US011053247B2

United States Patent
Dilger et al.

(10) Patent No.: US 11,053,247 B2
(45) Date of Patent: Jul. 6, 2021

(54) PYRIMIDINONES AS FACTOR XIA INHIBITORS

(71) Applicant: Bristol-Myers Squibb Company, Princeton, NJ (US)

(72) Inventors: Andrew K. Dilger, Ewing, NJ (US); James R. Corte, Yardley, PA (US); Indawati De Lucca, Pennington, NJ (US); Tianan Fang, Newtown, PA (US); Wu Yang, Princeton Junction, NJ (US); Yufeng Wang, Belle Mead, NJ (US); Kumar Balashanmuga Pabbisetty, Piscataway, NJ (US); William R. Ewing, Yardley, PA (US); Yeheng Zhu, Stockton, NJ (US); Ruth R. Wexler, Belle Mead, NJ (US); Donald J. P. Pinto, Churchville, PA (US); Michael J. Orwat, New Hope, PA (US); Leon M. Smith, II, Somerset, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/451,873

(22) Filed: Jun. 25, 2019

(65) Prior Publication Data
US 2020/0055854 A1 Feb. 20, 2020

Related U.S. Application Data

(63) Continuation of application No. 15/903,671, filed on Feb. 23, 2018, now Pat. No. 10,336,754, which is a continuation of application No. 15/221,142, filed on Jul. 27, 2016, now abandoned, which is a continuation of application No. 14/872,546, filed on Oct. 1, 2015, now Pat. No. 9,453,018.

(60) Provisional application No. 62/058,316, filed on Oct. 1, 2014, provisional application No. 62/058,293, filed on Oct. 1, 2014.

(51) Int. Cl.
| C07D 471/18 | (2006.01) |
| C07F 7/08 | (2006.01) |
| C07D 519/00 | (2006.01) |
| C07D 471/08 | (2006.01) |
| C07D 487/08 | (2006.01) |

(52) U.S. Cl.
CPC ......... *C07D 471/18* (2013.01); *C07D 471/08* (2013.01); *C07D 487/08* (2013.01); *C07D 519/00* (2013.01); *C07F 7/0814* (2013.01)

(58) Field of Classification Search
CPC .. C07D 471/18; C07D 487/08; C07D 471/08; C07D 519/00
See application file for complete search history.

(56) References Cited

U.S. PATENT DOCUMENTS

| 5,624,936 A | 4/1997 | deSolms |
| 5,869,682 A | 2/1999 | deSolms |
| 6,951,840 B2 | 10/2005 | Belvo et al. |
| 7,544,699 B2 | 6/2009 | Mjalli et al. |

FOREIGN PATENT DOCUMENTS

| CL | 2016001933 A1 | 3/2017 |
| CL | 2017000742 A1 | 11/2017 |
| CL | 2017000782 A1 | 11/2017 |
| CL | 2017000792 A1 | 11/2017 |
| DE | 40 34 829 A1 | 5/1992 |
| EP | 0 525 420 B1 | 5/1999 |
| EP | 1 016 663 A1 | 7/2000 |
| EP | 1 125 925 A1 | 8/2001 |
| EP | 3 089 979 B1 | 10/2017 |
| FR | 1525186 | 5/1968 |
| FR | 7155 M | 2/1970 |
| GB | 2497806 A | 6/2013 |
| JP | 2013-519678 A | 5/2013 |
| JP | 2014-521701 A | 8/2014 |
| JP | 2015-120685 A | 7/2015 |
| JP | 2017-504642 A | 2/2017 |

(Continued)

OTHER PUBLICATIONS

Al-Horani et al. in Expert Opinion if Therapeutic Patents 2016; 26(3):323-345 (Year: 2016).*
J. G. Cannon Chapter Nineteen in Burger's Medicinal Chemistry and Drug Discovery, Fifth Edition, vol. I: Principles and Practice, Wiley-Interscience 1995, pp. 783-802, 784 (Year: 1995).*
Wang et al. (May 1999) "Endogenous Bile Acids are Ligands for the Nuclear Receptor FXR/BAR", Molecular Cell, 3(5):543-553.
U.S. Appl. No. 15/115,314, filed Jul. 29, 2016, Corte, James R.
U.S. Appl. No. 15/115,319, filed Jul. 29, 2016, Dilger, Andrew K.
U.S. Appl. No. 15/115,327, filed Jul. 29, 2016, Corte, James R.

(Continued)

*Primary Examiner* — Dennis Heyer
(74) *Attorney, Agent, or Firm* — Mintz Levin Cohn Ferris Glovsky and Popeo, P.C.; Mark Pino; Pooja Varshneya

(57) ABSTRACT

The present invention provides compounds of Formula (1):

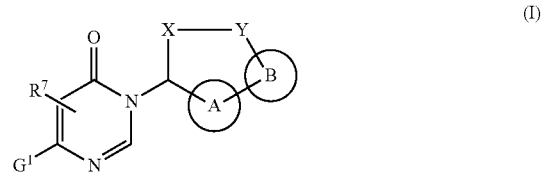

or stereoisomers, tautomers, or pharmaceutically acceptable salts thereof, wherein all the variables are as defined herein. These compounds are selective factor XIa inhibitors or dual inhibitors of FXIa and plasma kallikrein. This invention also relates to pharmaceutical compositions comprising these compounds and methods of treating thromboembolic and/or inflammatory disorders using the same.

9 Claims, No Drawings

(56) References Cited

FOREIGN PATENT DOCUMENTS

| | | |
|---|---|---|
| KR | 2015-0136294 A | 12/2015 |
| MX | 2016009230 A | 10/2016 |
| WO | WO 93/20099 A2 | 10/1993 |
| WO | WO 96/34010 A2 | 10/1996 |
| WO | WO 97/36891 A1 | 10/1997 |
| WO | WO 99/15530 A1 | 4/1999 |
| WO | WO 99/47545 A2 | 9/1999 |
| WO | WO 99/61444 A2 | 12/1999 |
| WO | WO 00/18733 A1 | 4/2000 |
| WO | WO 00/40571 A1 | 7/2000 |
| WO | WO 00/61608 A2 | 10/2000 |
| WO | WO 01/85695 A1 | 11/2001 |
| WO | WO 02/18369 A2 | 3/2002 |
| WO | WO 03/011222 A2 | 2/2003 |
| WO | WO 03/041641 A2 | 5/2003 |
| WO | WO 03/106438 A1 | 12/2003 |
| WO | WO 2004/080971 A1 | 9/2004 |
| WO | WO 2004/094372 A2 | 11/2004 |
| WO | WO 2005/014533 A2 | 2/2005 |
| WO | WO 2005/099709 A2 | 10/2005 |
| WO | WO 2005/123050 A2 | 12/2005 |
| WO | WO 2005/123680 A1 | 12/2005 |
| WO | WO 2006/017295 A2 | 2/2006 |
| WO | WO 2006/076575 A2 | 7/2006 |
| WO | WO 2006/089005 A2 | 8/2006 |
| WO | WO 2007/047608 A2 | 4/2007 |
| WO | WO 2007/054453 A2 | 5/2007 |
| WO | WO 2007/070816 A2 | 6/2007 |
| WO | WO 2007/070818 A1 | 6/2007 |
| WO | WO 2007/070826 A1 | 6/2007 |
| WO | WO 2007/076431 A1 | 7/2007 |
| WO | WO 2008/076805 A2 | 6/2008 |
| WO | WO 2008/079836 A2 | 7/2008 |
| WO | WO 2008/157162 A1 | 12/2008 |
| WO | WO 2009/114677 A1 | 9/2009 |
| WO | WO 2010/151317 A1 | 12/2010 |
| WO | WO 2011/002520 A2 | 1/2011 |
| WO | WO 2011/017296 A1 | 2/2011 |
| WO | WO 2011/100401 A1 | 8/2011 |
| WO | WO 2011/100402 A1 | 8/2011 |
| WO | WO 2013/009527 A2 | 1/2013 |
| WO | WO 2013/022814 A1 | 2/2013 |
| WO | WO 2013/022818 A1 | 2/2013 |
| WO | WO 2013/055984 A1 | 4/2013 |
| WO | WO 2013/056034 A1 | 4/2013 |
| WO | WO 2013/056060 A1 | 4/2013 |
| WO | WO 2013/093484 A1 | 6/2013 |
| WO | WO 2013/111107 A1 | 8/2013 |
| WO | WO 2013/111108 A1 | 8/2013 |
| WO | WO 2013/118805 A1 | 8/2013 |
| WO | WO 2013/167669 A1 | 11/2013 |
| WO | WO 2013/174937 A1 | 11/2013 |
| WO | WO 2014/014050 A1 | 1/2014 |
| WO | WO 2014/022766 A1 | 2/2014 |
| WO | WO 2014/022767 A1 | 2/2014 |
| WO | WO 2014/059202 A1 | 4/2014 |
| WO | WO 2014/059203 A1 | 4/2014 |
| WO | WO 2014/059214 A1 | 4/2014 |
| WO | WO 2014/108679 A1 | 7/2014 |
| WO | WO 2014/108685 A1 | 7/2014 |
| WO | WO 2014/120346 A1 | 8/2014 |
| WO | WO 2014/154794 A1 | 10/2014 |
| WO | WO 2014/160668 A1 | 10/2014 |
| WO | WO 2015/011087 A1 | 1/2015 |
| WO | WO 2015/044163 A1 | 4/2015 |
| WO | WO 2015/044165 A1 | 4/2015 |
| WO | WO 2015/044167 A1 | 4/2015 |
| WO | WO 2015/044169 A1 | 4/2015 |
| WO | WO 2015/044170 A1 | 4/2015 |
| WO | WO 2015/044172 A1 | 4/2015 |
| WO | WO 2015/044173 A1 | 4/2015 |
| WO | WO 2015/044174 A1 | 4/2015 |
| WO | WO 2015/047973 A1 | 4/2015 |
| WO | WO 2015/054087 A1 | 4/2015 |
| WO | WO 2015/107724 A1 | 7/2015 |
| WO | WO 2015/116882 A1 | 8/2015 |
| WO | WO 2015/116885 A1 | 8/2015 |
| WO | WO 2015/116886 A1 | 8/2015 |
| WO | WO 2015/120062 A2 | 8/2015 |
| WO | WO 2015/120777 A1 | 8/2015 |
| WO | WO 2015/123090 A1 | 8/2015 |
| WO | WO 2015/123091 A1 | 8/2015 |
| WO | WO 2015/123093 A1 | 8/2015 |
| WO | WO 2015/134998 A1 | 9/2015 |
| WO | WO 2015/160634 A1 | 10/2015 |
| WO | WO 2015/160636 A1 | 10/2015 |
| WO | WO 2015/183709 A1 | 12/2015 |
| WO | WO 2016/046157 | 3/2016 |
| WO | 2016/050358 A1 | 4/2016 |
| WO | 2016/050831 A1 | 4/2016 |
| WO | 2016/050841 A1 | 4/2016 |
| WO | WO 2016/053455 | 4/2016 |
| WO | WO 2016/093285 | 6/2016 |

OTHER PUBLICATIONS

Approaches of Classic Medicinal Chemistry, Optimizing Drug Binding Affinity: (Semi) Empirical Studies, http://www.chem.uzh.ch/zerbe/MedChem/MedChem4_MedChem.pdf (Mar. 18, 2012).

Boger, D.L. et al., "Thermal Atropisomerism of Aglucovancomycin Derivatives: Preparation of $(M,M,M)$- and $(P,M,M)$-Aglucovancomycins", J. Am. Chem. Soc., vol. 120, No. 35, pp. 8920-8926 (1998).

Caballero, J. et al., "Quantitative Structure-Activity Relationship Modeling of Growth Hormone Secretagogues Agonist Activity of Some Tetrahydroisoquinoline 1-Carboxamides", Chem. Biol. Drug. Des., vol. 69, pp. 48-55 (2007).

Chan, J.C.Y. et al., "The Characterization of Mice with a Targeted Combined Deficiency of Protein C and Factor XI", American Journal of Pathology, vol. 158, No. 2, pp. 469-479 (2001).

Chen, X. et al., Chapter 32: "The use of bioisosteric groups in lead optimization", Annual Reports in Medicinal Chemistry, vol. 38, pp. 333-346, Elsevier Inc., publ. (2003).

Cho, J.E. et al., "Characterization of Binding Mode for Human Coagulation Factor XI (FXI) Inhibitors", Bull. Korean Chem. Soc., vol. 34, No. 4, pp. 1212-1220 (2013).

Crosby, J.R. et al., "Antithrombotic Effect of Antisense Factor XI Oligonucleotide Treatment in Primates", Arterioscler. Thromb. Vasc. Biol., vol. 33, pp. 1670-1678 (2013), and vol. 33, pp. e127 and e130 (errata) (2013).

Evans, D.A. et al., "Total Syntheses of Vancomycin and Eremomycin Aglycons", Angew. Chem. Int. Ed., vol. 37, No. 19, pp. 2700-2704 (1998).

Gailani, D., "Gene Targeting in Hemostasis, Factor XI", Frontiers in Bioscience, vol. 6, pp. 201-207 (2001).

Gailani, D. et al., "A murine model of factor XI deficiency", Blood Coagulation and Fibrinolysis, vol. 8, pp. 134-144 (1997).

Gruber, A. et al., "Factor XI-dependence of surface- and tissue factor-initiated thrombus propagation in primates", Blood, vol. 102, No. 3, pp. 953-955 (2003).

Hoffman, M., "A cell-based model of coagulation and the role of factor VIIa", Blood Reviews, vol. 17, pp. S1-S5 (2003).

Jiang, G. et al., "Highly Efficient Oxidation of Amines to Imines by Singlet Oxygen and Its Application in Ugi-Type Reactions", Organic Letters, vol. 11, No. 20, pp. 4568-4571 (2009).

Li, J.J. et al., "Tetrahydroisoquinoline 1-carboxamides as growth hormone secretagogues", Bioorganic & Medicinal Chemistry Letters, vol. 15, pp. 1799-1802 (2005).

Matafonov, A. et al., "Evidence for factor IX-independent roles for factor XIa in blood coagulation", Journal of Thrombosis and Haemostasis, vol. 11, pp. 2118-2127 (2013).

MayoClinic.com, "Pulmonary Embolism: Prevention", http://www.mayoclinic.com/health/pulmonary-embolism/DS00429/DSECTION=prevention, accessed May 20, 2013.

Meijers, J.C.M. et al., "High Levels of Coagulation Factor XI as a Risk Factor for Venous Thrombosis", The New England Journal of Medicine, vol. 342, pp. 696-701 (2000).

(56) References Cited

OTHER PUBLICATIONS

Meng, D. et al., "Development of a novel tricyclic class of potent and selective FIXa inhibitors", Bioorganic & Medicinal Chemistry Letters (2015), doi: http://dx.doi.org/10.1016/j.bmcl.2015.07.078.

Minnema, M.C. et al., "Activation of Clotting Factors XI and IX in Patients with Acute Myocardial Infarction", Arterioscler. Thromb. Vasc. Biol., vol. 20, pp. 2489-2493 (2000).

Murakami, T. et al., "Evaluation of Factor XIa-$\alpha_1$-Antitrypsin in Plasma, a Contact Phase-Activated Coagulation Factor-Inhibitor Complex, in Patients with Coronary Artery Disease", Arteriosclerosis, Thrombosis, and Vascular Biology, vol. 15, No. 8, pp. 1107-1113 (1995).

Ngouansavanh, T. et al., "IBX-Mediated Oxidative Ugi-Type Multicomponent Reactions: Application to the N and C1 Functionalization of Tetrahydroisoquinoline", Angew. Chem. Int. Ed., vol. 46, pp. 5775-5778 (2007).

Rosen, E.D. et al., "FXI is Essential for Thrombus Formation Following FeCl$_3$-Induced Injury of the Carotid Artery in the Mouse", Thromb. Haemost., vol. 87, pp. 774-776 (2002).

Schumacher, W.A. et al., "Inhibition of Factor XIa as a New Approach to Anticoagulation", Arteriorscler. Thromb. Vasc. Biol., vol. 30, pp. 388-392 (2010).

Schuster, I. et al., "Convenient Synthesis of 1,2,3,4-Tetrahydroisoquinoline-1-Carboxylic Acid Derivatives via Isocyanide-Based Three-Component Reactions", Synthetic Communications, vol. 40, pp. 2488-2498 (2010).

Schuster, I. et al., "Synthesis of 1,2,3,4-Tetrahydroisoquinoline-1-Carboxylic Acid Derivatives *Via* Ugi Reactions", Letters in Organic Chemistry, vol. 4, No. 2, pp. 102-108 (2007).

Schuster, I. et al., "Synthesis of 1,2,3,4-Tetrahydroisoquinoline-1-carboxylic Acid Derivatives via Ugi Reactions", Magyar Kémiai Folyóirat (Hungarian Journal of Chemistry), vol. 116, No. 3, pp. 126-130 (2010).

Walsh, P.N., "Platelets and Factor XI Bypass the Contact System of Blood Coagulation", Thrombosis and Haemostasis, vol. 82, No. 2, pp. 234-242 (1999).

Wang, X. et al., "Effects of factor IX or factor XI deficiency on ferric chloride-induced carotid artery occlusion in mice", Journal of Thrombosis and Haemostasis, vol. 3, pp. 695-702 (2005).

Wu, Y.-J. et al., "Discovery of (*S,E*)-3-(2-fluorophenyl)-*N*-(1-(3-(pyridin-3-yloxy)phenyl)ethyl)-acrylamide as a potent and efficacious KCNQ2 (Kv7.2) opener for the treatment of neuropathic pain", Bioorganic & Medicinal Chemistry Letters, vol. 23, pp. 6188-6191 (2013).

\* cited by examiner

PYRIMIDINONES AS FACTOR XIA INHIBITORS

CROSS REFERENCE TO RELATED APPLICATIONS

This application is a continuation of U.S. application Ser. No. 15/903,671, filed on Feb. 23, 2018, which is a continuation of U.S. application Ser. No. 15/221,142, filed on Jul. 27, 2016 which is a continuation of U.S. application Ser. No. 14/872,546, filed on Oct. 1, 2015, now U.S. Pat. No. 9,453,018, issued Sep. 27, 2016, which is entitled to priority pursuant to 35 U.S.C. § 119(e) to U.S. provisional patent application Nos. 62/058,316 and 62/058,293, both filed on Oct. 1, 2014, which are incorporated herein in their entireties.

FIELD OF THE INVENTION

The present invention relates generally to novel macrocyclic compounds, and their analogues thereof, which are factor XIa inhibitors or dual inhibitors of factor XIa and plasma kallikrein, compositions containing them, and methods of using them, for example, for the treatment or prophylaxis of thromboembolic disorders, or for the treatment of retinal vascular permeability associated with diabetic retinopathy and diabetic macular edema.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and anti platelet agents such as aspirin and clopidogrel (PLAVTX®) The oral anticoagulant warfarin, inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation factor XIa (FXIa). Factor XIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D et al., *Arterioscler. Thromb. Vasc. Biol.*, 27:2507-2513 (2007).) The resulting burst of thrombin converts fibrinogen to fibrin that polymerizes to form the structural framework of a blood clot, and activates platelets, which are a key cellular component of coagulation (Hoffman, M., *Blood Reviews*, 17:S1-S5 (2003)). Therefore, factor XIa plays a key role in propagating this amplification loop and is thus an attractive target for anti-thrombotic therapy.

An alternative way of initiation of coagulation is operative when blood is exposed to artificial surfaces. This process is also termed contact activation. Surface absorption of factor XII leads to a conformational change in the factor XII molecule, thereby facilitating activation to proteolytic active factor XII molecules (factor XIIa and factor XIII). Factor XIIa (or XIII) has a number of target proteins, including plasma prekallikrein and factor XI.

Plasma prekallikrein is a zymogen of a trypsin-like serine protease and is present in plasma at 35 to 50 µg/mL. The gene structure is similar to that of factor XI. Overall, the amino acid sequence of plasma kallikrein has 58% homology to factor XI. Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastrointestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (Lehmann, A., "Ecallantide (DX-88), a plasma kallikrein inhibitor for the treatment of hereditary angioedema and the prevention of blood loss in on-pump cardiothoracic surgery", *Expert Opin. Biol. Ther.*, 8:1187-1199 (2008)).

The plasma kallikrein-kinin system is abnormally abundant in patients with advanced diabetic macular edema. It has been recently published that plasma kallikrein contributes to retinal vascular dysfunctions in diabetic rats (Clermont, A. et al., "Plasma kallikrein mediates retinal vascular dysfunction and induces retinal thickening in diabetic rats", *Diabetes*, 60:1590-1598 (2011)). Furthermore, administration of the plasma kallikrein inhibitor ASP-440 ameliorated both retinal vascular permeability and retinal blood flow abnormalities in diabetic rats. Therefore, a plasma kallikrein inhibitor should have utility as a treatment to reduce retinal vascular permeability associated with diabetic retinopathy and diabetic macular edema. Other complications of diabetes such as cerebral hemorrhage, nephropathy, cardiomyopathy and neuropathy, all of which have associations with plasma kallikrein may also be considered as targets for a plasma kallikrein inhibitor.

To date, no small molecule synthetic plasma kallikrein inhibitor has been approved for medical use. The large protein plasma kallikrein inhibitors present risks of anaphylactic reactions, as has been reported for Ecallantide. Thus there remains a need for compounds that inhibit plasma kallikrein, that do not induce anaphylaxis and that are orally available. Furthermore, the molecules in the known art feature a highly polar and ionizable guanidine or amidine functionality. It is well known that such functionalities may be limiting to gut permeability and therefore to oral availability.

SUMMARY OF THE INVENTION

The present invention provides novel macrocyclic compounds, their analogues, including stereoisomers, tautomers, pharmaceutically acceptable salts, or solvates thereof, which are useful as selective factor XIa inhibitors or dual inhibitors of factor XIa and plasma kallikrein.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of thromboembolic disorders.

The compounds of the invention may be used in the treatment of retinal vascular permeability associated with diabetic retinopathy and diabetic macular edema.

The compounds of the present invention may be used in therapy.

The compounds of the present invention may be used for the manufacture of a medicament for the treatment and/or prophylaxis of a thromboembolic disorder.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter aha, compounds of Formula (I):

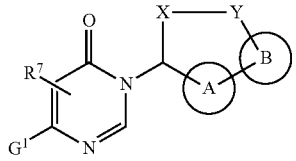

(I)

or stereoisomers, tautomers, pharmaceutically acceptable salts, solvates, or prodrugs thereof, wherein:

ring A is independently selected from 6-membered aryl and 5- to 6-membered heterocyclyl, wherein said aryl and heterocyclyl are optionally substituted with, where valence allows, one or more $R^4$;

ring B is 5- to 10-membered heterocyclyl optionally substituted with, where valence allows, one or more $R^3$ or 5- to 10-membered heterocyclyl comprising carbon atoms and 1-4 heteroatoms selected from N, $NR^{3c}$, O, and $S(O)_p$ and optionally substituted with, where valence allows, one or more $R^3$;

$G^1$ is independently selected from $C_{3\text{-}10}$ carbocyclyl and 5- to 10-membered heterocyclyl, wherein said carbocyclyl and heterocyclyl are optionally substituted with, where valence allows, one or more $R^8$;

X is independently selected from $C_{4\text{-}8}$ alkylene and $C_{4\text{-}8}$ alkenylene, wherein said alkylene and alkenylene are substituted with $R^1$ and $R^2$; alternatively one or more of the carbon atoms of said alkylene and alkenylene may be replaced by O, C=O, $S(=O)_p$, $S(=O)_pNH$, and $NR^{15}$;

Y is independently selected from $-CR^{13}NH-$, $-NHC(=O)-$, $-C(=O)NH-$, $-S(=O)_pNH-$, $-NHS(=O)_p-$, and $C_{1\text{-}2}$ alkylene;

$R^1$ and $R^2$ are independently selected from H, D, halogen, haloalkyl, $C_{1\text{-}6}$ alkyl (optionally substituted with $R^6$), hydroxyl, and alkoxy optionally substituted with $R^6$, and $C_{3\text{-}6}$ cycloalkyl optionally substituted with $R^6$; optionally, when $R^1$ and $R^2$ are attached to the same carbon atom, together they form an oxo group or $C_{3\text{-}6}$ cycloalkyl; optionally, when $R^1$ and $R^2$ are attached to carbon atoms adjacent to each other, together they form a bond or carbocyclyl; optionally, $R^1$ and $R^{15}$ or $R^2$ and $R^{15}$ taken together form a ring;

$R^3$ is independently selected from H, $NO_2$, O, halogen, haloalkyl, $C_{1\text{-}4}$ alkyl (optionally substituted with $R^6$), $C_{2\text{-}4}$ alkenyl (optionally substituted with $R^6$), $C_{2\text{-}4}$ alkynyl (optionally substituted with $R^6$),
CN, $-(CH_2)_n-OR^5$, $-(CH_2)_n-NR^5R^5$, $-(CH_2)_n-C(=O)R^5$, $-(CH_2)_n-C(=O)OR^5$, $-(CH_2)_n-NR^9C(=O)OR^5$, $-(CH_2)_n-NR^9C(=O)R^5$, $-(CH_2)_n-NR^9C(N=CN)NHR^5$, $-(CH_2)_n-NR^9C(NH)NHR^5$, $-(CH_2)_n-N=CR^9NR^5R^5$, $-(CH_2)_n-NR^9C(=O)NR^3R^5$, $-(CH_2)_n-C(=O)NR^5R^5$, $-(CH_2)_n-NR^9C(=S)NR^9C(=O)R^5$, $-(CH_2)_n-S(=O)_pR^5$, $-(CH_2)_n-S(=O)_pNR^5R^5$, $-(CH_2)_n-NR^9S(=O)_pNR^5R^5$, $-(CH_2)_n-NR^9S(=O)_pR^5$, $-(CH_2)_n-C_{3\text{-}10}$ carbocyclyl and $-(CH_2)_n$-4- to 10-membered heterocyclyl, wherein said carbocyclyl and heterocyclyl are optionally substituted with $R^6$; optionally, two adjacent $R^3$ groups on the heterocyclyl may form a ring optionally substituted with $R^6$;

$R^{3c}$ is independently selected from H, haloalkyl, $C_{1\text{-}4}$ alkyl (optionally substituted with $R^6$), $-(CH_2)_{1\text{-}2}-OH$, $C(=O)C_{1\text{-}4}$ alkyl, $-(CH_2)_{0\text{-}2}-C(=O)OH$, $-C(=O)OC_{1\text{-}4}$ alkyl, $S(=O)_pC_{1\text{-}6}$ alkyl, $-(CH_2)_n-C_{3\text{-}10}$ carbocyclyl and $-(CH_2)_n$-4- to 10-membered heterocyclyl, wherein said carbocyclyl and heterocyclyl are optionally substituted with $R^6$;

$R^4$ is independently selected from H, OH, $NH_2$, halogen, CN, $C_{1\text{-}4}$ alkyl, $C_{1\text{-}4}$ haloalkyl, $C_{1\text{-}4}$ alkoxy, $-CH_2OH$, $-C(=O)OH$, $-CH_2C(=O)OH$, $-CO_2(C_{1\text{-}4}$ alkyl), $-C(=O)NH_2$, $-C(=O)NH(C_{1\text{-}4}$ alkyl), $-C(=O)N(C_{1\text{-}4}$ alkyl)$_2$, $-S(=O)_2C_{1\text{-}4}$ alkyl, $-S(=O)_2NH_2$, $C_{3\text{-}6}$ cycloalkyl, aryl, and 5- to 6-membered heterocyclyl, wherein said cycloalkyl, aryl and heterocyclyl are optionally substituted with $R^6$;

$R^5$ is independently selected from H, $C_{1\text{-}4}$ alkyl (optionally substituted with halogen, hydroxyl, alkoxy, carboxy, hydroxy carbonyl, alkoxycarbonyl, amino, substituted amino), $-(CH_2)_n-C_{3\text{-}10}$ carbocyclyl and $-(CH_2)_n$-4- to 10-membered heterocyclyl, wherein said carbocyclyl and heterocyclyl are optionally substituted with $R^6$; alternatively, $R^5$ and $R^5$ together with the nitrogen atom to which they are both attached form a heterocyclic ring optionally substituted with $R^6$;

$R^6$ is independently selected from H, $-(CH_2)_n-OH$, =O, $-(CH_2)_nNH_2$, $-(CH_2)_nCN$, halogen, $C_{1\text{-}6}$ alkyl, $-(CH_2)_n-C(=O)OH$, $-(CH_2)_n-C(=O)NH_2$, $-(CH_2)_n-C(=O)OC_{1\text{-}4}$ alkyl, $-(CH_2)_n-OC_{1\text{-}4}$ alkyl, $-(CH_2)_n-C_{3\text{-}10}$ carbocyclyl, $-(CH_2)_n$-4- to 10-membered heterocyclyl, and $-O$-4- to 10-membered heterocyclyl, wherein said carbocyclyl and heterocyclyl are optionally substituted with $R^{10}$;

$R^7$ is independently selected from H, hydroxyl, alkoxy, halogen, amino, $C_{1\text{-}3}$haloalkyl, and $C_{1\text{-}3}$ alkyl;

$R^8$ is independently selected from H, halogen, $-(CH_2)_n$ CN, $C_{1\text{-}6}$ alkyl, amino, aminoalkyl, haloalkyl, hydroxyl, alkoxy, haloalkoxy, alkylcarbonyl, carboxyl, carboxyl ester, amide, haloalkylaminocarbonyl, arylalkylaminocarbonyl, haloalkylaminocarbonyl, alkoxy carbonyl amino, haloalkylcarbonylamino, arylamino, heteroaryl amino, arylalkylcarbonyl, aryloxy, heteroaryloxy, alkylthio, alkylsulfonyl, arylsulfonyl, heteroarylsulfonyl, sulfonamide, —$(CH_2)_n$-aryl, —$(CH_2)_n$—$C_{3-6}$ cycloalkyl, and —$(CH_2)_n$-4- to 12-membered heterocyclyl, wherein said aryl, cycloalkyl, and heterocyclyl are optionally substituted with $R^{10}$;

alternatively, two adjacent $R^8$ groups taken together form a heterocyclic ring optionally substituted with $R^{10}$;

$R^9$ is H or $C_{1-6}$ alkyl;

$R^{10}$ is independently selected from H, $C_{1-6}$ alkyl (optionally substituted with $R^{11}$), $C_{2-6}$ alkenyl, $C_{2-6}$ alkynyl, aryl (optionally substituted with $R^{11}$), —$(CH_2)_n$—$C_{3-6}$ cycloalkyl (optionally substituted with $R^{11}$), —$(CH_2)_n$—O-4- to 10-membered heterocyclyl (optionally substituted with $R^{11}$), halogen, —$(CH_2)_n CN$, $NO_2$, =O, $C(=O)NR^{12}R^{12}$, —$(CH_2)_n C(=O)OR^{12}$, $Si(C_{1-4}$ alkyl$)_3$, —$(CH_2)_n$—$OR^{12}$, —$(CH_2)_n$—$NR^{12}R^{12}$, —$S(=O)_p C_{1-6}$ alkyl, $NR^{12}S(=O)_p C_{1-6}$ alkyl, $S(=O)_p NR^{12}R^{12}$, and $C(=NOH)NH_2$;

$R^{11}$, at each occurrence, is independently selected from H, halogen, $C_{1-5}$ alkyl, —$(CH_2)_n$—OH, $C_{3-6}$ cycloalkyl, phenyl, and heterocyclyl;

$R^{12}$, at each occurrence, is independently selected from H, $C_{1-5}$ alkyl optionally substituted with $R^{11}$, $C_{3-6}$ cycloalkyl, phenyl, and heterocyclyl, or $R^{12}$ and $R^{12}$ together with the nitrogen atom to which they are both attached form a heterocyclic ring optionally substituted with $C_{1-4}$alkyl;

$R^{13}$ is, independently at each occurrence, selected from H, $C_{1-4}$ haloalkyl, $C_{1-4}$ alkyl, $C(=O)OH$, $C(=O)O(C_{1-4}$ alkyl), $C(=O)O(CH_2)_2O(C_{1-4}$ alkyl), $C(=O)O(C_{1-4}$ haloalkyl), $CH_2C(=O)OH$, $CH_2C(=O)O(C_{1-4}$ alkyl), $C(=O)NH_2$, $C(=O)NH(C_{1-4}$ alkyl), $C(=O)N(C_{1-4}$ alkyl$)_2$, and —$C(=O)NH(C_{1-4}$ alkoxy);

$R^{15}$ is H or $C_{1-6}$ alkyl;

n, at each occurrence, is an integer independently selected from 0, 1, 2, 3, and 4; and p, at each occurrence, is an integer independently selected from 0, 1, and 2.

In another aspect, the present invention provides compounds of Formula (I) or stereoisomers, tautomers, pharmaceutically acceptable salts, solvates, or prodrugs thereof, wherein:

ring A is independently selected from a 6-membered aryl and a 5- to 6-membered heterocycle, wherein said aryl and heterocycle are optionally substituted with, where valence allows, one or more $R^4$;

ring B is a 5- to 10-membered heterocycle optionally substituted with, where valence allows, one or more $R^3$;

$G^1$ is independently selected from a $C_{3-10}$ carbocycle and a 5- to 10-membered heterocycle, wherein said carbocycle and heterocycle are optionally substituted with, where valence allows, one or more $R^8$;

X is independently selected from $C_{4-5}$ alkylene and $C_{4-5}$ alkenylene, wherein said alkylene and alkenylene are substituted with $R^1$ and $R^2$; alternatively one or more of the carbon atoms of said alkylene and alkenylene may be replaced by O, C=O, $S(=O)_p$, $S(=O)_p NH$, NH, and $N(C_{1-4}$ alkyl);

Y is independently selected
from —$CR^{13}NH$—, —$NHC(=O)$—, —$C(=O)NH$—, —$S(=O)_p NH$—, —$NHS(=O)_p$—, and $C_{1-2}$ alkylene;

$R^1$ and $R^2$ are independently selected from H, halogen, haloalkyl, $C_{1-6}$ alkyl (optionally substituted with $R^6$), hydroxyl, and alkoxy (optionally substituted with $R^6$), and $C_{3-6}$ cycloalkyl optionally substituted with $R^6$; optionally, when $R^1$ and $R^2$ are attached to the same carbon atom, together they form an oxo group or $C_{3-6}$ cycloalkyl; optionally, when $R^1$ and $R^2$ are attached to carbon atoms adjacent to each other, together they form a bond or a carbocycle;

$R^3$ is independently selected from H, $NO_2$, =O, halogen, haloalkyl, $C_{1-4}$ alkyl (optionally substituted with $R^6$), $C_{2-4}$ alkenyl (optionally substituted with $R^6$), $C_{2-4}$ alkynyl (optionally substituted with $R^6$),
CN, —$(CH_2)_n$—$OR^5$, —$(CH_2)_n$—$NR^5R^5$, —$(CH_2)_n$—$C(=O)R^5$, —$(CH_2)_n$—$C(=O)OR^5$, —$(CH_2)_n$—$NR^9C(=O)OR^5$, —$(CH_2)_n$—$NR^9C(=O)R^5$, —$(CH_2)_n$—$NR^9C(N=CN)NHR^5$, —$(CH_2)_n$—$NR^9C(NH)NHR^5$, —$(CH_2)_n$—$N=CR^9NR^5R^5$, —$(CH_2)_n$—$NR^9C(=O)NR^5R^5$, —$(CH_2)_n$—$C(=O)NR^5R^5$, —$(CH_2)_n$—$NR^9C(=S)NR^9C(=O)R^5$, —$(CH_2)_n$—$S(=O)_p C_{1-6}$ alkyl optionally substituted with $R^{11}$, —$(CH_2)_n$—$S(=O)_p NR^5R^5$, —$(CH_2)_n$—$NR^9S(=O)_p NR^3R^5$, —$(CH_2)_n$—$NR^9S(=O)_p C_{1-6}$ alkyl optionally substituted with $R^{11}$, —$(CH_2)_n$—$C_{3-10}$ carbocycle and —$(CH_2)_n$-4- to 10-membered heterocycle, wherein said carbocycle and heterocycle are optionally substituted with $R^6$; optionally, two adjacent $R^3$ groups on the carbocycle and heterocycle may form a ring optionally substituted with $R^6$;

$R^4$ is independently selected from H, OH, $NH_2$, halogen, CN, $C_{1-4}$ alkyl, $C_{1-4}$ haloalkyl, CM alkoxy, —$CH_2OH$, —$C(=O)OH$, —$CH_2C(=O)OH$, —$CO_2(C_{1-4}$ alkyl), —$C(=O)NH_2$, —$C(=O)NH(C_{1-4}$ alkyl), —$C(=O)N(C_{1-4}$ alkyl$)_2$, —$S(=O)_2 C_{1-4}$ alkyl, $S(=O)_2 NH_2$, $C_{3-6}$ cycloalkyl, aryl, and 5- to 6-membered heterocycle, wherein said cycloalkyl, aryl and heterocycle are optionally substituted with $R^6$;

$R^5$ is independently selected from H, $C_{1-4}$ alkyl (optionally substituted with halogen, hydroxyl, alkoxy, carboxy, alkoxy carbonyl, amino, substituted amino), —$(CH_2)_n$—$C_{3-10}$ carbocycle and —$(CH_2)_n$-4- to 10-membered heterocycle, wherein said carbocycle and heterocycle are optionally substituted with $R^6$; alternatively, $R^5$ and $R^5$ together with the nitrogen atom to which they are both attached form a heterocyclic ring optionally substituted with $R^6$;

$R^6$ is independently selected from H, —$(CH_2)_n$—OH, =O, —$(CH_2)_n NH_2$, —$(CH_2)_n CN$, halogen, $C_{1-6}$ alkyl, —$(CH_2)_n$—$C(=O)OH$, —$(CH_2)_n$—$C(=O)OC_{1-4}$ alkyl, —$(CH_2)_n$—$OC_{1-4}$ alkyl, —$(CH_2)_n$—$C_{3-10}$ carbocycle, —$(CH_2)_n$-4- to 10-membered heterocycle, and —O-4- to 10-membered heterocycle, wherein said carbocycle and heterocycle are optionally substituted with $R^{10}$;

$R^7$ is independently selected from H, hydroxyl, alkoxy, halogen, amino, and $C_{1-3}$ alkyl;

$R^8$ is independently selected from H, halogen, CN, $NH_2$, $C_{1-6}$ alkyl, haloalkyl, haloalkylcarbonylamine, alkylcarbonyl, hydroxyl, alkoxy, haloalkoxy, —$(CH_2)_n$-aryl, —$(CH_2)_n$—$C_{3-6}$ cycloalkyl, and —$(CH_2)_n$-4- to 6-membered heterocycle, wherein said aryl, cycloalkyl, and heterocycle are optionally substituted with $R^{10}$;

alternatively, two adjacent $R^8$ groups form a heterocyclic ring optionally substituted with $R^{10}$;

$R^9$ is H or $C_{1-6}$ alkyl;

$R^{10}$ is independently selected from H, $C_{1-6}$ alkyl (optionally substituted with $R^{11}$), $C_{2-6}$ alkenyl, $C_{2-6}$ alkynyl, aryl, —$(CH_2)_n$—$C_{3-6}$ cycloalkyl (optionally substituted with $R^{11}$), —$(CH_2)_n$—O-4- to 10-membered heterocycle (optionally substituted with $R^{11}$), halogen, CN, $NC_2$, =O, $C(=O)NR^{12}R^{12}$, $C(=O)OH$, $Si(C_{1-4}$ alkyl$)_3$, —$(CH_2)_n$—$OR^{12}$, —$(CH_2)_n$—$NR^{12}R^{12}$, and $C(=NOH)NH_2$;

$R^{11}$, at each occurrence, is independently selected from H, halogen, $C_{1-5}$ alkyl, —$(CH_2)_n$—OH, $C_{3-6}$ cycloalkyl, phenyl, and heterocycle;

$R^{12}$, at each occurrence, is independently selected from H, $C_{1-5}$ alkyl, $C_{3-6}$ cycloalkyl, phenyl, and heterocycle, or $R^{12}$ and $R^{12}$ together with the nitrogen atom to which they are both attached form a heterocyclic ring optionally substituted with
$C_{1-4}$alkyl;

$R^{13}$ is, independently at each occurrence, selected from H, halogen, $C_{1-4}$ haloalkyl, $CO_2H$, $CO_2(C_{1-4}$ alkyl), $CO_2(CH_2)_2O(C_{1-4}$ alkyl), $CO_2(C_{1-4}$ haloalkyl), $CO_2(CH_2)_2SO_2(C_{1-4}$ alkyl), $CH_2CO_2H$, $CH_2CO_2(C_{1-4}$ alkyl), $CONH_2$, $CONH(C_{1-4}$ alkyl), $CON(C_{1-4}$ alkyl)$_2$, —$CONH(C_{1-4}$ alkoxy), —$CO_2(CH_2)_2O(C_{1-4}$ alkyl), —$CO_2(CH_2)_2N(C_{1-4}$ alkyl)$_2$, —$CONH(CH_2)_2O(C_{1-4}$ alkyl), —$CONH(CH_2)_2N(C_{1-4}$ alkyl)$_2$, —$CON(C_{1-4}$ alkyl)$(CH_2)_2O(C_{1-4}$ alkyl), —$CON(C_{1-4}$ alkyl)$(CH_2)_2N(C_{1-4}$ alkyl)$_2$, $C_{1-4}$ alkyl, —CONHBn, —CONH(OBn), —$(CO)_{0-1}(CH_2)_{0-3}$—$C_{3-6}$ carbocycle,
and —$(CH_2)_{0-1}$—$(CO)_{0-1}$—$(V)_{0-1}$—$(CH_2)_{0-2}$-(4- to 6-membered heterocycle comprising carbon atoms and 1-4 heteroatoms selected from N, NH, N($C_{1-4}$ alkyl), O, and S(O)$_p$), wherein said carbocycle and heterocycle are substituted with 0-2 $R^{14}$;

$R^{14}$ is, independently at each occurrence, selected from the group consisting of: halogen, OH, $CHF_2$, $CF_3$, $C_{1-4}$ alkoxy, $CH_2OH$, $CO_2H$, $CO_2(C_{1-4}$ alkyl), $CONH_2$, and $C_{1-4}$ alkyl;

V is independently selected from O, NH and N($C_{1-4}$ alkyl);

n, at each occurrence, is an integer independently selected from 0, 1, 2, 3, and 4; and p, at each occurrence, is an integer independently selected from 0, 1, and 2.

In another aspect, the present invention provides compounds of Formula (I) or stereoisomers, tautomers, pharmaceutically acceptable salts, solvates, or prodrugs thereof, wherein:

ring A is independently selected from a 6-membered aryl and a 5- to 6-membered heterocycle, wherein said aryl and heterocycle are optionally substituted with, where valence allows, one or more $R^4$;

ring B is a 5- to 10-membered heterocycle optionally substituted with, where valence allows, one or more $R^3$;

$G^1$ is independently selected from a $C_{3-10}$ carbocycle and a 5- to 10-membered heterocycle, wherein said carbocycle and heterocycle are optionally substituted with, where valence allows, one or more $R^8$;

X is independently selected from $C_{4-8}$ alkylene and $C_{4-8}$ alkenylene, wherein said alkylene and alkenylene are substituted with $R^1$ and $R^2$; alternatively one or more of the carbon atoms of said alkylene and alkenylene may be replaced by O, C=O, S(O)$_p$, S(O)$_p$NH, NH, and N($C_{1-4}$ alkyl);

Y is independently selected from —NH—C(O)— and —C(O)—NH—;

$R^1$ and $R^2$ are independently selected from H, halogen, haloalkyl, $C_{1-6}$ alkyl (optionally substituted with $R^6$), hydroxyl, and alkoxy (optionally substituted with $R^6$), and $C_{3-6}$ cycloalkyl optionally substituted with $R^6$; optionally, when $R^1$ and $R^2$ are attached to the same carbon atom, together they form an oxo group or $C_{3-6}$cycloalkyl; optionally, when $R^1$ and $R^2$ are attached to carbon atoms adjacent to each other, together they form a bond or a carbocycle;

$R^3$ is independently selected from H, $NO_2$, =O, halogen, haloalkyl, $C_{1-4}$alkyl (optionally substituted with $R^6$), $C_{2-4}$alkenyl (optionally substituted with $R^6$), $C_{2-4}$alkynyl (optionally substituted with $R^6$), CN, —$(CH_2)_n$—$OR^5$, —$(CH_2)_n$—$NR^5R^5$, —$(CH_2)_n$—$C(O)OR^5$, —$(CH_2)_n$—$NR^9C(O)OR^5$, —$(CH_2)_n$—$NR^9C(O)R^5$, —$(CH_2)_n$—$NR^9C(N$—CN)NHR$^5$, —$(CH_2)_n$—$NR^9C(NH)NHR^5$, —$(CH_2)_n$—$N$=$CR^9NR^5R^5$, —$(CH_2)_n$—$NR^9C(O)NR^5R^5$, —$(CH_2)_n$—$C(O)NR^5R^5$, —$(CH_2)_n$—$NR^9C(S)NR^9C(O)R^5$, —$(CH_2)_n$—$S(O)_pR^{12}$, —$(CH_2)_n$—$S(O)_pNR^5R^5$, —$(CH_2)_n$—$NR^9S(O)_pNR^5R^5$, —$(CH_2)_n$—$NR^9S(O)_pR^{12}$, —$(CH_2)_n$—$C_{3-10}$ carbocycle and —$(CH_2)_n$-4- to 10-membered heterocycle, wherein said carbocycle and heterocycle are optionally substituted with $R^6$; optionally, two adjacent $R^3$ groups on the carbocycle and heterocycle may form a ring optionally substituted with $R^6$;

$R^4$ is independently selected from H, OH, $NH_2$, halogen, CN, $C_{1-4}$ alkyl, $C_{1-4}$ haloalkyl, $C_{1-4}$ alkoxy, —$CH_2OH$, —$CO_2H$, —$CH_2CO_2H$, —$CO_2(C_{1-4}$ alkyl), —$C(O)NH_2$, —$C(O)NH(C_{1-4}$ alkyl), —$C(O)N(C_{1-4}$ alkyl)$_2$, $S(O)_2NH_2$, $C_{3-6}$ cycloalkyl, aryl, and 5- to 6-membered heterocycle, wherein said cycloalkyl, aryl and heterocycle are optionally substituted with $R^6$;

$R^5$ is independently selected from H, $C_{1-4}$ alkyl (optionally substituted with halogen, hydroxyl, alkoxy, carboxy, alkoxycarbonyl, amino, substituted amino), —$(CH_2)_n$—$C_{3-10}$ carbocycle and —$(CH_2)_n$-4- to 10-membered heterocycle, wherein said carbocycle and heterocycle are optionally substituted with $R^6$; alternatively, $R^5$ and $R^5$ together with the nitrogen atom to which they are both attached form a heterocyclic ring optionally substituted with $R^6$;

$R^6$ is independently selected from H, —$(CH_2)_n$—OH, =O, —$(CH_2)_nNH_2$, —$(CH_2)_nCN$, halogen, $C_{1-6}$ alkyl, —$(CH_2)_n$—C(=O)OH, —$(CH_2)_n$—C(=O)O$C_{1-4}$ alkyl, —$(CH_2)_n$—$OC_{1-4}$ alkyl, —$(CH_2)_n$—$C_{3-10}$ carbocycle, —$(CH_2)_n$-4- to 10-membered heterocycle, and —O-4- to 10-membered heterocycle, wherein said carbocycle and heterocycle are optionally substituted with $R^{10}$;

$R^7$ is independently selected from H, hydroxyl, alkoxy, halogen, amino, and $C_{1-3}$ alkyl;

$R^8$ is independently selected from H, halogen, CN, $NH_2$, $C_{1-6}$ alkyl, haloalkyl, haloalkylcarbonylamine, alkylcarbonyl, alkoxy, haloalkoxy, —$(CH_2)_n$-aryl, —$(CH_2)_n$—$C_{3-6}$ cycloalkyl, and —$(CH_2)_n$-4- to 6-membered heterocycle;

$R^9$ is H or $C_{1-6}$ alkyl;

$R^{10}$ is independently selected from H, $C_{1-6}$ alkyl (optionally substituted with $R^{11}$), $C_{2-6}$ alkenyl, $C_{2-6}$ alkynyl, —$(CH_2)_n$—$C_{3-6}$ cycloalkyl (optionally substituted with $R^{11}$), —O-4- to 10-membered heterocycle (optionally substituted with $R^{11}$), F, Cl, Br, CN, $NO_2$, =O, $CO_2H$, —$(CH_2)_n$—$OC_{1-5}$ alkyl, —$(CH_2)_n$—$OR^{11}$, and —$(CH_2)_n$—$NR^{11}R^{11}$;

$R^{11}$, at each occurrence, is independently selected from H, $C_{1-5}$ alkyl, —$(CH_2)_n$—OH, $C_{3-6}$ cycloalkyl, and phenyl, or $R^{11}$ and $R^{11}$ together with the nitrogen atom to which they are both attached form a heterocyclic ring optionally substituted with $C_{1-4}$alkyl;

$R^{12}$ is $C_{1-6}$ alkyl optionally substituted with $R^{11}$;

n, at each occurrence, is an integer independently selected from 0, 1, 2, 3, and 4; and p, at each occurrence, is an integer independently selected from 0, 1, and 2.

In another aspect, the present invention provides compounds of Formula (II):

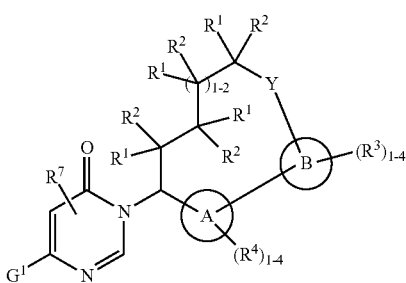

(II)

or stereoisomers, tautomers, pharmaceutically acceptable salts, solvates, or prodrugs thereof, wherein:

ring A is independently selected from a 6-membered aryl and a 5- to 6-membered heterocycle, wherein said aryl and heterocycle are substituted with 1-4 $R^4$;

ring B is a 5- to 10-membered heterocycle substituted with 1-4 $R^3$;

$G^1$ is independently selected from a $C_{3-10}$ carbocycle and a 5- to 10-membered heterocycle, wherein said carbocycle and heterocycle are substituted with 1-4 $R^8$;

Y is independently selected from —NH—C(O)— and —C(O)—NH—;

$R^1$ and $R^2$ are independently selected from H, halogen, haloalkyl, $C_{1-4}$ alkyl (optionally substituted with $R^6$), hydroxyl, and alkoxy (optionally substituted with $R^6$), and $C_{3-5}$ cycloalkyl optionally substituted with $R^6$;

$R^3$ is independently selected from H, =O, halogen, haloalkyl, $C_{1-4}$alkyl (optionally substituted with $R^6$), $C_{2-4}$ alkenyl (optionally substituted with $R^6$), $C_{2-4}$ alkynyl (optionally substituted with $R^6$), CN, $NO_2$, —$(CH_2)_n$—$OR^5$, —$(CH_2)_n$—$NR^5R^5$, —$(CH_2)_n$—C(O)$OR^5$, —$(CH_2)_n$—$NR^9C(O)OR^5$, —$(CH_2)_n$—$NR^9C(O)R^5$, —$(CH_2)_n$—$NR^9C(N$—CN)$NHR^5$, —$(CH_2)_n$—$NR^9C(NH)NHR^5$, —$(CH_2)_n$—N=$CR^9NR^5R^5$, —$(CH_2)_n$—$NR^9C(O)NR^5R^5$, —$(CH_2)_n$—$C(O)NR^5R^5$, —$(CH_2)_n$—$NR^9C(S)NR^9C(O)R^5$, —$(CH_2)_n$—$S(O)_pR^{12}$, —$(CH_2)_n$—$S(O)_pNR^5R^5$, —$(CH_2)_n$—$NR^9S(O)_pNR^5R^5$, —$(CH_2)_n$—$NR^9S(O)_pR^{12}$, —$(CH_2)_n$—$C_{3-10}$ carbocycle and —$(CH_2)_n$-4- to 10-membered heterocycle, wherein said carbocycle and heterocycle are optionally substituted with $R^6$; optionally, two adjacent $R^3$ groups on the carbocycle and heterocycle may form a ring optionally substituted with $R^6$;

$R^4$ is independently selected from H, OH, halogen, CN, $C_{1-4}$ alkyl, $C_{1-4}$ haloalkyl, $C_{1-4}$ alkoxy, —C(O)$NH_2$, —C(O)NH($C_{1-4}$ alkyl), —C(O)N($C_{1-4}$ alkyl)$_2$, $C_{3-6}$ cycloalkyl, aryl, and 5- to 6-membered heterocycle, wherein said cycloalkyl, aryl and heterocycle are optionally substituted with $R^6$;

$R^5$ is independently selected from H, $C_{1-4}$ alkyl (optionally substituted with halogen, hydroxyl, alkoxy, carboxy, alkoxycarbonyl, amino, substituted amino), $C_{3-10}$ carbocycle and 4- to 10-membered heterocycle, wherein said carbocycle and heterocycle are optionally substituted with $R^6$; alternatively, $R^5$ and $R^5$ together with the nitrogen atom to which they are both attached form a heterocyclic ring optionally substituted with $R^6$;

$R^6$ is independently selected from OH, =O, —$(CH_2)_nNH_2$, —$(CH_2)_nCN$, halogen, $C_{1-6}$ alkyl, —$(CH_2)_n$—C(=O)OH, —$(CH_2)_n$—C(=O)$OC_{1-4}$ alkyl, —$(CH_2)_n$—$OC_{1-4}$ alkyl, —$(CH_2)_n$—$C_{3-10}$ carbocycle, —$(CH_2)_n$-4- to 10-membered heterocycle, and —$(CH_2)_n$-4- to 10-membered heterocycle, wherein said carbocycle and heterocycle are optionally substituted with $R^{10}$;

$R^7$ is independently selected from H, hydroxyl, alkoxy, halogen, methyl, ethyl, and isopropyl;

$R^8$ is independently selected from H, halogen, CN, $NH_2$, $C_{1-6}$ alkyl, haloalkyl, alkylcarbonyl, alkoxy, haloalkoxy, —$(CH_2)_n$-aryl, —$(CH_2)_n$—$C_{3-6}$ cycloalkyl, and —$(CH_2)_n$-4- to 6-membered heterocycle;

$R^9$ is H or $C_{1-6}$ alkyl;

$R^{10}$ is independently selected from $C_{1-6}$ alkyl (optionally substituted with $R^{11}$), $C_{2-6}$ alkenyl, $C_{2-6}$ alkynyl, —$(CH_2)_n$—$C_{3-6}$ cycloalkyl, —O-4- to 10-membered heterocycle (optionally substituted with $R^{11}$), F, Cl, Br, CN, $NO_2$, =O, $CO_2H$, —$(CH_2)_n$—$OC_{1-5}$ alkyl, —$(CH_2)_n$—$OR^{11}$, and —$(CH_2)_n$—$NR^{11}R^{11}$;

$R^{11}$, at each occurrence, is independently selected from H, $C_{1-5}$ alkyl, —$(CH_2)_n$—OH, $C_{3-6}$ cycloalkyl, and phenyl, or $R^{11}$ and $R^{11}$ together with the nitrogen atom to which they are both attached form a heterocyclic ring optionally substituted with $C_{1-4}$alkyl;

$R^{12}$ is $C_{1-6}$ alkyl optionally substituted with $R^{11}$;

n, at each occurrence, is an integer independently selected from 0, 1, 2, 3, and 4; and p, at each occurrence, is an integer independently selected from 0, 1, and 2.

In another aspect, the present invention provides compounds of Formula (II), or stereoisomers, tautomers, pharmaceutically acceptable salts, solvates, or prodrugs thereof, wherein:

ring A is independently selected from

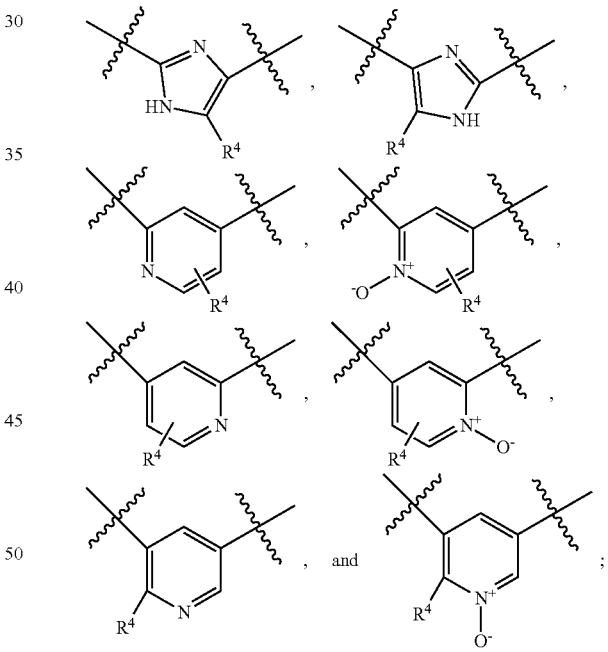

ring B is

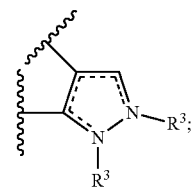

---- is an optional bond;

$G^1$ is independently selected from

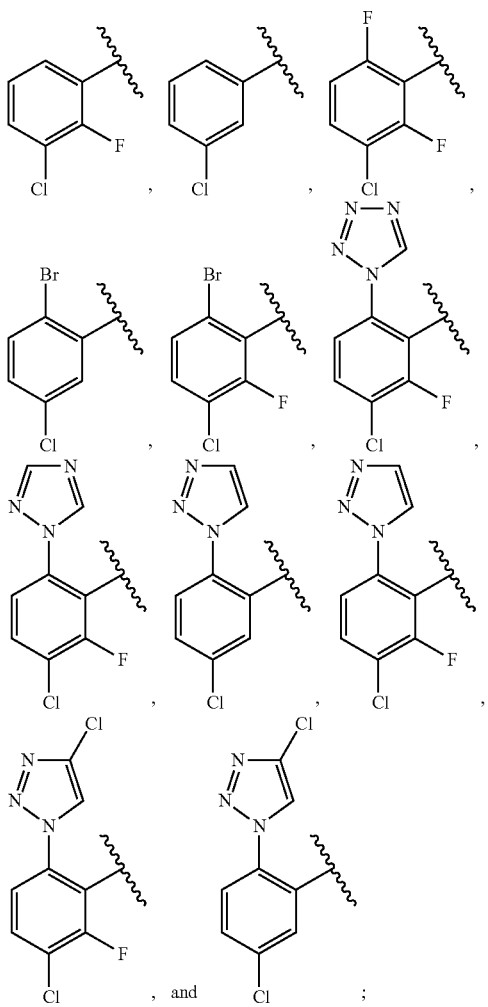

Y is —C(O)NH—;
$R^1$ and $R^2$ are independently selected from H and $C_{1-4}$ alkyl;
$R^3$ is independently selected from H, F, $C_{1-4}$ alkyl, haloalkyl, and —NHC(O)O$C_{1-4}$ alkyl; provided only one $R^3$ is present on the ring, and
$R^4$ is independently selected from H, and $C_{1-4}$ alkyl; and $R^7$ is H.

In another aspect, the present invention provides compounds of Formula (IIa):

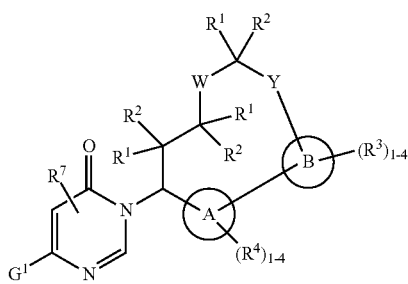

(IIa)

or stereoisomers, tautomers, pharmaceutically acceptable salts, solvates, or prodrugs thereof, wherein:

ring A is independently selected from 6-membered aryl and 5- to 6-membered heterocyclyl;

ring B is 5- to 10-membered heterocyclyl or 5- to 10-membered heterocyclyl comprising carbon atoms and 1-4 heteroatoms selected from N, $NR^{3c}$, O, and $S(O)_p$;

$G^1$ is independently selected from $C_{3-6}$ carbocyclyl and 5- to 10-membered heterocyclyl, wherein said carbocyclyl and heterocyclyl are substituted with 1-4 $R^8$;

W is independently selected from $(CR^1R^2)_{1-2}$, O, NH, and $N(C_{1-4}$ alkyl);

Y is independently selected from —$CR^{13}$NH—, —NHC(=O)— and —C(=O)NH—;

$R^1$ and $R^2$ are independently selected from H, D, halogen, haloalkyl, $C_{1-4}$ alkyl (optionally substituted with $R^6$), hydroxyl, and alkoxy (optionally substituted with $R^6$), and $C_{3-5}$ cycloalkyl optionally substituted with $R^6$;

$R^3$ is independently selected from H, halogen, $C_{1-4}$ alkyl (optionally substituted with $R^6$), CN, —$(CH_2)_n$—$OR^5$, —$(CH_2)_n$—$NR^5R^5$, —$(CH_2)_n$—C(=O)$R^5$, and —$(CH_2)_n$—C(=O)$OR^5$;

$R^{3c}$ is independently selected from H, haloalkyl, $C_{1-4}$ alkyl (optionally substituted with $R^6$), —$(CH_2)_{1-2}$—OH, C(=O)$C_{1-4}$ alkyl, —$(CH_2)_{1-2}$—C(=O)OH, —C(=O)O$C_{1-4}$ alkyl, $S(=O)_pC_{1-6}$ alkyl, —$(CH_2)_n$—$C_{3-10}$ carbocyclyl and —$(CH_2)_n$-4- to 10-membered heterocyclyl, wherein said carbocyclyl and heterocyclyl are optionally substituted with $R^6$;

$R^4$ is independently selected from H, OH, halogen, CN, $C_{1-4}$ alkyl, $C_{1-4}$ haloalkyl, $C_{1-4}$ alkoxy, —C(=O)$NH_2$, —C(=O)NH($C_{1-4}$ alkyl), —C(=O)N($C_{1-4}$ alkyl)$_2$, $C_{3-6}$ cycloalkyl, aryl, and 5- to 6-membered heterocyclyl, wherein said cycloalkyl, aryl and heterocyclyl are optionally substituted with $R^6$;

$R^5$ is independently selected from H, $C_{1-4}$ alkyl (optionally substituted with halogen, hydroxyl, alkoxy, carboxy, alkoxycarbonyl, amino, substituted amino), $C_{3-10}$ carbocyclyl and 4- to 10-membered heterocyclyl, wherein said carbocyclyl and heterocyclyl are optionally substituted with $R^6$;

$R^6$ is independently selected from H, OH, =O, —$(CH_2)_nNH_2$, —$(CH_2)_n$CN, halogen, $C_{1-6}$ alkyl, —$(CH_2)_n$—C(=O)OH, —$(CH_2)_n$—C(=O)O$C_{1-4}$ alkyl, —$(CH_2)_n$—O$C_{1-4}$ alkyl, —$(CH_2)_n$—C(=O)$NH_2$, —$(CH_2)_n$—$C_{3-10}$ carbocyclyl, —$(CH_2)_n$-4- to 10-membered heterocyclyl, and —$(CH_2)_n$-4- to 10-membered heterocyclyl, wherein said carbocyclyl and heterocyclyl are optionally substituted with $R^{10}$;

$R^7$ is independently selected from H, hydroxyl, halogen, $C_{1-2}$haloalkyl, and $C_{1-2}$alkyl;

$R^8$ is independently selected from H, halogen, CN, $NH_2$, $C_{1-6}$ alkyl, haloalkyl, haloalkylcarbonylamino, arylamino, heteroarylamino, hydroxycarbonyl, haloalkylaminocarbonyl, arylalkylcarbonyl, alkylcarbonyl, alkoxy, haloalkoxy, —$(CH_2)_n$-aryl, —$(CH_2)_n$—$C_{3-6}$ cycloalkyl, and —$(CH_2)_n$-4- to 12-membered heterocyclyl, wherein said aryl, cycloalkyl, and heterocyclyl are optionally substituted with $R^{10}$;

alternatively, two adjacent $R^8$ groups and $G_1$ form a fused heterocyclic group selected from

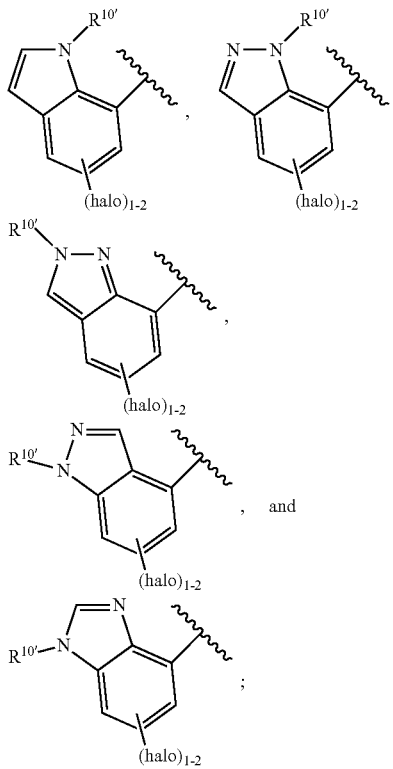

$R^9$ is H or $C_{1-6}$ alkyl;

$R^{10}$ is independently selected from H, $C_{1-6}$ alkyl (optionally substituted with $R^{11}$), $C_{2-6}$ alkenyl, $C_{2-6}$ alkynyl, aryl (optionally substituted with $R^{11}$), —$(CH_2)_n$—$C_{3-6}$ cycloalkyl (optionally substituted with $R^{11}$), —$(CH_2)_n$—O-4- to 10-membered heterocyclyl (optionally substituted with $R^{11}$), F, Cl, Br, —$(CH_2)_n$CN, $NO_2$, =O, C(=O)$NR^{12}R^{12}$, —$(CH_2)_nC(=O)OR^{12}$, Si($C_{1-4}$ alkyl)$_3$, —$(CH_2)_n$—$OR^{12}$, —$(CH_2)_n$—$NR^{12}R^{12}$, and —S(=O)$_p C_{1-6}$ alkyl, $NR^{12}S(=O)_p C_{1-6}$ alkyl, and S(=O)$_p NR^{12}R^{12}$;

$R^{10'}$ is independently selected from H, $C_{1-6}$ alkyl (optionally substituted with $R^{11}$), aryl, —$(CH_2)_n$—$C_{3-6}$ cycloalkyl (optionally substituted with $R^{11}$), and —$(CH_2)_n$—O-4- to 10-membered heterocyclyl (optionally substituted with $R^{11}$);

$R^{11}$, at each occurrence, is independently selected from H, halogen, $C_{1-5}$ alkyl, —$(CH_2)_n$—OH, $C_{3-6}$ cycloalkyl, and phenyl;

$R^{12}$, at each occurrence, is independently selected from H, $C_{1-5}$ alkyl optionally substituted with $R^1$, $C_{3-6}$ cycloalkyl, phenyl, and heterocyclyl, or $R^{12}$ and $R^{12}$ together with the nitrogen atom to which they are both attached form a heterocyclic ring optionally substituted with $C_{1-4}$alkyl;

$R^{13}$ is, independently at each occurrence, selected from H, $CF_3$, C(=O)OH, C(=O)O($C_{1-4}$ alkyl), and —C(=O)$NH_2$ ($C_{1-4}$ alkoxy);

n, at each occurrence, is an integer independently selected from 0, 1, 2, 3, and 4; and p, at each occurrence, is an integer independently selected from 0, 1, and 2.

In another aspect, the present invention provides compounds of Formula (IIb):

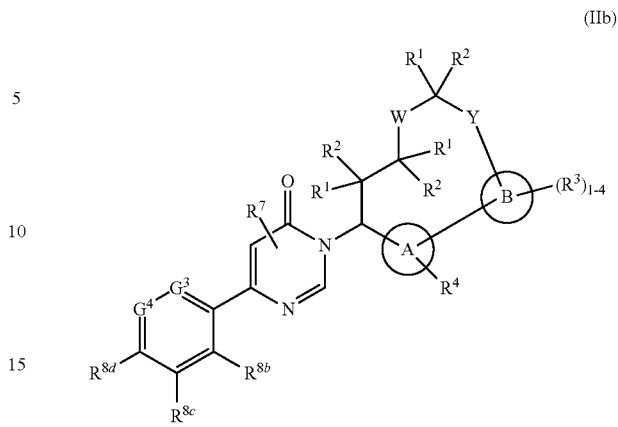

(IIb)

or stereoisomers, tautomers, pharmaceutically acceptable salts, solvates, or prodrugs thereof, wherein:

ring A is independently selected from phenyl and 5- to 6-membered heterocyclyl;

ring B is 5- to 10-membered heterocyclyl or 5- to 6-membered heterocyclyl comprising carbon atoms and 1-4 heteroatoms selected from N, $NR^{3c}$, O, and S(O)$_p$;

W is independently selected from $(CR^1R^2)_{1-2}$, O, NH, and N($C_{1-4}$ alkyl);

Y is independently selected from —$CH_2NH$—, —NHC(=O)— and —C(=O)NH—;

$G^3$ is independently selected from N and $CR^{8a}$;

$G^4$ is independently selected from N and $CR^{8e}$;

$R^1$ and $R^2$ are independently selected from H, D, halogen, $CF_3$, $C_{1-6}$ alkyl, and hydroxyl;

$R^3$ is independently selected from H, halogen, $C_{1-4}$alkyl (optionally substituted with $R^6$), CN, —$(CH_2)_n$—$OR^5$, —$(CH_2)_n$—$NR^5R^5$, —$(CH_2)_n$—C(=O)$R^5$, and —$(CH_2)_n$—C(=O)$OR^5$;

$R^{3c}$ is independently selected from H, haloalkyl, $C_{1-4}$ alkyl (optionally substituted with $R^6$), —$(CH_2)_{1-2}$—OH, C(=O)$C_{1-4}$ alkyl, —$(CH_2)_{1-2}$—C(=O)OH, —C(=O)O$C_{1-4}$ alkyl, S(=O)$_p C_{1-6}$ alkyl, —$(CH_2)_n$—$C_{3-10}$ carbocyclyl and —$(CH_2)_n$-4- to 10-membered heterocyclyl, wherein said carbocyclyl and heterocyclyl are optionally substituted with $R^6$;

$R^4$ is independently selected from H, OH, F, Cl, Br, $C_{1-4}$ alkyl, $C_{1-4}$ alkoxy, $CF_3$, CN, C(=O)$NH_2$, $C_{3-6}$ cycloalkyl, aryl, and 5- to 6-membered heterocyclyl, wherein said cycloalkyl, aryl and heterocyclyl are optionally substituted with $R^6$;

$R^5$ is independently selected from H, and $C_{1-4}$ alkyl optionally substituted with halogen and hydroxyl;

$R^6$ is independently selected from H, —$(CH_2)_n$—OH, =O, $NH_2$, —$(CH_2)_n$—CN, halogen, $C_{1-6}$ alkyl, —$(CH_2)_n$—C(=O)OH, —$(CH_2)_n$—C(=O)O$C_{1-4}$ alkyl, —$(CH_2)_n$—O$C_{1-4}$ alkyl, —$(CH_2)_n$—$C_{3-6}$ cycloalkyl, —$(CH_2)_n$-4- to 10-membered heterocyclyl, and —O—$(CH_2)_n$-4- to 10-membered heterocyclyl, wherein said cycloalkyl and heterocyclyl are optionally substituted with $R^{10}$;

$R^7$ is independently selected from H, F, Cl, Br, $CF_3$, and $CH_3$;

$R^{8a}$ is independently selected from H, F, Cl, Br, I, —$(CH_2)_n$CN, —$(CH_2)_n NH_2$, $C_{1-2}$alkyl, $C_{1-2}$haloalkyl, OH, O$C_{1-2}$alkyl, O$C_{1-2}$haloalkyl, C(=O)OH, C(=O)O$C_{1-3}$alkyl, C(=O)$NH_2$, C(=O)NH$C_{1-2}$haloalkyl, C(=O)NHarylalkyl, C(=O)$C_{1-3}$alkyl, NHC(=O)O$C_{1-4}$alkyl, NHC(=O)$C_{1-2}$haloalkyl, NH-aryl, NH-heteroaryl, aryl, $C_{3-6}$ cycloalkyl, and 4- to 12-membered heterocyclyl, wherein said aryl, cycloalkyl and heterocyclyl is optionally substituted with $R^{10}$;

$R^{8b}$ is independently selected from H and F;

$R^{8c}$ is independently selected from H, F, Cl, methyl, ethyl, isopropyl, $OCHF_2$, and $OCH_3$;

$R^{8d}$ is independently selected from H, F, and Cl;

$R^{8e}$ is independently selected from H, F, and Cl;

$R^{10}$ is independently selected from H, $C_{1-6}$ alkyl (optionally substituted with $R^{11}$), $C_{2-6}$ alkenyl, $C_{2-6}$ alkynyl, aryl (optionally substituted with $R^{11}$), —$(CH_2)_n$—$C_{3-6}$ cycloalkyl (optionally substituted with $R^{11}$), —$(CH_2)_n$—O-4- to 10-membered heterocyclyl (optionally substituted with $R^{11}$), F, Cl, Br, CN, $NO_2$, =O, $CONR^{12}R^{12}$, —$(CH_2)_nC(=O)$ $OR^{12}$, $Si(C_{1-4}$ alkyl$)_3$, —$(CH_2)_n$—$OR^{12}$, and —$(CH_2)_n$—$NR^{12}R^{12}$, —$S(=O)_pC_{1-6}$ alkyl, $NR^{12}S(=O)_pC_{1-6}$ alkyl, and $S(=O)_pNR^{12}R^{12}$;

$R^{11}$, at each occurrence, is independently selected from H, halogen, $C_{1-5}$ alkyl, —$(CH_2)_n$—OH, $C_{3-6}$ cycloalkyl, and phenyl;

$R^{12}$, at each occurrence, is independently selected from H, $C_{1-5}$ alkyl optionally substituted with $R^{11}$, $C_{3-6}$ cycloalkyl, phenyl, and heterocyclyl, or $R^{12}$ and $R^{12}$ together with the nitrogen atom to which they are both attached form a heterocyclic ring optionally substituted with $C_{1-4}$alkyl;

n, at each occurrence, is an integer independently selected from 0, 1, and 2; and p, at each occurrence, is an integer independently selected from 0, 1, and 2.

In another aspect, the present invention provides compounds of Formula (IIb), or stereoisomers, tautomers, pharmaceutically acceptable salts, solvates, or prodrugs thereof, wherein:

ring A is independently selected from phenyl and 5- to 6-membered heterocyclyl;

ring B is 5- to 6-membered heteroaryl comprising carbon atoms and 1-4 heteroatoms selected from N and $NR^{3c}$;

W is independently selected from $(CR^1R^2)_{1-2}$, O, NH, and $N(C_{1-4}$ alkyl);

Y is independently selected from —$CH_2NH$—, —$NHC(=O)$— and —$C(=O)NH$—;

$G^3$ is $CR^{8a}$;

$G^4$ is $CR^{8e}$;

$R^1$ and $R^2$ are independently selected from H, D, halogen, $CF_3$, $C_{1-6}$ alkyl, and hydroxyl;

$R^3$ is independently selected from H, halogen, $C_{1-4}$alkyl (optionally substituted with $R^6$), CN, —$(CH_2)_n$—$OR^5$, —$(CH_2)_n$—$C(=O)R^5$, and —$(CH_2)_n$—$C(=O)OR$;

$R^{3c}$ is independently selected from H, haloalkyl, $C_{1-4}$ alkyl (optionally substituted with $R^6$), —$(CH_2)_{1-2}$—OH, $C(=O)C_{1-4}$ alkyl, —$(CH_2)_{1-2}$—$C(=O)OH$, —$C(=O)$ $OC_{1-4}$ alkyl, $S(=O)_pC_{1-6}$ alkyl, —$(CH_2)_n$—$C_{3-10}$ carbocyclyl and —$(CH_2)_n$-4- to 10-membered heterocyclyl, wherein said carbocyclyl and heterocyclyl are optionally substituted with $R^6$;

$R^4$ is independently selected from H, OH, F, Cl, Br, $C_{1-4}$ alkyl, $C_{1-4}$ alkoxy, $CF_3$, CN, $C(=O)NH_2$, $C_{3-6}$ cycloalkyl, aryl, and 5- to 6-membered heterocyclyl, wherein said cycloalkyl, aryl and heterocyclyl are optionally substituted with $R^6$;

$R^5$ is independently selected from H and $C_{1-4}$ alkyl;

$R^6$ is independently selected from H, —$(CH_2)_n$—OH, =O, $NH_2$, —$(CH_2)_n$—CN, halogen, $C_{1-6}$ alkyl, —$(CH_2)_n$—$C(=O)OH$, —$(CH_2)_n$—$C(=O)OC_{1-4}$ alkyl, —$(CH_2)_n$—$OC_{1-4}$ alkyl, —$(CH_2)_n$—$C_{3-6}$ cycloalkyl, —$(CH_2)_n$-4- to 10-membered heterocyclyl, and —O—$(CH_2)_n$-4- to 10-membered heterocyclyl, wherein said cycloalkyl and heterocyclyl are optionally substituted with $R^{10}$;

$R^7$ is independently selected from H, F, Cl, Br, and methyl;

$R^{8a}$ is independently selected from H, F, Cl, Br, I, —$(CH_2)_nCN$, —$(CH_2)_nNH_2$, $CH_3CHF_2$, $CCH_3F_2$, $CF_3$, OH, $OCH_3$, $OCF_3$, $OCHF_2$, $C(=O)CH_3$, $C(=O)OH$, $C(=O)OCH_3$, $C(=O)NH_2$, $C(=O)NHCH_2CF_3$, $C(=O)NHCH_2Ph$, $NHC(=O)OCH_3$, $NHC(=O)CF_3$,

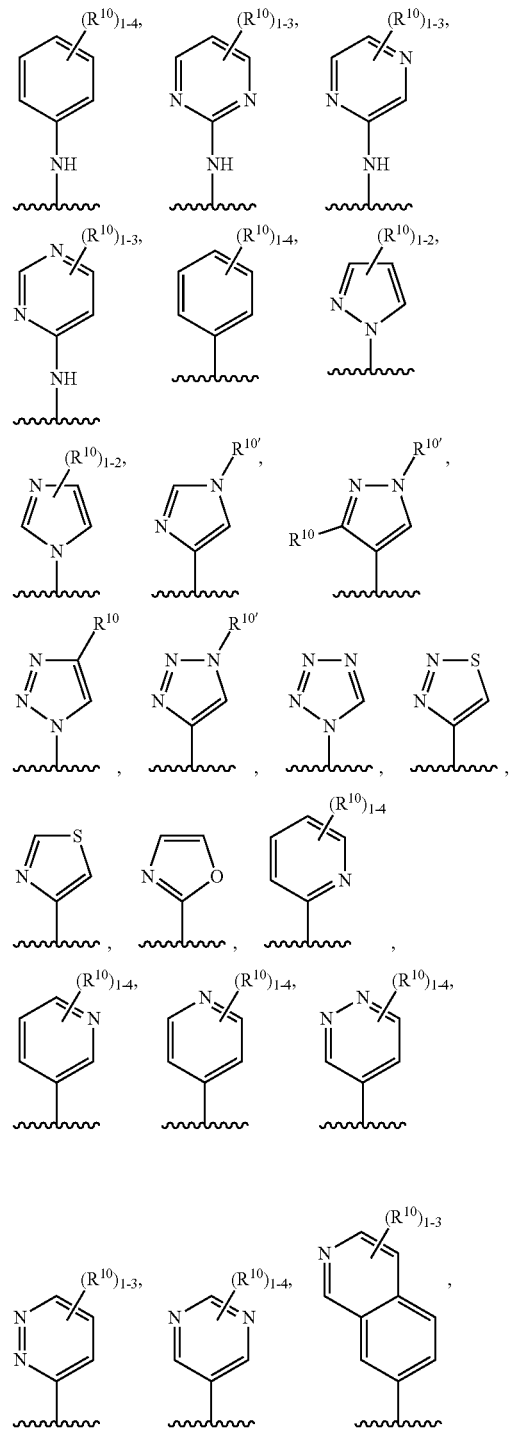

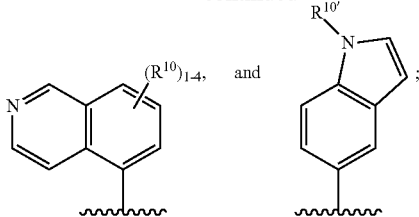

$R^{8b}$ is independently selected from H and F;

$R^{8c}$ is independently selected from H, F, Cl, methyl, ethyl, isopropyl, and OCH$_3$;

$R^{8d}$ is independently selected from H, F, and Cl;

$R^{8e}$ is independently selected from H, F, and Cl;

$R^{10}$ is independently selected from H, C$_{1-6}$ alkyl (optionally substituted with R$^{11}$), C$_{2-6}$ alkenyl, C$_{2-6}$ alkynyl, aryl (optionally substituted with R$^{11}$), —(CH$_2$)$_n$—C$_{3-6}$ cycloalkyl (optionally substituted with R$^{11}$), —(CH$_2$)$_n$—O-4- to 10-membered heterocyclyl (optionally substituted with R$^{11}$), F, Cl, Br, CN, NO$_2$, =O, CONR$^{12}$R$^{12}$, —(CH$_2$)$_n$—C(=O) OR$^{12}$, Si(C$_{1-4}$ alkyl)$_3$, —(CH$_2$)$_n$—OR$^{12}$, —(CH$_2$)$_n$— NR$^{12}$R$^{12}$, —S(=O)$_p$C$_{1-6}$ alkyl, NR$^{12}$S(=O)$_p$C$_{1-6}$ alkyl, and S(=O)$_p$NR$^{12}$R$^{12}$;

$R^{10'}$ is independently selected from H, C$_{1-6}$ alkyl (optionally substituted with R$^{11}$), aryl, —(CH$_2$)$_n$—C$_{3-6}$ cycloalkyl (optionally substituted with R$^{11}$), and —(CH$_2$)$_n$—O-4- to 10-membered heterocyclyl (optionally substituted with R$^{11}$);

$R^{11}$, at each occurrence, is independently selected from H, halogen, C$_{1-5}$ alkyl, —(CH$_2$)$_n$—OH, C$_{3-6}$ cycloalkyl, and phenyl;

$R^{12}$, at each occurrence, is independently selected from H, C$_{1-5}$ alkyl optionally substituted with R$^{11}$, C$_{3-6}$ cycloalkyl, phenyl, and heterocyclyl, or R$^{12}$ and R$^{12}$ together with the nitrogen atom to which they are both attached form a heterocyclic ring optionally substituted with C$_{1-4}$alkyl;

n, at each occurrence, is an integer independently selected from 0, 1, and 2; and p, at each occurrence, is an integer independently selected from 0, 1, and 2.

In another aspect, the present invention provides compounds of Formula (IIc):

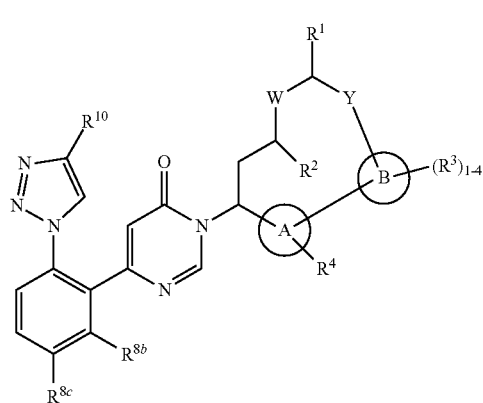

(IIc)

or stereoisomers, tautomers, pharmaceutically acceptable salts, solvates, or prodrugs thereof, wherein:

ring A is independently selected from phenyl and 5- to 6-membered heterocyclyl;

ring B is 5- to 6-membered heteroaryl comprising carbon atoms and 1-3 heteroatoms selected from N and NR$^{3c}$;

W is independently selected from (CR$^1$R$^2$)$_{1-2}$, O, NH, and N(C$_{1-4}$ alkyl);

Y is independently selected from —CH$_2$NH—, —NHC (=O)— and —C(=O)NH—;

R$^1$ and R$^2$ are independently selected from H, D, F, C$_{1-4}$ alkyl, and hydroxyl;

R$^3$ is independently selected from H, halogen, haloalkyl, C$_{1-4}$alkyl (optionally substituted with R$^6$), and CN;

R$^{3c}$ is independently selected from H, haloalkyl, C$_{1-4}$ alkyl (optionally substituted with R$^6$), —(CH$_2$)$_{1-2}$—OH, C(=O)C$_{1-4}$ alkyl, —(CH$_2$)$_{1-2}$—C(=O)OH, —C(=O) OC$_{1-4}$ alkyl, S(=O)$_p$C$_{1-6}$ alkyl, —(CH$_2$)$_n$—C$_{3-10}$ carbocyclyl and —(CH$_2$)$_n$-4- to 10-membered heterocyclyl, wherein said carbocyclyl and heterocyclyl are optionally substituted with R$^6$;

R$^4$ is independently selected from H, OH, F, Cl, Br, C$_{1-4}$ alkyl, C$_{1-4}$ alkoxy, CF$_3$, CN; C(=O)NH$_2$, C$_{3-6}$ cycloalkyl, aryl, and 5- to 6-membered heterocyclyl;

R$^6$ is independently selected from H, —(CH$_2$)$_n$—OH, =O, NH$_2$, —(CH$_2$)$_n$—CN, halogen, C$_{1-6}$ alkyl, —(CH$_2$)$_n$— C(=O)OH, —(CH$_2$)$_n$—C(=O)OC$_{1-4}$ alkyl, —(CH$_2$)$_n$— OC$_{1-4}$ alkyl, —(CH$_2$)$_n$—C$_{3-6}$ cycloalkyl, —(CH$_2$)$_n$-4- to 10-membered heterocyclyl, and —O—(CH$_2$)$_n$-4- to 10-membered heterocyclyl, wherein said cycloalkyl and heterocyclyl are optionally substituted with R$^{10}$;

$R^{8b}$ is independently selected from H and F;

$R^{8c}$ is independently selected from H, F, Cl, CH$_3$, and OCH$_3$;

$R^{10}$ is independently selected from H, C$_{1-6}$ alkyl (optionally substituted with R$^{11}$), C$_{2-6}$ alkenyl, C$_{2-6}$ alkynyl, aryl, —(CH$_2$)$_n$—C$_{3-6}$ cycloalkyl (optionally substituted with R$^{11}$), —(CH$_2$)$_n$—O-4- to 10-membered heterocyclyl (optionally substituted with R$^{11}$), F, Cl, Br, CN, NO$_2$, =O, C(=O)NR$^{12}$R$^{12}$, C(=O)OR$^{12}$, Si(C$_{1-4}$ alkyl)$_3$, —(CH$_2$)$_n$— OR$^{12}$, —(CH$_2$)$_n$—NR$^{12}$R$^{12}$, —S(=O)$_p$C$_{1-6}$ alkyl, NR$^{12}$S (=O)$_p$C$_{1-6}$ alkyl, and S(=O)$_p$NR$^{12}$R$^{12}$;

$R^{11}$, at each occurrence, is independently selected from H, halogen, C$_{1-5}$ alkyl, —(CH$_2$)$_n$—OH, C$_{3-6}$ cycloalkyl, and phenyl;

$R^{12}$, at each occurrence, is independently selected from H, C$_{1-5}$ alkyl, C$_{3-6}$ cycloalkyl, phenyl, and heterocyclyl, or R$^{12}$ and R$^{12}$ together with the nitrogen atom to which they are both attached form a heterocyclic ring optionally substituted with C$_{1-4}$alkyl;

n, at each occurrence, is an integer independently selected from 0, 1, and 2; and p, at each occurrence, is an integer independently selected from 0, 1, and 2.

In another aspect, the present invention provides compounds of Formula (IId):

(IId)

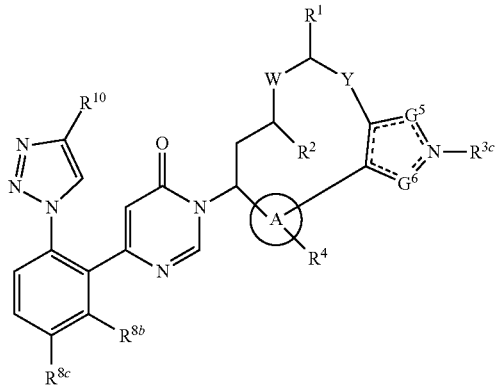

or stereoisomers, tautomers, pharmaceutically acceptable salts, solvates, or prodrugs thereof, wherein:

---- is an optional bond;

ring A is independently selected from phenyl and 5- to 6-membered heterocyclyl;

W is independently selected from $CHR^{1a}$, O, NH, and $N(C_{1-4}$ alkyl);

$G^5$ is independently selected from $CH_2$ and $NR^{3c}$;

$G^6$ is independently selected from $CH_2$ and $NR^{3c}$;

provided when $G^5$ is $CH_2$, $G^6$ is $NR^{3c}$; when $G^5$ is $NR^{3c}$, $G^6$ is $CH_2$ and only one $R^{3c}$ is present on the ring;

Y is independently selected from —NHC(=O)— and —C(=O)NH—;

$R^1$ is independently selected from H and $C_{1-4}$ alkyl;

$R^{1a}$ is independently selected from H, D, F, $CH_3$, and OH;

$R^2$ is independently selected from H, D, and OH;

$R^{3c}$ is independently selected from H, haloalkyl, $C_{1-4}$alkyl (optionally substituted with $R^6$), —$(CH_2)_{1-2}$—OH, C(=O)$C_{1-4}$ alkyl, —$(CH_2)_{1-2}$—C(=O)OH, —C(=O)O$C_{1-4}$ alkyl, $S(=O)_pC_{1-6}$ alkyl, phenyl optionally substituted with $R^6$, 5- to 6-membered heterocyclyl optionally substituted with $R^6$, and 5- to 6-membered heteroaryl optionally substituted with $R^6$;

$R^4$ is independently selected from H, OH, F, Cl, Br, $C_{1-4}$ alkyl, $C_{1-4}$ alkoxy, $CF_3$, CN, and C(=O)$NH_2$;

$R^6$ is independently selected from H, —$(CH_2)_n$—OH, =O, $NH_2$, —$(CH_2)_n$—CN, halogen, $C_{1-6}$ alkyl, —$(CH_2)_n$—C(=O)OH, —$(CH_2)_n$—C(=O)O$C_{1-4}$ alkyl, —$(CH_2)_n$—O$C_{1-4}$ alkyl, —$(CH_2)_n$—$C_{3-6}$ cycloalkyl, —$(CH_2)_n$-4- to 10-membered heterocyclyl, and —O—$(CH_2)_n$-4- to 10-membered heterocyclyl, wherein said cycloalkyl and heterocyclyl are optionally substituted with $R^{10}$;

$R^{8b}$ is independently selected from H and F;

$R^{8c}$ is independently selected from H, F, Cl, $CH_3$, and $OCH_3$;

$R^{10}$ is independently selected from H, $C_{1-6}$ alkyl (optionally substituted with $R^{11}$), aryl, —$(CH_2)_n$—$C_{3-6}$ cycloalkyl (optionally substituted with $R^{11}$), —$(CH_2)_n$—O-4- to 10-membered heterocyclyl (optionally substituted with $R^{11}$), F, Cl, Br, CN, $NO_2$, =O, C(=O)$NR^{12}R^{12}$, C(=O)$OR^{12}$, $Si(C_{1-4}$ alkyl$)_3$, —$(CH_2)_n$—$OR^{12}$, and —$(CH_2)_n$—$NR^{12}R^{12}$, —$S(=O)_pC_{1-6}$ alkyl, $NR^{12}S(=O)_pC_{1-6}$ alkyl, and $S(=O)_pNR^{12}R^{12}$;

$R^{11}$, at each occurrence, is independently selected from H, halogen, $C_{1-5}$ alkyl, —$(CH_2)_n$—OH, $C_{3-6}$ cycloalkyl, and phenyl;

$R^{12}$, at each occurrence, is independently selected from H, $C_{1-5}$ alkyl, $C_{3-6}$ cycloalkyl, phenyl, and heterocyclyl, or $R^{12}$ and $R^{12}$ together with the nitrogen atom to which they are both attached form a heterocyclic ring optionally substituted with $C_{1-4}$alkyl;

n, at each occurrence, is an integer independently selected from 0, 1, and 2; and p, at each occurrence, is an integer independently selected from 0, 1, and 2.

In another aspect, the present invention provides compounds of Formula (IIe):

(IIe)

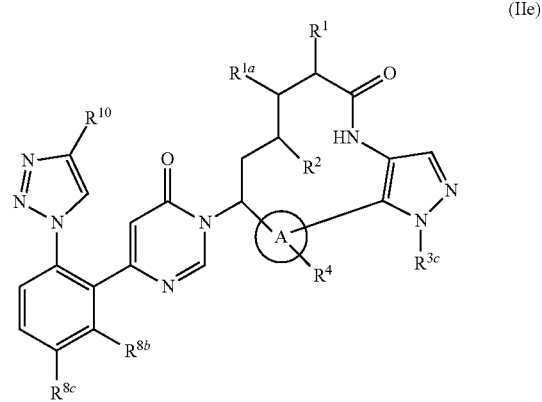

or stereoisomers, tautomers, pharmaceutically acceptable salts, solvates, or prodrugs thereof, wherein:

ring A is independently selected from

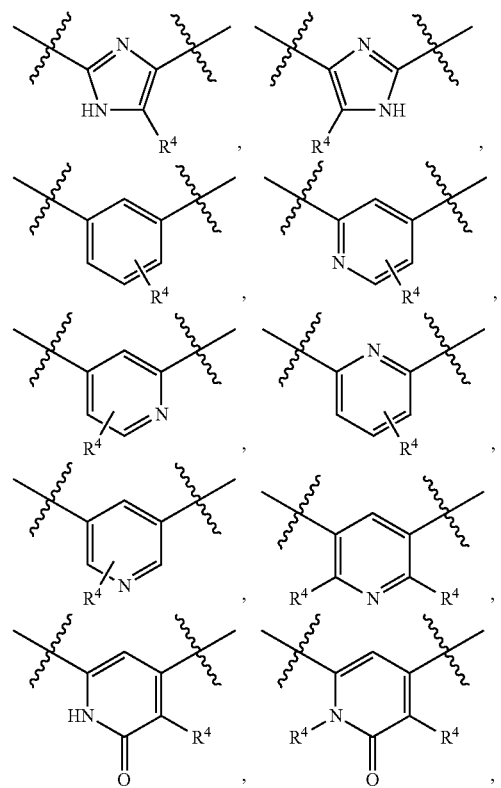

-continued

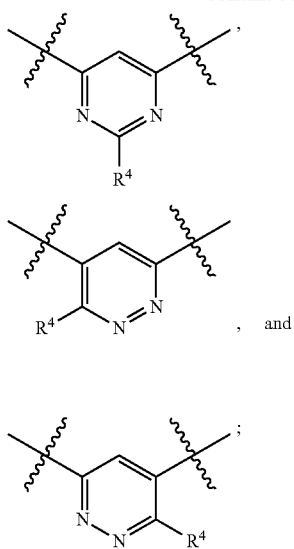

R[1] is independently selected from H and $C_{1-4}$ alkyl;

R[1a] is independently selected from H, D, F, $CH_3$, and OH;

R[2] is independently selected from H, D, and OH;

R[3c] is independently selected from H, $CHF_2$, $CD_3$, $CH_3$, $CH_2CH_2OH$, $CH_2C(=O)OH$, $SO_2CH_3$, phenyl optionally substituted with R[6], and 5- to 6-membered heteroaryl optionally substituted with R[6];

R[4] is independently selected from H, F, and $C(=O)NH_2$;

R[6] is independently selected from H, $—(CH_2)_n—OH$, $=O$, $NH_2$, $—(CH_2)_n—CN$, halogen, $C_{1-6}$ alkyl, $—(CH_2)_n—C(=O)OH$, $—(CH_2)_n—C(=O)OC_{1-4}$ alkyl, $—(CH_2)_n—OC_{1-4}$ alkyl, $—(CH_2)_n—C_{3-6}$ cycloalkyl, $—(CH_2)_n$-4- to 10-membered heterocyclyl, and $—O—(CH_2)_n$-4- to 10-membered heterocyclyl, wherein said cycloalkyl and heterocyclyl are optionally substituted with R[10];

R[8b] is independently selected from H and F;

R[8c] is independently selected from H, F, Cl, $CH_3$, and $OCH_3$;

R[10] is independently selected from H, $CF_3$, $CHF_2$, $CH_2F$, aryl, $—(CH_2)_n—C_{3-6}$ cycloalkyl (optionally substituted with R[11]), heteroaryl (optionally substituted with R[11]), $—(CH_2)_n—O$-4- to 10-membered heterocyclyl (optionally substituted with R[11]), F, Cl, Br, CN, $NO_2$, $=O$, $C(=O)NR^{12}R^{12}$, $—(CH_2)_n—C(=O)OR^{12}$, $Si(C_{1-4}$ alkyl$)_3$, $—(CH_2)_n—OR^{12}$, $—(CH_2)_n—NR^{12}R^{12}$, $—S(=O)_pC_{1-6}$ alkyl, $NR^{12}S(=O)_pC_{1-6}$ alkyl, and $S(=O)_pNR^{12}R^{12}$;

R[11], at each occurrence, is independently selected from H, halogen, $C_{1-5}$ alkyl, $—(CH_2)_n—OH$, $C_{3-6}$ cycloalkyl, and phenyl;

R[12], at each occurrence, is independently selected from H, $C_{1-5}$ alkyl, $C_{3-6}$ cycloalkyl, phenyl, and heterocyclyl, or R[12] and R[12] together with the nitrogen atom to which they are both attached form a heterocyclic ring optionally substituted with $C_{1-4}$alkyl; and n, at each occurrence, is an integer independently selected from 0, 1, and 2.

In another aspect, the present invention provides compounds of Formula (IIf):

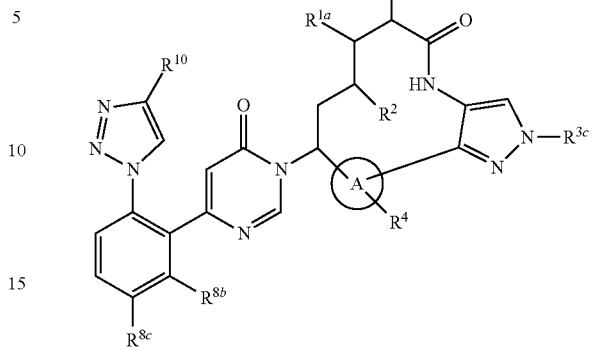

(IIf)

or stereoisomers, tautomers, pharmaceutically acceptable salts, solvates, or prodrugs thereof, wherein:
ring A is independently selected from

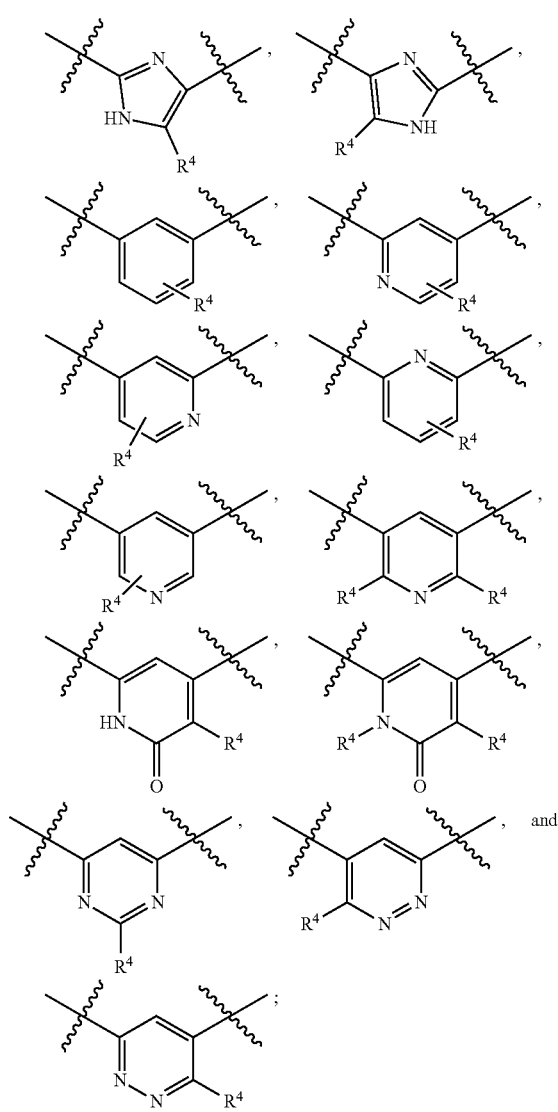

R[1] is independently selected from H and $C_{1-4}$ alkyl;

R[1a] is independently selected from H, D, F, $CH_3$, and OH;

R[2] is independently selected from H, D, and OH;

R[3c] is independently selected from H, $CHF_2$, $CD_3$, $CH_3$, $SO_2CH_3$, phenyl optionally substituted with R[6], and 5- to 6-membered heterocyclyl optionally substituted with R[6], 5- to 6-membered heteroaryl optionally substituted with R[6];

R[4] is independently selected from H and F;

R[6] is independently selected from OH, =O, $NH_2$, CN, halogen, $C_{1-6}$ alkyl, —$(CH_2)_n$—$C_{3-6}$ cycloalkyl, —$(CH_2)_n$-4- to 10-membered heterocyclyl, and —O—$(CH_2)_n$-4- to 10-membered heterocyclyl, wherein said cycloalkyl and heterocyclyl are optionally substituted with R[10];

R[8b] is independently selected from H and F;

R[8c] is independently selected from H, F, Cl, $CH_3$, and $OCH_3$;

R[10] is independently selected from H, $CF_3$, $CHF_2$, $C(CH_3)_2OH$, aryl, —$(CH_2)_n$—$C_{3-6}$ cycloalkyl (optionally substituted with R[11]), —$(CH_2)_n$—O-4- to 10-membered heterocyclyl (optionally substituted with R[11]), F, Cl, Br, CN, $NO_2$, =O, C(=O)NR[12]R[12], C(=O)OR[12], Si($C_{1-4}$ alkyl)$_3$, —$(CH_2)_n$—OR[12], —$(CH_2)_n$—NR[12]R[12], —S(=O)$_p$$C_{1-6}$ alkyl, NR[12]S(=O)$_p$$C_{1-6}$ alkyl, and S(=O)$_p$NR[12]R[12];

R[11], at each occurrence, is independently selected from H, halogen, $C_{1-5}$ alkyl, —$(CH_2)_n$—OH, $C_{3-6}$ cycloalkyl, and phenyl;

R[12], at each occurrence, is independently selected from H, $C_{1-5}$ alkyl, $C_{3-6}$ cycloalkyl, phenyl, and heterocyclyl, or R[12] and R[12] together with the nitrogen atom to which they are both attached form a heterocyclic ring optionally substituted with $C_{1-4}$alkyl; and n, at each occurrence, is an integer independently selected from 0, 1, and 2.

In another aspect, the present invention provides compounds of Formula (IIf): or stereoisomers, tautomers, pharmaceutically acceptable salts, solvates, or prodrugs thereof, wherein:

ring A is independently selected from

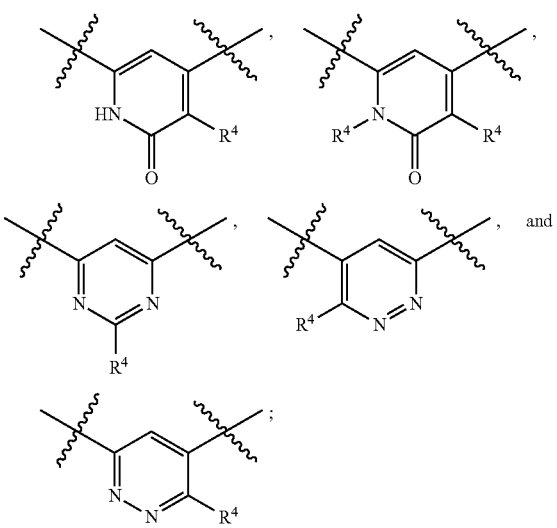

R[1] is independently selected from H and $C_{1-4}$ alkyl;

R[1a] is independently selected from H, D, F, $CH_3$, and OH;

R[2] is independently selected from H, D, and OH;

R[3c] is independently selected from H, $CHF_2$, $CD_3$, $CH_3$, $SO_2CH_3$, phenyl optionally substituted with R[6], and heterocyclyl selected from

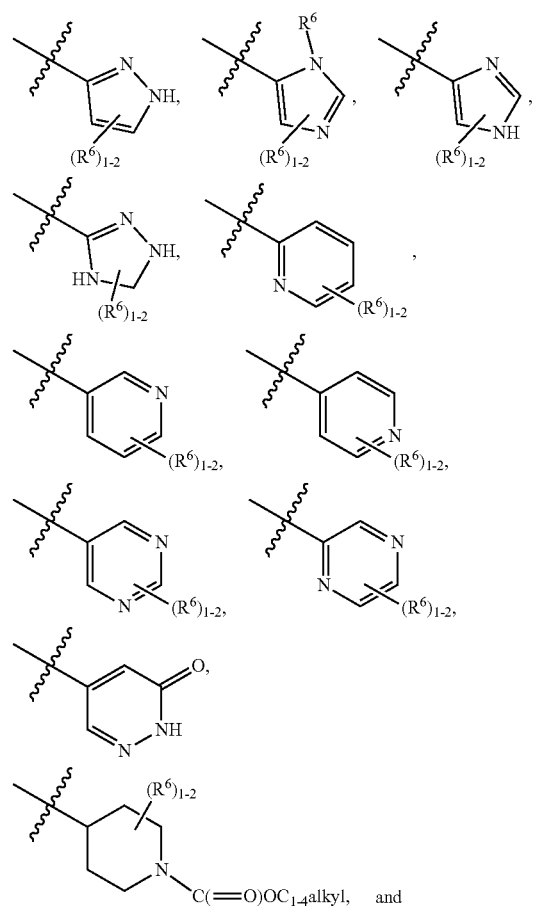

-continued

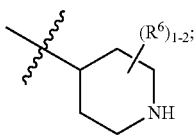

R⁴ is independently selected from H and F;

R⁶ is independently selected from H, OH, OC$_{1-4}$ alkyl, CN, F, Cl, and C$_{1-4}$ alkyl;

R$^{8b}$ is independently selected from H and F;

R$^{8c}$ is independently selected from H, F, Cl, CH$_3$, and OCH$_3$;

R$^{10}$ is independently selected from H, CF$_3$, CHF$_2$, C(CH$_3$)$_2$OH, aryl, —(CH$_2$)$_n$—C$_{3-6}$ cycloalkyl (optionally substituted with R$^{11}$), —(CH$_2$)$_n$—O-4- to 10-membered heterocyclyl (optionally substituted with R$^{11}$), F, Cl, Br, CN, NO$_2$, =O, C(=O)NR$^{12}$R$^{12}$, C(=O)OR$^{12}$, Si(C$_{1-4}$ alkyl)$_3$, —(CH$_2$)$_n$—OR$^{12}$, —(CH$_2$)$_n$—NR$^{12}$R$^{12}$, —S(=O)$_p$C$_{1-6}$ alkyl, NR$^{12}$S(=O)$_p$C$_{1-6}$ alkyl, and S(=O)$_p$NR$^{12}$R$^{12}$;

R$^{11}$, at each occurrence, is independently selected from H, halogen, C$_{1-5}$ alkyl, —(CH$_2$)$_n$—OH, C$_{3-6}$ cycloalkyl, and phenyl;

R$^{12}$, at each occurrence, is independently selected from H, C$_{1-5}$ alkyl, C$_{3-6}$ cycloalkyl, phenyl, and heterocyclyl, or R$^{12}$ and R$^{12}$ together with the nitrogen atom to which they are both attached form a heterocyclic ring optionally substituted with C$_{1-4}$alkyl; and n, at each occurrence, is an integer independently selected from 0, 1, and 2.

In another aspect, the present invention provides compounds of Formula (IIg):

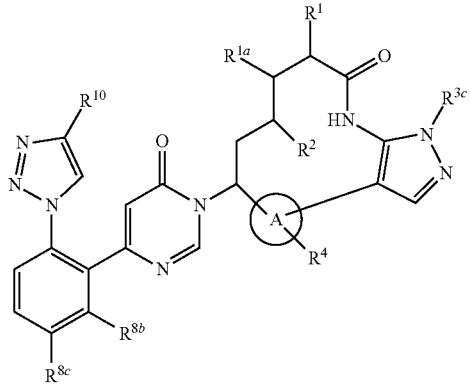

(IIg)

or stereoisomers, tautomers, pharmaceutically acceptable salts, solvates, or prodrugs thereof, wherein:

ring A is independently selected from

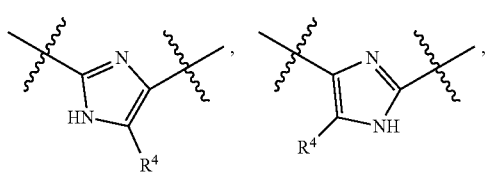

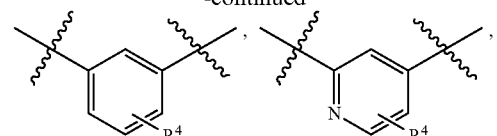

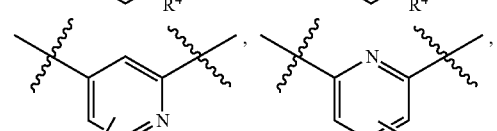

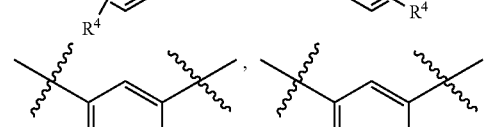

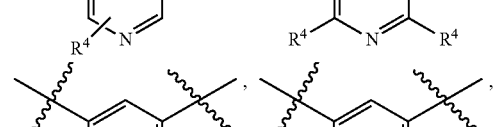

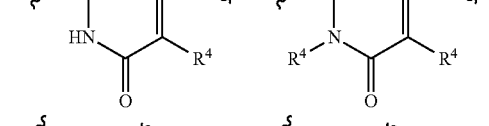

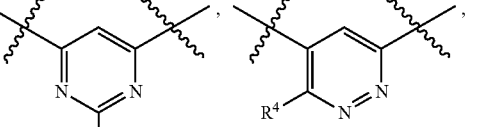

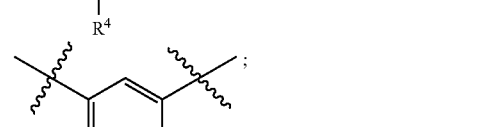

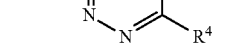, and

R$^1$ is independently selected from H and C$_{1-4}$ alkyl;

R$^{1a}$ is independently selected from H, F, CH$_3$, and OH;

R$^2$ is independently selected from H and OH;

R$^{3c}$ is independently selected from H, CHF$_2$, CD$_3$, and CH$_3$;

R$^4$ is independently selected from H and F;

R$^{8b}$ is independently selected from H and F;

R$^{8c}$ is independently selected from H, F, Cl, CH$_3$, and OCH$_3$;

R$^{10}$ is independently selected from H, CF$_3$, CHF$_2$, aryl, —(CH$_2$)$_n$—C$_{3-6}$ cycloalkyl (optionally substituted with R$^{11}$), —(CH$_2$)$_n$—O-4- to 10-membered heterocyclyl (optionally substituted with R$^{11}$), F, Cl, Br, CN, NO$_2$, =O, C(=O)NR$^{12}$R$^{12}$, C(=O)OR$^{12}$, Si(C$_{1-4}$ alkyl)$_3$, —(CH$_2$)$_n$—OR$^{12}$, —(CH$_2$)$_n$—NR$^{12}$R$^{12}$, —S(=O)$_p$C$_{1-6}$ alkyl, NR$^{12}$S(=O)$_p$C$_{1-6}$ alkyl, and S(=O)$_p$NR$^{12}$R$^{12}$;

R$^{11}$, at each occurrence, is independently selected from H, halogen, C$_{1-5}$ alkyl, —(CH$_2$)$_n$—OH, C$_{3-6}$ cycloalkyl, and phenyl;

R$^{12}$, at each occurrence, is independently selected from H, C$_{1-5}$ alkyl, C$_{3-6}$ cycloalkyl, phenyl, and heterocyclyl, or R$^{12}$ and R$^{12}$ together with the nitrogen atom to which they are both attached form a heterocyclic ring optionally substituted with C$_{1-4}$alkyl; and n, at each occurrence, is an integer independently selected from 0, 1, and 2.

In another aspect, the present invention provides compounds of Formula (IIIa):

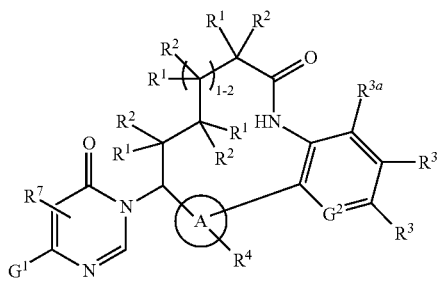 (IIIa)

or stereoisomers, tautomers, pharmaceutically acceptable salts, solvates, or prodrugs thereof, wherein:

ring A is independently selected from phenyl and a 5- to 6-membered heterocycle;

$G^1$ is independently selected from aryl, $C_{3-6}$cycloalkyl and a 5- to 6-membered heterocycle, wherein said aryl, cycloalkyl and heterocycle are substituted with 1-4 $R^8$;

$G^2$ is N;

$R^1$ and $R^2$ are independently selected from H, halogen, $CF_3$, $C_{1-6}$ alkyl, and hydroxyl;

$R^3$ is independently selected from H, halogen, haloalkyl, $C_{1-4}$alkyl (optionally substituted with $R^6$), $C_{2-4}$alkenyl (optionally substituted with $R^6$), CN, $NO_2$, —$(CH_2)_n$—$OR^5$, —$(CH_2)_n$—$NR^5R^5$, —$(CH_2)_n$—C(=O)OR^5$, —$(CH_2)_n$—NHC(=O)OR^5$, —$(CH_2)_n$—NHC(=O)R^5$, —$(CH_2)_n$—NHC(N=CN)NHR^5$, —$(CH_2)_n$—NHC(NH)NHR^5$, —$(CH_2)_n$—N=CHNR^5R^5$, —$(CH_2)_n$—NHC(=O)NR^5R^5$, —$(CH_2)_n$—C(=O)NR^5R^5$, —$(CH_2)_n$—NHC(S)NR^9C(=O)R^5$, —$(CH_2)_n$—S(=O)$_p$C$_{1-6}$ alkyl optionally substituted with $R^{11}$, —$(CH_2)_n$—S(=O)$_p$NR^5R^5$, —$(CH_2)_n$—NHS(=O)$_p$NR^5R^5$, —$(CH_2)_n$—NHS(=O)$_p$C$_{1-6}$ alkyl optionally substituted with $R^{11}$, —$(CH_2)_n$—C$_{3-10}$ carbocycle and —$(CH_2)_n$-4- to 10-membered heterocycle, wherein said carbocycle and heterocycle are optionally substituted with $R^6$; optionally, two adjacent $R^3$ groups on the carbocycle and heterocycle may form a ring optionally substituted with $R^6$;

$R^{3a}$ is independently selected from H and halogen;

$R^{3b}$ is independently selected from H, halogen, methyl, and CN;

$R^4$ is independently selected from H, OH, F, Cl, Br, $C_{1-4}$ alkyl, $C_{1-4}$ alkoxy, $CF_3$, CN, $C_{3-6}$ cycloalkyl, aryl, and 5- to 6-membered heterocycle, wherein said cycloalkyl, aryl and heterocycle are optionally substituted with $R^6$;

$R^5$ is independently selected from H, $C_{1-4}$ alkyl (optionally substituted with halogen, hydroxyl, alkoxy, carboxy, alkoxycarbonyl, amino, substituted amino), —$(CH_2)_n$—$C_{3-10}$ carbocycle and —$(CH_2)_n$-4- to 10-membered heterocycle, wherein said carbocycle and heterocycle are optionally substituted with $R^6$;

$R^6$ is independently selected from —$(CH_2)_n$—OH, =O, $NH_2$, —$(CH_2)_n$—CN, halogen, $C_{1-6}$ alkyl, —$(CH_2)_n$—C(=O)OH, —$(CH_2)_n$—C(=O)OC$_{1-4}$ alkyl, —$(CH_2)_n$—OC$_{1-4}$ alkyl, —$(CH_2)_n$—$C_{3-6}$ cycloalkyl, —$(CH_2)_n$-4- to 10-membered heterocycle, and —O—$(CH_2)_n$-4- to 10-membered heterocycle, wherein said cycloalkyl and heterocycle are optionally substituted with $R^{10}$;

$R^7$ is independently selected from H, F, Cl, and methyl;

$R^8$ is independently selected from H, halogen, CN, $NH_2$, $C_{1-6}$ alkyl, haloalkyl, alkylcarbonyl, alkoxy, haloalkoxy, aryl, $C_{3-6}$ cycloalkyl, and 4- to 6-membered heterocycle, wherein said aryl, cycloalkyl, and heterocycle are optionally substituted with $R^{10}$;

$R^{10}$ is independently selected from H, $C_{1-6}$ alkyl (optionally substituted with $R^{11}$), $C_{2-6}$ alkenyl, $C_{2-6}$ alkynyl, aryl, —$(CH_2)_n$—$C_{3-6}$ cycloalkyl (optionally substituted with $R^{11}$), —$(CH_2)_n$—O-4- to 10-membered heterocycle (optionally substituted with $R^{11}$), F, Cl, Br, CN, $NO_2$, =O, C(=O)NR^{12}R^{12}$, C(=O)OR^{12}$, Si(C$_{1-4}$ alkyl)$_3$, —$(CH_2)_n$—$OR^{12}$, and —$(CH_2)_n$—$NR^{12}R^{12}$;

$R^{11}$, at each occurrence, is independently selected from H, halogen, $C_{1-5}$ alkyl, —$(CH_2)_n$—OH, $C_{3-6}$ cycloalkyl, and phenyl;

$R^{12}$, at each occurrence, is independently selected from H, $C_{1-5}$ alkyl, $C_{3-6}$ cycloalkyl, phenyl, and heterocycle, or $R^{12}$ and $R^{12}$ together with the nitrogen atom to which they are both attached form a heterocyclic ring optionally substituted with $C_{1-4}$alkyl;

n, at each occurrence, is an integer independently selected from 0, 1, and 2; and p, at each occurrence, is an integer independently selected from 0, 1, and 2.

In another aspect, the present invention provides compounds of Formula (IIIb):

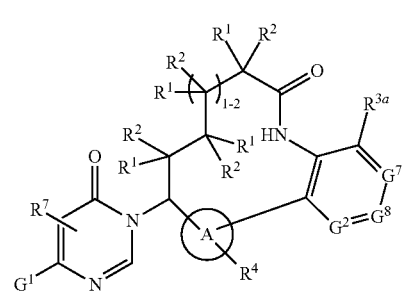 (IIIb)

or stereoisomers, tautomers, pharmaceutically acceptable salts, solvates, or prodrugs thereof, wherein:

ring A is independently selected from phenyl and 5- to 6-membered heterocyclyl;

$G^1$ is independently selected from aryl, $C_{3-6}$cycloalkyl and 5- to 6-membered heterocyclyl, wherein said aryl, cycloalkyl and heterocyclyl are substituted with 1-4 $R^8$;

$G^2$ is independently selected from N and $CR^{3b}$;

$G^7$ is independently selected from N and $CR^3$;

$G^8$ is independently selected from N and $CR^3$;

provided at least one of $G^2$, $G^6$, and $G^7$ is N;

$R^1$ and $R^2$ are independently selected from H, halogen, $CF_3$, $C_{1-6}$ alkyl, and hydroxyl;

$R^3$ is independently selected from H, halogen, haloalkyl, $C_{1-4}$alkyl (optionally substituted with $R^6$), $C_{2-4}$alkenyl (optionally substituted with $R^6$), CN, $NO_2$, —$(CH_2)_n$—$OR^5$, —$(CH_2)_n$—$NR^5R^5$, —$(CH_2)_n$—C(=O)OR^5$, —$(CH_2)_n$—NHC(=O)OR^5$, —$(CH_2)_n$—NHC(=O)R^5$, —$(CH_2)_n$—NHC(N—CN)NHR^5$, —$(CH_2)_n$—NHC(NH)NHR^5$, —$(CH_2)_n$—N=CHNR^5R^5$, —$(CH_2)_n$—NHC(=O)NR^5R^5$, —$(CH_2)_n$—C(=O)NR^5R^5$, —$(CH_2)_n$—NHC(S)NR^9C(=O)R^5$, —$(CH_2)_n$—S(=O)$_p$C$_{1-6}$ alkyl optionally substituted with $R^{11}$, —$(CH_2)_n$—S(=O)$_p$NR^5R^5$, —$(CH_2)_n$—NHS(=O)$_p$NR^5R^5$, —$(CH_2)_n$—NHS(=O)$_p$C$_{1-6}$ alkyl optionally substituted with $R^{11}$, —$(CH_2)_n$—$C_{3-10}$ carbocyclyl and —$(CH_2)_n$-4- to 10-membered heterocyclyl, wherein said carbocyclyl and heterocyclyl are optionally substituted with $R^6$; optionally, two adjacent $R^3$ groups on the carbocyclyl and heterocyclyl may form a ring optionally substituted with $R^6$;

$R^{3a}$ is independently selected from H and halogen;

$R^{3b}$ is independently selected from H, halogen, methyl, and CN;

$R^4$ is independently selected from H, OH, F, Cl, Br, $C_{1-4}$ alkyl, $C_{1-4}$ alkoxy, $CF_3$, CN, $C_{3-6}$ cycloalkyl, aryl, and 5- to 6-membered heterocyclyl, wherein said cycloalkyl, aryl and heterocyclyl are optionally substituted with $R^6$;

$R^5$ is independently selected from H, $C_{1-4}$ alkyl (optionally substituted with halogen, hydroxyl, alkoxy, carboxy, alkoxycarbonyl, amino, substituted amino), —$(CH_2)_n$—$C_{3-10}$ carbocyclyl and —$(CH_2)_n$-4- to 10-membered heterocyclyl, wherein said carbocyclyl and heterocyclyl are optionally substituted with $R^6$;

$R^6$ is independently selected from —$(CH_2)_n$—OH, =O, $NH_2$, —$(CH_2)_n$—CN, halogen, $C_{1-6}$ alkyl, —$(CH_2)_n$—C(=O)OH, —$(CH_2)_n$—C(=O)OC$_{1-4}$ alkyl, —$(CH_2)_n$—OC$_{1-4}$ alkyl, —$(CH_2)_n$—$C_{3-6}$ cycloalkyl, —$(CH_2)_n$-4- to 10-membered heterocyclyl, and —O—$(CH_2)_n$-4- to 10-membered heterocyclyl, wherein said cycloalkyl and heterocyclyl are optionally substituted with $R^{10}$;

$R^7$ is independently selected from H, F, Cl, and methyl;

$R^8$ is independently selected from H, halogen, CN, $NH_2$, $C_{1-6}$ alkyl, haloalkyl, alkylcarbonyl, alkoxy, haloalkoxy, aryl, $C_{3-6}$ cycloalkyl, and 4- to 12-membered heterocyclyl, wherein said aryl, cycloalkyl, and heterocyclyl are optionally substituted with $R^{10}$;

$R^{10}$ is independently selected from H, $C_{1-6}$ alkyl (optionally substituted with $R^{11}$), $C_{2-6}$ alkenyl, $C_{2-6}$ alkynyl, aryl, —$(CH_2)_n$—$C_{3-6}$ cycloalkyl (optionally substituted with $R^{11}$), —$(CH_2)_n$—O-4- to 10-membered heterocyclyl (optionally substituted with $R^{11}$), F, Cl, Br, CN, $NO_2$, =O, C(=O)NR$^{12}$R$^{12}$, C(=O)OR$^{12}$, Si(C$_{1-4}$ alkyl)$_3$, —$(CH_2)_n$—OR$^{12}$, —$(CH_2)_n$—NR$^{12}$R$^{12}$, —S(=O)$_p$C$_{1-6}$ alkyl, NR$^{12}$S(=O)$_p$C$_{1-6}$ alkyl, and S(=O)$_p$NR$^{12}$R$^{12}$;

$R^{11}$, at each occurrence, is independently selected from H, halogen, $C_{1-5}$ alkyl, —$(CH_2)_n$—OH, $C_{3-6}$ cycloalkyl, and phenyl;

$R^{12}$, at each occurrence, is independently selected from H, $C_{1-5}$ alkyl, $C_{3-6}$ cycloalkyl, phenyl, and heterocyclyl, or $R^{12}$ and $R^{12}$ together with the nitrogen atom to which they are both attached form a heterocyclic ring optionally substituted with $C_{1-4}$alkyl;

n, at each occurrence, is an integer independently selected from 0, 1, and 2; and p, at each occurrence, is an integer independently selected from 0, 1, and 2.

In another aspect, the present invention provides compounds of Formula (IVb):

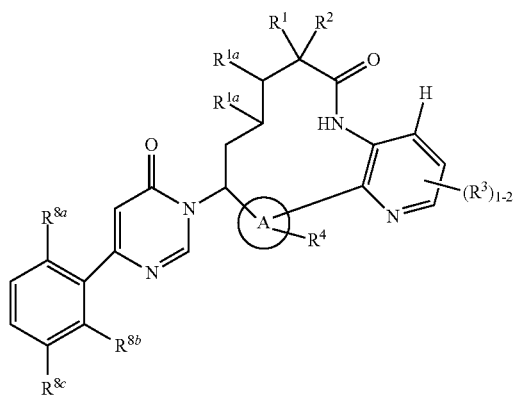

(IVb)

or stereoisomers, tautomers, pharmaceutically acceptable salts, solvates, or prodrugs thereof, wherein:

ring A is independently selected from

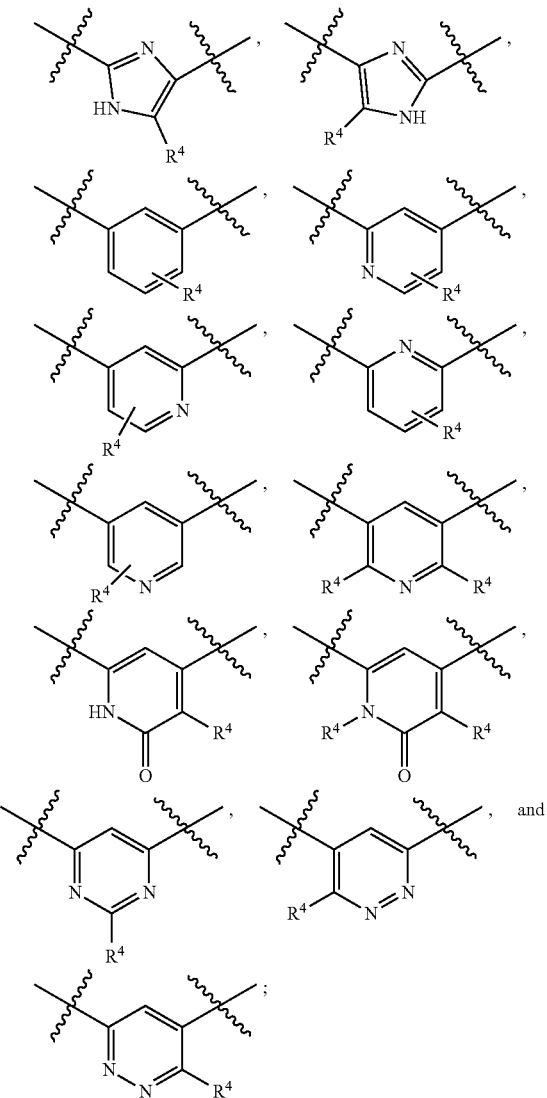

$R^1$ and $R^2$ are independently selected from H, F, $C_{1-4}$ alkyl, and OH;

$R^{1a}$, at each occurrence, is independently selected from H, F, $CH_3$, and OH;

$R^3$ is independently selected from H, F, Cl, Br, I, $C_{2-4}$alkenyl (optionally substituted C(=O)OH), CN, and —$(CH_2)_n$—OH;

$R^4$ is independently selected from H, OH, F, OC$_{1-4}$ alkyl, $C_{1-4}$ alkyl, CN, $C_{3-6}$ cycloalkyl, aryl, and 5- to 6-membered heterocyclyl, wherein said cycloalkyl, aryl and heterocyclyl are optionally substituted with $R^6$;

$R^6$ is independently selected from OH, $NH_2$, halogen, $C_{1-6}$ alkyl, $C_{3-6}$ cycloalkyl, —$(CH_2)_n$—C(=O)OH, —$(CH_2)_n$—C(=O)OC$_{1-4}$ alkyl, —$(CH_2)_n$—OC$_{1-4}$ alkyl, =O, $C_{3-6}$ cycloalkyl, 4- to 10-membered heterocyclyl, and —O-4- to 10-membered heterocyclyl, wherein said cycloalkyl and heterocyclyl are optionally substituted with $R^{10}$;

$R^{8a}$ is independently selected from H, F, Cl, Br, CN, $OCH_3$, $OCF_3$, $CH_3$, C(=O)CH$_3$, $CF_3$, $OCHF_2$, NHC(=O)

$C_{1-4}$ alkyl, aryl, $C_{3-6}$ cycloalkyl, and 4- to 12-membered heterocyclyl, wherein said aryl, cycloalkyl, and heterocyclyl are optionally substituted with $R^{10}$;

$R^{8b}$ is independently selected from H and F;

$R^{8c}$ is independently selected from H, F, Cl, $CH_3$, and $OCH_3$;

$R^{10}$ is independently selected from $C_{1-6}$ alkyl, —$C_{3-6}$ cycloalkyl, F, Cl, Br, $CF_3$, $CHF_2$, CN, and $OC_{1-5}$ alkyl; and n, at each occurrence, is an integer independently selected from 0, 1, and 2.

In another aspect, the present invention provides compounds of Formula (IIb), or stereoisomers, tautomers, pharmaceutically acceptable salts, solvates, or prodrugs thereof, wherein:

ring A is independently selected from

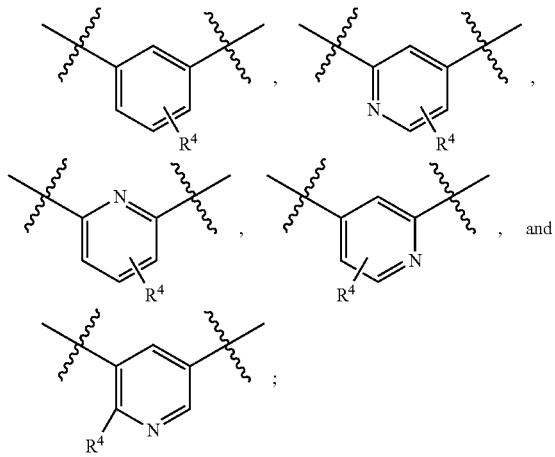

ring B is independently selected from

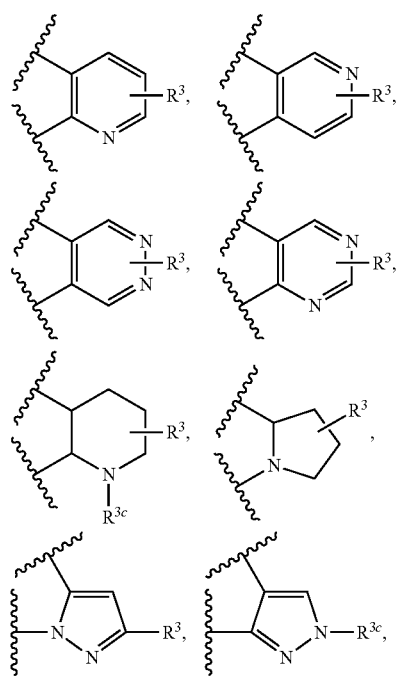

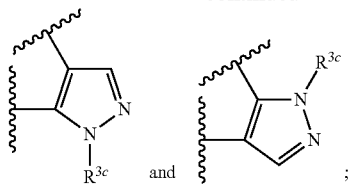

W is independently selected from $CHR^{1a}$, O, NH, and $N(C_{1-4}$ alkyl);

$R^1$ is independently selected from H and $C_{1-4}$ alkyl;

$R^{1a}$ is independently selected from H F, $CH_3$, and hydroxyl;

$R^2$ is independently selected from H and hydroxyl;

$R^3$ is independently selected from H, =O, F, $CHF_2$, $CF_3$, $OCF_3$, $OCHF_2$, $CH_3$, CN, —$(CH_2)_{0-2}$—OH, $OC_{1-4}$ alkyl, $C(=O)C_{1-4}$ alkyl, —$(CH_2)_{0-1}$—$C(=O)OH$, —$C(=O)OC_{1-4}$ alkyl, —$S(=O)_2C_{1-4}$ alkyl, and —$NHC(=O)OC_{1-4}$ alkyl;

$R^{3c}$ is independently selected from H, $CF_2H$, $CF_3$, $C_{1-4}$ alkyl, and $CD_3$;

$R^4$ is independently selected from H and F;

$R^{8b}$ is independently selected from H and F;

$R^{8c}$ is independently selected from H and Cl;

$R^{10}$ is independently selected from H, $C_{1-6}$ alkyl (optionally substituted with $R^{11}$), aryl, —$(CH_2)_n$—$C_{3-6}$ cycloalkyl (optionally substituted with $R^{11}$), —$(CH_2)_n$—O-4- to 10-membered heterocyclyl, F, Cl, Br, CN, $C(=O)NR^{12}R^{12}$, $Si(C_{1-4}$ alkyl$)_3$, and —$(CH_2)_n$—$OR^2$;

$R^{11}$, at each occurrence, is independently selected from H, halogen, and $C_{1-5}$ alkyl; and n, at each occurrence, is an integer independently selected from 0, 1, 2, 3, and 4; and other variables are as defined in Formula (IVb) above.

In another aspect, the present invention provides compounds of Formula (IIc), or stereoisomers, tautomers, pharmaceutically acceptable salts, solvates, or prodrugs thereof, wherein:

ring A is independently selected from

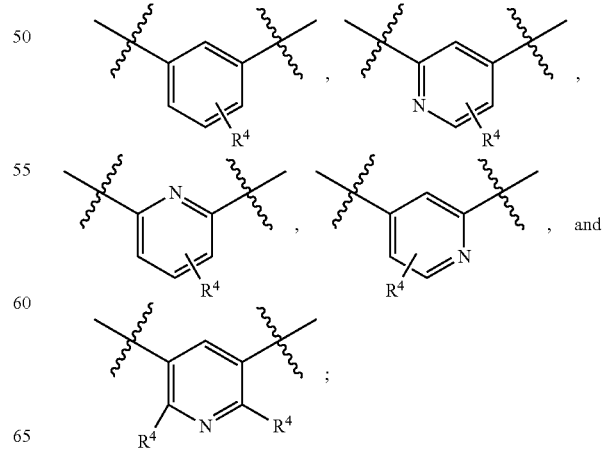

ring B is independently selected from

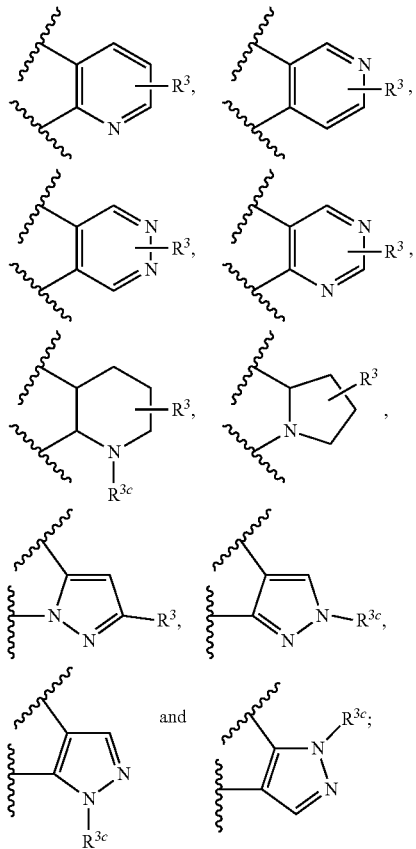

W is independently selected from CHR$^{1a}$, O, NH, and N(C$_{1-4}$ alkyl);
R$^1$ is independently selected from H and C$_{1-4}$ alkyl;
R$^{1a}$ is independently selected from H F, CH$_3$, and hydroxyl;
R$^2$ is independently selected from H and hydroxyl;
R$^3$ is independently selected from H, =O, F, CHF$_2$, CF$_3$, OCF$_3$, OCHF$_2$, CH$_3$, CN, —(CH$_2$)$_{0-2}$—OH, OC$_{1-4}$ alkyl, C(=O)C$_{1-4}$ alkyl, —(CH$_2$)$_{0-1}$—C(=O)OH, —C(=O)OC$_{1-4}$ alkyl, —S(=O)$_2$C$_{1-4}$ alkyl, and —NHC(=O)OC$_{1-4}$ alkyl;
R$^{3c}$ is independently selected from H, CF$_2$H, CF$_3$, C$_{1-4}$ alkyl, and CD$_3$;
R$^4$ is independently selected from H and F;
R$^{8b}$ is independently selected from H and F;
R$^{8c}$ is independently selected from H and Cl;
R$^{10}$ is independently selected from H, C$_{1-6}$ alkyl (optionally substituted with R$^{11}$), aryl, —(CH$_2$)$_n$—C$_{3-6}$ cycloalkyl (optionally substituted with R$^{11}$), —(CH$_2$)$_n$—O-4- to 10-membered heterocyclyl, F, Cl, Br, CN, C(=O)NR$^{12}$R$^{12}$, Si(C$_{1-4}$ alkyl)$_3$, and —(CH$_2$)$_n$—OR$^{12}$;
R$^{11}$, at each occurrence, is independently selected from H, halogen, and C$_{1-5}$ alkyl; and
n, at each occurrence, is an integer independently selected from 0, 1, 2, 3, and 4; and
other variables are as defined in Formula (IIc) above.

In another aspect, the present invention provides compounds of Formula (IIa), or stereoisomers, tautomers, pharmaceutically acceptable salts, solvates, or prodrugs thereof, wherein:

ring A is independently selected from

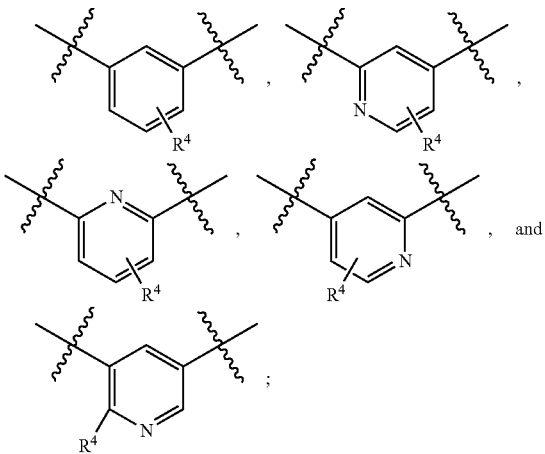

ring B is independently selected from

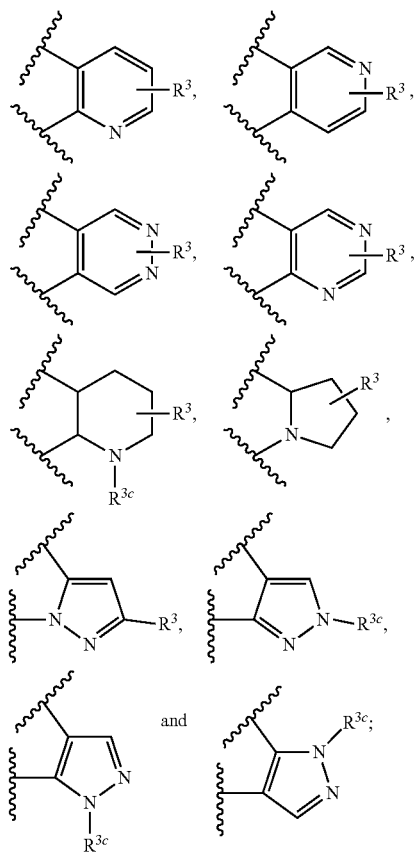

G$^1$ is independently selected from

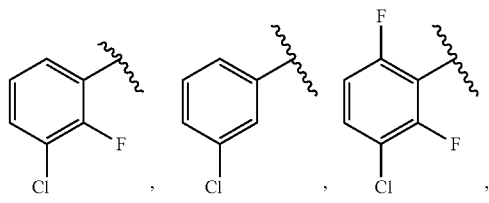

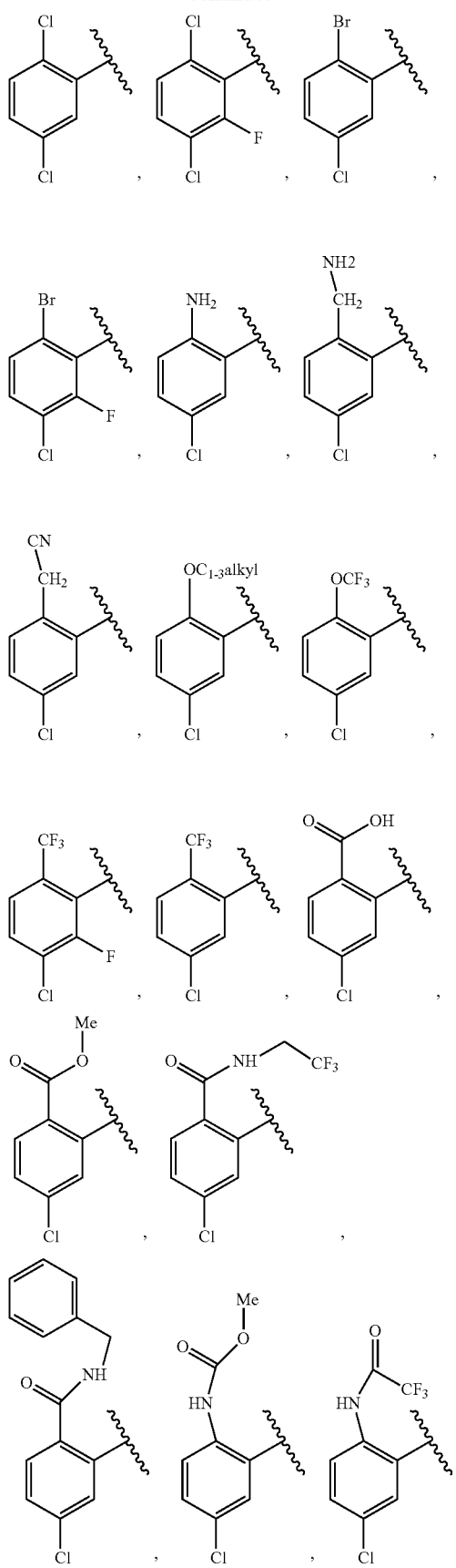
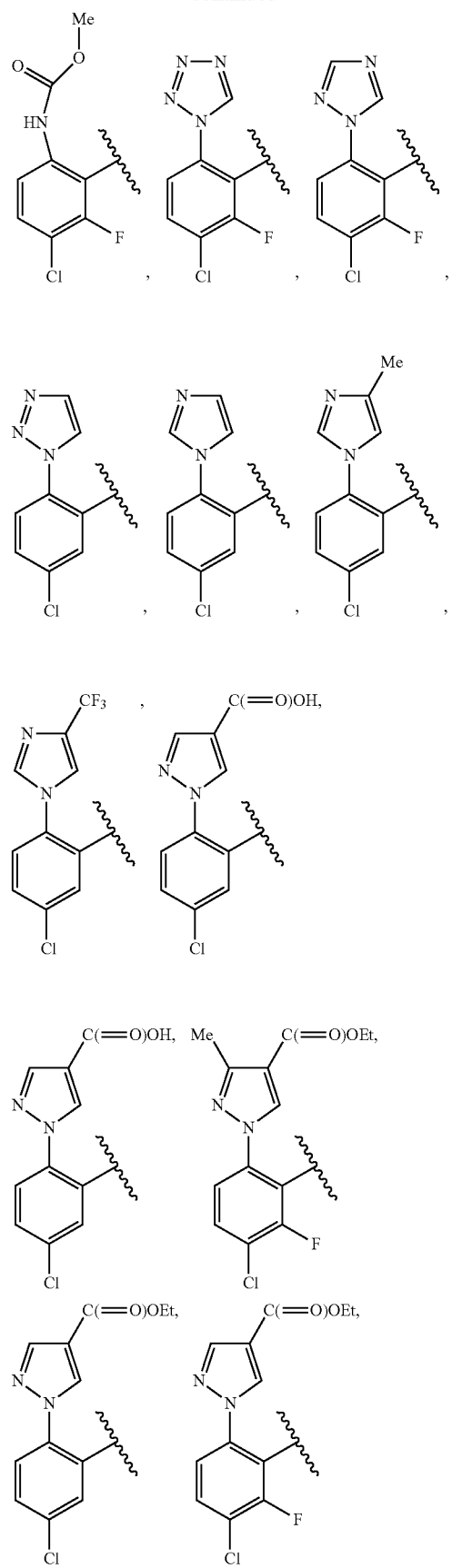

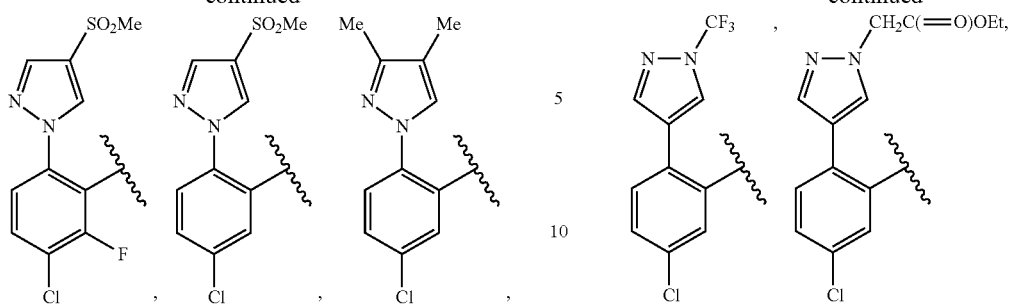
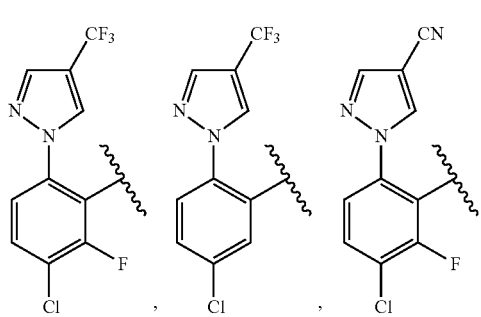
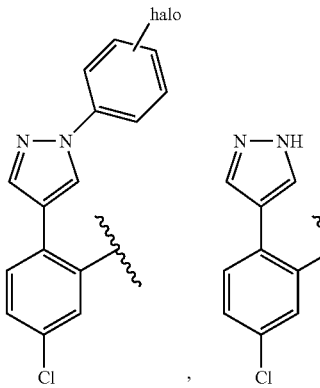
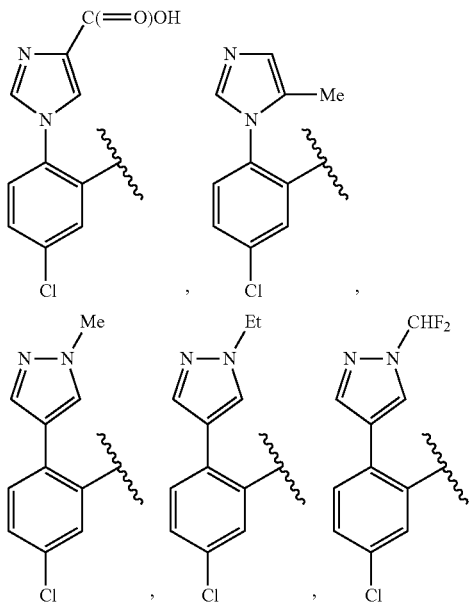

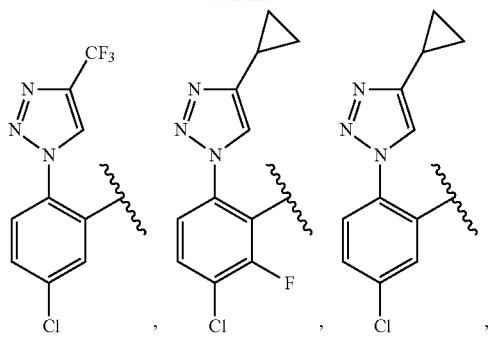
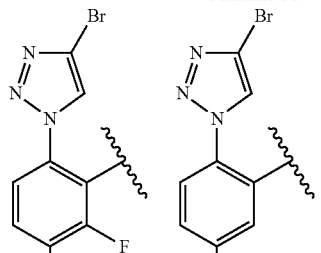
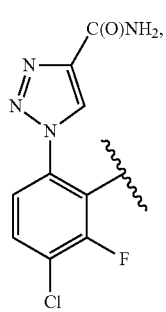
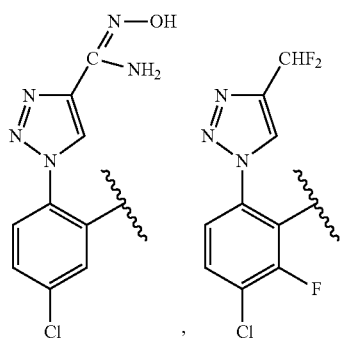
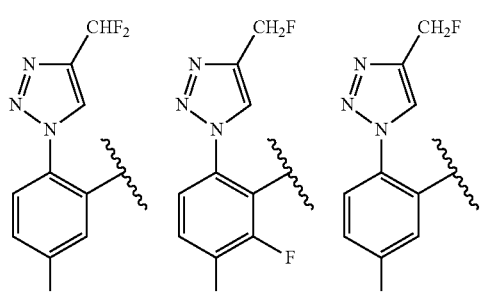
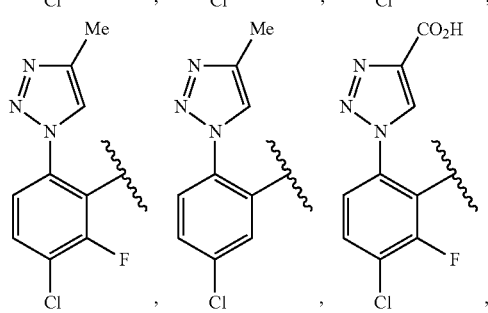

-continued
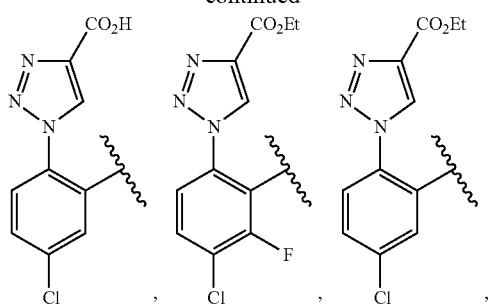
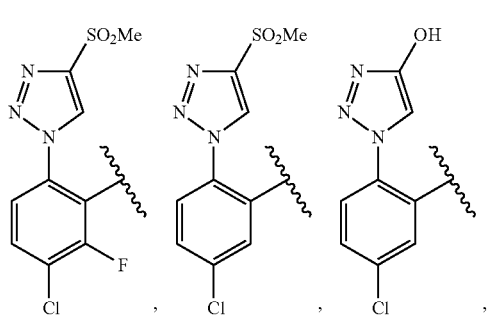
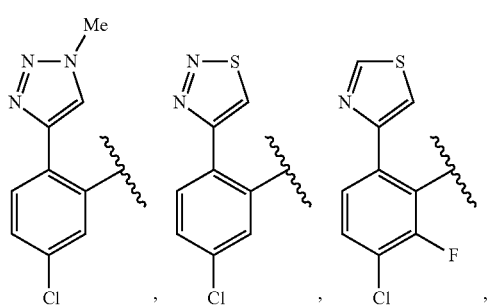
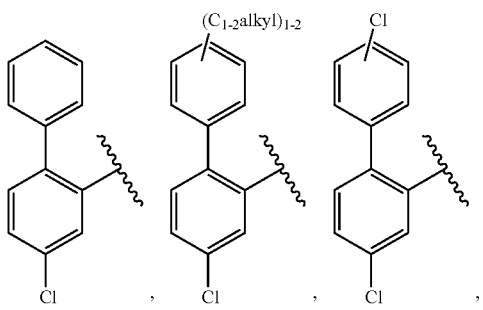
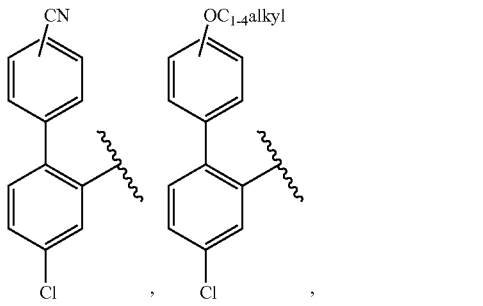
-continued
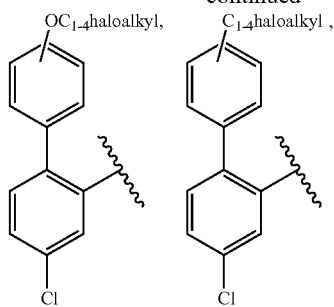
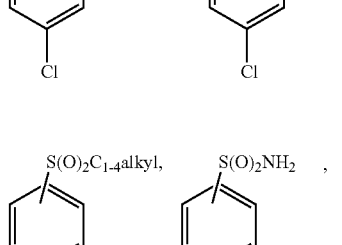
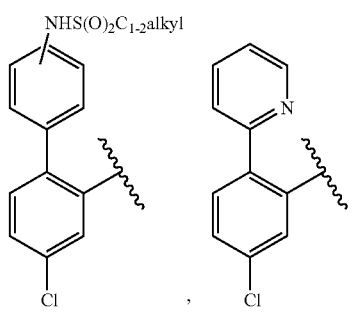
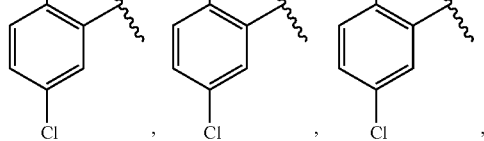

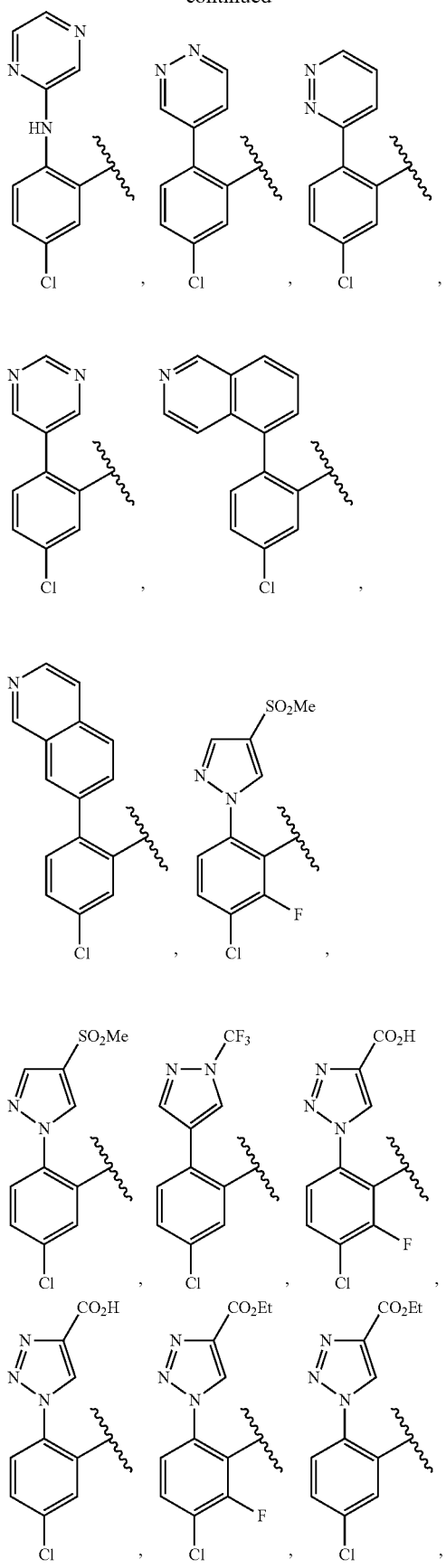
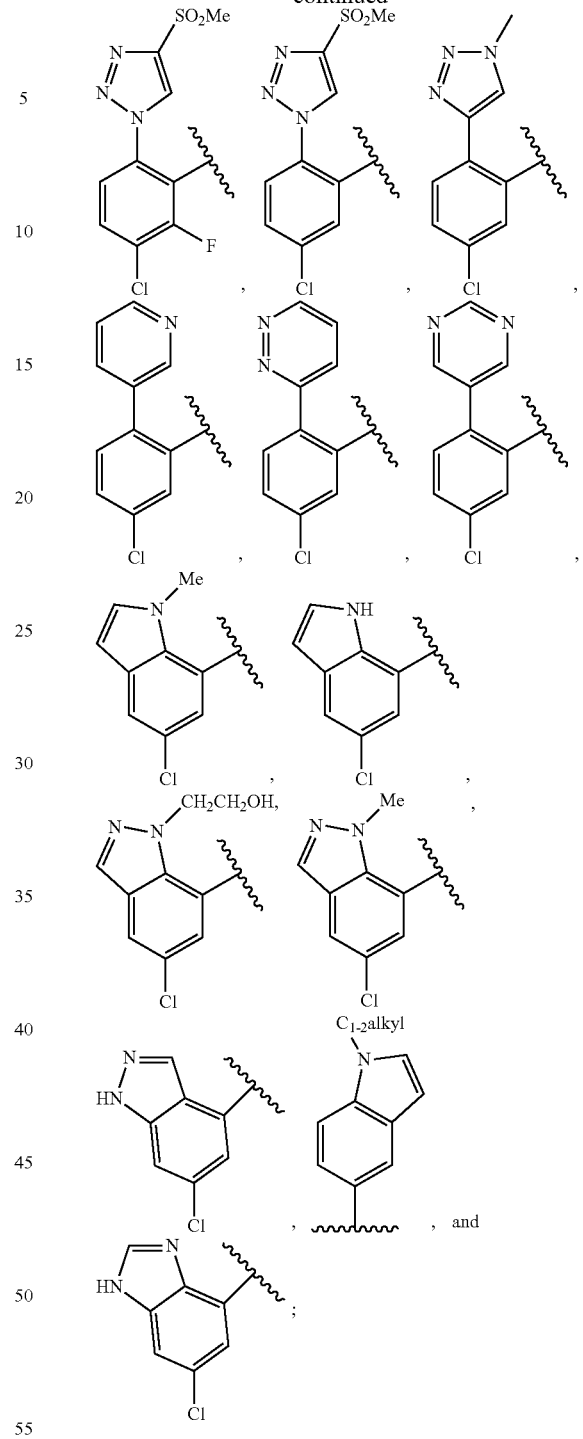
W is independently selected from CHR$^1$, O, NH, and N(C$_{1-4}$ alkyl);
Y is independently selected from —NH—, —NHC(=O)— and —C(=O)NH—;
R$^1$ and R$^2$ are independently selected from H, F, C$_{1-4}$ alkyl, and hydroxyl;
R$^3$ is independently selected from H, =O, F, CHF$_2$, CF$_3$, OCF$_3$, OCHF$_2$, CH$_3$, CN, —(CH$_2$)$_{0-2}$—OH, OC$_{1-4}$ alkyl, C(=O)C$_{1-4}$ alkyl, —(CH$_2$)$_{0-1}$—C(=O)OH, —C(=O)OC$_{1-4}$ alkyl, —S(=O)$_2$C$_{1-4}$ alkyl, and —NHC(=O)OC$_{1-4}$ alkyl;

$R^{3c}$ is independently selected from H, CF$_2$H, CF$_3$, C$_{1-4}$ alkyl, and CD$_3$;

$R^4$ is independently selected from H, F, and C$_{1-4}$ alkyl; and $R^7$ is H; and other variables are as defined in Formula (IIa) above.

In another aspect, the present invention provides compounds of Formula (V):

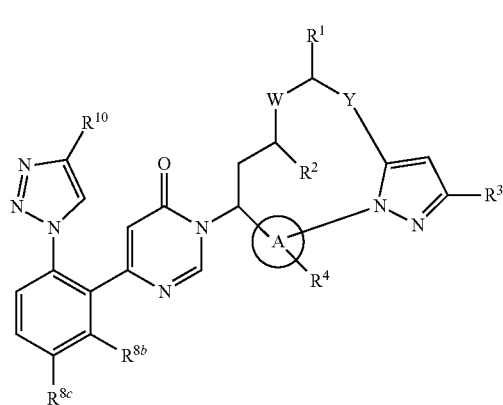

(V)

or stereoisomers, tautomers, pharmaceutically acceptable salts, solvates, or prodrugs thereof, wherein:

ring A is independently selected from phenyl and a 5- to 6-membered heterocyclyl;

W is independently selected from CHR$^{1a}$, O, NH, and N(C$_{1-4}$ alkyl);

$R^1$ is independently selected from H and C$_{1-4}$ alkyl;

$R^{1a}$ is independently selected from H and F;

$R^2$ is independently selected from H and hydroxyl;

$R^3$ is independently selected from H, haloalkyl, and C$_{1-4}$alkyl (optionally substituted with R$^6$), F, CN, C(=O)C$_{1-4}$ alkyl, C(=O)OH, —S(=O)$_2$C$_{1-4}$alkyl, and —NHC(=O)OC$_{1-4}$ alkyl;

$R^4$ is independently selected from H, OH, F, Cl, Br, C$_{1-4}$ alkyl, C$_{1-4}$ alkoxy, CF$_3$, and CN;

$R^5$ is independently selected from H, C$_{1-4}$ alkyl (optionally substituted with halogen, hydroxyl, alkoxy, carboxy, alkoxycarbonyl, amino, substituted amino), —(CH$_2$)$_n$—C$_{3-10}$ carbocyclyl and —(CH$_2$)$_n$-4- to 10-membered heterocyclyl, wherein said carbocyclyl and heterocyclyl are optionally substituted with R$^6$;

$R^6$ is independently selected from —(CH$_2$)$_n$—OH, =O, NH$_2$, —(CH$_2$)$_n$—CN, halogen, C$_{1-6}$ alkyl, —(CH$_2$)$_n$—C(=O)OH, —(CH$_2$)$_n$—C(=O)OC$_{1-4}$ alkyl, —(CH$_2$)$_n$—OC$_{1-4}$ alkyl, —(CH$_2$)$_n$—C$_{3-6}$ cycloalkyl, —(CH$_2$)$_n$-4- to 10-membered heterocyclyl, and —O—(CH$_2$)$_n$-4- to 10-membered heterocyclyl, wherein said cycloalkyl and heterocyclyl are optionally substituted with R$^{10}$;

$R^7$ is independently selected from H, F, Cl, and methyl;

$R^{8b}$ is independently selected from H and F;

$R^{8c}$ is independently selected from H, F, Cl, CH$_3$, and OCH$_3$;

$R^{10}$ is independently selected from H, C$_{1-6}$ alkyl (optionally substituted with R$^{11}$), C$_{2-6}$ alkenyl, C$_{2-6}$ alkynyl, aryl, —(CH$_2$)$_n$—C$_{3-6}$ cycloalkyl (optionally substituted with R$^{11}$), —(CH$_2$)$_n$—O-4- to 10-membered heterocyclyl (optionally substituted with R$^{11}$), F, Cl, Br, CN, NO$_2$, =O, C(=O)NR$^{12}$R$^{12}$, C(=O)OR$^{12}$, Si(C$_{1-4}$ alkyl)$_3$, —(CH$_2$)$_n$—OR$^{12}$, and —(CH$_2$)$_n$—NR$^{12}$R$^{12}$;

$R^{11}$, at each occurrence, is independently selected from H, halogen, C$_{1-5}$ alkyl, —(CH$_2$)$_n$—OH, C$_{3-6}$ cycloalkyl, and phenyl;

$R^{12}$, at each occurrence, is independently selected from H, C$_{1-5}$ alkyl, C$_{3-6}$ cycloalkyl, phenyl, and heterocyclyl, or R$^{12}$ and R$^{12}$ together with the nitrogen atom to which they are both attached form a heterocyclic ring optionally substituted with C$_{1-4}$alkyl; and n, at each occurrence, is an integer independently selected from 0, 1, and 2; and p, at each occurrence, is an integer independently selected from 0, 1, and 2.

In another aspect, the present invention provides compounds of Formula (VI):

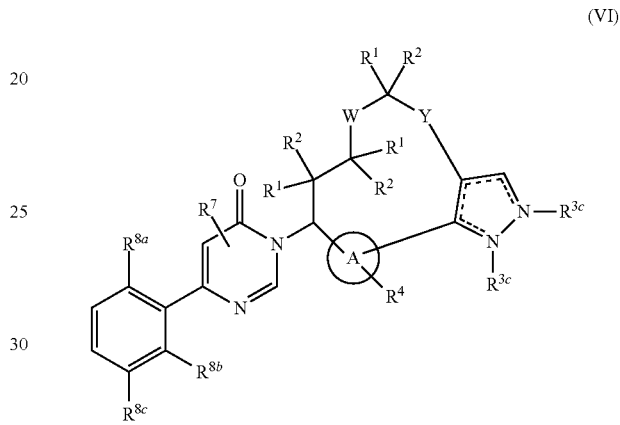

(VI)

or stereoisomers, tautomers, pharmaceutically acceptable salts, solvates, or prodrugs thereof, wherein:

ring A is independently selected from phenyl and a 5- to 6-membered heterocyclyl;

W is independently selected from (CR$^1$R$^2$)$_{1-2}$, O, NH, and N(C$_{1-4}$ alkyl);

Y is independently selected from —NH—, —NHC(=O)— and —C(=O)NH—;

$R^1$ and $R^2$ are independently selected from H, halogen, CF$_3$, C$_{1-6}$ alkyl, and hydroxyl;

$R^{3c}$ is independently selected from H, haloalkyl, and C$_{1-4}$alkyl (optionally substituted with R$^6$), —(CH$_2$)$_{1-2}$—OH, C(=O)C$_{1-4}$ alkyl, —(CH$_2$)$_{0-2}$—C(=O)OH, and —C(=O)OC$_{1-4}$ alkyl; only one R$^{3c}$ is present on the ring;

$R^4$ is independently selected from H, OH, F, Cl, Br, C$_{1-4}$ alkyl, C$_{1-4}$ alkoxy, CF$_3$, CN, C$_{3-6}$ cycloalkyl, aryl, and 5- to 6-membered heterocyclyl, wherein said cycloalkyl, aryl and heterocyclyl are optionally substituted with R$^6$;

$R^5$ is independently selected from H, C$_{1-4}$ alkyl (optionally substituted with halogen, hydroxyl, alkoxy, carboxy, alkoxycarbonyl, amino, substituted amino), —(CH$_2$)$_n$—C$_{3-10}$ carbocyclyl and —(CH$_2$)$_n$-4- to 10-membered heterocyclyl, wherein said carbocyclyl and heterocyclyl are optionally substituted with R$^6$;

$R^6$ is independently selected from —(CH$_2$)$_n$—OH, =O, NH$_2$, —(CH$_2$)$_n$—CN, halogen, C$_{1-6}$ alkyl, —(CH$_2$)$_n$—C(=O)OH, —(CH$_2$)$_n$—C(=O)OC$_{1-4}$ alkyl, —(CH$_2$)$_n$—OC$_{1-4}$ alkyl, —(CH$_2$)$_n$—C$_{3-6}$ cycloalkyl, —(CH$_2$)$_n$-4- to 10-membered heterocyclyl, and —O—(CH$_2$)$_n$-4- to 10-membered heterocyclyl, wherein said cycloalkyl and heterocyclyl are optionally substituted with R$^{10}$;

$R^7$ is independently selected from H, F, and methyl;

$R^{8a}$ is independently selected from H, F, Cl, Br, CN, $OCH_3$, $OCF_3$, $CH_3$, $C(=O)CH_3$, $CHF_2$, $CF_3$, $CCH_3F_2$, $OCHF_2$, aryl, $C_{3-6}$ cycloalkyl, and 4- to 6-membered heterocyclyl optionally substituted with $R^{10}$;

$R^{8b}$ is independently selected from H and F;

$R^{8c}$ is independently selected from H, F, Cl, $CH_3$, and $OCH_3$;

$R^{10}$ is independently selected from H, $C_{1-6}$ alkyl (optionally substituted with $R^{11}$), $C_{2-6}$ alkenyl, $C_{2-6}$ alkynyl, aryl, —$(CH_2)_n$—$C_{3-6}$ cycloalkyl (optionally substituted with $R^{11}$), —$(CH_2)_n$—O-4- to 10-membered heterocyclyl (optionally substituted with $R^{11}$), F, Cl, Br, CN, $NO_2$, =O, $CONR^{12}R^{12}$, $C(=O)OR^{12}$, $Si(C_{1-4}$ alkyl$)_3$, —$(CH_2)_n$—$OR^{12}$, and —$(CH_2)_n$—$NR^{12}R^{12}$;

$R^{11}$, at each occurrence, is independently selected from H, halogen, $C_{1-5}$ alkyl, —$(CH_2)_n$—OH, $C_{3-6}$ cycloalkyl, and phenyl;

$R^{12}$, at each occurrence, is independently selected from H, $C_{1-5}$ alkyl, $C_{3-6}$ cycloalkyl, phenyl, and heterocyclyl, or $R^{12}$ and $R^{12}$ together with the nitrogen atom to which they are both attached form a heterocyclic ring optionally substituted with $C_{1-4}$alkyl;

n, at each occurrence, is an integer independently selected from 0, 1, and 2; and p, at each occurrence, is an integer independently selected from 0, 1, and 2.

In another aspect, the present invention provides compounds of Formula (VII):

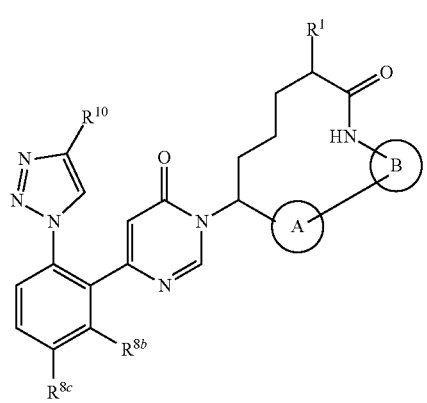

(VII)

or stereoisomers, tautomers, pharmaceutically acceptable salts, solvates, or prodrugs thereof, wherein:

ring A is independently selected from

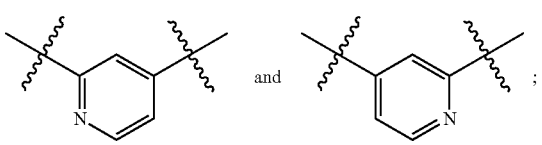 [SMILES: *c1ccnc(*)c1 ; *c1ccnc(*)c1]

ring B is independently selected from

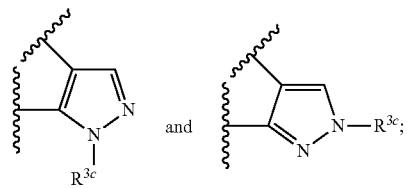

$R^1$ is independently selected from H and $C_{1-4}$ alkyl;

$R^{10}$ is independently selected from F, Cl, $CF_3$, $CHF_2$, and COOH;

$R^{3c}$ is independently selected from H, $CHF_2$, $CD_3$, $CH_3$, and

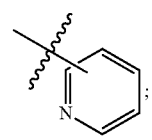

$R^{8b}$ is independently selected from H and F; and $R^{8c}$ is independently selected from H, F, Cl, $CH_3$, and $OCH_3$.

In another aspect, the present invention provides compounds of Formula (VII), or stereoisomers, tautomers, pharmaceutically acceptable salts, solvates, or prodrugs thereof, wherein:

ring A is independently selected from

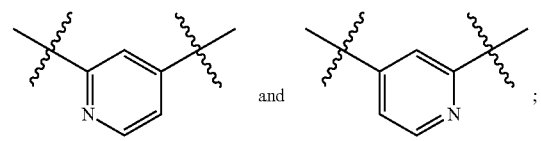 [SMILES: *c1ccnc(*)c1 ; *c1ccnc(*)c1]

ring B is independently selected from

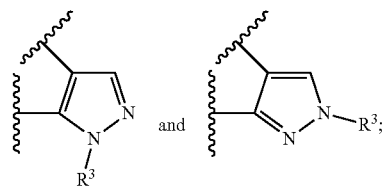

$R^1$ is independently selected from H and $C_{1-4}$ alkyl;

$R^{10}$ is independently selected from F, Cl, $CF_3$, $CHF_2$, and COOH;

$R^{3c}$ is independently selected from H, $CHF_2$, $CD_3$, and $CH_3$;

$R^{8b}$ is independently selected from H and F; and $R^{8c}$ is independently selected from H, F, Cl, $CH_3$, and $OCH_3$.

In another aspect, the present invention provides compounds of Formula (VIII):

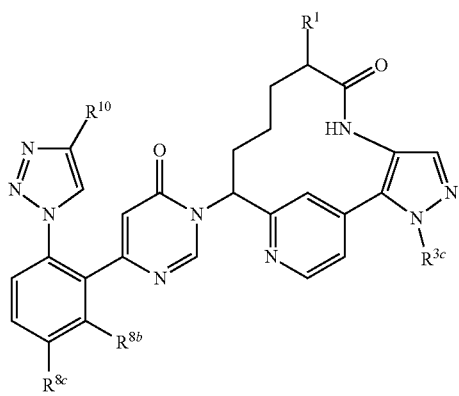

(VIII)

or stereoisomers, tautomers, pharmaceutically acceptable salts, solvates, or prodrugs thereof, wherein:
$R^1$ is $C_{1-4}$ alkyl;
$R^{10}$ is independently selected from F, Cl, $CF_3$, $CHF_2$ and COOH;
$R^{3c}$ is independently selected from $CHF_2$, $CD_3$, and $CH_3$;
$R^{8b}$ is H; and
$R^{8c}$ is independently selected from F and Cl.

In another aspect, the present invention provides compounds of Formula (VIII), or stereoisomers, tautomers, pharmaceutically acceptable salts, solvates, or prodrugs thereof, wherein:
$R^1$ is $C_{1-4}$ alkyl;
$R^{10}$ is independently selected from F, Cl, $CF_3$, $CHF_2$ and COOH;
$R^{3c}$ is independently selected from $CHF_2$, $CD_3$, and $CH_3$;
$R^{8b}$ is H; and
$R^{8c}$ is independently selected from F and Cl.

In another aspect, the present invention provides compounds of Formula (IX):

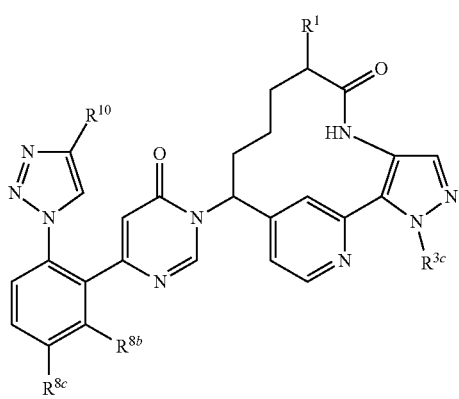

(IX)

or stereoisomers, tautomers, pharmaceutically acceptable salts, solvates, or prodrugs thereof, wherein:
$R^1$ is $C_{1-4}$ alkyl;
$R^{10}$ is independently selected from F, Cl, $CF_3$, $CHF_2$, and COOH;
$R^{3c}$ is independently selected from $CHF_2$, $CD_3$, and $CH_3$;
$R^{8b}$ is H; and
$R^{8c}$ is independently selected from F and Cl.

In another aspect, the present invention provides compounds of Formula (IX), or stereoisomers, tautomers, pharmaceutically acceptable salts, solvates, or prodrugs thereof, wherein:
$R^1$ is $C_{1-4}$ alkyl;
$R^{10}$ is independently selected from F, Cl, $CF_3$, $CHF_2$, and COOH;
$R^{3c}$ is independently selected from $CHF_2$, $CD_3$, and $CH_3$;
$R^{8b}$ is H; and
$R^{8c}$ is independently selected from F and Cl.

In another aspect, the present invention provides compounds of Formula (X):

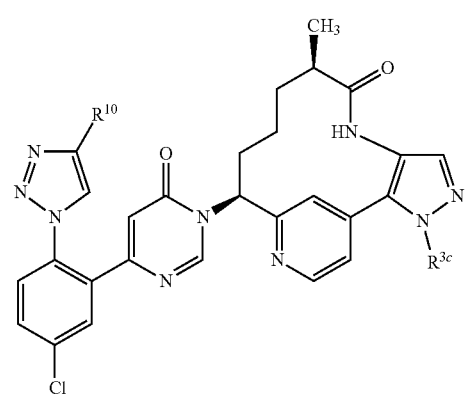

(X)

or stereoisomers, tautomers, pharmaceutically acceptable salts, solvates, or prodrugs thereof, wherein:
$R^{10}$ is independently selected from F, Cl, $CF_3$, $CHF_2$, and COOH; and
$R^{3c}$ is independently selected from $CHF_2$, $CD_3$, and $CH_3$.

In another aspect, the present invention provides compounds of Formula (VII), or stereoisomers, tautomers, pharmaceutically acceptable salts, solvates, or prodrugs thereof, wherein:
ring A is independently selected from

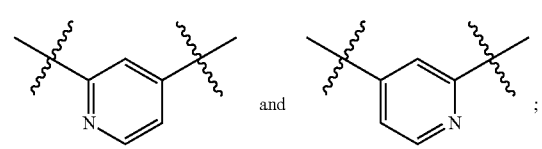 [SMILES: *c1ccnc(*)c1 ; *c1ccnc(*)c1]

ring B is

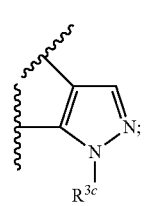

$R^1$ is independently selected from H and $C_{1-4}$ alkyl;
$R^{10}$ is COOH;
$R^{3c}$ is independently selected from H, $CHF_2$, $CD_3$, and $CH_3$;
$R^{8b}$ is independently selected from H and F; and
$R^{8c}$ is independently selected from H, F, Cl, $CH_3$, and $OCH_3$.

In another aspect, the present invention provides compounds selected from
51
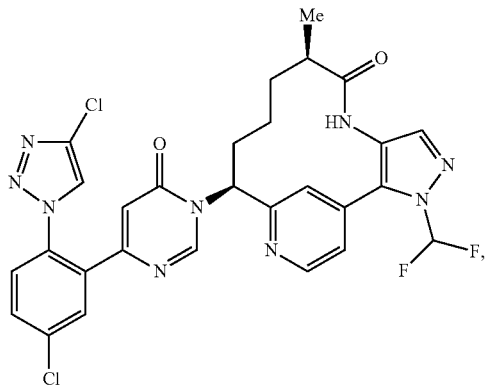
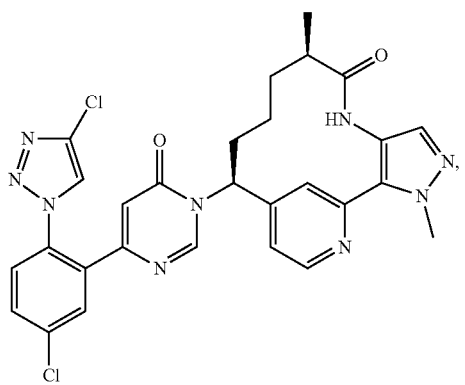
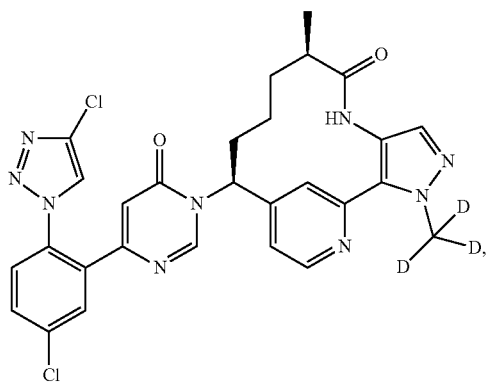
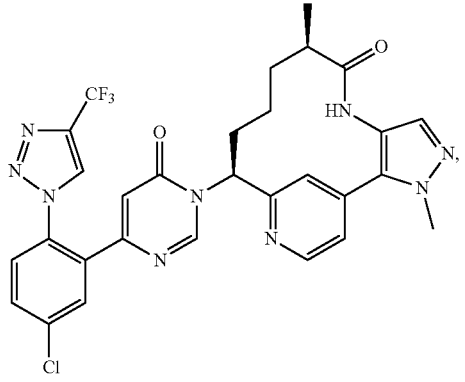
-continued
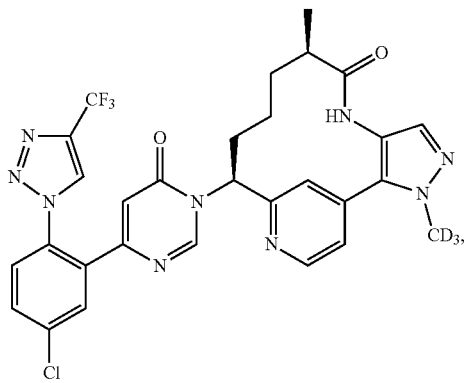
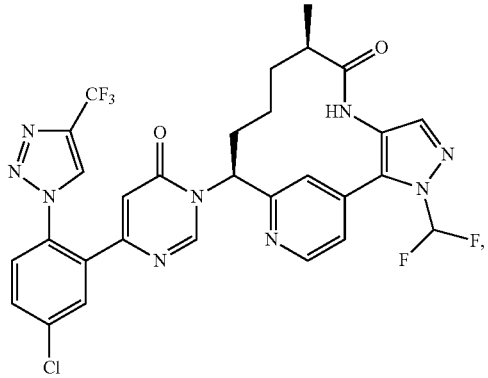
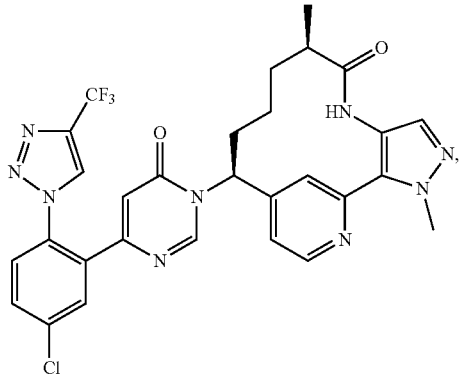
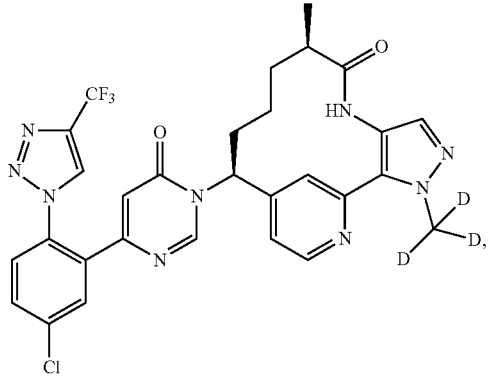

-continued

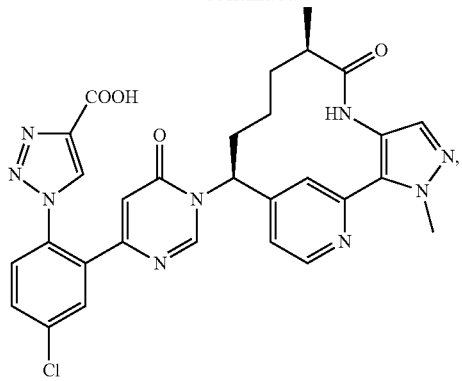

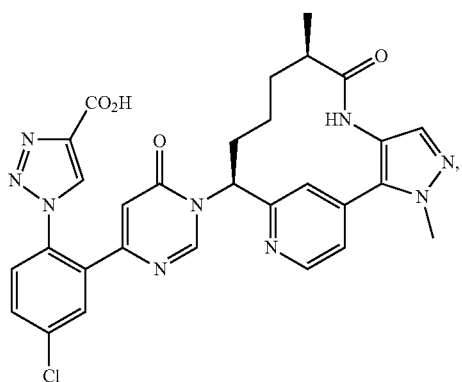

or a stereoisomer, a tautomer, a pharmaceutically acceptable salt, solvates, or prodrugs thereof.

In one embodiment, $G^1$ is independently selected from the group consisting of

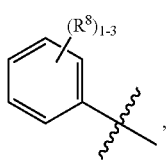, wherein $R^8$ is, independently at each occurrence, selected from the group consisting of H, halogen, CN, $C_{1-6}$ alkyl, haloalkyl, alkoxy, haloalkoxy, and 4- to 6-membered heterocyclyl.

In another embodiment, $G^1$ is

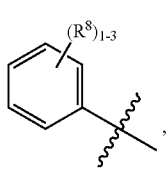, wherein $R^8$ is, independently at each occurrence, selected from the group consisting of H, halogen, CN, methyl, ethyl, $CF_3CHF_2$, OMe, OEt, $OCF_3$, $OCHF_2$, aryl, $C_{3-6}$ cycloalkyl, and 4- to 6-membered heterocyclyl.

In another embodiment, $G^1$ is

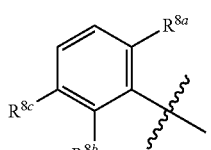

and selected from the group consisting of

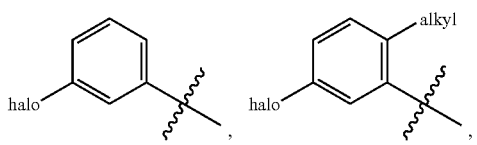

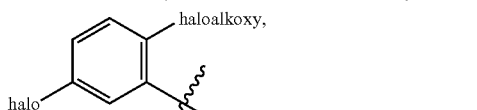

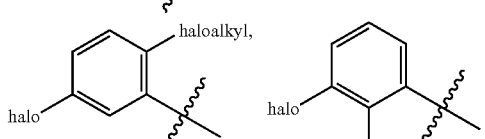

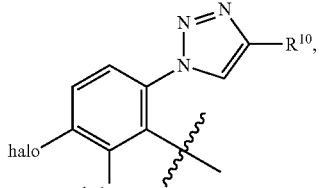

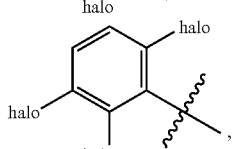

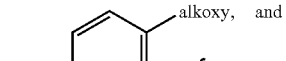

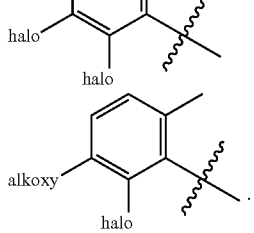

In another embodiment, $G^1$ is

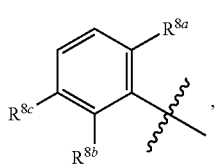, wherein $R^{8a}$ is independently selected from the group consisting of H, F, $OCH_3$, $OCHF_2$, and

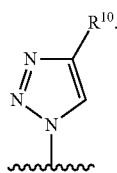

In another embodiment, $R^{8b}$ is independently selected from the group consisting of H, F and Cl.

In another embodiment, $R^{8b}$ is independently selected from the group consisting of H and F.

In another embodiment, $R^{8c}$ is Cl.

In another embodiment, $G^1$ is

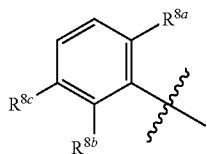

selected from the group consisting of

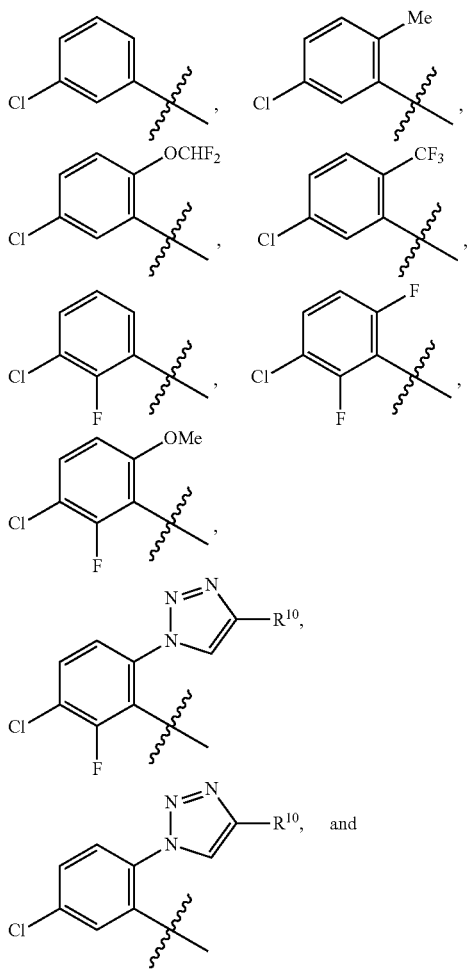

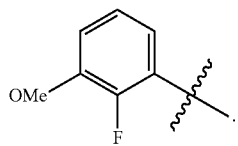

In another embodiment, $G^1$ is

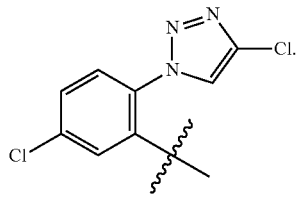 [SMILES: *c1cc(Cl)ccc1-n1cc(Cl)nn1]

In one embodiment, the present invention provides compounds of Formulae (I), (II), (IIa), (IIb), (IIc), (IId), (IIe), (IIf), (IIg), (IIIa), (IIIb), (IVb), (V), and (VI) or stereoisomers, tautomers, pharmaceutically acceptable salts, solvates, or prodrugs thereof, wherein ring A is independently selected from the group consisting of imidazole, oxadiazole, pyridine, pyridinone, pyridazine, pyridazinone, and phenyl.

In another embodiment,

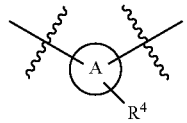

is independently selected from the group consisting of

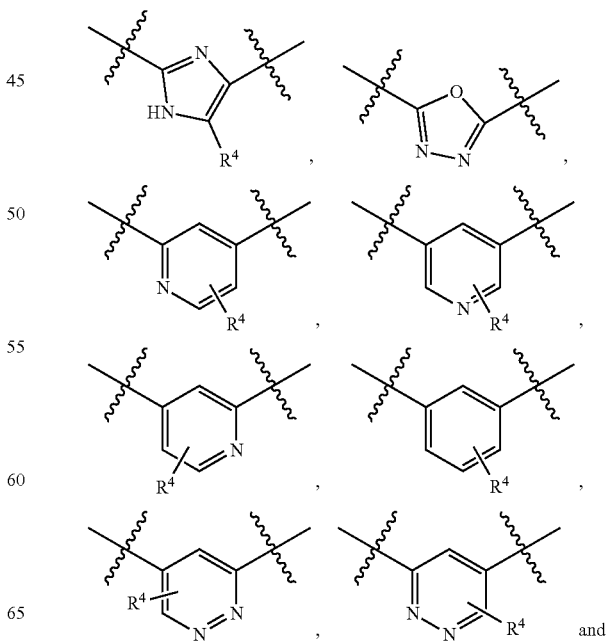

-continued

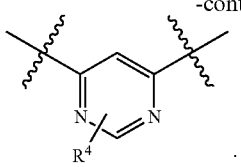

In another embodiment,

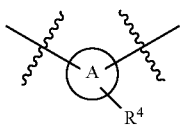

is independently selected from the group consisting of

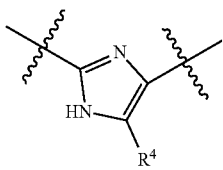 , 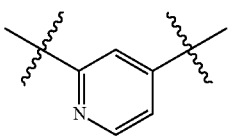 ,

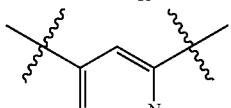 , 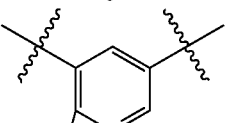 ,

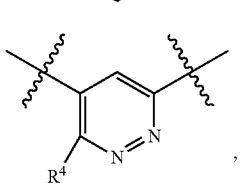 , and 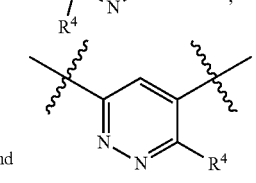 .

In another embodiment,

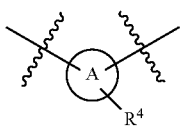

is independently selected from the group consisting of

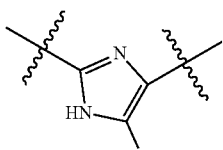 , 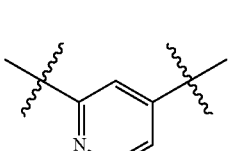 ,

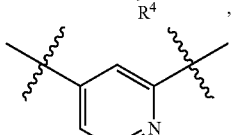 , and 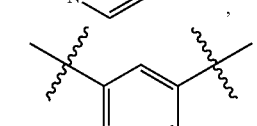 .

In still another embodiment,

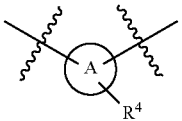

is independently selected from the group consisting of

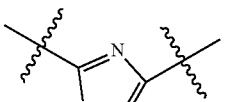 , 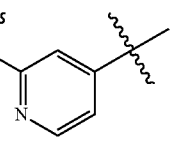 , and

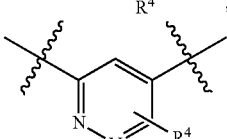 .

In another embodiment,

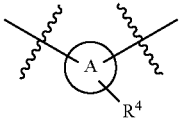 is 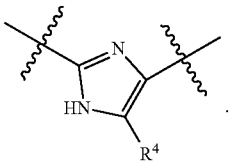 .

In another embodiment,

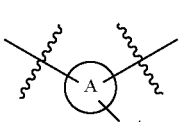 is 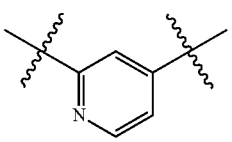 .

In another embodiment,

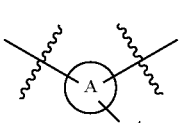 is 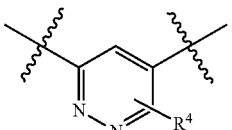 .

In another embodiment,

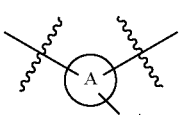 is 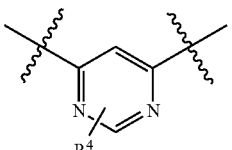 .

In another embodiment,

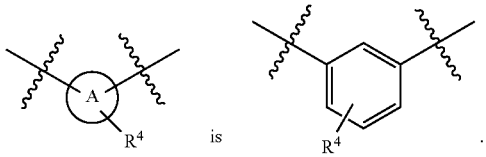 is 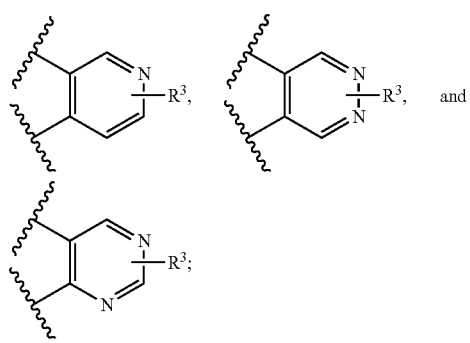

In another embodiment,

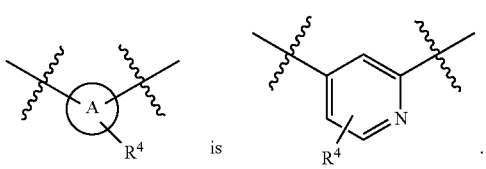 is .

In another embodiment,

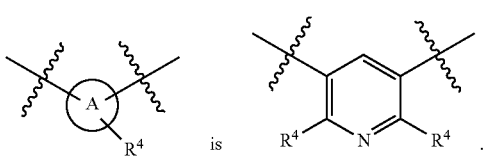 is .

In another embodiment, ring B is independently selected from

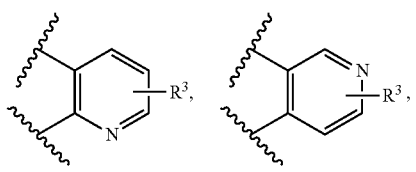

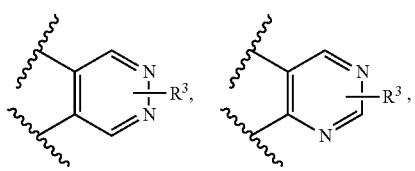

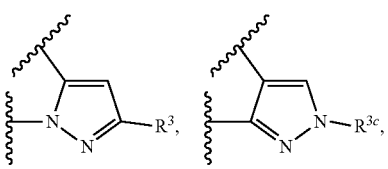

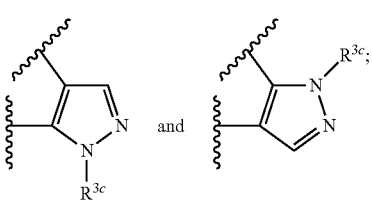

In another embodiment, ring B is independently selected from,

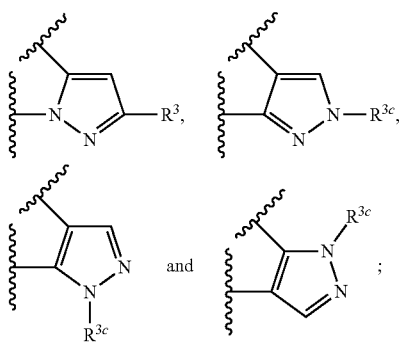

In another embodiment, ring B is independently selected from,

In another embodiment, ring B is

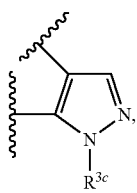

wherein $R^{3c}$ is independently selected from H, $CHF_2$, $CD_3$, $CH_3$, and $SO_2CH_3$.

In another embodiment, $R^1$ is independently selected from the group consisting of H, OH, F, and $C_{1-4}$ alkyl.

In another embodiment, $R^1$ is independently selected from the group consisting of H and $C_{1-4}$ alkyl.

In another embodiment, $R^1$ is independently selected from the group consisting of H and methyl, ethyl, and isopropyl.

In one embodiment, $R^2$ is, independently at each occurrence, selected from the group consisting of H and $C_{1-4}$ alkyl.

In another embodiment, $R^2$ is, independently at each occurrence, selected from the group consisting of H and methyl.

In another embodiment, one of $R^1$ and $R^2$ is H and the other is methyl;

In another embodiment, $R^1$ and $R^2$ together are =O;

In one embodiment, Ring B is 5-membered heteroaryl comprising carbon atoms and heteroatoms selected from N and $NR^{3c}$; $R^3$ is independently selected from H, halogen, $C_{1-4}$ alkyl (optionally substituted with $R^6$), CN, $-(CH_2)_n-OR^5$, $-(CH_2)_n-NR^5R^5$, $-(CH_2)_n-C(=O)R^5$, and $-(CH_2)_n-C(=O)OR^5$; $R^{3c}$ is independently selected from H, haloalkyl, $C_{1-4}$ alkyl (optionally substituted with $R^6$), —$(CH_2)_{1-2}$—OH, $C(=O)C_{1-4}$ alkyl, —$(CH_2)_{1-2}$—$C(=O)OH$, —$C(=O)OC_{1-4}$ alkyl, $S(=O)_pC_{1-6}$ alkyl, —$(CH_2)_n$—$C_{3-10}$ carbocyclyl and —$(CH_2)_n$-4- to 10-membered heterocyclyl, wherein said carbocyclyl and heterocyclyl are optionally substituted with $R^6$; $R^5$ is independently selected from H, $C_{1-4}$ alkyl (optionally substituted with halogen, hydroxyl, alkoxy, carboxy, alkoxycarbonyl), —$(CH_2)_n$—$C_{3-10}$ carbocyclyl and —$(CH_2)_n$-4- to 10-membered heterocyclyl, wherein said carbocyclyl and heterocyclyl are optionally substituted with $R^6$; $R^6$ is independently selected from OH, =O, —$(CH_2)_nNH_2$, —$(CH_2)_nCN$, halogen, $C_{1-6}$ alkyl, —$(CH_2)_n$—$C(=O)OH$, —$(CH_2)_n$—$C(=O)OC_{1-4}$ alkyl, —$(CH_2)_n$—$OC_{1-4}$ alkyl, —$(CH_2)_n$—$C_{3-10}$ carbocyclyl, —$(CH_2)_n$-4- to 10-membered heterocyclyl, and —$(CH_2)_n$-4- to 10-membered heterocyclyl, wherein said carbocyclyl and heterocyclyl are optionally substituted with $R^{10}$.

In another aspect, the present invention provides a compound selected from any subset list of compounds exemplified in the present application.

In another aspect, the present invention provides a compound selected from:
- (9R,13S)-13-(4-{5-chloro-2-[(pyrimidin-2-yl)amino]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one;
- ethyl 2-[4-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-pyrazol-1-yl]acetate;
- 2-[4-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-pyrazol-1-yl]acetic acid;
- 2-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)acetonitrile;
- (9R,13S)-13-{4-[5-chloro-2-(1-methyl-1H-pyrazol-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;
- (9R,13S)-13-{4-[5-chloro-2-(1,3-dimethyl-1H-pyrazol-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate;
- (10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-4,5,8-triazatricyclo[13.3.1.0$^{2,7}$]nonadeca-1(19),2(7),3,5,15,17-hexaen-9-one;
- 1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-pyrazole-4-carboxylic acid;
- (9R,13S)-13-[4-(2-bromo-5-chlorophenyl)-5-chloro-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one;
- (9R,13S)-13-{4-[3-chloro-2-fluoro-6-(1,3-thiazol-5-yl)phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one;
- (9R,13S)-13-{4-[3-chloro-2-fluoro-6-(1H-1,2,3-triazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate;
- (9R,13S)-13-(4-{5-chloro-2-[4-(trifluoromethyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate;
- (9R,13S)-13-{4-[5-chloro-2-(4-chloro-1H-1,2,3-triazol-1-yl)phenyl]-6-oxo-1,6-dihydropyrimidin-1-yl}-9-ethyl-3-methyl-3,4,7,15-tetraazatricyclo[12.3.1.0$^{2,6}$]octadeca-1(18),2(6),4,14,16-pentaen-8-one trifluoroacetate;
- (9R,13S)-13-{4-[5-chloro-2-(4-chloro-1H-1,2,3-triazol-1-yl)phenyl]-6-oxo-1,6-dihydropyrimidin-1-yl}-3-methyl-9-(propan-2-yl)-3,4,7,15-tetraazatricyclo[12.3.1.0$^{2,6}$]octadeca-1(18),2(6),4,14,16-pentaen-8-one trifluoroacetate;
- (9S,13S)-13-{4-[5-chloro-2-(4-chloro-1H-1,2,3-triazol-1-yl)phenyl]-6-oxo-1,6-dihydropyrimidin-1-yl}-3-methyl-9-(propan-2-yl)-3,4,7,15-tetraazatricyclo[12.3.1.0$^{2,6}$]octadeca-1(18),2(6),4,14,16-pentaen-8-one trifluoroacetate;
- (9S,13S)-13-{4-[3-chloro-6-(4-chloro-1H-1,2,3-triazol-1-yl)-2-fluorophenyl]-6-oxo-1,6-dihydropyrimidin-1-yl}-3-methyl-9-(propan-2-yl)-3,4,7,15-tetraazatricyclo[12.3.1.0$^{2,6}$]octadeca-1(18),2(6),4,14,16-pentaen-8-one trifluoroacetate;
- (9R,13S)-13-{4-[3-chloro-6-(difluoromethyl)-2-fluorophenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate;
- (9R,13S)-13-{4-[3-chloro-6-(1,1-difluoroethyl)-2-fluorophenyl]-6-oxo-1,6-ihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate;
- (9R,13S)-13-{4-[3-chloro-2-fluoro-6-(1H-1,2,3-triazol-1-yl)phenyl]-6-oxo-1,6-dihydropyrimidin-1-yl}-16-fluoro-3,9-dimethyl-3,4,7-triazatricyclo[12.3.1.0$^{2,6}$]octadeca-1(18),2(6),4,14,16-pentaen-8-one;
- (9R,13S)-13-[4-(3-chloro-2,6-difluorophenyl)-6-oxo-1,6-dihydropyrimidin-1-yl]-16-fluoro-3,9-dimethyl-3,4,7-triazatricyclo[12.3.1.0$^{2,6}$]octadeca-1(18),2(6),4,14,16-pentaen-8-one;
- (9R,13S)-13-{4-[3-chloro-2-fluoro-6-(1H-1,2,3-triazol-1-yl)phenyl]-6-oxo-1,6-dihydropyrimidin-1-yl}-3,9-dimethyl-3,4,7-triazatricyclo[12.3.1.0$^{2,6}$]octadeca-1(18),2(6),4,14,16-pentaen-8-one;
- (9R,13S)-13-{4-[5-chloro-2-(4-chloro-1H-1,2,3-triazol-1-yl)phenyl]-6-oxo-1,6-dihydropyrimidin-1-yl}-3,9-dimethyl-3,4,7-triazatricyclo[12.3.1.0$^{2,6}$]octadeca-1(18),2(6),4,14,16-pentaen-8-one;
- (9R)-13-{4-[3-chloro-2-fluoro-6-(1H-1,2,3-triazol-1-yl)phenyl]-6-oxo-1,6-dihydropyrimidin-1-yl}-3,9-dimethyl-3,4,7-triazatricyclo[12.3.1.0$^{2,6}$]octadeca-1(18),2(6),4,14,16-pentaen-8-one;
- (9R,13S)-13-{4-[5-chloro-2-(4-chloro-1H-1,2,3-triazol-1-yl)phenyl]-6-oxo-1,6-dihydropyrimidin-1-yl}-3-($^2H_3$)methyl-9-methyl-3,4,7-triazatricyclo[12.3.1.0$^{2,6}$]octadeca-1(18),2(6),4,14,16-pentaen-8-one;
- (10R,14S)-14-{4-[3-chloro-6-(4-chloro-1H-1,2,3-triazol-1-yl)-2-fluorophenyl]-6-oxo-1,6-dihydropyrimidin-1-yl}-10-methyl-3,8-diazatricyclo[13.3.1.0$^{2,7}$]nonadeca-1(19),2(7),3,5,15,17-hexaen-9-one trifluoroacetate;
- 1-(4-chloro-2-{1-[(9R,13S)-3-(difluoromethyl)-9-methyl-8-oxo-3,4,7-triazatricyclo[12.3.1.0$^{2,6}$]octadeca-1(18),2(6),4,14,16-pentaen-13-yl]-6-oxo-1,6-dihydropyrimidin-4-yl}-3-fluorophenyl)-1H-1,2,3-triazole-4-carbonitrile;
- (9R,13S)-13-(4-{5-chloro-2-[4-(difluoromethyl)-1H-1,2,3-triazol-1-yl]phenyl}-6-oxo-1,6-dihydropyrimidin-1-yl)-3-(difluoromethyl)-9-methyl-3,4,7-triazatricyclo[12.3.1.0$^{2,6}$]octadeca-1(18),2(6),4,14,16-pentaen-8-one;
- (9R,13S)-13-(4-{5-chloro-2-[4-(difluoromethyl)-1H-1,2,3-triazol-1-yl]phenyl}-6-oxo-1,6-dihydropyrimidin-1-yl)-

3-($^2$H$_3$)methyl-9-methyl-3,4,7-triazatricyclo[12.3.1.0$^{2,6}$]
octadeca-1(18),2(6),4,14,16-pentaen-8-one;
1-(4-chloro-3-fluoro-2-{1-[(9R,13S)-3-($^2$H$_3$)methyl-9-
methyl-8-oxo-3,4,7-triazatricyclo[12.3.1.0$^{2,6}$]octadeca-1
(18),2(6),4,14,16-pentaen-13-yl]-6-oxo-1,6-dihydropy-
rimidin-4-yl}phenyl)-1H-1,2,3-triazole-4-carbonitrile;
1-(4-chloro-2-{1-[(9R,13S)-3-(difluoromethyl)-9-methyl-8-
oxo-3,4,7-triazatricyclo[12.3.1.0$^{2,6}$]octadeca-1(18),2(6),
4,14,16-pentaen-13-yl]-6-oxo-1,6-dihydropyrimidin-4-
yl}phenyl)-1H-1,2,3-triazole-4-carbonitrile;
(9R,13S)-13-(4-{5-chloro-2-[4-(trifluoromethyl)-1H-1,2,3-
triazol-1-yl]phenyl}-6-oxo-1,6-dihydropyrimidin-1-yl)-
3-(difluoromethyl)-9-methyl-3,4,7-triazatricyclo
[12.3.1.0$^{2,6}$]octadeca-1(18),2(6),4,14,16-pentaen-8-one;
(10R,14S)-14-(4-{5-chloro-2-[4-(trifluoromethyl)-1H-1,2,
3-triazol-1-yl]phenyl}-6-oxo-1,6-dihydropyrimidin-1-
yl)-10-methyl-3,8-diazatricyclo[13.3.1.0$^{2,7}$]nonadeca-1
(19),2(7),3,5,15,17-hexaen-9-one;
(9R,13S)-13-{4-[5-chloro-2-(4-chloro-1H-1,2,3-triazol-1-
yl)phenyl]-6-oxo-1,6-dihydropyrimidin-1-yl}-3,9-dim-
ethyl-3,4,7,17-tetraazatricyclo[12.3.1.0$^{2,6}$]octadeca-1
(18),2(6),4,14,16-pentaen-8-one;
(9R,13S)-13-{4-[2-(4-bromo-1H-1,2,3-triazol-1-yl)-5-chlo-
rophenyl]-6-oxo-1,6-dihydropyrimidin-1-yl}-3-($^2$H$_3$)
methyl-9-methyl-3,4,7-triazatricyclo[12.3.1.0$^{2,6}$]octa-
deca-1(18),2(6),4,14,16-pentaen-8-one;
(9R,13S)-13-(4-{5-chloro-2-[4-(pyrimidin-2-yl)-1H-1,2,3-
triazol-1-yl]phenyl}-6-oxo-1,6-dihydropyrimidin-1-yl)-
3-($^2$H$_3$)methyl-9-methyl-3,4,7-triazatricyclo[12.3.1.0$^{2,6}$]
octadeca-1(18),2(6),4,14,16-pentaen-8-one;
(10R,14S)-14-(4-{5-chloro-2-[4-(trifluoromethyl)-1H-1,2,
3-triazol-1-yl]phenyl}-6-oxo-1,6-dihydropyrimidin-1-
yl)-4,10-dimethyl-3,8-diazatricyclo[13.3.1.0$^{2,7}$]nona-
deca-1(19),2(7),3,5,15,17-hexaen-9-one;
(10R,14S)-14-(4-{5-chloro-2-[4-(trifluoromethyl)-1H-1,2,
3-triazol-1-yl]phenyl}-6-oxo-1,6-dihydropyrimidin-1-
yl)-5-methoxy-10-methyl-3,8-diazatricyclo[13.3.1.0$^{2,7}$]
nonadeca-1(19),2(7),3,5,15,17-hexaen-9-one;
(10R,14S)-5-chloro-14-(4-{5-chloro-2-[4-(trifluoromethyl)-
1H-1,2,3-triazol-1-yl]phenyl}-6-oxo-1,6-dihydropyrimi-
din-1-yl)-10-methyl-3,8-diazatricyclo[13.3.1.0$^{2,7}$]nona-
deca-1(19),2(7),3,5,15,17-hexaen-9-one;
(9R,13S)-13-{4-[5-chloro-2-(4-chloro-1H-1,2,3-triazol-1-
yl)phenyl]-6-oxo-1,6-dihydropyrimidin-1-yl}-3,9-dim-
ethyl-3,4,7,16-tetraazatricyclo[12.3.1.0$^{2,6}$]octadeca-1
(18),2(6),4,14,16-pentaen-8-one;
(9R,13S)-13-{4-[5-chloro-2-(4-chloro-1H-1,2,3-triazol-1-
yl)phenyl]-6-oxo-1,6-dihydropyrimidin-1-yl}-3-(difluo-
romethyl)-9-methyl-8-oxo-3,4,7-triazatricyclo[12.3.1.
0$^{2,6}$]octadeca-1(18),2(6),4,14,16-pentaene-16-carboxam-
ide;
1-(4-chloro-2-{1-[(9R,13S)-3-($^2$H$_3$)methyl-9-methyl-8-
oxo-3,4,7-triazatricyclo[12.3.1.0$^{2,6}$]octadeca-1(18),2(6),
4,14,16-pentaen-13-yl]-6-oxo-1,6-dihydropyrimidin-4-
yl}phenyl)-1H-1,2,3-triazole-4-carboxamide;
(9R,13S)-13-{4-[3-chloro-6-(4-chloro-1H-1,2,3-triazol-1-
yl)-2-fluorophenyl]-6-oxo-1,6-dihydropyrimidin-1-yl}-9-
methyl-3,4,7-triazatricyclo[12.3.1.0$^{2,6}$]octadeca-1(18),2
(6),4,14,16-pentaen-8-one;
(9R,13S)-13-{4-[3-chloro-2-fluoro-6-(1H-1,2,3-triazol-1-
yl)phenyl]-6-oxo-1,6-dihydropyrimidin-1-yl}-3-(difluo-
romethyl)-9-methyl-3,4,7,15-tetraazatricyclo[12.3.1.0$^{2,6}$]
octadeca-1(18),2(6),4,14,16-pentaen-8-one
trifluoroacetate;
(9R,13S)-13-{4-[5-chloro-2-(4-chloro-1H-1,2,3-triazol-1-
yl)phenyl]-6-oxo-1,6-dihydropyrimidin-1-yl}-3-(difluoromethyl)-9-methyl-3,4,7,15-tetraazatricyclo[12.3.1.0$^{2,6}$]
octadeca-1(18),2(6),4,14,16-pentaen-8-one
trifluoroacetate;
(9R,13S)-13-{4-[3-chloro-6-(4-chloro-1H-1,2,3-triazol-1-
yl)-2-fluorophenyl]-6-oxo-1,6-dihydropyrimidin-1-yl}-3-
(difluoromethyl)-9-methyl-3,4,7,15-tetraazatricyclo
[12.3.1.0$^{2,6}$]octadeca-1(18),2(6),4,14,16-pentaen-8-one;
trifluoroacetate;
(9R,13S)-13-{4-[3-chloro-6-(4-chloro-1H-1,2,3-triazol-1-
yl)-2-fluorophenyl]-6-oxo-1,6-dihydropyrimidin-1-yl}-3-
(2-hydroxyethyl)-9-methyl-3,4,7,15-tetraazatricyclo
[12.3.1.0$^{2,6}$]octadeca-1(18),2(6),4,14,16-pentaen-8-one
trifluoroacetate;
(9R,13S)-13-(4-{5-chloro-2-[4-(difluoromethyl)-1H-1,2,3-
triazol-1-yl]phenyl}-6-oxo-1,6-dihydropyrimidin-1-yl)-
3-(2-hydroxy ethyl)-9-methyl-3,4,7,15-tetraazatricyclo
[12.3.1.0$^{2,6}$]octadeca-1(18),2(6),4,14,16-pentaen-8-one
trifluoroacetate;
(9R,13S)-13-{4-[5-chloro-2-(4-chloro-1H-1,2,3-triazol-1-
yl)phenyl]-6-oxo-1,6-dihydropyrimidin-1-yl}-3-(2-hy-
droxyethyl)-9-methyl-3,4,7,15-tetraazatricyclo[12.3.
1.0$^{2,6}$]octadeca-1(18),2(6),4,14,16-pentaen-8-one trifluo-
roacetate;
(9R,13S)-13-{4-[5-chloro-2-(1H-1,2,3,4-tetrazol-1-yl)phe-
nyl]-6-oxo-1,6-dihydropyrimidin-1-yl}-3-(2-hydroxy-
ethyl)-9-methyl-3,4,7,15-tetraazatricyclo[12.3.1.0$^{2,6}$]oc-
tadeca-1(18),2(6),4,14,16-pentaen-8-one trifluoroacetate;
(9R,13S)-13-(4-{5-chloro-2-[4-(trifluoromethyl)-1H-1,2,3-
triazol-1-yl]phenyl}-6-oxo-1,6-dihydropyrimidin-1-yl)-
3-(2-hydroxy ethyl)-9-methyl-3,4,7,15-tetraazatricyclo
[12.3.1.0$^{2,6}$]octadeca-1(18),2(6),4,14,16-pentaen-8-one
trifluoroacetate;
2-[(9R,13S)-13-{4-[3-chloro-6-(4-chloro-1H-1,2,3-triazol-
1-yl)-2-fluorophenyl]-6-oxo-1,6-dihydropyrimidin-1-yl}-
9-methyl-8-oxo-3,4,7,15-tetraazatricyclo[12.3.1.0$^{2,6}$]oc-
tadeca-1(18),2(6),4,14,16-pentaen-3-yl]acetic acid
trifluoroacetate;
2-[(9R,13S)-13-(4-{5-chloro-2-[4-(difluoromethyl)-1H-1,2,
3-triazol-1-yl]phenyl}-6-oxo-1,6-dihydropyrimidin-1-
yl)-9-methyl-8-oxo-3,4,7,15-tetraazatricyclo[12.3.1.0$^{2,6}$]
octadeca-1(18),2(6),4,14,16-pentaen-3-yl]acetic acid
trifluoroacetate;
2-[(9R,13S)-13-{4-[5-chloro-2-(4-chloro-1H-1,2,3-triazol-
1-yl)phenyl]-6-oxo-1,6-dihydropyrimidin-1-yl}-9-
methyl-8-oxo-3,4,7,15-tetraazatricyclo[12.3.1.0$^{2,6}$]octa-
deca-1(18),2(6),4,14,16-pentaen-3-yl]acetic acid
trifluoroacetate;
2-[(9R,13S)-13-{4-[5-chloro-2-(1H-1,2,3,4-tetrazol-1-yl)
phenyl]-6-oxo-1,6-dihydropyrimidin-1-yl}-9-methyl-8-
oxo-3,4,7,15-tetraazatricyclo[12.3.1.0$^{2,6}$]octadeca-1(18),
2(6),4,14,16-pentaen-3-yl]acetic acid trifluoroacetate;
2-[(9R,13S)-13-(4-{5-chloro-2-[4-(trifluoromethyl)-1H-1,2,
3-triazol-1-yl]phenyl}-6-oxo-1,6-dihydropyrimidin-1-
yl)-9-methyl-8-oxo-3,4,7,15-tetraazatricyclo[12.3.1.0$^{2,6}$]
octadeca-1(18),2(6),4,14,16-pentaen-3-yl]acetic acid
trifluoroacetate;
(9R,13S)-13-{4-[3-chloro-6-(4-chloro-1H-1,2,3-triazol-1-
yl)-2-fluorophenyl]-6-oxo-1,6-dihydropyrimidin-1-yl}-9-
methyl-3,4,7,15-tetraazatricyclo[12.3.1.0$^{2,6}$]octadeca-1
(18),2(6),4,14,16-pentaen-8-one trifluoroacetate;
(9R,13S)-13-{4-[5-chloro-2-(4-chloro-1H-1,2,3-triazol-1-
yl)phenyl]-6-oxo-1,6-dihydropyrimidin-1-yl}-9-methyl-
3,4,7,15-tetraazatricyclo[12.3.1.0$^{2,6}$]octadeca-1(18),2(6),
4,14,16-pentaen-8-one trifluoroacetate;
methyl (9R,13S)-13-{4-[5-chloro-2-(4-chloro-1H-1,2,3-tri-
azol-1-yl)phenyl]-6-oxo-1,6-dihydropyrimidin-1-yl}-9- methyl-8-oxo-2,3,7,15-tetraazatricyclo[12.3.1.0$^{2,6}$]octadeca-1(18),3,5,14,16-pentaene-4-carboxylate trifluoroacetate;

methyl (9R,13S)-13-(4-{5-chloro-2-[4-(difluoromethyl)-1H-1,2,3-triazol-1-yl]phenyl}-6-oxo-1,6-dihydropyrimidin-1-yl)-9-methyl-8-oxo-2,3,7,15-tetraazatricyclo[12.3.1.0$^{2,6}$]octadeca-1(18),3,5,14,16-pentaene-4-carboxylate trifluoroacetate;

(9R,13S)-13-{4-[5-chloro-2-(4-chloro-1H-1,2,3-triazol-1-yl)phenyl]-6-oxo-1,6-dihydropyrimidin-1-yl}-9-methyl-8-oxo-2,3,7,15-tetraazatricyclo[12.3.1.0$^{2,6}$]octadeca-1(18),3,5,14,16-pentaene-4-carboxylic acid trifluoroacetate;

(9R,13S)-13-(4-{5-chloro-2-[4-(difluoromethyl)-1H-1,2,3-triazol-1-yl]phenyl}-6-oxo-1,6-dihydropyrimidin-1-yl)-9-methyl-8-oxo-2,3,7,15-tetraazatricyclo[12.3.1.0$^{2,6}$]octadeca-1(18),3,5,14,16-pentaene-4-carboxylic acid trifluoroacetate;

(9R,13S)-13-{4-[5-chloro-2-(4-chloro-1H-1,2,3-triazol-1-yl)phenyl]-6-oxo-1,6-dihydropyrimidin-1-yl}-3-($^{2}H_{3}$)methyl-9-methyl-3,4,7,15-tetraazatricyclo[12.3.1.0$^{2,6}$]octadeca-1(18),2(6),4,14,16-pentaen-8-one trifluoroacetate;

(9R,13S)-13-{4-[3-chloro-6-(4-chloro-1H-1,2,3-triazol-1-yl)-2-fluorophenyl]-6-oxo-1,6-dihydropyrimidin-1-yl}-3-($^{2}H_{3}$)methyl-9-methyl-3,4,7,15-tetraazatricyclo[12.3.1.0$^{2,6}$]octadeca-1(18),2(6),4,14,16-pentaen-8-one trifluoroacetate;

(9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7-triazatricyclo[12.3.1.0$^{2,6}$]octadeca-1(18),2(6),4,14,16-pentaen-8-one;

(9R,13S)-13-{4-[3-chloro-6-(4-chloro-1H-1,2,3-triazol-1-yl)-2-fluorophenyl]-6-oxo-1,6-dihydropyrimidin-1-yl}-3-(difluoromethyl)-9-methyl-3,4,7-triazatricyclo[12.3.1.0$^{2,6}$]octadeca-1(18),2(6),4,14,16-pentaen-8-one;

(9R,13S)-13-{4-[3-chloro-6-(4-chloro-1H-1,2,3-triazol-1-yl)-2-fluorophenyl]-6-oxo-1,6-dihydropyrimidin-1-yl}-3,9-dimethyl(10,11-$^{2}H_{2}$)-3,4,7,15-tetraazatricyclo[12.3.1.0$^{2,6}$]octadeca-1(18),2(6),4,14,16-pentaen-8-one trifluoroacetate;

(9R,13S)-13-{4-[3-chloro-6-(4-chloro-1H-1,2,3-triazol-1-yl)-2-fluorophenyl]-6-oxo-1,6-dihydropyrimidin-1-yl}-3-($^{2}H_{3}$)methyl-9-methyl(10,11-$^{2}H_{2}$)-3,4,7,15-tetraazatricyclo[12.3.1.0$^{2,6}$]octadeca-1(18),2(6),4,14,16-pentaen-8-one trifluoroacetate;

(9R,13S)-13-{4-[3-chloro-6-(4-chloro-1H-1,2,3-triazol-1-yl)-2-fluorophenyl]-6-oxo-1,6-dihydropyrimidin-1-yl}-3-(difluoromethyl)-9-methyl(10,11-$^{2}H_{2}$)-3,4,7,15-tetraazatricyclo[12.3.1.0$^{2,6}$]octadeca-1(18),2(6),4,14,16-pentaen-8-one trifluoroacetate;

(9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl(10,11-$^{2}H_{2}$)-3,4,7,15-tetraazatricyclo[12.3.1.0$^{2,6}$]octadeca-1(18),2(6),4,14,16-pentaen-8-one trifluoroacetate;

(10R,14S)-14-{4-[5-chloro-2-(4-chloro-1H-1,2,3-triazol-1-yl)phenyl]-6-oxo-1,6-dihydropyrimidin-1-yl}-10-methyl-3,8,16-triazatricyclo[13.3.1.0$^{2,7}$]nonadeca-1(19),2(7),3,5,15,17-hexaen-9-one, bis-trifluoroacetate;

(9R,13S)-13-[4-(5-chloro-1-methyl-1H-indazol-7-yl)-6-oxo-1,6-dihydropyrimidin-1-yl]-3-($^{2}H_{3}$)methyl-9-methyl-3,4,7,15-tetraazatricyclo[12.3.1.0$^{2,6}$]octadeca-1(18),2(6),4,14,16-pentaen-8-one trifluoroacetate;

(9R,13S)-13-{4-[5-chloro-2-(1H-1,2,3-triazol-1-yl)phenyl]-6-oxo-1,6-dihydropyrimidin-1-yl}-3-(difluoromethyl)-9-methyl-3,4,7-triazatricyclo[12.3.1.0$^{2,6}$]octadeca-1(18),2(6),4,14,16-pentaen-8-one;

(9R,13S)-13-[4-(5-chloro-1-methyl-1H-indazol-7-yl)-6-oxo-1,6-dihydropyrimidin-1-yl]-3-(difluoromethyl)-9-methyl-3,4,7-triazatricyclo[12.3.1.0$^{2,6}$]octadeca-1(18),2(6),4,14,16-pentaen-8-one;

(10R,14S)-14-{4-[3-chloro-6-(4-chloro-1H-1,2,3-triazol-1-yl)-2-fluorophenyl]-6-oxo-1,6-dihydropyrimidin-1-yl}-10-methyl-3,8,16-triazatricyclo[13.3.1.0$^{2,7}$]nonadeca-1(19),2(7),3,5,15,17-hexaen-9-one bis-trifluoroacetate;

(9R,13S)-3-(difluoromethyl)-9-methyl-13-(4-{5-methyl-2-[4-(trifluoromethyl)-1H-1,2,3-triazol-1-yl]phenyl}-6-oxo-1,6-dihydropyrimidin-1-yl)-3,4,7,17-tetraazatricyclo[12.3.1.0$^{2,6}$]octadeca-1(18),2(6),4,14,16-pentaen-8-one;

(9R,13S)-13-{4-[5-chloro-2-(1H-1,2,3-triazol-1-yl)phenyl]-6-oxo-5-(trifluoromethyl)-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-3,8,16-triazatricyclo[13.3.1.0$^{2,7}$]nonadeca-1(19),2(7),3,5,15,17-hexaen-9-one, bis-trifluoroacetate;

(9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7,16-tetraazatricyclo[12.3.1.0$^{2,6}$]octadeca-1(18),2(6),4,14,16-pentaen-8-one;

6-[3-chloro-6-(4-chloro-1H-1,2,3-triazol-1-yl)-2-fluorophenyl]-3-[(9R,13S)-3,9-dimethyl-3,4,7,15-tetraazatricyclo[12.3.1.0$^{2,6}$]octadeca-1(18),2(6),4,14,16-pentaen-13-yl]-3,4-dihydropyrimidin-4-one;

(9S,13S)-13-{4-[5-chloro-2-(4-chloro-1H-1,2,3-triazol-1-yl)phenyl]-6-oxo-1,6-dihydropyrimidin-1-yl}-3-(difluoromethyl)-10-fluoro-9-methyl-3,4,7-triazatricyclo[12.3.1.0$^{2,6}$]octadeca-1(18),2(6),4,14,16-pentaen-8-one;

(9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-11-fluoro-9-methyl-3,4,7-triazatricyclo[12.3.1.0$^{2,6}$]octadeca-1(18),2(6),4,14,16-pentaen-8-one;

(9S,13S)-13-{4-[5-chloro-2-(4-chloro-1H-1,2,3-triazol-1-yl)phenyl]-6-oxo-1,6-dihydropyrimidin-1-yl}-10,16-difluoro-3,9-dimethyl-3,4,7-triazatricyclo[12.3.1.0$^{2,6}$]octadeca-1(18),2(6),4,14,16-pentaen-8-one;

(9S,13S)-13-(4-{5-chloro-2-[4-(trifluoromethyl)-1H-1,2,3-triazol-1-yl]phenyl}-6-oxo-1,6-dihydropyrimidin-1-yl)-10,16-difluoro-3,9-dimethyl-3,4,7-triazatricyclo[12.3.1.0$^{2,6}$]octadeca-1(18),2(6),4,14,16-pentaen-8-one;

(9R,13S)-13-{4-[5-chloro-2-(4-cyclopropyl-1H-1,2,3-triazol-1-yl)phenyl]-6-oxo-1,6-dihydropyrimidin-1-yl}-3-($Â^{2}Hâ,f$)methyl-9-methyl-3,4,7-triazatricyclo[12.3.1.0$^{2,6}$]octadeca-1(18),2(6),4,14,16-pentaen-8-one;

6-[3-chloro-6-(4-chloro-1H-1,2,3-triazol-1-yl)-2-fluorophenyl]-3-[(9R,13S)-3-(difluoromethyl)-9-methyl-3,4,7,15-tetraazatricyclo[12.3.1.0$^{2,6}$]octadeca-1(18),2(6),4,14,16-pentaen-13-yl]-3,4-dihydropyrimidin-4-one;

(9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-8-oxo-3,4,7-triazatricyclo[12.3.1.0$^{2,6}$]octadeca-1(18),2(6),4,14,16-pentaene-16-carbonitrile;

(9R,13S)-13-(4-{5-chloro-2-[4-(trimethylsilyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate;

(9R,13S)-13-[4-(3-chloro-2,6-difluorophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one trifluoroacetate;

(9R,13S)-13-{4-[5-chloro-2-(1H-1,2,3-triazol-1-yl)phenyl]-6-oxo-1,6-dihydropyrimidin-1-yl}-3,9-dimethyl-3,4,7, 15-tetraazatricyclo[12.3.1.0²,⁶]octadeca-1(18),2(6),4,14,16-pentaen-8-one trifluoroacetate;

(13S)-13-{4-[5-chloro-2-(4-chloro-1H-1,2,3-triazol-1-yl)phenyl]-6-oxo-1,6-dihydropyrimidin-1-yl}-3-(difluoromethyl)-3,4,7,15-tetraazatricyclo[12.3.1.0²,⁶]octadeca-1(18),2(6),4,14,16-pentaen-8-one trifluoroacetate;

(9S,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0²,⁶]octadeca-1(18),2(6),4,14,16-pentaen-8-one;

(9R,13S)-13-{4-[5-chloro-2-(4-methyl-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0²,⁶]octadeca-1(18),2(6),4,14,16-pentaen-8-one trifluoroacetate;

(9R,13S)-3-(difluoromethyl)-9-methyl-13-(4-{5-methyl-2-[4-(trifluoromethyl)-1H-1,2,3-triazol-1-yl]phenyl}-6-oxo-1,6-dihydropyrimidin-1-yl)-3,4,7,15-tetraazatricyclo[12.3.1.0²,⁶]octadeca-1(18),2(6),4,14,16-pentaen-8-one;

(9R,13S)-13-[4-(2-bromo-5-chlorophenyl)-6-oxo-1,6-dihydropyrimidin-1-yl]-3,9-dimethyl-3,4,7,15-tetraazatricyclo[12.3.1.0²,⁶]octadeca-1(18),2(6),4,14,16-pentaen-8-one;

(9R,13S)-13-{4-[3-chloro-2-fluoro-6-(4-methyl-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0²,⁶]octadeca-1(18),2(6),4,14,16-pentaen-8-one;

(9R,13S)-13-(4-{5-chloro-2-[1-(difluoromethyl)-1H-pyrazol-4-yl]phenyl}-6-oxo-1,6-dihydropyrimidin-1-yl)-3,9-dimethyl-3,4,7,15-tetraazatricyclo[12.3.1.0²,⁶]octadeca-1(18),2(6),4,14,16-pentaen-8-one;

(9R,13S)-13-[4-(3-fluoro-4-methylpyridin-2-yl)-6-oxo-1,6-dihydropyrimidin-1-yl]-3,9-dimethyl-3,4,7,15-tetraazatricyclo[12.3.1.0²,⁶]octadeca-1(18),2(6),4,14,16-pentaen-8-one;

(9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7,17-tetraazatricyclo[12.3.1.0²,⁶]octadeca-1(18),2(6),4,14,16-pentaen-8-one;

(9R,13S)-13-{4-[5-chloro-2-(4-chloro-1H-1,2,3-triazol-1-yl)phenyl]-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one trifluoroacetate;

(9R,13S)-13-{4-[3-chloro-6-(4-chloro-1H-1,2,3-triazol-1-yl)-2-fluorophenyl]-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one trifluoroacetate;

(9R,13S)-13-{4-[2-(4-bromo-1H-1,2,3-triazol-1-yl)-5-chlorophenyl]-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one trifluoroacetate;

1-(4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)-1H-1,2,3-triazole-4-carboxamide trifluoroacetate;

1-(4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)-1H-1,2,3-triazole-4-carbonitrile trifluoroacetate;

(10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-9-oxo-3,8-diazatricyclo[13.3.1.0²,⁷]nonadeca-1(19),2(7),3,5,15,17-hexaene-5-carbonitrile;

(9R,13S)-13-(4-{5-chloro-2-[4-({3H-[1,2,3]triazolo[4,5-b]pyridin-3-yloxy}methyl)-1H-1,2,3-triazol-1-yl]phenyl}-

6-oxo-1,6-dihydropyrimidin-1-yl)-3,9-dimethyl-3,4,7,15-tetraazatricyclo[12.3.1.0²,⁶]octadeca-1(18),2(6),4,14,16-pentaen-8-one trifluoroacetate;

(9R,13S)-13-(4-{5-chloro-2-[4-(hydroxylmethyl)-1H-1,2,3-triazol-1-yl]phenyl}-6-oxo-1,6-dihydropyrimidin-1-yl)-3,9-dimethyl-3,4,7,15-tetraazatricyclo[12.3.1.0²,⁶]octadeca-1(18),2(6),4,14,16-pentaen-8-one trifluoroacetate;

(9R,13S)-13-(4-{5-chloro-2-[4-(difluoromethyl)-1H-1,2,3-triazol-1-yl]phenyl}-6-oxo-1,6-dihydropyrimidin-1-yl)-3,9-dimethyl-3,4,7,15-tetraazatricyclo[12.3.1.0²,⁶]octadeca-1(18),2(6),4,14,16-pentaen-8-one trifluoroacetate;

(9R,13S)-13-(4-{5-chloro-2-[4-(trifluoromethyl)-1H-pyrazol-1-yl]phenyl}-6-oxo-1,6-dihydropyrimidin-1-yl)-3,9-dimethyl-3,4,7,15-tetraazatricyclo[12.3.1.0²,⁶]octadeca-1(18),2(6),4,14,16-pentaen-8-one trifluoroacetate;

(9R,13S)-13-(4-{5-chloro-2-[4-(fluoromethyl)-1H-1,2,3-triazol-1-yl]phenyl}-6-oxo-1,6-dihydropyrimidin-1-yl)-3,9-dimethyl-3,4,7,15-tetraazatricyclo[12.3.1.0²,⁶]octadeca-1(18),2(6),4,14,16-pentaen-8-one trifluoroacetate;

1-(4-chloro-2-{1-[(9R,13S)-3-(difluoromethyl)-9-methyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)-1H-1,2,3-triazole-4-carbonitrile trifluoroacetate;

(9R,13S)-13-(4-{5-chloro-2-[4-(trifluoromethyl)-1H-1,2,3-triazol-1-yl]phenyl}-6-oxo-1,6-dihydropyrimidin-1-yl)-3-(²H₃)methyl-9-methyl-3,4,7,15-tetraazatricyclo[12.3.1.0²,⁶]octadeca-1(18),2(6),4,14,16-pentaen-8-one trifluoroacetate;

(9R,13S)-13-(4-{5-chloro-2-[4-(difluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0²,⁶]octadeca-1(18),2(6),4,14,16-pentaen-8-one trifluoroacetate;

(9R,13S)-13-(4-{5-chloro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0²,⁶]octadeca-1(18),2(6),4,14,16-pentaen-8-one trifluoroacetate;

(9R,13S)-13-(4-{5-chloro-2-[4-(trifluoromethyl)-1H-1,2,3-triazol-1-yl]phenyl}-6-oxo-1,6-dihydropyrimidin-1-yl)-3-(²H₃)methyl-9-methyl-3,4,7-triazatricyclo[12.3.1.0²,⁶]octadeca-1(18),2(6),4,14,16-pentaen-8-one trifluoroacetate;

(9S,13R)-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0²,⁶]octadeca-1(18),2(6),4,14,16-pentaen-8-one;

(9R,13R)-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0²,⁶]octadeca-1(18),2(6),4,14,16-pentaen-8-one;

(9R,13S)-13-{4-[5-chloro-2-(pyridin-3-yl)phenyl]-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one;

(9R,13S)-13-(4-{5-chloro-2-[4-(2-hydroxypropan-2-yl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0²,⁶]octadeca-1(18),2(6),4,14,16-pentaen-8-one;

(9R,13S)-3-(difluoromethyl)-9-methyl-13-(6-oxo-4-{2-[4-(trifluoromethyl)-1H-1,2,3-triazol-1-yl]phenyl}-1,6-dihydropyrimidin-1-yl)-3,4,7,15-tetraazatricyclo[12.3.1.0²,⁶]octadeca-1(18),2(6),4,14,16-pentaen-8-one;

(9R,13S)-3-(difluoromethyl)-13-(4-{5-fluoro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0$^{2,6}$]octadeca-1(18),2(6),4,14,16-pentaen-8-one;

(9R,13S)-13-{4-[5-chloro-2-(4-hydroxy-1H-1,2,3-triazol-1-yl)phenyl]-6-oxo-1,6-ihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate;

5-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)pyridine-3-carbonitrile;

(9R,13S)-13-{4-[5-chloro-2-(4-cyclopropyl-1H-1,2,3-triazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate;

methyl 4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}benzoate;

(9R,13S)-13-{4-[3-chloro-6-(4-ethoxy-1H-1,2,3-triazol-1-yl)-2-fluorophenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate;

(9R,13S)-13-{4-[3-chloro-6-(4-cyclopropyl-1H-1,2,3-triazol-1-yl)-2-fluorophenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate;

(9R,13S)-13-{4-[3-chloro-2-fluoro-6-(trifluoromethyl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate;

(9R,13S)-13-{4-[3-chloro-6-(4-cyclopropyl-1H-1,2,3-triazol-1-yl)-2-fluorophenyl]-6-oxo-1,6-dihydropyrimidin-1-yl}-3-($^{2}$H$_3$)methyl-9-methyl-3,4,7-triazatricyclo[12.3.1.0$^{2,6}$]octadeca-1(18),2(6),4,14,16-pentaen-8-one;

(9R,13S)-13-(4-{3-chloro-2-fluoro-6-[4-(trifluoromethyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate;

1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}-3-fluorophenyl)-1H-1,2,3-triazole-4-carbonitrile trifluoroacetate;

(9R,13S)-13-(4-{3-chloro-2-fluoro-6-[4-(trifluoromethyl)-1H-1,2,3-triazol-1-yl]phenyl}-6-oxo-1,6-dihydropyrimidin-1-yl)-3-($^{2}$H$_3$)methyl-9-methyl-3,4,7,15-tetraazatricyclo[12.3.1.0$^{2,6}$]octadeca-1(18),2(6),4,14,16-pentaen-8-one trifluoroacetate;

1-(4-chloro-2-{1-[(9R,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}-3-fluorophenyl)-1H-1,2,3-triazole-4-carbonitrile trifluoroacetate;

(9R,13S)-13-{4-[3-chloro-6-(4-cyclopropyl-1H-1,2,3-triazol-1-yl)-2-fluorophenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one trifluoroacetate;

(9R,13S)-13-(4-{3-chloro-6-[4-(difluoromethyl)-1H-1,2,3-triazol-1-yl]-2-fluorophenyl}-6-oxo-1,6-dihydropyrimidin-1-yl)-3,9-(difluoromethyl)-9-methyl-3,4,7,15-tetraazatricyclo[12.3.1.0$^{2,6}$]octadeca-1(18),2(6),4,14,16-pentaen-8-one trifluoroacetate;

(9R,13S)-13-(4-{3-chloro-6-[4-(difluoromethyl)-1H-1,2,3-triazol-1-yl]-2-fluorophenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate;

(9R,13S)-13-[4-(3-chlorophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one;

4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}benzoic acid;

(9R,13S)-3-(difluoromethyl)-9-methyl-13-{6-oxo-4-[5-(propan-2-yl)-2-[4-(trifluoromethyl)-1H-1,2,3-triazol-1-yl]phenyl]-1,6-dihydropyrimidin-1-yl}-3,4,7,15-tetraazatricyclo[12.3.1.0$^{2,6}$]octadeca-1(18),2(6),4,14,16-pentaen-8-one;

(9R,13)-13-(4-{5-chloro-2-[4-(trifluoromethyl)-1H-1,2,3-triazol-1-yl]phenyl}-6-oxo-1,6-dihydropyrimidin-1-yl)-3-($^{2}$H$_3$)methyl-9-methyl-3,4,7,17-tetraazatricyclo[12.3.1.0$^{2,6}$]octadeca-1(18),2(6),4,14,16-pentaen-8-one;

(9R,13S)-13-(4-{5-chloro-2-[4-(trifluoromethyl)-1H-1,2,3-triazol-1-yl]phenyl}-6-oxo-1,6-dihydropyrimidin-1-yl)-3-(difluoromethyl)-9-methyl-8-oxo-3,4,7-triazatricyclo[12.3.1.0$^{2,6}$]octadeca-1(18),2(6),4,14,16-pentaene-16-carbonitrile;

(9R,13S)-13-(4-{5-chloro-2-[4-(trifluoromethyl)-1H-1,2,3-triazol-1-yl]phenyl}-6-oxo-1,6-dihydropyrimidin-1-yl)-3,9-dimethyl-3,4,7,17-tetraazatricyclo[12.3.1.0$^{2,6}$]octadeca-1(18),2(6),4,14,16-pentaen-8-one;

(9S,13S)-13-{4-[5-chloro-2-(4-chloro-1H-1,2,3-triazol-1-yl)phenyl]-6-oxo-1,6-dihydropyrimidin-1-yl}-10-fluoro-3,9-dimethyl-3,4,7,15-tetraazatricyclo[12.3.1.0$^{2,6}$]octadeca-1(18),2(6),4,14,16-pentaen-8-one trifluoroacetate;

(9R,13S)-3-(difluoromethyl)-13-(4-{5-ethyl-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0$^{2,6}$]octadeca-1(18),2(6),4,14,16-pentaen-8-one;

(9S,13S)-13-{4-[3-chloro-6-(4-chloro-1H-1,2,3-triazol-1-yl)-2-fluorophenyl]-6-oxo-1,6-dihydropyrimidin-1-yl}-10-fluoro-3,9-dimethyl-3,4,7,15-tetraazatricyclo[12.3.1.0$^{2,6}$]octadeca-1(18),2(6),4,14,16-pentaen-8-one trifluoroacetate;

(9R,13S)-13-{5-chloro-4-[5-chloro-2-(4-chloro-1H-1,2,3-triazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate;

(9R,13S)-3-(difluoromethyl)-13-(4-{4-fluoro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0$^{2,6}$]octadeca-1(18),2(6),4,14,16-pentaen-8-one;

(9R,13S)-13-{4-[5-chloro-2-(4-chloro-1H-1,2,3-triazol-1-yl)phenyl]-6-oxo-1,6-dihydropyrimidin-1-yl}-3-($^{2}$H$_3$)methyl-9-methyl-3,4,7,17-tetraazatricyclo[12.3.1.0$^{2,6}$]octadeca-1(18),2(6),4,14,16-pentaen-8-one;

(9R,13S)-13-[4-(3-chloro-2,6-difluorophenyl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one;

(9R,13S)-13-[4-(5-chloro-2-phenylphenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one;

(9R,13S)-13-(4-{5-chloro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,16-tetraazatricyclo[12.3.1.0$^{2,6}$]octadeca-1(18),2(6),4,14,16-pentaen-8-one;

(9R,13S)-13-[4-(5-chloro-1-ethyl-1H-indazol-7-yl)-6-oxo-1,6-dihydropyrimidin-1-yl]-3-(difluoromethyl)-9- methyl-3,4,7,15-tetraazatricyclo[12.3.1.0$^{2,6}$]octadeca-1(18),2(6),4,14,16-pentaen-8-one;

(9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0$^{2,6}$]octadeca-1(18),2(6),4,14,16-pentaen-8-one;

(9R,13S)-13-{4-[3-chloro-2-fluoro-6-(1H-1,2,3,4-tetrazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate;

(9R,13S)-13-{4-[3-chloro-2-fluoro-6-(1H-1,2,3,4-tetrazol-1-yl)phenyl]-6-oxo-1,6-dihydropyrimidin-1-yl}-3-(difluoromethyl)-9-methyl-3,4,7-triazatricyclo[12.3.1.0$^{2,6}$]octadeca-1(18),2(6),4,14,16-pentaen-8-one trifluoroacetate;

(9R,13S)-13-{4-[5-chloro-1-(2,2,2-trifluoroethyl)-1H-indazol-7-yl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one;

(9R,13S)-13-{4-[5-chloro-2-(1H-1,2,3,4-tetrazol-1-yl)phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one trifluoroacetate;

(9R,13S)-13-{4-[5-chloro-2-(1H-1,2,3,4-tetrazol-1-yl)phenyl]-6-oxo-1,6-dihydropyrimidin-1-yl}-3-(difluoromethyl)-9-methyl-3,4,7-triazatricyclo[12.3.1.0$^{2,6}$]octadeca-1(18),2(6),4,14,16-pentaen-8-one;

(9R,13S)-13-{4-[5-chloro-2-(4-chloro-1H-1,2,3-triazol-1-yl)phenyl]-5-fluoro-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-{5-bromo-4-[5-chloro-2-(4-chloro-1H-1,2,3-triazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-(4-{5-chloro-3-fluoro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one;

(10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-5,8-diazatricyclo[13.3.1.0$^{2,7}$]nonadeca-1(19),2(7),3,5,15,17-hexaen-9-one;

(10R,14S)-14-{4-[5-chloro-2-(4-chloro-1H-1,2,3-triazol-1-yl)phenyl]-6-oxo-1,6-dihydropyrimidin-1-yl}-10-methyl-5,8-diazatricyclo[13.3.1.0$^{2,7}$]nonadeca-1(19),2(7),3,5,15,17-hexaen-9-one;

(9R,13S)-13-[4-(6-chloro-1H-1,3-benzodiazol-4-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one;

methyl 4-[(9R,13S)-13-{4-[5-chloro-2-(4-chloro-1H-1,2,3-triazol-1-yl)phenyl]-6-oxo-1,6-dihydropyrimidin-1-yl}-9-methyl-8-oxo-3,4,7,15-tetraazatricyclo[12.3.1.0$^{2,6}$]octadeca-1(18),2,5,14,16-pentaen-4-yl]piperidine-1-carboxylate;

(9R,13S)-13-(4-{4-chloro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one;

(9R,13S)-13-{4-[5-chloro-2-(4-chloro-1H-1,2,3-triazol-1-yl)phenyl]-5-methyl-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-[4-(5-chloro-2-iodophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one;

(9R,13S)-13-{4-[3-chloro-2-fluoro-6-(4-phenyl-1H-1,2,3-triazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate;

N-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}-3-fluorophenyl)carbamate trifluoroacetate;

(9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-8-oxo-3,4,7,15-tetraazatricyclo[12.3.1.0$^{2,6}$]octadeca-1(18),2(6),4,14,16-pentaen-15-ium-15-olate;

(9R,13S)-13-(4-{5-chloro-2-[4-(pyridin-3-yl)-1H-1,2,3-triazol-1-yl]phenyl}-6-oxo-1,6-dihydropyrimidin-1-yl)-3-(difluoromethyl)-9-methyl-3,4,7-triazatricyclo[12.3.1.0$^{2,6}$]octadeca-1(18),2(6),4,14,16-pentaen-8-one trifluoroacetate;

(9R,13S)-13-{4-[5-chloro-2-(4-chloro-1H-1,2,3-triazol-1-yl)phenyl]-6-oxo-1,6-dihydropyrimidin-1-yl}-9-methyl-4-(pyridin-3-yl)-3,4,7,15-tetraazatricyclo[12.3.1.0$^{2,6}$]octadeca-1(18),2,5,14,16-pentaen-8-one;

(9R,13S)-13-{4-[5-chloro-2-(4-chloro-1H-1,2,3-triazol-1-yl)phenyl]-6-oxo-1,6-dihydropyrimidin-1-yl}-9-methyl-3-(pyridin-3-yl)-3,4,7,15-tetraazatricyclo[12.3.1.0$^{2,6}$]octadeca-1(18),2(6),4,14,16-pentaen-8-one;

(9R,13S)-13-{4-[5-chloro-2-(4-chloro-1H-1,2,3-triazol-1-yl)phenyl]-6-oxo-1,6-dihydropyrimidin-1-yl}-9-methyl-3-phenyl-3,4,7,15-tetraazatricyclo[12.3.1.0$^{2,6}$]octadeca-1(18),2(6),4,14,16-pentaen-8-one;

(9R,13S)-13-(4-{5-chloro-2-[4-(trifluoromethyl)-1H-1,2,3-triazol-1-yl]pyridin-3-yl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one;

(9R,13S)-13-(5-bromo-4-{5-chloro-2-[4-(trifluoromethyl)-1H-1,2,3-triazol-1-yl]pyridin-3-yl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one;

(9R,13S)-13-(4-{5-chloro-4-fluoro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one;

(9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-3-phenyl-3,4,7,15-tetraazatricyclo[12.3.1.0$^{2,6}$]octadeca-1(18),2(6),4,14,16-pentaen-8-one;

(9R,13S)-13-(4-{4,5-Dichloro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one;

(9R,13S)-13-{4-[5-chloro-2-(4-chloro-1H-1,2,3-triazol-1-yl)phenyl]-6-oxo-1,6-dihydropyrimidin-1-yl}-9-methyl-4-(1-methyl-1H-imidazol-5-yl)-3,4,7,15-tetraazatricyclo[12.3.1.0$^{2,6}$]octadeca-1(18),2,5,14,16-pentaen-8-one;

4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}-N-(2,2,2-trifluoroethyl)benzamide;

(9R,13S)-13-{4-[5-chloro-2-(4-chloro-1H-1,2,3-triazol-1-yl)phenyl]-6-oxo-1,6-dihydropyrimidin-1-yl}-5,9-dimethyl-4,5,7,15-tetraazatricyclo[12.3.1.0$^{2,6}$]octadeca-1 (18),2(6),3,14,16-pentaen-8-one;

(9R,13S)-13-(4-{5-chloro-2-[4-(trifluoromethyl)-1H-1,2,3-triazol-1-yl]phenyl}-6-oxo-1,6-dihydropyrimidin-1-yl)-5,9-dimethyl-4,5,7,15-tetraazatricyclo[12.3.1.0$^{2,6}$]octadeca-1(18),2(6),3,14,16-pentaen-8-one;

(9R,13S)-13-[4-(1-benzyl-5-chloro-1H-indazol-7-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one;

(9R,13S)-13-{4-[5-chloro-2-(1H-1,2,3-triazol-1-yl)phenyl]-5-methyl-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-{4-[5-chloro-2-(1-methyl-1H-pyrazol-3-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-{4-[5-chloro-2-(1H-imidazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-[4-(5-chloro-1H-indazol-7-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one;

(9R,13S)-13-{4-[5-chloro-2-(4-chloro-1H-1,2,3-triazol-1-yl)phenyl]-6-oxo-1,6-dihydropyrimidin-1-yl}-4-(6-methoxypyridin-3-yl)-9-methyl-3,4,7,15-tetraazatricyclo[12.3.1.0$^{2,6}$]octadeca-1(18),2,5,14,16-pentaen-8-one;

(10R,14S)-3-chloro-14-{4-[5-chloro-2-(4-chloro-1H-1,2,3-triazol-1-yl)phenyl]-6-oxo-1,6-dihydropyrimidin-1-yl}-10-methyl-5,8-diazatricyclo[13.3.1.0$^{2,7}$]nonadeca-1(19),2(7),3,5,15,17-hexaen-9-one;

(9R,13S)-13-{4-[5-chloro-2-(1H-pyrazol-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

N-benzyl-4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}benzamide;

(9R,13S)-13-{4-[5-chloro-2-(4-chloro-1H-1,2,3-triazol-1-yl)phenyl]-6-oxo-1,6-dihydropyrimidin-1-yl}-9-methyl-4-(pyridin-2-yl)-3,4,7,15-tetraazatricyclo[12.3.1.0$^{2,6}$]octadeca-1(18),2,5,14,16-pentaen-8-one;

1-(4-chloro-3-fluoro-2-{1-[(9R,13S)-3-($^{2}H_{3}$)methyl-9-methyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-pyrazole-4-carbonitrile;

1-(4-chloro-2-{1-[(9R,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}-3-fluorophenyl)-1H-pyrazole-4-carbonitrile;

(9R,13S)-13-{4-[5-chloro-2-(1-propyl-1H-pyrazol-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-{4-[5-chloro-2-(4-chloro-1H-1,2,3-triazol-1-yl)phenyl]-6-oxo-1,6-dihydropyrimidin-1-yl}-9-methyl-4-(pyridin-4-yl)-3,4,7,15-tetraazatricyclo[12.3.1.0$^{2,6}$]octadeca-1(18),2,5,14,16-pentaen-8-one;

(9R,13S)-13-{4-[5-chloro-2-(4-chloro-1H-1,2,3-triazol-1-yl)phenyl]-6-oxo-1,6-dihydropyrimidin-1-yl}-9-methyl-3-(pyridin-4-yl)-3,4,7,15-tetraazatricyclo[12.3.1.0$^{2,6}$]octadeca-1(18),2(6),4,14,16-pentaen-8-one;

1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-imidazole-4-carbonitrile;

N-(4-chloro-2-{1-[(9R,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-2,2,2-trifluoroacetamide;

(9R,13S)-13-(4-{5-chloro-2-[1-(propan-2-yl)-1H-pyrazol-4-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one;

(9R,13S)-13-{4-[5-(difluoromethoxy)-2-[4-(trifluoromethyl)-1H-1,2,3-triazol-1-yl]phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one;

(9R,13S)-3-(difluoromethyl)-13-(4-{5-methoxy-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0$^{2,6}$]octadeca-1(18),2(6),4,14,16-pentaen-8-one;

(9R,13S)-13-(4-{5-chloro-2-[1-(2-methylpropyl)-1H-pyrazol-4-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one;

(9R,13S)-13-{4-[2-(1-benzyl-1H-pyrazol-4-yl)-5-chlorophenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-{4-[5-chloro-2-(1-methyl-1H-1,2,3-triazol-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(10R,14S)-14-(4-{5-chloro-2-[4-(trifluoromethyl)-1H-1,2,3-triazol-1-yl]phenyl}-6-oxo-1,6-dihydropyrimidin-1-yl)-4-fluoro-10-methyl-5,8,16-triazatricyclo[13.3.1.0$^{2,7}$]nonadeca-1(19),2(7),3,5,15,17-hexaen-9-one;

(9R,13S)-13-(4-{5-chloro-2-[4-(trifluoromethyl)-1H-1,2,3-triazol-1-yl]phenyl}-6-oxo-1,6-dihydropyrimidin-1-yl)-4-(6-methoxypyridin-2-yl)-9-methyl-3,4,7,15-tetraazatricyclo[12.3.1.0$^{2,6}$]octadeca-1(18),2,5,14,16-pentaen-8-one;

(9R,13S)-13-(4-{5-chloro-2-[4-(trifluoromethyl)-1H-1,2,3-triazol-1-yl]phenyl}-6-oxo-1,6-dihydropyrimidin-1-yl)-4-(difluoromethyl)-9-methyl-3,4,7,15-tetraazatricyclo[12.3.1.0$^{2,6}$]octadeca-1(18),2,5,14,16-pentaen-8-one;

(9R,13S)-13-{4-[5-chloro-2-(1-cyclopropyl-1H-pyrazol-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-(4-{5-chloro-2-[1-(2,2,2-trifluoroethyl)-1H-pyrazol-4-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one;

3-[(9R,13S)-13-{4-[5-chloro-2-(4-chloro-1H-1,2,3-triazol-1-yl)phenyl]-6-oxo-1,6-dihydropyrimidin-1-yl}-9-methyl-8-oxo-3,4,7,15-tetraazatricyclo[12.3.1.0$^{2,6}$]octadeca-1(18),2,5,14,16-pentaen-4-yl]benzonitrile;

(9R,13S)-13-{4-[5-chloro-2-(5-methyl-1H-imidazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate;

(9R,13S)-13-{4-[5-chloro-2-(4-chloro-1H-1,2,3-triazol-1-yl)phenyl]-6-oxo-1,6-dihydropyrimidin-1-yl}-9-methyl-4-(1H-pyrazol-3-yl)-3,4,7,15-tetraazatricyclo[12.3.1.0$^{2,6}$]octadeca-1(18),2,5,14,16-pentaen-8-one;

(9R,13S)-13-{4-[5-chloro-2-(4-chloro-1H-1,2,3-triazol-1-yl)phenyl]-6-oxo-1,6-dihydropyrimidin-1-yl}-9-methyl-4-(pyrimidin-5-yl)-3,4,7,15-tetraazatricyclo[12.3.1.0$^{2,6}$]octadeca-1(18),2,5,14,16-pentaen-8-one;

(9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-4-(pyrazin-2-yl)-3,4,7,15-tetraazatricyclo[12.3.1.0$^2$16]octadeca-1(18),2,5,14,16-pentaen-8-one;

(9R,13S)-13-[4-(2-Amino-5-chlorophenyl)-6-oxo-1,6-dihydropyrimidin-1-yl]-3-(difluoromethyl)-9-methyl-3,4,7,15-tetraazatricyclo[12.3.1.0$^2$16]octadeca-1(18),2(6),4,14,16-pentaen-8-one;

(9R,13S)-13-(4-{3-chloro-6-[1-(difluoromethyl)-1H-pyrazol-4-yl]-2-fluorophenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one;

(9R,13S)-13-[4-(5-chloro-1H-indol-7-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one;

(9R,13S)-13-[4-(6-chloro-1H-indazol-4-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one;

(14S)-14-(4-{5-chloro-2-[4-(trifluoromethyl)-1H-1,2,3-triazol-1-yl]phenyl}-6-oxo-1,6-dihydropyrimidin-1-yl)-10-methyl-5,8,16-triazatricyclo[13.3.1.0$^{2,7}$]nonadeca-1(19),2(7),3,5,15,17-hexaen-9-one trifluoroacetate;

(9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-4-(6-oxo-1,6-dihydropyridazin-4-yl)-3,4,7,15-tetraazatricyclo[12.3.1.0$^{2,6}$]octadeca-1(18),2,5,14,16-pentaen-8-one;

(9R,13S)-13-(4-{5-chloro-2-[4-(trifluoromethyl)-1H-1,2,3-triazol-1-yl]phenyl}-6-oxo-1,6-dihydropyrimidin-1-yl)-4-(6-methoxypyrazin-2-yl)-9-methyl-3,4,7,15-tetraazatricyclo[12.3.1.0$^{2,6}$]octadeca-1(18),2,5,14,16-pentaen-8-one;

(9R,13S)-13-(4-{5-chloro-2-[4-(trifluoromethyl)-1H-1,2,3-triazol-1-yl]phenyl}-6-oxo-1,6-dihydropyrimidin-1-yl)-4-(5-fluoro-2-methoxypyridin-4-yl)-9-methyl-3,4,7,15-tetraazatricyclo[12.3.1.0$^{2,6}$]octadeca-1(18),2,5,14,16-pentaen-8-one;

(9R,13S)-13-(4-{5-chloro-2-[4-(trifluoromethyl)-1H-1,2,3-triazol-1-yl]phenyl}-6-oxo-1,6-dihydropyrimidin-1-yl)-3-(difluoromethyl)-9-methyl-8-oxo-3,4,7-triazatricyclo[12.3.1.0$^{2,6}$]octadeca-1(18),2(6),4,14,16-pentaene-17-carbonitrile;

(9R,13S)-13-{4-[5-chloro-2-(4-methyl-1H-imidazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-(4-{5-chloro-2-[4-(trifluoromethyl)-1H-1,2,3-triazol-1-yl]phenyl}-6-oxo-1,6-dihydropyrimidin-1-yl)-4-(5-fluoro-2-hydroxypyridin-4-yl)-9-methyl-3,4,7,15-tetraazatricyclo[12.3.1.0$^{2,6}$]octadeca-1(18),2,5,14,16-pentaen-8-one;

(9R,13S)-13-{4-[5-chloro-2-(1,3-oxazol-2-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-(4-{5-chloro-2-[(pyrazin-2-yl)amino]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one;

(9R,13S)-13-(4-{5-chloro-2-[4-(trifluoromethyl)-1H-1,2,3-triazol-1-yl]phenyl}-6-oxo-1,6-dihydropyrimidin-1-yl)-4-(4-hydroxypyrimidin-5-yl)-9-methyl-3,4,7,15-tetraazatricyclo[12.3.1.0$^{2,6}$]octadeca-1(18),2,5,14,16-pentaen-8-one;

ethyl 1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-3-methyl-1H-pyrazole-4-carboxylate;

(9R,13S)-13-{4-[5-chloro-2-(3,4-dimethyl-1H-pyrazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

ethyl 1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-pyrazole-4-carboxylate;

(9R,13S)-13-[4-(5-chloro-2-hydroxyphenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one;

(9R,13S)-13-(4-{5-chloro-2-[4-(trifluoromethyl)-1H-imidazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one;

(9R,13S)-13-{4-[5-chloro-2-(4-chloro-1H-1,2,3-triazol-1-yl)phenyl]-6-oxo-1,6-dihydropyrimidin-1-yl}-4-methanesulfonyl-9-methyl-3,4,7,15-tetraazatricyclo[12.3.1.0$^{2,6}$]octadeca-1(8),2,5,14,16-pentaen-8-one;

(9R,13S)-13-{4-[5-chloro-2-(4-chloro-1H-1,2,3-triazol-1-yl)phenyl]-6-oxo-1,6-dihydropyrimidin-1-yl}-3-methanesulfonyl-9-methyl-3,4,7,15-tetraazatricyclo[12.3.1.0$^{2,6}$]octadeca-1(8),2(6),4,14,16-pentaen-8-one;

(9R,13S)-13-(4-{2,3-difluoro-6-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one;

methyl 1-(4-chloro-2-{1-[(9R,13S)-3,9-dimethyl-8-oxo-3,4,7,15-tetraazatricyclo[12.3.1.0$^{2,6}$]octadeca-1(8),2(6),4,14,16-pentaen-13-yl]-6-oxo-1,6-dihydropyrimidin-4-yl}phenyl)-1H-imidazole-4-carboxylate;

(9R,13S)-13-[4-(2,5-dichlorophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one;

(9R,13R)-13-{4-[5-chloro-2-(4-chloro-1H-1,2,3-triazol-1-yl)phenyl]-6-oxo-1,6-dihydropyrimidin-1-yl}-3,9-dimethyl-3,4,7,18-tetraazatricyclo[12.3.1.0$^{2,6}$]octadeca-1(18),2(6),4,14,16-pentaen-8-one trifluoroacetate;

(9R,13S)-13-(4-{2,3-difluoro-6-[4-(trifluoromethyl)-1H-1,2,3-triazol-1-yl]phenyl}-6-oxo-1,6-dihydropyrimidin-1-yl)-3-($^2$H$_3$)methyl-9-methyl-3,4,7,17-tetraazatricyclo[12.3.1.0$^{2,6}$]octadeca-1(18),2(6),4,14,16-pentaen-8-one;

1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-imidazole-4-carboxylic acid;

(9R,13S)-13-{4-[5-chloro-2-(4-chloro-1H-1,2,3-triazol-1-yl)phenyl]-6-oxo-1,6-dihydropyrimidin-1-yl}-3,9-dimethyl-3,4,7,18-tetraazatricyclo[12.3.1.0$^{2,6}$]octadeca-1(18),2(6),4,14,16-pentaen-8-one;

(10R,14S)-14-{4-[5-chloro-2-(4-chloro-1H-1,2,3-triazol-1-yl)phenyl]-6-oxo-1,6-dihydropyrimidin-1-yl}-10-methyl-3,5,8-triazatricyclo[13.3.1.0$^{2,7}$]nonadeca-1(19),2(7),3,5,15,17-hexaen-9-one;

(9R,13S)-13-{4-[5-chloro-1-(2-hydroxyethyl)-1H-indazol-7-yl]-6-oxo-1,6-dihydropyrimidin-1-yl}-3-(difluoromethyl)-9-methyl-3,4,7,15-tetraazatricyclo[12.3.1.0$^{2,6}$]octadeca-1(8),2(6),4,14,16-pentaen-8-one;

(9R,13S)-13-[4-(5-chloro-1-methyl-1H-indol-7-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one;

(9R,13S)-13-{4-[5-chloro-2-(2-hydroxyethyl)-2H-indazol-7-yl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one;

(9R,13S)-13-[4-(6-chloro-1-methyl-1H-indazol-4-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one;

(9R,13S)-13-{4-[5-chloro-2-(4-chloro-1H-1,2,3-triazol-1-yl)phenyl]-6-oxo-1,6-dihydropyrimidin-1-yl}-4-(6-hydroxypyridin-3-yl)-9-methyl-3,4,7,15-tetraazatricyclo[12.3.1.0$^{2,6}$]octadeca-1(18),2,5,14,16-pentaen-8-one;

(9R,13S)-13-{4-[5-chloro-2-(1,2,3-thiadiazol-4-yl)phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one;

(9R,13S)-13-(4-{3-chloro-2-fluoro-6-[4-(trifluoromethyl)-1H-pyrazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one;

(9R,13S)-13-[4-(3-chloro-2,6-difluorophenyl)-6-oxo-1,6-dihydropyrimidin-1-yl]-9-methyl-3,4,7,15-tetraazatricyclo[12.3.1.0$^{2,6}$]octadeca-1(18),2(6),4,14,16-pentaen-8-one;

(9R,13S)-13-{4-[5-chloro-2-(1,2,3-thiadiazol-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-(4-{5-chloro-2-[4-(trifluoromethyl)-1H-1,2,3-triazol-1-yl]phenyl}-6-oxo-1,6-dihydropyrimidin-1-yl)-4-(2-hydroxypyridin-4-yl)-9-methyl-3,4,7,15-tetraazatricyclo[12.3.1.0$^{2,6}$]octadeca-1(18),2,5,14,16-pentaen-8-one;

(9R,13S)-13-[4-(3-chloro-2,6-difluorophenyl)-6-oxo-1,6-dihydropyrimidin-1-yl]-9-methyl-4-(pyrimidin-5-yl)-3,4,7,15-tetraazatricyclo[12.3.1.0$^{2,6}$]octadeca-1(18),2,5,14,16-pentaen-8-one;

(9R,13S)-13-{4-[5-chloro-2-(pyridazin-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-{4-[5-chloro-2-(4-chloro-1H-1,2,3-triazol-1-yl)phenyl]-6-oxo-1,6-dihydropyrimidin-1-yl}-4-(2-hydroxypyrimidin-5-yl)-9-methyl-3,4,7,15-tetraazatricyclo[12.3.1.0$^{2,6}$]octadeca-1(8),2,5,14,16-pentaen-8-one;

(10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-5,8,17-triazatricyclo[13.3.1.0$^{2,7}$]nonadeca-1(19),2(7),3,5,15,17-hexaen-9-one;

(9R,13S)-13-{4-[5-chloro-2-(4-chloro-H-1,2,3-triazol-1-yl)phenyl]-6-oxo-1,6-dihydropyrimidin-1-yl}-9-methyl-4-(piperidin-4-yl)-3,4,7,15-tetraazatricyclo[12.3.1.0$^{2,6}$]octadeca-1(18),2,5,14,16-pentaen-8-one;

1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}-3-fluorophenyl)-1H-pyrazole-4-carbonitrile;

(9R,13S)-13-{4-[5-chloro-2-(4-chloro-H-1,2,3-triazol-1-yl)phenyl]-6-oxo-1,6-dihydropyrimidin-1-yl}-4-(1H-imidazol-4-yl)-9-methyl-3,4,7,15-tetraazatricyclo[12.3.1.0$^{2,6}$]octadeca-1(18),2,5,14,16-pentaen-8-one;

(9R,13S)-13-{4-[5-chloro-2-(4-chloro-1H-1,2,3-triazol-1-yl)phenyl]-6-oxo-1,6-dihydropyrimidin-1-yl}-9-methyl-4-(1H-1,2,4-triazol-5-yl)-3,4,7,15-tetraazatricyclo[12.3.1.0$^{2,6}$]octadeca-1(18),2,5,14,16-pentaen-8-one;

N-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-2,2,2-trifluoroacetamide;

(9R,13S)-13-(4-{5-chloro-2-[4-(trifluoromethyl)-1H-1,2,3-triazol-1-yl]phenyl}-6-oxo-1,6-dihydropyrimidin-1-yl)-4-(2-hydroxypyridin-3-yl)-9-methyl-3,4,7,15-tetraazatricyclo[12.3.1.0$^{2,6}$]octadeca-1(18),2,5,14,16-pentaen-8-one;

(9R,13S)-13-{4-[5-chloro-2-(4-chloro-1H-1,2,3-triazol-1-yl)phenyl]-6-oxo-1,6-dihydropyrimidin-1-yl}-9-methyl-3-(1H-pyrazol-3-yl)-3,4,7,15-tetraazatricyclo[12.3.1.0$^{2,6}$]octadeca-1(18),2(6),4,14,16-pentaen-8-one;

(9R,13S)-13-[4-(2-amino-5-chlorophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one;

(9R,13S)-13-(4-{5-chloro-2-[(pyrimidin-4-yl)amino]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one;

(9R,13S)-13-{4-[2-(aminomethyl)-5-chlorophenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one;

(9R,13S)-13-{4-[5-chloro-2-(pyridin-2-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-(4-{5-chloro-2-[4-(trifluoromethyl)-1H-1,2,3-triazol-1-yl]phenyl}-6-oxo-1,6-dihydropyrimidin-1-yl)-4-(2-methoxypyridin-3-yl)-9-methyl-3,4,7,15-tetraazatricyclo[12.3.1.0$^{2,6}$]octadeca-1(18),2,5,14,16-pentaen-8-one;

(9R,13S)-13-(4-{5-chloro-2-[4-(trifluoromethyl)-1H-1,2,3-triazol-1-yl]phenyl}-6-oxo-1,6-dihydropyrimidin-1-yl)-3-(6-methoxypyrimidin-4-yl)-9-methyl-3,4,7,15-tetraazatricyclo[12.3.1.0$^{2,6}$]octadeca-1(18),2(6),4,14,16-pentaen-8-one;

(9R,13S)-13-(4-{5-chloro-2-[4-(trifluoromethyl)-1H-1,2,3-triazol-1-yl]phenyl}-6-oxo-1,6-dihydropyrimidin-1-yl)-4-(6-methoxypyrimidin-4-yl)-9-methyl-3,4,7,15-tetraazatricyclo[12.3.1.0$^{2,6}$]octadeca-1(18),2,5,14,16-pentaen-8-one;

(9R,13S)-13-(4-{5-chloro-2-[4-(trifluoromethyl)-1H-1,2,3-triazol-1-yl]phenyl}-6-oxo-1,6-dihydropyrimidin-1-yl)-4-(6-hydroxypyrimidin-4-yl)-9-methyl-3,4,7,15-tetraazatricyclo[12.3.1.0$^{2,6}$]octadeca-1(18),2,5,14,16-pentaen-8-one;

(9R,13S)-13-(4-{5-chloro-2-[4-(trifluoromethyl)-1H-1,2,3-triazol-1-yl]phenyl}-6-oxo-1,6-dihydropyrimidin-1-yl)-4-(2-methoxypyridin-4-yl)-9-methyl-3,4,7,15-tetraazatricyclo[12.3.1.0$^{2,6}$]octadeca-1(18),2,5,14,16-pentaen-8-one;

(9R,13S)-13-{4-[5-chloro-2-(4-methylphenyl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-{4-[5-chloro-2-(3-chlorophenyl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-{4-[5-chloro-2-(3-methoxyphenyl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-{4-[5-chloro-2-(2-methylphenyl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-(4-{5-chloro-2-[4-(trifluoromethoxy)phenyl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one;

(9R,13S)-13-{4-[5-chloro-2-(2-chlorophenyl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-(4-{5-chloro-2-[4-(trifluoromethyl)phenyl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one;

(9R,13S)-13-(4-{5-chloro-2-[4-(propan-2-ylsulfanyl)phenyl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one;

4-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)benzene-1-sulfonamide;

(9R,13S)-13-(4-{5-chloro-2-[4-(difluoromethoxy)phenyl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one;

N-[3-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)phenyl]methanesulfonamide;

3-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)benzonitrile;

(9R,13S)-13-(4-{5-chloro-2-[3-(trifluoromethoxy)phenyl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one;

(9R,13S)-13-{4-[5-chloro-2-(3-methanesulfonylphenyl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

methyl 4-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)benzoate;

(9R,13S)-13-{4-[5-chloro-2-(3-methylphenyl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

4-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)benzonitrile;

(9R,13S)-13-{4-[5-chloro-2-(1-methyl-1H-indol-5-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-{4-[5-chloro-2-(isoquinolin-5-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

methyl 3-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)benzoate;

N-[4-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)phenyl]methanesulfonamide;

(9R,13S)-13-(4-{5-chloro-2-[3-(trifluoromethyl)phenyl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one;

(9R,13S)-13-{4-[5-chloro-2-(4-methoxyphenyl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-{4-[5-chloro-2-(4-chlorophenyl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-{4-[5-chloro-2-(pyridin-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-{4-[5-chloro-2-(isoquinolin-7-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

(9R,13S)-13-{4-[5-chloro-2-(pyrimidin-5-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one;

ethyl 2-[4-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-pyrazol-1-yl]acetate;

(9R,13S)-13-{4-[5-chloro-2-(1-ethyl-1H-pyrazol-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one; and (9R,13S)-13-(4-{5-chloro-2-[1-(4-fluorophenyl)-1H-pyrazol-4-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one.

In another embodiment, the compounds of the present invention have Factor XIa or plasma kallikrein Ki values ≤10 μM.

In another embodiment, the compounds of the present invention have Factor XIa or plasma kallikrein Ki values ≤1 μM.

In another embodiment, the compounds of the present invention have Factor XIa or plasma kallikrein Ki values ≤0.5 μM.

In another embodiment, the compounds of the present invention have Factor XIa or plasma kallikrein Ki values ≤0.1 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s). In a preferred embodiment, the present invention provides pharmaceutical composition, wherein the additional therapeutic agent(s) are an anti-platelet agent or a combination thereof. Preferably, the anti-platelet agent(s) are clopidogrel and/or aspirin, or a combination thereof.

In another embodiment, the present invention provides a method for the treatment and/or prophylaxis of a thromboembolic disorder comprising administering to a patient in need of such treatment and/or prophylaxis a therapeutically effective amount of at least one of the compounds of the present invention or a stereoisomer, a tautomer, a pharmaceutically acceptable salt, or a solvate thereof.

In another embodiment, the present invention provides a compound of the present invention or a stereoisomer, a tautomer, a pharmaceutically acceptable salt, or a solvate thereof, for use in therapy.

In another embodiment, the present invention provides a compound of the present invention or a stereoisomer, a tautomer, a pharmaceutically acceptable salt, or a solvate thereof, for use in therapy for the treatment and/or prophylaxis of a thromboembolic disorder.

In another embodiment, the present invention also provides the use of a compound of the present invention or a stereoisomer, a tautomer, a pharmaceutically acceptable salt, or a solvate thereof, for the manufacture of a medicament for the treatment and/or prophylaxis of a thromboembolic disorder.

In another embodiment, the present invention provides a method for treatment and/or prophylaxis of a thromboembolic disorder, comprising: administering to a patient in need thereof a therapeutically effective amount of a first and second therapeutic agent, wherein the first therapeutic agent is a compound of the present invention or a stereoisomer, a tautomer, a pharmaceutically acceptable salt, or a solvate thereof, and the second therapeutic agent is at least one agent selected from a factor Xa inhibitor such as apixaban, rivaroxaban, betrixaban, edoxaban, an anti-coagulant agent, an anti-platelet agent, a thrombin inhibiting agent such as dabigatran, a thrombolytic agent, and a fibrinolytic agent. Preferably, the second therapeutic agent is at least one agent selected from warfarin, unfractionated heparin, low molecular weight heparin, synthetic pentasaccharide, hirudin, argatroban, aspirin, ibuprofen, naproxen, sulindac, indomethacin, mefenamate, droxicam, diclofenac, eribaxaban, sulfinpyrazone, piroxicam, ticlopidine, clopidogrel, tirofiban, eptifibatide, abciximab, melagatran, desulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof.

The thromboembolic disorder includes arterial cardiovascular thromboembolic disorders, venous cardiovascular thromboembolic disorders, arterial cerebrovascular thromboembolic disorders, and venous cerebrovascular thromboembolic disorders. Examples of the thromboembolic disorder include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for the treatment and/or prophylaxis of an inflammatory disorder comprising: administering to a patient in need of such treatment and/or prophylaxis a therapeutically effective amount of at least one of the compounds of the present invention or a stereoisomer, a tautomer, a pharmaceutically acceptable salt, or a solvate thereof. Examples of the inflammatory disorder include, but are not limited to, sepsis, acute respiratory distress syndrome, and systemic inflammatory response syndrome.

In another embodiment, the present invention provides a method for the prophylaxis of a disease or condition in which plasma kallikrein activity is implicated comprising administering to a patient in need of such treatment and/or prophylaxis a therapeutically effective amount of at least one of the compounds of the present invention or a stereoisomer, a tautomer, a pharmaceutically acceptable salt, or a solvate thereof.

The disease or condition in which plasma kallikrein activity is implicated includes, but not limited to, impaired visual acuity, diabetic retinopathy, diabetic macular edema, hereditary angioedema, diabetes, pancreatitis, nephropathy, cardio myopathy, neuropathy, inflammatory bowel disease, arthritis, inflammation, septic shock, hypotension, cancer, adult respiratory distress syndrome, disseminated intravascular coagulation, and cardiopulmonary bypass surgery.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment and/or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans-(or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond. "Alkyl" also includes deuteroalkyl such as $CD_3$.

"Alkenyl" or "alkenylene" is intended to include hydrocarbon chains of either straight or branched configuration having one or more, preferably one to three, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups; such as ethenyl, propenyl, butenyl, pentenyl, and hexenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Alkoxy also includes deuteroalkoxy such as $OCD_3$. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "amino", as used herein, refers to —$NH_2$.

The term "substituted amino", as used herein, refers to the defined terms below having the suffix "amino" such as "arylamino", "alkylamino", "arylamino", etc.

The term "alkoxycarbonyl", as used herein, refers to an alkoxy group attached to the parent molecular moiety through a carbonyl group.

The term "alkoxycarbonylamino", as used herein, refers to an —NHR wherein R is an alkoxycarbonyl group.

The term "alkylamino", as used herein refers to —NHR, wherein R is an alkyl group.

The term "alkylcarbonyl", as used herein, refers to an alkyl group attached to the parent molecular moiety through a carbonyl group.

The term "alkylcarbonylamino", as used herein, refers to —NHR wherein R is an alkylcarbonyl group.

The term "aminosulfonyl", as used herein, refers to —SO$_2$NH$_2$.

The term "arylalkyl", as used herein, refers to an alkyl group substituted with one, two, or three aryl groups.

The term "arylamino", as used herein, refers to —NHR wherein R is an aryl group.

The term "arylcarbonyl", as used herein, refers to an aryl group attached to the parent molecular moiety through a carbonyl group.

The term "arylcarbonylamino", as used herein refers to —NHR wherein R is an arylcarbonyl group.

The term "cyano", as used herein, refers to —CN.

The term "cycloalkylamino", as used herein, refers to —NHR wherein R is a cycloalkyl group.

The term "cycloalkylcarbonyl", as used herein, refers to a cycloalkyl group attached to the parent molecular moiety through a carbonyl group.

The term "cycloalkylcarbonylamino", as used herein, refers to —NHR wherein R is a cycloalkylcarbonyl group.

The term "cycloalkyloxy", as used herein, refers to a cycloalkyl group attached to the parent molecular moiety through an oxygen atom.

The term "dialkylamino", as used herein, refers to NR$_2$, wherein each R is an alkyl group. The two alkyl groups are the same or different.

The term "haloalkoxy", as used herein, refers to a haloalkyl group attached to the parent molecular moiety through an oxygen atom.

The term "haloalkyl", as used herein, refers to an alkyl group substituted by one, two, three, or four halogen atoms.

The term "haloalkylamino", as used herein, refers to —NHR wherein R is a haloalkyl group.

The term "carbonyl" refers to C(=O) or C(O).

The term "carboxyl" or "carboxyl" refers to C(=O)OH.

The terms "carboxyl ester" and "oxycarbonyl" refer to the groups —C(O)O-alkyl, —C(O)O-substituted alkyl, —C(O)O-alkenyl, —C(O)O-substituted alkenyl, —C(O)O-alkynyl, C(O)O-substituted alkynyl, —C(O)O-cycloalkyl, —C(O)O-substituted cycloalkyl, —C(O)O-aryl, —C(O)O-substituted aryl, —C(O)O-heteroaryl, —C(O)O-substituted heteroaryl, —C(O)O-heterocyclic, and —C(O)O-substituted heterocyclic.

The term "aminoacyl" or "amide", or the prefix "carbamoyl", "carboxamide", "substituted carbamoyl" or "substituted carboxamide" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic.

The term "haloalkylcarbonyl", as used herein, refers to a haloalkyl group attached to the parent molecular moiety through a carbonyl group.

The term "haloalkylcarbonylamino", as used herein, refers to —NHR wherein R is a haloalkylcarbonyl group.

The terms "alkylcarbonyl" refer to an alkyl or substituted alkyl bonded to a carbonyl.

The term "alkoxycarbonyl", as used herein, refers to an alkoxy group attached to the parent molecular moiety through a carbonyl group.

The term "hydroxy" or "hydroxyl" refers to OH.

As used herein the term "thiol" means —SH. A thiol may be substituted with a substituent disclosed herein, in particular alkyl(thioalkyl), aryl(thioaryl), or alkoxy(thioalkoxy).

As used herein the term "sulfonyl", used alone or linked to other terms such as alkylsulfonyl or arylsulfonyl, refers to the divalent radicals —SO$_2$—. In aspects of the invention a sulfonyl group, the sulfonyl group may be attached to a substituted or unsubstituted hydroxyl, alkyl group, ether group, alkenyl group, alkynyl group, aryl group, cycloalkyl group, cycloalkenyl group, cycloalkynyl group, heterocyclic group, carbohydrate, peptide, or peptide derivative.

The term "cycloalkyl" refers to cyclized alkyl groups, including mono-, bi- or poly-cyclic ring systems. "C$_3$ to C$_7$ cycloalkyl" or "C$_{3-7}$ cycloalkyl" is intended to include C$_3$, C$_4$, C$_5$, C$_6$, and C$_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocyclyls include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocyclyl (e.g., [2.2.2]bicyclooctane). Preferred carbocyclyls, unless otherwise specified, are cyclopropyl, cyclobutyl, cyclopentyl, cyclohexyl, phenyl, and indanyl. When the term "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997).

"$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, OCH$_3$, C$_1$, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocycle", "heterocyclyl" or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N—O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocyclyl may optionally be quaternized. It is preferred that when the total number of S and O atoms in the heterocyclyl exceeds 1, then these heteroatoms are not adjacent to one another. It is preferred that the total number of S and O atoms in the heterocyclyl is not more than 1. When the term "heterocyclyl" is used, it is intended to include heteroaryl.

Examples of heterocyclyls include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocyclyls.

Examples of 5- to 10-membered heterocyclyls include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocyclyls include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocyclyls.

As used herein, the term "bicyclic heterocyclyl" "bicyclic heterocyclyl" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocyclyl, a 6-membered heterocyclyl or a carbocyclyl (provided the first ring is not benzo when the second ring is a carbocyclyl).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocyclyl exceeds 1, then these heteroatoms are not adjacent to one another. It is preferred that the total number of S and O atoms in the heterocyclyl is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydroquinolinyl, 2,3-dihydrobenzofuranyl, chromanyl, 1,2,3,4-tetrahydroquinoxalinyl, and 1,2,3,4-tetrahydroquinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocyclyl. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology,* 112:309-396, Academic Press (1985);

b) Bundgaard, H., Chapter 5: "Design and Application of Prodrugs", *A Textbook of Drug Design and Development*, pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "RBF" for round bottom flask, "atm" for atmosphere, "psi" for pounds per square inch, "conc." for concentrate, "RCM" for ring-closing metathesis, "sat" or "sat'd" for saturated, "SFC" for supercritical fluid chromatography "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc or BOC tert-butyloxycarbonyl
Boc$_2$O di-tert-butyl dicarbonate
AcOH or HOAc acetic acid
AlCl$_3$ aluminum chloride
AIBN azobisisobutyronitrile
aqueous aq
BBr$_3$ boron tribromide
BCl$_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
Cbz carbobenzyloxy
DCM or CH$_2$Cl$_2$ dichloromethane
CH$_3$CN or ACN acetonitrile
CDCl$_3$ deutero-chloroform
CHCl$_3$ chloroform
mCPBA or m-CPBA meta-chloroperbenzoic acid
Cs$_2$CO$_3$ cesium carbonate
Cu(OAc)$_2$ copper (II) acetate
CuI copper(I) iodide
CuSO$_4$ copper(II) sulfate
Cy$_2$NMe N-cyclohexyl-N-methylcyclohexanamine
DBU 1,8-diazabicyclo[5.4.0]undec-7-ene
DCE 1,2-dichloroethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or diisopropylethylamine Hunig's base
DMAP 4-dimethylaminopyridine
DME 1,2-dimethoxy ethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylpholano)benzene
EDC N-(3-dimethylaminopropyl)-N'-ethylcarbodiimide
EDCI N-(3-dimethylaminopropyl)-N'-ethylcarbodiimide hydrochloride EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
$Et_3N$ or TEA triethylamine
EtOAc ethyl acetate
$Et_2O$ diethyl ether
EtOH ethanol
GMF glass microfiber filter
Grubbs II (1,3-bis(2,4,6-trimethylphenyl)-2-imidazolidinylidene)dichloro (phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperazine-1-ethanesulfonic acid
Hex hexane
HOBt or HOBT 1-hydroxybenzotriazole
$H_2O_2$ hydrogen peroxide
$H_2SO_4$ sulfuric acid
IBX 2-iodoxybenzoic acid
$InCl_3$ Indium(III) chloride
Jones reagent $CrO_3$ in aqueous $H_2SO_4$, 2 M
$K_2CO_3$ potassium carbonate
$K_2HPO_4$ potassium phosphate dibasic
$K_3PO_4$ potassium phosphate tribasic
KOAc potassium acetate
$K_3PO_4$ potassium phosphate
LAH lithium aluminum hydride
LG leaving group
LiOH lithium hydroxide
MeOH methanol
$MgSO_4$ magnesium sulfate
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ ammonia
$NH_4Cl$ ammonium chloride
$NH_4OH$ ammonium hydroxide
$NH_4COOH$ ammonium formate
NMM N-methylmorpholine
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
i-PrOH or IPA isopropanol
PS Polystyrene
rt room temperature
SEM-Cl 2-(trimethysilyl)ethoxymethyl chloride
$SiO_2$ silica oxide
$SnCl_2$ tin(II) chloride
TBAI tetra-n-butylammonium iodide
TBN t-butyl nitrite
TFA trifluoroacetic acid
THF tetrahydrofuran
$TMSCHN_2$ trimethylsilyldiazomethane
T3P® propane phosphonic acid anhydride
TRIS tris (hydroxymethyl) aminomethane
pTsOH p-toluenesulfonic acid The compounds of the present invention can be prepared in a number of ways known to one skilled in the art of organic synthesis, which are described in more detail in Section VI.

IV. Biology

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders and include acute coronary syndrome, unstable angina, myocardial infarction, atrial fibrillation, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, artificial heart valves, and hemodialysis membranes.

Some conditions contribute to the risk of developing thrombosis. For example, alterations of the vessel wall, changes in the flow of blood, and alterations in the composition of the vascular compartment. These risk factors are collectively known as Virchow's triad. (Colman, R. W. et al., eds., *Hemostasis and Thrombosis, Basic Principles and Clinical Practice*, Fifth Edition, p. 853, Lippincott Williams & Wilkins (2006)).

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in factor V (also known as factor V Leiden) and additional risk factors (e.g., pregnancy), are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e., heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al., *Blood*, 105:453-463 (2005)).

An alternative way of initiation of coagulation is operative when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., *Blood*, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact Activation Pathway", *Hemostasis and Thrombosis*, pp. 103-122, Lippincott Williams & Wilkins (2001); Schmaier, A. H., "Contact Activation", *Thrombosis and Hemorrhage*, pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., *J Exp. Med.*, 202:271-281 (2005); Kleinschmitz et al., *J. Exp. Med*, 203:513-518 (2006)). The fact that factor XI is down-stream from factor XIIa, combined with the identical phenotype of the XII and XI deficient mice suggest that the contact activation system could play a major role in factor XI activation in vivo.

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D., *Trends Cardiovasc. Med*, 10:198-204 (2000)).

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al., *Thromb. Res.*, 101:329-354 (2001).) Thus, inhibitors of factor XIa are expected to be anticoagulant and profibrinolytic.

Further evidence for the anti-thromboembolic effects of targeting factor XI is derived from mice deficient in factor XI. It has been demonstrated that complete fXI deficiency protected mice from ferric chloride ($FeCl_3$)-induced carotid artery thrombosis (Rosen et al., *Thromb. Haemost.*, 87:774-777 (2002); Wang et al., *J. Thromb. Haemost.*, 3:695-702 (2005)). Also, factor XI deficiency rescues the perinatal lethal phenotype of complete protein C deficiency (Chan et al., *Amer. J. Pathology*, 158:469-479 (2001)). Furthermore, baboon cross-reactive, function blocking antibodies to human factor XI protect against baboon arterial-venous shunt thrombosis (Gruber et al., *Blood*, 102:953-955 (2003)). Evidence for an antithrombotic effect of small molecule inhibitors of factor XIa is also disclosed in published U.S. Patent Publication No. 2004/0180855 A1. Taken together, these studies suggest that targeting factor XI will reduce the propensity for thrombotic and thromboembolic diseases.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or post-traumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of aPTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The aPTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D., *Frontiers in Bioscience*, 6:201-207 (2001); Gailani, D. et al., *Blood Coagulation and Fibrinolysis*, 8:134-144 (1997).) Taken together, these observations suggest that high levels of inhibition of factor XIa should be well tolerated. This is in contrast to gene targeting experiments with other coagulation factors, excluding factor XII.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA.

This study can be viewed as evidence that at least in a subpopulation of patients with AMI, factor XI activation contributes to thrombin formation (Minnema, M. C. et al., *Arterioscler. Thromb. Vasc. Biol.*, 20:2489-2493 (2000)). A second study establishes a positive correlation between the extent of coronary arteriosclerosis and factor XIa in complex with alpha 1 antitrypsin (Murakami, T. et al., *Arterioscler. Thromb. Vasc. Biol.*, 15:1107-1113 (1995)). In another study, Factor XI levels above the 90th percentile in patients were associated with a 2.2-fold increased risk for venous thrombosis (Meijers, J. C. M. et al., *N. Engl. J Med.*, 342:696-701 (2000)).

Also, it is preferred to find new compounds with improved activity in in vitro clotting assays, compared with known serine protease inhibitors, such as the activated partial thromboplastin time (aPTT) or prothrombin time (PT) assay. (for a description of the aPTT and PT assays see, Goodnight, S. H. et al., "Screening Tests of Hemostasis", *Disorders of Thrombosis and Hemostasis: A Clinical Guide*, Second Edition, pp. 41-51, McGraw-Hill, New York (2001)).

It is also desirable and preferable to find compounds with advantageous and improved characteristics compared with known serine protease inhibitors, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility.

Pre-clinical studies demonstrated significant antithrombotic effects of small molecule factor XIa inhibitors in rabbit and rat model of arterial and venous thrombosis, at doses that preserved hemostasis. (Wong P. C. et al., *Journal of Thrombosis and Thrombolysis*, 32(2):129-137 (August 2011); Schumacher, W. et al., *Journal of Thrombosis and Haemostasis*, 3(Suppl. 1):P1228 (2005); Schumacher, W. A. et al., *Eur. J Pharmacol.*, 167-174 (2007)). Furthermore, it was observed that in vitro prolongation of the aPTT by specific XIa inhibitors is a good predictor of efficacy in our thrombosis models. Thus, the in vitro aPTT test can be used as a surrogate for efficacy in vivo. Pre-clinical and clinical studies using FXI antisense (ASO) has been shown to be effective in various venous and arterial thrombosis models, comparable to warfarin or enoxaparin without increased bleeding (Bueller et al., DOI: 10.1056/NEJMoa1405760 (2014)).

As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

As used herein, "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit factor XIa and/or plasma kallikrein and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Risk factors for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population (Levitan, N. et al., *Medicine* (Baltimore), 78(5):285-291 (1999); Levine M. et al., *N. Engl. J. Med.*, 334(11):677-681 (1996); Blom, J. W. et al., *JAMA*, 293(6):715-722 (2005)). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and anti-angiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al., *British Journal of Surgery*, 88:913-930 (2001).)

A. In Vitro Assays

The effectiveness of compounds of the present invention as inhibitors of the coagulation Factors XIa, VIIa, IXa, Xa, XIIa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, Ki.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 25-200 pM (Haematologic Technologies) and the synthetic substrate S-2366 (pyroGlu-Pro-Arg-pNA; CHROMOGENIX® or AnaSpec) at a concentration of 0.0002-0.001 M.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 0.5-10 nM, recombinant soluble tissue factor at a concentration of 10-40 nM and the synthetic substrate H-D-Ile-Pro-Arg-pNA (S-2288; CHROMOGENIX® or BMPM-2; AnaSpec) at a concentration of 0.001-0.0075 M.

Factor IXa determinations were made in 0.005 M calcium chloride, 0.1 M sodium chloride, 0.0000001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; CHROMOGENIX®) at a concentration of 0.0002-0.00035 M.

Factor XIIa determinations were made in 0.05 M HEPES buffer at pH 7.4 containing 0.145 M NaCl, 0.05 M KCl, and 0.1% PEG 8000. Determinations were made using purified human Factor XIIa at a final concentration of 4 nM (American Diagnostica) and the synthetic substrate SPECTROZYME® #312 (H-D-CHT-Gly-L-Arg-pNA.2AcOH; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human plasma kallikrein (Enzyme Research Laboratories) at a final assay concentration of 200 pM and the synthetic substrate S-2302 (H-(D)-Pro-Phe-Arg-pNA; CHROMOGENIX®) at a concentration of 0.00008-0.0004 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; CHROMOGENIX® or AnaSpec) at a concentration of 0.0002-0.0004 M.

The Michaelis constant, $K_m$, for substrate hydrolysis by each protease, was determined at 25° C. or 37° C. in the absence of inhibitor. Values of Ki were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate Ki values:

$$(V_{max}*S)/(K_m+S)$$

$(v_o-v_s)/v_s = I/(K_i(1+S/K_m))$ for a competitive inhibitor with one binding site; or $$v_s/v_o = A+(B-A)/(1+(I/IC_{50})^n);\text{ and}$$

$Ki = IC_{50}/(1+S/K_m)$ for a competitive inhibitor where:

$v_o$ is the velocity of the control in the absence of inhibitor;
$v_s$ is the velocity in the presence of inhibitor;
$V_{max}$ is the maximum reaction velocity;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme: inhibitor complex;
S is the concentration of substrate; and
$K_m$ is the Michaelis constant for the substrate.

The selectivity of a compound may be evaluated by taking the ratio of the $K_i$ value for a given protease with the $K_i$ value for the protease of interest (i.e., selectivity for FXIa versus protease P=$K_i$ for protease P/$K_i$ for FXIa). Compounds with selectivity ratios >20 are considered selective.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5× or IC2×, the inhibitor concentration required to increase the clotting time by 50 or 100 percent, respectively. The IC1.5× or IC2× is found by linear interpolation from relative clotting time versus inhibitor concentration plots using inhibitor concentration that spans the IC1.5× or IC2×.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (SYSMEX®, Dade-Behring, Ill.). Similarly, clotting times can be determined from laboratory animal species or humans dosed with compounds of the invention.

Activated Partial Thromboplastin Time (aPTT) is determined using ACTIN® FSL (Dade-Behring, Ill.) following the directions in the package insert. Plasma (0.05 mL) is warmed to 37° C. for 1 minute. ACTIN® FSL (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Thromboplastin C Plus or INNOVIN®, Dade-Behring, Ill.) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

Equilibrium solubilities were determined in various aqueous solvents buffered to a specific pH. Approximately 1 mg of compound was used for equilibration in 100 to 300 µL of solvent. Samples were stirred at 300 RPM at room temperature (20±2° C.) for 24 hours. If solubilization of the entire solid was observed, additional compound was added to keep the solid in excess for the duration of the study. After 24 hours, microscopy was used to determine if there was a change in morphology to the excess solid. The supernatants were then filtered through a 0.22 m PVDF filter plate and diluted with acetonitrile for HPLC analysis. Calibration samples were also provided for HPLC analysis.

The extent to which compounds of the present invention bind to human serum proteins can be determined using dialysis methods and analytical techniques well known in the art and described in, for example, Plise, E. G. et al., "Semi-automated protein binding methodology using equilibrium dialysis and a novel mixed-matrix cassette approach", J. Pharm. Sci., 99(12):5070-5078 (2010); Waters, N.J. et al., "Validation of a rapid equilibrium dialysis approach for the measurement of plasma protein binding", J. Pharm. Sci., 97(10):4586-4595 (2008); Van Liempd, S. et al., "Development and Validation of a Higher-Throughput Equilibrium Dialysis Assay for Plasma Protein Binding", J. Lab. Autom., 16:56-67 (2011); Di, L. et al., "Impact of Recovery on Fraction Unbound Using Equilibrium Dialysis", J. Pharm. Sci., 101(3):1327-1335 (2011).

Compounds of the present invention were assayed in triplicate by combining with human serum to achieve a final concentration of 10 µM. Dialysis was performed for 5 hours at 37° C., in a 10% $CO_2$ atmosphere against 0.133 M sodium phosphate buffer adjusted to pH 7.4 using the two-chamber Rapid Equilibrium Dialysis Assay Plates from Thermo Fisher (Waltham, Mass.). Assay samples from buffer and serum chambers were collected at time zero ($T_{0[Serum]}$ and $T_{0[Buffer]}$) and at 5 hours post-incubation ($T_{5h[Serum]}$ and $T_{5h[Buffer]}$). Prior to analysis, dialyzed serum samples were diluted with 0.133 M sodium phosphate buffer adjusted to pH 7.4 and dialyzed buffer samples were diluted with human serum to result in the same final serum concentration in each sample. Subsequently, these samples were extracted by protein precipitation in acetonitrile containing two analytical internal standards (200 nM alprenolol and 600 nM tolbutamide). Precipitated proteins and supernatants were separated by centrifugation at 4000×g for 10 minutes. Sample supernatants were analyzed by LC-MS/MS and the peak area ratios of compound to the internal standard were determined for initial time zero samples ($T_{0[Serum]}$ and $T_{0[Buffer]}$) and for post-equilibrium samples ($T_{5h[Serum]}$ and $T_{5h[Buffer]}$). The percent free (free fraction), percent bound, and percent recovery results were calculated as follows:

Percent free=100×($T_{5h[Buffer]}/T_{5h[Serum]}$)

Percent bound=100−percent free

Percent recovery=100×(($T_{5h[Buffer]}$+$T_{5h[Serum]}$)/$T_{0[Serum]}$)

Matrix interference was assessed by measuring the LC-MS/MS area ratio of analyte/internal standard for assay matrix blank (50:50 serum:buffer). The analytical conditions were deemed acceptable for assessment of percent free when the area ratio of analyte/internal standard for assay matrix blank (50:50 serum:buffer) was less than 20% of the area ratio for the T5h[Buffer] sample.

The exemplified Examples disclosed below were tested in the Factor XIa assay described above and found having Factor XIa inhibitory activity. A range of Factor XIa inhibitory activity (Ki values) of ≤10 µM (10000 nM) was observed. Table 1 below lists Factor XIa Ki values measured at 37° C. for the following Examples.

TABLE 1

| Example No. | Factor XIa Ki (nM) |
| --- | --- |
| 353 | 0.1 |
| 354 | 0.6 |
| 362 | 0.2 |
| 363 | 0.2 |
| 367 | 0.1 |
| 368 | 0.1 |
| 369 | 0.1 |
| 370 | 0.1 |
| 371 | 0.1 |
| 372 | 0.2 |
| 373 | 0.2 |

The exemplified Examples disclosed below were tested in the Plasma Kallikrein assay described above and found having Plasma Kallikrein inhibitory activity. A range of Plasma Kallikrein inhibitory activity (Ki values) of ≤10 µM (10000 nM) was observed. Table 2 below lists Plasma Kallikrein Ki values measured at 37° C. for the following Examples.

TABLE 2

| Example No. | Plasma Kallikrein Ki (nM) |
| --- | --- |
| 353 | 28 |
| 354 | 10 |
| 362 | 23 |
| 363 | 22 |
| 367 | 24 |
| 368 | 32 |
| 369 | 33 |
| 370 | 17 |
| 371 | 19 |
| 372 | 35 |
| 373 | 37 |

The effectiveness of the compounds of the present invention as antithrombotic agents is also assessed in other assays such as aPTT, solubility, and human protein binding affinity described above. Compared to the phenyl P2' macrocycles disclosed in WO 2013/022814 and WO 2014/022766, the pyrazolyl P2' macrocycles of the present application exhibited surprising pharmacological activities. As shown in Table 3, the compounds of the present invention possess superior anticoagulant activity, solubility and bioavailability compared to the reference compounds.

TABLE 3

| Example No. | aPTT$_{1.5x}$ (μM) | Solubility at pH = 6.5 μg/mL | Human protein binding Free fraction |
|---|---|---|---|
| Example 1 from WO 2014/022766 | 1.50 | <0.001 (cryst.) | 0.7% |
| Example 100 from WO 2013/022814 | 1.33 | 0.005 (amphor.) | 5% |
| 353 | 0.50 | 6 (cryst.) | 9% |
| 362 | 0.37 | 16 (amphor.) | 17% |
| 363 | 0.34 | 159 (amphor.) | 25% |
| 367 | 0.32 | 100 (amphor.) | 21% |
| 368 | 0.36 | 82 (amphor.) | 21% |
| 369 | 0.52 | 2 (cryst.) | 8% |
| 370 | 0.42 | 106 (amphor.) | 24% |
| 371 | 0.37 | 44 (cryst.) | 26% |
| 372 | 0.22 | >3,000 (amphor.) | 25% |
| 373 | 0.24 | >3,400 (amphor.) | 11% |

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arteriovenous Shunt Thrombosis Models.

a. In Vivo Electrically-Induced Carotid Artery Thrombosis (ECAT) Model

The rabbit ECAT model, described by Wong et al. (*J. Pharmacol. Exp. Ther.*, 295:212-218 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The ED$_{50}$ (dose that increased average carotid blood flow over 90 min to 50% of the control) of compounds are estimated by a nonlinear least square regression program using the Hill sigmoid E$_{max}$ equation (DeltaGraph; SPSS Inc., Chicago, Ill.).

b. In Vivo Rabbit Arteriovenous (AV) Shunt Thrombosis Model

The rabbit AV shunt model, described by Wong et al. (Wong, P. C. et al., *J. Pharmacol. Exp. Ther.* 292:351-357 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID$_{50}$ values (dose that produces 50% inhibition of thrombus formation) are estimated by a nonlinear least square regression program using the Hill sigmoid E$_{max}$ equation (DeltaGraph; SPSS Inc., Chicago, Ill.).

The anti-inflammatory effect of these compounds can be demonstrated in an Evans Blue dye extravasation assay using C1-esterase inhibitor deficient mice. In this model, mice are dosed with a compound of the present invention, Evans Blue dye is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient. In one embodiment, the pharmaceutical composition is a solid formulation, e.g., a spray-dried composition, which may be used as is, or whereto the physician or the patient adds solvents, and/or diluents prior to use.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels. Solid dispersions are also called solid-state dispersions. In some embodiments, any compound described herein is formulated as a spray dried dispersion (SDD). An SDD is a single phase amorphous molecular dispersion of a drug in a polymer matrix. It is a solid solution prepared by dissolving the drug and a polymer in a solvent (e.g., acetone, methanol or the like) and spray drying the solution. The solvent rapidly evaporates from droplets which rapidly solidifies the polymer and drug mixture trapping the drug in amorphous form as an amorphous molecular dispersion.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 300 milligrams per dosage unit, and the second anti-coagulant in an amount of about 1 to about 500 milligrams per dosage unit.

Where the compounds of the present invention are administered in combination with an anti-platelet agent, by way of general guidance, typically a daily dosage may be about 0.01 to about 300 milligrams of the compound of the present invention and about 50 to about 150 milligrams of the anti-platelet agent, preferably about 0.1 to about 4 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 100 milligrams of the compound of the present invention, per kilogram of patient body weight and, in the case of the thrombolytic agents, the usual dosage of the thrombolytic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (aliskiren) and vasopepsidase inhibitors, an antiarrythmic agent selected from $I_{Kur}$ inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, GP Ib/IX blockers, protease activated receptor 1 (PAR-1) antagonists, protease activated receptor4 (PAR-4) antagonists, prostaglandin E2 receptor EP3 antagonists, collagen receptor antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX®), synthetic pentasaccharide, direct acting thrombin inhibitors including hirudin and argatroban, as well as other factor VIIa inhibitors, factor IXa inhibitors, factor Xa inhibitors (e.g., ARIXTRA®, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDs) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDs, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR-1) antagonists (e.g., E-5555, SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, are ADP (adenosine diphosphate) receptor antagonists, preferably antagonists of the purinergic receptors $P2Y_1$ and $P2Y_{12}$, with $P2Y_{12}$ being even more preferred. Preferred $P2Y_{12}$ receptor antagonists include clopidogrel, ticlopidine, prasugrel, ticagrelor, and cangrelor, and pharmaceutically acceptable salts or prodrugs thereof. Ticlopidine and clopidogrel are also preferred compounds since they are known to be more gentle than aspirin on the gastrointestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, omithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvastatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPARgamma modulators (e.g., rosiglitazone), compounds that have multiple functionality for modulating the activities of various combinations of PPARalpha, PPAR-gamma and PPARdelta, probucol or derivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXRbeta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention can also be combined with soluble guanylate cyclase inhibitors, Chymase inhibitors, ROMK inhibitors, ACE inhibitors, ATII inhibitors, ATR inhibitors, NEP inhibitors and other compounds to treat heart failure.

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor Vila, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 µM against the target protease and greater than or equal to 0.1 µM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Fourth Edition, Wiley-Interscience (2006)).

Representative pyrimidinone compounds 1a of this invention can be prepared as described in Scheme 1. Using a modified procedure described by Xiao (*Organic Letters*, 11:1421 (2009)), suitably substituted pyrimidin-4-ol derivatives 1b can be coupled with an appropriately substituted macrocycle amine ic in the presence of HATU and DBU in a solvent such as $CH_3CN$ to provide pyrimidinone compounds 1a. When ring A is a SEM-protected imidazole ring, an additional deprotection step employing 4N HCl in dioxane or TFA in DCM is used to afford compounds of this invention.

Scheme 1

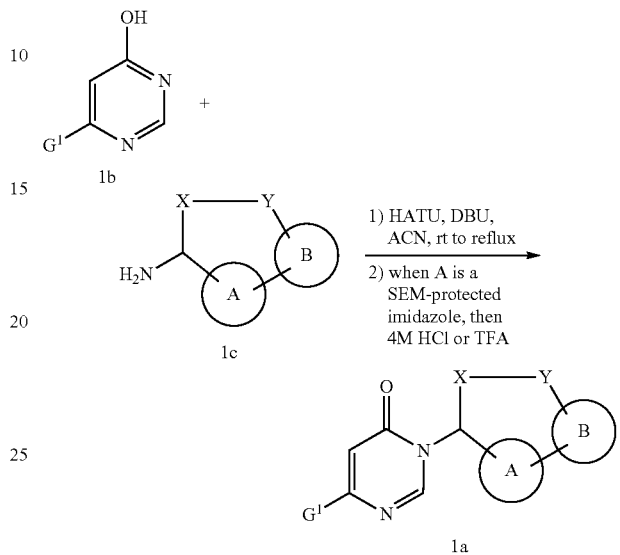

Scheme 2 describes the synthesis of suitably substituted pyrimidin-4-ol derivatives 1b. Suzuki-Miyaura coupling between 6-chloropyrimidin-4-ol (2a) and an appropriately substituted heteroaryl boronic acid or ester 2c in the presence of a base such as Hunig's base or potassium phosphate tribasic, in a solvent mixture, such as toluene and ethanol, or THF, using a precatalyst such as $Pd(PPh_3)_4$ or 2nd generation XPhos provides 1b. Alternatively, when 4-chloro-6-methoxypyrimidine 2b is used, an additional deprotection step, employing aqueous HBr at elevated temperatures, is required to provide pyrimidin-4-ol derivatives 1b.

Scheme 2

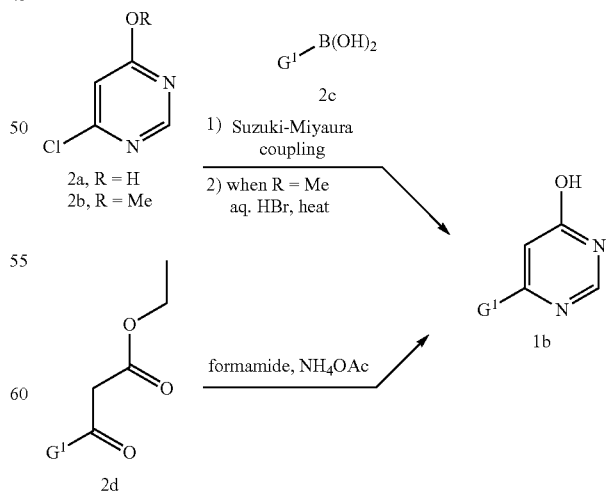

Intermediates for preparation of compounds of the present invention wherein ring A and B are a 6-membered heterocyclyl (example—pyridine) can be derived from appropriately substituted aldehydes 3a according to the general method outlined in Scheme 3. Condensation of aldehyde 3a (X=N, Y=Z=M=CH) prepared according to a modified procedure described by Negi (*Synthesis*, 991 (1996)), with (S)-2-methylpropane-2-sulfinamide in the presence of anhydrous copper sulfate or cesium carbonate in a solvent such as DCM gives the sulfinimine 3b (Ellman, J., *J. Org. Chem.*, 64:1278 (1999)). Using a modified procedure described by Kuduk (*Tetrahedron Letters*, 45:6641 (2004)), suitably substituted Grignard reagents, for example allylmagnesium bromide, can be added to sulfinimine 3b to give a sulfinamide 3c, as a mixture of diastereomers which can be separated at various stages of the sequence. The diastereoselectivity for the addition of allylmagnesium bromide to sulfinimine 3b can be improved by employing indium(III) chloride according to a modified procedure of Xu (Xu, M-H, *Organic Letters*, 10(6):1259 (2008)). Suzuki-Miyaura coupling between 4-chloropyridine 3c and an appropriately substituted heteroaryl boronic acid or ester 3e in the presence of a base such as potassium phosphate, in a solvent mixture, such as DMSO and H₂O, or DMF, using a precatalyst such as Pd(dppf)Cl₂·CH₂Cl₂ complex provides 3g. Alternatively, the Suzuki-Miyaura coupling between boronic acid 3d and an appropriately substituted heteroaryl halide 3f can be used to prepare 3g. Protecting group interconversion can be accomplished in two steps to give 3h. Alternatively, the protecting group interconversion can take place initially on 3c followed by the Suzuki-Miyaura coupling. The aniline 3h can then be coupled with an appropriately substituted carboxylic acid 3i using T3P® and a base, such as pyridine, to give the amide 3j. Using a modified procedure described by Lovely (*Tetrahedron Letters*, 44:1379 (2003)), 3j, following pretreatment with p-toluenesulfonic acid to form the pyridinium ion, can be cyclized via ring-closing metathesis using a catalyst, such as Second Generation Grubbs Catalyst in a suitable solvent, such as DCM, DCE, or toluene at elevated temperature, to give the pyridine-containing macrocycle 3k. The alkene can be reduced with hydrogen over either palladium on carbon or platinum oxide, and subsequent deprotection with TFA in DCM or 4M HCl in dioxane provides amine 3l. Compounds of the formula 3l can be converted to compounds in this invention according to Scheme 1.

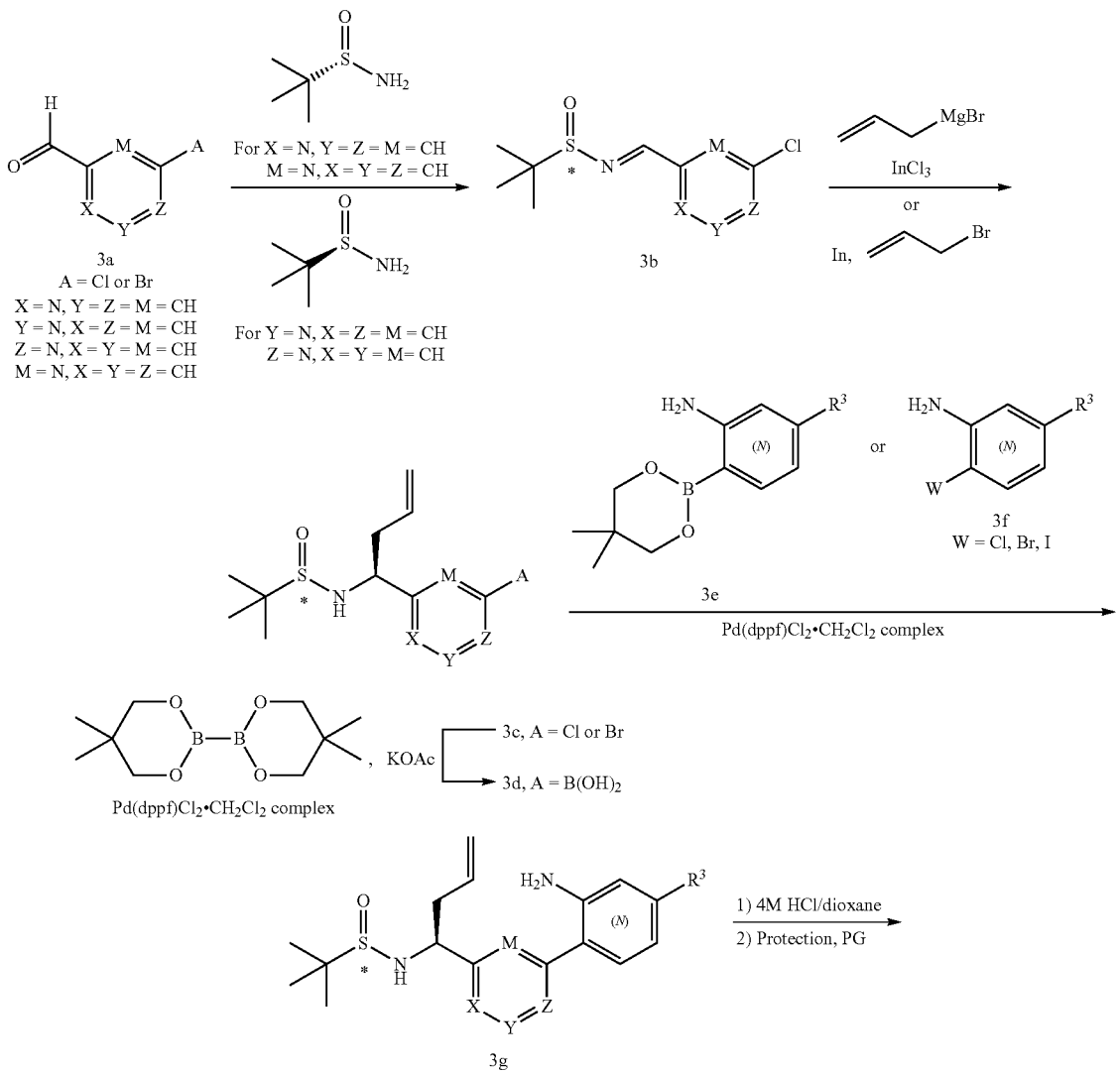

Scheme 3

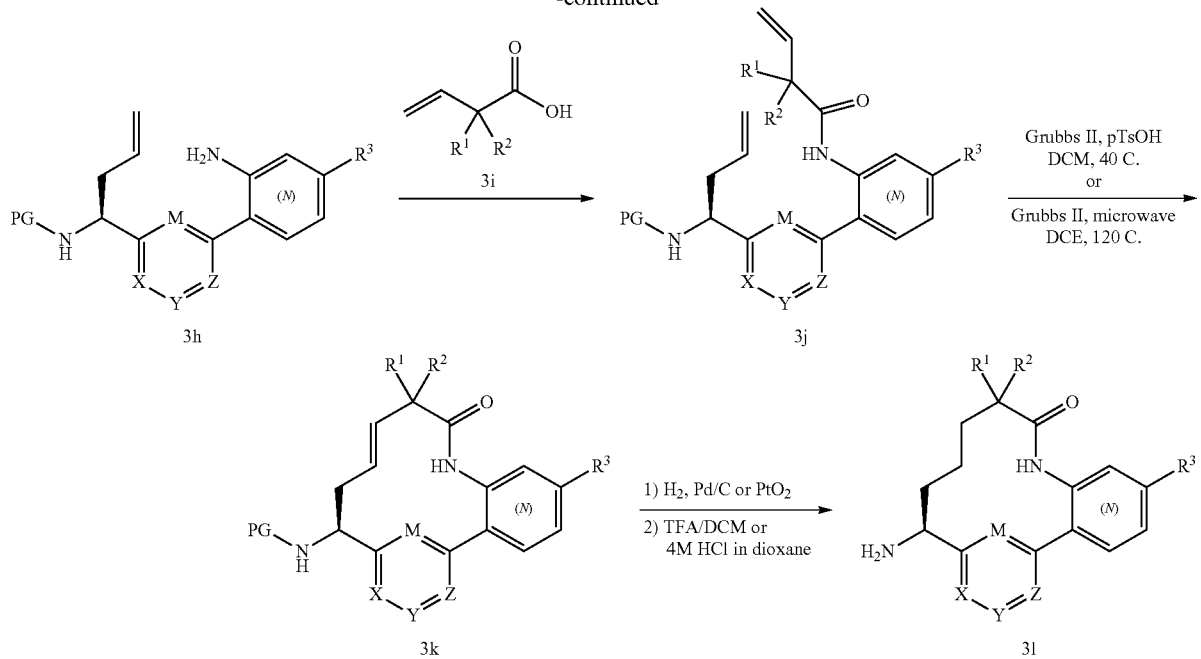

Methods for synthesis of a large variety of substituted pyridine compounds useful as starting materials for the preparation of compounds of the present invention are well known in the art and have been extensively reviewed. (For examples of methods useful for the preparation of pyridine starting materials see: Kroehnke, F., *Synthesis*, 1 (1976); Abramovitch, R. A., ed., "Pyridine and Its Derivatives", *The Chemistry of Heterocyclic Compounds*, 14(Suppl. 1-4), John Wiley & Sons, New York (1974); Boulton, A. J. et al., eds., *Comprehensive Heterocyclic Chemistry*, 2:165-524, Pergamon Press, New York (1984); McKillop, A., ed., *Comprehensive Heterocyclic Chemistry*, 5:1-300, Pergamon Press, New York (1996)).

In cases where suitably substituted boronic acids are not commercially available, a modification to this approach may be adopted wherein a heteroaryl halide is subjected to a palladium mediated coupling with a diboron species such as bis(pinacolato) diboron or bis(neopentyl glycolato)diboron to provide the corresponding 4,4,5,5-tetramethyl-[1,3,2]dioxaborolane or the 5,5-dimethyl-[1,3,2]dioxaborolane intermediates using the method of Ishiyama, T. et al. (*J. Org. Chem.*, 60(23):7508-7510 (1995)). Alternately, this same intermediate can be prepared by reaction of the intermediate halide with the corresponding dialkoxyhydroborane as described by Murata et al. (*J. Org. Chem.*, 62(19):6458-6459 (1997)). The boron pinacolate intermediates can be used in place of boronic acids for coupling to the aryl/heteroaryl halides or triflates or the boron pinacolate intermediate can be converted to the boronic acids. Alternately, the corresponding boronic acids can be prepared by metal-halogen exchange of the aryl/heteroaryl halide, quenching with a trialkoxyborate reagent, and aqueous workup to provide the boronic acids (Miyaura, N. et al., *Chem. Rev.*, 95:2457 (1995)).

It is also realized that the scope of intermediate synthesis can be further extended outside the use of Suzuki-Miyaura coupling methodology since the precursor heteroaryl halides or triflates described above are also precursors for Stille, Negishi, Hiyama, and Kumada-type cross coupling methodologies (Tsuji, J., *Transition Metal Reagents and Catalysts: Innovations in Organic Synthesis*, John Wiley & Sons (2000); Tsuji, J., *Palladium Reagents and Catalysts: Innovations in Organic Synthesis*, John Wiley & Sons (1996)).

Intermediates for preparation of compounds of the present invention wherein ring A is an imidazole ring, can be prepared from an appropriately N-protected allylglycine (4a) according to the general method outlined in Scheme 4 (Contour-Galcera et al., *Bioorg. Med. Chem. Lett.*, 11(5): 741-745 (2001)). Condensation of 4a with a suitably substituted alpha-bromo-ketone bearing a heteroaryl group (4b) in the presence of a suitable base such as potassium bicarbonate, potassium carbonate or cesium carbonate in a suitable solvent such as DMF provides a keto ester intermediate which can be cyclized to afford an imidazole (4c) by heating in the presence of excess ammonium acetate in a solvent such as toluene or xylene. This latter transformation can be conveniently carried out on small scale at 160° C. in a microwave reactor or on larger scale by refluxing the mixture while removing water via a Dean-Stark trap. The resulting imidazole intermediate (4c) is then protected by treatment with SEM-Cl in the presence of a base such as sodium hydride or dicyclohexylmethylamine in a solvent such as THF or DCM. The resulting heteroaryl bromide (4d) is then converted to the corresponding amino-heterocyclyl (4e) by heating in a sealed vessel with excess ammonium hydroxide, in the presence of copper iodide, a base such as potassium carbonate and a catalytic amount of proline in DMSO as solvent. Acylation of 4e with the appropriate alkenoic acid and a coupling agent such as T3P® or BOP reagent, or alternately, by treatment with an alkenoic acid chloride in the presence of a base such as TEA, DIPEA, or pyridine provides diene 4f, which undergoes ring closing metathesis by heating in dilute solution in the presence of p-toluene sulfonic acid and Second Generation Grubbs Catalyst in a suitable solvent such as DCM or DCE to provide the corresponding macrocycle (4g). Alternately, the RCM can be run in a microwave at elevated temperatures without pTsOH. Reduction of the double bond followed by bromination with NBS at room temperature affords 4h. Suzuki-Miyaura coupling with methylboronic acid or tetramethylstannane and removal of the protecting group (PG), provides intermediate 4i. Intermediate 4i can be converted to compounds of the present invention following the steps described in Scheme 1.

Scheme 4

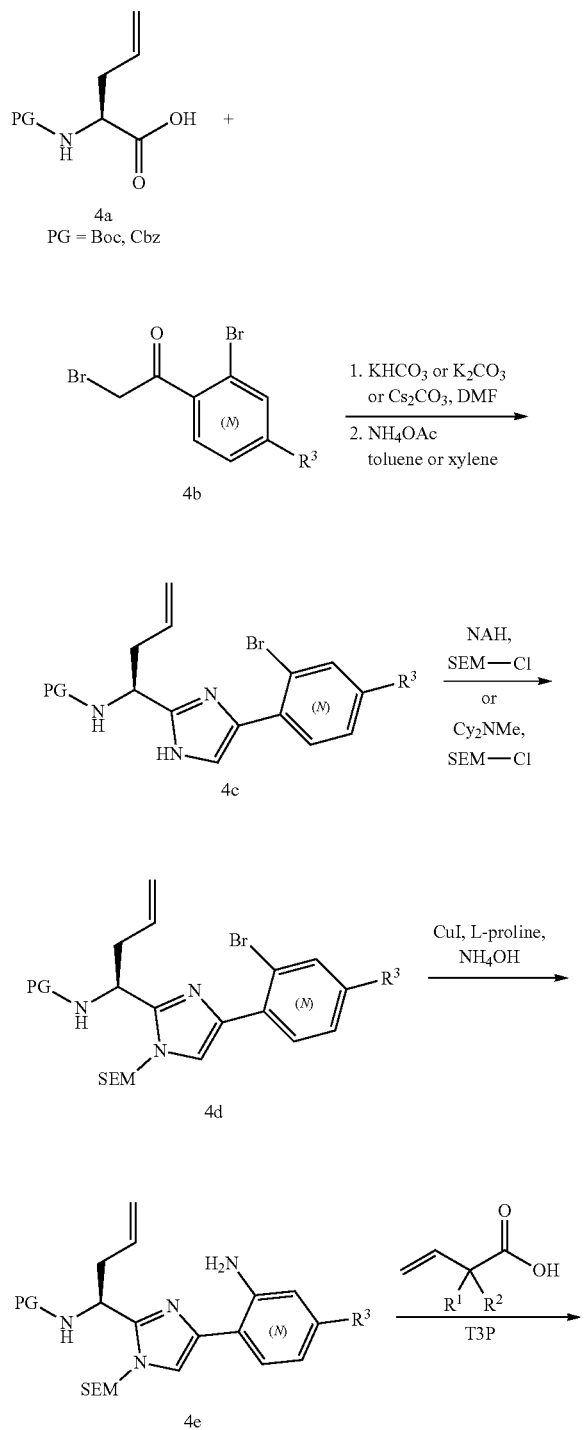

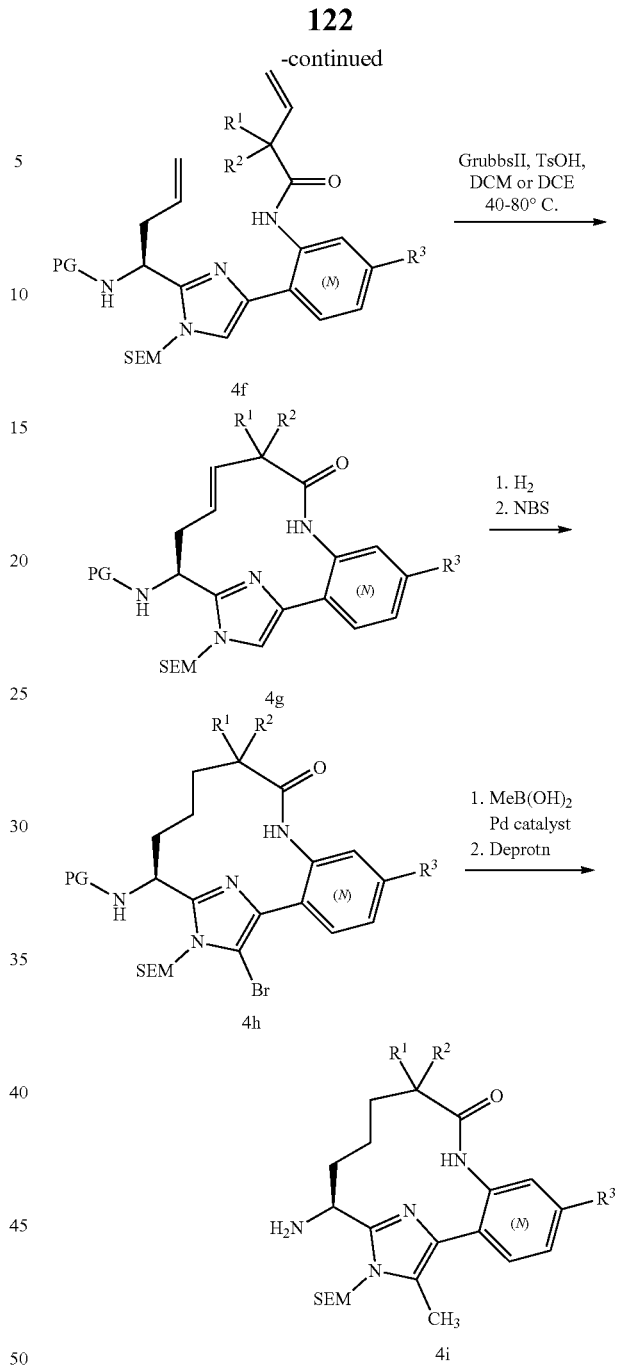

Scheme 5 describes the intermediates in the present invention where ring B is a heterocyclyl (example—pyrazole). Chloropyridine 3b undergoes protecting group interconversion to provide 5a which can be coupled to 4-nitropyrazoles 5b upon heating with a Pd(II) salt such as Pd(OAc)$_2$ in the presence of a phosphine ligand and a base such as potassium carbonate in a solvent such as DMF or DMA, as described by Sames (Goikhman, R., Jacques, T. L. and Sames, D., *J. Am. Chem. Soc.*, 131:3042 (2009)). Zinc/HOAc reduction of the nitropyrazole, 5c, followed by amidation with an appropriately substituted carboxylic acid, 5d, provides 5e. Macrocyclization is then accomplished via ring-closing metathesis using the Grubb's second generation ruthenium catalyst to yield 5f. Hydrogenation of the resulting olefin and protecting group cleavage yields amine 5g.

Compounds of the formulae 5g can be converted to compounds in this invention upon coupling with an appropriately substituted pyrimidin-4-ol derivative, 1b, according to Scheme 1.

Scheme 5

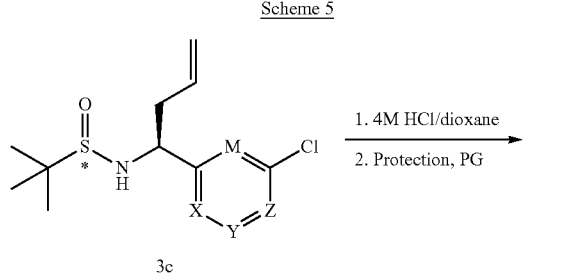

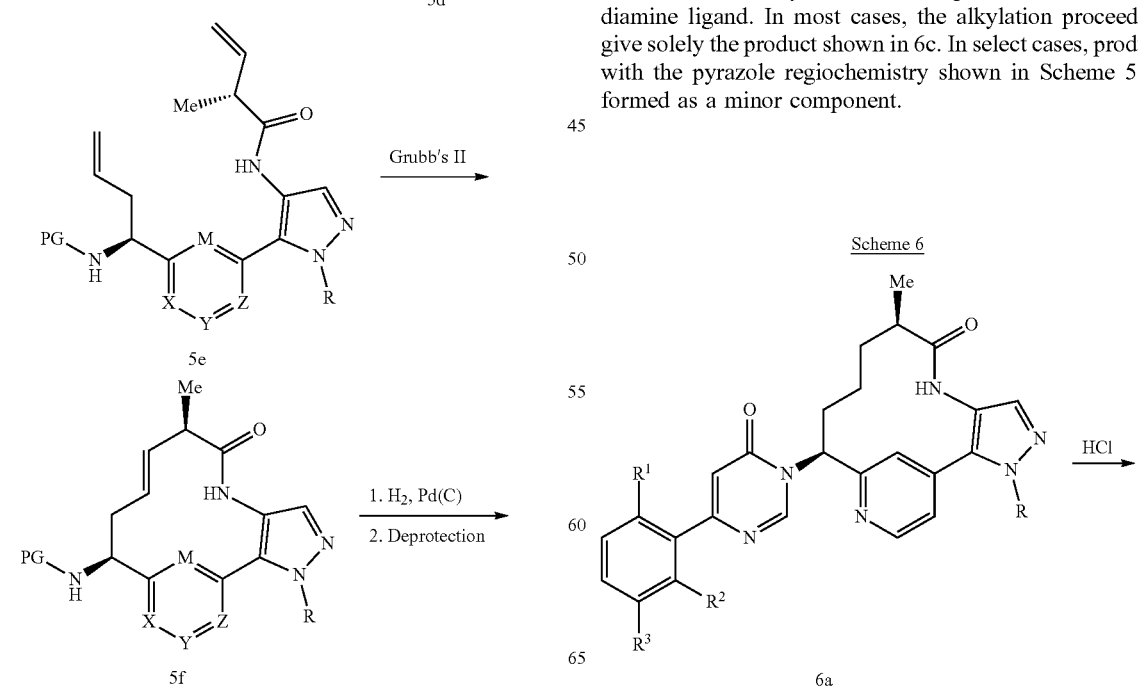

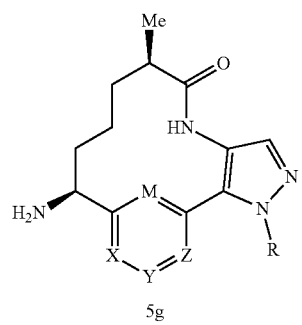

Compounds in this invention bearing alternate regiochemical pyrazole substitution can be synthesized as shown in Scheme 6. When R is an appropriate protective group (example—trimethylsilylethoxymethyl), deprotection of 6a to 6b can be followed by alkylation with an alkyl halide under basic conditions, upon reaction with a boronic acid in the presence of Cu(II) salts such as $Cu(OAc)_2$, or upon reaction with an aryl iodide in the presence of CuI and a diamine ligand. In most cases, the alkylation proceeds to give solely the product shown in 6c. In select cases, products with the pyrazole regiochemistry shown in Scheme 5 are formed as a minor component.

Compounds in this invention bearing alternate regiochemical pyrazole substitution can be synthesized as shown in Scheme 6. When R is an appropriate protective group (example—trimethylsilylethoxymethyl), deprotection of 6a to 6b can be followed by alkylation with an alkyl halide under basic conditions, upon reaction with a boronic acid in the presence of Cu(II) salts such as $Cu(OAc)_2$, or upon reaction with an aryl iodide in the presence of CuI and a diamine ligand. In most cases, the alkylation proceeds to give solely the product shown in 6c. In select cases, products with the pyrazole regiochemistry shown in Scheme 5 are formed as a minor component.

Scheme 6

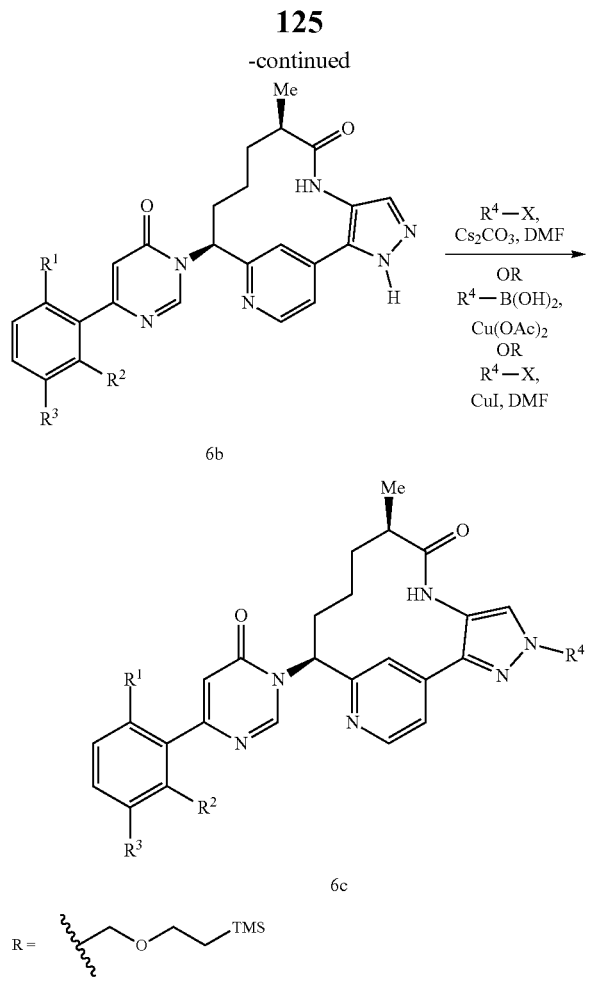

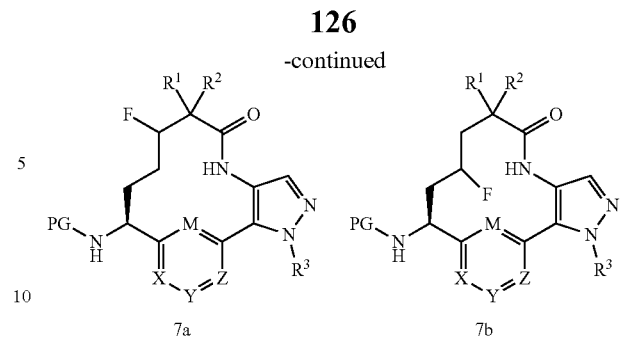

Intermediates for preparation of compounds of the present invention corresponding to Formula V can be prepared according to Scheme 8. Chloropyridine 5a is reacted with aqueous hydrazine to generate substituted hydrazine 8a. This hydrazine can be cyclized upon treatment with α-cyanoketones 8b to yield aminopyrazoles 8c. These intermediates (8c) can be elaborated to compounds of this invention according to the procedures described in Schemes 1 and 3.

Intermediates for preparation of compounds of the present invention wherein $R^{1a}$ is —F can be prepared according to Scheme 7. Olefin 5f can be subjected to hydrofluorination, yielding as many as four isomeric alkyl fluorides. Following separation of the isomers, deprotection of the amine protecting group is accomplished by the action of either TFA or HCl, as previously shown in Schemes 3-5. The intermediate 7a and 7b can be elaborated to compounds of this invention according to the procedure described in Scheme 1.

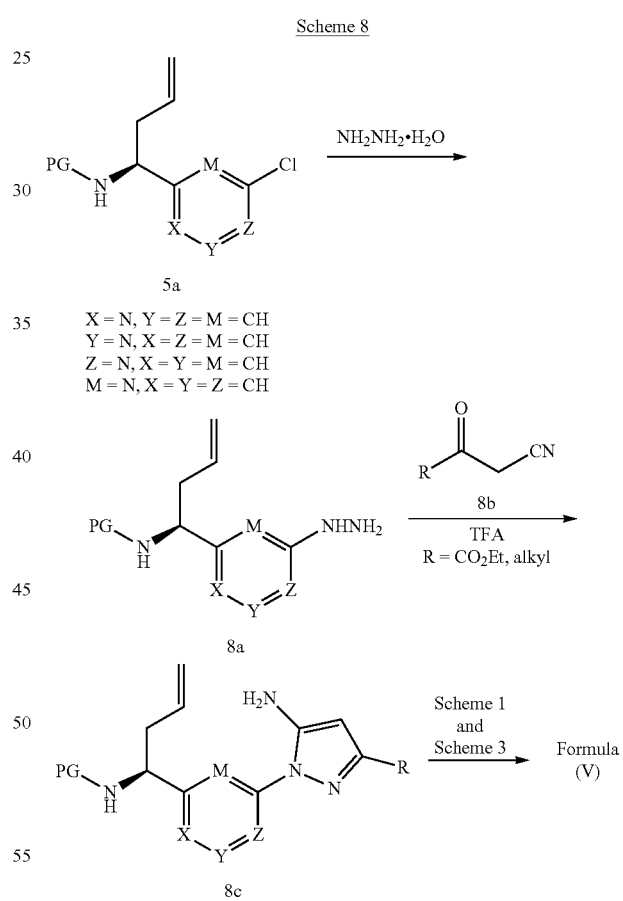

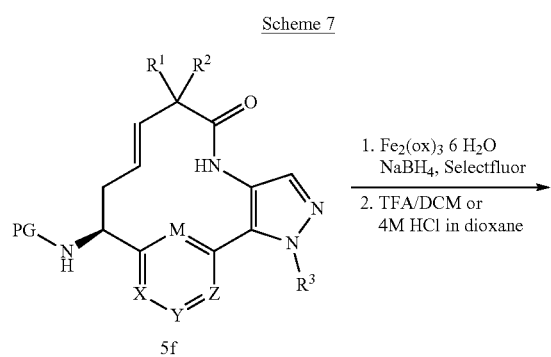

Scheme 9 describes the synthesis of suitably substituted pyrimidin-4-ol derivatives where $G^1$ is a substituted phenyl. Aniline 9a can be converted to a suitably substituted triazole 9b in a one pot, two step sequence. Specifically, the aniline 9a is converted to the aryl azide in situ followed by cycloaddition with a suitably substituted alkyne in the presence of a copper catalyst, such as $Cu_2O$, to provide 9b. Demethylation of 9b according to Scheme 2 provides the pyrimidin-4-ol derivatives 9c. When $R^{10}$ is a trimethylsilyl group, the silyl moiety can be converted to a chloride at elevated temperature with NCS in the presence of silica gel. Aniline 9a can be converted to the iodide 9d with p-TsOH, NaNO$_2$, and NaI. Subjecting iodide 9d to a variety of N-arylation or Suzuki-Miyaura couplings, followed by demethylation according to Scheme 2, gives additional pyrimidin-4-ol derivatives 9e. When R$^8$ is tetrazole, intermediate 9g can be prepared by first treatment of the aniline 9a with trimethoxymethane and sodium azide followed by demethylation according to Scheme 2.

Scheme 10 describes the synthesis of suitably substituted pyrimidin-4-ol derivatives where R$^8$ is a thiadiazole. Bromide 10a can be converted to acetyl compound 10b by coupling with 1-(trimethylsilyl)ethanone with Pd catalyst. 10b can react with ethyl hydrazinecarboxylate to form 10c, which upon treatment with SOCl$_2$ to give thiadiazole compound 10d. Intermediate 10e can be obtained by demethylation of 10d according to Scheme 2.

Scheme 9

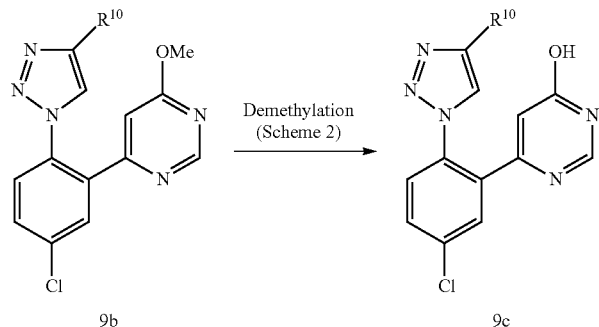

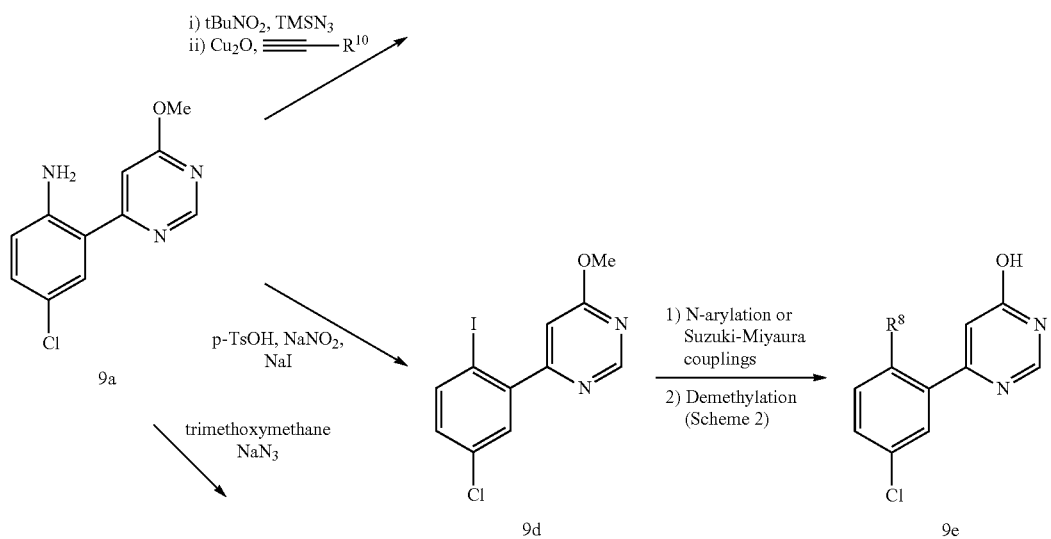

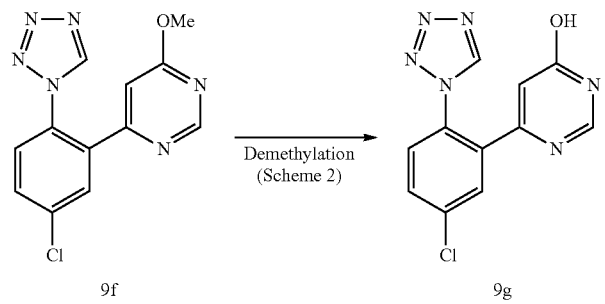

R$^8$ = aryl, heterocyclyl

Scheme 10

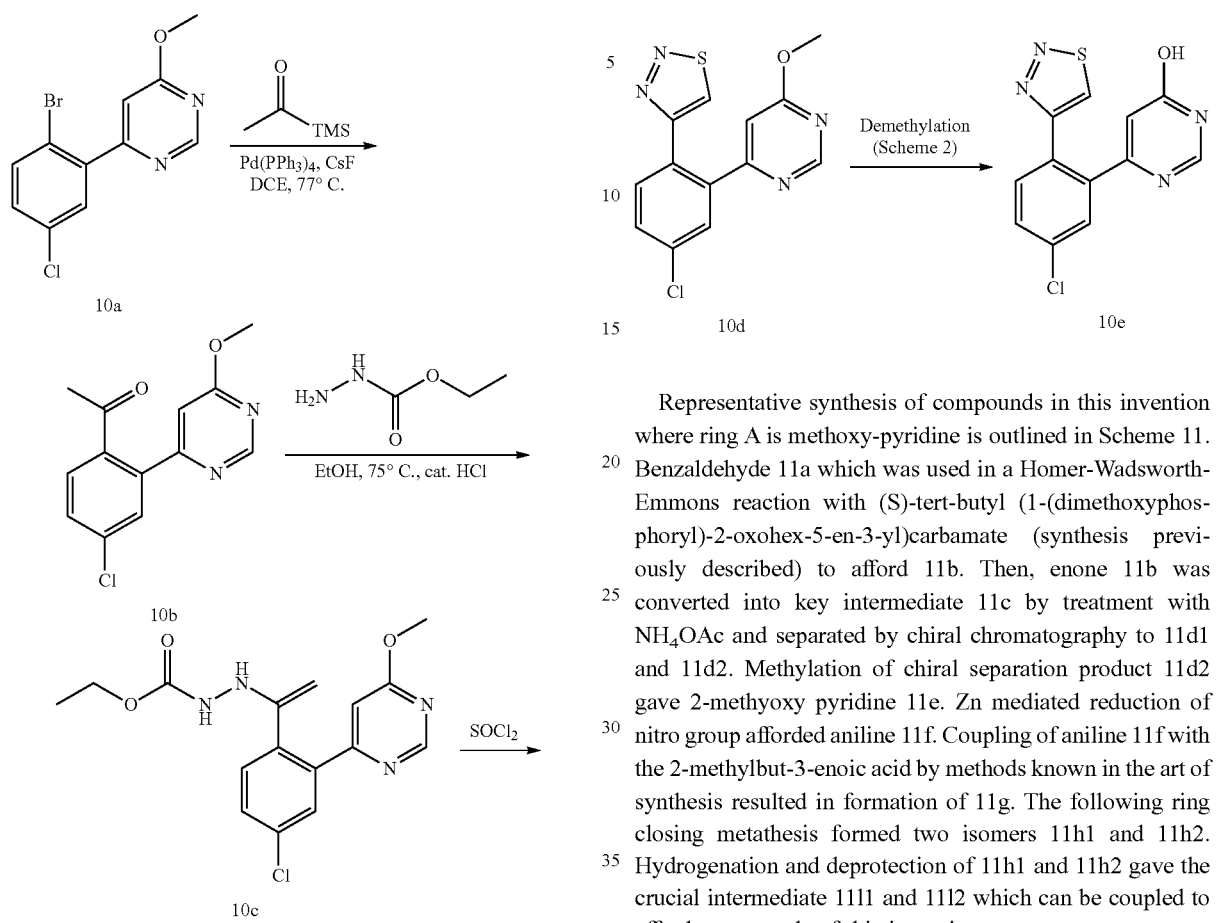

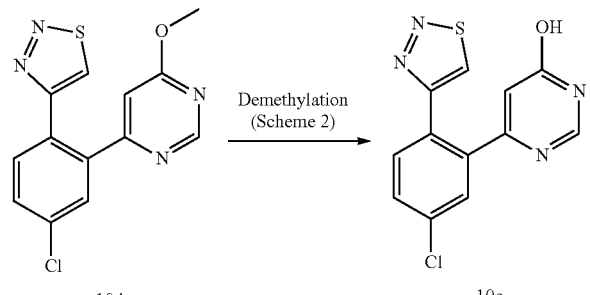

Representative synthesis of compounds in this invention where ring A is methoxy-pyridine is outlined in Scheme 11. Benzaldehyde 11a which was used in a Homer-Wadsworth-Emmons reaction with (S)-tert-butyl (1-(dimethoxyphosphoryl)-2-oxohex-5-en-3-yl)carbamate (synthesis previously described) to afford 11b. Then, enone 11b was converted into key intermediate 11c by treatment with NH₄OAc and separated by chiral chromatography to 11d1 and 11d2. Methylation of chiral separation product 11d2 gave 2-methyoxy pyridine 11e. Zn mediated reduction of nitro group afforded aniline 11f. Coupling of aniline 11f with the 2-methylbut-3-enoic acid by methods known in the art of synthesis resulted in formation of 11g. The following ring closing metathesis formed two isomers 11h1 and 11h2. Hydrogenation and deprotection of 11h1 and 11h2 gave the crucial intermediate 11I1 and 11I2 which can be coupled to afford compounds of this invention.

Scheme 11

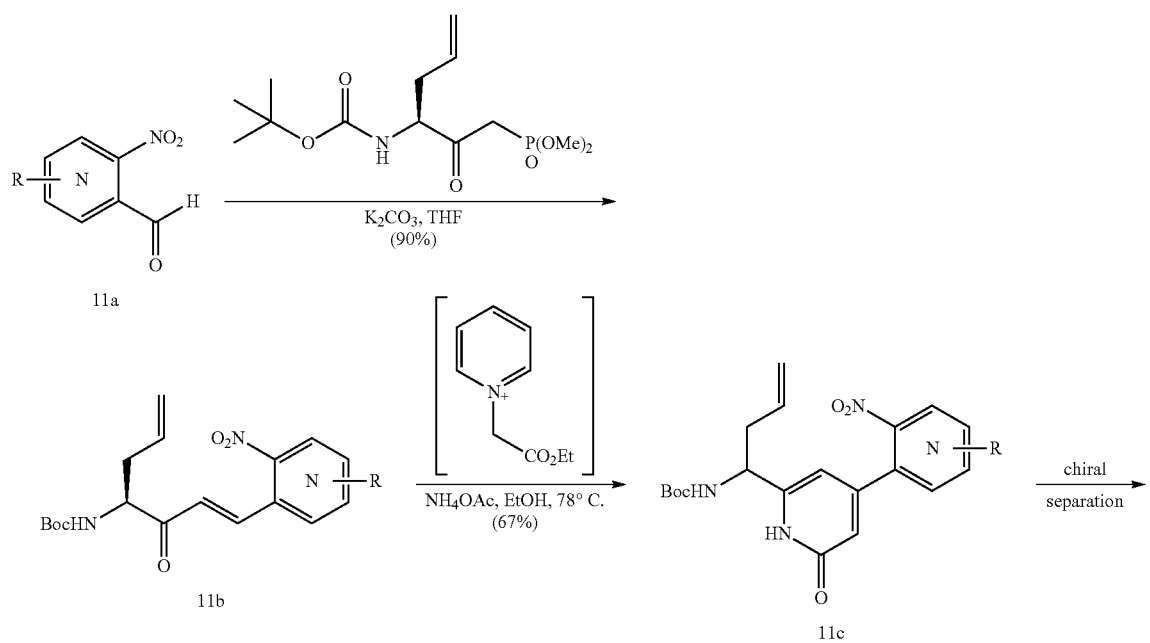

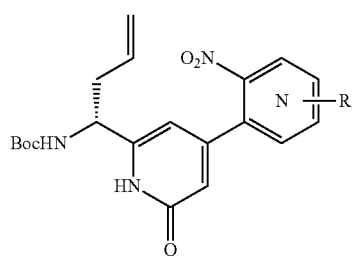
Peak 1
Enantiomer A
11d1
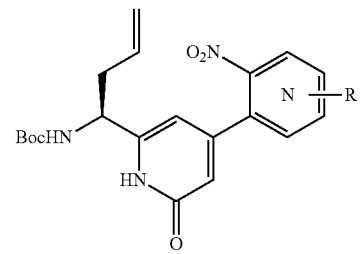
Peak 2
Enantiomer B
11d2
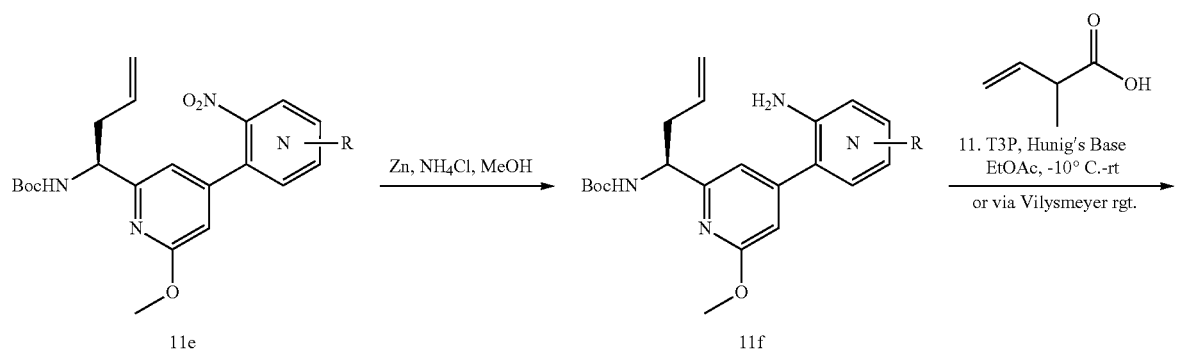
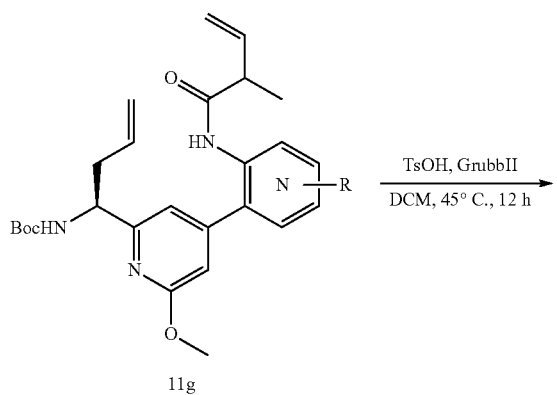
11g
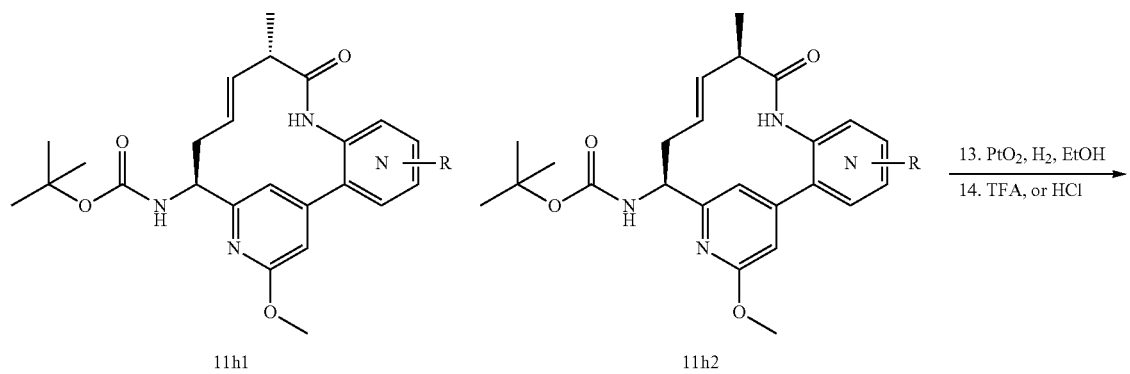

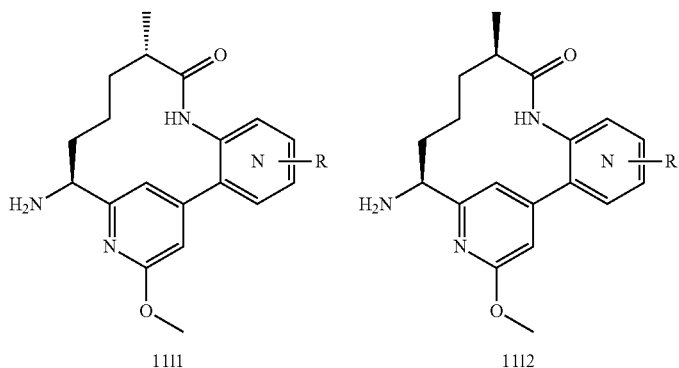
The corresponding pyridone compounds of this invention can also be prepared by the methodologies outlined in Schemes 12 to 14.
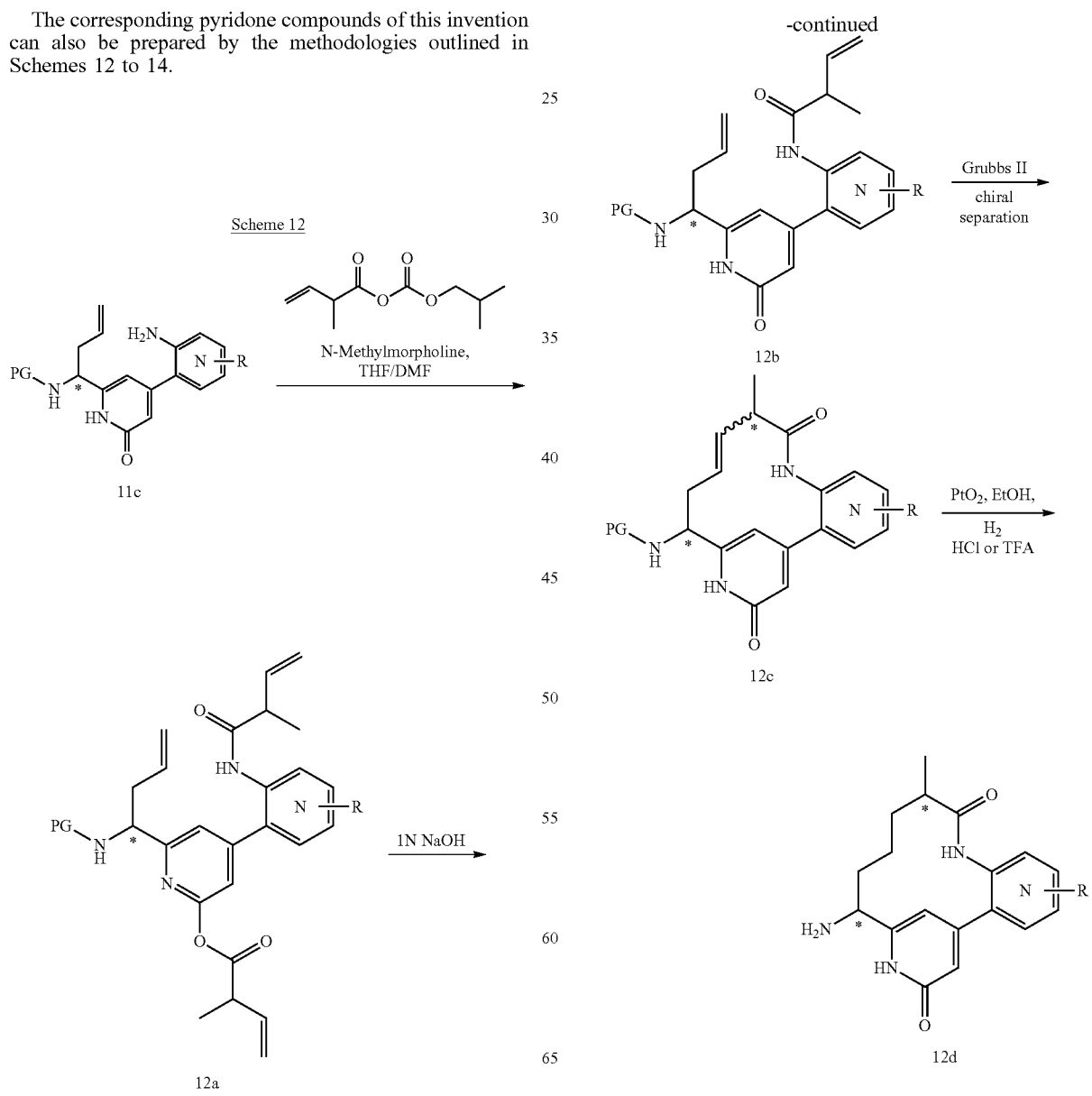

Scheme 13
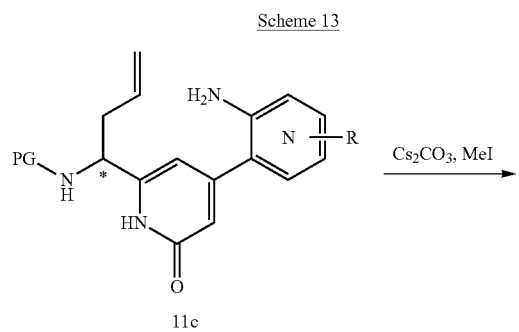
11c
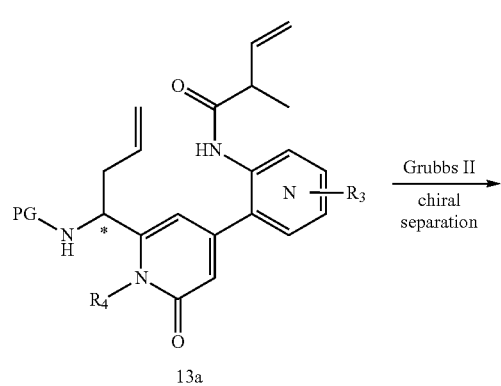
13a
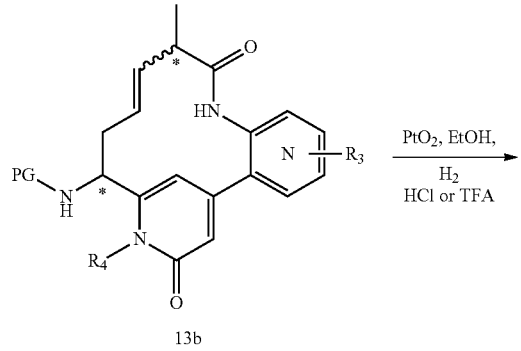
13b
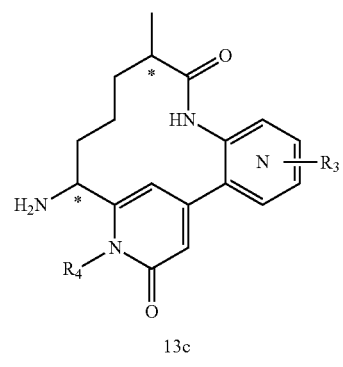
13c
Scheme 14
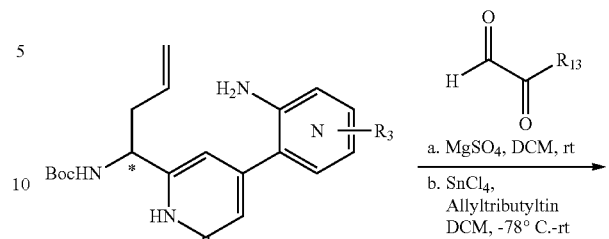
11c
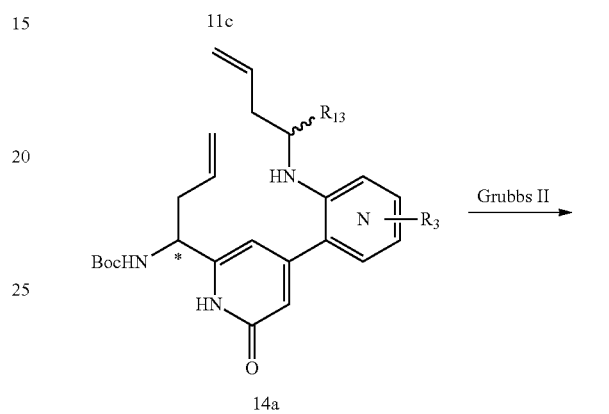
14a
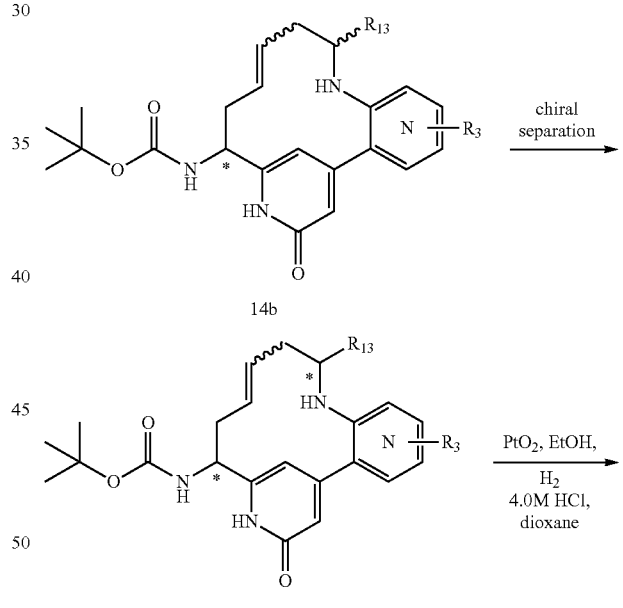
14b
14c
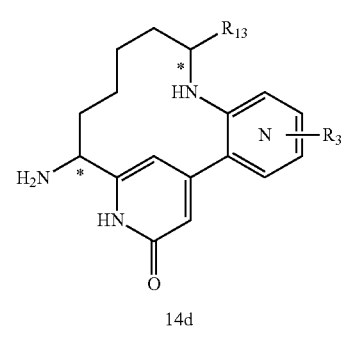
14d Other azole containing compounds of this invention can also be accessed via the schematic shown in Scheme 15 by following the procedure outlined for the pyridine/one ring systems.

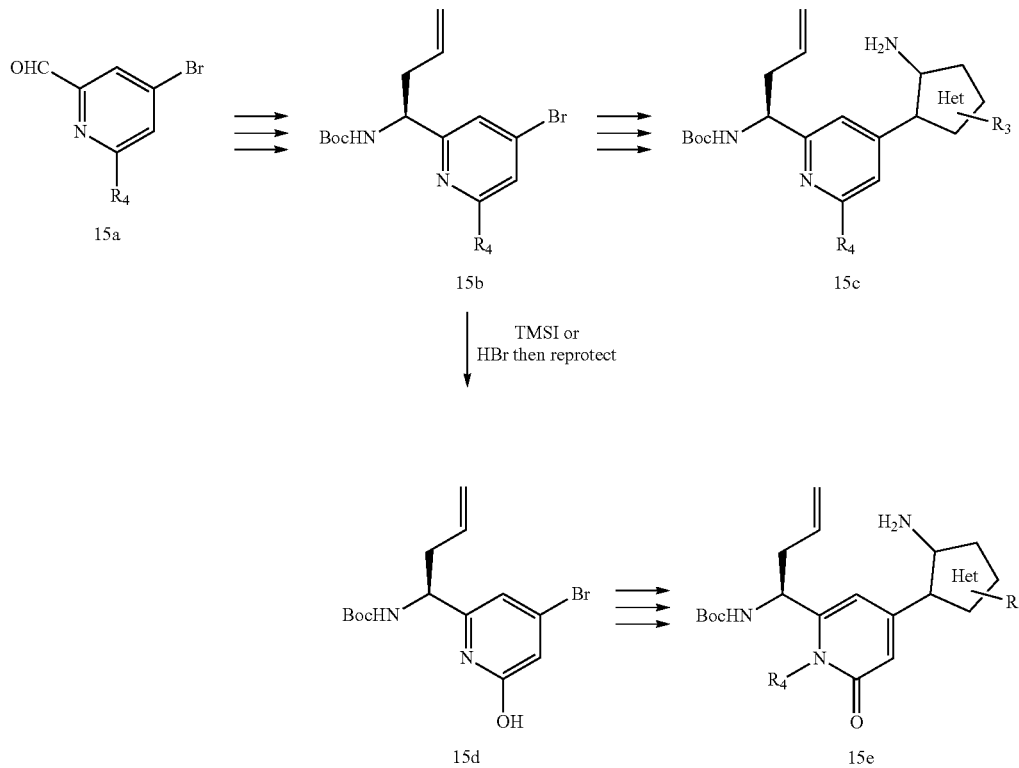

Scheme 15

R4 = OH, OMe

Alternatively, Examples 353-373 of the present invention can also be made by the following schemes.

Representative pyrimidinone compounds 1a of this invention can be prepared as described in Scheme 1A. Using a modified procedure described by Xiao (*Org. Lett.,* 11:1421 (2009)), suitably substituted pyrimidin-4-ol derivatives 1b can be coupled with an appropriately substituted macrocycle amine 1c in the presence of HATU and DBU in a solvent such as $CH_3CN$ to provide pyrimidinone compounds 1a. When ring A is a SEM-protected imidazole ring, an additional deprotection step employing 4M HCl in dioxane or TFA in DCM is required to afford compounds of this invention.

Scheme 1A

-continued

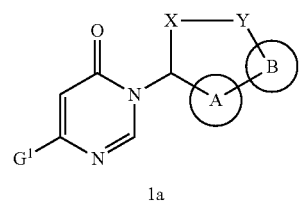

1a

Scheme 2A describes the synthesis of suitably substituted pyrimidin-4-ol derivatives 1b. Suzuki-Miyaura coupling between 6-chloropyrimidin-4-ol (2a) and an appropriately substituted aryl or heteroaryl boronic acid or ester 2c in the presence of a base such as Hunig's base or potassium phosphate tribasic, in a solvent mixture, such as toluene and ethanol, or THF, using a precatalyst such as $Pd(PPh_3)_4$ or $2^{nd}$ generation XPhos provides 1b. Alternatively, when 4-chloro-6-methoxypyrimidine 2b is used, an additional deprotection step, employing aqueous HBr at elevated temperatures, is required to provide pyrimidin-4-ol derivatives 1b.

Scheme 2A

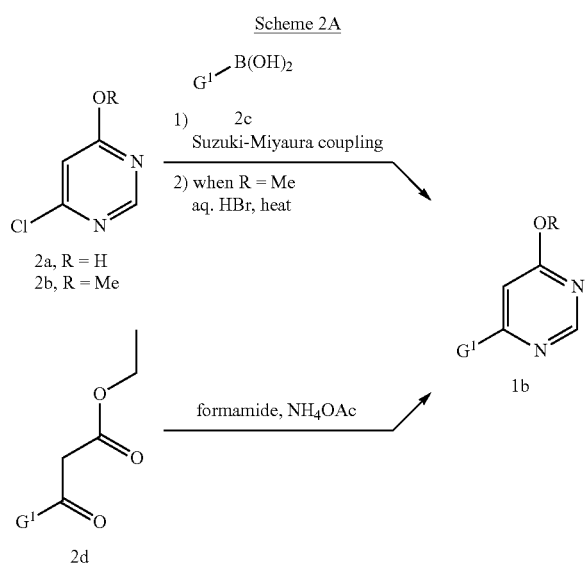

Intermediates for preparation of compounds of the present invention wherein ring A is a 6-membered heterocycle (example—pyridine) can be derived from appropriately substituted aldehydes 3a according to the general method outlined in Scheme 3A. Condensation of aldehyde 3a (X=N) prepared according to a modified procedure described by Negi (*Synthesis*, 991 (1996)), with (S)-2-methylpropane-2-sulfinamide in the presence of anhydrous copper sulfate or cesium carbonate in a solvent such as DCM gives the sulfinimine 3b (Ellman, J., *J. Org. Chem.*, 64:1278 (1999)). Using a modified procedure described by Kuduk (*Tetrahedron Letters*, 45:6641 (2004)), suitably substituted Grignard reagents, for example, allylmagnesium bromide, can be added to sulfinimine 3b to give a sulfinamide 3c, as a mixture of diastereomers which can be separated at various stages of the sequence. The diastereoselectivity for the addition of allyl magnesium bromide to sulfinimine 3b can be improved by employing indium(III) chloride according to a modified procedure of Xu (Xu, M.-H., *Org. Lett.*, 10(6): 1259 (2008)). Protecting group interconversion can be accomplished in two steps to give 3d. The critical subunit coupling is accomplished via methodology developed by Sames (*J. Am. Chem. Soc.*, 131:3042 (2009)). Treatment of chloropyridine 3d with N-protected nitropyrazole 3e in the presence of catalytic Pd(OAc)$_2$ and P(nBu)Ad$_2$ forges the desired arylpyrazole bond, forming 3f. Reduction of this nitropyrazole yields 3g. This aminopyrazole can then be coupled with an appropriately substituted carboxylic acid 3h using T3P® and a base, such as pyridine, to give the amide 3i. The diene can be cyclized via ring-closing metathesis using a catalyst, such as Grubbs (II), in a suitable solvent, such as EtOAc at elevated temperature, to give the pyridine-containing macrocycle 3j. The alkene can be reduced with hydrogen over either palladium on carbon or platinum oxide. The second coupling reaction is then carried out as described in Scheme 1 with pyrimidinol 3k to yield pyrimidinone 3l. Subsequent deprotection of the pyrazole with TFA in DCM or 4M HCl in dioxane provides followed by Ullmann coupling with an aryl iodide affords 3m as a major regioisomer. If 3n is formed, it is the minor component of the product mixture.

Scheme 3A

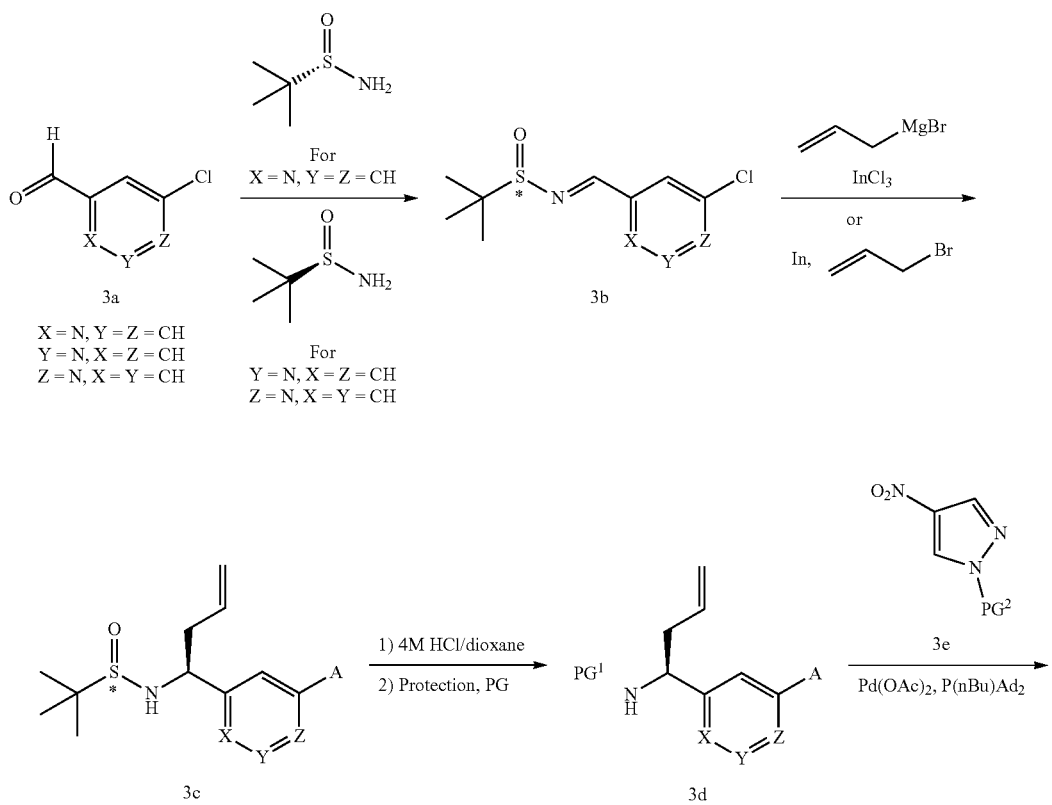

-continued

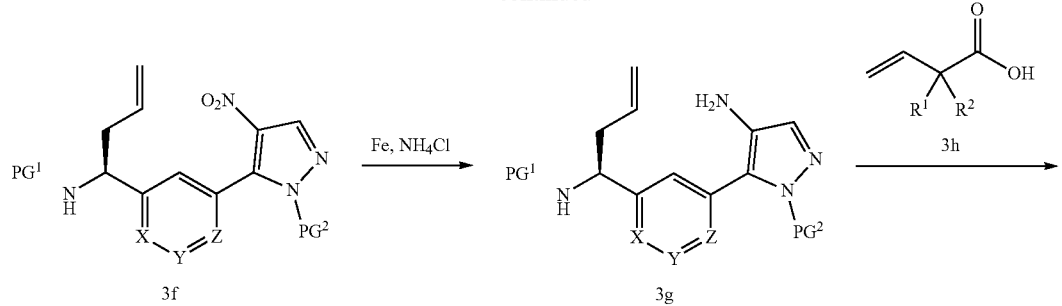

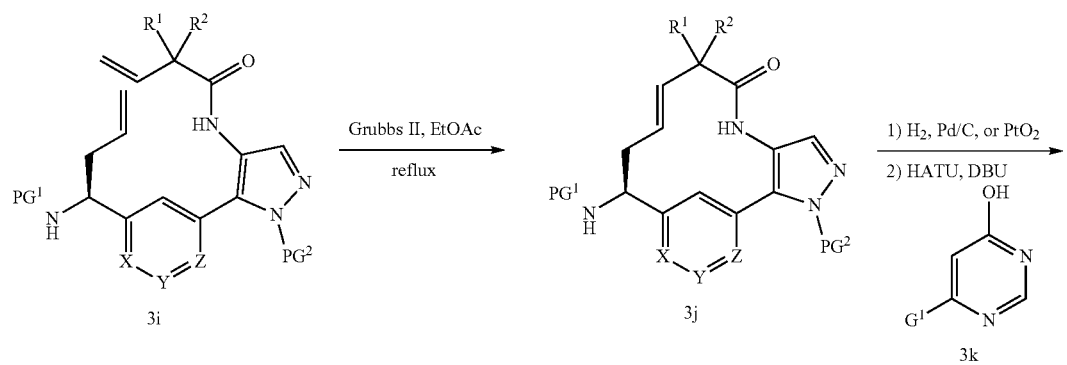

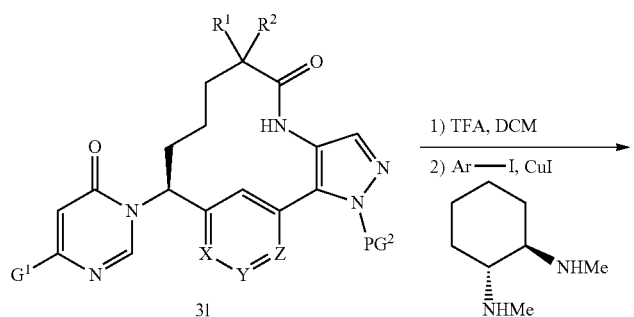

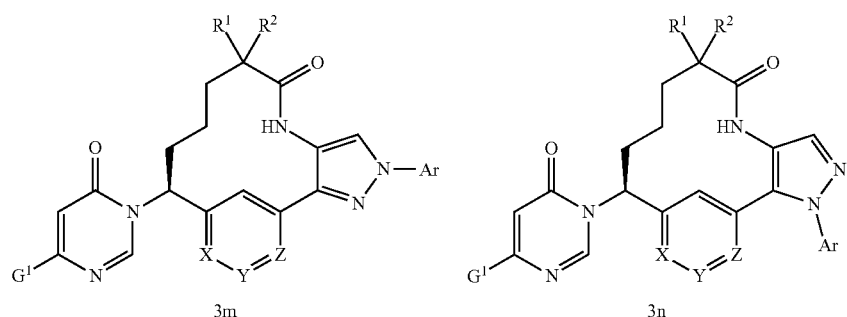

Compounds like 3n can be obtained as exclusive products following the synthetic procedures in Scheme 4A. All operations are analogous to those in Scheme 3 up until the pyrazole coupling reaction. Appropriately substituted nitro-pyrazoles 4a yield the shown regioisomeric pyrazoles 4b under the same conditions described in Scheme 3. Reduction to 4c, amidation with 3h to form 4d, and ring-closing metathesis to form macrocycle 4e occur in a similar fashion as well. Reduction of the olefin and deprotection are followed by pyrimidinol coupling, as described in Schemes 1A and 3A.

Scheme 4A

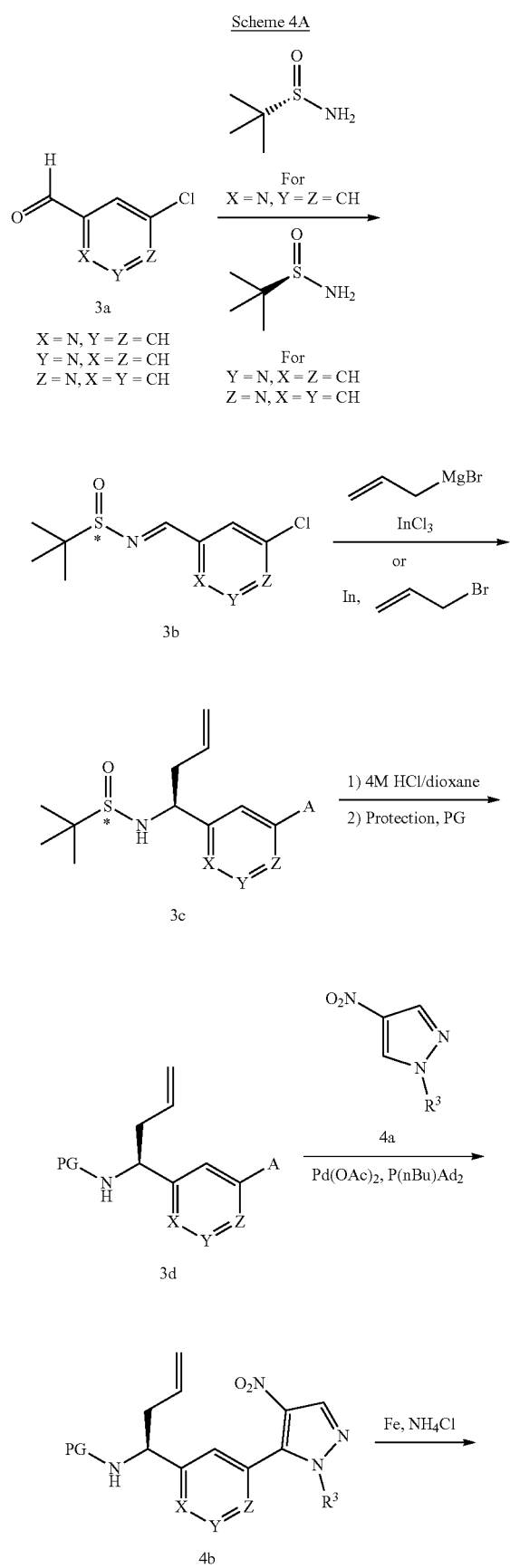

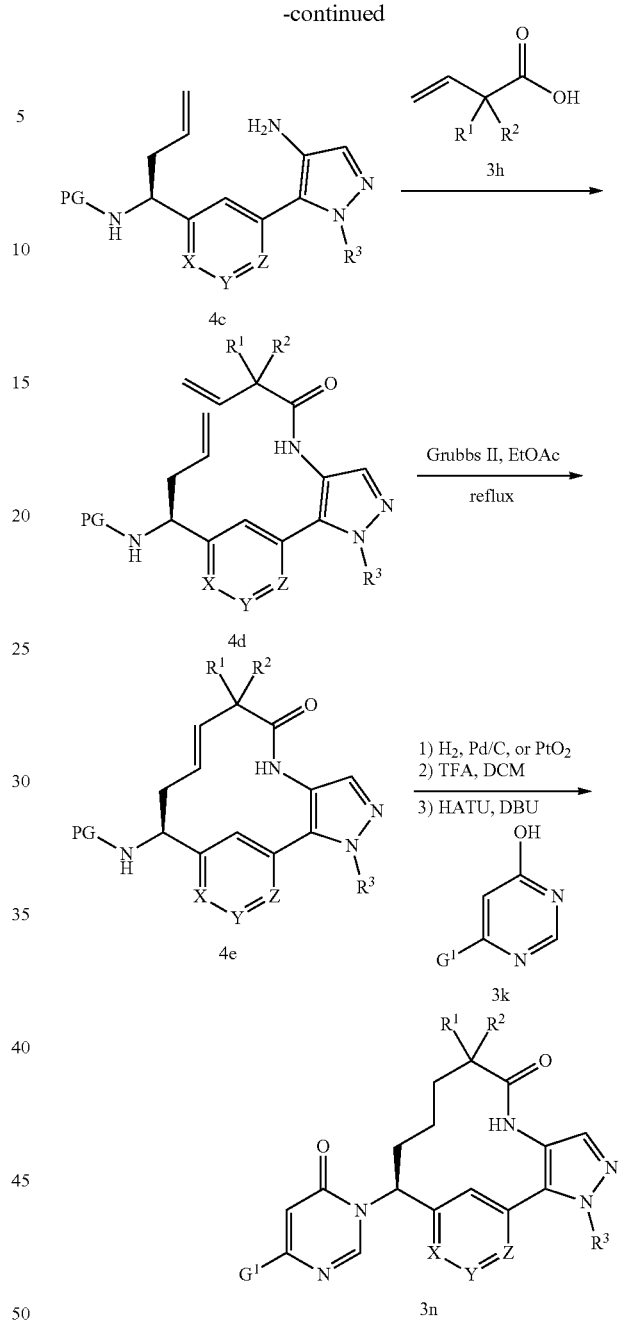

Purification of intermediates and final products was carried out via either normal or reverse phase chromatography. Normal phase chromatography was carried out using pre-packed $SiO_2$ cartridges eluting with either gradients of hexanes and EtOAc or DCM and MeOH unless otherwise indicated. Reverse phase preparative HPLC was carried out using C18 columns eluting with gradients of Solvent A (90% water, 10% MeOH, 0.1% TFA) and Solvent B (10% water, 90% MeOH, 0.1% TFA, UV 220 nm) or with gradients of Solvent A (90% water, 10% ACN, 0.1% TFA) and Solvent B (10% water, 90% ACN, 0.1% TFA, UV 220 nm) or with gradients of Solvent A (98% water, 2% ACN, 0.05% TFA) and Solvent B (98% ACN, 2% water, 0.05% TFA, UV 220 nm) (or) SunFire Prep C18 OBD 5μ 30×100 mm, 25 min gradient from 0-100% B. A=H2O/ACN/TFA 90:10:0.1. B=ACN/H2O/TFA 90:10:0.1

Unless otherwise stated, analysis of final products was carried out by reverse phase analytical HPLC.

Method A: Waters SunFire column (3.5 μm C18, 3.0×150 mm). Gradient elution (0.5 mL/min) from 10-100% Solvent B for 12 min and then 100% Solvent B for 3 min was used. Solvent A is (95% water, 5% acetonitrile, 0.05% TFA) and Solvent B is (5% water, 95% acetonitrile, 0.05% TFA, UV 254 nm).

Method B: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Method C: Waters Acquity UPLC BEH C18, 2.1×50 mm, 1.7-μm particles; Mobile Phase A: 5:95 acetonitrile:water with 0.1% TFA; Mobile Phase B: 95:5 acetonitrile:water with 0.1% TFA; Temperature: 50° C.; Gradient: 0-100% B over 3 minutes, then a 0.75-minute hold at 100% B; Flow: 1.11 mL/min Method X: ZORBAX® SB C18 column (4.6×75 mm). Gradient elution (2.5 mL/min) from 0-100% Solvent B for 8 min and then 100% Solvent B for 2 min was used. Solvent A is (90% water, 10% MeOH, 0.02% $H_3PO_4$) and Solvent B is (10% water, 90% MeOH, 0.02% $H_3PO_4$, UV 220 nm).

Intermediate 1

Preparation of N-(4-chloro-2-(6-hydroxypyrimidin-4-yl)phenyl)-2,2,2-trifluoroacetamide

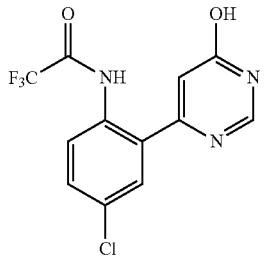 [SMILES: O=C(Nc1ccc(Cl)cc1-c1cc(O)ncn1)C(F)(F)F]

1A. Preparation of N-(4-chloro-2-(6-methoxypyrimidin-4-yl)phenyl)-2,2,2-trifluoroacetamide $Et_3N$ (2.1 mL, 15.3 mmol) was added to a solution of 4-chloro-2-(6-methoxypyrimidin-4-yl)aniline (3 g, 12.7 mmol) and TFAA (2.2 mL, 15.3 mmol) in DCM (100 mL). The solution was stirred for 1 h at rt. The solution was then concentrated to about 15 mL volume and purified by normal phase silica gel chromatography (hexanes-EtOAc gradient) to yield N-(4-chloro-2-(6-methoxypyrimidin-4-yl)phenyl)-2,2,2-trifluoroacetamide (4 g, 12.06 mmol, 95% yield) as a white powder.

1B. Preparation of N-(4-chloro-2-(6-hydroxypyrimidin-4-yl)phenyl)-2,2,2-trifluoroacetamide A clear, orange solution of N-(4-chloro-2-(6-methoxypyrimidin-4-yl)phenyl)-2,2,2-trifluoroacetamide (3.2 g, 9.65 mmol) in HOAc (20 ml) and 48% aq HBr (5.5 ml, 48.2 mmol) was warmed to 60° C. for 1.5 h. The reaction was cooled to rt and the solvents were removed in vacuo. EtOAc (100 mL) and sat aq $NaHCO_3$ were added to the residue. The aqueous layer was then extracted twice with EtOAc (50 mL). The combined organic layers were dried with $MgSO_4$ and concentrated. The residue was triturated with $Et_2O$ and filtered to yield N-(4-chloro-2-(6-hydroxypyrimidin-4-yl)phenyl)-2,2,2-trifluoroacetamide (1.2 g, 3.78 mmol, 39.2% yield) as a white powder.

Intermediate 2

Preparation of (R)-2-methylbut-3-enoic Acid

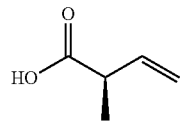

2A. Preparation of (R)-4-benzyl-3-((R)-2-methylbut-3-enoyl)oxazolidin-2-one

To the solution of 2-methylbut-3-enoic acid (5.59 g, 55.9 mmol) and NMM (6.14 mL, 55.9 mmol) in THF (62 mL) at 0° C. was added pivaloyl chloride (6.87 mL, 55.9 mmol) dropwise. The reaction mixture was cooled down to −78° C., and stirred for ~2 h. In a separate flask: To the solution of (R)-4-benzyloxazolidin-2-one (8.25 g, 46.6 mmol) in THF (126 mL) at −78° C. was added 2.5 M nBuLi in hexane (20.49 mL, 51.2 mmol) dropwise. After 35 min, this reaction was transferred via cannula to the first reaction. The reaction mixture was stirred at −78° C. for 2 h, then the cold bath was removed, and the reaction was quenched with sat $NH_4Cl$. The reaction was diluted with water and extracted with EtOAc (3×). The combined organic layers were washed with brine, dried over $Na_2SO_4$, filtered, and concentrated to give a yellow oil (15 g). Purification by silica gel chromatography afforded (R)-4-benzyl-3-((R)-2-methylbut-3-enoyl)oxazolidin-2-one (6.59 g, 55%) as a colorless oil. MS(ESI) m/z: 282.1 $(M+Na)^+$. $^1$H NMR (500 MHz, $CDCl_3$) δ 7.36-7.19 (m, 5H), 6.03-5.93 (m, 1H), 5.23-5.10 (m, 2H), 4.69-4.63 (m, 1H), 4.51-4.43 (m, 1H), 4.23-4.15 (m, 2H), 3.29 (dd, J 13.5, 3.3 Hz, 1H), 2.79 (dd, J=13.5, 9.6 Hz, 1H), 1.35 (d, J=6.9 Hz, 3H) ppm. The other diastereomer (R)-4-benzyl-3-((S)-2-methylbut-3-enoyl)oxazolidin-2-one (4.6 g, 38%) was also obtained as a white solid. MS(ESI) m/z: 260.1 $(M+H)^+$.

2B. Preparation of (R)-2-methylbut-3-enoic Acid

To a clear colorless solution of (R)-4-benzyl-3-((R)-2-methylbut-3-enoyl) oxazolidin-2-one (6.05 g, 23.33 mmol) in THF (146 mL) at 0° C. was added dropwise 30% aq $H_2O_2$ (9.53 mL, 93 mmol) followed by 2 N LiOH (23.33 mL, 46.7 mmol). After 30 min, the reaction was quenched with 25 mL of sat $Na_2SO_3$ and 25 mL of sat $NaHCO_3$. The reaction was then concentrated to remove the THF. The residue was diluted with water and extracted with $CHCl_3$ (3×). The aqueous layer was acidified with conc. HCl to pH ~3 and then it was extracted with EtOAc (3×). The EtOAc layers were combined, washed with brine, dried over $MgSO_4$, filtered and concentrated to afford (R)-2-methylbut-3-enoic acid (2.15 g, 92%) as a colorless oil. $^1$H NMR (500 MHz, $CDCl_3$) δ 10.84 (br. s., 1H), 5.94 (ddd, J=17.4, 10.1, 7.4 Hz, 1H), 5.22-5.13 (m, 2H), 3.23-3.15 (m, 1H), 1.31 (d, J=7.2 Hz, 3H) ppm.

Intermediate 3

Preparation of 6-(3-chloro-2-fluorophenyl)pyrimidin-4-ol

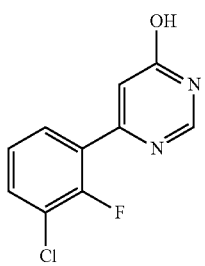 [SMILES: Oc1cc(-c2cccc(Cl)c2F)ncn1]

A microwave vial containing 6-chloropyrimidin-4-ol (0.100 g, 0.766 mmol), (3-chloro-2-fluorophenyl)boronic acid (0.534 g, 3.06 mmol), and Pd(PPh$_3$)$_4$ (0.089 g, 0.077 mmol) was purged with Ar for several min. Then degassed toluene (1.53 mL) and EtOH (1.53 mL) were added followed by DIEA (0.54 mL, 3.06 mmol). The vial was capped and the reaction was microwaved at 120° C. for 1 h. The resulting clear, orange solution was allowed to cool to rt and a precipitate formed. The yellow solid was removed by filtration, rinsing with 1:1 toluene/EtOH. A precipitate formed in the filtrate. The solid was collected by filtration, rinsed with cold 1:1 toluene/EtOH, air-dried, and dried under vacuum to give 6-(3-chloro-2-fluorophenyl)pyrimidin-4-ol (0.0357 g, 21% yield) as a white solid. MS(ESI) m/z: 225.1 (M+H)$^+$ and 227.1 (M+2+H)$^+$. $^1$H NMR (500 MHz, DMSO-d$_6$) δ 12.71 (br. s., 1H), 8.31 (d, J=1.1 Hz, 1H), 7.87 (ddd, J=8.0, 7.2, 1.7 Hz, 1H), 7.74-7.69 (m, 1H), 7.36 (td, J=8.0, 1.1 Hz, 1H), 6.72 (br. s, 1H). $^{19}$F NMR (471 MHz, DMSO-d$_6$) δ −117.48.

Intermediate 4

Preparation of 6-(3-chloro-2,6-difluorophenyl)pyrimidin-4-ol, Hydrobromide

4A. Preparation of 4-(3-chloro-2,6-difluorophenyl)-6-methoxypyrimidine

A flask containing 4-chloro-6-methoxypyrimidine (1.0 g, 6.92 mmol), (3-chloro-2,6-difluorophenyl)boronic acid (1.996 g, 10.38 mmol), and 2nd generation XPhos precatalyst (0.272 g, 0.346 mmol) was purged with Ar for several min, then degassed THF (13.84 mL) and degassed 0.5 M K$_3$PO$_4$ (27.7 mL, 13.84 mmol) were added. The resulting cloudy, pink reaction mixture was stirred vigorously at rt. After 2 h, the reaction was diluted with water and extracted with EtOAc (2×). The organic layers were combined and washed with brine, dried over Na$_2$SO$_4$, filtered and concentrated to give an orange-brown residue weighing 1.5 g. Purification by normal phase chromatography gave 4-(3-chloro-2,6-difluorophenyl)-6-methoxypyrimidine (0.242 g, 13.6% yield) as an off-white solid. MS(ESI) m/z: 257.0 (M+H)$^+$ and 259.0 (M+2+H)$^+$. $^1$H NMR (500 MHz, CD$_3$OD) δ 8.86 (d, J=1.1 Hz, 1H), 7.68-7.63 (m, 1H), 7.17 (td, J=9.0, 1.8 Hz, 1H), 7.10-7.08 (m, 1H), 4.07 (s, 3H). $^{19}$F NMR (471 MHz, CD$_3$OD) δ −115.84 (d, J=4.3 Hz), −116.49 (d, J=5.7 Hz).

4B. Preparation of 6-(3-chloro-2,6-difluorophenyl)pyrimidin-4-ol

A clear, yellow solution of 4-(3-chloro-2,6-difluorophenyl)-6-methoxypyrimidine (0.240 g, 0.935 mmol) in AcOH (9.35 mL) and 48% aq HBr (5.29 mL, 46.8 mmol) was warmed to 85° C. After 1 h, the reaction was cooled to rt and then it was concentrated to give a yellow solid. Et$_2$O (10 mL) was added resulting in a suspension. The solid was collected by filtration, rinsed with Et$_2$O, air-dried, and then dried under vacuum to give 6-(3-chloro-2,6-difluorophenyl)pyrimidin-4-ol (0.258 g, 85% yield) as an off-white solid. MS(ESI) m/z: 243.0 (M+H)$^+$ and 245.0 (M+2+H)$^+$. $^1$H NMR (500 MHz, DMSO-d$_6$) δ 8.33 (d, J=1.1 Hz, 1H), 7.77 (td, J=8.7, 5.6 Hz, 1H), 7.32 (td, J=9.1, 1.7 Hz, 1H), 6.63 (d, J=0.6 Hz, 1H). $^{19}$F NMR (471 MHz, DMSO-d$_6$) δ −113.79 (d, J=4.3 Hz), −113.88 (d, J=5.7 Hz).

Intermediate 5

Preparation of 6-(5-chloro-2-fluorophenyl)pyrimidin-4-ol

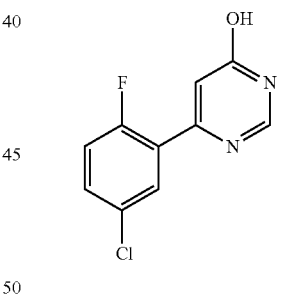

5A. Preparation of 4-(5-chloro-2-fluorophenyl)-6-methoxypyrimidine

A microwave vial containing 4-chloro-6-methoxypyrimidine (0.290 g, 2.007 mmol), (5-chloro-2-fluorophenyl)boronic acid (0.35 g, 2.007 mmol) and Na$_2$CO$_3$ (0.213 g, 2.007 mmol) in DME (10 mL), EtOH (1.250 mL) and water (1.250 mL) was purged with N$_2$ for several min. Then PdCl$_2$(dppf)-CH$_2$Cl$_2$ adduct (0.082 g, 0.100 mmol) was added and the vial was capped. The reaction was heated in a microwave at 100° C. for 1 h. The reaction mixture was then diluted with water and extracted with EtOAc. The organic layer was washed with brine and then concentrated to give an orange-brown residue. Purification by normal phase chromatography gave 4-(5-chloro-2-fluorophenyl)-6-methoxypyrimidine (400 mg, 84% yield) as white crystals. MS(ESI) m/z: 239.3

(M+H)+. ¹H NMR (400 MHz, CDCl₃) δ 8.86 (s, 1H), 8.16 (dd, J=6.7, 2.8 Hz, 1H), 7.39 (ddd, J=8.8, 4.2, 2.9 Hz, 1H), 7.28-7.23 (m, 1H), 7.12 (dd, J=10.8, 8.8 Hz, 1H), 4.04 (s, 3H).

5B. Preparation of 6-(5-chloro-2-fluorophenyl)pyrimidin-4-ol

A clear, yellow solution of 4-(5-chloro-2-fluorophenyl)-6-methoxypyrimidine (300 mg, 1.257 mmol) in AcOH (12.57 mL) and 48% aq HBr (7 mL, 61.9 mmol) was warmed to 85° C. After 0.5 h, the reaction was cooled to rt and concentrated under high vacuum to dryness. To the residue was added sat NaHCO₃ carefully to give a suspension. The solid was collected by filtration, rinsed with water, a small amount of acetone and air dried to give 6-(5-chloro-2-fluorophenyl)pyrimidin-4-ol (140 mg, 36.5% yield) as a white solid. MS(ESI) m/z: 225.2 (M+H)⁺. ¹H NMR (400 MHz, DMSO-d₆) δ 12.73 (br. s., 1H), 8.33 (d, J=0.9 Hz, 1H), 7.99 (dd, J=6.6, 2.9 Hz, 1H), 7.61 (ddd, J=6.6, 4.3, 2.1 Hz, 1H), 7.43 (dd, J=11.1, 8.9 Hz, 1H), 6.76 (s, 1H).

Intermediate 6

Preparation of (S)-(2-(1-((tert-butoxycarbonyl)amino)but-3-en-1-yl)pyridin-4-yl) boronic Acid

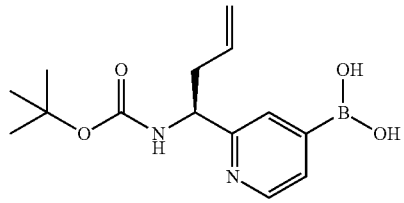 [SMILES: C=CC[C@H](NC(=O)OC(C)(C)C)c1cc(B(O)O)ccn1]

6A. Preparation of 4-chloro-2-[(E)-2-[(S)-2-methyl-propane-2-sulfinyl]ethenyl]pyridine To a solution of S-(−)-t-butyl-sulfinamide (0.856 g, 7.06 mmol) in DCM (14.1 mL) was added sequentially CuSO₄ (2.481 g, 15.54 mmol) and 4-chloropicolinaldehyde (1.0 g, 7.06 mmol). The resulting white suspension was stirred at rt. After 3 h, the brown suspension was filtered through CELITE®, eluting with DCM, to give a clear brown filtrate. Concentration of the filtrate gave a brown oil weighing 1.85 g. Purification by normal phase chromatography gave 1.31 g of 4-chloro-2-[(E)-2-[(S)-2-methylpropane-2-sulfinyl]ethenyl]pyridine as a clear, yellow oil. MS(ESI) m/z: 245.0 (M+H)⁺.

6B. Preparation of (S)—N—((S)-1-(4-chloropyridin-2-yl)but-3-enyl)-2-methylpropane-2-sulfinamide To a cooled (0-5° C.) mixture of InCl₃ (13.56 g, 61.3 mmol) in THF (170 mL) was added dropwise over 30 min 1 M allylmagnesium bromide in Et₂O (62 mL, 61.3 mmol). The reaction was allowed to warm to rt. After 1 h at rt, a solution of chloro-2-[(E)-2-[(S)-2-methylpropane-2-sulfinyl]ethenyl]pyridine (10 g, 40.9 mmol) in EtOH (170 mL) was added. After 3 h, the reaction was concentrated under vacuum at 50-55° C. The crude material was partitioned between EtOAc (200 mL) and water (50 mL) and the layers were separated. The aqueous layer was extracted with EtOAc (2×50 mL). The organic layers were combined and washed with brine (100 mL), dried over Na₂SO₄, filtered and concentrated to give (S)—N—((S)-1-(4-chloropyridin-2-yl)but-3-enyl)-2-methylpropane-2-sulfinamide (13.5 g, 106%) as a yellow oil. MS(ESI) m/z: 287.2 (M+H)⁺.

6C. Preparation of (S)-tert-butyl 1-(4-chloropyridin-2-yl)but-3-enylcarbamate (S)—N—((S)-1-(4-Chloropyridin-2-yl)but-3-enyl)-2-methylpropane-2-sulfinamide (75 g, 261 mmol) was dissolved in MeOH (1500 mL). 6 N aq HCl (750 mL, 4.5 mol) was added. The reaction was stirred at rt for 3 h and then was concentrated. The residue was diluted with water (2 L), washed with EtOAc (500 mL). The aqueous layer was basified with sat Na₂CO₃ solution and then extracted with EtOAc (3×1 L). The combined organic layers were washed with water (1 L) and brine (1 L), dried over Na₂SO₄, filtered and concentrated under vacuum at 50-55° C. to give crude product (43 g, 90%). MS(ESI) m/z: 183.2 (M+H)⁺. The crude product (42 g, 230 mmol) was dissolved in DCM (420 mL) and Et₃N (32.1 mL, 230 mmol) was added followed by dropwise addition of Boc₂O (53.4 mL, 230 mmol). The reaction was stirred at rt for 3 h. The reaction was diluted with DCM (1 L), washed with water (500 mL) and brine (500 mL). The organic layer was dried over Na₂SO₄, filtered, and concentrated. The crude product was then purified using silica gel chromatography to give (S)-tert-butyl 1-(4-chloropyridin-2-yl)but-3-enylcarbamate (61 g, 86%) as a pale yellow solid. MS(ESI) m/z: 283.2 (M+H)⁺.

6D. Preparation of (S)-(2-(1-((tert-butoxycarbonyl)amino)but-3-en-1-yl)pyridin-4-yl)boronic Acid Trifluoroacetate To a solution of 5,5,5',5'-tetramethyl-2,2'-bi(1,3,2-dioxaborinane) (1.198 g, 5.30 mmol) and (S)-tert-butyl 1-(4-chloropyridin-2-yl)but-3-enylcarbamate (1.0 g, 3.54 mmol), prepared as described in Intermediate 23, in DMSO (10 mL) was added KOAc (1.041 g, 10.61 mmol) and PdCl₂(dppf)-CH₂Cl₂ adduct (0.289 g, 0.354 mmol). The reaction was purged with Ar for 10 min. The reaction mixture was then sealed and stirred for 12 h at 85° C. The reaction mixture was cooled to rt and then it was diluted with EtOAc and washed with water. The aqueous layer was extracted with EtOAc. The organic layers were combined and was washed with brine, dried over Na₂SO₄, filtered, and concentrated. Purification by reverse phase chromatography afforded the (S)-(2-(1-((tert-butoxycarbonyl)amino)but-3-en-1-yl)pyridin-4-yl)boronic acid trifluoroacetate (1.1 g, 77%) as a white solid. MS(ESI) m/z: 293.2 (M+H)⁺. ¹H NMR (500 MHz, CD₃OD) δ 8.54 (d, J=5.8 Hz, 1H), 8.11 (s, 1H), 8.02 (dd, J=5.8, 0.6 Hz, 1H), 5.79 (ddt, J=17.1, 10.2, 7.1 Hz, 1H), 5.11-5.03 (m, 2H), 4.86 (t, J=7.0 Hz, 1H), 2.69-2.55 (m, 2H), 1.40 (br. s., 9H) ppm.

Intermediate 7

Preparation of 6-(3-chloro-2-fluoro-6-(1H-1,2,3-triazol-1-yl)phenyl)pyrimidin-4-ol

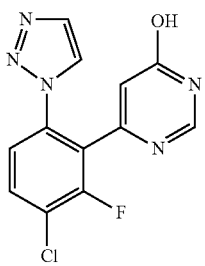 [SMILES: Oc1cc(-c2c(-n3ccnn3)ccc(Cl)c2F)ncn1]

7A. Preparation of N-(4-chloro-3-fluorophenyl)-2,2,2-trifluoroacetamide

To a cooled (−10° C.) suspension of 4-chloro-3-fluoroaniline (10.67 g, 73.3 mmol) and $Na_2CO_3$ (13.21 g, 125 mmol) in $Et_2O$ (300 mL) was added dropwise TFAA (12.23 mL, 88 mmol). The mixture was allowed to warm to rt overnight. The mixture was diluted with hexane (300 mL) and filtered. The filtrate was washed with ice water, 10% aq $NaHCO_3$, and brine, dried over $Na_2SO_4$, filtered, and concentrated to give N-(4-chloro-3-fluorophenyl)-2,2,2-trifluoroacetamide (17 g, 96% yield), as a pale, yellow solid. MS(ESI) m/z: 242.1 $(M+H)^+$.

7B. Preparation of (3-chloro-2-fluoro-6-(2,2,2-trifluoroacetamido)phenyl)boronic Acid To a cooled (−78° C.) clear, colorless solution of N-(4-chloro-3-fluorophenyl)-2,2,2-trifluoroacetamide (0.500 g, 2.070 mmol) in THF (8.28 mL) was added dropwise 2.5 M nBuLi in hexane (1.74 mL, 4.35 mmol) over 15 min keeping the internal temperature below −65° C. The resulting clear, yellow solution was stirred at −78° C. for 10 min. The reaction was allowed to warm to −50° C. over 1 h. The reaction was then cooled to −78° C. and B(O-i-Pr)$_3$ (1.051 mL, 4.55 mmol) was added dropwise. The reaction was stirred at −78° C. for 30 min and then the ice bath was removed and the reaction was allowed to warm to rt and stirred at rt for 1 h. After this time, the reaction was cooled to −5° C. and then quenched with the dropwise addition of 1.0 M HCl (5 mL) followed by the addition of water (5 mL). The resulting cloudy yellow reaction mixture was stirred at rt for 45 min. The reaction was diluted with EtOAc and the layers were separated. The organic layer was washed with brine, dried over $Na_2SO_4$, filtered and concentrated to give a pale, orange solid. The solid was partitioned between THF (10 mL) and 0.5 M HCl (20 mL) and stirred vigorously for 4 h. The layers were then separated and the clear, colorless aqueous layer was concentrated to give (3-chloro-2-fluoro-6-(2,2,2-trifluoroacetamido)phenyl)boronic acid (0.1599 g, 34.2% yield) as a white solid. MS(ESI) m/z: 189.9 $[M+H]^+$.

7C. Preparation of 4-chloro-3-fluoro-2-(6-methoxypyrimidin-4-yl)aniline

4-Chloro-3-fluoro-2-(6-methoxypyrimidin-4-yl)aniline was prepared according to the procedures described in Intermediate 3 using (3-chloro-2-fluoro-6-(2,2,2-trifluoroacetamido)phenyl)boronic acid. MS(ESI) m/z: 253.9 $(M+H)^+$. $^1$H NMR (500 MHz, $CD_3OD$) δ 8.82 (d, J=1.1 Hz, 1H), 7.18 (dd, J=8.8, 8.3 Hz, 1H), 7.01 (dd, J=3.0, 1.1 Hz, 1H), 6.61 (dd, J=8.9, 1.5 Hz, 1H), 4.04 (s, 3H). $^{19}$F NMR (471 MHz, $CD_3OD$) δ −119.92 (s, 1F).

7D. Preparation of 4-(3-chloro-2-fluoro-6-(1H-1,2,3-triazol-1-yl)phenyl)-6-methoxypyrimidine Trifluoroacetate In a microwave vial, 4-chloro-3-fluoro-2-(6-methoxypyrimidin-4-yl)aniline (0.045 g, 0.177 mmol) in $CH_3CN$ (1.8 mL), cooled to 0° C., was added isoamylnitrite (0.036 mL, 0.266 mmol), followed by the dropwise addition of $TMSN_3$ (0.035 mL, 0.266 mmol). Gas evolution was observed. After 5 min, the cold bath was removed, and the reaction was allowed to warm to rt. After 1 h, trimethylsilylacetylene (0.076 mL, 0.532 mmol) was added. The septum was replaced with a microwave cap and sealed. The reaction was heated in a microwave at 120° C. for a total of 4 h. The reaction was concentrated almost to dryness and then purified by reverse phase chromatography to give 4-(3-chloro-2-fluoro-6-(1H-1,2,3-triazol-1-yl)phenyl)-6-methoxypyrimidine (27 mg, 0.088 mmol) as a clear glass. MS(ESI) m/z: 306.3 $(M+H)^+$. $^1$H NMR (400 MHz, $CDCl_3$) δ 8.74 (d, J=0.4 Hz, 1H), 7.80 (d, J=0.9 Hz, 1H), 7.77-7.69 (m, 2H), 7.38 (dd, J=8.6, 1.5 Hz, 1H), 6.88 (s, 1H), 4.06 (s, 3H). $^{19}$F NMR (376 MHz, $CDCl_3$) δ −76.02 (s), −112.27 (s).

7E. Preparation of 6-(3-chloro-2-fluoro-6-(1H-1,2,3-triazol-1-yl)phenyl)pyrimidin-4-ol 6-(3-Chloro-2-fluoro-6-(1H-1,2,3-triazol-1-yl)phenyl)pyrimidin-4-ol was prepared according to the procedures in described in Intermediate 5 for the synthesis of 6-(5-chloro-2-fluorophenyl)pyrimidin-4-ol, by replacing 4-(5-chloro-2-fluorophenyl)-6-methoxypyrimidine with 4-(3-chloro-2-fluoro-6-(1H-1,2,3-triazol-1-yl)phenyl)-6-methoxypyrimidine. MS(ESI) m/z: 292.3 $(M+H)^+$. $^1$H NMR (400 MHz, $CD_3OD$) δ 8.20 (d, J=1.1 Hz, 1H), 8.06 (d, J=0.7 Hz, 1H), 7.89-7.81 (m, 1H), 7.80 (d, J=0.9 Hz, 1H), 7.54 (dd, J=8.6, 1.5 Hz, 1H), 6.52 (s, 1H).

Intermediate 8

Preparation of 6-(5-chloro-2-(1H-1,2,3-triazol-1-yl)phenyl)pyrimidin-4-ol

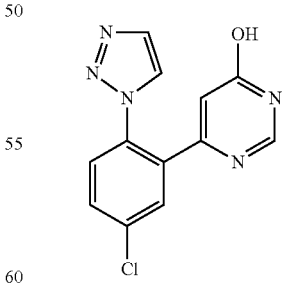

8A. Preparation of 4-chloro-2-(6-methoxypyrimidin-4-yl)aniline

4-Chloro-2-(6-methoxypyrimidin-4-yl)aniline was synthesized according to the procedure described in Intermediate 5, by replacing (5-chloro-2-fluorophenyl)boronic acid with 4-chloro-2-(4,4,5,5-tetramethyl-1,3,2-dioxaborolan-2-yl)aniline. MS(ESI) m/z: 236.3 (M+H)+. 1H NMR (400 MHz, CDCl3) δ 8.78 (s, 1H), 7.49 (d, J=2.4 Hz, 1H), 7.15 (dd, J=8.6, 2.4 Hz, 1H), 6.99 (d, J=0.9 Hz, 1H), 6.66 (d, J=8.6 Hz, 1H), 4.02 (s, 3H).

8B. Preparation of 6-(5-chloro-2-(1H-1,2,3-triazol-1-yl)phenyl)pyrimidin-4-ol 6-(5-Chloro-2-(1H-1,2,3-triazol-1-yl)phenyl)pyrimidin-4-ol was synthesized according to the procedures described for the synthesis of 6-(3-chloro-2-fluoro-6-(1H-1,2,3-triazol-1-yl)phenyl)pyrimidin-4-ol, by replacing 4-chloro-3-fluoro-2-(6-methoxypyrimidin-4-yl)aniline with 4-chloro-2-(6-methoxypyrimidin-4-yl)aniline. MS(ESI) m/z: 274.3 (M+H)+. 1H NMR (400 MHz, CD3OD) δ 8.51 (d, J=0.9 Hz, 1H), 8.35 (d, J=1.1 Hz, 1H), 7.92 (d, J=1.1 Hz, 1H), 7.88 (d, J=2.4 Hz, 1H), 7.83-7.78 (m, 1H), 7.74-7.69 (m, 1H), 6.39 (d, J=0.9 Hz, 1H).

Intermediate 9

Preparation of 6-[5-chloro-2-(4-chloro-1H-1,2,3-triazol-1-yl)phenyl]pyrimidin-4-ol

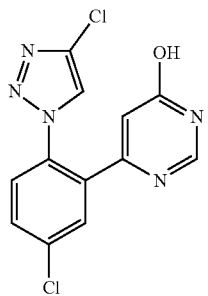 [SMILES: Oc1cc(-c2cc(Cl)ccc2-n2cc(Cl)nn2)ncn1]

9A. Preparation of 4-chloro-2-(tetramethyl-1,3,2-dioxaborolan-2-yl)aniline

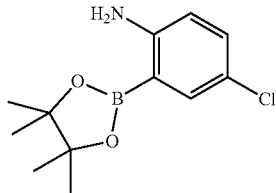 [SMILES: CC1(C)OB(c2cc(Cl)ccc2N)OC1(C)C]

In a 20 mL microwave vial was added 2-bromo-4-chloroaniline (3 g, 14.53 mmol), 4,4,5,5-tetramethyl-2-(tetramethyl-1,3,2-dioxaborolan-2-yl)-1,3,2-dioxaborolane (5.53 g, 21.80 mmol), KOAc (3.66 g, 37.3 mmol), Pd(dppf)Cl2—CH2Cl2 adduct (0.32 g, 0.44 mmol) and DMSO (9 mL). The resulting suspension was purged with N2, capped and heated at 80° C. for 22 h. The reaction was cooled to rt. Water was added to dissolve the salts, then the reaction was filtered. The remaining solid was suspended in DCM and the insoluble solid was filtered. The filtrate was concentrated and then purified by normal phase chromatography to give 4-chloro-2-(tetramethyl-1,3,2-dioxaborolan-2-yl)aniline (3.15 g, 86% yield) as a white solid. MS(ESI) m/z: 172.3 (M-C6H10+H)+. 1H NMR (400 MHz, CDCl3) δ 7.54 (d, J=2.6 Hz, 1H), 7.13 (dd, J=8.8, 2.6 Hz, 1H), 6.52 (d, J=8.6 Hz, 1H), 4.72 (br. s., 2H), 1.34 (s, 12H).

9B. Preparation of 4-chloro-2-(6-methoxypyrimidin-4-yl)aniline

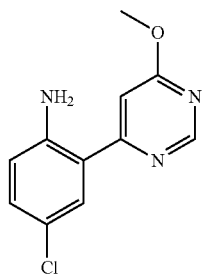 [SMILES: COc1cc(-c2cc(Cl)ccc2N)ncn1]

A RBF containing 4-chloro-6-methoxypyrimidine (3.13 g, 21.62 mmol), 4-chloro-2-(tetramethyl-1,3,2-dioxaborolan-2-yl)aniline (7.31 g, 21.62 mmol), Na2CO3 (2.29 g, 21.62 mmol), DME (86 ml), EtOH (10.81 ml) and water (10.81 ml) was equipped with a condenser. The mixture was purged with Ar for several min then Pd(dppf)Cl2—CH2Cl2 adduct (1.77 g, 2.16 mmol) was added. The reaction was heated at 90° C. for 5 h. The reaction was cooled to rt, diluted with water and extracted with EtOAc. The organic layer was washed with brine, concentrated and purified by normal phase chromatography to give 4-chloro-2-(6-methoxypyrimidin-4-yl)aniline (2.86 g, 56.1% yield) as yellow solid. MS(ESI) m/z: 236.0 (M+H)+. 1H NMR (500 MHz, CDCl3) δ 8.78 (d, J=1.1 Hz, 1H), 7.49 (d, J=2.5 Hz, 1H), 7.15 (dd, J=8.8, 2.5 Hz, 1H), 6.99 (d, J=1.1 Hz, 1H), 6.67 (d, J=8.8 Hz, 1H), 5.89 (br. s., 2H), 4.03 (s, 3H).

9C. Preparation of 4-{5-chloro-2-[4-(trimethylsilyl)-1H-1,2,3-triazol-1-yl]phenyl}-6-methoxypyrimidine

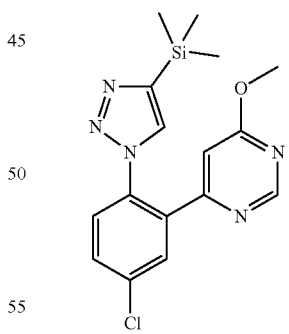

To a solution of 4-chloro-2-(6-methoxypyrimidin-4-yl)aniline (1.5 g, 6.36 mmol) in ACN (90 ml) at 0° C. was added 3-methylbutyl nitrite (1.28 ml, 9.55 mmol), followed by the dropwise addition of TMSN3 (1.26 ml, 9.55 mmol). Gas evolution was observed. After 10 min, the ice bath was removed, and the reaction was allowed to warm to rt. After 1 h, ethynyltrimethylsilane (2.72 ml, 19.09 mmol) and Cu2O (0.09 g, 0.64 mmol) were added and the reaction was stirred for an additional 1 h. The reaction was partitioned in EtOAc and sat NH4Cl, and the layers were separated. The organic layer was washed with brine, dried over MgSO$_4$, filtered and concentrated. Purification by normal phase chromatography gave 4-{5-chloro-2-[4-(trimethylsilyl)-1H-1,2,3-triazol-1-yl]phenyl}-6-methoxypyrimidine (2.13 g, 5.92 mmol, 93% yield) as a yellow solid. MS(ESI) m/z: 360.3 (M+H)+. $^1$H NMR (400 MHz, CDCl$_3$) δ 8.71 (d, J=1.1 Hz, 1H), 7.82 (d, J=2.2 Hz, 1H), 7.61-7.56 (m, 1H), 7.54-7.48 (m, 2H), 6.20 (d, J=1.1 Hz, 1H), 3.92 (s, 3H), 0.32-0.28 (m, 9H).

9D. Preparation of 4-[5-chloro-2-(4-chloro-1H-1,2,3-triazol-1-yl)phenyl]-6-methoxypyrimidine

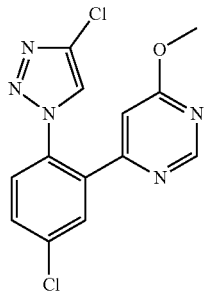 [SMILES: COc1cc(-c2cc(Cl)ccc2-n2cc(Cl)nn2)ncn1]

To a solution of 4-{5-chloro-2-[4-(trimethylsilyl)-1H-1,2,3-triazol-1-yl]phenyl}-6-methoxypyrimidine (1.56 g, 4.33 mmol) in ACN (28.9 ml) was added NCS (2.03 g, 15.17 mmol) and silica gel (6.51 g, 108 mmol). The reaction was stirred at 80° C. for 1 h. Then, the reaction was filtered to remove the silica gel and the collected silica gel was washed with EtOAc. The filtrate was washed with water (2×), brine and concentrated. Purification by normal phase chromatography gave 4-[5-chloro-2-(4-chloro-1H-1,2,3-triazol-1-yl)phenyl]-6-methoxypyrimidine (0.90 g, 64.5% yield) as a yellow foam. MS(ESI) m/z: 322.3 (M+H)+. $^1$H NMR (400 MHz, CDCl$_3$) δ 8.70 (d, J=1.1 Hz, 1H), 7.75 (d, J=2.4 Hz, 1H), 7.66-7.55 (m, 2H), 7.50 (d, J=8.6 Hz, 1H), 6.52 (d, J=0.9 Hz, 1H), 3.98 (s, 3H).

9E. Preparation of 6-[5-chloro-2-(4-chloro-1H-1,2,3-triazol-1-yl)phenyl]pyrimidin-4-ol

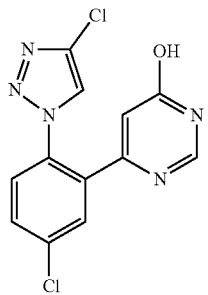 [SMILES: Oc1cc(-c2cc(Cl)ccc2-n2cc(Cl)nn2)ncn1]

To a solution of 4-[5-chloro-2-(4-chloro-1H-1,2,3-triazol-1-yl)phenyl]-6-methoxypyrimidine (900 mg, 2.79 mmol) in AcOH (6 ml) was added 48% aq HBr (3 ml, 26.5 mmol). The mixture was stirred at 85° C. for 1 h. The reaction was concentrated to dryness and then partitioned between EtOAc and sat NaHCO$_3$. The mixture was separated and the aqueous layer was extracted with EtOAc (2×). The organic layers were combined, concentrated, and then the residue was purified by normal phase chromatography to give a white solid. The solid was suspended in Et$_2$O, filtered and washed with Et$_2$O to give 6-[5-chloro-2-(4-chloro-1H-1,2,3-triazol-1-yl)phenyl]pyrimidin-4-ol (610 mg, 70.9% yield) as a white solid. MS(ESI) m/z: 308.3 (M+H)+. $^1$H NMR (400 MHz, CDCl$_3$) δ 7.96 (s, 1H), 7.74-7.67 (m, 2H), 7.62 (dd, J=8.5, 2.3 Hz, 1H), 7.47 (d, J=8.4 Hz, 1H), 6.44 (d, J=0.9 Hz, 1H).

Intermediate 10

Preparation of 6-(3-chloro-6-(4-chloro-1H-1,2,3-triazol-1-yl)-2-fluorophenyl) pyrimidin-4-ol

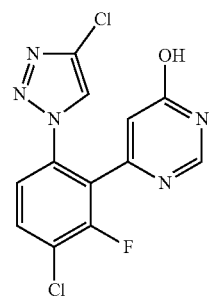 [SMILES: Oc1cc(-c2c(-n3cc(Cl)nn3)ccc(Cl)c2F)ncn1]

10A. Preparation of N-(4-chloro-3-fluorophenyl)-2,2,2-trifluoroacetamide

To a suspension of 4-chloro-3-fluoroaniline (10.67 g, 73.3 mmol) and Na$_2$CO$_3$ (24.5 g, 125 mmol) in Et$_2$O (300 mL) at −10° C. under N$_2$ was added TFAA (12.23 mL, 88 mmol) dropwise. The mixture was allowed to warm to rt and then stirred for 18 h. The reaction mixture was diluted with hexane (300 mL) and filtered. The filtrate was washed with ice water, 10% aq NaHCO$_3$, and brine, dried over Na$_2$SO$_4$, and concentrated. A pale yellow solid obtained as N-(4-chloro-3-fluorophenyl)-2,2,2-trifluoroacetamide (17 g, 96% yield). MS(ESI) m/z: 242.1 (M+H)+.

10B. Preparation of (6-amino-3-chloro-2-fluorophenyl)boronic Acid

To a cooled (−78° C.) clear, colorless solution of N-(4-chloro-3-fluorophenyl)-2,2,2-trifluoroacetamide (5 g, 20.70 mmol) in THF (69.0 ml) was added dropwise 2.5 M BuLi in hexane (16.56 ml, 41.4 mmol) over 15 min, keeping the internal temperature below −60° C. The resulting clear, yellow solution was stirred at −78° C. for 10 min, then the reaction was allowed to warm to −50° C. over 1 h. The resulting clear brown solution was cooled to −78° C. and then B(O-iPr)$_3$ (10.51 ml, 45.5 mmol) was added dropwise. The reaction was stirred at −78° C. for 10 min, and then the ice bath was removed and the reaction was allowed to warm to rt. The resulting orange suspension was stirred at rt for 2 h, then cooled in ice bath and quenched with 1 N HCl (40 ml). The reaction mixture was warmed to 40° C. for 1 h and then cooled to rt. The reaction was diluted with EtOAc and the layers were separated. The organic layer was washed with brine and concentrated. Purification by normal phase chromatography afforded (6-amino-3-chloro-2-fluorophenyl)boronic acid (3 g, 76.6% yield). MS(ESI) m/z: 190.1 (M+H)+.

10C. Preparation of 4-chloro-3-fluoro-2-(6-methoxypyrimidin-4-yl)aniline

Reaction was done in a 350 ml pressure bottle. A solution of 4-chloro-6-methoxypyrimidine (1.784 g, 12.34 mmol), (6-amino-3-chloro-2-fluorophenyl)boronic acid (3.3 g, 12.34 mmol) in toluene (25 ml) and EtOH (25 ml) was purged with $N_2$ for several min. DIEA (4.31 ml, 24.68 mmol) followed by Pd(Ph$_3$P)$_4$ (1.426 g, 1.234 mmol) were added. The flask was capped and the reaction was heated at 120° C. for 2 h, then cooled to rt, and concentrated. Purification by normal phase chromatography afforded 4-chloro-3-fluoro-2-(6-methoxypyrimidin-4-yl)aniline (2 g, 45.2% yield) as a yellow solid. MS(ESI) m/z: 254.0 (M+H)$^+$.

10D. Preparation of 4-(3-chloro-2-fluoro-6-(4-(trimethylsilyl)-1H-1,2,3-triazol-1-yl)phenyl)-6-methoxypyrimidine

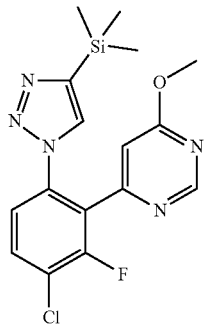 [SMILES: COc1cc(-c2c(-n3cc([Si](C)(C)C)nn3)ccc(Cl)c2F)ncn1]

To a cooled (0° C.), clear, yellow solution of 4-chloro-3-fluoro-2-(6-methoxypyrimidin-4-yl)aniline (2.1 g, 8.28 mmol) in ACN (118 ml) was added isoamylnitrite (1.67 ml, 12.42 mmol), followed by the dropwise addition of TMSN$_3$ (1.63 ml, 12.42 mmol). After 10 min, the cold bath was removed, and the reaction was allowed to warm to rt. After 2 h, ethynyltrimethylsilane (3.54 ml, 24.84 mmol) and Cu$_2$O (0.118 g, 0.83 mmol) were added, and the reaction was stirred at rt for 1.5 h. The reaction was then diluted with EtOAc and washed with sat NH$_4$Cl, brine, dried over MgSO$_4$, filtered and concentrated to give a brown oil. Purification by normal phase chromatography afforded 4-(3-chloro-2-fluoro-6-(4-(trimethylsilyl)-1H-1,2,3-triazol-1-yl)phenyl)-6-methoxypyrimidine (2.71 g, 87% yield) as a brown solid. MS(ESI) m/z: 378.1 (M+H)$^+$.

10E. Preparation of 4-(3-chloro-6-(4-chloro-1H-1,2,3-triazol-1-yl)-2-fluorophenyl)-6-methoxypyrimidine

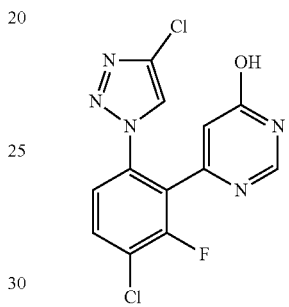

In a RBF equipped with stirring bar and condenser was added 4-(3-chloro-2-fluoro-6-(4-(trimethylsilyl)-1H-1,2,3-triazol-1-yl)phenyl)-6-methoxypyrimidine (2.71 g, 7.17 mmol), NCS (3.35 g, 25.1 mmol), and silica gel (10.77 g, 179 mmol), followed by ACN (47.8 ml). The reaction was heated at 80° C. for 1 h, and then cooled to rt. The reaction was filtered, and the filtrate was concentrated. The residue was redissolved in EtOAc and washed with sat NaHCO$_3$, water, brine, and concentrated. Purification by normal phase chromatography afforded 4-(3-chloro-6-(4-chloro-1H-1,2,3-triazol-1-yl)-2-fluorophenyl)-6-methoxypyrimidine (1.05 g, 43.0% yield) as a yellow solid. MS(ESI) m/z: 340.0 (M+H)$^+$. $^1$H NMR (400 MHz, CDCl$_3$) δ 8.68 (d, J=0.7 Hz, 1H), 7.71-7.62 (m, 2H), 7.37 (dd, J=8.6, 1.8 Hz, 1H), 6.84 (s, 1H), 4.02 (s, 3H).

10F. Preparation of 6-(3-chloro-6-(4-chloro-1H-1,2,3-triazol-1-yl)-2-fluorophenyl) pyrimidin-4-ol

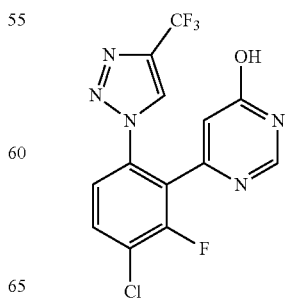

A clear, yellow solution of 4-(3-chloro-6-(4-chloro-1H-1,2,3-triazol-1-yl)-2-fluorophenyl)-6-methoxypyrimidine (1.05 g, 3.09 mmol) in HOAc (15.43 ml) and 48% aq HBr (17.46 ml, 154 mmol) was warmed to 65° C. for 3 h, and then cooled to rt and concentrated. The yellow gum was suspended in EtOAc and washed with sat NaHCO$_3$ (2×), brine, dried over Na$_2$SO$_4$, filtered, and concentrated. To the residue was added Et$_2$O (10 ml), and the resulting suspension was sonicated then filtered. The solid was rinsed with Et$_2$O (2 ml), air-dried with suction to afford 6-(3-chloro-6-(4-chloro-1H-1,2,3-triazol-1-yl)-2-fluorophenyl)pyrimidin-4-ol (0.79 g, 78% yield) as a white solid. MS(ESI) m/z: 326.3 (M+H)$^+$. $^1$H NMR (400 MHz, CD$_3$OD) δ 8.35 (s, 1H), 8.08 (d, J=0.7 Hz, 1H), 7.85 (dd, J=8.7, 7.6 Hz, 1H), 7.54 (dd, J=8.6, 1.5 Hz, 1H), 6.57 (s, 1H).

Intermediate 11

Preparation of 6-(3-chloro-2-fluoro-6-(4-(trifluoromethyl)-1H-1,2,3-triazol-1-yl)phenyl)pyrimidin-4-ol

11A. Preparation of 4-(3-chloro-2-fluoro-6-(4-(trifluoromethyl)-1H-1,2,3-triazol-1-yl)phenyl)-6-methoxypyrimidine To a cooled (0° C.), clear, yellow solution of 4-chloro-3-fluoro-2-(6-methoxypyrimidin-4-yl)aniline (0.2 g, 0.79 mmol) in ACN (11.26 ml) was added isoamylnitrite (0.16 mL, 1.18 mmol), followed by the dropwise addition of TMSN$_3$ (0.16 mL, 1.18 mmol). After 10 min, the cold bath was removed, and the reaction was allowed to warm to rt. After 2 h, Cu$_2$O (0.011 g, 0.079 mmol) was added. 3,3,3-Trifluoroprop-1-yne (0.5 mL, 0.79 mmol) gas was bubbled in through the reaction for 5 min, then the reaction was capped and stirred at rt. After 1 h, the reaction was diluted with EtOAc and washed with sat NH$_4$Cl, brine, dried over MgSO$_4$, filtered and concentrated to give a brown oil. Purification by normal phase chromatography afforded 4-(3-chloro-2-fluoro-6-(4-(trifluoromethyl)-1H-1,2,3-triazol-1-yl)phenyl)-6-methoxypyrimidine (0.24 g, 81% yield) as a yellow solid. MS(ESI) m/z: 374.3 (M+H)$^+$.

11B. Preparation of 6-(3-chloro-2-fluoro-6-(4-(trifluoromethyl)-1H-1,2,3-triazol-1-yl)phenyl)pyrimidin-4-ol A clear, yellow solution of 4-(3-chloro-2-fluoro-6-(4-(trifluoromethyl)-1H-1,2,3-triazol-1-yl)phenyl)-6-methoxypyrimidine (0.1 g, 0.268 mmol) in HOAc (1.34 ml) and 48% aq HBr (1.51 ml, 13.38 mmol) was warmed to 65° C. for 3 h, and then cooled to rt and concentrated. The yellow gum was suspended with EtOAc, washed with sat NaHCO$_3$ (2×), brine, dried over Na$_2$SO$_4$, filtered, and concentrated. To the residue was added Et$_2$O (3 ml) and the resulting suspension was sonicated, then filtered. The solid was rinsed with Et$_2$O (2 ml), air-dried with suction to afford 6-(3-chloro-2-fluoro-6-(4-(trifluoromethyl)-1H-1,2,3-triazol-1-yl)phenyl)pyrimidin-4-ol (0.07 g, 72.7% yield) as a white solid. MS(ESI) m/z: 360.0 (M+H)$^+$. $^1$H NMR (400 MHz, CD$_3$OD) δ 8.84 (s, 1H), 8.03 (br. s., 1H), 7.91-7.84 (m, 1H), 7.58 (dd, J=8.8, 1.5 Hz, 1H), 6.61 (br. s., 1H).

Intermediate 12

Preparation of 1-(4-chloro-3-fluoro-2-(6-hydroxypyrimidin-4-yl)phenyl)-1H-1,2,3-triazole-4-carbonitrile

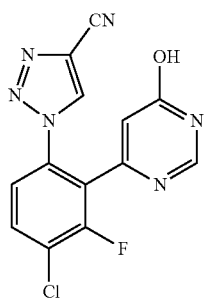 [SMILES: Oc1cc(-c2c(-n3cc(Cl)nn3)ccc(Cl)c2F)ncn1]

12A. Preparation of 1-(4-chloro-3-fluoro-2-(6-methoxypyrimidin-4-yl)phenyl)-1H-1,2,3-triazole-4-carboxamide To a cooled (0° C.), clear, yellow solution of 4-chloro-3-fluoro-2-(6-methoxypyrimidin-4-yl)aniline (1 g, 3.94 mmol) in ACN (56.3 ml) was added isoamylnitrite (0.79 ml, 5.91 mmol), followed by the dropwise addition of TMSN$_3$ (0.79 ml, 5.91 mmol). After 10 min, the cold bath was removed, and the reaction was allowed to warm to rt and stirred at rt for 1h. Next, propiolamide (0.817 g, 11.83 mmol) and Cu$_2$O (0.056 g, 0.394 mmol) were added. After 1 h, the yellow cloudy reaction was diluted with EtOAc, and washed with sat NH$_4$Cl, brine, dried over MgSO$_4$, filtered and concentrated to give a yellow solid. DCM (10 ml) was added and the resulting mixture was sonicated. The suspension was filtered and the solid was air-dried. A yellow solid obtained as 1-(4-chloro-3-fluoro-2-(6-methoxypyrimidin-4-yl)phenyl)-1H-1,2,3-triazole-4-carboxamide (1.003 g, 73.0% yield). MS(ESI) m/z: 349.0 (M+H)$^+$.

12B. Preparation of 1-(4-chloro-3-fluoro-2-(6-methoxypyrimidin-4-yl)phenyl)-1H-1,2,3-triazole-4-carbonitrile To a suspension of 1-(4-chloro-3-fluoro-2-(6-methoxypyrimidin-4-yl)phenyl)-1H-1,2,3-triazole-4-carboxamide (1.003 g, 2.88 mmol) in EtOAc (13 ml) was added TEA (1.20 ml, 8.63 mmol), followed by the dropwise addition of T3P® (50% in EtOAc) (5.14 ml, 8.63 mmol). The reaction was microwaved at 120° C. for 30 min and then it was cooled to rt. The reaction was diluted with EtOAc, washed with sat NaHCO$_3$, brine, dried over Na$_2$SO$_4$, filtered, and concentrated to afford a brown solid. Purification by normal phase chromatography afforded 1-(4-chloro-3-fluoro-2-(6-methoxypyrimidin-4-yl)phenyl)-1H-1,2,3-triazole-4-carbonitrile (0.815 g, 86% yield) as a yellow solid. MS(ESI) m/z: 331.1 (M+H)$^+$. $^1$H NMR (400 MHz, CDCl$_3$) δ 8.62 (d, J=1.1 Hz, 1H), 8.21 (s, 1H), 7.72 (dd, J=8.6, 7.5 Hz, 1H), 7.39 (dd, J=8.6, 1.8 Hz, 1H), 6.89 (dd, J=1.9, 1.2 Hz, 1H), 4.03 (s, 3H).

12C. Preparation of 1-(4-chloro-3-fluoro-2-(6-hydroxypyrimidin-4-yl)phenyl)-1H-1,2,3-triazole-4-carbonitrile To a suspension of 1-(4-chloro-3-fluoro-2-(6-methoxypyrimidin-4-yl)phenyl)-1H-1,2,3-triazole-4-carbonitrile (0.81 g, 2.449 mmol) in ACN (16.33 ml) was added TMSI (2.00 ml, 14.70 mmol) at rt then the clear solution was heated to 50° C. After 18 h, the reaction was cooled to rt. The reaction was poured into a 10% Na$_2$S$_2$O$_3$ solution and extracted with EtOAc (3×). The combined organic layers were washed with sat NaHCO$_3$, brine, dried over Na$_2$SO$_4$, filtered, and concentrated to give a residue. The residue was suspended in DCM (20 ml), filtered, and the solid was rinsed with DCM, and air-dried to afford 1-(4-chloro-3-fluoro-2-(6-hydroxypyrimidin-4-yl)phenyl)-1H-1,2,3-triazole-4-carbonitrile (0.73 g, 94% yield) as a white solid. MS(ESI) m/z: 317.1 (M+H)$^+$. $^1$H NMR (400 MHz, CD$_3$OD) δ 8.97 (s, 1H), 8.04 (s, 1H), 7.91-7.85 (m, 1H), 7.58 (dd, J=8.8, 1.5 Hz, 1H), 6.62 (s, 1H). $^{19}$F NMR (376 MHz, CD$_3$OD) δ −114.93 (s, 1F).

Intermediate 13

Preparation of 6-(5-chloro-2-(4-cyclopropyl-1H-1,2,3-triazol-1-yl)phenyl)pyrimidin-4-ol hydrobromide

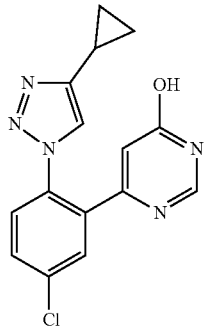 [SMILES: Oc1cc(-c2cc(Cl)ccc2-n2cc(C3CC3)nn2)ncn1]

13A. Preparation of 4-(5-chloro-2-(4-cyclopropyl-1H-1,2,3-triazol-1-yl)phenyl)-6-methoxypyrimidine To a cooled (0° C.), clear, yellow solution of 4-chloro-2-(6-methoxypyrimidin-4-yl)aniline (0.100 g, 0.42 mmol) in ACN (6.06 ml) was added isoamylnitrite (0.086 ml, 0.64 mmol), followed by the dropwise addition of TMSN$_3$ (0.084 ml, 0.64 mmol). After 10 min, the cold bath was removed, and the reaction was allowed to warm to rt and the reaction was stirred at rt for 1 h. Next, ethynylcyclopropane (0.120 g, 1.27 mmol) and Cu$_2$O (6.07 mg, 0.042 mmol) were added. The flask was equipped with a reflux condenser and the reaction was heated to 50° C. for 1 h, then the reaction was cooled to rt. The reaction was diluted with DCM and washed with sat NH$_4$Cl, brine, dried over MgSO$_4$, filtered and concentrated to give a brown oil. Purification by normal phase chromatography then reverse phase chromatography afforded 4-(5-chloro-2-(4-cyclopropyl-1H-1,2,3-triazol-1-yl)phenyl)-6-methoxypyrimidine (0.024 g, 17.3% yield) as a yellow oil. MS(ESI) m/z: 328.1 (M+H)$^+$. $^1$H NMR (400 MHz, CDCl$_3$) δ 8.75 (d, J=0.9 Hz, 1H), 7.79 (d, J=2.2 Hz, 1H), 7.61-7.56 (m, 1H), 7.51-7.47 (m, 1H), 7.29 (s, 1H), 6.35 (d, J=0.9 Hz, 1H), 3.96 (s, 3H), 1.96 (tt, J=8.4, 5.0 Hz, 1H), 1.02-0.95 (m, 2H), 0.88-0.81 (m, 2H).

13B. Preparation of 6-(5-chloro-2-(4-cyclopropyl-1H-1,2,3-triazol-1-yl)phenyl) pyrimidin-4-ol hydrobromide A clear, yellow solution of 4-(5-chloro-2-(4-cyclopropyl-1H-1,2,3-triazol-1-yl)phenyl)-6-methoxypyrimidine (0.024 g, 0.073 mmol) in HOAc (0.73 ml) and 48% aq HBr (0.41 ml, 3.66 mmol) was warmed to 65° C. for 3 h, and then cooled to rt and concentrated. The yellow gum was suspended in EtOAc and washed with brine, dried over Na$_2$SO$_4$, filtered, and concentrated. To the residue was added Et$_2$O (3 ml), sonicated, and filtered. The solid was rinsed with Et$_2$O (2 ml), air-dried with suction to afford 6-(5-chloro-2-(4-cyclopropyl-1H-1,2,3-triazol-1-yl)phenyl)pyrimidin-4-ol hydrobromide (0.03 g, 100% yield) as a yellow solid. MS(ESI) m/z: 314.0 (M+H)$^+$. $^1$H NMR (400 MHz, CD$_3$OD) δ 8.67 (d, J=0.7 Hz, 1H), 8.22 (s, 1H), 7.89 (d, J=2.4 Hz, 1H), 7.82 (dd, J=8.6, 2.2 Hz, 1H), 7.74 (d, J=8.6 Hz, 1H), 6.48 (d, J=0.9 Hz, 1H), 2.11-2.01 (m, 1H), 1.11-1.04 (m, 2H), 0.91-0.84 (m, 2H).

Intermediate 14

Preparation of 6-(3-chloro-6-(4-cyclopropyl-1H-1,2,3-triazol-1-yl)-2-fluorophenyl)pyrimidin-4-ol

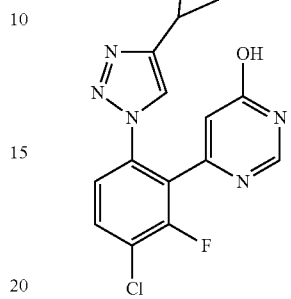

14A. Preparation of 4-(3-chloro-6-(4-cyclopropyl-1H-1,2,3-triazol-1-yl)-2-fluorophenyl)-6-methoxypyrimidine To a cooled (0° C.), clear, yellow solution of 4-chloro-3-fluoro-2-(6-methoxypyrimidin-4-yl)aniline (0.100 g, 0.39 mmol) in ACN (5.6 ml) was added isoamylnitrite (0.079 ml, 0.59 mmol), followed by the dropwise addition of TMSN$_3$ (0.078 ml, 0.59 mmol). After 10 min, the cold bath was removed, and the reaction was allowed to warm to rt. After 1 h, ethynylcyclopropane (0.112 g, 1.18 mmol) and Cu$_2$O (5.64 mg, 0.039 mmol) were added. The flask was equipped with a reflux condenser and the reaction was heated to 50° C. for 1 h, then the reaction was cooled to rt. The reaction was diluted with DCM and washed with sat NH$_4$Cl, brine, dried over MgSO$_4$, filtered and concentrated to give a brown oil. Purification by normal phase chromatography afforded 4-(3-chloro-6-(4-cyclopropyl-1H-1,2,3-triazol-1-yl)-2-fluorophenyl)-6-methoxypyrimidine (0.05 g, 36.7% yield) as a yellow oil. MS(ESI) m/z: 346.0 (M+H)$^+$. $^1$H NMR (400 MHz, CDCl$_3$) δ 8.69 (d, J=0.9 Hz, 1H), 7.63 (dd, J=8.6, 7.5 Hz, 1H), 7.35 (dd, J=8.6, 1.5 Hz, 1H), 7.30 (s, 1H), 6.76 (t, J=1.2 Hz, 1H), 4.00 (s, 3H), 1.90 (tt, J=8.4, 5.0 Hz, 1H), 0.98-0.91 (m, 2H), 0.82-0.76 (m, 2H).

14B. Preparation of 6-(3-chloro-6-(4-cyclopropyl-1H-1,2,3-triazol-1-yl)-2-fluorophenyl) pyrimidin-4-ol A clear, yellow solution of 4-(3-chloro-6-(4-cyclopropyl-1H-1,2,3-triazol-1-yl)-2-fluorophenyl)-6-methoxypyrimidine (0.05 g, 0.145 mmol) in HOAc (1.45 ml) and 48% aq HBr (0.82 ml, 7.23 mmol) was warmed to 65° C. for 3 h, and then the reaction was cooled to rt and concentrated. Purification by reverse phase chromatography afforded 6-(3-chloro-6-(4-cyclopropyl-1H-1,2,3-triazol-1-yl)-2-fluorophenyl)pyrimidin-4-ol (0.04 g, 83% yield) as a yellow solid. MS(ESI) m/z: 332.0 (M+H)$^+$. $^1$H NMR (400 MHz, CD$_3$OD) δ 8.09 (d, J=0.9 Hz, 1H), 7.91 (s, 1H), 7.82 (dd, J=8.6, 7.7 Hz, 1H), 7.49 (dd, J=8.8, 1.5 Hz, 1H), 6.50-6.47 (m, 1H), 1.97 (tt, J=8.5, 5.1 Hz, 1H), 1.01-0.95 (m, 2H), 0.81-0.75 (m, 2H). $^{19}$F NMR (376 MHz, CD$_3$OD) δ −115.39 (s).

Intermediate 15

Preparation of 6-{5-chloro-2-[4-(trifluoromethyl)-1H-1,2,3-triazol-1-yl]phenyl}pyrimidin-4-ol

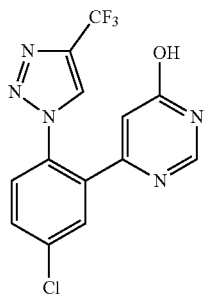

15A. Preparation of 4-{5-chloro-2-[4-(trifluoromethyl)-1H-1,2,3-triazol-1-yl]phenyl}-6-methoxypyrimidine

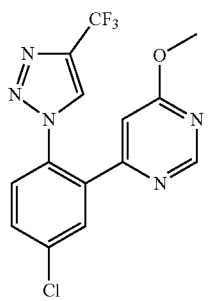

To a solution of 4-chloro-2-(6-methoxypyrimidin-4-yl)aniline (1.0 g, 4.24 mmol), prepared as described in Intermediate 9B, in ACN (60.6 ml) at 0° C. was added 3-methylbutyl nitrite (0.86 ml, 6.36 mmol) followed by the dropwise addition of TMSN₃ (0.84 ml, 6.36 mmol). Gas evolution was observed. After 10 min, the ice bath was removed, and the reaction was allowed to warm to rt. After 2 h, Cu₂O (61 mg, 0.42 mmol) was added followed by a slow bubbling of 3,3,3-trifluoroprop-1-yne gas over a period of 5 min. After an additional 10 min, the reaction was partitioned between DCM and sat NH₄Cl and then the layers were separated. The organic layer was washed with brine, dried over MgSO₄, filtered and concentrated. Purification by normal phase chromatography gave 4-{5-chloro-2-[4-(trifluoromethyl)-1H-1,2,3-triazol-1-yl]phenyl}-6-methoxypyrimidine (1.46 g, 97% yield) as a yellow solid. MS(ESI) m/z: 356.1 (M+H)⁺. ¹H NMR (400 MHz, CDCl₃) δ 8.62 (d, J=1.1 Hz, 1H), 8.00 (d, J=0.7 Hz, 1H), 7.75 (d, J=2.4 Hz, 1H), 7.66-7.60 (m, 1H), 7.52 (d, J=8.6 Hz, 1H), 6.60 (d, J=1.1 Hz, 1H), 3.98 (s, 3H). ¹⁹F NMR (376 MHz, CDCl₃) δ −61.10 (s).

15B. Preparation of 6-{5-chloro-2-[4-(trifluoromethyl)-1H-1,2,3-triazol-1-yl]phenyl}pyrimidin-4-ol

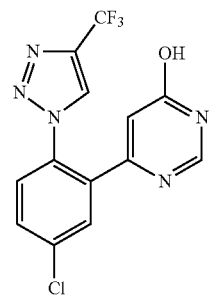

To a solution of 4-{5-chloro-2-[4-(trifluoromethyl)-1H-1,2,3-triazol-1-yl]phenyl}-6-methoxypyrimidine (1.46 g, 4.10 mmol) in AcOH (10 ml) was added 48% aq HBr (5 ml, 44.2 mmol). The mixture was stirred at 85° C. for 1 h. The reaction was concentrated to dryness and then partitioned between EtOAc and sat NaHCO₃. The layers were separated and the aqueous layer was extracted with EtOAc (2×). The organic layers were combined and washed with sat NaHCO₃, brine, dried over MgSO₄, filtered and the solvent was reduced under vacuum until some solid started to form. The resulting suspension was triturated with Et₂O. The solid was filtered and washed with Et₂O to give 6-{5-chloro-2-[4-(trifluoromethyl)-H-1,2,3-triazol-1-yl]phenyl}pyrimidin-4-ol (1 g, 71.3% yield) as a pale yellow solid. MS(ESI) m/z: 342.0 (M+H)⁺. 1H NMR (400 MHz, CD₃OD) δ 8.83 (d, J=0.7 Hz, 1H), 7.99 (d, J=0.9 Hz, 1H), 7.87 (d, J=2.2 Hz, 1H), 7.79-7.72 (m, 1H), 7.70-7.62 (m, 1H), 6.45 (d, J=0.9 Hz, 1H). ¹⁹F NMR (376 MHz, CD₃OD) δ −62.61 (s).

Intermediate 16

Preparation of 6-{5-chloro-2-[4-(difluoromethyl)-1H-1,2,3-triazol-1-yl]phenyl}pyrimidin-4-ol

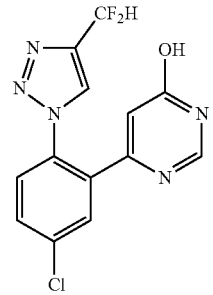

16A. Preparation of {1-[4-chloro-2-(6-methoxypyrimidin-4-yl)phenyl]-1H-1,2,3-triazol-4-yl}methanol

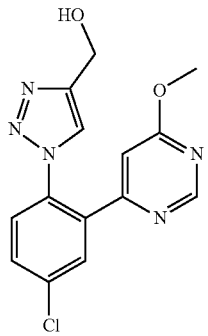 [SMILES: COc1cc(-c2cc(Cl)ccc2-n2cc(CO)nn2)ncn1]

{1-[4-Chloro-2-(6-methoxypyrimidin-4-yl)phenyl]-1H-1,2,3-triazol-4-yl}methanol (0.44 g, 52.5% yield) was prepared in a similar manner as the procedure described for the preparation of 4-{5-chloro-2-[4-(trimethylsilyl)-1H-1,2,3-triazol-1-yl]phenyl}-6-methoxypyrimidine, as described in Intermediate 9C, by replacing ethynyltrimethylsilane with propargyl alcohol (0.38 ml, 6.36 mmol). MS(ESI) m/z: 318.3 (M+H)+. $^{1}$H NMR (400 MHz, CDCl$_3$) δ 8.66 (d, J=1.1 Hz, 1H), 7.77 (d, J=2.2 Hz, 1H), 7.63 (s, 1H), 7.61-7.55 (m, 1H), 7.51-7.46 (m, 1H), 6.42 (d, J=1.1 Hz, 1H), 4.77 (d, J=5.9 Hz, 2H), 3.93 (s, 3H).

16B. Preparation of 1-[4-chloro-2-(6-methoxypyrimidin-4-yl)phenyl]-1H-1,2,3-triazole-4-carbaldehyde

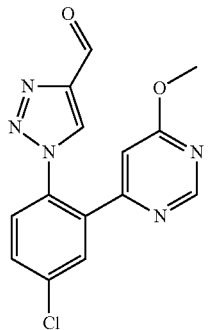 [SMILES: COc1cc(-c2cc(Cl)ccc2-n2cc(C=O)nn2)ncn1]

To a solution of {1-[4-chloro-2-(6-methoxypyrimidin-4-yl)phenyl]-1H-1,2,3-triazol-4-yl}methanol (95 mg, 0.3 mmol) in DMSO (1 mL) was added IBX (92 mg, 0.33 mmol) and the reaction was stirred at rt for 14 h. Water and sat NaHCO$_3$ were added and the mixture was extracted with EtOAc (2×). The organic layers were combined, concentrated and purified by normal phase chromatography to give 1-[4-chloro-2-(6-methoxy pyrimidin-4-yl)phenyl]-1H-1,2,3-triazole-4-carbaldehyde (82 mg, 87% yield) as a white solid. MS(ESI) m/z: 316.3 (M+H)+. $^{1}$H NMR (400 MHz, CDCl$_3$) δ 10.16 (s, 1H), 8.62 (d, J=1.1 Hz, 1H), 8.21 (s, 1H), 7.76 (d, J=2.2 Hz, 1H), 7.64 (dd, J=8.5, 2.3 Hz, 1H), 7.53 (d, J=8.4 Hz, 1H), 6.59 (d, J=1.1 Hz, 1H), 3.97 (s, 3H).

16C. Preparation of 4-{5-chloro-2-[4-(difluoromethyl)-1H-1,2,3-triazol-1-yl]phenyl}-6-methoxypyrimidine

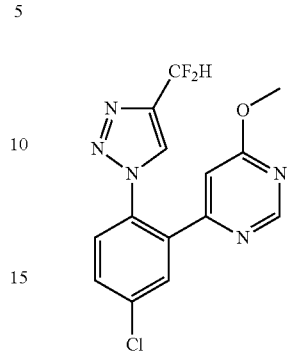

To a solution of 1-[4-chloro-2-(6-methoxypyrimidin-4-yl)phenyl]-1H-1,2,3-triazole-4-carbaldehyde (427 mg, 1.35 mmol) in DCM (30 ml) was added DAST (0.54 ml, 4.1 mmol) and the reaction was stirred overnight at rt. The reaction was quenched with water and extracted with DCM. The organic layer was concentrated and purified by normal phase chromatography to give 4-{5-chloro-2-[4-(difluoromethyl)-1H-1,2,3-triazol-1-yl]phenyl}-6-methoxypyrimidine (441 mg, 97% yield) as a yellow solid. MS(ESI) m/z: 338.3 (M+H)+. $^{1}$H NMR (400 MHz, CDCl$_3$) δ 8.65 (d, J=0.9 Hz, 1H), 7.89 (s, 1H), 7.76 (d, J=2.4 Hz, 1H), 7.62 (dd, J=8.5, 2.3 Hz, 1H), 7.55-7.47 (m, 1H), 6.89 (t, J=54.6 Hz, 1H), 6.52 (d, J=1.1 Hz, 1H), 4.03-3.87 (m, 3H). $^{19}$F NMR (376 MHz, CDCl$_3$) δ −112.40 (s).

16D. Preparation of 6-{5-chloro-2-[4-(difluoromethyl)-1H-1,2,3-triazol-1-yl]phenyl}pyrimidin-4-ol

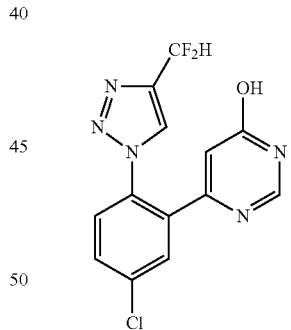

6-{5-Chloro-2-[4-(difluoromethyl)-1H-1,2,3-triazol-1-yl]phenyl}pyrimidin-4-ol (370 mg, 88% yield) was prepared in a similar manner as the procedure described for the preparation of 6-[5-chloro-2-(4-chloro-1H-1,2,3-triazol-1-yl)phenyl]pyrimidin-4-ol, as described in Intermediate 9E, by replacing 4-[5-chloro-2-(4-chloro-1H-1,2,3-triazol-1-yl)phenyl]-6-methoxypyrimidine with 4-{5-chloro-2-[4-(difluoromethyl)-1H-1,2,3-triazol-1-yl]phenyl}-6-methoxypyrimidine (441 mg, 1.31 mmol). MS(ESI) m/z: 324.3 (M+H)+. $^{1}$H NMR (400 MHz, CDCl$_3$) δ 8.04 (s, 1H), 7.86 (s, 1H), 7.71 (d, J=2.2 Hz, 1H), 7.67-7.61 (m, 1H), 7.51 (d, J=8.6 Hz, 1H), 6.92 (t, J=54.6 Hz, 1H), 6.43 (d, J=0.7 Hz, 1H). $^{19}$F NMR (376 MHz, CDCl$_3$) δ −112.69 (s).

Intermediate 17

Preparation of 6-[3-chloro-2-fluoro-6-(1H-1,2,3,4-tetrazol-1-yl)phenyl]pyrimidin-4-ol

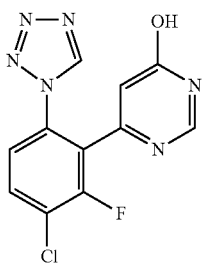 [SMILES: Oc1cc(-c2c(-n3cnnn3)ccc(Cl)c2F)ncn1]

17A. Preparation of 4-[3-chloro-2-fluoro-6-(1H-1,2,3,4-tetrazol-1-yl)phenyl]-6-methoxypyrimidine 4-Chloro-3-fluoro-2-(6-methoxypyrimidin-4-yl)aniline (300 mg, 1.183 mmol) dissolved in AcOH (3 mL) was added trimethoxymethane (377 mg, 3.55 mmol), stirred at rt. After 30 min, NaN$_3$ (231 mg, 3.55 mmol) was added and stirred at rt for 16 h. To the reaction mixture was added water and a precipitate formed. The mixture was filtered to collect the solid residue, and filtrate was extracted with EtOAc, and the organic later was washed with brine, dried over MgSO$_4$, filtered and concentrated to give a crude solid, which was then combined with original solid residue collected. The crude material was purified by normal phase chromatography to afford 4-(3-chloro-2-fluoro-6-(1H-tetrazol-1-yl)phenyl)-6-methoxypyrimidine (367 mg, 100% yield). MS(ESI) m/z: 307.08 (M+H)$^+$. $^1$H NMR (400 MHz, CDCl$_3$) δ 8.78 (s, 1H), 8.59 (d, J=1.1 Hz, 1H), 7.71 (dd, J=8.7, 7.4 Hz, 1H), 7.38 (dd, J=8.6, 1.8 Hz, 1H), 6.86 (dd, J=1.9, 1.2 Hz, 1H), 3.98 (s, 3H).

17B. Preparation of 6-[3-chloro-2-fluoro-6-(1H-1,2,3,4-tetrazol-1-yl)phenyl]pyrimidin-4-ol To a solution of 4-(3-chloro-2-fluoro-6-(1H-tetrazol-1-yl)phenyl)-6-methoxypyrimidine (50 mg, 0.163 mmol), NaI (244 mg, 1.630 mmol) dissolved in ACN (1.6 ml) was added TMSCl (0.2 ml, 1.630 mmol). The resulting reaction mixture was stirred at rt for 23 h. To the reaction mixture was added CELITE®, the slurry was filtered and the collected organics were concentrated to yield a crude solid. Purification by normal phase chromatography, followed by trituration with Et$_2$O, afforded 6-[3-chloro-2-fluoro-6-(1H-1,2,3,4-tetrazol-1-yl)phenyl]pyrimidin-4-ol (46 mg, 96% yield) as a white solid. MS(ESI) m/z: 293.08 (M+H)$^+$. $^1$H NMR (400 MHz, CD$_3$OD) δ 9.75 (s, 1H), 8.40 (s, 1H), 8.28 (dd, J=8.7, 7.6 Hz, 1H), 7.97 (dd, J=8.7, 1.7 Hz, 1H), 7.02 (s, 1H).

Intermediate 18

Preparation of 1-[4-chloro-2-(6-hydroxypyrimidin-4-yl)phenyl]-1H-1,2,3-triazole-4-carbonitrile

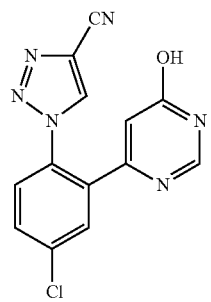 [SMILES: N#Cc1cn(-c2ccc(Cl)cc2-c2cc(O)ncn2)nn1]

18A. Preparation of 1-[4-chloro-2-(6-methoxypyrimidin-4-yl)phenyl]-1H-1,2,3-triazole-4-carboxamide

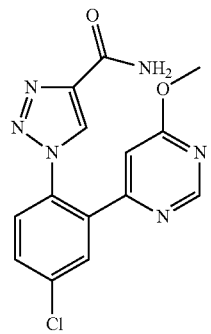 [SMILES: COc1cc(-c2cc(Cl)ccc2-n2cc(C(N)=O)nn2)ncn1]

1-[4-Chloro-2-(6-methoxypyrimidin-4-yl)phenyl]-1H-1,2,3-triazole-4-carboxamide (300 mg, 80% yield) was prepared in a similar manner as the procedure described for the preparation of 4-{5-chloro-2-[4-(trimethylsilyl)-1H-1,2,3-triazol-1-yl]phenyl}-6-methoxypyrimidine, as described in Intermediate 9C, by replacing ethynyltrimethylsilane with prop-2-ynamide (176 mg, 2.55 mmol). MS(ESI) m/z: 331.4 (M+H)$^+$. $^1$H NMR (400 MHz, CDCl$_3$) δ 8.66 (d, J=0.7 Hz, 1H), 8.16 (s, 1H), 7.76 (d, J=2.4 Hz, 1H), 7.62 (dd, J=8.5, 2.3 Hz, 1H), 7.51 (d, J=8.6 Hz, 1H), 7.05 (br. s., 1H), 6.53 (d, J=0.9 Hz, 1H), 5.66 (br. s., 1H), 3.97 (s, 3H).

18B. Preparation of 1-[4-chloro-2-(6-methoxypyrimidin-4-yl)phenyl]-1H-1,2,3-triazole-4-carbonitrile

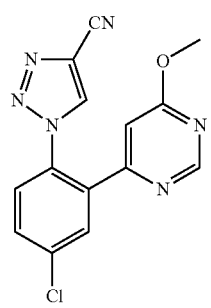 [SMILES: COc1cc(-c2cc(Cl)ccc2-n2cc(C#N)nn2)ncn1]

To a suspension of 1-[4-chloro-2-(6-methoxypyrimidin-4-yl)phenyl]-1H-1,2,3-triazole-4-carboxamide (91 mg, 0.28 mmol) and TEA (115 μl, 0.83 mmol) in EtOAc (6.88 ml) was added T3P® (50% in EtOAc) (0.49 ml, 0.83 mmol) dropwise. The reaction was microwaved at 120° C. for 1 h. Additional TEA (115 μl, 0.83 mmol) and T3P® (50% in EtOAc) (0.49 ml, 0.83 mmol) were added and the reaction was microwaved at 120° C. for an additional 30 min. The reaction was diluted with EtOAc and washed with water, sat NaHCO$_3$, brine, dried over MgSO$_4$, filtered, and concentrated. Purification by normal phase chromatography gave 1-[4-chloro-2-(6-methoxypyrimidin-4-yl)phenyl]-1H-1,2,3-triazole-4-carbonitrile (91 mg, 100% yield) as a white solid. MS(ESI) m/z: 313.3 (M+H)$^+$. $^1$H NMR (400 MHz, CDCl$_3$) δ 8.62 (d, J=0.9 Hz, 1H), 8.17 (s, 1H), 7.73 (d, J=2.4 Hz, 1H), 7.65 (dd, J=8.5, 2.3 Hz, 1H), 7.51 (d, J=8.6 Hz, 1H), 6.65 (d, J=1.1 Hz, 1H), 4.00 (s, 3H).

18C. Preparation of 1-[4-chloro-2-(6-hydroxypyrimidin-4-yl)phenyl]-1H-1,2,3-triazole-4-carbonitrile

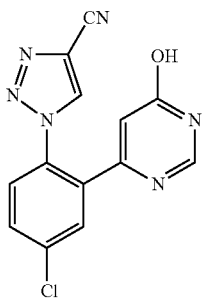 [SMILES: N#Cc1cn(-c2ccc(Cl)cc2-c2cc(O)ncn2)nn1]

To a suspension of 1-[4-chloro-2-(6-methoxypyrimidin-4-yl)phenyl]-1H-1,2,3-triazole-4-carbonitrile (91 mg, 0.29 mmol) in ACN (3 mL) was added TMSI (0.2 mL, 1.47 mmol) at rt and the solution was heated at 50° C. for 15 h. The reaction was poured into 10% Na$_2$S$_2$O$_3$ and sat NaHCO$_3$ then extracted with EtOAc (3×). The combined organic layers were washed with brine. On standing, a solid precipitated out from the organic layer. The solid was filtered and rinsed with EtOAc and air-dried to give 1-[4-chloro-2-(6-hydroxypyrimidin-4-yl)phenyl]-1H-1,2,3-triazole-4-carbonitrile (60 mg, 69.0% yield) as a white solid. MS(ESI) m/z: 299.3 (M+H)+. $^1$H NMR (400 MHz, CDCl$_3$) δ 8.22 (s, 1H), 7.91 (s, 1H), 7.72 (d, J=2.2 Hz, 1H), 7.66 (dd, J=8.5, 2.3 Hz, 1H), 7.49 (d, J=8.4 Hz, 1H), 6.55 (s, 1H).

Intermediate 19

Preparation of (9R,13S)-13-amino-9-methyl-3-{[2-(trimethylsilyl)ethoxy]methyl}-3,4,7,15-tetraazatricyclo[12.3.1.0$^{2,6}$]octadeca-1(18),2(6),4,14,16-pentaen-8-one

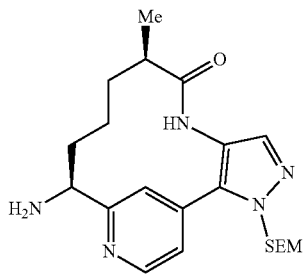 [SMILES: C[C@@H]1CCC[C@H](N)c2cc(ccn2)-c2c(cnn2COCC[Si](C)(C)C)NC1=O]

19A. Preparation of 4-nitro-1-((2-(trimethylsilyl)ethoxy)methyl)-1H-pyrazole

To a solution of 4-nitro-1H-pyrazole (5.0 g, 44.2 mmol) in THF (100 mL) at 0° C. was added N-cyclohexyl-N-methylcyclohexanamine (0.948 mL, 4.43 mmol) followed by dropwise addition of SEM-Cl (12.55 mL, 70.7 mmol). The reaction mixture was then allowed to gradually warm to rt and stirred overnight. The reaction mixture was concentrated and purified by normal phase chromatography to yield 4-nitro-1-((2-(trimethylsilyl)ethoxy)methyl)-1H-pyrazole as clear oil (2.4 g, 21% yield). $^1$H NMR (500 MHz, CDCl$_3$) δ 8.31 (s, 1H), 8.10 (s, 1H), 5.46 (s, 2H), 3.67-3.55 (m, 2H), 0.99-0.90 (m, 2H), 0.05-0.03 (m, 9H).

19B. Preparation of (S)-benzyl (1-(4-(4-nitro-1-((2-(trimethylsilyl)ethoxy)methyl)-1H-pyrazol-5-yl)pyridin-2-yl)but-3-en-1-yl)carbamate To a N$_2$ flushed pressure vial was added (S)-benzyl (1-(4-chloropyridin-2-yl)but-3-en-1-yl)carbamate, prepared as described in Intermediate 23, (1.9 g, 6.00 mmol), 4-nitro-1-((2-(trimethylsilyl)ethoxy)methyl)-1H-pyrazole, prepared as described in Intermediate 41A, (1.6 g, 6.60 mmol), di(adamant-1-yl)(butyl)phosphine (0.323 g, 0.90 mmol), PvOH (0.209 mL, 1.80 mmol) and K$_2$CO$_3$ (2.48 g, 17.9 mmol). To the above mixture was then added N,N-dimethylacetamide (45 mL) and the vial was purged with N$_2$ for 5 min. To this mixture was then added Pd(OAc)$_2$ (0.135 g, 0.600 mmol). The reaction mixture was again purged with N$_2$. The vial was sealed and heated in microwave at 120° C. for 1 h. The reaction mixture was cooled to rt and partitioned between 10% aqueous LiCl (15 mL) and EtOAc (30 mL). The aqueous layer was extracted with EtOAc (2×20 mL) and the combined organic layers were washed with brine (15 mL) and dried over MgSO$_4$. The crude product was then purified using normal phase chromatography to yield (S)-benzyl (1-(4-(4-nitro-1-((2-(trimethylsilyl)ethoxy)methyl)-1H-pyrazol-5-yl)pyridin-2-yl)but-3-en-1-yl)carbamate (1.92 g, 58% yield) as a brown oil. MS(ESI) m/z: 524.2 (M+H)$^+$.

19C. Preparation of (S)-benzyl(1-(4-(4-amino-1-((2-(trimethylsilyl)ethoxy)methyl)-1H-pyrazol-5-yl)pyridin-2-yl)but-3-en-1-yl)carbamate A solution of (S)-benzyl (1-(4-(4-nitro-1-((2-(trimethylsilyl)ethoxy)methyl)-1H-pyrazol-5-yl)pyridin-2-yl)but-3-en-1-yl)carbamate (1.92 g, 3.68 mmol), prepared as described in Intermediate 41B, in MeOH (20 mL) and AcOH (2 mL) was heated at 40° C. To the above clear solution was then slowly added Zn (0.481 g, 7.35 mmol, in 3 portions (50:25:25%)) and allowed to stir at the same temperature for 5 min. The reaction mixture was monitored by LCMS and once complete, to the cooled reaction mixture was added 2.0 g of K$_2$CO$_3$ (1 g for 1 mL AcOH) and 2 mL water. The reaction mixture was stirred for 5 min then filtered over a pad of CELITE® and concentrated to yield the crude product. The crude product was then partitioned between EtOAc (30 mL) and sat NaHCO$_3$(15 mL) solution. The organic layers are separated and dried over MgSO$_4$, filtered and concentrated. The crude product was then purified using normal phase chromatography to yield (S)-benzyl (1-(4-(4-amino-1-((2-(trimethylsilyl)ethoxy)methyl)-1H-pyrazol-5-yl)pyridin-2-yl)but-3-en-1-yl)carbamate (1.15 g, 63% yield) as pale yellow oil. MS(ESI) m/z: 494.4 (M+H)$^+$.

19D. Preparation of benzyl ((S)-1-(4-(4-((R)-2-methylbut-3-enamido)-1-((2-(trimethylsilyl)ethoxy)methyl)-1H-pyrazol-5-yl)pyridin-2-yl)but-3-en-1-yl)carbamate To a N₂ flushed, 3-necked, 250 mL RBF was added a solution (S)-benzyl (1-(4-(4-amino-1-((2-(trimethylsilyl)ethoxy)methyl)-1H-pyrazol-5-yl)pyridin-2-yl)but-3-en-1-yl)carbamate (1.15 g, 2.33 mmol), prepared as described in Example 41C, and EtOAc (15 mL). The solution was cooled to −10° C. and (R)-2-methylbut-3-enoic acid, as prepared in Intermediate 2, (350 mg, 3.49 mmol), pyridine (0.564 mL, 6.99 mmol) and T3P® (2.77 mL, 4.66 mmol) were added. The cooling bath was removed and the solution was allowed to warm to rt and then stir over a period of 20 h. Water (20 mL) and EtOAc (20 mL) were added and the mixture was stirred for 30 min. The organic phase was separated and the aqueous layer was extracted with EtOAc (20 mL). The combined organic extracts were washed with brine (15 mL), dried over Na₂SO₄, filtered and concentrated in vacuo. Purification by normal phase chromatography eluting with a gradient of hexanes/EtOAc gave benzyl ((S)-1-(4-(4-((R)-2-methylbut-3-enamido)-1-((2-(trimethylsilyl)ethoxy)methyl)-1H-pyrazol-5-yl)pyridin-2-yl)but-3-en-1-yl)carbamate (1.12 g, 79% yield). MS(ESI) m/z: 576.4 [M+H]⁺.

19E. Preparation of Benzyl N-[(9R,10E,13S)-9-methyl-8-oxo-3-{[2-(trimethylsilyl) ethoxy]methyl}-3,4,7,15-tetraazatricyclo[12.3.1.0²,⁶]octadeca-1(18), 2(6),4,10,14,16-hexaen-13-yl]carbamate To a N₂ flushed, 250 mL, 3-necked, RBF was added a solution of benzyl ((S)-1-(4-(4-((R)-2-methylbut-3-enamido)-1-((2-(trimethylsilyl)ethoxy)methyl)-1H-pyrazol-5-yl)pyridin-2-yl)but-3-en-1-yl)carbamate (1.12 g, 1.945 mmol), prepared as described in Intermediate 41D, in DCE (18 mL). The solution was sparged with Ar for 15 min. Second Generation Grubbs Catalyst (662 mg, 0.778 mmol) was added in one portion. The reaction mixture was heated at 120° C. in microwave for 30 min. After cooling to rt, the solvent was removed and the residue was purified by normal phase chromatography eluting with a gradient of DCM/MeOH to yield benzyl N-[(9R,10E,13S)-9-methyl-8-oxo-3-{[2-(trimethylsilyl)ethoxy]methyl}-3,4,7,15-tetraazatricyclo[12.3.1.0²,⁶]octadeca-1(18),2(6),4,10,14,16-hexaen-13-yl]carbamate (477 mg, 42% yield) as a tan solid. MS(ESI) m/z: 548.3 [M+H]⁺.

19F. Preparation of (9R,13S)-13-amino-9-methyl-3-{[2-(trimethylsilyl)ethoxy]methyl}-3,4,7,15-tetraazatricyclo[12.3.1.0²,⁶]octadeca-1(18),2(6),4,14,16-pentaen-8-one Pd/C (0.93 g, 0.871 mmol) was added to a 250 mL Parr hydrogenation flask containing a solution of benzyl N-[(9R,10E,13S)-9-methyl-8-oxo-3-{[2-(trimethylsilyl) ethoxy]methyl}-3,4,7,15-tetraazatricyclo[12.3.1.0²,⁶]octadeca-1(18),2(6),4,10,14,16-hexaen-13-yl]carbamate (477 mg, 0.871 mmol), prepared as described in Intermediate 41E, in EtOH (20 mL). The flask was purged with N₂ and pressurized to 55 psi of H₂ and allowed to stir for 4 h. The reaction was filtered through a pad of CELITE® and concentrated to yield (9R,13S)-13-amino-9-methyl-3-{[2-(trimethylsilyl)ethoxy]methyl}-3,4,7,15-tetraazatricyclo[12.3.1.0²,⁶]octadeca-1(18),2(6),4,14,16-pentaen-8-one (245 mg, 64% yield) as a tan solid. MS(ESI) m/z: 416.4 [M+H]⁺.

Intermediate 20

Preparation of 6-[5-chloro-2-(1H-1,2,3,4-tetrazol-1-yl)phenyl]pyrimidin-4-ol

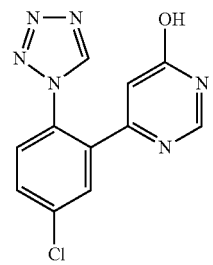 [SMILES: Oc1cc(-c2cc(Cl)ccc2-n2cnnn2)ncn1]

20A. Preparation of 4-[5-chloro-2-(1H-1,2,3,4-tetrazol-1-yl)phenyl]-6-methoxypyrimidine To a solution of 4-chloro-2-(6-methoxypyrimidin-4-yl)aniline (0.507 g, 2.151 mmol) dissolved in AcOH (5.4 ml) was added trimethoxymethane (0.685 g, 6.45 mmol) and the resulting solution was stirred at rt for 30 min. After that time NaN₃ (0.420 g, 6.45 mmol) was added and the reaction mixture was stirred at rt for 16 h. Water was added to form a precipitate. The precipitate was collected by filtration, and filtrate was extracted with EtOAc, which was then washed with brine, dried over MgSO₄, filtered and concentrated to give a crude solid. The combined solid residue was purified by normal phase chromatography to afford 4-(5-chloro-2-(1H-tetrazol-1-yl)phenyl)-6-methoxypyrimidine (0.59 g, 95% yield) as an off-white solid. MS(ESI) m/z: 289.08 (M+H)⁺. ¹H NMR (400 MHz, CDCl₃) δ 8.76 (s, 1H), 8.62 (d, J=0.9 Hz, 1H), 7.74 (d, J=2.2 Hz, 1H), 7.66 (dd, J=8.5, 2.3 Hz, 1H), 7.52 (d, J=8.4 Hz, 1H), 6.65 (d, J=1.1 Hz, 1H), 3.99 (s, 3H).

20B. Preparation of 6-[5-chloro-2-(1H-1,2,3,4-tetrazol-1-yl)phenyl]pyrimidin-4-ol To a solution of 4-(5-chloro-2-(1H-tetrazol-1-yl)phenyl)-6-methoxypyrimidine (0.59 g, 2.044 mmol), NaI (3.06 g, 20.44 mmol) in ACN (20.44 ml) was added TMSCl (2.6 ml, 20.44 mmol), and the reaction was stirred at rt for 16 h. CELITE® was added to the reaction mixture, the slurry was filtered, and concentrated to give a crude solid mixture. The solid was purified by normal phase chromatography, then recrystallized from EtOAc to give 6-[5-chloro-2-(1H-1,2,3,4-tetrazol-1-yl)phenyl]pyrimidin-4-ol (370 mg, 66% yield) as a white solid. MS(ESI) m/z: 275.08 (M+H)⁺. ¹H NMR (400 MHz, DMSO-d₆) δ 12.62 (br. s., 1H), 9.72 (s, 1H), 7.97 (d, J=0.7 Hz, 1H), 7.92 (d, J=2.2 Hz, 1H), 7.87-7.83 (m, 1H), 7.82-7.78 (m, 1H), 6.48 (d, J=0.7 Hz, 1H).

Intermediate 21

Preparation of 6-(3-chloro-6-(4-(difluoromethyl)-1H-1,2,3-triazol-1-yl)-2-fluorophenyl)pyrimidin-4-ol

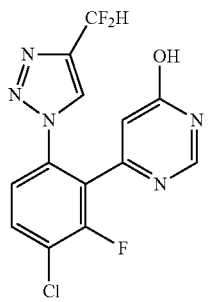 [SMILES: Oc1cc(-c2c(-n3cc(C(F)F)nn3)ccc(Cl)c2F)ncn1]

21A. Preparation of (1-(4-chloro-3-fluoro-2-(6-methoxypyrimidin-4-yl)phenyl)-1H-1,2,3-triazol-4-yl)methanol To a cooled (0° C.), clear, yellow solution of 4-chloro-3-fluoro-2-(6-methoxypyrimidin-4-yl)aniline (1.058 g, 4.17 mmol) in ACN (59.6 ml) was added isoamylnitrite (0.84 ml, 6.26 mmol), followed by the dropwise addition of $TMSN_3$ (0.82 ml, 6.26 mmol). After 10 min, the cold bath was removed, and the reaction was allowed to warm to rt. Propargyl alcohol (0.75 ml, 12.51 mmol) and $Cu_2O$ (0.060 g, 0.42 mmol) were added. After 1 h, the reaction was diluted with EtOAc and washed with sat $NH_4Cl$, brine, dried over $MgSO_4$, filtered and concentrated to give a brown oil. The crude product was purified by normal phase chromatography to give (1-(4-chloro-3-fluoro-2-(6-methoxypyrimidin-4-yl)phenyl)-1H-1,2,3-triazol-4-yl)methanol (0.8 g, 57.1% yield) as a yellow foam. MS(ESI) m/z: 336.1 $(M+H)^+$. $^1H$ NMR (400 MHz, $CDCl_3$) δ 8.65 (d, J=1.1 Hz, 1H), 7.69-7.62 (m, 2H), 7.37 (dd, J=8.6, 1.5 Hz, 1H), 6.81 (t, J=1.2 Hz, 1H), 4.76 (d, J=5.9 Hz, 2H), 4.00 (s, 3H), 2.18 (t, J=6.1 Hz, 1H).

21B. Preparation of I-(4-chloro-3-fluoro-2-(6-methoxypyrimidin-4-yl)phenyl)-1H-1,2,3-triazole-4-carbaldehyde To the solution of (1-(4-chloro-3-fluoro-2-(6-methoxypyrimidin-4-yl)phenyl)-1H-1,2,3-triazol-4-yl)methanol (0.8 g, 2.38 mmol) in DMSO (9.53 ml) was added IBX (0.734 g, 2.62 mmol), and the reaction was stirred at rt. After 18 h, water and sat $NaHCO_3$ were added and the reaction mixture was extracted with EtOAc (2×). The organic layers were combined and dried over $Na_2SO_4$, filtered, and concentrated. Purification by normal phase chromatography afforded 1-(4-chloro-3-fluoro-2-(6-methoxypyrimidin-4-yl)phenyl)-1H-1,2,3-triazole-4-carbaldehyde (0.64 g, 80% yield) as a white solid. MS(ESI) m/z: 334.4 $(M+H)^+$. $^1H$ NMR (400 MHz, $CDCl_3$) δ 10.12 (s, 1H), 8.60 (d, J=1.1 Hz, 1H), 8.25 (s, 1H), 7.71 (dd, J=8.6, 7.5 Hz, 1H), 7.39 (dd, J=8.6, 1.8 Hz, 1H), 6.88 (dd, J=1.8, 1.1 Hz, 1H), 4.01 (s, 3H).

21C. Preparation of 4-(3-chloro-6-(4-(difluoromethyl)-1H-1,2,3-triazol-1-yl)-2-fluorophenyl)-6-methoxypyrimidine To the solution of 1-(4-chloro-3-fluoro-2-(6-methoxypyrimidin-4-yl)phenyl)-1H-1,2,3-triazole-4-carbaldehyde (0.3 g, 0.9 mmol) in DCM (24 ml) was added DAST (0.54 ml, 4.09 mmol). The reaction was stirred at rt for 22 h. To the reaction was added water and the resulting mixture was extracted with DCM. The organic layer was washed with brine, dried over $Na_2SO_4$, filtered, and concentrated. Purification by normal phase chromatography afforded 4-(3-chloro-6-(4-(difluoromethyl)-1H-1,2,3-triazol-1-yl)-2-fluorophenyl)-6-methoxypyrimidine (0.256 g, 80% yield) as a white solid. MS(ESI) m/z: 356.1 $(M+H)^+$. $^1H$ NMR (400 MHz, $CDCl_3$) δ 8.62 (d, J=0.9 Hz, 1H), 7.94 (t, J=1.3 Hz, 1H), 7.69 (dd, J=8.6, 7.5 Hz, 1H), 7.39 (dd, J=8.6, 1.8 Hz, 1H), 7.00-6.69 (m, 2H), 4.00 (s, 3H).

21D. Preparation of 6-(3-chloro-6-(4-(difluoromethyl)-1H-1,2,3-triazol-1-yl)-2-fluorophenyl)pyrimidin-4-ol A clear, yellow solution of 4-(3-chloro-6-(4-(difluoromethyl)-1H-1,2,3-triazol-1-yl)-2-fluorophenyl)-6-methoxypyrimidine (0.256 g, 0.72 mmol) in HOAc (3.6 ml) and 48% aq HBr (4.07 ml, 36.0 mmol) was warmed to 65° C. for 3 h, and then the reaction was cooled to rt and concentrated. The yellow gum was suspended in EtOAc and washed with sat $NaHCO_3$(2×), brine, dried over $Na_2SO_4$, filtered, and concentrated. The residue was suspended in $Et_2O$ (3 ml), sonicated, and filtered. The solid was rinsed with $Et_2O$ (2 ml), air-dried with suction to afford 6-(3-chloro-6-(4-(difluoromethyl)-1H-1,2,3-triazol-1-yl)-2-fluorophenyl)pyrimidin-4-ol (0.23 g, 94% yield) as a yellow solid. MS(ESI) m/z: 342.0 $(M+H)^+$. $^1H$ NMR (400 MHz, $CD_3OD$) δ 8.56 (t, J=1.4 Hz, 1H), 8.05 (d, J=0.9 Hz, 1H), 7.86 (dd, J=8.6, 7.7 Hz, 1H), 7.57 (dd, J=8.7, 1.7 Hz, 1H), 6.98 (t, J=54.0 Hz, 1H), 6.58 (t, J=1.2 Hz, 1H). $^{19}F$ NMR (376 MHz, $CD_3OD$) δ −114.68 (s), −115.20 (s).

Intermediate 22

Preparation of 6-(5-chloro-1-methyl-1H-indazol-7-yl)pyrimidin-4-ol

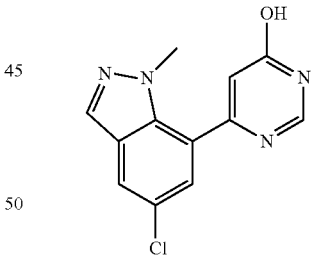

22A. Preparation of 7-bromo-5-chloro-1-methyl-1H-indazole

To a solution of 7-bromo-5-chloro-1H-indazole (5.0 g, 21.60 mmol) and $K_2CO_3$ (14.93 g, 108 mmol) in DMSO (24.91 ml) was added $CH_3I$ (1.62 ml, 25.9 mmol) at rt. The reaction mixture was stirred at rt overnight. Reaction was diluted with water and the resulting solid filtered through a Buchner funnel, washed with water, and dried under vacuum. The regioisomers were separate by normal phase chromatography eluting with a gradient of hexanes/EtOAc with the 1st isomer to elute off of the column being 7-bromo-5-chloro-1-methyl-1H-indazole (2.83 g, 53.4%) as confirmed by ¹H NMR and a negative NOE. MS(ESI) m/z: 245 (M+H)⁺ and 247 (M+2+H)⁺. ¹H NMR (400 MHz, DMSO-d₆) δ 8.12-8.09 (m, 1H), 7.88 (d, J=1.8 Hz, 1H), 7.67 (d, J=1.5 Hz, 1H), 4.32 (s, 3H).

22B. Preparation of 5-chloro-1-methyl-7-(4,4,5,5-tetramethyl-1,3,2-dioxaborolan-2-yl)-1H-indazole To a stirring solution of 7-bromo-5-chloro-1-methyl-1H-indazole (1.0 g, 4.07 mmol) in dioxane (20.37 ml) at rt was added 4,4,4',4',5,5,5',5'-octamethyl-2,2'-bi(1,3,2-dioxaborolane) (1.190 g, 4.68 mmol) and KOAc (1.839 g, 18.74 mmol). The reaction was purged with Ar (3×). Pd(dppf)Cl₂ DCM complex (0.266 g, 0.326 mmol) was added, the reaction was again purged with Ar, and heated to 90° C. After stirring overnight, the reaction mixture was cooled to rt, diluted with water, extracted with EtOAc (3×), washed with water, brine, dried over Na₂SO₄, filtered, and concentrated. The crude residue was purified by normal phase column chromatography eluting with a gradient of hexanes/EtOAc to give 5-chloro-1-methyl-7-(4,4,5,5-tetramethyl-1,3,2-dioxaborolan-2-yl)-1H-indazole (0.47 g, 39.4% yield) an oil which slowly solidified upon standing. MS(ESI) m/z: 293.0 (M+H)⁺ and 295.0 (M+2+H)⁺. ¹H NMR (400 MHz, CD₃OD) δ 7.94 (s, 1H), 7.80 (d, J=2.2 Hz, 1H), 7.71 (d, J=2.2 Hz, 1H), 4.23 (s, 3H), 1.40 (s, 12H).

22C. Preparation of 5-chloro-7-(6-methoxypyrimidin-4-yl)-1-methyl-1H-indazole To a large microwave vial was added 4-chloro-6-methoxypyrimidine (0.201 g, 1.391 mmol), 5-chloro-1-methyl-7-(4,4,5,5-tetramethyl-1,3,2-dioxaborolan-2-yl)-1H-indazole (0.407 g, 1.391 mmol), and 2 M aqNa₂CO₃ (0.70 ml, 1.391 mmol) in DME (5.56 ml)/EtOH (0.696 ml). The mixture was purged with Ar for several min, PdCl₂(dppf)-CH₂Cl₂ adduct (0.114 g, 0.139 mmol) added and then heated at 90° C. After 4 h, the reaction mixture was cooled to rt, diluted with water, and extracted with EtOAc. The organic layer washed with brine, dried over Na₂SO₄, filtered, and concentrated to give an orange-brown residue. The crude material was purified by normal phase column chromatography eluting with a gradient of hexanes/EtOAc to give 5-chloro-7-(6-methoxypyrimidin-4-yl)-1-methyl-1H-indazole (0.382, 100%) as a solid. MS(ESI) m/z: 275.1 (M+H)⁺ and 277.1 (M+2+H)⁺.

22D. Preparation of 6-(5-chloro-1-methyl-1H-indazol-7-yl)pyrimidin-4-ol

A clear, yellow solution of 5-chloro-7-(6-methoxypyrimidin-4-yl)-1-methyl-1H-indazole (0.382 g, 1.391 mmol) in AcOH (3 ml) and 48% aq HBr (1.639 ml, 14.49 mmol) was warmed to 85° C. After 3 h, the reaction mixture was concentrated. The residue was dissolved in EtOAc and washed with sat NaHCO₃. The aqueous layer was extracted with additional EtOAc, washed with brine, dried over Na₂SO₄, filtered, and concentrated. The resulting solid was suspended with Et₂O, filtered, and dried under vacuum to give 6-(5-chloro-1-methyl-1H-indazol-7-yl)pyrimidin-4-ol (0.085 g, 23.5%) as a white solid. MS(ESI) m/z: 261.0 (M+H)⁺ and 263.0 (M+2+H)⁺. ¹H NMR (400 MHz, DMSO-d₆) δ 12.78 (br. s., 1H), 8.32 (s, 1H), 8.13 (s, 1H), 7.97 (d, J=1.8 Hz, 1H), 7.46-7.36 (m, 1H), 6.66 (s, 1H), 3.87 (s, 3H).

Intermediate 23

Preparation of tert-butyl N-[(1S)-1-(4-chloropyridin-2-yl)but-3-en-1-yl]carbamate

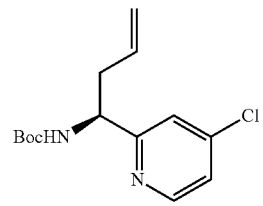 [SMILES: C=CC[C@H](NC(=O)OC(C)(C)C)c1cc(Cl)ccn1]

23A. Preparation of 4-chloro-2-[(E)-2-[(S)-2-methylpropane-2-sulfinyl]ethenyl]pyridine To a solution of S-(−)-t-butyl-sulfinamide (0.856 g, 7.06 mmol) in DCM (14.13 mL) was added sequentially CuSO₄ (2.481 g, 15.54 mmol) and 4-chloropicolinaldehyde (1.0 g, 7.06 mmol). The white suspension was stirred at rt. After 3 h, the brown suspension was filtered through CELITE®, eluting with DCM, to give a clear brown filtrate. Concentration gave crude product as a brown oil weighing 1.85 g. Purification by normal phase chromatography gave tert-butyl N-[(1S)-1-(4-chloropyridin-2-yl)but-3-en-1-yl]carbamate (1.31 g) as a clear, yellow oil. MS(ESI) m/z: 245.0 (M+H)⁺.

23B. Preparation of (R)—N-[(1S)-1-(4-chloropyridin-2-yl)but-3-en-1-yl]-2-methylpropane-2-sulfinamide To a cooled (0-5° C.) mixture of InCl₃ (13.56 g, 61.3 mmol) in THF (170 mL) was added dropwise over 30 min 1 M allylmagnesium bromide in Et₂O (62 mL, 61.3 mmol). The reaction was allowed to warm to rt. After 1 h, a solution of 4-chloro-2-[(E)-2-[(S)-2-methylpropane-2-sulfinyl]ethenyl]pyridine (10 g, 40.9 mmol) in EtOH (170 mL) was added to the reaction mixture. After 2-3 h, the reaction was concentrated under vacuum at 50-55° C. The crude material was partitioned between EtOAc (200 ml) and water (50 ml) and the layers were separated. The aqueous layer was extracted with EtOAc (2×50 ml). The organic layers were combined and washed with brine (100 ml), dried over Na₂SO₄, filtered and concentrated to give (R)—N-[(1S)-1-(4-chloropyridin-2-yl)but-3-en-1-yl]-2-methylpropane-2-sulfinamide (13.5 g, 106%) as a yellow oil. MS(ESI) m/z: 287.2 (M+H)⁺.

23C. Preparation of (1S)-1-(4-chloropyridin-2-yl)but-3-en-1-amine (R)—N-[(1S)-1-(4-Chloropyridin-2-yl)but-3-en-1-yl]-2-methylpropane-2-sulfinamide (75 g, 261 mmol) was dissolved in MeOH (1500 mL). 6 N HCl (750 ml, 4.5 mol) was added. The reaction was stirred at rt for 2-3 h and then was concentrated. The residue was diluted with water (2 L), washed with EtOAc (500 ml). The aqueous layer was basified with sat aq Na₂CO₃, then extracted into EtOAc (3×1 L). The combined organic layers were washed with water (1

L) and brine (1 L), dried over $Na_2SO_4$, filtered and conc. under vacuum at 50-55° C. to give (1S)-1-(4-chloropyridin-2-yl)but-3-en-1-amine (43g, 90%). MS(ESI) m/z: 183.2 $(M+H)^+$.

23D. Preparation of Tert-Butyl N-[(1S)-1-(4-chloropyridin-2-yl)but-3-en-1-yl]carbamate (1S)-1-(4-Chloropyridin-2-yl)but-3-en-1-amine (42g, 230 mmol) was dissolved in DCM (420 mL), $Et_3N$ (32.1 mL, 230 mmol) was added followed by dropwise addition of $BOC_2O$ (53.4 mL, 230 mmol). The reaction was stirred at rt for 2-3 h. The reaction was diluted with excess DCM (1 L), washed with water (500 ml) and brine (500 ml). The organic layer was dried over $Na_2SO_4$, filtered, and concentrated. The crude product was purified using silica gel chromatography to give tert-butyl N-[(1S)-1-(4-chloropyridin-2-yl)but-3-en-1-yl]carbamate (61 g, 86%) as a pale yellow solid. MS(ESI) m/z: 283.2 $(M+H)^+$. $^1H$ NMR (500 MHz, $CDCl_3$) δ 8.44 (d, 1H), 7.26-7.16 (dd, 2H), 5.69-5.61 (m, 1H), 5.59 (bs, 1H), 5.07-5.03 (m, 2H), 4.76 (bs, 1H), 2.62-2.55 (m, 2H), 1.42 (s, 9H).

Intermediate 24

Preparation of Tert-Butyl N-[(1S)-1-(3-bromophenyl)but-3-en-1-yl]carbamate

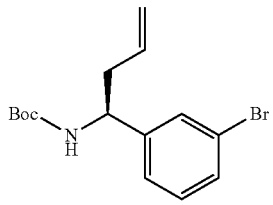 [SMILES: C=CC[C@H](NC(=O)OC(C)(C)C)c1cccc(Br)c1]

24A. Preparation of (R)—N-[(1E)-(3-bromophenyl)methylidene]-2-methylpropane-2-sulfinamide To 3-bromobenzaldehyde (7.8 g, 42.2 mmol) was added (R)-2-methylpropane-2-sulfinamide (5.11 g, 42.2 mmol), $Cs_2CO_3$ (20.60 g, 63.2 mmol) in DCM (211 ml) and the resulting reaction mixture was stirred for 5 days. The reaction mixture was then partitioned with brine (50 ml) and DCM (50 ml). The aqueous layer was extracted with DCM (2×50 ml). The combined organic layers were washed with brine (25 ml), dried ($Na_2SO_4$), filtered and concentrated. Purification by normal phase chromatography using hexanes and EtOAc as eluents gave (R)—N-[(1E)-(3-bromophenyl)methylidene]-2-methylpropane-2-sulfinamide (11.8 g, 97%) as an amber oil. $^1H$ NMR (400 MHz, $CDCl_3$) δ 8.53 (s, 1H), 8.02 (t, J=1.8 Hz, 1H), 7.74 (dt, J=7.7, 1.2 Hz, 1H), 7.64 (ddd, J=8.0, 2.0, 1.0 Hz, 1H), 7.36 (t, J=7.8 Hz, 1H), 1.34-1.22 (m, 9H). MS(ESI) m/z: 290 $(M+H)^+$.

24B. Preparation of (R)—N-[(1S)-1-(3-bromophenyl)but-3-en-1-yl]-2-methylpropane-2-sulfinamide To (R)—N-[(1E)-(3-bromophenyl)methylidene]-2-methylpropane-2-sulfinamide (11.8 g, 40.9 mmol) in THF (190 ml), in a 3 neck flask, cooled to 0° C., was added allyl bromide (3.90 ml, 45.0 mmol) and In (6.58 g, 57.3 mmol). After stirred at rt for 18 h, the reaction was heated to 50° C. for 6 h, then stirred at rt for 18 h. The reaction mixture was filtered through CELITE® and the filtrate was quenched with water (100 ml). A thick clear gelatinous material formed in the aqueous layer. The organics were extracted with EtOAc (4×75 ml). The combined organic layer was washed with brine, dried with $MgSO_4$, filtered and concentrated to give (R)—N-[(1S)-1-(3-bromophenyl)but-3-en-1-yl]-2-methylpropane-2-sulfinamide as a clear oil (9.6 g, 71%). $^1H$ NMR (400 MHz, $CDCl_3$) δ 7.48 (t, J=1.8 Hz, 1H), 7.41 (dt, J=7.6, 1.6 Hz, 1H), 7.26-7.18 (m, 2H), 5.79-5.66 (m, 1H), 5.23-5.16 (m, 2H), 4.46 (ddd, J=8.1, 5.6, 2.0 Hz, 1H), 3.69 (s, 1H), 2.63-2.53 (m, 1H), 2.53-2.40 (m, 1H), 1.23-1.19 (m, 9H).

24C. Preparation of Tert-Butyl N-[(1S)-1-(3-bromophenyl)but-3-en-1-yl]carbamate

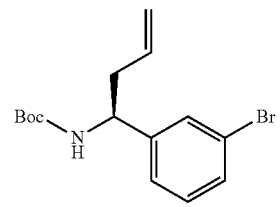 [SMILES: C=CC[C@H](NC(=O)OC(C)(C)C)c1cccc(Br)c1]

To (R)—N-[(1S)-1-(3-bromophenyl)but-3-en-1-yl]-2-methylpropane-2-sulfinamide (9.6 g, 29.1 mmol) in MeOH (300 ml) was added conc. HCl (4 ml). After 3 h, the reaction was concentrated and the residue was dissolved in DCM (300 ml), cooled to 0° C., and then TEA (16.20 ml, 116 mmol) and $Boc_{2O}$ (6.75 ml, 29.1 mmol) in DCM (20 ml) were added. After 18 h, additional $Boc_2O$ (1 g) was added and the reaction was stirred 4 h. The reaction was quenched with water (100 ml) and extracted with DCM (3×50 ml). The combined organic layers were washed with brine (50 ml), dried ($Na_2SO_4$), filtered and concentrated. Purification by normal phase chromatography using hexanes and EtOAc as eluents gave tert-butyl N-[(1S)-1-(3-bromophenyl)but-3-en-1-yl]carbamate (7.3 g, 77%) as a white solid. MS(ESI) m/z: 326.08 $(M+H)^+$.

Intermediate 25

Preparation of N-[(1S)-1-(3-bromo-5-fluorophenyl)but-3-en-1-yl]carbamate

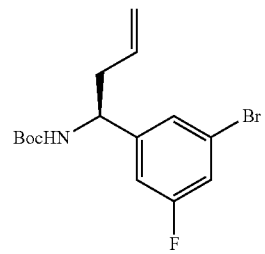 [SMILES: C=CC[C@H](NC(=O)OC(C)(C)C)c1cc(F)cc(Br)c1]

25A. Preparation of (R)—N-[(1E)-(3-bromo-5-fluorophenyl)methylidene]-2-methylpropane-2-sulfinamide To 3-bromo-5-fluorobenzaldehyde (25g, 123 mol) dissolved in DCM (200 mL) was added (R)-2-methylpropane- 2-sulfinamide (14.96 g, 123 mol) and Cs$_2$CO$_3$ (40.2 g, 123 mol). The reaction mixture was stirred at rt overnight. After this time, the reaction mixture was filtered and concentrated to give a yellow oil. The yellow oil was purified using a 120 g silica gel ISCO column eluted with hexanes and EtOAc to give (R)—N-[(1E)-(3-bromo-5-fluorophenyl)methylidene]-2-methylpropane-2-sulfinamide (35 g, 93%) as a yellow oil. $^1$H NMR (500 MHz, DMSO-d$_6$) δ 8.58-8.55 (m, 1H), 8.05-7.98 (m, 1H), 7.84-7.76 (m, 2H), 1.20 (s, 9H). LCMS m/z 306.1 (M+H).

25B. Preparation of (R)—N-[(1S)-1-(3-bromo-5-fluorophenyl)but-3-en-1-yl]-2-methylpropane-2-sulfinamide N-[(1E)-(3-Bromo-5-fluorophenyl)methylidene]-2,2-dimethylpropanamide (35 g, 114 mol) was dissolved in THF (500 mL) in a large 3 neck RB flask and flushed with Ar. The solution was cooled to 0° C. and In powder (18.4 g, 160 mol) was added followed by dropwise addition of allylbromide (15.2 g, 126 mol). The reaction was stirred at 0° C. for 2 h, then the ice bath was removed and the reaction mixture was stirred at rt overnight. The reaction was quenched with water (2 L) and the gelatinous material was filtered through CELITE®. The filtrate was concentrated to an oily mass. The crude material was dissolved in water (2 L) and the organics were extracted with EtOAc (4×200 mL), dried over MgSO$_4$, filtered and concentrated to give an oil. The oily liquid was purified via a silica gel ISCO column and eluted with DCM/MeOH to afford (R)—N-[(1S)-1-(3-bromo-5-fluorophenyl)but-3-en-1-yl]-2-methylpropane-2-sulfinamide (34.9 g, 88% yield) as a semi solid mass. LCMS m/z 348.2 (M+H). $^1$H NMR (500 MHz, DMSO-d$_6$) δ 7.44-7.38 (m, 2H), 7.26-7.20 (m, 1H), 5.79-5.65 (m, 1H), 5.46-5.42 (m, 1H), 5.04-4.98 (m, 2H), 4.41-4.34 (m, 1H), 2.69-2.59 (m, 1H), 2.49-2.43 (m, 1H), 1.09 (s, 9H).

25C. Preparation of N-[(1S)-1-(3-bromo-5-fluorophenyl)but-3-en-1-yl]carbamate To a cooled 0° C. solution of (R)—N-[(1S)-1-(3-bromo-5-fluorophenyl)but-3-en-1-yl]-2-methylpropane-2-sulfinamide (21.9 g, 100 mol) dissolved in MeOH (100 mL) was added conc. HCl (50 mL) dropwise and then the reaction was stirred at 0° C. for 48 h. After this time, the reaction mixture was concentrated to give a white solid mass. The residue was dissolved in water (1 L) and the organics were extracted with EtOAc (2×200 mL), dried over MgSO$_4$, filtered and concentrated to a brown oil (11.5 g). The aqueous layer was basified with NaOH and the organics were extracted with EtOAc (2×300 mL), dried over MgSO$_4$, filtered and concentrated to a brown oil (18 g). The combined oils were dissolved in DCM (500 mL) and to this was added Boc$_2$O (22 g) followed by TEA (15 mL) and the reaction mixture was stirred at rt overnight. The reaction mixture was concentrated and purified via a 330g silica gel Isco column eluting with hexanes and EtOAc to give a white solid. The white solid was triturated with hexanes and the precipitate was collected by filtration to give N-[(1S)-1-(3-bromo-5-fluorophenyl)but-3-en-1-yl]carbamate (29.5 g, 87% yield).

Intermediate 26

Preparation of N-[(1S)-1-(5-bromopyridin-3-yl)but-3-en-1-yl]carbamate

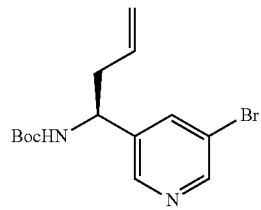 [SMILES: C=CC[C@H](NC(=O)OC(C)(C)C)c1cncc(Br)c1]

26A. Preparation of (R)—N-[(1E)-(5-chloropyridin-3-yl)methylidene]-2-methylpropane-2-sulfinamide 5-Bromonicotinaldehyde (6.6g, 35.9 mmol) was dissolved in DCM (200 mL). To the solution was added Cs$_2$CO$_3$ (11.68g, 35.9 mmol) and (R)-2-methylpropane-2-sulfinamide (4.34 g, 35.9 mol) and then the reaction mixture was stirred at rt overnight. The inorganics were filtered and the filtrate was concentrated to afford (R)—N-[(1E)-(5-chloropyridin-3-yl)methylidene]-2-methylpropane-2-sulfinamide as an oil (10.4g, 100% yield). LCMS m/z=291.3.

26B. Preparation of (R)—N-[(1S)-1-(5-chloropyridin-3-yl)but-3-en-1-yl]-2-methylpropane-2-sulfinamide To a solution of (R)—N-[(1E)-(5-chloropyridin-3-yl)methylidene]-2-methylpropane-2-sulfinamide (10.36 g, 35.8 mmol) in THF (150 mL) at 0° C. was added powdered In (5.76 g, 50.2 mmol) followed by allylbromide (3.72 mL, 43.0 mmol). The reaction mixture was sealed and was stirred vigorously at 0° C. for 1 h and then warmed to rt and stirred overnight. The reaction gradually turned from pale yellow to greenish yellow to dark greenish yellow with the indium metal forming fine particles. LCMS of the greenish black heterogenous solution showed the desired product peak and mass. The solution was filtered through a pad of CELITE® and washed with EtOAc. The solution was concentrated to afford a yellow solid mass. The solids were dissolved in MeOH (100 mL) and a solution of 4 N HCl in dioxane (25 mL) was added. The resultant solution was stirred at rt. After 6 h, conc. HCl (1 mL) was added and stirring was continued for 1 h. The reaction mixture was concentrated to give a yellow solid. The solid was dissolved in a mixture of THF and dioxane and DCM (1:1:1, 200 mL). To this solution was added TEA (20 mL) followed by Boc$_2$O (8.1 g, 37.1 mmol) and the reaction mixture was stirred overnight. LCMS confirmed the desired product formation. To the reaction mixture was added water (200 mL) and the mixture was filtered through a pad of CELITE® and washed with EtOAc (200 mL). The aqueous layer was extracted with EtOAc (2×100 mL). The combined organic layer was dried over MgSO$_4$, filtered and concentrated to give a reddish brown oil. The crude material was purified via a 80 g silica gel ISCO column and eluted with hexanes and EtOAc. (R)—N-[(1S)-1-(5-Chloropyridin-3-yl)but-3-en-1-yl]-2-methylpropane-2-sulfinamide was obtained as a pale yellow semi solid mass (4.3 g, 36.7% yield). LCMS m/z 327.1(M+H). $^1$H NMR (400 MHz, CDCl$_3$) δ 8.61-8.59 (m, 1H), 8.51-8.48 (m, 1H), 7.77-7.74 (m, 1H), 5.76-5.63 (m, 1H), 5.23-5.14 (m, 2H), 5.00-4.84 (m, 1H), 4.83-4.70 (m, 1H), 2.60-2.44 (m, 2H), 1.48-1.35 (m, 9H).

Intermediate 27

Preparation of tert-butyl N-[(1S)-1-(2-bromopyridin-4-yl)but-3-en-1-yl]carbamate

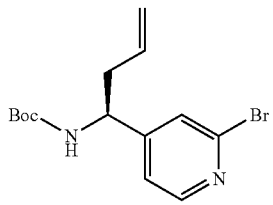

27A. Preparation of (R)—N-[(1E)-(2-bromopyridin-4-yl)methylidene]-2-methylpropane-2-sulfinamide

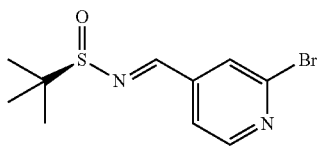

To a stirred suspension of (R)-2-methylpropane-2-sulfinamide (13.03 g, 108 mmol) and Cs$_2$CO$_3$ (52.5 g, 161 mmol) in DCM (400 ml) was added 2-bromopyridine-4-carbaldehyde (20 g, 108 mmol) over 10 min. The reaction mixture was then stirred for 18.5 h at rt. The reaction mixture was concentrated and the residue was diluted with EtOAc (50 ml) and washed with brine (3×20 ml). The organic layer was dried over MgSO$_4$, filtered and the filtrate concentrated. The residue was purified by normal phase chromatography using hexanes and EtOAc as eluents to afford (R)—N-[(1E)-(2-bromopyridin-4-yl)methylidene]-2-methylpropane-2-sulfinamide (27.2 g, 87%) as a white solid. MS(ESI) m/z: 289-291.0 (M+H)$^+$.

27B. Preparation of (R)—N-[(15)-1-(2-bromopyridin-4-yl)but-3-en-1-yl]-2-methylpropane-2-sulfonamide

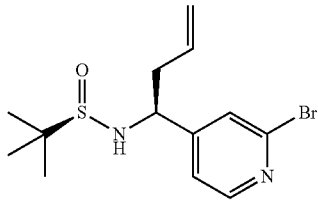 [SMILES: C=CC[C@H](N[S@](=O)C(C)(C)C)c1ccnc(Br)c1]

To a solution of (R)—N-[(1E)-(2-bromopyridin-4-yl)methylidene]-2-methylpropane-2-sulfinamide (0.73 g, 2.52 mmol) and In (0.435 g, 3.79 mmol) in THF (6 ml) was slowly added 3-bromoprop-1-ene (0.458 g, 3.79 mmol) and resulting solution was heated at 60° C. for 18 h. The reaction mixture was cooled, filtered through CELITE® and the filtrate was concentrated. To the residue was added EtOAc (100 ml) and 5% aq NaHCO$_3$(1 L) and an emulsion formed immediately. The suspension was filtered through paper. The organic layer was washed with brine, dried over Na$_2$SO$_4$, filtered, and concentrated. The residue was purified by normal phase chromatography using hexanes and EtOAc as eluents to afford (0.62 g, 74%) of (R)—N-[(1S)-1-(2-bromopyridin-4-yl)but-3-en-1-yl]-2-methylpropane-2-sulfonamide as a yellow liquid. MS(ESI) m/z: 331-333.0 (M+H)$^+$.

27C. Preparation of Tert-Butyl N-[(1S)-1-(2-bromopyridin-4-yl)but-3-en-1-yl]carbamate

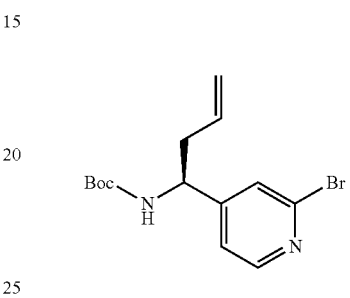

To a solution of (R)—N-[(1S)-1-(2-bromopyridin-4-yl)but-3-en-1-yl]-2-methylpropane-2-sulfinamide (1.38 g, 4.17 mmol) in MeOH (10 ml) was added 4 N HCl in dioxane (5.21 mL, 20.83 mmol). The reaction mixture was stirred for 1.5 h at rt, then was concentrated. To the resulting residue was added ACN (10 ml), TEA (5.8 ml, 41.7 mmol) and Boc$_{20}$ (1.818 g, 8.33 mmol). After 18 h, the reaction mixture was concentrated and the residue was taken up in EtOAc, washed with water, brine, dried over MgSO$_4$, filtered and concentrated. The resulting residue was purified by normal phase chromatography using hexanes and EtOAc as eluents to afford tert-butyl N-[(1S)-1-(2-bromopyridin-4-yl)but-3-en-1-yl]carbamate (0.80 g, 58.7%) as a pale yellow oil. MS(ESI) m/z: 324-326.1 (M+H)$^+$.

Intermediate 28

Preparation of (9R,13S)-13-amino-3,9-dimethyl-3,4,7,18-tetraazatricyclo[12.3.1.0$^{2,6}$]octadeca-1(18),2(6),4,14,16-pentaen-8-one

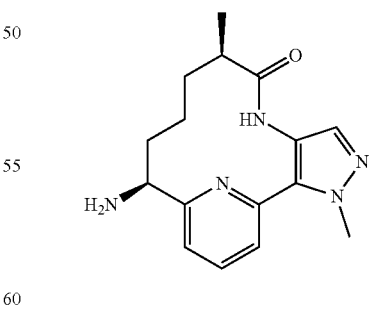

28A. Preparation of (S)—N-[(1E)-(6-chloropyridin-2-yl)methylidene]-2-methylpropane-2-sulfinamide To a solution of (S)-2-methylpropane-2-sulfinamide (1.712 g, 14.13 mmol) in DCM (61.4 mL) was added Cs$_2$CO$_3$ (6.91 g, 21.19 mmol) and 6-chloropicolinaldehyde (2.0 g, 14.13 mmol). The resulting white suspension was stirred at rt. After 17 h, the reaction was filtered. The filtrate was diluted with EtOAc (100 ml) and washed with brine (3×50 mL). The organic layer was dried over MgSO$_4$, filtered and concentrated to give (S)—N-[(1E)-(6-chloropyridin-2-yl)methylidene]-2-methylpropane-2-sulfinamide (3.58g, 100%) as a yellow oil. $^1$H NMR (400 MHz, CDCl$_3$) δ 8.65 (s, 1H), 7.99-7.94 (m, 1H), 7.79 (t, J=7.7 Hz, 1H), 7.45 (dd, J=7.9, 0.7 Hz, 1H), 1.28 (s, 10H).

28B. Preparation of (S)—N-[(1S)-1-(6-chloropyridin-2-yl)but-3-en-1-yl]-2-methylpropane-2-sulfinamide, and

28C. Preparation of (S)—N-[(1R)-1-(6-chloropyridin-2-yl)but-3-en-1-yl]-2-methylpropane-2-sulfinamide To a mixture of (S)—N-[(1E)-(6-chloropyridin-2-yl)methylidene]-2-methylpropane-2-sulfinamide (1.73 g, 7.07 mmol) and In (0.92 g, 10.60 mmol) in THF (17.7 ml) was slowly added 3-bromoprop-1-ene (0.92 g, 10.60 mmol). The reaction was heated at 60° C. overnight. The reaction mixture was cooled to rt, filtered through CELITE® and the filtrate was concentrated. The resulting residue was purified by normal phase chromatography, using hexanes and EtOAc, which gave a 5.6:1 of (S)—N-[(1S)-1-(6-chloropyridin-2-yl)but-3-en-1-yl]-2-methylpropane-2-sulfinamide: (S)—N-[(1R)-1-(6-chloropyridin-2-yl)but-3-en-1-yl]-2-methylpropane-2-sulfinamide (2.42 g, 58%) as a brown semi-solid. MS(ESI) m/z: 287.4 (M+H)$^+$.

28D. Preparation of (S)-2-methyl-N-[(1R)-1-[6-(1-methyl-4-nitro-1H-pyrazol-5-yl)pyridin-2-yl]but-3-en-1-yl]propane-2-sulfinamide (Diastereomer A), and

28E. Preparation of (S)-2-methyl-N-[(1S)-1-[6-(1-methyl-4-nitro-1H-pyrazol-5-yl)pyridin-2-yl]but-3-en-1-yl]propane-2-sulfinamide (Diastereomer B)

To a N$_2$ flushed pressure vial was added 5.6:1 of (S)—N-[(1S)-1-(6-chloropyridin-2-yl)but-3-en-1-yl]-2-methylpropane-2-sulfinamide: (S)—N-[(1R)-1-(6-chloropyridin-2-yl)but-3-en-1-yl]-2-methylpropane-2-sulfinamide (2.18 g, 7.60 mmol), 1-methyl-4-nitro-1H-pyrazole (0.966 g, 7.60 mmol), prepared as described in Intermediate 32A, di(adamant-1-yl)(butyl)phosphine (0.954 g, 2.66 mmol), PvOH (0.300 ml, 2.58 mmol), K$_2$CO$_3$ (3.62 g, 26.2 mmol), Pd(OAc)$_2$ (0.341 g, 1.52 mmol) and DMF (15.2 mL). The vial was purged with Ar. The vial was sealed and heated at 120° C. overnight. The reaction mixture was cooled to rt, partitioned between water and EtOAc, and the layers were separated. The aqueous layer was extracted with EtOAc (3×) and the organic layers were combined and concentrated. The crude product was purified using normal phase chromatography followed a second purification by reverse phase chromatography to give (S)-2-methyl-N-[(1R)-1-[6-(1-methyl-4-nitro-1H-pyrazol-5-yl)pyridin-2-yl]but-3-en-1-yl] propane-2-sulfinamide (Diastereomer A) (0.275 g, 13%), MS(ESI) m/z: 274.4 (M+H)$^+$; and (S)-2-methyl-N-[(1S)-1-[6-(1-methyl-4-nitro-1H-pyrazol-5-yl)pyridin-2-yl]but-3-en-1-yl]propane-2-sulfinamide (Diastereomer B) (1.2 g, 57%); MS(ESI) m/z: 274.4 (M+H)$^+$.

28F. Preparation of Tert-Butyl N-[(1S)-1-[6-(1-methyl-4-nitro-1H-pyrazol-5-yl)pyridin-2-yl]but-3-en-1-yl]carbamate (1S)-1-(6-(1-Methyl-4-nitro-1H-pyrazol-5-yl)pyridin-2-yl)but-3-en-1-amine (Diastereomer B) (1.2 g, 3.18 mmol) was dissolved in MeOH (5 mL) and dioxane (25 ml). 4 N HCl in dioxane (4.8 ml, 19.1 mmol) was added. The reaction was stirred at rt for 3 h and then was concentrated. The residue was coevaporated with toluene, dissolved in DCM (40 mL), and cooled to 0° C. TEA (4.43 mL, 31.8 mmol) was added followed by BOC$_2$O (0.738 mL, 3.18 mmol). The reaction was stirred at 0° C. for 15 min and then the reaction was allowed to warm to rt. After 2 h, the reaction was diluted with DCM, washed with sat NaHCO$_3$, brine, and concentrated. Purification by normal phase chromatography gave tert-butyl N-[(1S)-1-[6-(1-methyl-4-nitro-1H-pyrazol-5-yl) pyridin-2-yl]but-3-en-1-yl]carbamate (393 mg, 33% yield) as an orange oil. MS(ESI) m/z: 374.5 (M+H)$^+$. $^1$H NMR (400 MHz, CDCl$_3$) δ 8.19 (s, 1H), 7.84 (t, J=7.8 Hz, 1H), 7.55 (d, J=7.7 Hz, 1H), 7.38 (d, J=7.7 Hz, 1H), 5.77-5.58 (m, 1H), 5.40 (br. s., 1H), 5.13-5.01 (m, 2H), 4.92 (d, J=6.8 Hz, 1H), 3.86 (s, 3H), 2.71-2.51 (m, 2H), 1.43 (s, 9H).

28G. Preparation of Tert-Butyl N-[(1S)-1-[6-(4-amino-1-methyl-1H-pyrazol-5-yl)pyridin-2-yl]but-3-en-1-yl]carbamate To a solution of tert-butyl N-[(1S)-1-[6-(1-methyl-4-nitro-1H-pyrazol-5-yl) pyridin-2-yl]but-3-en-1-yl]carbamate (393 mg, 1.05 mmol) in MeOH (6.4 mL) was added AcOH (0.64 mL). The reaction mixture was heated to 45° C. then Zn powder (206 mg, 3.16 mmol) was added portionwise. After 1 h, additional Zn (198 mg) was added. Upon completion of the reaction, the mixture was cooled to rt, partitioned between DCM and sat NaHCO$_3$, and the layers were separated. The aqueous layer was extracted with DCM (2×). The organic layers were combined and washed with brine, dried over MgSO$_4$, filtered and concentrated to give tert-butyl N-[(1S)-1-[6-(4-amino-1-methyl-H-pyrazol-5-yl)pyridin-2-yl]but-3-en-1-yl]carbamate (343 mg, 95% yield) as a yellow foam. MS(ESI) m/z: 344.5 (M+H)$^+$. $^1$H NMR (400 MHz, CDCl$_3$) δ 7.74 (t, J=7.8 Hz, 1H), 7.39 (dd, J=7.8, 0.8 Hz, 1H), 7.25-7.18 (m, 1H), 7.14 (d, J=7.7 Hz, 1H), 5.70 (ddt, J=17.1, 10.2, 7.0 Hz, 1H), 5.46 (d, J=6.8 Hz, 1H), 5.13-4.99 (m, 2H), 4.89 (d, J=6.8 Hz, 1H), 4.01 (s, 3H), 2.71-2.53 (m, 2H), 1.49-1.30 (m, 9H).

28H. Preparation of Tert-Butyl N-[(1S)-1-(6-{1-methyl-4-[(2R)-2-methylbut-3-enamido]-1H-pyrazol-5-yl}pyridin-2-yl)but-3-en-1-yl]carbamate To tert-butyl N-[(1S)-1-[6-(4-amino-1-methyl-1H-pyrazol-5-yl) pyridin-2-yl]but-3-en-1-yl]carbamate (343 mg, 0.999 mmol) in EtOAc (3.33 ml) was added a solution of (R)-2-methylbut-3-enoic acid (0.150 g, 1.498 mmol), prepared as described in Intermediate 2, in EtOAc (1 ml). The mixture was cooled to 0° C. and pyridine (0.24 ml, 3.0 mmol) was added, followed by the addition of a solution of 50% T3P® in EtOAc (1.19 ml, 1.50 mmol). After 2 h, the reaction was partitioned between sat NaHCO$_3$ and EtOAc, and the layers were separated. The aqueous layer was extracted with EtOAc (2×). The organic layers were combined and washed with brine and then concentrated. Purification by normal phase chromatography gave tert-butyl N-[(1S)-1-(6-{1-methyl-4-[(2R)-2-methylbut-3-enamido]-1H-pyrazol-5-yl}pyridin-2-yl) but-3-en-1-yl]carbamate (360 mg, 85%) as a yellow solid. MS(ESI) m/z: 426.5 (M+H)$^+$. $^1$H NMR (400 MHz, CDCl$_3$) δ 9.35 (br. s., 1H), 8.30 (s, 1H), 7.82 (t, J=7.8 Hz, 1H), 7.40 (d, J=7.9 Hz, 1H), 7.32-7.19 (m, 1H), 6.01 (ddd, J=17.4, 10.0, 7.6 Hz, 1H), 5.78-5.57 (m, 1H), 5.35-5.04 (m, 5H), 4.91 (br. s., 1H), 4.06 (s, 3H), 3.26-3.06 (m, 1H), 2.81-2.54 (m, 2H), 1.54-1.30 (m, 12H).

28I. Preparation of Tert-Butyl N-[(9R,10E,13S)-3,9-dimethyl-8-oxo-3,4,7,18-tetraazatricyclo[12.3.1.0$^{2,6}$]octadeca-1(18),2(6),4,10,14,16-hexaen-13-yl]carbamate A solution of tert-butyl N-[(1S)-1-(6-{1-methyl-4-[(2R)-2-methylbut-3-enamido]-1H-pyrazol-5-yl}pyridin-2-yl) but-3-en-1-yl]carbamate (140 mg, 0.329 mmol) in EtOAc (25 ml) was purged with Ar for 20 min. Second Generation Grubbs Catalyst (0.112 g, 0.132 mmol) was added and the reaction mixture was heated at 80° C. overnight. The reaction mixture was cooled to rt and concentrated. Purification by normal phase chromatography and then by reverse phase chromatography was done. The fractions containing the desired product were made basic (pH ~8) with sat NaHCO$_3$ and then concentrated. The residue was partitioned between water and EtOAc, and the layers were separated. The aqueous layer was extracted with DCM (3×) and EtOAc (3×). The organic layers were combined and washed with brine, dried MgSO$_4$, filtered and concentrated to give tert-butyl N-[(9R,10E,13S)-3,9-dimethyl-8-oxo-3,4,7,18-tetraazatricyclo[12.3.1.0$^{2,6}$]octadeca-1(18),2(6),4,10,14,16-hexaen-13-yl]carbamate (96 mg, 66% yield). MS(ESI) m/z: 398.2 (M+H)$^+$. $^1$H NMR (400 MHz, CDCl$_3$) δ 11.12 (br. s., 1H), 8.08 (s, 1H), 7.84 (t, J=7.9 Hz, 1H), 7.39 (dd, J=7.9, 0.7 Hz, 1H), 7.32-7.24 (m, 1H), 5.98-5.83 (m, 1H), 5.55 (dd, J=15.7, 7.4 Hz, 1H), 5.41 (d, J=6.6 Hz, 1H), 5.04 (m, 1H), 4.10-4.03 (m, 3H), 3.15 (quin, J=7.3 Hz, 1H), 2.84-2.56 (m, 2H), 1.51-1.32 (m, 12H).

28J. Preparation of Tert-Butyl N-[(9R,13S)-3,9-dimethyl-8-oxo-3,4,7,18-tetraazatricyclo[12.3.1.0$^{2,6}$]octadeca-1(18),2(6),4,14,16-pentaen-13-yl]carbamate, and

28K. Preparation of Tert-Butyl N-[(9R,13S)-3,9-dimethyl-8-oxo-3,4,7,18-tetraazatricyclo[12.3.1.0$^{2,6}$]octadeca-2(6),4-dien-13-yl]carbamate A solution of tert-butyl N-[(9R,10E,13S)-3,9-dimethyl-8-oxo-3,4,7,18-tetraazatricyclo[12.3.1.0$^{2,6}$]octadeca-1(18),2(6),4,10,14,16-hexaen-13-yl]carbamate (0.096 g, 0.024 mmol) in EtOH (4 ml) was hydrogenated at 20 psi H$_2$ in the presence of PtO$_2$ (20 mg) for 20 h. The mixture was filtered, washing with MeOH and EtOAc. The filtrate was concentrated and then purified by reverse phase chromatography to give, following neutralization of the fractions and extraction, tert-butyl N-[(9R,13S)-3,9-dimethyl-8-oxo-3,4,7,18-tetraazatricyclo[12.3.1.0$^{2,6}$]octadeca-2(6),4-dien-13-yl]carbamate (20 mg, 20.4% yield), MS(ESI) m/z: 406.2 (M+H)$^+$; and tert-butyl N-[(9R,13S)-3,9-dimethyl-8-oxo-3,4,7,18-tetraazatricyclo[12.3.1.0$^{2,6}$]octadeca-1(18),2(6),4,14,16-pentaen-13-yl]carbamate (68 mg, 70.5% yield), MS(ESI) m/z: 400.2 (M+H)$^+$.

28L. Preparation of (9R,13S)-13-amino-3,9-dimethyl-3,4,7,18-tetraazatricyclo[12.3.1.0$^{2,6}$]octadeca-1(18),2(6),4,14,16-pentaen-8-one To a solution of tert-butyl N-[(9R,13S)-3,9-dimethyl-8-oxo-3,4,7,18-tetraazatricyclo[12.3.1.0$^{2,6}$]octadeca-1(18),2(6),4,14,16-pentaen-13-yl]carbamate (0.035 g, 0.088 mmol) in DCM (0.5 ml) was added TFA (0.2 mL, 2.60 mmol). After stirring for 1 h, the reaction mixture was concentrated to dryness, and coevaporated with CH$_3$CN. The residue was neutralized by dissolving in MeOH, passing through NaHCO$_3$ cartridge (StratoSpheres SPE; 500 mg, 0.90 mmol loading), and the filtrate concentrated to give (9R,13S)-13-amino-3,9-dimethyl-3,4,7,18-tetraazatricyclo[12.3.1.0$^{2,6}$]octadeca-1(18),2(6),4,14,16-pentaen-8-one (15 mg, 57% yield) as clear glass. MS(ESI) m/z: 300.5 (M+H)$^+$.

Intermediate 29

Preparation of (9R,13S)-13-amino-16-fluoro-3,9-dimethyl-3,4,7-triazatricyclo[12.3.1.0$^{2,6}$]octadeca-1(18),2(6),4,14,16-pentaen-8-one

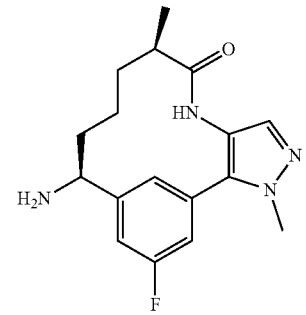 [SMILES: C[C@@H]1CCC[C@H](N)c2cc(F)cc(c2)-c2c(cnn2C)NC1=O]

29A. Preparation of Tert-Butyl N-[(1S)-1-[3-fluoro-5-(1-methyl-4-nitro-1H-pyrazol-5-yl)phenyl]but-3-en-1-yl]carbamate To tert-butyl N-[(1S)-1-(3-bromo-5-fluorophenyl)but-3-en-1-yl]carbamate (0.19 g, 0.552 mmol), 1-methyl-4-nitro-1H-pyrazole (0.070 g, 0.552 mmol), di(adamantan-1-yl)(butyl)phosphine (0.059 g, 0.166 mmol), pivalic acid (0.019 ml, 0.166 mmol), K$_2$CO$_3$ (0.229 g, 1.656 mmol) was added DMF (1.1 ml), and the mixture was purged with Ar. Pd(OAc)$_2$ (0.025 g, 0.110 mmol) was added and the reaction was heated at 120° C. for 18 h. The reaction was partitioned between water (15 ml) and EtOAc (30 ml). The aqueous layer was extracted with EtOAc (2×20 ml). The combined organic layers was washed with brine (15 ml), dried over MgSO$_4$, filtered and concentrated. The residue was purified by normal phase chromatography using hexanes and EtOAc as eluents to give tert-butyl N-[(1S)-1-[3-fluoro-5-(1-methyl-4-nitro-1H-pyrazol-5-yl)phenyl]but-3-en-1-yl]carbamate (0.123 g, 57%) as a yellow oil. $^1$H NMR (400 MHz, CDCl$_3$) δ 8.23-8.17 (m, 1H), 7.22-7.16 (m, 1H), 7.10 (s, 1H), 7.01 (dt, J=8.5, 1.9 Hz, 1H), 5.76-5.60 (m, 1H), 5.22-5.11 (m, 2H), 4.90 (br. s., 1H), 4.78 (br. s., 1H), 3.78-3.69 (m, 3H), 2.60-2.48 (m, 2H), 1.41 (br. s., 9H).

29B. Preparation of Tert-Butyl N-[(1S)-1-[3-(4-amino-1-methyl-1H-pyrazol-5-yl)-5-fluorophenyl]but-3-en-1-yl]carbamate To tert-butyl N-[(1S)-1-[3-fluoro-5-(1-methyl-4-nitro-1H-pyrazol-5-yl)phenyl]but-3-en-1-yl]carbamate (0.123 g, 0.315 mmol) dissolved in acetone (5 ml)/water (1 ml), cooled to 0° C., and NH₄Cl (0.084 g, 1.575 mmol) and Zn (0.206 g, 3.15 mmol) were added. The ice bath was removed. After 3 h, the reaction was filtered and filtrate was partitioned between water (10 ml) and EtOAc (30 ml). The aqueous layer was extracted with EtOAc (2×20 ml). The combined organic layers was washed with brine (10 ml), dried over MgSO₄, filtered and concentrated. The residue was purified by normal phase chromatography using DCM and 0-10% MeOH as eluents to give tert-butyl N-[(1S)-1-[3-(4-amino-1-methyl-1H-pyrazol-5-yl)-5-fluorophenyl]but-3-en-1-yl]carbamate (0.105 g, 92%). MS(ESI) m/z: 361.08 (M+H)⁺.

29C. Preparation of Tert-Butyl N-[(1S)-1-(3-fluoro-5-{1-methyl-4-[(2R)-2-methylbut-3-enamido]-1H-pyrazol-5-yl}phenyl)but-3-en-1-yl]carbamate To tert-butyl N-[(1S)-1-[3-(4-amino-1-methyl-1H-pyrazol-5-yl)-5-fluorophenyl]but-3-en-1-yl]carbamate (0.105 g, 0.291 mmol) in EtOAc (0.58 ml) was added (R)-2-methyl-but-3-enoic acid (0.035 g, 0.350 mmol), prepared as described in Intermediate 2, in 0.3 ml EtOAc. The mixture was cooled to 0° C. and Hunig's Base (0.153 ml, 0.874 mmol) followed by a solution of 50% T3P® in EtOAc (0.347 ml, 0.583 mmol) were added. After 4 h, the reaction was partitioned with sat NaHCO₃(5 ml) and EtOAc (5 ml). The aqueous layer was extracted with EtOAc (2×10 ml). The combined organic layers was washed with brine (5 ml), dried over MgSO₄, filtered and concentrated. The residue was purified by normal phase chromatography using hexanes and EtOAc as eluents to give the desired product (53.0 mg, 41%) as a yellow foam. MS(ESI) m/z: 443.5 (M+H)⁺.

29D. Preparation of Tert-Butyl N-[(9R,10E,13S)-16-fluoro-3,9-dimethyl-8-oxo-3,4,7-triazatricyclo[12.3.1.0²,⁶]octadeca-1(18),2(6),4,10,14,16-hexaen-13-yl]carbamate A solution of tert-butyl N-[(1S)-1-(3-fluoro-5-{1-methyl-4-[(2R)-2-methylbut-3-enamido]-1H-pyrazol-5-yl}phenyl)but-3-en-1-yl]carbamate (0.053 g, 0.120 mmol) in degassed DCE (10 ml) was heated to 120° C. for 30 min in a microwave in the presence of Second Generation Grubbs Catalyst (0.041 g, 0.048 mmol). The reaction mixture was directly purified by normal phase chromatography using hexanes and EtOAc as eluents to give tert-butyl N-[(9R,10E,13S)-16-fluoro-3,9-dimethyl-8-oxo-3,4,7-triazatricyclo[12.3.1.0²,⁶]octadeca-1(18),2(6),4,10,14,16-hexaen-13-yl]carbamate (27.0 mg, 54%) as a dark solid. MS(ESI) m/z: 415.4 (M+H)⁺.

29E. Preparation of (9R,13S)-13-amino-16-fluoro-3,9-dimethyl-3,4,7-triazatricyclo[12.3.1.0²,⁶]octadeca-1(18),2(6),4,14,16-pentaen-8-one A solution of tert-butyl N-[(9R,10E,13S)-16-fluoro-3,9-dimethyl-8-oxo-3,4,7-triazatricyclo[12.3.1.0²,⁶]octadeca-1(18),2(6),4,10,14,16-hexaen-13-yl]carbamate (0.027 g, 0.065 mmol) in EtOH (3 ml) was hydrogenated in the presence of PtO₂ (5 mg) for 6 h. After this time, the reaction was filtered through CELITE® and the filtrate was concentrated to tert-butyl N-[(9R,13S)-16-fluoro-3,9-dimethyl-8-oxo-3,4,7-triazatricyclo[12.3.1.0²,⁶]octadeca-1(18),2(6),4,14,16-pentaen-13-yl]carbamate (19 mg). The Boc protecting group was removed by dissolving the material in 3 ml of 50% TFA/DCM. After 2 h, the reaction mixture was concentrated and the residue was taken up in DCM and MeOH, and filtered through a basic cartridge. Concentration of the filtrate afforded (9R,13S)-13-amino-16-fluoro-3,9-dimethyl-3,4,7-triazatricyclo[12.3.1.0²,⁶]octadeca-1(18),2(6),4,14,16-pentaen-8-one (19 mg, 92%) as a dark solid. MS(ESI) m/z: 317.4 (M+H)⁺.

Intermediate 30

Preparation of (9R,13S)-13-amino-3-(difluoromethyl)-9-methyl-3,4,7,15-tetraazatricyclo[12.3.1.0²,⁶]octadeca-1(18),2(6),4,14,16-pentaen-8-one

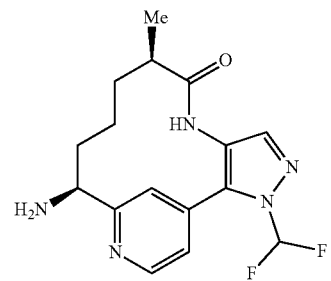 [SMILES: C[C@@H]1CCC[C@H](N)c2cc(ccn2)-c2c(cnn2C(F)F)NC1=O]

30A. Preparation of 1-(difluoromethyl)-4-nitro-1H-pyrazole

Cs₂CO₃ (14.41 g, 44.2 mmol) was suspended in a solution of 4-nitro-1H-pyrazole (5.00 g, 44.2 mmol) and DMF (40 mL). After heating to 120° C. for 5 min, solid sodium 2-chloro-2,2-difluoroacetate (13.48 g, 88 mmol) was added in 10 equal portions over 20 min. The reaction was complete after 10 min of additional heating. The mixture was added to a separatory funnel containing 100 mL water and extracted with Et₂O (2×50 mL). The combined organic layers were concentrated. Purification by normal-phase chromatography eluting with a gradient of hexanes/EtOAc yielded 1-(difluoromethyl)-4-nitro-1H-pyrazole (6.99 g, 42.9 mmol, 97% yield) as a clear, colorless oil. ¹H NMR (500 MHz, CDCl₃) δ 8.58 (s, 1H), 8.22 (s, 1H), 7.39-7.05 (t, J=60 Hz, 1H).

30B. Preparation of (S)-tert-butyl (1-(4-(1-(difluoromethyl)-4-nitro-1H-pyrazol-5-yl)pyridin-2-yl)but-3-en-1-yl)carbamate To a N₂ flushed, 500 mL RBF was added (S)-tert-butyl (1-(4-chloropyridin-2-yl)but-3-en-1-yl)carbamate, prepared as described in Intermediate 23, (10 g, 35.4 mmol), 1-(difluoromethyl)-4-nitro-1H-pyrazole, prepared as described in Intermediate 30A, (6.34 g, 38.9 mmol) and dioxane (100 mL). The solution was bubbled with N₂ for 5 min and Pd(OAc)₂ (0.40 g, 1.7 mmol), di(adamantan-1-yl)(butyl)phosphine (1.27 g, 3.5 mmol), K₂CO₃ (14.7 g, 106 mmol) and PvOH (1.08 g, 10.61 mmol) were added. The reaction mixture was bubbled with N₂ for 5 min, then heated to 100° C. for 3 h. Water (200 mL) was added. The reaction mixture was then extracted with EtOAc (2×200 mL). The combined organic extracts were washed with water (200 mL), brine (200 mL), dried over Na₂SO₄, filtered and concentrated. Purification by normal phase chromatography eluting with a gradient of hexanes/EtOAc afforded (S)-tert-butyl (1-(4-(1-(difluoromethyl)-4-nitro-1H-pyrazol-5-yl)pyridin-2-yl)but- 3-en-1-yl)carbamate (12.91 g, 31.5 mmol, 89% yield) as a yellowish oil. MS(ESI) m/z: 410.4 [M+H]$^+$. $^1$H NMR (400 MHz, CDCl$_3$) δ 8.80 (dd, J=5.1, 0.7 Hz, 1H), 8.36 (s, 1H), 7.34 (s, 1H), 7.31 (dd, J=5.1, 1.5 Hz, 1H), 7.27-6.91 (t, J=58 Hz, 1H), 5.79-5.63 (m, 1H), 5.16-5.03 (m, 2H), 4.92 (d, J=5.9 Hz, 1H), 2.67 (t, J=6.4 Hz, 2H), 1.46 (br. s., 9H).

30C. Preparation of (S)-tert-butyl (1-(4-(4-amino-1-(difluoromethyl)-1H-pyrazol-5-yl)pyridin-2-yl)but-3-en-1-yl)carbamate To a 100 mL, 3-necked RBF was added a solution of (S)-tert-butyl (1-(4-(1-(difluoromethyl)-4-nitro-1H-pyrazol-5-yl)pyridin-2-yl)but-3-en-1-yl)carbamate (0.78 g, 1.90 mmol) in MeOH (12 mL) and a solution of NH$_4$Cl (1.02 g, 19 mmol) in water (3 mL). To the solution was added Fe (0.53 g, 9.49 mmol). The reaction mixture was heated to 65° C. for 3 h. Water (50 mL) was added. After cooling to rt, the mixture was filtered through a CELITE® pad and rinsed with MeOH (200 mL). The filtrate was concentrated. The residue was partitioned between EtOAc (100 mL) and water (100 mL). The organic phase was separated, washed with water (100 mL), brine (100 mL), dried over Na$_2$SO$_4$, filtered and concentrated in vacuo. Purification by normal phase chromatography eluting with a gradient of DCM/MeOH yielded (S)-tert-butyl (1-(4-(4-amino-1-(difluoromethyl)-1H-pyrazol-5-yl)pyridin-2-yl)but-3-en-1-yl)carbamate (0.585 g, 1.54 mmol, 81% yield) as an oil. MS(ESI) m/z: 380.1 [M+H]$^+$. $^1$H NMR (400 MHz, CDCl$_3$) δ 8.70 (dd, J=5.0, 0.7 Hz, 1H), 7.43 (s, 1H), 7.36 (s, 1H), 7.32 (dd, J=5.1, 1.5 Hz, 1H), 7.28-6.97 (t, J=58 Hz, 1H), 5.80-5.66 (m, 1H), 5.65-5.53 (m, 1H), 5.13-5.03 (m, 2H), 4.87 (br. s., 1H), 3.22 (br. s., 2H), 2.65 (t, J=6.5 Hz, 2H), 1.52-1.37 (m, 9H).

30D. Preparation of Tert-Butyl ((S)-1-(4-(1-(difluoromethyl)-4-((R)-2-methylbut-3-enamido)-1H-pyrazol-5-yl)pyridin-2-yl)but-3-en-1-yl)carbamate To a N$_2$ flushed, 3-necked, 250 mL RBF was added a solution of (S)-tert-butyl (1-(4-(4-amino-1-(difluoromethyl)-1H-pyrazol-5-yl)pyridin-2-yl)but-3-en-1-yl)carbamate (5 g, 13.18 mmol) and EtOAc (50 mL). The solution was cooled to −10° C. and (R)-2-methylbut-3-enoic acid, as prepared in Intermediate 2, (1.72 g, 17.13 mmol), pyridine (4.26 mL, 52.7 mmol), and T3P® (23.54 mL, 39.5 mmol) were added. The cooling bath was removed and the solution was allowed to warm to rt and then stir over a period of 20 h. Water (30 mL) and EtOAc (30 mL) were added and the mixture was stirred for 30 min. The organic phase was separated and the aqueous layer was extracted with EtOAc (30 mL). The combined organic extracts were washed with brine (50 mL), dried over Na$_2$SO$_4$, filtered and concentrated. Purification by normal phase chromatography eluting with a gradient of hexanes/EtOAc gave tert-butyl ((S)-1-(4-(1-(difluoromethyl)-4-((R)-2-methylbut-3-enamido)-1H-pyrazol-5-yl)pyridin-2-yl)but-3-en-1-yl)carbamate (5.69 g, 12.33 mmol, 94% yield). MS(ESI) m/z: 462.2 [M+H]$^+$. $^1$H NMR (400 MHz, CDCl$_3$) δ 8.75 (dd, J=5.0, 0.6 Hz, 1H), 8.37 (s, 1H), 7.32 (t, J=59 Hz, 1H), 7.28 (br. s., 1H), 7.20 (s, 1H), 5.97-5.85 (m, 1H), 5.78-5.65 (m, 1H), 5.56-5.44 (m, 1H), 5.28-5.19 (m, 2H), 5.12 (d, J=2.0 Hz, 2H), 4.91-4.82 (m, 1H), 3.20-3.11 (m, 1H), 2.72-2.62 (m, 2H), 1.48-1.43 (s, 9H), 1.33 (d, J=6.8 Hz, 3H).

30E. Preparation of Tert-Butyl N-[(9R,10E,13S)-3-(difluoromethyl)-9-methyl-8-oxo-3,4,7,15-tetraazatricyclo[12.3.1.0$^{2,6}$]octadeca-1(18),2(6),4,10,14,16-hexaen-13-yl]carbamate To a N$_2$ flushed, 2 L, 3-necked, RBF was added a solution of tert-butyl ((S)-1-(4-(1-(difluoromethyl)-4-((R)-2-methyl-but-3-enamido)-1H-pyrazol-5-yl)pyridin-2-yl)but-3-en-1-yl)carbamate (3 g, 6.50 mmol) in EtOAc (1300 mL). The solution was sparged with Ar for 15 min. Second Generation Grubbs Catalyst (1.38 g, 1.63 mmol) was added in one portion. The reaction mixture was heated to reflux for 24 h. After cooling to rt, the solvent was removed and the residue was purified by normal phase chromatography eluting with a gradient of DCM/MeOH to yield tert-butyl N-[(9R,10E,13S)-3-(difluoromethyl)-9-methyl-8-oxo-3,4,7,15-tetraazatricyclo[12.3.1.0$^{2,6}$]octadeca-1(18),2(6),4,10,14,16-hexaen-13-yl]carbamate (2.13 g, 4.91 mmol, 76% yield) as a tan solid. MS(ESI) m/z: 434.4 [M+H]$^+$. $^1$H NMR (400 MHz, CDCl$_3$) δ 8.71 (d, J=5.1 Hz, 1H), 7.78 (s, 1H), 7.44-7.40 (m, 1H), 7.36 (br. s., 1H), 7.27 (t, J=58 Hz, 1H), 6.87 (s, 1H), 6.49-6.39 (m, 1H), 5.78 (s, 1H), 4.80 (br. s., 2H), 3.18-3.08 (m, 1H), 3.08-2.98 (m, 1H), 2.06-1.93 (m, 1H), 1.51 (s, 9H), 1.19 (d, J=6.6 Hz, 3H).

30F. Preparation of Tert-Butyl N-[(9R,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]carbamate Pd/C (0.60 g, 0.570 mmol) was added to a 250 mL Parr hydrogenation flask containing a solution of tert-butyl N-[(9R,10E,13S)-3-(difluoromethyl)-9-methyl-8-oxo-3,4,7,15-tetraazatricyclo[12.3.1.0$^{2,6}$]octadeca-1(18),2(6),4,10,14,16-hexaen-13-yl]carbamate (2.46 g, 5.68 mmol) in EtOH (100 mL). The flask was purged with N$_2$ and pressurized to 55 psi of H$_2$ allowed to stir for 18 h. The reaction was filtered through CELITE® and concentrated to yield tert-butyl N-[(9R,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]carbamate (2.17 g, 88% yield) as a tan solid. MS(ESI) m/z: 436.3 [M+H]$^+$. $^1$H NMR (400 MHz, DMSO-d$_6$) δ 9.32 (s, 1H), 8.71 (d, J=5.0 Hz, 1H), 7.96 (t, J=58 Hz, 1H), 7.43 (s, 1H), 7.32 (d, J=4.8 Hz, 1H), 7.22 (d, J=7.3 Hz, 1H), 4.66 (d, J=8.3 Hz, 1H), 2.62 (br. s., 1H), 1.88 (d, J=12.8 Hz, 1H), 1.77-1.59 (m, 2H), 1.42-1.28 (m, 9H), 1.15 (d, J=18.2 Hz, 2H), 0.83 (d, J=7.0 Hz, 3H).

Example 30G. Preparation of (9R,13S)-13-amino-3-(difluoromethyl)-9-methyl-3,4,7,15-tetraazatricyclo [12.3.1.0$^{2,6}$]octadeca-1(18),2(6),4,14,16-pentaen-8-one 4 N HCl in dioxane (3.88 mL, 15.5 mmol) was added to a solution of tert-butyl N-[(9R,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]carbamate (2.25 g, 5.2 mmol) in MeOH (10 mL). The reaction was allowed to stir at rt for 2 h. The reaction was cooled in an ice bath, and 7 N NH$_3$ in MeOH (13.3 mL, 93.0 mmol) was added. After 5 min, the reaction was diluted with CH$_2$Cl$_2$ (80 mL) and the solid that formed was filtered. The filtrate was concentrated to yield (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one (1.3 g, 3.88 mmol, 75% yield). MS(ESI) m/z: 336.3 [M+H]$^+$. $^1$H NMR (400 MHz, DMSO-d$_6$) δ 9.33 (s, 1H), 8.71 (d, J=5.0 Hz, 1H), 7.94 (t, J=58 Hz, 1H), 7.85 (s, 1H), 7.40 (s, 1H), 7.32 (d, J=5.0 Hz, 1H), 4.01 (dd, J=10.2, 5.1 Hz, 1H), 2.63-2.53 (m, 1H), 1.90-1.69 (m, 2H), 1.53-1.36 (m, 2H), 1.16-1.00 (m, 1H), 0.85 (d, J=7.0 Hz, 3H).

Intermediate 31

Preparation of (9R,13S)-13-amino-3,9-dimethyl-3,4,7-triazatricyclo[12.3.1.0$^{2,6}$]octadeca-1(18),2(6),4,14,16-pentaen-8-one, Hydrochloride

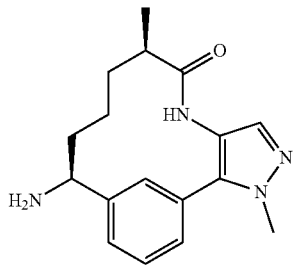 [SMILES: C[C@@H]1CCC[C@H](N)c2cccc(c2)-c2c(cnn2C)NC1=O]

31A. Preparation of Tert-Butyl N-[(1S)-1-[3-(1-methyl-4-nitro-1H-pyrazol-5-yl)phenyl]but-3-en-1-yl]carbamate To tert-butyl N-[(1S)-1-(3-bromophenyl)but-3-en-1-yl]carbamate (2 g, 6.13 mmol), 1-methyl-4-nitro-1H-pyrazole (0.779 g, 6.13 mmol), di(adamantan-1-yl)(butyl) phosphine (0.659 g, 1.839 mmol), pivalic acid (0.213 ml, 1.839 mmol), K$_2$CO$_3$ (2.54 g, 18.39 mmol) was added DMF (9 ml). The mixture was purged with Ar for 10 min and Pd(OAc)$_2$ (0.275 g, 1.226 mmol) was added. The reaction was heated at 120° C. for 15 h. The reaction was partitioned between water (50 ml) and EtOAc (50 ml) and solution was filtered through paper and the layers were separated. The aqueous layer was extracted with EtOAc (2×50 ml). The combined organic layers were washed with brine (50 ml), dried over MgSO$_4$, filtered and concentrated. The residue was purified by normal phase chromatography using hexanes and EtOAc as eluents to afford (S)-tert-butyl (1-(3-(1-methyl-4-nitro-1H-pyrazol-5-yl)phenyl)but-3-en-1-yl)carbamate (1.186 g, 3.18 mmol, 51.9% yield) as a yellow oil. MS(ESI) m/z: 371.1 (M–H)$^+$.

31B. Preparation of Tert-Butyl N-[(1S)-1-[3-(4-amino-1-methyl-1H-pyrazol-5-yl)phenyl]but-3-en-1-yl]carbamate To tert-butyl N-[(1S)-1-[3-(1-methyl-4-nitro-1H-pyrazol-5-yl)phenyl]but-3-en-1-yl]carbamate (0.097 g, 0.260 mmol) in acetone (5 ml)/water (1 ml), cooled to 0° C., was added NH$_4$Cl (0.070 g, 1.302 mmol) and Zn (0.170 g, 2.60 mmol). The ice bath was removed. After 3 h, the reaction was filtered and the filtrate was partitioned between water (10 ml) and EtOAc (30 ml). The aqueous layer was extracted with EtOAc (2×20 ml). The combined organic layers were washed with brine (10 ml), dried over MgSO$_4$, filtered and concentrated. The residue was purified by normal phase chromatography using DCM and 0-10% MeOH as eluents to afford tert-butyl N-[(1S)-1-[3-(4-amino-1-methyl-1H-pyrazol-5-yl)phenyl]but-3-en-1-yl]carbamate (76.6 mg, 86%). MS(ESI) m/z: 343.2 (M+H)$^+$.

31C. Preparation of Tert-Butyl N-[(1S)-1-(3-{1-methyl-4-[(2R)-2-methylbut-3-enamido]-1H-pyrazol-5-yl}phenyl)but-3-en-1-yl]carbamate To tert-butyl N-[(1S)-1-[3-(4-amino-1-methyl-1H-pyrazol-5-yl)phenyl]but-3-en-1-yl]carbamate (0.076 g, 0.222 mmol) in EtOAc (0.58 ml) was added (R)-2-methylbut-3-enoic acid (0.027 g, 0.266 mmol), prepared as described in Intermediate 2, in 0.3 mL EtOAc. The mixture was cooled to 0° C. and Hunig's Base (0.116 ml, 0.666 mmol) followed by a solution of 50% T3P® in EtOAc (0.264 ml, 0.444 mmol) were added. After 3 h, the reaction was partitioned with sat NaHCO$_3$(5 ml) and EtOAc (5 ml). The aqueous layer was extracted with EtOAc (2×10 ml). The combined organic layers were washed with brine (5 ml), dried over MgSO$_4$, filtered and concentrated. The residue was purified by normal phase chromatography using hexanes and EtOAc as eluents to afford tert-butyl N-[(1S)-1-(3-{1-methyl-4-[(2R)-2-methylbut-3-enamido]-1H-pyrazol-5-yl}phenyl)but-3-en-1-yl]carbamate (69 mg, 73%) as a yellow oil. MS(ESI) m/z: 425.2 (M+H)$^+$. $^1$H NMR (400 MHz, CDCl$_3$) δ 8.04 (s, 1H), 7.52-7.45 (m, 1H), 7.37 (d, J=7.9 Hz, 1H), 7.26-7.18 (m, 2H), 7.05 (br. s., 1H), 5.96-5.85 (m, 1H), 5.69 (ddt, J=17.0, 10.1, 7.0 Hz, 1H), 5.21-5.09 (m, 4H), 4.95 (br. s., 1H), 4.77 (br. s., 1H), 3.76 (s, 3H), 3.07 (quin, J=7.2 Hz, 1H), 2.61-2.48 (m, 2H), 1.45-1.38 (m, 9H), 1.30 (d, J=7.0 Hz, 3H).

31D. Preparation of Tert-Butyl N-[(9R,10E,13S)-3,9-dimethyl-8-oxo-3,4,7-triazatricyclo[12.3.1.0$^{2,6}$]octadeca-1(18),2(6),4,10,14,16-hexaen-13-yl]carbamate A solution of tert-butyl N-[(1S)-1-(3-{1-methyl-4-[(2R)-2-methylbut-3-enamido]-1H-pyrazol-5-yl}phenyl)but-3-en-1-yl]carbamate (0.069 g, 0.163 mmol) in degassed DCE (10 ml) was heated to 120° C. for 30 min in a microwave in the presence of Second Generation Grubbs Catalyst (0.055 g, 0.065 mmol). The reaction mixture was directly purified by normal phase chromatography twice using hexanes and EtOAc as eluents to afford desired tert-butyl N-[(9R,10E,13S)-3,9-dimethyl-8-oxo-3,4,7-triazatricyclo[12.3.1.0$^{2,6}$]octadeca-1(18),2(6),4,10,14,16-hexaen-13-yl]carbamate (33 mg, 51.2%) as a dark solid. MS(ESI) m/z: 397.1 (M+H)$^+$. $^1$H NMR (400 MHz, CDCl$_3$) δ 7.61-7.52 (m, 1H), 7.46-7.40 (m, 1H), 7.33-7.25 (m, 1H), 7.20 (d, J=7.5 Hz, 1H), 6.93 (br. s., 1H), 6.83 (s, 1H), 5.63 (ddd, J=15.1, 9.4, 5.6 Hz, 1H), 5.18 (br. s., 1H), 4.89 (dd, J=15.2, 8.8 Hz, 1H), 4.69 (br. s., 1H), 3.93-3.86 (m, 3H), 3.09-2.99 (m, 1H), 2.69-2.58 (m, 1H), 2.17-2.08 (m, 1H), 1.53-1.32 (m, 9H), 1.18 (d, J=6.8 Hz, 3H).

31E. Preparation of Tert-Butyl N-[(9R,13S)-3,9-dimethyl-8-oxo-3,4,7-triazatricyclo[12.3.1.0$^{2,6}$]octadeca-1(18),2(6),4,14,16-pentaen-13-yl]carbamate A solution of tert-butyl N-[(9R,10E,13S)-3,9-dimethyl-8-oxo-3,4,7-triazatricyclo[12.3.1.0$^{2,6}$]octadeca-1(18),2(6),4,10,14,16-hexaen-13-yl]carbamate (0.089 g, 0.224 mmol) in EtOH (5 ml) was hydrogenated under a H$_2$ atmosphere at 55 psi for 3 h. The reaction mixture was filtered through small plug of CELITE® and rinsed with EtOH/MeOH/DCM to give tert-butyl N-[(9R,13S)-3,9-dimethyl-8-oxo-3,4,7-triazatricyclo[12.3.1.0$^{2,6}$]octadeca-1(18),2(6),4,14,16-pentaen-13-yl]carbamate (89 mg, 99%) as a white solid. MS(ESI) m/z: 399.4 (M+H)$^+$. $^1$H NMR (400 MHz CDCl$_3$) δ 7.53-7.43 (m, 2H), 7.43-7.36 (m, 1H), 7.29 (s, 1H), 6.44 (s, 1H), 4.90 (br. s., 1H), 4.68 (br. s., 1H), 3.98 (s, 3H), 2.44 (br. s., 1H), 1.93 (d, J=7.7 Hz, 1H), 1.85-1.63 (m, 2H), 1.42 (br. s., 9H), 1.28-1.19 (m, 2H), 1.07 (d, J=6.8 Hz, 3H), 0.96 (br. s., 1H).

31F. Preparation of (9R,13S)-13-amino-3,9-dimethyl-3,4,7-triazatricyclo[12.3.1.0²,⁶]octadeca-1(18),2(6),4,14,16-pentaen-8-one Hydrochloride

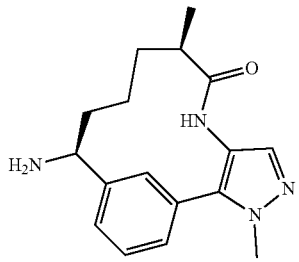 [SMILES: C[C@@H]1CCC[C@H](N)c2cccc(c2)-c2c(cnn2C)NC1=O]

tert-Butyl N-[(9R,13S)-3,9-dimethyl-8-oxo-3,4,7-triazatricyclo[12.3.1.0²,⁶]octadeca-1(18),2(6),4,14,16-pentaen-13-yl]carbamate (88 mg, 0.221 mmol) was deprotected with 4 N HCl in dioxane (3 ml) for 5 h. The reaction was concentrated to afford (70 mg, 95%) of (9R,13S)-13-amino-3,9-dimethyl-3,4,7-triazatricyclo[12.3.1.0²,⁶]octadeca-1 (18),2(6),4,14,16-pentaen-8-one hydrochloride as a dark solid. MS(ESI) m/z: 299.08 (M+H)⁺. ¹H NMR (500 MHz, CD₃OD) δ 7.81 (s, 1H), 7.77-7.70 (m, 1H), 7.70-7.58 (m, 3H), 4.46 (dd, J=12.0, 4.5 Hz, 1H), 4.19-4.07 (m, 3H), 3.45-3.26 (m, 1H), 2.75-2.59 (m, 1H), 2.21-2.09 (m, 1H), 1.99-1.86 (m, 2H), 1.58 (td, J=14.3, 8.3 Hz, 1H), 1.29-1.17 (m, 1H), 1.03 (d, J=6.9 Hz, 3H), 0.94-0.82 (m, 1H).

Intermediate 32

Preparation of (9R,13S)-13-amino-3,9-dimethyl-3,4,7,15-tetraazatricyclo[12.3.1.0²,⁶]

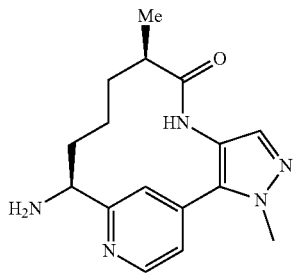 [SMILES: C[C@@H]1CCC[C@H](N)c2cc(ccn2)-c2c(cnn2C)NC1=O]

32A. Preparation of 1-methyl-4-nitro-1H-pyrazole

To a solution of 4-nitro-1H-pyrazole (2.5 g, 22.11 mmol) in THF (50 mL) was added NaH (0.973 g, 24.32 mmol) and the mixture was stirred at rt for 5 min. To this suspension was then added CH₃I (1.382 mL, 22.11 mmol) and stirred at rt overnight. The reaction mixture was then diluted with EtOAc (2×25 mL) and washed with brine (25 mL). The organic layer was concentrated, followed by purification using normal phase chromatography to yield 1-methyl-4-nitro-1H-pyrazole as white solid (1.9 g, 80% yield). ¹H NMR (400 MHz, CDCl₃) δ ppm 8.12 (s, 1H), 8.06 (s, 1H), 3.97 (s, 3H).

32B. Preparation of (S)-tert-butyl (1-(4-(1-methyl-4-nitro-1H-pyrazol-5-yl)pyridin-2-yl)but-3-en-1-yl)carbamate To a N₂ flushed pressure vial was added (S)-tert-butyl (1-(4-chloropyridin-2-yl)but-3-en-1-yl)carbamate, prepared as described in Intermediate 23, (3.0 g, 10.61 mmol), 1-methyl-4-nitro-1H-pyrazole (1.348 g, 10.61 mmol), di(adamant-1-yl)(butyl) phosphine (1.141 g, 3.18 mmol), PvOH (0.369 ml, 3.18 mmol), K₂CO₃ (4.40 g, 31.8 mmol) and DMF (21 mL). The reaction mixture was purged with N₂ for 5 min and Pd(OAc)₂ (0.476 g, 2.122 mmol) was added. The reaction mixture was purged with N₂. The vial was sealed and heated at 120° C. for 4 h. The reaction mixture was cooled to rt and partitioned between 10% aqueous LiCl (15 mL) and EtOAc (30 mL). The aqueous layer was extracted with EtOAc (2×20 mL) and the combined organic layers were washed with brine (15 mL), dried over MgSO₄, filtered and concentrated. The crude product was then purified using normal phase chromatography to yield (S)-tert-butyl (1-(4-(1-methyl-4-nitro-1H-pyrazol-5-yl)pyridin-2-yl) but-3-en-1-yl)carbamate (1.2 g, 29% yield) as a brown oil. MS(ESI) m/z: 374.4 (M+H)⁺.

32C. Preparation of (S)-tert-butyl (1-(4-(4-amino-1-methyl-1H-pyrazol-5-yl)pyridin-2-yl)but-3-en-1-yl) carbamate A solution of (S)-tert-butyl (1-(4-(1-methyl-4-nitro-1H-pyrazol-5-yl)pyridin-2-yl)but-3-en-1-yl)carbamate (1.2 g, 3.21 mmol) in MeOH (10 mL) and AcOH (1 mL) was heated to 40° C. To the above clear solution was then slowly added Zn (0.420 g, 6.43 mmol) in 3 portions (50:25:25%) and stirred at 40° C. for 5 min. The reaction mixture was monitored by LCMS and once complete, the solution was cooled to rt, and K₂CO₃ and 1 mL water were added. The reaction mixture was stirred for 5 min, then filtered through a pad of CELITE® and concentrated to yield the crude product. The crude product was partitioned between EtOAc (30 mL) and sat NaHCO₃(15 mL). The organic layers were separated and dried over MgSO₄. The crude product was purified using normal phase chromatography to yield (S)-tert-butyl (1-(4-(4-amino-1-methyl-1H-pyrazol-5-yl)pyridin-2-yl)but-3-en-1-yl)carbamate (0.88 g, 76% yield) as pale brown oil. MS(ESI) m/z: 344.4 (M+H)¹.

32D. Preparation of Tert-Butyl ((S)-1-(4-(1-methyl-4-((R)-2-methylbut-3-enamido)-1H-pyrazol-5-yl)pyridin-2-yl)but-3-en-1-yl)carbamate To a N₂ flushed, 3-necked, 250 mL RBF was added a solution of (S)-tert-butyl (1-(4-(4-amino-1-methyl-1H-pyrazol-5-yl)pyridin-2-yl)but-3-en-1-yl)carbamate (620 mg, 1.805 mmol) and EtOAc (15 mL). The solution was cooled to −10° C. and (R)-2-methylbut-3-enoic acid, as prepared in Intermediate 2, (271 mg, 2.71 mmol), pyridine (0.437 mL, 5.42 mmol) and T3P® (2.149 mL, 3.61 mmol) were added. The cooling bath was removed and the solution was allowed to warm to rt and then stir over a period of 20 h. Water (15 mL) and EtOAc (15 mL) were added and the mixture was stirred for 30 min. The organic phase was separated and the aqueous layer was extracted with EtOAc (15 mL). The combined organic extracts were washed with brine (15 mL), dried over Na₂SO₄, filtered and concentrated. Purification by normal phase chromatography eluting with a gradient of hexanes/EtOAc gave tert-butyl ((S)-1-(4-(1-methyl-4-((R)-

2-methylbut-3-enamido)-1H-pyrazol-5-yl)pyridin-2-yl)but-3-en-1-yl)carbamate (0.26 g, 34% yield). MS(ESI) m/z: 426.5 [M+H]+.

32E. Preparation of Tert-Butyl N-[(9R,10E,13S)-3,9-dimethyl-8-oxo-3,4,7,15-tetraazatricyclo[12.3.1.0²,⁶]octadeca-1(18),2(6),4,10,14,16-hexaen-13-yl]carbamate To a N₂ flushed, 250 mL, 3-necked RBF was added a solution of tert-butyl ((S)-1-(4-(1-methyl-4-((R)-2-methylbut-3-enamido)-1H-pyrazol-5-yl)pyridin-2-yl)but-3-en-1-yl)carbamate (266 mg, 0.625 mmol) in DCE (18 mL). The solution was sparged with Ar for 15 min. Second Generation Grubbs Catalyst (213 mg, 0.250 mmol) was added in one portion. The reaction mixture was heated to 120° C. in microwave for 30 min. After cooling to rt, the solvent was removed and the residue was purified by normal phase chromatography eluting with a gradient of DCM/MeOH to yield tert-butyl N-[(9R,10E,13S)-3,9-dimethyl-8-oxo-3,4,7,15-tetraazatricyclo[12.3.1.0²,⁶]octadeca-1(18),2(6),4,10,14,16-hexaen-13-yl]carbamate (60 mg, 23% yield) as a tan solid. MS(ESI) m/z: 398.4 [M+H]+.

32F. Preparation of Tert-Butyl N-[(9R,13S)-3,9-dimethyl-8-oxo-3,4,7,15-tetraazatricyclo[12.3.1.0²,⁶]octadeca-1(18),2(6),4,14,16-pentaen-13-yl]carbamate Pd/C (0.016 g, 0.015 mmol) was added to a 100 mL Parr hydrogenation flask containing a solution of tert-butyl N-[(9R,10E,13S)-3,9-dimethyl-8-oxo-3,4,7,15-tetraazatricyclo[12.3.1.0²,⁶]octadeca-1(18),2(6),4,10,14,16-hexaen-13-yl]carbamate (60 mg, 0.151 mmol) in EtOH (6 mL). The flask was purged with N₂ and pressurized to 55 psi of H₂ and allowed to stir for 5 h. The reaction was filtered through a pad of CELITE® and concentrated to yield tert-butyl N-[(9R,13S)-3,9-dimethyl-8-oxo-3,4,7,15-tetraazatricyclo[12.3.1.0²,⁶]octadeca-1(18),2(6),4,14,16-pentaen-13-yl]carbamate (48 mg, 76% yield) as a tan solid. MS(ESI) m/z: 400.5 [M+H]+.

32G. Preparation of (9R,13S)-13-amino-3,9-dimethyl-3,4,7,15-tetraazatricyclo[12.3.1.0²,⁶]octadeca-1(18),2(6),4,14,16-pentaen-8-one To a solution of tert-butyl N-[(9R,13S)-3,9-dimethyl-8-oxo-3,4,7,15-tetraazatricyclo[12.3.1.0²,⁶]octadeca-1(18),2(6),4,14,16-pentaen-13-yl]carbamate (48 mg, 0.120 mmol) in DCM (2.5 mL) was added TFA (0.6 mL, 7.79 mmol) and the reaction was stirred at rt for 1.5 h. The reaction mixture was then concentrated to give (9R,13S)-13-amino-3,9-dimethyl-3,4,7,15-tetraazatricyclo[12.3.1.0²,⁶]octadeca-1(18),2(6),4,14,16-pentaen-8-one bis trifluoroacetate (63 mg, 94% yield) as a brown solid which was then dissolved in MeOH (1 mL) to give a clear, brown solution. The solution was added to a pre-rinsed AGILENT® StratoSpheres SPE PL-HCO₃ MP Resin cartridge. Gravity filtration, eluting with MeOH, gave a clear, slightly yellow filtrate. Concentration provided (9R,13S)-13-amino-3,9-dimethyl-3,4,7,15-tetraazatricyclo[12.3.1.0²,⁶]octadeca-1(18),2(6),4,14,16-pentaen-8-one (25 mg, 93%) as a pale yellow solid. MS(ESI) m/z: 300.4 [M+H]+.

Intermediate 33

Preparation of (9R,13S)-13-amino-3-(²H₃)methyl-9-methyl-3,4,7,15-tetraazatricyclo[12.3.1.0²,⁶]octadeca-1(18),2(6),4,14,16-pentaen-8-one

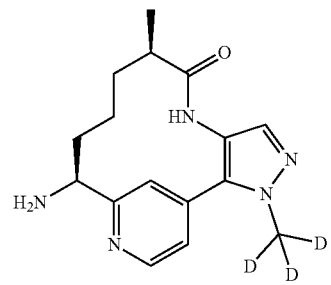 [SMILES: [2H]C([2H])([2H])n1ncc2c1-c1ccnc(c1)[C@@H](N)CCC[C@@H](C)C(=O)N2]

33A. Preparation of 1-(²H₃)methyl-4-nitro-1H-pyrazole

DIAD (5.59 mL, 28.7 mmol) was added to a solution of 4-nitro-1H-pyrazole (2.5 g, 22.11 mmol), CD₃OD (0.898 mL, 22.11 mmol), and Ph₃P (resin bound) (8.84 g, 26.5 mmol) in THF (40 ml) and stirred overnight. The reaction was quenched with water, extracted with EtOAc, washed with brine, dried over Na₂SO₄, filtered, and concentrated. The crude product was purified by normal phase chromatography eluting with a gradient of DCM/MeOH to afford 1-(²H₃)methyl-4-nitro-1H-pyrazole (1.92 g, 14.76 mmol, 66.7% yield) as a white solid. MS(ESI) m/z: 131.0 (M+H)+. ¹H NMR (400 MHz, CDCl₃) δ 8.13 (d, J=0.4 Hz, 1H), 8.05 (s, 1H).

33B. Preparation of Tert-Butyl N-[(1S)-1-{4-[1-(²H₃)methyl-4-nitro-1H-pyrazol-5-yl]pyridin-2-yl}but-3-en-1-yl]carbamate To a large microwave vial were added (S)-tert-butyl (1-(4-chloropyridin-2-yl)but-3-en-1-yl)carbamate (2.61 g, 9.22 mmol), 1-(²H₃)methyl-4-nitro-1H-pyrazole (1.0 g, 7.69 mmol), di(adamantan-1-yl)(butyl)phosphine (0.413 g, 1.15 mmol), K₂CO₃ (3.19 g, 23.06 mmol), pivalic acid (0.268 ml, 2.306 mmol) and DMF (15.37 ml). The reaction was purged with Ar for 10 min, Pd(OAc)₂ (0.173 g, 0.769 mmol) was added, the vial sealed, and stirred at 115° C. overnight. The reaction was then partitioned between EtOAc and H₂O. The aqueous layer was extracted with EtOAc (2×). The combined organic layer was washed with brine, dried over MgSO₄, filtered and concentrated. The residue was purified by normal phase chromatography eluting with a gradient of hexanes/EtOAc to give tert-butyl N-[(1S)-1-{4-[1-(²H₃)methyl-4-nitro-1H-pyrazol-5-yl]pyridin-2-yl}but-3-en-1-yl]carbamate (1.49 g, 3.96 mmol, 51.5% yield) as a lavender foam. MS(ESI) m/z: 377.0 (M+H)+. ¹H NMR (400 MHz, CDCl₃) δ 8.77 (d, J=4.8 Hz, 1H), 8.21 (s, 1H), 7.26 (s, 1H), 7.23 (dd, J=5.1, 1.5 Hz, 1H), 5.78-5.65 (m, 1H), 5.55 (d, J=6.8 Hz, 1H), 5.14-5.03 (m, 2H), 4.89 (d, J=6.8 Hz, 1H), 2.66 (t, J=6.6 Hz, 2H), 1.44 (s, 9H).

33C. Preparation of Tert-Butyl N-[(1S)-1-{4-[4-amino-1-(²H₃)methyl-1H-pyrazol-5-yl]pyridin-2-yl}but-3-en-1-yl]carbamate tert-Butyl N-[(1S)-1-{4-[1-(²H₃)methyl-4-nitro-1H-pyrazol-5-yl]pyridin-2-yl}but-3-en-1-yl]carbamate (1.45 g, 3.85 mmol) was dissolved in acetone (15 ml)/water (3 ml), cooled to 0° C. NH₄Cl (1.030 g, 19.26 mmol) and Zn (2.52 g, 38.5 mmol) were added and the ice bath was removed. After 1 h, the reaction was filtered and filtrate partitioned with water (30 ml) and EtOAc (50 ml). The aqueous layer was extracted with EtOAc (2×50 ml). The combined organic layers were washed with brine (20 ml), dried over MgSO₄, filtered, and concentrated. The residue was purified by normal phase eluting with a gradient of DCM/MeOH chromatography to afford tert-butyl N-[(1S)-1-{4-[4-amino-1-($^2$H₃)methyl-1H-pyrazol-5-yl]pyridin-2-yl}but-3-en-1-yl]carbamate (0.62 g, 46.5%). MS(ESI) m/z: 347.2 (M+H)⁺. ¹H NMR (400 MHz, CDCl₃) δ 8.67 (dd, J=5.1, 0.7 Hz, 1H), 7.26-7.23 (m, 2H), 7.21 (dd, J=5.1, 1.5 Hz, 1H), 5.79-5.66 (m, 1H), 5.58 (d, J=7.3 Hz, 1H), 5.11-5.05 (m, 2H), 4.86 (q, J=6.6 Hz, 1H), 2.64 (t, J=6.7 Hz, 2H), 1.44 (s, 9H).

33D. Preparation of Tert-Butyl N-[(1S)-1-{4-[1-($^2$H₃)methyl-4-[(2R)-2-methylbut-3-enamido]-1H-pyrazol-5-yl]pyridin-2-yl}but-3-en-1-yl]carbamate (R)-2-Methylbut-3-enoic acid (233 mg, 2.327 mmol), tert-butyl N-[(1S)-1-{4-[4-amino-1-($^2$H₃)methyl-1H-pyrazol-5-yl]pyridin-2-yl}but-3-en-1-yl]carbamate (620 mg, 1.79 mmol), pyridine (0.433 ml, 5.37 mmol) in EtOAc (17.900 ml) was cooled to −10° C. under Ar. T3P® (50% wt in EtOAc) (2.13 ml, 3.58 mmol) was added dropwise and then the reaction mixture was gradually warmed up to rt. After 3.5 h, the reaction mixture was diluted with EtOAc, washed with 1.5 M K₂HPO₄ followed by brine, dried over Na₂SO₄, filtered, and concentrated. The crude product was then purified by normal phase chromatography eluting with a gradient of hexanes/EtOAc to give tert-butyl N-[(1S)-1-{4-[1-($^2$H₃)methyl-4-[(2R)-2-methylbut-3-enamido]-1H-pyrazol-5-yl]pyridin-2-yl}but-3-en-1-yl]carbamate (529 mg, 1.234 mmol, 69.0% yield) as a yellow foam. MS(ESI) m/z: 429.2 (M+H)⁺.

33E. Preparation of Tert-Butyl N-[(9R,10E,13S)-3-($^2$H₃)methyl-9-methyl-8-oxo-3,4,7,15-tetraazatricyclo[12.3.1.0$^{2,6}$]octadeca-1(18),2(6),4,10,14,16-hexaen-13-yl]carbamate Five large microwave vials were charged in equal amounts with the following: tert-butyl N-[(1S)-1-{4-[1-($^2$H₃)methyl-4-[(2R)-2-methylbut-3-enamido]-1H-pyrazol-5-yl]pyridin-2-yl}but-3-en-1-yl]carbamate (0.51 g, 1.190 mmol) in degassed DCE (90 ml) was irradiated at 120° C. for 30 min in the presence of Second Generation Grubbs Catalyst (0.404 g, 0.476 mmol). The reactions were combined, concentrated, and the residue purified by normal phase column chromatography eluting with a gradient of hexanes/EtOAc to give tert-butyl N-[(9R,10E,13S)-3-($^2$H₃)methyl-9-methyl-8-oxo-3,4,7,15-tetraazatricyclo[12.3.1.0$^{2,6}$]octadeca-1(18),2(6),4,10,14,16-hexaen-13-yl]carbamate (0.124 g, 26.0%) as a brown solid. MS(ESI) m/z: 401.2 (M+H)⁺. ¹H NMR (400 MHz, CDCl₃) δ 8.66 (d, J=5.1 Hz, 1H), 7.52 (s, 1H), 7.19 (d, J=4.8 Hz, 1H), 6.80 (s, 1H), 6.37 (d, J=7.5 Hz, 1H), 5.68 (t, J=11.2 Hz, 1H), 4.82-4.63 (m, 2H), 3.12-2.93 (m, 2H), 1.93 (q, J=11.1 Hz, 1H), 1.48 (s, 9H), 1.15 (d, J=5.9 Hz, 3H).

33F. Preparation of Tert-Butyl N-[(9R,13S)-3-($^2$H₃)methyl-9-methyl-8-oxo-3,4,7,15-tetraazatricyclo[12.3.1.0$^{2,6}$]octadeca-1(18),2(6),4,14,16-pentaen-13-yl]carbamate PtO₂ (6.80 mg, 0.030 mmol) was added to a stirring solution of tert-butyl N-[(9R,10E,13S)-3-($^2$H₃)methyl-9-methyl-8-oxo-3,4,7,15-tetraazatricyclo[12.3.1.0$^{2,6}$]octadeca-1(18),2(6),4,10,14,16-hexaen-13-yl]carbamate (0.120 g, 0.300 mmol) in EtOH (10 ml). The suspension was subjected to a H₂ atmosphere (55 psi) for 1 h. The catalyst was filtered off through a plug of CELITE® and the filtrate concentrated to give tert-butyl N-[(9R,13S)-3-($^2$H₃)methyl-9-methyl-8-oxo-3,4,7,15-tetraazatricyclo[12.3.1.0$^{2,6}$]octadeca-1(18),2(6),4,14,16-pentaen-13-yl]carbamate (0.104 g, 86%). MS(ESI) m/z: 403.2 (M+H)⁺.

33G. Preparation of (9R,13S)-13-amino-3-($^2$H₃)methyl-9-methyl-3,4,7,15-tetraazatricyclo[12.3.1.0$^{2,6}$]octadeca-1(18),2(6),4,14,16-pentaen-8-one 4 M HCl in dioxane (1.62 ml) was added to a stirring solution of tert-butyl N-[(9R,13S)-3-($^2$H₃)methyl-9-methyl-8-oxo-3,4,7,15-tetraazatricyclo[12.3.1.0$^{2,6}$]octadeca-1(18),2(6),4,14,16-pentaen-13-yl]carbamate (0.100 g, 0.248 mmol) in MeOH (3 ml) and stirred overnight. The reaction mixture was concentrated to dryness and placed under high vacuum. The hydrochloride salt was free based by dissolution in MeOH, passed through a resin bound NaHCO₃ cartridge (StratoSpheres SPE; 500 mg, 0.90 mmol loading) and filtrate concentrated to give (9R,13S)-13-amino-3-($^2$H₃)methyl-9-methyl-3,4,7,15-tetraazatricyclo[12.3.1.0$^{2,6}$]octadeca-1(18),2(6),4,14,16-pentaen-8-one. MS(ESI) m/z: 303.4 (M+H)⁺.

Intermediate 34

Preparation of (9R,13S)-13-amino-3-($^2$H₃)methyl-9-methyl-3,4,7,17-tetraazatricyclo[12.3.1.0$^{2,6}$]octadeca-1(18),2(6),4,14,16-pentaen-8-one

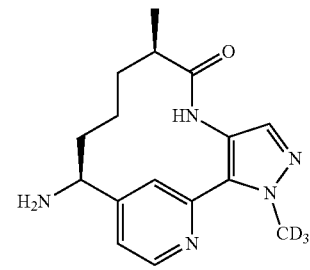 [SMILES: [2H]C([2H])([2H])n1ncc2c1-c1cc(ccn1)[C@@H](N)CCC[C@@H](C)C(=O)N2]

(9R,13S)-13-Amino-3-($^2$H₃)methyl-9-methyl-3,4,7,17-tetraazatricyclo[12.3.1.0$^{2,6}$]octadeca-1(18),2(6),4,14,16-pentaen-8-one was prepared in a similar manner as (9R,13S)-13-amino-3-c($^2$H₃)methyl-9-methyl-3,4,7,15-tetraazatricyclo[12.3.1.0$^{2,6}$]octadeca-1(18),2(6),4,14,16-pentaen-8-one, as described in Intermediate 33, replacing (S)-tert-butyl (1-(4-chloropyridin-2-yl)but-3-en-1-yl)carbamate, described in Intermediate 23, with (S)-tert-butyl (1-(2-bromopyridin-4-yl)but-3-en-1-yl)carbamate, described in Intermediate 27. MS(ESI) m/z: 303.3 (M+H)⁺. ¹H NMR (400 MHz, CD₃OD) δ 8.70 (d, J=5.3 Hz, 1H), 7.58 (s, 1H), 7.50-7.42 (m, 2H), 4.14-4.05 (m, 1H), 2.72 (td, J=6.7, 3.5 Hz, 1H), 2.06-1.94 (m, 2H), 1.65-1.50 (m, 2H), 1.41-1.26 (m, 1H), 1.02 (d, J=6.8 Hz, 3H), 0.70-0.53 (m, 1H).

Intermediate 35

Preparation of (9R,13S)-13-amino-3-(difluoromethyl)-9-methyl-3,4,7-triazatricyclo[12.3.1.0²,⁶]octadeca-1(18),2(6),4,14,16-pentaen-8-one

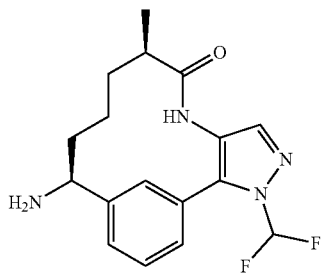 [SMILES: C[C@@H]1CCC[C@H](N)c2cccc(c2)-c2c(cnn2C(F)F)NC1=O]

35A. Preparation of Tert-Butyl N-[(1S)-1-{3-[1-(difluoromethyl)-4-nitro-1H-pyrazol-5-yl]phenyl}but-3-en-1-yl]carbamate To a solution of (S)-tert-butyl (1-(3-bromophenyl)but-3-en-1-yl)carbamate (4.0 g, 12.29 mmol), prepared as described in Intermediate 24, in DMF (40.9 ml), was added 1-(difluoromethyl)-4-nitro-1H-pyrazole (2.20 g, 13.49 mmol), di(adamantan-1-yl)(butyl) phosphine (0.659 g, 1.839 mmol), K₂CO₃ (5.08 g, 36.8 mmol) and pivalic acid (0.427 ml, 3.68 mmol). The resulting solution was purged with Ar for 10 min. Pd(OAc)₂ (0.275 g, 1.226 mmol) was added and the reaction mixture was stirred at 115° C. for 4 h. The reaction was cooled to rt, quenched with water (50 mL) and extracted with EtOAc (3×50 mL). The combined organic layers were washed with brine (50 mL), dried (MgSO₄), filtered, and concentrated. The residue was purified by normal phase column chromatography eluting with a gradient of heptane/EtOAc to give tert-butyl N-[(1S)-1-{3-[1-(difluoromethyl)-4-nitro-H-pyrazol-5-yl]phenyl}but-3-en-1-yl]carbamate (4.0 g, 80.0%). MS(ESI) m/z: 407 (M−H)⁻.

35B. Preparation of Tert-Butyl N-[(1S)-1-{3-[4-amino-1-(difluoromethyl)-1H-pyrazol-5-yl]phenyl}but-3-en-1-yl]carbamate tert-Butyl N-[(1S)-1-{3-[1-(difluoromethyl)-4-nitro-1H-pyrazol-5-yl]phenyl}but-3-en-1-yl]carbamate (4.0 g, 9.79 mmol) was dissolved in acetone (100 ml)/H₂O (24 ml) and then cooled to 0° C. To the solution was added NH₄Cl (2.62 g, 49.0 mmol) and Zn (6.40 g, 98 mmol) and the ice bath was removed. After 2 h, the reaction mixture was filtered and filtrate partitioned between water (30 ml) and EtOAc (50 ml). The aqueous layer was extracted with EtOAc (2×50 ml). The combined organic phase was washed with brine (20 ml), dried (MgSO₄), filtered, and concentrated. The residue was purified by normal phase chromatography eluting with a gradient of DCM/MeOH to give of tert-butyl N-[(1S)-1-{3-[4-amino-1-(difluoromethyl)-1H-pyrazol-5-yl]phenyl}but-3-en-1-yl]carbamate (3.33 g, 8.80 mmol, 90%) as a yellow oil. MS(ESI) m/z: 379.2 (M+H)⁺.

35C. Preparation of Tert-Butyl N-[(1S)-1-{3-[1-(difluoromethyl)-4-[(2R)-2-methylbut-3-enamido]-1H-pyrazol-5-yl]phenyl}but-3-en-1-yl]carbamate To a solution of tert-butyl N-[(1S)-1-{3-[4-amino-1-(difluoromethyl)-1H-pyrazol-5-yl]phenyl}but-3-en-1-yl]carbamate (3.3 g, 8.72 mmol) in EtOAc (20 ml) at 0° C. was added (R)-2-methylbut-3-enoic acid (1.048 g, 10.46 mmol), prepared as described in Intermediate 2, in EtOAc (10 ml), pyridine (2.116 ml, 26.2 mmol), and T3P®/50% EtOAc (10.38 ml, 17.44 mmol). After 4 h, the reaction was diluted with EtOAc, and washed with a solution of K₂HPO₄, followed by brine. The organic layer was dried over Na₂SO₄, filtered, and concentrated. The residue was purified normal phase column chromatography eluting with a gradient of hexanes/EtOAc to give tert-butyl N-[(1S)-1-{3-[1-(difluoromethyl)-4-[(2R)-2-methylbut-3-enamido]-1H-pyrazol-5-yl]phenyl}but-3-en-1-yl]carbamate (3.10 g, 6.73 mmol, 77% yield) as a yellow foam. MS(ESI) m/z: 461.2 (M+H)⁺.

35D. Preparation of Tert-Butyl N-[(9R,10E,13S)-3-(difluoromethyl)-9-methyl-8-oxo-3,4,7-triazatricyclo[12.3.1.0²,⁶]octadeca-1(18),2(6),4,10,14,16-hexaen-13-yl]carbamate To a solution of tert-butyl N-[(1S)-1-{3-[1-(difluoromethyl)-4-[(2R)-2-methylbut-3-enamido]-1H-pyrazol-5-yl]phenyl}but-3-en-1-yl]carbamate (3.0 g, 6.51 mmol) in degassed DCM (800 mL), was added Second Generation Grubbs Catalyst (2.212 g, 2.61 mmol) and the reaction was heated to 40° C. After stirring overnight, the mixture was concentrated and the residue was purified by normal phase column chromatography eluting with a gradient of hexanes/EtOAc to give tert-butyl N-[(9R,10E,13S)-3-(difluoromethyl)-9-methyl-8-oxo-3,4,7-triazatricyclo[12.3.1.0²,⁶]octadeca-1(18),2(6),4,10,14,16-hexaen-13-yl]carbamate (1.8 g, 63.9%). MS(ESI) m/z: 433.2 (M+H)⁺.

35E. Preparation of Tert-Butyl N-[(9R,13S)-3-(difluoromethyl)-9-methyl-8-oxo-3,4,7-triazatricyclo[12.3.1.0²,⁶]octadeca-1(18),2(6),4,14,16-pentaen-13-yl]carbamate To a solution of tert-butyl N-[(9R,10E,13S)-3-(difluoromethyl)-9-methyl-8-oxo-3,4,7-triazatricyclo[12.3.1.0²,⁶]octadeca-1(18),2(6),4,10,14,16-hexaen-13-yl]carbamate (1.3 g, 3.01 mmol) in EtOH (50 ml) was added PtO₂ (0.102 g, 0.451 mmol) and the reaction was hydrogenated at 55 psi for 4 h. The reaction mixture was filtered through a plug of CELITE® and the filtrate concentrated to give tert-butyl N-[(9R,13S)-3-(difluoromethyl)-9-methyl-8-oxo-3,4,7-triazatricyclo[12.3.1.0²,⁶]octadeca-1(18),2(6),4,14,16-pentaen-13-yl]carbamate (0.973 g, 74.5%). MS(ESI) m/z: 435.2 (M+H)⁺.

35F. Preparation of (9R,13S)-13-amino-3-(difluoromethyl)-9-methyl-3,4,7-triazatricyclo[12.3.1.0²,⁶]octadeca-1(18),2(6),4,14,16-pentaen-8-one To a solution of tert-butyl N-[(9R,13S)-3-(difluoromethyl)-9-methyl-8-oxo-3,4,7-triazatricyclo[12.3.1.0²,⁶]octadeca-1(18),2(6),4,14,16-pentaen-13-yl]carbamate (0.973 g, 2.239 mmol) in DCM (50 ml) was added TFA (5.18 ml, 67.2 mmol). After 3 h, the reaction mixture was concentrated to dryness. The residue was partitioned between sat NaHCO₃ and EtOAc. The aqueous phase was extracted with EtOAc (3×), washed with brine, dried over Na₂SO₄, filtered, and concentrated to give (9R,13S)-13-amino-3-(difluoromethyl)-9-methyl-3,4,7-triazatricyclo[12.3.1.0²,⁶]octadeca-1(18),2(6),4,14,16-pentaen-8-one (0.619 g, 83%). MS(ESI) m/z: 335 (M+H)⁺.

Intermediate 36

Preparation of (9R,13S)-13-amino-3-($^2H_3$)methyl-9-methyl-3,4,7-triazatricyclo[12.3.1.0$^{2,6}$]octadeca-1(18),2(6),4,14,16-pentaen-8-one

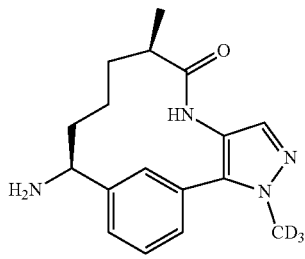 [SMILES: [2H]C([2H])([2H])n1ncc2c1-c1cccc(c1)[C@@H](N)CCC[C@@H](C)C(=O)N2]

36A. Preparation of Tert-Butyl N-[(1S)-1-{3-[1-($^2H_3$)methyl-4-nitro-1H-pyrazol-5-yl]phenyl}but-3-en-1-yl]carbamate To a solution of tert-butyl N-[(1S)-1-(3-bromophenyl)but-3-en-1-yl]carbamate (3.8 g, 11.65 mmol) in DMF (35 ml), was added 1-($^2H_3$)methyl-4-nitro-1H-pyrazole (1.667 g, 12.81 mmol), di(adamantan-1-yl)(butyl)phosphine (0.626 g, 1.747 mmol), K$_2$CO$_3$ (4.83 g, 34.9 mmol) and pivalic acid (0.406 ml, 3.49 mmol). The reaction was purged with Ar and Pd(OAc)$_2$ (0.262 g, 1.165 mmol) was added. The reaction was heated to 115° C. After 4 h, the reaction was diluted with 1:1 EtOAc/water (50 ml) and filtered through paper to remove Pd solids. The filtrate was extracted with EtOAc (2×50 ml). The combined organic layer was washed with water (20 ml), brine (20 ml), dried (MgSO$_4$), filtered and concentrated. The residue was purified by normal phase chromatography twice using hexanes and EtOAc as eluents to afford tert-butyl-N-[(1S)-1-{3-[1-($^2H_3$)methyl-4-nitro-1H-pyrazol-5-yl]phenyl}but-3-en-1-yl]carbamate (1.89 g, 43.2%) as a brown oil. MS(ESI) m/z: 374.4 (M−H)$^+$.

36B. Preparation of Tert-Butyl N-[(1S)-1-{3-[4-amino-1-($^2H_3$)methyl-1H-pyrazol-5-yl]phenyl}but-3-en-1-yl]carbamate To a cooled (0° C.) solution of tert-butyl N-[(1S)-1-{3-[1-($^2H_3$)methyl-4-nitro-1H-pyrazol-5-yl]phenyl}but-3-en-1-yl]carbamate (1.89 g, 5.03 mmol), dissolved in acetone (40 ml)/water (12 ml) was added NH$_4$Cl (1.346 g, 25.2 mmol) and Zn (3.29 g, 50.3 mmol). The ice bath was removed and the solution was allowed to warm to rt. After 3 h, the reaction was filtered through paper and the filtrate was partitioned between water (20 ml) and EtOAc (75 ml). The aqueous layer was extracted with EtOAc (2×50 ml). The combined organic layers were washed with brine (25 ml), dried (MgSO$_4$), filtered and concentrated. The residue was purified by normal phase chromatography using hexanes and EtOAc and then DCM/0-10% MeOH as eluents to afford tert-butyl N-[(1S)-1-{3-[4-amino-1-($^2H_3$)methyl-1H-pyrazol-5-yl]phenyl}but-3-en-1-yl]carbamate (0.84 g, 48.3%) as a light brown foam. MS(ESI) m/z: 346.5 (M+H)$^+$.

36C. Preparation of Tert-Butyl N-[(1S)-1-{3-[1-($^2H_3$)methyl-4-[(2R)-2-methylbut-3-enamido]-1H-pyrazol-5-yl]phenyl}but-3-en-1-yl]carbamate To tert-butyl N-[(1S)-1-{3-[4-amino-1-($^2H_3$)methyl-1H-pyrazol-5-yl]phenyl}but-3-en-1-yl]carbamate (0.7 g, 2.026 mmol) in EtOAc (6 ml) was added (R)-2-methylbut-3-enoic acid (0.26 g, 2.63 mmol), prepared as described in Intermediate 2, in 1 mL EtOAc. The mixture was cooled to 0° C. and pyridine (0.49 ml, 6.08 mmol) followed by a solution of 50% T3P® in EtOAc (2.41 ml, 4.05 mmol) were added. After 1 h, the reaction was partitioned with sat NaHCO$_3$ (30 ml) and EtOAc (50 ml). The aqueous layer was extracted with EtOAc (2×50 ml). The combined organic layers were washed with brine (25 ml), dried (MgSO$_4$), filtered and concentrated. The residue was purified by normal phase chromatography using hexanes and EtOAc as eluents to afford tert-butyl N-[(1S)-1-{3-[1-($^2H_3$)methyl-4-[(2R)-2-methylbut-3-enamido]-1H-pyrazol-5-yl]phenyl}but-3-en-1-yl]carbamate (0.69 g, 81%) as a rose oil. MS(ESI) m/z: 428.5 (M+H)$^+$. $^1$H NMR (400 MHz, CDCl$_3$) δ 8.07-7.93 (m, 1H), 7.53-7.44 (m, 1H), 7.37 (d, J=7.9 Hz, 1H), 7.28-7.09 (m, 3H), 5.89 (ddd, J=17.4, 9.9, 7.9 Hz, 1H), 5.76-5.60 (m, 1H), 5.25-5.11 (m, 4H), 5.07 (d, J=7.0 Hz, 1H), 4.77 (br. s., 1H), 3.08 (quin, J=7.2 Hz, 1H), 2.62-2.47 (m, 2H), 1.41 (br. s., 9H), 1.30 (s, 3H).

36D. Preparation of Tert-Butyl N-[(9R,10E,13S)-3-($^2H_3$)methyl-9-methyl-8-oxo-3,4,7-triazatricyclo[12.3.1.0$^{2,6}$]octadeca-1(18),2(6),4,10,14,16-hexaen-13-yl]carbamate To a degassed DCM (200 ml) solution of tert-butyl N-[(1S)-1-{3-[1-($^2H_3$)methyl-4-[(2R)-2-methylbut-3-enamido]-1H-pyrazol-5-yl]phenyl}but-3-en-1-yl]carbamate (0.699 g, 1.635 mmol) was added Second Generation Grubbs Catalyst (0.555 g, 0.654 mmol) and the resulting solution was heated to 40° C. for 24 h. The reaction mixture was concentrated and the residue was purified by normal phase chromatography using DCM and 0-10% MeOH as eluents to afford tert-butyl N-[(9R,10E,13S)-3-($^2H_3$)methyl-9-methyl-8-oxo-3,4,7-triazatricyclo[12.3.1.0$^{2,6}$]octadeca-1(18),2(6),4,10,14,16-hexaen-13-yl]carbamate (0.511 g, 78%) as a dark solid. MS(ESI) m/z: 400.2 (M+H)$^+$. $^1$H NMR (400 MHz, CDCl$_3$) δ 7.65-7.56 (m, 1H), 7.51-7.44 (m, 1H), 7.30 (d, J=7.9 Hz, 1H), 7.23 (d, J=7.7 Hz, 1H), 6.85 (s, 1H), 6.68 (s, 1H), 5.66 (ddd, J=15.2, 9.3, 5.6 Hz, 1H), 5.20-5.06 (m, 1H), 4.94 (dd, J=15.3, 8.5 Hz, 1H), 4.78-4.66 (m, 1H), 3.08-2.99 (m, 1H), 2.71-2.58 (1, 1H), 2.23-2.12 (m, 1H), 1.43 (br. s., 9H), 1.25-1.19 (1, 3H).

36E. Preparation of Tert-Butyl N-[(9R,13S)-3-($^2H_3$)methyl-9-methyl-8-oxo-3,4,7-triazatricyclo[12.3.1.0$^{2,6}$]octadeca-1(18),2(6),4,14,16-pentaen-13-yl]carbamate To a EtOH (20 ml) solution of tert-butyl N-[(9R,10E,13S)-3-($^2H_3$)methyl-9-methyl-8-oxo-3,4,7-triazatricyclo[12.3.1.0$^{2,6}$]octadeca-1(18),2(6),4,10,14,16-hexaen-13-yl]carbamate (0.40 g, 1.001 mmol) was added PtO$_2$ (0.023 g, 0.100 mmol). The reaction vessel was purged with H$_2$ and the reaction mixture was then hydrogenated at 55 psi. After 1.5 h under pressure, the reaction mixture was then allowed to sit overnight under N$_2$. The reaction was then filtered through CELITE® rinsing with DCM and EtOH. The filtrate was concentration of the afforded tert-butyl N-[(9R,13S)-3-($^2H_3$)methyl9-methyl-8-oxo-3,4,7-triazatricyclo[12.3.1.0$^{2,6}$]octadeca-1(18),2(6),4,14,16-pentaen-13-yl]carbamate (0.38 g, 95%) as a brown solid. MS(ESI) m/z: 402.5 (M+H)$^+$.

36F. Preparation of (9R,13S)-13-amino-3-($^2$H$_3$)methyl-9-methyl-3,4,7-triazatricyclo[12.3.1.0$^{2,6}$]octadeca-1(18),2(6),4,14,16-pentaen-8-one

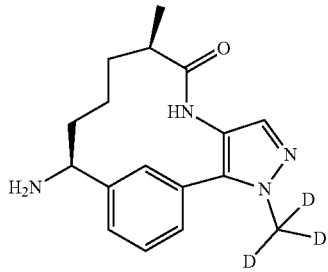 [SMILES: [2H]C([2H])([2H])n1ncc2c1-c1cccc(c1)[C@@H](N)CCC[C@@H](C)C(=O)N2]

To a dioxane (2 ml) and MeOH (2 ml) solution of tert-butyl N-[(9R,13S)-3-($^2$H$_3$)methyl-9-methyl-8-oxo-3,4,7-triazatricyclo[12.3.1.0$^{2,6}$]octadeca-1(18),2(6),4,14,16-pentaen-13-yl]carbamate (0.38 g, 0.946 mmol) was added 4 N HCl in dioxane (2 ml). After 4 h, the reaction was concentrated to near dryness. The dry residue was dissolved in MeOH/DCM and filtered through 500 mg basic cartridge and the filtrate was concentrated to afford (9R,13S)-13-amino-3-($^2$H$_3$)methyl-9-methyl-3,4,7-triazatricyclo[12.3.1.0$^{2,6}$]octadeca-1(18),2(6),4,14,16-pentaen-8-one (0.28 g, 98%) as a gray solid. MS(ESI) m/z: 302.5 (M+H)$^+$.

Intermediate 37

Preparation of (9R,13S)-13-amino-3-(difluoromethyl)-9-methyl-3,4,7,17-tetraazatricyclo[12.3.1.0$^{2,6}$]octadeca-1(18),2(6),4,14,16-pentaen-8-one

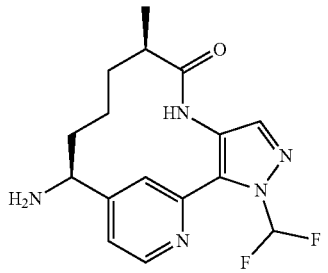 [SMILES: C[C@@H]1CCC[C@H](N)c2ccnc(c2)-c2c(cnn2C(F)F)NC1=O]

37A. Preparation of (S)-tert-butyl (1-(2-(1-(difluoromethyl)-4-nitro-1H-pyrazol-5-yl)pyridin-4-yl)but-3-en-1-yl)carbamate To a large microwave vial was added (S)-tert-butyl (1-(2-bromopyridin-4-yl)but-3-en-1-yl)carbamate (1.5 g, 4.58 mmol), prepared as described for Intermediate 27, 1-(difluoromethyl)-4-nitro-1H-pyrazole (0.822 g, 5.04 mmol), prepared as described for Intermediate 30A, DMF (15.3 mL), di(adamantan-1-yl)(butyl)phosphine (0.247 g, 0.688 mmol), K$_2$CO$_3$ (1.901 g, 13.75 mmol) and pivalic acid (0.160 mL, 1.375 mmol). The mixture was purged with Ar for 15 min. Pd(OAc)$_2$ (0.103 g, 0.458 mmol) was added, the vial sealed and stirred at 115° C. After 4h, the reaction was quenched with water (50 mL) and extracted with EtOAc (3×50 mL). The combined organic layers were washed with brine (50 mL), dried (MgSO$_4$), filtered, and concentrated to give a dark brown oil. The crude product was purified by normal phase chromatography using heptane and EtOAc as eluents to give (S)-tert-butyl (1-(2-(1-(difluoromethyl)-4-nitro-1H-pyrazol-5-yl)pyridin-4-yl)but-3-en-1-yl)carbamate (973 mg, 52%) as a orange solid. MS(ESI) m/z: 410.1 (M+H)$^+$. $^1$H NMR (500 MHz, CDCl$_3$) δ 8.73 (d, J=5.2 Hz, 1H), 8.38 (s, 1H), 7.74 (br. s., 1H), 7.63-7.48 (m, 1H), 7.44-7.37 (m, 1H), 5.69 (ddt, J=17.0, 10.1, 7.0 Hz, 1H), 5.24-5.17 (m, 2H), 2.62-2.50 (m, 2H), 1.45 (s, 9H).

37B. Preparation of (S)-tert-butyl (1-(2-(4-amino-1-(difluoromethyl)-1H-pyrazol-5-yl)pyridin-4-yl)but-3-en-1-yl)carbamate (S)-tert-Butyl (1-(2-(1-(difluoromethyl)-4-nitro-1H-pyrazol-5-yl)pyridin-4-yl)but-3-en-1-yl)carbamate (0.974 g, 2.379 mmol) was dissolved in acetone (15 mL)/water (3 mL), cooled to 0° C., and NH$_4$Cl (0.636 g, 11.90 mmol) and Zn (1.555 g, 23.79 mmol) were added. After stirring overnight at rt, the reaction mixture was filtered through a plug of CELITE® and the filtrate was concentrated. The residue was partitioned with water (30 mL) and EtOAc (50 mL). The aqueous layer was extracted with EtOAc (2×50 mL). The combined organic layers were washed with brine (20 mL) and dried (MgSO$_4$). The product was carried forward as is. MS(ESI) m/z: 380.1 (M+H)$^+$.

37C. Preparation of Tert-Butyl ((S)-1-(2-(1-(difluoromethyl)-4-((R)-2-methylbut-3-enamido)-1H-pyrazol-5-yl)pyridin-4-yl)but-3-en-1-yl)carbamate To a stirring solution of (S)-tert-butyl (1-(2-(4-amino-1-(difluoromethyl)-1H-pyrazol-5-yl)pyridin-4-yl)but-3-en-1-yl)carbamate (0.900 g, 2.372 mmol) in EtOAc (7.91 mL) at 0° C., (R)-2-methylbut-3-enoic acid (0.309 g, 3.08 mmol) in EtOAc (0.50 mL) T3P®/50% EtOAc (2.82 mL, 4.74 mmol) and pyridine (0.576 mL, 7.12 mmol) were added. After 5 h, the reaction mixture concentrated and purified by normal phase chromatography using hexanes and EtOAc as eluents to afford tert-butyl ((S)-1-(2-(1-(difluoromethyl)-4-((R)-2-methylbut-3-enamido)-1H-pyrazol-5-yl)pyridin-4-yl)but-3-en-1-yl)carbamate (680 mg, 62.1%) as an oil. MS(ESI) m/z: 462.2 (M+H)$^+$. $^1$H NMR (500 MHz, CDCl$_3$-d) δ 10.74 (br. s., 1H), 8.60 (s, 1H), 8.57 (d, J=5.2 Hz, 1H), 7.84 (s, 1H), 7.58-7.42 (m, 1H), 7.23-7.20 (m, 1H), 6.00 (ddd, J=17.3, 10.1, 8.1 Hz, 1H), 5.72-5.62 (m, 1H), 5.36-5.31 (m, 2H), 5.21-5.15 (m, 2H), 3.22 (quin, J=7.2 Hz, 1H), 2.59-2.47 (m, 2H), 1.48-1.37 (m, 12H).

37D. Preparation of Tert-Butyl N-[(9R,10E,13S)-3-(difluoromethyl)-9-methyl-8-oxo-3,4,7,17-tetraazatricyclo[12.3.1.0$^{2,6}$]octadeca-1(18),2(6),4,10,14,16-hexaen-13-yl]carbamate 3 large microwave vials received equal portions of the following: tert-butyl ((S)-1-(2-(1-(difluoromethyl)-4-((R)-2-methylbut-3-enamido)-1H-pyrazol-5-yl)pyridin-4-yl)but-3-en-1-yl)carbamate (0.680 g, 1.473 mmol) in degassed DCE (61.4 mL) in the presence of Second Generation Grubbs Catalyst (0.500 g, 0.589 mmol) was irradiated to 120° C. for 30 min in a μwave. The reaction mixture was concentrated and purified by normal phase chromatography using hexanes and EtOAc as eluents to give tert-butyl N-[(9R,10E,13S)-3-(difluoromethyl)-9-methyl-8-oxo-3,4,7,17-tetraazatricyclo[12.3.1.0$^{2,6}$]octadeca-1(18),2(6),4,10,14,16-hexaen-13-yl]carbamate (158 mg, 24.7%) as a brown film. MS(ESI) m/z: 434.2 (M+H)$^+$. $^1$H NMR (500 MHz, CDCl$_3$-d) δ 8.69

(d, J=5.0 Hz, 1H), 8.05-7.89 (m, 1H), 7.83 (s, 1H), 7.10 (s, 1H), 6.77 (br. s., 1H), 5.73 (ddd, J=15.2, 9.7, 5.1 Hz, 1H), 5.13-5.05 (1n, 2H), 3.19-3.10 (m, 1H), 2.73 (d, J=12.7 Hz, 1H), 2.24-2.15 (m, 1H), 1.46 (br. s., 9H), 1.30-1.24 (m, 4H).

37E. Preparation of Tert-Butyl N-[(9R,13S)-3-(difluoromethyl)-9-methyl-8-oxo-3,4,7,17-tetraazatricyclo[12.3.1.0$^{2,6}$]octadeca-1(18),2(6),4,14,16-pentaen-13-yl]carbamate PtO$_2$ (8.28 mg, 0.036 mmol) was added to a solution of tert-butyl N-[(9R,10E,13S)-3-(difluoromethyl)-9-methyl-8-oxo-3,4,7,17-tetraazatricyclo[12.3.1.0$^{2,6}$]octadeca-1(18),2(6),4,10,14,16-hexaen-13-yl]carbamate (0.158 g, 0.365 mmol) in EtOH (10 mL) and subjected to a H$_2$ atmosphere (55 psi). After 3 h, the catalyst was filtered through a pad of CELITE® and filtrate concentrated to give tert-butyl N-[(9R,13S)-3-(difluoromethyl)-9-methyl-8-oxo-3,4,7,17-tetraazatricyclo[12.3.1.0$^{2,6}$]octadeca-1(18),2(6),4,14,16-pentaen-13-yl]carbamate. MS(ESI) m/z: 436.1 (M+H)$^+$.

37F. Preparation of (9R,13S)-13-amino-3-(difluoromethyl)-9-methyl-3,4,7,17-tetraazatricyclo[12.3.1.0$^{2,6}$]octadeca-1(18),2(6),4,14,16-pentaen-8-one tert-Butyl N-[(9R,13S)-3-(difluoromethyl)-9-methyl-8-oxo-3,4,7,17-tetraazatricyclo[12.3.1.0$^{2,6}$]Octadeca-1(18),2(6),4,14,16-pentaen-13-yl]carbamate (0.159 g, 0.365 mmol) was dissolved in MeOH (0.50 mL) and treated with 4 M HCl in dioxane (1.83 mL, 7.30 mmol). After stirring for 14 h, the reaction mixture was concentrated to dryness. The amine HCl salt was free based by dissolving in MeOH and passing through 2 consecutive NaHCO$_3$ cartridges. The filtrate was concentrated (9R,13S)-13-amino-3-(difluoromethyl)-9-methyl-3,4,7,17-tetraazatricyclo[12.3.1.0$^{2,6}$]octadeca-1(18),2(6),4,14,16-pentaen-8-one (0.085 g, 69%). MS(ESI) m/z: 336.1 (M+H)$^+$.

Intermediate 38

Preparation of (10R,14S)-14-amino-10-methyl-3,8-diazatricyclo[13.3.1.0$^{2,7}$]nonadeca-1(19),2,4,6,15,17-hexaen-9-one

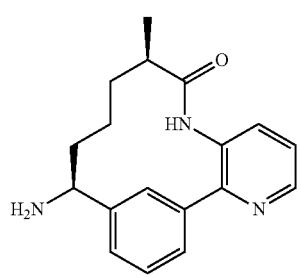 [SMILES: C[C@@H]1CCC[C@H](N)c2cccc(c2)-c2ncccc2NC1=O]

38A. Preparation of {3-[(1S)-1-{[(tert-butoxy)carbonyl]amino}but-3-en-1-yl]phenyl}boronic Acid To a solution of tert-butyl N-[(1S)-1-(3-bromophenyl)but-3-en-1-yl]carbamate, prepared as described in Intermediate 24, (2.36 g, 7.23 mmol) in dioxane (50 ml), was added 5,5,5',5'-tetramethyl-2,2'-bi(1,3,2-dioxaborinane) (1.798 g, 7.96 mmol), and KOAc (2.130 g, 21.70 mmol). The mixture was purged with Ar and PdCl$_2$(dppf)-CH$_2$Cl$_2$ adduct (0.295 g, 0.362 mmol) was added. The reaction mixture was heated to 90° C. for 18 h, then quenched with water (20 ml) and extracted with EtOAc (3×30 ml). The combined organic layers were washed with brine (20 ml), dried (Na$_2$SO$_4$), filtered and concentrated. The residue was absorbed on CELITE® and charged to a 100 g reverse phase cartridge which was eluted with a 25 min gradient from 10-100% Solvent B (Solvent A: 90% H$_2$O-10% MeCN-0.05% TFA; Solvent B: 90% MeCN-10% H$_2$O-0.05% TFA) to give {3-[(1S)-1-{[(tert-butoxy)carbonyl]amino}but-3-en-1-yl]phenyl}boronic acid as a tan solid. MS(ESI) m/z: 292.08 (M+H)$^+$.

38B. Preparation of Tert-Butyl N-[(1S)-1-[3-(3-aminopyridin-2-yl) phenyl]but-3-en-1-yl]carbamate {3-[(1S)-1-{[(tert-Butoxy)carbonyl]amino}but-3-en-1-yl]phenyl}boronic acid (0.36 g, 1.236 mmol), 2-bromopyridin-3-amine (0.214 g, 1.236 mmol), and 2 M aq Na$_2$CO$_3$ (3.09 ml, 6.18 mmol) were added to dioxane (8 ml) and purged with a stream of Ar for 10 min. Pd(PPh$_3$)$_4$ (0.143 g, 0.124 mmol) was added and the reaction mixture was irradiated in microwave at 120° C. for 30 min. The reaction was quenched with water (20 ml) and extracted with EtOAc (3×30 ml). The combined organic layers were washed with brine (15 ml), dried (MgSO$_4$), filtered and concentrated. The residue was purified via Isco 40g column eluting with DCM/0-10% MeOH to give a tan foam (0.352g (84%). The reaction mixture was filtered and concentrated and the residue was purified by normal phase chromatography using DCM and 0-10% MeOH as eluents to afford tert-butyl N-[(1S)-1-[3-(3-aminopyridin-2-yl)phenyl]but-3-en-1-yl]carbamate (0.352 g, 84%) as a tan solid. MS(ESI) m/z: 340.5 (M+H)$^+$. $^1$H NMR (400 MHz, CDCl$_3$) δ 8.13 (dd, J=4.1, 1.9 Hz, 1H), 7.62-7.54 (m, 2H), 7.44 (t, J=7.6 Hz, 1H), 7.26 (s, 2H), 7.12-7.00 (m, 2H), 5.82-5.57 (m, 1H), 5.23-5.02 (m, 1H), 4.91 (br. s., 1H), 4.80 (br. s., 1H), 3.82 (br. s., 2H), 2.81-2.41 (m, 2H), 1.51-1.34 (m, 9H).

38C. Preparation of Tert-Butyl N-[(1S)-1-(3-{3-[(2R)-2-methylbut-3-enamido]pyridin-2-yl}phenyl)but-3-en-1-yl]carbamate To a cooled (0° C.) EtOAc (6 mL) solution of tert-butyl N-[(1S)-1-[3-(3-minopyridin-2-yl)phenyl]but-3-en-1-yl]carbamate (0.334 g, 1.03 mmol) was added (R)-2-methylbut-3-enoic acid (0.135 g, 1.348 mmol), prepared as described in Intermediate 2, in 1 ml EtOAc, pyridine (0.252 ml, 3.11 mmol) and the dropwise addition of a 50% EtOAc solution of T3P® (1.235 ml, 2.074 mmol). After 1 h, the reaction was partitioned between sat NaHCO$_3$(30 ml) and EtOAc (50 ml). The aqueous layer was extracted with EtOAc (2×50 ml). The combined organic layers were washed with brine (25 ml) dried (MgSO$_4$), filtered and concentrated. The residue was purified by normal phase chromatography using hexanes and EtOAc as eluents to afford tert-butyl N-[(1S)-1-(3-{3-[(2R)-2-methylbut-3-enamido]pyridin-2-yl}phenyl)but-3-en-1-yl]carbamate (0.334 g, 76%) as a tan solid. MS(ESI) m/z: 428.5 (M+H)$^+$. $^1$H NMR (400 MHz, CDCl$_3$) δ 8.71 (dd, J=8.3, 1.2 Hz, 1H), 8.41 (dd, J=4.6, 1.5 Hz, 1H), 7.60 (br. s., 1H), 7.49-7.42 (m, 2H), 7.42-7.36 (m, 2H), 7.29 (dd, J=8.4, 4.8 Hz, 1H), 5.84-5.62 (m, 2H), 5.16-5.02 (m, 4H), 4.92 (br. s., 1H), 4.80 (br. s., 1H), 3.04 (quin, J=7.3 Hz, 1H), 2.62-2.48 (m, 2H), 1.51-1.35 (m, 9H), 1.32-1.25 (m, 3H).

38D. Preparation of Tert-Butyl N-[(10R,11E,14S)-10-methyl-9-oxo-3,8-diazatricyclo[13.3.1.0$^{2,7}$]nonadeca-1(19),2(7),3,5,11,15,17-heptaen-14-yl]carbamate Trifluoroacetate To a in degassed DCE (20 ml) solution of tert-butyl N-[(1S)-1-(3-{3-[(2R)-2-methylbut-3-enamido]pyridin-2-yl}phenyl)but-3-en-1-yl]carbamate (0.15 g, 0.356 mmol) was added Second Generation Grubbs Catalyst (0.121 g, 0.142 mmol) and the resulting solution was heated to 120° C. for 30 min in a microwave. The reaction was concentrated, and the residue purified by normal phase chromatography, then reverse phase preparative HPLC (PHENOMENEX® Luna Axia C18 5μ 30×100 mm column, 8-min gradient; Solvent A: 30% MeOH-70% H$_2$O-0.1% TFA; Solvent B: 90% MeOH-10% H$_2$O-0.1% TFA) to afford tert-butyl N-[(10R,11E,14S)-10-methyl-9-oxo-3,8-diazatricyclo[13.3.1.0$^{2,7}$]nonadeca-1(19),2(7),3,5,11,15,17-heptaen-14-yl]carbamate trifluoroacetate (71 mg, 39%) as a clear residue. MS(ESI) m/z: 394.5 (M+H)$^+$. $^1$H NMR (400 MHz, CDCl$_3$) δ 8.73 (d, J=4.4 Hz, 1H), 8.44 (d, J=7.9 Hz, 1H), 7.99-7.89 (m, 1H), 7.69-7.59 (m, 1H), 7.59-7.48 (m, 2H), 7.17-7.08 (m, 1H), 5.84-5.67 (m, 1H), 4.67-4.53 (m, 1H), 4.53-4.38 (m, 1H), 3.28-3.17 (m, 1H), 2.77-2.66 (m, 1H), 2.04 (q, J=11.4 Hz, 1H), 1.46 (br. s., 9H), 1.18-1.09 (m, 3H).

38E. Preparation of Tert-Butyl N-[(10R,14S)-10-methyl-9-oxo-3,8-diazatricyclo[13.3.1.0$^{2,7}$]nonadeca-1(19),2(7),3,5,15,17-hexaen-14-yl]carbamate To a EtOH (5 ml) solution of tert-butyl N-[(10R,11E,14S)-10-methyl-9-oxo-3,8-diazatricyclo[13.3.1.0$^{2,7}$]nonadeca-1 (19),2(7),3,5,11,15,17-heptaen-14-yl]carbamate (0.37 g, 0.940 mmol) (free base was prepared as in Example 38D) was added PtO$_2$ (21 mg) and the reaction mixture was purged with H$_2$ and was hydrogenated at 20-30 psi for 4 h. The reaction was filtered through CELITE® and the filtrate was concentrated to afford tert-butyl N-[(10R,14S)-10-methyl-9-oxo-3,8-diazatricyclo[13.3.1.0$^{2,7}$]nonadeca-1(19), 2(7),3,5,15,17-hexaen-14-yl]carbamate (0.37g, 99%) as a dark solid. MS(ESI) m/z: 396.3 (M+H)$^+$.

38F. Preparation of (10R,14S)-14-amino-10-methyl-3,8-diazatricyclo[13.3.1.0$^{2,7}$]nonadeca-1(19),2(7),3, 5,15,17-hexaen-9-one tert-Butyl N-[(10R,14S)-10-methyl-9-oxo-3,8-diazatricyclo[13.3.1.0$^{2,7}$]nonadeca-1(19),2 (7),3,5,15,17-hexaen-14-yl]carbamate (0.18 g, 0.455 mmol) was dissolved in 4 N HCl in dioxane (2 ml) and MeOH (2 ml). After 2 h, the reaction was concentrated, the residue was dissolved in DCM/MeOH and free-based by passing through a 500 mg basic cartridge (2×). Concentration of the filtrate afforded (10R,14)-14-amino-10-methyl-3,8-diazatricyclo[13.3.1.0$^{2,7}$]nonadeca-1 (19),2(7),3,5,15,17-hexaen-9-one (0.11g, 49%) as a dark brown film. MS(ESI) m/z: 296.3 (M+H)$^+$.

Intermediate 39

Preparation of (10R,14S)-14-amino-10-methyl-3,8, 16-triazatricyclo[13.3.1.0$^{2,7}$]nonadeca-1(19),2(7),3, 5,15,17-hexaen-9-one

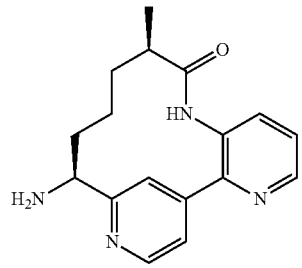 [SMILES: C[C@@H]1CCC[C@H](N)c2cc(ccn2)-c2ncccc2NC1=O]

39A. Preparation of (S)-tert-butyl (1-(3-amino-[2,4'-bipyridin]-2'-yl)but-3-en-1-yl)carbamate To a solution of (S)-(2-(1-((tert-butoxycarbonyl)amino) but-3-en-1-yl)pyridin-4-yl)boronic acid trifluoroacetate (0.60 g, 1.477 mmol) in dioxane (12 ml) was added 2-bromopyridin-3-amine (0.256 g, 1.477 mmol) and 2 M aq Na$_2$CO$_3$ (3.69 ml, 7.39 mmol). The reaction mixture was purged with a stream of Ar for 10 min. Pd(PPh$_3$)$_4$ (0.171 g, 0.148 mmol) was added and the mixture irradiated at 120° C. for 30 min. The reaction was partitioned between water and EtOAc. The organic layer was washed with brine, dried over Na$_2$SO$_4$, filtered and concentrated. The crude material was purified by normal phase column chromatography eluting with a gradient of DCM/MeOH to give (S)-tert-butyl (1-(3-amino-[2,4'-bipyridin]-2'-yl)but-3-en-1-yl)carbamate (0.500 g, 99% yield) as a brown oil. MS(ESI) m/z: 341.1 (M+H)$^+$.

39B. Preparation of Tert-Butyl ((S)-1-(3-((R)-2-methylbut-3-enamido)-[2,4'-bipyridin]-2'-yl)but-3-en-1-yl)carbamate A solution of (R)-2-methylbut-3-enoic acid (0.191 g, 1.909 mmol), prepared as described in Intermediate 2, (S)-tert-butyl (1-(3-amino-[2,4'-bipyridin]-2'-yl)but-3-en-1-yl)carbamate (0.500 g, 1.469 mmol), and pyridine (0.356 ml, 4.41 mmol) in EtOAc (14.69 ml) was cooled down to 0° C. under Ar followed by addition of T3P® (50% wt in EtOAc) (1.75 ml, 2.94 mmol), then the reaction mixture was gradually warmed up to rt. After stirring overnight, the mixture was diluted with EtOAc, washed with 1.5 M K$_2$HPO$_4$ followed by brine, dried over Na$_2$SO$_4$, filtered, and concentrated. The crude product was then purified by normal phase chromatography eluting with a gradient of hexanes/EtOAc to give tert-butyl ((S)-1-(3-((R)-2-methylbut-3-enamido)-[2, 4'-bipyridin]-2'-yl)but-3-en-1-yl)carbamate (0.458 g, 73.8% yield) as a yellow foam. MS(ESI) m/z: 423.2 (M+H)$^+$.

39C. Preparation of Tert-Butyl N-[(10R,11E,14S)-10-methyl-9-oxo-3,8,16-triazatricyclo[13.3.1.0$^{2,7}$] nonadeca-1(19),2(7),3,5,11,15,17-heptaen-14-yl] carbamate, bis-trifluoroacetate tert-Butyl ((S)-1-(3-((R)-2-methylbut-3-enamido)-[2,4'-bipyridin]-2'-yl)but-3-en-1-yl)carbamate (100 mg, 0.237 mmol) in degassed DCE (14.79 ml) in the presence of Second Generation Grubbs Catalyst (0.080 g, 0.095 mmol) was irradiated at 120° C. for 30 min. The reaction mixture was concentrated and purified by reverse phase chromatography to give the tert-butyl N-[(10R,11E,14S)-10-methyl-9-oxo-3,8,16-triazatricyclo[13.3.1.0$^{2,7}$]nonadeca-1(19),2(7),3,5,11,15,17-heptaen-14-yl]carbamate, bis-trifluoroacetate (39 mg, 26.5% yield) as brown oil. MS(ESI) m/z: 395.2 (M+H)$^{+}$.

39D. Preparation of Tert-Butyl N-[(10R,14S)-10-methyl-9-oxo-3,8,16-triazatricyclo[13.3.1.0$^{2,7}$]nonadeca-1(19),2(7),3,5,15,17-hexaen-14-yl]carbamate PtO$_2$ (2.245 mg, 9.89 μmol) was added to a stirring solution of tert-butyl N-[(10R,11E,14S)-10-methyl-9-oxo-3,8,16-triazatricyclo[13.3.1.0$^{2,7}$]nonadeca-1(19),2(7),3,5,11,15,17-heptaen-14-yl]carbamate, bis-trifluoroacetate (0.039 g, 0.099 mmol) in EtOH (10 ml) and subjected to a H$_2$ atmosphere (55 psi). After 4 h, the reaction mixture was filtered through a pad of CELITE® and the filtrate concentrated to give tert-butyl N-[(10R,14S)-10-methyl-9-oxo-3,8,16-triazatricyclo[13.3.1.0$^{2,7}$]nonadeca-1(19),2(7),3,5,15,17-hexaen-14-yl]carbamate. MS(ESI) m/z: 397.2 (M+H)$^{+}$.

39E. Preparation of (10R,14S)-14-amino-10-methyl-3,8,16-triazatricyclo[13.3.1.0$^{2,7}$]nonadeca-1(19),2(7),3,5,15,17-hexaen-9-one TFA (0.15 mL, 1.967 mmol) was added to a solution of tert-butyl N-[(10R,14S)-10-methyl-9-oxo-3,8,16-triazatricyclo[13.3.1.0$^{2,7}$]nonadeca-1(19),2(7),3,5,15,17-hexaen-14-yl]carbamate (0.039 g, 0.098 mmol) in DCM (2.0 ml). After stirring for 4 h, the reaction mixture was concentrated to dryness, and placed under high vacuum for 12 h. The residue was neutral by dissolving in MeOH, passing through NaHCO$_3$ cartridge (StratoSpheres SPE; 500 mg, 0.90 mmol loading), and concentrating the filtrate to give (10R,14S)-14-amino-10-methyl-3,8,16-triazatricyclo[13.3.1.0$^{2,7}$]nonadeca-1(19),2(7),3,5,15,17-hexaen-9-one. MS(ESI) m/z: 297.5 (M+H)$^{+}$.

Intermediate 40

Preparation of (9R,13S)-13-amino-3-(2-hydroxyethyl)-9-methyl-3,4,7,15-tetraazatricyclo[12.3.1.0$^{2,6}$]octadeca-1(18),2(6),4,14,16-pentaen-8-one

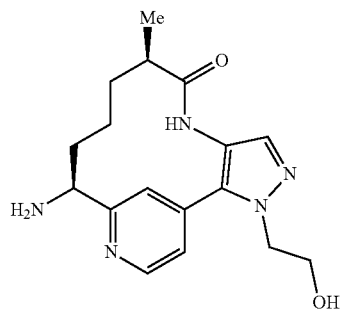 [SMILES: C[C@@H]1CCC[C@H](N)c2cc(ccn2)-c2c(cnn2CCO)NC1=O]

40A. Preparation of 1-(2-((tert-butyldimethylsilyl)oxy)ethyl)-4-nitro-1H-pyrazole To a solution of 4-nitro-1H-pyrazole (4.0 g, 35.4 mmol) in DMF (50 mL) was added Cs$_2$CO$_3$ (12.68 g, 38.9 mmol) and (2-bromoethoxy)(tert-butyl)dimethylsilane (8.35 mL, 38.9 mmol). The resulting suspension was heated to 60° C. for 2 h. The reaction mixture was then diluted with EtOAc (2×25 mL) and washed with 10% LiCl solution (25 mL). The organic layer was concentrated, and the residue purified using normal phase chromatography to yield 1-(2-((tert-butyldimethylsilyl)oxy)ethyl)-4-nitro-1H-pyrazole as white solid (8.6 g, 85% yield). MS(ESI) m/z: 272.4 (M+H)$^{+}$.

40B. Preparation of (S)-tert-butyl (1-(4-(1-(2-((tert-butyldimethylsilyl)oxy)ethyl)-4-nitro-1H-pyrazol-5-yl)pyridin-2-yl)but-3-en-1-yl)carbamate To a N$_2$ flushed pressure vial was added (S)-tert-butyl (1-(4-chloropyridin-2-yl)but-3-en-1-yl)carbamate, prepared as described in Intermediate 23, (3.0 g, 10.61 mmol), 1-(2-((tert-butyldimethylsilyl)oxy)ethyl)-4-nitro-1H-pyrazole, prepared as described in Intermediate 40A, (2.88 g, 10.61 mmol), di(adamant-1-yl)(butyl)phosphine (0.571 g, 1.59 mmol), PvOH (0.369 ml, 3.18 mmol), K$_2$CO$_3$ (4.40 g, 31.8 mmol), and DMF (20 mL). The vial was purged with N$_2$ for 5 min and Pd(OAc)$_2$ (0.238 g, 1.061 mmol) was added. The reaction mixture was again briefly purged with N$_2$. The vial was sealed and heated at 120° C. for 4 h. The reaction mixture was cooled to rt and partitioned between 10% aqueous LiCl (15 mL) and EtOAc (30 mL). The aqueous layer was extracted with EtOAc (2×20 mL) and the combined organic layers were washed with brine (15 mL), dried over MgSO$_4$, filtered and concentrated. The crude product was purified using normal phase chromatography to yield (S)-tert-butyl (1-(4-(1-(2-((tert-butyldimethylsilyl)oxy)ethyl)-4-nitro-1H-pyrazol-5-yl)pyridin-2-yl)but-3-en-1-yl)carbamate (1.4 g, 25% yield) as a brown oil. MS(ESI) m/z: 518.3 (M+H)$^{+}$.

40C. Preparation of (S)-tert-butyl (1-(4-(4-amino-1-(2-((tert-butyldimethylsilyl)oxy) ethyl)-1H-pyrazol-5-yl)pyridin-2-yl)but-3-en-1-yl)carbamate A solution of (S)-tert-butyl (1-(4-(1-(2-((tert-butyldimethylsilyl)oxy)ethyl)-4-nitro-1H-pyrazol-5-yl)pyridin-2-yl)but-3-en-1-yl)carbamate (2.4 g, 4.64 mmol) in MeOH (25 mL) and CH$_3$COOH (2.5 mL) was heated to 40° C. To the resulting clear solution was then slowly added Zn (0.606 g, 9.27 mmol, in 3 portions (50:25:25%)) and the reaction was stirred at 40° C. for 5 min. Additional Zn was added to the reaction. The reaction mixture was monitored by LCMS and once complete, to the cooled reaction mixture was then added 2.5 g of K$_2$CO$_3$ (1 g for 1 mL AcOH) and 2.5 mL water. The reaction mixture was then stirred for 5 min. The reaction mixture was then filtered over a pad of CELITE® and concentrated to yield the crude product. The crude product was partitioned between EtOAc (40 mL) and sat NaHCO$_3$(20 mL). The organic layers were separated, dried over MgSO$_4$, filtered and concentrated. The crude product was purified using normal phase chromatography to yield (S)-tert-butyl (1-(4-(4-amino-1-(2-((tert-butyldimethylsilyl)oxy)-1H-pyrazol-5-yl)pyridin-2-yl)but-3-en-1-yl)carbamate (1.9 g, 80% yield) as pale brown oil. MS(ESI) m/z: 488.6 (M+H)$^{+}$.

40D. Preparation of Tert-Butyl ((S)-1-(4-(1-(2-((tert-butyldimethylsilyl)oxy)ethyl)-4-((R)-2-methylbut-3-enamido)-1H-pyrazol-5-yl)pyridin-2-yl)but-3-en-1-yl)carbamate To a N$_2$ flushed, 3-necked, 250 mL RBF was added (S)-tert-butyl (1-(4-(4-amino-1-(2-((tert-butyldimethylsilyl)

oxy)ethyl)-1H-pyrazol-5-yl)pyridin-2-yl)but-3-en-1-yl)carbamate (1.9 g, 3.90 mmol) and EtOAc (25 mL). The solution was cooled to −10° C. and (R)-2-methylbut-3-enoic acid, as prepared in Intermediate 2, (390 mg, 3.90 mmol), pyridine (0.630 mL, 7.79 mmol) and T3P® (3.48 mL, 5.84 mmol) were added. The cooling bath was removed and the solution was allowed to warm to rt and then stirred for 20 h. Water (20 mL) and EtOAc (20 mL) were added and the mixture was stirred for 30 min. The organic phase was separated and the aqueous layer was extracted with EtOAc (20 mL). The combined organic extracts were washed with brine (15 mL), dried over $Na_2SO_4$, filtered and concentrated. Purification by normal phase chromatography eluting with a gradient of hexanes/EtOAc gave ((S)-1-(4-(1-(2-((tert-butyldimethylsilyl)oxy) ethyl)-4-((R)-2-methylbut-3-enamido)-1H-pyrazol-5-yl)pyridin-2-yl)but-3-en-1-yl)carbamate (0.68 g, 28% yield). MS(ESI) m/z: 570.1 $[M+H]^+$.

40E. Preparation of Tert-Butyl N-[(9R,10E,13S)-3-{2-[(tert-butyldimethylsilyl)oxy]ethyl}-9-methyl-8-oxo-3,4,7,15-tetraazatricyclo[12.3.1.0$^{2,6}$]octadeca-1(18),2(6),4,10,14,16-hexaen-13-yl]carbamate To a $N_2$ flushed, 250 mL, 3-necked, RBF was added a solution of tert-butyl ((S)-1-(4-(1-(2-((tert-butyldimethylsilyl)oxy)ethyl)-4-((R)-2-methylbut-3-enamido)-1H-pyrazol-5-yl)pyridin-2-yl)but-3-en-1-yl)carbamate (680 mg, 1.193 mmol) in EtOAc (56 mL). The solution was sparged with Ar for 15 min. Second Generation Grubbs Catalyst (253 mg, 0.298 mmol) was added in one portion. The reaction mixture was heated to reflux temperature for overnight. After cooling to rt, the solvent was removed and the residue was purified by normal phase chromatography eluting with a gradient of DCM/MeOH to yield tert-butyl N-[(9R,10E,13S)-3-{2-[(tert-butyldimethylsilyl)oxy]ethyl}-9-methyl-8-oxo-3,4,7,15-tetraazatricyclo[12.3.1.0$^{2,6}$]octadeca-1(18),2(6),4,10,14,16-hexaen-13-yl]carbamate (400 mg, 61% yield) as a tan solid. MS(ESI) m/z: 542.6 $[M+H]^+$.

40F. Preparation of Tert-Butyl N-[(9R,13S)-3-{2-[(tert-butyldimethylsilyl)oxy]ethyl}-9-methyl-8-oxo-3,4,7,15-tetraazatricyclo[12.3.1.0$^{2,6}$]octadeca-1(18),2(6),4,14,16-pentaen-13-yl]carbamate Pd/C (0.078 g, 0.074 mmol) was added to a 250 mL Parr hydrogenation flask containing a solution of tert-butyl N-[(9R,10E,13S)-3-{2-[(tert-butyldimethylsilyl)oxy]ethyl}-9-methyl-8-oxo-3,4,7,15-tetraazatricyclo[12.3.1.0$^{2,6}$]octadeca-1(18),2(6),4,10,14,16-hexaen-13-yl]carbamate (400 mg, 0.738 mmol) in EtOH (20 mL). The flask was purged with $N_2$ and pressurized to 55 psi of $H_2$ and allowed to stir for 4 h. The reaction was filtered through a pad of CELITE® and concentrated to yield tert-butyl N-[(9R,13S)-3-{2-[(tert-butyldimethyl silyl)oxy]ethyl}-9-methyl-8-oxo-3,4,7,15-tetraazatricyclo[12.3.1.0$^{2,6}$]octadeca-1(18),2(6),4,14,16-pentaen-13-yl]carbamate (375 mg, 92% yield) as a tan solid. MS(ESI) m/z: 544.6 $[M+H]^+$.

40G. (9R,13S)-13-Amino-3-(2-hydroxyethyl)-9-methyl-3,4,7,15-tetraazatricyclo[12.3.1.0$^{2,6}$]octadeca-1(18),2(6),4,14,16-pentaen-8-one To a solution of tert-butyl N-[(9R,13S)-3-{2-[(tert-butyldimethylsilyl)oxy]ethyl}-9-methyl-8-oxo-3,4,7,15-tetraazatricyclo[12.3.1.0$^{2,6}$]octadeca-1(18),2(6),4,14,16-pentaen-13-yl]carbamate (375 mg, 0.690 mmol) in MeOH (5 mL) was added 4 N HCl in dioxane (5 mL, 20.0 mmol) and the reaction mixture was stirred at rt for 1 h. The reaction mixture was then concentrated to give (9R,13S)-13-amino-3-(2-hydroxyethyl)-9-methyl-3,4,7,15-tetraazatricyclo[12.3.1.0$^{2,6}$]octadeca-1(18),2(6),4,14,16-pentaen-8-one, bis hydrochloride (220 mg, 96% yield) as a pale yellow solid which was then dissolved in MeOH (4 mL) to give a clear, pale yellow solution. The solution was added to a pre-rinsed AGILENT® StratoSpheres SPE PL-HCO$_3$ MP Resin cartridge. Gravity filtration, eluting with MeOH, gave a clear, slightly yellow filtrate. Concentration provided (9R,13S)-13-amino-3-(2-hydroxyethyl)-9-methyl-3,4,7,15-tetraazatricyclo[12.3.1.0$^{2,6}$]octadeca-1(18),2(6),4,14,16-pentaen-8-one (170 mg, 96%) as a pale yellow solid. MS(ESI) m/z: 330.5 $[M+H]^+$.

Intermediate 41

Preparation of (9R,13)-13-amino-16-fluoro-3,9-dimethyl-3,4,7-triazatricyclo[12.3.1.0$^{2,6}$]octadeca-1(18),2(6),4,14,16-pentaen-8-one

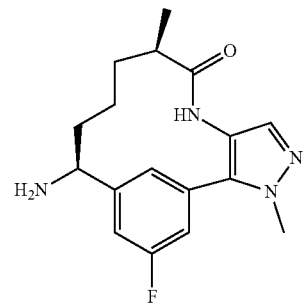 [SMILES: C[C@@H]1CCC[C@H](N)c2cc(F)cc(c2)-c2c(cnn2C)NC1=O]

41A. Preparation of Tert-Butyl N-[(1S)-1-[3-fluoro-5-(1-methyl-4-nitro-1H-pyrazol-5-yl)phenyl]but-3-en-1-yl]carbamate To a DMF (1 ml) solution of tert-butyl N-[(1S)-1-(3-bromo-5-fluorophenyl)but-3-en-1-yl]carbamate (0.19 g, 0.552 mmol), prepared as described in Intermediate 25, was added 1-methyl-4-nitro-1H-pyrazole (0.070 g, 0.552 mmol), di(adamantan-1-yl)(butyl) phosphine (0.059 g, 0.166 mmol), pivalic acid (0.019 ml, 0.166 mmol), $K_2CO_3$ (0.229 g, 1.656 mmol) and Pd(OAc)$_2$ (0.025 g, 0.110 mmol). The reaction mixture was purged with Ar, and heated at 120° C. After 18 h, the reaction was partitioned between water (15 ml) and EtOAc (30 ml). The aqueous layer was extracted with EtOAc (2×20 ml). The combined organic layers were washed with brine (15 ml), dried (MgSO$_4$), filtered and concentrated. The residue was purified by normal phase chromatography and was eluted with hexanes and EtOAc to afford tert-butyl N-[(1S)-1-[3-fluoro-5-(1-methyl-4-nitro-1H-pyrazol-5-yl)phenyl]but-3-en-1-yl]carbamate as a yellow oil (0.123 g, 57%). $^1$H NMR (400 MHz, CDCl$_3$) 8.23-8.17 (m, 1H), 7.22-7.16 (m, 1H), 7.10 (s, 1H), 7.01 (dt, J=8.5, 1.9 Hz, 1H), 5.76-5.60 (m, 1H), 5.22-5.11 (m, 2H), 4.90 (br. s., 1H), 4.78 (br. s., 1H), 3.78-3.69 (m, 3H), 2.60-2.48 (m, 2H), 1.41 (br. s., 9H).

41B. Preparation of Tert-Butyl N-[(1S)-1-[3-(4-amino-1-methyl-1H-pyrazol-5-yl)-5-fluorophenyl]but-3-en-1-yl]carbamate tert-Butyl N-[(1S)-1-[3-(4-amino-1-methyl-1H-pyrazol-5-yl)-5-fluorophenyl]but-3-en-1-yl]carbamate (0.123 g, 0.315 mmol) was dissolved in acetone (5 ml)/water (1 ml), cooled to 0° C., and NH$_4$Cl (0.084 g, 1.575 mmol) and Zn (0.206 g, 3.15 mmol) were added. The ice bath was removed and the reaction mixture was warmed to rt. After 3 h, the reaction was filtered and partitioned between water (10 ml) and EtOAc (30 ml). The aqueous layer was extracted with EtOAc (2×20 ml). The combined organic layers were washed with brine (10 ml), dried (MgSO$_4$), filtered and concentrated. The residue was purified by normal phase chromatography and was eluted with hexanes and EtOAc to afford tert-butyl N-[(1S)-1-[3-(4-amino-1-methyl-1H-pyrazol-5-yl)-5-fluorophenyl]but-3-en-1-yl]carbamate (0.105 g, 92%). MS(ESI) m/z: 361.08 (M+H)$^+$.

41C. Preparation of Tert-Butyl N-[(1S)-1-(3-fluoro-5-{1-methyl-4-[(2R)-2-methylbut-3-enamido]-1H-pyrazol-5-yl}phenyl)but-3-en-1-yl]carbamate To tert-butyl N-[(1S)-1-[3-(4-amino-1-methyl-1H-pyrazol-5-yl)-5-fluorophenyl]but-3-en-1-yl]carbamate (0.105 g, 0.291 mmol) was added EtOAc (0.6 ml), (R)-2-methylbut-3-enoic acid (0.035 g, 0.350 mmol), prepared as described in Intermediate 2, in 0.3 ml EtOAc. The reaction mixture was cooled to 0° C., and a 50% EtOAc solution of T3P® (0.347 ml, 0.583 mmol) and Hunig's Base (0.153 ml, 0.874 mmol) were added. After 4 h, the reaction was partitioned between sat NaHCO$_3$ (5 ml) and EtOAc (5 ml). The aqueous layer was extracted with EtOAc (2×10 ml). The combined organic layers were washed with brine (5 ml), dried (MgSO$_4$), filtered and concentrated. The residue was purified by normal phase chromatography and was eluted with hexanes and EtOAc to give tert-butyl N-[(1S)-1-(3-fluoro-5-{1-methyl-4-[(2R)-2-methylbut-3-enamido]-1H-pyrazol-5-yl}phenyl)but-3-en-1-yl]carbamate as a yellow foam (53 mg, 41%). MS(ESI) m/z: 443.5 (M+H)$^+$.

41D. Preparation of Tert-Butyl N-[(9R,10E,13S)-16-fluoro-3,9-dimethyl-8-oxo-3,4,7-triazatricyclo[12.3.1.0$^{2,6}$]octadeca-1(18),2(6),4,10,14,16-hexaen-13-yl]carbamate To a degassed DCE (10 ml) solution of tert-butyl N-[(1S)-1-(3-fluoro-5-{1-methyl-4-[(2R)-2-methylbut-3-enamido]-1H-pyrazol-5-yl}phenyl)but-3-en-1-yl]carbamate (0.053 g, 0.120 mmol) was added Second Generation Grubbs Catalyst (0.041 g, 0.048 mmol) and the reaction mixture was heated to 120° C. for 30 min in a microwave. The reaction mixture was directly purified by normal phase chromatography eluting with hexanes and EtOAc to afford tert-butyl N-[(9R,10E,13S)-16-fluoro-3,9-dimethyl-8-oxo-3,4,7-triazatricyclo[12.3.1.0$^{2,6}$]octadeca-1(18),2(6),4,10,14,16-hexaen-13-yl]carbamate as a dark solid (27 mg, 54%). MS(ESI) m/z: 415.4 (M+H)$^+$.

41E. Preparation of (9R,13S)-13-amino-16-fluoro-3,9-dimethyl-3,4,7-triazatricyclo[12.3.1.0$^{2,6}$]octadeca-1(18),2(6),4,14,16-pentaen-8-one

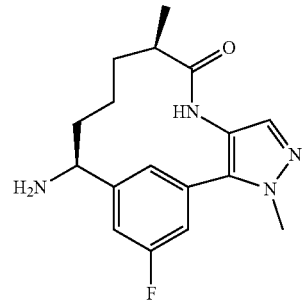 [SMILES: C[C@@H]1CCC[C@H](N)c2cc(F)cc(c2)-c2c(cnn2C)NC1=O]

To an EtOH (3 ml) solution of tert-butyl N-[(9R,10E,13S)-16-fluoro-3,9-dimethyl-8-oxo-3,4,7-triazatricyclo[12.3.1.0$^{2,6}$]octadeca-1(18),2(6),4,10,14,16-hexaen-13-yl]carbamate (0.027 g, 0.065 mmol) was added PtO$_2$ (5 mg). The reaction mixture was purged with H$_2$ and was then hydrogenated at 55 psi. After 6 h, the reaction mixture was filtered through CELITE® and concentrated to give 19 mg of a dark solid MS(ESI) m/z: 417.08 (M+H)$^+$. The dark solid residue was dissolved in 50% TFA/DCM (3 ml). After 3 h, the reaction mixture was concentrated, the residue was dissolved in DCM/MeOH, passed through a basic cartridge and concentrated to give (9R,13S)-13-amino-16-fluoro-3,9-dimethyl-3,4,7-triazatricyclo[12.3.1.0$^{2,6}$]octadeca-1(18),2(6),4,14,16-pentaen-8-one a dark solid (19 mg, 92%). MS(ESI) m/z: 317.4 (M+H)$^+$.

Intermediate 42

Preparation of (9R,13S)-13-amino-3,9-dimethyl-3,4,7,17-tetraazatricyclo[12.3.1.0$^{2,6}$]

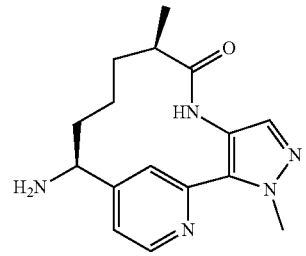 [SMILES: C[C@@H]1CCC[C@H](N)c2ccnc(c2)-c2c(cnn2C)NC1=O]

42A. Preparation of Tert-Butyl N-[(1S)-1-[2-(1-methyl-4-nitro-1H-pyrazol-5-yl)pyridin-4-yl]but-3-en-1-yl]carbamate To a large microwave vial was added tert-butyl N-[(1S)-1-(2-bromopyridin-4-yl) but-3-en-1-yl]carbamate (1.0 g, 3.06 mmol), prepared as described in Intermediate 27, 1-methyl-4-nitro-1H-pyrazole (0.427 g, 3.36 mmol), dioxane (10 ml), di(adamantan-1-yl)(butyl)phosphine (0.164 g, 0.458 mmol), K$_2$CO$_3$ (1.267 g, 9.17 mmol) and pivalic acid (0.106 ml, 0.917 mmol). The reaction was purged with Ar. Pd(OAc)$_2$ (0.069 g, 0.306 mmol) was added and the reaction was stirred at 100° C. After 4 h, heating was stopped and the reaction was stirred at rt for 72 h. The reaction was quenched with water (20 ml) and extracted with EtOAc (3×50 ml). The combined organic layers were washed with brine (20 ml), dried (MgSO$_4$), filtered, and concentrated. The residue was purified by normal phase chromatography using heptanes and EtOAc as eluents to give tert-butyl N-[(1S)-1-[2-(1-methyl-4-nitro-1H-pyrazol-5-yl) pyridin-4-yl]but-3-en-1-yl]carbamate (0.62 g, 54%) as a white foam. MS(ESI) m/z: 374.08 (M+H)$^+$. $^1$H NMR (500 MHz, CDCl$_3$) δ 8.73 (d, J=5.2 Hz, 1H), 8.28-8.15 (m, 1H), 7.66-7.54 (m, 1H), 7.43-7.34 (m, 1H), 5.76-5.63 (m, 1H), 5.26-5.16 (m, 2H), 4.99 (br. s., 1H), 4.83 (br. s., 1H), 3.97-3.85 (m, 3H), 2.66-2.46 (m, 2H), 1.45 (br. s., 9H).

42B. Preparation of Tert-Butyl N-[(1S)-1-[2-(4-amino-1-methyl-1H-pyrazol-5-yl)pyridin-4-yl]but-3-en-1-yl]carbamate To a cooled (0° C.) acetone (40 ml)/water (12 ml) solution of tert-butyl N-[(1S)-1-[2-(1-methyl-4-nitro-1H-pyrazol-5-yl)pyridin-4-yl]but-3-en-1-yl]carbamate (0.62 g, 1.660 mmol) was added NH$_4$Cl (0.444 g, 8.30 mmol) and Zn (1.086 g, 16.60 mmol). The ice bath was removed and the reaction was stirred 18 h. The reaction was filtered through paper and partitioned with water (20 ml) and EtOAc (75 ml). The aqueous layer was extracted with EtOAc (2×50 ml). The combined organic layers were washed with brine (25 ml), dried (MgSO$_4$), filtered and concentrated. The residue was purified by normal phase chromatography using DCM and 0-10% MeOH as eluents to give tert-butyl N-[(1S)-1-[2-(4-amino-1-methyl-1H-pyrazol-5-yl)pyridin-4-yl]but-3-en-1-yl]carbamate (0.46 g, 60%). MS(ESI) m/z: 344.5 (M+H)$^+$.

42C. Preparation of Tert-Butyl N-[(1S)-1-(2-{1-methyl-4-[(2R)-2-methylbut-3-enamido]-1H-pyrazol-5-yl}pyridin-4-yl)but-3-en-1-yl]carbamate To tert-butyl N-[(1S)-1-[2-(4-amino-1-methyl-1H-pyrazol-5-yl)pyridin-4-yl]but-3-en-1-yl]carbamate (0.6 g, 1.747 mmol) was added (R)-2-methylbut-3-enoic acid (0.189 g, 1.893 mmol), prepared as described in Intermediate 2, in EtOAc (5.8 ml), cooled to 0° C. Pyridine (0. 0.424 ml, 5.24 mmol) and a 50% EtOAc solution of T3P® (2.080 ml, 3.49 mmol) were added. After 24 h, the reaction was partitioned between sat NaHCO$_3$(10 ml) and EtOAc (20 ml). The aqueous layer was extracted with EtOAc (2×20 ml). The combined organic layers were washed with brine (10 ml), dried (MgSO$_4$), filtered and concentrated. The residue was purified by normal phase chromatography using hexanes and EtOAc as eluents to give tert-butyl N-[(1S)-1-(2-{1-methyl-4-[(2R)-2-methylbut-3-enamido]-1H-pyrazol-5-yl}pyridin-4-yl)but-3-en-1-yl]carbamate (0.35 g, 47%). MS(ESI) m/z: 426.1 (M+H)$^+$. $^1$H NMR (500 MHz, CDCl$_3$) δ 10.23 (br. s., 1H), 8.70-8.56 (m, 1H), 8.35 (d, J=1.1 Hz, 1H), 7.56-7.44 (m, 1H), 7.25-7.14 (m, 1H), 6.03 (ddd, J=17.2, 10.2, 8.0 Hz, 1H), 5.39-5.17 (m, 3H), 5.03-4.63 (m, 2H), 4.14-4.08 (m, 3H), 3.22 (quin, J=7.2 Hz, 1H), 2.66-2.49 (m, 1H), 1.84-1.72 (m, 1H), 1.50-1.40 (m, 9H), 1.42-1.37 (m, 3H), 1.06-0.93 (m, 1H).

42D. Preparation of Tert-Butyl N-[(9R,10E,13S)-3,9-dimethyl-8-oxo-3,4,7,17-tetraazatricyclo[12.3.1.0$^{2,6}$]octadeca-1(18),2(6),4,10,14,16-hexaen-13-yl]carbamate To a degassed DCE (20 ml) solution of tert-butyl N-[(1S)-1-(2-{1-methyl-4-[(2R)-2-methylbut-3-enamido]-1H-pyrazol-5-yl}pyridin-4-yl)but-3-en-1-yl]carbamate (0.160 g, 0.376 mmol) was added Second Generation Grubbs Catalyst (0.096 g, 0.113 mmol) and the reaction mixture was heated to 120° C. for 30 min in a microwave. The reaction mixture was concentrated and the residue was purified by normal phase chromatography using DCM and MeOH as eluents to afford desired product (29 mg, 19%) as a green film. MS(ESI) m/z: 398.3 (M+H)$^+$. $^1$H NMR (500 MHz, CDCl$_3$) δ 8.71 (d, J=4.7 Hz, 1H), 7.58 (s, 1H), 7.23 (d, J=13.8 Hz, 1H), 7.03-6.94 (m, 1H), 6.61 (s, 1H), 5.82-5.71 (m, 1H), 5.19-5.09 (m, 2H), 4.75 (br. s., 1H), 4.15-4.09 (m, 3H), 3.19-3.10 (m, 1H), 2.67 (br. s., 1H), 2.28-2.15 (m, 2H), 1.54-1.39 (m, 9H), 1.34-1.28 (m, 3H).

42E. Preparation of (9R,13S)-13-amino-3,9-dimethyl-3,4,7,17-tetraazatricyclo[12.3.1.0$^{2,6}$]octadeca-1(18),2(6),4,14,16-pentaen-8-one

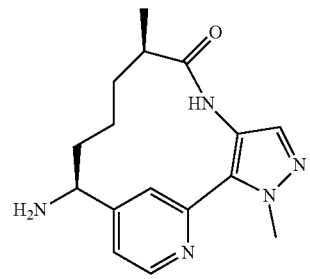 [SMILES: C[C@@H]1CCC[C@H](N)c2ccnc(c2)-c2c(cnn2C)NC1=O]

To an EtOH (3 mL) solution of tert-butyl N-[(9R,10E,13S)-3,9-dimethyl-8-oxo-3,4,7,17-tetraazatricyclo[12.3.1.0$^{2,6}$]octadeca-1(18),2(6),4,10,14,16-hexaen-13-yl]carbamate (29 mg, 0.073 mmol) was added PtO$_2$ (4 mg). The reaction mixture was purged with H$_2$, then was hydrogenated at 55 psi. After 3 h, the reaction mixture was filtered through a 0.45 M filter and concentrated to afford a dark solid (MS(ESI) m/z: 400.3 (M+H)$^+$). The dark solid residue was dissolved in 4 N HCl in dioxane (1 ml) and MeOH (1 ml). After 3 h, the mixture was concentrated and resultant HCl salt was dissolved in DCM/MeOH and passed through a basic cartridge to afford (9R,13S)-13-amino-3,9-dimethyl-3,4,7,17-tetraazatricyclo[12.3.1.0$^{2,6}$]octadeca-1(18),2(6),4,14,16-pentaen-8-one as a dark solid (21 mg, 96%). MS(ESI) m/z: 300.2 (M+H)$^+$.

Intermediate 43

Preparation of (9R,13S)-13-amino-3-(difluoromethyl)-9-methyl-3,4,7,16-tetraazatricyclo[12.3.1.0$^{2,6}$]octadeca-1(18),2(6),4,14,16-pentaen-8-one

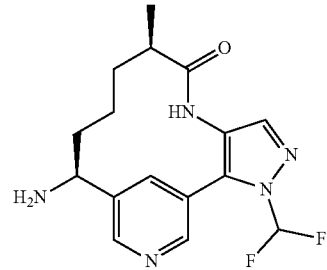

43A. Preparation of (S)-tert-butyl (1-(5-(1-(difluoromethyl)-4-nitro-1H-pyrazol-5-yl)pyridin-3-yl)but-3-en-1-yl)carbamate To a large microwave vial was added (S)-tert-butyl (1-(5-bromopyridin-3-yl)but-3-en-1-yl)carbamate (1.0 g, 3.06 mmol), prepared a described in Intermediate 26, 1-(difluoromethyl)-4-nitro-1H-pyrazole (0.548 g, 3.36 mmol), DMF (10.19 ml), di(adamantan-1-yl)(butyl)phosphine (0.164 g, 0.458 mmol), $K_2CO_3$ (1.267 g, 9.17 mmol) and pivalic acid (0.106 ml, 0.917 mmol). The reaction mixture was purged with Ar. After 10 min, $Pd(OAc)_2$ (0.069 g, 0.306 mmol) was added, the vessel sealed, and stirred at 115° C. After 4 h, the reaction was quenched with $H_2O$ (50 mL) and extracted with EtOAc (3×50 mL). The combined organic phase was washed with brine (50 mL), dried ($MgSO_4$), filtered, and concentrated. The crude material was purified by normal phase chromatography eluting with a gradient of heptane/EtOAc to give (S)-tert-butyl (1-(5-(1-(difluoromethyl)-4-nitro-1H-pyrazol-5-yl)pyridin-3-yl)but-3-en-1-yl)carbamate (1.25 g, 100%). MS(ESI) m/z: 410.2 $(M+H)^+$.

43B. Preparation of (S)-tert-butyl (1-(5-(4-amino-1-(difluoromethyl)-1H-pyrazol-5-yl)pyridin-3-yl)but-3-en-1-yl)carbamate (S)-tert-Butyl (1-(5-(1-(difluoromethyl)-4-nitro-H-pyrazol-5-yl)pyridin-3-yl)but-3-en-1-yl)carbamate (1.27 g, 3.10 mmol) was dissolved in acetone (15 ml)/water (3 ml), cooled to 0° C., and $NH_4Cl$ (0.830 g, 15.51 mmol) and Zn (2.028 g, 31.0 mmol) were added. The ice bath was removed. After 2 h, the reaction mixture was filtered and filtrate partitioned with water (30 ml) and EtOAc (50 ml). The aqueous layer was extracted with EtOAc (2×50 ml). The combined organic phase was washed with brine (20 ml), dried ($MgSO_4$), filtered, and concentrated. The residue was purified by normal phase chromatography eluting with a gradient of DCM/MeOH to give (S)-tert-butyl (1-(5-(4-amino-1-(difluoromethyl)-1H-pyrazol-5-yl)pyridin-3-yl)but-3-en-1-yl)carbamate (0.720 g, 61.2% yield) as a solid. MS(ESI) m/z: 380 $(M+H)^+$.

43C. Preparation of Tert-Butyl ((S)-1-(5-(1-(difluoromethyl)-4-((R)-2-methylbut-3-enamido)-1H-pyrazol-5-yl)pyridin-3-yl)but-3-en-1-yl)carbamate A solution of (S)-tert-butyl (1-(5-(4-amino-1-(difluoromethyl)-1H-pyrazol-5-yl)pyridin-3-yl)but-3-en-1-yl)carbamate (0.720 g, 1.898 mmol) in EtOAc (20 ml) was cooled to 0° C. and (R)-2-methylbut-3-enoic acid (0.228 g, 2.277 mmol), prepared as described in Intermediate 2, in EtOAc (10 ml), pyridine (0.460 ml, 5.69 mmol), and T3P® (50% wt in EtOAc) (2.259 ml, 3.80 mmol) were added. After 6 h, the reaction was partitioned with 1.5 M $K_2PO_4$ (50 mL) and EtOAc (50 mL). The aqueous layer was extracted with EtOAc (2×20 mL). The combined organic phase was washed with brine (50 mL), dried ($MgSO_4$), filtered, and concentrated. The residue was purified by normal chromatography eluting with a gradient of hexanes/EtOAc to give tert-butyl ((S)-1-(5-(1-(difluoromethyl)-4-((R)-2-methylbut-3-enamido)-1H-pyrazol-5-yl)pyridin-3-yl)but-3-en-1-yl)carbamate (0.386 g, 44.1% yield) as a yellow foam. MS(ESI) m/z: 462.2 $(M+H)^+$.

43D. Preparation of Tert-Butyl N-[(9R,10E,13S)-3-(difluoromethyl)-9-methyl-8-oxo-3,4,7,16-tetraazatricyclo[12.3.1.0$^{2,6}$]octadeca-1(18),2(6),4,10,14,16-hexaen-13-yl]carbamate To a RBF was added tert-butyl ((5)-1-(5-(1-(difluoromethyl)-4-((R)-2-methylbut-3-enamido)-1H-pyrazol-5-yl)pyridin-3-yl)but-3-en-1-yl)carbamate (0.190 g, 0.412 mmol), pTsOH (0.086 g, 0.453 mmol), and degassed DCE (103 ml). The clear yellow solution was warmed to 40° C. and degassed with Ar for 1 h. Second Generation Grubbs Catalyst (0.140 g, 0.165 mmol) was added and reaction stirred at 40° C. overnight. Additional Second Generation Grubbs Catalyst (0.2 eq.) was added and stirring continued. After stirring for a total of 48 h, the reaction mixture was cooled to rt, washed with sat $NaHCO_3$, brine, dried over $MgSO_4$, filtered, and concentrated. The crude product was purified by normal phase chromatography eluting with a gradient of DCM/MeOH to give tert-butyl N-[(9R,10E,13S)-3-(difluoromethyl)-9-methyl-8-oxo-3,4,7,16-tetraazatricyclo[12.3.1.0$^{2,6}$]octadeca-1(18),2(6),4,10,14,16-hexaen-13-yl]carbamate (0.020 g, 11.2%) as a brown oil. MS(ESI) m/z: 434.3 $(M+H)^+$.

43E. Preparation of Tert-Butyl N-[(9R,13S)-3-(difluoromethyl)-9-methyl-8-oxo-3,4,7,16-tetraazatricyclo[12.3.1.0$^{2,6}$]octadeca-1(18),2(6),4,14,16-pentaen-13-yl]carbamate To an EtOH (3 mL) solution of tert-butyl N-[(9R,10F,13S)-3-(difluoromethyl)-9-methyl-8-oxo-3,4,7,16-tetraazatricyclo[12.3.1.0$^{2,6}$]octadeca-1(18),2(6),4,10,14,16-hexaen-13-yl]carbamate (0.020, 0.046 mmol) was added $PtO_2$ (1.048 mg, 4.61 μmol) and the reaction was purged with $H_2$. The reaction mixture was subjected to a $H_2$ atmosphere (55 psi). After 2 h, the catalyst was filtered off through a plug of CELITE® and the filtrate concentrated to give tert-butyl N-[(9R,13S)-3-(difluoromethyl)-9-methyl-8-oxo-3,4,7,16-tetraazatricyclo[12.3.1.0$^{2,6}$]octadeca-1(18),2(6),4,14,16-pentaen-13-yl]carbamate. MS(ESI) m/z: 436.2 $(M+H)^+$.

43F. Preparation of (9R,13S)-13-amino-3-(difluoromethyl)-9-methyl-3,4,7,16-tetraazatricyclo [12.3.1.0$^{2,6}$]octadeca-1(18),2(6),4,14,16-pentaen-8-one tert-Butyl N-[(9R,13S)-3-(difluoromethyl)-9-methyl-8-oxo-3,4,7,16-tetraazatricyclo[12.3.1.0$^{2,6}$]octadeca-1(18),2(6),4,14,16-pentaen-13-yl]carbamate (0.020 g, 0.046 mmol) was dissolved in 4 N HCl in dioxane (0.230 ml, 0.919 mmol). A minimum amount of MeOH was added to aid dissolution. After 1 h, the reaction mixture was concentrated to dryness. The residue was dissolved in MeOH, passed through a $NaHCO_3$ cartridge (StratoSpheres SPE; 500 mg, 0.90 mmol loading), concentrated to give (9R,13S)-13-amino-3-(difluoromethyl)-9-methyl-3,4,7,16-tetraazatricyclo[12.3.1.0$^{2,6}$]octadeca-1(18),2(6),4,14,16-pentaen-8-one. MS(ESI) m/z: 336.2 $(M+H)^+$.

Intermediate 44

Preparation of 6-(2-bromo-5-chlorophenyl)pyrimidin-4-ol

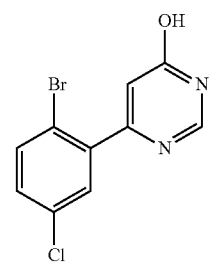

44A. Preparation of 4-(2-bromo-5-chlorophenyl)-6-methoxypyrimidine

To a suspension of 4-chloro-2-(6-methoxypyrimidin-4-yl) aniline (100 mg, 0.424 mmol) and TsOH—H$_2$O (97 mg, 0.509 mmol) in CH$_3$CN (20 mL) was added CuBr$_2$ (9.48 mg, 0.042 mmol). Then t-butyl nitrite (0.067 mL, 0.509 mmol) was added followed by tetrabutylammonium bromide (274 mg, 0.849 mmol) and the reaction was stirred at rt. After 2 h, water was added and the mixture was extracted with CH$_2$Cl$_2$ (2×). The organic layers were combined, dried over MgSO$_4$, filtered, and concentrated. Purification by normal phase chromatography gave 4-(2-bromo-5-chlorophenyl)-6-methoxypyrimidine (115 mg, 90% yield) as a white solid. MS(ESI) m/z: 299.2 (M+H)$^+$. $^1$H NMR (400 MHz, CDCl$_3$) δ 8.88 (d, J=1.1 Hz, 1H), 7.61 (d, J=8.6 Hz, 1H), 7.56 (d, J=2.6 Hz, 1H), 7.30-7.24 (m, 1H), 7.04 (d, J=1.1 Hz, 1H), 4.05 (s, 3H).

44B. Preparation of 6-(2-bromo-5-chlorophenyl)pyrimidin-4-ol 6-(2-Bromo-5-chlorophenyl)pyrimidin-4-ol was prepared according to the procedures described in Intermediate 5 for the synthesis of 6-(5-chloro-2-fluorophenyl) pyrimidin-4-ol, by replacing 6-(5-chloro-2-fluorophenyl)pyrimidin-4-ol with 4-(2-bromo-5-chlorophenyl)-6-methoxypyrimidine. MS(ESI) m/z: 285.2 (M+H)$^+$. $^1$H NMR (400 MHz, DMSO-d$_6$) δ 8.19 (s, 1H), 7.72 (d, J=8.6 Hz, 1H), 7.52 (d, J=2.6 Hz, 1H), 7.41 (dd, J=8.6, 2.6 Hz, 1H), 6.21 (s, 1H).

Example 45

Preparation of (9R,13S)-13-(4-{5-chloro-2-[(pyrimidin-2-yl)amino]phenyl}-6-oxo-1,6-dihydropyrimidin-1-yl)-3,9-dimethyl-3,4,7,15-tetraazatricyclo[12.3.1.0$^{2,6}$] octadeca-1(18),2(6),4,14,16-pentaen-8-one

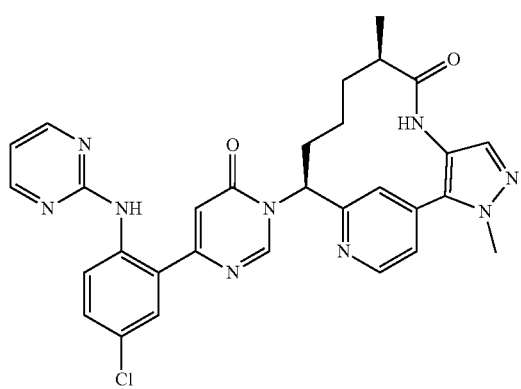 [SMILES: C[C@@H]1CCC[C@H](n2cnc(-c3cc(Cl)ccc3Nc3ncccn3)cc2=O)c2cc(ccn2)-c2c(cnn2C)NC1=O]

(9R,13S)-13-(4-{5-Chloro-2-[(pyrimidin-2-yl)amino] phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one, 2 trifluoroacetate (2.75 mg, 19% yield) was prepared in a similar manner as the procedure described in Example 314, by replacing 4-bromopyrimidine hydrochloride (6.78 mg, 0.035 mmol) with 2-bromopyrimidine (5.51 mg, 0.035 mmol). MS(ESI) m/z: 582.5 (M+H)$^+$. $^1$H NMR (400 MHz, CD$_3$OD) δ 9.12 (s, 1H), 8.74 (d, J=5.1 Hz, 1H), 8.46-8.42 (m, 3H), 7.73 (s, 1H), 7.66 (d, J=2.6 Hz, 1H), 7.54-7.48 (m, 2H), 7.43 (dd, J=8.9, 2.5 Hz, 1H), 6.85 (t, J=5.0 Hz, 1H), 6.79 (s, 1H), 6.06 (dd, J=12.7, 4.3 Hz, 1H), 4.05 (s, 3H), 2.78-2.67 (m, 1H), 2.42-2.31 (m, 1H), 2.16-2.02 (m, 2H), 1.69-1.44 (m, 2H), 1.02 (d, J=6.8 Hz, 3H), 0.80-0.63 (m, 1H). Analytical HPLC (Method A): RT=8.33 min, 97.9% purity; Factor XIa Ki=2,000 nM.

Example 46

Preparation of Ethyl 2-[4-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-pyrazol-1-yl]acetate

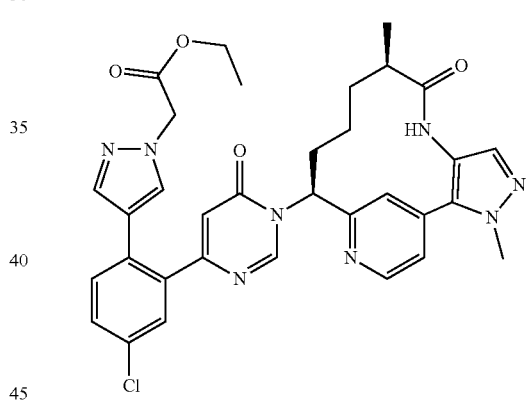

Ethyl 2-[4-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-pyrazol-1-yl]acetate trifluoroacetate (3.67 mg, 15% yield) was prepared in a similar manner as the procedure described in Example 49, by replacing 1-methyl-4-(4,4,5,5-tetramethyl-1,3,2-dioxaborolan-2-yl)-1H-pyrazole with ethyl 2-(4-(4,4,5,5-tetramethyl-1,3,2-dioxaborolan-2-yl)-1H-pyrazol-1-yl)acetate (13.67 mg, 0.049 mmol). MS(ESI) m/z: 641.5 (M+H)$^+$. $^1$H NMR (400 MHz, CD$_3$OD) δ 8.96 (s, 1H), 8.74 (d, J=5.3 Hz, 1H), 7.72 (s, 1H), 7.62 (s, 1H), 7.56-7.52 (m, 2H), 7.51-7.49 (m, 3H), 7.45 (s, 1H), 6.41 (s, 1H), 6.00 (dd, J=12.7, 4.1 Hz, 1H), 4.94 (s, 2H), 4.18 (q, J=7.1 Hz, 2H), 4.05 (s, 3H), 2.76-2.66 (m, 1H), 2.40-2.28 (m, 1H), 2.14-2.03 (m, 2H), 1.67-1.42 (m, 2H), 1.24 (t, J=7.2 Hz, 3H), 1.02 (d, J=6.8 Hz, 3H), 0.80-0.65 (m, 1H). Analytical HPLC (Method A): RT=7.92 min, 99.6% purity; Factor XIa Ki=25 nM, Plasma Kallikrein Ki=7,000 nM.

Example 47

Preparation of 2-[4-(4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)-1H-pyrazol-1-yl]acetic Acid

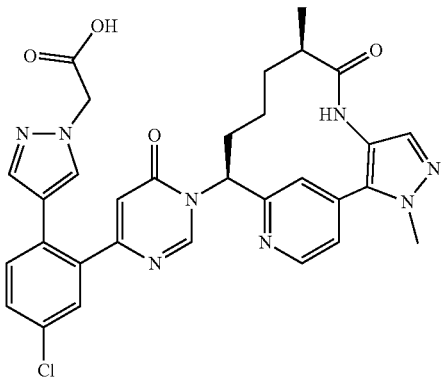 [SMILES: C[C@@H]1CCC[C@H](n2cnc(-c3cc(Cl)ccc3-c3cnn(CC(=O)O)c3)cc2=O)c2cc(ccn2)-c2c(cnn2C)NC1=O]

2-[4-(4-Chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)-1H-pyrazol-1-yl]acetic acid trifluoroacetate (8.6 mg, 35% yield) was also isolated from Example 46. MS(ESI) m/z: 613.5 (M+H)⁺. ¹H NMR (400 MHz, CD₃OD) δ 8.94 (s, 1H), 8.75 (d, J=5.3 Hz, 1H), 7.74 (s, 1H), 7.60 (s, 1H), 7.56-7.48 (m, 5H), 7.46 (s, 1H), 6.45 (d, J=0.4 Hz, 1H), 6.00 (dd, J=12.5, 4.2 Hz, 1H), 4.90 (s, 2H), 4.05 (s, 3H), 2.75-2.66 (m, 1H), 2.33 (tt, J=12.7, 4.5 Hz, 1H), 2.14-2.03 (m, 2H), 1.66-1.42 (m, 2H), 1.02 (d, J=6.8 Hz, 3H), 0.82-0.66 (m, 1H). Analytical HPLC (Method A): RT=6.68 min, 99.0% purity; Factor XIa Ki=12 nM, Plasma Kallikrein Ki=6,000 nM.

Example 48

Preparation of 2-(4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)acetonitrile

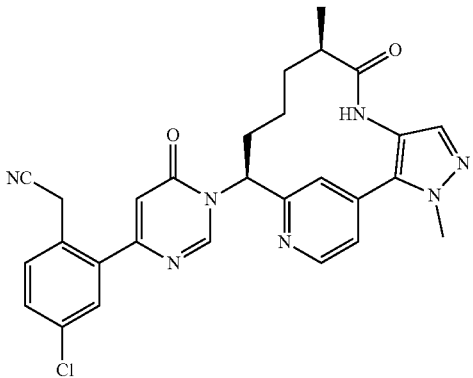 [SMILES: C[C@@H]1CCC[C@H](n2cnc(-c3cc(Cl)ccc3CC#N)cc2=O)c2cc(ccn2)-c2c(cnn2C)NC1=O]

2-(4-Chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)acetonitrile trifluoroacetate (2.2 mg, 11% yield) was prepared in a similar manner as the procedure described in Example 49, by replacing 1-methyl-4-(4,4,5,5-tetramethyl-1,3,2-dioxaborolan-2-yl)-1H-pyrazole with 4-(4,4,5,5-tetramethyl-1,3,2-dioxaborolan-2-yl)isoxazole (9.52 mg, 0.049 mmol). MS(ESI) m/z: 528.35 (M+H)⁺. ¹H NMR (500 MHz, CD₃OD) δ 9.04 (br. s., 1H), 8.74 (d, J=5.2 Hz, 1H), 7.73 (s, 1H), 7.59-7.49 (m, 5H), 6.65 (s, 1H), 6.06 (d, J=9.6 Hz, 1H), 4.18-4.08 (m, 2H), 4.06 (s, 3H), 2.78-2.68 (m, 1H), 2.42-2.33 (m, 1H), 2.16-2.03 (m, 2H), 1.68-1.58 (m, 1H), 1.55-1.45 (m, 1H), 1.02 (d, J=6.9 Hz, 3H), 0.79-0.65 (m, 1H). Analytical HPLC (Method C): RT=1.46 min, 100% purity; Factor XIa Ki=16 nM, Plasma Kallikrein Ki=850 nM.

Example 49

Preparation of (9R,13S)-13-{4-[5-chloro-2-(1-methyl-1H-pyrazol-4-yl)phenyl]-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one

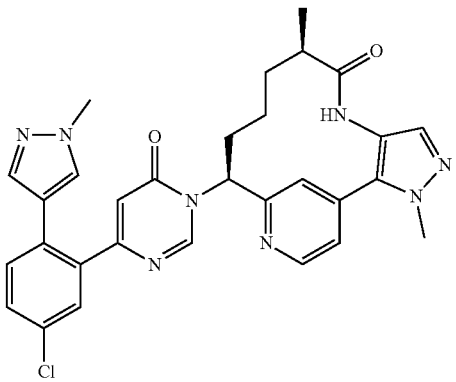 [SMILES: C[C@@H]1CCC[C@H](n2cnc(-c3cc(Cl)ccc3-c3cnn(C)c3)cc2=O)c2cc(ccn2)-c2c(cnn2C)NC1=O]

To a degassed solution of (9R,13S)-13-[4-(5-chloro-2-iodophenyl)-6-oxo-1,6-dihydropyrimidin-1-yl]-3,9-dimethyl-3,4,7,15-tetraazatricyclo[12.3.1.0²,⁶]octadeca-1(18),2(6),4,14,16-pentaen-8-one (15 mg, 0.024 mmol), prepared as described in Example 211, 1-methyl-4-(4,4,5,5-tetramethyl-1,3,2-dioxaborolan-2-yl)-1H-pyrazole (7.61 mg, 0.037 mmol), and K₂CO₃ (8.43 mg, 0.061 mmol) in 1,4-dioxane (0.6 ml) and water (0.2 ml) was added Pd(Ph₃P)₄ (2.82 mg, 2.440 μmol). The reaction was microwaved at 120° C. for 0.5 h, and then cooled to rt and concentrated. Purification by reverse phase chromatography afforded (9R,13S)-13-{4-[5-chloro-2-(1-methyl-1H-pyrazol-4-yl)phenyl]-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one trifluoroacetate (7.9 mg, 47% yield) as an off-white solid. MS(ESI) m/z: 569.6 (M+H)⁺. ¹H NMR (500 MHz, CD₃OD) δ 8.97 (s, 1H), 8.75 (d, J=5.2 Hz, 1H), 7.73 (s, 1H), 7.59 (s, 1H), 7.55-7.52 (m, 2H), 7.50-7.45 (m, 3H), 7.33 (s, 1H), 6.40 (d, J=0.6 Hz, 1H), 6.02 (dd, J=12.7, 3.9 Hz, 1H), 4.05 (s, 3H), 3.84 (s, 3H), 2.75-2.68 (m, 1H), 2.39-2.30 (m, 1H), 2.13-2.02 (m, 2H), 1.66-1.45 (m, 2H), 1.02 (d, J=7.2 Hz, 3H), 0.78-0.65 (m, 1H). Analytical HPLC (Method A): RT=7.01 min, 98.4% purity; Factor XIa Ki=14 nM, Plasma Kallikrein Ki=930 nM.

Example 50

Preparation of (9R,13S)-13-{4-[5-chloro-2-(1,3-dimethyl-1H-pyrazol-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one Trifluoroacetate

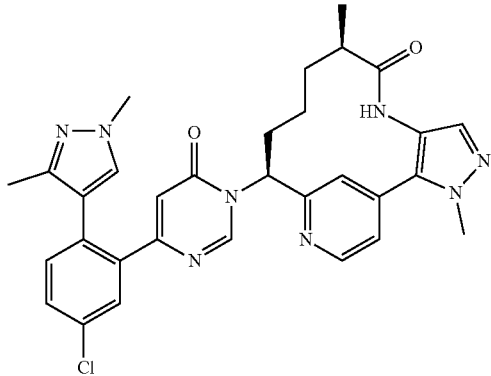

(9R,13S)-13-{4-[5-Chloro-2-(1,3-dimethyl-1H-pyrazol-4-yl)phenyl]-6-oxo-1,6-dihydropyrimidin-1-yl}-3,9-dimethyl-3,4,7,15-tetraazatricyclo[12.3.1.0$^{2,6}$]Octadeca-1(18),2(6),4,14,16-pentaen-8-one trifluoroacetate (11.3 mg, 49% yield) was prepared in a similar manner as the procedure described in Example 49, by replacing 1-methyl-4-(4,4,5,5-tetramethyl-1,3,2-dioxaborolan-2-yl)-1H-pyrazole with 1,3-dimethyl-4-(4,4,5,5-tetramethyl-1,3,2-dioxaborolan-2-yl)-1H-pyrazole (10.84 mg, 0.049 mmol). MS(ESI) m/z: 583.5 (M+H)$^+$. $^1$H NMR (400 MHz, CD$_3$OD) δ 8.95 (s, 1H), 8.73 (d, J=5.1 Hz, 1H), 7.73-7.69 (m, 2H), 7.55-7.47 (m, 4H), 7.33 (d, J=8.4 Hz, 1H), 6.24 (d, J=0.7 Hz, 1H), 5.97 (dd, J=12.7, 4.3 Hz, 1H), 4.05 (s, 3H), 3.81 (s, 3H), 2.76-2.65 (m, 1H), 2.39-2.28 (m, 1H), 2.13-1.97 (m, 2H), 1.90 (s, 3H), 1.66-1.42 (m, 2H), 1.01 (d, J=6.8 Hz, 3H), 0.80-0.63 (m, 1H). Analytical HPLC (Method A): RT=7.15 min, 99.6% purity; Factor XIa Ki=270 nM, Plasma Kallikrein Ki=5,200 nM.

Example 51

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-4,5,8-triazatricyclo[13.3.1.0$^{2,7}$]nonadeca-1(19),2(7),3,5,15,17-hexaen-9-one

51A. Preparation of 5-bromopyridazin-4-amine tert-Butyl N-(5-bromopyridazin-4-yl)carbamate (400 mg, 1.183 mmol) in DCM (15 mL) was added TFA (4.56 mL, 59.2 mmol). The reaction was stirred at rt overnight. Concentration gave 5-bromopyridazin-4-amine.trifluoroacetate as a dark brownish solid. MS(ESI) m/z: 174.2 (M+H)$^+$.

51B. Preparation of (10R,14S)-14-amino-10-methyl-4,5,8-triazatricyclo[13.3.1.0$^{2,7}$]nonadeca-1(19),2,4,6,15,17-hexaen-9-one (10R,14S)-14-Amino-10-methyl-4,5,8-triazatricyclo[13.3.1.0$^{2,7}$]nonadeca-1(19),2,4,6,15,17-hexaen-9-one was prepared in a similar manner as the procedure described in Intermediate 38, by replacing 2-bromopyridin-3-amine with 5-bromopyridazin-4-amine. MS(ESI) m/z: 297.5 (M+H)$^+$.

51C. Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-4,5,8-triazatricyclo[13.3.1.0$^{2,7}$]nonadeca-1(19),2(7),3,5,15,17-hexaen-9-one (10R,14S)-14-(4-{5-Chloro-2-[4-(trifluoromethyl)-1H-1,2,3-triazol-1-yl]phenyl}-6-oxo-1,6-dihydropyrimidin-1-yl)-10-methyl-4,5,8-triazatricyclo[13.3.1.0$^{2,7}$]nonadeca-1(19),2(7),3,5,15,17-hexaen-9-one trifluoroacetate (3.8 mg, 32.7% yield) was prepared in a similar manner as the procedure described in Example 56 by using (10R,14S)-14-amino-10-methyl-4,5,8-triazatricyclo[13.3.1.0$^{2,7}$]nonadeca-1(19),2,4,6,15,17-hexaen-9-one (4.5 mg, 0.015 mmol). $^1$H NMR (400 MHz, CD$_3$OD) δ 9.42 (s, 1H), 9.14 (s, 1H), 8.82-8.77 (m, 1H), 8.42 (s, 1H), 7.90-7.84 (m, 1H), 7.81 (s, 1H), 7.77-7.72 (m, 1H), 7.70-7.65 (m, 1H), 7.65-7.61 (m, 2H), 7.30-7.24 (m, 1H), 6.45 (d, J=0.7 Hz, 1H), 5.77 (dd, J=12.9, 4.3 Hz, 1H), 2.70-2.59 (m, 1H), 2.36-2.23 (m, 1H), 2.13-2.00 (m, 1H), 2.00-1.89 (m, 1H), 1.67-1.35 (m, 2H), 1.26-1.13 (m, 1H), 1.07 (d, J=6.8 Hz, 3H). MS(ESI) m/z: 621.0 (M+H)$^+$. Analytical HPLC (Method A): RT=8.24 min, purity=100%; Factor XIa Ki=5 nM, Plasma Kallikrein Ki=18 nM.

Example 52

Preparation of 1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-pyrazole-4-carboxylic Acid

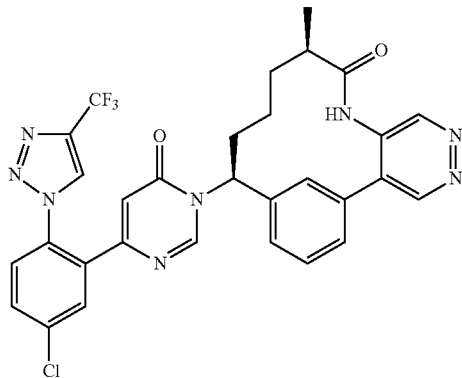 [SMILES: C[C@@H]1CCC[C@H](n2cnc(-c3cc(Cl)ccc3-n3cc(C(F)(F)F)nn3)cc2=O)c2cccc(c2)-c2cnncc2NC1=O]

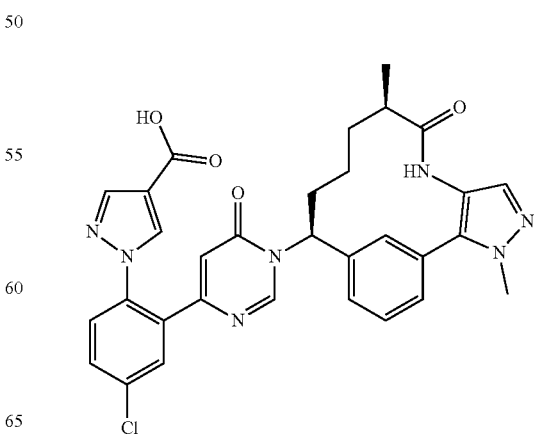

To a solution of ethyl 1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-pyrazole-4-carboxylate trifluoroacetate (7 mg, 0.011 mmol) in THF (56 μl) was added a solution of LiOH.H$_2$O (4.7 mg, 0.112 mmol) in water (56 μl). To the resulting cloudy mixture was added MeOH (1 drop). The reaction was stirred vigorously at rt for 3.5 h. The solution was acidified to pH 5 with 1.0 N HCl and then purified by reverse phase chromatography to give 1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-pyrazole-4-carboxylic acid trifluoroacetate (0.0024 g, 30% yield) as a white solid. MS(ESI) m/z: 599.1 (M+H)$^+$. $^1$H NMR (400 MHz, CD$_3$CN) δ 8.73-8.66 (m, 2H), 8.17 (s, 1H), 7.94 (s, 1H), 7.81 (d, J=2.2 Hz, 1H), 7.73-7.62 (m, 3H), 7.61-7.55 (m, 1H), 7.47-7.38 (m, 2H), 6.16 (d, J=0.9 Hz, 1H), 5.98 (dd, J=12.7, 3.9 Hz, 1H), 4.02 (s, 3H), 2.65 (m, 1H), 2.30-2.19 (m, 1H), 2.15-2.02 (m, 1H), 1.64-1.39 (m, 2H), 0.98 (d, J=6.8 Hz, 3H), 0.61 (m, 1H). Analytical HPLC (Method A): SunFire, RT=6.48 min, 99.3% purity; Factor XIa Ki=5 nM, Plasma Kallikrein Ki=2,400 nM.

Example 53

Preparation of (9R,13S)-13-[4-(2-bromo-5-chlorophenyl)-5-chloro-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one

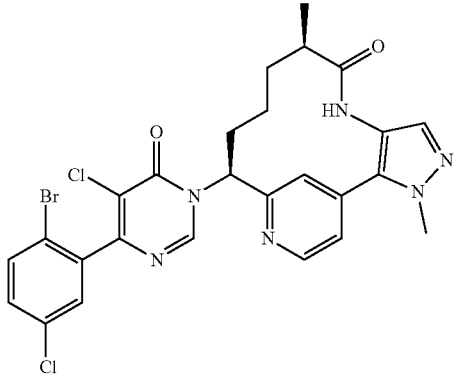 [SMILES: C[C@@H]1CCC[C@H](n2cnc(-c3cc(Cl)ccc3Br)c(Cl)c2=O)c2cc(ccn2)-c2c(cnn2C)NC1=O]

53A. Preparation of 6-(2-bromo-5-chlorophenyl)-5-chloropyrimidin-4-ol

To a suspension of 6-(2-bromo-5-chlorophenyl)pyrimidin-4-ol, prepared as described in Intermediate 44, (40 mg, 0.140 mmol) in MeCN (1401 μl) was added NCS (20.58 mg, 0.154 mmol). The reaction was heated at 60° C. for 4 h. The reaction mixture was concentrated and the crude residue was purified using normal phase chromatography to yield 6-(2-bromo-5-chlorophenyl)-5-chloropyrimidin-4-ol (42 mg, 94%) as a white solid. MS(ESI) m/z: 320.9 (M+H)$^+$.

53B. Preparation of (9R,13S)-13-[4-(2-bromo-5-chlorophenyl)-5-chloro-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one (9R,13S)-13-[4-(2-Bromo-5-chlorophenyl)-5-chloro-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one trifluoroacetate (8.3 mg, 41.1% yield) was prepared in a similar manner as the procedure described in Example 56, by using 6-(2-bromo-5-chlorophenyl)-5-chloropyrimidin-4-ol (8.6 mg, 0.027 mmol) and (9R,13S)-13-amino-3,9-dimethyl-3,4,7,15-tetraazatricyclo[12.3.1.0$^{2,6}$]octadeca-1(18),2(6),4,14,16-pentaen-8-one (8 mg, 0.027 mmol), prepared as described in Intermediate 32. MS(ESI) m/z: 603.0 (M+H)$^+$. $^1$H NMR (400 MHz, CD$_3$OD) δ 8.99 (s, 1H), 8.75 (d, J=5.1 Hz, 1H), 7.75 (s, 1H), 7.70 (d, J=8.6 Hz, 1H), 7.54 (dd, J=5.1, 1.5 Hz, 1H), 7.50 (s, 1H), 7.45-7.38 (m, 2H), 6.06 (dd, J=12.4, 4.1 Hz, 1H), 4.05 (s, 3H), 2.72 (td, J=6.7, 3.1 Hz, 1H), 2.45-2.31 (m, 1H), 2.19-2.03 (m, 2H), 1.70-1.43 (m, 2H), 1.02 (d, J=7.0 Hz, 3H), 0.73 (br. s., 1H). Analytical HPLC (Method A): RT=9.24 min, 100% purity; Factor XIa Ki=8 nM, Plasma Kallikrein Ki=1,200 nM.

Example 54

Preparation of (9R,13S)-13-{4-[3-chloro-2-fluoro-6-(1,3-thiazol-5-yl)phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one

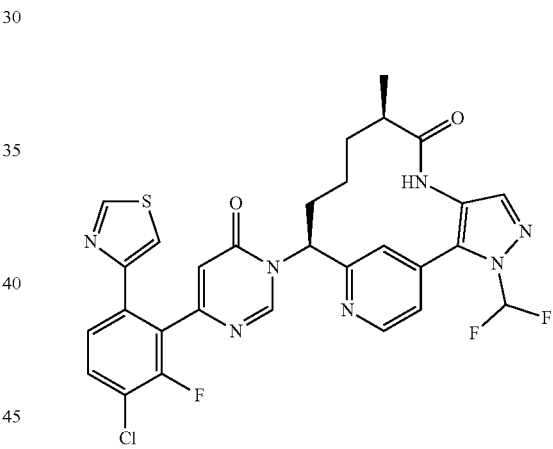

54A. Preparation of 4-(3-chloro-2-fluoro-6-iodophenyl)-6-methoxypyrimidine

4-Chloro-3-fluoro-2-(6-methoxypyrimidin-4-yl)aniline, prepared as described in Intermediate 10C (1 g, 3.94 mmol) in ACN (26.3 ml) was cooled to 0° C. and pTsOH.H$_2$O (1.875 g, 9.86 mmol) was added followed by addition of NaNO$_2$ (0.544 g, 7.88 mmol) and NaI (1.477 g, 9.86 mmol) in water (13.14 ml). After 1 h, the reaction was warmed to rt and stirred overnight. After this time, the reaction was partially concentrated to remove the ACN and NaHCO$_3$ was then added to neutralize the solution. The resulting solution was extracted with EtOAc. The combined organic layer was washed with sat Na$_2$S$_2$O$_3$ and brine, dried over MgSO$_4$, filtered, and concentrated to yield a solid, which was purified by normal phase chromatography to give 4-(3-chloro-2-fluoro-6-iodophenyl)-6-methoxypyrimidine (0.934 g, 65% yield). MS(ESI) m/z: 365.2 (M+H)$^+$.

54B. Preparation of 6-(3-chloro-2-fluoro-6-iodophenyl)pyrimidin-4-ol 6-(3-Chloro-2-fluoro-6-iodophenyl)pyrimidin-4-ol was prepared according to the procedures as described in Intermediate 4B for the synthesis of 6-(3-chloro-2,6-difluorophenyl)pyrimidin-4-ol, by replacing 4-(3-chloro-2,6-difluorophenyl)-6-methoxypyrimidine, prepared as described in Intermediate 4A, with 4-(3-chloro-2-fluoro-6-iodophenyl)-6-methoxypyrimidine. MS(ESI) m/z: 350.8 (M+H)$^+$.

54C. Preparation of (9R,13S)-13-[4-(3-chloro-2-fluoro-6-iodophenyl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one (9R,13S)-13-[4-(3-Chloro-2-fluoro-6-iodophenyl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one was prepared in a similar manner as the procedure described in Example 56, using 6-(3-chloro-2-fluoro-6-iodophenyl)pyrimidin-4-ol (62.7 mg, 0.179 mmol) and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one (60 mg, 0.179 mmol), prepared as described in Intermediate 30. MS(ESI) m/z: 667.1 (M+H)$^+$.

54D. Preparation of (9R,13S)-13-{4-[3-chloro-2-fluoro-6-(1,3-thiazol-5-yl)phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one To a microwave tube was added (9R,13S)-13-[4-(3-chloro-2-fluoro-6-iodophenyl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one (20 mg, 0.030 mmol), 5-(4,4,5,5-tetramethyl-1,3,2-dioxaborolan-2-yl)thiazole (9.47 mg, 0.045 mmol), K$_3$PO$_4$ (29.9 µl, 0.090 mmol) and THF (299 µl). The solution was bubbled through with Ar for several min then (DtBPF)PdCl$_2$ (0.974 mg, 1.495 µmol) was added. The reaction was sealed and heated at 90° C. overnight. The solution was cooled to rt and Ar was again bubbled through the solution for several minutes and additional 5-(4,4,5,5-tetramethyl-1,3,2-dioxaborolan-2-yl)thiazole (9.47 mg, 0.045 mmol) and Pd(PPh$_3$)$_4$ (3.46 mg, 2.99 µmol) were added. The solution was heated in a microwave at 120° C. for 30 min. The solution was then filtered and the residue was purified by reverse phase chromatography to give (9R,13S)-13-{4-[3-chloro-2-fluoro-6-(1,3-thiazol-5-yl)phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one (0.67 mg, 2.9%). $^1$H NMR (400 MHz, CD$_3$OD) δ 9.02 (s, 1H), 8.95 (s, 1H), 8.77 (d, J=5.1 Hz, 1H), 7.80 (s, 1H), 7.74 (s, 1H), 7.72-7.60 (m, 3H), 7.59-7.50 (m, 2H), 7.46 (dd, J=8.4, 1.3 Hz, 1H), 6.55 (s, 1H), 6.05 (dd, J=12.9, 4.3 Hz, 1H), 2.71 (dt, J=6.6, 3.3 Hz, 1H), 2.40-2.26 (m, 1H), 2.12-1.97 (m, 2H), 1.70-1.41 (m, 2H), 1.00 (d, J=7.0 Hz, 3H), 0.66 (br. s., 1H). MS(ESI) m/z: 625.9 (M+H)$^+$. Analytical HPLC (Method A): RT=8.51 min, purity=96.4%; Factor XIa Ki=1.7 nM, Plasma Kallikrein Ki=230 nM.

Example 55

Preparation of (9R,13S)-13-{4-[3-chloro-2-fluoro-6-(1H-1,2,3-triazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one Trifluoroacetate

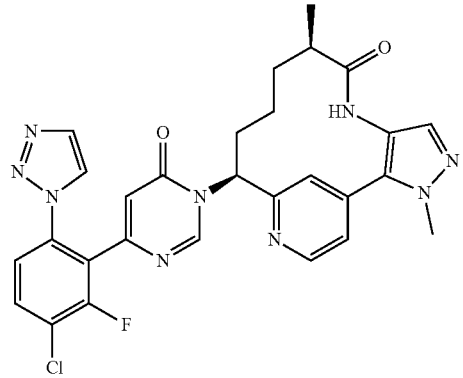 [SMILES: C[C@@H]1CCC[C@H](n2cnc(-c3c(-n4ccnn4)ccc(Cl)c3F)cc2=O)c2cc(ccn2)-c2c(cnn2C)NC1=O]

55A. Preparation of 1-methyl-4-nitro-1H-pyrazole

To a solution of 4-nitro-1H-pyrazole (2.5 g, 22.11 mmol) in THF (50 mL) was added NaH (0.973 g, 24.32 mmol) and the mixture was stirred at rt for 5 min. To this suspension was added MeI (1.382 mL, 22.11 mmol) and the resulting solution was stirred at rt overnight. The reaction mixture was then diluted with EtOAc and washed with brine. The organic layer was concentrated, followed by purification using normal phase chromatography to yield 1-methyl-4-nitro-1H-pyrazole as a white solid (1.9 g, 80%). $^1$H NMR (400 MHz, CDCl$_3$) δ ppm 8.12 (s, 1H), 8.06 (s, 1H), 3.97 (s, 3H).

55B. Preparation of (S)-tert-butyl (1-(4-(1-methyl-4-nitro-1H-pyrazol-5-yl)pyridin-2-yl)but-3-en-1-yl)carbamate To a pressure vial was added (S)-tert-butyl 1-(4-chloropyridin-2-yl)but-3-enylcarbamate, prepared as described in Intermediate 23, (3.0 g, 10.61 mmol), 1-methyl-4-nitro-1H-pyrazole (1.348 g, 10.61 mmol), di(adamant-1-yl)(butyl)phosphine (1.141 g, 3.18 mmol), pivalic acid (0.369 mL, 3.18 mmol) and K$_2$CO$_3$ (4.40 g, 31.8 mmol). To the above mixture was added DMF (21 mL) and the vial was purged and evacuated (3×) with Ar. To this mixture was added Pd(OAc)$_2$ (0.476 g, 2.122 mmol). The vial was sealed and heated at 120° C. overnight. The reaction mixture was cooled to rt, filtered and partitioned between 10% aqueous LiCl (15 mL) and EtOAc (30 mL). The aqueous layer was extracted with EtOAc (2×20 mL) and the combined organic layers were washed with brine (15 mL), dried over MgSO$_4$, filtered and concentrated. The crude product was then purified using normal phase chromatography to yield (S)-tert-butyl (1-(4-(1-methyl-4-nitro-1H-pyrazol-5-yl)pyridin-2-yl)but-3-en-1-yl)carbamate (1.2 g, 29% yield) as a brown oil. MS(ESI) m/z: 374.4 (M+H)$^+$.

55C. Preparation of (S)-tert-butyl (1-(4-(4-amino-1-methyl-1H-pyrazol-5-yl)pyridin-2-yl)but-3-en-1-yl)carbamate A solution of (S)-tert-butyl (1-(4-(1-methyl-4-nitro-1H-pyrazol-5-yl)pyridin-2-yl)but-3-en-1-yl)carbamate (1.2 g, 3.21 mmol) in MeOH (10 mL) and CH$_3$COOH (1 ml) was heated to 60° C. To the above clear solution was then slowly added Zn (0.420 g, 6.43 mmol) and the solution was allowed to stir at 60° C. for an additional 15 min. The reaction mixture was then filtered through CELITE® and concentrated to yield crude product. The crude product was then purified using normal phase chromatography to yield (S)-tert-butyl (1-(4-(4-amino-1-methyl-1H-pyrazol-5-yl)pyridin-2-yl)but-3-en-1-yl)carbamate (0.88 g, 76% yield) as a pale brown oil. MS(ESI) m/z: 344.4 (M+H)$^+$.

55D. Preparation of Tert-Butyl ((S)-1-(4-(1-methyl-4-((R)-2-methylbut-3-enamido)-1H-pyrazol-5-yl)pyridin-2-yl)but-3-en-1-yl)carbamate To a solution of (R)-4-benzyl-3-((R)-2-methylbut-3-enoyl)oxazolidin-2-one (385 mg, 3.84 mmol), prepared as described in Intermediate 2A, (S)-tert-butyl (1-(4-(4-amino-1-methyl-1H-pyrazol-5-yl)pyridin-2-yl)but-3-en-1-yl)carbamate (880 mg, 2.56 mmol) and pyridine (0.620 mL, 7.69 mmol) in EtOAc (40 mL) at −10° C. under Ar was added T3P® (50% wt in EtOAc) (3.05 mL, 5.12 mmol) dropwise. The reaction mixture was stirred at −10° C. and was allowed to gradually warm up to rt. The reaction mixture was stirred at rt for 2 h, then diluted with EtOAc and washed with sat aq NaHCO$_3$ and brine. The organic layers were pooled together, dried over MgSO$_4$, filtered and concentrated. The crude product was then purified using normal phase chromatography to yield tert-butyl ((S)-1-(4-(1-methyl-4-((R)-2-methylbut-3-enamido)-1H-pyrazol-5-yl)pyridin-2-yl)but-3-en-1-yl)carbamate (0.6 g, 52% yield) as a yellow oil. MS(ESI) m/z: 426.5 (M+H)$^+$.

55E. Preparation of Tert-Butyl N-[(9R,10E,13S)-3,9-dimethyl-8-oxo-3,4,7,15-tetraazatricyclo[12.3.1.0$^{2,6}$]octadeca-1(18),2(6),4,10,14,16-hexaen-13-yl]carbamate A solution of tert-butyl ((S)-1-(4-(1-methyl-4-((R)-2-methylbut-3-enamido)-1H-pyrazol-5-yl)pyridin-2-yl)but-3-en-1-yl)carbamate (600 mg, 1.410 mmol) in DCE (18 mL) was purged with Ar (3×). Second Generation Grubbs Catalyst (480 mg, 0.564 mmol) was added and Ar was again bubbled into the reaction mixture and evacuated (3×). The reaction mixture was then heated at 120° C. in a microwave vial for 30 min. The reaction mixture was then concentrated and the crude residue was purified using normal phase chromatography to yield tert-butyl N-[(9R,10E,13S)-3,9-dimethyl-8-oxo-3,4,7,15-tetraazatricyclo[12.3.1.0$^{2,6}$]octadeca-1(18),2(6),4,10,14,16-hexaen-13-yl]carbamate (118 mg, 20% yield) as a brown oil. MS(ESI) m/z: 398.5 (M+H)$^1$.

55F. Preparation of Tert-Butyl N-[(9R,13S)-3,9-dimethyl-8-oxo-3,4,7,15-tetraazatricyclo[12.3.1.0$^{2,6}$]octadeca-1(18),2(6),4,14,16-pentaen-13-yl]carbamate To a degassed solution of tert-butyl N-[(9R,10E,13S)-3,9-dimethyl-8-oxo-3,4,7,15-tetraazatricyclo[12.3.1.0$^{2,6}$]octadeca-1(18),2(6),4,10,14,16-hexaen-13-yl]carbamate (118 mg, 0.297 mmol) in EtOH (12 mL) was added Pd/C (31.6 mg, 0.030 mmol) and the reaction mixture was then stirred under H$_2$ at 55 psi for 5 h. The reaction mixture was then filtered though CELITE® and concentrated to yield tert-butyl N-[(9R,13S)-3,9-dimethyl-8-oxo-3,4,7,15-tetraazatricyclo[12.3.1.0$^{2,6}$]octadeca-1(18),2(6),4,14,16-pentaen-13-yl]carbamate. (92 mg, 72%) as a brown oil. MS(ESI) m/z: 400.4 (M+H)$^+$.

55G. Preparation of (9R,13S)-13-amino-3,9-dimethyl-3,4,7,15-tetraazatricyclo[12.3.1.0$^{2,6}$]octadeca-1(18),2(6),4,14,16-pentaen-8-one, dihydrochloride To a solution of tert-butyl N-[(9R,13S)-3,9-dimethyl-8-oxo-3,4,7,15-tetraazatricyclo[12.3.1.0$^{2,6}$]octadeca-1(18),2(6),4,14,16-pentaen-13-yl]carbamate (92 mg, 0.230 mmol) in MeOH (3 mL) was added 4 M HCl in dioxane (3 mL, 12 mmol) and the reaction was stirred at rt for 1.5 h. The reaction mixture was concentrated to yield (9R,13S)-13-amino-3,9-dimethyl-3,4,7,15-tetraazatricyclo[12.3.1.0$^{2,6}$]octadeca-1(18),2(6),4,14,16-pentaen-8-one dihydrochloride (86 mg) as yellow solid. MS(ESI) m/z: 300.4 (M+H)$^+$.

55H. Preparation of (9R,13S)-13-{4-[3-chloro-2-fluoro-6-(1H-1,2,3-triazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (9R,13S)-13-{4-[3-Chloro-2-fluoro-6-(1H-1,2,3-triazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate was prepared according to the procedure described in Example 56, by using (9R,13S)-13-amino-3,9-dimethyl-3,4,7,15-tetraazatricyclo[12.3.1.0$^{2,6}$]octadeca-1(18),2(6),4,14,16-pentaen-8-one dihydrochloride and 6-(3-chloro-2-fluoro-6-(1H-1,2,3-triazol-1-yl)phenyl)pyrimidin-4-ol, prepared as described in Intermediate 7. MS(ESI) m/z: 574.3 (M+H)$^1$. $^1$H NMR (400 MHz, CD$_3$OD) δ 8.82 (s, 1H), 8.73 (d, J=5.3 Hz, 1H), 8.19 (d, J=1.1 Hz, 1H), 7.85 (dd, J=8.6, 7.7 Hz, 1H), 7.78 (d, J=1.1 Hz, 1H), 7.70 (s, 1H), 7.56-7.50 (m, 2H), 7.49 (s, 1H), 6.53 (s, 1H), 5.98 (dd, J=12.8, 4.2 Hz, 1H), 4.05 (s, 3H), 2.70 (td, J=6.7, 3.2 Hz, 1H), 2.27 (ddt, J=12.7, 8.5, 4.3 Hz, 1H), 2.14-1.92 (m, 2H), 1.66-1.53 (m, 1H), 1.46 (ddd, J=15.1, 10.0, 5.3 Hz, 1H), 1.00 (d, J=7.0 Hz, 3H), 0.68 (m, 1H). Analytical HPLC (method A): RT=6.41 min, purity=93%; Factor XIa Ki=1.0 nM, Plasma Kallikrein Ki=24 nM.

Example 56

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one Trifluoroacetate

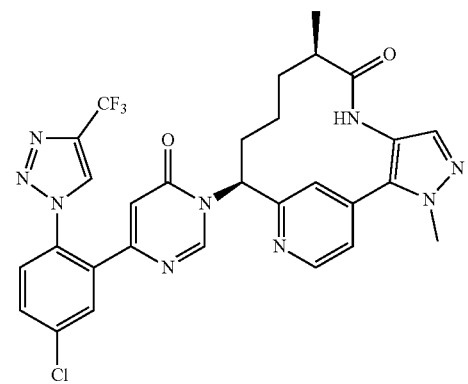 [SMILES: C[C@@H]1CCC[C@H](n2cnc(-c3cc(Cl)ccc3-n3cc(C(F)(F)F)nn3)cc2=O)c2cc(ccn2)-c2c(cnn2C)NC1=O]

To a scintillation vial containing 6-{5-chloro-2-[4-(trifluoromethyl)-1H-1,2,3-triazol-1-yl]phenyl}pyrimidin-4-ol (22.8 mg, 0.067 mmol), prepared as described in Intermediate 15, HATU (33.0 mg, 0.087 mmol) in anhydrous ACN (0.5 mL) was added DBU (15 mL, 0.100 mmol). After 30 min, a solution of (9R,13S)-13-amino-3,9-dimethyl-3,4,7,15-tetraazatricyclo[12.3.1.0$^{2,6}$]octadeca-1(18),2(6),4,14,16-pentaen-8-one (20 mg, 0.067 mmol), prepared as described in Intermediate 32, in 0.5 ml CH$_3$CN and DMF (0.1 ml) was added. The resulting solution was stirred at rt for 2 h then purified by reverse phase chromatography to give (9R,13S)-13-(4-{5-chloro-2-[4-(trifluoromethyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate (26.98 mg, 53.1% yield) as a white solid. MS(ESI) m/z: 624.3 (M+H)$^+$. $^1$H NMR (400 MHz, CD$_3$OD) δ 8.81 (d, J=0.7 Hz, 1H), 8.75 (s, 1H), 8.70 (d, J=5.3 Hz, 1H), 7.89 (d, J=2.4 Hz, 1H), 7.77-7.72 (m, 1H), 7.72-7.66 (m, 2H), 7.53 (dd, J=5.1, 1.5 Hz, 1H), 7.49 (s, 1H), 6.43 (s, 1H), 6.02-5.93 (m, 1H), 4.04 (s, 3H), 2.70 (td, J=6.7, 3.3 Hz, 1H), 2.27 (tt, J=12.7, 4.4 Hz, 1H), 2.12-1.94 (m, 2H), 1.66-1.52 (m, 1H), 1.45 (ddd, J=15.0, 9.8, 5.0 Hz, 1H), 1.00 (d, J=7.0 Hz, 3H), 0.69 (br. s., 1H). $^{19}$F NMR (376 MHz, CD$_3$OD) d −62.54 (s), −77.44 (s). Analytical HPLC (Method A): RT=11.02 min, purity=96.7%; Factor XIa Ki=1.4 nM, Plasma Kallikrein Ki=24 nM.

Example 57

Preparation of (9R,13S)-13-{4-[5-chloro-2-(4-chloro-1H-1,2,3-triazol-1-yl)phenyl]-6-oxo-1,6-dihydropyrimidin-1-yl}-9-ethyl-3-methyl-3,4,7,15-tetraazatricyclo[12.3.1.0$^{2,6}$]octadeca-1(18),2(6),4,14,16-pentaen-8-one Trifluoroacetate

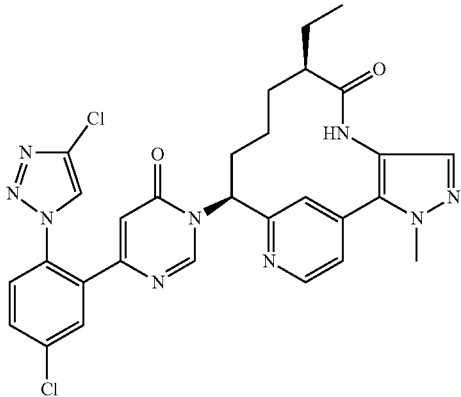 [SMILES: CC[C@@H]1CCC[C@H](n2cnc(-c3cc(Cl)ccc3-n3cc(Cl)nn3)cc2=O)c2cc(ccn2)-c2c(cnn2C)NC1=O]

57A. Preparation of 2-ethylbut-3-enoic Acid

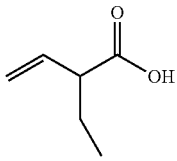

To a dry flask was added 2 M DIA in THF (8.28 mL, 58.1 mmol) and THF (50 mL). The reaction was cooled to −78° C. and 1.6 M nBuLi in hexanes (23.23 mL, 58.1 mmol) was added dropwise. The reaction was stirred at −78° C. for 30 min. But-3-enoic acid (2.00 g, 23.23 mmol) was added to the reaction and the reaction was stirred at −78° C. for 30 min. After this time, EtI (5.44 g, 34.8 mmol) was added. The reaction was slowly warmed to rt and stirred at rt overnight. The reaction was then quenched with sat NH$_4$Cl (3 mL). The pH of the reaction was adjusted to <4 using 1 N HCl. The reaction was then extracted with EtOAc (2×30 mL). The combined organic layer was washed with water (20 mL) and brine (20 mL), dried over MgSO$_4$, filtered and concentrated. The residue was purified using ISCO system (0-60% EtOAc/Hex gradient) to give 2-ethylbut-3-enoic acid (450 mg, 2.37 mmol, 10.2% yield) as a clear liquid. $^1$H NMR (400 MHz, CDCl$_3$) δ 5.89-5.75 (m, 1H), 5.22-5.18 (m, 1H), 5.16 (s, 1H), 2.95 (q, J=7.5 Hz, 1H), 1.83 (dt, J=13.9, 7.2 Hz, 1H), 1.61 (dt, J=13.6, 7.4 Hz, 1H), 0.95 (t, J=7.4 Hz, 3H).

57B. Preparation of Tert-Butyl ((1S)-1-(4-(4-(2-ethylbut-3-enamido)-1-methyl-1H-pyrazol-5-yl)pyridin-2-yl)but-3-en-1-yl)carbamate

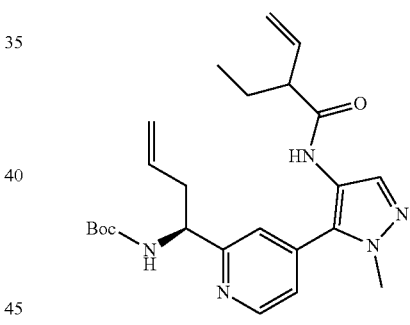

To a RBF was added (S)-tert-butyl (1-(4-(4-amino-1-methyl-1H-pyrazol-5-yl)pyridin-2-yl)but-3-en-1-yl)carbamate, prepared as described in Intermediate 32C, (1000 mg, 2.91 mmol), EtOAc (20 mL), 2-ethylbut-3-enoic acid (332 mg, 2.91 mmol), and pyridine (0.71 mL, 8.74 mmol). The solution was cooled in a brine/ice bath and 50% T3P® (2.60 mL, 4.37 mmol) was added. The reaction was stirred at 0° C. for 10 min and then at rt for 60 min. The reaction was diluted with EtOAc (30 mL) and washed with sat NaHCO$_3$ (20 mL), water (30 mL) and brine (30 mL). The organic layer was separated, dried over MgSO$_4$, filtered and concentrated. The residue was purified using ISCO system (0-100% EtOAc/Hex gradient) to give tert-butyl ((1S)-1-(4-(4-(2-ethylbut-3-enamido)-1-methyl-1H-pyrazol-5-yl)pyridin-2-yl)but-3-en-1-yl)carbamate (1.10 g, 2.50 mmol, 86% yield) as a diastereomer mixture as a yellow solid. MS(ESI) m/z: 440.0 (M+H)$^+$.

57C. Preparation of Tert-Butyl N-[(9R,10E,13S)-9-ethyl-3-methyl-8-oxo-3,4,7,15-tetraazatricyclo[12.3.1.0²,⁶]octadeca-1(18),2(6),4,10,14,16-hexaen-13-yl]carbamate

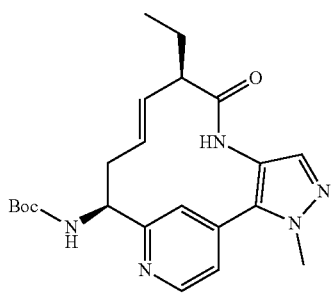 [SMILES: CC[C@@H]1/C=C/C[C@H](NC(=O)OC(C)(C)C)c2cc(ccn2)-c2c(cnn2C)NC1=O]

To a microwave vial was added tert-butyl ((1S)-1-(4-(4-(2-ethylbut-3-enamido)-1-methyl-1H-pyrazol-5-yl)pyridin-2-yl)but-3-en-1-yl)carbamate (500 mg, 1.138 mmol) and DCE (12 mL). The reaction was purged with Ar for 1 min. Then Second Generation Grubbs Catalyst (386 mg, 0.455 mmol) was added to the solution. The reaction was sealed and heated in microwave at 120° C. for 30 min. The reaction was concentrated and the residue was purified using ISCO system (0-10% MeOH/CH$_2$Cl$_2$ gradient). Two products were isolated. The fast eluting product was tert-butyl N-[(9R,10E)-9-ethyl-3-methyl-8-oxo-3,4,7,15-tetraazatricyclo[12.3.1.0²,⁶]octadeca-1(18),2(6),4,10,14,16-hexaen-13-yl]carbamate (75 mg, 0.182 mmol, 16.0% yield), MS(ESI) m/z: 412.2 (M+H)⁺ which was carried forward and the slow eluting product was the other diastereomer, tert-butyl N-[(9S,10E)-9-ethyl-3-methyl-8-oxo-3,4,7,15-tetraazatricyclo[12.3.1.0²,⁶]octadeca-1(18),2(6),4,10,14,16-hexaen-13-yl]carbamate (75 mg, 0.182 mmol, 16.0% yield), MS(ESI) m/z: 412.2 (M+H)⁺.

57D. Preparation of Tert-Butyl N-[(9R,13S)-9-ethyl-3-methyl-8-oxo-3,4,7,15-tetraazatricyclo[12.3.1.0²,⁶]octadeca-1(18),2(6),4,14,16-pentaen-13-yl]carbamate

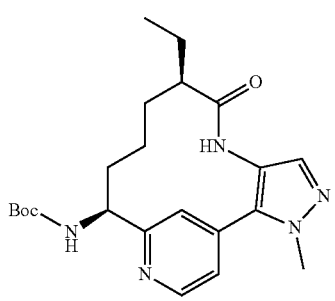 [SMILES: CC[C@@H]1CCC[C@H](NC(=O)OC(C)(C)C)c2cc(ccn2)-c2c(cnn2C)NC1=O]

To a 3-neck RBF was added tert-butyl N-[(9R,10E)-9-ethyl-3-methyl-8-oxo-3,4,7,15-tetraazatricyclo[12.3.1.0²,⁶]octadeca-1(18),2(6),4,10,14,16-hexaen-13-yl]carbamate (115 mg, 0.279 mmol), EtOH (10 mL) and PtO$_2$ (31.7 mg, 0.140 mmol). The reaction was stirred under a H$_2$ atmosphere (balloon pressure) for 1 h. The reaction was carefully filtered through CELITE® and concentrated. The residue was purified using ISCO system (0-10% MeOH/CH$_2$Cl$_2$ gradient) to give tert-butyl N-[(9R,13S)-9-ethyl-3-methyl-8-oxo-3,4,7,15-tetraazatricyclo[12.3.1.0²,⁶]octadeca-1(18),2(6),4,14,16-pentaen-13-yl]carbamate (75 mg, 0.181 mmol, 64.9% yield) as a light brown solid. MS(ESI) m/z: 414.2 (M+H)⁺.

57E. Preparation of (9R,13S)-13-amino-9-ethyl-3-methyl-3,4,7,15-tetraazatricyclo[12.3.1.0²,⁶]octadeca-1(18),2(6),4,14,16-pentaen-8-one

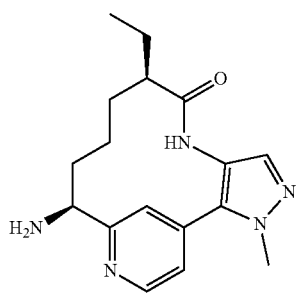 [SMILES: CC[C@@H]1CCC[C@H](N)c2cc(ccn2)-c2c(cnn2C)NC1=O]

To a RBF was added tert-butyl N-[(9R,13)-9-ethyl-3-methyl-8-oxo-3,4,7,15-tetraazatricyclo[12.3.1.0²,⁶]Octadeca-1(18),2(6),4,14,16-pentaen-13-yl]carbamate (75 mg, 0.181 mmol), dioxane (3 mL), 4 N HCl (18.14 mmol) and MeOH (0.5 mL). The reaction was stirred at rt for 5 min. The reaction was concentrated and the residue was purified using reverse phase preparative HPLC to give (9R,13S)-13-amino-9-ethyl-3-methyl-3,4,7,15-tetraazatricyclo[12.3.1.0²,⁶]octadeca-1(18),2(6),4,14,16-pentaen-8-one, trihydrochloride. The product was dissolved in MeOH (1 mL) to give a clear, brown solution. The solution was added to a pre-rinsed AGILENT® StratoSpheres SPE PL-HCO$_3$ MP Resin cartridge. Gravity filtration, eluting with MeOH, gave a clear, slightly brown filtrate. Concentration provided (9R,13S)-13-amino-9-ethyl-3-methyl-3,4,7,15-tetraazatricyclo[12.3.1.0²,⁶]octadeca-1(18),2(6),4,14,16-pentaen-8-one (75 mg, 0.177 mmol, 98% yield) as a beige solid. MS(ESI) m/z: 314.2 (M+H)⁺.

57F. Preparation of (9R,13S)-13-{4-[5-chloro-2-(4-chloro-1H-1,2,3-triazol-1-yl)phenyl]-6-oxo-1,6-dihydropyrimidin-1-yl}-9-ethyl-3-methyl-3,4,7,15-tetraazatricyclo[12.3.1.0²,⁶]octadeca-1(18),2(6),4,14,16-pentaen-8-one Trifluoroacetate

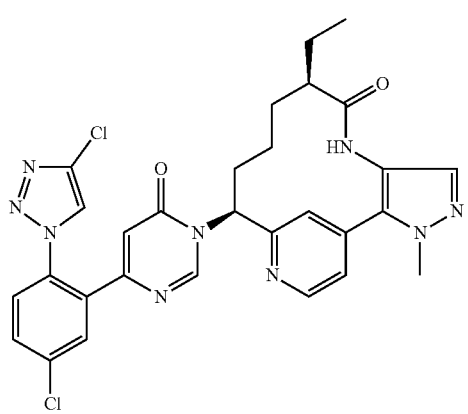 [SMILES: CC[C@@H]1CCC[C@H](n2cnc(-c3cc(Cl)ccc3-n3cc(Cl)nn3)cc2=O)c2cc(ccn2)-c2c(cnn2C)NC1=O]

(9R,13S)-13-{4-[5-Chloro-2-(4-chloro-1H-1,2,3-triazol-1-yl)phenyl]-6-oxo-1,6-dihydropyrimidin-1-yl}-9-ethyl-3-methyl-3,4,7,15-tetraazatricyclo[12.3.1.0²,⁶]octadeca-1(18),2(6),4,14,16-pentaen-8-one trifluoroacetate (5 mg, 6.82 μmol, 26.3% yield) was prepared in a similar manner as the procedure described in Example 56 by using 6-(5-chloro-2-(4-chloro-1H-1,2,3-triazol-1-yl)phenyl)pyrimidin-4-ol (8 mg, 0.026 mmol), prepared as described in Intermediate 9, and (9R)-13-amino-9-ethyl-3-methyl-3,4,7,15-tetraazatricyclo[12.3.1.0²,⁶]octadeca-1(18),2(6),4,14,16-pentaen-8-one (8 mg, 0.026 mmol). $^1$H NMR (400 MHz, CD$_3$OD) δ 8.87 (s, 1H), 8.72 (d, J=5.1 Hz, 1H), 7.89 (s, 1H), 7.76 (d, J=2.4 Hz, 1H), 7.64 (dd, J=8.5, 2.3 Hz, 1H), 7.59 (s, 1H), 7.52 (d, J=8.6 Hz, 1H), 7.46 (s, 1H), 7.36 (dd, J=5.1, 1.5 Hz, 1H), 6.37 (s, 1H), 6.06 (dd, J=12.5, 4.6 Hz, 1H), 4.03 (s, 3H), 2.46-2.36 (m, 1H), 2.26-2.12 (m, 1H), 2.03-1.92 (m, 2H), 1.69-1.56 (m, 2H), 1.45 (d, J=4.8 Hz, 1H), 1.32-1.20 (m, 1H), 0.86 (t, J=7.4 Hz, 3H), 0.69-0.57 (m, 1H); MS(ESI) m/z: 604.2 (M+H)⁺. Analytical HPLC (Method A): RT=7.23 min, purity=97.0%; Factor XIa Ki=0.36 nM, Plasma Kallikrein Ki=37 nM.

Example 58

Preparation of (9R,13S)-13-{4-[5-chloro-2-(4-chloro-1H-1,2,3-triazol-1-yl)phenyl]-6-oxo-1,6-dihydropyrimidin-1-yl}-3-methyl-9-(propan-2-yl)-3,4,7,15-tetraazatricyclo[12.3.1.0²,⁶]octadeca-1(18),2(6),4,14,16-pentaen-8-one Trifluoroacetate

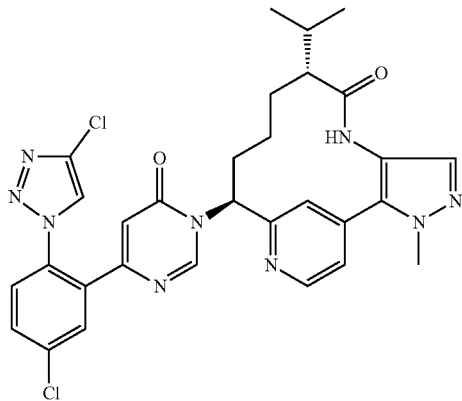 [SMILES: CC(C)[C@H]1CCC[C@H](n2cnc(-c3cc(Cl)ccc3-n3cc(Cl)nn3)cc2=O)c2cc(ccn2)-c2c(cnn2C)NC1=O]

58A. Preparation of 2-isopropylbut-3-enoic Acid

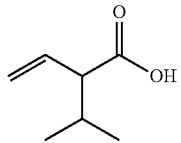

To a flame-dry RBF was added 2 M DIA in THF (3.64 ml, 25.6 mmol) and THF (58.1 ml). The reaction was cooled to −78° C. and 1.6 M nBuLi in hexane (15.97 ml, 25.6 mmol) was added. The reaction was stirred at −78° C. for 30 min. But-3-enoic acid (0.990 ml, 11.62 mmol) was added and the reaction was stirred for additional 30 min. Then at −78° C., iPrI (1.74 ml, 17.42 mmol) was added and the reaction was slowly warmed to rt over 2 h and then stirred at rt overnight. The reaction was quenched with sat NH$_4$Cl (15 ml). The pH of the solution was adjusted to <4 using 1 N HCl. The reaction was extracted with EtOAc (3×30 mL). The combined EtOAc layer was washed with brine (40 mL), dried over MgSO$_4$, filtered and concentrated. The residue was purified using ISCO system (0-50% EtOAc/Hex gradient) to give 2-isopropylbut-3-enoic acid (800 mg, 6.24 mmol, 53.7% yield) as a clear liquid. $^1$H NMR (400 MHz, CDCl$_3$) δ 5.98-5.65 (m, 1H), 5.33-5.05 (m, 2H), 2.73 (t, J=8.8 Hz, 1H), 2.08-1.95 (m, 1H), 1.09-0.74 (m, 6H).

58B. Preparation of Tert-Butyl ((1S-[1-(4-{1-methyl-4-[2-(propan-2-yl)but-3-enamido]-1H-pyrazol-5-yl}pyridin-2-yl)but-3-en-1-yl]carbamate

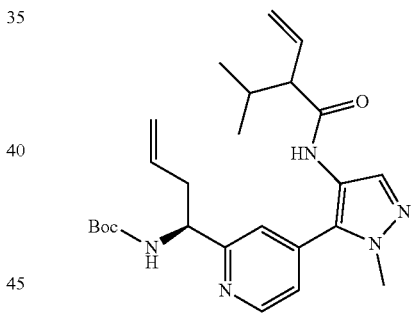

To a RBF was added (S)-tert-butyl (1-(4-(4-amino-1-methyl-1H-pyrazol-5-yl)pyridin-2-yl)but-3-en-1-yl)carbamate, prepared as described in Intermediate 32C, (765 mg, 2.228 mmol), EtOAc (20 mL), 2-isopropylbut-3-enoic acid (286 mg, 2.228 mmol), and pyridine (0.540 mL, 6.68 mmol). The solution was cooled in a brine/ice bath and 50% T3P® (1.989 mL, 3.34 mmol) was added. The reaction was stirred at 0° C. for 10 min and then at rt for 60 min. Reaction was diluted with EtOAc (30 mL) and washed with sat NaHCO$_3$(20 mL), water (30 mL) and brine (30 mL). The organic layer was separated, dried over MgSO$_4$, filtered and concentrated. The residue was purified using ISCO system (0-100% EtOAc/Hex gradient) to give tert-butyl ((1S)-1-(4-(4-(2-isopropylbut-3-enamido)-1-methyl-1H-pyrazol-5-yl)pyridin-2-yl)but-3-en-1-yl)carbamate (850 mg, 1.874 mmol, 84% yield) as a diastereomer mixture as a yellow solid. MS(ESI) m/z: 454.2 (M+H)⁺.

58C1 and 58C2. Preparation of Tert-Butyl N-[(9S,10E,13S)-3-methyl-8-oxo-9-(propan-2-yl)-3,4,7,15-tetraazatricyclo[12.3.1.0$^{2,6}$]octadeca-1(18),2(6),4,10,14,16-hexaen-13-yl]carbamate, and tert-butyl N-[(9R,10E,13S)-3-methyl-8-oxo-9-(propan-2-yl)-3,4,7,15 tetraazatricyclo[12.3.1.0$^{2,6}$]octadeca-1(18),2(6),4,10,14,16-hexaen-13-yl]carbamate

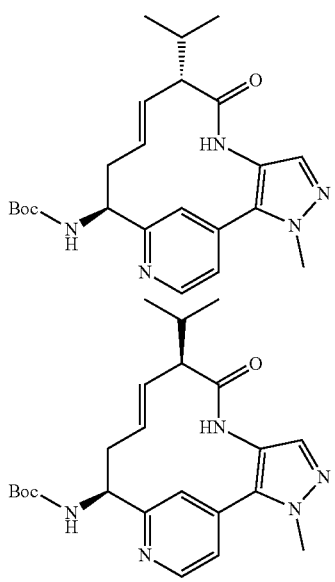

To a microwave vial was added tert-butyl ((1S)-1-(4-(4-(2-isopropylbut-3-enamido)-1-methyl-H-pyrazol-5-yl)pyridin-2-yl)but-3-en-1-yl)carbamate (250 mg, 0.551 mmol) and DCE (15 mL). The reaction was purged with Ar for 1 min. Then Second Generation Grubbs Catalyst (187 mg, 0.220 mmol) was added. The reaction was sealed and heated at microwave at 120° C. for 60 min. The reaction was then concentrated and the residue was purified using reverse phase preparative HPLC to give 58C$_1$, tert-butyl N-[(9S,10E,13S)-3-methyl-8-oxo-9-(propan-2-yl)-3,4,7,15-tetraazatricyclo[12.3.1.0$^{2,6}$]Octadeca-1(18),2(6),4,10,14,16-hexaen-13-yl]carbamate trifluoroacetate (50 mg, 0.093 mmol, 16.8% yield), (ESI) m/z: 426.2 (M+H)$^+$, which has a shorter retention time and 58C2, tert-butyl N-[(9R,10E,13S)-3-methyl-8-oxo-9-(propan-2-yl)-3,4,7,15-tetraazatricyclo[12.3.1.0$^{2,6}$]octadeca-1(18),2(6),4,10,14,16-hexaen-13-yl]carbamate trifluoroacetate (50 mg, 0.093 mmol, 16.8% yield), MS(ESI) m/z: 426.2 (M+H)$^+$ which had a longer retention time.

58D. Preparation of Tert-Butyl N-[(9R,13S)-3-methyl-8-oxo-9-(propan-2-yl)-3,4,7,15-tetraazatricyclo[12.3.1.0$^{2,6}$]octadeca-1(18),2(6),4,14,16-pentaen-13-yl]carbamate

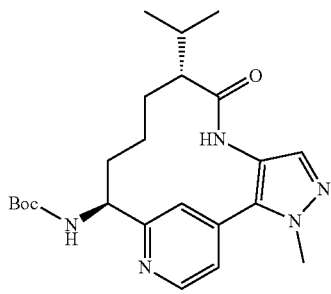 [SMILES: CC(C)[C@H]1CCC[C@H](NC(=O)OC(C)(C)C)c2cc(ccn2)-c2c(cnn2C)NC1=O]

To a 3-neck RBF was added tert-butyl N-[(9S,10E,13S)-3-methyl-8-oxo-9-(propan-2-yl)-3,4,7,15-tetraazatricyclo[12.3.1.0$^{2,6}$]octadeca-1(18),2(6),4,10,14,16-hexaen-13-yl]carbamate trifluoroacetate (20 mg, 0.037 mmol), EtOH (3 mL) and PtO$_2$ (4.21 mg, 0.019 mmol). The reaction was stirred under a H$_2$ atmosphere (balloon pressure) for 1 h. The reaction was carefully filtered through CELITE® and the filtrate was concentrated to give tert-butyl N-[(9R,13S)-3-methyl-8-oxo-9-(propan-2-yl)-3,4,7,15-tetraazatricyclo[12.3.1.0$^{2,6}$]octadeca-1(18),2(6),4,14,16-pentaen-13-yl]carbamate (12 mg, 0.028 mmol, 76% yield). MS(ESI) m/z: 428.2 (M+H)$^+$.

58E. Preparation of (9R,13S)-13-amino-3-methyl-9-(propan-2-yl)-3,4,7,15-tetraazatricyclo[12.3.1.0$^{2,6}$]octadeca-1(18),2(6),4,14,16-pentaen-8-one

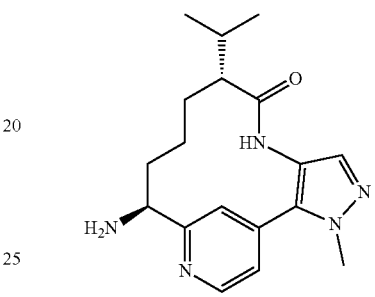

To a round RBF flask was added tert-butyl N-[(9R,13S)-3-methyl-8-oxo-9-(propan-2-yl)-3,4,7,15-tetraazatricyclo[12.3.1.0$^{2,6}$]octadeca-1(18),2(6),4,14,16-pentaen-13-yl]carbamate (20 mg, 0.047 mmol), dioxane (3 mL), 4 N HCl in dioxane (0.14 mL, 4.68 mmol) and MeOH (0.5 mL). The reaction was stirred at rt for 5 min. The reaction was concentrated and the residue was purified using reverse phase preparative HPLC to give (9R,13S)-13-amino-3-methyl-9-(propan-2-yl)-3,4,7,15-tetraazatricyclo[12.3.1.0$^{2,6}$]octadeca-1(18),2(6),4,14,16-pentaen-8-one hydrochloride. The product was added to a pre-rinsed AGILENT® StratoSpheres SPE PL-HCO$_3$ MP Resin cartridge. Gravity filtration, eluting with MeOH, gave a clear, slightly brown filtrate. Concentration provided (9R,13S)-13-amino-3-methyl-9-(propan-2-yl)-3,4,7,15-tetraazatricyclo[12.3.1.0$^{2,6}$]octadeca-1(18),2(6),4,14,16-pentaen-8-one (7 mg, 0.016 mmol, 34.3% yield) as a solid. MS(ESI) m/z: 328.2 (M+H)$^+$.

58F. Preparation of (9R,13S)-13-{4-[5-chloro-2-(4-chloro-1H-1,2,3-triazol-1-yl)phenyl]-6-oxo-1,6-dihydropyrimidin-1-yl}-3-methyl-9-(propan-2-yl)-3,4,7,15-tetraazatricyclo[12.3.1.0$^{2,6}$]octadeca-1(18),2(6),4,14,16-pentaen-8-one trifluoroacetate

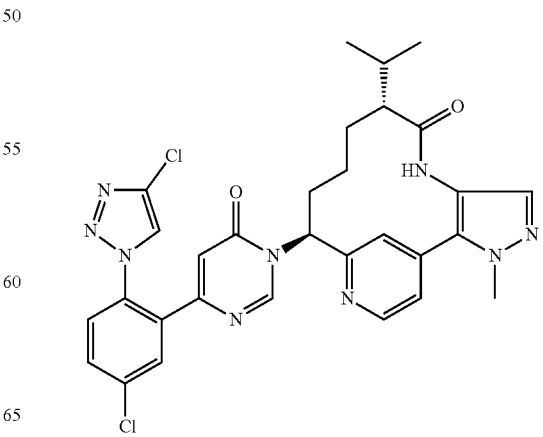

(9R,13S)-13-{4-[5-Chloro-2-(4-chloro-1H-1,2,3-triazol-1-yl)phenyl]-6-oxo-1,6-dihydropyrimidin-1-yl}-3-methyl-9-(propan-2-yl)-3,4,7,15-tetraazatricyclo[12.3.1.0$^{2,6}$]octadeca-1(18),2(6),4,14,16-pentaen-8-one trifluoroacetate (6 mg, 8.03 µmol, 40.4% yield) was prepared in a similar manner as the procedure described in Example 56 by using 6-(5-chloro-2-(4-chloro-1H-1,2,3-triazol-1-yl)phenyl)pyrimidin-4-ol (6.12 mg, 0.020 mmol), prepared as described in Intermediate 9, and (9R,13S)-13-amino-3-methyl-9-(propan-2-yl)-3,4,7,15-tetraazatricyclo[12.3.1.0$^{2,6}$]octadeca-1(18),2(6),4,14,16-pentaen-8-one (6.5 mg, 0.020 mmol). $^1$H NMR (400 MHz, CD$_3$OD) δ 8.75 (s, 1H), 8.69 (d, J=5.1 Hz, 1H), 8.07-8.01 (m, 1H), 7.82-7.78 (m, 1H), 7.71-7.66 (m, 1H), 7.65 (s, 1H), 7.60-7.57 (m, 1H), 7.52-7.47 (m, 1H), 7.36 (dd, J=5.1, 1.5 Hz, 1H), 6.41 (d, J=0.7 Hz, 1H), 6.09 (dd, J=12.4, 4.3 Hz, 1H), 4.04 (s, 3H), 2.16 (tt, J=12.6, 4.2 Hz, 1H), 2.06-1.71 (m, 5H), 1.60-1.48 (m, 1H), 1.03 (dd, J=6.4, 3.7 Hz, 6H), 0.82 (q, J=11.4 Hz, 1H); MS(ESI) m/z: 618.2 (M+H)$^+$. Analytical HPLC (Method A): RT=11.50 min, purity=98.0%; Factor XIa Ki=56 nM, Plasma Kallikrein Ki=3,300 nM.

Example 59

(9S,13S)-13-{4-[5-Chloro-2-(4-chloro-1H-1,2,3-triazol-1-yl)phenyl]-6-oxo-1,6-dihydropyrimidin-1-yl}-3-methyl-9-(propan-2-yl)-3,4,7,15-tetraazatricyclo[12.3.1.0$^{2,6}$]octadeca-1(18),2(6),4,14,16-pentaen-8-one Trifluoroacetate

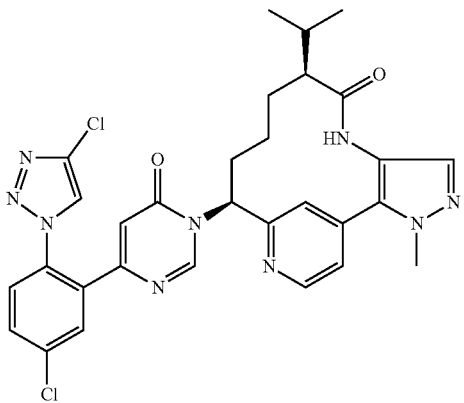 [SMILES: CC(C)[C@@H]1CCC[C@H](n2cnc(-c3cc(Cl)ccc3-n3cc(Cl)nn3)cc2=O)c2cc(ccn2)-c2c(cnn2C)NC1=O]

59A. Preparation of Tert-Butyl N-[(9S,13S)-3-methyl-8-oxo-9-(propan-2-yl)-3,4,7,15-tetraazatricyclo[12.3.1.0$^{2,6}$]octadeca-1(18),2(6),4,14,16-pentaen-13-yl]carbamate

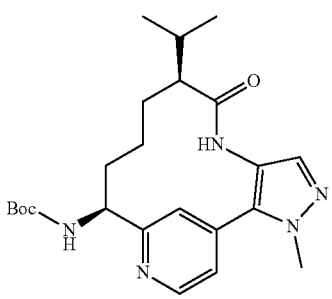 [SMILES: CC(C)[C@@H]1CCC[C@H](NC(=O)OC(C)(C)C)c2cc(ccn2)-c2c(cnn2C)NC1=O]

To a 3-neck RBF was added tert-butyl N-[(9R,10E,13S)-3-methyl-8-oxo-9-(propan-2-yl)-3,4,7,15-tetraazatricyclo[12.3.1.0$^{2,6}$]octadeca-1(18),2(6),4,10,14,16-hexaen-13-yl]carbamate trifluoroacetate (15 mg, 0.028 mmol), prepared as described in Example 58C2, EtOH (3 mL) and PtO$_2$ (3.16 mg, 0.014 mmol). The reaction was stirred under a H$_2$ atmosphere (balloon pressure) for 1 h. The reaction was carefully filtered through CELITE® and the filtrate was concentrated to give tert-butyl N-[(9S,13S)-3-methyl-8-oxo-9-(propan-2-yl)-3,4,7,15-tetraazatricyclo[12.3.1.0$^{2,6}$]octadeca-1(18),2(6),4,14,16-pentaen-13-yl]carbamate (10 mg, 0.023 mmol, 84% yield) as a brown solid. MS(ESI) m/z: 618.2 (M+H)$^+$.

59B. Preparation of (9S,13S)-13-amino-3-methyl-9-(propan-2-yl)-3,4,7,15-tetraazatricyclo[12.3.1.0$^{2,6}$]octadeca-1(18),2(6),4,14,16-pentaen-8-one

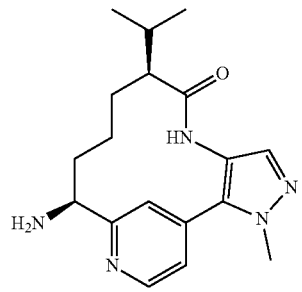 [SMILES: CC(C)[C@@H]1CCC[C@H](N)c2cc(ccn2)-c2c(cnn2C)NC1=O]

To a RBF was added tert-butyl N-[(9S,13S)-3-methyl-8-oxo-9-(propan-2-yl)-3,4,7,15-tetraazatricyclo[12.3.1.0$^{2,6}$]octadeca-1(18),2(6),4,14,16-pentaen-13-yl]carbamate (20 mg, 0.047 mmol), dioxane (3 mL), 4 N HCl in dioxane (0.142 mL, 4.68 mmol) and MeOH (0.5 mL). The reaction was stirred at rt for 5 min. The reaction was concentrated and the residue was purified using reverse phase preparative HPLC to give (9S,13S)-13-amino-3-methyl-9-(propan-2-yl)-3,4,7,15-tetraazatricyclo[12.3.1.0$^{2,6}$]octadeca-1(18),2(6),4,14,16-pentaen-8-one hydrochloride. The product was added to a pre-rinsed AGILENT® StratoSpheres SPE PL-HCO$_3$ MP Resin cartridge. Gravity filtration, eluting with MeOH, gave a clear, slightly brown filtrate. Concentration provided (9S,13S)-13-amino-3-methyl-9-(propan-2-yl)-3,4,7,15-tetraazatricyclo[12.3.1.0$^{2,6}$]octadeca-1(18),2(6),4,14,16-pentaen-8-one (1.5 mg, 3.43 µmol, 7.34% yield) as a beige solid. MS(ESI) m/z: 328.2 (M+H)$^+$.

59C. Preparation of (9S,13S)-13-{4-[5-chloro-2-(4-chloro-1H-1,2,3-triazol-1-yl)phenyl]-6-oxo-1,6-dihydropyrimidin-1-yl}-3-methyl-9-(propan-2-yl)-3,4,7,15-tetraazatricyclo[12.3.1.0$^{2,6}$]octadeca-1(18),2(6),4,14,16-pentaen-8-one trifluoroacetate

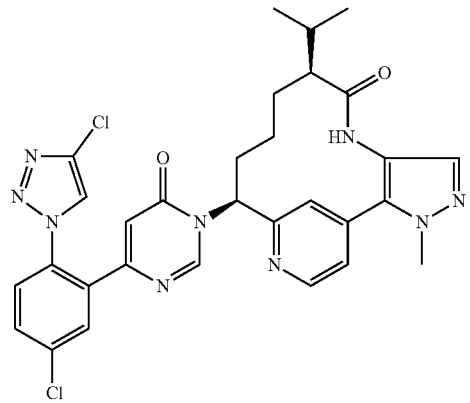 [SMILES: CC(C)[C@@H]1CCC[C@H](n2cnc(-c3cc(Cl)ccc3-n3cc(Cl)nn3)cc2=O)c2cc(ccn2)-c2c(cnn2C)NC1=O]

(9S,13S)-13-{4-[5-Chloro-2-(4-chloro-1H-1,2,3-triazol-1-yl)phenyl]-6-oxo-1,6-dihydropyrimidin-1-yl}-3-methyl-9-(propan-2-yl)-3,4,7,15-tetraazatricyclo[12.3.1.0²,⁶]octadeca-1(18),2(6),4,14,16-pentaen-8-one trifluoroacetate (0.6 mg, 0.778 μmol, 21.23% yield) was prepared in a similar manner as the procedure described in Example 56 by using 6-(5-chloro-2-(4-chloro-1H-1,2,3-triazol-1-yl)phenyl)pyrimidin-4-ol (1.129 mg, 3.66 μmol), prepared as described in Intermediate 9, and (9S,13S)-13-amino-3-methyl-9-(propan-2-yl)-3,4,7,15-tetraazatricyclo[12.3.1.0²,⁶]octadeca-1(18),2(6),4,14,16-pentaen-8-one (1.2 mg, 3.66 μmol). ¹H NMR (400 MHz, CD₃OD) δ 8.80 (s, 1H), 8.76 (d, J=5.1 Hz, 1H), 8.38-8.36 (m, 1H), 7.92 (d, J=2.2 Hz, 1H), 7.79-7.75 (m, 1H), 7.73 (s, 1H), 7.70-7.65 (m, 1H), 7.55 (dd, J=5.1, 1.5 Hz, 1H), 7.52 (s, 1H), 6.40 (s, 1H), 5.98 (d, J=9.2 Hz, 1H), 4.08 (s, 3H), 2.46-2.27 (m, 2H), 2.17-2.01 (m, 3H), 1.87-1.67 (m, 3H), 1.43 (br. s., 1H), 0.97 (d, J=6.6 Hz, 3H), 0.92 (d, J=6.4 Hz, 3H); MS(ESI) m/z: 618.2 (M+H)⁺. Analytical HPLC (Method A): RT=11.52 min, purity=95.0%; Factor XIa Ki=3.5 nM, Plasma Kallikrein Ki=370 nM.

Example 60

Preparation of (9S,13S)-13-{4-[3-chloro-6-(4-chloro-1H-1,2,3-triazol-1-yl)-2-fluorophenyl]-6-oxo-1,6-dihydropyrimidin-1-yl}-3-methyl-9-(propan-2-yl)-3,4,7,15-tetraazatricyclo[12.3.1.0²,⁶]octadeca-1(18),2(6),4,14,16-pentaen-8-one Trifluoroacetate

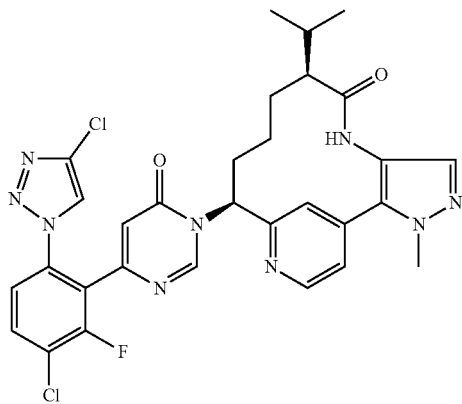 [SMILES: CC(C)[C@@H]1CCC[C@H](n2cnc(-c3c(-n4cc(Cl)nn4)ccc(Cl)c3F)cc2=O)c2cc(ccn2)-c2c(cnn2C)NC1=O]

(9S,13S)-13-{4-[3-Chloro-6-(4-chloro-1H-1,2,3-triazol-1-yl)-2-fluorophenyl]-6-oxo-1,6-dihydropyrimidin-1-yl}-3-methyl-9-(propan-2-yl)-3,4,7,15-tetraazatricyclo[12.3.1.0²,⁶]octadeca-1(18),2(6),4,14,16-pentaen-8-one trifluoroacetate (0.8 mg, 1.013 μmol, 3.32% yield) was prepared in a similar manner as the procedure described in Example 56 by using 6-(3-chloro-6-(4-chloro-1H-1,2,3-triazol-1-yl)-2-fluorophenyl) pyrimidin-4-ol (12.43 mg, 0.031 mmol) prepared as described in Intermediate 10 and (9S,13S)-13-amino-3-methyl-9-(propan-2-yl)-3,4,7,15-tetraazatricyclo[12.3.1.0²,⁶]octadeca-1(18),2(6),4,14,16-pentaen-8-one (10 mg, 0.031 mmol). ¹H NMR (400 MHz, CD₃OD) δ 8.80 (s, 1H), 8.75 (d, J=5.1 Hz, 1H), 8.27 (s, 1H), 7.87-7.83 (m, 1H), 7.69 (s, 1H), 7.56-7.49 (m, 2H), 7.48 (s, 1H), 6.61 (s, 1H), 6.01 (d, J=8.8 Hz, 1H), 4.06 (s, 3H), 2.33-2.24 (m, 1H), 2.13-1.99 (m, 3H), 2.14-1.97 (m, 4H), 1.83-1.69 (m, 2H), 1.42 (br. s., 1H), 1.33-1.23 (m, 1H), 0.94 (d, J=6.8 Hz, 3H), 0.89 (d, J=6.4 Hz, 3H); MS(ESI) m/z: 636.2 (M+H)⁺. Analytical HPLC (Method A): RT=11.266 min, purity=95.0%; Factor XIa Ki=0.53 nM, Plasma Kallikrein Ki=40 nM.

Example 61

Preparation of (9R,13S)-13-{4-[3-chloro-6-(difluoromethyl)-2-fluorophenyl]-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one Trifluoroacetate

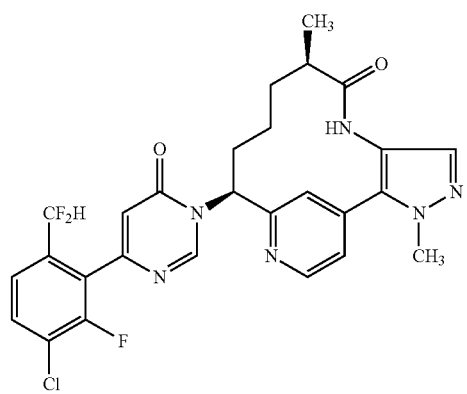 [SMILES: C[C@@H]1CCC[C@H](n2cnc(-c3c(C(F)F)ccc(Cl)c3F)cc2=O)c2cc(ccn2)-c2c(cnn2C)NC1=O]

61A. Preparation of 2-(3-chloro-6-(difluoromethyl)-2-fluorophenyl)-4,4,5,5-tetramethyl-1,3,2-dioxaborolane

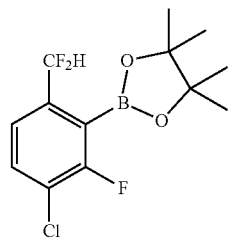 [SMILES: CC1(C)OB(c2c(C(F)F)ccc(Cl)c2F)OC1(C)C]

To a dry RBF was added 1-chloro-4-(difluoromethyl)-2-fluorobenzene (180 mg, 0.997 mmol) and THF (3 mL). The reaction was cooled to −78° C. and 2 M LDA in THF (0.498 mL, 0.997 mmol) was added dropwise. The reaction turned to dark red immediately after the addition. The reaction was stirred at −78° C. for 5 min and 2-isopropoxy-4,4,5,5-tetramethyl-1,3,2-dioxaborolane (371 mg, 1.994 mmol) was added in one portion. The reaction was stirred at −78° C. for 20 min. The colored changed to pale yellow. The reaction was partitioned between EtOAc (30 mL) and water (20 mL). The organic layer was separated, washed with water (20 mL) and brine (20 mL), dried over MgSO₄, filtered and concentrated. The residue was purified using ISCO system (0-30% EtOAc/Hex gradient) to give 2-(3-chloro-6-(difluoromethyl)-2-fluorophenyl)-4,4,5,5-tetramethyl-1,3,2-dioxaborolane (125 mg, 0.408 mmol, 40.9% yield) as a light brown oil. ¹H NMR (400 MHz, CDCl₃) δ 7.45 (t, J=7.8 Hz, 1H), 7.29 (d, J=8.4 Hz, 1H), 7.10-6.74 (m, 1H), 1.31 (s, 12H).

61B. Preparation of 4-(3-chloro-6-(difluoromethyl)-2-fluorophenyl)-6-methoxypyrimidine

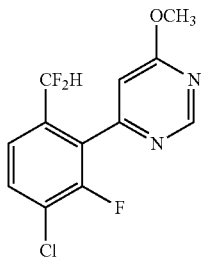 [SMILES: COc1cc(-c2c(C(F)F)ccc(Cl)c2F)ncn1]

To a microwave vial was added 2-(3-chloro-6-(difluoromethyl)-2-fluorophenyl)-4,4,5,5-tetramethyl-1,3,2-dioxaborolane (120 mg, 0.391 mmol), 4-chloro-6-methoxypyrimidine (56.6 mg, 0.391 mmol), toluene (2 mL), EtOH (1 mL) and 2 M $Na_2CO_3$ (0.587 mL, 1.174 mmol). The reaction was purged with Ar and $Pd(PPh_3)_4$(45 mg, 0.039 mmol) was added. The reaction was sealed and stirred in a microwave at 120° C. for 1 h. The reaction was partitioned between EtOAc (20 mL) and water (20 mL). The organic layer was separated, washed with water (10 mL) and brine (15 mL), dried over $MgSO_4$, filtered and concentrated. The residue was purified using ISCO system (0-30% EtOAc/Hex gradient) to give 4-(3-chloro-6-(difluoromethyl)-2-fluorophenyl)-6-methoxypyrimidine (40 mg, 0.139 mmol, 35.4% yield) as a white solid. $^1$H NMR (400 MHz, $CDCl_3$) δ 8.88 (d, J=0.9 Hz, 1H), 7.64-7.57 (m, 1H), 7.56-7.50 (m, 1H), 7.11-6.76 (m, 2H), 4.06 (s, 3H).

61C. Preparation of 6-(3-chloro-6-(difluoromethyl)-2 fluorophenyl)pyrimidin-4-ol

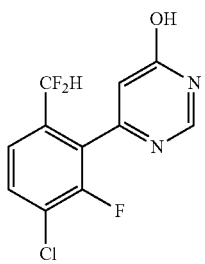 [SMILES: Oc1cc(-c2c(C(F)F)ccc(Cl)c2F)ncn1]

To a RBF was added 4-(3-chloro-6-(difluoromethyl)-2-fluorophenyl)-6-methoxypyrimidine (40 mg, 0.139 mmol), AcOH (0.5 mL) and 48% HBr (0.784 mL, 6.93 mmol). The reaction was stirred at 85° C. for 45 min. Then toluene (25 mL) was added and the reaction was concentrated. The residue was then partitioned between EtOAc (25 mL) and sat aq $NaHCO_3$(25 mL). The organic layer was separated, washed with water (15 mL) and brine (15 mL), dried over $MgSO_4$, filtered and concentrated. The residue was purified using ISCO system (0-100% EtOAc/Hex gradient) to give 6-(3-chloro-6-(difluoromethyl)-2-fluorophenyl)pyrimidin-4-ol (36 mg, 0.131 mmol, 95% yield) as a white solid. $^1$H NMR (400 MHz, $CDCl_3$) δ 13.25 (br. s., 1H), 8.28 (s, 1H), 7.70-7.57 (m, 1H), 7.53 (d, J=8.4 Hz, 1H), 7.16-6.79 (m, 1H), 6.72 (br. s., 1H).

61D. Preparation of (9R,13S)-13-{4-[3-chloro-6-(difluoromethyl)-2-fluorophenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one Trifluoroacetate

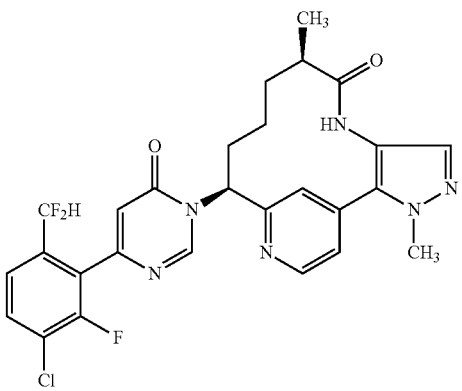 [SMILES: C[C@@H]1CCC[C@H](n2cnc(-c3c(C(F)F)ccc(Cl)c3F)cc2=O)c2cc(ccn2)-c2c(cnn2C)NC1=O]

(9R,13S)-13-{4-[3-Chloro-6-(difluoromethyl)-2-fluorophenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (3.1 mg, 4.44 μmol, 7.38% yield) was prepared in a similar manner as the procedure described in Example 56 using 6-(3-chloro-6-(difluoromethyl)-2-fluorophenyl)pyrimidin-4-ol (16.51 mg, 0.060 mmol). $^1$H NMR (400 MHz, $CD_3OD$) δ 8.78 (d, J=5.3 Hz, 1H), 7.80-7.74 (m, 2H), 7.60 (d, J=8.6 Hz, 1H), 7.56 (dd, J=5.3, 1.5 Hz, 1H), 7.53 (s, 1H), 7.16-6.84 (m, 1H), 6.67 (s, 1H), 6.08 (dd, J=12.8, 4.2 Hz, 1H), 4.08 (s, 3H), 2.75 (td, J=6.8, 3.2 Hz, 1H), 2.40 (tt, J=12.7, 4.6 Hz, 1H), 2.19-2.05 (m, 2H), 1.71-1.60 (m, 1H), 1.53 (ddd, J=15.0, 9.9, 5.5 Hz, 1H), 1.05 (d, J=7.0 Hz, 3H), 0.76 (br. s., 1H); MS(ESI) m/z: 557.1 (M+H)$^+$. Analytical HPLC (Method A): RT=7.516 min, purity=96.0%; Factor XIa Ki=2.5 nM, Plasma Kallikrein Ki=45 nM.

Example 62

Preparation of (9R,13S)-13-{4-[3-chloro-6-(1,1-difluoroethyl)-2-fluorophenyl]-6-oxo-1,6-ihydropyrimidin-1-yl}-3,9-dimethyl-3,4,7,15-tetraazatricyclo[12.3.1.0$^{2,6}$]octadeca-1(18),2(6),4,14,16-pentaen-8-one Trifluoroacetate

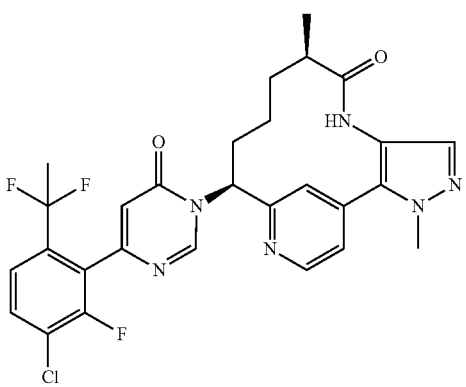 [SMILES: C[C@@H]1CCC[C@H](n2cnc(-c3c(C(C)(F)F)ccc(Cl)c3F)cc2=O)c2cc(ccn2)-c2c(cnn2C)NC1=O]

62A. Preparation of 1-chloro-4-(1,1-difluoroethyl)-2-fluorobenzene

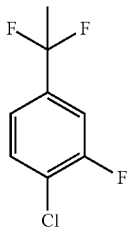

To a sealed tube was added 1-(4-chloro-3-fluorophenyl)ethanone (1 g, 5.79 mmol), CH$_2$Cl$_2$ (10 mL) and DAST (2.297 mL, 17.38 mmol). The reaction was sealed and stirred at 45° C. for 8 h. The reaction was carefully quenched with cold sat NaHCO$_3$ over 30 min until the pH was greater than 7. The organic layer was separated, washed with water, dried over MgSO$_4$, filtered and concentrated. The reside was purified using ISCO system (0-10% EtOAC/Hex gradient) to give 1-chloro-4-(1,1-difluoroethyl)-2-fluorobenzene (300 mg, 1.54 mmol, 26.6% yield) as a light brown liquid. $^1$H NMR (400 MHz, CDCl$_3$) δ 7.49-7.42 (m, 1H), 7.32-7.27 (m, 1H), 7.25-7.20 (m, 1H), 1.90 (t, J=18.2 Hz, 3H).

62B. Preparation of 2-(3-chloro-6-(1,1-difluoroethyl)-2-fluorophenyl)-4,4,5,5-tetramethyl-1,3,2-dioxaborolane

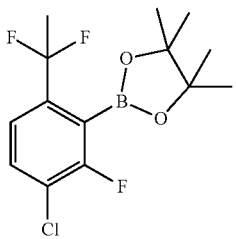

To a dry RBF was added 1-chloro-4-(1,1-difluoroethyl)-2-fluorobenzene (230 mg, 1.182 mmol) and THF (3 mL). The reaction was cooled to −78° C. and 2 M LDA solution (0.71 mL, 1.418 mmol) was added dropwise. The reaction turned to red after the addition. The reaction was stirred at −78° C. for 5 min and then 2-isopropoxy-4,4,5,5-tetramethyl-1,3,2-dioxaborolane (440 mg, 2.364 mmol) was added in one portion. The reaction was stirred at −78° C. for additional 20 min. The color changed to pale yellow. The reaction was partitioned between EtOAc (30 mL) and water (20 mL). The organic layer was separated, washed with water (20 mL) and brine (20 mL), dried over MgSO$_4$, filtered and concentrated. The residue was purified using ISCO system (0-30% EtOAc/Hex gradient) to give 2-(3-chloro-6-(1,1-difluoroethyl)-2-fluorophenyl)-4,4,5,5-tetramethyl-1,3,2-dioxaborolane (330 mg, 1.030 mmol, 87% yield) as a clear oil. $^1$H NMR (400 MHz, CDCl$_3$) δ 7.43 (t, J=7.9 Hz, 1H), 7.18 (d, J=8.4 Hz, 1H), 1.93 (t, J=18.3 Hz, 3H), 1.38 (s, 12H).

62C. Preparation of 4-(3-chloro-6-(1,1-difluoroethyl)-2-fluorophenyl)-6-methoxypyrimidine

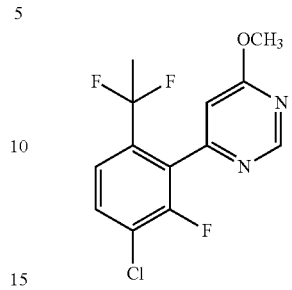

To a microwave vial was added 2-(3-chloro-6-(1,1-difluoroethyl)-2-fluorophenyl)-4,4,5,5-tetramethyl-1,3,2-dioxaborolane (325 mg, 1.014 mmol), 4-chloro-6-methoxypyrimidine (147 mg, 1.014 mmol), toluene (4 mL), EtOH (2 mL) and 2 M Na$_2$CO$_3$ (1.52 mL, 3.04 mmol). The reaction was purged with Ar and Pd(PPh$_3$)$_4$ (116.7 mg, 0.101 mmol) was added. The reaction was sealed and stirred in microwave at 120° C. for 1 h. The reaction was partitioned between EtOAc (20 mL) and water (20 mL). The organic layer was separated, washed with water (10 mL) and brine (15 mL), dried over MgSO$_4$, filtered and concentrated. The residue was purified using ISCO system (0-30% EtOAc/Hex gradient) to give 4-(3-chloro-6-(1,1-difluoroethyl)-2-fluorophenyl)-6-methoxypyrimidine (40 mg, 0.132 mmol, 13.03% yield) as a white solid. $^1$H NMR (400 MHz, CDCl$_3$) δ 8.84 (d, J=1.1 Hz, 1H), 7.52 (d, J=7.3 Hz, 1H), 7.36 (dd, J=8.6, 1.3 Hz, 1H), 6.81 (s, 1H), 4.05 (s, 3H), 1.91 (t, J=18.6 Hz, 3H); MS(ESI) m/z: 303.0, 305.0 (M+H)$^+$.

62D. Preparation of 6-(3-chloro-6-(1,1-difluoroethyl)-2-fluorophenyl)pyrimidin-4-ol

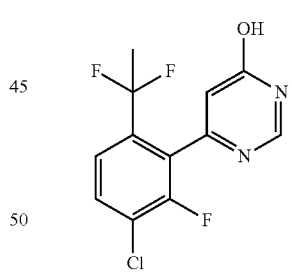

To a RBF was added 4-(3-chloro-6-(1,1-difluoroethyl)-2-fluorophenyl)-6-methoxypyrimidine (35 mg, 0.116 mmol), AcOH (0.5 mL) and HBr (0.654 mL, 5.78 mmol). The reaction was stirred at 85° C. for 45 min. Then toluene (25 mL) was added and the reaction was concentrated. The residue was partitioned between EtOAc (25 mL) and sat NaHCO$_3$ (25 mL). The organic layer was separated, washed with water (15 mL) and brine (15 mL), dried over MgSO$_4$, filtered and concentrated. The residue was purified using ISCO system (0-100% EtOAc/Hex gradient) to give 6-(3-chloro-6-(1,1-difluoroethyl)-2-fluorophenyl)pyrimidin-4-ol (28 mg, 0.097 mmol, 84% yield) as a white solid. MS(ESI) m/z: 289, 291.0 (M+H)$^+$.

62E. Preparation of (9R,13S)-13-{4-[3-chloro-6-(1,1-difluoroethyl)-2-fluorophenyl]-6-oxo-1,6-ihydropyrimidin-1-yl}-3,9-dimethyl-3,4,7,15-tetraazatricyclo[12.3.1.0²,⁶]octadeca-1(18),2(6),4,14,16-pentaen-8-one trifluoroacetate

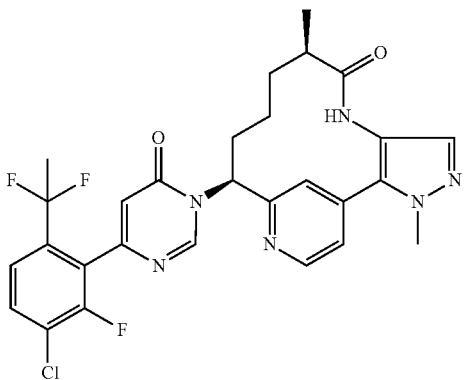 [SMILES: C[C@@H]1CCC[C@H](n2cnc(-c3c(C(C)(F)F)ccc(Cl)c3F)cc2=O)c2cc(ccn2)-c2c(cnn2C)NC1=O]

(9R,13S)-13-{4-[3-Chloro-6-(1,1-difluoroethyl)-2-fluorophenyl]-6-oxo-1,6-ihydropyrimidin-1-yl}-3,9-dimethyl-3,4,7,15-tetraazatricyclo[12.3.1.0²,⁶]octadeca-1(18),2(6),4,14,16-pentaen-8-one trifluoroacetate (30 mg, 0.042 mmol, 69.9% yield) was prepared in a similar manner as the procedure described in Example 56 by replacing 6-{5-chloro-2-[4-(trifluoromethyl)-1H-1,2,3-triazol-1-yl]phenyl}pyrimidin-4-ol with 6-(3-chloro-6-(1,1-difluoroethyl)-2-fluorophenyl)pyrimidin-4-ol (22.2 mg, 0.06 mmol). ¹H NMR (400 MHz, CD₃OD) δ 8.99 (br. s., 1H), 8.74 (d, J=4.2 Hz, 1H), 7.78 (s, 1H), 7.65 (t, J=7.8 Hz, 1H), 7.58 (d, J=3.7 Hz, 1H), 7.50-7.39 (m, 2H), 6.53 (s, 1H), 6.01 (d, J=9.9 Hz, 1H), 4.02 (s, 3H), 2.67 (br. s., 1H), 2.43-2.31 (m, 1H), 2.06 (br. s., 1H), 1.89 (t, J=18.6 Hz, 3H), 1.66-1.53 (m, 1H), 1.45 (br. s., 1H), 0.98 (d, J=6.8 Hz, 3H), 0.73 (br. s., 1H); MS(ESI) m/z: 636.2 (M+H)⁺. Analytical HPLC (Method A): RT=11.078 min, purity=96.0%; Factor XIa Ki=16 nM, Plasma Kallikrein Ki=240 nM.

Example 63

Preparation of (9R,13S)-13-{4-[3-chloro-2-fluoro-6-(1H-1,2,3-triazol-1-yl)phenyl]-6-oxo-1,6-dihydropyrimidin-1-yl}-16-fluoro-3,9-dimethyl-3,4,7-triazatricyclo[12.3.1.0²,⁶]octadeca-1(18),2(6),4,14,16-pentaen-8-one

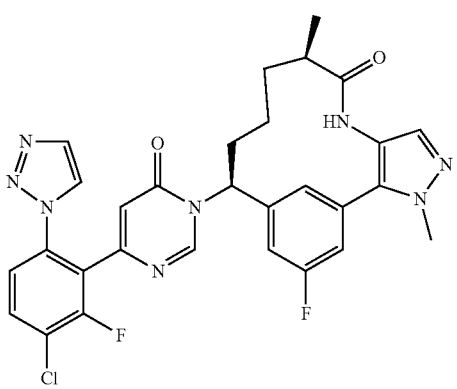 [SMILES: C[C@@H]1CCC[C@H](n2cnc(-c3c(-n4ccnn4)ccc(Cl)c3F)cc2=O)c2cc(F)cc(c2)-c2c(cnn2C)NC1=O]

To 6-[3-chloro-2-fluoro-6-(1H-1,2,3-triazol-1-yl)phenyl]pyrimidin-4-ol (0.018 g, 0.060 mmol), prepared as described in Intermediate 7, was added HATU (0.030 g, 0.078 mmol) and a solution of DBU (0.014 mL, 0.090 mmol) in CH₃CN (0.5 ml). After 30 min, (9R,13S)-13-amino-16-fluoro-3,9-dimethyl-3,4,7-triazatricyclo[12.3.1.0²,⁶]octadeca-1(18),2(6),4,14,16-pentaen-8-one (0.019 g, 0.060 mmol), prepared as described in Intermediate 29, was added. After 18 h, the reaction was diluted with DMF, filtered and concentrated. The residue was purified by reverse phase HPLC using PHENOMENEX® Luna 5U 30×100 mm (10:90 ACN/H₂O to 90:10 AcN/H₂O, 0.1% TFA) (20% B start 10 min gradient). The desired fractions were concentrated and freeze-dried to afford (9R,13S)-13-{4-[3-chloro-2-fluoro-6-(1H-1,2,3-triazol-1-yl)phenyl]-6-oxo-1,6-dihydropyrimidin-1-yl}-16-fluoro-3,9-dimethyl-3,4,7-triazatricyclo[12.3.1.0²,⁶]octadeca-1(18),2(6),4,14,16-pentaen-8-one (4.5 mg, 12%) as a white solid. MS(ESI) m/z: 591.3 (M+H)⁺. ¹H NMR (400 MHz, CD₃OD) δ 8.25 (s, 1H), 8.20 (d, J=1.1 Hz, 1H), 7.91-7.84 (m, 1H), 7.84-7.77 (m, 2H), 7.60-7.49 (m, 3H), 7.38 (d, J=8.6 Hz, 1H), 7.12 (d, J=9.5 Hz, 1H), 6.59 (s, 1H), 5.79 (dd, J=12.9, 3.2 Hz, 1H), 4.08-4.00 (m, 3H), 2.52 (td, J=6.8, 3.4 Hz, 1H), 2.41-2.29 (m, 1H), 2.15-2.04 (m, 1H), 1.90 (d, J=4.8 Hz, 1H), 1.65-1.45 (m, 2H), 1.29-1.19 (m, 1H), 1.14 (d, J=6.8 Hz, 3H). Analytical HPLC (Method A) RT=7.41 min, purity=95%; Factor XIa Ki=0.25 nM, Plasma Kallikrein Ki=34 nM.

Example 64

Preparation of (9R,13S)-13-[4-(3-chloro-2,6-difluorophenyl)-6-oxo-1,6-dihydropyrimidin-1-yl]-16-fluoro-3,9-dimethyl-3,4,7-triazatricyclo[12.3.1.0²,⁶]octadeca-1(18),2(6),4,14,16-pentaen-8-one

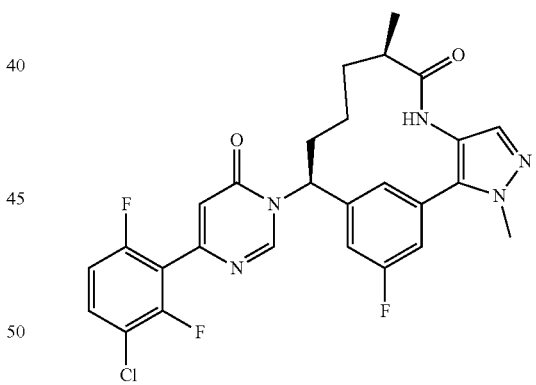

To a solution of 6-(3-chloro-2,6-difluorophenyl)pyrimidin-4-ol hydrobromide (0.017 g, 0.053 mmol), prepared as described in Intermediate 4, in CH₃CN (1 ml), was added HATU (0.026 g, 0.068 mmol) and DBU (0.028 mL, 0.184 mmol). After 1 h, (9R,13S)-13-amino-6-fluoro-3,9-dimethyl-3,4,7-triazatricyclo[12.3.1.0²,⁶]octadeca-1(18),2(6),4,14,16-pentaen-8-one, (0.019 g, 0.053 mmol), prepared as described in Intermediate 29, was added. After 18 h, the reaction was diluted with DMF, filtered and concentrated. The residue was purified by reverse phase HPLC, then preparative LCMS to give (9R,13S)-13-[4-(3-chloro-2,6-difluorophenyl)-6-oxo-1,6-dihydropyrimidin-1-yl]-16-fluoro-3,9-dimethyl-3,4,7-triazatricyclo[12.3.1.0²,⁶]octadeca-1(18),2(6),4,14,16-pentaen-8-one (3.4 mg, 11.9%).

MS(ESI) m/z: 542.1 (M+H)+. 1H NMR ((500 MHz, DMSO-d6) δ 9.23 (s, 1H), 8.69 (br. s., 1H), 7.84-7.73 (m, 1H), 7.61-7.50 (m, 2H), 7.45 (s, 1H), 7.38-7.32 (m, 1H), 7.29-7.19 (m, 1H), 6.74 (s, 1H), 5.66 (d, J=12.5 Hz, 1H), 3.98 (s, 3H), 2.42 (br. s., 1H), 2.10-1.97 (m, 1H), 1.88 (br. s., 1H), 1.45 (d, J=7.3 Hz, 1H), 1.21 (br. s., 1H), 1.11 (br. s., 1H), 0.97 (d, J=6.4 Hz, 3H). Analytical HPLC (Method C) RT=1.50 min., purity=99%; Factor XIa Ki=26 nM, Plasma Kallikrein Ki=450 nM.

Example 65

Preparation of (9R,13S)-13-{4-[3-chloro-2-fluoro-6-(1H-1,2,3-triazol-1-yl)phenyl]-6-oxo-1,6-dihydropyrimidin-1-yl}-3,9-dimethyl-3,4,7-triazatricyclo[12.3.1.0$^{2,6}$]octadeca-1(18),2(6),4,14,16-pentaen-8-one

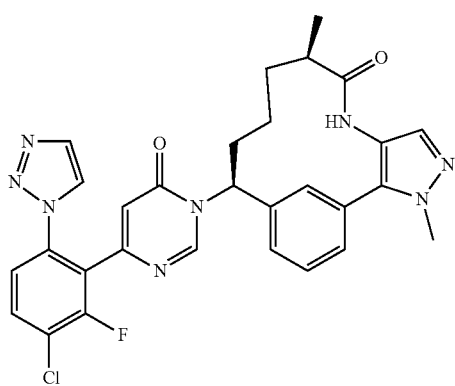 [SMILES: C[C@@H]1CCC[C@H](n2cnc(-c3c(-n4ccnn4)ccc(Cl)c3F)cc2=O)c2cccc(c2)-c2c(cnn2C)NC1=O]

To 6-[3-chloro-2-fluoro-6-(1H-1,2,3-triazol-1-yl)phenyl]pyrimidin-4-ol (13.07 mg, 0.045 mmol), prepared as described in Intermediate 7, was added HATU (22.14 mg, 0.058 mmol) and a solution of DBU (0.017 mL, 0.112 mmol) in ACN (0.5 ml). After 30 min, (9R,13S)-13-amino-3,9-dimethyl-3,4,7-triazatricyclo[12.3.1.0$^{2,6}$]octadeca-1(18),2(6),4,14,16-pentaen-8-one, hydrochloride (15 mg, 0.045 mmol), prepared as described in Intermediate 31, was added and the reaction was stirred for 18 h. The reaction was then diluted with DMF, filtered and concentrated. The residue was purified by reverse phase HPLC, then, preparative LCMS to give (9R,13S)-13-{4-[3-chloro-2-fluoro-6-(1H-1,2,3-triazol-1-yl)phenyl]-6-oxo-1,6-dihydropyrimidin-1-yl}-3,9-dimethyl-3,4,7-triazatricyclo[12.3.1.0$^{2,6}$]octadeca-1(18),2(6),4,14,16-pentaen-8-one (3.2 mg, 12%). MS(ESI) m/z: 573.3 (M+H)+. 1H NMR (500 MHz, DMSO-d6) δ 9.15 (s, 1H), 8.43-8.32 (m, 2H), 8.00-7.93 (m, 2H), 7.84 (s, 1H), 7.68-7.59 (m, 2H), 7.59-7.50 (m, 2H), 7.41 (s, 1H), 7.28-6.99 (m, 2H), 6.56 (s, 1H), 5.60 (d, J=11.3 Hz, 1H), 4.03-3.90 (m, 3H), 2.32 (br. s., 1H), 1.94-1.79 (m, 2H), 1.41 (d, J=5.2 Hz, 1H), 1.14 (br. s., 2H), 0.96 (d, J=6.4 Hz, 3H). Analytical HPLC (Method C) RT=1.41 min., purity=98%; Factor XIa Ki=0.23 nM, Plasma Kallikrein Ki=22 nM.

Example 66

Preparation of (9R,13S)-13-{4-[5-chloro-2-(4-chloro-1H-1,2,3-triazol-1-yl)phenyl]-6-oxo-1,6-dihydropyrimidin-1-yl}-3,9-dimethyl-3,4,7-triazatricyclo[12.3.1.0$^{2,6}$]octadeca-1(18),2(6),4,14,16-pentaen-8-one

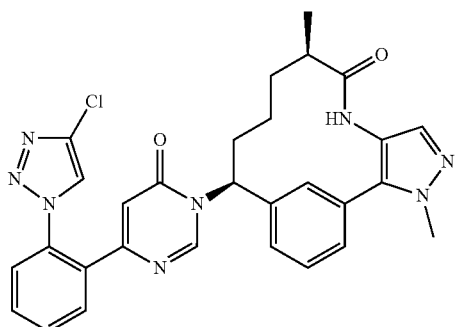

To a 1-dram vial containing a white suspension of 6-[5-chloro-2-(4-chloro-1H-1,2,3-triazol-1-yl)phenyl]pyrimidin-4-ol (0.026 g, 0.084 mmol), prepared as described in Intermediate 9, in CH3CN (0.5 ml) was added HATU (0.041 g, 0.109 mmol) and DBU (0.019 mL, 0.126 mmol). After 30 min, (9R,13S)-13-amino-3,9-dimethyl-3,4,7-triazatricyclo[12.3.1.0$^{2,6}$]octadeca-1(18),2(6),4,14,16-pentaen-8-one (0.025 g, 0.084 mmol), prepared as described in Intermediate 31, which had been free-based through a basic cartridge in DCM/MeOH and dried, in CH3CN/DMF (0.5 ml) was added. After 18 h, the reaction was diluted with DMF, filtered and purified by reverse phase HPLC using PHENOMENEX® Luna 5U 30×100 mm (10:90 MeOH/H2O to 90:10 MeOH/H2O, 0.1% TFA) (20% B start 10 min gradient) to afford (9R,13S)-13-{4-[5-chloro-2-(4-chloro-1H-1,2,3-triazol-1-yl)phenyl]-6-oxo-1,6-dihydropyrimidin-1-yl}-3,9-dimethyl-3,4,7-triazatricyclo[12.3.1.0$^{2,6}$]octadeca-1(18),2(6),4,14,16-pentaen-8-one (13.9 mg, 280% yield) as a white solid. MS(ESI) m/z: 589.2 (M+H)+. 1H NMR (400 MHz, CD3OD) δ 8.37-8.33 (m, 1H), 8.19 (s, 1H), 7.88 (d, J=2.4 Hz, 1H), 7.80-7.72 (m, 2H), 7.67-7.55 (m, 3H), 7.52 (s, 1H), 7.34 (d, J=7.3 Hz, 1H), 6.43 (d, J=0.7 Hz, 1H), 5.84 (dd, J=13.1, 3.2 Hz, 1H), 4.04 (s, 3H), 2.55-2.46 (m, 1H), 2.41-2.30 (m, 1H), 2.17-2.05 (m, 1H), 1.92-1.84 (m, 1H), 1.66-1.53 (m, 2H), 1.22 (br. s., 1H), 1.16 (d, J=6.8 Hz, 3H). Analytical HPLC (Method A) RT=8.25 min., purity=95%; Factor XIa Ki=0.1 nM, Plasma Kallikrein Ki=8 nM.

Example 67

Preparation of (9R)-13-{4-[3-chloro-2-fluoro-6-(1H-1,2,3-triazol-1-yl)phenyl]-6-oxo-1,6-dihydropyrimidin-1-yl}-3,9-dimethyl-3,4,7-triazatricyclo[12.3.1.0²,⁶]octadeca-1(18),2(6),4,14,16-pentaen-8-one

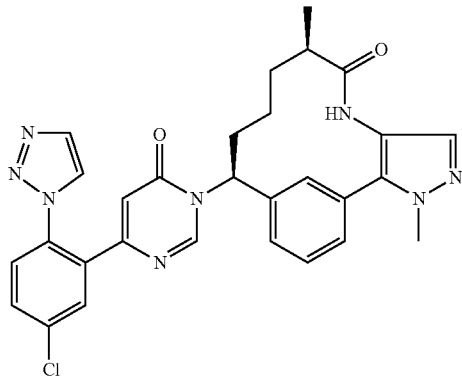 [SMILES: C[C@@H]1CCC[C@H](n2cnc(-c3cc(Cl)ccc3-n3ccnn3)cc2=O)c2cccc(c2)-c2c(cnn2C)NC1=O]

Purification of Example 65 by reverse phase HPLC, then, preparative LCMS also gave (9R)-13-{4-[3-chloro-2-fluoro-6-(1H-1,2,3-triazol-1-yl)phenyl]-6-oxo-1,6-dihydropyrimidin-1-yl}-3,9-dimethyl-3,4,7-triazatricyclo[12.3.1.0²,⁶]octadeca-1(18),2(6),4,14,16-pentaen-8-one as the first eluting diastereomer (1.4 mg, 5.4%). MS(ESI) m/z: 573.3 (M+H)⁺. ¹H NMR (500 MHz, DMSO-d₆)¹H NMR (500 MHz, DMSO-d₆) δ 9.08 (s, 1H), 8.71 (s, 1H), 8.39 (s, 1H), 8.04-7.94 (m, 1H), 7.86 (s, 1H), 7.70-7.58 (m, 2H), 7.58-7.48 (m, 2H), 7.42 (s, 1H), 7.25-7.03 (m, 2H), 6.61 (s, 1H), 5.60 (d, J=13.1 Hz, 1H), 3.98 (s, 2H), 2.41-2.30 (m, 2H), 1.82 (br. s., 1H), 1.68 (d, J=10.1 Hz, 1H), 1.37 (d, J=11.0 Hz, 1H), 1.11 (br. s., 2H), 1.07 (d, J=6.4 Hz, 3H). Analytical HPLC (Method C) RT=1.39 min., purity=100%; Factor XIa Ki=5 nM, Plasma Kallikrein Ki=256 nM.

Example 68

Preparation of (9R,13S)-13-{4-[5-chloro-2-(4-chloro-1H-1,2,3-triazol-1-yl)phenyl]-6-oxo-1,6-dihydropyrimidin-1-yl}-3-(²H₃)methyl-9-methyl-3,4,7-triazatricyclo[12.3.1.0²,⁶]octadeca-1(18),2(6),4,14,16-pentaen-8-one

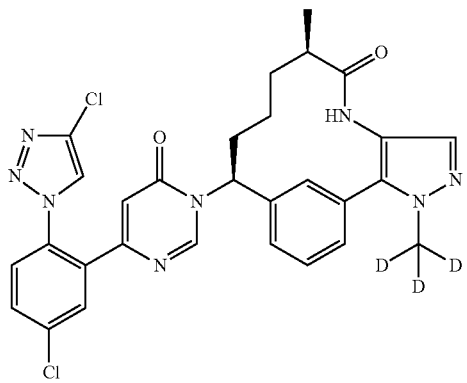 [SMILES: [2H]C([2H])([2H])n1ncc2c1-c1cccc(c1)[C@@H](n1cnc(-c3cc(Cl)ccc3-n3cc(Cl)nn3)cc1=O)CCC[C@@H](C)C(=O)N2]

To a solution of 6-[5-chloro-2-(4-chloro-1H-1,2,3-triazol-1-yl)phenyl]pyrimidin-4-ol (0.031 g, 0.100 mmol), prepared as described in Intermediate 9, in CH₃CN (0.8 ml) was added HATU (0.049 g, 0.129 mmol) and DBU (0.023 mL, 0.149 mmol) After 30 min, (9R,13S)-13-amino-3-(²H₃)methyl-9-methyl-3,4,7-triazatricyclo[12.3.1.0²,⁶]octadeca-1(18),2(6),4,14,16-pentaen-8-one 0.03 g, 0.100 mmol), prepared as described in Intermediate 36, was added (rinsed in with 0.2 ml DMF). After 18 h, the reaction was diluted with DMF, filtered and concentrated. The residue was purified by reverse phase HPLC using PHENOMENEX® Luna 5U 30×100 mm (10:90 MeOH/H₂O to 90:10 MeOH/H₂O, 0.1% TFA) (25% B start, 14 min gradient). The desired fractions were concentrated and freeze-dried to afford (9R,13S)-13-{4-[5-chloro-2-(4-chloro-1H-1,2,3-triazol-1-yl)phenyl]-6-oxo-1,6-dihydropyrimidin-1-yl}-3-(²H₃)methyl-9-methyl-3,4,7-triazatricyclo[12.3.1.0²,⁶]octadeca-1(18),2(6),4,14,16-pentaen-8-one (19.6 mg, 33% yield) as a tan solid. MS(ESI) m/z: 592.4 (M+H)⁺. ¹H NMR (400 MHz, CD₃OD) δ 8.33 (s, 1H), 8.18 (s, 1H), 7.87 (d, J=2.2 Hz, 1H), 7.80-7.71 (m, 2H), 7.68-7.55 (m, 3H), 7.54-7.50 (m, 1H), 7.33 (d, J=7.5 Hz, 1H), 6.42 (s, 1H), 5.83 (dd, J=12.8, 3.1 Hz, 1H), 2.56-2.45 (m, 1H), 2.38-2.29 (m, 1H), 2.18-2.06 (m, 1H), 1.94-1.82 (m, 1H), 1.67-1.52 (m, 2H), 1.22 (br. s., 1H), 1.15 (d, J=6.8 Hz, 3H). Analytical HPLC (Method A) RT=8.44 min, 95% purity; Factor XIa Ki=0.1 nM, Plasma Kallikrein Ki=6 nM.

Example 69

Preparation of (10R,14S)-14-{4-[3-chloro-6-(4-chloro-1H-1,2,3-triazol-1-yl)-2-fluorophenyl]-6-oxo-1,6-dihydropyrimidin-1-yl}-10-methyl-3,8-diazatricyclo[13.3.1.0²,⁷]nonadeca-1(19),2(7),3,5,15,17-hexaen-9-one trifluoroacetate

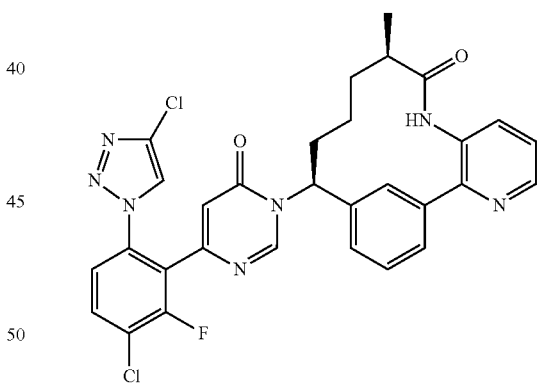

To a solution of 6-[3-chloro-6-(4-chloro-1H-1,2,3-triazol-1-yl)-2-fluorophenyl]pyrimidin-4-ol (4.42 mg, 0.014 mmol), prepared as described in Intermediate 10, in CH₃CN (0.2 ml) was added HATU (6.69 mg, 0.018 mmol) and DBU (3.06 μl, 0.020 mmol). After 30 min, (10R,14S)-14-amino-10-methyl-3,8-diazatricyclo[13.3.1.0²,⁷]nonadeca-1(19),2(7),3,5,15,17-hexaen-9-one (0.004 g, 0.014 mmol), prepared as described in Intermediate 38, was added with DMF (0.2 ml). After 18 h, the reaction was diluted with DMF, filtered and concentrated. The residue was purified by reverse phase HPLC using PHENOMENEX® Luna 5U 30×100 mm (10:90 ACN/H₂O to 90:10 ACN/H₂O, 0.1% TFA) (20% B start, 14 min gradient) to afford (10R,14S)-14-{4-[3-chloro-6-(4-chloro-1H-1,2,3-triazol-1-yl)-2-fluorophenyl]-6-oxo-1,6-dihydropyrimidin-1-yl}-10-methyl-3,8-diazatricyclo[13.3.1.0²,⁷]nonadeca-1(19),2(7),3,5,15,17-hexaen-9-one trifluoroacetate (2 mg, 20% yield) as a white solid. MS(ESI) r/z: 604.4 (M+H)⁺. ¹H NMR (400 MHz, CD₃OD) δ 8.69-8.65 (m, 1H), 8.38-8.30 (m, 2H), 8.00-7.91 (m, 2H), 7.91-7.84 (m, 1H), 7.74 (d, J=7.9 Hz, 1H), 7.69-7.63 (m, 2H), 7.55 (dd, J=8.6, 1.5 Hz, 1H), 7.36 (d, J=7.7 Hz, 1H), 6.64 (s, 1H), 5.83 (dd, J=12.9, 3.4 Hz, 1H), 2.55 (t, J=6.7 Hz, 1H), 2.40-2.29 (m, 1H), 2.21-2.10 (m, 1H), 1.89 (br. s., 1H), 1.65-1.51 (m, 2H), 1.33 (d, J=9.7 Hz, 1H), 1.15 (d, J=6.8 Hz, 3H). Analytical HPLC (Method A) RT=6.32 min. Purity=100%; Factor XIa Ki=1.1 nM, Plasma Kallikrein Ki=54 nM.

Example 70

Preparation of 1-(4-chloro-2-{1-[(9R,13S)-3-(difluoromethyl)-9-methyl-8-oxo-3,4,7-triazatricyclo[12.3.1.0²,⁶]octadeca-1(18),2(6),4,14,16-pentaen-13-yl]-6-oxo-1,6-dihydropyrimidin-4-yl}-3-fluorophenyl)-1H-1,2,3-triazole-4-carbonitrile

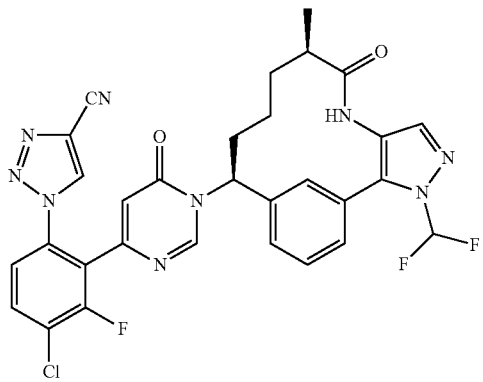 [SMILES: C[C@@H]1CCC[C@H](n2cnc(-c3c(-n4cc(C#N)nn4)ccc(Cl)c3F)cc2=O)c2cccc(c2)-c2c(cnn2C(F)F)NC1=O]

To a solution of 1-[4-chloro-3-fluoro-2-(6-hydroxypyrimidin-4-yl)phenyl]-1H-1,2,3-triazole-4-carbonitrile (13.0 mg, 0.041 mmol), prepared as described in Intermediate 12, in CH₃CN (0.4 ml) was added HATU (0.020 g, 0.053 mmol) and DBU (9.28 µl, 0.062 mmol). After 0.5 h, (9R,13S)-13-amino-3-(difluoromethyl)-9-methyl-3,4,7-triazatricyclo[12.3.1.0²,⁶]octadeca-1(18),2(6),4,14,16-pentaen-8-one (14.0 mg, 0.041 mmol), prepared as described in Intermediate 35, was added with DMF (0.2 ml). Additional CH₃CN (0.2 ml) and DMF (0.2 ml) were added to rinse the vials and dissolve reagents. After 18 h, the reaction was diluted with DMF, filtered and concentrated. The residue was purified by reverse phase HPLC using PHENOMENEX® Luna 5U 30×100 mm (10:90 ACN/H₂O to 90:10 ACN/H₂O, 0.1% TFA) (20% B start, 14 min gradient) to afford 1-(4-chloro-2-{1-[(9R,13S)-3-(difluoromethyl)-9-methyl-8-oxo-3,4,7-triazatricyclo[12.3.1.0²,⁶]octadeca-1(18),2(6),4,14,16-pentaen-13-yl]-6-oxo-1,6-dihydropyrimidin-4-yl}-3-fluorophenyl)-1H-1,2,3-triazole-4-carbonitrile (6 mg, 24.7% yield) as a white solid. MS(ESI) m/z: 643.3 (M+H)⁺. ¹H NMR (400 MHz, CD₃OD) δ 8.96 (br. s., 1H), 8.22 (br. s., 1H), 7.90 (d, J=6.8 Hz, 1H), 7.79 (br. s., 2H), 7.71-7.55 (m, 4H), 7.39 (br. s., 1H), 6.71 (br. s., 1H), 5.84 (d, J=9.9 Hz, 1H), 2.52 (br. s., 1H), 2.37 (br. s., 1H), 2.19-2.01 (m, 1H), 2.01-1.87 (m, 1H), 1.59 (br. s., 2H), 1.23 (br. s., 1H), 1.17 (br. s., 3H). Analytical HPLC (Method A) rt=8.83 min, purity=99%; Factor XIa Ki=0.1 nM, Plasma Kallikrein Ki=4 nM.

Example 71

Preparation of (9R,13S)-13-(4-{5-chloro-2-[4-(difluoromethyl)-1H-1,2,3-triazol-1-yl]phenyl}-6-oxo-1,6-dihydropyrimidin-1-yl)-3-(difluoromethyl)-9-methyl-3,4,7-triazatricyclo[12.3.1.0²,⁶]octadeca-1(18),2(6),4,14,16-pentaen-8-one

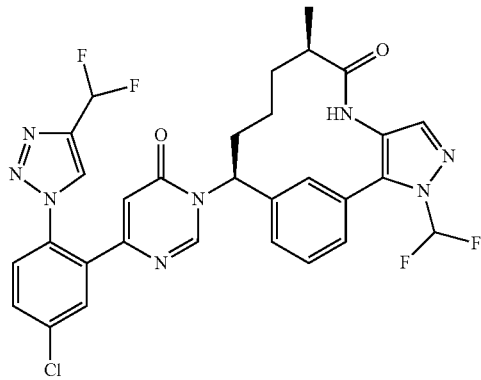 [SMILES: C[C@@H]1CCC[C@H](n2cnc(-c3cc(Cl)ccc3-n3cc(C(F)F)nn3)cc2=O)c2cccc(c2)-c2c(cnn2C(F)F)NC1=O]

To a solution of 6-{5-chloro-2-[4-(difluoromethyl)-1H-1,2,3-triazol-1-yl]phenyl}pyrimidin-4-ol (0.014 g, 0.043 mmol), prepared as described in Intermediate 16, in CH₃CN (0.4 ml) was added HATU (0.021 g, 0.056 mmol) and DBU (9.78 µl, 0.065 mmol). After 30 min, (9R,13S)-13-amino-3-(difluoromethyl)-9-methyl-3,4,7-triazatricyclo[12.3.1.0²,⁶]octadeca-1(18),2(6),4,14,16-pentaen-8-one (0.14 g, 0.043 mmol), prepared as described in Intermediate 35, was added with DMF (0.2 ml). Additional CH₃CN (0.2 ml) and DMF (0.2 ml) were added to rinse vials and dissolve reagents. After 18 h, the reaction was diluted with DMF, filtered and concentrated. The residue was purified by reverse phase HPLC using PHENOMENEX® Luna 5U 30×100 mm (10:90 ACN/H₂O to 90:10 ACN/H₂O, 0.1% TFA) (20% B start, 14 min gradient) to afford (9R,13S)-13-(4-{5-chloro-2-[4-(difluoromethyl)-1H-1,2,3-triazol-1-yl]phenyl}-6-oxo-1,6-dihydropyrimidin-1-yl)-3-(difluoromethyl)-9-methyl-3,4,7-triazatricyclo[12.3.1.0²,⁶]octadeca-1(18),2(6),4,14,16-pentaen-8-one (9.9 mg, 35.7%) as a white solid. MS(ESI) m/z: 641.5 (M+H)⁺. ¹H NMR (400 MHz, CD₃OD) δ 8.53 (t, J=1.3 Hz, 1H), 8.19 (s, 1H), 7.88 (d, J=2.4 Hz, 1H), 7.82-7.72 (m, 3H), 7.68 (s, 1H), 7.65-7.56 (m, 3H), 7.38 (d, J=7.5 Hz, 1H), 7.20-6.81 (m, 1H), 6.42 (d, J=0.7 Hz, 1H), 5.82 (dd, J=12.8, 3.3 Hz, 1H), 2.50 (ddd, J=10.2, 6.9, 3.4 Hz, 1H), 2.35 (d, J=12.5 Hz, 1H), 2.19-2.08 (m, 1H), 1.97-1.86 (m, 1H), 1.65-1.52 (m, 2H), 1.27-1.20 (m, 1H), 1.16 (d, J=6.8 Hz, 3H). Analytical HPLC (Method A) RT=8.79 min, purity=100%; Factor XIa Ki=0.17 nM, Plasma Kallikrein Ki=46 nM.

Example 72

Preparation of (9R,13S)-13-(4-{5-chloro-2-[4-(difluoromethyl)-1H-1,2,3-triazol-1-yl]phenyl}-6-oxo-1,6-dihydropyrimidin-1-yl)-3-($^2$H$_3$)methyl-9-methyl-3,4,7-triazatricyclo[12.3.1.0$^{2,6}$]octadeca-1(18),2(6),4,14,16-pentaen-8-one

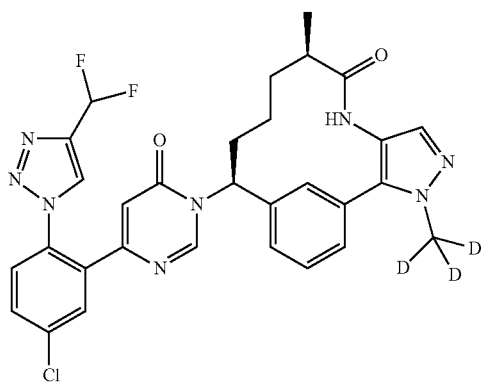 [SMILES: [2H]C([2H])([2H])n1ncc2c1-c1cccc(c1)[C@@H](n1cnc(-c3cc(Cl)ccc3-n3cc(C(F)F)nn3)cc1=O)CCC[C@@H](C)C(=O)N2]

To a solution of 6-{5-chloro-2-[4-(difluoromethyl)-1H-1,2,3-triazol-1-yl]phenyl}pyrimidin-4-ol (0.014 g, 0.043 mmol), prepared as described in Intermediate 16, in CH$_3$CN (0.4 ml) was added HATU (0.021 g, 0.056 mmol) and DBU (9.78 μl, 0.065 mmol). After 30 min, (9R,13S)-13-amino-3-($^2$H$_3$)methyl-9-methyl-3,4,7-tri azatricyclo[12.3.1.0$^{2,6}$]octadeca-1(18),2(6),4,14,16-pentaen-8-one (0.13 g, 0.043 mmol) prepared as described in Intermediate 36, was added with DMF (0.2 ml). Additional CH$_3$CN (0.2 ml) and DMF (0.4 ml) were added to dissolve reagents. After 18 h, the reaction was diluted with DMF, filtered and concentrated. The residue was purified by reverse phase HPLC using PHENOMENEX® Luna 5U 30×100 mm (10:90 ACN/H$_2$O to 90:10 ACN/H$_2$O, 0.1% TFA) (20% B start, 14 min gradient) to afford (9R,13S)-13-(4-{5-chloro-2-[4-(difluoromethyl)-1H-1,2,3-triazol-1-yl]phenyl}-6-oxo-1,6-dihydropyrimidin-1-yl)-3-($^2$H$_3$)methyl-9-methyl-3,4,7-triazatricyclo[12.3.1.0$^{2,6}$]octadeca-1(18),2(6),4,14,16-pentaen-8-one (10.5 mg, 39%) as a white solid. MS(ESI) m/z: 608.3 (M+H)$^+$. $^1$H NMR (400 MHz, CD$_3$OD) δ 8.52 (t, J=1.3 Hz, 1H), 8.14 (s, 1H), 7.93-7.87 (m, 1H), 7.75 (dd, J=8.5, 2.3 Hz, 2H), 7.72-7.66 (m, 1H), 7.64-7.54 (m, 2H), 7.54-7.50 (m, 1H), 7.35-7.30 (m, 1H), 7.14-6.83 (m, 1H), 6.43 (d, J=0.7 Hz, 1H), 5.83 (dd, J=13.0, 3.3 Hz, 1H), 2.49 (dt, J=6.9, 3.4 Hz, 1H), 2.40-2.27 (m, 1H), 2.09 (d, J=12.3 Hz, 1H), 1.95-1.84 (m, 1H), 1.67-1.52 (m, 2H), 1.21 (d, J=6.8 Hz, 1H), 1.16 (d, J=6.8 Hz, 3H) Analytical HPLC (Method A) RT=7.94 min, purity=99%; Factor XIa Ki=0.15 nM, Plasma Kallikrein Ki=21 nM.

Example 73

Preparation of 1-(4-chloro-3-fluoro-2-{1-[(9R,13S)-3-($^2$H$_3$)methyl-9-methyl-8-oxo-3,4,7-triazatricyclo[12.3.1.0$^{2,6}$]octadeca-1(18),2(6),4,14,16-pentaen-13-yl]-6-oxo-1,6-dihydropyrimidin-4-yl}phenyl)-1H-1,2,3-triazole-4-carbonitrile

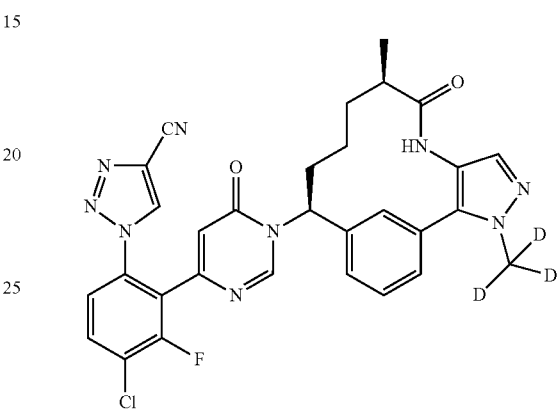

To a solution of 1-[4-chloro-3-fluoro-2-(6-hydroxypyrimidin-4-yl)phenyl]-1H-1,2,3-triazole-4-carbonitrile (0.010 g, 0.032 mmol), prepared as described in Intermediate 12, in CH$_3$CN (0.4 ml) was added HATU (0.016 g, 0.041 mmol) and DBU (7.14 μl, 0.047 mmol). After 30 min, (9R,13S)-13-amino-3-($^2$H$_3$)methyl-9-methyl-3,4,7-triazatricyclo[12.3.1.0$^{2,6}$]octadeca-1(18),2(6),4,14,16-pentaen-8-one (0.095 g, 0.032 mmol), prepared as described in Intermediate 36, was added with DMF (0.2 ml). Additional CH$_3$CN (0.2 ml) and DMF (0.2 ml) were added to dissolve reagents. After 18 h, the reaction was diluted with DMF, filtered and concentrated. The residue was purified by reverse phase HPLC using PHENOMENEX® Luna 5U 30×100 mm (10:90 ACN/H$_2$O to 90:10 ACN/H$_2$O, 0.1% TFA) (20% B start, 14 min gradient) to afford 1-(4-chloro-3-fluoro-2-{1-[(9R,13S)-3-($^2$H$_3$)methyl-9-methyl-8-oxo-3,4,7-triazatricyclo[12.3.1.0$^{2,6}$]octadeca-1(18),2(6),4,14,16-pentaen-13-yl]-6-oxo-1,6-dihydropyrimidin-4-yl}phenyl)-1H-1,2,3-triazole-4-carbonitrile (4.7 mg, 24%) as a white solid. MS(ESI) m/z: 601.3 (M+H)$^+$. $^1$H NMR (400 MHz, CD$_3$OD) δ 8.94 (s, 1H), 8.16 (s, 1H), 7.90 (dd, J=8.7, 7.6 Hz, 1H), 7.77 (s, 1H), 7.70-7.56 (m, 3H), 7.56-7.49 (m, 1H), 7.32 (d, J=7.7 Hz, 1H), 6.79-6.66 (m, 1H), 5.85 (dd, J=12.7, 3.2 Hz, 1H), 2.50 (ddd, J=10.2, 6.7, 3.5 Hz, 1H), 2.39-2.30 (m, 1H), 2.20-2.06 (m, 1H), 1.90 (dd, J=9.6, 4.5 Hz, 1H), 1.69-1.53 (m, 2H), 1.28-1.22 (m, 1H), 1.16 (d, J=6.8 Hz, 3H). Analytical HPLC (Method A) RT=7.99 min, purity=97%; Factor XIa Ki=0.15 nM, Plasma Kallikrein Ki=9 nM.

Example 74

Preparation of 1-(4-chloro-2-{1-[(9R,13S)-3-(difluoromethyl)-9-methyl-8-oxo-3,4,7-triazatricyclo[12.3.1.0²,⁶]octadeca-1(18),2(6),4,14,16-pentaen-13-yl]-6-oxo-1,6-dihydropyrimidin-4-yl}phenyl)-1H-1,2,3-triazole-4-carbonitrile

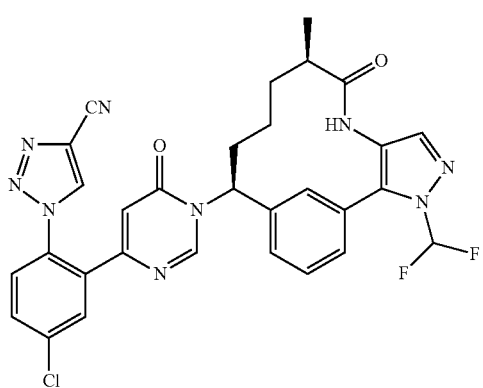 [SMILES: C[C@@H]1CCC[C@H](n2cnc(-c3cc(Cl)ccc3-n3cc(C#N)nn3)cc2=O)c2cccc(c2)-c2c(cnn2C(F)F)NC1=O]

To a solution of 1-[4-chloro-2-(6-hydroxypyrimidin-4-yl)phenyl]-1H-1,2,3-triazole-4-carbonitrile (0.016 g, 0.054 mmol), prepared as described in Intermediate 18, in CH$_3$CN (0.4 ml) was added HATU (0.026 g, 0.070 mmol) and DBU (0.012 mL, 0.080 mmol). After 30 min, (9R,13S)-13-amino-3-(difluoromethyl)-9-methyl-3,4,7-triazatricyclo[12.3.1.0²,⁶]octadeca-1(18),2(6),4,14,16-pentaen-8-one (0.018 g, 0.054 mmol), prepared as described in Intermediate 35, was added with DMF (0.5 ml). After 18 h, the reaction was diluted with DMF, filtered and concentrated. The residue was purified by reverse phase HPLC using PHENOMENEX® Luna 5U 30×100 mm (10:90 ACN/H$_2$O to 90:10 ACN/H$_2$O, 0.1% TFA) (20% B start, 14 min gradient) to afford 1-(4-chloro-2-{1-[(9R,13S)-3-(difluoromethyl)-9-methyl-8-oxo-3,4,7-triazatricyclo[12.3.1.0²,⁶]octadeca-1(18),2(6),4,14,16-pentaen-13-yl]-6-oxo-1,6-dihydropyrimidin-4-yl}phenyl)-1H-1,2,3-triazole-4-carbonitrile (11.7 mg, 34%) as a white solid. MS(ESI) m/z: 616.2 (M+H)$^+$. $^1$H NMR (400 MHz, CD$_3$OD) δ 8.96 (s, 1H), 8.19 (s, 1H), 7.94-7.89 (m, 1H), 7.84-7.74 (m, 4H), 7.72-7.66 (m, 1H), 7.66-7.61 (m, 1H), 7.60-7.55 (m, 1H), 7.40 (d, J=7.5 Hz, 1H), 6.52 (s, 1H), 5.83 (dd, J=12.9, 3.4 Hz, 1H), 2.50 (td, J=6.6, 3.7 Hz, 1H), 2.42-2.31 (m, 1H), 2.17-2.07 (m, 1H), 1.90 (dd, J=10.0, 4.7 Hz, 1H), 1.63-1.53 (m, 2H), 1.28-1.20 (m, 1H), 1.16 (d, J=6.8 Hz, 3H). Analytical HPLC (Method A) RT=8.82, purity=97%; Factor XIa Ki=0.1 nM, Plasma Kallikrein Ki=10 nM.

Example 75

Preparation of (9R,13)-13-(4-{5-chloro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7-triazatricyclo[12.3.1.0²,⁶]octadeca-1(18),2(6),4,14,16-pentaen-8-one

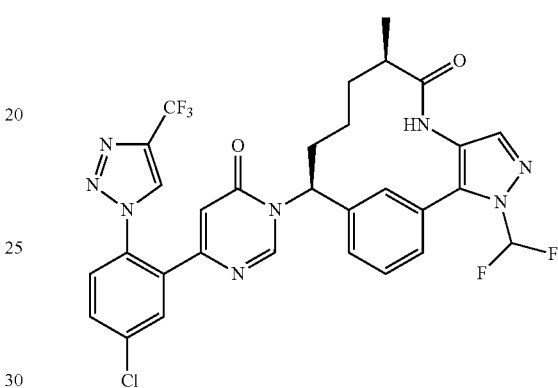

To a solution of 6-{5-chloro-2-[4-(trifluoromethyl)-1H-1,2,3-triazol-1-yl]phenyl}pyrimidin-4-ol (0.029 g, 0.084 mmol), prepared as described in Intermediate 15, in CH$_3$CN (0.8 ml) was added HATU (0.041 g, 0.109 mmol) and DBU (0.019 mL, 0.126 mmol). After 30 min, (9R,13)-13-amino-3-(difluoromethyl)-9-methyl-3,4,7-triazatricyclo[12.3.1.0²,⁶]octadeca-1(18),2(6),4,14,16-pentaen-8-one (0.028 g, 0.084 mmol), prepared as described in Example 35, was added with DMF (0.4 ml). The reaction was stirred 4 h then was diluted with DMF, filtered and concentrated. The residue was purified by reverse phase HPLC using PHENOMENEX® Luna 5U 30×100 mm (10:90 ACN/H$_2$O to 90:10 ACN/H$_2$O, 0.1% TFA) (20% B start, 14 min gradient) to afford (9R,13S)-13-(4-{5-chloro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7-triazatricyclo[12.3.1.0²,⁶]octadeca-1(18),2(6),4,14,16-pentaen-8-one (18.8 mg, 34%) as a white solid. MS(ESI) m/z: 659.03 (M+H)$^+$. $^1$H NMR (400 MHz, CD$_3$OD) δ 8.81 (d, J=0.7 Hz, 1H), 8.18 (s, 1H), 7.89 (d, J=2.4 Hz, 1H), 7.82-7.74 (m, 3H), 7.70 (s, 1H), 7.64-7.56 (m, 3H), 7.42-7.36 (m, 1H), 6.49 (d, J=0.7 Hz, 1H), 5.83 (dd, J=12.9, 3.2 Hz, 1H), 2.50 (ddd, J=10.2, 6.8, 3.4 Hz, 1H), 2.35 (d, J=12.3 Hz, 1H), 2.15-2.06 (m, 1H), 1.94-1.85 (m, 1H), 1.65-1.51 (m, 2H), 1.31-1.20 (m, 1H), 1.16 (d, J=6.8 Hz, 3H). Analytical HPLC (Method A) RT=9.40 min, purity=100%; Factor XIa Ki=0.1 nM, Plasma Kallikrein Ki=15 nM.

Example 76

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-3,8-diazatricyclo[13.3.1.0$^{2,7}$]nonadeca-1(19),2(7),3,5,15,17-hexaen-9-one

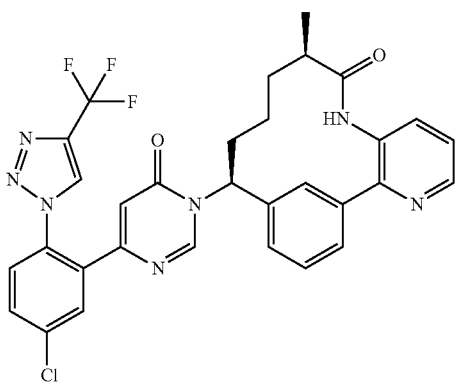 [SMILES: C[C@@H]1CCC[C@H](n2cnc(-c3cc(Cl)ccc3-n3cc(C(F)(F)F)nn3)cc2=O)c2cccc(c2)-c2ncccc2NC1=O]

To a solution of 6-{5-chloro-2-[4-(trifluoromethyl)-1H-1,2,3-triazol-1-yl]phenyl}pyrimidin-4-ol (0.035 g, 0.102 mmol), prepared as described in Intermediate 15, in CH$_3$CN (0.4 ml) was added HATU (0.050 g, 0.132 mmol) and DBU (0.023 mL, 0.152 mmol). After 30 min, (10R,14S)-14-amino-10-methyl-3,8-diazatricyclo[13.3.1.0$^{2,7}$]nonadeca-1(19),2(7),3,5,15,17-hexaen-9-one (0.030 g, 0.102 mmol), prepared as described in Intermediate 38, was added with DMF (0.6 ml). After 18 h, the reaction was diluted with DMF, filtered and concentrated. The residue was purified by preparative LCMS using (5:95 ACN/H$_2$O to 95:5 ACN/H$_2$O, 0.1% TFA) to afford (10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-3,8-diazatricyclo[13.3.1.0$^{2,7}$]nonadeca-1(19),2(7),3,5,15,17-hexaen-9-one (8.6 mg, 11.1%). MS(ESI) m/z: 620.08 (M+H)$^+$. $^1$H NMR (400 MHz, CD$_3$OD) δ 8.81-8.72 (m, 1H), 8.59 (d, J=4.3 Hz, 1H), 8.16 (s, 1H), 7.88-7.83 (m, 2H), 7.78-7.65 (m, 4H), 7.58-7.53 (m, 1H), 7.53-7.48 (m, 1H), 7.28 (d, J=7.6 Hz, 1H), 6.43 (s, 1H), 5.88-5.72 (m, 1H), 2.49 (br. s., 1H), 2.27 (d, J=10.4 Hz, 1H), 2.10 (d, J=10.1 Hz, 1H), 1.85 (d, J=8.9 Hz, 1H), 1.55 (d, J=9.8 Hz, 2H), 1.28 (br. s., 1H), 1.13 (d, J=6.7 Hz, 3H). Analytical HPLC (Method C) RT=1.55 min, purity=97%; Factor XIa Ki=1.7 nM, Plasma Kallikrein Ki=130 nM.

Example 77

Preparation of (9R,13S)-13-{4-[5-chloro-2-(4-chloro-1H-1,2,3-triazol-1-yl)phenyl]-6-oxo-1,6-dihydropyrimidin-1-yl}-3,9-dimethyl-3,4,7,17-tetraazatricyclo[12.3.1.0$^{2,6}$]octadeca-1(18),2(6),4,14,16-pentaen-8-one

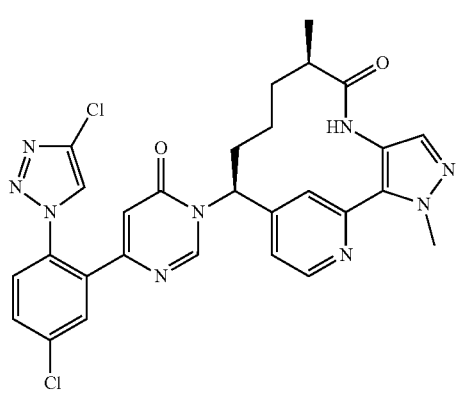 [SMILES: C[C@@H]1CCC[C@H](n2cnc(-c3cc(Cl)ccc3-n3cc(Cl)nn3)cc2=O)c2ccnc(c2)-c2c(cnn2C)NC1=O]

To a solution of 6-[5-chloro-2-(4-chloro-1H-1,2,3-triazol-1-yl)phenyl]pyrimidin-4-ol (0.019 g, 0.060 mmol), prepared as described in Intermediate 9, in CH$_3$CN (0.4 ml) was added HATU (0.030 g, 0.078 mmol) and DBU (0.014 mL, 0.090 mmol). After 30 min, (9R,13S)-13-amino-3,9-dimethyl-3,4,7,17-tetraazatricyclo[12.3.1.0$^{2,6}$]octadeca-1(18),2(6),4,14,16-pentaen-8-one, prepared as described in Intermediate 42, was added with DMF (0.2 ml). After 18 h, the reaction was diluted with DMF, filtered and concentrated. The residue was purified by reverse phase HPLC using PHENOMENEX® Luna 5U 30×100 mm (10:90 ACN/H$_2$O to 90:10 ACN/H$_2$O, 0.1% TFA) (20% B start, 14 min gradient) to afford (9R,13S)-13-{4-[5-chloro-2-(4-chloro-1H-1,2,3-triazol-1-yl)phenyl]-6-oxo-1,6-dihydropyrimidin-1-yl}-3,9-dimethyl-3,4,7,17-tetraazatricyclo[12.3.1.0$^{2,6}$]octadeca-1(18),2(6),4,14,16-pentaen-8-one (11.9 mg, 27%) as an off-white solid. MS(ESI) m/z: 590.3 (M+H)$^+$. $^1$H NMR (400 MHz, CD$_3$OD) δ d 8.78-8.70 (m, 1H), 8.41-8.33 (m, 2H), 7.92-7.85 (m, 2H), 7.80-7.73 (m, 1H), 7.71-7.65 (m, 1H), 7.51 (s, 1H), 7.21 (dd, J=5.3, 1.8 Hz, 1H), 6.50-6.42 (m, 1H), 5.77 (dd, J=12.5, 3.1 Hz, 1H), 4.23-4.16 (m, 3H), 2.69-2.58 (m, 1H), 2.41 (dd, J=7.5, 4.2 Hz, 1H), 2.22-2.09 (m, 1H), 2.07-1.96 (m, 1H), 1.74-1.60 (m, 1H), 1.38 (d, J=7.7 Hz, 2H), 1.15 (d, J=7.0 Hz, 3H). Analytical HPLC (Method A) RT=7.38 min, purity=96%; Factor XIa Ki=0.2 nM, Plasma Kallikrein Ki=23 nM.

Example 78

Preparation of (9R,13S)-13-{4-[2-(4-bromo-1H-1,2,3-triazol-1-yl)-5-chlorophenyl]-6-oxo-1,6-dihydropyrimidin-1-yl}-3-($^2$H$_3$)methyl-9-methyl-3,4,7-triazatricyclo[12.3.1.0$^{2,6}$]octadeca-1(18),2(6),4,14,16-pentaen-8-one

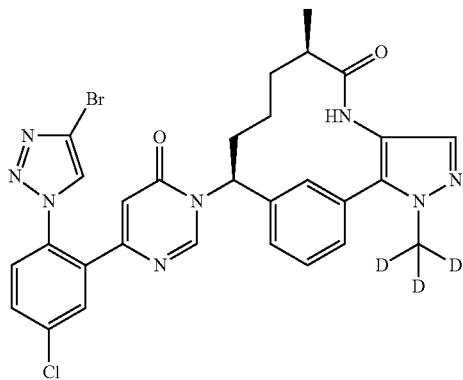 [SMILES: [2H]C([2H])([2H])n1ncc2c1-c1cccc(c1)[C@@H](n1cnc(-c3cc(Cl)ccc3-n3cc(Br)nn3)cc1=O)CCC[C@@H](C)C(=O)N2]

To 6-[2-(4-bromo-1H-1,2,3-triazol-1-yl)-5-chlorophenyl]pyrimidin-4-ol (0.05 g, 0.142 mmol) and HATU (0.070 g, 0.184 mmol) in a small vial was added DBU (0.032 mL, 0.213 mmol) in CH$_3$CN (0.8 ml). After 30 min, (9R,13S)-13-amino-3-($^2$H$_3$)methyl-9-methyl-3,4,7-triazatricyclo[12.3.1.0$^{2,6}$]octadeca-1(18),2(6),4,14,16-pentaen-8-one (0.043 g, 0.142 mmol), prepared as described in Intermediate 36, was added and the vial was rinsed with DMF (0.2 ml). After 18 h, the reaction was diluted with DMF, filtered and purified by reverse phase HPLC using PHENOMENEX® Luna 5U 30×100 mm (10:90 MeOH/H$_2$O to 90:10 MeOH/H$_2$O, 0.1% TFA) (20% B start, 14 min gradient) to afford (9R,13S)-13-{4-[2-(4-bromo-1H-1,2,3-triazol-1-yl)-5-chlorophenyl]-6-oxo-1,6-dihydropyrimidin-1-yl}-3-($^2$H$_3$)methyl-9-methyl-3,4,7-triazatricyclo[12.3.1.0$^{2,6}$]octadeca-1(18),2(6),4,14,16-pentaen-8-one (30 mg, 33%) as a white solid. This compound was used in subsequent reaction and a small amount (4 mg, white solid after freeze-drying) was isolated by preparative LCMS using (5:95 AcN/H$_2$O to 95:5 AcN/H$_2$O, 10 mM NH$_4$OAc). MS(ESI) m/z: 638.4 (M+H)$^+$. $^1$H NMR (400 MHz, CD$_3$OD) δ 8.25 (s, 1H), 8.06 (s, 1H), 7.75 (d, J=2.4 Hz, 1H), 7.68-7.59 (m, 2H), 7.56-7.43 (m, 3H), 7.40-7.36 (m, 1H), 7.21 (d, J=7.5 Hz, 1H), 6.30 (s, 1H), 5.71 (dd, J=12.7, 3.2 Hz, 1H), 2.43-2.32 (m, 1H), 2.28-2.18 (m, 1H), 1.98 (d, J=12.3 Hz, 1H), 1.84-1.73 (m, 1H), 1.56-1.41 (m, 2H), 1.10 (br. s., 1H), 1.03 (d, J=6.8 Hz, 3H). Analytical HPLC (Method C) RT=1.60 min, purity=96%; Factor XIa Ki=0.1 nM, Plasma Kallikrein Ki=7 nM.

Example 79

Preparation of (9R,13S)-13-(4-{5-chloro-2-[4-(pyrimidin-2-yl)-1H-1,2,3-triazol-1-yl]phenyl}-6-oxo-1,6-dihydropyrimidin-1-yl)-3-($^2$H$_3$)methyl-9-methyl-3,4,7-triazatricyclo[12.3.1.0$^{2,6}$]octadeca-1(18),2(6),4,14,16-pentaen-8-one

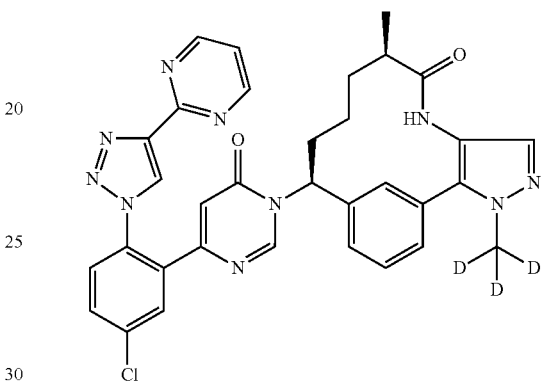

(9R,13S)-13-{4-[2-(4-Bromo-1H-1,2,3-triazol-1-yl)-5-chlorophenyl]-6-oxo-1,6-dihydropyrimidin-1-yl}-3-($^2$H$_3$)methyl-9-methyl-3,4,7-triazatricyclo[12.3.1.0$^{2,6}$]octadeca-1(18),2(6),4,14,16-pentaen-8-one 0.014 g, 0.022 mmol), prepared as described in Example 78, pyrimidin-2-ylboronic acid (2.59 mg, 0.021 mmol), and 2.0 M aq Na$_2$CO$_3$ (0.033 mL, 0.066 mmol) were added to dioxane (0.6 ml) and the resulting solution was purged with a stream of Ar. Pd(PPh$_3$)$_4$ (1.270 mg, 1.099 μmol) was then added and the mixture was heated to 120° C. in a microwave for 30 min. The reaction was concentrated and the residue was diluted with DMF, filtered and reconcentrated. The residue was purified by preparative LCMS using (5:95 ACN/H$_2$O to 95:5 ACN/H$_2$O, 10 mM NH$_4$OAc) to give (9R,13S)-13-(4-{5-chloro-2-[4-(pyrimidin-2-yl)-1H-1,2,3-triazol-1-yl]phenyl}-6-oxo-1,6-dihydropyrimidin-1-yl)-3-($^2$H$_3$)methyl-9-methyl-3,4,7-triazatricyclo[12.3.1.0$^{2,6}$]octadeca-1(18),2(6),4,14,16-pentaen-8-one (2.5 mg, 25%). MS(ESI) m/z: 636.08 (M+H)$^+$. $^1$H NMR (400 MHz, CD$_3$OD) δ 9.16-9.11 (m, 2H), 9.06 (s, 1H), 8.75-8.65 (m, 1H), 8.02 (s, 1H), 7.85-7.77 (m, 1H), 7.71-7.63 (m, 1H), 7.63-7.58 (m, 2H), 7.45-7.35 (m, 3H), 7.16 (s, 1H), 6.37-6.30 (m, 1H), 5.69 (d, J=9.2 Hz, 1H), 2.35 (s, 1H), 2.18 (d, J=9.9 Hz, 1H), 1.95 (d, J=7.9 Hz, 1H), 1.73 (s, 1H), 1.44 (d, J=9.5 Hz, 2H), 1.19 (m, 1H), 1.02 (d, J=6.8 Hz, 3H). Analytical HPLC (Method C) RT=1.43 min, purity=95%; Factor XIa Ki=1.0 nM, Plasma Kallikrein Ki=150 nM.

Example 80

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-4,10-dimethyl-3,8-diazatricyclo[13.3.1.0$^{2,7}$]nonadeca-1(19),2(7),3,5,15,17-hexaen-9-one

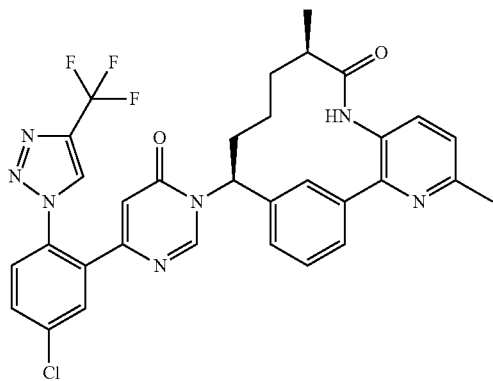 [SMILES: Cc1ccc2c(n1)-c1cccc(c1)[C@@H](n1cnc(-c3cc(Cl)ccc3-n3cc(C(F)(F)F)nn3)cc1=O)CCC[C@@H](C)C(=O)N2]

80A. Preparation of Tert-Butyl N-[(1S)-1-[3-(5,5-dimethyl-1,3,2-dioxaborinan-2-yl) phenyl]but-3-en-1-yl]carbamate To a RBF was added tert-butyl N-[(1S)-1-(3-bromophenyl)but-3-en-1-yl]carbamate (2.6 g, 7.97 mmol), 5,5,5',5'-tetramethyl-2,2'-bi(1,3,2-dioxaborinane (1.980 g, 8.77 mmol), and KOAc (2.347 g, 23.91 mmol) in dioxane (35 ml). The mixture was purged with Ar for 10 min, then PdCl$_2$(dppf)-DCM adduct (0.325 g, 0.398 mmol) was added and the reaction was stirred at 90° C. for 4 h. The reaction was partitioned between EtOAc (50 ml) and water (40 ml). The organic layer was separated, washed with water (15 ml), brine (30 ml), dried over MgSO$_4$, filtered and concentrated. The residue was purified by normal phase chromatography using hexanes and EtOAc as eluents to afford tert-butyl N-[(1S)-1-[3-(5,5-dimethyl-1,3,2-dioxaborinan-2-yl)phenyl]but-3-en-1-yl]carbamate (2.62 g, 92%) as a white solid. MS(ESI) m/z: 292.08 (M+H)$^+$.

80B. Preparation of Tert-Butyl N-[(1S)-1-[3-(3-amino-6-methylpyridin-2-yl)phenyl]but-3-en-1-yl]carbamate tert-Butyl N-[(1S)-1-[3-(5,5-dimethyl-1,3,2-dioxaborinan-2-yl)phenyl]but-3-en-1-yl]carbamate (0.67 g, 1.865 mmol), 2-bromo-6-methylpyridin-3-amine (0.349 g, 1.865 mmol), and 2 M aq Na$_2$CO$_3$ (4 mL, 8.00 mmol) were added to dioxane (9 ml) and the solution was purged with a stream of Ar for 10 min. Pd(PPh$_3$)$_4$ (0.108 g, 0.093 mmol) was added and the mixture was irradiated in a microwave at 120° C. for 30 min. The reaction was quenched with water (20 ml) and extracted with EtOAc (3×30 ml). The combined organic layers were washed with brine (15 ml), dried (MgSO$_4$), filtered and concentrated. The residue was purified by normal phase chromatography using DCM and 0-10% MeOH as eluents to afford tert-butyl N-[(1S)-1-[3-(3-amino-6-methylpyridin-2-yl)phenyl]but-3-en-1-yl]carbamate (0.94g, 100%, 70% purity) as a brown oil. MS(ESI) m/z: 354.5 (M+H)$^+$.

80C. Preparation of Tert-Butyl N-[(1S)-1-(3-{6-methyl-3-[(2R)-2-methylbut-3-enamido]pyridin-2-yl}phenyl)but-3-en-1-yl]carbamate To a solution of tert-butyl N-[(1S)-1-[3-(3-amino-6-methylpyridin-2-yl)phenyl]but-3-en-1-yl]carbamate (0.65 g, 1.83 mmol) in EtOAc (0.58 ml), was added (R)-2-methylbut-3-enoic acid (0.239 g, 2.391 mmol), prepared as described in Intermediate 2, in 0.3 ml EtOAc. The resulting solution was cooled to 0° C. and pyridine (0.446 ml, 5.52 mmol) and a 50% EtOAc solution of T3P® (2.189 ml, 3.68 mmol) were added. After 3 h, the reaction was quenched with sat NaHCO$_3$(15 ml) and extracted with EtOAc (3×20 ml). The combined organic layers were washed with brine (15 ml) and dried (MgSO$_4$). The mixture was filtered and concentrated and the residue was purified by normal phase chromatography using DCM and 0-10% MeOH as eluents to afford tert-butyl N-[(1S)-1-(3-{6-Methyl-3-[(2R)-2-methylbut-3-enamido]pyridin-2-yl}phenyl)but-3-en-1-yl]carbamate (0.65 g, 82%) as a tan foam. MS(ESI) m/z: 436.08 (M+H)$^+$. $^1$H NMR (500 MHz, CDCl$_3$) δ 8.56 (d, J=8.5 Hz, 1H), 7.54-7.46 (m, 2H), 7.42 (s, 1H), 7.37 (d, J=1.4 Hz, 2H), 7.17 (d, J=8.5 Hz, 1H), 5.90-5.67 (m, 2H), 5.22-5.03 (m, 4H), 5.00-4.75 (m, 3H), 3.05 (t, J=7.3 Hz, 1H), 2.62 (br. s. and m, 4H), 1.50-1.39 (m, 9H), 1.28 (d, J=7.2 Hz, 3H).

80D. Preparation of Tert-Butyl N-[(10R,11E,14S)-4,10-dimethyl-9-oxo-3,8-diazatricyclo[13.3.1.0$^{2,7}$]nonadeca-1(19),2(7),3,5,11,15,17-heptaen-14-yl]carbamate To a solution of tert-butyl N-[(1S)-1-(3-{6-methyl-3-[(2R)-2-methylbut-3-enamido]pyridin-2-yl}phenyl)but-3-en-1-yl]carbamate (0.2 g, 0.459 mmol) in degassed DCE (20 ml) was added Second Generation Grubbs Catalyst (0.156 g, 0.184 mmol) and the resulting reaction mixture was heated to 120° C. for 30 min in a microwave. The reaction mixture was directly purified by normal phase chromatography using DCM and 0-10% MeOH as eluents to afford tert-butyl N-[(10R,11E,14S)-4,10-dimethyl-9-oxo-3,8-diazatricyclo[13.3.1.0$^{2,7}$]nonadeca-1 (19),2(7),3,5,11,15,17-heptaen-14-yl]carbamate (0.19g, 100%) as a dark solid. MS(ESI) m/z: 408.08 (M+H)$^+$.

80E. Preparation of (10R,14S)-14-amino-4,10-dimethyl-3,8-diazatricyclo[13.3.1.0$^{2,7}$]nonadeca-1(19),2(7),3,5,15,17-hexaen-9-one

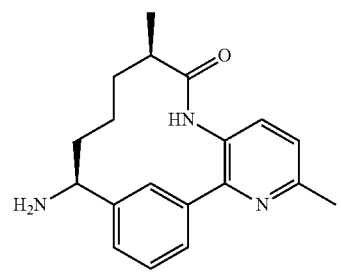 [SMILES: Cc1ccc2c(n1)-c1cccc(c1)[C@@H](N)CCC[C@@H](C)C(=O)N2]

tert-Butyl N-[(10R,11E,14S)-4,10-dimethyl-9-oxo-3,8-diazatricyclo[13.3.1.0$^{2,7}$]nonadeca-1(19),2(7),3,5,11,15,17-heptaen-14-yl]carbamate (0.187 g, 0.459 mmol) was hydrogenated in EtOH (3 ml) in the presence of PtO₂ at 20-30 psi. After 4 h, the reaction mixture was filtered through CELITE® and concentrated to afford a dark solid (MS(ESI) m/z: 410.3 (M+H)⁺) which was then deprotected with 4 N HCl in dioxane (2 ml) and MeOH (2 ml). The resultant HCl salt was dissolved in DCM/MeOH and passed through a basic cartridge to afford (0.16g, 118%) of a crude dark solid containing as the major component, (10R,14S)-14-amino-4,10-dimethyl-3,8-diazatricyclo[13.3.1.0$^{2,7}$]nonadeca-1(19),2(7),3,5,15,17-hexaen-9-one, which was used in next step without purification. MS(ESI) m/z: 310.3 (M+H)⁺.

80F. Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-4,10-dimethyl-3,8-diazatricyclo[13.3.1.0$^{2,7}$]nonadeca-1(19),2(7),3,5,15,17-hexaen-9-one

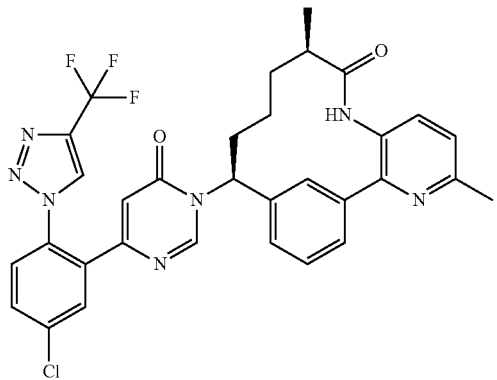 [SMILES: Cc1ccc2c(n1)-c1cccc(c1)[C@@H](n1cnc(-c3cc(Cl)ccc3-n3cc(C(F)(F)F)nn3)cc1=O)CCC[C@@H](C)C(=O)N2]

To 6-{5-chloro-2-[4-(trifluoromethyl)-1H-1,2,3-triazol-1-yl]phenyl}pyrimidin-4-ol (0.033 g, 0.097 mmol), prepared as described in Intermediate 15, and HATU (0.048 g, 0.126 mmol) in a small vial was added DBU (0.022 mL, 0.145 mmol) in ACN (0.4 ml). After 30 min, (10R,14S)-14-amino-4,10-dimethyl-3,8-diazatricyclo[13.3.1.0$^{2,7}$]nonadeca-1(19),2(7),3,5,15,17-hexaen-9-one (0.033 g, 0.097 mmol) was added with DMF (0.2 ml). The reaction was stirred for 18 h. The reaction was diluted with DMF, filtered and purified by preparative LCMS using (5:95 ACN/H₂O to 95:5 ACN/H₂O, 10 mM NH₄OAc) to afford (10R,14S)-14-(4-{5-chloro-2-[4-(trifluoromethyl)-1H-1,2,3-triazol-1-yl]phenyl}-6-oxo-1,6-dihydropyrimidin-1-yl)-4,10-dimethyl-3,8-diazatricyclo[13.3.1.0$^{2,7}$]nonadeca-1(19),2(7),3,5,15,17-hexaen-9-one (5.8 mg, 7.7% yield) as a white solid. MS(ESI) m/z: 634.4 (M+H)⁺. ¹H NMR (500 MHz, CD₃OD) δ 8.75 (s, 1H), 8.12 (s, 1H), 7.86-7.82 (m, 2H), 7.77-7.64 (m, 3H), 7.62-7.54 (m, 2H), 7.34 (d, J=8.2 Hz, 1H), 7.29 (d, J=7.9 Hz, 1H), 6.43 (s, 1H), 5.86-5.73 (m, 1H), 2.61 (s, 3H), 2.45 (br. s., 1H), 2.26 (d, J=9.5 Hz, 1H), 2.11 (br. s., 1H), 1.82 (br. s., 1H), 1.64-1.49 (m, 2H), 1.28-1.21 (m, 1H), 1.13 (d, J=6.7 Hz, 3H). Analytical HPLC (Method C) RT=1.54 min, purity=97%; Factor XIa Ki=2.2 nM, Plasma Kallikrein Ki=260 nM.

Example 81

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-5-methoxy-10-methyl-3,8-diazatricyclo[13.3.1.0$^{2,7}$]nonadeca-1(19),2(7),3,5,15,17-hexaen-9-one

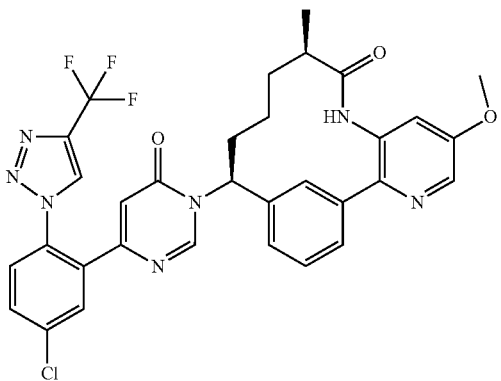 [SMILES: COc1cnc2c(c1)NC(=O)[C@H](C)CCC[C@H](n1cnc(-c3cc(Cl)ccc3-n3cc(C(F)(F)F)nn3)cc1=O)c1cccc-2c1]

81A. Preparation of Tert-Butyl N-[(1S)-1-[3-(3-amino-5-methoxypyridin-2-yl)phenyl]but-3-en-1-yl]carbamate tert-Butyl N-[(1S)-1-[3-(5,5-dimethyl-1,3,2-dioxaborinan-2-yl)phenyl]but-3-en-1-yl]carbamate (0.348 g, 0.969 mmol), 2-bromo-5-methoxypyridin-3-amine (0.197 g, 0.969 mmol), and 2.0 M aq Na₂CO₃ (2.422 mL, 4.84 mmol) were added to dioxane (8 ml) and the solution was purged with a stream of Ar for 10 min. Pd(PPh₃)₄ (0.056 g, 0.048 mmol) was added and the mixture irradiated in microwave at 120° C. for 30 min. The reaction was quenched with water (20 ml) and extracted with EtOAc (3×30 ml). The combined organic layers were washed with brine (15 ml), dried (MgSO₄), filtered and concentrated. The residue was purified by normal phase chromatography using DCM and 0-10% MeOH as eluents to afford tert-butyl N-[(1S)-1-[3-(3-amino-5-methoxypyridin-2-yl)phenyl]but-3-en-1-yl]carbamate (0.391g, 100%) as a tan foam. MS(ESI) m/z: 370.08 (M+H)⁺. ¹H NMR (500 MHz, CDCl₃) δ 7.89 (d, J=2.5 Hz, 1H), 7.60-7.52 (m, 2H), 7.45 (t, J=7.6 Hz, 1H), 7.33-7.29 (m, 1H), 6.62 (d, J=2.5 Hz, 1H), 5.73 (ddt, J=17.1, 10.1, 7.0 Hz, 1H), 5.21-5.06 (m, 2H), 4.93 (br. s., 1H), 4.81 (br. s., 1H), 3.92-3.86 (m, 4H), 3.77-3.71 (m, 1H), 2.64-2.52 (m, 2H), 1.44 (br. s., 9H).

81B. Preparation of Tert-Butyl N-[(1S)-1-(3-{5-methoxy-3-[(2R)-2-methylbut-3-enamido]pyridin-2-yl}phenyl)but-3-en-1-yl]carbamate To tert-butyl N-[(1S)-1-[3-(3-amino-5-methoxypyridin-2-yl)phenyl]but-3-en-1-yl]carbamate (0.358 g, 0.972 mmol) was added (R)-2-methylbut-3-enoic acid (0.126 g, 1.263 mmol), prepared as described in Intermediate 2, in EtOAc (3 ml). The resulting solution was cooled to 0° C. Pyridine (0.236 ml, 2.91 mmol) and a 50% EtOAc solution of T3P® (1.157 ml, 1.943 mmol) were added. The reaction was partitioned between sat NaHCO₃(10 ml) and EtOAc (20 ml). The aqueous layer was extracted with EtOAc (2×20 ml). The combined organic layers were washed with brine (25 ml), dried (MgSO₄), filtered and concentrated. The residue was purified by normal phase chromatography using heptanes and EtOAc as eluents to afford tert-butyl N-[(1S)-1-(3-{5-methoxy-3-[(2R)-2-methylbut-3-enamido]pyridin-2-yl}phenyl)but-3-en-1-yl]carbamate (0.347g, 79%) as a white foam. MS(ESI) m/z: 452.08 (M+H)⁺. ¹H NMR (500 MHz, CDCl₃) δ 8.47 (d, J=2.8 Hz, 1H), 8.16 (d, J=2.8 Hz, 1H), 7.65 (br. s., 1H), 7.53-7.46 (m, 1H), 7.46-7.41 (m, 1H), 7.37 (dt, J=7.5, 1.9 Hz, 2H), 5.86-5.65 (m, 2H), 5.19-5.07 (m, 4H), 4.93 (br. s., 1H), 4.82 (br. s., 1H), 3.93 (s, 3H), 3.07 (quin, J=7.3 Hz, 1H), 2.62-2.51 (m, 2H), 1.50-1.41 (m, 9H), 1.32-1.29 (m, 3H).

81C. Preparation of Tert-Butyl N-[(10R,11E,14S)-5-methoxy-10-methyl-9-oxo-3,8-diazatricyclo[13.3.1.0²,⁷]nonadeca-1 (19),2(7),3,5,11,15,17-heptaen-14-yl]carbamate A solution of tert-butyl N-[(1S)-1-(3-{5-methoxy-3-[(2R)-2-methylbut-3-enamido]pyridin-2-yl}phenyl)but-3-en-1-yl]carbamate (0.189 g, 0.419 mmol) in degassed DCE (20 ml) in the presence of Second Generation Grubbs Catalyst (0.107 g, 0.126 mmol) was heated to 120° C. for 30 min in a microwave. The reaction mixture was directly purified by normal phase chromatography using DCM and 0-10% MeOH as eluents to afford tert-butyl N-[(10R,11E,14S)-5-methoxy-10-methyl-9-oxo-3,8-diazatricyclo[13.3.1.0²,⁷]nonadeca-1 (19),2(7),3,5,11,15,17-heptaen-14-yl]carbamate (0.17g, 96%) as a dark brown oil. MS(ESI) m/z: 424.1 (M+H)⁺.

81D. Preparation of (10R,14S)-14-amino-5-methoxy-10-methyl-3,8-diazatricyclo[13.3.1.0²,⁷]nonadeca-1(19),2(7),3,5,15,17-hexaen-9-one

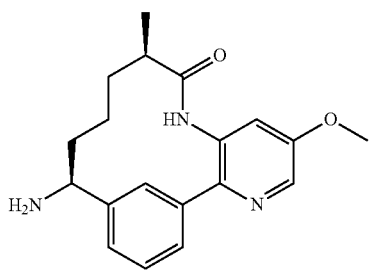 [SMILES: COc1cnc2c(c1)NC(=O)[C@H](C)CCC[C@H](N)c1cccc-2c1]

tert-Butyl N-[(10R,11E,14S)-5-methoxy-10-methyl-9-oxo-3,8-diazatricyclo[13.3.1.0²,⁷]nonadeca-1(19),2(7),3,5,11,15,17-heptaen-14-yl]carbamate (0.177 g, 0.418 mmol) was hydrogenated in EtOH (3 ml) in the presence of PtO₂ (20 mg) over 8 h. The resultant thick sludge was filtered through CELITE® and rinsed with DCM, MeOH and EtOH to afford 0.121g of a dark solid. MS(ESI) m/z: 426.4 (M+H)⁺. Deprotection was performed with 4 N HCl in dioxane (2 ml) in MeOH (4 ml) over 3 h. The reaction mixture was concentrated and the residue was taken up in DCM/MeOH and filtered through a basic cartridge to give (10R,14S)-14-amino-5-methoxy-10-methyl-3,8-diazatricyclo[13.3.1.0²,⁷]nonadeca-1(19),2(7),3,5,15,17-hexaen-9-one as a dark solid (0.108g, 79%). MS(ESI) m/z: 326.4 (M+H)⁺.

81E. Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-5-methoxy-10-methyl-3,8-diazatricyclo[13.3.1.0²,⁷]nonadeca-1(19),2(7),3,5,15,17-hexaen-9-one

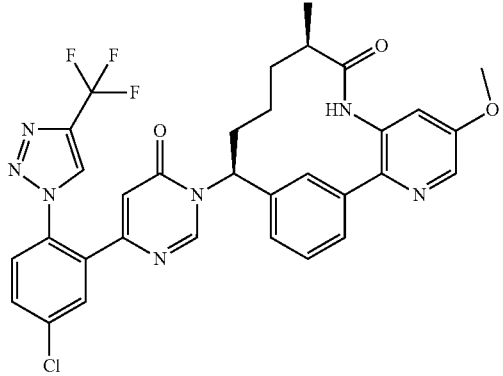 [SMILES: COc1cnc2c(c1)NC(=O)[C@H](C)CCC[C@H](n1cnc(-c3cc(Cl)ccc3-n3cc(C(F)(F)F)nn3)cc1=O)c1cccc-2c1]

To 6-{5-chloro-2-[4-(trifluoromethyl)-1H-1,2,3-triazol-1-yl]phenyl}pyrimidin-4-ol (0.032 g, 0.092 mmol), prepared as described in Intermediate 15, and HATU (0.046 g, 0.120 mmol) in a small vial was added DBU (0.021 mL, 0.138 mmol) in ACN (0.4 ml). After 30 min, (10R,14S)-14-amino-5-methoxy-10-methyl-3,8-diazatricyclo[13.3.1.0²,⁷]nonadeca-1(19),2(7),3,5,15,17-hexaen-9-one (0.030 g, 0.092 mmol) was added with DMF (0.4 ml). After 18 h, the reaction was diluted with DMF, filtered and concentrated. The residue was purified twice by reverse phase HPLC using PHENOMENEX® Luna 5U 30×100 mm (10:90 ACN/H₂O to 90:10 ACN/H₂O, 0.1% TFA) (20% B start, 14 min gradient) to afford (10R,14S)-14-(4-{5-chloro-2-[4-(trifluoromethyl)-1H-1,2,3-triazol-1-yl]phenyl}-6-oxo-1,6-dihydropyrimidin-1-yl)-5-methoxy-10-methyl-3,8-diazatricyclo[13.3.1.0²,⁷]nonadeca-1(19),2(7),3,5,15,17-hexaen-9-one (3.7 mg, 4.8%) as a white solid. MS(ESI) m/z: 650.3 (M+H)⁺. ¹H NMR (400 MHz, CD₃OD) δ 8.82 (d, J=0.7 Hz, 1H), 8.39 (d, J=2.6 Hz, 1H), 8.25 (s, 1H), 7.89 (d, J=2.2 Hz, 1H), 7.86 (s, 1H), 7.80-7.74 (m, 1H), 7.71-7.63 (m, 2H), 7.62-7.55 (m, 2H), 7.29 (d, J=7.9 Hz, 1H), 6.47 (d, J=0.7 Hz, 1H), 5.81 (dd, J=13.0, 3.5 Hz, 1H), 4.03-4.01 (m, 3H), 2.60-2.49 (m, 1H), 2.34-2.26 (m, 1H), 2.18-2.08 (m, 1H), 1.94-1.85 (m, 1H), 1.62-1.46 (m, 2H), 1.33 (d, J=9.7 Hz, 1H), 1.15 (d, J=6.8 Hz, 3H). Analytical HPLC (Method A) RT=8.44, purity=93%; Factor XIa Ki=22 nM, Plasma Kallikrein Ki=950 nM.

Example 82

Preparation of (10R,14S)-5-chloro-14-(4-{5-chloro-2-[4-(trifluoromethyl)-1H-1,2,3-triazol-1-yl]phenyl}-6-oxo-1,6-dihydropyrimidin-1-yl)-10-methyl-3,8-diazatricyclo[13.3.1.0²,⁷]nonadeca-1(19),2(7),3,5,15,17-hexaen-9-one

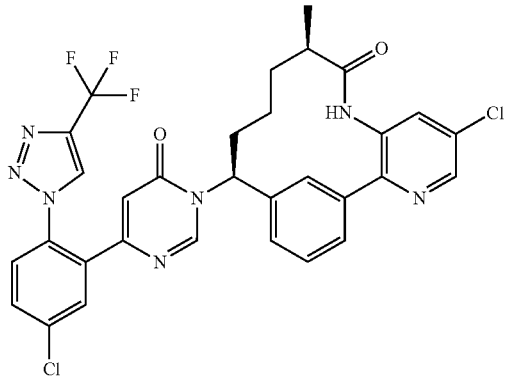 [SMILES: C[C@@H]1CCC[C@H](n2cnc(-c3cc(Cl)ccc3-n3cc(C(F)(F)F)nn3)cc2=O)c2cccc(c2)-c2ncc(Cl)cc2NC1=O]

82A. Preparation of Tert-Butyl N-[(1S)-1-[3-(3-amino-5-chloropyridin-2-yl)phenyl]but-3-en-1-yl]carbamate tert-Butyl N-[(1S)-1-[3-(5,5-dimethyl-1,3,2-dioxaborinan-2-yl)phenyl]but-3-en-1-yl]carbamate (0.339 g, 0.944 mmol), 2-bromo-5-chloropyridin-3-amine (0.196 g, 0.944 mmol), and 2.0 M aq $Na_2CO_3$ (2.36 mL, 4.72 mmol) were added to dioxane (8 ml) and the resulting solution was purged with a stream of Ar for 10 min. $Pd(PPh_3)_4$ (0.055 g, 0.047 mmol) was added and the mixture irradiated on microwave at 120° C. for 30 min. The reaction was quenched with water (20 ml) and extracted with EtOAc (3×30 ml). The combined organic layers were washed with brine (15 ml), dried ($Na_2SO_4$), filtered and concentrated. The residue was purified by normal phase chromatography using DCM and 0-10% MeOH as eluents to afford tert-butyl N-[(1S)-1-[3-(3-amino-5-chloropyridin-2-yl) phenyl]but-3-en-1-yl]carbamate (0.375g, 106%) as a tan foam. MS(ESI) m/z: 374.3 $(M+H)^+$. $^1$H NMR (500 MHz, $CDCl_3$) δ 8.08 (d, J=2.2 Hz, 1H), 7.60-7.52 (m, 2H), 7.48-7.43 (m, 1H), 7.34 (d, J=7.7 Hz, 1H), 7.07 (d, J=1.9 Hz, 1H), 5.72 (ddt, J=17.1, 10.1, 7.0 Hz, 1H), 5.21-5.09 (m, 2H), 4.93 (br. s., 1H), 4.81 (br. s., 1H), 3.94 (br. s., 2H), 2.63-2.51 (m, 2H), 1.43 (br. s., 9H).

82B. Preparation of Tert-Butyl N-[(1S)-1-(3-{5-chloro-3-[(2R)-2-methylbut-3-enamido]pyridin-2-yl}phenyl)but-3-en-1-yl]carbamate To tert-butyl N-[(1S)-1-[3-(3-amino-5-chloropyridin-2-yl)phenyl]but-3-en-1-yl]carbamate (0.358 g, 0.958 mmol) was added (R)-2-methylbut-3-enoic acid (0.125 g, 1.245 mmol), prepared as described in Intermediate 2, in 3 ml EtOAc, and the resulting solution was cooled to 0° C. Pyridine (0.232 ml, 2.87 mmol) and a 50% EtOAc solution of T3P® (1.140 ml, 1.915 mmol) were then added. After 4 h, the reaction was partitioned with sat $NaHCO_3$(10 ml) and EtOAc (10 ml). The aqueous layer was extracted with EtOAc (2×20 ml). The combined organic layers were washed with brine (10 ml), dried ($Na_2SO_4$), filtered and concentrated. The residue was purified by normal phase chromatography using heptanes and EtOAc as eluents to give tert-butyl N-[(1S)-1-(3-{5-chloro-3-[(2R)-2-methylbut-3-enamido]pyridin-2-yl}phenyl)but-3-en-1-yl]carbamate (0.31 g, 71%) as a white foam. MS(ESI) m/z: 456.08 $(M+H)^+$. $^1$H NMR (500 MHz, $CDCl_3$) δ 8.88 (d, J=2.2 Hz, 1H), 8.38 (d, J=2.2 Hz, 1H), 7.65 (br. s., 1H), 7.56-7.49 (m, 1H), 7.45-7.40 (m, 2H), 7.39-7.33 (m, 1H), 5.82-5.66 (m, 2H), 5.21-5.11 (m, 2H), 5.11-5.06 (m, 2H), 4.93 (br. s., 1H), 4.82 (br. s., 1H), 3.08 (quin, J=7.2 Hz, 1H), 2.64-2.50 (m, 2H), 1.46-1.41 (m, 9H), 1.30 (d, J=7.2 Hz, 3H).

82C. Preparation of Tert-Butyl N-[(10R,11E,14S)-5-chloro-10-methyl-9-oxo-3,8-diazatricyclo[13.3.1.0$^{2,7}$]nonadeca-1 (19),2(7),3,5,11,15,17-heptaen-14-yl]carbamate A solution of Second Generation Grubbs Catalyst (0.107 g, 0.126 mmol) and tert-butyl N-[(1S)-1-(3-{5-chloro-3-[(2R)-2-methylbut-3-enamido]pyridin-2-yl}phenyl)but-3-en-1-yl]carbamate (0.191 g, 0.419 mmol) in degassed DCE (20 ml) was heated to 120° C. for 30 min in a microwave. The reaction mixture was concentrated and the crude material was directly purified by normal phase chromatography using DCM and 0-10% MeOH as eluents to afford tert-butyl N-[(10R,11E,14S)-5-chloro-10-methyl-9-oxo-3,8-diazatricyclo[13.3.1.0$^{2,7}$]nonadeca-1(19),2(7),3,5,11,15,17-heptaen-14-yl]carbamate (0.17 g, 95%) as a dark brown oil. MS(ESI) m/z: 428.2 $(M+H)^+$.

82D. Preparation of (10R,14S)-14-amino-5-chloro-10-methyl-3,8-diazatricyclo[13.3.1.0$^{2,7}$]nonadeca-1(19),2(7),3,5,15,17-hexaen-9-one

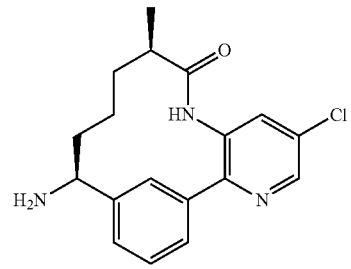 [SMILES: C[C@@H]1CCC[C@H](N)c2cccc(c2)-c2ncc(Cl)cc2NC1=O]

tert-Butyl N-[(10R,11E,14S)-5-chloro-10-methyl-9-oxo-3,8-diazatricyclo[13.3.1.0$^{2,7}$]nonadeca-1(19),2(7),3,5,11, 15,17-heptaen-14-yl]carbamate (0.17 g, 0.397 mmol) was hydrogenated in EtOH (3 ml) in the presence of $PtO_2$ (20 mg) for 8 h. MS(ESI) m/z: 430.3 $(M+H)^+$. The thick sludge was filtered through CELITE® and rinsed with DCM/MeOH/EtOH to afford 0.169 g of a dark solid. Deprotection was carried out with 4 N HCl in dioxane (2 ml) and MeOH (2 ml) over 4 h. After this time the solution was concentrated and the residue was taken up in DCM/MeOH and passed through a basic cartridge to give (10R,14S)-14-amino-5-chloro-10-methyl-3,8-diazatricyclo[13.3.1.0$^{2,7}$]nonadeca-1(19),2(7),3,5,15,17-hexaen-9-one as a crude product (0.159g, 121%) that was used 'as is'. MS(ESI) m/z: 330.08 $(M+H)^+$.

82E. Preparation of (10R,14S)-5-chloro-14-(4-{5-chloro-2-[4-(trifluoromethyl)-H-1,2,3-triazol-1-yl]phenyl}-6-oxo-1,6-dihydropyrimidin-1-yl)-10-methyl-3,8-diazatricyclo[13.3.1.0$^{2,7}$]nonadeca-1(19),2(7),3,5,15,17-hexaen-9-one

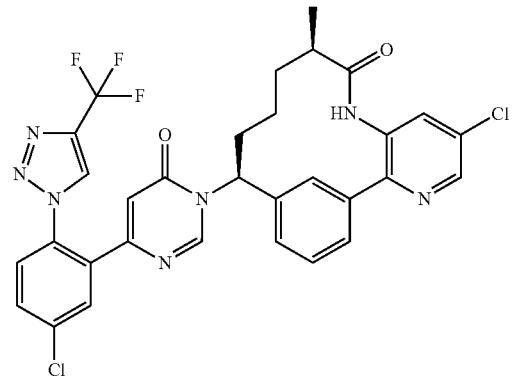 [SMILES: C[C@@H]1CCC[C@H](n2cnc(-c3cc(Cl)ccc3-n3cc(C(F)(F)F)nn3)cc2=O)c2cccc(c2)-c2ncc(Cl)cc2NC1=O]

To HATU (0.045 g, 0.118 mmol) and 6-{5-chloro-2-[4-(trifluoromethyl)-1H-1,2,3-triazol-1-yl]phenyl}pyrimidin-4-ol (0.031 g, 0.091 mmol), prepared as described in Intermediate 15, in a small vial was added DBU (0.021 mL, 0.136 mmol) in $CH_3CN$ (0.4 ml). After 30 min, tert-butyl N-[(10R,11E,14S)-5-chloro-10-methyl-9-oxo-3,8-diazatricyclo[13.3.1.0$^{2,7}$]nonadeca-1 (19),2(7),3,5,11,15,17-heptaen-14-yl]carbamate (0.030 g, 0.091 mmol) was added with DMF (0.4 ml). After 18 h, the reaction was diluted with DMF, filtered and concentrated The residue was purified twice by reverse phase HPLC using PHENOMENEX® Luna 5U 30×100 mm (10:90 ACN/H$_2$O to 90:10 ACN/H$_2$O, 0.1% TFA) (20% B start, 14 min gradient) to afford (10R,14S)-5-chloro-14-(4-{5-chloro-2-[4-(trifluoromethyl)-1H-1,2,3-triazol-1-yl]phenyl}-6-oxo-1,6-dihydropyrimidin-1-yl)-10-methyl-3,8-diazatricyclo[13.3.1.0$^{2,7}$]nonadeca-1 (19),2(7),3,5,15,17-hexaen-9-one (3.0 mg, 4.2% yield) as a tan solid. MS(ESI) m/z: 654.3 (M+H)$^+$. $^1$H NMR (400 MHz, CD$_3$OD) δ 8.81 (d, J=0.7 Hz, 1H), 8.67-8.62 (m, 1H), 8.23 (s, 1H), 7.93-7.84 (m, 3H), 7.79-7.67 (m, 3H), 7.63-7.54 (m, 1H), 7.29 (d, J=7.9 Hz, 1H), 6.47 (d, J=0.9 Hz, 1H), 5.82 (dd, J=12.9, 3.6 Hz, 1H), 2.58-2.48 (m, 1H), 2.40-2.24 (m, 1H), 2.11 (d, J=9.7 Hz, 1H), 1.99-1.87 (m, 1H), 1.55 (d, J=9.0 Hz, 2H), 1.33 (d, J=9.7 Hz, 1H), 1.15 (d, J=6.8 Hz, 3H). Analytical HPLC (Method A) RT=9.88 min, purity=98%; Factor XIa Ki=3.5 nM, Plasma Kallikrein Ki=240 nM.

Example 83

Preparation of (9R,13S)-13-{4-[5-chloro-2-(4-chloro-1H-1,2,3-triazol-1-yl)phenyl]-6-oxo-1,6-dihydropyrimidin-1-yl}-3,9-dimethyl-3,4,7,16-tetraazatricyclo[12.3.1.0$^{2,6}$]octadeca-1(18),2(6),4,14,16-pentaen-8-one

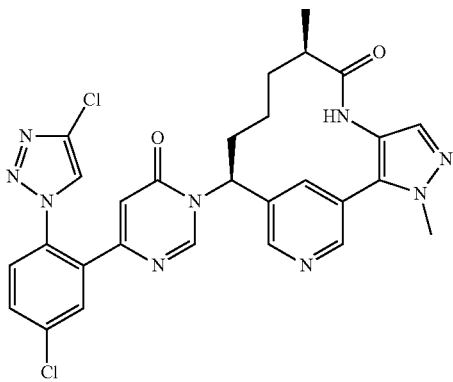 [SMILES: C[C@@H]1CCC[C@H](n2cnc(-c3cc(Cl)ccc3-n3cc(Cl)nn3)cc2=O)c2cncc(c2)-c2c(cnn2C)NC1=O]

83A. Preparation of Tert-Butyl N-[(1S)-1-[5-(1-methyl-4-nitro-1H-pyrazol-5-yl) pyridin-3-yl]but-3-en-1-yl]carbamate To a solution of tert-butyl N-[(1S)-1-(5-bromopyridin-3-yl)but-3-en-1-yl]carbamate (1.0 g, 3.06 mmol), prepared as described in Intermediate 26, in dioxane (10 ml) was added 1-methyl-4-nitro-1H-pyrazole (0.427 g, 3.36 mmol), di(adamantan-1-yl)(butyl)phosphine (0.164 g, 0.458 mmol), K$_2$CO$_3$ (1.267 g, 9.17 mmol) and pivalic acid (0.106 ml, 0.917 mmol). The reaction mixture was purged with Ar. Pd(OAc)$_2$ (0.069 g, 0.306 mmol) was added and the solution was stirred at 100° C. After 4 h, the reaction was quenched with water (20 ml) and extracted with EtOAc (3×50 ml). The combined organic layers were washed with brine (20 ml), dried (MgSO$_4$), filtered, and concentrated. The residue was purified by normal phase chromatography using heptanes and EtOAc as eluents to give tert-butyl N-[(1S)-1-[5-(1-methyl-4-nitro-1H-pyrazol-5-yl)pyridin-3-yl]but-3-en-1-yl]carbamate (0.85 g, 74%) as a white foam. MS(ESI) m/z: 374.5 (M+H)$^+$. $^1$H NMR (500 MHz, CDCl$_3$) δ 8.74 (d, J=1.9 Hz, 1H), 8.57 (d, J=1.9 Hz, 1H), 8.25 (s, 1H), 7.72 (t, J=1.9 Hz, 1H), 5.73 (ddt, J=17.1, 10.2, 7.2 Hz, 1H), 5.26-5.17 (m, 2H), 4.99 (br. s., 1H), 4.93-4.84 (m, 1H), 3.80 (s, 3H), 2.75-2.52 (m, 2H), 1.43 (br. s., 9H).

83B. Preparation of Tert-Butyl N-[(1S)-1-[5-(4-amino-1-methyl-1H-pyrazol-5-yl)pyridin-3-yl]but-3-en-1-yl]carbamate To a solution of tert-butyl N-[(1S)-1-[5-(1-methyl-4-nitro-1H-pyrazol-5-yl) pyridin-3-yl]but-3-en-1-yl]carbamate (0.85g, 2.276) in acetone (60 ml)/water (15 ml) at 0° C. was added NH$_4$Cl (0.609 g, 11.38 mmol) and Zn (1.488 g, 22.76 mmol). The ice bath was removed and the reaction was stirred 18 h. The reaction was filtered through paper and partitioned between water (20 ml) and EtOAc (75 ml). The aqueous layer was extracted with EtOAc (2×50 ml). The combined organic layers were washed with brine (25 ml), dried (MgSO$_4$), filtered, and concentrated. Thr residue was purified by normal phase chromatography using hexanes and EtOAc as eluents to give tert-butyl N-[(1S)-1-[5-(4-amino-1-methyl-1H-pyrazol-5-yl)pyridin-3-yl]but-3-en-1-yl]carbamate (0.64 g, 65% yield). MS(ESI) m/z: 344.5 (M+H)$^+$.

83C. Preparation of Tert-Butyl N-[(1S)-1-(5-{1-methyl-4-[(2R)-2-methylbut-3-enamido]-1H-pyrazol-5-yl}pyridin-3-yl)but-3-en-1-yl]carbamate To a solution of tert-butyl N-[(1S)-1-(5-{1-methyl-4-[(2R)-2-methylbut-3-enamido]-1H-pyrazol-5-yl}pyridin-3-yl) but-3-en-1-yl]carbamate (0.5 g, 1.45 mmol) in EtOAc (4 ml) was added a solution of (R)-2-methylbut-3-enoic acid (0.189 g, 1.893 mmol), prepared as described in Intermediate 2, in 0.3 ml EtOAc. The reaction mixture was cooled to 0° C. and pyridine (0.353 ml, 4.37 mmol) and a 50% EtOAc solution of T3P® (1.733 ml, 2.91 mmol) were added. After 3 h, the reaction was partitioned between sat NaHCO$_3$(15 ml) and EtOAc (20 ml). The aqueous layer was extracted with EtOAc (2×20 ml). The combined organic layers were washed with brine (10 ml), dried (MgSO$_4$), filtered and concentrated. The residue was purified by normal phase chromatography using DCM and 0-10% MeOH as eluents to give tert-butyl N-[(1S)-1-(5-{1-methyl-4-[(2R)-2-methylbut-3-enamido]-1H-pyrazol-5-yl}pyridin-3-yl)but-3-en-1-yl]carbamate (0.48 g, 77% yield) as a pink solid. MS(ESI) m/z: 426.5 (M+H)$^+$. $^1$H NMR (500 MHz, CDCl$_3$) δ 8.66 (d, J=2.2 Hz, 1H), 8.51 (d, J=1.9 Hz, 1H), 7.99 (s, 1H), 7.62 (t, J=2.1 Hz, 1H), 6.95 (br. s., 1H), 5.91 (ddd, J=17.2, 10.0, 8.0 Hz, 1H), 5.79-5.66 (m, 1H), 5.25-5.13 (m, 4H), 4.95 (br. s., 1H), 4.82 (br. s., 1H), 3.85-3.77 (m, 3H), 3.10 (quin, J=7.2 Hz, 1H), 2.68-2.51 (m, 2H), 1.50-1.37 (m, 9H), 1.37-1.29 (m, 3H).

83D. Preparation of Tert-Butyl N-[(9R,10E,13S)-3,9-dimethyl-8-oxo-3,4,7,16-tetraazatricyclo[12.3.1.0$^{2,6}$]octadeca-1(18),2(6),4,10,14,16-hexaen-13-yl] carbamate To a solution of tert-butyl N-[(1S)-1-(5-{1-methyl-4-[(2R)-2-methylbut-3-enamido]-1H-pyrazol-5-yl}pyridin-3-yl)but-3-en-1-yl]carbamate (0.153 g, 0.36 mmol) in DCM (90 ml) was added pTsOH.H$_2$O (0.075 g, 0.396 mmol) and the mixture was degassed for 10 min, then heated to 40° C. for 1 h. Second Generation Grubbs Catalyst (0.122 g, 0.144 mmol) was added and the reaction was heated at 40° C. for 24 h. The reaction was quenched with sat NaHCO₃ (15 ml) and extracted with DCM (3×20 ml). The combined organic layers were washed with brine (30 ml), dried (MgSO₄), filtered and concentrated. The residue purified by normal phase chromatography using DCM and MeOH as eluents to afford tert-butyl N-[(9R,10E,13S)-3,9-dimethyl-8-oxo-3,4,7,16-tetraazatricyclo[12.3.1.0²,⁶]octadeca-1(18),2(6),4,10,14,16-hexaen-13-yl]carbamate (20 mg, 14%) as a brown solid. MS(ESI) m/z: 398.2 (M+H)⁺. ¹H NMR (500 MHz, CDCl₃) δ 8.60 (s, 1H), 7.57 (s, 1H), 7.25-7.17 (m, 1H), 6.98 (s, 1H), 6.52 (br. s., 1H), 5.78-5.65 (m, 1H), 5.14 (br. s., 1H), 5.04-4.96 (m, 1H), 4.79 (br. s., 1H), 3.97 (s, 3H), 3.85-3.74 (m, 1H), 3.06 (br. s., 1H), 2.61 (br. s., 4H), 1.46 (br. s., 9H), 1.30-1.23 (m, 3H).

83E. Preparation of (9R,13S)-13-amino-3,9-dimethyl-3,4,7,16-tetraazatricyclo[12.3.1.0²,⁶]octadeca-1(18),2(6),4,14,16-pentaen-8-one

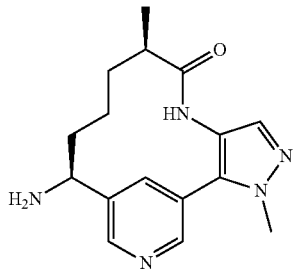 [SMILES: C[C@@H]1CCC[C@H](N)c2cncc(c2)-c2c(cnn2C)NC1=O]

tert-Butyl N-[(9R,10E,13S)-3,9-dimethyl-8-oxo-3,4,7,16-tetraazatricyclo[12.3.1.0²,⁶]octadeca-1(18),2(6),4,10,14,16-hexaen-13-yl]carbamate (20 mg, 0.050 mmol) was hydrogenated in EtOH (3 ml) in the presence of PtO₂ (4 mg) at 55 psi. After 4 h, the reaction mixture was filtered through CELITE® and concentrated to afford 16 mg of a dark solid (MS(ESI) m/z: 400.08 (M+H)⁺ which was then deprotected with 4 N HCl in dioxane (1 ml) and MeOH (1 ml). After 3 h, the mixture was concentrated and the resultant HCl salt was dissolved in DCM/MeOH and passed through a basic cartridge to afford (9R,13S)-13-amino-3,9-dimethyl-3,4,7,16-tetraazatricyclo[12.3.1.0²,⁶]octadeca-1(18),2(6),4,14,16-pentaen-8-one (15 mg, 100%) as a dark solid.

83F. Preparation of (9R,13S)-13-{4-[5-chloro-2-(4-chloro-1H-1,2,3-triazol-1-yl)phenyl]-6-oxo-1,6-dihydropyrimidin-1-yl}-3,9-dimethyl-3,4,7,16-tetraazatricyclo[12.3.1.0²,⁶]octadeca-1(18),2(6),4,14,16-pentaen-8-one

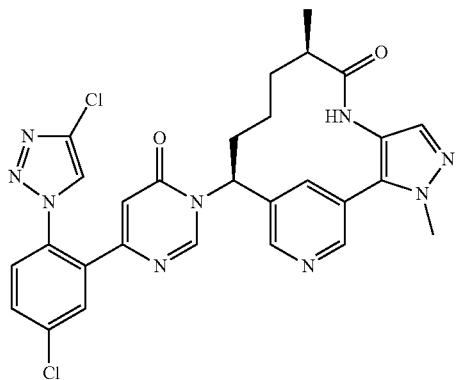 [SMILES: C[C@@H]1CCC[C@H](n2cnc(-c3cc(Cl)ccc3-n3cc(Cl)nn3)cc2=O)c2cncc(c2)-c2c(cnn2C)NC1=O]

To 6-[5-chloro-2-(4-chloro-1H-1,2,3-triazol-1-yl)phenyl]pyrimidin-4-ol (0.015 g, 0.050 mmol), prepared as described in Intermediate 15, and HATU (0.025 g, 0.065 mmol) in a small vial was added DBU (0.011 mL, 0.075 mmol) in CH₃CN (0.4 ml). After 30 min, (9R,13S)-13-amino-3,9-dimethyl-3,4,7,16-tetraazatricyclo[12.3.1.0²,⁶]octadeca-1(18),2(6),4,14,16-pentaen-8-one (0.015 g, 0.050 mmol) was added with DMF (0.2 ml). After 18 h, the reaction was diluted with DMF, filtered and purified by reverse phase HPLC using PHENOMENEX® Luna 5U 30×100 mm (10:90 ACN/H₂O to 90:10 ACN/H₂O, 0.1% TFA) (20% B start, 14 min gradient) to afford (9R,13S)-13-{4-[5-chloro-2-(4-chloro-1H-1,2,3-triazol-1-yl)phenyl]-6-oxo-1,6-dihydropyrimidin-1-yl}-3,9-dimethyl-3,4,7,16-tetraazatricyclo[12.3.1.0²,⁶]octadeca-1(18),2(6),4,14,16-pentaen-8-one (4.1 mg, 11%) as an off-white solid. MS(ESI) m/z: 590.3 (M+H)⁺. ¹H NMR (400 MHz, CD₃OD) δ 8.83 (d, J=1.8 Hz, 1H), 8.64 (d, J=2.0 Hz, 1H), 8.42-8.34 (m, 2H), 8.30 (s, 1H), 7.95-7.86 (m, 1H), 7.81-7.72 (m, 1H), 7.69-7.63 (m, 1H), 7.60-7.53 (m, 1H), 6.49-6.42 (m, 1H), 5.79 (dd, J=13.0, 3.1 Hz, 1H), 4.13 (s, 3H), 2.56-2.45 (m, 2H), 2.24-2.14 (m, 1H), 1.89 (br. s., 1H), 1.65-1.53 (m, 2H), 1.23-1.14 (m, 3H), 1.10 (br. s., 1H). Analytical HPLC (Method A) rt=6.29 min, purity=98%; Factor XIa Ki=0.2 nM, Plasma Kallikrein Ki=43 nM.

Example 84

Preparation of (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-8-oxo-3,4,7-triazatricyclo[12.3.1.0²,⁶]octadeca-1(18),2(6),4,14,16-pentaene-16-carboxamide

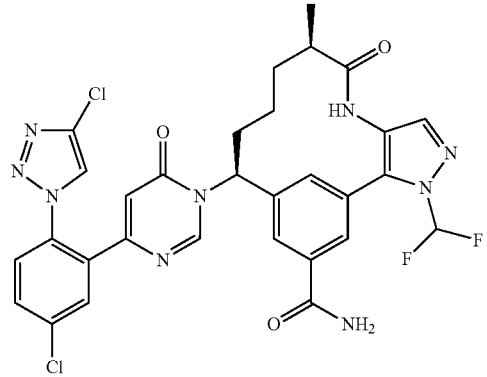 [SMILES: C[C@@H]1CCC[C@H](n2cnc(-c3cc(Cl)ccc3-n3cc(Cl)nn3)cc2=O)c2cc(C(N)=O)cc(c2)-c2c(cnn2C(F)F)NC1=O]

84A. Preparation of 3-bromo-5-[(1E)-{[(R)-2-methylpropane-2-sulfinyl]imino}methyl]benzamide To 3-formylbenzonitrile (3.49 g, 26.6 mmol) in con. H₂SO₄ (12 ml) was heated to 60° C., NBS (5.68 g, 31.9 mmol) was added in 3 portions. The reaction was stirred for 2 h. The reaction was quenched by pouring into ice water. The product was filtered off and dried. The collected crude product was used 'as is' in next step. The crude material was combined with (R)-2-methylpropane-2-sulfinamide (1.382 g, 11.40 mmol), Cs₂CO₃ (5.57 g, 17.10 mmol) in DCM (57.0 ml) and stirred 18 h. The reaction thickened to a gel, was diluted with DCM and stirring was resumed for 3 h. The reaction was partitioned between brine (40 ml) and DCM (50 ml). The insoluble gel was filtered off. The aqueous layer was extracted with DCM (2×20 ml). The combined organic layers were dried (Na$_2$SO$_4$), filtered and concentrated. The residue was purified by normal phase chromatography using heptanes and EtOAc as eluents to afford 3-bromo-5-[(1E)-{[(R)-2-methylpropane-2-sulfinyl]imino}methyl]benzamide (3.3 g). $^1$H NMR (400 MHz, DMSO-d$_6$) δ 8.58 (s, 1H), 8.42 (s, 1H), 8.34 (br. s., 1H), 8.26 (s, 2H), 7.68 (br. s., 1H), 1.20 (s, 9H).

84B. Preparation of 3-bromo-5-[(1S)-1-{[(R)-2-methylpropane-2-sulfinyl]amino}but-3-en-1-yl]benzamide To 3-bromo-5-[(1E)-{[(R)-2-methylpropane-2-sulfinyl]imino}methyl]benzamide (3.3 g, 9.96 mmol) in THF (75 ml) was added In (1.716 g, 14.94 mmol) and 3-bromoprop-1-ene (1.30 ml, 14.94 mmol). The reaction was stirred at rt. After, 72 h, the reaction became a gray suspension and LCMS showed it was not complete. An additional 4 g of In and 2.6 ml of 3-bromoprop-1-ene were added. After an additional week the reaction was filtered and the filtrate concentrated to give 4 g of crude 3-bromo-5-[(1S)-1-{[(R)-2-methylpropane-2-sulfinyl]amino}but-3-en-1-yl]benzamide. MS(ESI) m/z: 373-375.1 (M+H)$^+$.

84C. Preparation of Tert-Butyl N-[(1S)-1-(3-bromo-5-carbamoylphenyl)but-3-en-1-yl]carbamate To 3-bromo-5-[(1S)-1-{[(R)-2-methylpropane-2-sulfinyl]amino}but-3-en-1-yl]benzamide (3.7 g, 9.91 mmol) in (1:1) dioxane/MeOH (50 ml) was added 15 ml of conc. HCl. The reaction was stirred for 24 h, then concentrated. The residue was dissolved in DCM (50 ml) and cooled to 0° C. TEA (8.29 ml, 59.5 mmol) and BOC$_2$O (2.301 ml, 9.91 mmol) were added. An additional amount of 1 N NaOH was added to ensure reaction was basic. After 24 h, the thick reaction was filtered giving a gummy solid. Both the gummy solid and filtrate were combined and partitioned between water (100 ml) and EtOAc (150 ml). The aqueous layer was extracted with EtOAc (2×50 ml). The combined organic layers were washed with brine (50 ml), dried (Na$_2$SO$_4$), filtered and concentrated. The residue was purified by normal phase chromatography using hexanes and EtOAc as eluents to afford tert-butyl N-[(1S)-1-(3-bromo-5-carbamoylphenyl)but-3-en-1-yl]carbamate (0.92 g, 25%). MS(ESI) m/z: 311-313.3 (M+H-t-butyl)$^+$. $^1$H NMR (400 MHz, CDCl$_3$) δ 7.88-7.79 (m, 1H), 7.74 (br. s., 1H), 7.56 (t, J=1.5 Hz, 1H), 6.66 (br. s., 1H), 6.40 (br. s., 1H), 5.74-5.59 (m, 1H), 5.28-5.19 (m, 1H), 5.17-5.12 (m, 1H), 4.71 (br. s., 1H), 2.57-2.45 (m, 3H), 1.49-1.34 (m, 9H).

84D. Preparation of Tert-Butyl N-[(1S)-1-{3-carbamoyl-5-[1-(difluoromethyl)-4-nitro-1H-pyrazol-5-yl]phenyl}but-3-en-1-yl]carbamate To a solution of (S)-tert-butyl (1-(3-bromo-5-carbamoylphenyl)but-3-en-1-yl)carbamate (0.2 g, 0.542 mmol) in dioxane (3 ml) was added 1-(difluoromethyl)-4-nitro-1H-pyrazole (0.106 g, 0.650 mmol), di(adamantan-1-yl)(butyl)phosphine (0.029 g, 0.081 mmol), K$_2$CO$_3$ (0.225 g, 1.625 mmol) and pivalic acid (0.019 ml, 0.162 mmol). The reaction was purged with Ar. Afterwards, Pd(OAc)$_2$ (0.012 g, 0.054 mmol) was added and the reaction was heated to 100° C. After 18 h, the reaction was partitioned with water (20 ml) and EtOAc (20 ml) and filtered. The filtrate was extracted with EtOAc (2×20 ml). The combined organic layers were washed with brine (15 ml), dried (MgSO$_4$), filtered, and concentrated. The residue was purified by normal phase chromatography using heptanes and EtOAc as eluents to afford tert-butyl N-[(1S)-1-{3-carbamoyl-5-[1-(difluoromethyl)-4-nitro-1H-pyrazol-5-yl]phenyl}but-3-en-1-yl]carbamate (0.177 g, 72.4%) as a yellow oil. MS(ESI) m/z: 450.1 (M−H)$^+$. $^1$H NMR (500 MHz, CDCl$_3$) δ 8.34 (s, 1H), 7.99-7.91 (m, 1H), 7.85-7.77 (m, 1H), 7.58-7.52 (m, 1H), 7.16-6.82 (m, 1H), 6.07 (br. s., 1H), 5.75-5.55 (m, 2H), 5.20-5.08 (m, 2H), 4.96 (br. s., 1H), 4.82 (br. s., 1H), 2.62-2.46 (m, 2H), 1.40 (d, J=7.2 Hz, 9H).

84E. Preparation of Tert-Butyl N-[(1S)-1-{3-carbamoyl-5-[1-(difluoromethyl)-4-[(2R)-2-methylbut-3-enamido]-1H-pyrazol-5-yl]phenyl}but-3-en-1-yl]carbamate To tert-butyl N-[(1S)-1-{3-carbamoyl-5-[1-(difluoromethyl)-4-nitro-1H-pyrazol-5-yl]phenyl}but-3-en-1-yl]carbamate (0.177 g, 0.392 mmol) in acetone (40 ml)/water (12 ml), cooled to 0° C., was added NH$_4$Cl (0.105 g, 1.960 mmol) and Zn (0.256 g, 3.92 mmol). After 18 h at rt, the reaction was filtered through paper and the filtrate was partitioned with water (20 ml) and EtOAc (25 ml). The aqueous layer was extracted with EtOAc (2×25 ml). The combined organic layers were washed with brine (25 ml), dried (MgSO$_4$) filtered and concentrated. To the crude yellow oil in EtOAc (3 ml) at 0° C., was added (R)-2-methylbut-3-enoic acid (0.051 g, 0.510 mmol), prepared as described in Intermediate 2, pyridine (0.095 mL, 1.176 mmol) and a 50% EtOAc solution of T3P® (0.233 mL, 0.784 mmol). After 24 h, the reaction was partitioned between sat NaHCO$_3$ (10 ml) and EtOAc (20 ml). The aqueous layer was extracted with EtOAc (2×20 ml). The combined organic layers were washed with brine (25 ml), dried (MgSO$_4$), filtered and concentrated. The was residue was purified by normal phase chromatography using hexanes and EtOAc as eluents to afford tert-butyl N-[(1S)-1-{3-carbamoyl-5-[1-(difluoromethyl)-4-[(2R)-2-methylbut-3-enamido]-1H-pyrazol-5-yl]phenyl}but-3-en-1-yl]carbamate (0.113 g, 57%) as a yellow oil. MS(ESI) m/z: 448.3 (M+H-t-butyl)$^+$.

84F. Preparation of Tert-Butyl N-[(9R,10E,13S)-16-carbamoyl-3-(difluoromethyl)-9-methyl-8-oxo-3,4,7-triazatricyclo[12.3.1.0$^{2,6}$]octadeca-1(18),2(6),4,10,14,16-hexaen-13-yl]carbamate To a solution of tert-butyl N-[(1S)-1-{3-carbamoyl-5-[1-(difluoromethyl)-4-[(2R)-2-methylbut-3-enamido]-1H-pyrazol-5-yl]phenyl}but-3-en-1-yl]carbamate (0.113 g, 0.224 mmol) in degassed DCE (11 ml) was added Second Generation Grubbs Catalyst (0.08 g, 0.094 mmol) and the resulting solution was heated to 120° C. for 30 min in a microwave. The reaction was directly purified by normal phase chromatography using DCM and 0-10% MeOH as eluents gave tert-butyl N-[(9R,10E,13S)-16-carbamoyl-3-(difluoromethyl)-9-methyl-8-oxo-3,4,7-triazatricyclo [12.3.1.0$^{2,6}$]octadeca-1(18),2(6),4,10,14,16-hexaen-13-yl]carbamate (33 mg, 31%) as a tan solid. MS(ESI) m/z: 420.2 (M+H-t-butyl)$^+$. $^1$H NMR (400 MHz, CD$_3$OD) δ 7.95 (s, 1H), 7.82-7.78 (m, 2H), 7.10 (s, 1H), 5.73 (ddd, J=15.2, 10.5, 4.7 Hz, 1H), 4.65 (d, J=9.5 Hz, 1H), 4.54 (dd, J=15.2, 9.2 Hz, 1H), 3.19-3.09 (m, 1H), 2.70 (dt, J=12.1, 3.5 Hz, 1H), 2.03 (q, J=11.4 Hz, 1H), 1.46 (br. s., 9H), 1.08 (d, J=6.8 Hz, 3H).

84G. Preparation of (9R,13S)-13-amino-3-(difluoromethyl)-9-methyl-8-oxo-3,4,7-triazatricyclo[12.3.1.0²,⁶]octadeca-1(18),2(6),4,14,16-pentaene-16-carboxamide

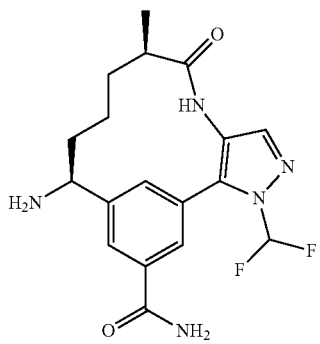 [SMILES: C[C@@H]1CCC[C@H](N)c2cc(C(N)=O)cc(c2)-c2c(cnn2C(F)F)NC1=O]

tert-Butyl N-[(9R,10E,13S)-16-carbamoyl-3-(difluoromethyl)-9-methyl-8-oxo-3,4,7-triazatricyclo[12.3.1.0²,⁶]octadeca-1(18),2(6),4,10,14,16-hexaen-13-yl]carbamate (0.033 g, 0.069 mmol) was hydrogenated in EtOH (1 ml) in the presence of PtO₂ (5 mg). After 4 h, the reaction was filtered through 0.45 ELM filter to afford 0.022 g of a tan solid. MS(ESI) m/z: 422.3 (M+H-t-butyl)⁺. The intermediate was deprotected in MeOH (1 ml) with 4 N HCl in dioxane (0.5 ml). After 3 h, the reaction was concentrated. The residue was taken up in DCM/MeOH and passed through a basic cartridge and concentrated to afford (9R,13S)-13-amino-3-(difluoromethyl)-9-methyl-8-oxo-3,4,7-triazatricyclo[12.3.1.0²,⁶]octadeca-1(18),2(6),4,14,16-pentaene-16-carboxamide (22 mg, 84%) as a brown solid. MS(ESI) m/z: 378.2(M+H)⁺.

84H. Preparation of (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-8-oxo-3,4,7-triazatricyclo[12.3.1.0²,⁶]octadeca-1(18),2(6),4,14,16-pentaene-16-carboxamide

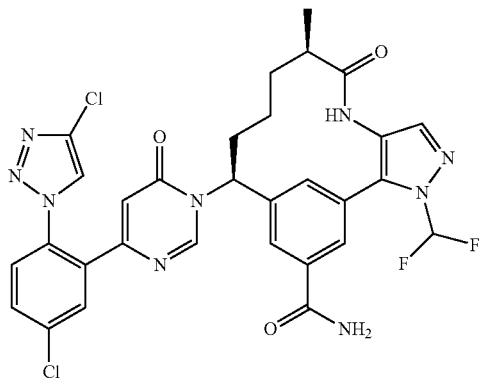 [SMILES: C[C@@H]1CCC[C@H](n2cnc(-c3cc(Cl)ccc3-n3cc(Cl)nn3)cc2=O)c2cc(C(N)=O)cc(c2)-c2c(cnn2C(F)F)NC1=O]

To 6-[5-chloro-2-(4-chloro-1H-1,2,3-triazol-1-yl)phenyl]pyrimidin-4-ol (0.018 g, 0.058 mmol), prepared as described in Intermediate 9, and HATU (0.029 g, 0.076 mmol) in a small vial was added DBU (0.013 mL, 0.087 mmol) in ACN (0.4 ml). After 30 min, (9R,13S)-13-amino-3-(difluoromethyl)-9-methyl-8-oxo-3,4,7-triazatricyclo[12.3.1.0²,⁶]octa-deca-1(18),2(6),4,14,16-pentaene-16-carboxamide (0.022g, 0.058 mmol) was added with DMF (0.2 ml). After 18 h, the reaction was diluted with DMF, filtered and purified by reverse phase HPLC using PHENOMENEX® Luna 5U 30×100 mm (10:90 ACN/H₂O to 90:10 ACN/H₂O, 0.1% TFA) (20% B start, 14 min gradient) to afford (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-8-oxo-3,4,7-triazatricyclo[12.3.1.0²,⁶]octadeca-1(18),2(6),4,14,16-pentaene-16-carboxamide (10 mg, 25%) as a white solid. MS(ESI) m/z: 668.3 (M+H)⁺. ¹H NMR (400 MHz, CD₃OD) δ 8.36 (s, 1H), 8.30 (s, 1H), 8.04 (s, 1H), 7.96 (s, 1H), 7.91-7.86 (m, 2H), 7.85-7.78 (m, 1H), 7.77-7.71 (m, 1H), 7.70-7.63 (m, 2H), 6.47-6.40 (m, 1H), 5.84 (dd, J=12.9, 3.4 Hz, 1H), 2.52 (ddd, J=10.0, 6.7, 3.5 Hz, 1H), 2.47-2.38 (m, 1H), 2.21-2.11 (m, 1H), 1.98-1.86 (m, 1H), 1.67-1.47 (m, 2H), 1.22 (d, J=6.8 Hz, 1H), 1.16 (d, J=6.8 Hz, 3H). Analytical HPLC (Method A) RT=7.39 min, purity=98%; Factor XIa Ki=0.1 nM, Plasma Kallikrein Ki=18 nM.

Example 85

Preparation of 1-(4-chloro-2-{1-[(9R,13S)-3-(²H₃)methyl-9-methyl-8-oxo-3,4,7-triazatricyclo[12.3.1.0²,⁶]octadeca-1(18),2(6),4,14,16-pentaen-13-yl]-6-oxo-1,6-dihydropyrimidin-4-yl}phenyl)-1H-1,2,3-triazole-4-carboxamide

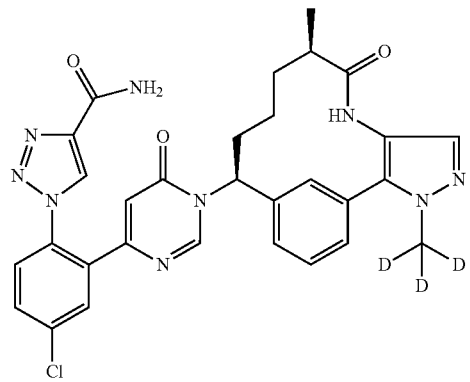 [SMILES: [2H]C([2H])([2H])n1ncc2c1-c1cccc(c1)[C@@H](n1cnc(-c3cc(Cl)ccc3-n3cc(C(N)=O)nn3)cc1=O)CCC[C@@H](C)C(=O)N2]

85A. Preparation of 1-[4-chloro-2-(6-hydroxypyrimidin-4-yl)phenyl]-1H-1,2,3-triazole-4-carboxamide

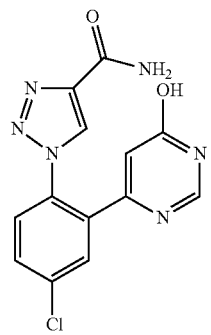 [SMILES: NC(=O)c1cn(-c2ccc(Cl)cc2-c2cc(O)ncn2)nn1]

To a suspension of 1-[4-chloro-2-(6-methoxypyrimidin-4-yl)phenyl]-1H-1,2,3-triazole-4-carboxamide (60 mg, 0.18 mmol) in ACN (1 ml) was added TMSI (12 µL, 0.88 mmol). The solution was heated at 70° C. for 3 h. The reaction was cooled to rt and poured into a 10% $Na_2S_2O_3$ solution. The insoluble yellow solid that formed was filtered and washed with water to give crude 1-[4-chloro-2-(6-hydroxypyrimidin-4-yl)phenyl]-1H-1,2,3-triazole-4-carboxamide (30 mg, 41.8% yield). MS(ESI) m/z: 317.3 $(M+H)^+$. $^1H$ NMR (400 MHz, $CD_3OD$) δ 8.57 (s, 1H), 8.02 (s, 1H), 7.85 (d, J=2.4 Hz, 1H), 7.76-7.71 (m, 1H), 7.70-7.64 (m, 1H), 6.39 (s, 1H).

85B. Preparation of 1-(4-chloro-2-{1-[(9R,13S)-3-($^2H_3$)methyl-9-methyl-8-oxo-3,4,7-triazatricyclo[12.3.1.0$^{2,6}$]octadeca-1(18),2(6),4,14,16-pentaen-13-yl]-6-oxo-1,6-dihydropyrimidin-4-yl}phenyl)-1H-1,2,3-triazole-4-carboxamide To 1-[4-chloro-2-(6-hydroxypyridin-4-yl)phenyl]-1H-1,2,3-triazole-4-carboxamide (0.004 g, 0.013 mmol) and HATU (6.24 mg, 0.016 mmol) in a small vial was added DBU (2.86 µl, 0.019 mmol) in $CH_3CN$ (0.8 ml). After 30 min, solid (9R,13S)-13-amino-3-($^2H_3$)methyl-9-methyl-3,4,7-triazatricyclo[12.3.1.0$^{2,6}$]octadeca-1(18),2(6),4,14,16-pentaen-8-one (0.038 g, 0.013 mmol), prepared as described in Intermediate 16, was added (rinsed with 0.2 ml DMF). The reaction was stirred 18 h, then diluted with DMF, filtered and concentrated. The residue was purified by preparative LCMS using (5:95 ACN/$H_2O$ to 95:5 ACN/$H_2O$, 10 mM $NH_4OAc$) to afford 1-(4-chloro-2-{1-[(9R,13S)-3-($^2H_3$)methyl-9-methyl-8-oxo-3,4,7-triazatricyclo[12.3.1.0$^{2,6}$]octadeca-1(18),2(6),4,14,16-pentaen-13-yl]-6-oxo-1,6-dihydropyrimidin-4-yl}phenyl)-1H-1,2,3-triazole-4-carboxamide (3.1 mg, 38% yield) as a white solid. MS(ESI) m/z: 601.08 $(M+H)^+$. $^1H$ NMR (500 MHz, $CD_3OD$) δ 8.47-8.41 (m, 1H), 8.03 (s, 1H), 7.76 (d, J=2.2 Hz, 1H), 7.67-7.60 (m, 2H), 7.60-7.53 (m, 1H), 7.52-7.41 (m, 2H), 7.41-7.36 (m, 1H), 7.19 (d, J=7.4 Hz, 1H), 6.37-6.28 (m, 1H), 5.69 (d, J=9.6 Hz, 1H), 4.45 (br. s., 1H), 2.40-2.34 (m, 1H), 2.27-2.19 (m, 1H), 1.82-1.73 (m, 1H), 1.52-1.41 (m, 2H), 1.15-1.10 (m, 1H), 1.07-1.01 (m, 3H). Analytical HPLC (Method C) RT=1.31 min, purity=95%; Factor XIa Ki=0.3 nM, Plasma Kallikrein Ki=60 nM.

Example 86

Preparation of (9R,13S)-13-{4-[3-chloro-6-(4-chloro-1H-1,2,3-triazol-1-yl)-2-fluorophenyl]-6-oxo-1,6-dihydropyrimidin-1-yl}-9-methyl-3,4,7-triazatricyclo[12.3.1.0$^{2,6}$]octadeca-1(18),2(6),4,14,16-pentaen-8-one

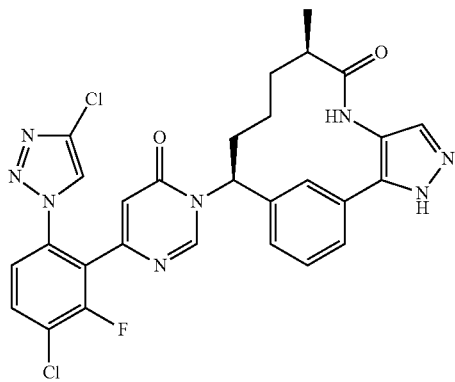 [SMILES: C[C@@H]1CCC[C@H](n2cnc(-c3c(-n4cc(Cl)nn4)ccc(Cl)c3F)cc2=O)c2cccc(c2)-c2[nH]ncc2NC1=O]

86A. Preparation of 4-nitro-1-{[2-(trimethylsilyl)ethoxy]methyl}-1H-pyrazole

To a solution of 4-nitro-1H-pyrazole (5.1 g, 45.1 mmol) in THF (50 mL) at 0° C. was added N-cyclohexyl-N-methylcyclohexanamine (19.32 mL, 90 mmol) followed by dropwise addition of SEM-Cl (12 mL, 67.7 mmol). The reaction mixture was slowly allowed to warm to rt and stirred for 18 h. The reaction mixture was concentrated and the residue was purified by normal phase chromatography using hexanes and EtOAc as eluents to afford 4-nitro-1-{[2-(trimethylsilyl)ethoxy]methyl}-1H-pyrazole (4.6 g, 43% yield) as a yellow oil. MS(ESI) m/z: 244 $(M-H)^+$. $^1H$ NMR (500 MHz, $CD_3Cl$) δ 8.30 (s, 1H), 8.10 (s, 1H), 5.45 (s, 2H), 3.67-3.57 (m, 2H), 1.01-0.90 (m, 2H), 0.04-0.00 (m, 9H).

86B. Preparation of Tert-Butyl N-[(1S)-1-[3-(4-nitro-1-{[2-(trimethylsilyl)ethoxy]methyl}-1H-pyrazol-5-yl)phenyl]but-3-en-1-yl]carbamate To a solution of tert-butyl N-[(1S)-1-(3-bromophenyl)but-3-en-1-yl]carbamate (0.4 g, 1.226 mmol) in DMF (3.07 ml) was added di(adamantan-1-yl)(butyl)phosphine (0.066 g, 0.184 mmol), 4-nitro-1-{[2-(trimethylsilyl)ethoxy]methyl}-1H-pyrazole (0.298 g, 1.226 mmol), $K_2CO_3$ (0.508 g, 3.68 mmol) and pivalic acid (0.043 ml, 0.368 mmol). The reaction was purged with Ar for 10 min, then, $Pd(OAc)_2$ (0.028 g, 0.123 mmol) was added and the reaction was heated to 115° C. for 3 h. The reaction mixture was diluted with EtOAc/water and filtered through paper to remove Pd. The filtrate was extracted (2×20 ml) EtOAc. The combined organic layer was washed with water (15 ml), brine (15 ml), dried ($MgSO_4$), filtered and concentrated. The residue was purified by normal phase chromatography using hexanes and EtOAc as eluents to afford tert-butyl N-[(1S)-1-[3-(4-nitro-1-{[2-(trimethylsilyl)ethoxy]methyl}-1H-pyrazol-5-yl)phenyl]but-3-en-1-yl]carbamate (0.315 g, 53%) as a yellow oil. MS(ESI) m/z: 487.3 $(M-H)^+$. $^1H$ NMR (500 MHz, $CD_3Cl$) δ 8.23 (s, 1H), 7.53-7.40 (m, 4H), 5.69 (ddt, J=17.1, 10.1, 7.2 Hz, 1H), 5.25 (s, 2H), 5.17-5.10 (m, 2H), 4.90 (br. s., 1H), 4.81 (br. s., 1H), 3.75-3.64 (m, 2H), 2.55 (br. s., 2H), 1.48 (br. s., 9H), 0.96-0.88 (m, 2H), 0.07-0.02 (m, 9H).

86C. Preparation of Tert-Butyl N-[(1S)-1-[3-(4-amino-1-{[2-(trimethylsilyl)ethoxy]methyl}-1H-pyrazol-5-yl)phenyl]but-3-en-1-yl]carbamate tert-Butyl N-[(1S)-1-[3-(4-nitro-1-{[2-(trimethylsilyl)ethoxy]methyl}-1H-pyrazol-5-yl) phenyl]but-3-en-1-yl]carbamate (0.315 g, 0.645 mmol) was dissolved in acetone (40 ml)/water (12 ml), cooled to 0° C. $NH_4Cl$ (0.172 g, 3.22 mmol) and Zn (0.421 g, 6.45 mmol) were added. The ice bath was removed. After 3 h, the reaction was partitioned with water (20 ml) and EtOAc (75 ml) and filtered through paper. The aqueous layer was extracted with EtOAc (2×50 ml). The combined organic layers were washed with brine (25 ml), dried ($MgSO_4$), filtered and concentrated. The residue was purified by normal phase chromatography using hexanes and EtOAc as eluents to afford tert-butyl N-[(1S)-1-[3-(4-amino-1-{[2-(trimethylsilyl)ethoxy]methyl}-1H-pyrazol-5-yl)phenyl]but-3-en-1-yl]carbamate (0.269 g, 91%) as a yellow oil. MS(ESI) m/z: 459.5 $(M-H)^+$. $^1H$ NMR (400 MHz, $CDCl_3$) δ 7.54-7.42 (m, 3H), 7.34-7.28 (m, 2H), 5.72 (ddt, J=17.0, 10.1, 7.0 Hz, 1H), 5.33-5.26 (m, 2H), 5.18-5.07 (m, 2H), 4.95 (br. s., 1H), 4.81 (br. s., 1H), 3.73-3.60 (m, 2H), 3.03 (br. s., 2H), 2.63-2.52 (m, 2H), 1.50-1.36 (m, 9H), 0.97-0.88 (m, 2H), 0.04-0.03 (m, 9H).

86D. Preparation of Tert-Butyl N-[(1S)-1-(3-{4-[(2R)-2-methylbut-3-enamido]-1-{[2-(trimethylsilyl)ethoxy]methyl}-1H-pyrazol-5-yl}phenyl)but-3-en-1-yl]carbamate To tert-butyl N-[(1S)-1-[3-(4-amino-1-{[2-(trimethylsilyl)ethoxy]methyl}-1H-pyrazol-5-yl)phenyl]but-3-en-1-yl]carbamate (0.269 g, 0.586 mmol) in EtOAc (1 ml) was added (R)-2-methylbut-3-enoic acid (0.076 g, 0.762 mmol), prepared as described in Intermediate 2, in 1 mL EtOAc and the solution was cooled to 0° C. To the reaction mixture was added pyridine (0.142 ml, 1.759 mmol) and 50% EtOAc solution of T3P® (0.698 ml, 1.173 mmol). After 1 h, the reaction was partitioned between sat NaHCO$_3$(10 ml) and EtOAc (30 ml). The aqueous layer was extracted with EtOAc (2×20 ml). The combined organic layers were washed with brine (10 ml), dried (MgSO$_4$), filtered and concentrated. The residue was purified by normal phase chromatography using hexanes and EtOAc as eluents to afford tert-butyl N-[(1S)-1-(3-{4-[(2R)-2-methylbut-3-enamido]-1-{[2-(trimethylsilyl)ethoxy]methyl}-1H-pyrazol-5-yl}phenyl)but-3-en-1-yl]carbamate (0.241 g, 76%) as a pink oil. MS(ESI) m/z: 541.6 (M−H)$^+$. $^1$H NMR (400 MHz, CDCl$_3$) δ 8.18 (s, 1H), 7.53-7.41 (m, 2H), 7.41-7.35 (m, 2H), 7.18 (br. s., 1H), 5.92 (ddd, J=17.2, 10.1, 7.9 Hz, 1H), 5.81-5.65 (m, 1H), 5.37-5.30 (m, 2H), 5.25-5.10 (m, 4H), 4.93 (br. s., 1H), 4.82-4.73 (m, 1H), 3.75-3.66 (m, 2H), 3.12 (quin, J=7.2 Hz, 1H), 2.63-2.49 (m, 2H), 1.48-1.39 (m, 9H), 1.35-1.31 (m, 3H), 1.00-0.90 (m, 2H), 0.03-0.02 (m, 9H).

86E. Preparation of Tert-Butyl N-[(9R,10E,13S)-9-methyl-8-oxo-3-{[2-(trimethylsilyl)ethoxy]methyl}-3,4,7-triazatricyclo[12.3.1.0$^{2,6}$]octadeca-1(18),2(6),4,10,14,16-hexaen-13-yl]carbamate A solution of tert-butyl N-[(1S)-1-(3-{4-[(2R)-2-methylbut-3-enamido]-1-{[2-(trimethylsilyl)ethoxy]methyl}-1H-pyrazol-5-yl}phenyl)but-3-en-1-yl]carbamate (0.241 g, 0.446 mmol) in DCM (55 ml), purged with Ar for 15 min. Second Generation Grubbs Catalyst (0.151 g, 0.178 mmol) was added and the reaction was heated to 40° C. After 24 h, the reaction mixture was concentrated and the residue was purified by normal phase chromatography using DCM and 0-10% MeOH and then, again with hexanes and EtOAc as eluents to afford tert-butyl N-[(9R,10E,13S)-9-methyl-8-oxo-3-{[2-(trimethylsilyl)ethoxy]methyl}-3,4,7-triazatricyclo[12.3.1.0$^{2,6}$]octadeca-1(18),2(6),4,10,14,16-hexaen-13-yl]carbamate (0.224 g, 98%) as a dark solid. MS(ESI) m/z: 513.5 (M+H)$^+$.

86F. Preparation of Tert-Butyl N-[(9R,13S)-9-methyl-8-oxo-3-{[2-(trimethylsilyl)ethoxy]methyl}-3,4,7-triazatricyclo[12.3.1.0$^{2,6}$]octadeca-1(18),2(6),4,14,16-pentaen-13-yl]carbamate tert-Butyl N-[(9R,10E,13S)-9-methyl-8-oxo-3-{[2-(trimethylsilyl)ethoxy]methyl}-3,4,7-triazatricyclo[12.3.1.0$^{2,6}$]octadeca-1(18),2(6),4,10,14,16-hexaen-13-yl]carbamate (0.16 g, 0.312 mmol) was hydrogenated at 55 psi in EtOH (4 ml), in the presence of PtO$_2$ (7.09 mg, 0.031 mmol). After 3 h, the reaction was filtered through CELITE® and concentrated to afford tert-butyl N-[(9R,13S)-9-methyl-8-oxo-3-{[2-(trimethylsilyl) ethoxy]methyl}-3,4,7-triazatricyclo[12.3.1.0$^{2,6}$]octadeca-1(18),2(6),4,14,16-pentaen-13-yl]carbamate (0.15g, 93%) desired product as a gray solid. MS(ESI) m/z: 515.5 (M+H)$^+$.

86G. and 86H. Preparation of (9R,13S)-13-amino-9-methyl-3-{[2-(trimethylsilyl)ethoxy]methyl}-3,4,7-triazatricyclo[12.3.1.0$^{2,6}$]octadeca-1(18),2(6),4,14,16-pentaen-8-one, and (9R,13S)-13-amino-9-methyl-3,4,7-triazatricyclo[12.3.1.0$^{2,6}$]octadeca-1(18),2(6),4,14,16-pentaen-8-one

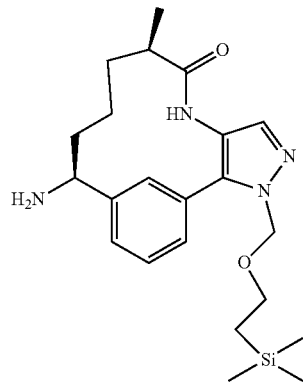

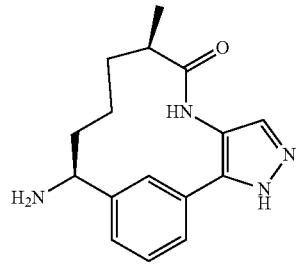

tert-Butyl N-[(9R,13S)-9-methyl-8-oxo-3-{[2-(trimethylsilyl)ethoxy]methyl}-3,4,7-triazatricyclo[12.3.1.0$^{2,6}$]octadeca-1(18),2(6),4,14,16-pentaen-13-yl]carbamat (0.15 g, 0.291 mmol) was heated in water (10 ml) in a microwave for 30 min at 150° C. The water was decanted from a tarry material and freeze-dried to afford a mixture of (9R,13S)-13-amino-9-methyl-3-{[2-(trimethylsilyl)ethoxy]methyl}-3,4,7-triazatricyclo[12.3.1.0$^{2,6}$]octadeca-1(18),2(6),4,14,16-pentaen-8-one (MS(ESI) m/z: 415.5 (M+H)$^+$)) and (9R,13S)-13-amino-9-methyl-3,4,7-triazatricyclo[12.3.1.0$^{2,6}$]octadeca-1(18),2(6),4,14,16-pentaen-8-one one (MS(ESI) m/z: 285.5 (M+H)$^+$) (29 mg) which was carried on to the next step 'as is'.

86I. Preparation of (9R,13S)-13-{4-[3-chloro-6-(4-chloro-1H-1,2,3-triazol-1-yl)-2-fluorophenyl]-6-oxo-1,6-dihydropyrimidin-1-yl}-9-methyl-3,4,7-triazatricyclo[12.3.1.0$^{2,6}$]octadeca-1(18),2(6),4,14,16-pentaen-8-one

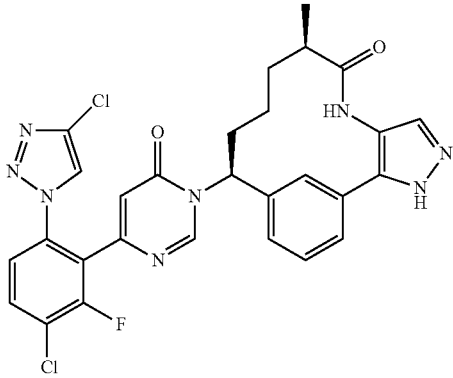 [SMILES: C[C@@H]1CCC[C@H](n2cnc(-c3c(-n4cc(Cl)nn4)ccc(Cl)c3F)cc2=O)c2cccc(c2)-c2[nH]ncc2NC1=O]

To 6-[3-chloro-6-(4-chloro-1H-1,2,3-triazol-1-yl)-2-fluorophenyl]pyrimidin-4-ol (0.015 g, 0.046 mmol), prepared as described in Intermediate 10, and HATU (0.023 g, 0.059 mmol) in a small vial was added DBU (10.34 µl, 0.069 mmol) in CH$_3$CN (0.8 ml). After 30 min, the mixture of (9R,13S)-13-amino-9-methyl-3-{[2-(trimethylsilyl)ethoxy]methyl}-3,4,7-triazatricyclo[12.3.1.0$^{2,6}$]octadeca-1(18),2(6),4,14,16-pentaen-8-one and (9R,13S)-13-amino-9-methyl-3,4,7-triazatricyclo[12.3.1.0$^{2,6}$]octadeca-1(18),2(6),4,14,16-pentaen-8-one (13 mg) in DMF (0.8 ml) was added and the reaction was stirred for 24 h. The reaction was diluted with DMF, filtered and purified by reverse phase HPLC using PHENOMENEX® Luna 5U 30×100 mm (10:90 MeOH/H$_2$O to 90:10 MeOH/H$_2$O, 0.1% TFA) (25% B start, 14 min gradient) to afford (9R,13S)-13-{4-[3-chloro-6-(4-chloro-1H-1,2,3-triazol-1-yl)-2-fluorophenyl]-6-oxo-1,6-dihydropyrimidin-1-yl}-9-methyl-3,4,7-triazatricyclo[12.3.1.0$^{2,6}$]octadeca-1(18),2(6),4,14,16-pentaen-8-one (2 mg, 7% yield) as a white solid. MS(ESI) m/z: 593.4 (M+H)$^+$. $^1$H NMR (400 MHz, CD$_3$OD) δ 8.29 (s, 1H), 8.11 (s, 1H), 7.91-7.82 (m, 2H), 7.70-7.65 (m, 1H), 7.62 (s, 1H), 7.56-7.46 (m, 3H), 7.10 (d, J=7.5 Hz, 1H), 6.67-6.62 (m, 1H), 5.93-5.86 (m, 1H), 2.65-2.57 (m, 1H), 2.29 (d, J=11.4 Hz, 1H), 2.11 (d, J=10.3 Hz, 1H), 1.98 (br. s., 1H), 1.65 (d, J=5.9 Hz, 1H), 1.59-1.50 (m, 1H), 1.40 (br. s., 1H), 1.15 (d, J=6.8 Hz, 3H). Analytical HPLC (Method A) RT=7.38 min, purity=90%; Factor XIa Ki=1.8 nM, Plasma Kallikrein Ki=90 nM.

Example 87

Preparation of (9R,13S)-13-{4-[3-chloro-2-fluoro-6-(1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one trifluoroacetate

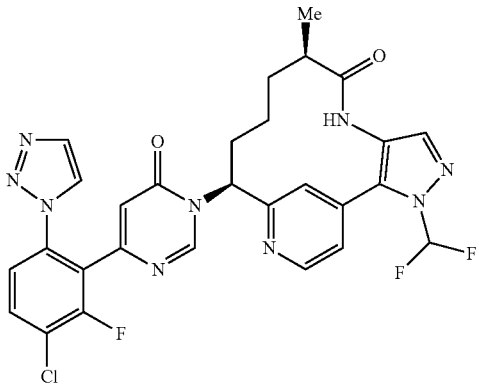 [SMILES: C[C@@H]1CCC[C@H](n2cnc(-c3c(-n4ccnn4)ccc(Cl)c3F)cc2=O)c2cc(ccn2)-c2c(cnn2C(F)F)NC1=O]

(9R,13S)-13-{4-[3-Chloro-2-fluoro-6-(1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one trifluoroacetate was prepared in a similar manner as the procedures described in Example 56, by using 6-(3-chloro-2-fluoro-6-(1H-1,2,3-triazol-1-yl)phenyl)pyrimidin-4-ol (0.034 g, 0.116 mmol), prepared as described in Intermediate 7, and (9R,13S)-13-amino-3-(difluoromethyl)-9-methyl-3,4,7,15-tetraazatricyclo[12.3.1.0$^{2,6}$]Octadeca-1(18),2(6),4,14,16-pentaen-8-one (0.039 g, 0.116 mmol), prepared as described in Intermediate 30, to yield (9R,13S)-13-{4-[3-chloro-2-fluoro-6-(1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one trifluoroacetate. MS(ESI) m/z: 610.2 [M+H]$^+$. $^1$H NMR (500 MHz, CD$_3$OD) δ 8.57 (s, 1H), 8.43 (d, J=5.2 Hz, 1H), 7.87 (d, J=1.1 Hz, 1H), 7.53 (dd, J=8.5, 7.7 Hz, 1H), 7.50-7.41 (m, 3H), 7.39-7.32 (m, 2H), 7.25-7.18 (m, 3H), 6.22 (s, 1H), 5.75-5.65 (m, 1H), 2.43-2.35 (m, 1H), 2.01-1.91 (m, 1H), 1.76-1.64 (m, 8H), 1.32-1.22 (m, 1H), 1.21-1.10 (m, 1H), 0.67 (d, J=7.2 Hz, 3H). Analytical HPLC (Method A): RT=7.59 min, purity=97.5%; Factor XIa Ki=0.22 nM, Plasma Kallikrein Ki=42 nM.

Example 88

Preparation of (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one trifluoroacetate

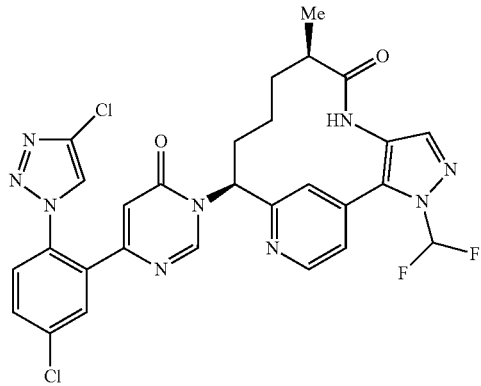 [SMILES: C[C@@H]1CCC[C@H](n2cnc(-c3cc(Cl)ccc3-n3cc(Cl)nn3)cc2=O)c2cc(ccn2)-c2c(cnn2C(F)F)NC1=O]

(9R,13S)-13-{4-[5-Chloro-2-(4-chloro-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one trifluoroacetate was prepared in a similar manner as the procedures described in Example 56, by using 6-(5-chloro-2-(4-chloro-1H-1,2,3-triazol-1-yl)phenyl)pyrimidin-4-ol (0.019 g, 0.062 mmol), prepared as described in Intermediate 9, and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one (0.021 g, 0.062 mmol), prepared as described in Intermediate 30, to yield (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one trifluoroacetate. MS(ESI) m/z: 626.2

[M+H]+. 1H NMR (500 MHz, CD3OD) δ 8.91-8.83 (m, 1H), 8.78-8.71 (m, 1H), 8.33 (s, 1H), 7.88 (d, J=2.5 Hz, 1H), 7.74 (s, 2H), 7.69-7.67 (m, 1H), 7.65 (s, 1H), 7.63 (t, J=58 Hz, 1H), 7.52-7.50 (m, 1H), 6.36 (d, J=0.8 Hz, 1H), 6.06-5.95 (m, 1H), 2.76-2.65 (m, 1H), 2.36-2.21 (m, 1H), 2.08-1.93 (m, 2H), 1.63-1.53 (m, 1H), 1.53-1.42 (m, 1H), 0.99 (d, J=6.9 Hz, 3H). Analytical HPLC (Method A): RT=8.87 min, purity=99.7%; Factor XIa Ki=0.12 nM, Plasma Kallikrein Ki=30 nM.

Example 89

Preparation of (9R,13S)-13-{4-[3-chloro-6-(4-chloro-1H-1,2,3-triazol-1-yl)-2-fluorophenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one; Trifluoroacetate

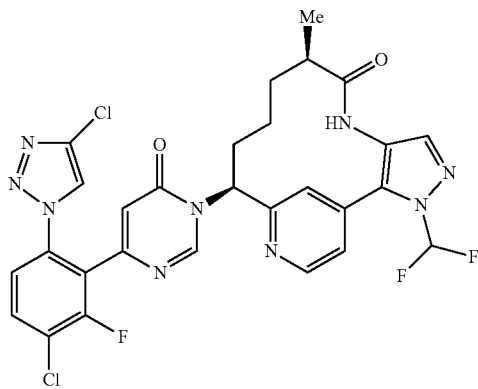 [SMILES: C[C@@H]1CCC[C@H](n2cnc(-c3c(-n4cc(Cl)nn4)ccc(Cl)c3F)cc2=O)c2cc(ccn2)-c2c(cnn2C(F)F)NC1=O]

(9R,13S)-13-{4-[3-Chloro-6-(4-chloro-1H-1,2,3-triazol-1-yl)-2-fluorophenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one trifluoroacetate was prepared in a similar manner as the procedures described in Example 56, by using 6-(3-chloro-6-(4-chloro-1H-1,2,3-triazol-1-yl)-2-fluorophenyl)pyrimidin-4-ol (0.025 g, 0.063 mmol), prepared as described in Intermediate 10, and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one (0.021 g, 0.063 mmol), prepared as described in Intermediate 30, to yield (9R,13S)-13-{4-[3-chloro-6-(4-chloro-1H-1,2,3-triazol-1-yl)-2-fluorophenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one trifluoroacetate. MS(ESI) m/z: 644.3 [M+H]+. 1H NMR (400 MHz, CD3OD) δ 8.92-8.84 (m, 1H), 8.80-8.72 (m, 1H), 8.32 (s, 1H), 7.89-7.82 (m, 1H), 7.75 (s, 1H), 7.74-7.70 (m, 1H), 7.66 (t, J=58 Hz, 1H), 7.54 (d, J=1.5 Hz, 2H), 6.60 (s, 1H), 6.07-5.97 (m, 1H), 2.76-2.65 (m, 1H), 2.36-2.23 (m, 1H), 2.09-1.96 (m, 2H), 1.65-1.42 (m, 2H), 1.00 (d, J=7.0 Hz, 3H). Analytical HPLC (Method A): RT=8.36 min, purity=98.8%; Factor XIa Ki=0.1 nM, Plasma Kallikrein Ki=11 nM.

Example 90

Preparation of (9R,13S)-13-{4-[3-chloro-6-(4-chloro-1H-1,2,3-triazol-1-yl)-2-fluorophenyl]-6-oxo-1,6-dihydropyrimidin-1-yl}-3-(2-hydroxy ethyl)-9-methyl-3,4,7,15-tetraazatricyclo[12.3.1.0$^{2,6}$]octadeca-1(18),2(6),4,14,16-pentaen-8-one Trifluoroacetate

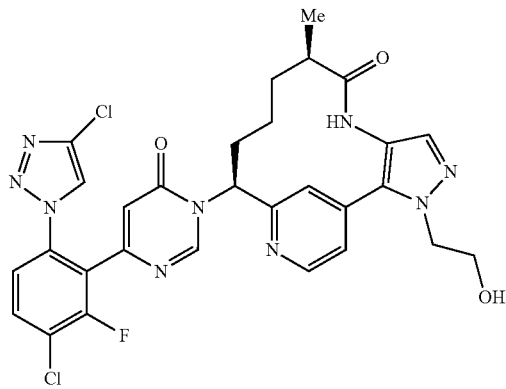 [SMILES: C[C@@H]1CCC[C@H](n2cnc(-c3c(-n4cc(Cl)nn4)ccc(Cl)c3F)cc2=O)c2cc(ccn2)-c2c(cnn2CCO)NC1=O]

(9R,13S)-13-{4-[3-Chloro-6-(4-chloro-1H-1,2,3-triazol-1-yl)-2-fluorophenyl]-6-oxo-1,6-dihydropyrimidin-1-yl}-3-(2-hydroxyethyl)-9-methyl-3,4,7,15-tetraazatricyclo[12.3.1.0$^{2,6}$]octadeca-1(18),2(6),4,14,16-pentaen-8-one trifluoroacetate was prepared in a similar manner as the procedures described in Example 56, by using 6-(3-chloro-6-(4-chloro-1H-1,2,3-triazol-1-yl)-2-fluorophenyl)pyrimidin-4-ol (0.054 g, 0.167 mmol), prepared as described in Intermediate 10, and (9R,13S)-13-amino-3-(2-hydroxyethyl)-9-methyl-3,4,7,15-tetraazatricyclo[12.3.1.0$^{2,6}$]octadeca-1(18),2(6),4,14,16-pentaen-8-one (0.055 g, 0.167 mmol), prepared as described in Intermediate 40. The crude product was purified by prep HPLC to give (9R,13S)-13-{4-[3-chloro-6-(4-chloro-1H-1,2,3-triazol-1-yl)-2-fluorophenyl]-6-oxo-1,6-dihydropyrimidin-1-yl}-3-(2-hydroxy ethyl)-9-methyl-3,4,7,15-tetraazatricyclo[12.3.1.0$^{2,6}$]octadeca-1(18),2(6),4,14,16-pentaen-8-one trifluoroacetate. (45 mg, 34% yield) as tan solid. 1H NMR (400 MHz, CD3OD) δ 8.82 (s, 1H), 8.75 (d, J=5.3 Hz, 1H), 8.36-8.32 (m, 1H), 7.87 (dd, J=8.6, 7.7 Hz, 1H), 7.81 (dd, J=5.1, 1.5 Hz, 1H), 7.73 (s, 1H), 7.61-7.53 (m, 2H), 6.00 (dd, J=12.7, 4.3 Hz, 1H), 4.51-4.33 (m, 1H), 4.13-3.86 (m, 2H), 3.39-3.35 (m, 2H), 2.71 (td, J=6.8, 3.1 Hz, 1H), 2.43-2.25 (m, 1H), 2.13-1.97 (m, 1H), 1.68-1.40 (m, 2H), 1.03 (d, J=6.8 Hz, 6H), 0.75 (br. s., 1H). MS(ESI) m/z: 638.5 [M+H]+. Analytical HPLC (Method A): RT=7.32 min, purity=>95.0%; Factor XIa Ki=0.34 nM, Plasma Kallikrein Ki=28 nM.

Example 91

Preparation of (9R,13)-13-(4-{5-chloro-2-[4-(difluoromethyl)-1H-1,2,3-triazol-1-yl]phenyl}-6-oxo-1,6-dihydropyrimidin-1-yl)-3-(2-hydroxyethyl)-9-methyl-3,4,7,15-tetraazatricyclo[12.3.1.0$^{2,6}$]octadeca-1(18),2(6),4,14,16-pentaen-8-one trifluoroacetate

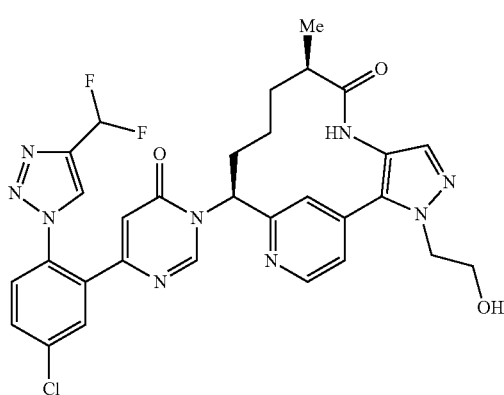 [SMILES: C[C@@H]1CCC[C@H](n2cnc(-c3cc(Cl)ccc3-n3cc(C(F)F)nn3)cc2=O)c2cc(ccn2)-c2c(cnn2CCO)NC1=O]

(9R,13S)-13-(4-{5-Chloro-2-[4-(difluoromethyl)-1H-1,2,3-triazol-1-yl]phenyl}-6-oxo-1,6-dihydropyrimidin-1-yl)-3-(2-hydroxyethyl)-9-methyl-3,4,7,15-tetraazatricyclo[12.3.1.0$^{2,6}$]octadeca-1(18),2(6),4,14,16-pentaen-8-one trifluoroacetate was prepared in a similar manner as the procedures described in Example 56, by using 6-(5-chloro-2-(4-(difluoromethyl)-1H-1,2,3-triazol-1-yl)phenyl)pyrimidin-4-ol (0.049 g, 0.152 mmol), prepared as described in Intermediate 16, and (9R,13S)-13-amino-3-(2-hydroxyethyl)-9-methyl-3,4,7,15-tetraazatricyclo[12.3.1.0$^{2,6}$]octadeca-1(18),2(6),4,14,16-pentaen-8-one (0.050 g, 0.152 mmol), prepared as described in Intermediate 40. The crude product was purified by prep HPLC to yield (9R,13S)-13-(4-{5-chloro-2-[4-(difluoromethyl)-1H-1,2,3-triazol-1-yl]phenyl}-6-oxo-1,6-dihydropyrimidin-1-yl)-3-(2-hydroxyethyl)-9-methyl-3,4,7,15-tetraazatricyclo[12.3.1.0$^{2,6}$]octadeca-1(18),2(6),4,14,16-pentaen-8-one trifluoroacetate (32 mg, 27% yield) as a white solid. $^1$H NMR (400 MHz, CD$_3$OD) δ 8.75 (s, 1H), 8.69 (d, J=5.1 Hz, 1H), 8.56-8.50 (m, 1H), 7.87 (d, J=2.4 Hz, 1H), 7.79-7.61 (m, 4H), 7.55 (s, 1H), 7.16-6.80 (m, 1H), 6.34 (d, J=0.4 Hz, 1H), 5.95 (dd, J=12.7, 4.1 Hz, 1H), 4.47-4.28 (m, 2H), 4.09-3.87 (m, 2H), 2.67 (td, J=6.8, 3.0 Hz, 1H), 2.34-2.19 (m, 1H), 2.09-1.91 (m, 2H), 1.65-1.34 (m, 2H), 1.00 (d, J=6.8 Hz, 3H), 0.70 (br. s., 1H). MS(ESI) m/z: 636.5 [M+H]$^+$. Analytical HPLC (Method A): RT=7.32 min, purity=>95.0%; Factor XIa Ki=2.8 nM, Plasma Kallikrein Ki=220 nM.

Example 92

Preparation of (9R,13S)-13-{4-[5-chloro-2-(4-chloro-1H-1,2,3-triazol-1-yl)phenyl]-6-oxo-1,6-dihydropyrimidin-1-yl}-3-(2-hydroxyethyl)-9-methyl-3,4,7,15-tetraazatricyclo[12.3.1.0$^{2,6}$]octadeca-1(18),2(6),4,14,16-pentaen-8-one trifluoroacetate

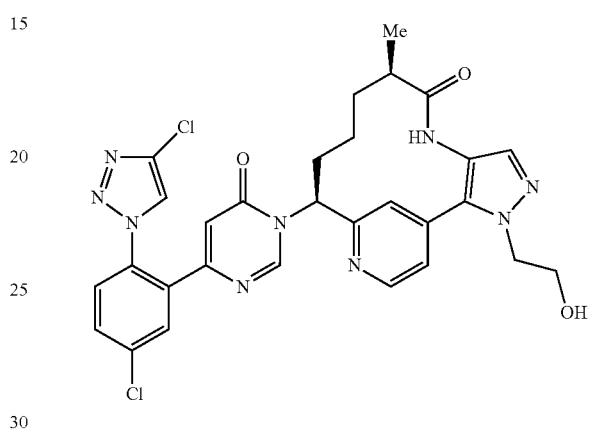

(9R,13S)-13-{4-[5-Chloro-2-(4-chloro-1H-1,2,3-triazol-1-yl)phenyl]-6-oxo-1,6-dihydropyrimidin-1-yl}-3-(2-hydroxyethyl)-9-methyl-3,4,7,15-tetraazatricyclo[12.3.1.0$^{2,6}$]octadeca-1(18),2(6),4,14,16-pentaen-8-one trifluoroacetate was prepared in a similar manner as the procedures described in Example 56, by using 6-(5-chloro-2-(4-chloro-1H-1,2,3-triazol-1-yl)phenyl)pyrimidin-4-ol (0.042 g, 0.137 mmol), prepared as described in Intermediate 9, and (9R,13S)-13-amino-3-(2-hydroxyethyl)-9-methyl-3,4,7,15-tetraazatricyclo[12.3.1.0$^{2,6}$]octadeca-1(18),2(6),4,14,16-pentaen-8-one (0.045 g, 0.137 mmol), prepared as described in Intermediate 40. The crude product was purified by prep HPLC to yield (9R,13S)-13-{4-[5-chloro-2-(4-chloro-1H-1,2,3-triazol-1-yl)phenyl]-6-oxo-1,6-dihydropyrimidin-1-yl}-3-(2-hydroxyethyl)-9-methyl-3,4,7,15-tetraazatricyclo[12.3.1.0$^{2,6}$]octadeca-(18),2(6),4,14,16-pentaen-8-one (65 mg, 61% yield) as white solid. $^1$H NMR (400 MHz, CD$_3$OD) δ 8.79 (s, 1H), 8.73 (d, J=5.1 Hz, 1H), 8.40-8.30 (m, 1H), 7.88 (d, J=2.2 Hz, 1H), 7.81 (dd, J=5.1, 1.5 Hz, 1H), 7.76-7.70 (m, 2H), 7.67-7.61 (m, 1H), 7.58 (s, 1H), 6.37 (d, J=0.4 Hz, 1H), 5.96 (dd, J=12.5, 4.2 Hz, 1H), 4.46-4.33 (m, 2H), 4.09-3.91 (m, 3H), 3.35 (s, 1H), 2.69 (td, J=6.8, 3.0 Hz, 1H), 2.39-2.24 (m, 1H), 2.12-1.94 (m, 2H), 1.66-1.40 (m, 2H), 1.02 (d, J=7.0 Hz, 3H), 0.73 (br. s., 1H). MS(ESI) m/z: 620.5 [M+H]$^+$. Analytical HPLC (Method A): RT=7.29 min, purity=>95.0%; Factor XIa Ki=1.3 nM, Plasma Kallikrein Ki=130 nM.

Example 93

Preparation of (9R,13S)-13-{4-[5-chloro-2-(1H-1,2,3,4-tetrazol-1-yl)phenyl]-6-oxo-1,6-dihydropyrimidin-1-yl}-3-(2-hydroxyethyl)-9-methyl-3,4,7,15-tetraazatricyclo[12.3.1.0$^{2,6}$]octadeca-1(18),2(6),4,14,16-pentaen-8-one trifluoroacetate

Example 94

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-3-(2-hydroxyethyl)-9-methyl-3,4,7,15-tetraazatricyclo[12.3.1.0$^{2,6}$]octadeca-1(18),2(6),4,14,16-pentaen-8-one trifluoroacetate

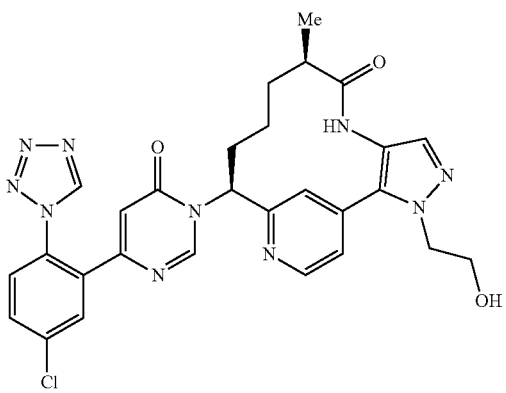 [SMILES: C[C@@H]1CCC[C@H](n2cnc(-c3cc(Cl)ccc3-n3cnnn3)cc2=O)c2cc(ccn2)-c2c(cnn2CCO)NC1=O]

(9R,13S)-13-{4-[5-Chloro-2-(1H-1,2,3,4-tetrazol-1-yl)phenyl]-6-oxo-1,6-dihydropyrimidin-1-yl}-3-(2-hydroxyethyl)-9-methyl-3,4,7,15-tetraazatricyclo[12.3.1.0$^{2,6}$]octadeca-1(18),2(6),4,14,16-pentaen-8-one trifluoroacetate was prepared in a similar manner as the procedures described in Example 56, by using 6-(5-chloro-2-(1H-tetrazol-1-yl)phenyl)pyrimidin-4-ol (0.037 g, 0.137 mmol), prepared as described in Intermediate 20, and (9R,13S)-13-amino-3-(2-hydroxyethyl)-9-methyl-3,4,7,15-tetraazatricyclo[12.3.1.0$^{2,6}$]octadeca-1(18),2(6),4,14,16-pentaen-8-one (0.045 g, 0.137 mmol), prepared as described in Intermediate 40. The crude product was purified by prep HPLC to yield (9R,13S)-13-{4-[5-chloro-2-(1H-1,2,3,4-tetrazol-1-yl)phenyl]-6-oxo-1,6-dihydropyrimidin-1-yl}-3-(2-hydroxyethyl)-9-methyl-3,4,7,15-tetraazatricyclo[12.3.1.0$^{2,6}$]octadeca-1(18),2(6),4,14,16-pentaen-8-one (52 mg, 52% yield) as a pale white solid. $^1$H NMR (400 MHz, CD$_3$OD) δ 9.42 (s, 1H), 8.68 (d, J=5.1 Hz, 2H), 7.88 (d, J=2.2 Hz, 1H), 7.78-7.72 (m, 2H), 7.67 (d, J=8.4 Hz, 2H), 7.55 (s, 1H), 6.49 (s, 1H), 5.93 (d, J=8.8 Hz, 1H), 4.45-4.29 (m, 2H), 4.08-3.88 (m, 3H), 3.32 (s, 1H), 2.66 (d, J=7.0 Hz, 1H), 2.24 (t, J=13.0 Hz, 1H), 2.08-1.88 (m, 2H), 1.65-1.49 (m, 1H), 1.41 (br. s., 1H), 0.98 (d, J=6.8 Hz, 3H), 0.67 (br. s., 1H). MS(ESI) m/z: 587.5 [M+H]$^+$. Analytical HPLC (Method A): RT=6.40 min, purity=>95.0%; Factor XIa Ki=0.65 nM, Plasma Kallikrein Ki=45 nM.

(9R,13S)-13-(4-{5-Chloro-2-[4-(trifluoromethyl)-1H-1,2,3-triazol-1-yl]phenyl}-6-oxo-1,6-dihydropyrimidin-1-yl)-3-(2-hydroxyethyl)-9-methyl-3,4,7,15-tetraazatricyclo[12.3.1.0$^{2,6}$]octadeca-1(18),2(6),4,14,16-pentaen-8-one trifluoroacetate was prepared in a similar manner as the procedures described in Example 56, by using 6-{5-chloro-2-[4-(trifluoromethyl)-1H-1,2,3-triazol-1-yl]phenyl}pyrimidin-4-ol (47 mg, 0.137 mmol), prepared as described in Intermediate 15, and (9R,13S)-13-amino-3-(2-hydroxyethyl)-9-methyl-3,4,7,15-tetraazatricyclo[12.3.1.0$^{2,6}$]octadeca-1(18),2(6),4,14,16-pentaen-8-one (0.045 g, 0.137 mmol), prepared as described in Intermediate 40. The crude product was purified by prep HPLC to yield (9R,13S)-13-(4-{5-chloro-2-[4-(trifluoromethyl)-1H-1,2,3-triazol-1-yl]phenyl}-6-oxo-1,6-dihydropyrimidin-1-yl)-3-(2-hydroxyethyl)-9-methyl-3,4,7,15-tetraazatricyclo[12.3.1.0$^{2,6}$]octadeca-1(18),2(6),4,14,16-pentaen-8-one (67 mg, 61% yield) as a white solid. $^1$H NMR (400 MHz, CD$_3$OD) δ 8.79 (s, 1H), 8.72 (s, 1H), 8.68-8.61 (m, 1H), 7.88-7.82 (m, 1H), 7.78-7.69 (m, 2H), 7.68-7.61 (m, 2H), 7.54 (s, 1H), 6.40 (s, 1H), 5.93 (dd, J=12.7, 4.1 Hz, 1H), 4.42-4.27 (m, 2H), 4.03-3.86 (m, 2H), 2.65 (dt, J=6.8, 3.3 Hz, 1H), 2.33-2.15 (m, 1H), 2.07-1.87 (m, 2H), 1.64-1.48 (m, 1H), 1.41 (td, J=10.0, 5.2 Hz, 1H), 1.01-0.93 (m, 3H), 0.66 (br. s., 1H). MS(ESI) m/z: 654.5 [M+H]$^+$. Analytical HPLC (Method A): RT=8.10 min, purity=>95.0%; Factor XIa Ki=1.1 nM, Plasma Kallikrein Ki=130 nM.

Example 95

Preparation of 2-[(9R,13S)-13-{4-[3-chloro-6-(4-chloro-1H-1,2,3-triazol-1-yl)-2-fluorophenyl]-6-oxo-1,6-dihydropyrimidin-1-yl}-9-methyl-8-oxo-3,4,7,15-tetraazatricyclo[12.3.1.0$^{2,6}$]octadeca-1(18),2(6),4,14,16-pentaen-3-yl]acetic Acid Trifluoroacetate

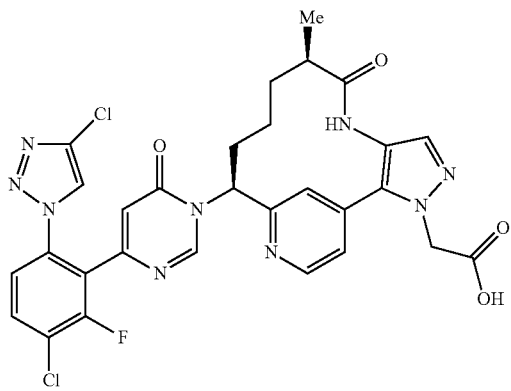 [SMILES: C[C@@H]1CCC[C@H](n2cnc(-c3c(-n4cc(Cl)nn4)ccc(Cl)c3F)cc2=O)c2cc(ccn2)-c2c(cnn2CC(=O)O)NC1=O]

A solution of (9R,13S)-13-{4-[3-chloro-6-(4-chloro-1H-1,2,3-triazol-1-yl)-2-fluorophenyl]-6-oxo-1,6-dihydropyrimidin-1-yl}-3-(2-hydroxyethyl)-9-methyl-3,4,7,15-tetraazatricyclo[12.3.1.0$^{2,6}$]octadeca-1(18),2(6),4,14,16-pentaen-8-one trifluoroacetate (0.034 g, 0.053 mmol), prepared as described in Example 90, in acetone (2 mL) was cooled to 0° C. To this cooled mixture was then added 2.86 M solution of Jones reagent (0.037 mL, 0.107 mmol) and the resulting reaction mixture was allowed to warm to rt over a period of 2 h. The reaction mixture was then quenched with 0.5 mL of IPA and concentrated. The resulting residue was purified by prep HPLC purification to afford 2-[(9R,13S)-13-{4-[3-chloro-6-(4-chloro-1H-1,2,3-triazol-1-yl)-2-fluorophenyl]-6-oxo-1,6-dihydropyrimidin-1-yl}-9-methyl-8-oxo-3,4,7,15-tetraazatricyclo[12.3.1.0$^{2,6}$]octadeca-1(18),2(6),4,14,16-pentaen-3-yl]acetic acid trifluoroacetate (8 mg, 19% yield) as a white solid. $^1$H NMR (400 MHz, CD$_3$OD) δ 8.85 (s, 1H), 8.74 (d, J=5.1 Hz, 1H), 8.34 (s, 1H), 7.87 (dd, J=8.6, 7.5 Hz, 1H), 7.72 (s, 1H), 7.61-7.53 (m, 2H), 7.49 (dd, J=5.1, 1.5 Hz, 1H), 6.62 (s, 1H), 6.04 (dd, J=12.3, 4.2 Hz, 1H), 5.27-5.06 (m, 2H), 2.72 (dt, J=6.7, 3.4 Hz, 1H), 2.30 (t, J=12.7 Hz, 1H), 2.15-1.97 (m, 2H), 1.69-1.41 (m, 2H), 1.03 (d, J=7.0 Hz, 3H), 0.71 (br. s., 1H). MS(ESI) m/z: 652.2 [M+H]$^+$. Analytical HPLC (Method A): RT=7.45 min, purity=>95.0%; Factor XIa Ki=0.11 nM, Plasma Kallikrein Ki=12 nM.

Example 96

Preparation of 2-[(9R,13S)-13-(4-{5-chloro-2-[4-(difluoromethyl)-1H-1,2,3-triazol-1-yl]phenyl}-6-oxo-1,6-dihydropyrimidin-1-yl)-9-methyl-8-oxo-3,4,7,15-tetraazatricyclo[12.3.1.0$^{2,6}$]octadeca-1(18),2(6),4,14,16-pentaen-3-yl]acetic acid Trifluoroacetate

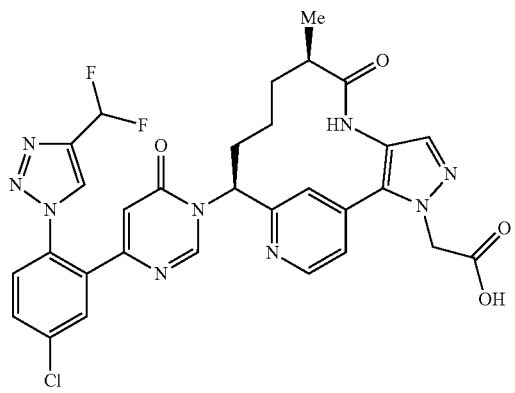 [SMILES: C[C@@H]1CCC[C@H](n2cnc(-c3cc(Cl)ccc3-n3cc(C(F)F)nn3)cc2=O)c2cc(ccn2)-c2c(cnn2CC(=O)O)NC1=O]

2-[(9R,13S)-13-(4-{5-Chloro-2-[4-(difluoromethyl)-1H-1,2,3-triazol-1-yl]phenyl}-6-oxo-1,6-dihydropyrimidin-1-yl)-9-methyl-8-oxo-3,4,7,15-tetraazatricyclo[12.3.1.0$^{2,6}$]octadeca-1(18),2(6),4,14,16-pentaen-3-yl]acetic acid was prepared in a similar manned as the procedure described in Example 95, using (9R,13S)-13-(4-{5-chloro-2-[4-(difluoromethyl)-1H-1,2,3-triazol-1-yl]phenyl}-6-oxo-1,6-dihydropyrimidin-1-yl)-3-(2-hydroxyethyl)-9-methyl-3,4,7,15-tetraazatricyclo[12.3.1.0$^{2,6}$]octadeca-1(18),2(6),4,14,16-pentaen-8-one trifluoroacetate (0.024 g, 0.038 mmol), prepared as described in Example 91, to yield 2-[(9R,13S)-13-(4-{5-chloro-2-[4-(difluoromethyl)-1H-1,2,3-triazol-1-yl]phenyl}-6-oxo-1,6-dihydropyrimidin-1-yl)-9-methyl-8-oxo-3,4,7,15-tetraazatricyclo[12.3.1.0$^{2,6}$]octadeca-1(18),2(6),4,14,16-pentaen-3-yl]acetic acid trifluoroacetate (6 mg, 20% yield) as a white solid. $^1$H NMR (400 MHz, CD$_3$OD) δ 8.83 (s, 1H), 8.72 (d, J=5.1 Hz, 1H), 8.56 (s, 1H), 7.91 (d, J=2.4 Hz, 1H), 7.80-7.74 (m, 1H), 7.72-7.66 (m, 2H), 7.59 (s, 1H), 7.49 (dd, J=5.1, 1.3 Hz, 1H), 7.19-6.86 (m, 1H), 6.38 (s, 1H), 6.03 (dd, J=12.7, 4.3 Hz, 1H), 5.27-5.06 (m, 2H), 2.72 (dt, J=6.6, 3.3 Hz, 1H), 2.34-2.22 (m, 1H), 2.13-1.94 (m, 2H), 1.68-1.40 (m, 2H), 1.03 (d, J=7.0 Hz, 3H), 0.71 (br. s., 1H). MS(ESI) m/z: 650.3 [M+H]$^+$. Analytical HPLC (Method A): RT=7.52 min, purity=>95.0%; Factor XIa Ki=0.65 nM, Plasma Kallikrein Ki=78 nM.

Example 97

Preparation of 2-[(9R,13S)-13-{4-[5-chloro-2-(4-chloro-1H-1,2,3-triazol-1-yl)phenyl]-6-oxo-1,6-dihydropyrimidin-1-yl}-9-methyl-8-oxo-3,4,7,15-tetraazatricyclo[12.3.1.0$^{2,6}$]octadeca-1(18),2(6),4,14,16-pentaen-3-yl]acetic Acid Trifluoroacetate

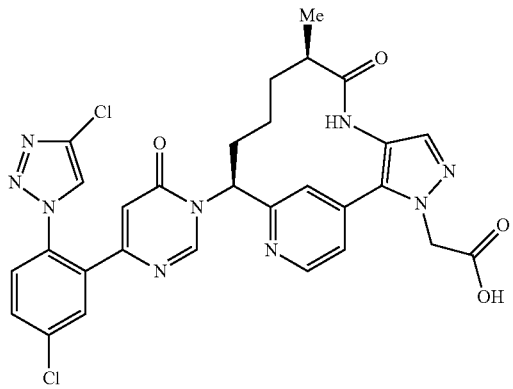 [SMILES: C[C@@H]1CCC[C@H](n2cnc(-c3cc(Cl)ccc3-n3cc(Cl)nn3)cc2=O)c2cc(ccn2)-c2c(cnn2CC(=O)O)NC1=O]

2-[(9R,13)-13-{4-[5-Chloro-2-(4-chloro-1H-1,2,3-triazol-1-yl)phenyl]-6-oxo-1,6-dihydropyrimidin-1-yl}-9-methyl-8-oxo-3,4,7,15-tetraazatricyclo[12.3.1.0$^{2,6}$]octadeca-1(18),2(6),4,14,16-pentaen-3-yl]acetic acid trifluoroacetate was prepared in a similar manned as the procedure described in Example 95, using (9R,13S)-13-{4-[5-chloro-2-(4-chloro-1H-1,2,3-triazol-1-yl)phenyl]-6-oxo-1,6-dihydropyrimidin-1-yl}-3-(2-hydroxyethyl)-9-methyl-3,4,7,15-tetraazatricyclo[12.3.1.0$^{2,6}$]octadeca-1(18),2(6),4,14,16-pentaen-8-one trifluoroacetate (0.038 g, 0.061 mmol), prepared as described in Example 92, to yield 2-[(9R,13)-13-{4-[5-chloro-2-(4-chloro-1H-1,2,3-triazol-1-yl)phenyl]-6-oxo-1,6-dihydropyrimidin-1-yl}-9-methyl-8-oxo-3,4,7,15-tetraazatricyclo[12.3.1.0$^{2,6}$]octadeca-1(18),2(6),4,14,16-pentaen-3-yl]acetic acid trifluoroacetate (8 mg, 17% yield) as a white solid. $^{1}$H NMR (400 MHz, CD$_3$OD) δ 8.85 (s, 1H), 8.73 (d, J=5.1 Hz, 1H), 8.36 (s, 1H), 7.92-7.88 (m, 1H), 7.79-7.64 (m, 3H), 7.59 (s, 1H), 7.49 (dd, J=5.1, 1.3 Hz, 1H), 6.38 (s, 1H), 6.03 (dd, J=12.5, 4.0 Hz, 1H), 5.27-5.04 (m, 2H), 2.72 (i, 1H), 2.30 (m, 1H), 2.14-1.97 (m, 2H), 1.69-1.42 (m, 2H), 1.03 (d, J=6.8 Hz, 3H), 0.71 (br. s., 1H). MS(ESI) m/z: 634.3 [M+H]$^+$. Analytical HPLC (Method A): RT=7.49 min, purity=>95.0%; Factor XIa Ki=0.38 nM, Plasma Kallikrein Ki=52 nM.

Example 98

Preparation of 2-[(9R,13S)-13-{4-[5-chloro-2-(1H-1,2,3,4-tetrazol-1-yl)phenyl]-6-oxo-1,6-dihydropyrimidin-1-yl}-9-methyl-8-oxo-3,4,7,15-tetraazatricyclo[12.3.1.0$^{2,6}$]octadeca-1(18),2(6),4,14,16-pentaen-3-yl]acetic Acid Trifluoroacetate

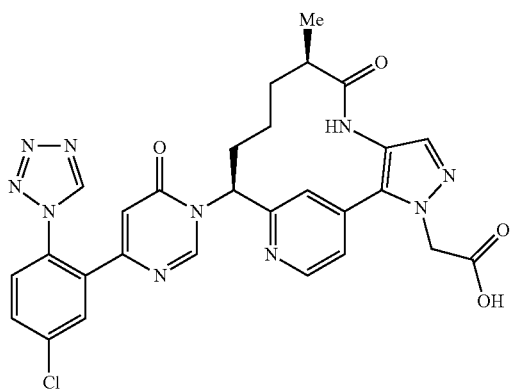 [SMILES: C[C@@H]1CCC[C@H](n2cnc(-c3cc(Cl)ccc3-n3cnnn3)cc2=O)c2cc(ccn2)-c2c(cnn2CC(=O)O)NC1=O]

2-[(9R,13S)-13-{4-[5-Chloro-2-(1H-1,2,3,4-tetrazol-1-yl)phenyl]-6-oxo-1,6-dihydropyrimidin-1-yl}-9-methyl-8-oxo-3,4,7,15-tetraazatricyclo[12.3.1.0$^{2,6}$]octadeca-1(18),2(6),4,14,16-pentaen-3-yl]acetic acid trifluoroacetate was prepared in a similar manned as the procedure described in Example 95, using (9R,13S)-13-{4-[5-chloro-2-(1H-1,2,3,4-tetrazol-1-yl)phenyl]-6-oxo-1,6-dihydropyrimidin-1-yl}-3-(2-hydroxyethyl)-9-methyl-3,4,7,15-tetraazatricyclo[12.3.1.0$^{2,6}$]octadeca-1(18),2(6),4,14,16-pentaen-8-one trifluoroacetate (0.020 g, 0.034 mmol), prepared as described in Example 93, to yield 2-[(9R,13S)-13-{4-[5-chloro-2-(1H-1,2,3,4-tetrazol-1-yl)phenyl]-6-oxo-1,6-dihydropyrimidin-1-yl}-9-methyl-8-oxo-3,4,7,15-tetraazatricyclo[12.3.1.0$^{2,6}$]octadeca-1(18),2(6),4,14,16-pentaen-3-yl]acetic acid trifluoroacetate (5.1 mg, 20% yield) as a white solid. $^{1}$H NMR (400 MHz, CD$_3$OD) δ 9.45 (s, 1H), 8.80-8.68 (m, 2H), 7.95-7.90 (m, 1H), 7.83-7.76 (m, 1H), 7.74-7.67 (m, 2H), 7.59 (s, 1H), 7.49 (dd, J=5.1, 1.3 Hz, 1H), 6.53 (s, 1H), 6.01 (dd, J=12.5, 4.0 Hz, 1H), 5.28-5.05 (m, 2H), 2.71 (m, 1H), 2.27 (m, 1H), 2.13-1.95 (m, 2H), 1.66-1.39 (m, 2H), 1.03 (d, J=7.0 Hz, 3H), 0.72 (br. s., 1H). MS(ESI) m/z: 601.3 [M+H]$^+$. Analytical HPLC (Method A): RT=6.62 min, purity=>95.0%; Factor XIa Ki=0.16 nM, Plasma Kallikrein Ki=20 nM.

Example 99

Preparation of 2-[(9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-8-oxo-3,4,7,15-tetraazatricyclo[12.3.1.0$^{2,6}$]octadeca-1(18),2(6),4,14,16-pentaen-3-yl]acetic Acid Trifluoroacetate

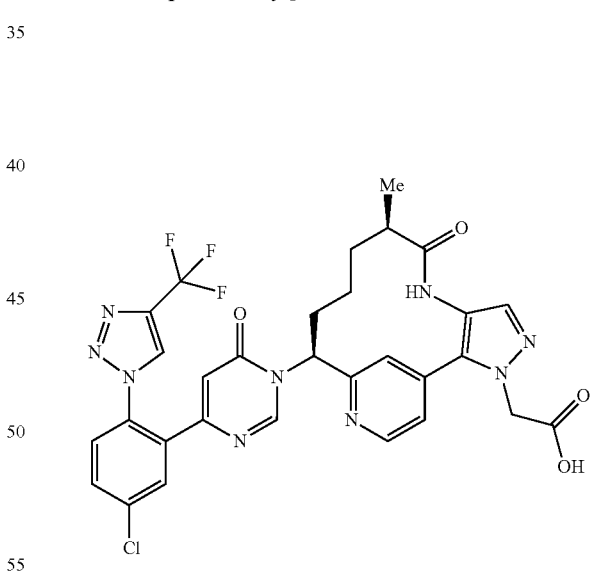

2-[(9R,13S)-13-(4-{5-Chloro-2-[4-(trifluoromethyl)-1H-1,2,3-triazol-1-yl]phenyl}-6-oxo-1,6-dihydropyrimidin-1-yl)-9-methyl-8-oxo-3,4,7,15-tetraazatricyclo[12.3.1.0$^{2,6}$]octadeca-1(18),2(6),4,14,16-pentaen-3-yl]acetic acid trifluoroacetate was prepared in a similar manned as the procedure described in Example 95, using (9R,13S)-13-(4-{5-chloro-2-[4-(trifluoromethyl)-1H-1,2,3-triazol-1-yl]phenyl}-6-oxo-1,6-dihydropyrimidin-1-yl)-3-(2-hydroxyethyl)-9-methyl-3,4,7,15-tetraazatricyclo[12.3.1.0$^{2,6}$]octadeca-1(18),2(6),4,14,16-pentaen-8-one trifluoroacetate (0.038 g, 0.058 mmol), prepared as described in Example 94, to yield 2-[(9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-8-oxo-3,4,7,15-tetraazatricyclo[12.3.1.0$^{2,6}$]octadeca-1(18),2(6),4,14,16-pentaen-3-yl]acetic acid trifluoroacetate (7.5 mg, 16% yield) as a white solid. $^1$H NMR (400 MHz, CD$_3$OD) δ 8.84 (s, 1H), 8.80 (s, 1H), 8.73-8.68 (m, 1H), 7.92 (d, J=2.4 Hz, 1H), 7.80-7.75 (m, 1H), 7.71 (m, 2H), 7.58 (s, 1H), 7.49 (dd, J=5.1, 1.3 Hz, 1H), 6.46 (s, 1H), 6.03 (dd, J=12.4, 4.1 Hz, 1H), 5.26-5.06 (m, 2H), 2.77-2.66 (m, 1H), 2.27 (m, 1H), 2.13-1.94 (m, 2H), 1.67-1.40 (m, 2H), 1.02 (d, J=6.8 Hz, 3H), 0.71 (br. s., 1H). MS(ESI) m/z: 668.3 [M+H]+; Factor XIa Ki=0.29 nM, Plasma Kallikrein Ki=52 nM.

Example 100

Preparation of (9R,13S)-13-{4-[3-chloro-6-(4-chloro-1H-1,2,3-triazol-1-yl)-2-fluorophenyl]-6-oxo-1,6-dihydropyrimidin-1-yl}-9-methyl-3,4,7,15-tetraazatricyclo[12.3.1.0$^{2,6}$]octadeca-1(18),2(6),4,14,16-pentaen-8-one Trifluoroacetate

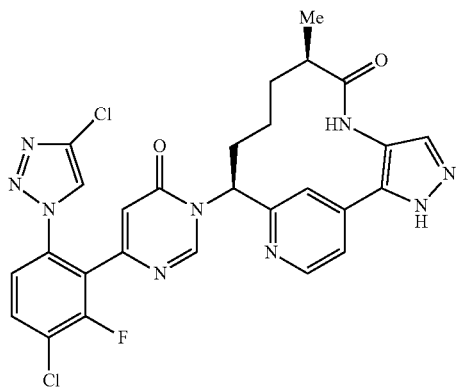 [SMILES: C[C@@H]1CCC[C@H](n2cnc(-c3c(-n4cc(Cl)nn4)ccc(Cl)c3F)cc2=O)c2cc(ccn2)-c2[nH]ncc2NC1=O]

100A. Preparation of (9R,13S)-13-{4-[3-chloro-6-(4-chloro-1H-1,2,3-triazol-1-yl)-2-fluorophenyl]-6-oxo-1,6-dihydropyrimidin-1-yl}-9-methyl-3-{[2-(trimethylsilyl)ethoxy]methyl}-3,4,7,15-tetraazatricyclo[12.3.1.0$^{2,6}$]octadeca-1(18),2(6),4,14,16-pentaen-8-one (9R,13S)-13-{4-[3-Chloro-6-(4-chloro-1H-1,2,3-triazol-1-yl)-2-fluorophenyl]-6-oxo-1,6-dihydropyrimidin-1-yl}-9-methyl-3-{[2-(trimethylsilyl)ethoxy]methyl}-3,4,7,15-tetraazatricyclo[12.3.1.0$^{2,6}$]octadeca-1(18),2(6),4,14,16-pentaen-8-one was prepared in a similar manner as the procedures described in Example 56, by using 6-(3-chloro-6-(4-chloro-1H-1,2,3-triazol-1-yl)-2-fluorophenyl)pyrimidin-4-ol (0.027 g, 0.083 mmol), prepared as described in Intermediate 10, and benzyl N-[(9R,13S)-9-methyl-8-oxo-3-{[2-(trimethylsilyl)ethoxy]methyl}-3,4,7,15-tetraazatricyclo[12.3.1.0$^{2,6}$]octadeca-1(18),2(6),4,14,16-pentaen-13-yl]carbamate (0.034 g, 0.081 mmol), prepared as described in Intermediate 41, to yield (9R,13S)-13-{4-[3-chloro-6-(4-chloro-1H-1,2,3-triazol-1-yl)-2-fluorophenyl]-6-oxo-1,6-dihydropyrimidin-1-yl}-9-methyl-3-{[2-(trimethylsilyl)ethoxy]methyl}-3,4,7,15-tetraazatricyclo[12.3.1.0$^{2,6}$]octadeca-1(18),2(6),4,14,16-pentaen-8-one (10 mg, 14% yield) as pale white solid. MS(ESI) m/z: 723.5 [M+H]$^+$.

100B. Preparation of (9R,13S)-13-{4-[3-chloro-6-(4-chloro-1H-1,2,3-triazol-1-yl)-2-fluorophenyl]-6-oxo-1,6-dihydropyrimidin-1-yl}-9-methyl-3,4,7,15-tetraazatricyclo[12.3.1.0$^{2,6}$]octadeca-1(18),2(6),4,14,16-pentaen-8-one trifluoroacetate To a solution of (9R,13S)-13-{4-[3-chloro-6-(4-chloro-1H-1,2,3-triazol-1-yl)-2-fluorophenyl]-6-oxo-1,6-dihydropyrimidin-1-yl}-9-methyl-3-{[2-(trimethylsilyl)ethoxy]methyl}-3,4,7,15-tetraazatricyclo[12.3.1.0$^{2,6}$]octadeca-1(18),2(6),4,14,16-pentaen-8-one (10 mg, 0.014 mmol), in DCM (0.8 mL) was added TFA (0.2 mL, 2.60 mmol) and the resulting solution was stirred at rt for 30 min. The reaction mixture was then concentrated and the residue was purified by prep HPLC purification to give (9R,13S)-13-{4-[3-chloro-6-(4-chloro-1H-1,2,3-triazol-1-yl)-2-fluorophenyl]-6-oxo-1,6-dihydropyrimidin-1-yl}-9-methyl-3,4,7,15-tetraazatricyclo[12.3.1.0$^{2,6}$]octadeca-1(18),2(6),4,14,16-pentaen-8-one trifluoroacetate (4.8 mg, 46% yield) as a pale pink solid. $^1$H NMR (400 MHz, CD$_3$OD) δ 8.74-8.59 (m, 2H), 8.42-8.30 (m, 1H), 7.99 (s, 1H), 7.88 (dd, J=8.6, 7.7 Hz, 1H), 7.77 (s, 1H), 7.67 (dd, J=5.3, 1.3 Hz, 1H), 7.58 (dd, J=8.6, 1.5 Hz, 1H), 6.65 (s, 1H), 6.07 (d, J=8.4 Hz, 1H), 2.90-2.74 (m, 1H), 2.44-2.18 (m, 2H), 2.14-2.02 (m, 1H), 1.83-1.67 (m, 1H), 1.63-1.47 (m, 1H), 1.11 (d, J=6.8 Hz, 3H), 1.00 (br. s., 1H). MS(ESI) m/z: 594.5 [M+H]$^+$. Analytical HPLC (Method A): RT=7.11 min, purity=>95.0%; Factor XIa Ki=1.6 nM, Plasma Kallikrein Ki=85 nM.

Example 101

Preparation of (9R,13S)-13-{4-[5-chloro-2-(4-chloro-1H-1,2,3-triazol-1-yl)phenyl]-6-oxo-1,6-dihydropyrimidin-1-yl}-9-methyl-3,4,7,15-tetraazatricyclo[12.3.1.0$^{2,6}$]octadeca-1(18),2(6),4,14,16-pentaen-8-one Trifluoroacetate

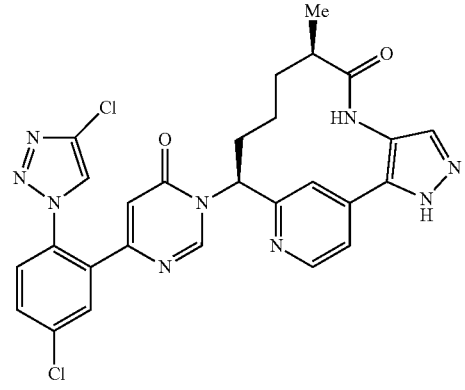 [SMILES: C[C@@H]1CCC[C@H](n2cnc(-c3cc(Cl)ccc3-n3cc(Cl)nn3)cc2=O)c2cc(ccn2)-c2[nH]ncc2NC1=O]

101A. Preparation of (9R,13S)-13-{4-[5-chloro-2-(4-chloro-1H-1,2,3-triazol-1-yl) phenyl]-6-oxo-1,6-dihydropyrimidin-1-yl}-9-methyl-3-{[2-(trimethylsilyl)ethoxy]methyl}-3,4,7,15-tetraazatricyclo[12.3.1.0$^{2,6}$]octadeca-1(18),2(6),4,14,16-pentaen-8-one (9R,13S)-13-{4-[5-Chloro-2-(4-chloro-1H-1,2,3-triazol-1-yl)phenyl]-6-oxo-1,6-dihydropyrimidin-1-yl}-9-methyl-3-{[2-(trimethylsilyl)ethoxy]methyl}-3,4,7,15-tetraazatricyclo[12.3.1.0$^{2,6}$]octadeca-1(18),2(6),4,14,16-pentaen-8- one was prepared in a similar manner as the procedure described in Example 56, by using 6-(5-chloro-2-(4-chloro-1H-1,2,3-triazol-1-yl)phenyl)pyrimidin-4-ol (0.034 g, 0.110 mmol), prepared as described in Intermediate 9, and benzyl N-[(9R,13S)-9-methyl-8-oxo-3-{[2-(trimethylsilyl)ethoxy]methyl}-3,4,7,15-tetraazatricyclo[12.3.1.0$^{2,6}$]octadeca-1(18),2(6),4,14,16-pentaen-13-yl]carbamate (0.046 g, 0.110 mmol), prepared as described in Intermediate 41, to give (9R,13)-13-{4-[5-chloro-2-(4-chloro-1H-1,2,3-triazol-1-yl)phenyl]-6-oxo-1,6-dihydropyrimidin-1-yl}-9-methyl-3-{[2-(trimethylsilyl) ethoxy]methyl}-3,4,7,15-tetraazatricyclo[12.3.1.0$^{2,6}$]octadeca-1(18),2(6),4,14,16-pentaen-8-one (12 mg, 14% yield) as pale yellow solid. MS(ESI) m/z: 706.5 [M+H]$^+$.

101B. Preparation of (9R,13S)-13-{4-[5-chloro-2-(4-chloro-1H-1,2,3-triazol-1-yl) phenyl]-6-oxo-1,6-dihydropyrimidin-1-yl}-9-methyl-3,4,7,15-tetraazatricyclo[12.3.1.0$^{2,6}$]octadeca-1(18),2(6),4,14,16-pentaen-8-one Trifluoroacetate To a solution of (9R,13S)-13-{4-[5-chloro-2-(4-chloro-1H-1,2,3-triazol-1-yl)phenyl]-6-oxo-1,6-dihydropyrimidin-1-yl}-9-methyl-3-{[2-(trimethylsilyl)ethoxy]methyl}-3,4,7,15-tetraazatricyclo[12.3.1.0$^{2,6}$]octadeca-1(18),2(6),4,14,16-pentaen-8-one (12 mg, 0.017 mmol) in DCM (0.8 mL) was added TFA (0.2 mL, 2.60 mmol) and the reaction was stirred at rt for 30 min. The reaction mixture was then concentrated and the residue was purified by prep HPLC purification to give (9R,13S)-13-{4-[5-chloro-2-(4-chloro-1H-1,2,3-triazol-1-yl)phenyl]-6-oxo-1,6-dihydropyrimidin-1-yl}-9-methyl-3,4,7,15-tetraazatricyclo[12.3.1.0$^{2,6}$]octadeca-1(18),2(6),4,14,16-pentaen-8-one trifluoroacetate (5.3 mg, 43% yield) as a pale pink solid. $^1$H NMR (400 MHz, CD$_3$OD) δ 8.72-8.57 (m, 2H), 8.37 (s, 1H), 7.99 (s, 1H), 7.91 (d, J=2.2 Hz, 1H), 7.82-7.72 (m, 2H), 7.70-7.63 (m, 2H), 6.41 (s, 1H), 6.11-5.95 (m, 1H), 2.81 (td, J=6.8, 3.4 Hz, 1H), 2.44-2.17 (m, 2H), 2.15-2.01 (m, 1H), 1.80-1.65 (m, 1H), 1.62-1.46 (m, 1H), 1.11 (d, J=7.0 Hz, 3H), 1.01 (br. s., 1H). MS(ESI) m/z: 576.4 [M+H]$^+$. Analytical HPLC (Method A): RT=6.98 min, purity=>95.0%; Factor XIa Ki=4.2 nM, Plasma Kallikrein Ki=300 nM.

Example 102

Preparation of methyl (9R,13S)-13-{4-[5-chloro-2-(4-chloro-1H-1,2,3-triazol-1-yl) phenyl]-6-oxo-1,6-dihydropyrimidin-1-yl}-9-methyl-8-oxo-2,3,7,15-tetraazatricyclo[12.3.1.0$^{2,6}$]octadeca-1(18),3,5,14,16-pentaene-4-carboxylate Trifluoroacetate

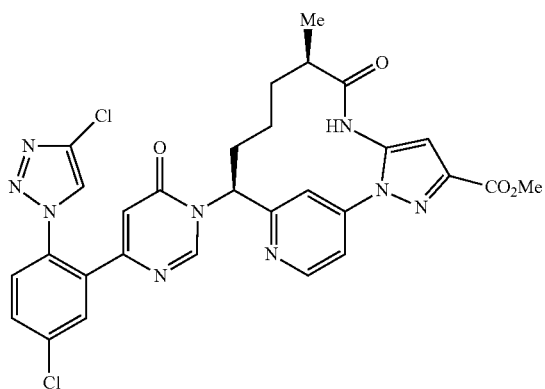 [SMILES: COC(=O)c1cc2n(n1)-c1ccnc(c1)[C@@H](n1cnc(-c3cc(Cl)ccc3-n3cc(Cl)nn3)cc1=O)CCC[C@@H](C)C(=O)N2]

102A. Preparation of (S)-tert-butyl (1-(4-hydrazinylpyridin-2-yl)but-3-en-1-yl) Carbamate A vial with a Teflon septum cap was charged with a solution of (S)-tert-butyl (1-(4-chloropyridin-2-yl)but-3-en-1-yl)carbamate (2 g, 7.0 mmol), prepared as described in Intermediate 23, and 35% aq hydrazine (10 mL, 111 mmol, 15.75 equiv) in EtOH (10 mL). The solution was heated by an aluminum block at 115° C. for 18 h. The reaction was concentrated to give a pink oil. The residue was purified by normal phase silica gel chromatography to give (S)-tert-butyl (1-(4-hydrazinylpyridin-2-yl)but-3-en-1-yl)carbamate (1.67 g, 85% yield) as a yellow, foam. $^1$H NMR (400 MHz, CDCl$_3$) δ 8.22 (d, J=5.7 Hz, 1H), 6.60 (s, 1H), 6.57 (dd, J=5.5, 2.4 Hz, 1H), 5.79-5.54 (m, 3H), 5.14-4.99 (m, 2H), 4.74-4.62 (m, 1H), 2.59 (t, J=6.7 Hz, 2H), 1.52-1.40 (m, 9H). MS(ESI) m/z: 279.2 (M+H)$^+$.

102B. Preparation of (S)-ethyl 5-amino-1-(2-(1-((tert-butoxycarbonyl)amino)but-3-en-1-yl)pyridin-4-yl)-1H-pyrazole-3-carboxylate Sodium (Z)-1-cyano-3-ethoxy-3-oxoprop-1-en-2-olate (0.29 g, 1.8 mmol) was suspended in a solution of (S)-tert-butyl (1-(4-hydrazinylpyridin-2-yl)but-3-en-1-yl) carbamate (0.50 g, 1.8 mmol) in EtOH (15 ml). TFA (0.4 ml, 5.39 mmol, 3 equiv) was added dropwise and the solid slowly dissolved upon heating to 80° C. Stirring was continued at 80° C. for 2 h, then the reaction was cooled to rt. The reaction was concentrated to an oil and the residue dissolved in EtOAc. The organic layer was washed with pH=7 phosphate buffer, separated and the organic layer was concentrated to yield an oil. Purification of the crude oil by normal phase silica gel chromatography yielded (S)-ethyl 5-amino-1-(2-(1-((tert-butoxy carbonyl)amino)but-3-en-1-yl)pyridin-4-yl)-1H-pyrazole-3-carboxylate (0.7 g, 97% yield) as a clear, colorless, thick oil. $^1$H NMR (400 MHz, CDCl$_3$) δ 8.71-8.67 (m, 1H), 7.64 (d, J=2.0 Hz, 1H), 7.60 (dd, J=5.4, 2.1 Hz, 1H), 6.20 (s, 1H), 5.79-5.66 (m, 1H), 5.56-5.42 (m, 1H), 5.15-5.06 (m, 3H), 4.93-4.82 (m, 1H), 4.44 (q, J=7.1 Hz, 2H), 4.03 (br. s., 2H), 2.66 (m, 2H), 1.46 (s, 9H), 1.45-1.41 (t, J=7.1 Hz, 3H). MS(ESI) m/z: 402.2 (M+H)$^+$.

102C. Preparation of ethyl 1-(2-((S)-1-((tert-butoxycarbonyl)amino)but-3-en-1-yl) pyridin-4-yl)-5-((R)-2-methylbut-3-enamido)-1H-pyrazole-3-carboxylate To a N$_2$ flushed, 3-necked, 250 mL RBF was added a solution (S)-ethyl 5-amino-1-(2-(1-((tert-butoxycarbonyl)amino)but-3-en-1-yl)pyridin-4-yl)-1H-pyrazole-3-carboxylate (1.75 g, 4.36 mmol) and EtOAc (15 mL). The solution was cooled to −10° C. and (R)-2-methylbut-3-enoic acid (436 mg, 4.36 mmol), as prepared in Intermediate 2, pyridine (0.705 mL, 8.72 mmol) and T3P® (3.89 mL, 6.54 mmol) were added. The cooling bath was removed and the solution was allowed to warm to rt and then stir for 20 h. Water (20 mL) and EtOAc (20 mL) were added and the mixture was stirred for 30 min. The organic phase was separated and the aqueous layer was extracted with EtOAc (20 mL). The combined organic extracts were washed with brine (15 mL), dried over Na$_2$SO$_4$, filtered and concentrated. Purification by normal phase chromatography eluting with a gradient of DCM/MeOH gave ethyl 1-(2-((S)-1-((tert-butoxy carbonyl)amino)but-3-en-1-yl)pyridin-4-yl)-5-((R)-2-methylbut-3-enamido)-1H-pyrazole-3-carboxylate (1.81 g, 86% yield) as a white foaming solid. MS(ESI) m/z: 484.5

102D. Preparation of ethyl (10E,13S)-13-{[(tert-butoxy)carbonyl]amino}-9-methyl-8-oxo-2,3,7,15-tetraazatricyclo[12.3.1.0$^{2,6}$]octadeca-1(18),3,5,10,14,16-hexaene-4-carboxylate To a N$_2$ flushed, 250 mL, 3-necked, RBF was added a solution of ethyl 1-(2-((S)-1-((tert-butoxycarbonyl)amino)but-3-en-1-yl)pyridin-4-yl)-5-((R)-2-methylbut-3-enamido)-1H-pyrazole-3-carboxylate (1.81 g, 3.74 mmol) and CH$_3$SO$_3$H (0.23 ml, 3.56 mmol) in DCM (30 mL). The resulting solution heated to 40° C. The solution was sparged with Ar for 15 min. Second Generation Grubbs Catalyst (253 mg, 0.298 mmol) dissolved in DCM (10 mL) was added dropwise over a period of 10 min at 40° C. The reaction mixture was heated at 40° C. for overnight. After cooling to rt, the solvent was removed and the residue was purified by normal phase chromatography eluting with a gradient of DCM/MeOH to yield ethyl (10E,13S)-13-{[(tert-butoxy)carbonyl]amino}-9-methyl-8-oxo-2,3,7,15-tetraazatricyclo[12.3.1.0$^{2,6}$]octadeca-1(18),3,5,10,14,16-hexaene-4-carboxylate (670 mg, 39% yield) as a gray solid. MS(ESI) m/z: 556.5 [M+H]$^+$.

102E. Preparation of ethyl (13S)-13-{[(tert-butoxy)carbonyl]amino}-9-methyl-8-oxo-2,3,7,15-tetraazatricyclo[12.3.1.0$^{2,6}$]octadeca-1(18),3,5,14,16-pentaene-4-carboxylate Pd/C (0.16 g, 0.147 mmol) was added to a 250 mL Parr hydrogenation flask containing a solution of ethyl (10E,13S)-13-{[(tert-butoxy)carbonyl]amino}-9-methyl-8-oxo-2,3,7,15-tetraazatricyclo[12.3.1.0$^{2,6}$]octadeca-1(18),3,5,10,14,16-hexaene-4-carboxylate (670 mg, 1.471 mmol) in EtOH (15 mL). The flask was purged with N$_2$ and pressurized to 55 psi of H$_2$ and allowed to stir overnight. The reaction was filtered through a pad of CELITE® and concentrated to yield ethyl (13S)-13-{[(tert-butoxy) carbonyl]amino}-9-methyl-8-oxo-2,3,7,15-tetraazatricyclo[12.3.1.0$^{2,6}$]octadeca-1(18),3,5,14,16-pentaene-4-carboxylate (500 mg, 70% yield) as a tan solid. MS(ESI) m/z: 458.4 [M+H]$^+$.

102F. Ethyl (9R,13S)-13-amino-9-methyl-8-oxo-2,3,7,15-tetraazatricyclo[12.3.1.0$^{2,6}$]octadeca-1(18),3,5,14,16-pentaene-4-carboxylate, Bis Hydrochloride To a solution of ethyl (13S)-13-{[(tert-butoxy)carbonyl]amino}-9-methyl-8-oxo-2,3,7,15-tetraazatricyclo[12.3.1.0$^{2,6}$]octadeca-1(18),3,5,14,16-pentaene-4-carboxylate (500 mg, 1.093 mmol) in MeOH (5 mL) was added 4 M HCl in dioxane (5 mL, 20.0 mmol) and the resulting solution was stirred at rt for 1 h. The reaction mixture was then concentrated to give ethyl (9R,13S)-13-amino-9-methyl-8-oxo-2,3,7,15-tetraazatricyclo[12.3.1.0$^{2,6}$]octadeca-1(18),3,5,14,16-pentaene-4-carboxylate, bis hydrochloride (380 mg, 97% yield, mixture of methyl and ethyl esters) as a pale yellow solid. Additionally, also observed was the formation of methyl (9R,13S)-13-amino-9-methyl-8-oxo-2,3,7,15-tetraazatricyclo[12.3.1.0$^{2,6}$]octadeca-1(18),3,5,14,16-pentaene-4-carboxylate, bis hydrochloride due to transesterification of the ethyl ester to methyl ester as MeOH was used as solvent. The mixture of ethyl (9R,13S)-13-amino-9-methyl-8-oxo-2,3,7,15-tetraazatricyclo[12.3.1.0$^{2,6}$]octadeca-1(18),3,5,14,16-pentaene-4-carboxylate, bis hydrochloride and methyl (9R,13S)-13-amino-9-methyl-8-oxo-2,3,7,15-tetraazatricyclo[12.3.1.0$^{2,6}$]octadeca-1(18),3,5,14,16-pentaene-4-carboxylate, bis hydrochloride were dissolved in MeOH (4 mL) to give a clear, pale brown solution. The solution was added to a pre-rinsed AGI-LENT® StratoSpheres SPE PL-HCO$_3$ MP Resin cartridge. Gravity filtration, eluting with MeOH, gave a clear, slightly yellow filtrate. Concentration provided ethyl (9R,13S)-13-amino-9-methyl-8-oxo-2,3,7,15-tetraazatricyclo[12.3.1.0$^{2,6}$]octadeca-1(18),3,5,14,16-pentaene-4-carboxylate (MS (ESI) m/z: 330.5 [M+H]+) and methyl (9R,13S)-13-amino-9-methyl-8-oxo-2,3,7,15-tetraazatricyclo[12.3.1.0$^{2,6}$]octadeca-1(18),3,5,14,16-pentaene-4-carboxylate (295 mg, 97%) carboxylate (MS(ESI) m/z: 344.3 [M+H]$^+$) mixture as a pale brown solid.

102G. Preparation of Methyl (9R,13S)-13-{4-[5-chloro-2-(4-chloro-1H-1,2,3-triazol-1-yl)phenyl]-6-oxo-1,6-dihydropyrimidin-1-yl}-9-methyl-8-oxo-2,3,7,15-tetraazatricyclo[12.3.1.0$^{2,6}$]octadeca-1(18),3,5,14,16-pentaene-4-carboxylate Trifluoroacetate

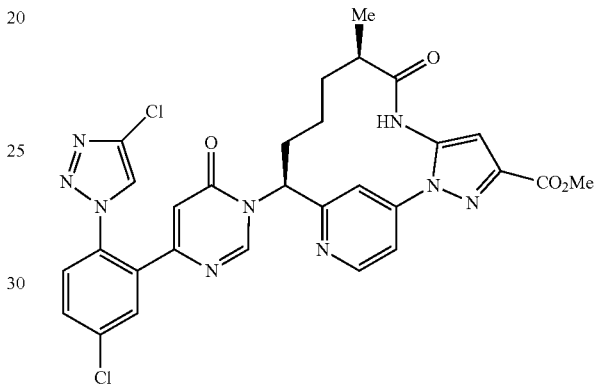

Methyl (9R,13S)-13-{4-[5-chloro-2-(4-chloro-1H-1,2,3-triazol-1-yl)phenyl]-6-oxo-1,6-dihydropyrimidin-1-yl}-9-methyl-8-oxo-2,3,7,15-tetraazatricyclo[12.3.1.0$^{2,6}$]octadeca-1(18),3,5,14,16-pentaene-4-carboxylate trifluoroacetate was prepared in a similar manner as the procedure described in Example 56, using 6-(5-chloro-2-(4-chloro-1H-1,2,3-triazol-1-yl)phenyl)pyrimidin-4-ol (0.035 g, 0.115 mmol), prepared as described in Intermediate 9, and the mixture of ethyl (9R,13S)-13-amino-9-methyl-8-oxo-2,3,7,15-tetraazatricyclo[12.3.1.0$^{2,6}$]octadeca-1(18),3,5,14,16-pentaene-4-carboxylate and methyl (9R,13S)-13-amino-9-methyl-8-oxo-2,3,7,15-tetraazatricyclo[12.3.1.0$^{2,6}$]octadeca-1(18),3,5,14,16-pentaene-4-carboxylate (0.041 g, 0.115 mmol) to yield a mixture of methyl (9R,13$-13-{4-[5-chloro-2-(4-chloro-1H-1,2,3-triazol-1-yl)phenyl]-6-oxo-1,6-dihydropyrimidin-1-yl}-9-methyl-8-oxo-2,3,7,15-tetraazatricyclo[12.3.1.0$^{2,6}$]octadeca-1(18),3,5,14,16-pentaene-4-carboxylate and ethyl (9R,13S)-13-{4-[5-chloro-2-(4-chloro-1H-1,2,3-triazol-1-yl)phenyl]-6-oxo-1,6-dihydropyrimidin-1-yl}-9-methyl-8-oxo-2,3,7,15-tetraazatricyclo[12.3.1.0$^{2,6}$]octadeca-1(18),3,5,14,16-pentaene-4-carboxylate which were further purified by prep HPLC to yield the desired methyl (9R,13S)-13-{4-[5-chloro-2-(4-chloro-1H-1,2,3-triazol-1-yl)phenyl]-6-oxo-1,6-dihydropyrimidin-1-yl}-9-methyl-8-oxo-2,3,7,15-tetraazatricyclo[12.3.1.0$^{2,6}$]octadeca-1(18),3,5,14,16-pentaene-4-carboxylate trifluoroacetate (7 mg, 8% yield) as white solid. $^1$H NMR (400 MHz, CD$_3$OD) δ 8.95 (s, 1H), 8.74 (d, J=5.3 Hz, 1H), 8.34 (s, 1H), 7.89 (d, J=2.2 Hz, 1H), 7.82 (d, J=1.8 Hz, 1H), 7.77-7.70 (m, 1H), 7.68-7.58 (m, 2H), 6.84 (s, 1H), 6.37 (s, 1H), 6.12 (dd, J=12.4, 5.0 Hz, 1H), 3.94 (s, 3H), 2.84 (br. s., 1H), 2.34-2.12 (m, 2H), 2.08-1.92 (m, 1H), 1.80-1.48 (m, 2H), 0.98 (d, J=6.8 Hz, 3H), 0.45 (br. s., 1H). MS(ESI) m/z: 634.3 [M+H]⁺. Analytical HPLC (Method A): RT=9.07 min, purity=>95.0%; Factor XIa Ki=11 nM, Plasma Kallikrein Ki=360 nM.

Example 103

Preparation of Methyl (9R,13S)-13-(4-{5-chloro-2-[4-(difluoromethyl)-1H-1,2,3-triazol-1-yl]phenyl}-6-oxo-1,6-dihydropyrimidin-1-yl)-9-methyl-8-oxo-2,3,7,15-tetraazatricyclo[12.3.1.0²,⁶]octadeca-1(18),3,5,14,16-pentaene-4-carboxylate Trifluoroacetate

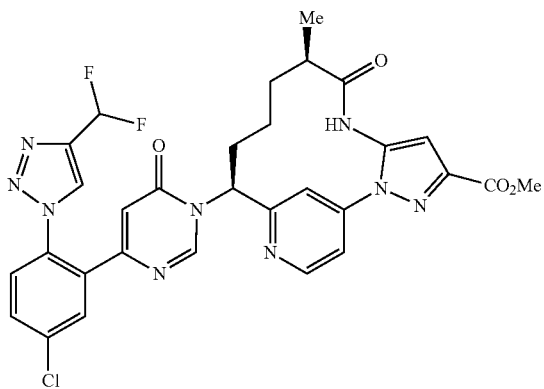 [SMILES: COC(=O)c1cc2n(n1)-c1ccnc(c1)[C@@H](n1cnc(-c3cc(Cl)ccc3-n3cc(C(F)F)nn3)cc1=O)CCC[C@@H](C)C(=O)N2]

Methyl (9R,13S)-13-(4-{5-chloro-2-[4-(difluoromethyl)-1H-1,2,3-triazol-1-yl]phenyl}-6-oxo-1,6-dihydropyrimidin-1-yl)-9-methyl-8-oxo-2,3,7,15-tetraazatricyclo[12.3.1.0²,⁶]octadeca-1(18),3,5,14,16-pentaene-4-carboxylate trifluoroacetate was prepared in a similar manner as the procedure described in Example 56, by using 6-(5-chloro-2-(4-(difluoromethyl)-1H-1,2,3-triazol-1-yl)phenyl)pyrimidin-4-ol (0.037 g, 0.115 mmol), prepared as described in Intermediate 16, and the mixture of ethyl (9R,13S)-13-amino-9-methyl-8-oxo-2,3,7,15-tetraazatricyclo[12.3.1.0²,⁶]octadeca-1(18),3,5,14,16-pentaene-4-carboxylate and methyl (9R,13S)-13-amino-9-methyl-8-oxo-2,3,7,15-tetraazatricyclo[12.3.1.0²,⁶]octadeca-1(18),3,5,14,16-pentaene-4-carboxylate (0.041 g, 0.115 mmol), prepared as described in Example 102F, to yield a mixture of methyl (9R,13S)-13-(4-{5-chloro-2-[4-(difluoromethyl)-1H-1,2,3-triazol-1-yl]phenyl}-6-oxo-1,6-dihydropyrimidin-1-yl)-9-methyl-8-oxo-2,3,7,15-tetraazatricyclo[12.3.1.0²,⁶]octadeca-1(18),3,5,14,16-pentaene-4-carboxylate and ethyl (9R,13S)-13-(4-{5-chloro-2-[4-(difluoromethyl)-1H-1,2,3-triazol-1-yl]phenyl}-6-oxo-1,6-dihydropyrimidin-1-yl)-9-methyl-8-oxo-2,3,7,15-tetraazatricyclo[12.3.1.0²,⁶]octadeca-1(18),3,5,14,16-pentaene-4-carboxylate which was further purified by prep HPLC to yield methyl (9R,13S)-13-(4-{5-chloro-2-[4-(difluoromethyl)-1H-1,2,3-triazol-1-yl]phenyl}-6-oxo-1,6-dihydropyrimidin-1-yl)-9-methyl-8-oxo-2,3,7,15-tetraazatricyclo[12.3.1.0²,⁶]octadeca-1(18),3,5,14,16-pentaene-4-carboxylate trifluoroacetate (7 mg, 8% yield) as white solid. ¹H NMR (400 MHz, CD₃OD) δ 8.95 (s, 1H), 8.75 (d, J=5.3 Hz, 1H), 8.59-8.55 (m, 1H), 7.93 (d, J=2.4 Hz, 1H), 7.84 (d, J=2.0 Hz, 1H), 7.80-7.74 (m, 1H), 7.73-7.68 (m, 1H), 7.64 (dd, J=5.5, 2.0 Hz, 1H), 7.19-6.88 (m, 1H), 6.86 (s, 1H), 6.39 (s, 1H), 6.14 (dd, J=12.5, 5.1 Hz, 1H), 3.97 (s, 3H), 2.85 (d, J=6.8 Hz, 1H), 2.36-2.13 (m, 2H), 2.08-1.92 (m, 1H), 1.77-1.51 (m, 2H), 1.01 (d, J=6.8 Hz, 3H), 0.45 (d, J=13.6 Hz, 1H). MS(ESI) m/z: 650.3 [M+H]⁺. Analytical HPLC (Method A): RT=8.98 min, purity=>95.0%; Factor XIa Ki=6.5 nM, Plasma Kallikrein Ki=200 nM.

Example 104

Preparation of (9R,13)-13-{4-[5-chloro-2-(4-chloro-1H-1,2,3-triazol-1-yl)phenyl]-6-oxo-1,6-dihydropyrimidin-1-yl}-9-methyl-8-oxo-2,3,7,15-tetraazatricyclo[12.3.1.0²,⁶]octadeca-1(18),3,5,14,16-pentaene-4-carboxylic Acid Trifluoroacetate

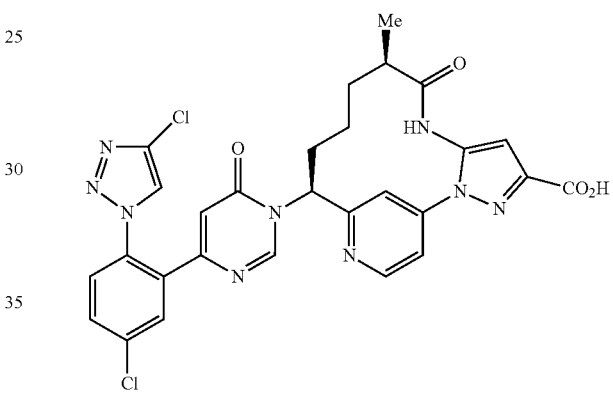

Ethyl (9R,13S)-13-{4-[5-chloro-2-(4-chloro-1H-1,2,3-triazol-1-yl)phenyl]-6-oxo-1,6-dihydropyrimidin-1-yl}-9-methyl-8-oxo-2,3,7,15-tetraazatricyclo[12.3.1.0²,⁶]octadeca-1(18),3,5,14,16-pentaene-4-carboxylate (0.035 g, 0.054 mmol), prepared as described in Example 102, was hydrolyzed using 2 M LiOH solution (0.08 mL, 0.162 mmol) at rt for 1 h. The reaction was neutralized using 1 N HCl and concentrated. The crude product was purified using prep HPLC to yield (9R,13S)-13-{4-[5-chloro-2-(4-chloro-1H-1,2,3-triazol-1-yl)phenyl]-6-oxo-1,6-dihydropyrimidin-1-yl}-9-methyl-8-oxo-2,3,7,15-tetraazatricyclo[12.3.1.0²,⁶]octadeca-1(18),3,5,14,16-pentaene-4-carboxylic acid trifluoroacetate (20 mg, 48% yield) as a white solid. ¹H NMR (400 MHz, CD₃OD) δ 8.98 (s, 1H), 8.76 (d, J=5.3 Hz, 1H), 8.36 (s, 1H), 7.92 (d, J=2.2 Hz, 1H), 7.85 (d, J=2.0 Hz, 1H), 7.79-7.73 (m, 1H), 7.70-7.63 (m, 2H), 6.85 (s, 1H), 6.40 (d, J=0.7 Hz, 1H), 6.15 (dd, J=12.4, 5.0 Hz, 1H), 2.88 (d, J=8.8 Hz, 1H), 2.38-2.15 (m, 2H), 2.10-1.94 (m, 1H), 1.80-1.52 (m, 2H), 1.01 (d, J=6.8 Hz, 3H), 0.48 (br. s., 1H). MS(ESI) m/z: 620.3 [M+H]⁺. Analytical HPLC (Method A): RT=7.96 min, purity=>95.0%; Factor XIa Ki=1.7 nM, Plasma Kallikrein Ki=470 nM.

Example 105

Preparation of (9R,13S)-13-(4-{5-chloro-2-[4-(difluoromethyl)-1H-1,2,3-triazol-1-yl]phenyl}-6-oxo-1,6-dihydropyrimidin-1-yl)-9-methyl-8-oxo-2,3,7,15-tetraazatricyclo[12.3.1.0²,⁶]Octadeca-1(18),3,5,14,16-pentaene-4-carboxylic Acid Trifluoroacetate

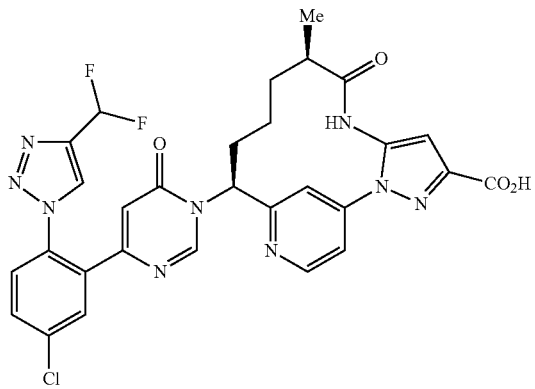 [SMILES: C[C@@H]1CCC[C@H](n2cnc(-c3cc(Cl)ccc3-n3cc(C(F)F)nn3)cc2=O)c2cc(ccn2)-n2nc(C(=O)O)cc2NC1=O]

Ethyl (9R,13S)-13-(4-{5-chloro-2-[4-(difluoromethyl)-1H-1,2,3-triazol-1-yl]phenyl}-6-oxo-1,6-dihydropyrimidin-1-yl)-9-methyl-8-oxo-2,3,7,15-tetraazatricyclo[12.3.1.0²,⁶]octadeca-1(18),3,5,14,16-pentaene-4-carboxylate (0.035 g, 0.053 mmol), prepared as described in Example 103, was hydrolyzed using 2 M LiOH (0.079 mL, 0.158 mmol) at rt for 1 h. The reaction was neutralized using 1 N HCl and concentrated. The crude product was purified using prep HPLC purification to yield (9R,13S)-13-(4-{5-chloro-2-[4-(difluoromethyl)-1H-1,2,3-triazol-1-yl]phenyl}-6-oxo-1,6-dihydropyrimidin-1-yl)-9-methyl-8-oxo-2,3,7,15-tetraazatricyclo[12.3.1.0²,⁶]octadeca-1(18),3,5,14,16-pentaene-4-carboxylic acid trifluoroacetate (10 mg, 24% yield) as a white solid. $^1$H NMR (400 MHz, CD$_3$OD) δ 8.96 (s, 1H), 8.75 (d, J=5.3 Hz, 1H), 8.60-8.55 (m, 1H), 7.93 (d, J=2.2 Hz, 1H), 7.85 (d, J=1.8 Hz, 1H), 7.80-7.74 (m, 1H), 7.73-7.62 (m, 2H), 7.20-6.89 (m, 1H), 6.85 (s, 1H), 6.39 (s, 1H), 6.15 (dd, J=12.5, 4.8 Hz, 1H), 2.93-2.82 (m, 1H), 2.34-2.14 (m, 2H), 2.09-1.95 (m, 1H), 1.77-1.52 (m, 2H), 1.01 (d, J=6.8 Hz, 3H), 0.46 (d, J=10.1 Hz, 1H). MS(ESI) m/z: 636.3 [M+H]⁺. Analytical HPLC (Method A): RT=7.97 min, purity=>95.0%; Factor XIa Ki=0.92 nM, Plasma Kallikrein Ki=470 nM.

Example 106

Preparation of (9R,13S)-13-{4-[5-chloro-2-(4-chloro-1H-1,2,3-triazol-1-yl)phenyl]-6-oxo-1,6-dihydropyrimidin-1-yl}-3-(²H$_3$)methyl-9-methyl-3,4,7,15-tetraazatricyclo[12.3.1.0²,⁶]octadeca-1(18),2(6),4,14,16-pentaen-8-one Trifluoroacetate

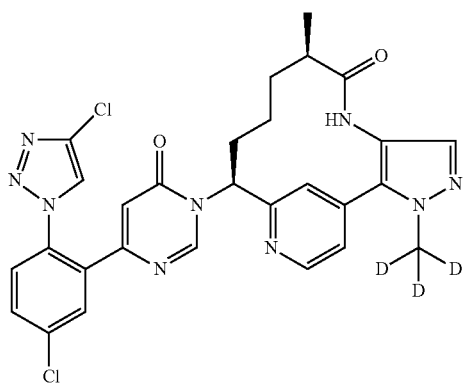 [SMILES: [2H]C([2H])([2H])n1ncc2c1-c1ccnc(c1)[C@@H](n1cnc(-c3cc(Cl)ccc3-n3cc(Cl)nn3)cc1=O)CCC[C@@H](C)C(=O)N2]

To a vial (4 ml) containing a suspension 6-(5-chloro-2-(4-chloro-1H-1,2,3-triazol-1-yl)phenyl)pyrimidin-4-ol (0.028 g, 0.089 mmol), prepared as described in Intermediate 9, in ACN (1 ml) was added HATU (0.044 g, 0.116 mmol) and DBU (0.020 ml, 0.134 mmol). After 20 min, (9R,13S)-13-amino-3-(²H$_3$)methyl-9-methyl-3,4,7,15-tetraazatricyclo[12.3.1.0²,⁶]octadeca-1(18),2(6),4,14,16-pentaen-8-one (0.027 g, 0.089 mmol), prepared as described in Intermediate 33, in DMF (1.0 ml) was added at rt. After 4 h, the crude mixture was purified by reverse phase chromatography (PHENOMENEX® Luna Axia C18 5μ, 30×100 mm column, Solvent A: 20% ACN-80% H$_2$O-0.1% TFA; Solvent B: 80% ACN-20% H$_2$O-0.1% TFA) to give (9R,13S)-13-{4-[5-chloro-2-(4-chloro-1H-1,2,3-triazol-1-yl)phenyl]-6-oxo-1,6-dihydropyrimidin-1-yl}-3-(²H$_3$)methyl-9-methyl-3,4,7,15-tetraazatricyclo[12.3.1.0²,⁶]octadeca-1(18),2(6),4,14,16-pentaen-8-one trifluoroacetate (19 mg, 28.6%) as a white solid. MS(ESI) m/z: 593.1 (M+H)⁺. $^1$H NMR (500 MHz, CD$_3$OD) δ 8.84 (s, 1H), 8.75 (d, J=5.0 Hz, 1H), 8.36 (s, 1H), 7.91 (d, J=2.5 Hz, 1H), 7.76 (dd, J=8.5, 2.2 Hz, 1H), 7.71 (s, 1H), 7.67 (d, J=8.5 Hz, 1H), 7.56-7.50 (m, 2H), 6.39 (s, 1H), 6.01 (dd, J=12.5, 4.0 Hz, 1H), 2.73 (td, J=6.6, 3.0 Hz, 1H), 2.32 (ddt, J=12.8, 8.6, 4.4 Hz, 1H), 2.13-1.99 (m, 2H), 1.67-1.59 (m, 1H), 1.53-1.45 (m, 1H), 1.03 (d, J=6.9 Hz, 3H), 0.71 (br. s., 1H). Analytical HPLC (Method A): RT=8.55 min, purity=99.0%; Factor XIa Ki=0.27 nM, Plasma Kallikrein Ki=27 nM.

Example 107

Preparation of (9R,13S)-13-{4-[3-chloro-6-(4-chloro-1H-1,2,3-triazol-1-yl)-2-fluorophenyl]-6-oxo-1,6-dihydropyrimidin-1-yl}-3-(²H$_3$)methyl-9-methyl-3,4,7,15-tetraazatricyclo[12.3.1.0²,⁶]octadeca-1(18),2(6),4,14,16-pentaen-8-one Trifluoroacetate

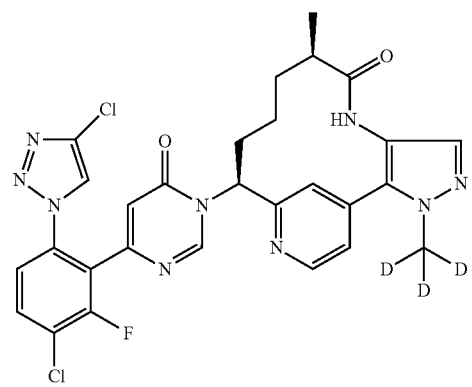 [SMILES: [2H]C([2H])([2H])n1ncc2c1-c1ccnc(c1)[C@@H](n1cnc(-c3c(-n4cc(Cl)nn4)ccc(Cl)c3F)cc1=O)CCC[C@@H](C)C(=O)N2]

To a vial (4 ml) containing a suspension 6-[3-chloro-6-(4-chloro-1H-1,2,3-triazol-1-yl)-2-fluorophenyl]pyrimidin-4-ol hydrobromide (0.034 g, 0.083 mmol), prepared as described in Intermediate 10, in ACN (1 ml) was added HATU (0.041 g, 0.107 mmol) and DBU (0.034 ml, 0.223 mmol). After 30 min, (9R,13S)-13-amino-3-(²H$_3$)methyl-9-methyl-3,4,7,15-tetraazatricyclo[12.3.1.0²,⁶]octadeca-1(18),2(6),4,14,16-pentaen-8-one (0.027 g, 0.089 mmol), prepared as described in Intermediate 33, in DMF (1.0 ml) was added at rt. After 2 h, the crude mixture was purified by reverse phase chromatography (PHENOMENEX® Luna Axia C18 5μ 30×100 mm column, Solvent A: 20% ACN-80% H$_2$O-0.1% TFA; Solvent B: 80% ACN-20% H$_2$O-0.1% TFA) to give (9R,13S)-13-{4-[3-chloro-6-(4-chloro-1H-1,2,3-triazol-1-yl)-2-fluorophenyl]-6-oxo-1,6-dihydropyrimidin-1-yl}-3-($^2$H$_3$)methyl-9-methyl-3,4,7,15-tetraazatricyclo[12.3.1.0$^{2,6}$]octadeca-1(18),2(6),4,14,16-pentaen-8-one trifluoroacetate (20.3 mg, 32.2%) as a white solid. MS(ESI) m/z: 611.2 (M+H)$^+$ and 613.1 (M+2+H)$^+$. $^1$H NMR (400 MHz, CD$_3$OD) δ 8.85 (s, 1H), 8.78 (d, J=5.1 Hz, 1H), 8.36 (s, 1H), 7.93-7.87 (m, 1H), 7.75 (s, 1H), 7.60-7.55 (m, 2H), 7.53 (s, 1H), 6.64 (s, 1H), 6.03 (dd, J=12.7, 4.1 Hz, 1H), 2.74 (td, J=6.6, 3.1 Hz, 1H), 2.38-2.29 (m, 1H), 2.14-2.01 (m, 2H), 1.69-1.61 (m, 1H), 1.54-1.46 (m, 1H), 1.05 (d, J=7.0 Hz, 3H), 0.78-0.70 (m, 1H). Analytical HPLC (Method A): RT=8.66 min, purity=96.8%; Factor XIa Ki=0.1 nM, Plasma Kallikrein Ki=8 nM.

Example 108

Preparation of (9R,13)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7-triazatricyclo[12.3.1.0$^{2,6}$]octadeca-1(18),2(6),4,14,16-pentaen-8-one

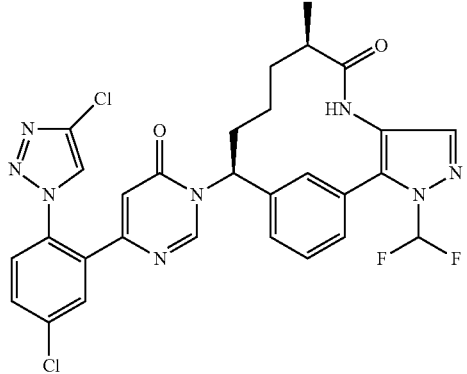 [SMILES: C[C@@H]1CCC[C@H](n2cnc(-c3cc(Cl)ccc3-n3cc(Cl)nn3)cc2=O)c2cccc(c2)-c2c(cnn2C(F)F)NC1=O]

To a vial (4 ml) containing a suspension 6-(5-chloro-2-(4-chloro-1H-1,2,3-triazol-1-yl)phenyl)pyrimidin-4-ol (0.023 g, 0.075 mmol), prepared as described in Intermediate 9, in ACN (1 ml) was added HATU (0.037 g, 0.097 mmol) and DBU (0.017 ml, 0.112 mmol). After 30 min, (9R,13S)-13-amino-3-(difluoromethyl)-9-methyl-3,4,7-triazatricyclo[12.3.1.0$^{2,6}$]octadeca-1(18),2(6),4,14,16-pentaen-8-one (0.025 g, 0.075 mmol), prepared as described in Intermediate 35, in DMF (1.0 ml) was added at rt. After stirring overnight, the crude mixture was concentrated and the residue purified by reverse phase chromatography (PHENOMENEX® Luna Axia C18 5μ 30×100 mm column, Solvent A: 20% ACN-80% H$_2$O-0.1% TFA; Solvent B: 80% ACN-20% H$_2$O-0.1% TFA) to give (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7-triazatricyclo[12.3.1.0$^{2,6}$]octadeca-1(18),2(6),4,14,16-pentaen-8-one (11 mg, 22.4%) as a white solid. MS(ESI) m/z: 625.1 (M+H)$^+$. $^1$H NMR (400 MHz, CD$_3$OD) δ 8.84 (s, 1H), 8.75 (d, J=5.0 Hz, 1H), 8.36 (s, 1H), 7.91 (d, J=2.5 Hz, 1H), 7.76 (dd, J=8.5, 2.2 Hz, 1H), 7.71 (s, 1H), 7.67 (d, J=8.5 Hz, 1H), 7.56-7.50 (m, 2H), 6.39 (s, 1H), 6.01 (dd, J=12.5, 4.0 Hz, 1H), 2.73 (td, J=6.6, 3.0 Hz, 1H), 2.32 (ddt, J=12.8, 8.6, 4.4 Hz, 1H), 2.13-1.99 (m, 2H), 1.67-1.59 (m, 1H), 1.53-1.45 (m, 1H), 1.03 (d, J=6.9 Hz, 3H), 0.71 (br. s., 1H). Analytical HPLC (Method A): RT=10.12 min, purity=98.0%; Factor XIa Ki=0.1 nM, Plasma Kallikrein Ki=16 nM.

Example 109

Preparation of (9R,13S)-13-{4-[3-chloro-6-(4-chloro-1H-1,2,3-triazol-1-yl)-2-fluorophenyl]-6-oxo-1,6-dihydropyrimidin-1-yl}-3-(difluoromethyl)-9-methyl-3,4,7-triazatricyclo[12.3.1.0$^{2,6}$]octadeca-1(18),2(6),4,14,16-pentaen-8-one

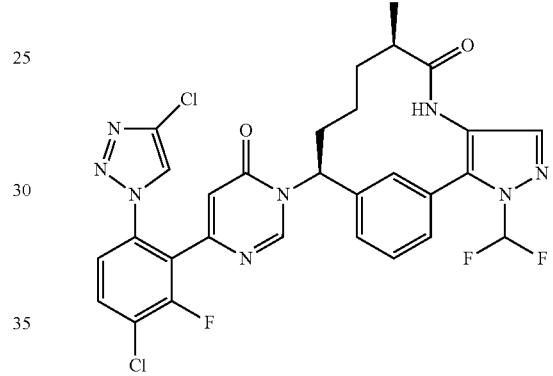

To a vial (4 ml) containing a suspension 6-[3-chloro-6-(4-chloro-1H-1,2,3-triazol-1-yl)-2-fluorophenyl]pyrimidin-4-ol (0.020 g, 0.060 mmol), prepared as described in Intermediate 10, in ACN (1 ml) was added HATU (0.030 g, 0.107 mmol) and DBU (0.014 ml, 0.090 mmol). After 30 min, (9R,13S)-13-amino-3-(difluoromethyl)-9-methyl-3,4,7-triazatricyclo[12.3.1.0$^{2,6}$]octadeca-1(18),2(6),4,14,16-pentaen-8-one (0.020 g, 0.060 mmol), prepared as described in Intermediate 35, in DMF (1.0 ml) was added at rt. After 2 h, the crude mixture was purified by reverse phase chromatography (PHENOMENEX® Luna Axia C18 5μ 30×100 mm column, Solvent A: 20% ACN-80% H$_2$O-0.1% TFA; Solvent B: 80% ACN-20% H$_2$O-0.1% TFA) to give (9R,13S)-13-{4-[3-chloro-6-(4-chloro-1H-1,2,3-triazol-1-yl)-2-fluorophenyl]-6-oxo-1,6-dihydropyrimidin-1-yl}-3-(difluoromethyl)-9-methyl-3,4,7-triazatricyclo[12.3.1.0$^{2,6}$]octadeca-1(18),2(6),4,14,16-pentaen-8-one (7.5 mg, 19.1%) as a white solid. MS(ESI) m/z: 643.1 (M+H)$^+$. $^1$H NMR (400 MHz, CD$_3$OD) δ 8.33 (s, 1H), 8.26 (s, 1H), 7.91-7.77 (m, 3H), 7.67-7.49 (m, 4H), 7.41 (d, J=7.7 Hz, 1H), 6.66 (s, 1H), 5.85 (dd, J=12.9, 3.2 Hz, 1H), 2.53 (td, J=6.8, 3.2 Hz, 1H), 2.43-2.34 (m, 1H), 2.21-2.10 (m, 1H), 1.98-1.88 (m, 1H), 1.65-1.53 (m, 2H), 1.29-1.15 (m, 4H). Analytical HPLC (Method A): RT=10.18 min, purity=98.5%; Factor XIa Ki=0.1 nM, Plasma Kallikrein Ki=5 nM.

Example 110

Preparation of (9R,13S)-13-{4-[3-chloro-6-(4-chloro-1H-1,2,3-triazol-1-yl)-2-fluorophenyl]-6-oxo-1,6-dihydropyrimidin-1-yl}-3,9-dimethyl(10,11-$^2$H$_2$)-3,4,7,15-tetraazatricyclo[12.3.1.0$^{2,6}$]octadeca-1(18),2(6),4,14,16-pentaen-8-one Trifluoroacetate

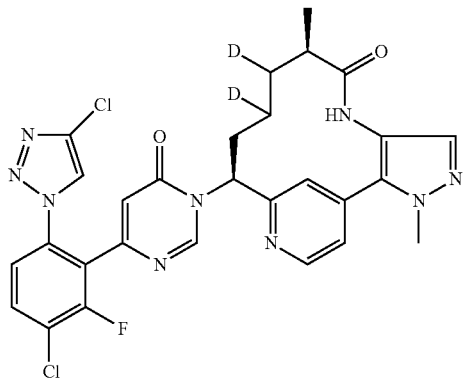 [SMILES: [2H]C1C[C@H](n2cnc(-c3c(-n4cc(Cl)nn4)ccc(Cl)c3F)cc2=O)c2cc(ccn2)-c2c(cnn2C)NC(=O)[C@H](C)C1[2H]]

110A. Preparation of Tert-Butyl N-[(9R,13S)-3,9-dimethyl-8-oxo(10,11-$^2$H$_2$)-3,4,7,15-tetraazatricyclo[12.3.1.0$^{2,6}$]octadeca-1(18),2(6),4,14,16-pentaen-13-yl]carbamate To a solution of tert-butyl N-[(9R,10E,13S)-3,9-dimethyl-8-oxo-3,4,7,15-tetraazatricyclo[12.3.1.0$^{2,6}$]octadeca-1(18),2(6),4,10,14,16-hexaen-13-yl]carbamate (165 mg, 0.415 mmol), prepared as described in Intermediate 32E, in CD$_3$OD (7 ml), under N$_2$ was added Pd/C (44.2 mg, 0.042 mmol), and the resulting solution was purged and refilled with N$_2$, then purged and refilled with D$_2$ (3×). The solution was stirred at rt at 50 psi D$_2$ for 29 h. The reaction mixture was filtered through CELITE® followed by a syringe filter. The filtrate was concentrated to dryness and dried further under vacuum to give tert-butyl N-[(9R,13S)-3,9-dimethyl-8-oxo(10,11-$^2$H$_2$)-3,4,7,15-tetraazatricyclo[12.3.1.0$^{2,6}$]octadeca-1(18),2(6),4,14,16-pentaen-13-yl]carbamate as a light brown solid. MS(ESI) m/z: 402.3 (M+H)$^+$. $^1$H NMR (400 MHz, CD$_3$OD) δ 8.68 (d, J=5.3 Hz, 1H), 7.49-7.43 (m, 3H), 4.77 (dd, J=11.0, 5.3 Hz, 1H), 4.05 (s, 3H), 2.75-2.65 (m, 1H), 1.94 (br. s., 1H), 1.90-1.80 (m, 1H), 1.73-1.61 (m, 1H), 1.54 (t, J=5.8 Hz, 1H), 1.42 (s, 9H), 0.94 (d, J=6.8 Hz, 3H).

110B. Preparation of (9R,13S)-13-amino-3,9-dimethyl(10,11-2H$_2$)-3,4,7,15-tetraazatricyclo[12.3.1.0$^{2,6}$]octadeca-1(18),2(6),4,14,16-pentaen-8-one CF$_3$COOD (0.230 ml, 2.99 mmol) was added to a solution of tert-butyl N-[(9R,13S)-3,9-dimethyl-8-oxo(10,11-$^2$H$_2$)-3,4,7,15-tetraazatricyclo[12.3.1.0$^{2,6}$]octadeca-1(18),2(6),4,14,16-pentaen-13-yl]carbamate (0.040 g, 0.100 mmol) in CD$_2$Cl$_2$ (1 ml, 15.67 mmol) at rt. After 1 h, the reaction mixture was concentrated. The residue was dissolved in MeOH and free based by passing through two consecutive resin bound NaHCO$_3$ cartridges (StratoSpheres SPE; 500 mg, 0.90 mmol loading) and concentrated. (9R,13S)-13-Amino-3,9-dimethyl(10,11-$^2$H$_2$)-3,4,7,15-tetraazatricyclo[12.3.1.0$^{2,6}$]octadeca-1(18),2(6),4,14,16-pentaen-8-one, was carried forward 'as is' to next reaction. MS(ESI) m/z: 302.2 (M+H)$^+$.

110C. Preparation of (9R,13S)-13-{4-[3-chloro-6-(4-chloro-1H-1,2,3-triazol-1-yl)-2-fluorophenyl]-6-oxo-1,6-dihydropyrimidin-1-yl}-3,9-dimethyl(10,11-$^2$H$_2$)-3,4,7,15-tetraazatricyclo[12.3.1.0$^{2,6}$]octadeca-1(18),2(6),4,14,16-pentaen-8-one Trifluoroacetate To a vial (4 ml) containing a suspension 6-[3-chloro-6-(4-chloro-1H-1,2,3-triazol-1-yl)-2-fluorophenyl]pyrimidin-4-ol (0.027 g, 0.083 mmol), prepared as described in Intermediate 10, in ACN (1 ml) was added HATU (0.041 g, 0.108 mmol) and DBU (0.019 ml, 0.124 mmol). After 30 min, (9R,13S)-13-amino-3,9-dimethyl(10,11-$^2$H$_2$)-3,4,7,15-tetraazatricyclo[12.3.1.0$^{2,6}$]octadeca-1(18),2(6),4,14,16-pentaen-8-one, in DMF (1.0 ml) was added at rt. After 2 h, the crude mixture was purified by reverse phase chromatography (PHENOMENEX® Luna Axia C18 5µ 30×100 mm column, Solvent A: 20% ACN-80% H$_2$O-0.1% TFA; Solvent B: 80% ACN-20% H$_2$O-0.1% TFA) to give (9R,13S)-13-{4-[3-chloro-6-(4-chloro-1H-1,2,3-triazol-1-yl)-2-fluorophenyl]-6-oxo-1,6-dihydropyrimidin-1-yl}-3,9-dimethyl(10,11-$^2$H$_2$)-3,4,7,15-tetraazatricyclo[12.3.1.0$^{2,6}$]octadeca-1(18),2(6),4,14,16-pentaen-8-one trifluoroacetate (22 mg, 35.9%) as a white solid. MS(ESI) m/z: 610.2 (M+H)$^+$. $^1$H NMR (400 MHz, CD$_3$OD) δ 8.84 (s, 1H), 8.77 (d, J=5.1 Hz, 1H), 8.35 (s, 1H), 7.88 (dd, J=8.7, 7.6 Hz, 1H), 7.74 (s, 1H), 7.61-7.54 (m, 2H), 7.52 (s, 1H), 6.63 (s, 1H), 6.02 (dd, J=12.8, 4.0 Hz, 1H), 4.08 (s, 3H), 2.72 (t, J=6.8 Hz, 1H), 2.36-2.29 (m, 1H), 2.07-2.00 (m, 1H), 1.61 (t, J=6.3 Hz, 1H), 1.47 (d, J=3.7 Hz, 1H), 1.03 (d, J=6.8 Hz, 3H). Analytical HPLC (Method A): RT=7.94 min, purity=99.3%; Factor XIa Ki=0.1 nM, Plasma Kallikrein Ki=8 nM.

Example 111

Preparation of (9R,13S)-13-{4-[3-chloro-6-(4-chloro-1H-1,2,3-triazol-1-yl)-2-fluorophenyl]-6-oxo-1,6-dihydropyrimidin-1-yl}-3-($^2$H$_3$)methyl-9-methyl(10,11-$^2$H$_2$)-3,4,7,15-tetraazatricyclo[12.3.1.0$^{2,6}$]octadeca-1(18),2(6),4,14,16-pentaen-8-one Trifluoroacetate

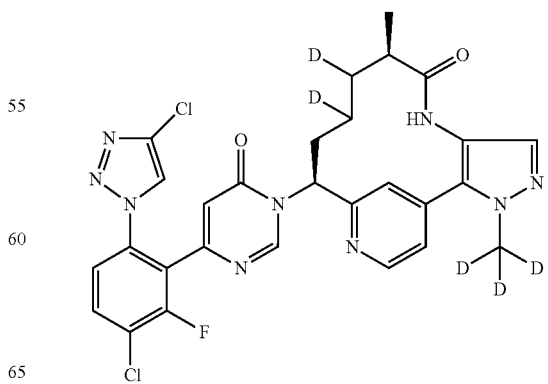

111A. Preparation of Tert-Butyl N-[(9R,13S)-3-($^2$H$_3$)methyl-9-methyl-8-oxo(10,11-$^2$H$_2$)3,4,7,15-tetraazatricyclo[12.3.1.0$^{2,6}$]octadeca-1(18),2(6),4,14,16-pentaen-13-yl]carbamate tert-Butyl N-[(9R,10E,13S)-3-($^2$H$_3$)methyl-9-methyl-8-oxo-3,4,7,15-tetraazatricyclo[12.3.1.0$^{2,6}$]octadeca-1(18),2(6),4,10,14,16-hexaen-13-yl]carbamate (153 mg, 0.382 mmol), prepared as described in Example 33E, in CD$_3$OD (7 ml), under N$_2$ was added Pd/C (0.0382 mmol), the resulting solution was purged and refilled with N$_2$, then refilled with D$_2$ (3×), and stirred at rt at 50 psi D$_2$ for 65 h. The reaction mixture was filtered through CELITER followed by a syringe filter. The filtrate was concentrated to dryness and dried further under vacuum to give tert-butyl N-[(9R,13S)-3-($^2$H$_3$)methyl-9-methyl-8-oxo(10,11-$^2$H$_2$)3,4,7,15 tetraazatricyclo[12.3.1.0$^{2,6}$]octadeca-1(18),2(6),4,14,16-pentaen-13-yl]carbamate as a light brown solid (143.4 mg, 88.2%). MS(ESI) m/z: 405.3 (M+H)$^+$. $^1$H NMR (400 MHz, CD$_3$OD) δ 8.68 (d, J=5.1 Hz, 1H), 7.50-7.42 (m, 3H), 4.80-4.73 (m, 1H), 3.61 (q, J=7.0 Hz, 1H), 2.76-2.65 (m, 1H), 1.96-1.80 (m, 1H), 1.72-1.61 (m, 1H), 1.54 (t, J=5.6 Hz, 1H), 1.42 (s, 9H), 1.18 (t, J=7.0 Hz, 1H), 0.94 (d, J=7.0 Hz, 3H).

111B. Preparation of (9R,13S)-13-amino-3-($^2$H$_3$)methyl-9-methyl(10,11-$^2$H$_2$)-3,4,7,15-tetraazatricyclo[12.3.1.0$^{2,6}$]octadeca-1(18),2(6),4,14,16-pentaen-8-one CF$_3$COOD (0.229 ml, 2.97 mmol) was added to a solution tert-butyl N-[(9R,13S)-3-($^2$H$_3$)methyl-9-methyl-8-oxo(10,11-$^2$H$_2$)3,4,7,15-tetraazatricyclo[12.3.1.0$^{2,6}$]octadeca-1(18),2(6),4,14,16-pentaen-13-yl]carbamate (0.040 g, 0.099 mmol) in CD$_2$Cl$_2$ (1 ml, 15.67 mmol) at rt. After 1 h, the reaction mixture was concentrated to dryness. The residue was dissolved in MeOH and free based by passing through two consecutive resin bound NaHCO$_3$ cartridges (StratoSpheres SPE; 500 mg, 0.90 mmol loading) and concentrated. The product, (9R,13S)-13-amino-3-($^2$H$_3$)methyl-9-methyl(10,11-$^2$H$_2$)-3,4,7,15-tetraazatricyclo[12.3.1.0$^{2,6}$]octadeca-1(18),2(6),4,14,16-pentaen-8-one, was carried forward 'as is' to next reaction. MS(ESI) m/z: 305.2 (M+H)$^+$.

111C. Preparation of (9R,13S)-13-{4-[3-chloro-6-(4-chloro-1H-1,2,3-triazol-1-yl)-2-fluorophenyl]-6-oxo-1,6-dihydropyrimidin-1-yl}-3-($^2$H$_3$)methyl-9-methyl(10,11-$^2$H$_2$)-3,4,7,15-tetraazatricyclo[12.3.1.0$^{2,6}$]octadeca-1(18),2(6),4,14,16-pentaen-8-one Trifluoroacetate To a vial (4 ml) containing a suspension 6-[3-chloro-6-(4-chloro-1H-1,2,3-triazol-1-yl)-2-fluorophenyl]pyrimidin-4-ol (0.027 g, 0.083 mmol), prepared as described in Intermediate 10, in ACN (1 ml) was added HATU (0.041 g, 0.108 mmol) and DBU (0.019 ml, 0.124 mmol). After 30 min, (9R,13S)-13-amino-3-($^2$H$_3$)methyl-9-methyl (10,11-$^2$H$_2$)-3,4,7,15-tetraazatricyclo[12.3.1.0$^{2,6}$]octadeca-1(18),2(6),4,14,16-pentaen-8-one (0.025 g, 0.082 mmol) in DMF (1.0 ml) was added at rt. After 2 h, the crude mixture was purified by reverse phase chromatography (PHENOMENEX® Luna Axia C18 5μ 30×100 mm column, Solvent A: 20% ACN-80% H$_2$O-0.1% TFA; Solvent B: 80% ACN-20% H$_2$O-0.1% TFA) to give (9R,13S)-13-{4-[3-chloro-6-(4-chloro-1H-1,2,3-triazol-1-yl)-2-fluorophenyl]-6-oxo-1,6-dihydropyrimidin-1-yl}-3-($^2$H$_3$)methyl-9-methyl(10,11-$^2$H$_2$)-3,4,7,15-tetraazatricyclo[12.3.1.0$^{2,6}$]octadeca-1(18),2(6),4,14,16-pentaen-8-one trifluoroacetate (19.2 mg, 30.8%) as a white solid. MS(ESI) m/z: 613.2 (M+H)$^+$. $^1$H NMR (400 MHz, CD$_3$OD) δ 8.90-8.75 (m, 2H), 8.35 (s, 1H), 7.87 (d, J=7.7 Hz, 1H), 7.76 (br. s., 1H), 7.64-7.52 (m, 3H), 6.63 (s, 1H), 6.00 (d, J=12.1 Hz, 1H), 2.76-2.68 (m, 1H), 2.37-2.29 (m, 1H), 2.08-2.02 (m, 1H), 1.61 (t, J=6.2 Hz, 1H), 1.46 (d, J=4.4 Hz, 1H), 1.03 (d, J=6.8 Hz, 3H). Analytical HPLC (Method A): RT=7.90 min, purity=99.1%; Factor XIa Ki=0.1 nM, Plasma Kallikrein Ki=8 nM.

Example 112

Preparation of (9R,13S)-13-{4-[3-chloro-6-(4-chloro-1H-1,2,3-triazol-1-yl)-2-fluorophenyl]-6-oxo-1,6-dihydropyrimidin-1-yl}-3-(difluoromethyl)-9-methyl(10,11-$^2$H$_2$)-3,4,7,15-tetraazatricyclo[12.3.1.0$^{2,6}$]octadeca-1(18),2(6),4,14,16-pentaen-8-one Trifluoroacetate

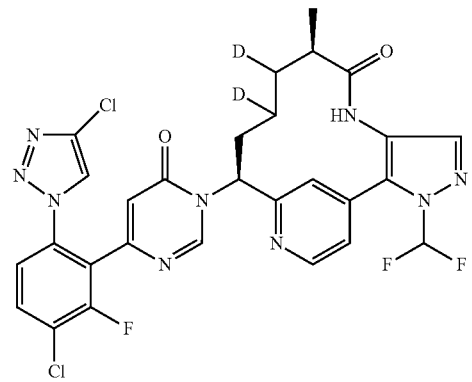 [SMILES: [2H]C1C[C@H](n2cnc(-c3c(-n4cc(Cl)nn4)ccc(Cl)c3F)cc2=O)c2cc(ccn2)-c2c(cnn2C(F)F)NC(=O)[C@H](C)C1[2H]]

112A. Preparation of Tert-Butyl N-[(9R,13S)-3-(difluoromethyl)-9-methyl-8-oxo(10,11-$^2$H$_2$)-3,4,7,15-tetraazatricyclo[12.3.1.0$^{2,6}$]octadeca-1(18),2(6),4,14,16-pentaen-13-yl]carbamate tert-Butyl N-[(9R,10E,13S)-3-(difluoromethyl)-9-methyl-8-oxo-3,4,7,15-tetraazatricyclo[12.3.1.0$^{2,6}$]octadeca-1(18),2(6),4,10,14,16-hexaen-13-yl]carbamate (180 mg, 0.415 mmol), prepared as described in Example 30E, in CD$_3$OD (7 ml), under N$_2$ was added Pd/C (0.0415 mmol), the resulting solution was purged and refilled with N$_2$ and refilled with D$_2$ (3×), then stirred at rt at 50 psi D$_2$ for 60 h. The reaction mixture was filtered through CELITE® followed by a syringe filter. The filtrate was concentrated to dryness and dried further under vacuum to give tert-butyl N-[(9R,13S)-3-(difluoromethyl)-9-methyl-8-oxo(10,11-$^2$H$_2$)-3,4,7,15-tetraazatricyclo[12.3.1.0$^{2,6}$]octadeca-1(18),2(6),4,14,16-pentaen-13-yl]carbamate as a light brown solid (167 mg, 88.9%). MS(ESI) m/z: 438.3 (M+H)$^+$. $^1$H NMR (400 MHz, CD$_3$OD) δ 8.70 (d, J=5.5 Hz, 1H), 7.79 (s, 1H), 7.72 (s, 1H), 7.65 (d, J=2.0 Hz, 1H), 7.52-7.44 (m, 4H), 3.61 (q, J=7.0 Hz, 1H), 2.69 (t, J=6.8 Hz, 2H), 1.91-1.82 (m, 2H), 1.74-1.64 (m, 2H), 1.53 (t, J=5.8 Hz, 2H), 1.42 (s, 13H), 1.33-1.14 (m, 6H), 0.94 (d, J=7.0 Hz, 6H).

112B. Preparation of (9R,13S)-13-amino-3-(difluoromethyl)-9-methyl(10,11-$^2$H$_2$)-3,4,7,15-tetraazatricyclo[12.3.1.0$^{2,6}$]octadeca-1(18),2(6),4,14,16-pentaen-8-one CF$_3$COOD (0.211 ml, 2.74 mmol) was added to a solution tert-butyl N-[(9R,13S)-3-(difluoromethyl)-9-methyl-8-oxo (10,11-²H₂)-3,4,7,15-tetraazatricyclo[12.3.1.0²,⁶]octadeca-1(18),2(6),4,14,16-pentaen-13-yl]carbamate (0.040 g, 0.091 mmol) in CD₂Cl₂ (1 ml, 15.67 mmol) at rt. After 1 h, the reaction mixture was concentrated to dryness. The residue was dissolved in MeOH and free based by passing through two consecutive resin bound NaHCO₃ cartridges (Strato-Spheres SPE; 500 mg, 0.90 mmol loading) and concentrated. The product, (9R,13S)-13-amino-3-(difluoromethyl)-9-methyl(10,11-²H₂)-3,4,7,15-tetraazatricyclo[12.3.1.0²,⁶]octadeca-1(18),2(6),4,14,16-pentaen-8-one was carried forward as is to next reaction. MS(ESI) m/z: 338.2 (M+H)⁺.

112C. Preparation of (9R,13S)-13-{4-[3-chloro-6-(4-chloro-1H-1,2,3-triazol-1-yl)-2-fluorophenyl]-6-oxo-1,6-dihydropyrimidin-1-yl}-3-(difluoromethyl)-9-methyl(10,11-²H₂)-3,4,7,15-tetraazatricyclo[12.3.1.0²,⁶]octadeca-1(18),2(6),4,14,16-pentaen-8-one Trifluoroacetate To a vial (4 ml) containing a suspension 6-[3-chloro-6-(4-chloro-1H-1,2,3-triazol-1-yl)-2-fluorophenyl]pyrimidin-4-ol (0.024 g, 0.074 mmol), prepared as described in Intermediate 10, in ACN (1 ml) was added HATU (0.037 g, 0.096 mmol) and DBU (0.017 ml, 0.111 mmol). After 30 min, (9R,13S)-13-amino-3-(difluoromethyl)-9-methyl(10,11-²H₂)-3,4,7,15-tetraazatricyclo[12.3.1.0²,⁶]octadeca-1(18),2(6),4,14,16-pentaen-8-one (0.025 g, 0.074 mmol) in DMF (1.0 ml) was added at rt. After 2 h, the crude mixture was purified by reverse phase chromatography (PHENOMENEX® Luna Axia C18 5µ 30×100 mm column, Solvent A: 20% ACN-80% H₂O-0.1% TFA; Solvent B: 80% ACN-20% H₂O-0.1% TFA) to give (9R,13S)-13-{4-[3-chloro-6-(4-chloro-1H-1,2,3-triazol-1-yl)-2-fluorophenyl]-6-oxo-1,6-dihydropyrimidin-1-yl}-3-(difluoromethyl)-9-methyl(10,11-²H₂)-3,4,7,15-tetraazatricyclo[12.3.1.0²,⁶]octadeca-1(18),2(6),4,14,16-pentaen-8-one trifluoroacetate (16.8 mg, 29.8%) as a white solid. MS(ESI) m/z: 646.3 (M+H)⁺. ¹H NMR (400 MHz, CD₃OD) δ 8.91 (s, 1H), 8.78 (d, J=5.1 Hz, 1H), 8.34 (s, 1H), 7.91-7.85 (m, 1H), 7.83-7.67 (m, 3H), 7.58-7.52 (m, 2H), 6.63 (s, 1H), 6.04 (dd, J=12.8, 4.6 Hz, 1H), 2.73 (quin, J=6.8 Hz, 1H), 2.31 (td, J=12.8, 4.0 Hz, 1H), 2.07-1.99 (m, 1H), 1.59 (t, J=6.1 Hz, 1H), 1.48 (d, J=4.8 Hz, 1H), 1.01 (d, J=6.8 Hz, 3H). Analytical HPLC (Method A): RT=8.81 min, purity=100%; Factor XIa Ki=0.1 nM, Plasma Kallikrein Ki=6 nM.

Example 113

Preparation of (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl(10,11-²H₂)-3,4,7,15-tetraazatricyclo[12.3.1.0²,⁶]octadeca-1(18),2(6),4,14,16-pentaen-8-one Trifluoroacetate

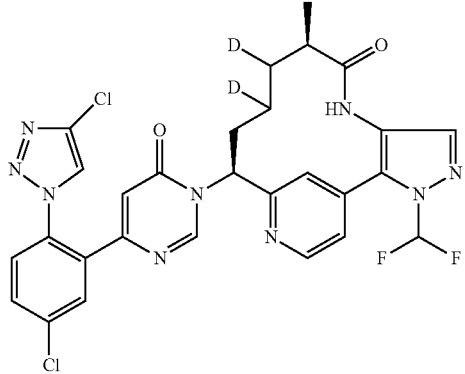 [SMILES: [2H]C1C[C@H](n2cnc(-c3cc(Cl)ccc3-n3cc(Cl)nn3)cc2=O)c2cc(ccn2)-c2c(cnn2C(F)F)NC(=O)[C@H](C)C1[2H]]

(9R,13S)-13-{4-[5-Chloro-2-(4-chloro-1H-1,2,3-triazol-1-yl)phenyl]-6-oxo-1,6-dihydropyrimidin-1-yl}-3-(difluoromethyl)-9-methyl(10,11-²H₂)-3,4,7,15-tetraazatricyclo[12.3.1.0²,⁶]octadeca-1(18),2(6),4,14,16-pentaen-8-one was prepared in a similar manner as the procedure described in Example 112, by using 6-(5-chloro-2-(4-chloro-1H-1,2,3-triazol-1-yl)phenyl)pyrimidin-4-ol (0.023 g, 0.075 mmol), prepared in Intermediate 9, to give (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl(10,11-²H₂)-3,4,7,15-tetraazatricyclo[12.3.1.0²,⁶]octadeca-1(18),2(6),4,14,16-pentaen-8-one trifluoroacetate as a white solid (20.4 mg, 36.3%). MS(ESI) m/z: 628.1 (M+H)⁺. ¹H NMR (400 MHz, CD₃OD) 8.91 (s, 1H), 8.77 (d, J=5.1 Hz, 1H), 8.36 (s, 1H), 7.91 (d, J=2.4 Hz, 1H), 7.83-7.65 (m, 5H), 7.58-7.52 (m, 1H), 6.39 (d, J=0.4 Hz, 1H), 6.03 (dd, J=12.8, 4.6 Hz, 1H), 2.74 (t, J=6.7 Hz, 1H), 2.32 (td, J=-12.9, 4.0 Hz, 1H), 2.07-1.98 (m, 1H), 1.59 (t, J=6.2 Hz, 1H), 1.48 (d, J=4.8 Hz, 1H), 1.02 (d, J=7.0 Hz, 3H). Analytical HPLC (Method A): RT=8.81 min, purity=99.3%; Factor XIa Ki=0.1 nM, Plasma Kallikrein Ki=25 nM.

Example 114

Preparation of (10R,14S)-14-{4-[5-chloro-2-(4-chloro-1H-1,2,3-triazol-1-yl)phenyl]-6-oxo-1,6-dihydropyrimidin-1-yl}-10-methyl-3,8,16-triazatricyclo[13.3.1.0²,⁷]nonadeca-1(19),2(7),3,5,15,17-hexaen-9-one, Bis-Trifluoroacetate

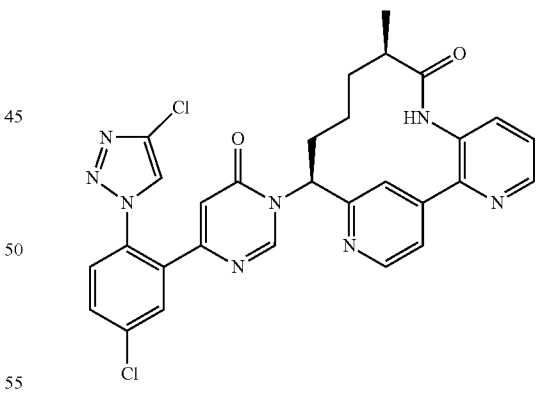

To a vial (4 ml) containing a suspension 6-(5-chloro-2-(4-chloro-1H-1,2,3-triazol-1-yl)phenyl)pyrimidin-4-ol (0.021 g, 0.067 mmol), prepared as described in Intermediate 9, in ACN (1 ml) was added HATU (0.033 g, 0.088 mmol) and DBU (0.015 ml, 0.101 mmol). After 30 min, (10R,14S)-14-amino-10-methyl-3,8,16-triazatricyclo[13.3.1.0²,⁷]nonadeca-1(19),2(7),3,5,15,17-hexaen-9-one (0.020 g, 0.067 mmol), prepared as described in Intermediate 38, in DMF (1.0 ml) was added at rt. After 4 h, the crude mixture was purified by reverse phase chromatography (PHENOMENEX® Luna Axia C18 5μ 30×100 mm column, Solvent A: 20% ACN-80% H₂O-0.1% TFA; Solvent B: 80% ACN-20% H₂O-0.1% TFA) to give (10R,14S)-14-{4-[5-chloro-2-(4-chloro-1H-1,2,3-triazol-1-yl)phenyl]-6-oxo-1,6-dihydropyrimidin-1-yl}-10-methyl-3,8,16-triazatricyclo[13.3.1.0²,⁷]nonadeca-1(19),2(7),3,5,15,17-hexaen-9-one, bis-trifluoroacetate (3.7 mg, 6.72%) as a white solid. MS(ESI) m/z: 587.1 (M+H)⁺. ¹H NMR (500 MHz, CD₃OD) δ 9.02 (s, 1H), 8.77 (d, J=4.8 Hz, 1H), 8.66 (d, J=4.8 Hz, 1H), 8.37 (s, 1H), 7.94-7.88 (m, 2H), 7.79-7.74 (m, 2H), 7.71-7.67 (m, 2H), 7.59 (dd, J=8.1, 4.8 Hz, 1H), 6.39 (s, 1H), 6.09 (dd, J=12.8, 5.1 Hz, 1H), 2.76 (br. s., 1H), 2.28 (t, J=12.8 Hz, 1H), 2.10-2.03 (m, 2H), 1.62-1.53 (m, 2H), 1.01 (d, J=7.0 Hz, 3H), 0.66 (br. s., 1H). Analytical HPLC (Method A): RT=7.60 min, purity=99.0%; Factor XIa Ki=3.3 nM, Plasma Kallikrein Ki=200 nM.

Example 115

Preparation of (9R,13S)-13-[4-(5-chloro-1-methyl-1H-indazol-7-yl)-6-oxo-1,6-dihydropyrimidin-1-yl]-3-(²H₃)methyl-9-methyl-3,4,7,15-tetraazatricyclo[12.3.1.0²,⁶]octadeca-1(18),2(6),4,14,16-pentaen-8-one Trifluoroacetate

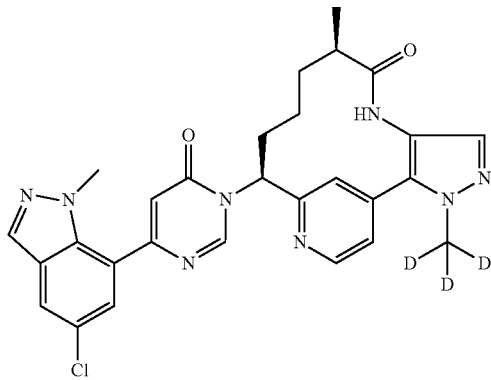 [SMILES: [2H]C([2H])([2H])n1ncc2c1-c1ccnc(c1)[C@@H](n1cnc(-c3cc(Cl)cc4cnn(C)c34)cc1=O)CCC[C@@H](C)C(=O)N2]

To a vial (4 ml) containing a suspension 6-(5-chloro-1-methyl-1H-indazol-7-yl)pyrimidin-4-ol (0.017 g, 0.066 mmol), prepared as described in Intermediate 22, in ACN (1 ml) was added HATU (0.033 g, 0.086 mmol) and DBU (0.015 ml, 0.099 mmol). After 30 min, (9R,13S)-13-amino-3-(²H₃)methyl-9-methyl-3,4,7,15-tetraazatricyclo[12.3.1.0²,⁶]octadeca-1(18),2(6),4,14,16-pentaen-8-one (0.020 g, 0.066 mmol), prepared as described in Intermediate 33, in DMF (1.0 ml) was added at rt. After 4 h, the crude mixture was purified by reverse phase chromatography (PHENOMENEX® Luna Axia C18 5μ 30×100 mm column, Solvent A: 20% ACN-80% H₂O-0.1% TFA; Solvent B: 80% ACN-20% H₂O-0.1% TFA) to give (9R,13S)-13-[4-(5-chloro-1-methyl-1H-indazol-7-yl)-6-oxo-1,6-dihydropyrimidin-1-yl]-3-(²H₃)methyl-9-methyl-3,4,7,15-tetraazatricyclo[12.3.1.0²,⁶]octadeca-1(18),2(6),4,14,16-pentaen-8-one trifluoroacetate (7.2 mg, 16.3%) as a white solid. MS(ESI) m/z: 587.1 (M+H)⁺. ¹H NMR (500 MHz, CD₃OD) δ 9.10 (s, 1H), 8.81 (d, J=5.3 Hz, 1H), 8.11 (s, 1H), 7.94 (d, J=2.0 Hz, 1H), 7.87 (s, 1H), 7.66 (d, J=5.1 Hz, 1H), 7.59-7.55 (m, 1H), 7.50 (d, J=1.8 Hz, 1H), 6.80 (s, 1H), 6.10 (dd, J=12.4, 4.1 Hz, 1H), 4.01-3.96 (m, 3H), 2.76 (dd, J=6.6, 3.1 Hz, 1H), 2.51-2.46 (m, 1H), 2.22-2.11 (m, 2H), 1.72-1.67 (m, 1H), 1.56 (br. s., 1H), 1.08 (d, J=7.0 Hz, 3H), 0.85 (br. s., 1H). Analytical HPLC (Method A): RT=7.41 min, purity=100.0%; Factor XIa Ki=113 nM.

Example 116

Preparation of (9R,13S)-13-{4-[5-chloro-2-(1H-1,2,3-triazol-1-yl)phenyl]-6-oxo-1,6-dihydropyrimidin-1-yl}-3-(difluoromethyl)-9-methyl-3,4,7-triazatricyclo[12.3.1.0²,⁶]octadeca-1(18),2(6),4,14,16-pentaen-8-one

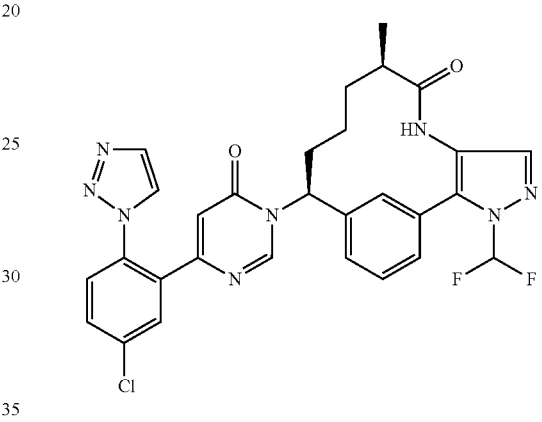

To a vial (4 ml) containing a suspension 6-[5-chloro-2-(1H-1,2,3-triazol-1-yl) phenyl]pyrimidin-4-ol (0.016 g, 0.060 mmol), prepared as described in Intermediate 8, in ACN (1 ml) was added HATU (0.030 g, 0.078 mmol) and DBU (0.014 ml, 0.090 mmol). After 30 min (9R,13S)-13-amino-3-(difluoromethyl)-9-methyl-3,4,7-triazatricyclo[12.3.1.0²,⁶]octadeca-1(18),2(6),4,14,16-pentaen-8-one (0.020 g, 0.060 mmol), prepared as described in Intermediate 35, in DMF (1.0 ml) was added at rt. After 4 h, the crude mixture was purified by reverse phase chromatography (PHENOMENEX® Luna Axia C18 5μ 30×100 mm column, Solvent A: 20% ACN-80% H₂O-0.1% TFA; Solvent B: 80% ACN-20% H₂O-0.1% TFA) to give (9R,13S)-13-[4-(5-chloro-1-methyl-1H-indazol-7-yl)-6-oxo-1,6-dihydropyrimidin-1-yl]-3-(²H₃)methyl-9-methyl-3,4,7,15-tetraazatricyclo[12.3.1.0²,⁶]octadeca-1(18),2(6),4,14,16-pentaen-8-one as a white solid. MS(ESI) m/z: 591.3 (M+H)⁺. ¹H NMR (400 MHz, CD₃OD) δ 8.22 (d, J=1.8 Hz, 2H), 7.90-7.72 (m, 5H), 7.66-7.50 (m, 4H), 7.41 (d, J=7.5 Hz, 1H), 6.27 (s, 1H), 5.83 (dd, J=12.9, 3.4 Hz, 1H), 2.57-2.47 (m, 1H), 2.41-2.31 (m, 1H), 2.18-2.06 (m, 1H), 1.90 (dd, J=9.5, 5.1 Hz, 1H), 1.64-1.52 (m, 2H), 1.27-1.11 (m, 4H). Analytical HPLC (Method A): RT=8.82 min, purity=98.4%; Factor XIa Ki=0.72 nM, Plasma Kallikrein Ki=120 nM.

Example 117

Preparation of (9R,13S)-13-[4-(5-chloro-1-methyl-1H-indazol-7-yl)-6-oxo-1,6-dihydropyrimidin-1-yl]-3-(difluoromethyl)-9-methyl-3,4,7-triazatricyclo[12.3.1.0$^{2,6}$]octadeca-1(18),2(6),4,14,16-pentaen-8-one

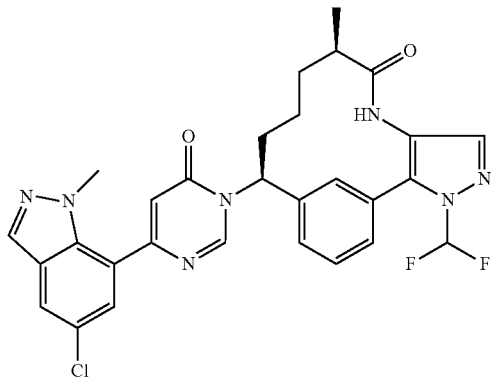 [SMILES: C[C@@H]1CCC[C@H](n2cnc(-c3cc(Cl)cc4cnn(C)c34)cc2=O)c2cccc(c2)-c2c(cnn2C(F)F)NC1=O]

To a vial (4 ml) containing a suspension of 6-(5-chloro-1-methyl-1H-indazol-7-yl) pyrimidin-4-ol. (0.016 g, 0.060 mmol), prepared as described in Intermediate 22, in ACN (1 ml) was added HATU (0.030 g, 0.078 mmol) and DBU (0.014 ml, 0.090 mmol). After 30 min (9R,13S)-13-amino-3-(difluoromethyl)-9-methyl-3,4,7-triazatricyclo[12.3.1.0$^{2,6}$]octadeca-1(18),2(6),4,14,16-pentaen-8-one (0.020 g, 0.060 mmol), prepared as described in Intermediate 35, in DMF (1.0 ml) was added at rt. After 4 h, the crude mixture was purified by reverse phase chromatography (PHENOMENEX® Luna Axia C18 5μ 30×100 mm column, Solvent A: 20% ACN-80% H$_2$O-0.1% TFA; Solvent B: 80% ACN-20% H$_2$O-0.1% TFA) to give (9R,13S)-13-[4-(5-chloro-1-methyl-1H-indazol-7-yl)-6-oxo-1,6-dihydropyrimidin-1-yl]-3-(difluoromethyl)-9-methyl-3,4,7-triazatricyclo[12.3.1.0$^{2,6}$]octadeca-1(18),2(6),4,14,16-pentaen-8-one (11 mg, 30.2%) as a white solid. MS(ESI) m/z: 578.2 (M+H)$^+$. $^1$H NMR (400 MHz, CD$_3$OD) δ 8.36 (s, 1H), 7.95 (s, 1H), 7.79-7.74 (m, 2H), 7.66 (s, 1H), 7.54-7.38 (m, 4H), 7.34 (d, J=2.0 Hz, 1H), 6.67 (s, 1H), 5.83 (dd, J=13.0, 3.3 Hz, 1H), 3.79 (s, 3H), 2.41-2.32 (m, 2H), 2.11 (d, J=12.5 Hz, 1H), 1.83-1.76 (m, 1H), 1.53-1.45 (m, 2H), 1.16-1.03 (m, 4H). Analytical HPLC (Method A): RT=9.56 min, purity=100%; Factor XIa Ki=90 nM, Plasma Kallikrein Ki=3,800 nM.

Example 118

Preparation of (10R,14S)-14-{4-[3-chloro-6-(4-chloro-1H-1,2,3-triazol-1-yl)-2-fluorophenyl]-6-oxo-1,6-dihydropyrimidin-1-yl}-10-methyl-3,8,16-triazatricyclo[13.3.1.0$^{2,7}$]nonadeca-1(19),2(7),3,5,15,17-hexaen-9-one bis-trifluoroacetate

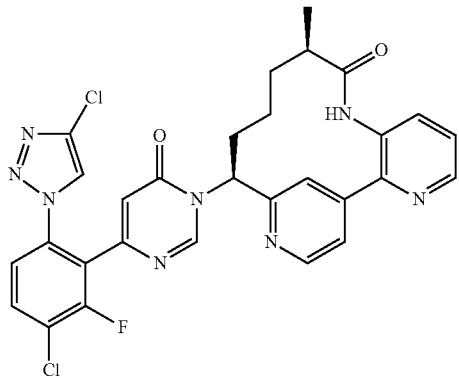 [SMILES: C[C@@H]1CCC[C@H](n2cnc(-c3c(-n4cc(Cl)nn4)ccc(Cl)c3F)cc2=O)c2cc(ccn2)-c2ncccc2NC1=O]

To a vial (4 ml) containing a suspension 6-[3-chloro-6-(4-chloro-1H-1,2,3-triazol-1-yl)-2-fluorophenyl]pyrimidin-4-ol (0.028 g, 0.084 mmol), prepared as described in Intermediate 10, in ACN (1 ml) was added HATU (0.042 g, 0.11 mmol) and DBU (0.019 ml, 0.127 mmol). After 30 min, 10R,14S)-14-amino-10-methyl-3,8,16-triazatricyclo[13.3.1.0$^{2,7}$]nonadeca-1(19),2(7),3,5,15,17-hexaen-9-one (0.025 g, 0.084 mmol), prepared as described in Intermediate 39, in DMF (1.0 ml) was added at rt. After stirring overnight, the crude mixture was purified by reverse phase chromatography (PHENOMENEX) Luna Axia C18 5μ 30×100 mm column, Solvent A: 20% ACN-80% H$_2$O-0.1% TFA; Solvent B: 80% ACN-20% H$_2$O-0.1% TFA) to give, after concentration and lyophilization (10R,14S)-14-{4-[3-chloro-6-(4-chloro-1H-1,2,3-triazol-1-yl)-2-fluorophenyl]-6-oxo-1,6-dihydropyrimidin-1-yl}-10-methyl-3,8,16-triazatricyclo[13.3.1.0$^{2,7}$]nonadeca-1(19),2(7),3,5,15,17-hexaen-9-one, bis-trifluoroacetate (13 mg, 17.6%) as a white solid. MS(ESI) m/k: 611.2 (M+H)$^+$ and 613.1 (M+2+H)$^+$. $^1$H NMR (400 MHz, CD$_3$OD) δ $^1$H NMR (500 MHz, CD$_3$OD-d$_4$) d 8.98 (s, 1H), 8.86-8.83 (m, 1H), 8.75-8.71 (m, 1H), 8.37 (s, 1H), 7.98 (s, 1H), 7.95-7.87 (m, 2H), 7.79-7.71 (m, 2H), 7.59-7.57 (m, 1H), 6.64 (s, 1H), 6.08 (dd, J=12.4, 5.0 Hz, 1H), 2.77 (br. s., 1H), 2.35-2.28 (m, 1H), 2.13-2.02 (m, 2H), 1.61-1.55 (m, 2H), 1.29 (d, J=6.9 Hz, 1H), 1.00 (d, J=7.2 Hz, 3H), 0.66 (br. s., 1H). Analytical HPLC (Method A): RT=7.11 min, purity=97.5%; Factor XIa Ki=1.4 nM, Plasma Kallikrein Ki=73 nM.

Example 119

Preparation of (9R,13S)-3-(difluoromethyl)-9-methyl-13-(4-{5-methyl-2-[4-(trifluoromethyl)-1H-1,2,3-triazol-1-yl]phenyl}-6-oxo-1,6-dihydropyrimidin-1-yl)-3,4,7,17-tetraazatricyclo[12.3.1.0$^{2,6}$]octadeca-1(18),2(6),4,14,16-pentaen-8-one

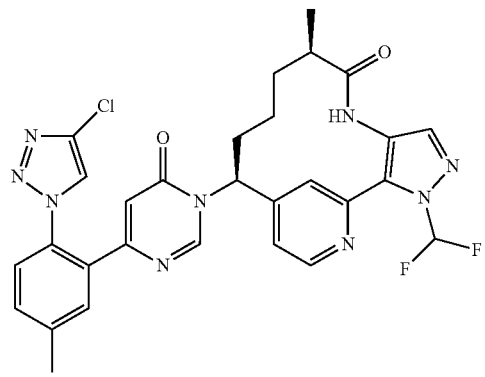 [SMILES: Cc1ccc(-n2cc(Cl)nn2)c(-c2cc(=O)n([C@H]3CCC[C@@H](C)C(=O)Nc4cnn(C(F)F)c4-c4cc3ccn4)cn2)c1]

119A. Preparation of 4-methyl-2-(4,4,5,5-tetramethyl-1,3,2-dioxaborolan-2-yl)aniline 2-Bromo-4-methylaniline (3 g, 16.12 mmol), bis(pinacolato)diboron (6.14 g, 24.19 mmol), KOAc (4.07 g, 41.4 mmol) were added to DMSO (9 mL) under N₂ atm and then degassed for 10 min. Pd(dppf)Cl₂CH₂Cl₂ Adduct (0.395 g, 0.484 mmol) was added and the resulting suspension was stirred overnight at 80° C. The reaction mixture was partitioned between DCM and water. The organic layer was washed with brine, dried over Na₂SO₄, filtered, and concentrated then purified normal phase chromatography using hexane and EtOAc as eluents to give 4-methyl-2-(4,4,5,5-tetramethyl-1,3,2-dioxaborolan-2-yl)aniline (3.52 g, 94% yield) as a clear oil which solidified into a white solid upon standing. MS(ESI) m/z: 152.3 (M-C₆H₁₀+H)⁺. ¹H NMR (400 MHz, CDCl₃-d) δ 7.43 (d, J=1.8 Hz, 1H), 7.04 (dd, J=8.3, 2.3 Hz, 1H), 6.55 (d, J=8.1 Hz, 1H), 4.60 (br. s., 2H), 2.23-2.20 (m, 3H), 1.38-1.32 (m, 12H).

119B. Preparation of 2-(6-methoxypyrimidin-4-yl)-4-methylaniline

To a RBF equipped with a reflux condenser containing DME (42.9 mL), EtOH (5.36 mL) was added 4-chloro-6-methoxypyrimidine (1.55 g, 10.72 mmol), 4-methyl-2-(4,4,5,5-tetramethyl-1,3,2-dioxaborolan-2-yl)aniline (2.5 g, 10.72 mmol) and 2 M aq Na₂CO₃ (5.36 mL, 10.72 mmol). The mixture was purged with Ar for 10 min then PdCl₂(dppf)-CH₂Cl₂ Adduct (0.876 g, 1.072 mmol) was added and the reaction mixture heated at 90° C. After 2 h, the reaction was diluted with water and extracted with EtOAc. The organic layer washed with brine and concentrated to give a brown oil. The crude product was purified by normal phase chromatography using heptane and EtOAc as eluents to give 2-(6-methoxypyrimidin-4-yl)-4-methylaniline (670 mg, 29%) as a solid. MS(ESI) m/z: 216.1 (M+H)⁺. ¹H NMR (500 MHz, CDCl₃-d) δ 8.79 (d, J=1.1 Hz, 1H), 7.33 (d, J=1.4 Hz, 1H), 7.08-7.01 (m, 2H), 6.67 (d, J=8.3 Hz, 1H), 5.68 (br. s., 2H), 4.03 (s, 3H), 2.29 (s, 3H).

119C. Preparation of 4-methoxy-6-(5-methyl-2-(4-(trifluoromethyl)-1H-1,2,3-triazol-1-yl)phenyl)pyrimidine To a cooled (0° C.), clear, yellow solution of 2-(6-methoxypyrimidin-4-yl)-4-methylaniline (0.670 g, 3.11 mmol) in ACN (44.5 mL) was added isoamylnitrite (0.63 mL, 4.67 mmol), followed by dropwise addition of TMSN₃ (0.62 mL, 4.67 mmol). After 10 min, the cold bath was removed, and the reaction allowed to warm to rt. After 4.5 h, Cu₂O (0.045 g, 0.311 mmol) was added. After a few min, 3,3,3-trifluoroprop-1-yne (0.293 g, 3.11 mmol) gas was bubbled into the dark green solution at rt. After 1 h, the reaction was diluted with DCM and washed with sat NH₄Cl, brine, dried over MgSO₄, filtered and concentrated to give a brown oil. The crude product was purified by normal phase chromatography using heptane and EtOAc as eluents to give 4-methoxy-6-(5-methyl-2-(4-(trifluoromethyl)-1H-1,2,3-triazol-1-yl)phenyl)pyrimidine (941 mg, 90%) as a solid. MS(ESI) m/z: 336.1 (M+H)⁺. ¹H NMR (500 MHz, CDCl₃-d) δ 8.63 (s, 1H), 7.98 (s, 1H), 7.56 (s, 1H), 7.45 (s, 2H), 6.58 (s, 1H), 3.97 (s, 3H), 2.53 (s, 3H).

119D. Preparation of 6-(5-methyl-2-(4-(trifluoromethyl)-1H-1,2,3-triazol-1-yl)phenyl) pyrimidin-4-ol A clear, yellow solution of 4-methoxy-6-(5-methyl-2-(4-(trifluoromethyl)-1H-1,2,3-triazol-1-yl)phenyl)pyrimidine (0.941 g, 2.81 mmol) in AcOH (14.03 mL) and 48% aq HBr (15.88 mL, 140 mmol) was warmed to 85° C. After 3 h, the reaction was cooled to rt and concentrated. The yellow gum dissolved in EtOAc, washed with sat NaHCO₃, brine, dried over Na₂SO₄, filtered, and concentrated. Et₂O (3 mL) was added, sonicated, and filtered. The solid rinsed with Et₂O (5 mL), air-dried with suction overnight to afford 6-(5-methyl-2-(4-(trifluoromethyl)-1H-1,2,3-triazol-1-yl)phenyl)pyrimidin-4-ol (0.609 g, 67.5% yield) as a light yellow solid. MS(ESI) m/z: 322.1 (M+H)⁺. ¹H NMR (400 MHz, CDCl₃) δ 12.90 (br. s., 1H), 8.06 (s, 1H), 7.93 (d, J=0.7 Hz, 1H), 7.57-7.40 (m, 3H), 6.51 (d, J=0.9 Hz, 1H), 2.53 (s, 3H).

119E. Preparation of (9R,13S)-3-(difluoromethyl)-9-methyl-13-(4-{5-methyl-2-[4-(trifluoromethyl)-1H-1,2,3-triazol-1-yl]phenyl})-6-oxo-1,6-dihydropyrimidin-1-yl)-3,4,7,17-tetraazatricyclo[12.3.1.0²,⁶]octadeca-1(18),2(6),4,14,16-pentaen-8-one Trifluoroacetate (9R,13S)-3-(Difluoromethyl)-9-methyl-13-(4-{5-methyl-2-[4-(trifluoromethyl)-1H-1,2,3-triazol-1-yl]phenyl}-6-oxo-1,6-dihydropyrimidin-1-yl)-3,4,7,17-tetraazatricyclo[12.3.1.0²,⁶]octadeca-1(18),2(6),4,14,16-pentaen-8-one trifluoroacetate (13 mg, 23%) was prepared in a similar manner as Example 56, using 6-(5-methyl-2-(4-(trifluoromethyl)-1H-1,2,3-triazol-1-yl)phenyl)pyrimidin-4-ol and (9R,13S)-13-amino-3-(difluoromethyl)-9-methyl-3,4,7,17-tetraazatricyclo[12.3.1.0²,⁶]octadeca-1(18),2(6),4,14,16-pentaen-8-one, prepared as described in Intermediate 37. MS(ESI) m/z: 640.2 (M+H)⁺. ¹H NMR (400 MHz, CD₃OD) δ 8.67 (s, 1H), 8.62-8.57 (m, 1H), 8.31-8.10 (m, 3H), 8.00-7.83 (m, 2H), 7.69 (s, 2H), 7.45 (d, J=0.9 Hz, 2H), 7.02 (dd, J=5.1, 1.5 Hz, 1H), 6.39 (s, 1H), 5.71-5.62 (m, 1H), 2.60-2.53 (m, 1H), 2.42 (s, 3H), 2.27 (d, J=6.6 Hz, 1H), 2.03-1.93 (m, 2H), 1.56 (dd, J=13.4, 5.1 Hz, 1H), 1.31-1.19 (m, 2H), 1.03 (d, J=6.8 Hz, 3H). Analytical HPLC (Method A): RT=8.90 min, purity=99%; Factor XIa Ki=1.1 nM, Plasma Kallikrein Ki=340 nM.

Example 120

Preparation of (9R,13S)-13-{4-[5-chloro-2-(1H-1,2,3-triazol-1-yl)phenyl]-6-oxo-5-(trifluoromethyl)-1,6-dihydropyrimidin-1-yl}-3,9-dimethyl-3,4,7,15-tetraazatricyclo[12.3.1.0²,⁶]octadeca-1(18),2(6),4,14,16-pentaen-8-one

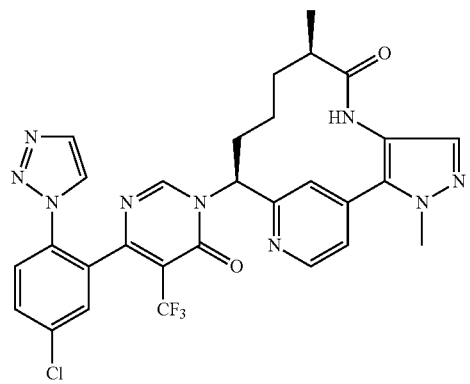 [SMILES: C[C@@H]1CCC[C@H](n2cnc(-c3cc(Cl)ccc3-n3ccnn3)c(C(F)(F)F)c2=O)c2cc(ccn2)-c2c(cnn2C)NC1=O]

A TFA/DMSO solution was prepared by dissolving TFA (10 μL) in DMSO (2.5 mL). To a separate vial containing a mixture of (9R,13S)-13-{4-[5-chloro-2-(1H-1,2,3-triazol-1-yl)phenyl]-6-oxo-1,6-dihydropyrimidin-1-yl}-3,9-dimethyl-3,4,7,15-tetraazatricyclo[12.3.1.0²,⁶]octadeca-1(18),2 (6),4,14,16-pentaen-8-one trifluoroacetate (0.0084 g, 0.013 mmol), prepared as described in Example 133, and Zn(SO₂CF₃)₂ (8.31 mg, 0.025 mmol) was added DMSO (0.25 mL). Next, 0.25 mL of the TFA/DMSO solution was added to give a clear, yellow solution. Then, 70% aq t-BuOOH (5.21 µl, 0.038 mmol) was added. After 2 h, additional Zn(SO₂CF₃)₂ (16.6 mg, 0.050 mmol) was added. After 30 min, additional 70% aq t-BuOOH (10.4 µl, 0.076 mmol) was added. After 1 h, the reaction was stopped. MeOH (1.5 mL) was added to the reaction mixture and it was purified by reverse phase chromatography to provide (9R,13S)-13-{4-[5-chloro-2-(1H-1,2,3-triazol-1-yl)phenyl]-6-oxo-5-(trifluoromethyl)-1,6-dihydropyrimidin-1-yl}-3,9-dimethyl-3,4,7,15-tetraazatricyclo[12.3.1.0²,⁶]octadeca-1 (18),2(6),4,14,16-pentaen-8-one (0.0024 g, 30% yield) as a white solid. MS(ESI) m/z: 624.4 (M+H)⁺, 626.4 (M+2H)⁺. A mixture of atropisomers were observed by ¹H NMR and ¹⁹F NMR. ¹H NMR (500 MHz, CD₃OD) δ 9.09-9.06 (m, 0.5H), 9.03-9.00 (m, 0.5H), 8.75 (d, J=5.0 Hz, 0.5H), 8.72 (d, J=5.0 Hz, 0.5H), 8.33 (s, 0.5H), 8.25 (s, 0.5H), 7.87 (br. s., 0.5H), 7.80 (br. s., 0.5H), 7.76-7.67 (m, 3H), 7.64 (d, J=2.2 Hz, 0.5H), 7.61 (d, J=2.2 Hz, 0.5H), 7.55-7.48 (m, 2H), 6.06-5.97 (m, 1H), 4.06 (s, 1.5H), 4.05 (s, 1.5H), 2.77-2.68 (m, 1H), 2.33-2.24 (m, 1H), 2.14-1.99 (m, 2H), 1.65-1.56 (m, 1H), 1.56-1.44 (m, 1H), 1.02-0.97 (m, 3H), 0.68-0.55 (m, 1H). ¹⁹F NMR (471 MHz, CD₃OD) δ −60.90 (s, 1F), −60.94 (s, 1F). Analytical HPLC (Method A): RT=7.55 min, purity=97.9%; Factor XIa Ki=110 nM.

Example 121

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-3,8,16-triazatricyclo[13.3.1.0²,⁷]nonadeca-1(19),2(7),3,5,15,17-hexaen-9-one, bis-trifluoroacetate

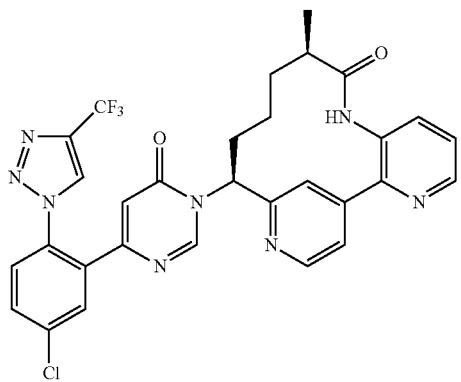 [SMILES: C[C@@H]1CCC[C@H](n2cnc(-c3cc(Cl)ccc3-n3cc(C(F)(F)F)nn3)cc2=O)c2cc(ccn2)-c2ncccc2NC1=O]

To a vial (4 ml) containing a suspension 6-{5-chloro-2-[4-(trifluoromethyl)-1H-1,2,3-triazol-1-yl]phenyl}pyrimidin-4-ol (0.027 g, 0.078 mmol), prepared as described in Intermediate 15, in ACN (2 ml) was added HATU (0.038 g, 0.101 mmol) and DBU (0.018 ml, 0.116 mmol). After 30 min, (10R,14S)-14-amino-10-methyl-3,8,16-triazatricyclo[13.3.1.0²,⁷]nonadeca-1(19),2(7),3,5,15,17-hexaen-9-one (0.023 g, 0.078 mmol), prepared as described in Intermediate 39, in ACN (1.0 ml) was added at rt. After 4 h, the crude mixture was purified by reverse phase chromatography (PHENOMENEX® Luna Axia C18 5µ 30×100 mm column, Solvent A: 20% ACN-80% H₂O-0.1% TFA; Solvent B: 80% ACN-20% H₂O-0.1% TFA) to give (10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-3,8,16-triazatricyclo[13.3.1.0²,⁷]nonadeca-1(19),2(7),3,5,15,17-hexaen-9-one, bis-trifluoroacetate (18 mg, 26.8%) as a white solid. MS(ESI) m/z: 621.2 (M+H)⁺ and 623.1 (M+2+H)⁺. ¹H NMR (500 MHz, CD₃OD) δ 8.82 (s, 1H), 8.72 (d, J=0.8 Hz, 1H), 8.63 (d, J=5.0 Hz, 1H), 8.54 (dd, J=5.0, 1.4 Hz, 1H), 7.80-7.78 (m, 2H), 7.70 (dd, J=8.1, 1.5 Hz, 1H), 7.68-7.64 (m, 1H), 7.61-7.57 (m, 2H), 7.51 (dd, J=8.0, 5.0 Hz, 1H), 6.33 (d, J=0.8 Hz, 1H), 5.95 (dd, J=12.7, 4.7 Hz, 1H), 2.66-2.61 (m, 1H), 2.13 (t, J=12.7 Hz, 1H), 1.91 (t, J=9.9 Hz, 2H), 1.47-1.39 (m, 2H), 0.87 (d, J=7.2 Hz, 3H). Analytical HPLC (Method A): RT=8.18 min, purity=98.3%; Factor XIa Ki=2.8 nM, Plasma Kallikrein Ki=190 nM.

Example 122

Preparation of (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7,16-tetraazatricyclo[12.3.1.0¹,⁶]octadeca-1(18),2(6),4,14,16-pentaen-8-one

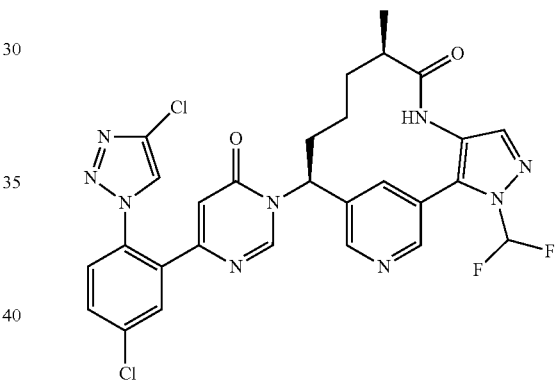

To a vial (4 ml) containing a suspension 6-(5-chloro-2-(4-chloro-1H-1,2,3-triazol-1-yl)phenyl)pyrimidin-4-ol (0.014 g, 0.046 mmol), prepared as described in Intermediate 9, in ACN (1 ml) was added HATU (0.019 g, 0.051 mmol) and DBU (0.009 ml, 0.060 mmol). After 20 min, (9R,13S)-13-amino-3-(difluoromethyl)-9-methyl-3,4,7,16-tetraazatricyclo[12.3.1.0²,⁶]octadeca-1(18),2(6),4,14,16-pentaen-8-one (0.0155 g, 0.046 mmol), prepared as described in Intermediate 43, in DMF (1.0 ml) was added at rt. After 3 h, the crude mixture was purified by reverse phase (PHENOMENEX® Luna Axia C18 30×100 mm column, Solvent A: 20% ACN-80% H₂O-0.1% TFA; Solvent B: 80% ACN-20% H₂O-0.1% TFA) to give (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7,16-tetraazatricyclo[12.3.1.0²,⁶]octadeca-1(18),2(6),4,14,16-pentaen-8-one (1.7 mg, 5.86%). MS(ESI) m/z: 626 (M+H)⁺. ¹H NMR (500 MHz, DMSO-d₆) δ 9.35 (s, 1H), 8.74 (s, 1H), 8.63 (d, J=1.7 Hz, 1H), 8.60-8.53 (m, 2H), 8.12-7.97 (m, 2H), 7.93-7.86 (m, 2H), 7.85-7.71 (m, 2H), 6.41 (s, 1H), 5.57 (d, J=9.9 Hz, 1H), 2.46-2.39 (m, 1H), 2.04-1.95 (m, 1H), 1.79 (d, J=10.7 Hz, 1H), 1.42 (d, J=6.9 Hz, 1H), 1.24 (br. s., 1H), 0.99 (d, J=6.6 Hz, 4H). Analytical HPLC (Method C): RT=1.52 min, purity=100.0%; Factor XIa Ki=0.16 nM, Plasma Kallikrein Ki=34 nM.

Example 123

Preparation of 6-[3-chloro-6-(4-chloro-1H-1,2,3-triazol-1-yl)-2-fluorophenyl]-3-[(9R,13S)-3,9-dimethyl-3,4,7,15-tetraazatricyclo[12.3.1.0$^{2,6}$]octadeca-1(18),2(6),4,14,16-pentaen-13-yl]-3,4-dihydropyrimidin-4-one

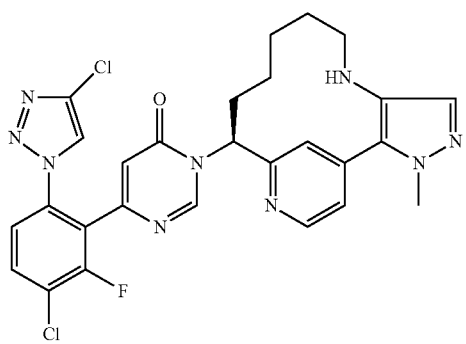 [SMILES: Cn1ncc2c1-c1ccnc(c1)[C@@H](n1cnc(-c3c(-n4cc(Cl)nn4)ccc(Cl)c3F)cc1=O)CCCCCN2]

123A. Preparation of (9R,13S)-3,9-dimethyl-3,4,7,15-tetraazatricyclo[12.3.1.0$^{2,6}$]octadeca-1(18),2(6),4,14,16-pentaen-13-amine To a solution of (9R,13S)-13-amino-3,9-dimethyl-3,4,7,15-tetraazatricyclo[12.3.1.0$^{2,6}$]octadeca-1(18),2(6),4,14,16-pentaen-8-one dihydrochloride (45 mg, 0.121 mmol), prepared as described in Intermediate 32, in THF (3022 μl) was added BH$_3$.THF complex (1813 μl, 1.813 mmol). The reaction was sealed and heated at 60° C. for 4.5 h. MeOH was added, followed by addition of 1.25 M HCl in MeOH (2 ml). The mixture was sealed and heated at 60° C. for 1 h. Another 0.5 mL of HCl in MeOH was added and heated at 60° C. for 1 h then cooled down to rt overnight. Another 0.5 mL of 4 N HCl in dioxane was added and the solution was heated at 65° C. for 5 h. The reaction mixture was concentrated. The residue was dissolved in MeOH, purified by reverse phase prep HPLC. After concentration and passing through NaHCO$_3$ cartridge, (9R,13S)-3,9-dimethyl-3,4,7,15-tetraazatricyclo[12.3.1.0$^{2,6}$]octadeca-1(18),2(6),4,14,16-pentaen-13-amine (28 mg, 81%) was obtained as an colorless oil. MS(ESI) m/z: 286.5 (M+H)$^+$.

123B. Preparation of 6-[3-chloro-6-(4-chloro-1H-1,2,3-triazol-1-yl)-2-fluorophenyl]-3-[(9R,13S)-3,9-dimethyl-3,4,7,15-tetraazatricyclo[12.3.1.0$^{2,6}$]octadeca-1(18),2(6),4,14,16-pentaen-13-yl]-3,4-dihydropyrimidin-4-one 6-[3-Chloro-6-(4-chloro-1H-1,2,3-triazol-1-yl)-2-fluorophenyl]-3-[(9R,13S)-3,9-dimethyl-3,4,7,15-tetraazatricyclo[12.3.1.0$^{2,6}$]octadeca-1(18),2(6),4,14,16-pentaen-13-yl]-3,4-dihydropyrimidin-4-one trifluoroacetate (12.5 mg, 30.4% yield) was prepared in a similar manner as the procedure described in Example 56 by using (9R,13S)-3,9-dimethyl-3,4,7,15-tetraazatricyclo[12.3.1.0$^{2,6}$]octadeca-1(18),2(6),4,14,16-pentaen-13-amine (6.5 mg, 0.020 mmol). $^1$H NMR (400 MHz, CDCl$_3$) δ 8.95 (s, 1H), 8.84 (d, J=5.1 Hz, 1H), 8.35 (s, 1H), 8.09-8.04 (m, 1H), 7.90-7.83 (m, 1H), 7.64 (s, 1H), 7.59-7.53 (m, 2H), 6.62 (s, 1H), 6.17 (dd, J=12.5, 4.8 Hz, 1H), 4.02 (s, 3H), 2.97 (d, J=10.6 Hz, 1H), 2.53 (br. s., 1H), 2.34-2.19 (m, 1H), 2.17-2.05 (m, 1H), 2.04-1.75 (m, 2H), 1.56 (t, J=12.3 Hz, 1H), 1.23 (br. s., 1H), 0.86 (d, J=7.3 Hz, 3H), 0.75-0.40 (m, 1H). MS(ESI) m/z: 594.2 (M+H)$^+$. Analytical HPLC (Method A): RT=6.97 min, purity=99.1%; Factor XIa Ki=2 nM, Plasma Kallikrein Ki=690 nM.

Example 124

Preparation of (9S,13S)-13-{4-[5-chloro-2-(4-chloro-1H-1,2,3-triazol-1-yl)phenyl]-6-oxo-1,6-dihydropyrimidin-1-yl}-3-(difluoromethyl)-10-fluoro-9-methyl-3,4,7-triazatricyclo[12.3.1.0$^{2,6}$]octadeca-1(18),2(6),4,14,16-pentaen-8-one

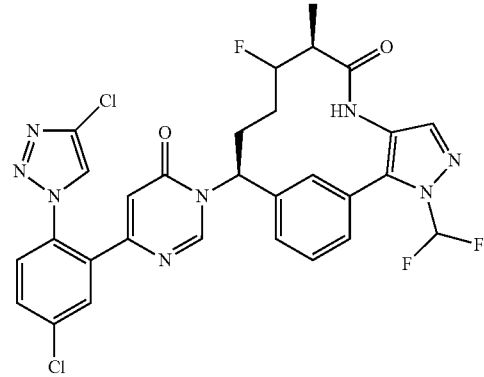 [SMILES: C[C@H]1C(=O)Nc2cnn(C(F)F)c2-c2cccc(c2)[C@@H](n2cnc(-c3cc(Cl)ccc3-n3cc(Cl)nn3)cc2=O)CCC1F]

124A. Preparation of Tert-Butyl N-[(9S,13S)-3-(difluoromethyl)-10-fluoro-9-methyl-8-oxo 3,4,7-triazatricyclo[12.3.1.0$^{2,6}$]octadeca-1(18),2(6),4,14,16-pentaen-13-yl]carbamate Fe$_2$(C$_2$O$_4$)$_3$.6H$_2$O (2.797 g, 5.78 mmol) was added to a RBF containing H$_2$O (30 ml). The suspension was warmed by a water bath (50° C.) to aid dissolution. After 3 h, the clear yellow solution was cooled to 0° C. and purged with Ar. After 20 min, SELECTFLUOR® (2.048 g, 5.78 mmol) in ACN (5 ml) was added followed by dropwise addition of tert-butyl N-[(9R,10E,13S)-3-(difluoromethyl)-9-methyl-8-oxo-3,4,7-triazatricyclo[12.3.1.0$^{2,6}$]octadeca-1(18),2(6),4,10,14,16-hexaen-13-yl]carbamate (0.500 g, 1.156 mmol), prepared as described in Example 35D, in ACN (10 ml). After 5 min, NaBH$_4$ (0.350 g, 9.25 mmol) was added in two separate portions over a 5 min period. After 15 min, the reaction mixture was allowed to come to rt. After 1 h, the reaction mixture was quenched with aqueous NH$_4$OH (28-30%; 15 mL). After 30 min, the reaction mixture was filtered and the collected solids washed with EtOAc. The combined organics was washed with brine, dried over Na$_2$SO$_4$, filtered, and concentrated to give a crude mixture of isomers. The material was subjected chiral purification using CHIRALPAK® IC, 21×250 mm, 5μ, using 10% MeOH/90% CO$_2$ at 75 ml/min, 150 Bar, 40° C. The early eluting isomer was assigned as tert-butyl N-[(9S,13S)-3-(difluoromethyl)-10-fluoro-9-methyl-8-oxo-3,4,7-triazatricyclo[12.3.1.0$^{2,6}$]octadeca-1(18),2(6),4,14,16-pentaen-13-yl]carbamate (99.5% ee; 38 mg, 7.26%) and the second eluting isomer, tert-butyl N-[(9R,13S)-3-(difluoromethyl)-11-fluoro-9-methyl-8-oxo- 3,4,7-triazatricyclo[12.3.1.0²,⁶]octadeca-1(18),2(6),4,14,16-pentaen-13-yl]carbamate (99.5% ee; 34 mg, 6.50%). MS(ESI) m/z: 397 (M-tBu)⁺.

124B. (9S,13S)-13-{4-[5-Chloro-2-(4-chloro-1H-1,2,3-triazol-1-yl)phenyl]-6-oxo-1,6-dihydropyrimidin-1-yl}-3-(difluoromethyl)-10-fluoro-9-methyl-3,4,7-triazatricyclo[12.3.1.0²,⁶]octadeca-1(18),2(6),4,14,16-pentaen-8-one The early eluting isomer tert-butyl N-[(9S,13S)-3-(difluoromethyl)-10-fluoro-9-methyl-8-oxo-3,4,7-triazatricyclo [12.3.1.0²,⁶]octadeca-1(18),2(6),4,14,16-pentaen-13-yl]carbamate (0.038 g, 0.084 mmol) was treated with HCl (4.0 M in dioxane) (0.420 ml, 1.680 mmol). A minimum amount of MeOH was added to aid dissolution. After 2 h, the reaction mixture was concentrated to dryness. The residue was dissolved in MeOH and passed through a NaHCO₃ cartridge (StratoSpheres SPE; 500 mg, 0.90 mmol loading). The filtrate was concentrated and the free base temporarily set aside. Separately, flask containing a white suspension of 6-(5-chloro-2-(4-chloro-1H-1,2,3-triazol-1-yl)phenyl) pyrimidin-4-ol (0.026 g, 0.084 mmol), prepared as described in Intermediate 9, in ACN (1.120 ml) was added HATU (0.035 g, 0.092 mmol) and DBU (0.016 ml, 0.109 mmol). After 20 min, the free base in DMF (1 mL) was added and the resulting suspension was stirred at rt overnight. The reaction mixture was purified reverse phase chromatography (SunFire C18 5μ 30×100 mm column, 10-minute gradient; Solvent A: 20% ACN-80% H₂O-0.1% TFA; Solvent B: 80% ACN-20% H₂O-0.1% TFA). The pure fractions were liberated of organics and the remaining aqueous phase freeze-dried to give (9S,13S)-13-{4-[5-chloro-2-(4-chloro-1H-1,2,3-triazol-1-yl)phenyl]-6-oxo-1,6-dihydropyrimidin-1-yl}-3-(difluoromethyl)-10-fluoro-9-methyl-3,4,7-triazatricyclo[12.3.1.0²,⁶]octadeca-1(18),2(6),4,14,16-pentaen-8-one (18.2 mg, 33.3%) as a white solid. MS(ESI) m/z: 643 (M+H)⁺. ¹H NMR (500 MHz, CD₃OD) δ 8.83 (s, 1H), 8.40-8.38 (m, 1H), 7.93 (d, J=2.2 Hz, 1H), 7.80-7.75 (m, 2H), 7.71-7.68 (m, 1H), 7.66-7.62 (m, 3H), 7.54 (d, J=7.7 Hz, 1H), 7.28 (d, J=8.0 Hz, 1H), 6.46 (d, J=0.8 Hz, 1H), 5.92 (dd, J=13.3, 4.5 Hz, 1H), 5.38-5.25 (m, 1H), 3.19-3.14 (m, 1H), 2.48-2.41 (m, 1H), 2.27 (ddt, J=12.9, 8.7, 4.2 Hz, 1H), 1.85-1.75 (m, 1H), 1.05 (d, J=6.9 Hz, 3H), 0.99-0.83 (m, 1H). Analytical HPLC (Method A): RT=9.3 min, purity=99.5%; Factor XIa Ki=0.1 nM, Plasma Kallikrein Ki=24 nM.

Example 125

Preparation of (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-11-fluoro-9-methyl-3,4,7-triazatricyclo[12.3.1.0²,⁶]octadeca-1(18),2(6),4,14,16-pentaen-8-one

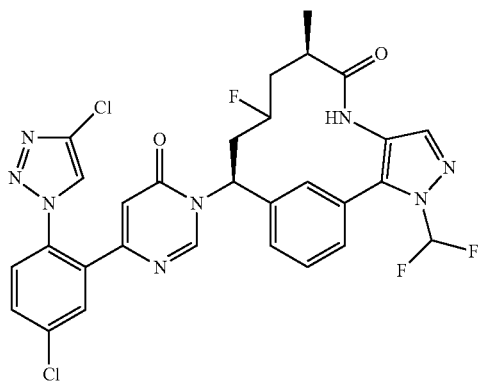 [SMILES: C[C@@H]1CC(F)C[C@H](n2cnc(-c3cc(Cl)ccc3-n3cc(Cl)nn3)cc2=O)c2cccc(c2)-c2c(cnn2C(F)F)NC1=O]

The second eluting isomer from Example 124A, tert-butyl N-[(9R,13S)-3-(difluoromethyl)-11-fluoro-9-methyl-8-oxo-3,4,7-triazatricyclo[12.3.1.0²,⁶]octadeca-1(18),2(6),4,14,16-pentaen-13-yl]carbamate (0.034 g, 0.075 mmol) was treated with HCl (4.0 M in dioxane) (0.376 ml, 1.50 mmol). A minimum amount of MeOH was added to aid dissolution. After 2 h, the reaction mixture was concentrated to dryness. The residue was dissolved in MeOH and passed through a NaHCO₃ cartridge (StratoSpheres SPE; 500 mg, 0.90 mmol loading). The filtrate was concentrated and the free base temporarily set aside. Separately, a flask containing a white suspension of 6-(5-chloro-2-(4-chloro-1H-1,2,3-triazol-1-yl)phenyl)pyrimidin-4-ol (0.023 g, 0.075 mmol), prepared as described in Intermediate 9, in ACN (1.120 ml) was added HATU (0.031 g, 0.083 mmol) and DBU (0.015 ml, 0.098 mmol). After 20 min, the free base in DMF (1 mL) was added and the resulting suspension was stirred at rts overnight. The reaction mixture was purified reverse phase chromatography (SunFire C18 5μ 30×100 mm column, 10-minute gradient; Solvent A: 20% ACN-80% H₂O-0.1% TFA; Solvent B: 80% ACN-20% H₂O-0.1% TFA). The pure fractions were concentrated to remove most of the ACN and the remaining aqueous phase freeze-dried to give (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-11-fluoro-9-methyl-3,4,7-triazatricyclo[12.3.1.0²,⁶]octadeca-1(18),2(6),4,14,16-pentaen-8-one (8.9 mg, 18.2%) as a white solid. MS(ESI) m/z: 643 (M+H)⁺. ¹H NMR (500 MHz, CD₃OD) δ 8.35 (s, 1H), 8.20 (s, 1H), 7.88 (d, J=2.5 Hz, 1H), 7.80 (s, 1H), 7.76-7.74 (m, 1H), 7.70 (s, 1H), 7.69-7.60 (m, 3H), 7.57-7.51 (m, 1H), 6.44 (d, J=0.8 Hz, 1H), 6.11 (dd, J=13.1, 2.9 Hz, 1H), 4.55-4.40 (m, 1H), 2.96-2.83 (m, 1H), 2.76-2.69 (m, 1H), 2.47-2.38 (m, 1H), 2.21-2.12 (m, 1H), 2.03-1.92 (m, 1H), 1.26 (d, J=6.6 Hz, 3H). Analytical HPLC (Method A): 9.41 min, purity=99.5%; Factor XIa Ki=20 nM, Plasma Kallikrein Ki=2,400 nM.

Example 126

Preparation of (9S,13S)-13-{4-[5-chloro-2-(4-chloro-1H-1,2,3-triazol-1-yl)phenyl]-6-oxo-1,6-dihydropyrimidin-1-yl}-10,16-difluoro-3,9-dimethyl-3,4,7-triazatricyclo[12.3.1.0²,⁶]octadeca-1(18),2(6),4,14,16-pentaen-8-one

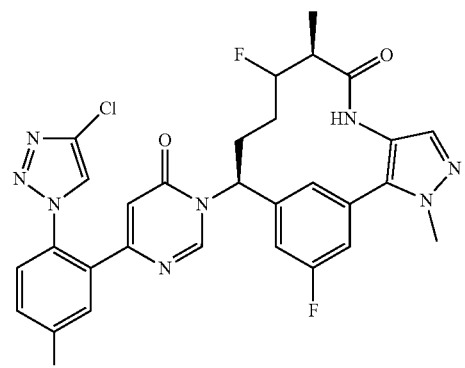

126A. Preparation of N-[(9S,13S)-10,16-difluoro-3,9-dimethyl-8-oxo-3,4,7-triazatricyclo[12.3.1.0²,⁶] octadeca-1(18),2(6),4,14,16-pentaen-13-yl]carbamate Fe₂(C₂O₄)₃.6H₂O (2.16 g, 4.46 mmol) was added to a RBF containing H₂O (30 ml). The suspension was warmed by a water bath (50° C.) to aid dissolution. After 3 h, the clear yellow solution was cooled to 0° C. and purged with Ar. After 20 min, SELECTFLUOR® (1.58 g, 4.46 mmol) in ACN (5 ml) was added followed by dropwise addition of tert-butyl N-[(9R,10E,13S)-16-fluoro-3,9-dimethyl-8-oxo-3,4,7-triazatricyclo[12.3.1.0$^{2,6}$]octadeca-1(18),2(6),4,10,14,16-hexaen-13-yl]carbamate (0.370 g, 0.893 mmol), prepared as described in Intermediate 29D, in ACN (10 ml). After 5 min, NaBH$_4$ (0.270 g, 7.14 mmol) was added in two separate portions over a 5 min period. After 15 min, the reaction mixture was allowed to warm to rt. After 1 h, the reaction mixture was quenched with 28-30% aq NH$_4$OH (15 mL). After 30 min, the reaction mixture was filtered, solids washed with EtOAc, organics washed with brine, dried over Na$_2$SO$_4$, filtered, and concentrated to give a crude mixture of isomers. The material was subjected chiral purification using CHIRALPAK® IC, 21×250 mm, 5 t, using 10% EtOH/90% C$_{O2}$ at 45 ml/min, 150 Bar, 40° C. The early eluting isomer was assigned tert-butyl N-[(9S,13S)-10,16-difluoro-3,9-dimethyl-8-oxo-3,4,7-triazatricyclo[12.3.1.0$^{2,6}$]octadeca-1(18),2(6),4,14,16-pentaen-13-yl]carbamate (99.5% ee; 68 mg, 17.50%) and the second eluting isomer, tert-butyl N-[(9R,13S)-11,16-difluoro-3,9-dimethyl-8-oxo-3,4,7-triazatricyclo[12.3.1.0$^{2,6}$]octadeca-1(18),2(6),4,14,16-pentaen-13-yl]carbamate (99.5% ee; 32 mg, 8.3%). 435 (M+H)$^+$.

126B. Preparation of (9S,13S)-13-{4-[5-chloro-2-(4-chloro-1H-1,2,3-triazol-1-yl) phenyl]-6-oxo-1,6-dihydropyrimidin-1-yl}-10,16-difluoro-3,9-dimethyl-3,4,7-triazatricyclo[12.3.1.0$^{2,6}$]octadeca-1(18),2(6),4,14,16-pentaen-8-one The early eluting isomer assigned tert-butyl N-[(9S,13S)-10,16-difluoro-3,9-dimethyl-8-oxo-3,4,7-triazatricyclo[12.3.1.0$^{2,6}$]octadeca-1(18),2(6),4,14,16-pentaen-13-yl]carbamate (0.034 g, 0.078 mmol) was treated with 4. M HCl in dioxane (0.391 ml, 1.570 mmol). A minimum amount of MeOH was added to aid dissolution. After 2 h, the reaction mixture was concentrated to dryness. The residue was dissolved in MeOH and passed through a NaHCO$_3$ cartridge (StratoSpheres SPE; 500 mg, 0.90 mmol loading). The filtrate was concentrated and the free base temporarily set aside. Separately, to a flask containing a white suspension of 6-(5-chloro-2-(4-chloro-1H-1,2,3-triazol-1-yl) phenyl)pyrimidin-4-ol (0.024 g, 0.078 mmol), prepared as described in Intermediate 9, in ACN (1.120 ml) was added HATU (0.033 g, 0.086 mmol) and DBU (0.015 ml, 0.102 mmol). After 20 min, the free base in DMF (1 mL) was added and the resulting suspension was stirred at rt overnight. The reaction mixture was purified reverse phase chromatography (SunFire C18 5μ 30×100 mm column, 10-minute gradient; Solvent A: 20% ACN-80% H$_2$O-0.1% TFA; Solvent B: 80% ACN-20% H$_2$O-0.1% TFA). The pure fractions were concentrated to remove most of the ACN and the remaining aqueous phase freeze-dried to give (9S,13S)-13-{4-[5-chloro-2-(4-chloro-1H-1,2,3-triazol-1-yl) phenyl]-6-oxo-1,6-dihydropyrimidin-1-yl}-10,16-difluoro-3,9-dimethyl-3,4,7-triazatricyclo[12.3.1.0$^{2,6}$]octadeca-1(18),2(6),4,14,16-pentaen-8-one (18.5 mg, 37.5%) as a white solid. MS(ESI) m/z: 643 (M+H)$^+$. $^1$H NMR (500 MHz, CD$_3$OD) δ 8.81 (s, 1H), 8.39 (s, 1H), 7.94 (d, J=2.5 Hz, 1H), 7.80-7.76 (m, 1H), 7.72-7.68 (m, 1H), 7.50 (s, 1H), 7.40 (s, 1H), 7.31 (dt, J=9.0, 1.8 Hz, 1H), 7.06-7.02 (m, 1H), 6.44 (s, 1H), 5.91 (dd, J=13.5, 4.4 Hz, 1H), 5.37-5.25 (m, 1H), 4.04 (s, 3H), 3.16 (ddd, J=11.3, 7.1, 3.9 Hz, 1H), 2.48-2.41 (m, 1H), 2.30-2.24 (m, 1H), 1.88-1.77 (m, 1H), 1.05 (d, J=6.9 Hz, 3H), 0.99- 0.86 (m, 1H). Analytical HPLC (Method A): RT=8.84 min, purity=99.5%; Factor XIa Ki=0.1 nM, Plasma Kallikrein Ki=12 nM.

Example 127

Preparation of (9S,13S)-13-(4-{5-chloro-2-[4-(trifluoromethyl)-1H-1,2,3-triazol-1-yl]phenyl}-6-oxo-1,6-dihydropyrimidin-1-yl)-10,16-difluoro-3,9-dimethyl-3,4,7-triazatricyclo[12.3.1.0$^{2,6}$]octadeca-1(18),2(6),4,14,16-pentaen-8-one

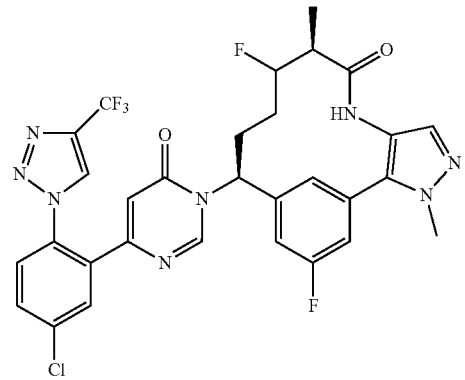 [SMILES: C[C@H]1C(=O)Nc2cnn(C)c2-c2cc(F)cc(c2)[C@@H](n2cnc(-c3cc(Cl)ccc3-n3cc(C(F)(F)F)nn3)cc2=O)CCC1F]

The early eluting isomer assigned tert-butyl N-[(9S,13S)-10,16-difluoro-3,9-dimethyl-8-oxo-3,4,7-triazatricyclo[12.3.1.0$^{2,6}$]octadeca-1(18),2(6),4,14,16-pentaen-13-yl]carbamate (0.034 g, 0.078 mmol), prepared as described in Example 126A was treated with HCl (4.0 M in dioxane) (0.391 ml, 1.570 mmol). A minimum amount of MeOH was added to aid dissolution. After 2 h, the reaction mixture was concentrated to dryness. The residue was dissolved in MeOH and passed through a NaHCO$_3$ cartridge (StratoSpheres SPE; 500 mg, 0.90 mmol loading). The filtrate was concentrated and the free base temporarily set aside. Separately, flask containing a white suspension of 6-{5-chloro-2-[4-(trifluoromethyl)-1H-1,2,3-triazol-1-yl]phenyl}pyrimidin-4-ol (0.027 g, 0.078 mmol), prepared as described in Intermediate 15, in ACN (1.120 ml) was added HATU (0.033 g, 0.086 mmol) and DBU (0.015 ml, 0.102 mmol). After 20 min, the free base in DMF (1 mL) was added and the resulting suspension was stirred at rt overnight. The reaction mixture was purified reverse phase chromatography (SunFire C18 5μ 30×100 mm column, 10-minute gradient; Solvent A: 20% ACN-80% H$_2$O-0.1% TFA; Solvent B: 80% ACN-20% H$_2$O-0.1% TFA). The pure fractions were liberated of organics and the remaining aqueous phase freeze-dried to give (9S,13S)-13-{4-[5-chloro-2-(4-chloro-1H-1,2,3-triazol-1-yl)phenyl]-6-oxo-1,6-dihydropyrimidin-1-yl}-10,16-difluoro-3,9-dimethyl-3,4,7-triazatricyclo[12.3.1.0$^{2,6}$]octadeca-1(18),2(6),4,14,16-pentaen-8-one (23 mg, 44.2%) as a white solid. MS(ESI) m/z: 659.2 (M+H)$^+$. $^1$H NMR (500 MHz, CD$_3$OD) δ 8.87 (d, J=0.8 Hz, 1H), 8.77 (s, 1H), 7.95 (d, J=2.2 Hz, 1H), 7.82-7.78 (m, 1H), 7.76-7.71 (m, 1H), 7.50 (s, 1H), 7.39 (s, 1H), 7.33-7.28 (m, 1H), 6.99 (dt, J=9.3, 1.8 Hz, 1H), 6.51 (d, J=0.8 Hz, 1H), 5.91 (dd, J=13.3, 4.5 Hz, 1H), 5.37-5.24 (m, 1H), 4.07-4.02 (m, 3H), 3.15 (ddd, J=11.5, 7.2, 3.9 Hz, 1H), 2.42 (tt, J=13.2, 4.0 Hz, 1H), 2.23 (tt, J=13.0, 4.0 Hz, 1H), 1.85-1.78 (m, 1H), 1.05 (d, J=6.9 Hz, 3H), 0.96-0.87 (m, 1H). Analytical HPLC (Method A): RT=9.26 min, purity=99.7%; Factor XIa Ki=0.1 nM, Plasma Kallikrein Ki=10 nM.

Example 128

Preparation of (9R,13S)-13-{4-[5-chloro-2-(4-cyclopropyl-1H-1,2,3-triazol-1-yl)phenyl]-6-oxo-1,6-dihydropyrimidin-1-yl}-3-($Å^2H$, f)methyl-9-methyl-3,4,7-triazatricyclo[12.3.1.0$^{2,6}$]octadeca-1(18),2(6),4,14,16-pentaen-8-one

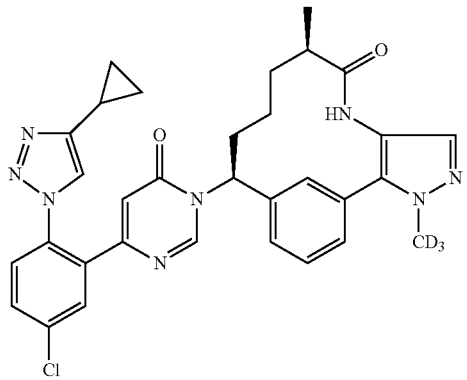 [SMILES: [2H]C([2H])([2H])n1ncc2c1-c1cccc(c1)[C@@H](n1cnc(-c3cc(Cl)ccc3-n3cc(C4CC4)nn3)cc1=O)CCC[C@@H](C)C(=O)N2]

(9R,13S)-13-{4-[5-Chloro-2-(4-cyclopropyl-1H-1,2,3-triazol-1-yl)phenyl]-6-oxo-1,6-dihydropyrimidin-1-yl}-3-($^2H_3$)methyl-9-methyl-3,4,7-triazatricyclo[12.3.1.0$^{2,6}$]octadeca-1(18),2(6),4,14,16-pentaen-8-one (1.68 mg, 15% yield) was prepared in a similar manner as the procedure described in Example 167, using (9R,13S)-13-amino-3-($^2H_3$)methyl-9-methyl-3,4,7,15-tetraazatricyclo[12.3.1.0$^{2,6}$]octadeca-1(18),2(6),4,14,16-pentaen-8-one (5.35 mg, 0.018 mmol), prepared as described in Intermediate 33. MS(ESI) m/z: 598.3 (M+H)$^+$. $^1$H NMR (400 MHz, CD$_3$OD) δ 8.17 (s, 1H), 7.86 (s, 1H), 7.83 (d, J=2.4 Hz, 1H), 7.75 (s, 1H), 7.68 (dd, J=8.4, 2.4 Hz, 1H), 7.59-7.55 (m, 3H), 7.49 (s, 1H), 7.32 (d, J=7.3 Hz, 1H), 6.23 (s, 1H), 5.81 (dd, J=13.1, 3.4 Hz, 1H), 2.53-2.26 (m, 2H), 2.13-1.80 (m, 3H), 1.63-1.49 (m, 2H), 1.27-1.09 (m, 4H), 1.01-0.91 (m, 2H), 0.78-0.69 (m, 2H). Analytical HPLC (Method A): RT=8.15 min, purity=95.3%; Factor XIa Ki=2 nM, Plasma Kallikrein Ki=280 nM

Example 129

Preparation of 6-[3-chloro-6-(4-chloro-1H-1,2,3-triazol-1-yl)-2-fluorophenyl]-3-[(9R,13S)-3-(difluoromethyl)-9-methyl-3,4,7,15-tetraazatricyclo[12.3.1.0$^{2,6}$]octadeca-1(18),2(6),4,14,16-pentaen-13-yl]-3,4-dihydropyrimidin-4-one

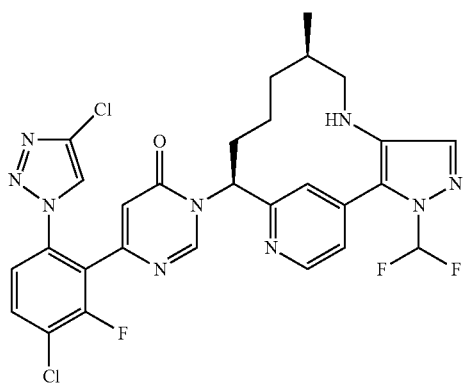 [SMILES: C[C@@H]1CCC[C@H](n2cnc(-c3c(-n4cc(Cl)nn4)ccc(Cl)c3F)cc2=O)c2cc(ccn2)-c2c(cnn2C(F)F)NC1]

6-[3-Chloro-6-(4-chloro-1H-1,2,3-triazol-1-yl)-2-fluorophenyl]-3-[(9R,13S)-3-(difluoromethyl)-9-methyl-3,4,7,15-tetraazatricyclo[12.3.1.0$^{2,6}$]octadeca-1(18),2(6),4,14,16-pentaen-13-yl]-3,4-dihydropyrimidin-4-one was prepared in a similar manner as the procedure described in Example 123 by using (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one, prepared as described in Intermediate 30. $^1$H NMR (400 MHz, CD$_3$OD δ 8.99 (s, 1H), 8.73 (d, J=5.3 Hz, 1H), 8.32 (s, 1H), 8.30 (s, 1H), 7.86 (dd, J=8.6, 7.7 Hz, 1H), 7.57 (s, 1H), 7.56-7.52 (m, 2H), 7.49 (d, J=5.1 Hz, 1H), 6.61 (s, 1H), 6.18 (dd, J=12.5, 5.1 Hz, 1H), 2.67 (d, J=11.7 Hz, 1H), 2.36-2.22 (m, 1H), 2.19-1.99 (m, 3H), 1.82 (br. s., 1H), 1.49 (br. s., 1H), 1.24 (m, 1H), 0.76 (d, J=7.3 Hz, 3H), 0.45 (br. s., 1H). MS(ESI) m/z: 630.2 (M+H)$^+$. Analytical HPLC (Method A): RT=11.06 min, purity=99.3%; Factor XIa Ki=0.8 nM, Plasma Kallikrein Ki=880 nM.

Example 130

Preparation of (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-8-oxo-3,4,7-triazatricyclo[12.3.1.0$^{2,6}$]octadeca-1(18),2(6),4,14,16-pentaene-16-carbonitrile

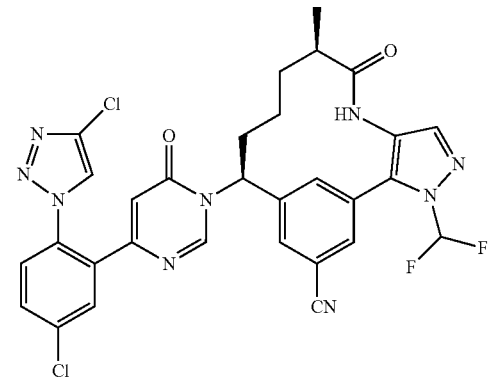 [SMILES: C[C@@H]1CCC[C@H](n2cnc(-c3cc(Cl)ccc3-n3cc(Cl)nn3)cc2=O)c2cc(C#N)cc(c2)-c2c(cnn2C(F)F)NC1=O]

To (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-8-oxo-3,4,7-triazatricyclo[12.3.1.0$^{2,6}$]octadeca-1(18),2(6),4,14,16-pentaene-16-carboxamide, described in Example 84, (0.004 g, 5.98 μmol) in ACN (0.3 mL), cooled to 0° C., was added several drops of pyridine, then POCl$_3$ (0.91 mg, 5.98 μmol). After 2 h, the reaction was concentrated and purified by preparative LCMS to afford (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-8-oxo-3,4,7-triazatricyclo[12.3.1.0$^{2,6}$]octadeca-1(18),2(6),4,14,16-pentaene-16-carboxamide (1.7 mg, 43%) as a white solid. MS(ESI) m/z: 650.3 (M+H)$^+$. $^1$H NMR (500 MHz, DMSO-d$_6$) δ 9.39 (s, 1H), 8.71 (s, 1H), 8.56 (s, 1H), 7.95 (d, J=1.4 Hz, 2H), 7.89 (t, J=2.9 Hz, 3H), 7.87-7.80 (m, 2H), 7.77-7.71 (m, 1H), 6.40 (s, 1H), 5.55 (d, J=10.5 Hz, 1H), 1.98-1.79 (m, 2H), 1.52-1.36 (m, 1H), 1.12 (br. s., 1H), 1.04-0.98 (m, 1H), 0.96 (d, J=6.9 Hz, 3H). Analytical HPLC (Method C) RT=1.76 min., purity=99%; Factor XIa Ki=0.2 nM, Plasma Kallikrein Ki=29 nM.

Example 131

Preparation of (9R,13S)-13-(4-{5-chloro-2-[4-(trimethylsilyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one Trifluoroacetate

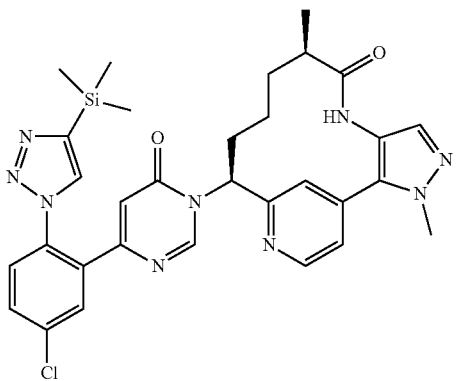 [SMILES: C[C@@H]1CCC[C@H](n2cnc(-c3cc(Cl)ccc3-n3cc([Si](C)(C)C)nn3)cc2=O)c2cc(ccn2)-c2c(cnn2C)NC1=O]

131A. Preparation of 6-{5-chloro-2-[4-(trimethylsilyl)-1H-1,2,3-triazol-1-yl]phenyl}pyrimidin-4-ol, Hydrobromide A clear, yellow solution of 4-{5-chloro-2-[4-(trimethylsilyl-1H-1,2,3-triazol-1-yl]phenyl}-6-methoxypyrimidine (0.027 g, 0.075 mmol), prepared as described in Intermediate 9, in AcOH (0.75 ml) and 48% aq HBr (0.42 ml, 3.75 mmol) was warmed to 65° C. After 1.5 h, the reaction was concentrated. MeOH was added and the reaction mixture concentrated. This was repeated (2×) to give an 86:14 mixture 6-{5-chloro-2-[4-(trimethylsilyl)-1H-1,2,3-triazol-1-yl]phenyl}pyrimidin-4-ol, hydrobromide and 6-[5-chloro-2-(1H-1,2,3-triazol-1-yl)phenyl]pyrimidin-4-ol, hydrobromide (0.0294 g, 92% yield) as an off-white solid. MS(ESI) m/z: 346.0 (M+H)$^+$.

131B. Preparation of (9R,13S)-13-(4-{5-chloro-2-[4-(trimethylsilyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one Trifluoroacetate (9R,13S)-13-(4-{5-Chloro-2-[4-(trimethylsilyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate (0.0087 g, 16% yield) was prepared in a similar manner as the procedure described in Example 128, by using 6-{5-chloro-2-[4-(trimethylsilyl)-1H-1,2,3-triazol-1-yl]phenyl}pyrimidin-4-ol hydrobromide and (9R,13S)-13-amino-3,9-dimethyl-3,4,7,15-tetraazatricyclo[12.3.1.0$^{2,6}$]octadeca-1(18),2(6),4,14,16-pentaen-8-one, prepared as described in Intermediate 32. MS(ESI) m/z: 628.4 (M+H)$^+$ and 630.5 (M+2+H)$^+$. $^1$H NMR (400 MHz, CD$_3$OD) δ 8.84 (s, 1H), 8.71 (d, J=5.1 Hz, 1H), 8.17 (s, 1H), 7.88 (d, J=2.4 Hz, 1H), 7.72 (dd, J=8.6, 2.4 Hz, 1H), 7.66 (s, 1H), 7.63 (d, J=8.4 Hz, 1H), 7.51 (dd, J=5.2, 1.4 Hz, 1H), 7.48 (s, 1H), 6.13 (s, 1H), 5.98 (dd, J=12.7, 4.3 Hz, 1H), 4.04 (s, 3H), 2.74-2.66 (m, 1H), 2.32-2.21 (m, 1H), 2.12-1.90 (m, 2H), 1.66-1.53 (m, 1H), 1.53-1.39 (m, 1H), 0.99 (d, J=7.0 Hz, 3H), 0.73-0.58 (m, 1H), 0.29 (m, 9H). $^{19}$F NMR (376 MHz, CD$_3$OD) δ −77.51 (br. s., 1F). Analytical HPLC (Method X): RT=6.62 min, purity=93.5%; Factor XIa Ki=29 nM, Plasma Kallikrein Ki=760 nM.

Example 132

Preparation of (9R,13S)-13-[4-(3-chloro-2,6-difluorophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one trifluoroacetate

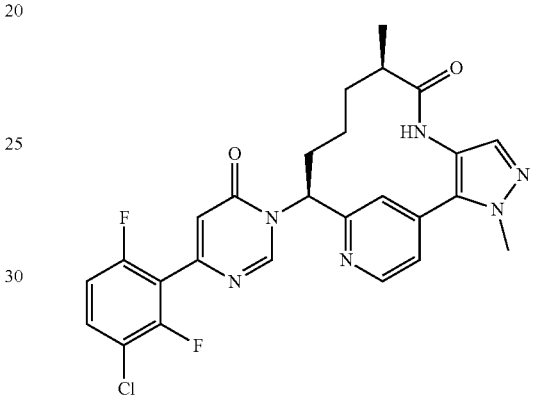

To a 1-dram vial containing a white suspension of 6-(3-chloro-2,6-difluorophenyl) pyrimidin-4-ol (0.013 g, 0.054 mmol), prepared as described in Intermediate 4, and HATU (0.027 g, 0.070 mmol) in ACN (0.54 ml) was added DBU (0.012 ml, 0.081 mmol). The resulting bright yellow solution was stirred at rt for 20 min. Over time this solution became a dull yellow-orange color. Then a clear, brown solution of (9R,13S)-13-amino-3,9-dimethyl-3,4,7,15-tetraazatricyclo[12.3.1.0$^{2,6}$]octadeca-1(18),2(6),4,14,16-pentaen-8-one, 2 HCl (0.020 g, 0.054 mmol), prepared as described in Intermediate 32, and DBU (0.016 ml, 0.107 mmol) in DMF (0.54 ml) was added. After 2.5 h, the reaction was stopped. Purification by reverse phase chromatography gave (9R,13S)-13-[4-(3-chloro-2,6-difluorophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one trifluoroacetate (0.0152 g, 43% yield) as an off-white solid. MS(ESI) m/z: 525.1 (M+H)$^+$. $^1$H NMR (500 MHz, CD$_3$OD) δ 9.04 (s, 1H), 8.75 (d, J=5.0 Hz, 1H), 7.73 (s, 1H), 7.63 (ddd, J=9.1, 8.3, 5.5 Hz, 1H), 7.55-7.51 (m, 1H), 7.50 (s, 1H), 7.14 (td, J=9.1, 1.7 Hz, 1H), 6.66 (d, J=0.6 Hz, 1H), 6.10-6.02 (m, 1H), 4.05 (s, 3H), 2.76-2.68 (m, 1H), 2.37 (tt, J=12.8, 4.5 Hz, 1H), 2.15-2.04 (m, 2H), 1.68-1.58 (m, 1H), 1.56-1.45 (m, 1H), 1.02 (d, J=6.9 Hz, 3H), 0.80-0.65 (m, 1H). $^{19}$F NMR (471 MHz, CD$_3$OD) δ −77.53 (s), −114.79 (d, J=4.3 Hz), −115.50 (d, J=4.3 Hz). Analytical HPLC (Method A): RT=7.37 min, purity=99.7%; Factor XIa Ki=33 nM, Plasma Kallikrein Ki=290 nM.

Example 133

Preparation of (9R,13S)-13-{4-[5-chloro-2-(1H-1,2,3-triazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one Trifluoroacetate

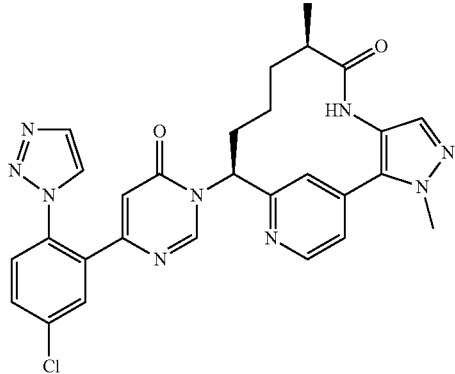 [SMILES: C[C@@H]1CCC[C@H](n2cnc(-c3cc(Cl)ccc3-n3ccnn3)cc2=O)c2cc(ccn2)-c2c(cnn2C)NC1=O]

(9R,13S)-13-{4-[5-Chloro-2-(1H-1,2,3-triazol-1-yl)phenyl]-6-oxo-1,6-dihydropyrimidin-1-yl)}-3,9-dimethyl-3,4,7,15-tetraazatricyclo[12.3.1.0$^{2,6}$]octadeca-1(18),2(6),4,14,16-pentaen-8-one trifluoroacetate (14 mg, 38% yield) was prepared in a similar manner as the procedure described in Example 132, by replacing 6-(3-chloro-2,6-difluorophenyl)pyrimidin-4-ol with 6-[5-chloro-2-(1H-1,2,3-triazol-1-yl)phenyl]pyrimidin-4-ol (0.015 g, 0.054 mmol), prepared as described in Intermediate 8. MS(ESI) m/z: 558.4 (M+H)$^+$. $^1$H NMR (500 MHz, CD$_3$OD) δ 8.83 (s, 1H), 8.71 (d, J=5.0 Hz, 1H), 8.21 (s, 1H), 7.89 (d, J=2.2 Hz, 1H), 7.84 (br. s., 1H), 7.72 (dd, J=8.4, 2.3 Hz, 1H), 7.67 (s, 1H), 7.62 (d, J=8.5 Hz, 1H), 7.51 (dd, J=5.1, 1.5 Hz, 1H), 7.48 (s, 1H), 6.18 (s, 1H), 6.00-5.93 (m, 1H), 4.04 (s, 3H), 2.73-2.66 (m, 1H), 2.31-2.23 (m, 1H), 2.11-1.91 (m, 2H), 1.64-1.54 (m, 1H), 1.51-1.40 (m, 1H), 1.00 (d, J=6.9 Hz, 3H), 0.72-0.59 (m, 1H). $^{19}$F NMR (471 MHz, CD$_3$OD) δ −77.37 (s). Analytical HPLC (Method A): RT=6.22 min, purity=99.2%; Factor XIa Ki=1.8 nM, Plasma Kallikrein Ki=110 nM.

Example 134

Preparation of (13S)-13-{4-[5-chloro-2-(4-chloro-1H-1,2,3-triazol-1-yl)phenyl]-6-oxo-1,6-dihydropyrimidin-1-yl}-3-(difluoromethyl)-3,4,7,15-tetraazatricyclo[12.3.1.0$^{2,6}$]octadeca-1(18),2(6),4,14,16-pentaen-8-one Trifluoroacetate

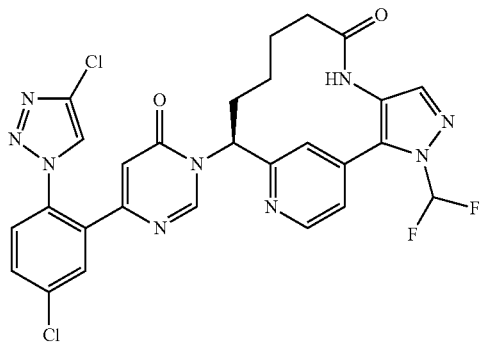 [SMILES: O=C1CCCC[C@H](n2cnc(-c3cc(Cl)ccc3-n3cc(Cl)nn3)cc2=O)c2cc(ccn2)-c2c(cnn2C(F)F)N1]

134A. Preparation of Tert-Butyl N-[(1S)-1-{4-[4-(but-3-enamido)-1-(difluoromethyl)-1H-pyrazol-5-yl]pyridin-2-yl}but-3-en-1-yl]carbamate To a cooled (−5° C.) yellow solution of tert-butyl N-[(1S)-1-{4-[4-amino-1-(difluoromethyl)-1H-pyrazol-5-yl]pyridin-2-yl}but-3-en-1-yl]carbamate (0.608 g, 1.60 mmol), prepared as described in Intermediate 30C, in EtOAc (10.1 ml) was added but-3-enoic acid (0.14 ml, 1.60 mmol) and pyridine (0.26 ml, 3.21 mmol). Next, T3P® (50% in EtOAc, 1.43 ml, 2.40 mmol) was added dropwise. The resulting orange solution was allowed to warm to rt. After 2 h, the reaction was diluted with EtOAc and washed with sat NaHCO$_3$, brine, dried over Na$_2$SO$_4$, filtered and concentrated to give a yellow foam weighing 0.702 g. Purification by normal phase chromatography gave tert-butyl N-[(1S)-1-{4-[4-(but-3-enamido)-1-(difluoromethyl)-1H-pyrazol-5-yl]pyridin-2-yl}but-3-en-1-yl]carbamate (0.374 g, 52% yield) as a white foam. MS(ESI) m/z: 448.2 (M+H)$^+$. $^1$H NMR (500 MHz, CD$_3$OD) δ 8.65 (d, J=4.7 Hz, 1H), 8.04 (s, 1H), 7.44 (s, 1H), 7.40 (t, J=58.0 Hz, 1H), 7.36 (d, J=4.4 Hz, 1H), 5.92 (ddt, J=17.1, 10.2, 7.0 Hz, 1H), 5.80 (ddt, J=17.2, 10.2, 6.9 Hz, 1H), 5.19-5.13 (m, 2H), 5.12-5.03 (m, 2H), 4.81-4.75 (m, 1H), 3.08 (d, J=6.9 Hz, 2H), 2.67-2.59 (m, 1H), 2.54-2.46 (m, 1H), 1.42 (s, 9H). $^{19}$F NMR (471 MHz, CD$_3$OD) δ −93.82 (br. s).

134B. Preparation of Tert-Butyl N-[(10E,13S)-3-(difluoromethyl)-8-oxo-3,4,7,15-tetraazatricyclo[12.3.1.0$^{2,6}$]octadeca-1(18),2(6),4,10,14,16-hexaen-13-yl]carbamate A solution of tert-butyl N-[(1S)-1-{4-[4-(but-3-enamido)-1-(difluoromethyl)-1H-pyrazol-5-yl]pyridin-2-yl}but-3-en-1-yl]carbamate (0.374 g, 0.836 mmol) in DCE (20.89 ml) was purged with Ar (3×). To the reaction mixture was added Second Generation Grubbs Catalyst (0.284 g, 0.334 mmol). The microwave vial was sealed and the reaction was heated in a microwave at 115° C. for 1 h. The reaction was cooled to rt and concentrated. The residue was purified by normal phase chromatography to give tert-butyl N-[(10E,13S)-3-(difluoromethyl)-8-oxo-3,4,7,15-tetraazatricyclo[12.3.1.0$^{2,6}$]octadeca-1(18),2(6),4,10,14,16-hexaen-13-yl]carbamate (0.106 g, 30% yield) as a brown residue. MS(ESI) m/z: 420.1 (M+H)$^+$.

134C. Preparation of Tert-Butyl N-[(13S)-3-(difluoromethyl)-8-oxo-3,4,7,15-tetraazatricyclo[12.3.1.0$^{2,6}$]octadeca-1(18),2(6),4,14,16-pentaen-13-yl]carbamate A clear, orange-brown solution of tert-butyl N-[(10E,13S)-3-(difluoromethyl)-8-oxo-3,4,7,15-tetraazatricyclo[12.3.1.0$^{2,6}$]octadeca-1(18),2(6),4,10,14,16-hexaen-13-yl]carbamate (0.105 g, 0.250 mmol) in EtOH (5.0 ml) was purged with Ar for several min. Next, 10% Pd/C (0.027 g, 0.025 mmol) was added and the suspension was pressurized with H$_2$ gas to 55 psi. After 17 h, CELITE® was added. The reaction was filtered through a nylon filter, eluting with EtOH to give a clear, orange solution. The filtrate was concentrated to give a clear, orange residue. Purification by reverse phase chromatography gave, after neutralization of the fractions with sat NaHCO$_3$ and concentration, a white solid. The solid was partitioned between EtOAc and water, and the layers were separated. The aqueous layer was extracted with EtOAc. The organic layers were combined and washed with brine, dried over Na$_2$SO$_4$, filtered and concentrated to give tert-butyl N-[(13S)-3-(difluoromethyl)-8-oxo-3,4,7,15-tetraazatricyclo[12.3.1.0$^{2,6}$]octadeca-1(18),2(6),4,14,16-pentaen-13-yl]carbamate (0.0518 g, 49% yield) as a white solid. MS(ESI) m/z: 422.1 (M+H)$^+$.

134D. Preparation of (13S)-13-amino-3-(difluoromethyl)-3,4,7,15-tetraazatricyclo[12.3.1.0$^{2,6}$]octadeca-1(18),2(6),4,14,16-pentaen-8-one, Bis-Hydrochloride A clear, colorless solution of tert-butyl N-[(13S)-3-(difluoromethyl)-8-oxo-3,4,7,15-tetraazatricyclo[12.3.1.0$^{2,6}$]octadeca-1(18),2(6),4,14,16-pentaen-13-yl]carbamate (0.0518 g, 0.123 mmol) in 4 M HCl in dioxane (1.54 ml, 6.15 mmol) was stirred at rt. After 5 min, a white precipitate formed. After 1 h, the reaction was concentrated to give (13S)-13-amino-3-(difluoromethyl)-3,4,7,15-tetraazatricyclo[12.3.1.0$^{2,6}$]octadeca-1(18),2(6),4,14,16-pentaen-8-one, bis-hydrochloride (0.0503 g, 104% yield) as an off-white solid. MS(ESI) m/z: 322.1 (M+H)$^+$. $^1$H NMR (500 MHz, CD$_3$OD) δ 8.82 (d, J=5.2 Hz, 1H), 7.72 (s, 1H), 7.59 (dd, J=60.0, 57.2 Hz, 1H), 7.58 (d, J=5.2 Hz, 1H), 7.54 (s, 1H), 4.61 (dd, J=11.1, 5.1 Hz, 1H), 2.45 (ddd, J=12.6, 7.4, 2.3 Hz, 1H), 2.22-2.13 (m, 1H), 2.06-1.99 (m, 1H), 1.87-1.71 (m, 2H), 1.67-1.57 (m, 1H), 1.52-1.42 (m, 1H), 0.84-0.73 (m, 1H). $^{19}$F NMR (471 MHz, CD$_3$OD) δ −89.17 (d, J=228.9 Hz, 1F), −98.00 (d, J=227.5 Hz, 1F).

134E. Preparation of (13S)-13-{4-[5-chloro-2-(4-chloro-1H-1,2,3-triazol-1-yl)phenyl]-6-oxo-1,6-dihydropyrimidin-1-yl}-3-(difluoromethyl)-3,4,7,15-tetraazatricyclo[12.3.1.0$^{2,6}$]octadeca-1(18),2(6),4,14,16-pentaen-8-one Trifluoroacetate To a 1-dram vial containing a yellow suspension of 6-(5-chloro-2-(4-chloro-1H-1,2,3-triazol-1-yl)phenyl)pyrimidin-4-ol (0.016 g, 0.051 mmol), prepared as described in Intermediate 9, and HATU (0.025 g, 0.066 mmol) in ACN (0.51 ml) was added DBU (0.011 ml, 0.076 mmol). The resulting yellow-orange solution was stirred at rt for 20 min. Over time the solution became a dull yellow-orange color. Then a clear, yellow solution of (13S)-13-amino-3-(difluoromethyl)-3,4,7,15-tetraazatricyclo[12.3.1.0$^{2,6}$]octadeca-1(18),2(6),4,14,16-pentaen-8-one, bis-hydrochloride (0.020 g, 0.051 mmol) and DBU (0.015 ml, 0.101 mmol) in DMF (0.51 ml) were added. The reaction was stirred at rt. After 3 h, the reaction was quenched with sat NH$_4$Cl. The mixture was partitioned between EtOAc and water and the layers were separated. The aqueous layer was extracted with EtOAc (2×). The organic layers were combined and washed with sat NaHCO$_3$, brine, dried over Na$_2$SO$_4$, filtered and concentrated to give a clear, yellow residue weighing 0.040 g. Purification by reverse phase chromatography gave (13S)-13-{4-[5-chloro-2-(4-chloro-1H-1,2,3-triazol-1-yl)phenyl]-6-oxo-1,6-dihydropyrimidin-1-yl}-3-(difluoromethyl)-3,4,7,15-tetraazatricyclo[12.3.1.0$^{2,6}$]octadeca-1(18),2(6),4,14,16-pentaen-8-one trifluoroacetate (0.0175 g, 47% yield) as a white solid. MS(ESI) m/z: 612.2 (M+H)$^+$ and 614.1 (M+2+H)$^+$. $^1$H NMR (500 MHz, DMSO-d$_6$, 60° C.) δ 9.28 (s, 1H), 8.78 (d, J=0.5 Hz, 1H), 8.72 (d, J=5.0 Hz, 1H), 8.64 (s, 1H), 7.91 (d, J=2.2 Hz, 1H), 7.89 (t, J=57.8 Hz, 1H), 7.86 (s, 1H), 7.81-7.78 (m, 1H), 7.72 (d, J=8.5 Hz, 1H), 7.64 (d, J=0.6 Hz, 1H), 7.42 (dd, J=5.1, 1.2 Hz, 1H), 6.32 (d, J=0.8 Hz, 1H), 5.93 (dd, J=12.7, 4.4 Hz, 1H), 2.41-2.36 (m, 1H), 2.29-2.20 (m, 1H), 2.00-1.87 (m, 3H), 1.64-1.53 (m, 1H), 1.44-1.33 (m, 1H), 0.76-0.66 (m, 1H). $^{19}$F NMR (471 MHz, DMSO-d$_6$) δ −73.75 (br. s), −90.34 (d, J=227.4 Hz), −95.01 (d, J=228.9 Hz). Analytical HPLC (Method A): RT=7.78 min, purity=99.8%.

Example 135

Preparation of (9S,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one

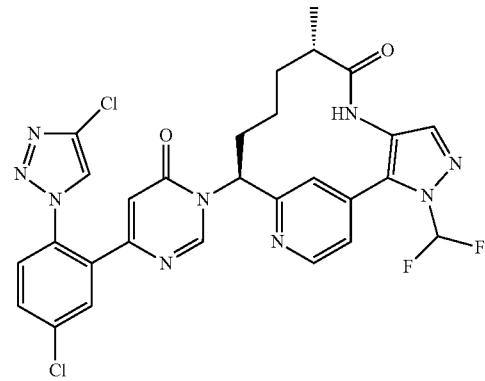 [SMILES: C[C@H]1CCC[C@H](n2cnc(-c3cc(Cl)ccc3-n3cc(Cl)nn3)cc2=O)c2cc(ccn2)-c2c(cnn2C(F)F)NC1=O]

135A. Preparation of Tert-Butyl ((1S)-1-(4-(1-(difluoromethyl)-4-(2-methylbut-3-enamido)-1H-pyrazol-5-yl)pyridin-2-yl)but-3-en-1-yl)carbamate To a N$_2$ flushed, 3-necked, 250 mL RBF was added a solution of (S)-tert-butyl (1-(4-(4-amino-1-(difluoromethyl)-1H-pyrazol-5-yl)pyridin-2-yl)but-3-en-1-yl)carbamate (1.8 g, 4.74 mmol), prepared as described in Intermediate 30C, and EtOAc (20 mL). The solution was cooled to −10° C. and (±)-2-methylbut-3-enoic acid (0.475 g, 4.74 mmol), pyridine (0.767 mL, 9.49 mmol), and T3P® (4.24 mL, 7.12 mmol) were added. The cooling bath was removed and the solution was allowed to warm to rt and then stir over a period of 20 h. Water (15 mL) and EtOAc (15 mL) were added and the mixture was stirred for 30 min. The organic phase was separated and the aqueous layer was extracted with EtOAc (30 mL). The combined organic extracts were washed with brine (50 mL), dried over Na$_2$SO$_4$, filtered and concentrated. Purification by normal phase chromatography eluting with a gradient of hexanes/EtOAc gave racemic tert-butyl ((1S)-1-(4-(1-(difluoromethyl)-4-(2-methylbut-3-enamido)-1H-pyrazol-5-yl)pyridin-2-yl)but-3-en-1-yl)carbamate (1.7 g, 3.50 mmol, 74% yield). MS(ESI) m/z: 462.4 [M+H]$^+$.

135B1. Preparation of Tert-Butyl N-[(9R,10E,13S)-3-(difluoromethyl)-9-methyl-8-oxo-3,4,7,15-tetraazatricyclo[12.3.1.0$^2$, $^6$]octadeca-1(18),2(6),4,10,14,16-hexaen-13-yl]carbamate, and 135B2. tert-Butyl N-[(9S,10E,13S)-3-(difluoromethyl)-9-methyl-8-oxo-3,4,7,15-tetraazatricyclo[12.3.1.0$^{2,6}$]octadeca-1(18),2(6),4,10,14,16-hexaen-13-yl]carbamate To a N$_2$ flushed, 500 mL, 3-necked, RBF was added a solution of tert-butyl ((1S)-1-(4-(1-(difluoromethyl)-4-(2-methylbut-3-enamido)-1H-pyrazol-5-yl)pyridin-2-yl)but-3- en-1-yl)carbamate (1.7 g, 3.68 mmol) in EtOAc (175 mL). The solution was sparged with Ar for 15 min. Second Generation Grubbs Catalyst (0.782 g, 0.921 mmol) was added in one portion. The reaction mixture was heated to reflux for 24 h. After cooling to rt, the solvent was removed and the residue was purified by normal phase chromatography eluting with a gradient of DCM/MeOH to yield (separated the diastereomers) tert-butyl N-[(9R,10E,13S)-3-(difluoromethyl)-9-methyl-8-oxo-3,4,7,15-tetraazatricyclo[12.3.1.0$^{2,6}$]octadeca-1(18),2(6),4,10,14,16-hexaen-13-yl]carbamate (0.33 g, 0.75 mmol, 20% yield) and tert-butyl N-[(9S,10E,13S)-3-(difluoromethyl)-9-methyl-8-oxo-3,4,7,15-tetraazatricyclo[12.3.1.0$^{2,6}$]octadeca-1(18),2(6),4,10,14,16-hexaen-13-yl]carbamate (0.34 g, 0.77 mmol, 21% yield) as a tan solid. Both diastereomers: MS(ESI) m/z: 434.3 [M+H]$^+$.

135C. Preparation of Tert-Butyl N-[(9S,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]carbamate Pd/C (0.082 g, 0.078 mmol) was added to a 100 mL Parr hydrogenation flask containing a solution of tert-butyl N-[(9S,10E,13S)-3-(difluoromethyl)-9-methyl-8-oxo-3,4,7,15-tetraazatricyclo[12.3.1.0$^{2,6}$]octadeca-1(18),2(6),4,10,14,16-hexaen-13-yl]carbamate (0.33 g, 0.775 mmol) in EtOH (15 mL). The flask was purged with N$_2$ and pressurized to 55 psi of H$_2$ and allowed to stir for 5 h. The reaction was filtered through CELITE® and concentrated to yield tert-butyl N-[(9S,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]carbamate (0.3 g, 0.654 mmol, 84% yield) as a tan solid. MS(ESI) m/z: 436.3 [M+H]$^+$.

135D. Preparation of (9S,13S)-13-amino-3-(difluoromethyl)-9-methyl-3,4,7,15-tetraazatricyclo[12.3.1.0$^{2,6}$]octadeca-1(18),2(6),4,14,16-pentaen-8-one 4 N HCl in dioxane (5.00 mL, 20.0 mmol) was added to a solution of tert-butyl N-[(9S,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]carbamate (0.300 g, 0.689 mmol) in MeOH (5 mL). The reaction was allowed to stir at rt for 1 h. The reaction was concentrated to yield (9S,13S)-13-amino-3-(difluoromethyl)-9-methyl-3,4,7,15-tetraazatricyclo[12.3.1.0$^{2,6}$]octadeca-1(18),2(6),4,14,16-pentaen-8-one bis-hydrochloride (0.24 g, 0.644 mmol, 93% yield) as a brown solid which was then dissolved in MeOH (1 mL) to give a clear, brown solution. The solution was added to a pre-rinsed AGILENT® StratoSpheres SPE PL-HCO$_3$ MP Resin cartridge. Gravity filtration, eluting with MeOH, gave a clear, slightly yellow filtrate. Concentration provided (9S,13)-13-amino-3-(difluoromethyl)-9-methyl-3,4,7,15-tetraazatricyclo[12.3.1.0$^{2,6}$]octadeca-1(18),2(6),4,14,16-pentaen-8-one (0.18 g, 94%) as a pale yellow solid. MS(ESI) m/z: 336.3 [M+H]$^+$.

135E. Preparation of (9S,13S)-13-{4-[5-chloro-2-(4-chloro-1H-1,2,3-triazol-1-yl) phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one Trifluoroacetate (9S,13S)-13-{4-[5-Chloro-2-(4-chloro-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one trifluoroacetate was prepared in a similar manner as the procedures described in Example 56, by using 6-(5-chloro-2-(4-chloro-1H-1,2,3-triazol-1-yl)phenyl)pyrimidin-4-ol (0.221 g, 0.716 mmol), prepared as described in Intermediate 9, and (9S,13S)-13-amino-3-(difluoromethyl)-9-methyl-3,4,7,15-tetraazatricyclo[12.3.1.0$^{2,6}$]octadeca-1(18),2(6),4,14,16-pentaen-8-one (0.021 g, 0.062 mmol) to yield (9S,13S)-13-{4-[5-chloro-2-(4-chloro-1H-1,2,3-triazol-1-yl) phenyl]-6-oxo-1,6-dihydropyrimidin-1-yl}-3-(difluoromethyl)-9-methyl-3,4,7,15-tetraazatricyclo[12.3.1.0$^{2,6}$]Octadeca-1(18),2(6),4,14,16-pentaen-8-one trifluoroacetate (0.16 g, 0.205 mmol, 29% yield). $^1$H NMR (400 MHz, CD$_3$OD) δ 8.85 (s, 1H), 8.75 (d, J=5.1 Hz, 1H), 8.37 (s, 1H), 7.93 (d, J=2.2 Hz, 1H), 7.85-7.75 (m, 3H), 7.72-7.67 (m, 1H), 7.62 (s, 1H), 7.57-7.48 (m, 1H), 6.43 (s, 1H), 6.08 (dd, J=12.9, 4.3 Hz, 1H), 2.41-2.30 (m, 1H), 2.29-2.17 (m, 1H), 2.09-1.90 (m, 2H), 1.68-1.52 (m, 2H), 1.28 (d, J=6.8 Hz, 3H), 0.93-0.81 (m, 1H). MS(ESI) m/z: 626.3 [M+H]$^+$. Analytical HPLC (Method A): RT=9.03 min, purity=>95.0%; Factor XIa Ki=1.7 nM, Plasma Kallikrein Ki=35 nM.

Example 136

Preparation of (9R,13S)-13-{4-[5-chloro-2-(4-methyl-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one Trifluoroacetate

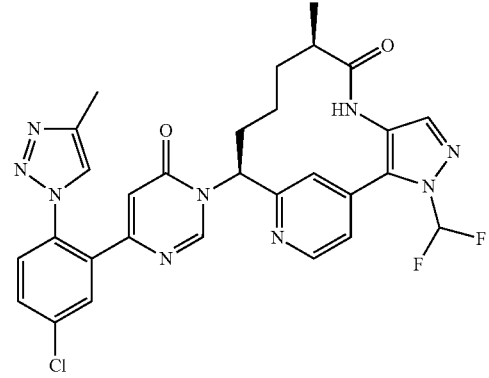 [SMILES: Cc1cn(-c2ccc(Cl)cc2-c2cc(=O)n([C@H]3CCC[C@@H](C)C(=O)Nc4cnn(C(F)F)c4-c4ccnc3c4)cn2)nn1]

136A. Preparation of 4-[5-chloro-2-(4-methyl-1H-1,2,3-triazol-1-yl)phenyl]-6-methoxypyrimidine Trifluoroacetate To a cooled (0° C.), clear, yellow solution of 4-chloro-2-(6-methoxypyrimidin-4-yl)aniline (0.095 g, 0.403 mmol), prepared as described in Intermediate 8A, in EtOH (5.0 ml) was added Hunig's base (0.42 ml, 2.42 mmol). After 10 min, a suspension of N'-[(2E)-1,1-dichloropropan-2-ylidene]-4-methylbenzene-1-sulfonohydrazide (0.242 g, 0.52 mmol) in ACN (3.3 ml) was added dropwise. The resulting orange solution was allowed to warm to rt. After 23 h, the reaction was stopped and concentrated to give a dark brown oil. Purification by reverse phase chromatography gave, after concentration, 4-[5-chloro-2-(4-methyl-1H-1,2,3-triazol-1-yl)phenyl]-6-methoxypyrimidine trifluoroacetate (0.0499 g, 30% yield) as a clear, yellow oil. MS(ESI) m/z: 302.1 (M+H)+. 1H NMR (500 MHz, CD3OD) δ 8.64 (d, J=1.1 Hz, 1H), 7.88 (d, J=0.8 Hz, 1H), 7.85 (d, J=2.2 Hz, 1H), 7.73 (dd, J=8.5, 2.2 Hz, 1H), 7.62 (d, J=8.5 Hz, 1H), 6.59 (d, J=1.1 Hz, 1H), 3.97 (s, 3H), 2.33 (d, J=0.8 Hz, 3H).

136B. Preparation of 6-[5-chloro-2-(4-methyl-1H-1,2,3-triazol-1-yl)phenyl]pyrimidin-4-ol A clear, yellow solution of 4-(5-chloro-2-(4-methyl-1H-1,2,3-triazol-1-yl)phenyl)-6-methoxypyrimidine, TFA (0.0499 g, 0.12 mmol) in AcOH (1.20 ml) and 48% aq HBr (0.68 ml, 6.00 mmol) was warmed to 85° C. After 1 h, the reaction was cooled to rt and then was concentrated to give a yellow solid. The yellow solid was suspended in EtOAc and sat NaHCO3 was added. The layers were separated and the aqueous layer was extracted with EtOAc (2×). The organic layers were combined and washed with brine, dried over Na2SO4, filtered and concentrated to give an off-white solid weighing 0.032 g. The solid was suspended in EtOAc (1 mL) and sonicated. The solid was collected by filtration, rinsed with EtOAc, air-dried, and dried under vacuum to give 6-[5-chloro-2-(4-methyl-1H-1,2,3-triazol-1-yl)phenyl]pyrimidin-4-ol (0.0144 g, 40% yield) as an off-white solid. MS(ESI) m/z: 288.1 (M+H)+. 1H NMR (500 MHz, CD3OD) δ 8.07 (s, 1H), 7.92 (s, 1H), 7.84 (d, J=2.2 Hz, 1H), 7.71 (dd, J=8.5, 2.5 Hz, 1H), 7.60 (d, J=8.5 Hz, 1H), 6.22 (s, 1H), 2.36 (s, 3H).

136C. Preparation of (9R,13S)-13-{4-[5-chloro-2-(4-methyl-1H-1,2,3-triazol-1-yl) phenyl]-6-oxo-1,6-dihydropyrimidin-1-yl}-3-(difluoromethyl)-9-methyl-3,4,7,15-tetraazatricyclo[12.3.1.0$^{2,6}$] Octadeca-1(18),2(6),4,14,16-pentaen-8-one Trifluoroacetate (9R,13S)-13-{4-[5-Chloro-2-(4-methyl-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0$^{2,6}$] octadeca-1(18),2(6),4,14,16-pentaen-8-one trifluoroacetate (0.0070 g, 32% yield) was prepared in a similar manner as the procedure described in Example 56, by using 6-[5-chloro-2-(4-methyl-1H-1,2,3-triazol-1-yl)phenyl]pyrimidin-4-ol and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one, prepared in Intermediate 30. MS(ESI) m/z: 606.3 (M+H)+ and 608.2 (M+2+H)+. 1H NMR (500 MHz, CD3OD) δ 8.91 (s, 1H), 8.73 (d, J=5.2 Hz, 1H), 7.91 (d, J=0.8 Hz, 1H), 7.88 (d, J=2.5 Hz, 1H), 7.73 (s, 1H), 7.70 (dd, J=8.5, 2.5 Hz, 1H), 7.68-7.67 (m, 1H), 7.65 (t, J=60.0 Hz, 1H), 7.59 (d, J=8.5 Hz, 1H), 7.53-7.51 (m, 1H), 6.18 (d, J=0.8 Hz, 1H), 6.02-5.97 (m, 1H), 2.74-2.66 (m, 1H), 2.35-2.24 (m, 4H), 2.08-1.94 (m, 2H), 1.63-1.53 (m, 1H), 1.53-1.42 (m, 1H), 0.99 (d, J=6.9 Hz, 3H), 0.67-0.52 (m, 1H). 19F NMR (471 MHz, CD3OD) δ −74.24 (s), −75.74 (s), −77.66 (s). Analytical HPLC (Method A): RT=7.55 min, purity=99.8%; Factor XIa Ki=2.2 nM, Plasma Kallikrein Ki=630 nM.

Example 137

Preparation of (9R,13S)-3-(difluoromethyl)-9-methyl-13-(4-{5-methyl-2-[4-(trifluoromethyl)-1H-1,2,3-triazol-1-yl]phenyl}-6-oxo-1,6-dihydropyrimidin-1-yl)-3,4,7,15-tetraazatricyclo[12.3.1.0$^{2,6}$] octadeca-1(18),2(6),4,14,16-pentaen-8-one

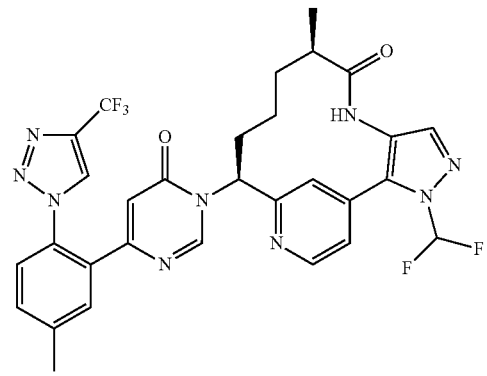 [SMILES: Cc1ccc(-n2cc(C(F)(F)F)nn2)c(-c2cc(=O)n([C@H]3CCC[C@@H](C)C(=O)Nc4cnn(C(F)F)c4-c4ccnc3c4)cn2)c1]

(9R,13S)-3-(Difluoromethyl)-9-methyl-13-(4-{5-methyl-2-[4-(trifluoromethyl)-1H-1,2,3-triazol-1-yl]phenyl}-6-oxo-1,6-dihydropyrimidin-1-yl)-3,4,7,15-tetraazatricyclo [12.3.1.0$^{2,6}$]octadeca-1(18),2(6),4,14,16-pentaen-8-one trifluoroacetate (11 mg, 24%) was prepared in a similar manner as Example 56 using 6-(5-methyl-2-(4-(trifluoromethyl)-1H-1,2,3-triazol-1-yl)phenyl)pyrimidin-4-ol, prepared as described in Example 119D and (9R,13S)-13-amino-3-(difluoromethyl)-9-methyl-9-ethyl-3,4,7,15-tetraazatricyclo[12.3.1.0$^{2,6}$]octadeca-1(18),2(6),4,14,16-pentaen-8-one, prepared as described in Intermediate 30. MS(ESI) m/z: 640.2 (M+H)+. 1H NMR (400 MHz, CD3OD) δ 8.85-8.74 (m, 3H), 7.84-7.67 (m, 4H), 7.59-7.53 (m, 3H), 6.47 (s, 1H), 6.05 (dd, J=12.8, 4.4 Hz, 1H), 2.75 (dd, J=6.7, 3.0 Hz, 1H), 2.56 (s, 3H), 2.35-2.27 (m, 1H), 2.10-1.99 (m, 2H), 1.64-1.50 (m, 2H), 1.03 (d, J=6.8 Hz, 3H), 0.65 (br. s., 1H)Analytical HPLC (Method A): RT=8.85 min, purity=99%; Factor XIa Ki=0.32 nM, Plasma Kallikrein Ki=132 nM.

Example 138

Preparation of (9R,13S)-13-[4-(2-bromo-5-chlorophenyl)-6-oxo-1,6-dihydropyrimidin-1-yl]-3,9-dimethyl-3,4,7,15-tetraazatricyclo[12.3.1.0$^{2,6}$]octadeca-1 (18),2(6),4,14,16-pentaen-8-one

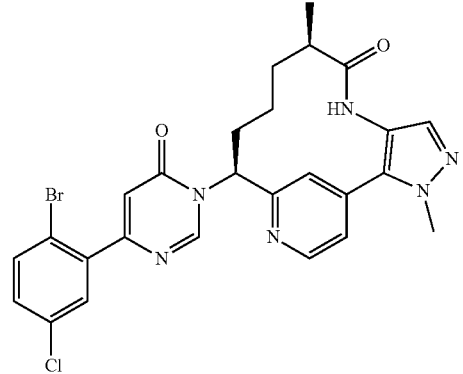 [SMILES: C[C@@H]1CCC[C@H](n2cnc(-c3cc(Cl)ccc3Br)cc2=O)c2cc(ccn2)-c2c(cnn2C)NC1=O]

(9R,13S)-13-[4-(2-Bromo-5-chlorophenyl)-6-oxo-1,6-dihydropyrimidin-1-yl]-3,9-dimethyl-3,4,7,15-tetraazatricyclo[12.3.1.0²,⁶]octadeca-1(18),2(6),4,14,16-pentaen-8-one trifluoroacetate (160 mg, 46.8% yield) was prepared in a similar manner as the procedure described in Example 56, by replacing 6-{5-chloro-2-[4-(trifluoromethyl)-1H-1,2,3-triazol-1-yl]phenyl}pyrimidin-4-ol (22.8 mg, 0.067 mmol), prepared as described in Intermediate 15, with 6-(2-bromo-5-chlorophenyl)pyrimidin-4-ol (143 mg, 0.501 mmol), prepared as described in Intermediate 44. MS(ESI) m/z: 567.1 (M+H)⁺. ¹H NMR (400 MHz, CD₃OD) δ 9.04 (s, 1H), 8.75 (d, J=5.3 Hz, 1H), 7.76 (s, 1H), 7.70 (d, J=8.6 Hz, 1H), 7.61-7.54 (m, 2H), 7.50 (s, 1H), 7.38 (dd, J=8.6, 2.4 Hz, 1H), 6.70 (s, 1H), 6.05 (dd, J=12.5, 4.0 Hz, 1H), 4.05 (s, 3H), 2.78-2.66 (m, 1H), 2.44-2.33 (m, 1H), 2.16-2.03 (m, 2H), 1.70-1.43 (m, 2H), 1.02 (d, J=6.8 Hz, 3H), 0.82-0.66 (m, 1H). Analytical HPLC (Method A): RT=8.45 min, 99.9% purity; Factor XIa Ki=23 nM, Plasma Kallikrein Ki=420 nM.

Example 139

Preparation of (9R,13S)-13-{4-[3-chloro-2-fluoro-6-(4-methyl-1H-1,2,3-triazol-1-yl) phenyl]-6-oxo-1,6-dihydropyrimidin-1-yl}-3-(difluoromethyl)-9-methyl-3,4,7,15-tetraazatricyclo[12.3.1.0²,⁶] octadeca-1(18),2(6),4,14,16-pentaen-8-one

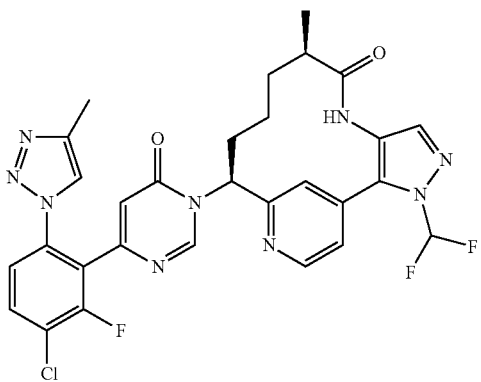 [SMILES: Cc1cn(-c2ccc(Cl)c(F)c2-c2cc(=O)n([C@H]3CCC[C@@H](C)C(=O)Nc4cnn(C(F)F)c4-c4ccnc3c4)cn2)nn1]

(9R,13S)-13-{4-[3-Chloro-2-fluoro-6-(4-methyl-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0²,⁶]octadeca-1(18),2(6),4,14,16-pentaen-8-one (0.0174 g, 62% yield) was prepared in a similar manner as the procedure described in Example 56, by using 6-[3-chloro-2-fluoro-6-(4-methyl-1H-1,2,3-triazol-1-yl)phenyl]pyrimidin-4-ol, prepared in Example 137B, and (9R,13S)-13-amino-3-(difluoromethyl)-9-methyl-3,4,7,15-tetraazatricyclo[12.3.1.0²,⁶]octadeca-1(18),2 (6),4,14,16-pentaen-8-one, prepared as described in Intermediate 30. MS(ESI) m/z: 624.3 (M+H)⁺ and 626.2 (M+2+H)⁺. ¹H NMR (500 MHz, CD₃OD) δ 9.52 (s, 1H), 8.90 (s, 1H), 8.75 (d, J=5.2 Hz, 1H), 7.89 (d, J=0.8 Hz, 1H), 7.82 (dd, J=8.7, 7.6 Hz, 1H), 7.74 (d, J=0.8 Hz, 1H), 7.69 (br. s, 1H), 7.65 (t, J=58.0 Hz, 1H), 7.53-7.49 (m, 2H), 6.52 (s, 1H), 6.05-5.99 (m, 1H), 2.77-2.66 (m, 1H), 2.34-2.23 (m, 4H), 2.09-1.95 (m, 2H), 1.64-1.53 (m, 1H), 1.53-1.42 (m, 1H), 0.99 (d, J=7.2 Hz, 3H), 0.69-0.53 (m, 1H). ¹⁹F NMR (471 MHz, CD₃OD) δ −74.25 (s), −75.75 (s), −115.22 (s). Analytical HPLC (Method A): RT=7.54 min, purity=99.8%; Factor XIa Ki=0.63 nM, Plasma Kallikrein Ki=119 nM.

Example 140

Preparation of (9R,13S)-13-(4-{5-chloro-2-[1-(difluoromethyl)-1H-pyrazol-4-yl]phenyl}-6-oxo-1,6-dihydropyrimidin-1-yl)-3,9-dimethyl-3,4,7,15-tetraazatricyclo[12.3.1.0²,⁶]octadeca-1(18),2(6),4,14,16-pentaen-8-one

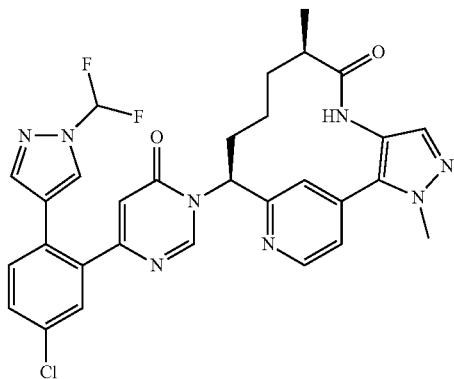 [SMILES: C[C@@H]1CCC[C@H](n2cnc(-c3cc(Cl)ccc3-c3cnn(C(F)F)c3)cc2=O)c2cc(ccn2)-c2c(cnn2C)NC1=O]

140A. Preparation of 4-(5-chloro-2-(1-(difluoromethyl)-1H-pyrazol-4-yl)phenyl)-6-methoxypyrimidine To a sealable vial was added 4-(2-bromo-5-chlorophenyl)-6-methoxypyrimidine (0.08 g, 0.267 mmol), 1-(difluoromethyl)-4-(4,4,5,5-tetramethyl-1,3,2-dioxaborolan-2-yl)-1H-pyrazole (0.072 g, 0.294 mmol), 3 M aq KH₂PO₄ (0.27 ml, 0.81 mmol) and THF (2.67 ml). Ar was bubbled through the reaction mixture for several min and (DtBPF)PdCl₂ (8.70 mg, 0.013 mmol) was added. The vial was sealed and heated at 90° C. for 15 h. The reaction was cooled to rt, diluted with EtOAc, washed with brine, dried over Na₂SO₄, filtered, and concentrated. Purification by normal phase chromatography afforded 4-(5-chloro-2-(1-(difluoromethyl)-1H-pyrazol-4-yl)phenyl)-6-methoxypyrimidine (0.05 g, 56% yield) as a white solid. MS(ESI) m/z: 337.2 (M+H)⁺. ¹H NMR (400 MHz, CDCl₃) δ 8.81 (d, J=0.9 Hz, 1H), 7.69 (s, 1H), 7.54 (d, J=2.2 Hz, 1H), 7.48-7.43 (m, 1H), 7.41-7.35 (m, 2H), 7.17 (t, J=54.0 Hz, 1H), 6.61 (d, J=1.1 Hz, 1H), 3.99 (s, 3H).

140B. Preparation of 6-(5-chloro-2-(1-(difluoromethyl)-1H-pyrazol-4-yl)phenyl) pyrimidin-4-ol A clear solution of 4-(5-chloro-2-(1-(difluoromethyl)-1H-pyrazol-4-yl)phenyl)-6-methoxypyrimidine (0.05 g, 0.148 mmol) in HOAc (0.742 ml) and 48% aq HBr (0.84 ml, 7.42 mmol) was warmed to 65° C. After 3 h, the reaction was cooled to rt and concentrated. The residue was dissolved in EtOAc, washed with sat NaHCO₃, brine, dried over Na₂SO₄, filtered, and concentrated. Et₂O (3 ml) was added and the mixture was sonicated. The solid was collected by filtration and rinsed with Et₂O (2 ml), air-dried to give 6-(5-chloro-2-(1-(difluoromethyl)-1H-pyrazol-4-yl)phenyl) pyrimidin-4-ol (0.03 g, 63% yield) as a white solid. MS(ESI) m/z: 323.2 (M+H)⁺. ¹H NMR (400 MHz, CD₃OD) δ 8.20 (d, J=1.1 Hz, 1H), 8.05 (s, 1H), 7.61-7.27 (m, 5H), 6.40 (d, J=1.1 Hz, 1H).

140C. Preparation of (9R,13S)-13-(4-{5-chloro-2-[1-(difluoromethyl)-1H-pyrazol-4-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate (9R,13S)-13-(4-{5-Chloro-2-[1-(difluoromethyl)-1H-pyrazol-4-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate (10 mg, 32% yield) was prepared in a similar manner as the procedure described in Example 56, by using 6-(5-chloro-2-(1-(difluoromethyl)-1H-pyrazol-4-yl)phenyl)pyrimidin-4-ol (14.01 mg, 0.043 mmol). MS(ESI) m/z: 605.2 (M+H)$^+$. $^1$H NMR (400 MHz, CD$_3$OD) δ 8.95 (s, 1H), 8.74 (d, J=5.3 Hz, 1H), 8.04 (s, 1H), 7.72 (s, 1H), 7.60-7.25 (m, 7H), 6.42 (s, 1H), 6.02 (dd, J=12.7, 4.3 Hz, 1H), 4.05 (s, 3H), 2.76-2.66 (m, 1H), 2.39-2.27 (m, 1H), 2.14-1.99 (m, 2H), 1.67-1.42 (m, 2H), 1.02 (d, J=6.8 Hz, 3H), 0.81-0.65 (m, 1H). Analytical HPLC (Method A): RT=8.18 min, 98.5% purity; Factor XIa Ki=9 nM, Plasma Kallikrein Ki=910 nM.

Example 141

Preparation of (9R,13S)-13-[4-(3-fluoro-4-methylpyridin-2-yl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one

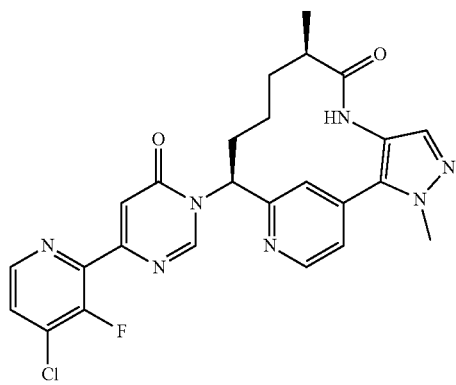 [SMILES: C[C@@H]1CCC[C@H](n2cnc(-c3nccc(Cl)c3F)cc2=O)c2cc(ccn2)-c2c(cnn2C)NC1=O]

141A. Preparation of 4-methoxy-6-(tributylstannyl)pyrimidine

To a RBF was added 4-chloro-6-methoxypyrimidine (3.15 g, 21.79 mmol), 1,1,1,2,2,2-hexabutyldistannane (10.92 mL, 21.79 mmol), toluene (50 mL) and Pd(PPh$_3$)$_4$ (1.259 g, 1.090 mmol). The reaction was purged with Ar and then stirred at 120° C. overnight. The reaction was then partitioned between EtOAc (30 ml) and water (25 ml). The organic layer was separated, washed with sat NaCl (20 ml), dried over MgSO$_4$, filtered and concentrated. The crude product was purified using ISCO system (0-30% EtOAc/Hex gradient) to give 4-methoxy-6-(tributylstannyl)pyrimidine (200 mg, 0.501 mmol, 2.3% yield) as a clear liquid. $^1$H NMR (400 MHz, CDCl$_3$) δ 8.85 (d, J=1.1 Hz, 1H), 6.94 (d, J=1.1 Hz, 1H), 3.97 (s, 3H), 1.60-1.55 (m, 6H), 1.36-1.32 (m, 6H), 1.20-1.13 (m, 6H), 0.96-0.91 (m, 9H); MS(ESI) m/z: 401.1 (M+H)$^+$.

141B. Preparation of 4-(3-fluoro-4-methylpyridin-2-yl)-6-methoxypyrimidine Trifluoroacetate To a sealed tube was added 2-bromo-3-fluoro-4-methylpyridine (25.7 mg, 0.135 mmol), 4-methoxy-6-(tributylstannyl)pyrimidine (45 mg, 0.113 mmol), toluene (1.5 mL) and Pd(PPh$_3$)$_4$ (13.03 mg, 0.011 mmol). The reaction was purged with Ar and then sealed and stirred at 120° C. overnight. The reaction was partitioned between EtOAc (25 ml) and water (20 ml). The organic layer was separated, washed with sat NaCl (10 ml), dried over MgSO$_4$, filtered and concentrated. The crude product was purified using prep-HPLC to give 4-(3-fluoro-4-methylpyridin-2-yl)-6-methoxypyrimidine trifluoroacetate (20 mg, 0.060 mmol, 53.2% yield) as a purple salt. $^1$H NMR (400 MHz, CDCl$_3$) δ 9.22 (s, 1H), 8.59 (d, J=4.2 Hz, 1H), 7.56 (s, 1H), 7.51 (br. s., 1H), 4.23 (s, 3H), 2.51 (s, 3H); MS(ESI) m/z: 220.1 (M+H)$^+$.

141C. Preparation of 6-(3-fluoro-4-methylpyridin-2-yl)pyrimidin-4-ol

To a RBF was added 4-(3-fluoro-4-methylpyridin-2-yl)-6-methoxypyrimidine (20 mg, 0.060 mmol), AcOH (0.5 mL) and HBr (0.34 mL, 3.00 mmol). The reaction was stirred at 85° C. for 45 min. Then toluene (25 ml) was added and the reaction was concentrated. The residue was then partitioned between EtOAc (25 ml) and sat NaHCO$_3$ (25 ml). The organic layer was separated, washed with water (15 ml) and sat NaCl (15 ml), dried over MgSO$_4$, filtered and concentrated, to give 6-(3-fluoro-4-methylpyridin-2-yl)pyrimidin-4-ol (10 mg, 0.049 mmol, 81% yield) as an oil. MS(ESI) m/z: 206.1 (M+H)$^+$.

141D. Preparation of (9R,13S)-13-[4-(3-fluoro-4-methylpyridin-2-yl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one trifluoroacetate (9R,13S)-13-[4-(3-Fluoro-4-methylpyridin-2-yl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one trifluoroacetate (14 mg, 22 μmol, 41.4% yield) was prepared in a similar manner as the procedure described in Example 56 by using 6-(3-fluoro-4-methylpyridin-2-yl)pyrimidin-4-ol (15.3 mg, 0.053 mmol) and (9R,13S)-13-amino-3,9-dimethyl-3,4,7,15-tetraazatricyclo[12.3.1.0$^{2,6}$]octadeca-1(18),2(6),4,14,16-pentaen-8-one (16 mg, 0.053 mmol), prepared as described in Intermediate 32. $^1$H NMR (400 MHz, CD$_3$OD) δ 9.21 (br. s., 1H), 8.76 (d, J=4.4 Hz, 1H), 8.49 (br. s., 1H), 7.77 (s, 1H), 7.66 (br. s., 1H), 7.56 (d, J=3.7 Hz, 1H), 7.52 (s, 1H), 7.15 (br. s., 1H), 6.10 (d, J=9.9 Hz, 1H), 4.07 (s, 3H), 2.74 (d, J=12.3 Hz, 1H), 2.51 (br. s., 3H), 2.40 (br. s., 1H), 2.13 (br. s., 2H), 1.66 (br. s., 1H), 1.54 (br. s., 1H), 1.04 (d, J=6.8 Hz, 3H), 0.75 (br. s., 1H); MS(ESI) m/z: 488.2 (M+H)$^+$. Analytical HPLC (Method A): RT=6.97 min, purity=97.0%; Factor XIa Ki=110 nM, Plasma Kallikrein Ki=2,200 nM.

Example 142

Preparation of (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7,17-tetraazatricyclo[12.3.1.0²,⁶]octadeca-1(18),2(6),4,14,16-pentaen-8-one

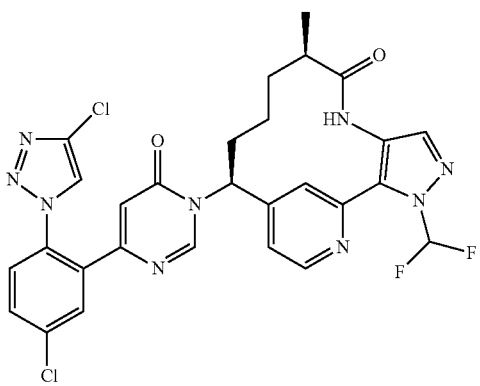 [SMILES: C[C@@H]1CCC[C@H](n2cnc(-c3cc(Cl)ccc3-n3cc(Cl)nn3)cc2=O)c2ccnc(c2)-c2c(cnn2C(F)F)NC1=O]

(9R,13S)-13-{4-[5-Chloro-2-(4-chloro-1H-1,2,3-triazol-1-yl)phenyl]-6-oxo-1,6-dihydropyrimidin-1-yl}-3-(difluoromethyl)-9-methyl-3,4,7,17-tetraazatricyclo[12.3.1.0²,⁶]octadeca-1(18),2(6),4,14,16-pentaen-8-one trifluoroacetate (14.2 mg, 24%) was prepared in a similar manner as Example 56, by using 6-[5-chloro-2-(4-chloro-1H-1,2,3-triazol-1-yl)phenyl]pyrimidin-4-ol, prepared as described in Intermediate 9, and (9R,13S)-13-amino-3-(difluoromethyl)-9-methyl-3,4,7,17-tetraazatricyclo[12.3.1.0²,⁶]octadeca-1(18),2(6),4,14,16-pentaen-8-one, prepared as described in Intermediate 37. MS(ESI) m/z: 626.1 (M+H)⁺ and 628.1 (M+2+H)⁺. ¹H NMR (400 MHz, CDCl₃) δ 8.62 (d, J=5.1 Hz, 1H), 8.35-8.13 (m, 3H), 7.85 (s, 2H), 7.71-7.62 (m, 1H), 7.57-7.53 (m, 1H), 7.09-7.03 (m, 1H), 6.36-6.30 (m, 1H), 5.67-5.63 (m, 1H), 2.59-2.54 (m, 1H), 2.31-2.24 (m, 1H), 2.04-1.94 (m, 2H), 1.59-1.54 (m, 1H), 1.30-1.21 (m, 2H), 1.03 (d, J=6.8 Hz, 3H). Analytical HPLC (Method A): RT=8.54 min, purity=99%; Factor XIa Ki=0.4 nM, Plasma Kallikrein Ki=90 nM.

Example 143

Preparation of (9R,13S)-13-{4-[5-chloro-2-(4-chloro-1H-1,2,3-triazol-1-yl)phenyl]-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one Trifluoroacetate

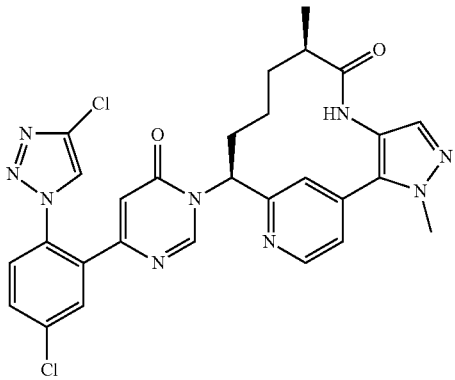

(9R,13S)-13-{4-[5-Chloro-2-(4-chloro-1H-1,2,3-triazol-1-yl)phenyl]-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one trifluoroacetate (9.7 mg, 21% yield) was prepared in a similar manner as the procedure described in Example 56, by replacing 6-{5-chloro-2-[4-(trifluoromethyl)-1H-1,2,3-triazol-1-yl]phenyl}pyrimidin-4-ol with 6-[5-chloro-2-(4-chloro-1H-1,2,3-triazol-1-yl)phenyl]pyrimidin-4-ol (20 mg, 0.065 mmol), prepared as described in Intermediate 9. MS(ESI) m/z: 590.1 (M+H)⁺. ¹H NMR (500 MHz, CD₃OD) δ 8.82 (s, 1H), 8.72 (d, J=5.0 Hz, 1H), 8.33 (s, 1H), 7.88 (d, J=2.5 Hz, 1H), 7.73 (dd, J=8.5, 2.2 Hz, 1H), 7.68 (s, 1H), 7.64 (d, J=8.5 Hz, 1H), 7.52-7.49 (m, 1H), 7.49 (s, 1H), 6.36 (s, 1H), 5.98 (dd, J=12.5, 3.7 Hz, 1H), 4.04 (s, 3H), 2.70 (td, J=6.5, 3.0 Hz, 1H), 2.33-2.24 (m, 1H), 2.12-1.95 (m, 2H), 1.65-1.55 (m, 1H), 1.52-1.42 (m, 1H), 1.00 (d, J=6.9 Hz, 3H), 0.74-0.61 (m, 1H). Analytical HPLC (Method A): RT=11.54 min, purity=99%; Factor XIa Ki=0.17 nM, Plasma Kallikrein Ki=20 nM.

Example 144

Preparation of (9R,13S)-13-{4-[3-chloro-6-(4-chloro-1H-1,2,3-triazol-1-yl)-2-fluorophenyl]-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one Trifluoroacetate

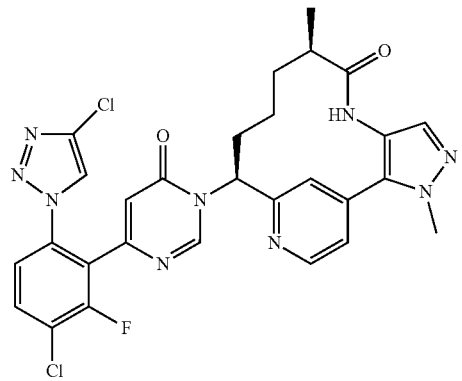 [SMILES: C[C@@H]1CCC[C@H](n2cnc(-c3c(-n4cc(Cl)nn4)ccc(Cl)c3F)cc2=O)c2cc(ccn2)-c2c(cnn2C)NC1=O]

(9R,13S)-13-{4-[3-Chloro-6-(4-chloro-1H-1,2,3-triazol-1-yl)-2-fluorophenyl]-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one trifluoroacetate (9.9 mg, 22% yield) was prepared in a similar manner as the procedure described in Example 56, by using 6-[3-chloro-6-(4-chloro-1H-1,2,3-triazol-1-yl)-2-fluorophenyl]pyrimidin-4-ol (20 mg, 0.061 mmol), prepared as described in Intermediate 10. MS(ESI) m/z: 608.1 (M+H)⁺. ¹H NMR (500 MHz, CD₃OD) δ 8.83 (s, 1H), 8.73 (d, J=5.2 Hz, 1H), 8.32 (s, 1H), 7.85 (dd, J=8.5, 7.7 Hz, 1H), 7.68 (s, 1H), 7.55 (dd, J=8.7, 1.5 Hz, 1H), 7.51 (dd, J=5.2, 1.7 Hz, 1H), 7.49 (s, 1H), 6.60 (s, 1H), 6.00 (dd, J=12.8, 4.0 Hz, 1H), 4.05 (s, 3H), 2.75-2.64 (m, 1H), 2.29 (t, J=12.9 Hz, 1H), 2.14-1.95 (m, 2H), 1.67-1.55 (m, 1H), 1.52-1.40 (m, 1H), 1.00 (d, J=6.9 Hz, 3H), 0.67 (m, 1H). ¹⁹F NMR (471 MHz, CD₃OD) δ −76.98 (s), −115.06 (s). Analytical HPLC (Method A): RT=11.58 min, purity=98.5%; Factor XIa Ki=0.1 nM, Plasma Kallikrein Ki=6 nM.

Example 145

Preparation of (9R,13S)-13-{4-[2-(4-bromo-1H-1,2,3-triazol-1-yl)-5-chlorophenyl]-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one Trifluoroacetate

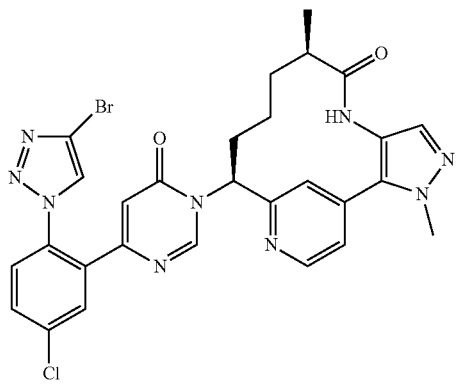 [SMILES: C[C@@H]1CCC[C@H](n2cnc(-c3cc(Cl)ccc3-n3cc(Br)nn3)cc2=O)c2cc(ccn2)-c2c(cnn2C)NC1=O]

145A. Preparation of 4-[5-chloro-2-(4-bromo-1H-1,2,3-triazol-1-yl)phenyl]-6-methoxypyrimidine

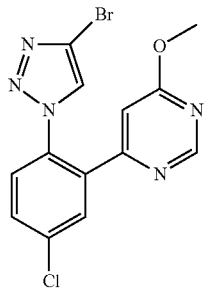 [SMILES: COc1cc(-c2cc(Cl)ccc2-n2cc(Br)nn2)ncn1]

4-[2-(4-Bromo-1H-1,2,3-triazol-1-yl)-5-chlorophenyl]-6-methoxypyrimidine (114 mg, 56.0% yield) was prepared in a similar manner as the procedure described for the preparation of 4-[5-chloro-2-(4-chloro-1H-1,2,3-triazol-1-yl)phenyl]-6-methoxypyrimidine, as described in Intermediate 9D, by replacing NCS with NBS (346 mg, 1.945 mmol). MS(ESI) m/z: 368.3 (M+H)⁺. 1H NMR (400 MHz, CDCl₃) δ 8.69 (d, J=0.9 Hz, 1H), 7.75 (d, J=2.4 Hz, 1H), 7.66 (s, 1H), 7.61 (dd, J=8.5, 2.3 Hz, 1H), 7.49 (d, J=8.4 Hz, 1H), 6.52 (d, J=1.1 Hz, 1H), 3.98 (s, 3H).

145B. Preparation of 6-[2-(4-bromo-1H-1,2,3-triazol-1-yl)-5-chlorophenyl]pyrimidin-4-ol

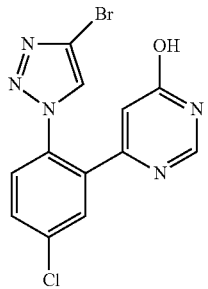 [SMILES: Oc1cc(-c2cc(Cl)ccc2-n2cc(Br)nn2)ncn1]

6-[2-(4-Bromo-1H-1,2,3-triazol-1-yl)-5-chlorophenyl]pyrimidin-4-ol (47 mg, 42.9% yield) was prepared in a similar manner as the procedure described in Intermediate 9E, by replacing 4-[5-chloro-2-(4-chloro-1H-1,2,3-triazol-1-yl)phenyl]-6-methoxypyrimidine with 4-[2-(4-bromo-1H-1,2,3-triazol-1-yl)-5-chlorophenyl]-6-methoxypyrimidine (114 mg, 0.311 mmol). MS(ESI) m/z: 354.2 (M+H)⁺. 1H NMR (400 MHz, CDCl₃) δ 8.01 (s, 1H), 7.76 (s, 1H), 7.73 (d, J=2.2 Hz, 1H), 7.62 (dd, J=8.5, 2.1 Hz, 1H), 7.47 (d, J=8.4 Hz, 1H), 6.42 (s, 1H).

145C. Preparation of (9R,13S)-13-{4-[2-(4-bromo-1H-1,2,3-triazol-1-yl)-5-chlorophenyl]-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one Trifluoroacetate

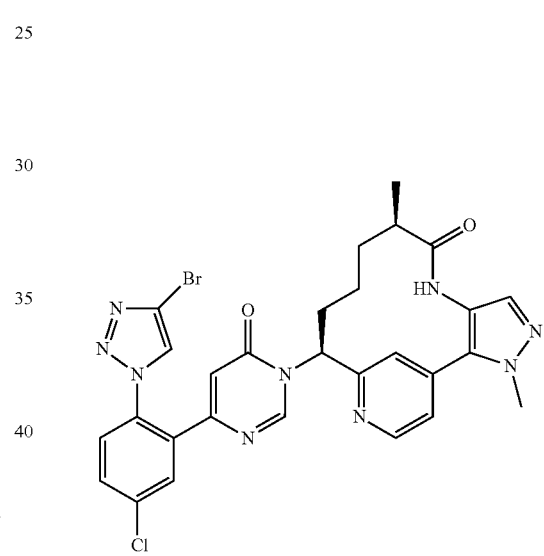

(9R,13S)-13-{4-[2-(4-Bromo-1H-1,2,3-triazol-1-yl)-5-chlorophenyl]-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one trifluoroacetate (18.7 mg, 36.3% yield) was prepared in a similar manner as the procedure described in Example 56, by using 6-[2-(4-bromo-1H-1,2,3-triazol-1-yl)-5-chlorophenyl]pyrimidin-4-ol (23.6 mg, 0.067 mmol). MS(ESI) m/z: 636.3 (M+H)⁺. 1H NMR (400 MHz, CD₃OD) δ 8.80 (s, 1H), 8.73 (d, J=5.3 Hz, 1H), 8.37 (s, 1H), 7.87 (d, J=2.4 Hz, 1H), 7.75-7.68 (m, 2H), 7.65-7.60 (m, 1H), 7.53 (dd, J=5.1, 1.5 Hz, 1H), 7.49 (s, 1H), 6.35 (s, 1H), 5.97 (dd, J=12.7, 4.3 Hz, 1H), 4.05 (s, 3H), 2.75-2.65 (m, 1H), 2.35-2.22 (m, 1H), 2.12-1.95 (m, 2H), 1.66-1.53 (m, 1H), 1.51-1.38 (m, 1H), 1.00 (d, J=7.0 Hz, 3H), 0.77-0.60 (m, 1H). Analytical HPLC (Method A): RT=10.12 min, purity=96.9%; Factor XIa Ki=0.13 nM, Plasma Kallikrein Ki=18 nM.

Examples 146 and 147

Preparation of 1-(4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)-1H-1,2,3-triazole-4-carboxamide Trifluoroacetate, and 1-(4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)-1H-1,2,3-triazole-4-carbonitrile Trifluoro Acetate

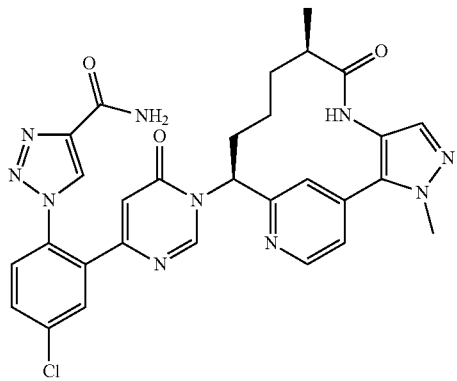

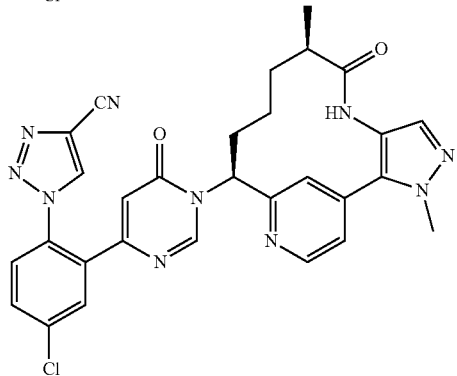

146A. Preparation of 1-[4-chloro-2-(6-methoxypyrimidin-4-yl)phenyl]-1H-1,2,3-triazole-4-carboxamide, and 147A. Preparation of 1-[4-chloro-2-(6-methoxypyrimidin-4-yl)phenyl]-1H-1,2,3-triazole-4-carbonitrile

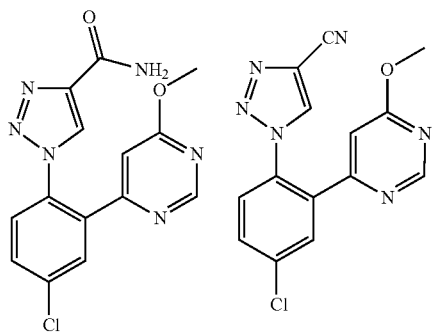

To a suspension of 1-[4-chloro-2-(6-methoxypyrimidin-4-yl)phenyl]-1H-1,2,3-triazole-4-carboxamide (150 mg, 0.45 mmol), prepared as described in Intermediate 18A, in DCM (1 mL) was added TFAA (0.3 mL, 2.12 mmol) at rt and the reaction was stirred for 1 h. The reaction was concentrated to dryness, partitioned between sat NaHCO₃ and EtOAc, and the layers were separated. The aqueous layer was extracted with EtOAc (2×). The combined organic layers were concentrated and then purified by normal phase chromatography to give 1-(4-chloro-2-(6-methoxypyrimidin-4-yl)phenyl)-1H-1,2,3-triazole-4-carboxamide (80 mg, 53.3% yield). MS(ESI) m/z: 331.3 (M+H)⁺; and 1-(4-chloro-2-(6-methoxypyrimidin-4-yl)phenyl)-1H-1,2,3-triazole-4-carboxamide (60.5 mg, 21.3% yield) which were used as is in the next step. MS(ESI) m/z: 331.3.

146B. Preparation of 1-[4-chloro-2-(6-hydroxypyrimidin-4-yl)phenyl]-1H-1,2,3-triazole-4-carboxamide, and 147B. Preparation of 1-[4-chloro-2-(6-hydroxypyrimidin-4-yl)phenyl]-1H-1,2,3-triazole-4-carbonitrile

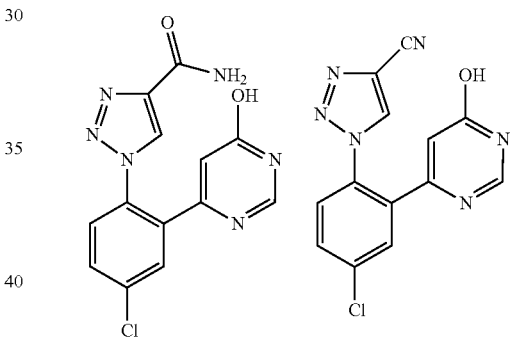

To a suspension of a 1:1 mixture of 1-(4-chloro-2-(6-methoxypyrimidin-4-yl)phenyl)-1H-1,2,3-triazole-4-carbonitrile and 1-(4-chloro-2-(6-methoxypyrimidin-4-yl)phenyl)-1H-1,2,3-triazole-4-carboxamide (60.5 mg, 0.194 mmol) in ACN (1 mL) was added TMSI (12 μL, 0.88 mmol) and the solution was heated at 50° C. overnight. The reaction was poured into 10% aq Na₂S₂O₃ s and extracted with EtOAc (3×). The combined organic layers were concentrated to dryness then suspended in DCM. The insoluble yellow solid was filtered to give a 5:3 mixture of 1-[4-chloro-2-(6-hydroxypyrimidin-4-yl)phenyl]-1H-1,2,3-triazole-4-carboxamide and 1-[4-chloro-2-(6-hydroxypyrimidin-4-yl)phenyl]-1H-1,2,3-triazole-4-carbonitrile (15 mg) which was used as in is the next step. MS(ESI) m/z: 317.3, 299.3 (M+H)⁺. The filtrate was concentrated then purified by normal phase chromatography to give 1-[4-chloro-2-(6-hydroxypyrimidin-4-yl)phenyl]-1H-1,2,3-triazole-4-carbonitrile (20 mg, 34.6% yield) as a yellow solid. MS(ESI) m/z: 299.3 ¹H NMR (400 MHz, CDCl₃) δ 8.23 (s, 1H), 7.93 (s, 1H), 7.73 (d, J=2.2 Hz, 1H), 7.66 (dd, J=8.4, 2.2 Hz, 1H), 7.49 (d, J=8.4 Hz, 1H), 6.54 (s, 1H).

146C. Preparation of 1-(4-chloro-2-{1[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)-1H-1,2,3-triazole-4-carboxamide Trifluoroacetate, and 147C. Preparation of 1-(4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)-1H-1,2,3-triazole-4-carbonitrile Trifluoroacetate

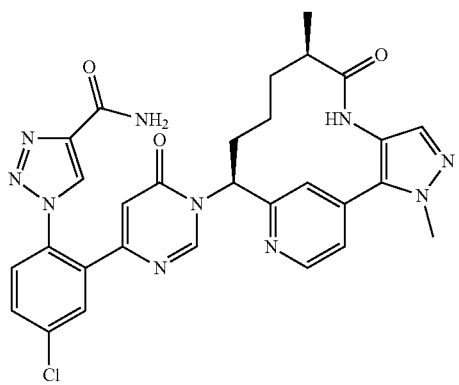

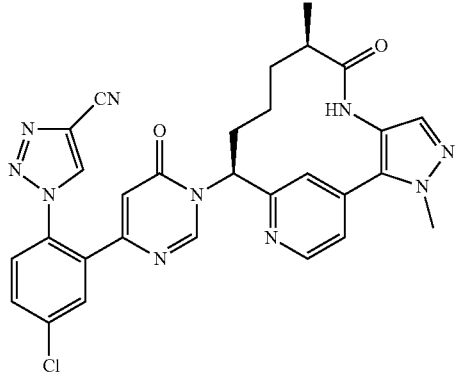

To a scintillation vial containing a mixture of 1-(4-chloro-2-(6-hydroxypyrimidin-4-yl)phenyl)-1H-1,2,3-triazole-4-carbonitrile and 1-[4-chloro-2-(6-hydroxypyrimidin-4-yl)phenyl]-1H-1,2,3-triazole-4-carboxamide (15 mg, 0.050 mmol) in ACN (1 mL), was added HATU (24.8 mg, 0.065 mmol) and DBU (11 μL, 0.075 mmol). After 20 min, a solution of (9R,13S)-13-amino-3,9-dimethyl-3,4,7,15-tetraazatricyclo[12.3.1.0²,⁶]octadeca-1(18),2(6),4,14,16-pentaen-8-one (18.4 mg, 0.061 mmol), prepared as described in Intermediate 32, in ACN (0.5 ml) and DMF (0.1 ml) was added. The resulting solution was stirred at rt for 2 h then purified by reverse phase chromatography to give two products. 1-(4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)-1H-1,2,3-triazole-4-carboxamide trifluoroacetate (3.8 mg, 10.5% yield) as a white solid. MS(ESI) m/z: 599.4 (M+H)⁺. ¹H NMR (400 MHz, CD₃OD) δ 8.79 (s, 1H), 8.71 (d, J=5.1 Hz, 1H), 8.56 (s, 1H), 7.88 (d, J=2.4 Hz, 1H), 7.76-7.71 (m, 1H), 7.69-7.64 (m, 2H), 7.51 (dd, J=5.2, 1.4 Hz, 1H), 7.48 (s, 1H), 6.35 (s, 1H), 5.96 (dd, J=12.8, 4.2 Hz, 1H), 4.04 (s, 3H), 2.75-2.63 (m, 1H), 2.33-2.21 (m, 1H), 2.12-1.92 (m, 2H), 1.66-1.53 (m, 1H), 1.52-1.40 (m, 1H), 1.00 (d, J=6.8 Hz, 3H), 0.74-0.60 (m, 1H). Analytical HPLC (Method A): RT=8.06 min, purity=98.4%; Factor XIa Ki=0.44 nM, Plasma Kallikrein Ki=99 nM.

1-(4-Chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)-1H-1,2,3-triazole-4-carbonitrile trifluoroacetate (1.7 mg, 4.9% yield) as a white solid. MS(ESI) m/z: 581.3 (M+H)⁺. ¹H NMR (400 MHz, CD₃OD) δ 8.93 (s, 1H), 8.73 (d, J=4.6 Hz, 2H), 7.90 (d, J=2.4 Hz, 1H), 7.79-7.73 (m, 1H), 7.71-7.67 (m, 2H), 7.51 (dd, J=5.1, 1.5 Hz, 1H), 7.49 (s, 1H), 6.46 (d, J=0.7 Hz, 1H), 5.97 (dd, J=12.7, 4.1 Hz, 1H), 4.05 (s, 3H), 2.70 (m, 1H), 2.34-2.21 (m, 1H), 2.13-1.94 (m, 2H), 1.67-1.53 (m, 1H), 1.52-1.39 (m, 1H), 1.01 (d, J=6.8 Hz, 3H), 0.71 (m, 1H). Analytical HPLC (Method A): RT=10.08 min, purity=99.2%; Factor XIa Ki=0.11 nM, Plasma Kallikrein Ki=20 nM.

Example 148

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-9-oxo-3,8-diazatricyclo[13.3.1.0²,⁷]nonadeca-1(19),2(7),3,5,15,17-hexaene-5-carbonitrile

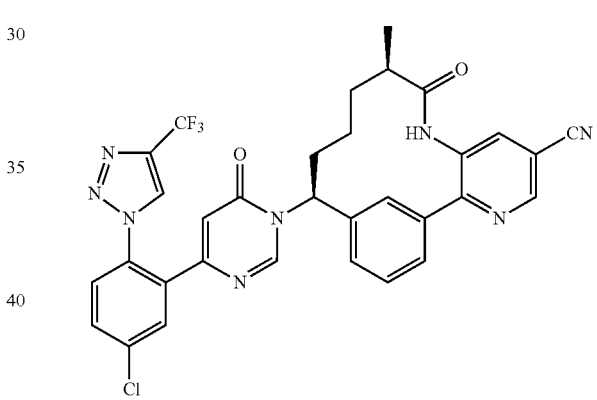

148A. Preparation of Tert-Butyl N-[(10R,14S)-5-bromo-10-methyl-9-oxo-3,8-diazatricyclo[13.3.1.0²,⁷]nonadeca-1(19),2(7),3,5,15,17-hexaen-14-yl]carbamate

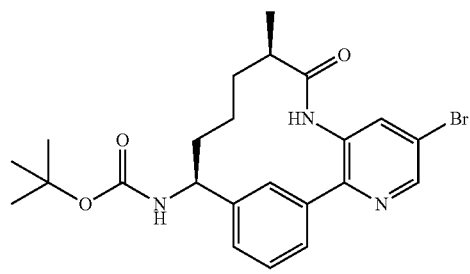 [SMILES: C[C@@H]1CCC[C@H](NC(=O)OC(C)(C)C)c2cccc(c2)-c2ncc(Br)cc2NC1=O]

tert-Butyl N-[(10R,14S)-5-bromo-10-methyl-9-oxo-3,8-diazatricyclo[13.3.1.0²,⁷]nonadeca-1(19),2(7),3,5,15,17-hexaen-14-yl]carbamate was prepared (0.1 g, 49% yield, dark solid) in a similar manner as Example 81C replacing 2-bromo-5-methoxypyridin-3-amine with 2,5-dibromopyridin-3-amine. LCMS (M+H)+ 474-476.08.

148B. Preparation of Tert-Butyl N-[(10R,14S)-5-cyano-10-methyl-9-oxo-3,8-diazatricyclo[13.3.1.0²,⁷]nonadeca-1(19),2(7),3,5,15,17-hexaen-14-yl]carbamate To tert-butyl N-[(10R,14S)-5-bromo-10-methyl-9-oxo-3,8-diazatricyclo[13.3.1.0²,⁷]nonadeca-1(19),2(7),3,5,15,17-hexaen-14-yl]carbamate (0.1 g, 0.211 mmol) in a microwave tube was added Zn(CN)$_2$ (0.037 g, 0.316 mmol), Zn (4.13 mg, 0.063 mmol) and DMF (2.1 ml). The mixture was purged with Ar for several min. Pd(t-Bu$_3$P)$_2$ (10.77 mg, 0.021 mmol) was added. The reaction was sealed and heated at 80° C. for 18 h. The reaction was partitioned with water (10 ml) and EtOAc (30 ml). The aqueous layer was extracted with EtOAc (2×10 ml). The combined organic layers were washed with brine (10 ml), dried (MgSO$_4$), filtered and concentrated. The residue was purified normal phase chromatography using 100% DCM to 10% MeOH as eluents to give tert-butyl N-[(10R,14S)-5-cyano-10-methyl-9-oxo-3,8-diazatricyclo[13.3.1.0²,⁷]nonadeca-1(19),2(7),3,5,15,17-hexaen-14-yl]carbamate (20 mg, 22.56% yield). LCMS (M+H)+ 421.3.

148C. Preparation of (10R,14S)-14-amino-10-methyl-9-oxo-3,8-diazatricyclo[13.3.1.0²,⁷]nonadeca-1(19),2(7),3,5,15,17-hexaene-5-carbonitrile

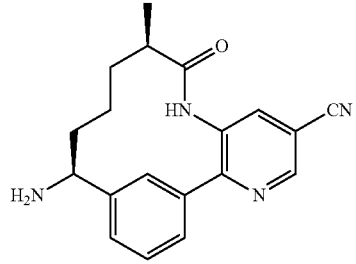 [SMILES: C[C@@H]1CCC[C@H](N)c2cccc(c2)-c2ncc(C#N)cc2NC1=O]

tert-Butyl N-[(10R,14S)-5-cyano-10-methyl-9-oxo-3,8-diazatricyclo[13.3.1.0²,⁷]nonadeca-1(19),2(7),3,5,15,17-hexaen-14-yl]carbamate (0.02 g, 0.048 mmol), Example 148B, was deprotected and the free-base was produced in a similar manner as Example 81D to afford (10R,14S)-14-amino-10-methyl-9-oxo-3,8-diazatricyclo[13.3.1.0²,⁷]nonadeca-1(19),2(7),3,5,15,17-hexaene-5-carbonitrile (13 mg, 85%) as a tan solid. LCMS (M+H)+321.3.

148D. Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-9-oxo-3,8-diazatricyclo[13.3.1.0²,⁷]nonadeca-1(19),2(7),3,5,15,17-hexaene-5-carbonitrile To 6-{5-chloro-2-[4-(trifluoromethyl)-1H-1,2,3-triazol-1-yl]phenyl}pyrimidin-4-ol, described in Intermediate 15, (0.014 g, 0.041 mmol) and HATU (0.020 g, 0.053 mmol) in a small vial was added DBU (9.17 µl, 0.061 mmol) in ACN (0.2 mL). After 30 min, (10R,14S)-14-amino-10-methyl-9-oxo-3,8-diazatricyclo[13.3.1.0²,⁷]nonadeca-1(19),2(7),3,5,15,17-hexaene-5-carbonitrile was added in DMF (0.4 ml). After 18 h, the reaction was diluted with DMF, filtered and concentrated. The residue was purified by reverse phase HPLC using PHENOMENEX® Luna 5U 30×100 mm (10: 90 ACN/H$_2$O to 90:10 ACN/H$_2$O, 0.1% TFA) (20% B start, 14 min gradient) to afford (10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-9-oxo-3,8-diazatricyclo[13.3.1.0²,⁷]nonadeca-1(19),2(7),3,5,15,17-hexaene-5-carbonitrile (4.9 mg, 14%) as a white solid. MS(ESI) m/z: 645.4 (M+H)+. ¹H NMR (400 MHz, CD$_3$OD) δ 8.98-8.94 (m, 1H), 8.80 (s, 1H), 8.30-8.24 (m, 1H), 8.18-8.13 (m, 1H), 7.96-7.91 (m, 1H), 7.81-7.76 (m, 2H), 7.74-7.68 (m, 1H), 7.60 (t, J=7.7 Hz, 1H), 7.32 (s, 1H), 6.49-6.46 (m, 1H), 5.81 (dd, J=12.7, 3.4 Hz, 1H), 2.56 (d, J=7.0 Hz, 1H), 2.31 (d, J=5.1 Hz, 1H), 2.16-2.08 (m, 1H), 1.93 (d, J=7.3 Hz, 1H), 1.58 (d, J=7.3 Hz, 1H), 1.46 (d, J=6.8 Hz, 1H), 1.37 (br. s., 1H), 1.26-1.21 (m, 1H), 1.17 (s, 3H). Analytical HPLC (Method A) RT=9.37 min, purity=90%; Factor XIa Ki=1.8 nM, Plasma Kallikrein Ki=120 nM.

Example 149

Preparation of (9R,13S)-13-(4-{5-chloro-2-[4-({3H-[1,2,3]triazolo[4,5-b]pyridin-3-yloxy}methyl)-1H-1,2,3-triazol-1-yl]phenyl}-6-oxo-1,6-dihydropyrimidin-1-yl)-3,9-dimethyl-3,4,7,15-tetraazatricyclo[12.3.1.0²,⁷]octadeca-1(18),2(6),4,14,16-pentaen-8-one Trifluoroacetate

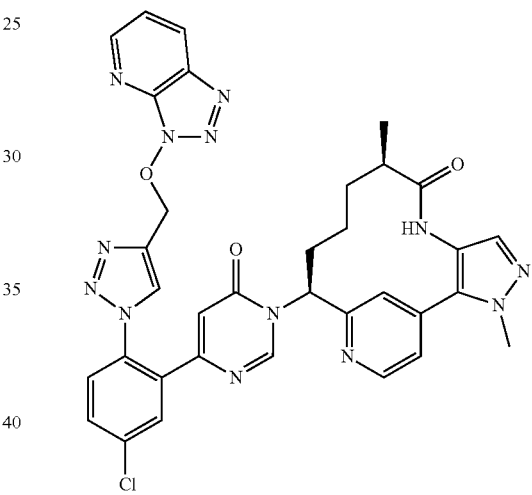

149A. Preparation of 4-{5-chloro-2-[4-(fluoromethyl)-1H-1,2,3-triazol-1-yl]phenyl}-6-methoxypyrimidine

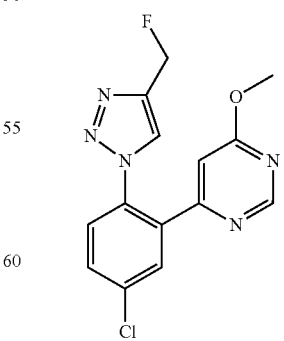

To a solution of {1-[4-chloro-2-(6-methoxypyrimidin-4-yl)phenyl]-1H-1,2,3-triazol-4-yl}methanol (95 mg, 0.3 mmol), prepared as described in Intermediate 16A, in DCM (6 ml) was added DAST (0.040 mL, 0.300 mmol) and the reaction was stirred at rt for 2 h. The reaction was quenched with water, and extracted with DCM. The organic layer was concentrated and purified by normal phase chromatography to give 4-{5-chloro-2-[4-(fluoromethyl)-1H-1,2,3-triazol-1-yl]phenyl}-6-methoxypyrimidine (56 mg, 0.175 mmol, 58.4% yield) as a clear oil. MS(ESI) m/z: 320.0 (M+H)+. $^1$H NMR (400 MHz, CDCl$_3$) δ 8.68 (d, J=1.1 Hz, 1H), 7.77 (d, J=2.2 Hz, 1H), 7.73 (d, J=2.6 Hz, 1H), 7.64-7.57 (m, 1H), 7.53-7.48 (m, 1H), 6.46 (d, J=1.1 Hz, 1H), 5.57 (s, 1H), 5.45 (s, 1H), 3.98-3.87 (m, 3H). $^{19}$F NMR (376 MHz, CDCl$_3$) δ −208.23 (s).

149B. Preparation of 6-{2-[4-(bromomethyl)-1H-1,2,3-triazol-1-yl]-5-chlorophenyl}pyrimidin-4-ol

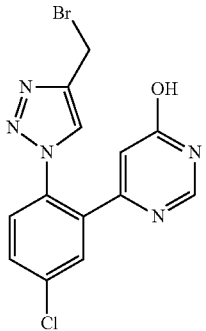 [SMILES: Oc1cc(-c2cc(Cl)ccc2-n2cc(CBr)nn2)ncn1]

A solution of 4-{5-chloro-2-[4-(fluoromethyl)-1H-1,2,3-triazol-1-yl]phenyl}-6-methoxypyrimidine (56 mg, 0.175 mmol) in 33% HBr in AcOH (0.5 ml, 4.14 mmol) was heated at 85° C. for 1 h. The reaction was concentrated to half the volume then, 48% aq HBr (0.2 ml) was added and heated at 85° C. for 1 h. The reaction was concentrated, and the residue was partitioned between EtOAc and sat NaHCO$_3$. The layers were separated and the aqueous layer was extracted with EtOAc (2×). The combined organic layers were concentrated and purified by normal phase chromatography to give 6-{2-[4-(bromomethyl)-1H-1,2,3-triazol-1-yl]-5-chlorophenyl}pyrimidin-4-ol. MS(ESI) m/z: 368.2 (M+H)+. $^1$H NMR (400 MHz, CDCl$_3$) δ 7.87 (d, J=0.9 Hz, 1H), 7.79 (s, 1H), 7.70 (d, J=2.2 Hz, 1H), 7.65-7.57 (m, 1H), 7.55-7.46 (m, 1H), 6.38 (d, J=1.1 Hz, 1H), 4.60 (s, 2H).

149C. Preparation of (9R,13S)-13-(4-{5-chloro-2-[4-({3H-[1,2,3]triazolo[4,5-b]pyridin-3-yloxy}methyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate

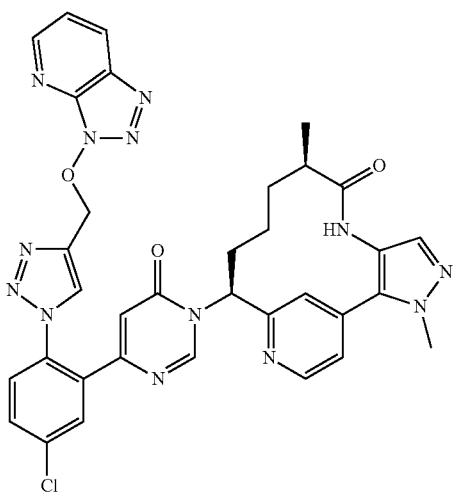 [SMILES: C[C@@H]1CCC[C@H](n2cnc(-c3cc(Cl)ccc3-n3cc(COn4nnc5cccnc54)nn3)cc2=O)c2cc(ccn2)-c2c(cnn2C)NC1=O]

(9R,13S)-13-(4-{5-Chloro-2-[4-({3H-[1,2,3]triazolo[4,5-b]pyridin-3-yloxy}methyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate (12.1 mg, 42.1% yield) was prepared in a similar manner as the procedure described in Example 56, by using 6-{2-[4-(bromomethyl)-1H-1,2,3-triazol-1-yl]-5-chlorophenyl}pyrimidin-4-ol (12.3 mg, 0.033 mmol). MS(ESI) m/z: 704.24 (M+H)+. $^1$H NMR (500 MHz, DMSO-d$_6$) δ 9.23 (s, 1H), 8.82-8.71 (m, 2H), 8.66-8.60 (m, 2H), 8.57 (d, J=8.2 Hz, 1H), 7.89 (d, J=2.4 Hz, 1H), 7.81 (dd, J=8.5, 2.1 Hz, 1H), 7.65-7.59 (m, 2H), 7.56 (dd, J=8.4, 4.4 Hz, 1H), 7.51 (d, J=4.6 Hz, 1H), 7.46 (s, 1H), 6.37 (s, 1H), 5.86 (d, J=11.3 Hz, 1H), 5.77 (s, 2H), 4.03-3.91 (m, 3H), 3.55 (m, 1H), 2.62 (m, 1H), 2.23 (m, 1H), 2.05 (d, J=10.4 Hz, 1H), 1.86-1.73 (m, 1H), 1.41 (m, 1H), 1.29 (m, 1H), 0.85 (d, J=6.7 Hz, 3H), 0.39 (m, 1H). Analytical HPLC (Method C): RT=1.41 min, purity=95%; Factor XIa Ki=3.4 nM, Plasma Kallikrein Ki=310 nM.

Example 150

Preparation of (9R,13S)-13-(4-{5-chloro-2-[4-(hydroxylmethyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate

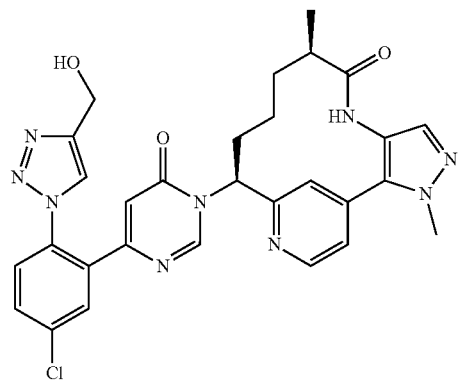

150A. Preparation of 6-{5-chloro-2-[4-(hydroxymethyl)-1H-1,2,3-triazol-1-yl]phenyl}pyrimidin-4-ol

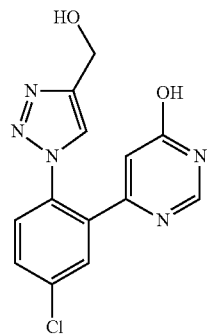 [SMILES: OCc1cn(-c2ccc(Cl)cc2-c2cc(O)ncn2)nn1]

A solution of {1-[4-chloro-2-(6-methoxypyrimidin-4-yl)phenyl]-1H-1,2,3-triazol-4-yl}methanol (65 mg, 0.205 mmol), prepared as described in Intermediate 16A, in 33% HBr in AcOH (0.6 ml, 4.97 mmol) was heated at 85° C. for 1 h. The reaction was concentrated to half the volume, then 48% aq HBr (0.2 ml) was added and heated at 85° C. for 1 h. The reaction was concentrated, and the residue was partitioned between EtOAc and sat NaHCO$_3$. The layers were separated and the aqueous layer was extracted with EtOAc (2×). The combined organic layers were concentrated and purified by normal phase chromatography to give 6-{5-chloro-2-[4-(hydroxymethyl)-1H-1,2,3-triazol-1-yl]phenyl}pyrimidin-4-ol (13 mg, 20.9% yield). MS(ESI) m/z: 304.4(M+H)$^+$. $^1$H NMR (400 MHz, CDCl$_3$) δ 7.99 (s, 1H), 7.76 (s, 2H), 7.59 (dd, J=8.5, 2.3 Hz, 1H), 7.49 (d, J=8.4 Hz, 1H), 6.18 (s, 1H), 4.83-4.76 (m, 2H).

150B. Preparation of (9R,13S)-13-(4-{5-chloro-2-[4-(hydroxymethyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate

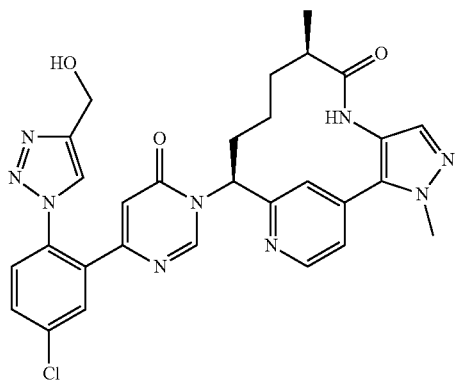 [SMILES: C[C@@H]1CCC[C@H](n2cnc(-c3cc(Cl)ccc3-n3cc(CO)nn3)cc2=O)c2cc(ccn2)-c2c(cnn2C)NC1=O]

(9R,13S)-13-(4-{5-Chloro-2-[4-(hydroxymethyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate (1.5 mg, 4.7% yield) was prepared in a similar manner as the procedure described in Example 56, by using 6-(5-chloro-2-(4-(hydroxylmethyl)-1H-1,2,3-triazol-1-yl)phenyl)pyrimidin-4-ol (13.19 mg, 0.043 mmol). MS(ESI) m/z: 586.20 (M+H)$^+$. $^1$H NMR (500 MHz, DMSO-d$_6$) δ 9.26 (s, 1H), 8.82 (s, 1H), 8.68 (d, J=4.9 Hz, 1H), 8.23 (s, 1H), 7.89 (d, J=1.8 Hz, 1H), 7.78 (d, J=6.4 Hz, 1H), 7.68-7.61 (m, 2H), 7.56 (d, J=5.2 Hz, 1H), 7.47 (s, 1H), 6.15 (s, 1H), 5.90-5.82 (m, 1H), 4.57 (d, J=4.9 Hz, 2H), 4.00 (s, 3H), 2.68-2.60 (m, 1H), 2.32-2.22 (m, 1H), 2.07 (m, 1H), 1.88-1.78 (m, 1H), 1.50-1.43 (m, 1H), 1.40-1.29 (m, 1H), 0.88 (d, J=6.7 Hz, 3H), 0.46-0.35 (m, 1H). Analytical HPLC (Method C): RT=1.19 min, purity=92%; Factor XIa Ki=7.3 nM, Plasma Kallikrein Ki=1,400 nM.

Example 151

Preparation of (9R,13S)-13-(4-{5-chloro-2-[4-(difluoromethyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate

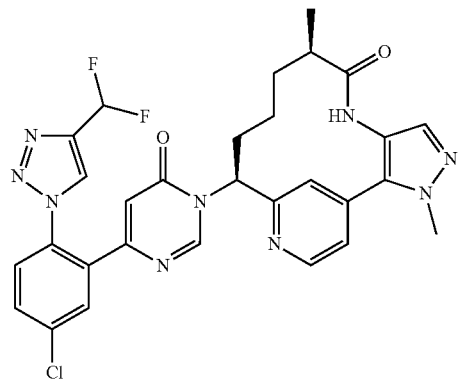 [SMILES: C[C@@H]1CCC[C@H](n2cnc(-c3cc(Cl)ccc3-n3cc(C(F)F)nn3)cc2=O)c2cc(ccn2)-c2c(cnn2C)NC1=O]

(9R,13S)-13-(4-{5-Chloro-2-[4-(difluoromethyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate (10 mg, 20.4% yield) was prepared in a similar manner as the procedure described in Example 56, by using 6-{5-chloro-2-[4-(difluoromethyl)-1H-1,2,3-triazol-1-yl]phenyl}pyrimidin-4-ol (21.62 mg, 0.067 mmol), prepared as described in Intermediate 16. MS(ESI) m/z: 606.2 (M+H)$^+$. $^1$H NMR (400 MHz, CD$_3$OD) δ 8.77 (s, 1H), 8.71 (d, J=5.1 Hz, 1H), 8.53 (t, J=1.3 Hz, 1H), 7.88 (d, J=2.4 Hz, 1H), 7.77-7.72 (m, 1H), 7.69 (s, 1H), 7.68-7.64 (m, 1H), 7.52 (dd, J=5.1, 1.5 Hz, 1H), 7.49 (s, 1H), 7.14-6.84 (m, 1H), 6.35 (s, 1H), 5.97 (dd, J=12.5, 4.2 Hz, 1H), 4.04 (s, 3H), 2.70 (td, J=6.7, 3.1 Hz, 1H), 2.27 (qd, J=8.5, 4.7 Hz, 1H), 2.12-1.92 (m, 2H), 1.65-1.53 (m, 1H), 1.45 (ddd, J=14.6, 9.8, 5.3 Hz, 1H), 1.00 (d, J=6.8 Hz, 3H), 0.69 (m, 1H). $^{19}$F NMR (376 MHz, CD$_3$OD) δ −77.76 (s), −114.46 (s). Analytical HPLC (Method A): RT=7.81 min, purity=98.7%; Factor XIa Ki=0.27 nM, Plasma Kallikrein Ki=54 nM.

Example 152

Preparation of (9R,13S)-13-(4-{5-chloro-2-[4-(trifluoromethyl)-1H-pyrazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one Trifluoroacetate

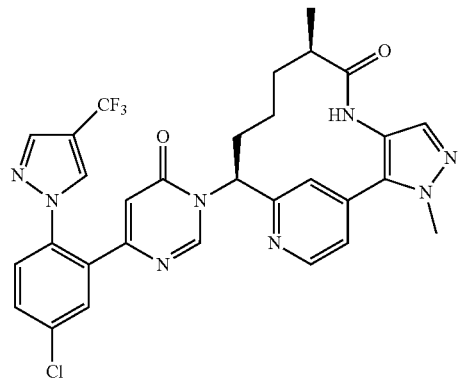 [SMILES: C[C@@H]1CCC[C@H](n2cnc(-c3cc(Cl)ccc3-n3cc(C(F)(F)F)cn3)cc2=O)c2cc(ccn2)-c2c(cnn2C)NC1=O]

152A. Preparation of 4-{5-chloro-2-[4-(trifluoromethyl)-1H-pyrazol-1-yl]phenyl}-6-methoxypyrimidine

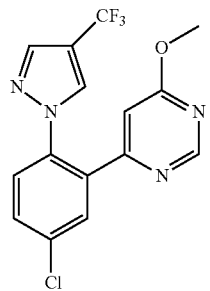 [SMILES: COc1cc(-c2cc(Cl)ccc2-n2cc(C(F)(F)F)cn2)ncn1]

To a solution of 4-(trifluoromethyl)-1H-pyrazole (34.2 mg, 0.251 mmol) in DMF (698 µl) was added NaH (12.57 mg, 0.314 mmol) in 2 portions and the reaction was stirred at rt for 30 min. 4-(5-Chloro-2-fluorophenyl)-6-methoxypyrimidine (50 mg, 0.210 mmol), prepared as described in Intermediate 5A, was added and the solution was stirred at rt for 2 h and then heated at 85° C. overnight. The reaction mixture was quenched with water and MeOH, then concentrated. Purification by normal phase chromatography gave 4-{5-chloro-2-[4-(trifluoromethyl)-1H-pyrazol-1-yl]phenyl}-6-methoxypyrimidine (60 mg, 32.3% yield). MS(ESI) m/z: 355.3 (M+H)+. 1H NMR (400 MHz, CDCl3) δ 8.73 (d, J=0.9 Hz, 1H), 7.81 (s, 1H), 7.77 (d, J=2.4 Hz, 1H), 7.70 (s, 1H), 7.59-7.53 (m, 1H), 7.51-7.47 (m, 1H), 6.36 (d, J=1.1 Hz, 1H), 3.98-3.94 (m, 3H).

152B. Preparation of 6-(5-chloro-2-(4-(trifluoromethyl)-1H-pyrazol-1-yl)phenyl) pyrimidin-4-ol

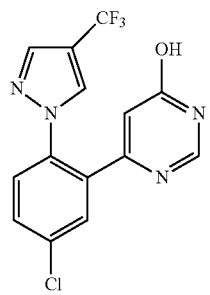 [SMILES: Oc1cc(-c2cc(Cl)ccc2-n2cc(C(F)(F)F)cn2)ncn1]

6-{5-Chloro-2-[4-(trifluoromethyl)-1H-pyrazol-1-yl]phenyl}pyrimidin-4-ol (23 mg, 25.5% yield) was prepared in a similar manner as the procedure described in Intermediate 9E, by using 4-{5-chloro-2-[4-(trifluoromethyl)-1H-pyrazol-1-yl]phenyl}-6-methoxypyrimidine (60 mg, 0.169 mmol). MS(ESI) m/z: 341.3(M+H)+. 1H NMR (400 MHz, CDCl3) δ 7.97 (s, 1H), 7.90 (d, J=0.7 Hz, 1H), 7.82 (s, 1H), 7.70 (d, J=2.2 Hz, 1H), 7.63-7.55 (m, 1H), 7.53-7.47 (m, 1H), 6.27 (d, J=0.9 Hz, 1H).

152C. Preparation of (9R,13S)-13-(4-{5-chloro-2-[4-(trifluoromethyl)-1H-pyrazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate

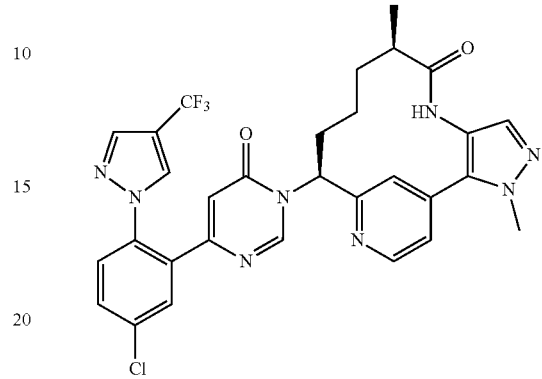

(9R,13S)-13-(4-{5-Chloro-2-[4-(trifluoromethyl)-1H-pyrazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate (20 mg, 40.2% yield) was prepared in a similar manner as the procedure described in Example 56, by using 6-{5-chloro-2-[4-(trifluoromethyl)-1H-pyrazol-1-yl]phenyl}pyrimidin-4-ol (22.76 mg, 0.067 mmol). MS(ESI) m/z: 623.2 (M+H)+. 1H NMR (400 MHz, CD3OD) δ 8.85 (s, 1H), 8.71 (d, J=5.1 Hz, 1H), 8.32 (s, 1H), 7.90-7.80 (m, 2H), 7.71-7.64 (m, 2H), 7.62-7.57 (m, 1H), 7.52 (dd, J=5.2, 1.7 Hz, 1H), 7.49 (s, 1H), 6.20 (d, J=0.7 Hz, 1H), 5.98 (dd, J=12.7, 4.3 Hz, 1H), 4.05 (s, 3H), 2.70 (td, J=6.7, 3.2 Hz, 1H), 2.30 (tt, J=12.7, 4.4 Hz, 1H), 2.13-1.94 (m, 2H), 1.68-1.53 (m, 1H), 1.47 (ddd, J=14.9, 9.8, 5.3 Hz, 1H), 1.01 (d, J=6.8 Hz, 3H), 0.70 (m, 1H). 19F NMR (376 MHz, CD3OD) δ −57.99 (s), −77.75 (s). Analytical HPLC (Method A): RT=8.98 min, purity=99.1%; Factor XIa Ki=10 nM, Plasma Kallikrein Ki=4,900 nM.

Example 153

Preparation of (9R,13)-13-(4-{5-chloro-2-[4-(fluoromethyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate

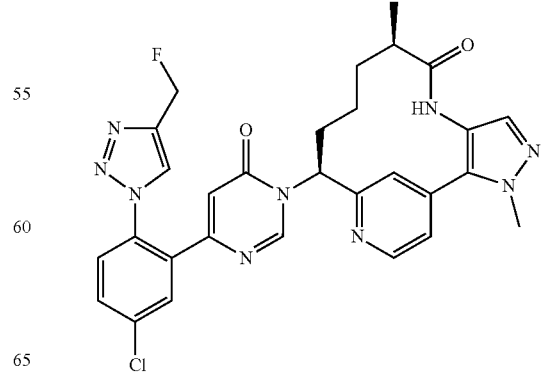

153A. Preparation of 6-{5-chloro-2-[4-(fluoromethyl)-1H-1,2,3-triazol-1-yl]phenyl}pyrimidin-4-ol

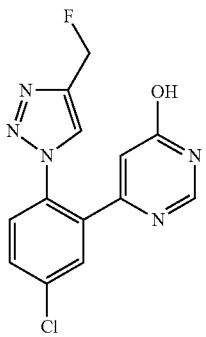 [SMILES: Oc1cc(-c2cc(Cl)ccc2-n2cc(CF)nn2)ncn1]

A solution of 4-{5-chloro-2-[4-(fluoromethyl)-1H-1,2,3-triazol-1-yl]phenyl}-6-methoxypyrimidine (35 mg, 0.109 mmol), prepared as described in Example 149A in ACN (1 mL) was treated with TMSI (75 μL, 0.55 mmol) and heated at 50° C. for 6 h. The reaction was poured into 10% aq Na$_2$S$_2$O$_3$. Sat NaHCO$_3$ was added and the mixture was extracted with EtOAc (2×). The combined organic layers were washed with brine, concentrated, and purified by normal phase chromatography to give 6-{5-chloro-2-[4-(fluoromethyl)-1H-1,2,3-triazol-1-yl]phenyl}pyrimidin-4-ol (14 mg, 41.8% yield). MS(ESI) m/z: 306.4(M+H)$^+$. $^1$H NMR (400 MHz, CDCl$_3$) δ 7.98 (s, 1H), 7.84 (d, J=2.4 Hz, 1H), 7.74 (d, J=2.4 Hz, 1H), 7.62 (dd, J=8.5, 2.3 Hz, 1H), 7.49 (d, J=8.4 Hz, 1H), 6.36 (s, 1H), 5.55 (d, J=48.2 Hz, 1H). $^{19}$F NMR (376 MHz, CDCl$_3$) δ −208.21 (s).

153B. Preparation of (9R,13S)-13-(4-{5-chloro-2-[4-(fluoromethyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one Trifluoroacetate

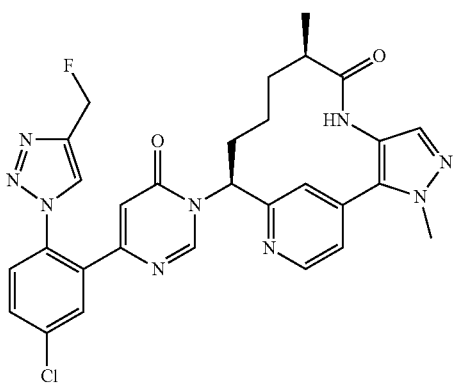 [SMILES: C[C@@H]1CCC[C@H](n2cnc(-c3cc(Cl)ccc3-n3cc(CF)nn3)cc2=O)c2cc(ccn2)-c2c(cnn2C)NC1=O]

(9R,13S)-13-(4-{5-Chloro-2-[4-(fluoromethyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate (12 mg, 37% yield) was prepared in a similar manner as the procedure described in Example 56, by replacing 6-{5-chloro-2-[4-(trifluoromethyl)-1H-1,2,3-triazol-1-yl]phenyl}pyrimidin-4-ol with 6-{5-chloro-2-[4-(fluoromethyl)-1H-1,2,3-triazol-1-yl]phenyl}pyrimidin-4-ol (14 mg, 0.046 mmol). MS(ESI) m/z: 588.3 (M+H)$^+$. $^1$H NMR (400 MHz, CD$_3$OD) δ 8.79 (s, 1H), 8.71 (d, J=5.1 Hz, 1H), 8.35 (d, J=3.1 Hz, 1H), 7.88 (d, J=2.4 Hz, 1H), 7.75-7.70 (m, 1H), 7.68 (s, 1H), 7.66-7.62 (m, 1H), 7.52 (dd, J=5.3, 1.5 Hz, 1H), 7.48 (s, 1H), 6.29 (s, 1H), 5.96 (dd, J=12.5, 4.2 Hz, 1H), 5.47 (d, J=48.6 Hz, 2H), 4.04 (s, 3H), 2.70 (td, J=6.7, 3.3 Hz, 1H), 2.33-2.20 (m, 1H), 2.12-1.92 (m, 2H), 1.66-1.53 (m, 1H), 1.52-1.37 (m, 1H), 1.00 (d, J=7.0 Hz, 3H), 0.69 (m, 1H). $^{19}$F NMR (376 MHz, CD$_3$OD) δ −77.74 (s), −207.90 (s). Analytical HPLC (Method A): RT=7.01 min, purity=98.5%; Factor XIa Ki=1.4 nM, Plasma Kallikrein Ki=150 nM.

Example 154

Preparation of 1-(4-chloro-2-{1-[(9R,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-1,2,3-triazole-4-carbonitrile Trifluoroacetate

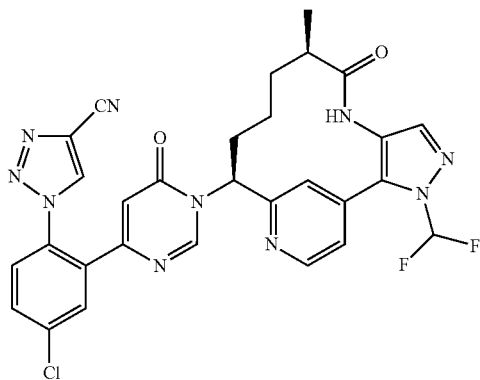 [SMILES: C[C@@H]1CCC[C@H](n2cnc(-c3cc(Cl)ccc3-n3cc(C(F)(F)F)nn3)cc2=O)c2cc(ccn2)-c2c(cnn2C(F)F)NC1=O]

1-(4-Chloro-2-{1-[(9R,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-1,2,3-triazole-4-carbonitrile trifluoroacetate (8 mg, 18% yield) was prepared in a similar manner as the procedure described in Example 56, by using 1-[4-chloro-2-(6-hydroxypyrimidin-4-yl)phenyl]-1H-1,2,3-triazole-4-carbonitrile (17.81 mg, 0.060 mmol), prepared as described in Intermediate 18. MS(ESI) m/z: 617.2 (M+H). $^1$H NMR (400 MHz, CD$_3$OD) δ 8.93 (s, 1H), 8.79 (s, 1H), 8.75 (d, J=5.1 Hz, 1H), 7.89 (d, J=2.2 Hz, 1H), 7.81-7.63 (m, 5H), 7.54-7.48 (m, 1H), 6.47 (d, J=0.7 Hz, 1H), 5.99 (dd, J=12.8, 4.4 Hz, 1H), 2.76-2.65 (m, 1H), 2.34-2.22 (m, 1H), 2.09-1.94 (m, 2H), 1.65-1.40 (m, 2H), 0.99 (d, J=6.8 Hz, 3H), 0.71-0.54 (m, 1H). Analytical HPLC (Method A): RT=9.04 min, purity=99.0%; Factor XIa Ki=0.1 nM, Plasma Kallikrein Ki=17 nM.

Example 155

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-3-($^2H_3$)methyl-9-methyl-3,4,7,15-tetraazatricyclo[12.3.1.0$^{2,6}$]octadeca-1(18),2(6),4,14,16-pentaen-8-one Trifluoroacetate

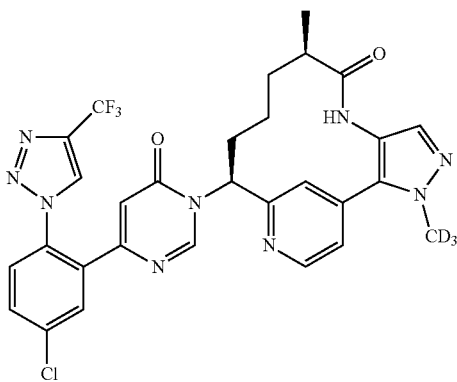 [SMILES: [2H]C([2H])([2H])n1ncc2c1-c1cccc(c1)[C@@H](n1cnc(-c3cc(Cl)ccc3-n3cc(C(F)(F)F)nn3)cc1=O)CCC[C@@H](C)C(=O)N2]

(9R,13S)-13-(4-{5-Chloro-2-[4-(trifluoromethyl)-1H-1,2,3-triazol-1-yl]phenyl}-6-oxo-1,6-dihydropyrimidin-1-yl)-3-($^2H_3$)methyl-9-methyl-3,4,7,15-tetraazatricyclo [12.3.1.0$^{2,6}$]octadeca-1(18),2(6),4,14,16-pentaen-8-one trifluoroacetate (11 mg, 30% yield) was prepared in a similar manner as the procedure described in Example 56, by using (9R,13S)-13-amino-3-($^2H_3$)methyl-9-methyl-3,4,7,15-tetraazatricyclo[12.3.1.0$^{2,6}$]octadeca-1(18),2(6),4,14,16-pentaen-8-one (15 mg, 0.050 mmol), prepared as described in Intermediate 33. MS(ESI) m/z: 627.3 (M+H). $^1$H NMR (400 MHz, CD$_3$OD) δ 8.81 (s, 1H), 8.77-8.66 (m, 2H), 7.89 (d, J=2.2 Hz, 1H), 7.79-7.64 (m, 3H), 7.59-7.51 (m, 1H), 7.49 (s, 1H), 6.44 (s, 1H), 5.97 (dd, J=12.4, 3.9 Hz, 1H), 2.76-2.62 (m, J=6.5, 3.4, 3.4 Hz, 1H), 2.34-2.21 (m, 1H), 2.12-1.94 (m, 2H), 1.68-1.53 (m, 1H), 1.51-1.39 (m, 1H), 1.00 (d, J=6.8 Hz, 3H), 0.78-0.63 (m, 1H). Analytical HPLC (Method A): RT=8.64 min, purity=99.4%; Factor XIa Ki=0.14 nM, Plasma Kallikrein Ki=33 nM.

Example 156

Preparation of (9R,13S)-13-(4-{5-chloro-2-[4-(difluoromethyl)-H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one Trifluoroacetate

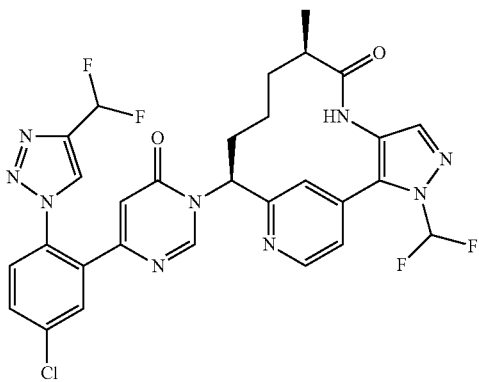

(9R,13S)-13-(4-{5-Chloro-2-[4-(difluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo [12.3.1.0$^{2,6}$]octadeca-1(18),2(6),4,14,16-pentaen-8-one trifluoroacetate (22 mg, 57% yield) was prepared in a similar manner as the procedure described in Example 56, using 6-{5-chloro-2-[4-(difluoromethyl)-1H-1,2,3-triazol-1-yl]phenyl}pyrimidin-4-ol (16.41 mg, 0.051 mmol), prepared as described in Intermediate 16, and (9R,13S)-13-amino-3-(difluoromethyl)-9-methyl-3,4,7,15-tetraazatricyclo [12.3.1.0$^{2,6}$]octadeca-1(18),2(6),4,14,16-pentaen-8-one (17 mg, 0.051 mmol), prepared as described in Intermediate 30. MS(ESI) m/z: 642.3 (M+H). $^1$H NMR (400 MHz, CD$_3$OD) δ 8.84 (s, 1H), 8.72 (d, J=5.1 Hz, 1H), 8.53 (t, J=1.4 Hz, 1H), 7.89 (d, J=2.2 Hz, 1H), 7.81-7.62 (m, 5H), 7.54-7.48 (m, 1H), 6.99 (t, J=54.4 Hz, 1H), 6.35 (d, J=0.7 Hz, 1H), 6.00 (dd, J=12.9, 4.7 Hz, 1H), 2.70 (td, J=6.7, 3.0 Hz, 1H), 2.33-2.19 (m, 1H), 2.08-1.93 (m, 2H), 1.64-1.51 (m, 1H), 1.51-1.39 (m, 1H), 0.99 (d, J=7.0 Hz, 3H), 0.68-0.52 (m, 1H). Analytical HPLC (Method A): RT=10.94 min, purity=99.0%; Factor XIa Ki=0.22 nM, Plasma Kallikrein Ki=50 nM.

Example 157

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one Trifluoroacetate

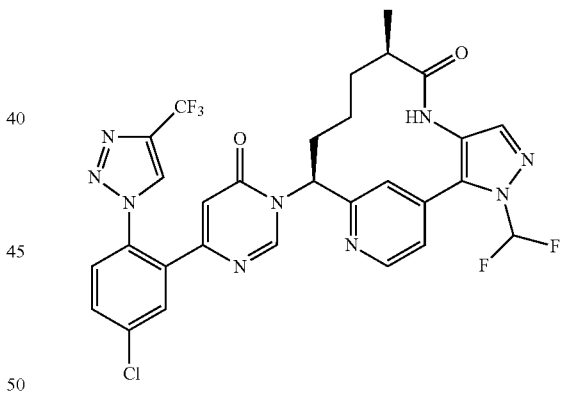

(9R,13S)-13-(4-{5-Chloro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo [12.3.1.0$^{2,6}$]octadeca-1(18),2(6),4,14,16-pentaen-8-one trifluoroacetate (20 mg, 50% yield) was prepared in a similar manner as the procedure described in Example 56, by using (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one (17 mg, 0.051 mmol), prepared as described in Intermediate 30. MS(ESI) m/z: 660.3 (M+H). $^1$H NMR (400 MHz, CD$_3$OD) δ 8.81 (d, J=3.7 Hz, 2H), 8.71 (d, J=5.1 Hz, 1H), 7.89 (d, J=2.2 Hz, 1H), 7.81-7.62 (m, 5H), 7.56-7.46 (m, 1H), 6.44 (s, 1H), 6.00 (dd, J=12.7, 4.5 Hz, 1H), 2.70 (td, J=6.5, 3.0 Hz, 1H), 2.32-2.20 (m, 1H), 2.10-1.91 (m, 2H), 1.65-1.51 (m, 1H), 1.51-1.39 (m, 1H), 0.99 (d, J=6.8 Hz, 3H), 0.70-0.51 (m, 1H). Analytical HPLC

Example 158

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-3-($^2$H$_3$)methyl-9-methyl-3,4,7-triazatricyclo[12.3.1.0$^{2,6}$]octadeca-1(18),2(6),4,14,16-pentaen-8-one Trifluoroacetate

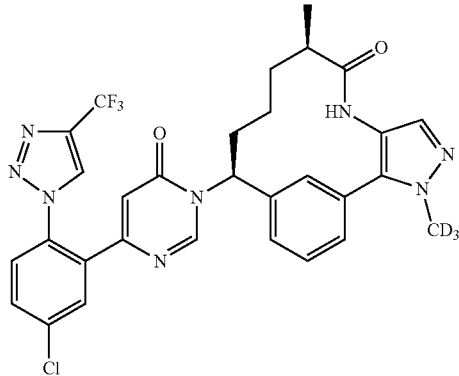

(9R,13S)-13-(4-{5-Chloro-2-[4-(trifluoromethyl)-1H-1,2,3-triazol-1-yl]phenyl}-6-oxo-1,6-dihydropyrimidin-1-yl)-3-($^2$H$_3$)methyl-9-methyl-3,4,7-triazatricyclo[12.3.1.0$^{2,6}$]octadeca-1(18),2(6),4,14,16-pentaen-8-one trifluoroacetate (12 mg, 36% yield) was prepared in a similar manner as the procedure described in Example 56, by using (9R,13S)-13-amino-3-($^2$H$_3$)methyl-9-methyl-3,4,7-triazatricyclo[12.3.1.0$^{2,6}$]octadeca-1(18),2(6),4,14,16-pentaen-8-one (16 mg, 0.053 mmol), prepared as described in Intermediate 36. MS(ESI) m/z: 626.3 (M+H)$^+$. $^1$H NMR (400 MHz, CD$_3$OD) δ 8.76 (d, J=0.7 Hz, 1H), 8.10 (s, 1H), 7.86 (d, J=2.2 Hz, 1H), 7.76-7.71 (m, 2H), 7.69-7.63 (m, 1H), 7.60-7.50 (m, 2H), 7.49 (s, 1H), 7.31-7.24 (m, 1H), 6.47 (d, J=0.4 Hz, 1H), 5.81 (dd, J=12.8, 3.3 Hz, 1H), 2.46 (ddd, J=10.3, 6.8, 3.6 Hz, 1H), 2.38-2.23 (m, 1H), 2.13-1.98 (m, 1H), 1.91-1.78 (m, 1H), 1.63-1.47 (m, 2H), 1.27-1.15 (m, 1H), 1.13 (d, J=6.8 Hz, 3H). Analytical HPLC (Method A): RT=9.06 min, purity=99.2%; Factor XIa Ki=0.1 nM, Plasma Kallikrein Ki=8 nM.

Example 159

Preparation of (9S,13R)-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one

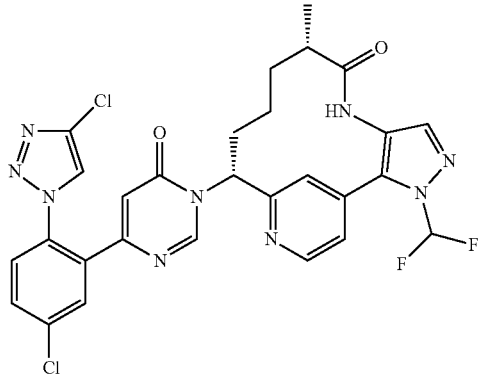 [SMILES: C[C@H]1CCC[C@@H](n2cnc(-c3cc(Cl)ccc3-n3cc(Cl)nn3)cc2=O)c2cc(ccn2)-c2c(cnn2C(F)F)NC1=O]

159A. Preparation of (R)—N-((4-chloropyridin-2-yl)methylene)-2-methylpropane-2-sulfinamide To a RBF was added 4-chloropicolinaldehyde (5.0 g, 35.3 mmol), CH$_2$Cl$_2$ (100 mL), (R)-2-methylpropane-2-sulfinamide (5.14 g, 42.4 mmol) and Cs$_2$CO$_3$ (34.5 g, 106 mmol). The reaction was stirred at rt overnight. The reaction was filtered through CELITE®. The filtrate was concentrated and the residue was purified using ISCO system (0-50% EtOAc/Hep gradient) to give (R)—N-((4-chloropyridin-2-yl)methylene)-2-methylpropane-2-sulfinamide (6.36 g, 26.0 mmol, 73.6% yield) as a clear oil. $^1$H NMR (400 MHz, CDCl$_3$) δ 8.71 (s, 1H), 8.67 (dd, J=5.3, 0.4 Hz, 1H), 8.05 (dd, J=2.0, 0.4 Hz, 1H), 7.44 (dd, J=5.3, 2.0 Hz, 1H), 1.33 (s, 9H); MS(ESI) m/z: 245.1 (M+H)$^+$.

159B. Preparation of (R)—N—((R)-1-(4-chloropyridin-2-yl)but-3-en-1-yl)-2-methylpropane-2-sulfinamide To a RBF was added (R)—N-((4-chloropyridin-2-yl)methylene)-2-methylpropane-2-sulfinamide (6.39 g, 26.1 mmol), THF (40 mL), 3-bromoprop-1-ene (3.39 mL, 39.2 mmol) and In (4.50 g, 39.2 mmol). The reaction was stirred at 60° C. overnight. The reaction was then partitioned between EtOAc (100 ml) and water (50 ml). The organic layer was separated, washed with sat NaCl (50 ml), dried over MgSO$_4$, filtered and concentrated. The residue was purified using ISCO system (0-100% EtOAc/Hep gradient) to give (R)—N—((R)-1-(4-chloropyridin-2-yl)but-3-en-1-yl)-2-methylpropane-2-sulfinamide (5.67 g, 19.8 mmol, 76% yield) as a clear oil. $^1$H NMR (500 MHz, CDCl$_3$) δ 8.50-8.41 (m, 1H), 7.36-7.30 (m, 1H), 7.26-7.18 (m, 1H), 5.71 (ddt, J=17.1, 10.3, 6.9 Hz, 1H), 5.12-4.99 (m, 2H), 4.77 (d, J=7.4 Hz, 1H), 4.48 (q, J=6.8 Hz, 1H), 2.66-2.51 (m, 2H), 1.30-1.27 (m, 9H); MS(ESI) m/z: 287.1 (M+H)$^+$.

159C. Preparation of (R)-tert-butyl (1-(4-chloropyridin-2-yl)but-3-en-1-yl)carbamate To a RBF was added (R)—N—((R)-1-(4-chloropyridin-2-yl)but-3-en-1-yl)-2-methylpropane-2-sulfinamide (5.67 g, 19.77 mmol), MeOH (100 mL) and 4 N HCl in dioxane (24.71 mL, 99 mmol). The reaction was stirred at rt for 30 min. The reaction was then concentrated to give a white solid. To this solid was added CH$_2$Cl$_2$ (100 mL), Et$_3$N (5.51 mL, 39.5 mmol) and (Boc)$_2$0 (5.51 mL, 23.72 mmol). The reaction was stirred at rt overnight. The reaction was diluted with CH$_2$Cl$_2$ (100 ml) and washed with water (100 ml) and sat NaCl (100 ml), dried over MgSO$_4$, filtered and concentrated. The residue was purified using ISCO system (0-50% EtOAc/Hex gradient) to give (R)-tert-butyl (1-(4-chloropyridin-2-yl)but-3-en-1-yl)carbamate (4.92 g, 17.40 mmol, 88% yield) as a clear oil. $^1$H NMR (500 MHz, CDCl$_3$) δ 8.47 (d, J=5.2 Hz, 1H), 7.27 (d, J=1.7 Hz, 1H), 7.21 (dd, J=5.2, 1.9 Hz, 1H), 5.80-5.60 (m, 1H), 5.49 (d, J=5.8 Hz, 1H), 5.15-5.00 (m, 2H), 4.81 (d, J=6.1 Hz, 1H), 2.67-2.50 (m, 2H), 1.50-1.39 (m, 9H); MS(ESI) m/z: 283.1 (M+H)$^+$.

159D. Preparation of (R)-tert-butyl (1-(4-(1-(difluoromethyl)-4-nitro-1H-pyrazol-5-yl)pyridin-2-yl)but-3-en-1-yl)carbamate To a RBF was added (R)-tert-butyl (1-(4-chloropyridin-2-yl)but-3-en-1-yl) carbamate (2.54 g, 15.56 mmol), di(adamantan-1-yl)(butyl)phosphine (0.507 g, 1.415 mmol), K$_2$CO$_3$ (5.87 g, 42.4 mmol), pivalic acid (0.433 g, 4.24 mmol) and dioxane (50 mL). The reaction mixture was purged with Ar for 5 min. To this mixture was added Pd(OAc)$_2$ (0.159 g, 0.707 mmol) and the reaction was heated at 100° C. for 4 h. The reaction was then partitioned with water (200 mL) and EtOAc (200 mL). The organic layer was separated and washed with water (200 mL) and sat NaCl (200 mL), dried over MgSO$_4$, filtered and concentrated to give the crude product which was then purified using ISCO system (0-60% EtOAc/Hex gradient) to give (R)-tert-butyl (1-(4-(1-(difluoromethyl)-4-nitro-1H-pyrazol-5-yl)pyridin-2-yl)but-3-en-1-yl)carbamate (4.12 g, 10.06 mmol, 71.1% yield) as a yellow oil. $^1$H NMR (500 MHz, CDCl$_3$) δ 8.82-8.78 (m, 1H), 8.36 (s, 1H), 7.34 (s, 1H), 7.32-7.30 (m, 1H), 7.23-6.96 (m, 1H), 5.76-5.65 (m, 1H), 5.59 (d, J=5.8 Hz, 1H), 5.14-5.04 (m, 2H), 4.93 (d, J=5.8 Hz, 1H), 2.67 (t, J=6.1 Hz, 2H), 1.46 (br. s., 9H); MS(ESI) m/z: 410.1 (M+H)$^+$.

159E. Preparation of (R)-tert-butyl (1-(4-(4-amino-1-(difluoromethyl)-1H-pyrazol-5-yl)pyridin-2-yl)but-3-en-1-yl)carbamate To a round bottom was added (R)-tert-butyl (1-(4-(1-(difluoromethyl)-4-nitro-1H-pyrazol-5-yl)pyridin-2-yl)but-3-en-1-yl)carbamate (4.12 g, 10.06 mmol), Zn (2.63 g, 40.3 mmol) MeOH (40 mL) and AcOH (4 mL). The reaction was heated in at 40° C. for 10 min. The reaction was then cooled to rt and partitioned between EtOAc (100 ml) and sat NaHCO$_3$(100 ml). The organic layer was separated, washed with water (100 ml) and sat NaCl (100 ml), dried over MgSO$_4$, filtered and concentrated. The residue was purified using ISCO system (0-30% MeOH/CH$_2$Cl$_2$ gradient) to give (R)-tert-butyl (1-(4-(4-amino-1-(difluoromethyl)-1H-pyrazol-5-yl)pyridin-2-yl)but-3-en-1-yl)carbamate (3.37 g, 8.88 mmol, 88% yield) as a yellow oil. $^1$H NMR (500 MHz, CDCl$_3$) δ 8.73-8.68 (m, 1H), 7.43 (s, 1H), 7.36 (s, 1H), 7.33 (d, J=5.0 Hz, 1H), 7.26-7.00 (m, 1H), 5.80-5.67 (m, 1H), 5.59 (br. s., 1H), 5.10 (s, 1H), 5.07 (d, J=4.4 Hz, 1H), 4.88 (d, J=6.1 Hz, 1H), 2.66 (t, J=6.2 Hz, 2H), 1.50-1.40 (m, 9H); MS(ESI) m/z: 380.1 (M+H)$^+$.

159F. Preparation of Tert-Butyl ((1R)-1-(4-(1-(difluoromethyl)-4-(2-methylbut-3-enamido)-1H-pyrazol-5-yl)pyridin-2-yl)but-3-en-1-yl)carbamate To a RBF was added (R)-tert-butyl (1-(4-(4-amino-1-(difluoromethyl)-1H-pyrazol-5-yl)pyridin-2-yl)but-3-en-1-yl)carbamate (3.37 g, 8.88 mmol), EtOAc (20 mL), 2-methylbut-3-enoic acid (0.889 g, 8.88 mmol) and pyridine (1.44 mL, 17.76 mmol). The solution was cooled in an ice bath and 2,4,6-tripropyl-1,3,5,2,4,6-trioxatriphosphorinane-2,4,6-trioxide (7.93 mL, 13.32 mmol) was added. The reaction was stirred at 0° C. for 2 h. The reaction was then partitioned between EtOAc (100 ml) and sat NaHCO$_3$(100 ml). The organic layer was separated, washed with water (100 ml) and brine (100 ml), dried over MgSO$_4$, filtered and concentrated. The residue was purified using ISCO system (0-80% EtOAc/Hex gradient) to give tert-butyl ((1R)-1-(4-(1-(difluoromethyl)-4-(2-methylbut-3-enamido)-1H-pyrazol-5-yl)pyridin-2-yl)but-3-en-1-yl)carbamate (3.33 g, 7.22 mmol, 81% yield) as a yellow oil. It was a mixture of 2 diastereomers. $^1$H NMR (500 MHz, CDCl$_3$) δ 8.74 (d, J=5.0 Hz, 1H), 8.36 (d, J=2.2 Hz, 1H), 7.34-7.30 (m, 1H), 7.28-7.24 (m, 1H), 7.22-7.06 (m, 2H), 5.98-5.83 (m, 1H), 5.76-5.65 (m, 1H), 5.51 (br. s., 1H), 5.28-5.18 (m, 2H), 5.15-5.03 (m, 2H), 4.86 (br. s., 1H), 3.22-3.04 (m, 1H), 2.66 (br. s., 2H), 1.50-1.42 (m, 9H), 1.33 (dd, J=7.0, 4.5 Hz, 3H); MS(ESI) m/z: 462.2 (M+H)$^+$.

159G and 159H. Preparation of Tert-Butyl N-[(9S,13R)-3-(difluoromethyl)-9-methyl-8-oxo-3,4,7,15-tetraazatricyclo[12.3.1.0$^{2,6}$]octadeca-1(18),2(6),4,10,14,16-hexaen-13-yl]carbamate, and tert-butyl N-[(9R,13R)-3-(difluoromethyl)-9-methyl-8-oxo-3,4,7,15-tetraazatricyclo[12.3.1.0$^{2,6}$]octadeca-1(18),2(6),4,10,14,16-hexaen-13-yl]carbamate To a RBF was added tert-butyl ((1R)-1-(4-(1-(difluoromethyl)-4-(2-methylbut-3-enamido)-1H-pyrazol-5-yl)pyridin-2-yl)but-3-en-1-yl)carbamate (3.33 g, 7.22 mmol) and EtOAc. Second Generation Grubbs Catalyst (1.531 g, 1.804 mmol) was added to the reaction. The reaction was refluxed under Ar for 2 days. The reaction was concentrated. The residue was purified using ISCO system (0-100% EtOAc/Hex gradient and then 100% EtOAc). Two diastereomers were separated. The compound that came off the column first was 159G, tert-butyl N-[(9S,13R)-3-(difluoromethyl)-9-methyl-8-oxo-3,4,7,15-tetraazatricyclo[12.3.1.0$^{2,6}$]octadeca-1(18),2(6),4,10,14,16-hexaen-13-yl]carbamate (490 mg, 1.13 mmol, 15.7% yield). $^1$H NMR (400 MHz, CDCl$_3$) δ 8.72 (d, J=5.1 Hz, 1H), 7.80 (s, 1H), 7.42 (s, 1H), 7.27 (m, 1H), 7.20 (br. s., 1H), 6.87 (s, 1H), 6.41 (d, J=7.5 Hz, 1H), 5.77 (ddd, J=15.2, 11.0, 4.0 Hz, 1H), 4.89-4.70 (m, 2H), 3.19-3.08 (m, 1H), 3.03 (d, J=12.5 Hz, 1H), 2.03-1.92 (m, 1H), 1.50 (s, 9H), 1.20 (d, J=6.6 Hz, 3H); MS(ESI) m/z: 434.1 (M+H)$^+$. The compound that came off the column second was 159H, tert-butyl N-[(9R,13R)-3-(difluoromethyl)-9-methyl-8-oxo-3,4,7,15-tetraazatricyclo[12.3.1.0$^{2,6}$]octadeca-1(18),2(6),4,10,14,16-hexaen-13-yl]carbamate (460 mg, 1.06 mmol, 14.7% yield). $^1$H NMR (400 MHz, CDCl$_3$) δ 8.71 (d, J=5.1 Hz, 1H), 7.83 (s, 1H), 7.37 (d, J=5.1 Hz, 1H), 7.26 (d, J=2.6 Hz, 1H), 6.89 (s, 1H), 6.68 (br. s., 1H), 6.28 (br. s., 1H), 5.84-5.69 (m, 1H), 5.47-5.32 (m, 1H), 4.82 (br. s., 1H), 3.11-2.90 (m, 2H), 2.15-1.98 (m, 1H), 1.52-1.44 (m, 9H), 1.37 (d, J=6.6 Hz, 3H); MS(ESI) m/z: 434.1 (M+H)$^+$.

159I. Preparation of Tert-Butyl N-[(9S,13R)-3-(difluoromethyl)-9-methyl-8-oxo-3,4,7,15-tetraazatricyclo[12.3.1.0$^{2,6}$]octadeca-1(18),2(6),4,14,16-pentaen-13-yl]carbamate To a 3-neck RBF wad added tert-butyl N-[(9S,13R)-3-(difluoromethyl)-9-methyl-8-oxo-3,4,7,15-tetraazatricyclo[12.3.1.0$^{2,6}$]octadeca-1(18),2(6),4,10,14,16-hexaen-13-yl]carbamate (485 mg, 1.119 mmol), EtOH (35 mL) and PtO$_2$ (127 mg, 0.559 mmol). The reaction was stirred under a H$_2$ balloon for 1 h. The reaction was carefully filtered through CELITE® and the filtrate was concentrated. The residue was purified using ISCO system (0-10% MeOH/CH$_2$Cl$_2$ gradient) to give tert-butyl N-[(9S,13R)-3-(difluoromethyl)-9-methyl-8-oxo-3,4,7,15-tetraazatricyclo[12.3.1.0$^{2,6}$]octadeca-1(18),2(6),4,14,16-pentaen-13-yl]carbamate (370 mg, 0.850 mmol, 76% yield) as a beige solid. $^1$H NMR (400 MHz, CDCl$_3$) δ 8.75 (d, J=5.1 Hz, 1H), 7.63 (s, 1H), 7.46 (s, 1H), 7.35 (s, 1H), 7.31 (m, J=3.5 Hz, 1H), 6.81 (br. s., 1H), 5.81 (d, J=7.9 Hz, 1H), 4.88 (br. s., 1H), 2.62 (td, J=6.5, 2.6 Hz, 1H), 2.13-1.99 (m, 1H), 1.90-1.77 (m, 1H), 1.69-1.62 (m, 1H), 1.56-1.51 (m, 1H), 1.49-1.41 (m, 9H), 1.31-1.17 (m, 1H), 1.03 (d, J=6.8 Hz, 3H), 0.41 (d, J=12.1 Hz, 1H); MS(ESI) m/z: 436.1 (M+H)$^+$.

159J. Preparation of (9S,13R)-13-amino-3-(difluoromethyl)-9-methyl-3,4,7,15-tetraazatricyclo[12.3.1.0²,⁶]octadeca-1(18),2(6),4,14,16-pentaen-8-one To a RBF was added tert-butyl N-[(9S,13R)-3-(difluoromethyl)-9-methyl-8-oxo-3,4,7,15-tetraazatricyclo[12.3.1.0²,⁶]octadeca-1(18),2(6),4,14,16-pentaen-13-yl]carbamate (370 mg, 0.850 mmol), dioxane (1 mL), MeOH (1 mL) and 4 N HCl (6.37 mL, 25.5 mmol). The reaction was stirred at rt for 1h. The reaction was concentrated to give the product as HCl salt. This HCl salt was dissolved in MeOH and was added to a pre-rinsed AGILENT® StratoSpheres SPE PL-HCO₃ MP Resin cartridge. Gravity filtration, eluting with MeOH, gave a clear, slightly brown filtrate. Concentration provided (9S,13R)-13-amino-3-(difluoromethyl)-9-methyl-3,4,7,15-tetraazatricyclo[12.3.1.0²,⁶]octadeca-1(18),2(6),4,14,16-pentaen-8-one (285 mg, 0.850 mmol, 100% yield) as a light brown solid. MS(ESI) m/z: 336.1 (M+H)⁺.

159K. Preparation of (9S,13R)-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0²,⁶]octadeca-1(18),2(6),4,14,16-pentaen-8-one (9S,13R)-{4-[5-Chloro-2-(4-chloro-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0²,⁶]octadeca-1(18),2(6),4,14,16-pentaen-8-one (230 mg, 360 μmol, 42.3% yield) was prepared in a similar manner as the procedure described in Example 56 by using 6-(5-chloro-2-(4-chloro-1H-1,2,3-triazol-1-yl)phenyl)pyrimidin-4-ol (331 mg, 0.850 mmol), prepared as described in Intermediate 9, and (9S,13R)-13-amino-3-(difluoromethyl)-9-methyl-3,4,7,15-tetraazatricyclo[12.3.1.0²,⁶]octadeca-1(18),2(6),4,14,16-pentaen-8-one (285 mg, 0.850 mmol). ¹H NMR (400 MHz, CD₃OD) δ 8.90 (s, 1H), 8.76 (d, J=5.1 Hz, 1H), 8.35 (s, 1H), 7.90 (d, J=2.4 Hz, 1H), 7.78-7.73 (m, 2H), 7.71 (d, J=0.7 Hz, 1H), 7.68 (t, 1H), 7.65 (s, 1H), 7.55-7.53 (m, 1H), 6.39 (d, J=0.9 Hz, 1H), 6.03 (dd, J=12.8, 4.4 Hz, 1H), 2.73 (td, J=6.5, 3.0 Hz, 1H), 2.31 (tt, J=12.8, 4.3 Hz, 1H), 2.11-1.97 (m, 2H), 1.67-1.44 (m, 2H), 1.01 (d, J=7.0 Hz, 3H), 0.64 (br. s., 1H); MS(ESI) m/z: 626.1 (M+H)⁺. Analytical HPLC (Method A): RT=7.96 min, purity=95.0%; Factor XIa Ki=14 nM, Plasma Kallikrein Ki=880 nM.

Example 160

Preparation of (9R,13R)-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0²,⁶]octadeca-1(18),2(6),4,14,16-pentaen-8-one

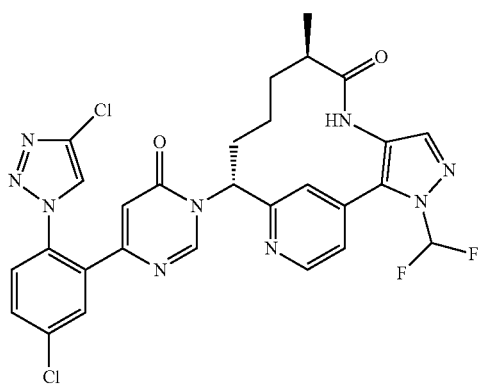 [SMILES: C[C@@H]1CCC[C@@H](n2cnc(-c3cc(Cl)ccc3-n3cc(Cl)nn3)cc2=O)c2cc(ccn2)-c2c(cnn2C(F)F)NC1=O]

160A. Preparation of Tert-Butyl N-[(9R,13R)-3-(difluoromethyl)-9-methyl-8-oxo-3,4,7,15-tetraazatricyclo[12.3.1.0²,⁶]octadeca-1(18),2(6),4,14,16-pentaen-13-yl]carbamate To a 3-neck RBF wad added tert-butyl N-[(9R,13R)-3-(difluoromethyl)-9-methyl-8-oxo-3,4,7,15-tetraazatricyclo[12.3.1.0²,⁶]octadeca-1(18),2(6),4,10,14,16-hexaen-13-yl]carbamate (450 mg, 1.038 mmol), EtOH (35 mL) and PtO₂ (118 mg, 0.519 mmol). The reaction was stirred under a H₂ balloon for 1 h. The reaction was carefully filtered through CELITE® and the filtrate was concentrated. The residue was purified using ISCO system (0-10% MeOH/CH₂Cl₂ gradient) to give tert-butyl N-[(9R,13R)-3-(difluoromethyl)-9-methyl-8-oxo-3,4,7,15-tetraazatricyclo[12.3.1.0²,⁶]octadeca-1(18),2(6),4,14,16-pentaen-13-yl]carbamate (300 mg, 0.689 mmol, 66.4% yield) as a beige solid. ¹H NMR (400 MHz, CDCl₃) δ 8.73 (d, J=5.3 Hz, 1H), 7.69 (s, 1H), 7.40 (d, J=5.1 Hz, 1H), 7.30 (m, J=4.2 Hz, 1H), 6.49 (br. s., 1H), 5.90 (d, J=7.0 Hz, 1H), 4.88 (br. s., 1H), 2.25-2.14 (m, 1H), 2.07 (d, J=9.5 Hz, 1H), 1.91-1.77 (m, 1H), 1.47 (s, 11H), 1.27 (d, J=6.8 Hz, 3H), 0.74 (d, J=11.2 Hz, 1H); MS(ESI) m/z: 436.1 (M+H)⁺.

160B. Preparation of (9R,13R)-13-amino-3-(difluoromethyl)-9-methyl-3,4,7,15-tetraazatricyclo[12.3.1.0²,⁶]octadeca-1(18),2(6),4,14,16-pentaen-8-one To a RBF was added tert-butyl N-[(9R,13R)-3-(difluoromethyl)-9-methyl-8-oxo-3,4,7,15-tetraazatricyclo[12.3.1.0²,⁶]octadeca-1(18),2(6),4,14,16-pentaen-13-yl]carbamate (300 mg, 0.689 mmol), dioxane (1 mL), MeOH (1 mL) and 4 N HCl (6.37 mL, 25.5 mmol). The reaction was stirred at rt for 1 h. The reaction was concentrated to give the product as HCl salt. This HCl salt was dissolved in MeOH and was added to a pre-rinsed AGILENT® StratoSpheres SPE PL-HCO₃ MP Resin cartridge. Gravity filtration, eluting with MeOH, gave a clear, slightly brown filtrate. Concentration provided (9R,13R)-13-amino-3-(difluoromethyl)-9-methyl-3,4,7,15-tetraazatricyclo[12.3.1.0²,⁶]octadeca-1(18),2(6),4,14,16-pentaen-8-one (220 mg, 0.656 mmol, 95% yield) as a light brown solid. MS(ESI) m/z: 336.1 (M+H)⁺.

160C. Preparation of (9R,13R)-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0²,⁶]octadeca-1(18),2(6),4,14,16-pentaen-8-one (9R,13R)-{4-[5-Chloro-2-(4-chloro-H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0²,⁶]octadeca-1(18),2(6),4,14,16-pentaen-8-one (140 mg, 219 μmol, 33.4% yield) was prepared in a similar manner as the procedure described in Example 56 by using 6-(5-chloro-2-(4-chloro-1H-1,2,3-triazol-1-yl)phenyl)pyrimidin-4-ol (255 mg, 0.656 mmol), prepared as described in Intermediate 9, and (9R,13R)-13-amino-3-(difluoromethyl)-9-methyl-3,4,7,15-tetraazatricyclo[12.3.1.0²,⁶]octadeca-1(18),2(6),4,14,16-pentaen-8-one (225 mg, 0.656 mmol). ¹H NMR (400 MHz, CD$_3$OD) δ 8.83 (s, 1H), 8.74 (d, J=5.1 Hz, 1H), 8.36 (s, 1H), 7.91 (d, J=2.2 Hz, 1H), 7.79 (s, 1H), 7.78-7.74 (m, 1H), 7.69 (t, 1H), 7.68-7.66 (m, 1H), 7.60 (s, 1H), 7.51 (d, J=4.8 Hz, 1H), 6.42 (d, J=0.7 Hz, 1H), 6.07 (dd, J=12.7, 4.3 Hz, 1H), 2.38-2.28 (m, 1H), 2.25-2.15 (m, 1H), 2.05-1.90 (m, 2H), 1.64-1.50 (m, 2H), 1.27 (d, J=6.8 Hz, 3H), 0.83 (d, J=13.6 Hz, 1H); MS(ESI) m/z: 626.1 (M+H)$^+$. Analytical HPLC (Method A): RT=10.37 min, purity=97.0%; Factor XIa Ki=18 nM, Plasma Kallikrein Ki=3,200 nM.

Example 161

Preparation of (9R,13S)-13-{4-[5-chloro-2-(pyridin-3-yl)phenyl]-6-oxo-1,6-dihydropyrimidin-1-yl}-3,9-dimethyl-3,4,7,15-tetraazatricyclo[12.3.1.0$^{2,6}$]octa-deca-1(18),2(6),4,14,16-pentaen-8-one

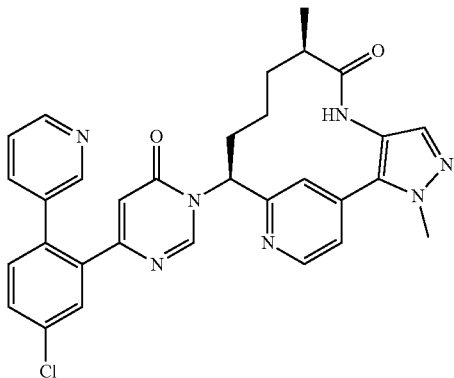 [SMILES: C[C@@H]1CCC[C@H](n2cnc(-c3cc(Cl)ccc3-c3cccnc3)cc2=O)c2cc(ccn2)-c2c(cnn2C)NC1=O]

In a microwave vial was added (9R,13S)-13-[4-(2-bromo-5-chlorophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one (0.02 g, 0.035 mmol), prepared in Example 138, pyridin-3-ylboronic acid (4.76 mg, 0.039 mmol), 3 M aq K$_3$PO$_4$ (0.035 ml, 0.106 mmol) and THF (1 ml). Ar was bubbled through the reaction for several min and then (DtBPF)PdCl$_2$ (1.15 mg, 1.761 µmol) was added. The reaction mixture was microwaved at 150° C. for 1 h, cooled to rt, and concentrated. Purification by reverse phase chromatography afforded (9R,13S)-13-{4-[5-chloro-2-(pyridin-3-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (3.21 mg, 12% yield) as a yellow solid. MS(ESI) m/z: 566.2 (M+H)$^+$. $^1$H NMR (500 MHz, CD$_3$OD) δ 8.79-8.68 (m, 4H), 8.34 (dt, J=8.2, 1.7 Hz, 1H), 7.90 (dd, J=8.0, 5.8 Hz, 1H), 7.81 (d, J=2.2 Hz, 1H), 7.71-7.66 (m, 2H), 7.57 (d, J=8.3 Hz, 1H), 7.53-7.47 (m, 2H), 6.52 (d, J=0.5 Hz, 1H), 5.98-5.90 (m, 1H), 4.04 (s, 3H), 2.74-2.64 (m, 1H), 2.30-2.19 (m, 1H), 2.10-1.93 (m, 2H), 1.63-1.53 (m, 1H), 1.50-1.40 (m, 1H), 1.00 (d, J=6.9 Hz, 3H), 0.77-0.61 (m, 1H). Analytical HPLC (Method A): RT=4.22 min, 99.8% purity; Factor XIa Ki=100 nM, Plasma Kallikrein Ki=5,700 nM.

Example 162

Preparation of (9R,13S)-13-(4-{5-chloro-2-[4-(2-hydroxypropan-2-yl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one

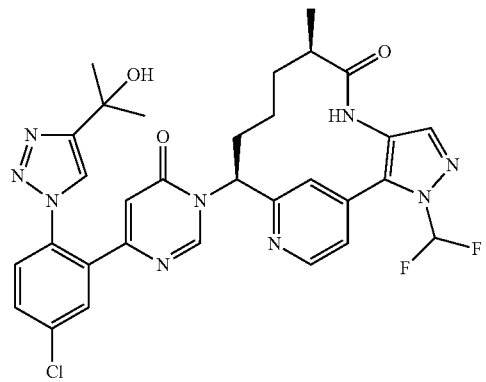 [SMILES: C[C@@H]1CCC[C@H](n2cnc(-c3cc(Cl)ccc3-n3cc(C(C)(C)O)nn3)cc2=O)c2cc(ccn2)-c2c(cnn2C(F)F)NC1=O]

162A. Preparation of 6-{5-chloro-2-[4-(2-hydroxypropan-2-yl)-1H-1,2,3-triazol-1-yl]phenyl}pyrimidin-4-ol

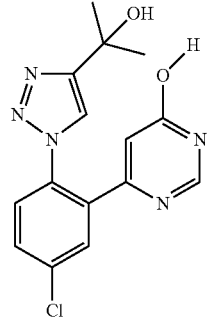 [SMILES: CC(C)(O)c1cn(-c2ccc(Cl)cc2-c2cc(O)ncn2)nn1]

6-{5-Chloro-2-[4-(2-hydroxypropan-2-yl)-1H-1,2,3-triazol-1-yl]phenyl}pyrimidin-4-ol was prepared by the condensation of an ACN (5 ml) solution consisting of 6-(2-azido-5-chlorophenyl)pyrimidin-4-ol (0.9g, 3.44 mmol) and 2-methylbut-3-yn-2-ol (0.289 g, 3.44 mmol) in the presence Cu$_2$O (0.05 g). The product, after ISCO silica gel chromatography with hexane:EtOAc as eluants, was obtained as an oil (0.5 g). $^1$H NMR (400 MHz, CDCl$_3$) δ 8.60-8.57 (m, 1H), 7.65-7.59 (m, 1H), 7.56-7.53 (m, 1H), 7.37-7.32 (m, 1H), 6.76-6.72 (m, 1H), 3.95 (s, 3H), 3.43-3.30 (m, 1H), 1.52 (s, 6H). The oil was then dissolved in AcOH (1 ml) and to this was added 48% aq HBr (0.5 ml) and the reaction was sealed. The reaction mixture was heated at 80° C. for 2 h and then concentrated to a gummy solid and water (10 ml) was added. A solid precipitated and was collected by decanting the solution. The solid was washed several times with water and the residue was dissolved in MeOH and the solution was concentrated to give 6-{5-chloro-2-[4-(2-hydroxypropan-2-yl)-1H-1,2,3-triazol-1-yl]phenyl}pyrimidin-4-ol (0.15 g, 13%) as a foam. LCMS m/z=332.1(M+H)$^1$. $^1$H NMR (400 MHz, CDCl$_3$) δ 11.51-11.06 (m, 1H), 8.33-8.09 (m, 1H), 7.90-7.78 (m, 1H), 7.71 (t, J=7.9 Hz, 1H), 7.39-7.29 (m, 1H), 6.87-6.68 (m, 1H), 5.80-5.66 (m, 1H), 5.27-5.17 (m, 1H), 2.12 (s, 6H).

162B. Preparation of (9R,13S)-13-(4-{5-chloro-2-[4-(2-hydroxypropan-2-yl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one (9R,13S)-13-(4-{5-Chloro-2-[4-(2-hydroxypropan-2-yl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one was prepared (4.2 mg, 21% yield) as a solid via the coupling of 6-{5-chloro-2-[4-(2-hydroxypropan-2-yl)-1H-1,2,3-triazol-1-yl]phenyl}pyrimidin-4-ol (0.01 g, 0.030 mmol) and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one (0.010 g, 0.030 mmol) using the HATU, DBU coupling methodology as described in Example 56. MS m/z=651.1(M+H)$^+$. $^1$H NMR (500 MHz, DMSO-d$_6$) δ 9.46-9.40 (m, 1H), 8.88-8.82 (m, 1H), 8.72-8.65 (m, 1H), 8.40-8.36 (m, 1H), 8.01-7.93 (m, 2H), 7.89 (s, 1H), 7.72-7.68 (m, 1H), 7.68-7.61 (m, 1H), 7.46-7.40 (m, 1H), 6.63-6.57 (m, 1H), 5.94-5.85 (m, 1H), 5.70-5.64 (m, 1H), 5.15-5.08 (m, 1H), 2.71-2.61 (m, 1H), 2.56 (s, 3H), 2.35-2.16 (m, 1H), 2.08-2.04 (m, 4H), 2.07-1.79 (m, 1H), 1.56-1.26 (m, 1H), 0.93-0.79 (d, 3H), 0.44-0.24 (m, 1H). Analytical HPLC (Method B): RT=1.75 min, purity=97%; Factor XIa Ki=1 nM, Plasma Kallikrein Ki=230 nM.

Example 163

Preparation of (9R,13S)-3-(difluoromethyl)-9-methyl-13-(6-oxo-4-{2-[4-(trifluoromethyl)-1H-1,2,3-triazol-1-yl]phenyl}-1,6-dihydropyrimidin-1-yl)-3,4,7,15-tetraazatricyclo[2.3.1.0$^{2,6}$]octadeca-1(18),2(6),4,14,16-pentaen-8-one

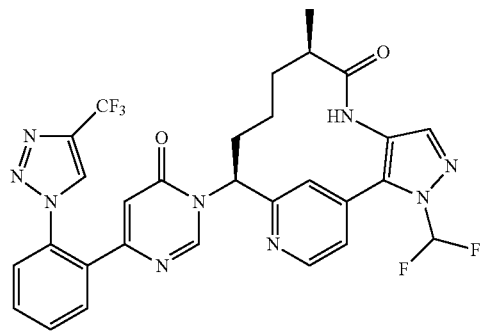 [SMILES: C[C@@H]1CCC[C@H](n2cnc(-c3ccccc3-n3cc(C(F)(F)F)nn3)cc2=O)c2cc(ccn2)-c2c(cnn2C(F)F)NC1=O]

(9R,13S)-3-(Difluoromethyl)-9-methyl-13-(6-oxo-4-{2-[4-(trifluoromethyl)-1H-1,2,3-triazol-1-yl]phenyl}-1,6-dihydropyrimidin-1-yl)-3,4,7,15-tetraazatricyclo[12.3.1.0$^{2,6}$]octadeca-1(18),2(6),4,14,16-pentaen-8-one was prepared (1.6 mg, 6.2% yield) as a solid via the coupling of 6-{2-[4-(trifluoromethyl)-1H-1,2,3-triazol-1-yl]phenyl}pyrimidin-4-ol (0.012 g, 0.04 mmol) and (9R,13S)-13-amino-3-(difluoromethyl)-9-methyl-3,4,7,15-tetraazatricyclo[12.3.1.0$^{2,6}$]octadeca-1(18),2(6), 4,14,16-pentaen-8-one (0.013 g, 0.04 mmol) using the HATU, DBU coupling methodology as described in Example 56. LCMS m/z=626.2 (M+H)$^+$. $^1$H NMR (500 MHz, DMSO-d$_6$) δ 9.46-9.42 (m, 1H), 9.20-9.15 (m, 1H), 8.76-8.67 (m, 2H), 7.89-7.83 (m, 2H), 7.80-7.73 (m, 3H), 7.70-7.64 (m, 1H), 7.46-7.39 (m, 1H), 6.42-6.36 (m, 1H), 5.94-5.86 (m, 1H), 2.70-2.60 (m, 1H), 2.31-2.18 (m, 1H), 2.10-1.94 (m, 1H), 1.88-1.77 (m, 1H), 1.52-1.28 (m, 2H), 0.91-0.82 (d, 3H), 0.49-0.19 (m, 1H). Analytical HPLC (Method B) RT=1.65 min, purity=96%; Factor XIa Ki=10 nM, Plasma Kallikrein Ki=5,900 nM.

Example 164

Preparation of (9R,13S)-3-(difluoromethyl)-13-(4-{5-fluoro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0$^{2,6}$]octadeca-1(18),2(6),4,14,16-pentaen-8-one

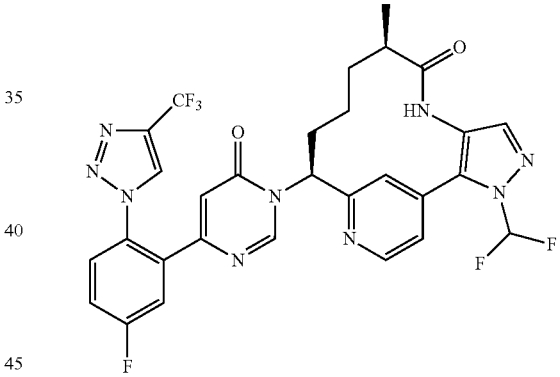

(9R,13S)-3-(Difluoromethyl)-13-(4-{5-fluoro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0$^{2,6}$]octadeca-1(18),2(6),4,14,16-pentaen-8-one was prepared (8 mg, 26% yield) as a solid via the coupling of 6-{5-fluoro-2-[4-(trifluoromethyl)-1H-1,2,3-triazol-1-yl]phenyl}pyrimidin-4-ol (0.015 g, 0.05 mmol) and (9R,13S)-13-amino-3-(difluoromethyl)-9-methyl-3,4,7,15-tetraazatricyclo[12.3.1.0$^{2,6}$]octadeca-1(18),2(6), 4,14,16-pentaen-8-one (0.015 g, 0.05 mmol) using the HATU, DBU coupling methodology described in Example 56. LCMS m/z=644.2 (M+H). $^1$H NMR (400 MHz, CD$_3$OD) δ 8.80-8.72 (m, 3H), 7.82-7.78 (m, 1H), 7.75-7.70 (m, 2H), 7.66-7.60 (m, 2H), 7.52-7.43 (m, 1H), 6.44-6.41 (m, 1H), 6.01-5.95 (m, 1H), 2.75-2.66 (m, 1H), 2.38-2.25 (m, 1H), 2.08-1.92 (m, 2H), 1.64-1.39 (m, 2H), 1.07-0.95 (d, 3H), 0.79-0.54 (m, 1H). Analytical HPLC (Method A) RT=8.22 min, purity=99%; Factor XIa Ki=5 nM, Plasma Kallikrein Ki=1,100 nM.

Example 165

Preparation of (9R,13S)-13-{4-[5-chloro-2-(4-hydroxy-1H-1,2,3-triazol-1-yl)phenyl]-6-oxo-1,6-ihydropyrimidin-1-yl}-3,9-dimethyl-3,4,7,15-tetraazatricyclo[12.3.1.0²,⁶]octadeca-1(18),2(6),4,14,16-pentaen-8-one Trifluoroacetate

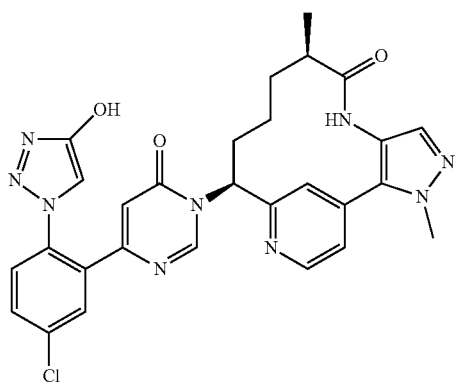 [SMILES: C[C@@H]1CCC[C@H](n2cnc(-c3cc(Cl)ccc3-n3cc(O)nn3)cc2=O)c2cc(ccn2)-c2c(cnn2C)NC1=O]

165A. Preparation of 6-(5-chloro-2-(4-hydroxy-1H-1,2,3-triazol-1-yl)phenyl)pyrimidin-4-ol To a solution of 6-(5-chloro-2-(4-ethoxy-1H-1,2,3-triazol-1-yl)phenyl)pyrimidin-4-ol, hydrobromide (0.027 g, 0.068 mmol) in DCM (1 ml) was added AlCl$_3$ (0.090 g, 0.68 mmol). The reaction was microwaved at 100° C. for 10 min, cooled to rt. Next the reaction was cooled in a dry ice/acetone bath and MeOH (1 ml) was added slowly. The reaction was allowed to warm to rt and the reaction was stirred until a solution formed. 1 N HCl (1 ml) was added and the resulting mixture was concentrated to dryness. Purification by reverse phase chromatography afforded 6-(5-chloro-2-(4-hydroxy-1H-1,2,3-triazol-1-yl)phenyl)pyrimidin-4-ol (0.012 g, 61.2% yield) as a white solid. MS(ESI) m/z: 290.3 (M+H)$^+$. $^1$H NMR (400 MHz, CD$_3$OD) δ 8.11 (s, 1H), 7.82 (d, J=2.4 Hz, 1H), 7.72-7.67 (m, 1H), 7.62-7.57 (m, 1H), 7.44 (s, 1H), 6.27 (d, J=0.7 Hz, 1H).

165B. Preparation of (9R,13S)-13-{4-[5-chloro-2-(4-hydroxy-1H-1,2,3-triazol-1-yl) phenyl]-6-oxo-1,6-ihydropyrimidin-1-yl}-3,9-dimethyl-3,4,7,15-tetraazatricyclo[12.3.1.0²,⁶]octadeca-1(18),2(6),4,14,16-pentaen-8-one trifluoroacetate (9R,13S)-13-{4-[5-Chloro-2-(4-hydroxy-1H-1,2,3-triazol-1-yl)phenyl]-6-oxo-1,6-ihydropyrimidin-1-yl}-3,9-dimethyl-3,4,7,15-tetraazatricyclo[12.3.1.0²,⁶]octadeca-1(18),2(6),4,14,16-pentaen-8-one trifluoroacetate (1.42 mg, 4.9% yield) was prepared in a similar manner as the procedure described in Example 162, using 6-(5-chloro-2-(4-hydroxy-1H-1,2,3-triazol-1-yl)phenyl)pyrimidin-4-ol (0.012 g, 0.041 mmol) and (9R,13S)-13-amino-3,9-dimethyl-3,4,7,15-tetraazatricyclo[12.3.1.0²,⁶]octadeca-1(18),2(6),4,14,16-pentaen-8-one (0.012 g, 0.041 mmol) prepared as described in Intermediate 32. MS(ESI) m/z: 572.3 (M+H)$^+$. $^1$H NMR (500 MHz, CD$_3$OD) δ 8.88 (s, 1H), 8.72 (d, J=5.2 Hz, 1H), 7.87 (d, J=2.2 Hz, 1H), 7.71-7.68 (m, 2H), 7.59 (d, J=8.5 Hz, 1H), 7.52 (dd, J=5.2, 1.7 Hz, 1H), 7.49 (s, 1H), 7.43 (s, 1H), 6.22 (d, J=0.8 Hz, 1H), 5.98 (dd, J=12.7, 4.1 Hz, 1H), 4.05 (s, 3H), 2.75-2.66 (m, 1H), 2.36-2.25 (m, 1H), 2.11-1.96 (m, 2H), 1.65-1.55 (m, 1H), 1.52-1.41 (m, 1H), 1.00 (d, J=6.9 Hz, 3H), 0.75-0.61 (m, 1H). Analytical HPLC (Method A): RT=6.12 min, 97.7% purity; Factor XIa Ki=13 nM, Plasma Kallikrein Ki=750 nM.

Example 166

Preparation of 5-(4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)pyridine-3-carbonitrile

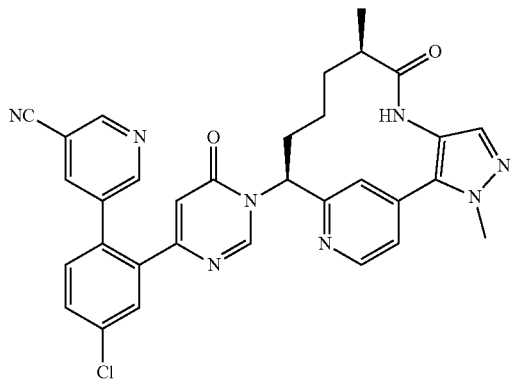 [SMILES: C[C@@H]1CCC[C@H](n2cnc(-c3cc(Cl)ccc3-c3cncc(C#N)c3)cc2=O)c2cc(ccn2)-c2c(cnn2C)NC1=O]

5-(4-Chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)pyridine-3-carbonitrile, 2 trifluoroacetate (1.5 mg, 5% yield) was prepared in a similar manner as the procedure described in Example 161, by replacing pyridin-3-ylboronic acid (4.76 mg, 0.039 mmol) with (5-cyanopyridin-3-yl)boronic acid (5.73 mg, 0.039 mmol). MS(ESI) m/z: 591.2 (M+H)$^+$. $^1$H NMR (500 MHz, CD$_3$OD) δ 8.84 (d, J=1.9 Hz, 1H), 8.79 (s, 1H), 8.72 (d, J=5.2 Hz, 1H), 8.64 (d, J=2.2 Hz, 1H), 8.08 (t, J=2.1 Hz, 1H), 7.75 (d, J=2.2 Hz, 1H), 7.67-7.62 (m, 2H), 7.54-7.47 (m, 3H), 6.43 (d, J=0.8 Hz, 1H), 6.00-5.94 (m, 1H), 4.04 (s, 3H), 2.74-2.66 (m, 1H), 2.31-2.23 (m, 1H), 2.11-1.94 (m, 2H), 1.64-1.54 (m, 1H), 1.51-1.42 (m, 1H), 1.00 (d, J=6.9 Hz, 3H), 0.75-0.60 (m, 1H). Analytical HPLC (Method A): RT=6.86 min, 99.5% purity; Factor XIa Ki=58 nM, Plasma Kallikrein Ki=6,500 nM.

Example 167

Preparation of (9R,13S)-13-{4-[5-chloro-2-(4-cyclopropyl-1H-1,2,3-triazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one Trifluoroacetate

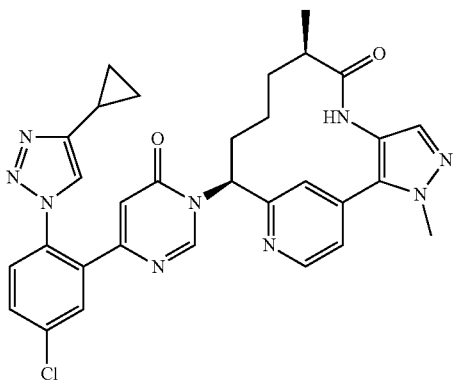 [SMILES: C[C@@H]1CCC[C@H](n2cnc(-c3cc(Cl)ccc3-n3cc(C4CC4)nn3)cc2=O)c2cc(ccn2)-c2c(cnn2C)NC1=O]

(9R,13S)-13-{4-[5-Chloro-2-(4-cyclopropyl-1H-1,2,3-triazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (3.96 mg, 9.6% yield) was prepared in a similar manner as the procedure described in Example 162, using 6-(5-chloro-2-(4-cyclopropyl-H-1,2,3-triazol-1-yl)phenyl)pyrimidin-4-ol hydrobromide (0.022 g, 0.057 mmol), prepared as described in Intermediate 13 and (9R,13S)-13-amino-3,9-dimethyl-3,4,7,15-tetraazatricyclo[12.3.1.0$^{2,6}$]octadeca-1(18),2(6),4,14,16-pentaen-8-one (0.017 g, 0.057 mmol) prepared as described in Intermediate 32. MS(ESI) m/z: 596.1 (M+H)$^+$. $^1$H NMR (400 MHz, CD$_3$OD) δ 8.85 (s, 1H), 8.72 (d, J=5.1 Hz, 1H), 7.88-7.86 (m, 2H), 7.72-7.67 (m, 2H), 7.59 (d, J=8.6 Hz, 1H), 7.51 (dd, J=5.1, 1.5 Hz, 1H), 7.49 (s, 1H), 6.17 (d, J=0.9 Hz, 1H), 5.98 (dd, J=12.7, 4.3 Hz, 1H), 4.04 (s, 3H), 2.75-2.66 (m, 1H), 2.34-2.24 (m, 1H), 2.12-1.93 (m, 3H), 1.66-1.40 (m, 2H), 1.03-0.94 (m, 5H), 0.81-0.58 (m, 3H). Analytical HPLC (Method A): RT=7.43 min, 98.0% purity; Factor XIa Ki=3.2 nM, Plasma Kallikrein Ki=210 nM.

Example 168

Preparation of Methyl 4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}benzoate

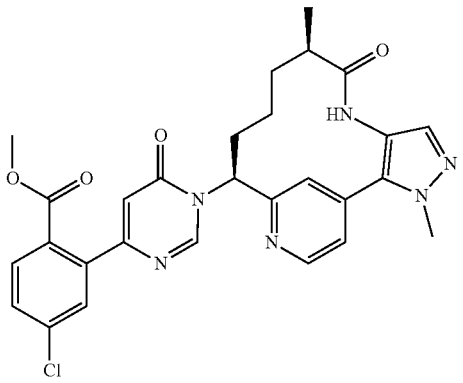 [SMILES: COC(=O)c1ccc(Cl)cc1-c1cc(=O)n([C@H]2CCC[C@@H](C)C(=O)Nc3cnn(C)c3-c3ccnc2c3)cn1]

168A. Preparation of methyl 4-chloro-2-(6-methoxypyrimidin-4-yl)benzoate, and 168B. Preparation 4-chloro-2-(6-methoxypyrimidin-4-yl)benzoic Acid A suspension of 4-chloro-6-methoxypyrimidine (0.067 g, 0.466 mmol) and (5-chloro-2-(methoxycarbonyl)phenyl)boronic acid (0.1 g, 0.466 mmol) in ACN (1.8 ml) was purged with Ar for several min, then 2 M Na$_2$CO$_3$ aq (0.47 ml, 0.94 mmol) was added, followed by Pd(Ph$_3$P)$_4$ (0.027 g, 0.023 mmol). The vial was capped and microwaved at 130° C. for 0.5 h, then cooled to rt. The reaction was diluted with EtOAc, washed with brine, dried over Na$_2$SO$_4$, filtered, and concentrated. Purification by normal phase chromatography afforded methyl 4-chloro-2-(6-methoxypyrimidin-4-yl)benzoate (0.086 g, 66% yield) as a colorless oil. MS(ESI) m/z: 279.0 (M+H)$^+$. The aqueous layer from the work-up was neutralized with 1 N HCl to afford a white cloudy suspension. The mixture was filtered, and the solid was rinsed with water and air-dried to afford 4-chloro-2-(6-methoxypyrimidin-4-yl)benzoic acid (0.026 g, 21% yield) as a white solid. MS(ESI) m/z: 265.0 (M+H)$^+$.

168C. Preparation of Methyl 4-chloro-2-(6-hydroxypyrimidin-4-yl)benzoate

Methyl 4-chloro-2-(6-hydroxypyrimidin-4-yl)benzoate (0.046 g, 56% yield) was prepared in a similar manner as the procedure described in Example 140B, by replacing 4-(5-chloro-2-(1-(difluoromethyl)-1H-pyrazol-4-yl)phenyl)-6-methoxypyrimidine with methyl 4-chloro-2-(6-methoxypyrimidin-4-yl)benzoate (0.086 g, 0.309 mmol). MS(ESI) m/z: 265.1 (M+H)$^+$. 1H NMR (500 MHz, CD$_3$OD) δ 8.19 (d, J=1.1 Hz, 1H), 7.83 (d, J=8.3 Hz, 1H), 7.62-7.57 (m, 2H), 6.57 (d, J=0.8 Hz, 1H), 3.76 (s, 3H).

168D. Preparation of Methyl 4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}benzoate Trifluoroacetate Methyl 4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}benzoate trifluoroacetate (0.067 g, 58% yield) was prepared in a similar manner as the procedure described in Example 56, by using methyl 4-chloro-2-(6-hydroxypyrimidin-4-yl)benzoate (0.046 g, 0.174 mmol), prepared as described in Example 168C. MS(ESI) m/z: 547.2 (M+H)$^+$. $^1$H NMR (500 MHz, CD$_3$OD) δ 8.99 (s, 1H), 8.74 (d, J=5.2 Hz, 1H), 7.83 (d, J=8.3 Hz, 1H), 7.75 (s, 1H), 7.62 (d, J=1.9 Hz, 1H), 7.59 (dd, J=8.3, 2.2 Hz, 1H), 7.55 (dd, J=5.2, 1.7 Hz, 1H), 7.50 (s, 1H), 6.62 (s, 1H), 6.07 (dd, J=12.7, 4.1 Hz, 1H), 4.05 (s, 3H), 3.75 (s, 3H), 2.76-2.68 (m, 1H), 2.41-2.33 (m, 1H), 2.14-2.03 (m, 2H), 1.67-1.58 (m, 1H), 1.55-1.45 (m, 1H), 1.02 (d, J=6.9 Hz, 3H), 0.79-0.66 (m, 1H). Analytical HPLC (Method A): RT=6.69 min, 99.9% purity; Factor XIa Ki=27 nM, Plasma Kallikrein Ki=650 nM.

Example 169

Preparation of (9R,13S)-13-{4-[3-chloro-6-(4-ethoxy-1H-1,2,3-triazol-1-yl)-2-fluorophenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate

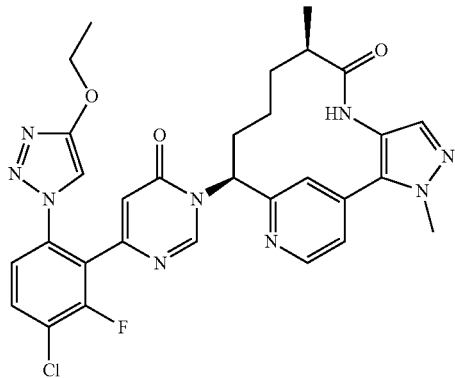 [SMILES: CCOc1cn(-c2ccc(Cl)c(F)c2-c2cc(=O)n([C@H]3CCC[C@@H](C)C(=O)Nc4cnn(C)c4-c4ccnc3c4)cn2)nn1]

(9R,13S)-13-{4-[3-Chloro-6-(4-ethoxy-1H-1,2,3-triazol-1-yl)-2-fluorophenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (22 mg, 41.7% yield) was prepared in a similar manner as the procedure described in Example 162, using 6-(3-chloro-6-(4-ethoxy-1H-1,2,3-triazol-1-yl)-2-fluorophenyl)pyrimidin-4-ol, hydrobromide (0.030 g, 0.072 mmol) and (9R,13S)-13-amino-3,9-dimethyl-3,4,7,15-tetraazatricyclo[12.3.1.0$^{2,6}$]octadeca-1(18),2(6),4,14,16-pentaen-8-one (0.025 g, 0.072 mmol) prepared as described in Intermediate 32. MS(ESI) m/z: 618.4 (M+H)$^+$. $^1$H NMR (400 MHz, CD$_3$OD) δ 8.87 (s, 1H), 8.73 (d, J=5.1 Hz, 1H), 7.82 (t, J=8.1 Hz, 1H), 7.71 (s, 1H), 7.66 (s, 1H), 7.56-7.47 (m, 3H), 6.54 (s, 1H), 6.00 (dd, J=12.5, 4.0 Hz, 1H), 4.13 (q, J=7.0 Hz, 2H), 4.05 (s, 3H), 2.76-2.65 (m, 1H), 2.36-2.24 (m, 1H), 2.14-1.95 (m, 2H), 1.67-1.54 (m, 1H), 1.53-1.41 (m, 1H), 1.35 (t, J=7.0 Hz, 3H), 1.00 (d, J=6.8 Hz, 3H), 0.77-0.59 (m, 1H). $^{19}$F NMR (376 MHz, CD$_3$OD) δ −77.75 (s), −115.15 (s). Analytical HPLC (Method A): RT=7.32 min, 99.7% purity; Factor XIa Ki=0.88 nM, Plasma Kallikrein Ki=95 nM.

Example 170

Preparation of (9R,13)-13-{4-[3-chloro-6-(4-cyclopropyl-1H-1,2,3-triazol-1-yl)-2-fluorophenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one Trifluoroacetate

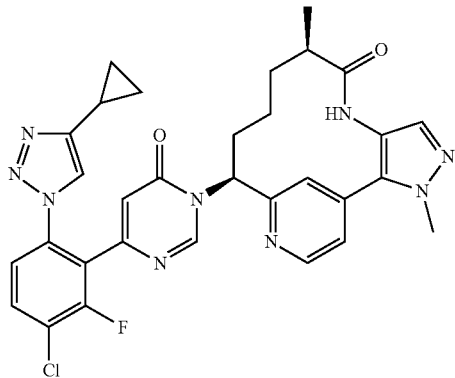 [SMILES: C[C@@H]1CCC[C@H](n2cnc(-c3c(-n4cc(C5CC5)nn4)ccc(Cl)c3F)cc2=O)c2cc(ccn2)-c2c(cnn2C)NC1=O]

(9R,13S)-13-{4-[3-Chloro-6-(4-cyclopropyl-1H-1,2,3-triazol-1-yl)-2-fluorophenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (0.02 g, 42.8% yield) was prepared in a similar manner as the procedure described in Example 160, by using 6-(3-chloro-6-(4-cyclopropyl-1H-1,2,3-triazol-1-yl)-2-fluorophenyl)pyrimidin-4-ol (0.021 g, 0.063 mmol), prepared as described in Intermediate 14, and (9R,13S)-13-amino-3,9-dimethyl-3,4,7,15-tetraazatricyclo[12.3.1.0$^{2,6}$]octadeca-1(18),2(6),4,14,16-pentaen-8-one (0.022 g, 0.063 mmol) prepared as described in Intermediate 32. MS(ESI) m/z: 614.4 (M+H)$^+$. $^1$H NMR (400 MHz, CD$_3$OD) δ 8.85 (s, 1H), 8.74 (d, J=5.1 Hz, 1H), 7.88-7.78 (m, 2H), 7.71 (s, 1H), 7.57-7.47 (m, 3H), 6.51 (s, 1H), 6.00 (dd, J=12.7, 4.1 Hz, 1H), 4.05 (s, 3H), 2.76-2.65 (m, 1H), 2.37-2.24 (m, 1H), 2.14-1.89 (m, 3H), 1.67-1.39 (m, 2H), 1.05-0.90 (m, 5H), 0.77-0.60 (m, 3H). $^{19}$F NMR (376 MHz, CD$_3$OD) δ −77.75 (s), −115.19 (s). Analytical HPLC (Method A): RT=7.35 min, 99.2% purity; Factor XIa Ki=0.93 nM, Plasma Kallikrein Ki=95 nM.

Example 171

Preparation of (9R,13S)-13-{4-[3-chloro-2-fluoro-6-(trifluoromethyl)phenyl]-6-oxo-1,6-dihydropyrimidin-1-yl}-3,9-dimethyl-3,4,7,15-tetraazatricyclo[12.3.1.0$^2$16]octadeca-1(18),2(6),4,14,16-pentaen-8-one Trifluoroacetate

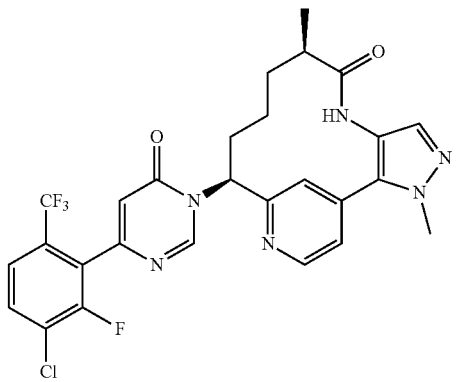 [SMILES: C[C@@H]1CCC[C@H](n2cnc(-c3c(C(F)(F)F)ccc(Cl)c3F)cc2=O)c2cc(ccn2)-c2c(cnn2C)NC1=O]

(9R,13S)-13-{4-[3-Chloro-2-fluoro-6-(trifluoromethyl)phenyl]-6-oxo-1,6-dihydropyrimidin-1-yl)}-3,9-dimethyl-3,4,7,15-tetraazatricyclo[12.3.1.0$^{2,6}$]octadeca-1(18),2(6),4,14,16-pentaen-8-one trifluoroacetate (0.016 g, 40.1% yield) was prepared in a similar manner as the procedure described in Example 162, using 6-(3-chloro-2-fluoro-6-(trifluoromethyl)phenyl)pyrimidin-4-ol hydrobromide (0.021 g, 0.057 mmol) and (9R,13S)-13-amino-3,9-dimethyl-3,4,7,15-tetraazatricyclo[12.3.1.0$^{2,6}$]octadeca-1(18),2(6),4,14,16-pentaen-8-one (0.02 g, 0.057 mmol) prepared as described in Intermediate 32. MS(ESI) m/z: 575.3 (M+H)$^+$. $^1$H NMR (400 MHz, CD$_3$OD) δ 9.05 (s, 1H), 8.77 (d, J=5.1 Hz, 1H), 7.85-7.79 (m, 1H), 7.75 (s, 1H), 7.66 (d, J=8.6 Hz, 1H), 7.55 (dd, J=5.3, 1.5 Hz, 1H), 7.50 (s, 1H), 6.60 (s, 1H), 6.08 (dd, J=12.7, 4.3 Hz, 1H), 4.06 (s, 3H), 2.77-2.67 (m, 1H), 2.45-2.34 (m, 1H), 2.16-2.04 (m, 2H), 1.70-1.44 (m, 2H), 1.02 (d, J=7.0 Hz, 3H), 0.81-0.64 (m, 1H). $^{19}$F NMR (376 MHz, CD$_3$OD) δ −59.04 (s), −77.76 (s), −115.37 (s). Ana-

Example 172

Preparation of (9R,13S)-13-{4-[3-chloro-6-(4-cyclopropyl-1H-1,2,3-triazol-1-yl)-2-fluorophenyl]-6-oxo-1,6-dihydropyrimidin-1-yl}-3-($^2$H$_3$)methyl-9-methyl-3,4,7-triazatricyclo[12.3.1.0$^{2,6}$]octadeca-1(18),2(6),4,14,16-pentaen-8-one

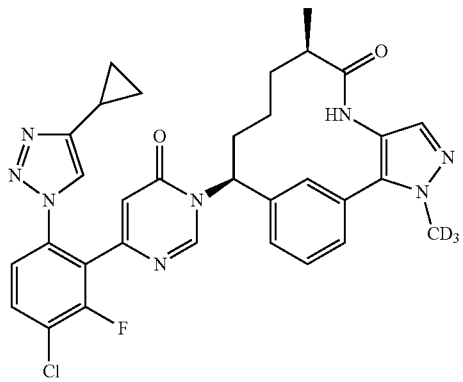 [SMILES: [2H]C([2H])([2H])n1ncc2c1-c1cccc(c1)[C@@H](n1cnc(-c3c(-n4cc(C5CC5)nn4)ccc(Cl)c3F)cc1=O)CCC[C@@H](C)C(=O)N2]

(9R,13S)-13-{4-[3-Chloro-6-(4-cyclopropyl-1H-1,2,3-triazol-1-yl)-2-fluorophenyl]-6-oxo-1,6-dihydropyrimidin-1-yl}-3-($^2$H$_3$)methyl-9-methyl-3,4,7-triazatricyclo[12.3.1.0$^{2,6}$]octadeca-1(18),2(6),4,14,16-pentaen-8-one (5.4 mg, 22.0% yield) was prepared in a similar manner as the procedure described in Example 160, using 6-(3-chloro-6-(4-cyclopropyl-1H-1,2,3-triazol-1-yl)-2-fluorophenyl)pyrimidin-4-ol (0.013 g, 0.040 mmol), prepared as described in Intermediate 14, and (9R,13S)-13-amino-3-($^2$H$_3$)methyl-9-methyl-3,4,7-triazatricyclo[12.3.1.0$^{2,6}$]octadeca-1(18),2(6),4,14,16-pentaen-8-one (0.012 g, 0.040 mmol), prepared as described in Intermediate 36. MS(ESI) m/z: 616.3 (M+H)$^+$. $^1$H NMR (400 MHz, CD$_3$OD) δ 8.17 (s, 1H), 7.84-7.73 (m, 3H), 7.62-7.54 (m, 2H), 7.50-7.46 (m, 2H), 7.32 (d, J=7.5 Hz, 1H), 6.55 (s, 1H), 5.82 (dd, J=12.8, 3.1 Hz, 1H), 2.52-2.42 (m, 1H), 2.38-2.27 (m, 1H), 2.15-2.03 (m, 1H), 1.97-1.81 (m, 2H), 1.62-1.49 (m, 2H), 1.26-1.10 (m, 4H), 1.00-0.90 (m, 2H), 0.73-0.63 (m, 2H). Analytical HPLC (Method A): RT=8.18 min, 100% purity; Factor XIa Ki=0.36 nM, Plasma Kallikrein Ki=45 nM.

Example 173

Preparation of (9R,13S)-13-(4-{3-chloro-2-fluoro-6-[4-(trifluoromethyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate

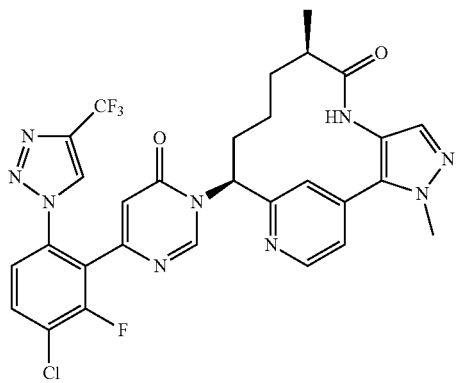 [SMILES: C[C@@H]1CCC[C@H](n2cnc(-c3c(-n4cc(C(F)(F)F)nn4)ccc(Cl)c3F)cc2=O)c2cc(ccn2)-c2c(cnn2C)NC1=O]

(9R,13S)-13-(4-{3-Chloro-2-fluoro-6-[4-(trifluoromethyl)-1H-1,2,3-triazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate (0.0215 g, 56.3% yield) was prepared in a similar manner as the procedure described in Example 160, using 6-(3-chloro-2-fluoro-6-(4-(trifluoromethyl)-1H-1,2,3-triazol-1-yl)phenyl)pyrimidin-4-ol (0.018 g, 0.050 mmol), prepared as described in Intermediate 11, and (9R,13S)-13-amino-3,9-dimethyl-3,4,7,15-tetraazatricyclo[12.3.1.0$^{2,6}$]octadeca-1(18),2(6),4,14,16-pentaen-8-one (0.015 g, 0.050 mmol), prepared as described in Intermediate 32. MS(ESI) m/z: 642.3 (M+H)$^+$. $^1$H NMR (400 MHz, CD$_3$OD) δ 8.82 (s, 1H), 8.78 (s, 1H), 8.70 (d, J=5.1 Hz, 1H), 7.91-7.83 (m, 1H), 7.70 (s, 1H), 7.59 (dd, J=8.6, 1.3 Hz, 1H), 7.53 (dd, J=5.2, 1.4 Hz, 1H), 7.48 (s, 1H), 6.65 (s, 1H), 6.00 (dd, J=12.7, 4.1 Hz, 1H), 4.05 (s, 3H), 2.74-2.64 (m, 1H), 2.33-2.22 (m, 1H), 2.12-1.93 (m, 2H), 1.66-1.39 (m, 2H), 1.00 (d, J=7.0 Hz, 3H), 0.75-0.58 (m, 1H). $^{19}$F NMR (376 MHz, CD$_3$OD) δ −62.57 (s), −77.74 (s), −114.95 (s). Analytical HPLC (Method A): RT=8.64 min, 99.6% purity, Factor XIa Ki=0.11 nM, Plasma Kallikrein Ki=13 nM.

Example 174

Preparation of 1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}-3-fluorophenyl)-1H-1,2,3-triazole-4-carbonitrile Trifluoroacetate

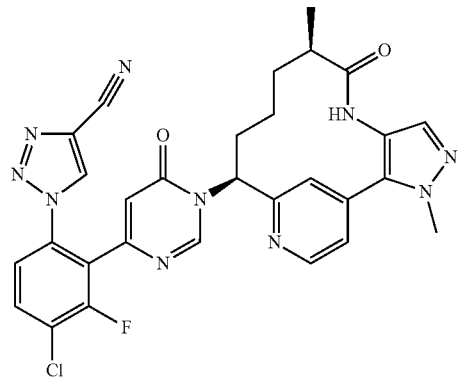 [SMILES: C[C@@H]1CCC[C@H](n2cnc(-c3c(-n4cc(C#N)nn4)ccc(Cl)c3F)cc2=O)c2cc(ccn2)-c2c(cnn2C)NC1=O]

1-(4-Chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-3-yl]-6-oxo-1,6-dihydropyrimidin-4-yl}-3-fluorophenyl)-1H-1,2,3-triazole-4-carbonitrile trifluoroacetate (0.0105 g, 0.015 mmol, 23.13% yield) was prepared in a similar manner as the procedure described in Example 160, using 1-(4-chloro-3-fluoro-2-(6-hydroxypyrimidin-4-yl)phenyl)-1H-1,2,3-triazole-4-carbonitrile (0.02 g, 0.063 mmol), prepared as described in Intermediate 12, and (9R,13S)-13-amino-3,9-dimethyl-3,4,7,15-tetraazatricyclo[12.3.1.0$^{2,6}$]octadeca-1(18),2(6),4,14,16-pentaen-8-one (0.019 g, 0.063 mmol) prepared as described in Intermediate 32. MS(ESI) m/z: 599.2 (M+H)$^+$. $^1$H NMR (400 MHz, CD$_3$OD) δ 8.93 (s, 1H), 8.78-8.74 (m, 2H), 7.93-7.86 (m, 1H), 7.70 (s, 1H), 7.60 (dd, J=8.7, 1.4 Hz, 1H), 7.53 (dd, J=5.1, 1.5 Hz, 1H), 7.49 (s, 1H), 6.65 (s, 1H), 5.99 (dd, J=12.4, 3.6 Hz, 1H), 4.05 (s, 3H), 2.75-2.65 (m, 1H), 2.35-2.23 (m, 1H), 2.13-1.95 (m, 2H), 1.67-1.41 (m, 2H), 1.01 (d, J=6.8 Hz, 3H), 0.78-0.60 (m, 1H). ¹⁹F NMR (376 MHz, CD₃OD) δ −77.72 (s), −114.94 (s). Analytical HPLC (Method A): RT=7.85 min, 99.2% purity; Factor XIa Ki=0.1 nM, Plasma Kallikrein Ki=6 nM.

Example 175

Preparation of (9R,13S)-13-(4-{3-chloro-2-fluoro-6-[4-(trifluoromethyl)-1H-1,2,3-triazol-1-yl]phenyl}-6-oxo-1,6-dihydropyrimidin-1-yl)-3-(²H₃)methyl-9-methyl-3,4,7,15-tetraazatricyclo[12.3.1.0²,⁶]octadeca-1(18),2(6),4,14,16-pentaen-8-one Trifluoroacetate

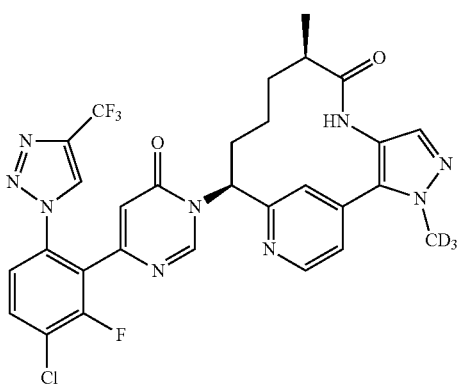 [SMILES: [2H]C([2H])([2H])n1ncc2c1-c1ccnc(c1)[C@@H](n1cnc(-c3c(-n4cc(C(F)(F)F)nn4)ccc(Cl)c3F)cc1=O)CCC[C@@H](C)C(=O)N2]

(9R,13S)-13-(4-{3-Chloro-2-fluoro-6-[4-(trifluoromethyl)-1H-1,2,3-triazol-1-yl]phenyl}-6-oxo-1,6-dihydropyrimidin-1-yl)-3-(²H₃)methyl-9-methyl-3,4,7,15-tetraazatricyclo[12.3.1.0²,⁶]octadeca-1(18),2(6),4,14,16-pentaen-8-one trifluoroacetate (0.018 g, 44.8% yield) was prepared in a similar manner as the procedure described in Example 160, using 6-(3-chloro-2-fluoro-6-(4-(trifluoromethyl)-1H-1,2,3-triazol-1-yl)phenyl)pyrimidin-4-ol (0.019 g, 0.053 mmol), prepared as described in Intermediate 11, and (9R,13S)-13-amino-3-(²H₃)methyl-9-methyl-3,4,7,15-tetraazatricyclo[12.3.1.0²,⁶]octadeca-1(18),2(6),4,14,16-pentaen-8-one (0.016 g, 0.053 mmol) prepared as described in Intermediate 33. MS(ESI) m/z: 645.3 (M+H)⁺. ¹H NMR (400 MHz, CD₃OD) δ 8.81 (d, J=0.7 Hz, 1H), 8.78 (s, 1H), 8.71 (d, J=5.1 Hz, 1H), 7.87 (dd, J=8.6, 7.7 Hz, 1H), 7.70 (s, 1H), 7.59 (dd, J=8.7, 1.4 Hz, 1H), 7.53 (dd, J=5.1, 1.5 Hz, 1H), 7.49 (s, 1H), 6.64 (s, 1H), 6.00 (dd, J=12.7, 4.3 Hz, 1H), 2.75-2.65 (m, 1H), 2.33-2.22 (m, 1H), 2.12-1.92 (m, 2H), 1.66-1.40 (m, 2H), 1.00 (d, J=6.8 Hz, 3H), 0.78-0.60 (m, 1H). ¹⁹F NMR (376 MHz, CD₃OD) δ −62.59 (s), −77.76 (s), −114.95 (s). Analytical HPLC (Method A): RT=8.44 min, 100% purity; Factor XIa Ki=0.11 nM, Plasma Kallikrein Ki=12 nM.

Example 176

Preparation of 1-(4-chloro-2-{1-[(9R,13S)-3-(difluoromethyl)-9-methyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}-3-fluorophenyl)-1H-1,2,3-triazole-4-carbonitrile Trifluoroacetate

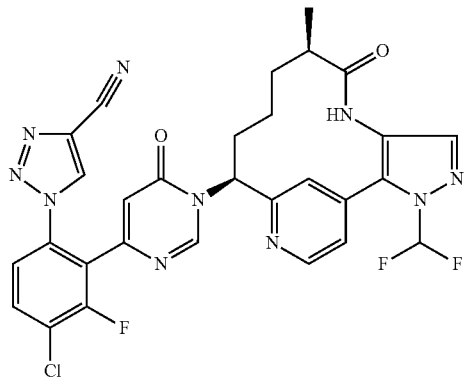 [SMILES: C[C@@H]1CCC[C@H](n2cnc(-c3c(-n4cc(C#N)nn4)ccc(Cl)c3F)cc2=O)c2cc(ccn2)-c2c(cnn2C(F)F)NC1=O]

1-(4-Chloro-2-{1-[(9R,13S)-3-(difluoromethyl)-9-methyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}-3-fluorophenyl)-1H-1,2,3-triazole-4-carbonitrile trifluoroacetate (9 mg, 20.1% yield) was prepared in a similar manner as the procedure described in Example 160, using 1-(4-chloro-3-fluoro-2-(6-hydroxypyrimidin-4-yl)phenyl)-1H-1,2,3-triazole-4-carbonitrile (18.89 mg, 0.060 mmol), prepared as described in Intermediate 12, and (9R,13S)-13-amino-3-(difluoromethyl)-9-methyl-3,4,7,15-tetraazatricyclo[12.3.1.0²,⁶]octadeca-1(18),2(6),4,14,16-pentaen-8-one (20 mg, 0.060 mmol) prepared as described in Intermediate 30. MS(ESI) m/z: 635.2 (M+H)⁺. ¹H NMR (400 MHz, CD₃OD) δ 8.92 (s, 1H), 8.81 (s, 1H), 8.77 (d, J=5.3 Hz, 1H), 7.92-7.85 (m, 1H), 7.81-7.48 (m, 5H), 6.65 (s, 1H), 6.00 (dd, J=12.7, 4.5 Hz, 1H), 2.76-2.65 (m, 1H), 2.34-2.22 (m, 1H), 2.10-1.95 (m, 2H), 1.64-1.41 (m, 2H), 0.99 (d, J=6.8 Hz, 3H), 0.73-0.55 (m, 1H). ¹⁹F NMR (376 MHz, CD₃OD) δ −77.28 (s), −90.87-92.15 (m), −96.05-−97.42 (m), −114.86 (s). Analytical HPLC (Method A): RT=9.02 min, 99.6% purity; Factor XIa Ki=0.1 nM, Plasma Kallikrein Ki=7 nM.

Example 177

Preparation of (9R,13S)-13-{4-[3-chloro-6-(4-cyclopropyl-1H-1,2,3-triazol-1-yl)-2-fluorophenyl]-6-oxo-1,6-dihydropyrimidin-1-yl}-3-(difluoromethyl)-9-methyl-3,4,7,15-tetraazatricyclo[12.3.1.0²,⁶]octadeca-1(18),2(6),4,14,16-pentaen-8-one Trifluoroacetate

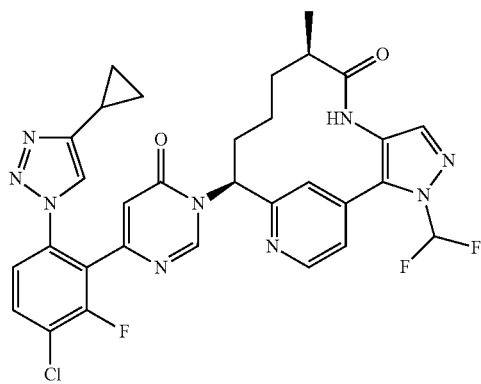 [SMILES: C[C@@H]1CCC[C@H](n2cnc(-c3c(-n4cc(C5CC5)nn4)ccc(Cl)c3F)cc2=O)c2cc(ccn2)-c2c(cnn2C(F)F)NC1=O]

(9R,13S)-13-{4-[3-Chloro-6-(4-cyclopropyl-1H-1,2,3-triazol-1-yl)-2-fluorophenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one trifluoroacetate (7.07 mg, 20.6% yield) was prepared in a similar manner as the procedure described in Example 160, using 6-(3-chloro-6-(4-cyclopropyl-1H-1,2,3-triazol-1-yl)-2-fluorophenyl) pyrimidin-4-ol (0.015 g, 0.045 mmol), prepared as described in Intermediate 14, and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one (0.015 g, 0.045 mmol) prepared as described in Intermediate 30. MS(ESI) m/z: 650.5 (M+H)$^+$. $^1$H NMR (400 MHz, CD$_3$OD) δ 8.92 (s, 1H), 8.76 (d, J=5.1 Hz, 1H), 7.86-7.47 (m, 7H), 6.50 (s, 1H), 6.04 (dd, J=12.5, 4.4 Hz, 1H), 2.77-2.66 (m, 1H), 2.35-2.24 (m, 1H), 2.10-1.87 (m, 3H), 1.66-1.41 (m, 2H), 1.02-0.89 (m, 5H), 0.73-0.50 (m, 3H). $^{19}$F NMR (376 MHz, CD$_3$OD) δ −77.68 (s), −90.26--91.77 (m), −95.81--97.73 (m), −115.24 (s). Analytical HPLC (Method A): RT=8.74 min, 99.8% purity; Factor XIa Ki=0.50 nM, Plasma Kallikrein Ki=120 nM.

Example 178

Preparation of (9R,13S)-13-(4-{3-chloro-6-[4-(difluoromethyl)-1H-1,2,3-triazol-1-yl]-2-fluorophenyl}-6-oxo-1,6-dihydropyrimidin-1-yl)-3-(difluoromethyl)-9-methyl-3,4,7,15-tetraazatricyclo[12.3.1.0$^{2,6}$]Octadeca-1(18),2(6),4,14,16-pentaen-8-one Trifluoroacetate

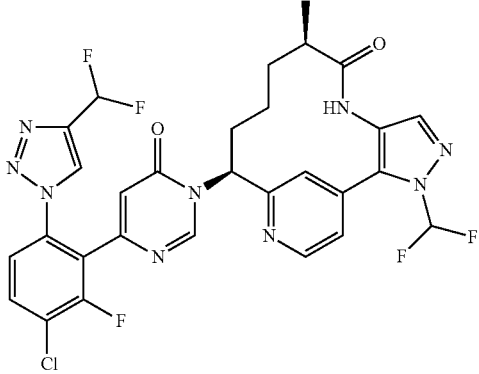 [SMILES: C[C@@H]1CCC[C@H](n2cnc(-c3c(-n4cc(C(F)F)nn4)ccc(Cl)c3F)cc2=O)c2cc(ccn2)-c2c(cnn2C(F)F)NC1=O]

(9R,13S)-13-(4-{3-Chloro-6-[4-(difluoromethyl)-1H-1,2,3-triazol-1-yl]-2-fluorophenyl}-6-oxo-1,6-dihydropyrimidin-1-yl)-3-(difluoromethyl)-9-methyl-3,4,7,15-tetraazatricyclo[12.3.1.0$^{2,6}$]Octadeca-1(18),2(6),4,14,16-pentaen-8-one trifluoroacetate (0.016 g, 46.0% yield) was prepared in a similar manner as the procedure described in Example 160, using 6-(3-chloro-6-(4-(difluoromethyl)-1H-1,2,3-triazol-1-yl)-2-fluorophenyl)pyrimidin-4-ol (0.015 g, 0.045 mmol), prepared as described in Intermediate 21, and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one (15 mg, 0.045 mmol), prepared as described in Intermediate 30. MS(ESI) m/z: 660.5 (M+H)$^+$. $^1$H NMR (400 MHz, CD$_3$OD) δ 8.86 (s, 1H), 8.73 (d, J=5.1 Hz, 1H), 8.52 (t, J=1.4 Hz, 1H), 7.86 (dd, J=8.6, 7.5 Hz, 1H), 7.80-7.48 (m, 5H), 6.96 (t, J=54.0 Hz, 1H), 6.60 (s, 1H), 6.02 (dd, J=12.5, 4.4 Hz, 1H), 2.76-2.66 (m, 1H), 2.32-2.20 (m, 1H), 2.09-1.92 (m, 2H), 1.65-1.40 (m, 2H), 0.99 (d, J=7.0 Hz, 3H), 0.69-0.52 (m, 1H). $^{19}$F NMR (376 MHz, CD$_3$OD) δ −77.73 (s), −90.24--92.35 (m), −95.39--97.64 (m), −114.57 (d, J=10.3 Hz), −115.06 (s). Analytical HPLC (Method A): RT=8.91 min, 99.6% purity; Factor XIa Ki=0.1 nM, Plasma Kallikrein Ki=16 nM.

Example 179

Preparation of (9R,13S)-13-(4-{3-chloro-6-[4-(difluoromethyl)-1H-1,2,3-triazol-1-yl]-2-fluorophenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one Trifluoroacetate

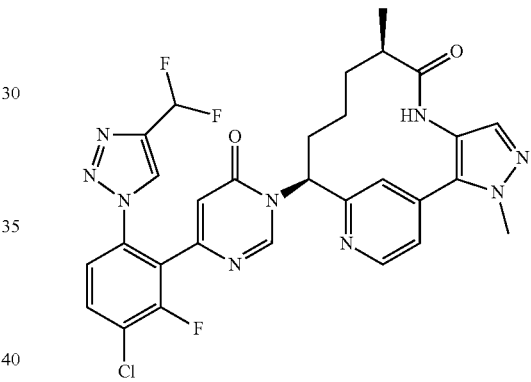

(9R,13S)-13-(4-{3-Chloro-6-[4-(difluoromethyl)-1H-1,2,3-triazol-1-yl]-2-fluorophenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate (0.015 g, 43.3% yield) was prepared in a similar manner as the procedure described in Example 160, using 6-(3-chloro-6-(4-(difluoromethyl)-1H-1,2,3-triazol-1-yl)-2-fluorophenyl)pyrimidin-4-ol (0.016 g, 0.047 mmol), prepared as described in Intermediate 21, and (9R,13S)-13-amino-3,9-dimethyl-3,4,7,15-tetraazatricyclo[12.3.1.0$^{2,6}$]octadeca-1(18),2(6),4,14,16-pentaen-8-one (0.014 g, 0.047 mmol) prepared as described in Intermediate 32. MS(ESI) m/z: 624.5 (M+H)$^+$. $^1$H NMR (400 MHz, CD$_3$OD) δ 8.79 (s, 1H), 8.72 (d, J=5.1 Hz, 1H), 8.52 (t, J=1.3 Hz, 1H), 7.86 (dd, J=8.6, 7.7 Hz, 1H), 7.70 (s, 1H), 7.59-7.51 (m, 2H), 7.48 (s, 1H), 6.97 (t, J=54.0 Hz, 1H), 6.60 (s, 1H), 5.99 (dd, J=12.7, 4.3 Hz, 1H), 4.05 (s, 3H), 2.75-2.64 (m, 1H), 2.34-2.21 (m, 1H), 2.12-1.93 (m, 2H), 1.66-1.39 (m, 2H), 1.00 (d, J=6.8 Hz, 3H), 0.78-0.59 (m, 1H). $^{19}$F NMR (376 MHz, CD$_3$OD) δ −77.74 (s), −114.52 (d, J=8.0 Hz), −115.03 (s). Analytical HPLC (Method A): RT=7.79 min, 99.6% purity; Factor XIa Ki=0.14 nM, Plasma Kallikrein Ki=16 nM.

Example 180

Preparation of (9R,13S)-3-[4-(3-chlorophenyl)-6-oxo-1,6-dihydropyrimidin-1-yl]-3,9-dimethyl-3,4,7,15-tetraazatricyclo[12.3.1.0$^{2,6}$]Octadeca-1 (18),2(6),4,14,16-pentaen-8-one

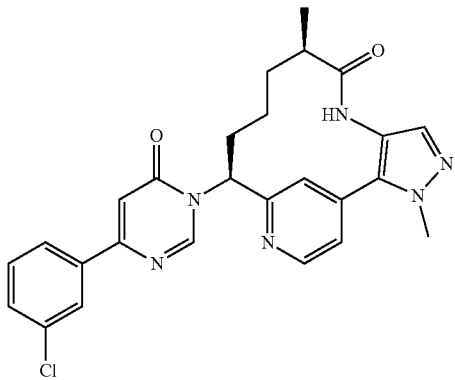 [SMILES: C[C@@H]1CCC[C@H](n2cnc(-c3cccc(Cl)c3)cc2=O)c2cc(ccn2)-c2c(cnn2C)NC1=O]

(9R,13S)-13-[4-(3-Chlorophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one trifluoroacetate (3.35 mg, 15% yield) was prepared in a similar manner as the procedure described in Example 161, by replacing pyridin-3-ylboronic acid (4.76 mg, 0.039 mmol) with lithium 4-methyl-1-(1-methyl-1H-1,2,3-triazol-4-yl)-2,6,7-trioxa-1-borabicyclo[2.2.2]octan-1-uide (8.41 mg, 0.039 mmol). MS(ESI) m/z: 489.3 (M+H)$^+$. $^1$H NMR (500 MHz, CD$_3$OD) δ 9.01 (s, 1H), 8.73 (d, J=5.2 Hz, 1H), 8.08 (t, J=1.7 Hz, 1H), 7.94 (dt, J=7.5, 1.6 Hz, 1H), 7.73 (s, 1H), 7.54-7.44 (m, 4H), 6.93 (d, J=0.5 Hz, 1H), 6.04 (dd, J=12.5, 4.0 Hz, 1H), 4.05 (s, 3H), 2.76-2.68 (m, 1H), 2.42-2.32 (m, 1H), 2.15-2.02 (m, 2H), 1.67-1.57 (m, 1H), 1.55-1.45 (m, 1H), 1.02 (d, J=6.9 Hz, 3H), 0.81-0.65 (m, 1H). Analytical HPLC (Method A): RT=7.33 min, 99.0% purity; Factor XIa Ki=360 nM, Plasma Kallikrein Ki=6,800 nM.

Example 181

Preparation of 4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}benzoic Acid

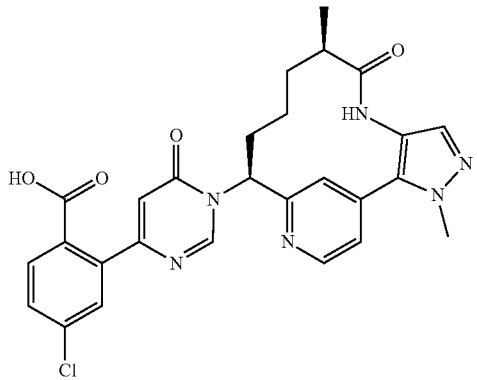 [SMILES: C[C@@H]1CCC[C@H](n2cnc(-c3cc(Cl)ccc3C(=O)O)cc2=O)c2cc(ccn2)-c2c(cnn2C)NC1=O]

To the solution of methyl 4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}benzoate trifluoroacetate (0.02 g, 0.030 mmol), prepared as described in Example 168, in DCM (0.5 ml) at 0° C. was added BBr$_3$ (0.029 ml, 0.30 mmol). The reaction became a yellow suspension. After 10 min, the cold bath was removed, and the reaction was stirred at rt. After 18 h, the reaction was cooled to 0° C. and carefully quenched with MeOH. The reaction was warmed to rt and then concentrated. Purification by reverse phase chromatography afforded 4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}benzoic acid trifluoroacetate (0.011 g, 56% yield) as a white solid. MS(ESI) m/z: 533.1 (M+H)$^+$. $^1$H NMR (400 MHz, CD$_3$OD) δ 9.00 (s, 1H), 8.74 (d, J=5.1 Hz, 1H), 7.90 (d, J=9.0 Hz, 1H), 7.73 (s, 1H), 7.61-7.56 (m, 2H), 7.53 (dd, J=5.3, 1.5 Hz, 1H), 7.50 (s, 1H), 6.58 (s, 1H), 6.07 (dd, J=12.8, 4.2 Hz, 1H), 4.05 (s, 3H), 2.77-2.67 (m, 1H), 2.41-2.30 (m, 1H), 2.16-2.00 (m, 2H), 1.68-1.57 (m, 1H), 1.55-1.43 (m, 1H), 1.01 (d, J=7.0 Hz, 3H), 0.79-0.62 (m, 1H). Analytical HPLC (Method A): RT=5.54 min, 99.9% purity; Factor XIa Ki=500 nM.

Example 182

Preparation of (9R,13S)-3-(difluoromethyl)-9-methyl-13-{6-oxo-4-[5-(propan-2-yl)-2-[4-(trifluoromethyl)-1H-1,2,3-triazol-1-yl]phenyl]-1,6-dihydropyrimidin-1-yl}-3,4,7,15-tetraazatricyclo[12.3.1.0$^{2,6}$]octadeca-1(18),2(6),4,14,16-pentaen-8-one

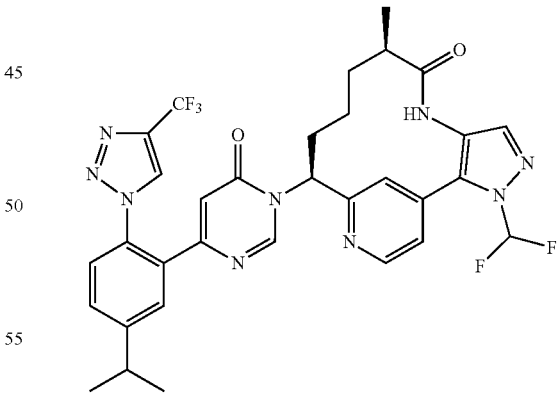

182A. Preparation of 4-isopropyl-2-(4,4,5,5-tetramethyl-1,3,2-dioxaborolan-2-yl)aniline 4-Isopropyl-2-(4,4,5,5-tetramethyl-1,3,2-dioxaborolan-2-yl)aniline (1.21 g, 99%) was prepared in a similar manner as Example 119A starting from 2-bromo-4-isopropylaniline. MS(ESI) m/z: 180 (M-C$_6$H$_{10}$+H).

182B. Preparation 4-isopropyl-2-(6-methoxypyrimidin-4-yl)aniline

4-Isopropyl-2-(6-methoxypyrimidin-4-yl)aniline (511 mg, 46%) was prepared in a similar manner as Example 119B using 4-isopropyl-2-(4,4,5,5-tetramethyl-1,3,2-dioxaborolan-2-yl)aniline. MS(ESI) m/z: 244.1 (M+H)$^+$.

182C. Preparation of 4-(5-isopropyl-2-(4-(trifluoromethyl)-1H-1,2,3-triazol-1-yl) phenyl)-6-methoxypyrimidine 4-(5-Isopropyl-2-(4-(trifluoromethyl)-1H-1,2,3-triazol-1-yl)phenyl)-6-methoxypyrimidine (522 mg, 68%) was prepared in a similar manner as Example 119C using 4-isopropyl-2-(6-methoxypyrimidin-4-yl)aniline. MS(ESI) m/z: 364.1 (M+H)$^+$.

182D. Preparation of 6-(5-isopropyl-2-(4-(trifluoromethyl)-1H-1,2,3-triazol-1-yl)phenyl) pyrimidin-4-ol 6-(5-Isopropyl-2-(4-(trifluoromethyl)-1H-1,2,3-triazol-1-yl)phenyl)pyrimidin-4-ol (459 mg, 91%) was prepared in a similar manner as Example 119D using 4-(5-isopropyl-2-(4-(trifluoromethyl)-1H-1,2,3-triazol-1-yl)phenyl)-6-methoxypyrimidine. MS(ESI) m z: 350.1 (M+H)$^+$. $^1$H NMR (400 MHz, CDCl$_3$) δ 12.53 (br. s., 1H), 8.06 (s, 1H), 7.92 (s, 1H), 7.58-7.50 (m, 2H), 7.47-7.44 (m, 1H), 6.54 (s, 1H), 3.15-3.03 (m, 1H), 1.38-1.30 (m, 6H).

182E. Preparation of (9R,13S)-3-(difluoromethyl)-9-methyl-13-{6-oxo-4-[5-(propan-2-yl)-2-[4-(trifluoromethyl)-1H-1,2,3-triazol-1-yl]phenyl]-1,6-dihydropyrimidin-1-yl}-3,4,7,15-tetraazatricyclo[12.3.1.0$^{2,6}$]octadeca-1(18),2(6),4,14,16-pentaen-8-one, Trifluoroacetate (9R,13S)-3-(Difluoromethyl)-9-methyl-13-{6-oxo-4-[5-(propan-2-yl)-2-[4-(trifluoromethyl)-1H-1,2,3-triazol-1-yl]phenyl]-1,6-dihydropyrimidin-1-yl}-3,4,7,15-tetraazatricyclo[12.3.1.0$^{2,6}$]octadeca-1(18),2(6),4,14,16-pentaen-8-one, trifluoroacetate (1.6 mg, 3.4%) was prepared in a similar manner as Example 56 using 6-(5-isopropyl-2-(4-(trifluoromethyl)-1H-1,2,3-triazol-1-yl)phenyl)pyrimidin-4-ol (21 mg, 0.060 mmol) and of (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one (20 mg, 0.060 mmol), prepared as described in Intermediate 30. MS(ESI) m/z: 668.2 (M+H)$^+$. $^1$H NMR (500 MHz, DMSO-d$_6$) δ 9.39 (s, 1H), 9.17 (s, 1H), 8.76 (s, 1H), 8.70 (d, J=5.2 Hz, 1H), 8.09-7.94 (m, 1H), 7.91-7.80 (m, 1H), 7.73-7.60 (m, 3H), 7.43 (d, J=4.7 Hz, 1H), 6.39 (s, 1H), 5.90 (d, J=10.2 Hz, 1H), 3.09 (dt, J=13.9, 6.8 Hz, 1H), 2.64 (d, J=3.3 Hz, 1H), 2.29 (t, J=12.7 Hz, 1H), 2.09-2.01 (m, 1H), 1.87-1.80 (m, 1H), 1.52-1.43 (m, 1H), 1.30 (d, J=6.9 Hz, 5H), 0.87 (d, J=6.9 Hz, 2H), 0.37 (br. s., 1H). Analytical HPLC (Method C): RT=2.00 min, 100% purity; Factor XIa Ki=500 nM.

Example 183

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-3-($^2$H$_3$)methyl-9-methyl-3,4,7,17-tetraazatricyclo[12.3.1.0$^{2,6}$]octadeca-1(18),2(6),4,14,16-pentaen-8-one

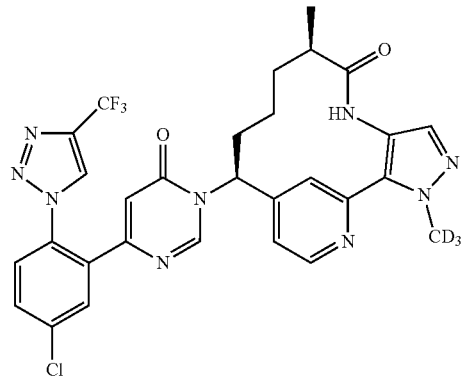

(9R,13S)-13-(4-{5-Chloro-2-[4-(trifluoromethyl)-1H-1,2,3-triazol-1-yl]phenyl}-6-oxo-1,6-dihydropyrimidin-1-yl)-3-($^2$H$_3$)methyl-9-methyl-3,4,7,17-tetraazatricyclo[12.3.1.0$^{2,6}$]octadeca-1(18),2(6),4,14,16-pentaen-8-one (0.068 g, 18.7%) as a white solid, was prepared in a similar manner as the procedure described in Example 56 by using 6-(5-chloro-2-(4-(trifluoromethyl)-1H-1,2,3-triazol-1-yl)phenyl) pyrimidin-4-ol (0.188 g, 0.549 mmol), as described in Intermediate 15, and (9R,13S)-13-amino-3-($^2$H$_3$)methyl-9-methyl-3,4,7,17-tetraazatricyclo[12.3.1.0$^{2,6}$]octadeca-1(18),2(6),4,14,16-pentaen-8-one (0.166 g, 0.549 mmol), as described in Intermediate 34. MS(ESI) m/z: 627.5 (M+H)$^+$. $^1$H NMR (400 MHz, CD$_3$OD) δ 8.84 (d, J=0.7 Hz, 1H), 8.72 (d, J=5.1 Hz, 1H), 8.29 (s, 1H), 7.91 (d, J=2.4 Hz, 1H), 7.86 (s, 1H), 7.82-7.76 (m, 1H), 7.74-7.69 (m, 1H), 7.51 (s, 1H), 7.16 (dd, J=5.2, 1.7 Hz, 1H), 6.53 (d, J=0.9 Hz, 1H), 5.78 (dd, J=12.4, 3.0 Hz, 1H), 2.70-2.57 (m, 1H), 2.40 (d, J=12.8 Hz, 1H), 2.15-2.08 (m, 1H), 2.04-1.94 (m, 1H), 1.64 (d, J=6.8 Hz, 1H), 1.48-1.32 (m, 2H), 1.15 (d, J=6.8 Hz, 3H). Analytical HPLC (Method A) RT=8.04 min, purity=95%; Factor XIa Ki=0.15 nM, Plasma Kallikrein Ki=18 nM.

Example 184

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-3-(difluoromethyl)-9-methyl-8-oxo-3,4,7-triazatricyclo[12.3.1.0$^{2,6}$]octadeca-1(18),2(6),4,14,16-pentaene-16-carbonitrile

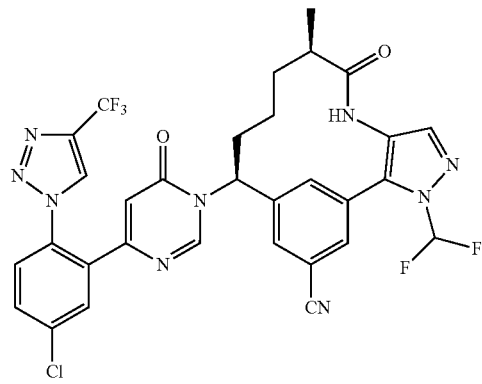 [SMILES: C[C@@H]1CCC[C@H](n2cnc(-c3cc(Cl)ccc3-n3cc(C(F)(F)F)nn3)cc2=O)c2cc(C#N)cc(c2)-c2c(cnn2C(F)F)NC1=O]

(9R,13S)-13-(4-{5-Chloro-2-[4-(trifluoromethyl)-1H-1,2,3-triazol-1-yl]phenyl}-6-oxo-1,6-dihydropyrimidin-1-yl)-3-(difluoromethyl)-9-methyl-8-oxo-3,4,7-triazatricyclo[12.3.1.0$^{2,6}$]octadeca-1(18),2(6),4,14,16-pentaene-16-carbonitrile (8 mg, 13.5%) as a white solid, was prepared in a similar manner as (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-8-oxo-3,4,7-triazatricyclo[12.3.1.0$^{2,6}$]octadeca-1(18),2(6),4,14,16-pentaene-16-carbonitrile, as described in Example 130, by replacing 6-[5-chloro-2-(4-chloro-1H-1,2,3-triazol-1-yl)phenyl]pyrimidin-4-ol with 6-{5-chloro-2-[4-(trifluoromethyl)-1H-1,2,3-triazol-1-yl]phenyl}pyrimidin-4-ol, as described in Intermediate 15. LCMS(ESI) m/z: 684.2 (M+H)$^+$. $^1$H NMR (400 MHz, CD$_3$OD) δ 8.82 (d, J=0.7 Hz, 1H), 8.32 (s, 1H), 8.03 (s, 1H), 7.90 (d, J=2.4 Hz, 2H), 7.83-7.75 (m, 3H), 7.73-7.43 (m, 2H), 6.48 (d, J=0.4 Hz, 1H), 5.76 (dd, J=13.1, 3.4 Hz, 1H), 2.60-2.42 (m, 2H), 2.17-2.05 (m, 1H), 1.88 (dt, J=7.2, 3.7 Hz, 1H), 1.64-1.53 (m, 1H), 1.42 (d, J=8.1 Hz, 1H), 1.20 (br. s., 1H), 1.13 (d, J=6.8 Hz, 3H). Analytical HPLC (Method A) RT=9.31 min, purity=98%; Factor XIa Ki=0.10 nM, Plasma Kallikrein Ki=15 nM.

Example 185

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-3,9-dimethyl-3,4,7,17-tetraazatricyclo[12.3.1.0$^{2,6}$]octadeca-1(18),2(6),4,14,16-pentaen-8-one

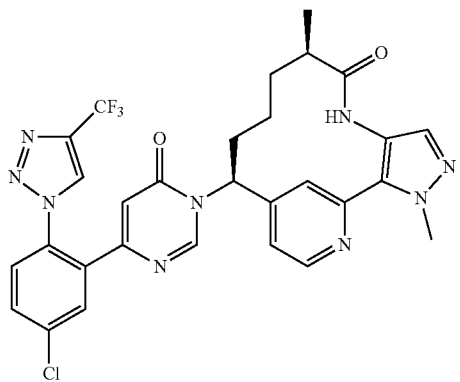 [SMILES: C[C@@H]1CCC[C@H](n2cnc(-c3cc(Cl)ccc3-n3cc(C(F)(F)F)nn3)cc2=O)c2ccnc(c2)-c2c(cnn2C)NC1=O]

(9R,13S)-13-(4-{5-Chloro-2-[4-(trifluoromethyl)-1H-1,2,3-triazol-1-yl]phenyl}-6-oxo-1,6-dihydropyrimidin-1-yl)-3,9-dimethyl-3,4,7,17-tetraazatricyclo[12.3.1.0$^{2,6}$]octadeca-1(18),2(6),4,14,16-pentaen-8-one (0.16 g, 27%), as a white solid, was prepared in a similar manner as Example 56, using 6-(5-chloro-2-(4-(trifluoromethyl)-1H-1,2,3-triazol-1-yl)phenyl)pyrimidin-4-ol (0.308 g, 0.902 mmol), as described in Intermediate 15, and (9R,13S)-13-amino-3,9-dimethyl-3,4,7,17-tetraazatricyclo[12.3.1.0$^{2,6}$]octadeca-1(18),2(6),4,14,16-pentaen-8-one (0.27 g, 0.902 mmol), as described in Intermediate 42. LCMS(ESI) m/z: 624.5 (M+H)$^+$. $^1$H NMR (400 MHz, CD$_3$OD) δ 8.84 (d, J=0.9 Hz, 1H), 8.71 (d, J=5.5 Hz, 1H), 8.29 (s, 1H), 7.91 (d, J=2.2 Hz, 1H), 7.86 (s, 1H), 7.80-7.75 (m, 1H), 7.73-7.70 (m, 1H), 7.51 (s, 1H), 7.16 (dd, J=5.2, 1.7 Hz, 1H), 6.53 (d, J=0.7 Hz, 1H), 5.78 (dd, J=12.5, 3.1 Hz, 1H), 4.18 (s, 3H), 2.69-2.55 (m, 1H), 2.40 (d, J=11.9 Hz, 1H), 2.11 (dd, J=13.3, 3.6 Hz, 1H), 2.00 (dd, J=14.0, 3.6 Hz, 1H), 1.64 (d, J=7.0 Hz, 1H), 1.50-1.29 (m, 2H), 1.15 (d, J=6.8 Hz, 3H). Analytical HPLC (Method A) RT=8.07 min, purity=95%; Factor XIa Ki=0.14 nM, Plasma Kallikrein Ki=18 nM.

Example 186

Preparation of (9S,13S)-13-{4-[5-chloro-2-(4-chloro-1H-1,2,3-triazol-1-yl)phenyl]-6-oxo-1,6-dihydropyrimidin-1-yl}-10-fluoro-3,9-dimethyl-3,4,7,15-tetraazatricyclo[12.3.1.0$^{2,6}$]octadeca-1(18),2(6),4,14,16-pentaen-8-one Trifluoroacetate

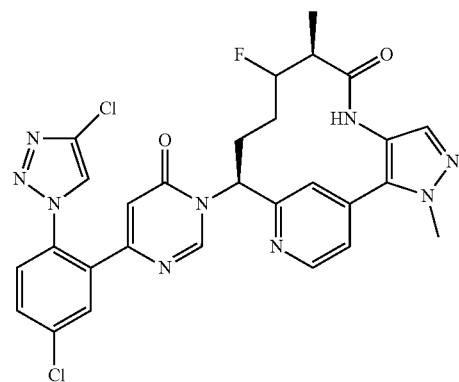 [SMILES: C[C@H]1C(=O)Nc2cnn(C)c2-c2ccnc(c2)[C@@H](n2cnc(-c3cc(Cl)ccc3-n3cc(Cl)nn3)cc2=O)CCC1F]

186A. Preparation of Tert-Butyl N-[(9S,13S)-10-fluoro-3,9-dimethyl-8-oxo-3,4,7,15-tetraazatricyclo[12.3.1.0$^{2,6}$]octadeca-1(18),2(6),4,14,16-pentaen-13-yl]carbamate

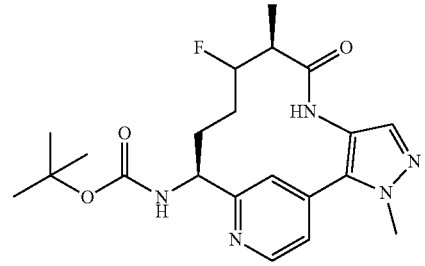 [SMILES: C[C@H]1C(=O)Nc2cnn(C)c2-c2ccnc(c2)[C@@H](NC(=O)OC(C)(C)C)CCC1F]

Fe$_2$(C$_2$O$_4$)$_3$.6H$_2$O (1.910 g, 3.95 mmol) was dissolved in water (75 mL) then purged with Ar (3×). SELECTFLUOR® (1398 mg, 3.95 mmol) was added, followed by tert-butyl N-[(9R,10E,13S)-3,9-dimethyl-8-oxo-3,4,7,15-tetraazatricyclo[12.3.1.0$^{2,6}$]octadeca-1(18),2(6),4,10,14,16-hexaen-13-yl]carbamate, prepared as described in Intermediate 32E (523 mg, 1.32 mmol), in ACN (75 mL). NaBH$_4$ (398 mg, 10.53 mmol) was added portionwise and the solution was stirred at rt for 1 h. The reaction mixture was quenched with 30% aq NH$_4$OH (40 ml), extracted with 500 ml 10% MeOH in DCM. The combined organic extracts were washed with brine, dried over MgSO$_4$, filtered, concentrated. The residue was purified by reverse phase chromatography to give a mixture of tert-butyl N-[(9S,13S)-10-fluoro-3,9-dimethyl-8-oxo-3,4,7,15-tetraazatricyclo[12.3.1.0$^{2,6}$]octadeca-1(18),2(6),4,14,16-pentaen-13-yl]carbamate and tert-butyl N-[(9R,13S)-11-fluoro-3,9-dimethyl-8-oxo-3,4,7,15-tetraazatricyclo[12.3.1.0$^{2,6}$]octadeca-1(18),2(6),4,14,16- pentaen-13-yl]carbamate (130 mg) as a solid. Further purification with chiral reverse phase chromatography gave tert-butyl N-[(9S,13S)-10-fluoro-3,9-dimethyl-8-oxo-3,4,7,15-tetraazatricyclo[12.3.1.0$^{2,6}$]Octadeca-1(18),2(6),4,14,16-pentaen-13-yl]carbamate (59 mg, 10% yield) as a single isomer as a white solid. 186B. Preparation of (9S,13S)-13-amino-10-fluoro-3,9-dimethyl-3,4,7,15-tetraazatricyclo[12.3.1.0$^{2,6}$]octadeca-1(18),2(6),4,14,16-pentaen-8-one

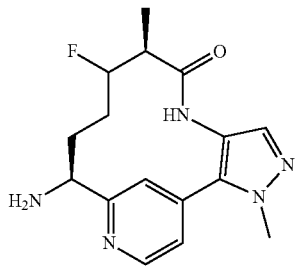 [SMILES: C[C@H]1C(=O)Nc2cnn(C)c2-c2ccnc(c2)[C@@H](N)CCC1F]

To a solution of tert-butyl N-[(9S,13S)-10-fluoro-3,9-dimethyl-8-oxo-3,4,7,15-tetraazatricyclo[12.3.1.0$^{2,6}$]octadeca-1(18),2(6),4,14,16-pentaen-13-yl]carbamate (96 mg, 0.230 mmol) in DCM (2 mL) was added TFA (0.709 mL, 9.20 mmol). The reaction mixture was stirred at rt for 2 h, then was concentrated to give (9S,13S)-13-amino-10-fluoro-3,9-dimethyl-3,4,7,15-tetraazatricyclo[12.3.1.0$^{2,6}$]octadeca-1(18),2(6),4,14,16-pentaen-8-one trifluoroacetate as a pale yellow solid, which was then dissolved in MeOH, passed through PL-HCOs MP SPE 500 mg per 6 ml tube, and rinsed with MeOH, The filtrate was concentrated to give (9S,13S)-13-amino-10-fluoro-3,9-dimethyl-3,4,7,15-tetraazatricyclo[12.3.1.0$^{2,6}$]octadeca-1(18),2(6),4,14,16-pentaen-8-one (72 mg, 99% yield). MS(ESI) m/z: 318.08 (M+H)$^+$.

186C. Preparation of (9S,13S)-13-{4-[5-chloro-2-(4-chloro-1H-1,2,3-triazol-1-yl) phenyl]-6-oxo-1,6-dihydropyrimidin-1-yl}-10-fluoro-3,9-dimethyl-3,4,7,15-tetraazatricyclo[12.3.1.0$^{2,6}$]octadeca-1(18),2(6),4,14,16-pentaen-8-one Trifluoroacetate ((9S,13S)-13-{4-[5-Chloro-2-(4-chloro-1H-1,2,3-triazol-1-yl)phenyl]-6-oxo-1,6-dihydropyrimidin-1-yl}-10-fluoro-3,9-dimethyl-3,4,7,15-tetraazatricyclo[12.3.1.0$^{2,6}$]octadeca-1(18),2(6),4,14,16-pentaen-8-one) trifluoroacetate (7.7 mg, 39% yield) was prepared in a similar manner as the procedure described in Example 184, by replacing methyl (10R,14S)-14-amino-10-methyl-9-oxo-8,16-diazatricyclo[13.3.1.0$^{2,7}$]nonadeca-1(19),2(7),3,5,15,17-hexaene-4-carboxylate with (9S,13S)-13-amino-10-fluoro-3,9-dimethyl-3,4,7,15-tetraazatricyclo[12.3.1.0$^{2,6}$]octadeca-1(18),2(6),4,14,16-pentaen-8-one. MS(ESI) m/z: 608.08 (M+H)$^+$. $^1$H NMR (400 MHz, CD$_3$OD) δ 9.10 (s, 1H), 8.77 (d, J=5.3 Hz, 1H), 8.36 (s, 1H), 7.91 (d, J=2.4 Hz, 1H), 7.78-7.73 (m, 1H), 7.69-7.64 (m, 1H), 7.56 (d, J=0.9 Hz, 1H), 7.53-7.46 (m, 2H), 6.39 (d, J=0.7 Hz, 1H), 6.25 (dd, J=12.1, 5.9 Hz, 1H), 5.46-5.23 (m, 1H), 4.05 (s, 3H), 3.22-3.11 (m, 1H), 2.36-2.19 (m, 2H), 1.86-1.68 (m, 1H), 1.00 (d, J=6.8 Hz, 3H), 0.75-0.51 (m, 1H) Analytical HPLC (Method A): RT=8.33 min, purity=>97%; Factor XIa Ki=0.37 nM, Plasma Kallikrein Ki=30 nM.

Example 187

Preparation of (9R,13S)-3-(difluoromethyl)-13-(4-{5-ethyl-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0$^{2,6}$]octadeca-1(18),2(6),4,14,16-pentaen-8-one

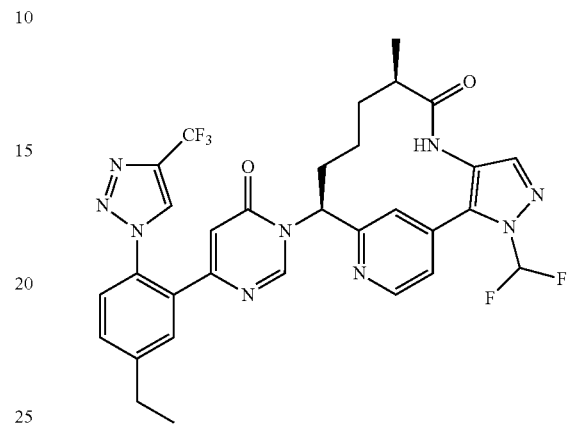

187A. Preparation of 4-ethyl-2-(4,4,5,5-tetramethyl-1,3,2-dioxaborolan-2-yl)aniline 4-Ethyl-2-(4,4,5,5-tetramethyl-1,3,2-dioxaborolan-2-yl)aniline (0.638 g, 52%) was prepared in a similar manner as Example 119A starting from 2-bromo-4-ethylaniline. MS(ESI) m/z: 166.0 (M-C$_6$H$_{10}$+H)$^+$. $^1$H NMR (400 MHz, chloroform-d) δ 7.44 (d, J=2.2 Hz, 1H), 7.08 (dd, J=8.3, 2.3 Hz, 1H), 6.57 (d, J=8.4 Hz, 1H), 4.60 (br. s., 2H), 1.38-1.33 (m, 12H), 1.27 (s, 2H), 1.21-1.16 (m, 3H).

187B. Preparation 4-ethyl-2-(6-methoxypyrimidin-4-yl)aniline

4-Ethyl-2-(6-methoxypyrimidin-4-yl)aniline (611 mg, 60%) was prepared in a similar manner as Example 119B using 4-ethyl-2-(4,4,5,5-tetramethyl-1,3,2-dioxaborolan-2-yl)aniline. MS(ESI) m/z: 230.1 (M+H)$^+$.

187C. Preparation of 4-(5-ethyl-2-(4-(trifluoromethyl)-1H-1,2,3-triazol-1-yl)phenyl)-6-methoxypyrimidine 4-(5-Ethyl-2-(4-(trifluoromethyl)-1H-1,2,3-triazol-1-yl)phenyl)-6-methoxypyrimidine (430 mg, 46%) was prepared in a similar manner as Example 119C using 4-ethyl-2-(6-methoxypyrimidin-4-yl)aniline. MS(ESI) m/z: 350.1 (M+H)$^+$.

187D. Preparation of 6-(5-isopropyl-2-(4-(trifluoromethyl)-1H-1,2,3-triazol-1-yl)phenyl) pyrimidin-4-ol 6-(5-Ethyl-2-(4-(trifluoromethyl)-1H-1,2,3-triazol-1-yl)phenyl)pyrimidin-4-ol (345 mg, 84%) was prepared in a similar manner as Example 119D using 4-(5-ethyl-2-(4-(trifluoromethyl)-1H-1,2,3-triazol-1-yl)phenyl)-6-methoxypyrimidine. MS(ESI) m/z: 336.1 (M+H)$^+$. $^1$H NMR (400

MHz, CDCl₃) δ 12.80 (br. s., 1H), 8.06 (s, 1H), 7.93 (s, 1H), 7.59-7.41 (m, 3H), 6.53 (s, 1H), 2.83 (q, J=7.7 Hz, 2H), 1.34 (t, J=7.6 Hz, 3H).

187E. Preparation of (9R,13S)-3-(difluoromethyl)-13-(4-{5-ethyl-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0²,⁶]octadeca-1(18),2(6),4,14,16-pentaen-8-one trifluoroacetate (9R,13S)-3-(Difluoromethyl)-13-(4-{5-ethyl-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0²,⁶]octadeca-1(18),2(6),4,14,16-pentaen-8-one trifluoroacetate (0.9 mg, 2.0%) was prepared in a similar manner as Example 56 using 6-(5-ethyl-2-(4-(trifluoromethyl)-1H-1,2,3-triazol-1-yl)phenyl)pyrimidin-4-ol (21 mg, 0.060 mmol) and (9R,13S)-13-amino-3-(difluoromethyl)-9-methyl-3,4,7,15-tetraazatricyclo[12.3.1.0²,⁶]octadeca-1(18), 2(6),4,14,16-pentaen-8-one (20 mg, 0.060 mmol), prepared as described in Intermediate 30. MS(ESI) m/z: 654.2 (M+H)⁺. ¹H NMR (500 MHz, DMSO-d₆) δ 9.40 (s, 1H), 9.18 (s, 1H), 8.78-8.65 (m, 2H), 8.09-7.93 (m, 1H), 7.90-7.83 (m, 1H), 7.72-7.65 (m, 3H), 7.59 (dd, J=8.2, 1.5 Hz, 1H), 7.43 (d, J=4.9 Hz, 1H), 6.38 (s, 1H), 5.90 (d, J=9.5 Hz, 1H), 2.79 (q, J=7.4 Hz, 2H), 2.69-2.61 (m, 1H), 2.28 (t, J=12.5 Hz, 1H), 2.09-2.00 (m, 1H), 1.89-1.79 (m, 1H), 1.47 (dt, J=12.2, 6.4 Hz, 1H), 1.38-1.23 (m, 4H), 0.88 (d, J=6.7 Hz, 3H), 0.36 (br. s., 1H). Analytical HPLC (Method C): RT=1.896 min, 100% purity; Factor XIa Ki=110 nM.

Example 188

Preparation of (9S,13S)-13-{4-[3-chloro-6-(4-chloro-1H-1,2,3-triazol-1-yl)-2-fluorophenyl]-6-oxo-1,6-dihydropyrimidin-1-yl}-10-fluoro-3,9-dimethyl-3,4,7,15-tetraazatricyclo[12.3.1.0²,⁶]octadeca-1(18), 2(6),4,14,16-pentaen-8-one Trifluoroacetate

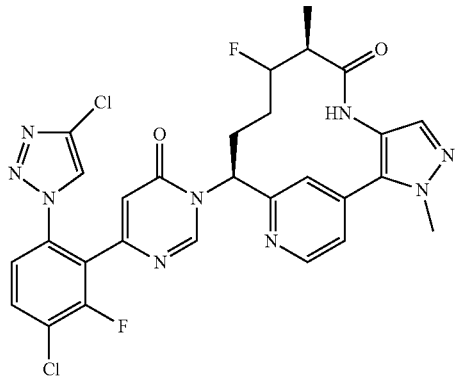 [SMILES: C[C@H]1C(=O)Nc2cnn(C)c2-c2ccnc(c2)[C@@H](n2cnc(-c3c(-n4cc(Cl)nn4)ccc(Cl)c3F)cc2=O)CCC1F]

(9S,13S)-13-{4-[3-Chloro-6-(4-chloro-1H-1,2,3-triazol-1-yl)-2-fluorophenyl]-6-oxo-1,6-dihydropyrimidin-1-yl}-10-fluoro-3,9-dimethyl-3,4,7,15-tetraazatricyclo[12.3.1.0²,⁶]octadeca-1(18),2(6),4,14,16-pentaen-8-one (9.33 mg, 32% yield) was prepared in a similar manner as the procedure described in Example 186 by replacing 6-[5-chloro-2-(4-chloro-1H-1,2,3-triazol-1-yl)phenyl]pyrimidin-4-ol with 6-[3-chloro-6-(4-chloro-1H-1,2,3-triazol-1-yl)-2-fluorophenyl]pyrimidin-4-ol, prepared as described in Intermediate 10. MS(ESI) m/z: 626.1 (M+H)⁺. ¹H NMR (400 MHz, CD₃OD) δ 9.10 (s, 1H), 8.78 (d, J=5.1 Hz, 1H), 8.34 (s, 1H), 7.88 (dd, J=8.7, 7.6 Hz, 1H), 7.60-7.54 (m, 2H), 7.53-7.48 (m, 2H), 6.63 (s, 1H), 6.27 (dd, J=11.8, 6.3 Hz, 1H), 5.44-5.25 (m, 1H), 4.05 (s, 3H), 3.23-3.12 (m, 1H), 2.35-2.21 (m, 2H), 1.85-1.69 (m, 1H), 1.00 (d, J=6.8 Hz, 3H), 0.75-0.52 (m, 1H). Analytical HPLC (Method A): RT=8.41 min, purity=>99%; Factor XIa Ki=0.15 nM, Plasma Kallikrein Ki=19 nM.

Example 189

Preparation of (9R,13S)-13-{5-chloro-4-[5-chloro-2-(4-chloro-1H-1,2,3-triazol-1-yl) phenyl]-6-oxo-1,6-dihydropyrimidin-1-yl}-3,9-dimethyl-3,4,7,15-tetraazatricyclo[12.3.1.0²,⁶]octadeca-1(18),2(6),4,14, 16-pentaen-8-one Trifluoroacetate

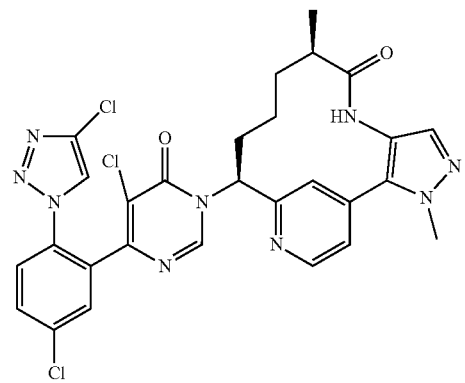 [SMILES: C[C@@H]1CCC[C@H](n2cnc(-c3cc(Cl)ccc3-n3cc(Cl)nn3)c(Cl)c2=O)c2cc(ccn2)-c2c(cnn2C)NC1=O]

189A. Preparation of 5-chloro-6-[5-chloro-2-(4-chloro-1H-1,2,3-triazol-1-yl)phenyl]pyrimidin-4-ol To a solution of 6-(5-chloro-2-(4-chloro-1H-1,2,3-triazol-1-yl)phenyl)pyrimidin-4-ol (100 mg, 0.325 mmol), prepared as described in Intermediate 9, in ACN (3.24 mL) was added Palau'chlor (82 mg, 0.389 mmol). The reaction was stirred at 60° C. for 4 h and then the reaction was cooled to rt and concentrated. Purification by normal phase chromatography, using EtOAc/Hex, gave a white solid weighing 0.135 g. Purification by reverse phase chromatography, gave a white solid. The solid was partitioned between sat NaHCO₃ and EtOAc and the layers were separated. The aqueous layer was extracted with EtOAc. The organic layers were combined, dried over MgSO₄, filtered and concentrated to give 5-chloro-6-[5-chloro-2-(4-chloro-H-1,2,3-triazol-1-yl)phenyl]pyrimidin-4-ol (63 mg, 57%) as a beige solid. MS(ESI) m/z: 342 (M+H)⁺, 344.1 (M+2+H)⁺, and 346.0 (M+4+H)⁺. ¹H NMR (400 MHz, CDCl₃) δ 8.09 (s, 1H), 7.75 (s, 1H), 7.66-7.61 (m, 2H), 7.55-7.50 (m, 1H).

189B. Preparation of (9R,13S)-13-{5-chloro-4-[5-chloro-2-(4-chloro-1H-1,2,3-triazol-1-yl)phenyl]-6-oxo-1,6-dihydropyrimidin-1-yl}-3,9-dimethyl-3,4,7, 15-tetraazatricyclo[12.3.1.0²,⁶]octadeca-1(18),2(6),4, 14,16-pentaen-8-one Trifluoroacetate (9R,13S)-13-{5-Chloro-4-[5-chloro-2-(4-chloro-1H-1,2,3-triazol-1-yl)phenyl]-6-oxo-1,6-dihydropyrimidin-1-yl}-3,9-dimethyl-3,4,7,15-tetraazatricyclo[12.3.1.0²,⁶]octadeca-1

(1S),2(6),4,14,16-pentaen-8-one trifluoroacetate (0.0071 g, 23%) was prepared in a similar manner as the procedure described in Example 56, by replacing 6-{5-chloro-2-[4-(trifluoromethyl)-1H-1,2,3-triazol-1-yl]phenyl}pyrimidin-4-ol with 5-chloro-6-[5-chloro-2-(4-chloro-1H-1,2,3-triazol-1-yl)phenyl]pyrimidin-4-ol. MS(ESI) m/z: 624 (M+H)+, 626.3 (M+2+H)+, and 628.2 (M+4+H)+. $^1$H NMR (500 MHz, DMSO-$d_6$) δ 9.15 (s, 1H), 8.83 (s, 1H), 8.75 (s, 1H), 8.63 (d, J=5.0 Hz, 1H), 7.83-7.73 (m, 3H), 7.62 (s, 1H), 7.53 (dd, J=5.1, 1.5 Hz, 1H), 7.40 (s, 1H), 5.88-5.78 (m, 1H), 3.95 (s, 3H), 2.62-2.52 (m, 1H), 2.32-2.21 (m, 1H), 2.08-1.98 (m, 1H), 1.87-1.78 (m, 1H), 1.47-1.36 (m, 1H), 1.33-1.21 (m, 1H), 0.81 (d, J=6.9 Hz, 3H), 0.45-0.29 (m, 1H). Analytical HPLC (Method A): RT=8.03 min, purity=99.5%; Factor XIa Ki=0.46 nM, Plasma Kallikrein Ki=29 nM.

Example 190

Preparation of (9R,13S)-3-(difluoromethyl)-13-(4-{4-fluoro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0$^{2,6}$]octadeca-1(18),2(6),4,14,16-pentaen-8-one

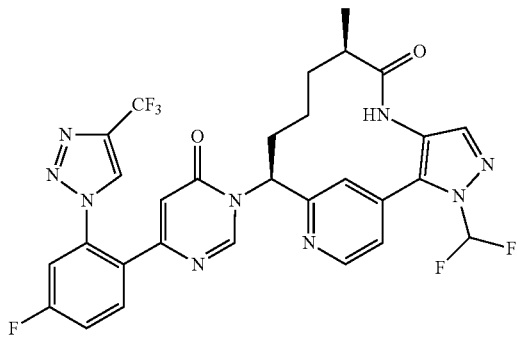 [SMILES: C[C@@H]1CCC[C@H](n2cnc(-c3ccc(F)cc3-n3cc(C(F)(F)F)nn3)cc2=O)c2cc(ccn2)-c2c(cnn2C(F)F)NC1=O]

(9R,13S)-3-(Difluoromethyl)-13-(4-{4-fluoro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0$^{2,6}$]octadeca-1(18),2(6),4,14,16-pentaen-8-one was prepared (0.72 mg, 6% yield as a solid via the coupling of 6-{4-fluoro-2-[4-(trifluoromethyl)-1H-1,2,3-triazol-1-yl]phenyl}pyrimidin-4-ol (0.006 g, 0.018 mmol) and (9R,13S)-13-amino-3-(difluoromethyl)-9-methyl-3,4,7,15-tetraazatricyclo[12.3.1.0$^{2,6}$]octadeca-1(18),2(6), 4,14,16-pentaen-8-one (0.006 g, 0.018 mmol) using the HATU, DBU coupling methodology as described in Example 56. LCMS m/z=644.2 (M+H)+. $^1$H NMR (400 MHz, CD$_3$OD) δ 8.83-8.77 (m, 2H), 8.73-8.69 (m, 1H), 7.91-7.86 (m, 1H), 7.75-7.72 (m, 2H), 7.68-7.49 (m, 4H), 6.05-5.96 (m, 1H), 2.75-2.62 (m, 1H), 2.30-2.18 (m, 1H), 2.05-1.94 (m, 2H), 1.64-1.36 (d, 3H), 1.02-0.94 (m, 1H). Analytical HPLC (Method A) RT=8.75 min, purity=98%; Factor XIa Ki=110 nM.

Example 191

Preparation of (9R,13S)-13-{4-[5-chloro-2-(4-chloro-1H-1,2,3-triazol-1-yl)phenyl]-6-oxo-1,6-dihydropyrimidin-1-yl}-3-($^2$H$_3$)methyl-9-methyl-3,4,7,17-tetraazatricyclo[12.3.1.0$^{2,6}$]octadeca-1(18),2(6),4,14,16-pentaen-8-one

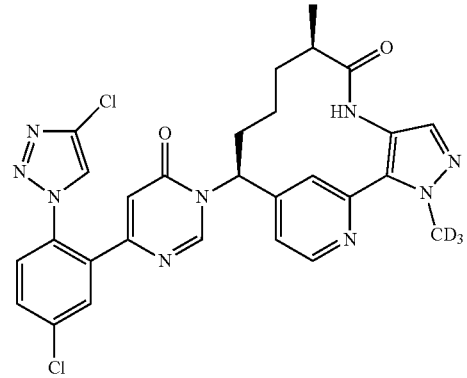 [SMILES: [2H]C([2H])([2H])n1ncc2c1-c1cc(ccn1)[C@@H](n1cnc(-c3cc(Cl)ccc3-n3cc(Cl)nn3)cc1=O)CCC[C@@H](C)C(=O)N2]

(9R,13S)-13-{4-[5-Chloro-2-(4-chloro-1H-1,2,3-triazol-1-yl)phenyl]-6-oxo-1,6-dihydropyrimidin-1-yl}-3-($^2$H$_3$)methyl-9-methyl-3,4,7,17-tetraazatricyclo[12.3.1.0$^{2,6}$]octadeca-1(18),2(6),4,14,16-pentaen-8-one (10.8 mg, 18.4%), as a white solid, was prepared in a similar manner as Example 56, using 6-[5-chloro-2-(4-chloro-1H-1,2,3-triazol-1-yl)phenyl]pyrimidin-4-ol (0.024 g, 0.079 mmol), as described in Intermediate 9, and (9R,13S)-13-amino-3-($^2$H$_3$)methyl-9-methyl-3,4,7,17-tetraazatricyclo[12.3.1.0$^{2,6}$]octadeca-1(18),2(6),4,14,16-pentaen-8-one (0.024 g, 0.079 mmol), as described in Intermediate 34. LCMS(ESI) m/z: 593.3 (M+H)+. $^1$H NMR (400 MHz, CD$_3$OD) δ 8.78-8.69 (m, 1H), 8.42-8.33 (m, 2H), 7.92-7.86 (m, 2H), 7.80-7.74 (m, 1H), 7.69-7.64 (m, 1H), 7.52 (s, 1H), 7.21 (dd, J=5.3, 1.5 Hz, 1H), 6.51-6.43 (m, 1H), 5.77 (dd, J=12.5, 3.3 Hz, 1H), 2.62 (ddd, J=9.5, 6.7, 3.4 Hz, 1H), 2.48-2.38 (m, 1H), 2.22-2.11 (m, 1H), 2.06-1.97 (m, 1H), 1.69-1.59 (m, 1H), 1.42-1.33 (m, 2H), 1.15 (d, J=6.8 Hz, 3H). Analytical HPLC (Method A) RT=7.77 min, purity=96%; Factor XIa Ki=0.19 nM, Plasma Kallikrein Ki=22 nM.

Example 192

Preparation of (9R,13S)-13-[4-(3-chloro-2,6-difluorophenyl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one

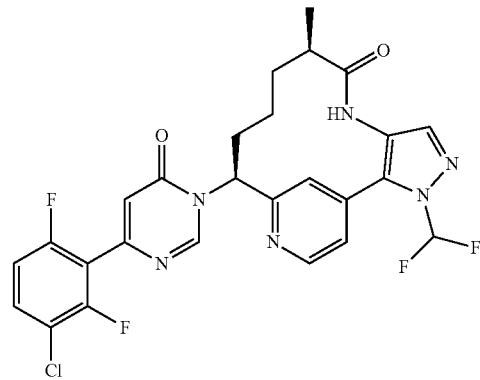 [SMILES: C[C@@H]1CCC[C@H](n2cnc(-c3c(F)ccc(Cl)c3F)cc2=O)c2cc(ccn2)-c2c(cnn2C(F)F)NC1=O]

192A. Preparation of 6-(3-chloro-2,6-difluorophenyl)pyrimidin-4-ol 6-(3-Chloro-2,6-difluorophenyl)pyrimidin-4-ol hydrobromide, prepared as described in Intermediate 4, was partitioned between EtOAc and sat NaHCO$_3$. The layers were separated and the organic layer was washed with brine, dried over Na$_2$SO$_4$, filtered and concentrated to give a white solid. The solid was suspended in Et$_2$O and sonicated. The solid was collected by filtration, rinsed with Et$_2$O, and dried under vacuum to give 6-(3-chloro-2,6-difluorophenyl)pyrimidin-4-ol as a white solid. MS(ESI) m/z: 243.0 (M+H)$^+$ and 245.0 (M+2+H)$^+$.

192B. Preparation of (9R,13S)-13-[4-(3-chloro-2,6-difluorophenyl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one (9R,13S)-13-[4-(3-Chloro-2,6-difluorophenyl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one trifluoroacetate (0.0092 g, 30%) was prepared in a similar manner as the procedures described in Example 56, by using 6-(3-chloro-2,6-difluorophenyl)pyrimidin-4-ol (10.8 mg, 0.045 mmol) and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one (0.015 g, 0.045 mmol), prepared as described in Intermediate 30. MS(ESI) m/z: 561.1 (M+H)$^+$ and 563.1 (M+2+H)$^+$. $^1$H NMR (500 MHz, CD$_3$OD) δ 9.09 (s, 1H), 8.77 (d, J=5.0 Hz, 1H), 7.79-7.72 (m, 2.25H), 7.67-7.60 (m, 1.5H), 7.56-7.52 (m, 1.25H), 7.14 (dt, J=9.1, 1.9 Hz, 1H), 6.67 (s, 1H), 6.11-6.04 (m, 1H), 2.76-2.69 (m, 1H), 2.42-2.33 (m, 1H), 2.13-2.02 (m, 2H), 1.66-1.56 (m, 1H), 1.56-1.46 (m, 1H), 1.01 (d, J=6.9 Hz, 3H), 0.73-0.60 (m, 1H). $^{19}$F NMR (471 MHz, CD$_3$OD) δ −114.75 (d, J=4.3 Hz), −115.47 (d, J=4.3 Hz), −77.66 (s). Analytical HPLC (Method A): RT=8.38 min, purity=99.7%; Factor XIa Ki=30 nM, Plasma Kallikrein Ki=670 nM.

Example 193

Preparation of (9R,13S)-13-[4-(5-chloro-2-phenylphenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one

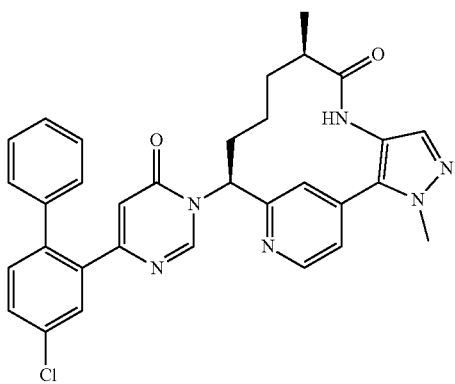

(9R,13S)-13-[4-(5-Chloro-2-phenylphenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one trifluoroacetate (5 mg, 21% yield) was prepared in a similar manner as the procedure described in Example 161, by replacing pyridin-3-ylboronic acid (4.76 mg, 0.039 mmol) with phenylboronic acid (4.72 mg, 0.039 mmol). MS(ESI) m/z: 565.4 (M+H)$^+$. $^1$H NMR (500 MHz, CD$_3$OD) δ 8.92 (s, 1H), 8.72 (d, J=5.0 Hz, 1H), 7.71 (d, J=2.2 Hz, 1H), 7.66 (s, 1H), 7.55-7.50 (m, 2H), 7.48 (s, 1H), 7.41 (d, J=8.3 Hz, 1H), 7.34-7.26 (m, 3H), 7.24-7.20 (m, 2H), 6.08 (d, J=0.8 Hz, 1H), 5.94 (dd, J=12.5, 4.0 Hz, 1H), 4.04 (s, 3H), 2.73-2.65 (m, 1H), 2.34-2.24 (m, 1H), 2.10-1.94 (m, 2H), 1.63-1.54 (m, 1H), 1.52-1.41 (m, 1H), 1.00 (d, J=6.9 Hz, 3H), 0.74-0.59 (m, 1H). Analytical HPLC (Method A): RT=12.43 min, 98.2% purity; Factor XIa Ki=160 nM, Plasma Kallikrein Ki=4,700 nM.

Example 194

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,16-tetraazatricyclo[12.3.1.0$^{2,6}$]octadeca-1(18),2(6),4,14,16-pentaen-8-one

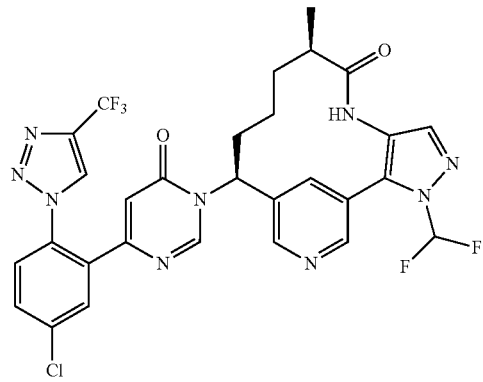 [SMILES: C[C@@H]1CCC[C@H](n2cnc(-c3cc(Cl)ccc3-n3cc(C(F)(F)F)nn3)cc2=O)c2cncc(c2)-c2c(cnn2C(F)F)NC1=O]

(9R,13S)-13-(4-{5-Chloro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,16-tetraazatricyclo[12.3.1.0$^{2,6}$]octadeca-1(18),2(6),4,14,16-pentaen-8-one trifluoroacetate (5 mg, 4.9%) was prepared in a similar manner as Example 56 using 6-{5-chloro-2-[4-(trifluoromethyl)-1H-1,2,3-triazol-1-yl]phenyl}pyrimidin-4-ol, prepared as described in Intermediate 15, and (9R,13S)-13-amino-3-(difluoromethyl)-9-methyl-3,4,7,16-tetraazatricyclo[12.3.1.0$^{2,6}$]octadeca-1(18),2(6),4,14,16-pentaen-8-one, prepared as described in Intermediate 43. MS(ESI) m/z: 660.2 (M+H)$^+$. $^1$H NMR (400 MHz, methanol-d$_4$) δ 8.84 (d, J=0.7 Hz, 1H), 8.78 (s, 1H), 8.65 (d, J=2.0 Hz, 1H), 8.34 (s, 1H), 8.27 (t, J=1.9 Hz, 1H), 7.92 (d, J=2.2 Hz, 1H), 7.82-7.77 (m, 2H), 7.73-7.70 (m, 1H), 6.50 (d, J=0.7 Hz, 1H), 5.79 (dd, J=12.9, 3.4 Hz, 1H), 2.58-2.48 (m, 2H), 2.22-2.14 (m, 1H), 1.92-1.87 (m, 1H), 1.64-1.57 (m, 2H), 1.17 (d, J=6.8 Hz, 3H), 1.12-1.03 (m, 1H). Analytical HPLC (Method A): RT=8.10 min, purity=90%; Factor XIa Ki=0.13 nM, Plasma Kallikrein Ki=66 nM.

Example 195

Preparation of (9R,13S)-13-[4-(5-chloro-1-ethyl-1H-indazol-7-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one

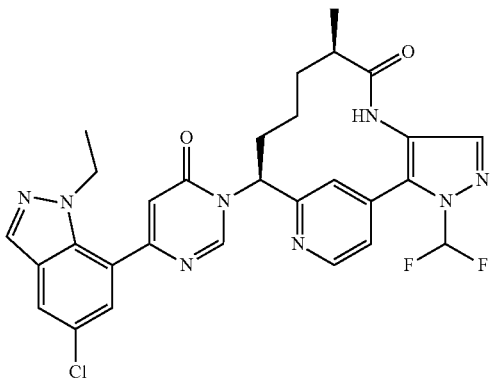 [SMILES: CCn1ncc2cc(Cl)cc(-c3cc(=O)n([C@H]4CCC[C@@H](C)C(=O)Nc5cnn(C(F)F)c5-c5ccnc4c5)cn3)c21]

195A. Preparation of 6-(5-chloro-1-methyl-1H-indazol-7-yl)pyrimidin-4-ol 6-(5-Chloro-1-methyl-1H-indazol-7-yl)pyrimidin-4-ol was prepared in a similar manner as Intermediate 22 replacing MeI with EtI. MS(ESI) m/z: 275.1 (M+H)$^+$ and 277.1 (M+2+H)$^+$.

195B. Preparation of (9R,13)-13-[4-(5-chloro-1-ethyl-1H-indazol-7-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one Trifluoroacetate (9R,13S)-13-[4-(5-Chloro-1-ethyl-1H-indazol-7-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one, trifluoroacetate (10.8 mg, 25%) was prepared in a similar manner as Example 56 using 6-(5-chloro-1-methyl-1H-indazol-7-yl)pyrimidin-4-ol and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one, prepared as described in Intermediate 30. MS(ESI) m/z: 593.2 (M+H)$^+$. $^1$H NMR (400 MHz, CD$_3$OD) δ 9.12 (s, 1H), 8.76 (d, J=5.1 Hz, 1H), 8.10 (s, 1H), 7.89 (d, J=2.0 Hz, 1H), 7.83-7.73 (m, 2H), 7.69-7.50 (m, 2H), 7.45-7.41 (m, 1H), 6.73 (s, 1H), 6.12 (dd, J=12.9, 4.3 Hz, 1H), 4.39-4.26 (m, 2H), 2.77-2.72 (m, 1H), 2.44-2.35 (m, 1H), 2.14-2.05 (m, 2H), 1.65-1.50 (m, 2H), 1.23 (t, J=7.2 Hz, 3H), 1.01 (d, J=7.0 Hz, 2H), 0.67 (br. s., 1H). Analytical HPLC (Method A): RT=8.69 min, purity=>99%; Factor XIa Ki=110 nM, Plasma Kallikrein Ki=8,400 nM.

Example 196

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0$^{2,6}$]octadeca-1(18),2(6),4,14,16-pentaen-8-one

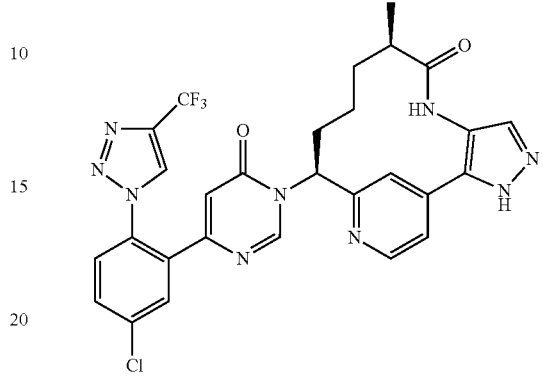

196A. Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-3-{[2-(trimethylsilyl)ethoxy]methyl}-3,4,7,15-tetraazatricyclo[12.3.1.0$^{2,6}$]octadeca-1(18),2(6),4,14,16-pentaen-8-one (9R,13S)-13-(4-{5-Chloro-2-[4-(trifluoromethyl)-1H-1,2,3-triazol-1-yl]phenyl}-6-oxo-1,6-dihydropyrimidin-1-yl)-9-methyl-3-{[2-(trimethylsilyl)ethoxy]methyl}-3,4,7,15-tetraazatricyclo[12.3.1.0$^{2,6}$]octadeca-1(18),2(6),4,14,16-pentaen-8-one (760 mg, 0.975 mmol, 74% yield) was prepared in a similar manner as the procedures described in Example 56, by using 6-(5-chloro-2-(4-(trifluoromethyl)-1H-1,2,3-triazol-1-yl)phenyl) pyrimidin-4-ol (0.452 g, 1.323 mmol), prepared as described in Intermediate 15, and (9R,13S)-9-methyl-3-{[2-(trimethylsilyl)ethoxy]methyl}-3,4,7,15-tetraazatricyclo[12.3.1.0$^{2,6}$]octadeca-1(18),2(6),4,14,16-pentaen-8-one (0.550 g, 1.323 mmol), prepared as described in Intermediate 19. MS(ESI) m/z: 740.6 [M+H]$^+$.

196B. Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0$^{2,6}$]octadeca-1(18),2(6),4,14,16-pentaen-8-one trifluoroacetate To a solution of (9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-3-{[2-(trimethylsilyl)ethoxy]methyl}-3,4,7,15-tetraazatricyclo[12.3.1.0$^{2,6}$]octadeca-1(18),2(6),4,14,16-pentaen-8-one (760 mg, 1.027 mmol), in DCM (4.0 mL) was added TFA (1.0 mL, 12.98 mmol) and the resulting solution was stirred at rt for 30 min. The reaction mixture was then concentrated and the residue was purified by prep HPLC purification to give (9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0$^{2,6}$]octadeca-1(18),2(6),4,14,16-pentaen-8-one trifluoroacetate (480 mg, 92% yield). $^1$H NMR (500 MHz, DMSO-d$_6$) δ 9.26 (s, 1H), 9.21 (s, 1H), 8.63 (br. s., 1H), 8.49 (br. s., 1H), 7.96 (d, J=1.5 Hz, 1H), 7.87-7.78 (m, 2H), 7.47 (br. s., 1H), 7.24-6.98 (m, 1H), 6.48

(s, 1H), 5.97 (br. s., 1H), 3.45-3.36 (m, 2H), 2.72 (br. s., 1H), 2.32-2.15 (m, 2H), 1.80 (br. s., 1H), 1.52 (br. s., 1H), 1.38 (br. s., 1H), 0.92 (d, J=6.7 Hz, 3H), 0.59 (br. s., 1H). MS(ESI) m/z: 610.1 [M+H]$^+$. Analytical HPLC (Method B): RT=1.57 min, purity=97.0%; Factor XIa Ki=1.9 nM, Plasma Kallikrein Ki=205 nM.

Example 197

Preparation of (9R,13S)-13-{4-[3-chloro-2-fluoro-6-(1H-1,2,3,4-tetrazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate

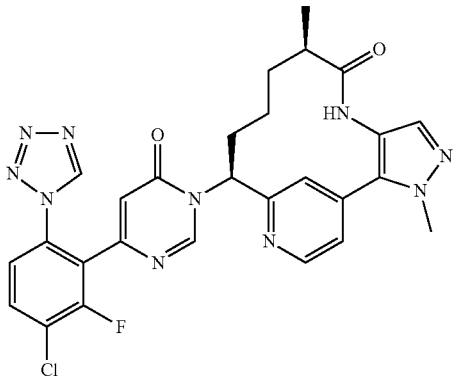 [SMILES: C[C@@H]1CCC[C@H](n2cnc(-c3c(-n4cnnn4)ccc(Cl)c3F)cc2=O)c2cc(ccn2)-c2c(cnn2C)NC1=O]

(9R,13S)-13-{4-[3-Chloro-2-fluoro-6-(1H-1,2,3,4-tetrazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (6.9 mg, 16% yield) was prepared in a similar manner as the procedure described in Example 196 by using (9R,13S)-13-amino-3,9-dimethyl-3,4,7,15-tetraazatricyclo[12.3.1.0$^{2,6}$]octadeca-1(18),2(6),4,14,16-pentaen-8-one, prepared as described in Intermediate 32. MS(ESI) m/z: 575.2 (M+H)$^+$. $^1$H NMR (400 MHz, CD$_3$OD) δ 9.46 (br. s., 1H), 8.76 (d, J=8.1 Hz, 2H), 7.91 (d, J=6.8 Hz, 1H), 7.80 (br. s., 1H), 7.62 (d, J=7.0 Hz, 2H), 7.53 (br. s., 1H), 6.70 (br. s., 1H), 5.95 (br. s., 1H), 4.09 (br. s., 3H), 2.71 (br. s., 1H), 2.32 (br. s., 1H), 2.05 (br. s., 2H), 1.62 (br. s., 1H), 1.46 (br. s., 1H), 1.03 (br. s., 3H), 0.77 (br. s., 1H) Analytical HPLC (Method A): RT=6.71 min, purity=>99%; Factor XIa Ki=0.1 nM, Plasma Kallikrein Ki=8 nM.

Example 198

Preparation of (9R,13S)-13-{4-[3-chloro-2-fluoro-6-(1H-1,2,3,4-tetrazol-1-yl)phenyl]-6-oxo-1,6-dihydropyrimidin-1-yl}-3-(difluoromethyl)-9-methyl-3,4,7-triazatricyclo[12.3.1.0$^{2,6}$]octadeca-1(18),2(6),4,14,16-pentaen-8-one Trifluoroacetate

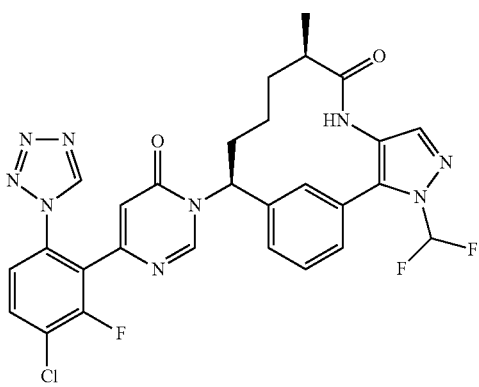 [SMILES: C[C@@H]1CCC[C@H](n2cnc(-c3c(-n4cnnn4)ccc(Cl)c3F)cc2=O)c2cccc(c2)-c2c(cnn2C(F)F)NC1=O]

(9R,13S)-13-{4-[3-Chloro-2-fluoro-6-(1H-1,2,3,4-tetrazol-1-yl)phenyl]-6-oxo-1,6-dihydropyrimidin-1-yl}-3-(difluoromethyl)-9-methyl-3,4,7-triazatricyclo[12.3.1.0$^{2,6}$]octadeca-1(18),2(6),4,14,16-pentaen-8-one trifluoroacetate (9.7 mg, 33% yield) was prepared in a similar manner as the procedure described in Example 196 by using (9R,13S)-13-amino-3-(difluoromethyl)-9-methyl-3,4,7-triazatricyclo[12.3.1.0$^{2,6}$]octadeca-1(18),2(6),4,14,16-pentaen-8-one, prepared as described in Intermediate 35. MS(ESI) m/z: 610.3 (M+H)$^+$. $^1$H NMR (400 MHz, CD$_3$OD) δ 9.42 (s, 1H), 8.17 (s, 1H), 7.89 (dd, J=8.7, 7.6 Hz, 1H), 7.81-7.75 (m, 2H), 7.65-7.46 (m, 4H), 7.38 (d, J=7.7 Hz, 1H), 6.71 (d, J=0.9 Hz, 1H), 5.81 (dd, J=12.9, 3.4 Hz, 1H), 2.56-2.44 (m, 1H), 2.40-2.25 (m, 1H), 2.17-2.05 (m, 1H), 1.94-1.82 (m, 1H), 1.63-1.47 (m, 2H), 1.27-1.17 (m, 1H), 1.15 (d, J=6.8 Hz, 3H). Analytical HPLC (Method A): RT=8.62 min, purity=99%; Factor XIa Ki=0.1 nM, Plasma Kallikrein Ki=4 nM.

Example 199

Preparation of (9R,13S)-13-{4-[5-chloro-1-(2,2,2-trifluoroethyl)-1H-indazol-7-yl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one

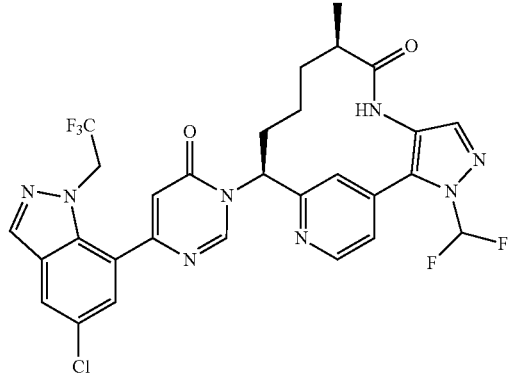 [SMILES: C[C@@H]1CCC[C@H](n2cnc(-c3cc(Cl)cc4cnn(CC(F)(F)F)c34)cc2=O)c2cc(ccn2)-c2c(cnn2C(F)F)NC1=O]

199A. Preparation of 6-(5-chloro-1-(2,2,2-trifluoroethyl)-1H-indazol-7-yl)pyrimidin-4-ol 6-(5-Chloro-1-(2,2,2-trifluoroethyl)-1H-indazol-7-yl)pyrimidin-4-ol (25 mg, 62%) was prepared in a similar manner as Intermediate 22 replacing MeI with 2-bromo-1,1,1-trifluoroethane. MS(ESI) m/z: 329 (M+H)$^+$ and 331 (M+2+H)$^+$.

199B. Preparation of (9R,13S)-13-{4-[5-chloro-1-(2,2,2-trifluoroethyl)-1H-indazol-7-yl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one Trifluoroacetate (9R,13S)-13-{4-[5-Chloro-1-(2,2,2-trifluoroethyl)-1H-indazol-7-yl]-6-oxo-1,6-dihydropyrimidin-1-yl}-3-(difluoromethyl)-9-methyl-3,4,7,15-tetraazatricyclo[12.3.1.0$^{2,6}$]

octadeca-1(18),2(6),4,14,16-pentaen-8-one trifluoroacetate (14.5 mg, 25%) was prepared in a similar manner as Example 56 using 6-(5-chloro-1-(2,2,2-trifluoroethyl)-1H-indazol-7-yl)pyrimidin-4-ol and (9R,13S)-13-amino-3-(difluoromethyl)-9-methyl-3,4,7,15-tetraazatricyclo[12.3.1.0²,⁶]octadeca-1(18),2(6),4,14,16-pentaen-8-one, prepared as described in Intermediate 30. MS(ESI) m/z: 647.2 (M+H)⁺ and 649.2 (M+2H)⁺. ¹H NMR (400 MHz, CD₃OD) δ 9.17 (s, 1H), 8.74 (d, J=5.1 Hz, 1H), 8.27-8.19 (m, 1H), 7.97 (d, J=2.0 Hz, 1H), 7.84-7.72 (m, 2H), 7.68-7.57 (m, 2H), 7.56-7.51 (m, 1H), 6.77 (s, 1H), 6.14 (dd, J=12.9, 4.3 Hz, 1H), 5.51-5.37 (m, 2H), 2.77-2.70 (m, 1H), 2.45-2.35 (m, 1H), 2.08 (t, J=12.4 Hz, 2H), 1.64-1.51 (m, 2H), 1.00 (d, J=6.8 Hz, 3H), 0.68 (br. s., 1H). Analytical HPLC (Method A): RT=9.21 min, purity=>99%; Factor XIa Ki=57 nM, Plasma Kallikrein Ki=1,500 nM.

Example 200

Preparation of (9R,13S3)-13-{4-[5-chloro-2-(1H-1,2,3,4-tetrazol-1-yl)phenyl]-6-oxo-1,6-dihydropyrimidin-1-yl}-3-(difluoromethyl)-9-methyl-3,4,7,15-tetraazatricyclo[12.3.1.0²,⁶]octadeca-1(18),2(6),4,14,16-pentaen-8-one trifluoroacetate

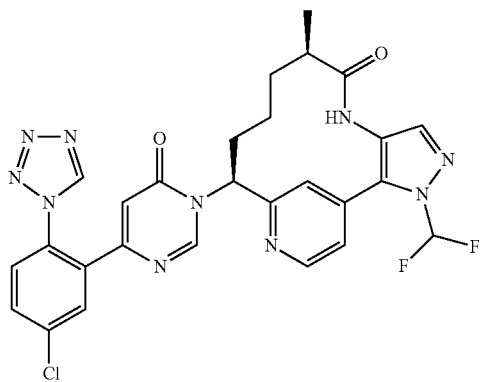 [SMILES: C[C@@H]1CCC[C@H](n2cnc(-c3cc(Cl)ccc3-n3cnnn3)cc2=O)c2cc(ccn2)-c2c(cnn2C(F)F)NC1=O]

(9R,13S)-13-{4-[5-Chloro-2-(1H-1,2,3,4-tetrazol-1-yl)phenyl]-6-oxo-1,6-dihydropyrimidin-1-yl}-3-(difluoromethyl)-9-methyl-3,4,7,15-tetraazatricyclo[12.3.1.0²,⁶]octadeca-1(18),2(6),4,14,16-pentaen-8-one trifluoroacetate (22.1 mg, 44% yield) was prepared in a similar manner as the procedure described in Example 198 by replacing 6-[3-chloro-2-fluoro-6-(1H-1,2,3,4-tetrazol-1-yl)phenyl]pyrimidin-4-ol with 6-[5-chloro-2-(1H-1,2,3,4-tetrazol-1-yl)phenyl]pyrimidin-4-ol, prepare as described in Intermediate 20. MS(ESI) m/z: 593.2 (M+H)⁺. ¹H NMR (400 MHz, CD₃OD) δ 9.38 (s, 1H), 8.73-8.65 (m, 2H), 7.84 (d, J=2.2 Hz, 1H), 7.79-7.42 (m, 6H), 6.46 (s, 1H), 5.88 (dd, J=12.5, 4.2 Hz, 1H), 2.71-2.58 (m, 1H), 2.32-2.19 (m, 1H), 2.04-1.89 (m, 2H), 1.60-1.47 (m, 1H), 1.45-1.30 (m, 1H), 0.94 (d, J=6.8 Hz, 3H), 0.60 (br. s., 1H). Analytical HPLC (Method A): RT=7.93 min, purity=>99%; Factor XIa Ki=0.1 nM, Plasma Kallikrein Ki=10 nM.

Example 201

Preparation of (9R,13S)-13-{4-[5-chloro-2-(1H-1,2,3,4-tetrazol-1-yl)phenyl]-6-oxo-1,6-dihydropyrimidin-1-yl}-3-(difluoromethyl)-9-methyl-3,4,7-triazatricyclo[12.3.1.0²,⁶]octadeca-1(18),2(6),4,14,16-pentaen-8-one

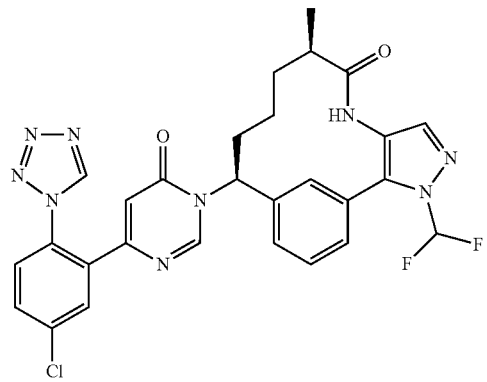 [SMILES: C[C@@H]1CCC[C@H](n2cnc(-c3cc(Cl)ccc3-n3cnnn3)cc2=O)c2cccc(c2)-c2c(cnn2C(F)F)NC1=O]

(9R,13S)-13-{4-[5-Chloro-2-(1H-1,2,3,4-tetrazol-1-yl)phenyl]-6-oxo-1,6-dihydropyrimidin-1-yl}-3-(difluoromethyl)-9-methyl-3,4,7-triazatricyclo[12.3.1.0²,⁶]octadeca-1(18),2(6),4,14,16-pentaen-8-one (10.5 mg, 40% yield) was prepared in a similar manner as the procedure described in Example 200 by replacing (9R,13S)-13-amino-3-(difluoromethyl)-9-methyl-3,4,7,15-tetraazatricyclo[12.3.1.0²,⁶]octadeca-1(18),2(6),4,14,16-pentaen-8-one with (9R,13S)-13-amino-3-(difluoromethyl)-9-methyl-3,4,7-triazatricyclo[12.3.1.0²,⁶]octadeca-1(18),2(6),4,14,16-pentaen-8-one, prepare as described in Intermediate 35. MS(ESI) m/z: 592.3 (M+H)⁺. ¹H NMR (400 MHz, CD₃OD) δ 9.39 (s, 1H), 8.09 (s, 1H), 7.86 (d, J=2.4 Hz, 1H), 7.78-7.42 (m, 7H), 7.34 (d, J=7.5 Hz, 1H), 6.51 (s, 1H), 5.76 (dd, J=12.8, 3.1 Hz, 1H), 2.51-2.38 (m, 1H), 2.36-2.21 (m, 1H), 2.11-1.99 (m, 1H), 1.90-1.77 (m, 1H), 1.58-1.41 (m, 2H), 1.21-1.03 (m, 4H) Analytical HPLC (Method A): RT=8.50 min, purity=>99%; Factor XIa Ki=0.1 nM, Plasma Kallikrein Ki=6 nM.

Example 202

Preparation of (9R,13S)-13-{4-[5-chloro-2-(4-chloro-1H-1,2,3-triazol-1-yl)phenyl]-5-fluoro-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one

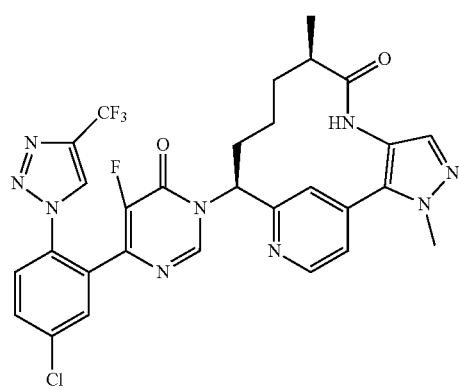

202A. Preparation of 6-(5-chloro-2-(4-chloro-1H-1,2,3-triazol-1-yl)phenyl)-5-fluoropyrimidin-4-ol To a solution of 6-(5-chloro-2-(4-chloro-1H-1,2,3-triazol-1-yl)phenyl)pyrimidin-4-ol (100 mg, 0.325 mmol) in CH$_3$CN (2 mL) was added SELECTFLUOR® (115 mg, 0.325 mmol). The mixture was stirred at rt for 1.5 h then DMF (0.5 ml) was added to solubilize the mixture. The reaction was heated at 85° C. overnight. The reaction mixture was purified using reverse phase chromatography. After the pure fractions were concentrated, the residue was partitioned between EtOAc and sat NaHCO$_3$ and the layers were separated. The aqueous layer was extracted with EtOAc (2×). The combined organic layers were dried with MgSO$_4$, filtered, and concentrated to give 6-(5-chloro-2-(4-chloro-1H-1,2,3-triazol-1-yl)phenyl)-5-fluoropyrimidin-4-ol (13 mg, 12.3% yield) as an off-white foam. MS(ESI) m/z: 326.1 (M+H)$^+$. $^1$H NMR (400 MHz, CDCl$_3$) δ 7.94 (s, 1H), 7.79 (s, 1H), 7.76 (d, J=2.2 Hz, 1H), 7.66 (dd, J=8.5, 2.3 Hz, 1H), 7.49 (d, J=8.6 Hz, 1H).

202B. Preparation of (9R,13S)-13-{4-[5-chloro-2-(4-chloro-1H-1,2,3-triazol-1-yl) phenyl]-5-fluoro-6-oxo-1,6-dihydropyrimidin-1-yl}-3,9-dimethyl-3,4,7,15-tetraazatricyclo[12.3.1.0$^{2,6}$]Octadeca-1(18),2(6),4,14,16-pentaen-8-one Trifluoroacetate (9R,13S)-13-{4-[5-Chloro-2-(4-chloro-1H-1,2,3-triazol-1-yl)phenyl]-5-fluoro-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (3 mg, 10% yield) was prepared in a similar manner as the procedure described in Example 56, using 6-(5-chloro-2-(4-chloro-1H-1,2,3-triazol-1-yl)phenyl)-5-fluoropyrimidin-4-ol. MS(ESI) m/z: 608.1 (M+H)$^+$. $^1$H NMR (400 MHz, CD$_3$OD) δ 8.78-8.68 (m, 1H), 8.41 (s, 1H), 7.86 (d, J=2.4 Hz, 1H), 7.81-7.74 (m, 1H), 7.71 (d, J=8.6 Hz, 2H), 7.52 (dd, J=5.1, 1.5 Hz, 1H), 7.49 (s, 1H), 6.00 (dd, J=12.4, 3.9 Hz, 1H), 4.05 (s, 3H), 2.70 (m, 1H), 2.36-2.23 (m, 1H), 2.14-1.96 (m, 2H), 1.67-1.54 (m, 1H), 1.53-1.41 (m, 1H), 1.01 (d, J=7.0 Hz, 3H), 0.68 (m, 1H). $^{19}$F NMR (376 MHz, CD$_3$OD) δ −77.46 (s), −147.07 (s). Analytical HPLC (Method A): RT=9.43 min, purity=93%; Factor XIa Ki=0.12 nM, Plasma Kallikrein Ki=13 nM.

Example 203

Preparation of (9R,13)-13-{5-bromo-4-[5-chloro-2-(4-chloro-1H-1,2,3-triazol-1-yl) phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

203A. Preparation of 6-(5-chloro-2-(4-chloro-1H-1,2,3-triazol-1-yl)phenyl)-5-fluoropyrimidin-4-ol To a solution of 6-(5-chloro-2-(4-chloro-1H-1,2,3-triazol-1-yl)phenyl)pyrimidin-4-ol (100 mg, 0.325 mmol) in CH$_3$CN (2 mL) was added NBS (63.5 mg, 0.357 mmol). The mixture was stirred at rt for 1.5 h. The reaction was partitioned between DCM and water and the layers were separated. The aqueous layer was extracted with DCM (2×). The combined organic layers was concentrated and then purified on normal phase chromatography to give 5-bromo-6-(5-chloro-2-(4-chloro-1H-1,2,3-triazol-1-yl)phenyl)pyrimidin-4-ol (117 mg, 93% yield) as white foam. MS(ESI) m/z: 388.0 (M+H)$^+$. $^1$H NMR (400 MHz, CDCl$_3$) δ 8.11 (s, 1H), 7.71 (s, 1H), 7.66-7.63 (m, 1H), 7.63-7.62 (m, 1H), 7.53 (d, J=8.4 Hz, 1H).

203B. Preparation of (9R,13S)-13-{5-bromo-4-[5-chloro-2-(4-chloro-1H-1,2,3-triazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one Trifluoroacetate (9R,13)-13-{5-Bromo-4-[5-chloro-2-(4-chloro-H-1,2,3-triazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (4 mg, 13% yield) was prepared in a similar manner as the procedure described in Example 56, by using 5-bromo-6-(5-chloro-2-(4-chloro-1H-1,2,3-triazol-1-yl)phenyl)pyrimidin-4-ol, prepared as described in Example 203A. MS(ESI) m/z: 670.0 (M+H)$^+$. $^1$H NMR (400 MHz, CD$_3$OD) δ 8.87 (s, 1H), 8.73 (d, J=5.1 Hz, 1H), 8.35 (s, 1H), 7.80-7.64 (m, 4H), 7.57-7.45 (m, 2H), 5.99 (dd, J=12.8, 3.7 Hz, 1H), 4.05 (s, 3H), 2.72 (m, 1H), 2.40-2.22 (m, 1H), 2.14-2.00 (m, 2H), 1.69-1.55 (m, 1H), 1.49 (t, J=10.0 Hz, 1H), 1.01 (d, J=6.8 Hz, 3H), 0.69 (m, 1H). Analytical HPLC (Method A): RT=11.12 min, purity=99%; Factor XIa Ki=4.6 nM, Plasma Kallikrein Ki=220 nM.

Example 204

Preparation of (9R,13S)-13-(4-{5-chloro-3-fluoro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one

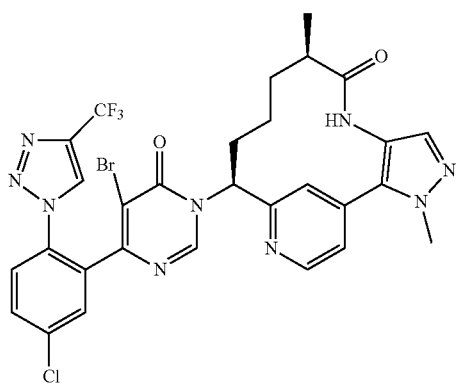 [SMILES: C[C@@H]1CCC[C@H](n2cnc(-c3cc(Cl)ccc3-n3cc(C(F)(F)F)nn3)c(Br)c2=O)c2cc(ccn2)-c2c(cnn2C)NC1=O]

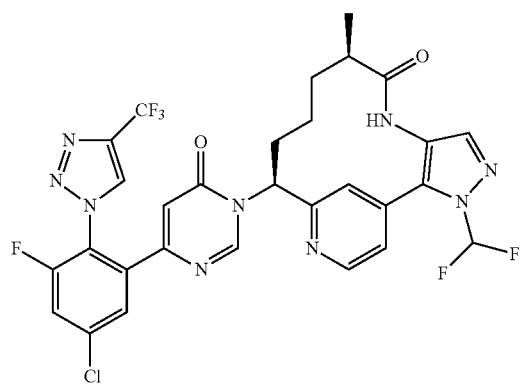 [SMILES: C[C@@H]1CCC[C@H](n2cnc(-c3cc(Cl)cc(F)c3-n3cc(C(F)(F)F)nn3)cc2=O)c2cc(ccn2)-c2c(cnn2C(F)F)NC1=O]

204A. Preparation of 6-(5-chloro-3-fluoro-2-(4-(trifluoromethyl)-1H-1,2,3-triazol-1-yl) phenyl)pyrimidin-4-ol 6-(5-Chloro-3-fluoro-2-(4-(trifluoromethyl)-1H-1,2,3-triazol-1-yl)phenyl) pyrimidin-4-ol was prepared in a similar manner as Intermediate 15, starting from 2-bromo-4-chloro-6-fluoroaniline instead of 2-bromo-4-chloroaniline. MS(ESI) m/z: 360.0 (M+H)+.

204B. Preparation of (9R,13S)-13-(4-{5-chloro-3-fluoro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one Trifluoroacetate (9R,13S)-13-(4-{5-Chloro-3-fluoro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one trifluoroacetate (25 mg, 23.4%) was prepared in a similar manner as Example 56 using 6-(5-chloro-3-fluoro-2-(4-(trifluoromethyl)-1H-1,2,3-triazol-1-yl)phenyl) pyrimidin-4-ol and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one, prepared as described in Intermediate 30. MS(ESI) m/z: 575.1 (M+H)+. $^1$H NMR (400 MHz, CD$_3$OD) δ 8.83 (s, 1H), 8.70 (s, 1H), 8.60 (d, J=5.3 Hz, 1H), 7.72-7.53 (m, 5H), 7.43-7.38 (m, 1H), 6.36 (d, J=0.7 Hz, 1H), 5.89 (dd, J=12.7, 4.5 Hz, 1H), 2.60 (td, J=6.7, 3.0 Hz, 1H), 2.14 (tt, J=12.8, 4.2 Hz, 1H), 1.98-1.82 (m, 2H), 1.53-1.30 (m, 2H), 0.88 (d, J=7.0 Hz, 3H), 0.51 (br. s., 1H). Analytical HPLC (Method A): RT=9.04 min, purity=99.5%; Factor XIa Ki=6.8 nM, Plasma Kallikrein Ki=2,700 nM.

Example 205

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-5,8-diazatricyclo[13.3.1.0$^{2,7}$]nonadeca-1(19),2(7),3,5,15,17-hexaen-9-one

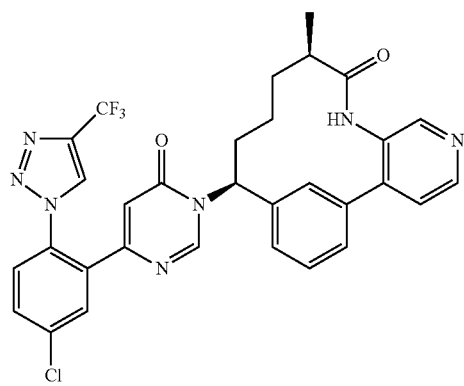 [SMILES: C[C@@H]1CCC[C@H](n2cnc(-c3cc(Cl)ccc3-n3cc(C(F)(F)F)nn3)cc2=O)c2cccc(c2)-c2ccncc2NC1=O]

(10R,14S)-14-(4-{5-Chloro-2-[4-(trifluoromethyl)-1H-1,2,3-triazol-1-yl]phenyl}-6-oxo-1,6-dihydropyrimidin-1-yl)-10-methyl-5,8-diazatricyclo[13.3.1.0$^{2,7}$]nonadeca-1(19),2(7),3,5,15,17-hexaen-9-one trifluoroacetate (0.0076 g, 36%) was prepared according to the procedures described in Example 46 by using 6-{5-chloro-2-[4-(trifluoromethyl)-1H-1,2,3-triazol-1-yl]phenyl}pyrimidin-4-ol, prepared as described in Example 15B, (10R,14S)-14-amino-10-methyl-5,8-diazatricyclo[13.3.1.0$^{2,7}$]nonadeca-1(19),2(7),3,5,15,17-hexaen-9-one, prepared as described in Intermediate 38, and 4-bromopyridin-3-amine in Intermediate 38B. MS(ESI) m/z: 620.1 (M+H)+. $^1$H NMR (400 MHz, CD$_3$OD) δ 8.81 (d, J=0.7 Hz, 1H), 8.77 (s, 2H), 8.29 (s, 1H), 8.08 (d, J=5.7 Hz, 1H), 7.91-7.84 (m, 2H), 7.82-7.60 (m, 4H), 7.42-7.34 (m, 1H), 6.49 (d, J=0.4 Hz, 1H), 5.80 (dd, J=13.0, 3.5 Hz, 1H), 2.64-2.51 (m, 1H), 2.39-2.26 (m, 1H), 2.18-2.06 (m, 1H), 1.99-1.88 (m, 1H), 1.63-1.30 (m, 3H), 1.16 (d, J=6.8 Hz, 3H). Analytical HPLC (Method A): RT=6.87 min, purity=90%; Factor XIa Ki=0.11 nM, Plasma Kallikrein Ki=11 nM.

Example 206

Preparation of (10R,14S)-14-{4-[5-chloro-2-(4-chloro-1H-1,2,3-triazol-1-yl)phenyl]-6-oxo-1,6-dihydropyrimidin-1-yl}-10-methyl-5,8-diazatricyclo[13.3.1.0$^{2,7}$]nonadeca-1(19),2(7),3,5,15,17-hexaen-9-one

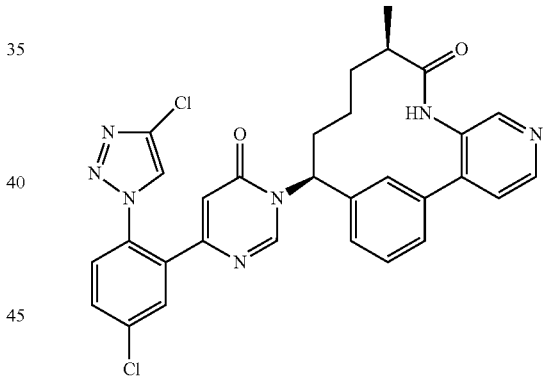

(10R,14S)-14-{4-[5-Chloro-2-(4-chloro-1H-1,2,3-triazol-1-yl)phenyl]-6-oxo-1,6-dihydropyrimidin-1-yl}-10-methyl-5,8-diazatricyclo[13.3.1.0$^{2,7}$]nonadeca-1(19),2(7),3,5,15,17-hexaen-9-one trifluoroacetate (0.0062 g, 31%) was prepared according to the procedures described in Example 205 by using 6-[5-chloro-2-(4-chloro-1H-1,2,3-triazol-1-yl)phenyl]pyrimidin-4-ol, prepared as described in Intermediate 9E. MS(ESI) m/z: 586.1 (M+H)+. $^1$H NMR (400 MHz, CD$_3$OD) δ 8.70 (d, J=5.3 Hz, 1H), 8.64 (s, 1H), 8.37-8.28 (m, 2H), 7.93-7.84 (m, 3H), 7.75 (dd, J=8.6, 2.2 Hz, 1H), 7.68-7.61 (m, 3H), 7.43-7.35 (m, 1H), 6.42 (s, 1H), 5.82 (dd, J=13.0, 3.5 Hz, 1H), 2.63-2.52 (m, 1H), 2.41-2.28 (m, 1H), 2.20-2.08 (m, 1H), 1.98-1.87 (m, 1H), 1.65-1.45 (m, 2H), 1.41-1.29 (m, 1H), 1.17 (d, J=7.0 Hz, 3H). Analytical HPLC (Method A): RT=6.26 min, purity=90%; Factor XIa Ki=0.2 nM, Plasma Kallikrein Ki=17 nM.

Example 207

Preparation of (9R,13S)-13-[4-(6-chloro-1H-1,3-benzodiazol-4-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one

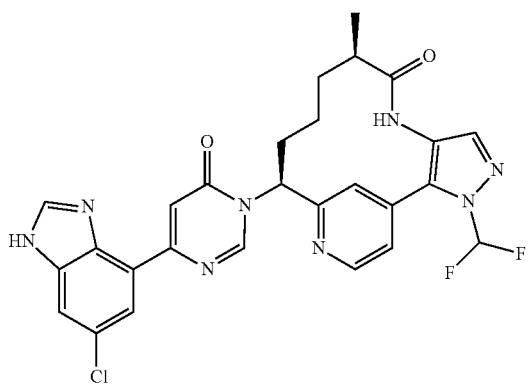 [SMILES: C[C@@H]1CCC[C@H](n2cnc(-c3cc(Cl)cc4[nH]cnc34)cc2=O)c2cc(ccn2)-c2c(cnn2C(F)F)NC1=O]

207A. Preparation of 6-chloro-4-(4,4,5,5-tetramethyl-1,3,2-dioxaborolan-2-yl)-1H-benzo[d]imidazole 4-Bromo-6-chloro-1H-benzo[d]imidazole (0.600 g, 2.59 mmol), 4,4,4',4',5,5,5',5'-octamethyl-2,2'-bi(1,3,2-dioxaborolane) (0.790 g, 3.11 mmol), KOAc (0.763 g, 7.78 mmol) were added to dioxane (10.9 mL). After bubbling Ar through the solution for 2 min, Pd(dppf)Cl$_2$CH$_2$Cl$_2$ complex (0.106 g, 0.130 mmol) was added and the mixture heated at 110° C. overnight. The reaction mixture was cooled to rt and partitioned between EtOAc and water. The organic phase separated and washed with sat NaHCO$_3$ and brine, dried over MgSO$_4$, filtered, concentrated to yield a crude dark solid product which was carried forward to the next reaction. MS(ESI) m/z: 197.0 (M-C$_6$H$_{10}$+H)$^+$.

207B. Preparation of 6-chloro-4-(6-methoxypyrimidin-4-yl)-1H-benzo[d]imidazole 4-Chloro-6-methoxypyrimidine (0.562 g, 3.89 mmol), 6-chloro-4-(4,4,5,5-tetramethyl-1,3,2-dioxaborolan-2-yl)-1H-benzo[d]imidazole (0.722 g, 2.59 mmol) and 2 M aq Na$_2$CO$_3$ (0.549 g, 5.18 mmol) in DME (20.74 mL), EtOH (2.59 mL) was purged with Ar for several min. Then PdCl$_2$(dppf)-CH$_2$Cl$_2$ Adduct (0.212 g, 0.259 mmol) was added and heated to 90° C. After 2 h, the reaction was cooled to rt, diluted with water and extracted with EtOAc. The organic layer washed with brine, dried over Na$_2$SO$_4$, filtered, and concentrated to give a brown oil. The crude material was purified by normal phase chromatography using EtOAc and MeOH as eluants to give 6-chloro-4-(6-methoxypyrimidin-4-yl)-1H-benzo[d]imidazole (148 mg, 22%). MS(ESI) m/z: 261.1 (M+H)$^+$ and 263.1 (M+2+H)$^+$. $^1$H NMR (500 MHz, DMSO-d$_6$) δ 8.93 (d, J=1.1 Hz, 1H), 8.42 (s, 1H), 8.36 (br. s., 1H), 8.20 (d, J=1.9 Hz, 1H), 7.84 (s, 1H), 4.02 (s, 3H).

207C. Preparation of 6-(6-chloro-H-benzo[d]imidazol-4-yl)pyrimidin-4-ol

To a clear solution of 6-chloro-4-(6-methoxypyrimidin-4-yl)-1H-benzo[d]imidazole (0.148 g, 0.568 mmol) in AcOH (2.88 ml) was added 63% aq HBr (0.548 ml, 4.54 mmol) and the reaction mixture was heated to 80° C. After 1 h, the solution was cooled to rt, diluted with EtOAc (10 ml), then quenched with sat aq NaHCO$_3$(20 ml). The aqueous layer was extracted with EtOAc (3×10 ml). The combined organic layer washed with brine (10 ml), dried over Na$_2$SO$_4$, filtered and concentrated. The crude product was triturated with pet. ether, filtered, and dried under vacuum to give 6-(6-chloro-1H-benzo[d]imidazol-4-yl)pyrimidin-4-ol as a beige color solid. MS(ESI) m/z: 247 (M+H)$^+$ and 249 (M+2+H)$^+$. $^1$H NMR (400 MHz, DMSO-d$_6$) δ 8.39 (s, 1H), 8.35-8.28 (m, 1H), 8.03 (d, J=2.0 Hz, 1H), 7.78 (d, J=2.2 Hz, 2H).

207D. Preparation of (9R,13S)-13-[4-(6-chloro-1H-1,3-benzodiazol-4-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one Trifluoroacetate (9R,13S)-13-[4-(6-Chloro-1H-1,3-benzodiazol-4-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one trifluoroacetate (0.7 mg, 0.77%) was prepared in a similar manner as Example 56 using 6-(6-chloro-1H-benzo[d]imidazol-4-yl)pyrimidin-4-ol and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one, prepared as described in Intermediate 30. MS(ESI) m/z: 565 (M+H)$^+$. $^1$H NMR (500 MHz, DMSO-d$_6$) δ 9.43 (s, 1H), 9.07 (br. s., 1H), 8.76 (d, J=4.6 Hz, 1H), 8.43 (br. s., 1H), 8.10 (d, J=17.7 Hz, 1H), 7.99-7.90 (m, 2H), 7.82-7.73 (m, 2H), 7.44 (d, J=4.6 Hz, 1H), 5.99 (d, J=11.0 Hz, 1H), 2.09 (d, J=8.9 Hz, 1H), 1.98 (br. s., 1H), 1.55 (br. s., 4H), 1.40 (br. s., 1H), 0.90 (d, J=6.7 Hz, 3H). Analytical HPLC (Method C): RT=1.20 min, purity=100%; Factor XIa Ki=120 nM.

Example 208

Preparation of methyl 4-[(9R,13S)-13-{4-[5-chloro-2-(4-chloro-1H-1,2,3-triazol-1-yl) phenyl]-6-oxo-1,6-dihydropyrimidin-1-yl}-9-methyl-8-oxo-3,4,7,15-tetraazatricyclo[12.3.1.0$^{2,6}$]octadeca-1(18),2,5,14,16-pentaen-4-yl]piperidine-1-carboxylate

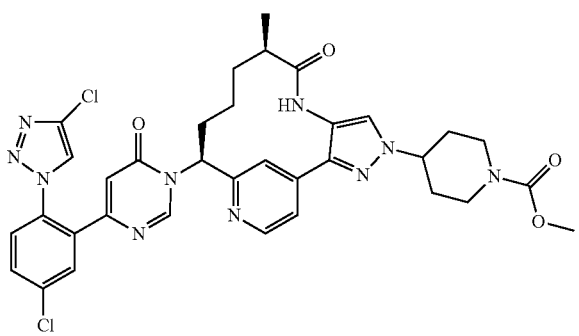 [SMILES: COC(=O)N1CCC(n2cc3c(n2)-c2ccnc(c2)[C@@H](n2cnc(-c4cc(Cl)ccc4-n4cc(Cl)nn4)cc2=O)CCC[C@@H](C)C(=O)N3)CC1]

(9R,13S)-13-{4-[5-Chloro-2-(4-chloro-1H-1,2,3-triazol-1-yl)phenyl]-6-oxo-1,6-dihydropyrimidin-1-yl}-9-methyl-4-(piperidin-4-yl)-3,4,7,15-tetraazatricyclo[12.3.1.0$^{2,6}$]octadeca-1(18),2,5,14,16-pentaen-8-one, prepared as described in Example 328 (0.015 g, 0.023 mmol), methyl chloroformate (2.2 mg, 0.023 mmol), and Et₃N (0.016 mL, 0.114 mmol) were dissolved in THF (1 mL) and stirred at rt for 3 h, then concentrated. The residue was purified by reverse phase chromatography to give methyl 4-[(9R,13S)-13-{4-[5-chloro-2-(4-chloro-1H-1,2,3-triazol-1-yl)phenyl]-6-oxo-1,6-dihydropyrimidin-1-yl}-9-methyl-8-oxo-3,4,7,15-tetraazatricyclo[12.3.1.0$^{2,6}$]octadeca-1(18),2,5,14,16-pentaen-4-yl]piperidine-1-carboxylate (10 mg, 61%) as a white solid. MS(ESI) m/z: 717.2 (M+H)⁺. ¹H NMR (400 MHz, CD₃OD) δ 8.69-8.64 (m, 1H), 8.63-8.57 (m, 1H), 8.36 (s, 1H), 7.91 (d, J=2.4 Hz, 2H), 7.83 (s, 1H), 7.79-7.72 (m, 1H), 7.68 (s, 1H), 7.67-7.65 (m, 1H), 7.65-7.61 (m, 1H), 6.40 (d, J=0.4 Hz, 1H), 6.11-5.99 (m, 1H), 4.52-4.41 (m, 1H), 4.34-4.22 (m, 2H), 3.74 (s, 3H), 3.17-2.97 (m, 2H), 2.86-2.75 (m, 1H), 2.36-2.13 (m, 4H), 2.13-1.97 (m, 3H), 1.81-1.63 (m, 1H), 1.61-1.48 (m, 1H), 1.09 (d, J=7.0 Hz, 3H). Analytical HPLC (Method A): RT=7.40 min, purity=99%; Factor XIa Ki=7 nM, Plasma Kallikrein Ki=460 nM.

Example 209

Preparation of (9R,13S)-13-(4-{4-chloro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]Octadeca-1(18),2(6),4,14,16-pentaen-8-one

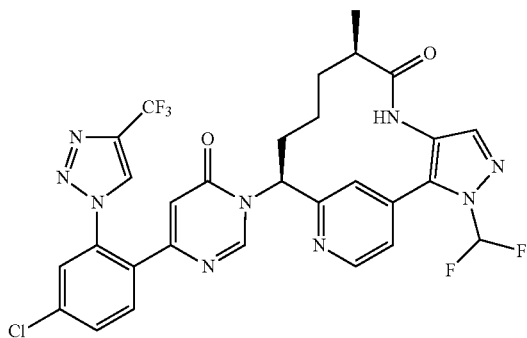 [SMILES: C[C@@H]1CCC[C@H](n2cnc(-c3ccc(Cl)cc3-n3cc(C(F)(F)F)nn3)cc2=O)c2cc(ccn2)-c2c(cnn2C(F)F)NC1=O]

(9R,13S)-13-(4-{4-Chloro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one (4 mg, 20% yield), was prepared as a solid via the coupling of 6-{4-chloro-2-[4-(trifluoromethyl)-1H-1,2,3-triazol-1-yl]phenyl}pyrimidin-4-ol (0.01 g, 0.028 mmol) and (9R,13S)-13-amino-3-(difluoromethyl)-9-methyl-3,4,7,15-tetraazatricyclo[12.3.1.0$^{2,6}$]octadeca-1(18),2(6), 4,14,16-pentaen-8-one (0.01 g, 0.028 mmol) using the HATU, DBU coupling methodology as described in Example 56. LCMS m/z=660.2 (M+H). ¹H NMR (400 MHz, CD₃OD) δ 8.87-8.80 (m, 2H), 8.76-8.71 (m, 1H), 7.86-7.83 (m, 2H), 7.82-7.80 (m, 1H), 7.77-7.76 (m, 1H), 7.72-7.66 (m, 2H), 7.55-7.52 (m, 1H), 6.49-6.46 (s, 1H), 6.08-5.99 (m, 1H), 2.78-2.68 (m, 1H), 2.36-2.21 (m, 1H), 2.12-1.99 (m, 3H), 1.69-1.41 (m, 4H), 1.05-0.96 (d, 3H), 0.74-0.54 (m, 1H). Analytical HPLC (Method A) RT=8.77 min, purity=95%; Factor XIa Ki=48 nM.

Example 210

Preparation of (9R,13S)-13-{4-[5-chloro-2-(4-chloro-1H-1,2,3-triazol-1-yl)phenyl]-5-methyl-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

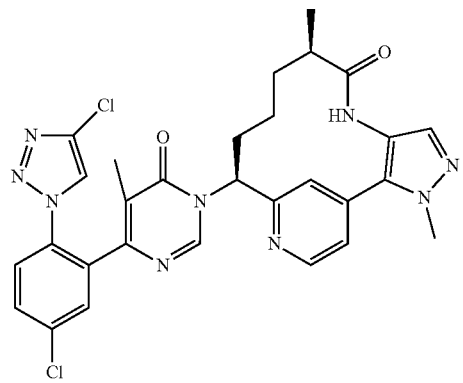 [SMILES: Cc1c(-c2cc(Cl)ccc2-n2cc(Cl)nn2)ncn([C@H]2CCC[C@@H](C)C(=O)Nc3cnn(C)c3-c3ccnc2c3)c1=O]

210A. Preparation of 4-chloro-2-(6-methoxy-5-methylpyrimidin-4-yl)aniline

4-Chloro-2-(6-methoxy-5-methylpyrimidin-4-yl)aniline (230 mg, 73% yield) was prepared in a similar manner as the procedure described in Intermediate 9B, by replacing 4-chloro-6-methoxypyrimidine with 4-chloro-6-methoxy-5-methylpyrimidine (200 mg, 1.261 mmol). MS(ESI) m/z: 250.1 (M+H)⁺. ¹H NMR (500 MHz, CDCl₃) δ 8.68 (s, 1H), 7.15 (dd, J=8.6, 2.6 Hz, 1H), 7.09 (d, J=2.6 Hz, 1H), 6.72 (d, J=8.6 Hz, 1H), 4.25 (br. s., 2H), 4.06 (s, 3H), 2.14 (s, 3H), 1.33-1.20 (m, 12H).

210B. Preparation of 4-(5-chloro-2-(4-(trimethylsilyl)-1H-1,2,3-triazol-1-yl)phenyl)-6-methoxy-5-methylpyrimidine 4-(5-Chloro-2-(4-(trimethylsilyl)-1H-1,2,3-triazol-1-yl) phenyl)-6-methoxy-5-methylpyrimidine (70 mg, 20% yield) was prepared in a similar manner as the procedure described in Intermediate 9C, by replacing 4-chloro-2-(6-methoxypyrimidin-4-yl)aniline with 4-chloro-2-(6-methoxy-5-methylpyrimidin-4-yl)aniline (230 mg, 0.921 mmol). MS(ESI) m/z: 374.4 (M+H)⁺. ¹H NMR (400 MHz, CDCl₃) δ 8.36 (s, 1H), 7.44-7.29 (m, 2H), 7.25 (d, J=2.2 Hz, 1H), 7.12 (s, 1H), 3.76-3.70 (m, 3H), 0.04-0.05 (m, 9H).

210C. Preparation of 4-(5-chloro-2-(4-chloro-1H-1,2,3-triazol-1-yl)phenyl)-6-methoxy-5-methylpyrimidine 4-(5-Chloro-2-(4-chloro-1H-1,2,3-triazol-1-yl)phenyl)-6-methoxy-5-methylpyrimidine (29 mg, 46% yield) was prepared in a similar manner as the procedure described in Intermediate 9D, by replacing 4-{5-chloro-2-[4-(trimethylsilyl)-1H-1,2,3-triazol-1-yl]phenyl}-6-methoxypyrimidine with 4-(5-chloro-2-(4-(trimethylsilyl)-1H-1,2,3-triazol-1-yl) phenyl)-6-methoxy-5-methylpyrimidine (70 mg, 0.187 mmol). MS(ESI) m/z: 336.4 (M+H)⁺. ¹H NMR (400 MHz, CDCl$_3$) δ 8.60 (s, 1H), 7.61-7.58 (m, 2H), 7.50 (s, 1H), 7.47 (d, J=2.0 Hz, 1H), 4.02 (s, 3H), 1.83 (s, 3H).

210D. Preparation of 6-(5-chloro-2-(4-chloro-1H-1,2,3-triazol-1-yl)phenyl)-5-methylpyrimidin-4-ol 6-(5-Chloro-2-(4-chloro-1H-1,2,3-triazol-1-yl)phenyl)-5-methylpyrimidin-4-ol (10 mg, 36% yield) was prepared in a similar manner as the procedure described in Intermediate 9E, by replacing 4-[5-chloro-2-(4-chloro-1H-1,2,3-triazol-1-yl)phenyl]-6-methoxypyrimidine with 4-(5-chloro-2-(4-chloro-1H-1,2,3-triazol-1-yl)phenyl)-6-methoxy-5-methylpyrimidine (29 mg, 0.086 mmol). MS(ESI) m/z: 322.0 (M+H)$^+$. $^1$H NMR (400 MHz, CD$_3$OD) δ 8.25 (s, 1H), 7.98 (s, 1H), 7.72 (d, J=2.0 Hz, 1H), 7.71 (d, J=0.4 Hz, 1H), 7.66 (dd, J=2.1, 0.6 Hz, 1H), 1.79 (s, 3H).

210E. Preparation of (9R,13S)-13-{4-[5-chloro-2-(4-chloro-1H-1,2,3-triazol-1-yl) phenyl]-5-methyl-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one Trifluoroacetate (9R,13S)-13-{4-[5-Chloro-2-(4-chloro-1H-1,2,3-triazol-1-yl)phenyl]-5-methyl-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (8.8 mg, 37% yield) was prepared in a similar manner as the procedure described in Example 56, by using 6-(5-chloro-2-(4-chloro-1H-1,2,3-triazol-1-yl)phenyl)-5-methylpyrimidin-4-ol (0.010 g, 0.031 mmol). MS(ESI) m/z: 604.1 (M+H)$^+$. $^1$H NMR (400 MHz, CD$_3$OD) δ 8.79-8.70 (m, 2H), 8.27 (s, 1H), 7.78 (s, 1H), 7.77-7.69 (m, 2H), 7.68 (d, J=2.0 Hz, 1H), 7.60 (dd, J=5.3, 1.5 Hz, 1H), 7.50 (s, 1H), 5.95 (dd, J=12.5, 4.2 Hz, 1H), 4.06 (s, 3H), 2.70 (m, 1H), 2.40-2.29 (m, 1H), 2.13-1.99 (m, 2H), 1.77 (s, 3H), 1.67-1.55 (m, 1H), 1.47 (m, 1H), 1.02 (d, J=6.8 Hz, 3H), 0.77 (m, 1H); Analytical HPLC (Method A): RT=7.79 min, purity=93%; Factor XIa Ki=3.5 nM, Plasma Kallikrein Ki=240 nM.

Example 211

Preparation of (9R,13S)-13-[4-(5-chloro-2-iodophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one

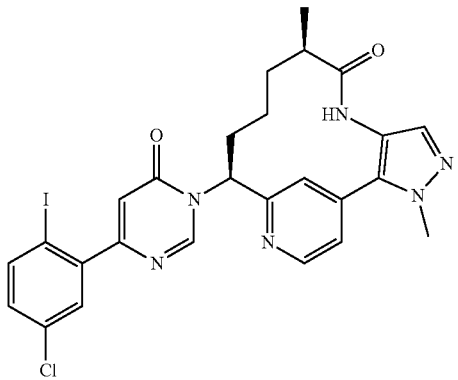 [SMILES: C[C@@H]1CCC[C@H](n2cnc(-c3cc(Cl)ccc3I)cc2=O)c2cc(ccn2)-c2c(cnn2C)NC1=O]

211A. Preparation of 4-(5-chloro-2-iodophenyl)-6-methoxypyrimidine

The solution of 4-chloro-2-(6-methoxypyrimidin-4-yl)aniline (2 g, 8.49 mmol), prepared as described in Intermediate 8A, in ACN (56.6 ml) was cooled to 0° C., then p-TsOH.H$_2$O (4.04 g, 21.22 mmol) was added. A solution of NaNO$_2$ (1.171 g, 16.97 mmol) and NaI (3.18 g, 21.22 mmol) in water (28.3 ml) was added slowly and the reaction turned into a dark brown solution. After a few min, the reaction turned cloudy. The reaction was stirred at 0° C. for 1 h, then the reaction was warmed to rt. After 18 h, the reaction was quenched with sat NaHCO$_3$ and extracted with EtOAc. The organic layer was washed with sat aq Na$_2$S$_2$O$_3$, brine, dried over Na$_2$SO$_4$, filtered, and concentrated to yield a solid. Purification by normal phase chromatography afforded 4-(5-chloro-2-iodophenyl)-6-methoxypyrimidine (2.13 g, 72% yield) as a white solid. MS(ESI) m/z: 347.2 (M+H)$^+$. $^1$H NMR (500 MHz, CDCl$_3$) δ 8.87 (d, J=1.1 Hz, 1H), 7.88 (d, J=8.3 Hz, 1H), 7.44 (d, J=2.8 Hz, 1H), 7.11 (dd, J=8.5, 2.8 Hz, 1H), 6.93 (d, J=1.4 Hz, 1H), 4.06 (s, 3H).

211B. Preparation of 6-(5-chloro-2-iodophenyl)pyrimidin-4-ol 6-(5-Chloro-2-iodophenyl)pyrimidin-4-ol (0.24 g, 100% yield) was prepared in a similar manner as the procedure described in Example 140B, by replacing 4-(5-chloro-2-(1-(difluoromethyl)-1H-pyrazol-4-yl)phenyl)-6-methoxypyrimidine with 4-(5-chloro-2-iodophenyl)-6-methoxypyrimidine (0.25 g, 0.721 mmol), and the reaction time was 1 h at 85° C. MS(ESI) m/z: 333.0 (M+H)$^+$. $^1$H NMR (400 MHz, CD$_3$OD) δ 8.27 (d, J=0.9 Hz, 1H), 7.95 (d, J=8.6 Hz, 1H), 7.47 (d, J=2.6 Hz, 1H), 7.21 (dd, J=8.6, 2.6 Hz, 1H), 6.54 (d, J=0.9 Hz, 1H).

211C. Preparation of (9R,13S)-13-[4-(5-chloro-2-iodophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one Trifluoroacetate (9R,13S)-13-[4-(5-Chloro-2-iodophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one trifluoroacetate (125 mg, 68% yield) was prepared in a similar manner as the procedure described in Example 56, by using 6-(5-chloro-2-iodophenyl)pyrimidin-4-ol (100 mg, 0.301 mmol). MS(ESI) m/z: 615.4 (M+H)$^+$. $^1$H NMR (400 MHz, CD$_3$OD) δ 9.05 (s, 1H), 8.75 (d, J=5.3 Hz, 1H), 7.95 (d, J=8.4 Hz, 1H), 7.74 (s, 1H), 7.54 (dd, J=5.1, 1.5 Hz, 1H), 7.51-7.49 (m, 2H), 7.21 (dd, J=8.5, 2.5 Hz, 1H), 6.60 (s, 1H), 6.07 (dd, J=12.8, 4.4 Hz, 1H), 4.05 (s, 3H), 2.77-2.68 (m, 1H), 2.38 (tt, J=12.7, 4.3 Hz, 1H), 2.16-2.02 (m, 2H), 1.68-1.44 (m, 2H), 1.02 (d, J=6.8 Hz, 3H), 0.79-0.64 (m, 1H). Analytical HPLC (Method A): RT=8.71 min, 99.6% purity; Factor XIa Ki=12 nM, Plasma Kallikrein Ki=140 nM.

Example 212

Preparation of (9R,13S)-13-{4-[3-chloro-2-fluoro-6-(4-phenyl-1H-1,2,3-triazol-1-yl) phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one Trifluoroacetate

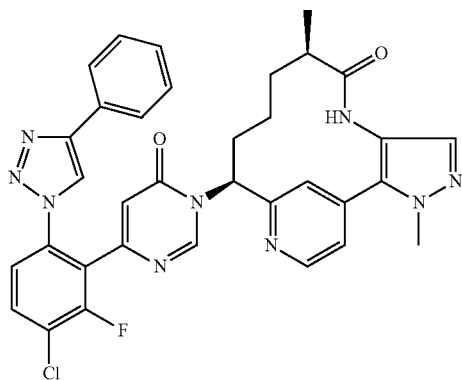 [SMILES: C[C@@H]1CCC[C@H](n2cnc(-c3c(-n4cc(-c5ccccc5)nn4)ccc(Cl)c3F)cc2=O)c2cc(ccn2)-c2c(cnn2C)NC1=O]

(9R,13S)-13-{4-[3-Chloro-2-fluoro-6-(4-phenyl-1H-1,2,3-triazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one (3 mg, 19% yield) was prepared in a similar manner as the procedure described in Example 56, by using 6-[3-chloro-2-fluoro-6-(4-phenyl-1H-1,2,3-triazol-1-yl)phenyl]pyrimidin-4-ol (9 mg, 0.024 mmol), prepared as described in Intermediate 9, and (9R,13S)-13-amino-3,9-dimethyl-3,4,7,15-tetraazatricyclo[12.3.1.0$^{2,6}$]octadeca-1(18),2(6),4,14,16-pentaen-8-one (7.3 mg, 0.024 mmol). LCMS m/z 650.3(M+H). $^1$H NMR (400 MHz, CD$_3$OD) δ 8.81-8.77 (m, 1H), 8.62-8.57 (m, 1H), 8.56-8.54 (m, 1H), 7.93-7.87 (m, 1H), 7.84-7.78 (m, 3H), 7.66-7.62 (dd, 1H), 7.61-7.57 (m, 1H), 7.52 (bs, 1H), 7.49-7.44 (m, 2H), 7.43-7.38 (m, 1H), 6.68-6.64 (m, 1H), 5.98-5.94 (m, 1H), 4.07 (s, 3H), 2.75-2.61 (m, 1H), 2.39-2.22 (m, 1H), 2.10-1.99 (m, 2H), 1.65-1.53 (m, 1H), 1.49-1.33 (m, 1H), 1.07-1.00 (d, 3H), 0.86-0.67 (m, 1H); Factor XIa Ki=0.81 nM, Plasma Kallikrein Ki=28 nM.

Example 213

Preparation of N-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}-3-fluorophenyl)carbamate Trifluoroacetate

213A. Preparation of N-[4-chloro-3-fluoro-2-(6-methoxypyrimidin-4-yl)phenyl]carbamate 4-Chloro-3-fluoro-2-(6-methoxypyrimidin-4-yl)aniline (0.024 g, 0.095 mmol), was dissolved in DCM (5 ml). To this solution was added sequentially TEA (1 mL) followed by methyl chloroformate (8.94 mg, 0.095 mmol) and the solution was stirred at rt. After 2 h, the reaction was concentrated in vacuo to an oil and quenched with dilute HCl (5 mL). The organics were extracted with EtOAc (2×25 mL), dried with MgSO$_4$ and evaporated to an oil. LCMS m/z 312.1(M+H). $^1$H NMR (400 MHz, CDCl$_3$) δ 10.30-10.24 (m, 1H), 8.84-8.81 (m, 1H), 8.00-7.92 (m, 1H), 7.40-7.32 (m, 1H), 7.05-7.01 (m, 1H), 3.98 (s, 3H), 3.67 (s, 3H). The crude product was taken in a small vial and dissolved in AcOH (1 mL) and to this was added 48% HBr (0.1 mL) and heated at 80° C. until reaction was complete. The reaction mixture was concentrated and quenched with water (25 mL), extracted with EtOAc (2×25 mL). The combined organic layers was dried and evaporated to give N-[4-chloro-3-fluoro-2-(6-methoxypyrimidin-4-yl)phenyl]carbamate as a white film (13 mg). LCMS m/z 299.1(M+H).

213B. Preparation of N-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}-3-fluorophenyl)carbamate N-(4-Chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}-3-fluorophenyl)carbamate (1.1 mg, 4.21% yield) was prepared following the procedure described in Example 56 by using N-[4-chloro-3-fluoro-2-(6-hydroxypyrimidin-4-yl)phenyl]carbamate (13 mg, 0.044 mmol), (9R,13)-13-amino-3,9-dimethyl-3,4,7,15-tetraazatricyclo[12.3.1.0$^{2,6}$]octadeca-1(18),2(6),4,14,16-pentaen-8-one (15 mg, 0.044 mmol). LCMS m/z 580.1(M+H). $^1$H NMR (500 MHz, DMSO-d$_6$) δ 9.39-9.34 (m, 1H), 9.24-9.21 (m, 1H), 9.05-9.02 (m, 1H), 8.74-8.70 (m, 1H), 7.74-7.57 (m, 3H), 7.49 (s, 1H), 6.61-6.55 (m, 1H), 5.99-5.87 (m, 1H), 4.04-3.98 (m, 3H), 3.65-3.59 (m, 3H), 2.70-2.62 (m, 1H), 2.40-2.32 (m, 1H), 2.18-2.09 (m, 1H), 1.96-1.85 (m, 1H), 1.53-1.30 (m, 2H), 0.94-0.87 (m, 3H), 0.56-0.36 (m, 1H). Ortho RT. 1.605 min purity 97%; Factor XIa Ki=110 nM.

Example 214

Preparation of (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-8-oxo-3,4,7,15-tetraazatricyclo[12.3.1.0$^{2,6}$]octadeca-1(18),2(6),4,14,16-pentaen-15-ium-15-olate

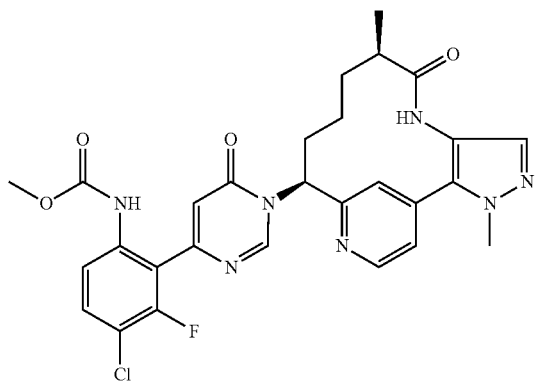 [SMILES: COC(=O)Nc1ccc(Cl)c(F)c1-c1cc(=O)n([C@H]2CCC[C@@H](C)C(=O)Nc3cnn(C)c3-c3ccnc2c3)cn1]
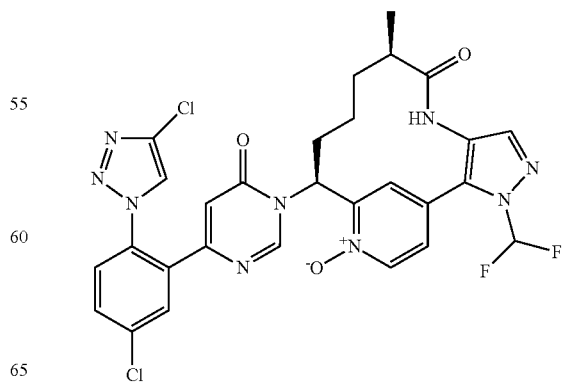

(9R,13S)-13-{4-[5-Chloro-2-(4-chloro-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0²,⁶]octadeca-1(18),2(6),4,14,16-pentaen-8-one, prepared as described in Example 88, was dissolved in EtOAc (2 mL) and m-CPBA (0.021 g, 0.120 mmol) was added at rt. After stirring overnight, the reaction was concentrated and purified by reverse phase chromatography to give (9R,13S)-13-{4-[5-chloro-2-(4-chloro-1H-1,2,3-triazol-1-yl) phenyl]-6-oxo-1,6-dihydropyrimidin-1-yl}-3-(difluoromethyl)-9-methyl-8-oxo-3,4,7,15-tetraazatricyclo[12.3.1.0²,⁶]octadeca-1(18),2(6),4,14,16-pentaen-15-ium-15-olate (11 mg, 15%) as a white solid. MS(ESI) m/z: 642.2 (M+H)⁺. ¹H NMR (500 MHz, DMSO-d₆) δ 9.54 (s, 1H), 8.71 (s, 1H), 8.40 (d, J=6.7 Hz, 2H), 7.98-7.86 (m, 3H), 7.85-7.76 (m, 2H), 7.72 (d, J=8.5 Hz, 1H), 7.55 (d, J=5.2 Hz, 1H), 6.32 (s, 1H), 5.49-5.31 (m, 1H), 2.48-2.34 (m, 1H), 2.03-1.92 (m, 1H), 1.82-1.70 (m, 1H), 1.48-1.36 (m, 1H), 1.06 (d, J=6.1 Hz, 3H), 1.01-0.85 (m, 1H). Analytical HPLC (Method C): RT=1.45 min, purity=100%; Factor XIa Ki=0.35 nM, Plasma Kallikrein Ki=74 nM.

Example 215

Preparation of (9R,13S)-13-(4-{5-chloro-2-[4-(pyridin-3-yl)-1H-1,2,3-triazol-1-yl]phenyl}-6-oxo-1,6-dihydropyrimidin-1-yl)-3-(difluoromethyl)-9-methyl-3,4,7-triazatricyclo[12.3.1.0²,⁶]octadeca-1(18),2(6),4,14,16-pentaen-8-one Trifluoroacetate

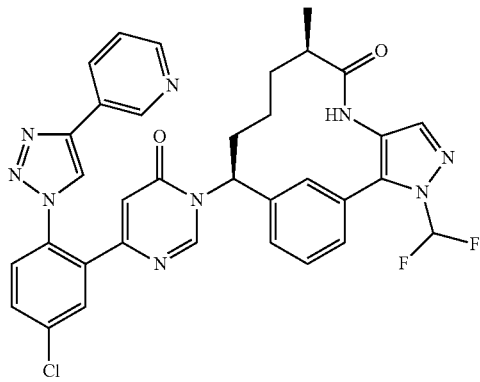 [SMILES: C[C@@H]1CCC[C@H](n2cnc(-c3cc(Cl)ccc3-n3cc(-c4cccnc4)nn3)cc2=O)c2cccc(c2)-c2c(cnn2C(F)F)NC1=O]

215A. Preparation of 6-{5-chloro-2-[4-(pyridin-3-yl)-1H-1,2,3-triazol-1-yl]phenyl}pyrimidin-4-ol

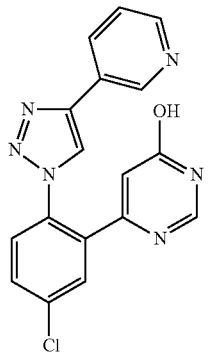 [SMILES: Oc1cc(-c2cc(Cl)ccc2-n2cc(-c3cccnc3)nn2)ncn1]

4-Chloro-2-(6-methoxypyrimidin-4-yl)aniline (0.1 g, 0.424 mmol) was dissolved in ACN (5 mL) and cooled to 0° C. To this solution was added isopentylnitrite ((0.075 g, 0.636 mmol) followed by the addition of TMSN₃ (0.073 g, 0.636 mmol). The reaction mixture was stirred at 0° C. for 0.5 h then allowed to warm to rt and stirred overnight. To the solution was added Cu₂O (6.1 mg, 0.042 mmol) followed by 3-ethynylpyridine (0.044 g, 0.424 mmol) and stirred at rt. The reaction turned milky gray to clear in about 2 min. After 1 h, the reaction was concentrated and directly purified via a 12 g silica gel ISCO column using hexane/EtOAc as eluants to give 6-{5-chloro-2-[4-(pyridin-3-yl)-1H-1,2,3-triazol-1-yl]phenyl}pyrimidin-4-ol (0.069 g) as a yellowish orange liquid. LCMS m/z 355.1 (M+H). ¹H NMR (500 MHz, CDCl₃) δ 8.89-8.86 (m, 1H), 7.91-7.88 (m, 1H), 7.49-7.45 (m, 1H), 7.29 (s, 5H), 7.27-7.20 (m, 2H), 4.10-4.04 (m, 3H). The product was dissolved in AcOH (1 mL) and 48% aq HBr (0.2 mL) was added, sealed and heated at 80° C. for 2 h. The reaction was concentrated and quenched with sat NaHCO₃(25 mL) and extracted with EtOAc (2×25 mL). The organic extracts were combined, dried over MgSO₄, filtered and concentrated to afford 6-{5-chloro-2-[4-(pyridin-3-yl)-1H-1,2,3-triazol-1-yl]phenyl}pyrimidin-4-ol as an oil (0.011 g, 7% yield). LCMS m/z 351.1 (M+H).

215B. Preparation of (9R,13S)-13-(4-{5-chloro-2-[4-(pyridin-3-yl)-1H-1,2,3-triazol-1-yl]phenyl}-6-oxo-1,6-dihydropyrimidin-1-yl)-3-(difluoromethyl)-9-methyl-3,4,7-triazatricyclo[12.3.1.0²,⁶]octadeca-1(18),2(6),4,14,16-pentaen-8-one Trifluoroacetate (9R,13S)-13-(4-{5-Chloro-2-[4-(pyridin-3-yl)-1H-1,2,3-triazol-1-yl]phenyl}-6-oxo-1,6-dihydropyrimidin-1-yl)-3-(difluoromethyl)-9-methyl-3,4,7-triazatricyclo[12.3.1.0²,⁶]octadeca-1(18),2(6),4,14,16-pentaen-8-one trifluoroacetate was prepared (3.5 mg, 14.1%) following the procedure described in Example 56 by using 6-{5-chloro-2-[4-(pyridin-3-yl)-1H-1,2,3-triazol-1-yl]phenyl}pyrimidin-4-ol (12 mg, 0.034 mmol) and (9R,13S)-13-amino-3-(difluoromethyl)-9-methyl-3,4,7-triazatricyclo[12.3.1.0²,⁶]octadeca-1(18),2(6),4,14,16-pentaen-8-one (11 mg, 0.034 mmol). LCMS m/z 668.1 (M+H). ¹H NMR (500 MHz, DMSO-d₆) δ 9.45-9.41 (m, 1H), 9.13-9.09 (m, 1H), 9.02-8.97 (m, 1H), 8.69-8.62 (m, 1H), 8.53-8.47 (m, 1H), 8.35-8.29 (m, 1H), 7.99-7.95 (m, 2H), 7.93-7.83 (m, 4H), 7.75-7.70 (m, 1H), 7.64-7.59 (m, 1H), 7.55-7.50 (m, 1H), 7.49-7.42 (m, 1H), 7.41-7.32 (m, 1H), 7.29-7.23 (m, 1H), 6.50-6.46 (m, 1H), 5.71-5.59 (m, 1H), 2.55-2.29 (m, 2H), 1.99-1.81 (m, 2H), 1.54-1.39 (m, 1H), 1.28-1.06 (m, 2H), 1.05-0.98 (d, 3H), 0.50-0.31 (m, 1H). Orthogonal RT. 1.652 purity>92%; Factor XIa Ki=0.48 nM, Plasma Kallikrein Ki=75 nM.

Example 216

Preparation of (9R,13S)-13-{4-[5-chloro-2-(4-chloro-1H-1,2,3-triazol-1-yl)phenyl]-6-oxo-1,6-dihydropyrimidin-1-yl}-9-methyl-4-(pyridin-3-yl)-3,4,7,15-tetraazatricyclo[12.3.1.0²,⁶]octadeca-1(18),2,5,14,16-pentaen-8-one

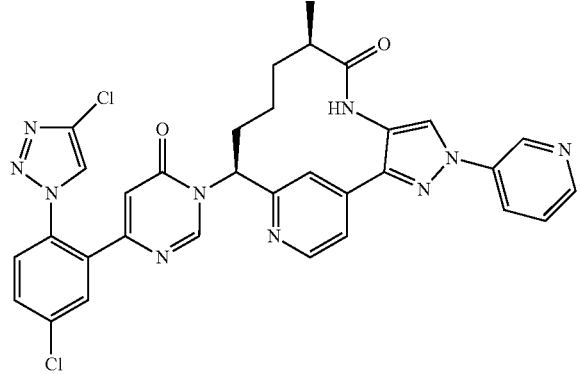 [SMILES: C[C@@H]1CCC[C@H](n2cnc(-c3cc(Cl)ccc3-n3cc(Cl)nn3)cc2=O)c2cc(ccn2)-c2nn(-c3cccnc3)cc2NC1=O]

(9R,13S)-13-{4-[5-Chloro-2-(4-chloro-1H-1,2,3-triazol-1-yl)phenyl]-6-oxo-1,6-dihydropyrimidin-1-yl}-9-methyl-3,4,7,15-tetraazatricyclo[12.3.1.0²,⁶]octadeca-1(18),2(6),4,14,16-pentaen-8-one, prepared as described in Example 101, (0.09 g, 0.156 mmol), (1R,2R)—N1,N2-dimethylcyclohexane-1,2-diamine (0.022 g, 0.156 mmol), Cs₂CO₃ (0.102 g, 0.312 mmol), and 3-iodopyridine (0.032 g, 0.156 mmol) were added to a 5 mL microwave vial. DMF (2 mL) was added and the vial was purged with Ar (3×). CuI (2 mg, 10.50 μmol) was added, the vial was sealed with a microwave vial cap and the reaction was heated in a microwave reactor at 120° C. for 30 min. The reaction was then purified by reverse phase chromatography to yield (9R,13S)-13-{4-[5-chloro-2-(4-chloro-1H-1,2,3-triazol-1-yl)phenyl]-6-oxo-1,6-dihydropyrimidin-1-yl}-9-methyl-4-(pyridin-3-yl)-3,4,7,15-tetraazatricyclo[12.3.1.0²,⁶]octadeca-1(18),2,5,14,16-pentaen-8-one trifluoroacetate (52 mg, 42% yield) as a tan solid. MS(ESI) m/z: 653.6 (M+H)⁺. ¹H NMR (400 MHz, CD₃OD) δ 9.34-9.21 (m, 1H), 8.81-8.73 (m, 1H), 8.72-8.64 (m, 2H), 8.60 (s, 2H), 8.37 (s, 1H), 8.02-7.96 (m, 1H), 7.96-7.89 (m, 1H), 7.87-7.80 (m, 1H), 7.80-7.73 (m, 2H), 7.72-7.63 (m, 1H), 6.47-6.35 (m, 1H), 6.20-6.03 (m, 1H), 2.96-2.82 (m, 1H), 2.42-2.22 (m, 2H), 2.17-2.01 (m, 1H), 1.83-1.70 (m, 1H), 1.70-1.52 (m, 1H), 1.42-1.26 (m, 1H), 1.11 (d, J=7.0 Hz, 3H), 0.97-0.85 (m, 2H). Analytical HPLC (Method A): RT=6.69 min, purity=97.5%; Factor XIa Ki=0.57 nM, Plasma Kallikrein Ki=10 nM.

Example 217

Preparation of (9R,13S)-13-{4-[5-chloro-2-(4-chloro-1H-1,2,3-triazol-1-yl)phenyl]-6-oxo-1,6-dihydropyrimidin-1-yl}-9-methyl-3-(pyridin-3-yl)-3,4,7,15-tetraazatricyclo[12.3.1.0²,⁶]octadeca-1(18),2(6),4,14,16-pentaen-8-one

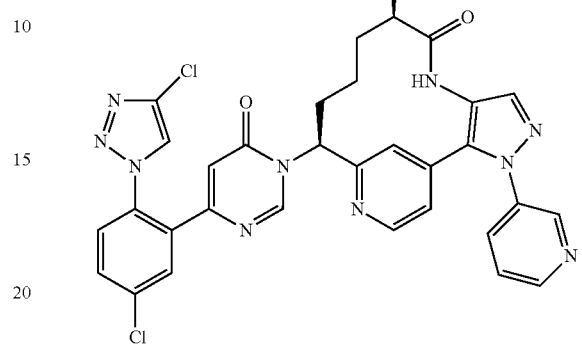

(9R,13S)-13-{4-[5-Chloro-2-(4-chloro-1H-1,2,3-triazol-1-yl)phenyl]-6-oxo-1,6-dihydropyrimidin-1-yl}-9-methyl-3-(pyridin-3-yl)-3,4,7,15-tetraazatricyclo[12.3.1.0²,⁶]octadeca-1(18),2(6),4,14,16-pentaen-8-one trifluoroacetate was synthesized as a minor product (24 mg, 19% yield) from the reaction to generate (9R,13S)-13-{4-[5-chloro-2-(4-chloro-1H-1,2,3-triazol-1-yl)phenyl]-6-oxo-1,6-dihydropyrimidin-1-yl}-9-methyl-4-(pyridin-3-yl)-3,4,7,15-tetraazatricyclo[12.3.1.0²,⁶]octadeca-1(18),2,5,14,16-pentaen-8-one, Example 216. MS(ESI) m/z: 653.6 (M+H)⁺. ¹H NMR (400 MHz, CD₃OD) δ 9.27-9.27 (m, 1H), 9.30-9.21 (m, 1H), 8.63 (s, 6H), 8.39 (s, 1H), 8.17-8.09 (m, 1H), 7.95-7.90 (m, 1H), 7.88-7.83 (m, 1H), 7.82-7.73 (m, 3H), 7.71-7.65 (m, 1H), 6.50-6.37 (m, 1H), 5.95-5.80 (m, 1H), 2.78-2.60 (m, 1H), 2.55-2.39 (m, 1H), 2.15-1.98 (m, 2H), 1.83-1.65 (m, 1H), 1.61-1.44 (m, 2H), 1.32 (d, J=7.0 Hz, 5H). Analytical HPLC (Method A): RT=6.45 min, purity=95%; Factor XIa Ki=74 nM, Plasma Kallikrein Ki=600 nM.

Example 218

Preparation of (9R,13S)-13-{4-[5-chloro-2-(4-chloro-1H-1,2,3-triazol-1-yl)phenyl]-6-oxo-1,6-dihydropyrimidin-1-yl}-9-methyl-3-phenyl-3,4,7,15-tetraazatricyclo[12.3.1.0²,⁶]octadeca-1(18),2(6),4,14,16-pentaen-8-one

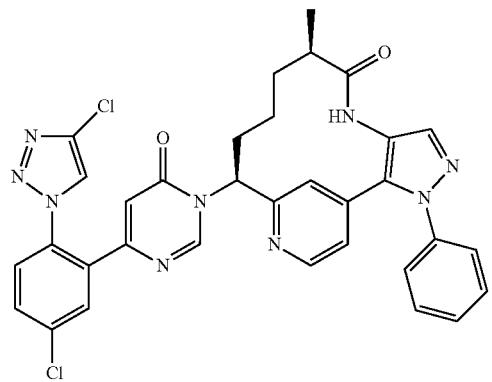 [SMILES: C[C@@H]1CCC[C@H](n2cnc(-c3cc(Cl)ccc3-n3cc(Cl)nn3)cc2=O)c2cc(ccn2)-c2c(cnn2-c2ccccc2)NC1=O]

218A. Preparation of 4-nitro-1-phenyl-1H-pyrazole

To a 3-neck flask was added 4-nitro-1H-pyrazole (3.0 g, 26.5 mmol), phenylboronic acid (5.18 g, 42.4 mmol), NaOH (1.061 g, 26.5 mmol), CuCl$_2$ (0.357 g, 2.65 mmol) and MeOH (25 mL). The above reaction mixture was then refluxed overnight while bubbling air through it. The solvent was then removed under vacuum and the crude product was purified by silica gel chromatography to yield 4-nitro-1-phenyl-1H-pyrazole (3.5 g, 17.58 mmol, 66% yield) as a white solid. MS(ESI) m/z: 190.1 [M+H]$^+$.

218B. Preparation of (S)-tert-butyl (1-(4-(4-nitro-1-phenyl-1H-pyrazol-5-yl)pyridin-2-yl)but-3-en-1-yl)carbamate To a N$_2$ flushed, 500 mL RBF was added (S)-tert-butyl (1-(4-chloropyridin-2-yl) but-3-en-1-yl)carbamate, prepared as described in Intermediate 23, (2.5 g, 8.84 mmol), 4-nitro-1-phenyl-1H-pyrazole (1.67 g, 8.84 mmol) and dioxane (50 mL). The solution was bubbled with N$_2$ for 5 min and Pd(OAc)$_2$ (0.1 g, 0.442 mmol), di(adamantan-1-yl)(butyl)phosphine (0.317 g, 0.884 mmol), K$_2$CO$_3$ (3.67 g, 26.5 mmol) and PvOH (0.271 g, 0.265 mmol) were added. The reaction mixture was bubbled with N$_2$ for 5 min, then heated to 100° C. for 3 h. Water (200 mL) was added. The reaction mixture was extracted with EtOAc (2×200 mL). The combined organic extracts were washed with water (200 mL), brine (200 mL), dried over Na$_2$SO$_4$, filtered and concentrated. Purification by normal phase chromatography eluting with a gradient of hexanes/EtOAc afforded (S)-tert-butyl (1-(4-(4-nitro-1-phenyl-1H-pyrazol-5-yl)pyridin-2-yl)but-3-en-1-yl)carbamate (3.0 g, 6.54 mmol, 74% yield) as a slightly yellow oil. MS(ESI) m/z: 436.5 [M+H]$^+$.

218C. Preparation of (9R,13S)-13-amino-9-methyl-3-phenyl-3,4,7,15-tetraazatricyclo[12.3.1.0$^{2,6}$]octadeca-1(18),2(6),4,14,16-pentaen-8-one (9R,13)-13-Amino-9-methyl-3-phenyl-3,4,7,15-tetraazatricyclo[12.3.1.0$^{2,6}$]octadeca-1(18),2(6),4,14,16-pentaen-8-one was prepared in the similar manner as described in Intermediate 30, by using (S)-tert-butyl (1-(4-(4-nitro-1-phenyl-1H-pyrazol-5-yl)pyridin-2-yl)but-3-en-1-yl)carbamate. (0.11 g, 0.34 mmol, 90% yield). MS(ESI) m/z: 362.5 [M+H]$^+$.

218D. (9R,13S3)-13-{4-[5-Chloro-2-(4-chloro-1H-1,2,3-triazol-1-yl)phenyl]-6-oxo-1,6-dihydropyrimidin-1-yl}-9-methyl-3-phenyl-3,4,7,15-tetraazatricyclo[12.3.1.0$^{2,6}$]octadeca-1(18),2(6),4,14,16-pentaen-8-one Trifluoroacetate (9R,13S)-13-{4-[5-Chloro-2-(4-chloro-1H-1,2,3-triazol-1-yl)phenyl]-6-oxo-1,6-dihydropyrimidin-1-yl}-9-methyl-3-phenyl-3,4,7,15-tetraazatricyclo[12.3.1.0$^{2,6}$]octadeca-1(18),2(6),4,14,16-pentaen-8-one trifluoroacetate (0.024 g, 0.030 mmol, 33% yield) was prepared in a similar manner as the procedures described in Example 56, by using 6-(5-chloro-2-(4-chloro-1H-1,2,3-triazol-1-yl)phenyl)pyrimidin-4-ol (0.028 g, 0.091 mmol), prepared as described in Intermediate 9, and (9R,13S)-13-amino-9-methyl-3-phenyl-3,4,7,15-tetraazatricyclo[12.3.1.0$^{2,6}$]octadeca-1(18),2(6),4,14,16-pentaen-8-one (0.033 g, 0.091 mmol). $^1$H NMR (400 MHz, CD$_3$OD) δ 8.81 (s, 1H), 8.39 (d, J=5.3 Hz, 1H), 8.32 (s, 1H), 7.87 (d, J=2.4 Hz, 2H), 7.76-7.68 (m, 2H), 7.65-7.60 (m, 1H), 7.51-7.38 (m, 5H), 6.66 (dd, J=5.1, 1.5 Hz, 1H), 6.37 (s, 1H), 6.02 (dd, J=12.7, 4.3 Hz, 1H), 3.34 (s, 1H), 2.76 (td, J=6.5, 3.1 Hz, 1H), 2.36-2.23 (m, 1H), 2.18-2.08 (m, 1H), 2.06-1.91 (m, 1H), 1.74-1.56 (m, 1H), 1.55-1.39 (m, 1H), 1.02 (d, J=7.0 Hz, 3H), 0.65 (br. s., 1H). MS(ESI) m/z: 652.6 [M+H]$^+$. Analytical HPLC (Method A): RT=9.41 min, purity=>95.0%; Factor XIa Ki=83 nM, Plasma Kallikrein Ki=2,700 nM.

Example 219

Preparation of (9R,13S)-13-(4-{5-chloro-2-[4-(trifluoromethyl)-1H-1,2,3-triazol-1-yl]pyridin-3-yl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one

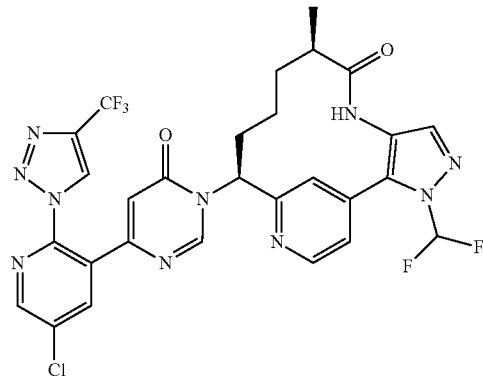 [SMILES: C[C@@H]1CCC[C@H](n2cnc(-c3cc(Cl)cnc3-n3cc(C(F)(F)F)nn3)cc2=O)c2cc(ccn2)-c2c(cnn2C(F)F)NC1=O]

(9R,13S)-13-(4-{5-Chloro-2-[4-(trifluoromethyl)-1H-1,2,3-triazol-1-yl]pyridin-3-yl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one (4 mg, 3% yield) as a solid was prepared in via the coupling of 6-{5-chloro-2-[4-(trifluoromethyl)-1H-1,2,3-triazol-1-yl]pyridin-3-yl}pyrimidin-4-ol (0.014 g, 0.04 mmol) and (9R,13S)-13-amino-3-(difluoromethyl)-9-methyl-3,4,7,15-tetraazatricyclo[12.3.1.0$^{2,6}$]octadeca-1(18),2(6), 4,14,16-pentaen-8-one (0.014 g, 0.04 mmol) using the HATU, DBU coupling methodology as described in Example 56. MS m/z=661.2 (M+H)$^1$. $^1$H NMR (400 MHz, CD$_3$OD) δ 9.30-9.27 (m, 1H), 9.08-9.03 (m, 1H), 8.79 (s, 2H), 8.37-8.33 (m, 1H), 7.78-7.74 (m, 2H), 7.70-7.67 (m, 1H), 7.59-7.51 (m, 1H), 6.14-6.00 (m, 1H), 2.81-2.68 (m, 1H), 2.47-2.29 (m, 1H), 2.16-2.01 (m, 2H), 1.70-1.46 (m, 2H), 1.07-0.96 (d, 3H), 0.75-0.55 (m, 1H). Analytical HPLC (Method A) RT=11.3 min, purity=98%; Factor XIa Ki=35 nM, Plasma Kallikrein Ki=7,200 nM.

Example 220

Preparation of (9R,13S)-13-(5-bromo-4-{5-chloro-2-[4-(trifluoromethyl)-1H-1,2,3-triazol-1-yl]pyridin-3-yl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one

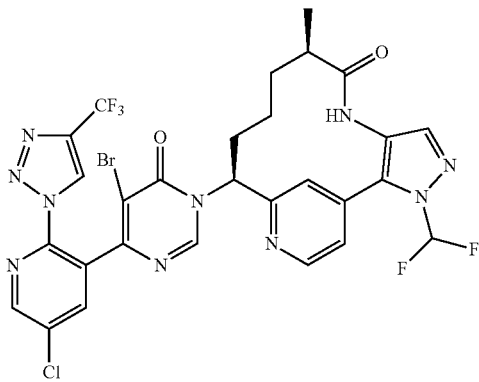 [SMILES: C[C@@H]1CCC[C@H](n2cnc(-c3cc(Cl)cnc3-n3cc(C(F)(F)F)nn3)c(Br)c2=O)c2cc(ccn2)-c2c(cnn2C(F)F)NC1=O]

(9R,13S)-13-(5-Bromo-4-{5-chloro-2-[4-(trifluoromethyl)-1H-1,2,3-triazol-1-yl]pyridin-3-yl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one was isolated as a by-product of Example 219 (3 mg, 9% yield) as a solid, via the coupling of 6-{5-chloro-2-[4-(trifluoromethyl)-1H-1,2,3-triazol-1-yl]pyridin-3-yl}pyrimidin-4-ol containing 5-bromo-6-{5-chloro-2-[4-(trifluoromethyl)-1H-1,2,3-triazol-1-yl]pyridin-3-yl}pyrimidin-4-ol (0.014 g, 0.04 mmol) and (9R,13S)-13-amino-3-(difluoromethyl)-9-methyl-3,4,7,15-tetraazatricyclo[12.3.1.0$^{2,6}$]octadeca-1(18),2(6), 4,14,16-pentaen-8-one (0.014 g, 0.04 mmol) using the HATU, DBU coupling methodology as described in Example 56. MS m/z=740.4(M+H)$^+$. Analytical HPLC (Method A) RT=12.2 min, purity=93%; Factor XIa Ki=250 nM, Plasma Kallikrein Ki=7,000 nM.

Example 221

Preparation of (9R,13S)-13-(4-{5-chloro-4-fluoro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one

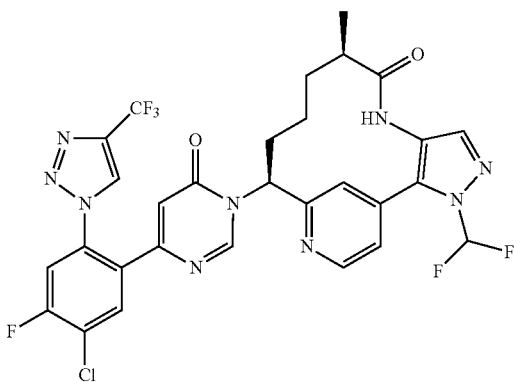 [SMILES: C[C@@H]1CCC[C@H](n2cnc(-c3cc(Cl)c(F)cc3-n3cc(C(F)(F)F)nn3)cc2=O)c2cc(ccn2)-c2c(cnn2C(F)F)NC1=O]

(9R,13S)-13-(4-{5-Chloro-4-fluoro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one (4 mg, 15% yield) as a solid was prepared via the coupling of 6-{5-chloro-4-fluoro-2-[4-(trifluoromethyl)-1H-1,2,3-triazol-1-yl]phenyl}pyrimidin-4-ol (0.013 g, 0.036 mmol) and (9R,13S)-13-amino-3-(difluoromethyl)-9-methyl-3,4,7,15-tetraazatricyclo[12.3.1.0$^{2,6}$]octadeca-1(18), 2(6), 4,14,16-pentaen-8-one (0.012 g, 0.036 mmol) using the HATU, DBU coupling methodology as previously described. MS m/z=678.1 (M+H). $^1$H NMR (400 MHz, CD$_3$OD) δ 8.88-8.82 (m, 2H), 8.75-8.72 (m, 1H), 8.10-8.04 (m, 1H), 7.76 (s, 2H), 7.72-7.65 (m, 1H), 7.56-7.51 (m, 1H), 6.46 (s, 1H), 6.09-5.96 (m, 1H), 4.07-3.99 (m, 1H), 3.53-3.44 (m, 1H), 2.81-2.64 (m, 1H), 2.37-2.21 (m, 1H), 2.09-1.96 (m, 2H), 1.68-1.42 (m, 2H), 1.02 (d, J=7.0 Hz, 3H); Factor XIa Ki=4.7 nM, Plasma Kallikrein Ki=1,300 nM.

Example 222

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-3-phenyl-3,4,7,15-tetraazatricyclo[12.3.1.0$^{2,6}$]octadeca-1(18),2(6),4,14,16-pentaen-8-one

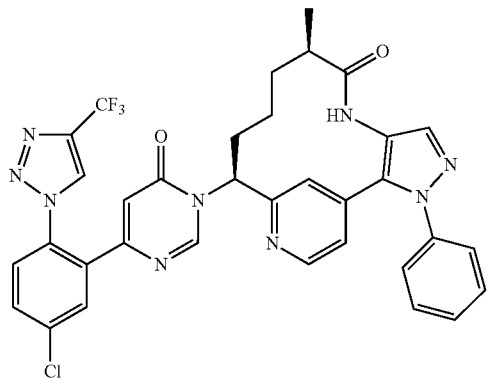 [SMILES: C[C@@H]1CCC[C@H](n2cnc(-c3cc(Cl)ccc3-n3cc(C(F)(F)F)nn3)cc2=O)c2cc(ccn2)-c2c(cnn2-c2ccccc2)NC1=O]

(9R,13S)-13-(4-{5-Chloro-2-[4-(trifluoromethyl)-1H-1,2,3-triazol-1-yl]phenyl}-6-oxo-1,6-dihydropyrimidin-1-yl)-9-methyl-3-phenyl-3,4,7,15-tetraazatricyclo[12.3.1.0$^{2,6}$]octadeca-1(18),2(6),4,14,16-pentaen-8-one trifluoroacetate (4.5 mg, 0.005 mmol, 6% yield) was prepared in a similar manner as the procedures described in Example 56, by using 6-{5-chloro-2-[4-(trifluoromethyl)-1H-1,2,3-triazol-1-yl]phenyl}pyrimidin-4-ol (0.031 g, 0.091 mmol), prepared as described in Intermediate 15, and (9R,13S)-13-amino-9-methyl-3-phenyl-3,4,7,15-tetraazatricyclo[12.3.1.0$^{2,6}$]octadeca-1(18),2(6),4,14,16-pentaen-8-one (0.033 g, 0.091 mmol), prepared as described in Example 218C. $^1$H NMR (400 MHz, CD$_3$OD) δ 8.80 (d, J=0.9 Hz, 1H), 8.77 (s, 1H), 8.37 (d, J=5.3 Hz, 1H), 7.89 (d, J=2.2 Hz, 1H), 7.86 (s, 1H), 7.78-7.72 (m, 2H), 7.71-7.66 (m, 1H), 7.50-7.39 (m, 5H), 6.66 (dd, J=5.1, 1.5 Hz, 1H), 6.45 (d, J=0.7 Hz, 1H), 6.03 (dd, J=12.7, 4.3 Hz, 1H), 3.35 (s, 1H), 2.76 (td, J=6.6, 3.1 Hz, 1H), 2.27 (tt, J=12.7, 4.5 Hz, 1H), 2.18-2.06 (m, 1H), 2.05-1.92 (m, 1H), 1.70-1.55 (m, 1H), 1.54-1.41 (m, 1H), 1.03 (d, J=6.8 Hz, 3H), 0.66 (br. s., 1H). MS(ESI) m/z: 686.6 [M+H]$^+$. Analytical HPLC (Method A): RT=10.03 min, purity=>95.0%; Factor XIa Ki=48 nM, Plasma Kallikrein Ki=3,700 nM.

Example 223

Preparation of (9R,13S)-13-(4-{4,5-dichloro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one

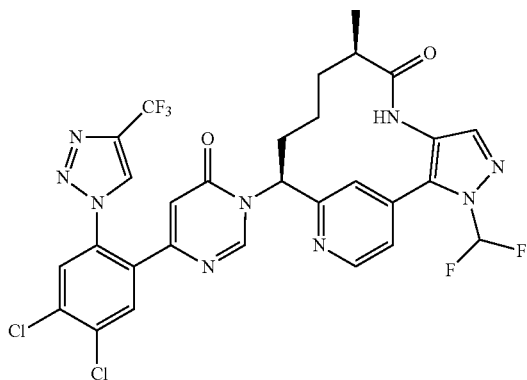 [SMILES: C[C@@H]1CCC[C@H](n2cnc(-c3cc(Cl)c(Cl)cc3-n3cc(C(F)(F)F)nn3)cc2=O)c2cc(ccn2)-c2c(cnn2C(F)F)NC1=O]

(9R,13S)-13-(4-{4,5-Dichloro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one (5 mg, 22% yield) as a solid was prepared via the coupling of 6-{4,5-dichloro-2-[4-(trifluoromethyl)-1H-1,2,3-triazol-1-yl]phenyl}pyrimidin-4-ol (0.012 g, 0.03 mmol) and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one (0.011 g, 0.03 mmol) using the HATU, DBU coupling methodology as described in Example 56. MS m/z=694.1 (M+H)$^+$. $^1$H NMR (400 MHz, CD$_3$OD) δ 8.88-8.83 (m, 2H), 8.75-8.71 (m, 1H), 8.10-8.08 (m, 1H), 8.02 (s, 1H), 7.76 (s, 1H), 7.72-7.69 (m, 1H), 7.56-7.51 (m, 1H), 6.47 (d, J=0.7 Hz, 1H), 6.08-6.00 (m, 1H), 2.80-2.63 (m, 1H), 2.36-2.16 (m, 1H), 2.11-1.96 (m, 2H), 1.67-1.42 (m, 2H), 1.06-0.95 (d, 3H), 0.71-0.53 (m, 1H). Analytical HPLC (Method A) RT=13.3 min, purity=98%; Factor XIa Ki=11 nM, Plasma Kallikrein Ki=4,500 nM.

Example 224

Preparation of (9R,13S)-13-{4-[5-chloro-2-(4-chloro-1H-1,2,3-triazol-1-yl)phenyl]-6-oxo-1,6-dihydropyrimidin-1-yl}-9-methyl-4-(1-methyl-1H-imidazol-5-yl)-3,4,7,15-tetraazatricyclo[12.3.1.0$^{2,6}$]octadeca-1(18),2,5,14,16-pentaen-8-one

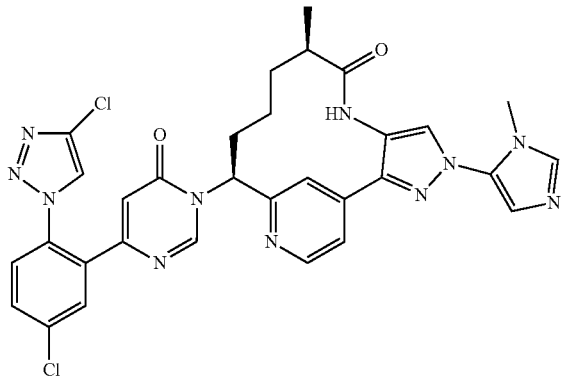 [SMILES: C[C@@H]1CCC[C@H](n2cnc(-c3cc(Cl)ccc3-n3cc(Cl)nn3)cc2=O)c2cc(ccn2)-c2nn(-c3cncn3C)cc2NC1=O]

(9R,13S)-13-{4-[5-Chloro-2-(4-chloro-1H-1,2,3-triazol-1-yl)phenyl]-6-oxo-1,6-dihydropyrimidin-1-yl}-9-methyl-4-(1-methyl-1H-imidazol-5-yl)-3,4,7,15-tetraazatricyclo[12.3.1.0$^{2,16}$]octadeca-1(18),2,5,14,16-pentaen-8-one (21 mg, 18%) as a peach solid was prepared in a similar manner as the procedure described in Example 216, by using 5-iodo-1-methyl-1H-imidazole. MS(ESI) m/z: 656.2 (M+H)$^+$. $^1$H NMR (400 MHz, CD$_3$OD) δ 9.06-9.01 (m, 1H), 8.82-8.77 (m, 1H), 8.70-8.65 (m, 1H), 8.37 (s, 1H), 8.22-8.20 (m, 1H), 7.99-7.97 (m, 1H), 7.97-7.94 (m, 1H), 7.93-7.90 (m, 1H), 7.79-7.74 (m, 1H), 7.70-7.66 (m, 1H), 7.66-7.62 (m, 1H), 6.42-6.38 (m, 1H), 6.17-6.06 (m, 1H), 3.98 (s, 3H), 2.94-2.83 (m, 1H), 2.39-2.22 (m, 2H), 2.12-2.00 (m, 1H), 1.81-1.69 (m, 1H), 1.68-1.54 (m, 1H), 1.13-1.05 (m, 3H), 0.87-0.74 (m, 1H). Analytical HPLC (Method A): RT=5.81 min, purity=91%; Factor XIa Ki=4.5 nM, Plasma Kallikrein Ki=220 nM.

Example 225

Preparation of 4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}-N-(2,2,2-trifluoroethyl)benzamide

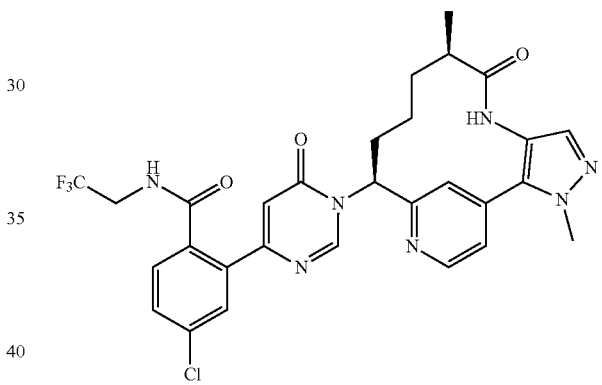

225A. Preparation of 4-chloro-2-(6-methoxypyrimidin-4-yl)-N-(2,2,2-trifluoroethyl) Benzamide To a RBF was added 4-chloro-2-(6-methoxypyrimidin-4-yl)benzoic acid (0.374 g, 1.413 mmol), prepared as described in Example 168B, EtOAc (7.07 ml), 2,2,2-CF$_3$CH$_2$NH$_2$ (0.14 g, 1.413 mmol), and pyridine (0.229 ml, 2.83 mmol). The solution was cooled in a MeOH/ice bath and 50% w/w 2,4,6-tripropyl-1,3,5,2,4,6-trioxatriphosphorinane-2,4,6-trioxide in EtOAc (1.26 ml, 2.120 mmol) was added. The reaction was allowed to warm to rt. After 18 h, the reaction was diluted with EtOAc, washed with sat NaHCO$_3$, brine, dried over Na$_2$SO$_4$, filtered, and concentrated. DCM (~10 ml) was added, plus a few drops of MeOH to afford a yellow suspension. The solid was filtered off, and the filtrate was purified by normal phase chromatography to afford 4-chloro-2-(6-methoxypyrimidin-4-yl)-N-(2,2,2-trifluoroethyl)benzamide (0.155 g, 32% yield) as a white solid. MS(ESI) m/z: 346.4 (M+H)$^+$.

225B. Preparation of 4-chloro-2-(6-hydroxypyrimidin-4-yl)-N-(2,2,2-trifluoroethyl) Benzamide To a solution of 4-chloro-2-(6-methoxypyrimidin-4-yl)-N-(2,2,2-trifluoroethyl) benzamide (0.05 g, 0.145 mmol) in ACN (0.96 ml) was added TMSI (0.118 ml, 0.868 mmol). The reaction was heated to 50° C. After 6 h, the reaction was cooled to rt, poured into a 10% aq $Na_2S_2O_3$, and extracted with EtOAc (3×). The combined organic layers were washed with sat $NaHCO_3$, brine, dried over $Na_2SO_4$, filtered, and concentrated. Purification by normal phase chromatography afforded 4-chloro-2-(6-hydroxypyrimidin-4-yl)-N-(2,2,2-trifluoroethyl)benzamide (0.02 g, 42% yield) as a white solid. MS(ESI) m/z: 332.3 $(M+H)^+$. 1H NMR (400 MHz, $CD_3OD$) δ 8.14 (d, J=0.9 Hz, 1H), 7.69 (d, J=2.0 Hz, 1H), 7.59-7.55 (m, 1H), 7.54-7.49 (m, 1H), 6.63 (d, J=0.9 Hz, 1H), 3.98 (q, J=9.5 Hz, 2H). $^{19}F$ NMR (376 MHz, $CD_3OD$) δ −73.22 (s).

225C. Preparation of 4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}-N-(2,2,2-trifluoroethyl)benzamide Trifluoroacetate 4-Chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}-N-(2,2,2-trifluoroethyl)benzamide trifluoroacetate (4.8 mg, 11% yield) was prepared in a similar manner as the procedure described in Example 56, by replacing 6-{5-chloro-2-[4-(trifluoromethyl)-1H-1,2,3-triazol-1-yl]phenyl}pyrimidin-4-ol with 4-chloro-2-(6-hydroxypyrimidin-4-yl)-N-(2,2,2-trifluoroethyl)benzamide (0.02 g, 0.060 mmol). MS(ESI) m/z: 614.5 $(M+H)^+$. $^1H$ NMR (400 MHz, $CD_3OD$) δ 8.95 (s, 1H), 8.73 (d, J=5.3 Hz, 1H), 7.72-7.71 (m, 2H), 7.59-7.55 (m, 1H), 7.54-7.48 (m, 3H), 6.66 (s, 1H), 6.05 (dd, J=12.5, 4.2 Hz, 1H), 4.08-3.90 (m, 5H), 2.76-2.67 (m, 1H), 2.39-2.28 (m, 1H), 2.15-1.98 (m, 2H), 1.68-1.42 (m, 2H), 1.01 (d, J=7.0 Hz, 3H), 0.79-0.62 (m, 1H). $^{19}F$ NMR (376 MHz, $CD_3OD$) δ −73.10 (s), −77.67 (s). Analytical HPLC (Method A): RT=6.78 min, 98.2% purity; Factor XIa Ki=23 nM, Plasma Kallikrein Ki=3,400 nM.

Example 226

Preparation of (9R,13S)-13-{4-[5-chloro-2-(4-chloro-1H-1,2,3-triazol-1-yl)phenyl]-6-oxo-1,6-dihydropyrimidin-1-yl}-5,9-dimethyl-4,5,7,15-tetraazatricyclo[12.3.1.0$^{2,6}$]octadeca-1(18),2(6),3,14,16-pentaen-8-one

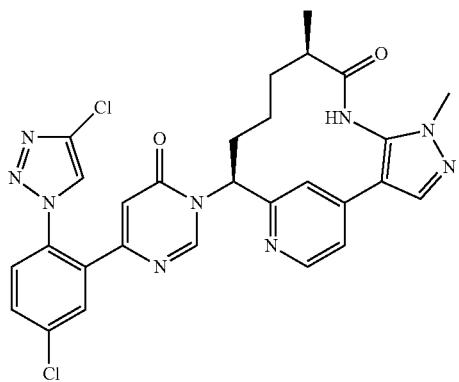 [SMILES: C[C@@H]1CCC[C@H](n2cnc(-c3cc(Cl)ccc3-n3cc(Cl)nn3)cc2=O)c2cc(ccn2)-c2cnn(C)c2NC1=O]

226A. Preparation of N-[(1S)-1-[4-(5-amino-1-methyl-1H-pyrazol-4-yl)pyridin-2-yl]but-3-en-1-yl]carbamate In a microwave vial was added (S)-(2-(1-((tert-butoxycarbonyl)amino)but-3-en-1-yl)pyridin-4-yl)boronic acid (500 mg, 1.712 mmol), 4-bromo-1-methyl-1H-pyrazol-5-amine (301 mg, 1.712 mmol), (DtBPF)PdCl$_2$ (55.8 mg, 0.086 mmol), 3 M $K_3PO_4$ (1.712 mL, 5.13 mmol), and THF (18 mL). The reaction mixture was purged with Ar (3×), then heated at 130° C. in a microwave for 30 min The reaction mixture was then cooled to rt, diluted with EtOAc and washed with brine (2×15 mL). The crude product was then subjected to silica gel chromatography to yield N-[(1S)-1-[4-(5-amino-1-methyl-1H-pyrazol-4-yl)pyridin-2-yl]but-3-en-1-yl]carbamate (0.5 g, 1.383 mmol, 81% yield). MS(ESI) m/z: 344.5 $(M+H)^+$.

226B. Preparation of (9R,13S)-13-amino-5,9-dimethyl-4,5,7,15-tetraazatricyclo[12.3.1.0$^{2,6}$]octadeca-1(18),2(6),3,14,16-pentaen-8-one (9R,13S)-13-Amino-5,9-dimethyl-4,5,7,15-tetraazatricyclo[12.3.1.0$^{2,6}$]octadeca-1(18),2(6),3,14,16-pentaen-8-one (83 mg, 0.263 mmol, 88% yield) was prepared in a similar manner as the procedure described in Intermediate 32, by replacing Intermediate 32C with N-[(1S)-1-[4-(5-amino-1-methyl-1H-pyrazol-4-yl)pyridin-2-yl]but-3-en-1-yl]carbamate and continuing through the rest of the sequence as described in the preparation of Intermediate 32.

226C. Preparation of (9R,13S)-13-{4-[5-chloro-2-(4-chloro-1H-1,2,3-triazol-1-yl) phenyl]-6-oxo-1,6-dihydropyrimidin-1-yl}-5,9-dimethyl-4,5,7,15-tetraazatricyclo[12.3.1.0$^{2,6}$]octadeca-1(18),2(6),3,14,16-pentaen-8-one Trifluoroacetate (9R,13S)-13-{4-[5-Chloro-2-(4-chloro-1H-1,2,3-triazol-1-yl)phenyl]-6-oxo-1,6-dihydropyrimidin-1-yl}-5,9-dimethyl-4,5,7,15-tetraazatricyclo[12.3.1.0$^{2,6}$]octadeca-1(18),2(6),3,14,16-pentaen-8-one trifluoroacetate (24 mg, 0.032 mmol, 34% yield) was prepared in a similar manner as the procedure described in Example 56 by using 6-(5-chloro-2-(4-chloro-1H-1,2,3-triazol-1-yl)phenyl)pyrimidin-4-ol (28.8 mg, 0.094 mmol), prepared as described in Intermediate 9, and (9R,13S)-13-amino-5,9-dimethyl-4,5,7,15-tetraazatricyclo[12.3.1.0$^{2,6}$]octadeca-1(18),2(6),3,14,16-pentaen-8-one (28.0 mg, 0.094 mmol). $^1H$ NMR (400 MHz, $CD_3OD$) δ 8.56 (d, J=5.7 Hz, 2H), 8.37 (s, 1H), 8.05 (br. s., 1H), 7.95 (br. s., 1H), 7.89 (d, J=2.4 Hz, 1H), 7.78-7.71 (m, 1H), 7.69-7.61 (m, 2H), 6.40 (s, 1H), 5.94 (br. s., 1H), 3.82 (s, 3H), 2.88 (d, J=18.3 Hz, 1H), 2.36 (br. s., 1H), 2.29-2.07 (m, 2H), 1.76 (d, J=7.3 Hz, 1H), 1.55 (br. s., 1H), 1.15 (br. s., 3H), 1.00 (br. s., 1H). MS(ESI) m/z: 590.5 $[M+H]^+$. Analytical HPLC (Method A): RT=7.04 min, purity=>95.0%; Factor XIa Ki=106 nM.

Example 227

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-5,9-dimethyl-4,5,7,15-tetraazatricyclo[12.3.1.0$^{2,6}$]octadeca-1(18),2(6),3,14,16-pentaen-8-one

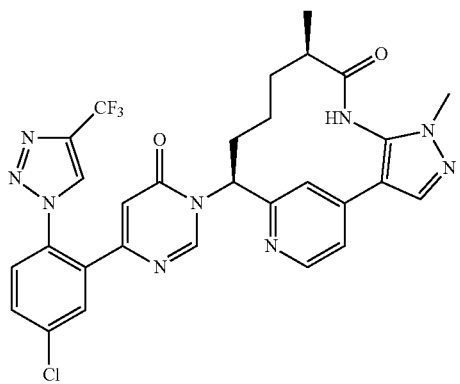 [SMILES: C[C@@H]1CCC[C@H](n2cnc(-c3cc(Cl)ccc3-n3cc(C(F)(F)F)nn3)cc2=O)c2cc(ccn2)-c2cnn(C)c2NC1=O]

(9R,13S)-13-(4-{5-Chloro-2-[4-(trifluoromethyl)-1H-1,2,3-triazol-1-yl]phenyl}-6-oxo-1,6-dihydropyrimidin-1-yl)-5,9-dimethyl-4,5,7,15-tetraazatricyclo[12.3.1.0$^{2,6}$]octadeca-1(18),2(6),3,14,16-pentaen-8-one trifluoroacetate (21 mg, 0.027 mmol, 29% yield) was prepared in a similar manner as the procedure described in Example 226 by replacing 6-(5-chloro-2-(4-chloro-1H-1,2,3-triazol-1-yl)phenyl)pyrimidin-4-ol with 6-(5-chloro-2-(4-(trifluoromethyl)-1H-1,2,3-triazol-1-yl)phenyl)pyrimidin-4-ol (32.0 mg, 0.094 mmol), prepared as described in Intermediate 15. $^1$H NMR (400 MHz, CD$_3$OD) δ 8.84 (s, 1H), 8.55-8.42 (m, 2H), 8.02 (br. s., 1H), 7.97-7.86 (m, 2H), 7.78-7.71 (m, 1H), 7.70-7.59 (m, 2H), 6.44 (s, 1H), 5.93 (br. s., 1H), 3.79 (s, 3H), 2.99-2.81 (m, 1H), 2.32 (br. s., 1H), 2.26-2.04 (m, 2H), 1.73 (d, J=7.3 Hz, 1H), 1.52 (br. s., 1H), 1.26-1.07 (m, 3H), 0.99 (br. s., 1H). MS(ESI) m/z: 624.5 [M+H]$^+$. Analytical HPLC (Method A): RT=7.83 min, purity=>95.0%; Factor XIa Ki=97 nM.

Example 228

Preparation of (9R,13S)-13-[4-(1-benzyl-5-chloro-1H-indazol-7-yl)-6-oxo-1,6-dihydropyrimidin-1-yl]-3-(difluoromethyl)-9-methyl-3,4,7,15-tetraazatricyclo[12.3.1.0$^{2,6}$]

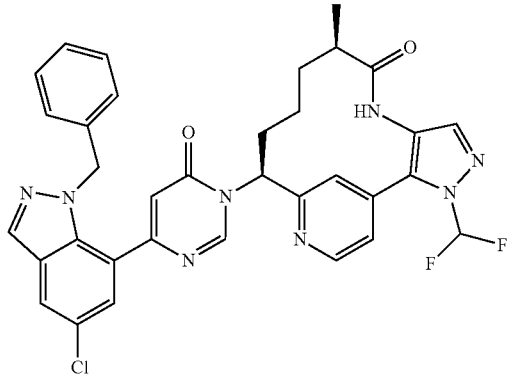 [SMILES: C[C@@H]1CCC[C@H](n2cnc(-c3cc(Cl)cc4cnn(Cc5ccccc5)c34)cc2=O)c2cc(ccn2)-c2c(cnn2C(F)F)NC1=O]

228A. Preparation of 6-(1-benzyl-5-chloro-1H-indazol-7-yl)pyrimidin-4-ol 6-(1-Benzyl-5-chloro-1H-indazol-7-yl)pyrimidin-4-ol (32 mg, 32%) was prepared in a similar manner as Intermediate 22 by replacing MeI with BnBr. MS(ESI) m/z: 337 (M+H)$^+$ and 339 (M+2+H)$^+$.

228B. Preparation of (9R,13S)-13-[4-(1-benzyl-5-chloro-1H-indazol-7-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one Trifluoroacetate (9R,13S)-13-[4-(1-Benzyl-5-chloro-1H-indazol-7-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one trifluoroacetate (4 mg, 9.7%) was prepared in a similar manner as Example 56 using 6-(1-benzyl-5-chloro-1H-indazol-7-yl)pyrimidin-4-ol and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one, prepared as described in Intermediate 30. MS(ESI) m/z: 655 (M+H)$^+$ and 657 (M+2+H)$^+$. $^1$H NMR (400 MHz, methanol-d$_4$) δ 8.99 (s, 1H), 8.69 (d, J=5.1 Hz, 1H), 8.47-8.39 (m, 1H), 8.28 (d, J=2.0 Hz, 1H), 8.11 (s, 1H), 7.89-7.82 (m, 1H), 7.72 (d, J=13.6 Hz, 2H), 7.41 (d, J=5.1 Hz, 1H), 7.35-7.21 (m, 4H), 6.05-5.94 (m, 1H), 5.65 (s, 2H), 2.65 (d, J=6.2 Hz, 1H), 2.40-2.30 (m, 1H), 2.07-1.92 (m, 2H), 1.56-1.33 (m, 3H), 0.90 (d, J=7.0 Hz, 3H), 0.53 (br. s., 1H). Analytical HPLC (Method A): RT=10.76 min, purity=>95%; Factor XIa Ki=110 nM.

Example 229

Preparation of (9R,13S)-13-{4-[5-chloro-2-(1H-1,2,3-triazol-1-yl)phenyl]-5-methyl-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

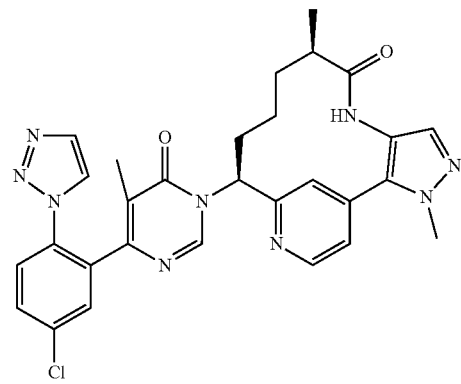 [SMILES: Cc1c(-c2cc(Cl)ccc2-n2ccnn2)ncn([C@H]2CCC[C@@H](C)C(=O)Nc3cnn(C)c3-c3ccnc2c3)c1=O]

229A. Preparation of 6-(5-chloro-2-(4-(trimethylsilyl)-1H-1,2,3-triazol-1-yl)phenyl)-5-methylpyrimidin-4-ol 6-(5-Chloro-2-(4-(trimethylsilyl)-1H-1,2,3-triazol-1-yl)phenyl)-5-methylpyrimidin-4-ol (53 mg, 50% yield) was prepared in a similar manner as the procedure described in Intermediate 18C, by replacing 1-[4-chloro-2-(6-methoxypyrimidin-4-yl)phenyl]-1H-1,2,3-triazole-4-carbonitrile with 4-(5-chloro-2-(4-(trimethylsilyl)-1H-1,2,3-triazol-1-yl)

phenyl)-6-methoxy-5-methylpyrimidine (0.110 g, 0.294 mmol). MS(ESI) m/z: 560.4 (M+H)+.

229B. Preparation of 6-(5-chloro-2-(1H-1,2,3-triazol-1-yl)phenyl)-5-methylpyrimidin-4-ol To a solution of 6-(5-chloro-2-(4-(trimethylsilyl)-1H-1,2,3-triazol-1-yl)phenyl)-5-methylpyrimidin-4-ol (53 mg, 0.147 mmol) in THF (5 mL) was added 1 M TBAF in THF (0.162 mL, 0.162 mmol) at rt. After 3 h, the solution was concentrated and partitioned between EtOAc and water and the layers were separated. The aqueous layer was extracted with EtOAc (2×). The combined organic layer was concentrated and then purified by normal phase chromatography to give 6-(5-chloro-2-(1H-1,2,3-triazol-1-yl)phenyl)-5-methylpyrimidin-4-ol (14 mg, 33% yield) as an orange glass. MS(ESI) m/z: 288.4 (M+H)+. $^1$H NMR (400 MHz, CDCl$_3$) δ 8.02 (s, 1H), 7.71 (d, J=0.9 Hz, 1H), 7.64-7.58 (m, 3H), 7.51 (t, J=1.3 Hz, 1H), 1.76 (s, 3H).

229C. Preparation of (9R,13S)-13-{4-[5-chloro-2-(1H-1,2,3-triazol-1-yl)phenyl]-5-methyl-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one Trifluoroacetate (9R,13S)-13-{4-[5-Chloro-2-(1H-1,2,3-triazol-1-yl)phenyl]-5-methyl-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (13 mg, 37% yield) was prepared in a similar manner as the procedure described in Example 56, by replacing 6-{5-chloro-2-[4-(trifluoromethyl)-1H-1,2,3-triazol-1-yl]phenyl}pyrimidin-4-ol with 6-(5-chloro-2-(1H-1,2,3-triazol-1-yl)phenyl)-5-methylpyrimidin-4-ol (0.014 g, 0.049 mmol). MS(ESI) m/z: 570.1 (M+H)+. $^1$H NMR (400 MHz, CD$_3$OD) δ8.89 (s, 1H), 8.76 (d, J=5.5 Hz, 1H), 8.17 (d, J=0.9 Hz, 1H), 7.84 (s, 1H), 7.80-7.71 (m, 3H), 7.70-7.64 (m, 2H), 7.51 (s, 1H), 5.93 (dd, J=12.5, 4.2 Hz, 1H), 4.07 (s, 3H), 2.70 (td, J=6.8, 3.3 Hz, 1H), 2.36 (ddt, J=12.6, 8.4, 4.3 Hz, 1H), 2.14-2.00 (m, 2H), 1.69 (s, 3H), 1.66-1.55 (m, 1H), 1.53-1.39 (m, 1H), 1.03 (d, J=7.0 Hz, 3H), 0.79 (m, 1H). Analytical HPLC (Method A): RT=6.51 min, purity=99%; Factor XIa Ki=63 nM, Plasma Kallikrein Ki=2,200 nM.

Example 230

Preparation of (9R,13S)-13-{4-[5-chloro-2-(1-methyl-1H-pyrazol-3-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

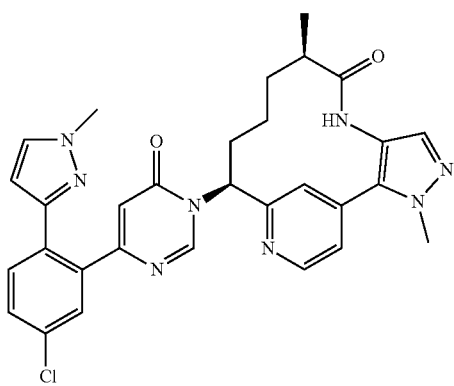 [SMILES: C[C@@H]1CCC[C@H](n2cnc(-c3cc(Cl)ccc3-c3ccn(C)n3)cc2=O)c2cc(ccn2)-c2c(cnn2C)NC1=O]

(9R,13S)-13-{4-[5-Chloro-2-(1-methyl-1H-pyrazol-3-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (1.14 mg, 7% yield) was prepared in a similar manner as the procedure described in Example 49, by replacing 1-methyl-4-(4,4,5,5-tetramethyl-1,3,2-dioxaborolan-2-yl)-1H-pyrazole with 1-methyl-3-(4,4,5,5-tetramethyl-1,3,2-dioxaborolan-2-yl)-1H-pyrazole (7.61 mg, 0.037 mmol). MS(ESI) m/z: 569.5 (M+H)+. $^1$H NMR (400 MHz, CD$_3$OD) δ 8.91 (s, 1H), 8.71 (d, J=5.1 Hz, 1H), 7.87 (d, J=2.2 Hz, 1H), 7.67 (s, 1H), 7.61 (dd, J=8.3, 2.3 Hz, 1H), 7.52-7.47 (m, 2H), 7.46-7.42 (m, 2H), 6.26 (d, J=2.0 Hz, 1H), 6.13 (s, 1H), 6.00-5.92 (m, 1H), 4.04 (s, 3H), 3.50 (s, 3H), 2.75-2.66 (m, 1H), 2.35-2.24 (m, 1H), 2.13-1.94 (m, 2H), 1.65-1.42 (m, 2H), 1.00 (d, J=6.8 Hz, 3H), 0.76-0.60 (m, 1H). Analytical HPLC (Method A): RT=7.34 min, 98.4% purity; Factor XIa Ki=800 nM.

Example 231

Preparation of (9R,13S)-13-{4-[5-chloro-2-(1H-imidazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

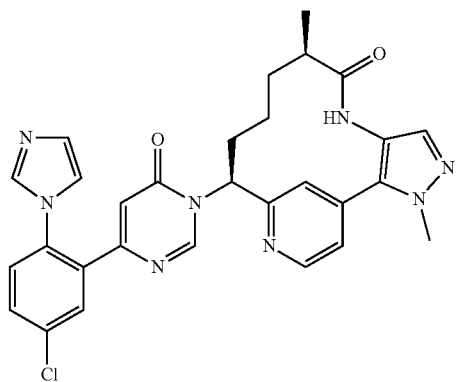 [SMILES: C[C@@H]1CCC[C@H](n2cnc(-c3cc(Cl)ccc3-n3ccnc3)cc2=O)c2cc(ccn2)-c2c(cnn2C)NC1=O]

To the solution of 1H-imidazole (8.86 mg, 0.130 mmol) and (9R,13S)-13-[4-(5-chloro-2-iodophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one trifluoroacetate (0.02 g, 0.033 mmol), prepared as described in Example 211, in DMSO (1 ml) was added CuI (0.62 mg, 3.25 μmol), L-proline (0.75 mg, 6.51 μmol), and K$_2$CO$_3$ (0.013 g, 0.098 mmol). The reaction was heated at 80° C. for 3 h and cooled to rt. Purification by reverse phase chromatography afforded (9R,13S)-13-{4-[5-chloro-2-(1H-imidazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (11 mg, 43% yield) as a yellow solid. MS(ESI) m/z: 555.5 (M+H)+. $^1$H NMR (500 MHz, CD$_3$OD) δ 9.19 (s, 1H), 8.77-8.67 (m, 2H), 7.92 (d, J=2.5 Hz, 1H), 7.81-7.75 (m, 1H), 7.73-7.64 (m, 4H), 7.54-7.48 (m, 2H), 6.62 (s, 1H), 6.00-5.91 (m, 1H), 4.04 (s, 3H), 2.74-2.64 (m, 1H), 2.32-2.21 (m, 1H), 2.11-1.92 (m, 2H), 1.64-1.39 (m, 2H), 1.01 (d, J=6.9 Hz, 3H), 0.79-0.63 (m, 1H). Analytical HPLC (Method A): RT=4.41 min, 99.9% purity; Factor XIa Ki=23 nM, Plasma Kallikrein Ki=1,100 nM.

Example 232

Preparation of (9R,13S)-13-[4-(5-chloro-1H-indazol-7-yl)-6-oxo-1,6-dihydropyrimidin-1-yl]-3-(difluoromethyl)-9-methyl-3,4,7,15-tetraazatricyclo[12.3.1.0²,⁶]octadeca-1(18),2(6),4,14,16-pentaen-8-one

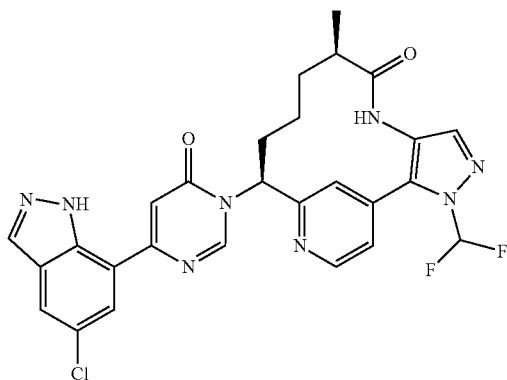 [SMILES: C[C@@H]1CCC[C@H](n2cnc(-c3cc(Cl)cc4cn[nH]c34)cc2=O)c2cc(ccn2)-c2c(cnn2C(F)F)NC1=O]

232A. Preparation of 6-(5-chloro-1H-indazol-7-yl)pyrimidin-4-ol 6-(5-Chloro-1H-indazol-7-yl)pyrimidin-4-ol (13.8 mg, 17%) was prepared in a similar manner to Example 207C starting from 7-bromo-5-chloro-1H-indazole instead of 4-bromo-6-chloro-1H-benzo[d]imidazole. MS(ESI) m/z: 247 (M+H)⁺ and 249 (M+2+H)¹. ¹H NMR (400 MHz, CDCl₃) δ 8.41 (d, J=0.9 Hz, 1H), 8.15 (s, 1H), 8.02 (d, J=1.8 Hz, 1H), 7.99 (d, J=1.8 Hz, 1H), 7.14 (d, J=0.7 Hz, 1H).

232B. Preparation of (9R,13S)-13-[4-(5-chloro-1H-indazol-7-yl)-6-oxo-1,6-dihydropyrimidin-1-yl]-3-(difluoromethyl)-9-methyl-3,4,7,15-tetraazatricyclo[12.3.1.0²,⁶]octadeca-1(18),2(6),4,14,16-pentaen-8-one trifluoroacetate (9R,13S)-13-[4-(5-Chloro-1H-indazol-7-yl)-6-oxo-1,6-dihydropyrimidin-1-yl]-3-(difluoromethyl)-9-methyl-3,4,7,15-tetraazatricyclo[12.3.1.0²,⁶]octadeca-1(18),2(6),4,14,16-pentaen-8-one trifluoroacetate (5 mg, 13%) was prepared in a similar manner as Example 56 using 6-(5-chloro-1H-indazol-7-yl)pyrimidin-4-ol and (9R,13S)-13-amino-3-(difluoromethyl)-9-methyl-3,4,7,15-tetraazatricyclo[12.3.1.0²,⁶]octadeca-1(18),2(6),4,14,16-pentaen-8-one, prepared as described in Intermediate 30. MS(ESI) m/z: 565 (M+H)⁺ and 567 (M+2+H)⁺. ¹H NMR (400 MHz, DMSO-d₆) δ 13.40 (br. s., 1H), 9.37 (s, 1H), 9.00 (s, 1H), 8.70 (d, J=5.1 Hz, 1H), 8.14 (br. s., 1H), 8.07-8.02 (m, 1H), 7.98 (d, J=1.5 Hz, 1H), 7.93-7.74 (m, 2H), 7.69 (s, 1H), 7.38 (d, J=5.1 Hz, 1H), 7.19 (br. s., 1H), 5.93 (d, J=9.5 Hz, 1H), 2.65-2.60 (m, 1H), 2.26 (d, J=1.8 Hz, 1H), 2.06-1.91 (m, 2H), 1.49-1.30 (m, 2H), 0.83 (d, J=6.8 Hz, 3H), 0.35 (br. s., 1H). Analytical HPLC (Method A): RT=11.43 min, purity=>95%; Factor XIa Ki=110 nM, Plasma Kallikrein Ki=4,300 nM.

Example 233

Preparation of (9R,13S)-13-{4-[5-chloro-2-(4-chloro-1H-1,2,3-triazol-1-yl)phenyl]-6-oxo-1,6-dihydropyrimidin-1-yl}-4-(6-methoxypyridin-3-yl)-9-methyl-3,4,7,15-tetraazatricyclo[12.3.1.0²,⁶]octadeca-1(18),2,5,14,16-pentaen-8-one

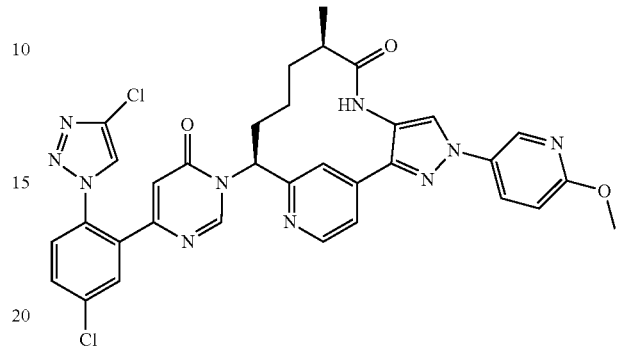

(9R,13S)-13-{4-[5-Chloro-2-(4-chloro-1H-1,2,3-triazol-1-yl)phenyl]-6-oxo-1,6-dihydropyrimidin-1-yl}-4-(6-methoxypyridin-3-yl)-9-methyl-3,4,7,15-tetraazatricyclo[12.3.1.0²,⁶]octadeca-1(18),2,5,14,16-pentaen-8-one was prepared in a similar manner as the procedure described in Example 216, by using 5-iodo-2-methoxypyridine to give (9R,13S)-13-{4-[5-chloro-2-(4-chloro-1H-1,2,3-triazol-1-yl)phenyl]-6-oxo-1,6-dihydropyrimidin-1-yl}-4-(6-methoxypyridin-3-yl)-9-methyl-3,4,7,15-tetraazatricyclo[12.3.1.0²,⁶]octadeca-1(18),2,5,14,16-pentaen-8-one trifluoroacetate as a brown solid (12 mg, 23%). MS(ESI) m/z: 683.5 (M+H)⁺. ¹H NMR (400 MHz, CD₃OD) δ 8.74-8.69 (m, 1H), 8.68-8.62 (m, 2H), 8.36 (d, J=7.4 Hz, 2H), 8.21-8.14 (m, 1H), 8.02-7.97 (m, 1H), 7.92 (d, J=2.2 Hz, 1H), 7.75 (d, J=2.5 Hz, 2H), 7.67 (d, J=8.5 Hz, 1H), 7.01-6.94 (m, 1H), 6.41 (d, J=0.8 Hz, 1H), 6.13-6.03 (m, 1H), 4.00 (s, 3H), 2.90-2.81 (m, 1H), 2.38-2.22 (m, 2H), 2.05 (s, 1H), 1.81-1.69 (m, 1H), 1.64-1.52 (m, 1H), 1.40-1.28 (m, 1H), 1.11 (d, J=6.9 Hz, 3H). Analytical HPLC (Method A): RT=9.08 min, purity=95%; Factor XIa Ki=1.1 nM, Plasma Kallikrein Ki=16 nM.

Example 234

Preparation of (1R,14S)-3-chloro-14-{4-[5-chloro-2-(4-chloro-1H-1,2,3-triazol-1-yl) phenyl]-6-oxo-1,6-dihydropyrimidin-1-yl}-10-methyl-5,8-diazatricyclo[13.3.1.0²,⁷]nonadeca-1(19),2(7),3,5,15,17-hexaen-9-one

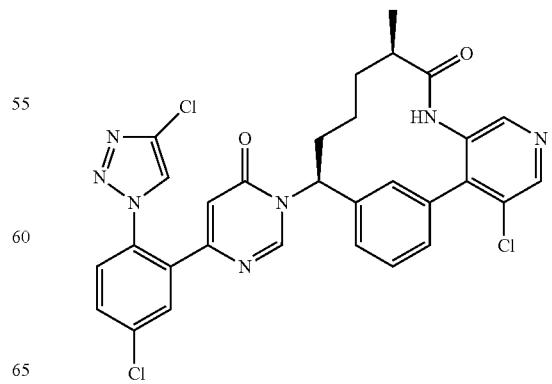

(10R,14S)-3-Chloro-14-{4-[5-chloro-2-(4-chloro-1H-1,2,3-triazol-1-yl)phenyl]-6-oxo-1,6-dihydropyrimidin-1-yl}-10-methyl-5,8-diazatricyclo[13.3.1.0²,⁷]nonadeca-1(19),2(7),3,5,15,17-hexaen-9-one trifluoroacetate (0.0069 g, 44%) was prepared according to the procedures described in Example 206 by using (10R,14S)-14-amino-3-chloro-10-methyl-5,8-diazatricyclo[13.3.1.0²,⁷]nonadeca-1(19),2(7),3,5,15,17-hexaen-9-one, prepared as described in Intermediate 38, by replacing 2-bromopyridin-3-amine with 4-bromo-5-chloropyridin-3-amine in Intermediate 38B. MS(ESI) m/z: 620.1 (M+H)⁺. ¹H NMR (500 MHz, CD₃OD, 60° C.) δ 9.00 (s, 1H), 8.75 (s, 1H), 8.71-8.60 (m, 1H), 8.56 (s, 1H), 8.16 (d, J=2.5 Hz, 1H), 8.03 (dd, J=8.4, 2.3 Hz, 1H), 7.97-7.82 (m, 4H), 7.73 (br. s., 1H), 6.70 (s, 1H), 6.04 (dd, J=12.8, 3.2 Hz, 1H), 2.73-2.55 (m, 2H), 2.52-2.41 (m, 1H), 2.00 (d, J=9.1 Hz, 2H), 1.85-1.58 (m, 1H), 1.47 (d, J=6.6 Hz, 3H), 1.45-1.23 (m, 1H). Analytical HPLC (Method A): RT=9.14 min, purity>99%; Factor XIa Ki=0.29 nM, Plasma Kallikrein Ki=80 nM.

Example 235

Preparation of (9R,13S)-13-{4-[5-chloro-2-(1H-pyrazol-4-yl)phenyl]-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one

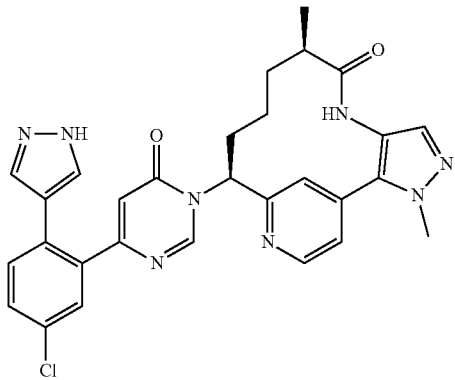 [SMILES: C[C@@H]1CCC[C@H](n2cnc(-c3cc(Cl)ccc3-c3cn[nH]c3)cc2=O)c2cc(ccn2)-c2c(cnn2C)NC1=O]

(9R,13S)-13-{4-[5-Chloro-2-(1H-pyrazol-4-yl)phenyl]-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one trifluoroacetate (2.97 mg, 14% yield) was prepared in a similar manner as the procedure described in Example 49, by replacing 1-methyl-4-(4,4,5,5-tetramethyl-1,3,2-dioxaborolan-2-yl)-1H-pyrazole with tert-butyl 4-(4,4,5,5-tetramethyl-1,3,2-dioxaborolan-2-yl)-1H-pyrazole-1-carboxylate (14.35 mg, 0.049 mmol). MS(ESI) m/z: 555.5 (M+H)⁺. ¹H NMR (400 MHz, CD₃OD) δ 8.97 (s, 1H), 8.75 (d, J=-5.1 Hz, 1H), 7.70 (s, 1H), 7.57-7.47 (m, 7H), 6.37 (s, 1H), 6.02 (dd, J=-12.5, 4.4 Hz, 1H), 4.05 (s, 3H), 2.76-2.67 (m, 1H), 2.39-2.28 (m, 1H), 2.15-1.98 (m, 2H), 1.67-1.43 (m, 2H), 1.01 (d, J=7.0 Hz, 3H), 0.80-0.63 (m, 1H). Analytical HPLC (Method A): RT=6.50 min, 99.7% purity; Factor XIa Ki=14 nM, Plasma Kallikrein Ki=550 nM.

Example 236

Preparation of N-benzyl-4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}benzamide

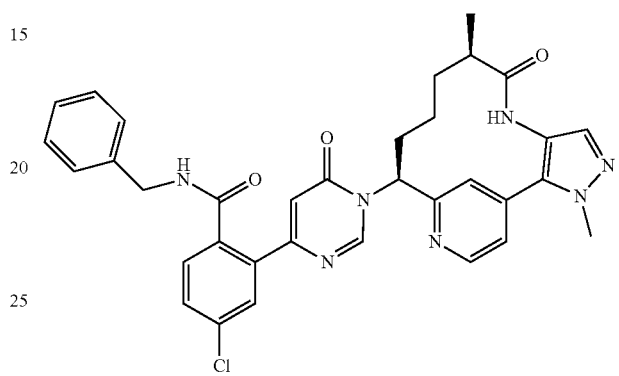

To a cooled (0° C.) solution of phenylmethanamine (0.081 ml, 0.741 mmol) in DCE (1.48 ml) was added dropwise a 2.0 M Al(Me)₃ in hexane (0.36 ml, 0.72 mmol). A white plume of gas formed above the reaction mixture. Gas evolution was observed in the solution. The resulting clear solution was stirred at 0° C. for 15 min, and then warmed to rt for 2 h. Next a solution of methyl 4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}benzoate (0.049 g, 0.074 mmol), prepared as described in Example 168, in DCE (1 ml) was added and the resulting clear, yellow reaction was heated to 40° C. After 5 h, the reaction was cooled to rt and the reaction was added to a cold (0° C.), vigorously stirred suspension of DCM/sat Rochelle's salt. The biphasic mixture was stirred for 10-15 min and then the layers were separated. The aqueous layer was extracted with DCM. The combined organic layers were washed with 1.0 N HCl, brine, dried over Na₂SO₄, filtered and concentrated. Purification by reverse phase chromatography afforded N-benzyl-4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}benzamide trifluoroacetate (6 mg, 11% yield) as a yellow solid. MS(ESI) m/z: 622.6 (M+H)¹. ¹H NMR (400 MHz, CD₃OD) δ 8.80 (s, 1H), 8.71 (d, J=5.1 Hz, 1H), 7.72 (s, 1H), 7.69 (s, 1H), 7.55-7.49 (m, 4H), 7.34-7.15 (m, 5H), 6.66 (s, 1H), 6.02 (dd, J=12.5, 4.2 Hz, 1H), 4.51-4.39 (m, 2H), 4.05 (s, 3H), 2.78-2.67 (m, 1H), 2.34-2.21 (m, 1H), 2.16-2.05 (m, 1H), 2.03-1.92 (m, 1H), 1.69-1.42 (m, 2H), 1.02 (d, J=6.8 Hz, 3H), 0.77-0.59 (m, 1H). Analytical HPLC (Method A): RT=7.27 min, 97.9% purity; Factor XIa Ki=23 nM, Plasma Kallikrein Ki=1,600 nM.

Example 237

Preparation of (9R,13S)-13-{4-[5-chloro-2-(4-chloro-1H-1,2,3-triazol-1-yl)phenyl]-6-oxo-1,6-dihydropyrimidin-1-yl}-9-methyl-4-(pyridin-2-yl)-3,4,7,15-tetraazatricyclo[12.3.1.0$^{2,6}$]octadeca-1(18),2,5,14,16-pentaen-8-one

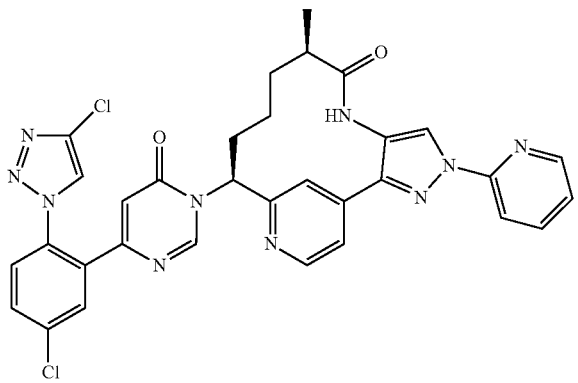 [SMILES: C[C@@H]1CCC[C@H](n2cnc(-c3cc(Cl)ccc3-n3cc(Cl)nn3)cc2=O)c2cc(ccn2)-c2nn(-c3ccccn3)cc2NC1=O]

(9R,13S)-13-{4-[5-Chloro-2-(4-chloro-1H-1,2,3-triazol-1-yl)phenyl]-6-oxo-1,6-dihydropyrimidin-1-yl}-9-methyl-4-(pyridin-2-yl)-3,4,7,15-tetraazatricyclo[12.3.1.0$^{2,6}$]octadeca-1(18),2,5,14,16-pentaen-8-one was prepared in a similar manner as the procedure described in Example 216, by using 2-iodopyridine to give (9R,13S)-13-{4-[5-chloro-2-(4-chloro-1H-1,2,3-triazol-1-yl)phenyl]-6-oxo-1,6-dihydropyrimidin-1-yl}-9-methyl-4-(pyridin-2-yl)-3,4,7,15-tetraazatricyclo[12.3.1.0$^{2,6}$]octadeca-1(18),2,5,14,16-pentaen-8-one trifluoroacetate (44 mg, 47%). MS(ESI) m/z: 653.5 (M+H)$^+$. $^1$H NMR (500 MHz, DMSO-d$_6$) δ 9.56-9.54 (m, 1H), 9.54 (s, 1H), 8.80 (s, 1H), 8.73-8.73 (m, 1H), 8.75 (s, 1H), 8.68 (s, 1H), 8.64 (d, J=5.2 Hz, 1H), 8.53 (d, J=4.9 Hz, 1H), 8.12-8.02 (m, 2H), 8.00-7.90 (m, 2H), 7.88-7.81 (m, 1H), 7.81-7.72 (m, 1H), 7.63 (dd, J=5.0, 1.1 Hz, 1H), 7.49-7.39 (m, 1H), 6.39 (s, 1H), 6.12-5.95 (m, 1H), 2.88-2.73 (m, 1H), 2.40-2.22 (m, 2H), 1.92-1.78 (m, 1H), 1.64-1.51 (m, 1H), 1.50-1.37 (m, 1H), 0.95 (d, J=6.7 Hz, 3H), 0.65-0.40 (m, 1H). Analytical HPLC (Method C): RT=1.75 min, purity=100%; Factor XIa Ki=8 nM, Plasma Kallikrein Ki=150 nM.

Example 238

Preparation of 1-(4-chloro-3-fluoro-2-{1-[(9R,13S)-3-($^2$H$_3$)methyl-9-methyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-pyrazole-4-carbonitrile

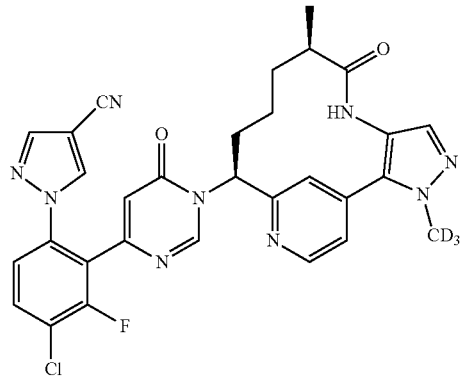 [SMILES: [2H]C([2H])([2H])n1ncc2c1-c1ccnc(c1)[C@@H](n1cnc(-c3c(-n4cc(C#N)cn4)ccc(Cl)c3F)cc1=O)CCC[C@@H](C)C(=O)N2]

238A. Preparation of 4-(3-chloro-2-fluoro-6-iodophenyl)-6-methoxypyrimidine To a suspension of 4-chloro-3-fluoro-2-(6-methoxypyrimidin-4-yl)aniline (2 g, 7.88 mmol) in CH$_3$CN (90 ml) at 0° C. was added pTsOH—H$_2$O (3.75 g, 19.71 mmol) followed by the dropwise addition of a solution of NaNO$_2$ (1.088 g, 15.77 mmol) and NaI (2.95 g, 19.71 mmol) in water (22.5 ml). The reaction was allowed to warm to rt and stir overnight. The reaction was quenched with sat NaHCO$_3$, and extracted with EtOAc. The organic layer was washed with sat Na$_2$S$_2$O$_3$, brine, dried with MgSO$_4$, filtered, and concentrated. Purification by normal phase chromatography gave 4-(3-chloro-2-fluoro-6-iodophenyl)-6-methoxypyrimidine (2.18 g, 76% yield) as viscous, yellow oil. MS(ESI) m/z: 365.1 (M+H)$^+$. $^1$H NMR (400 MHz, CDCl$_3$) δ 8.92 (d, J=0.9 Hz, 1H), 7.68 (dd, J=8.4, 1.5 Hz, 1H), 7.20 (dd, J=8.5, 7.4 Hz, 1H), 6.78 (s, 1H), 4.07 (s, 3H).

238B. Preparation of 6-(3-chloro-2-fluoro-6-iodophenyl)pyrimidin-4-ol

To a suspension of 4-(3-chloro-2-fluoro-6-iodophenyl)-6-methoxypyrimidine (0.22 g, 0.603 mmol) in ACN (6.03 ml) was added TMSI (0.411 ml, 3.02 mmol). The resulting clear, yellow solution was heated to 50° C. for 15 h. Additional TMSI (0.4 ml) was added and the reaction was heated 50° C. for 7 h. The reaction was poured into a 10% Na$_2$S$_2$O$_3$ and sat NaHCO$_3$, extracted with EtOAc (2×), and a mixture of DCM and MeOH. The organic layers were combined and concentrated. Purification by normal phase chromatography gave 6-(3-chloro-2-fluoro-6-iodophenyl)pyrimidin-4-ol (190 mg, 90% yield) as a yellow glass. MS(ESI) m/z: 351.1 (M+H)$^+$. $^1$H NMR (400 MHz, CD$_3$OD) δ 8.33 (d, J=1.1 Hz, 1H), 7.77 (dd, J=8.6, 1.5 Hz, 1H), 7.34 (dd, J=8.6, 7.5 Hz, 1H), 6.51 (d, J=0.9 Hz, 1H), 4.85 (br. s., 1H).

238C. Preparation of 1-(4-chloro-3-fluoro-2-(6-hydroxypyrimidin-4-yl)phenyl)-1H-pyrazole-4-carbonitrile To a suspension of 1H-pyrazole-4-carbonitrile (50.5 mg, 0.542 mmol), K$_3$PO$_4$ (233 mg, 1.084 mmol) and 6-(3-chloro-2-fluoro-6-iodophenyl)pyrimidin-4-ol (190 mg, 0.542 mmol) in dioxane (0.24 mL) was added (1R,2R)—N$_1$,N$_2$-dimethylcyclohexane-1,2-diamine (38.6 mg, 0.271 mmol). The vial was then purged with Ar, CuI (5.16 mg, 0.027 mmol) was added, and the vial was sealed. The reaction mixture was heated at 80° C. After 16 h, the reaction was cooled to rt, filtered, and the filtrate was concentrated. Purification by reverse phase chromatography gave 1-(4-chloro-3-fluoro-2-(6-hydroxypyrimidin-4-yl)phenyl)-1H-pyrazole-4-carbonitrile (74 mg, 43% yield) as an off-white solid. MS(ESI) m/z: 316.3 (M+H)$^+$. $^1$H NMR (400 MHz, CD$_3$OD) δ 8.54 (s, 1H), 8.09 (d, J=0.9 Hz, 1H), 7.97 (s, 1H), 7.80 (dd, J=8.7, 7.8 Hz, 1H), 7.50 (dd, J=8.7, 1.7 Hz, 1H), 6.51 (t, J=1.1 Hz, 1H).

238D. Preparation of 1-(4-chloro-3-fluoro-2-{1-[(9R,13S)-3-($^2$H$_3$)methyl-9-methyl-8-oxo-3,4,7,15-tetraazatricyclo[12.3.1.0$^{2,6}$]octadeca-1(18),2(6),4,14,16-pentaen-3-yl]-6-oxo-1,6-dihydropyrimidin-4-yl}phenyl)-1H-pyrazole-4-carbonitrile, Trifluoroacetate 1-(4-Chloro-3-fluoro-2-{1-[(9R,13S)-3-($^2$H$_3$)methyl-9-methyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-pyrazole-4-carbonitrile trifluoroacetate (9.5 mg, 41% yield) was prepared in a similar manner as the procedure described in Example 56, by using 1-(4-chloro-3-fluoro-2-(6-hydroxypyrimidin-4-yl)phenyl)-1H-pyrazole-4-carbonitrile (10 mg, 0.032 mmol) and (9R,13S)-13-amino-3-($^2$H$_3$)methyl-9-methyl-3,4,7,15-tetraazatricyclo[12.3.1.0$^{2,6}$]octadeca-1(18),2(6),4,14,16-pentaen-8-one (9.58 mg, 0.032 mmol), prepared as described in Intermediate 33. MS(ESI) m/z: 601.0 (M+H)$^+$. $^1$H NMR (400 MHz, CD$_3$OD) δ 8.81 (s, 1H), 8.76 (d, J=5.1 Hz, 1H), 8.46 (s, 1H), 7.94 (s, 1H), 7.80 (dd, J=8.6, 7.7 Hz, 1H), 7.69 (s, 1H), 7.55-7.48 (m, 3H), 6.54 (s, 1H), 6.00 (dd, J=13.0, 4.2 Hz, 1H), 2.70 (dt, J=6.7, 3.2 Hz, 1H), 2.36-2.25 (m, 1H), 2.15-1.95 (m, 2H), 1.67-1.55 (m, 1H), 1.55-1.41 (m, 1H), 1.01 (d, J=6.8 Hz, 3H), 0.72 (m, 1H). Analytical HPLC (Method A): RT=7.58 min, purity=98.5%; Factor XIa Ki=2.4 nM, Plasma Kallikrein Ki=1,500 nM.

Example 239

Preparation of 1-(4-chloro-2-{1-[(9R,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}-3-fluorophenyl)-1H-pyrazole-4-carbonitrile

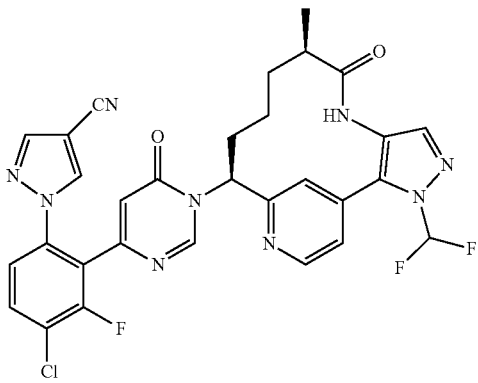 [SMILES: C[C@@H]1CCC[C@H](n2cnc(-c3c(-n4cc(C#N)cn4)ccc(Cl)c3F)cc2=O)c2cc(ccn2)-c2c(cnn2C(F)F)NC1=O]

1-(4-Chloro-2-{1-[(9R,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}-3-fluorophenyl)-1H-pyrazole-4-carbonitrile was prepared in a similar manner as the procedure described in Example 238, by replacing (9R,13S)-13-amino-3-($^2$H$_3$)methyl-9-methyl-3,4,7,15-tetraazatricyclo[12.3.1.0$^{2,6}$]octadeca-1(18),2(6),4,14,16-pentaen-8-one, prepared as described in Intermediate 33, with (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one (10.62 mg, 0.032 mmol), prepared as described in Example 30G. MS(ESI) m/z: 634.0 (M+H)$^+$. $^1$H NMR (400 MHz, CD$_3$OD) δ 8.86 (s, 1H), 8.78 (d, J=5.1 Hz, 1H), 8.47 (s, 1H), 7.94 (s, 1H), 7.83-7.77 (m, 1H), 7.74 (s, 1H), 7.70 (s, 1H), 7.65 (s, 1H), 7.52 (dd, J=8.7, 1.4 Hz, 2H), 6.55 (s, 1H), 6.01 (dd, J=12.7, 4.1 Hz, 1H), 2.76-2.65 (m, 1H), 2.31 (t, J=13.0 Hz, 1H), 2.10-1.95 (m, 2H), 1.65-1.42 (m, 2H), 1.00 (d, J=7.0 Hz, 3H), 0.67 (m, 1H). Analytical HPLC (Method A): SunFire, RT=8.75 min, 98.8% purity; Factor XIa Ki=1.0 nM, Plasma Kallikrein Ki=1,100 nM.

Example 240

Preparation of (9R,13S)-13-{4-[5-chloro-2-(1-propyl-1H-pyrazol-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

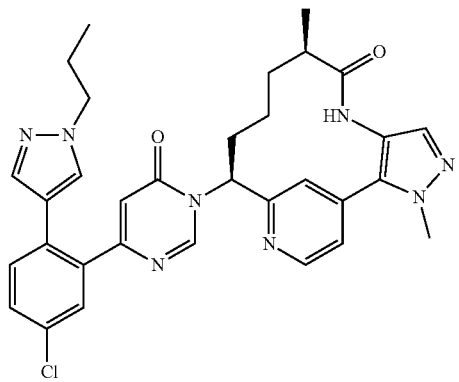 [SMILES: CCCn1cc(-c2ccc(Cl)cc2-c2cc(=O)n([C@H]3CCC[C@@H](C)C(=O)Nc4cnn(C)c4-c4ccnc3c4)cn2)cn1]

(9R,13S)-13-{4-[5-Chloro-2-(1-propyl-1H-pyrazol-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (14.3 mg, 62% yield) was prepared in a similar manner as the procedure described in Example 49, by replacing 1-methyl-4-(4,4,5,5-tetramethyl-1,3,2-dioxaborolan-2-yl)-1H-pyrazole with 1-propyl-4-(4,4,5,5-tetramethyl-1,3,2-dioxaborolan-2-yl)-1H-pyrazole (11.52 mg, 0.049 mmol). MS(ESI) m/z: 597.4 (M+H)$^+$. $^1$H NMR (400 MHz, CD$_3$OD) δ 9.01 (s, 1H), 8.75 (d, J=5.1 Hz, 1H), 7.74 (s, 1H), 7.58-7.52 (m, 3H), 7.50-7.47 (m, 3H), 7.42 (s, 1H), 6.40 (d, J=0.4 Hz, 1H), 6.02 (dd, J=12.7, 4.3 Hz, 1H), 4.07-4.01 (m, 5H), 2.76-2.67 (m, 1H), 2.40-2.29 (m, 1H), 2.13-2.00 (m, 2H), 1.77 (sxt, J=7.2 Hz, 2H), 1.67-1.43 (m, 2H), 1.02 (d, J=6.8 Hz, 3H), 0.79 (t, J=7.4 Hz, 3H), 0.75-0.66 (m, 1H). Analytical HPLC (Method A): RT=8.12 min, 100% purity; Factor XIa Ki=35 nM, Plasma Kallikrein Ki=3,800 nM.

Example 241

Preparation of (9R,13S)-13-{4-[5-chloro-2-(4-chloro-1H-1,2,3-triazol-1-yl)phenyl]-6-oxo-1,6-dihydropyrimidin-1-yl}-9-methyl-4-(pyridin-4-yl)-3,4,7,15-tetraazatricyclo[12.3.1.0$^{2,6}$]octadeca-1(18),2,5,14,16-pentaen-8-one

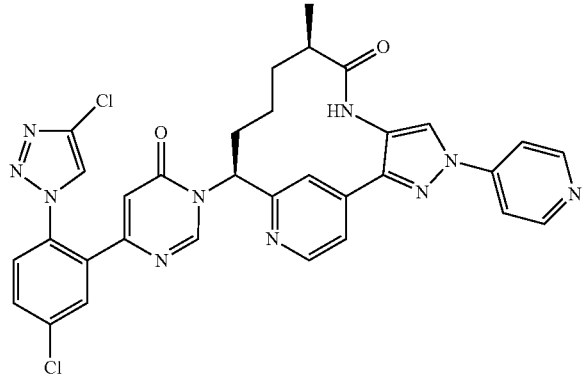 [SMILES: C[C@@H]1CCC[C@H](n2cnc(-c3cc(Cl)ccc3-n3cc(Cl)nn3)cc2=O)c2cc(ccn2)-c2nn(-c3ccncc3)cc2NC1=O]

(9R,13S)-13-{4-[5-Chloro-2-(4-chloro-1H-1,2,3-triazol-1-yl)phenyl]-6-oxo-1,6-dihydropyrimidin-1-yl}-9-methyl-4-(pyridin-4-yl)-3,4,7,15-tetraazatricyclo[12.3.1.0²,⁶]octadeca-1(18),2,5,14,16-pentaen-8-one was prepared in a similar manner as the procedure described in Example 216, by using 4-iodopyridine to give (9R,13S)-13-{4-[5-chloro-2-(4-chloro-1H-1,2,3-triazol-1-yl)phenyl]-6-oxo-1,6-dihydropyrimidin-1-yl}-9-methyl-4-(pyridin-4-yl)-3,4,7,15-tetraazatricyclo[12.3.1.0²,⁶]octadeca-1(18),2,5,14,16-pentaen-8-one trifluoroacetate (29 mg, 30% yield). MS(ESI) m/z: 653.6 (M+H)⁺. ¹H NMR (500 MHz, DMSO-d₆) δ 9.57 (s, 1H), 8.86 (s, 1H), 8.72 (s, 1H), 8.67 (s, 1H), 8.58 (d, J=4.9 Hz, 1H), 8.04 (br. s., 2H), 7.91-7.82 (m, 2H), 7.80-7.73 (m, 1H), 7.73-7.65 (m, 1H), 7.57 (d, J=5.2 Hz, 1H), 6.31 (s, 1H), 6.01-5.87 (m, 1H), 2.80-2.67 (m, 1H), 2.22 (d, J=7.3 Hz, 2H), 1.80 (br. s., 1H), 1.59-1.45 (m, 1H), 1.44-1.29 (m, 1H), 0.87 (d, J=7.0 Hz, 3H), 0.59-0.36 (m, 1H). Analytical HPLC (Method C): RT=1.42 min, purity=98%; Factor XIa Ki=0.58 nM, Plasma Kallikrein Ki=20 nM.

Example 242

Preparation of (9R,13S)-13-{4-[5-chloro-2-(4-chloro-1H-1,2,3-triazol-1-yl)phenyl]-6-oxo-1,6-dihydropyrimidin-1-yl}-9-methyl-3-(pyridin-4-yl)-3,4,7,15-tetraazatricyclo[12.3.1.0²,⁶]octadeca-1(18),2(6),4,14,16-pentaen-8-one

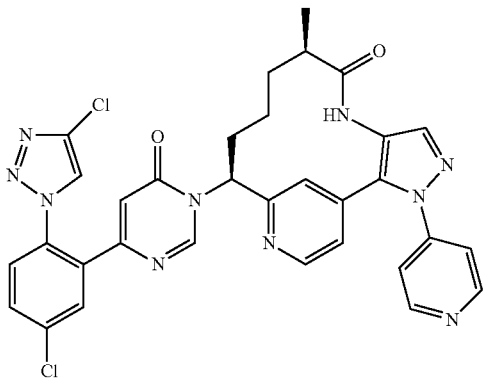

(9R,13S)-13-{4-[5-Chloro-2-(4-chloro-1H-1,2,3-triazol-1-yl)phenyl]-6-oxo-1,6-dihydropyrimidin-1-yl}-9-methyl-3-(pyridin-4-yl)-3,4,7,15-tetraazatricyclo[12.3.1.0²,⁶]octadeca-1(18),2(6),4,14,16-pentaen-8-one was synthesized as a minor product (2 mg, 2.4%) from the reaction to generate (9R,13S)-13-{4-[5-chloro-2-(4-chloro-1H-1,2,3-triazol-1-yl)phenyl]-6-oxo-1,6-dihydropyrimidin-1-yl}-9-methyl-4-(pyridin-4-yl)-3,4,7,15-tetraazatricyclo[12.3.1.0²,⁶]octadeca-1(18),2,5,14,16-pentaen-8-one, Example 241. MS(ESI) m/z: 653.6 (M+H)⁺. ¹H NMR (500 MHz, DMSO-d₆) δ 8.98 (br. s., 1H), 8.74 (br. s., 2H), 8.65 (br. s., 3H), 8.03-7.91 (m, 3H), 7.88-7.66 (m, 5H), 6.41 (br. s., 1H), 5.91-5.79 (m, 1H), 3.90 (br. s., 1H), 3.45 (br. s., 2H), 2.41-2.30 (m, 2H), 2.10-2.04 (m, 1H), 2.03-1.95 (m, 1H), 1.94-1.81 (m, 2H), 1.67 (br. s., 2H), 1.54 (br. s., 3H), 1.30 (br. s., 4H), 1.21 (br. s., 4H). Analytical HPLC (Method C): RT=1.37 min, purity=100%; Factor XIa Ki=22 nM, Plasma Kallikrein Ki=470 nM.

Example 243

Preparation of 1-(4-chloro-2-{1-[(9R,13S)-3,9-dimethyl-8-oxo-3,4,7,15-tetraazatricyclo[12.3.1.0²,⁶]octadeca-1(18),2(6),4,14,14,16-pentaen-13-yl]-6-oxo-1,6-dihydropyrimidin-4-yl}phenyl)-1H-imidazole-4-carbonitrile

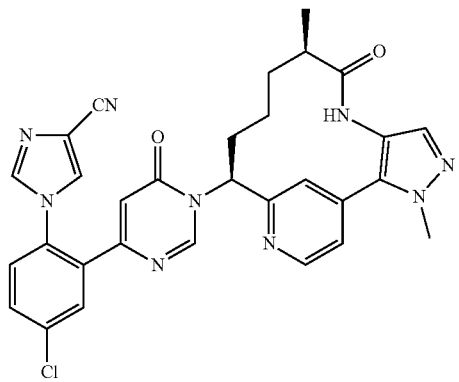

1-(4-Chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)-1H-imidazole-4-carbonitrile trifluoroacetate (9.7 mg, 37% yield) was prepared in a similar manner as the procedure described in Example 231, by replacing 1H-imidazole with 1H-imidazole-4-carbonitrile (0.012 g, 0.130 mmol). MS(ESI) m/z: 580.20 (M+H)⁺. ¹H NMR (500 MHz, DMSO-d₆) δ 9.22 (s, 1H), 8.82 (s, 1H), 8.69 (d, J=5.2 Hz, 1H), 8.29 (s, 1H), 8.04 (s, 1H), 7.88 (d, J=2.4 Hz, 1H), 7.78 (dd, J=8.5, 2.1 Hz, 1H), 7.70-7.66 (m, 2H), 7.59 (d, J=4.9 Hz, 1H), 7.48 (s, 1H), 6.37 (s, 1H), 5.89 (d, J=10.7 Hz, 1H), 4.01 (s, 3H), 2.69-2.61 (m, 1H), 2.39-2.27 (m, 1H), 2.11 (t, J=12.5 Hz, 1H), 1.89-1.80 (m, 1H), 1.53-1.42 (m, 1H), 1.39-1.29 (m, 1H), 0.89 (d, J=7.0 Hz, 3H), 0.50-0.34 (m, 1H). Analytical HPLC (Method B): RT=8.12 min, 100% purity; Factor XIa Ki=53 nM, Plasma Kallikrein Ki=3,400 nM.

Example 244

Preparation of N-(4-chloro-2-{1-[(9R,13S)-3-(difluoromethyl)-9-methyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)-2,2,2-trifluoroacetamide

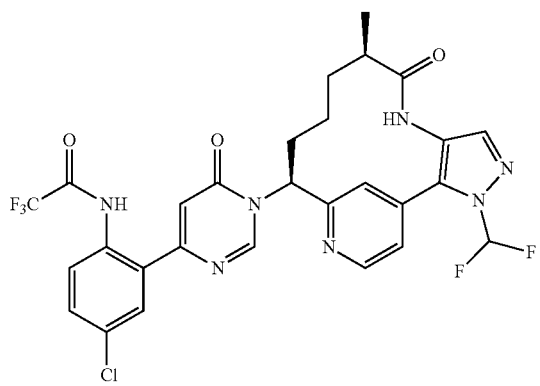 [SMILES: C[C@@H]1CCC[C@H](n2cnc(-c3cc(Cl)ccc3NC(=O)C(F)(F)F)cc2=O)c2cc(ccn2)-c2c(cnn2C(F)F)NC1=O]

N-(4-Chloro-2-{1-[(9R,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-2,2,2-trifluoroacetamide was prepared in a similar manner as the procedure described in Example 56, using N-(4-chloro-2-(6-hydroxypyrimidin-4-yl)phenyl)-2,2,2-trifluoroacetamide (0.19 g, 0.60 mmol), prepared as described in Intermediate 1, and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one (0.20 g, 0.60 mmol), prepared as described in Intermediate 30, to give N-(4-chloro-2-{1-[(9R,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-2,2,2-trifluoroacetamide (222 mg, 58%) as white powder. MS(ESI) m/z: 636.5 (M+H)$^+$. $^1$H NMR (400 MHz, CD$_3$OD) δ 9.23 (s, 1H), 8.89 (s, 1H), 8.56 (d, J=5.1 Hz, 1H), 7.74-7.69 (m, 3H), 7.55 (s, 1H), 7.46-7.39 (m, 1H), 7.24 (d, J=5.1 Hz, 1H), 6.74 (s, 1H), 5.83-5.70 (m, 1H), 2.55-2.40 (m, 1H), 2.27-2.12 (m, 1H), 1.89 (s, 1H), 1.81-1.66 (m, 1H), 1.38-1.24 (m, 1H), 1.24-1.11 (m, 1H), 0.70 (d, J=7.0 Hz, 3H). Analytical HPLC (Method A): RT=10.89 min, purity=99%; Factor XIa Ki=3.9 nM, Plasma Kallikrein Ki=260 nM.

Example 245

Preparation of (9R,13S)-13-(4-{5-chloro-2-[1-(propan-2-yl)-1H-pyrazol-4-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one

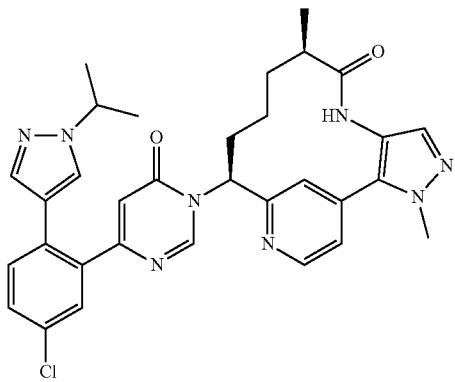 [SMILES: CC(C)n1cc(-c2ccc(Cl)cc2-c2cc(=O)n([C@H]3CCC[C@@H](C)C(=O)Nc4cnn(C)c4-c4ccnc3c4)cn2)cn1]

(9R,13S)-13-(4-{5-Chloro-2-[1-(propan-2-yl)-1H-pyrazol-4-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate (15.5 mg, 67% yield) was prepared in a similar manner as the procedure described in Example 49, by replacing 1-methyl-4-(4,4,5,5-tetramethyl-1,3,2-dioxaborolan-2-yl)-1H-pyrazole with 1-isopropyl-4-(4,4,5,5-tetramethyl-1,3,2-dioxaborolan-2-yl)-1H-pyrazole (11.52 mg, 0.049 mmol). MS(ESI) m/z: 597.4 (M+H)$^+$. $^1$H NMR (400 MHz, CD$_3$OD) δ 9.02 (s, 1H), 8.75 (d, J=5.1 Hz, 1H), 7.74 (s, 1H), 7.62 (s, 1H), 7.56 (dd, J=5.2, 1.7 Hz, 1H), 7.54-7.52 (m, 1H), 7.50-7.47 (m, 3H), 7.39 (s, 1H), 6.40 (d, J=0.4 Hz, 1H), 6.02 (dd, J=12.7, 4.3 Hz, 1H), 4.46 (spt, J=6.7 Hz, 1H), 4.05 (s, 3H), 2.76-2.66 (m, 1H), 2.41-2.30 (m, 1H), 2.14-2.00 (m, 2H), 1.67-1.37 (m, 8H), 1.02 (d, J=6.8 Hz, 3H), 0.80-0.64 (m, 1H). Analytical HPLC (Method A): RT=8.07 min, 100% purity; Factor XIa Ki=44 nM, Plasma Kallikrein Ki=5,600 nM.

Example 246

Preparation of (9R,13S)-13-{4-[5-(difluoromethoxy)-2-[4-(trifluoromethyl)-1H-1,2,3-triazol-1-yl]phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one

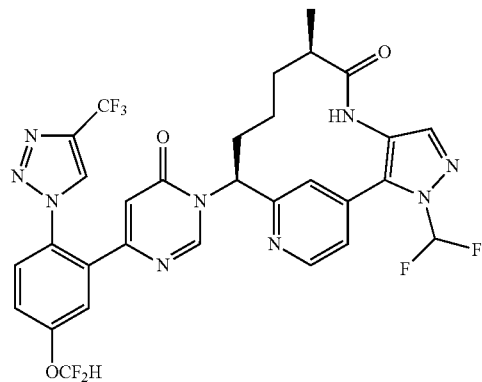

(9R,13S)-13-{4-[5-(Difluoromethoxy)-2-[4-(trifluoromethyl)-1H-1,2,3-triazol-1-yl]phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one (13 mg, 60% yield) as a solid was prepared via the coupling of 6-[5-(difluoromethoxy)-2-[4-(trifluoromethyl)-1H-1,2,3-triazol-1-yl]phenyl]pyrimidin-4-ol (0.012 g, 0.03 mmol) and (9R,13S)-13-amino-3-(difluoromethyl)-9-methyl-3,4,7,15-tetraazatricyclo[12.3.1.0$^{2,6}$]octadeca-1(18),2(6), 4,14,16-pentaen-8-one (0.011 g, 0.03 mmol) using the HATU, DBU coupling methodology as described in Example 56. MS m/z=692.1 (M+H)$^+$. $^1$H NMR (500 MHz, DMSO-d$_6$) δ 9.39 (s, 1H), 9.22 (s, 1H), 8.78 (s, 1H), 8.70 (d, J=5.2 Hz, 1H), 7.97-7.81 (m, 1H), 7.71-7.64 (m, 2H), 7.59-7.53 (m, 2H), 7.50-7.46 (m, 1H), 7.45-7.41 (m, 1H), 6.47-6.41 (m, 1H), 5.95-5.85 (m, 1H), 2.71-2.59 (m, 1H), 2.35-2.23 (m, 1H), 2.07-1.98 (m, 1H), 1.90-1.74 (m, 1H), 1.52-1.24 (m, 2H), 0.88 (d, J=6.7 Hz, 3H), 0.46-0.19 (m, 1H). Analytical HPLC (Method B) RT=1.8 min, purity=100%; Factor XIa Ki=110 nM.

Example 247

Preparation of (9R,13S)-3-(difluoromethyl)-13-(4-{5-methoxy-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[2.3.1.0$^{2,6}$]octadeca-1(18),2(6),4,14,16-pentaen-8-one

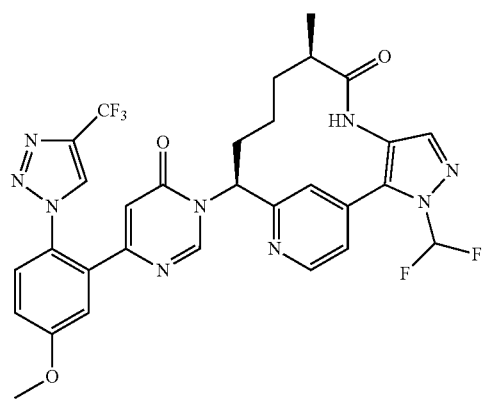 [SMILES: COc1ccc(-n2cc(C(F)(F)F)nn2)c(-c2cc(=O)n([C@H]3CCC[C@@H](C)C(=O)Nc4cnn(C(F)F)c4-c4ccnc3c4)cn2)c1]

(9R,13S)-3-(Difluoromethyl)-13-(4-{5-methoxy-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0$^{2,6}$]octadeca-1(18),2(6),4,14,16-pentaen-8-one (12 mg, 50% yield) as a solid was prepared via the coupling of 6-{5-methoxy-2-[4-(trifluoromethyl)-1H-1,2,3-triazol-1-yl]phenyl}pyrimidin-4-ol (0.012 g, 0.03 mmol) and (9R,13S)-13-amino-3-(difluoromethyl)-9-methyl-3,4,7,15-tetraazatricyclo[12.3.1.0$^{2,6}$]octadeca-1(18),2(6), 4,14,16-pentaen-8-one (0.012 g, 0.03 mmol) using the HATU, DBU coupling methodology as described in Example 56. MS m/z=656.2 (M+H)$^+$. $^1$H NMR (500 MHz, DMSO-d$_6$) δ 9.16-9.12 (m, 1H), 8.91-8.88 (m, 1H), 8.52-8.48 (m, 1H), 8.47-8.43 (m, 1H), 7.66-7.63 (m, 2H), 7.60-7.55 (m, 1H), 7.46-7.42 (m, 1H), 7.20-7.16 (m, 1H), 7.14-7.10 (m, 1H), 7.05-7.00 (m, 1H), 6.21-6.12 (m, 1H), 5.72-5.54 (m, 1H), 2.46-2.38 (m, 1H), 2.09-1.98 (m, 1H), 1.86-1.69 (m, 1H), 1.63-1.47 (m, 1H), 1.29-1.00 (m, 2H), 0.65-0.58 (d, 3H), 0.20-0.04 (m, 1H). Analytical HPLC (Method B) RT=1.72 min, purity=100%; Factor XIa Ki=7.7 nM, Plasma Kallikrein Ki=2,400 nM.

Example 248

Preparation of (9R,13S)-13-(4-{5-chloro-2-[1-(2-methylpropyl)-1H-pyrazol-4-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one

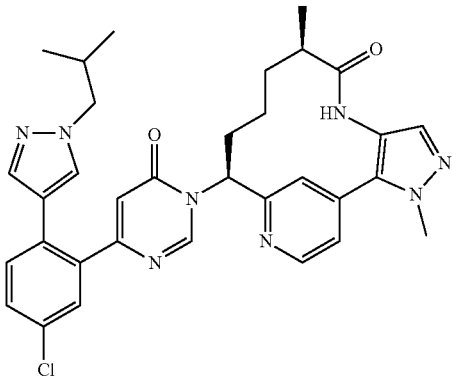 [SMILES: CC(C)Cn1cc(-c2ccc(Cl)cc2-c2cc(=O)n([C@H]3CCC[C@@H](C)C(=O)Nc4cnn(C)c4-c4ccnc3c4)cn2)cn1]

(9R,13S)-13-(4-{5-Chloro-2-[1-(2-methylpropyl)-1H-pyrazol-4-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate (7.6 mg, 32% yield) was prepared in a similar manner as the procedure described in Example 49, by replacing 1-methyl-4-(4,4,5,5-tetramethyl-1,3,2-dioxaborolan-2-yl)-1H-pyrazole with 1-isobutyl-4-(4,4,5,5-tetramethyl-1,3,2-dioxaborolan-2-yl)-1H-pyrazole (12.20 mg, 0.049 mmol). MS(ESI) m/z: 611.4 (M+H)$^+$. $^1$H NMR (400 MHz, CD$_3$OD) δ 9.00 (s, 1H), 8.75 (d, J=5.3 Hz, 1H), 7.72 (s, 1H), 7.57-7.47 (m, 6H), 7.42 (s, 1H), 6.37 (d, J=0.4 Hz, 1H), 6.02 (dd, J=12.8, 4.2 Hz, 1H), 4.05 (s, 3H), 3.91-3.81 (m, 2H), 2.76-2.67 (m, 1H), 2.34 (tt, J=12.7, 4.3 Hz, 1H), 2.14-1.98 (m, 3H), 1.67-1.43 (m, 2H), 1.01 (d, J=6.8 Hz, 3H), 0.83-0.63 (m, 7H). Analytical HPLC (Method A): RT=8.63 min, 100% purity; Factor XIa Ki=73 nM, Plasma Kallikrein Ki=8,900 nM.

Example 249

Preparation of (9R,13S)-13-{4-[2-(1-benzyl-1H-pyrazol-4-yl)-5-chlorophenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

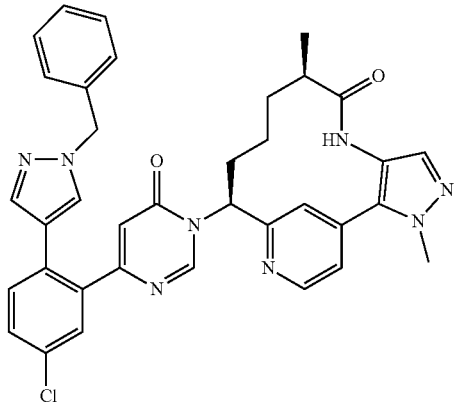 [SMILES: C[C@@H]1CCC[C@H](n2cnc(-c3cc(Cl)ccc3-c3cnn(Cc4ccccc4)c3)cc2=O)c2cc(ccn2)-c2c(cnn2C)NC1=O]

(9R,13S)-13-{4-[2-(1-Benzyl-1H-pyrazol-4-yl)-5-chlorophenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (2.68 mg, 11% yield) was prepared in a similar manner as the procedure described in Example 49, by replacing 1-methyl-4-(4,4,5,5-tetramethyl-1,3,2-dioxaborolan-2-yl)-1H-pyrazole with 1-benzyl-4-(4,4,5,5-tetramethyl-1,3,2-dioxaborolan-2-yl)-1H-pyrazole (13.86 mg, 0.049 mmol). MS(ESI) m/z: 645.4 (M+H)$^+$. $^1$H NMR (400 MHz, CD$_3$OD) δ 8.95 (s, 1H), 8.67 (d, J=5.1 Hz, 1H), 7.70 (s, 1H), 7.59 (s, 1H), 7.54-7.45 (m, 6H), 7.29-7.19 (m, 3H), 7.09-7.05 (m, 2H), 6.36 (d, J=0.7 Hz, 1H), 6.00 (dd, J=12.7, 4.1 Hz, 1H), 5.27 (s, 2H), 4.02 (s, 3H), 2.77-2.68 (m, 1H), 2.34-2.23 (m, 1H), 2.15-2.05 (m, 1H), 2.01-1.90 (m, 1H), 1.67-1.42 (m, 2H), 1.02 (d, J=6.8 Hz, 3H), 0.76-0.60 (m, 1H). Analytical HPLC (Method A): RT=8.90 min, 100% purity; Factor XIa Ki=100 nM.

Example 250

Preparation of (9R,13S)-13-{4-[5-chloro-2-(1-methyl-1H-1,2,3-triazol-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

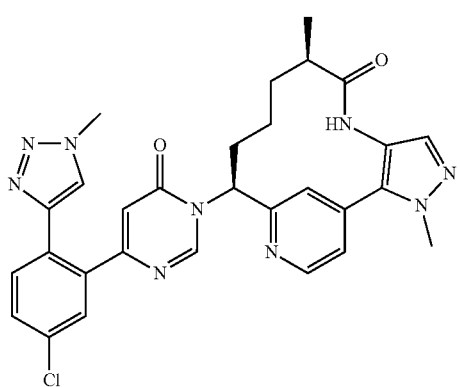 [SMILES: C[C@@H]1CCC[C@H](n2cnc(-c3cc(Cl)ccc3-c3cn(C)nn3)cc2=O)c2cc(ccn2)-c2c(cnn2C)NC1=O]

250A. Preparation of 4-(5-chloro-2-ethynylphenyl)-6-methoxypyrimidine

A flame-dried flask containing 4-(5-chloro-2-iodophenyl)-6-methoxypyrimidine (0.520 g, 1.50 mmol), prepared as described in Example 211, and Pd(PPh$_3$)$_4$ (0.087 g, 0.075 mmol) was purged with Ar for several min. Next, degassed THF (7.50 ml) and tributylstannylacetylene (0.651 ml, 2.25 mmol) were added. The resulting clear, burgundy solution was stirred at rt. After 15 h, the dark purple reaction was diluted with EtOAc and washed with brine, dried over Na$_2$SO$_4$, filtered and concentrated to give a purple solid. Purification by normal phase chromatography, using 0-10% EtOAc/Hex, gave 4-(5-chloro-2-ethynylphenyl)-6-methoxypyrimidine (0.176 g, 48%) as an off-white solid. MS(ESI) m/z: 244.9 (M+H)$^+$.

250B. Preparation of 4-(5-chloro-2-{1-[(trimethylsilyl)methyl]-1H-1,2,3-triazol-4-yl}phenyl)-6-methoxypyrimidine A sealed vial containing a mixture of TMSN$_3$ (0.091 ml, 0.61 mmol), 4-(5-chloro-2-ethynylphenyl)-6-methoxypyrimidine (0.050 g, 0.20 mmol), sodium ascorbate (8.10 mg, 0.041 mmol), and CuSO$_4$ (3.26 mg, 0.020 mmol) was stirred at 60° C. After 2 h, the dark black reaction was cooled to rt. The mixture was diluted with EtOAc (15 mL), and the turbid solution was washed water (3×), brine, dried over Na$_2$SO$_4$, filtered and concentrated to give 0.110 g of crude product as a black oil. Purification by normal phase chromatography using 0-40% EtOAc/Hex, gave 4-(5-chloro-2-{1-[(trimethylsilyl) methyl]-1H-1,2,3-triazol-4-yl}phenyl)-6-methoxypyrimidine (0.0191 g, 25%) as a yellow residue. MS(ESI) m/z: 374.0 (M+H)$^+$.

250C. Preparation of 4-[5-chloro-2-(1-methyl-1H-1,2,3-triazol-4-yl)phenyl]-6-methoxypyrimidine To a cooled (0° C.) clear yellow solution of 4-(5-chloro-2-(1-((trimethylsilyl) methyl)-1H-1,2,3-triazol-4-yl)phenyl)-6-methoxypyrimidine (0.019 g, 0.051 mmol) in THF (0.508 ml) and water (1.831 µl, 0.102 mmol) was added dropwise 1.0 M TBAF in THF (0.061 ml, 0.061 mmol). The reaction was stirred at 0° C. for 1 h and then warmed to rt. After 2 h, additional 1.0 M TBAF in THF (0.061 ml, 0.061 mmol) was added. After 51 h, additional 1.0 M TBAF in THF (0.51 ml, 0.51 mmol) was added. After 44 h, the reaction was diluted with EtOAc and washed with sat NH$_4$Cl, brine, dried over Na$_2$SO$_4$, filtered and concentrated to give 4-(5-chloro-2-(1-methyl-1H-1,2,3-triazol-4-yl)phenyl)-6-methoxypyrimidine (0.015 g, 98%) as a yellow residue. MS(ESI) m/z: 302.0 (M+H)$^+$.

250D. Preparation of 6-[5-chloro-2-(1-methyl-1H-1,2,3-triazol-4-yl)phenyl]pyrimidin-4-ol A clear, yellow solution of 4-(5-chloro-2-(1-methyl-1H-1,2,3-triazol-4-yl)phenyl)-6-methoxypyrimidine (0.015 g, 0.050 mmol) in AcOH (0.50 ml) and 48% aq HBr (0.28 ml, 2.486 mmol) was warmed to 85° C. After 1 h, the reaction was cooled to rt and then concentrated to give a brown solid. The brown solid was suspended in EtOAc and filtered to give and off-white solid. Purification by reverse phase chromatography gave, after free-basing with sat NaHCO$_3$, 6-[5-chloro-2-(1-methyl-1H-1,2,3-triazol-4-yl) phenyl]pyrimidin-4-ol (0.0090 g, 63%) as a white solid. MS(ESI) m/z: 288.0 (M+H)$^+$. $^1$H NMR (500 MHz, CD$_3$OD) δ 8.21 (s, 1H), 7.90 (s, 1H), 7.72 (d, J=8.3 Hz, 1H), 7.60 (d, J=2.2 Hz, 1H), 7.58 (dd, J=8.3, 2.2 Hz, 1H), 6.38 (s, 1H), 4.09 (s, 3H).

250E. Preparation of (9R,13S)-13-{4-[5-chloro-2-(1-methyl-1H-1,2,3-triazol-4-yl) phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (9R,13S)-13-{4-[5-Chloro-2-(1-methyl-1H-1,2,3-triazol-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (0.0055 g, 25%) was prepared in a similar manner as the procedure described in Example 56, by replacing 6-{5-chloro-2-[4-(trifluoromethyl)-1H-1,2,3-triazol-1-yl]phenyl}pyrimidin-4-ol with 6-[5-chloro-2-(1-methyl-1H-1,2,3-triazol-4-yl)phenyl]pyrimidin-4-ol. MS(ESI) m/z: 570.1 (M+H)$^+$ and 572.0 (M+2+H)$^+$. $^1$H NMR (500 MHz, CD$_3$OD) δ 8.94 (s, 1H), 8.75 (d, J=5.2 Hz, 1H), 7.90 (s, 1H), 7.74 (s, 1H), 7.70 (d, J=8.3 Hz, 1H), 7.63 (d, J=2.2 Hz, 1H), 7.59-7.54 (m, 2H), 7.50 (s, 1H), 6.40 (d, J=0.6 Hz, 1H), 6.04-5.99 (m, 1H), 4.08 (s, 3H), 4.05 (s, 3H), 2.76-2.67 (m, 1H), 2.40-2.29 (m, 1H), 2.15-2.01 (m, 2H), 1.68-1.56 (m, 1H), 1.55-1.43 (m, 1H), 1.02 (d, J=7.2 Hz, 3H), 0.79-0.64 (m, 1H). Analytical HPLC (Method A): RT=6.30 min, purity=100%; Factor XIa Ki=11 nM, Plasma Kallikrein Ki=2,000 nM.

Example 251

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-4-fluoro-10-methyl-5,8,16-triazatricyclo[13.3.1.0$^{2,7}$]nonadeca-1(19),2(7),3,5,15,17-hexaen-9-one

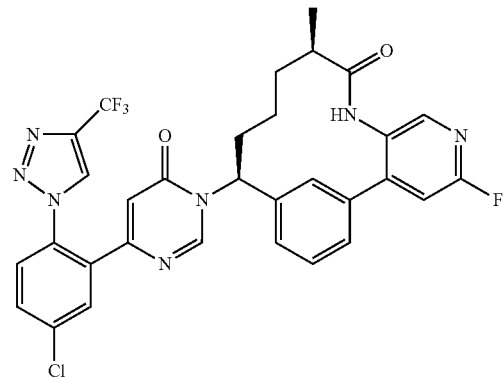 [SMILES: C[C@@H]1CCC[C@H](n2cnc(-c3cc(Cl)ccc3-n3cc(C(F)(F)F)nn3)cc2=O)c2cccc(c2)-c2cc(F)ncc2NC1=O]

251A. Preparation of Tert-Butyl N-(6-fluoro-4-iodopyridin-3-yl)carbamate

BuLi (11.31 ml, 28.3 mmol) was added dropwise to a stirred, cooled (−78° C.) solution of tert-butyl (6-fluoropyridin-3-yl)carbamate (2 g, 9.42 mmol) and TMEDA (4.27 ml, 28.3 mmol) in Et$_2$O (47.1 ml). The mixture was allowed to warm to −10° C. and stirred for 2 h. The mixture was recooled to −78° C. and a cooled (−10° C.) solution of 12

(4.90 g, 19.32 mmol) in Et₂O (25 mL) was added dropwise. The mixture was allowed to warm to rt and stirred for 2 days. Sat aq NH₄Cl was added and the mixture was extracted with Et₂O and EtOAc. The combined organic fractions were washed with Na₂S₂O₃, brine, dried over MgSO₄, filtered and concentrated to give a brownish oil, which was purified by normal phase chromatography to give tert-butyl N-(6-fluoro-4-iodopyridin-3-yl)carbamate (0.859 g, 27% yield). MS(ESI) m/z: 338.9 (M+H)⁺.

251B. Preparation of 6-fluoro-4-iodopyridin-3-amine

To a solution of N-(6-fluoro-4-iodopyridin-3-yl)carbamate (400 mg, 1.183 mmol) in DCM (15 mL) was added TFA (4.56 mL, 59.2 mmol). The reaction was stirred at rt for 1 h. Concentration gave 6-fluoro-4-iodopyridin-3-amine.trifluoroacetate (551 mg, 100%) as a pale yellow solid. MS(ESI) m/z: 238.9 (M+H)⁺.

251C. Preparation of (10R,14S)-14-amino-4-fluoro-10-methyl-5,8,16-triazatricyclo[13.3.1.0²,⁷]nonadeca-1(19),2,4,6,15,17-hexaen-9-one (10R,14S)-14-Amino-4-fluoro-10-methyl-5,8,16-triazatricyclo[13.3.1.0²,⁷]nonadeca-1(19),2,4,6,15,17-hexaen-9-one was prepared in a similar manner as the procedure described in Intermediate 39, by replacing 2-bromopyridin-3-amine with 6-fluoro-4-iodopyridin-3-amine. MS(ESI) m/z: 315.4 (M+H)⁺.

251D. Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-4-fluoro-10-methyl-5,8,16-triazatricyclo[13.3.1.0²,⁷]nonadeca-1(19),2(7),3,5,15,17-hexaen-9-one (10R,14S)-14-(4-{5-Chloro-2-[4-(trifluoromethyl)-1H-1,2,3-triazol-1-yl]phenyl}-6-oxo-1,6-dihydropyrimidin-1-yl)-4-fluoro-10-methyl-5,8,16-triazatricyclo[13.3.1.0²,⁷]nonadeca-1(19),2(7),3,5,15,17-hexaen-9-one trifluoroacetate (7.3 mg, 33.7% yield) was prepared in a similar manner as the procedure described in Example 56 by using (10R,14S)-14-amino-4-fluoro-10-methyl-5,8,16-triazatricyclo[13.3.1.0²,⁷]nonadeca-1(19),2,4,6,15,17-hexaen-9-one (8.8 mg, 0.028 mmol). ¹H NMR (400 MHz, CD₃OD) δ 8.91 (s, 1H), 8.83-8.79 (m, 1H), 8.71 (d, J=5.1 Hz, 1H), 8.13-8.09 (m, 1H), 7.89 (d, J=2.4 Hz, 1H), 7.78-7.65 (m, 3H), 7.48 (dd, J=5.1, 1.8 Hz, 1H), 7.37 (d, J=2.2 Hz, 1H), 6.42 (d, J=0.7 Hz, 1H), 6.04 (dd, J=12.5, 4.8 Hz, 1H), 2.79-2.65 (m, 1H), 2.27-2.14 (m, 1H), 2.07-1.92 (m, 2H), 1.60-1.37 (m, 2H), 0.95 (d, J=6.8 Hz, 3H), 0.57 (br. s., 1H). MS(ESI) m/z: 639.0 (M+H)⁺. Analytical HPLC (Method A): RT=9.64 min, purity=100%; Factor XIa Ki=0.53 nM, Plasma Kallikrein Ki=71 nM.

Example 252

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-4-(6-methoxypyridin-2-yl)-9-methyl-3,4,7,15-tetraazatricyclo[12.3.1.0²,⁶]octadeca-1(18),2,5,14,16-pentaen-8-one

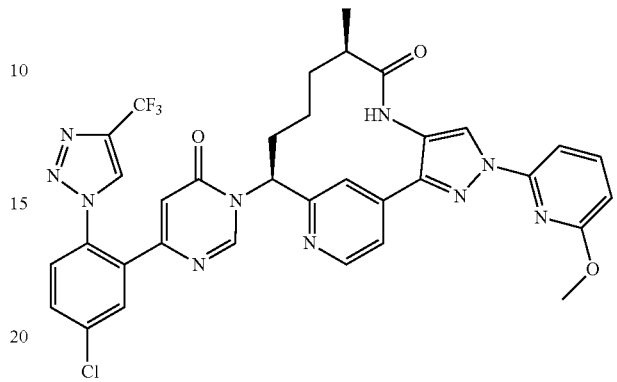

(9R,13S)-13-(4-{5-Chloro-2-[4-(trifluoromethyl)-1H-1,2,3-triazol-1-yl]phenyl}-6-oxo-1,6-dihydropyrimidin-1-yl)-4-(6-methoxypyridin-2-yl)-9-methyl-3,4,7,15-tetraazatricyclo[12.3.1.0²,⁶]octadeca-1(18),2,5,14,16-pentaen-8-one (9.5 mg, 17%) was prepared in a similar manner as the procedure described in Example 216, by using 2-iodo-6-methoxypyridine (31 mg, 0.131 mmol) and (9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0²,⁶]octadeca-1(18),2(6),4,14,16-pentaen-8-one (0.04 g, 0.066 mmol), as described in Example 196. MS(ESI) m/z: 717.4 (M+H)⁺. ¹H NMR (500 MHz, DMSO-d₆) δ 9.57 (s, 1H), 9.21 (s, 1H), 8.71 (d, J=15.6 Hz, 2H), 8.59 (d, J=5.2 Hz, 1H), 8.03-7.90 (m, 3H), 7.90-7.74 (m, 2H), 7.68-7.49 (m, 2H), 6.83 (d, J=7.9 Hz, 1H), 6.50 (s, 1H), 6.01 (br. s., 1H), 3.98 (s, 3H), 2.79 (br. s., 1H), 2.38-2.15 (m, 2H), 1.85 (br. s., 1H), 1.58 (br. s., 1H), 1.42 (br. s., 1H), 0.95 (d, J=6.7 Hz, 3H), 0.57 (br. s., 1H). Analytical HPLC (Method C): RT=2.07 min, purity=100%; Factor XIa Ki=23 nM, Plasma Kallikrein Ki=1,100 nM.

Example 253

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-4-(difluoromethyl)-9-methyl-3,4,7,15-tetraazatricyclo[12.3.1.0²,⁶]octadeca-1(18),2,5,14,16-pentaen-8-one

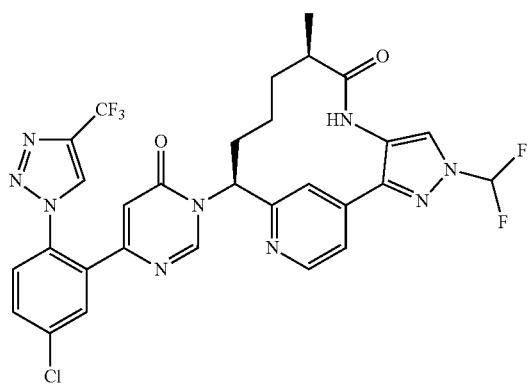 [SMILES: C[C@@H]1CCC[C@H](n2cnc(-c3cc(Cl)ccc3-n3cc(C(F)(F)F)nn3)cc2=O)c2cc(ccn2)-c2nn(C(F)F)cc2NC1=O]

(9R,13S)-13-(4-{5-Chloro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0²,⁶]octadeca-1(18),2(6),4,14,16-pentaen-8-one, prepared as described in Example 196, (0.02 g, 0.033 mmol), sodium 2-chloro-2,2-difluoroacetate (50 mg, 0.33 mmol), Cs$_2$CO$_3$ (0.021 g, 0.066 mmol), and DMF (2 mL) were added to a 5 mL microwave vial. The reaction was heated to 130° C. for 30 min in a microwave. The mixture was concentrated to dryness and the residue was purified by reverse phase chromatography to give (9R,13S)-13-(4-{5-chloro-2-[4-(trifluoromethyl)-1H-1,2,3-triazol-1-yl]phenyl}-6-oxo-1,6-dihydropyrimidin-1-yl)-4-(difluoromethyl)-9-methyl-3,4,7,15-tetraazatricyclo[12.3.1.0²,⁶]octadeca-1(18),2,5,14,16-pentaen-8-one (2 mg, 8%). MS(ESI) m/z: 660.1 (M+H)$^+$. $^1$H NMR (500 MHz, DMSO-d$_6$) δ 9.54 (s, 1H), 9.21 (s, 1H), 8.70 (s, 1H), 8.58 (d, J=4.9 Hz, 1H), 8.41 (s, 1H), 7.96 (br. s., 1H), 7.92-7.68 (m, 4H), 7.53 (d, J=4.9 Hz, 1H), 6.49 (s, 1H), 6.12-5.90 (m, 1H), 2.85-2.69 (m, 1H), 2.24 (d, J=11.9 Hz, 2H), 1.89-1.76 (m, 1H), 1.63-1.49 (m, 1H), 1.47-1.35 (m, 1H), 0.92 (d, J=6.7 Hz, 3H), 0.61-0.38 (m, 1H). Analytical HPLC (Method C): RT=1.82 min, purity=100%; Factor XIa Ki=8 nM, Plasma Kallikrein Ki=360 nM.

Example 254

Preparation of (9R,13S)-13-{4-[5-chloro-2-(1-cyclopropyl-1H-pyrazol-4-yl)phenyl]-6-oxo-1,6-dihydropyrimidin-1-yl}-3,9-dimethyl-3,4,7,15-tetraazatricyclo[12.3.1.0²,⁶]

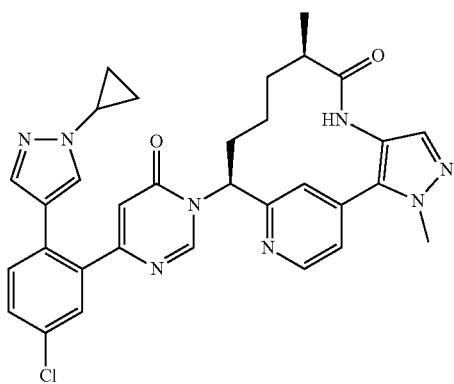 [SMILES: C[C@@H]1CCC[C@H](n2cnc(-c3cc(Cl)ccc3-c3cnn(C4CC4)c3)cc2=O)c2cc(ccn2)-c2c(cnn2C)NC1=O]

(9R,13S)-13-{4-[5-Chloro-2-(1-cyclopropyl-1H-pyrazol-4-yl)phenyl]-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one trifluoroacetate (10 mg, 43% yield) was prepared in a similar manner as the procedure described in Example 49, by replacing 1-methyl-4-(4,4,5,5-tetramethyl-1,3,2-dioxaborolan-2-yl)-1H-pyrazole with 1-cyclopropyl-4-(4,4,5,5-tetramethyl-1,3,2-dioxaborolan-2-yl)-1H-pyrazole (11.42 mg, 0.049 mmol). MS(ESI) m/z: 595.4 (M+H)$^+$. $^1$H NMR (400 MHz, CD$_3$OD) δ 8.99 (s, 1H), 8.76 (d, J=5.3 Hz, 1H), 7.73 (s, 1H), 7.64 (s, 1H), 7.57-7.52 (m, 2H), 7.50 (s, 1H), 7.47-7.46 (m, J=1.1 Hz, 2H), 7.33 (d, J=0.7 Hz, 1H), 6.39 (s, 1H), 6.03 (dd, J=12.5, 4.2 Hz, 1H), 4.05 (s, 3H), 3.63-3.56 (m, 1H), 2.76-2.67 (m, 1H), 2.35 (tt, J=12.7, 4.3 Hz, 1H), 2.14-2.01 (m, 2H), 1.67-1.44 (m, 2H), 1.04-0.97 (m, 7H), 0.79-0.64 (m, 1H). Analytical HPLC (Method A): RT=7.82 min, 99.9% purity; Factor XIa Ki=8 nM, Plasma Kallikrein Ki=1,700 nM.

Example 255

Preparation of (9R,13S)-13-(4-{5-chloro-2-[1-(2,2,2-trifluoroethyl)-1H-pyrazol-4-yl]phenyl}-6-oxo-1,6-dihydropyrimidin-1-yl)-3,9-dimethyl-3,4,7,15-tetraazatricyclo[12.3.1.0²,⁶]octadeca-1(18),2(6),4,14,16-pentaen-8-one

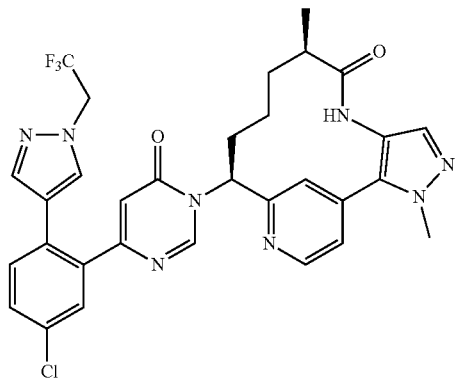 [SMILES: C[C@@H]1CCC[C@H](n2cnc(-c3cc(Cl)ccc3-c3cnn(CC(F)(F)F)c3)cc2=O)c2cc(ccn2)-c2c(cnn2C)NC1=O]

255A. Preparation of 4-(4,4,5,5-tetramethyl-1,3,2-dioxaborolan-2-yl)-1-(2,2,2-trifluoroethyl)-1H-pyrazole To a stirred solution of 4-(4,4,5,5-tetramethyl-1,3,2-dioxaborolan-2-yl)-1H-pyrazole (100 mg, 0.515 mmol) in DMF (1 ml) were added Cs$_2$CO$_3$ (252 mg, 0.773 mmol) and 2,2,2-trifluoroethyl trifluoromethanesulfonate (0.144 ml, 1.031 mmol) at rt. After stirring at 100° C. for 2 h, the reaction mixture was evaporated to dryness, partitioned between EtOAc and water, and the layers were separated. The organic layer was dried over Na$_2$SO$_4$, filtered, and concentrated to afford 4-(4,4,5,5-tetramethyl-1,3,2-dioxaborolan-2-yl)-1-(2,2,2-trifluoroethyl)-1H-pyrazole (0.111 g, 78% yield). MS(ESI) m/z: 277.4 (M+H)$^+$.

255B. Preparation of (9R,13S)-13-(4-{5-chloro-2-[1-(2,2,2-trifluoroethyl)-1H-pyrazol-4-yl]phenyl}-6-oxo-1,6-dihydropyrimidin-1-yl)-3,9-dimethyl-3,4,7,15-tetraazatricyclo[12.3.1.0²,⁶]octadeca-1(18),2(6),4,14,16-pentaen-8-one trifluoroacetate (9R,13S)-13-(4-{5-Chloro-2-[1-(2,2,2-trifluoroethyl)-1H-pyrazol-4-yl]phenyl}-6-oxo-1,6-dihydropyrimidin-1-yl)-3,9-dimethyl-3,4,7,15-tetraazatricyclo[12.3.1.0²,⁶]octadeca-1(18),2(6),4,14,16-pentaen-8-one trifluoroacetate (10.6 mg, 43% yield) was prepared in a similar manner as the procedure described in Example 49, by replacing 1-methyl-4-(4,4,5,5-tetramethyl-1,3,2-dioxaborolan-2-yl)-1H-pyrazole with 4-(4,4,5,5-tetramethyl-1,3,2-dioxaborolan-2-yl)-1-(2,2,2-trifluoroethyl)-1H-pyrazole (13.47 mg, 0.049 mmol), prepared as described in Example 255A. MS(ESI) m/z: 637.5 (M+H)$^+$. $^1$H NMR (400 MHz, CD$_3$OD) δ 8.97 (s, 1H), 8.74 (d, J=5.3 Hz, 1H), 7.74-7.67 (m, 2H), 7.56-7.49 (m, 6H), 6.40 (s, 1H), 6.03 (dd, J=12.7, 4.3 Hz, 1H), 4.92-4.82 (m, 2H), 4.05 (s, 3H), 2.76-2.67 (m, 1H), 2.39-2.28 (m, 1H), 2.14-1.99 (m, 2H), 1.67-1.43 (m, 2H), 1.02 (d, J=7.0 Hz, 3H), 0.79-0.64 (m, 1H). Analytical HPLC (Method A): RT=8.26 min, 99.5% purity; Factor XIa Ki=52 nM, Plasma Kallikrein Ki=5,500 nM.

Example 256

Preparation of 3-[(9R,13S)-13-{4-[5-chloro-2-(4-chloro-1H-1,2,3-triazol-1-yl)phenyl]-6-oxo-1,6-dihydropyrimidin-1-yl}-9-methyl-8-oxo-3,4,7,15-tetraazatricyclo[12.3.1.0$^{2,6}$]octadeca-1(18),2,5,14,16-pentaen-4-yl]benzonitrile

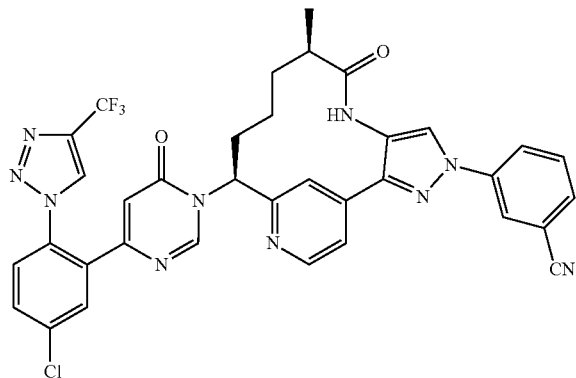 [SMILES: C[C@@H]1CCC[C@H](n2cnc(-c3cc(Cl)ccc3-n3cc(C(F)(F)F)nn3)cc2=O)c2cc(ccn2)-c2nn(-c3cccc(C#N)c3)cc2NC1=O]

3-[(9R,13S)-13-{4-[5-Chloro-2-(4-chloro-1H-1,2,3-triazol-1-yl)phenyl]-6-oxo-1,6-dihydropyrimidin-1-yl}-9-methyl-8-oxo-3,4,7,15-tetraazatricyclo[12.3.1.0$^{2,6}$]octadeca-1(18),2,5,14,16-pentaen-4-yl]benzonitrile trifluoroacetate was prepared in a similar manner as the procedure described in Example 216, by using 3-iodobenzonitrile (3.97 mg, 0.017 mmol) to give 3-[(9R,13S)-13-{4-[5-chloro-2-(4-chloro-1H-1,2,3-triazol-1-yl)phenyl]-6-oxo-1,6-dihydropyrimidin-1-yl}-9-methyl-8-oxo-3,4,7,15-tetraazatricyclo[12.3.1.0$^{2,6}$]octadeca-1(18),2,5,14,16-pentaen-4-yl]benzonitrile trifluoroacetate (4.5 mg, 33% yield). $^1$H NMR (500 MHz, DMSO-d$_6$) δ 9.60 (s, 1H), 8.76-8.65 (m, 2H), 8.60 (d, J=5.2 Hz, 1H), 8.36 (s, 1H), 8.25 (d, J=8.2 Hz, 1H), 7.93-7.86 (m, 2H), 7.84-7.69 (m, 4H), 7.63 (d, J=4.3 Hz, 1H), 6.34 (s, 1H), 5.98 (br. s., 1H), 2.78 (br. s., 1H), 2.54 (s, 1H), 2.24 (d, J=7.3 Hz, 2H), 1.85 (br. s., 1H), 1.56 (br. s., 1H), 1.41 (br. s., 1H), 0.93 (d, J=6.7 Hz, 3H), 0.55 (br. s., 1H). MS(ESI) m/z: 677.1 [M+H]$^+$. Analytical HPLC (Method B): RT=1.91 min, purity=100.0%; Factor XIa Ki=2.0 nM, Plasma Kallikrein Ki=30 nM.

Example 257

Preparation of (9R,13S)-13-{4-[5-chloro-2-(5-methyl-1H-imidazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one Trifluoroacetate

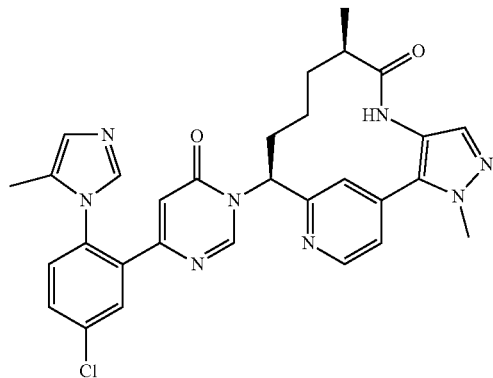 [SMILES: Cc1cncn1-c1ccc(Cl)cc1-c1cc(=O)n([C@H]2CCC[C@@H](C)C(=O)Nc3cnn(C)c3-c3ccnc2c3)cn1]

(9R,13S)-13-{4-[5-Chloro-2-(5-methyl-1H-imidazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (2.3 mg, 9% yield) was prepared in a similar manner as the procedure described in Example 231, by replacing 1H-imidazole with 4-methyl-1H-imidazole (10.68 mg, 0.130 mmol). MS(ESI) m/z: 569.20 (M+H)$^+$. $^1$H NMR (500 MHz, DMSO-d$_6$) δ 9.22 (s, 1H), 8.89 (br. s., 1H), 8.78 (s, 1H), 8.67 (d, J=4.9 Hz, 1H), 8.01 (d, J=2.4 Hz, 1H), 7.86 (dd, J=8.5, 2.1 Hz, 1H), 7.75 (d, J=8.5 Hz, 1H), 7.66 (s, 1H), 7.59 (d, J=4.9 Hz, 1H), 7.50-7.40 (m, 2H), 6.41 (br. s., 1H), 5.86 (d, J=10.4 Hz, 1H), 4.01 (s, 3H), 2.68-2.60 (m, 1H), 2.32-2.22 (m, 1H), 2.16-2.05 (m, 1H), 2.01 (s, 3H), 1.88-1.76 (m, 1H), 1.52-1.27 (m, 2H), 0.88 (d, J=6.7 Hz, 3H), 0.50-0.37 (m, 1H). Analytical HPLC (Method B): RT=1.49 min, 100% purity; Factor XIa Ki=7,500 nM.

Example 258

Preparation of (9R,13S)-13-{4-[5-chloro-2-(4-chloro-1H-1,2,3-triazol-1-yl)phenyl]-6-oxo-1,6-dihydropyrimidin-1-yl}-9-methyl-4-(1H-pyrazol-3-yl)-3,4,7,15-tetraazatricyclo[12.3.1.0$^{2,6}$]octadeca-1(18),2,5,14,16-pentaen-8-one

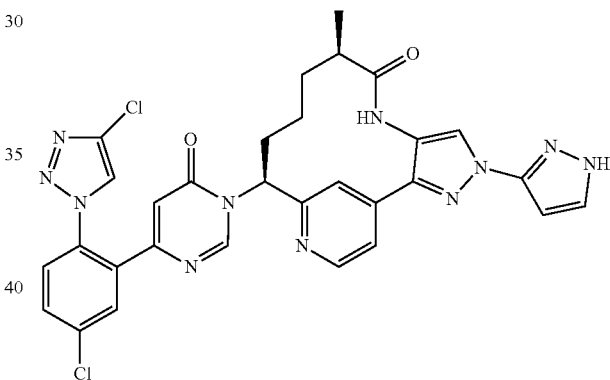

(9R,13S)-13-{4-[5-Chloro-2-(4-chloro-1H-1,2,3-triazol-1-yl)phenyl]-6-oxo-1,6-dihydropyrimidin-1-yl}-9-methyl-4-(1H-pyrazol-3-yl)-3,4,7,15-tetraazatricyclo[12.3.1.0$^{2,6}$]octadeca-1(18),2,5,14,16-pentaen-8-one trifluoroacetate was prepared in a similar manner as the procedure described in Example 216, by using 3-iodo-1-trityl-1H-pyrazole (18.9 mg, 0.043 mmol) followed by deprotection using 50% TFA in DCM and Et$_3$SiH as a scavenger to yield (9R,13S)-13-{4-[5-chloro-2-(4-chloro-1H-1,2,3-triazol-1-yl)phenyl]-6-oxo-1,6-dihydropyrimidin-1-yl}-9-methyl-4-(1H-pyrazol-3-yl)-3,4,7,15-tetraazatricyclo[12.3.1.0$^{2,6}$]octadeca-1(18),2,5,14,16-pentaen-8-one trifluoroacetate (4.8 mg, 3.2 µmol, 6% yield). $^1$H NMR (500 MHz, DMSO-d$_6$) δ 9.45 (s, 1H), 8.76-8.69 (m, 1H), 8.57 (d, J=4.9 Hz, 1H), 8.31 (s, 1H), 8.10 (br. s., 1H), 7.93 (d, J=2.1 Hz, 1H), 7.88 (s, 1H), 7.82 (dd, J=8.5, 2.1 Hz, 1H), 7.77-7.70 (m, 1H), 7.52 (d, J=4.9 Hz, 1H), 7.30-7.02 (m, 3H), 6.37 (s, 1H), 5.97 (br. s., 1H), 2.76 (br. s., 1H), 2.27 (d, J=10.7 Hz, 2H), 1.84 (br. s., 1H), 1.55 (br. s., 1H), 1.41 (br. s., 1H), 0.93 (d, J=6.7 Hz, 3H), 0.56 (br. s., 1H). MS(ESI) m/z: 642.3 [M+H]$^+$. Analytical HPLC (Method B): RT=1.51 min, purity=100.0%; Factor XIa Ki=0.29 nM, Plasma Kallikrein Ki=18 nM.

Example 259

Preparation of (9R,13S)-13-{4-[5-chloro-2-(4-chloro-1H-1,2,3-triazol-1-yl)phenyl]-6-oxo-1,6-dihydropyrimidin-1-yl}-9-methyl-4-(pyrimidin-5-yl)-3,4,7,15-tetraazatricyclo[12.3.1.0²,⁶]octadeca-1(18),2,5,14,16-pentaen-8-one

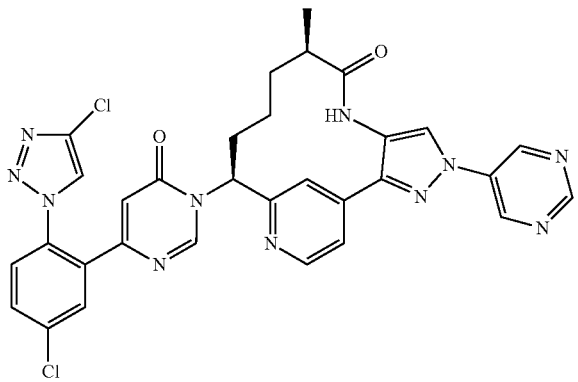 [SMILES: C[C@@H]1CCC[C@H](n2cnc(-c3cc(Cl)ccc3-n3cc(Cl)nn3)cc2=O)c2cc(ccn2)-c2nn(-c3cncnc3)cc2NC1=O]

(9R,13S)-13-{4-[5-Chloro-2-(4-chloro-1H-1,2,3-triazol-1-yl)phenyl]-6-oxo-1,6-dihydropyrimidin-1-yl}-9-methyl-4-(pyrimidin-5-yl)-3,4,7,15-tetraazatricyclo[12.3.1.0²,⁶]octadeca-1(18),2,5,14,16-pentaen-8-one trifluoroacetate was prepared in a similar manner as the procedure described in Example 216, by using 5-iodopyrimidine (21.4 mg, 0.104 mmol) to give (9R,13S)-13-{4-[5-chloro-2-(4-chloro-1H-1,2,3-triazol-1-yl)phenyl]-6-oxo-1,6-dihydropyrimidin-1-yl}-9-methyl-4-(pyrimidin-5-yl)-3,4,7,15-tetraazatricyclo[12.3.1.0²,⁶]octadeca-1(18),2,5,14,16-pentaen-8-one trifluoroacetate (15 mg, 36%). $^1$H NMR (400 MHz, CD$_3$OD) δ 9.58 (s, 1H), 9.40 (s, 2H), 9.20 (s, 1H), 8.85-8.72 (m, 3H), 8.64 (d, J=5.3 Hz, 1H), 7.98-7.91 (m, 2H), 7.87-7.80 (m, 1H), 7.79-7.73 (m, 1H), 7.65 (dd, J=5.1, 1.3 Hz, 1H), 6.39 (s, 1H), 6.02 (d, J=9.5 Hz, 1H), 2.82 (br. s., 1H), 2.37-2.23 (m, 2H), 1.94-1.80 (m, 1H), 1.58 (br. s., 1H), 1.43 (br. s., 1H), 0.99-0.91 (d, J=7.0 Hz, 3H), 0.56 (br. s., 1H). MS(ESI) m/z: 654.6 [M+H]⁺. Analytical HPLC (Method A): RT=7.96 min, purity=>95.0%; Factor XIa Ki=0.63 nM, Plasma Kallikrein Ki=17 nM.

Example 260

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-4-(pyrazin-2-yl)-3,4,7,15-tetraazatricyclo[12.3.1.0²,⁶]octadeca-1(18),2,5,14,16-pentaen-8-one

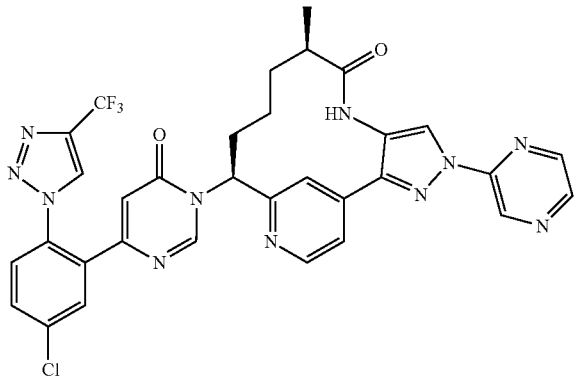 [SMILES: C[C@@H]1CCC[C@H](n2cnc(-c3cc(Cl)ccc3-n3cc(C(F)(F)F)nn3)cc2=O)c2cc(ccn2)-c2nn(-c3cnccn3)cc2NC1=O]

(9R,13S)-13-(4-{5-Chloro-2-[4-(trifluoromethyl)-1H-1,2,3-triazol-1-yl]phenyl}-6-oxo-1,6-dihydropyrimidin-1-yl)-9-methyl-4-(pyrazin-2-yl)-3,4,7,15-tetraazatricyclo[12.3.1.0²,⁶]octadeca-1(18),2,5,14,16-pentaen-8-one trifluoroacetate (9.0 mg, 34%) was prepared in a similar manner as the procedure described in Example 216, by using 2-iodopyrazine (6.75 mg, 0.033 mmol) and (9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0²,⁶]octadeca-1(18),2(6),4,14,16-pentaen-8-one (20.0 mg, 0.033 mmol), as described in Example 196. $^1$H NMR (500 MHz, DMSO-d$_6$) δ 9.60 (s, 1H), 9.33 (s, 1H), 9.22 (s, 1H), 8.76-8.65 (m, 2H), 8.63-8.56 (m, 2H), 7.95 (d, J=16.5 Hz, 2H), 7.88-7.78 (m, 2H), 7.66 (d, J=4.9 Hz, 1H), 7.27-6.98 (m, 1H), 6.49 (s, 1H), 6.03 (d, J=9.5 Hz, 1H), 2.79 (br. s., 1H), 2.37-2.18 (m, 2H), 1.83 (br. s., 1H), 1.56 (br. s., 1H), 1.42 (br. s., 1H), 0.93 (d, J=6.7 Hz, 3H), 0.52 (br. s., 1H). MS(ESI) m/z: 688.0 [M+H]⁺. Analytical HPLC (Method B): RT=1.923 min, purity=>100.0%; Factor XIa Ki=2.6 nM, Plasma Kallikrein Ki=54 nM.

Example 261

Preparation of (9R,13S)-13-[4-(2-amino-5-chlorophenyl)-6-oxo-1,6-dihydropyrimidin-1-yl]-3-(difluoromethyl)-9-methyl-3,4,7,15-tetraazatricyclo[12.3.1.0²,⁶]octadeca-1(18),2(6),4,14,16-pentaen-8-one

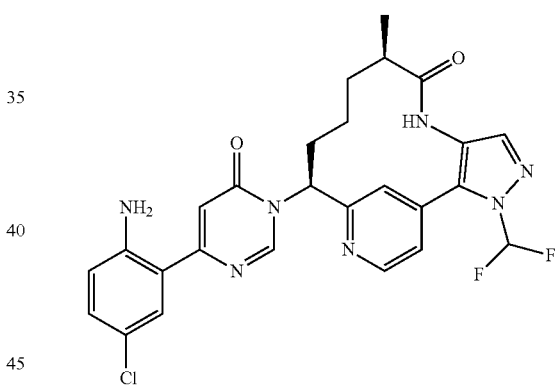

N-(4-Chloro-2-{1-[(9R,13S)-3-(difluoromethyl)-9-methyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)-2,2,2-trifluoroacetamide, prepared as described in Example 244, (0.2 g, 0.31 mmol) was dissolved in 1.25 M HCl in MeOH (5 ml, 6.25 mmol). The reaction was heated to 75° C. for 1 h, then cooled to rt and concentrated to dryness. The product was purified by recrystallizing from CH$_3$CN—H$_2$O to give (9R,13S)-13-[4-(2-amino-5-chlorophenyl)-6-oxo-1,6-dihydropyrimidin-1-yl]-3-(difluoromethyl)-9-methyl-3,4,7,15-tetraazatricyclo[12.3.1.0²,⁶]octadeca-1(18),2(6),4,14,16-pentaen-8-one (160 mg, 89%) as a yellow solid. MS(ESI) m/z: 540.5 (M+H)⁺. $^1$H NMR (500 MHz, DMSO-d$_6$) δ 9.40 (s, 1H), 9.00 (s, 1H), 8.75 (d, J=5.09 Hz, 1H), 7.96 (t, J=57.75 Hz, 1H), 7.90 (s, 1H), 7.73 (s, 1H), 7.46 (d, J=2.49 Hz, 1H), 7.43 (dd, J=4.92, 0.85 Hz, 1H), 7.14 (dd, J=8.80, 2.51 Hz, 1H), 6.76 (d, J=8.73 Hz, 1H), 6.70 (s, 1H), 6.43 (s, 2H), 5.95 (dd, 12.17, 3.13 Hz, 1H), 2.67 (m, 1H), 2.34 (tm, J=12.83 Hz, 1H), 2.08 (tm, J=13.09 Hz, 1H), 1.93 (m, 1H), 1.48 (m, 1H), 1.37 (m, 1H), 0.89 (d, J=6.87 Hz, 3H), 0.39 (br-s, 1H). Analytical HPLC (Method A): RT=7.75 min, purity=94%; Factor XIa Ki=170 nM, Plasma Kallikrein Ki=5,700 nM.

Example 262

Preparation of (9R,13S)-13-(4-{3-chloro-6-[1-(difluoromethyl)-1H-pyrazol-4-yl]-2-fluorophenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one

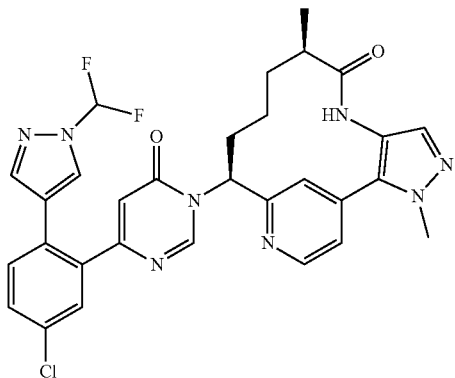

262A. Preparation of 6-(3-chloro-6-(1-(difluoromethyl)-1H-pyrazol-4-yl)-2-fluorophenyl)pyrimidin-4-ol 6-(3-Chloro-6-(1-(difluoromethyl)-1H-pyrazol-4-yl)-2-fluorophenyl)pyrimidin-4-ol (0.032 g, 85% yield) was prepared in a similar manner as the procedures described in Example 140A and 140B, by replacing 4-(2-bromo-5-chlorophenyl)-6-methoxypyrimidine (0.08 g, 0.267 mmol) with 4-(6-bromo-3-chloro-2-fluorophenyl)-6-methoxypyrimidine (0.1 g, 0.315 mmol). MS(ESI) m/z: 341.4 (M+H)$^+$. $^1$H NMR (500 MHz, CD$_3$OD) δ 8.35 (s, 1H), 8.06 (s, 1H), 7.67-7.60 (m, 2H), 7.45 (t, J=59.4 Hz, 1H), 7.40 (dd, J=8.3, 1.4 Hz, 1H), 6.52 (s, 1H).

262B. Preparation of (9R,13S)-13-(4-{3-chloro-6-[1-(difluoromethyl)-1H-pyrazol-4-yl]-2-fluorophenyl})-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate (9R,13S)-13-(4-{3-Chloro-6-[1-(difluoromethyl)-1H-pyrazol-4-yl]-2-fluorophenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate (11.7 mg, 36% yield) was prepared in a similar manner as the procedure described in Example 56, by replacing 6-{5-chloro-2-[4-(trifluoromethyl)-1H-1,2,3-triazol-1-yl]phenyl}pyrimidin-4-ol (22.8 mg, 0.067 mmol) with 6-(3-chloro-6-(1-(difluoromethyl)-1H-pyrazol-4-yl)-2-fluorophenyl)pyrimidin-4-ol (14.79 mg, 0.043 mmol). MS(ESI) m/z: 623.6 (M+H)$^+$. $^1$H NMR (500 MHz, CD$_3$OD) δ 8.99 (s, 1H), 8.75 (d, J=5.2 Hz, 1H), 8.00 (s, 1H), 7.73 (s, 1H), 7.64-7.58 (m, 2H), 7.55-7.28 (m, 4H), 6.51 (s, 1H), 6.04 (dd, J=12.7, 3.9 Hz, 1H), 4.05 (s, 3H), 2.75-2.67 (m, 1H), 2.36 (tt, J=12.7, 4.3 Hz, 1H), 2.13-2.02 (m, 2H), 1.66-1.45 (m, 2H), 1.02 (d, J=7.2 Hz, 3H), 0.83-0.66 (m, 1H). $^{19}$F NMR (471 MHz, CD$_3$OD) δ −77.75 (s), −96.25 (s), −117.96 (s). Analytical HPLC (Method A): RT=8.18 min, 98.0% purity; Factor XIa Ki=4.5 nM, Plasma Kallikrein Ki=340 nM.

Example 263

Preparation of (9R,13S)-13-[4-(5-chloro-1H-indol-7-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one

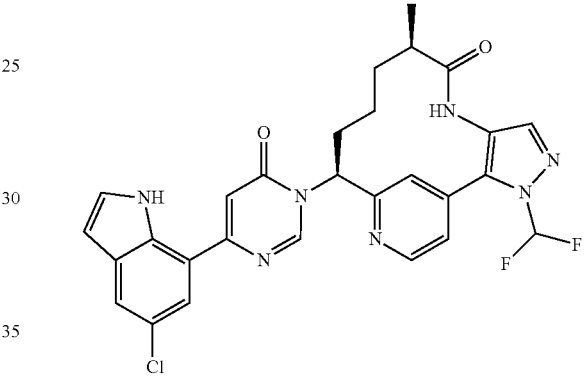

263A. Preparation of 6-(5-chloro-1H-indol-7-yl)pyrimidin-4-ol 6-(5-Chloro-1H-indol-7-yl)pyrimidin-4-ol was prepared in a similar manner as described for Example 207C by replacing 4-bromo-6-chloro-1H-benzo[d]imidazole with 7-bromo-5-chloro-1H-indole. MS(ESI) m/z: 246 (M+H)$^+$.

263B. (9R,13S)-13-[4-(5-Chloro-1H-indol-7-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one Trifluoroacetate (9R,13S)-13-[4-(5-Chloro-1H-indol-7-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one trifluoroacetate was prepared (0.61 mg, 1.3%) in a similar manner as described in Example 56 by using 6-(5-chloro-1H-indol-7-yl)pyrimidin-4-ol and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one, prepared as described in Intermediate 30. MS(ESI) m/z: 564 (M+H)$^+$ and 566 (M+2H)$^+$. Analytical HPLC (Method A): RT=9.71 min, purity=>90%; Factor XIa Ki=4,600 nM.

Example 264

Preparation of (9R,13S)-13-[4-(6-chloro-1H-indazol-4-yl)-6-oxo-1,6-dihydropyrimidin-1-yl]-3-(difluoromethyl)-9-methyl-3,4,7,15-tetraazatricyclo[12.3.1.0²,⁶]octadeca-1(18),2(6),4,14,16-pentaen-8-one

Example 265

Preparation of (14S)-14-(4-{5-chloro-2-[4-(trifluoromethyl)-1H-1,2,3-triazol-1-yl]phenyl}-6-oxo-1,6-dihydropyrimidin-1-yl)-10-methyl-5,8,16-triazatricyclo[13.3.1.0²,⁷]nonadeca-1(19),2(7),3,5,15,17-hexaen-9-one Trifluoroacetate

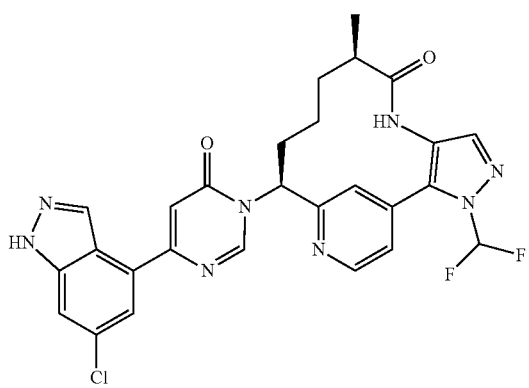 [SMILES: C[C@@H]1CCC[C@H](n2cnc(-c3cc(Cl)cc4[nH]ncc34)cc2=O)c2cc(ccn2)-c2c(cnn2C(F)F)NC1=O]

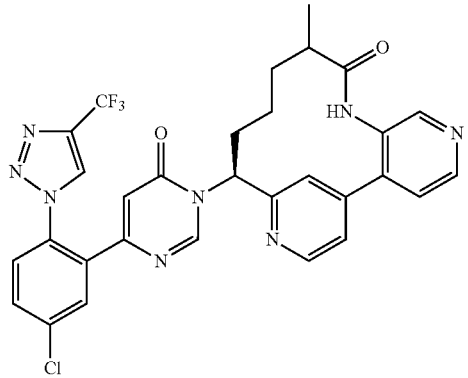 [SMILES: CC1CCC[C@H](n2cnc(-c3cc(Cl)ccc3-n3cc(C(F)(F)F)nn3)cc2=O)c2cc(ccn2)-c2ccncc2NC1=O]

264A. Preparation of 6-(6-chloro-1H-indazol-4-yl)pyrimidin-4-ol 6-(6-Chloro-1H-indazol-4-yl)pyrimidin-4-ol was prepared in a similar manner as described for Example 207C by replacing 4-bromo-6-chloro-1H-benzo[d]imidazole with 4-bromo-6-chloro-1H-indazole. MS(ESI) m/z: 247 (M+H)⁺.

264B. Preparation of (9R,13S)-13-[4-(6-chloro-1H-indazol-4-yl)-6-oxo-1,6-dihydropyrimidin-1-yl]-3-(difluoromethyl)-9-methyl-3,4,7,15-tetraazatricyclo[12.3.1.0²,⁶]octadeca-1(18),2(6),4,14,16-pentaen-8-one Trifluoroacetate (9R,13S)-13-[4-(6-Chloro-1H-indazol-4-yl)-6-oxo-1,6-dihydropyrimidin-1-yl]-3-(difluoromethyl)-9-methyl-3,4,7,15-tetraazatricyclo[12.3.1.0²]octadeca-1(18),2(6),4,14,16-pentaen-8-one trifluoroacetate (4 mg, 9.4%) was prepared in a similar manner as Example 56 by using 6-(6-chloro-1H-indazol-4-yl)pyrimidin-4-ol and (9R,13S)-13-amino-3-(difluoromethyl)-9-methyl-3,4,7,15-tetraazatricyclo[12.3.1.0²,⁶]octadeca-1(18),2(6),4,14,16-pentaen-8-one, prepared as described in Intermediate 30. MS(ESI) m/z: 565 (M+H)⁺. ¹H NMR (400 MHz, DMSO-d₆) δ 9.35 (s, 1H), 9.05 (s, 1H), 8.69 (d, J=5.3 Hz, 1H), 8.53 (s, 1H), 7.90-7.84 (m, 2H), 7.75-7.68 (m, 4H), 7.40-7.35 (m, 2H), 7.02 (s, 1H), 2.62-2.58 (m, 1H), 2.36-2.30 (m, 1H), 2.06-2.01 (m, 1H), 1.93-1.87 (m, 1H), 1.47-1.42 (m, 1H), 1.34-1.29 (m, 1H), 0.83 (d, J=6.8 Hz, 3H). Analytical HPLC (Method A): RT=7.32 min, purity=95%; Factor XIa Ki=260 nM.

265A. Preparation of (S)-(2-(1-((tert-butoxycarbonyl)amino)but-3-en-1-yl)pyridin-4-yl)boronic Acid, Trifluoroacetate To a solution of 5,5,5',5'-tetramethyl-2,2'-bi(1,3,2-dioxaborinane) (1.198 g, 5.30 mmol) and (S)-tert-butyl (1-(4-chloropyridin-2-yl)but-3-en-1-yl)carbamate (1.0 g, 3.54 mmol), prepared as described in Intermediate 23, in DMSO (10 mL) was added KOAc (1.041 g, 10.61 mmol) under Ar. PdCl₂(dppf)-CH₂Cl₂ adduct (0.289 g, 0.354 mmol) and the mixture was purged with Ar for an additional 10 min then stirred at 85° C. After 12 h, the reaction mixture was diluted with EtOAc and washed with water. The aqueous layer was extracted with EtOAc. The combined organic layers were washed with brine, dried over Na₂SO₄, filtered, and concentrated. The dark oil purified by reverse phase chromatography to give, after concentration and lyophilization, (S)-(2-(1-((tert-butoxycarbonyl)amino)but-3-en-1-yl)pyridin-4-yl)boronic acid trifluoroacetate (1.05 g, 2.59 mmol, 73.1% yield) as a white solid. MS(ESI) m/z: 293.2 (M+H)⁺.

265B. Preparation of (S)-tert-butyl (1-(3'-amino-[4,4'-bipyridin]-2-yl)but-3-en-1-yl) Carbamate To a solution of (S)-(2-(1-((tert-butoxycarbonyl)amino)but-3-en-1-yl)pyridin-4-yl)boronic acid, trifluoroacetate (1.0 g, 2.462 mmol) and 4-bromopyridin-3-amine (0.511 g, 2.95 mmol) in dioxane (17 mL) was added 2 M aq Na₂CO₃ (4.92 mL, 9.85 mmol). The mixture was purged with a stream of Ar for 5 min. Pd(PPh₃)₄ (0.285 g, 0.246 mmol) was added and the reaction was irradiated at 120° C. for 1 h. The reaction was quenched with water (40 mL) and extracted with EtOAc (2×). The combined organic layers were washed with brine, dried over MgSO₄, filtered, and concentrated. The crude material was purified by normal phase column chromatography eluting with a gradient of DCM/MeOH to give (S)-tert-butyl (1-(3'-amino-[4,4'-bipyridin]-2-yl)but-3-en-1-yl)carbamate (0.736 g, 88% yield) as a brown oil. MS(ESI) m/z: 341.2 (M+H)$^+$. $^1$H NMR (500 MHz, CDCl$_3$) δ 8.68 (d, J=4.7 Hz, 1H), 8.19 (s, 1H), 8.10 (d, J=5.0 Hz, 1H), 7.35 (s, 1H), 7.29 (dd, J=5.1, 1.5 Hz, 1H), 7.02 (d, J=5.0 Hz, 1H), 5.79-5.68 (m, 1H), 5.62-5.52 (m, 1H), 5.11-5.04 (m, 2H), 4.90-4.80 (m, 1H), 3.83 (br. s., 2H), 2.64 (t, J=6.7 Hz, 2H), 1.45 (s, 9H).

265C. Preparation of Tert-Butyl ((S)-1-(3'-((R)-2-methylbut-3-enamido)-[4,4'-bipyridin]-2-yl)but-3-en-1-yl)carbamate To a solution of (S)-tert-butyl (1-(3'-amino-[4,4'-bipyridin]-2-yl)but-3-en-1-yl) carbamate (736 mg, 2.16 mmol) in EtOAc (21.6 mL) was added (R)-2-methylbut-3-enoic acid (303 mg, 3.03 mmol). After cooling to 0° C., pyridine (0.525 mL, 6.49 mmol) was added followed by T3P®/50% EtOAc (2.57 mL, 4.32 mmol) dropwise. The reaction was slowly warmed to rt overnight. The reaction mixture was diluted with water and extracted with EtOAc (2×). The combined organic layers were washed with brine, dried over MgSO$_4$, filtered, and concentrated. The crude material was purified by normal phase column chromatography eluting with a gradient of DCM/MeOH to give of tert-butyl ((S)-1-(3'-((R)-2-methylbut-3-enamido)-[4,4'-bipyridin]-2-yl)but-3-en-1-yl) carbamate (815 mg, 89%). MS(ESI) m/z: 423.2 (M+H)$^+$. $^1$H NMR (500 MHz, CDCl$_3$) δ 9.45 (s, 1H), 8.70 (d, J=5.0 Hz, 1H), 8.49 (d, J=5.0 Hz, 1H), 7.24 (br. s., 1H), 7.21 (s, 1H), 7.18-7.14 (1m, 2H), 5.80 (ddd, J=17.1, 10.1, 8.3 Hz, 1H), 5.74-5.66 (m, 1H), 5.54-5.48 (m, 1H), 5.15-5.05 (m, 4H), 4.92-4.85 (m, 1H), 3.08 (quin, J=7.2 Hz, 1H), 2.69-2.61 (m, 2H), 1.45 (s, 9H), 1.31-1.28 (m, 3H).

265D. Preparation of Tert-Butyl N-[(11E,14S)-10-methyl-9-oxo-5,8,16-triazatricyclo[13.3.1.0$^{2,7}$]nonadeca-1(19),2(7),3,5,11,15,17-heptaen-14-yl]carbamate To a solution of tert-butyl((S)-1-(3'-((R)-2-methylbut-3-enamido)-[4,4'-bipyridin]-2-yl)but-3-en-1-yl)carbamate (400 mg, 0.947 mmol) in freshly opened and degassed DCM (500 mL) was added p-TsOH—H$_2$O (378 mg, 1.988 mmol). A stream of N$_2$ was bubbled for 10 min before heating the solution at 40° C. under a nitrogen atmosphere. After 1 h, Second Generation Grubbs Catalyst (201 mg, 0.237 mmol) dissolved in degassed DCM (20 ml) was added to the reaction mixture dropwise and heating continued at 40° C. overnight. The reaction mixture was quenched with 1.5 M K$_2$HPO$_3$ (30 mL) followed by separation of the organic phase and concentration. The crude residue was purified by reverse phase chromatography and concentration of product fractions. The residue was dissolved in MeOH, neutralized by passing through NaHCO$_3$ resin cartridges (2×) and concentrating the filtrate to afford tert-butyl N-[(11E,14S)-10-methyl-9-oxo-5,8,16-triazatricyclo[13.3.1.0$^{2,7}$]nonadeca-1(19),2(7),3,5,11,15,17-heptaen-14-yl]carbamate (24.6 mg, 6.59% yield) as brown film. MS(ESI) m/z: 395 (M+H)$^+$.

265E. Preparation of Tert-Butyl N-[(14S)-10-methyl-9-oxo-5,8,16-triazatricyclo[13.3.1.0$^{2,7}$]nonadeca-1(19),2(7),3,5,15,17-hexaen-14-yl]carbamate PtO$_2$ (0.018 g, 0.079 mmol) was added to a stirring solution of tert-butyl N-[(11E,14S)-10-methyl-9-oxo-5,8,16-triazatricyclo[13.3.1.0$^{2,7}$]nonadeca-1(19),2(7),3,5,11,15,17-heptaen-14-yl]carbamate (0.031 g, 0.079 mmol) in EtOH (3 mL) and subjected to a H$_2$ atmosphere (55 psi) for 3 h. The catalyst was filtered off through a plug of CELITE® and filtrate concentrated to give tert-butyl N-[(14S)-10-methyl-9-oxo-5,8,16-triazatricyclo[13.3.1.0$^{2,7}$]nonadeca-1(19),2(7),3,5,15,17-hexaen-14-yl]carbamate as a brown film (yield assumed quantitative). MS(ESI) m/z: 397 (M+H)$^+$.

265F. Preparation of (14S)-14-amino-10-methyl-5,8,16-triazatricyclo[13.3.1.0$^{2,7}$]nonadeca-1(19),2(7),3,5,15,17-hexaen-9-one TFA (0.18 mL, 2.35 mmol) was added to a stirring solution of tert-butyl N-[(14S)-10-methyl-9-oxo-5,8,16-triazatricyclo[13.3.1.0$^{2,7}$]nonadeca-1(19),2(7),3,5,15,17-hexaen-14-yl]carbamate (31 mg, 0.078 mmol). After 6 h, the reaction mixture was concentrated and the residue placed under vacuum overnight. The residue was dissolved in MeOH, passed a NaHCO$_3$ resin cartridge, and concentrated to give (14S)-14-amino-10-methyl-5,8,16-triazatricyclo[13.3.1.0$^{2,7}$]nonadeca-1(19),2(7),3,5,15,17-hexaen-9-one as a brown film. The material was carried forward to the next reaction without further purification. MS(ESI) m/z: 297.3 (M+H)$^+$.

265G. Preparation of (14S)-14-(4-{5-chloro-2-[4-(trifluoromethyl)-1H-1,2,3-triazol-1-yl]phenyl}-6-oxo-1,6-dihydropyrimidin-1-yl)-10-methyl-5,8,16-triazatricyclo[13.3.1.0$^{2,7}$]nonadeca-1(19),2(7),3,5,15,17-hexaen-9-onetrifluoracetate (14S)-14-(4-{5-Chloro-2-[4-(trifluoromethyl)-1H-1,2,3-triazol-1-yl]phenyl}-6-oxo-1,6-dihydropyrimidin-1-yl)-10-methyl-5,8,16-triazatricyclo[13.3.1.0$^{2,7}$]nonadeca-1(19),2(7),3,5,15,17-hexaen-9-one, trifluoroacetate was prepared (10.4 mg, 16.5%) in a similar manner as Example 56 using (14S)-14-amino-10-methyl-5,8,16-triazatricyclo[13.3.1.0$^{2,7}$]nonadeca-1(19),2(7),3,5,15,17-hexaen-9-one and 6-{5-chloro-2-[4-(trifluoromethyl)-1H-1,2,3-triazol-1-yl]phenyl}pyrimidin-4-ol, prepared as described in Intermediate 15. The compound exists as an apparent diastereomeric mixture according to NMR data. MS(ESI) m/z: 621.2 (M+H)$^+$. $^1$H NMR (400 MHz, CD$_3$OD) δ 8.88-8.81 (m, 4H), 8.75-8.69 (m, 3H), 8.07 (br. s., 1H), 8.03 (br. s., 1H), 7.96 (d, J=2.2 Hz, 1H), 7.95-7.93 (m, 1H), 7.84-7.82 (m, 1H), 7.80-7.79 (m, 1H), 7.76-7.73 (m, 2H), 7.59 (dd, J=5.0, 1.7 Hz, 1H), 7.47 (dd, J=5.1, 1.8 Hz, 1H), 7.27 (s, 1H), 6.49-6.45 (m, 2H), 6.09 (dd, J=12.4, 4.7 Hz, 1H), 5.94-5.83 (m, 2H), 4.61 (dd, J=15.2, 9.7 Hz, 1H), 2.94-2.86 (m, 1H), 2.79-2.70 (m, 1H), 2.26 (s, 1H), 2.03 (d, J=13.0 Hz, 1H), 1.35-1.28 (m, 1H), 1.15 (d, J=6.6 Hz, 3H), 1.00 (d, J=6.8 Hz, 2H). Analytical HPLC (Method A): RT=5.22 min, purity=98%.

Example 267

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-4-(6-oxo-1,6-dihydropyridazin-4-yl)-3,4,7,15-tetraazatricyclo[12.3.1.0²,⁶]octadeca-1(18),2,5,14,16-pentaen-8-one

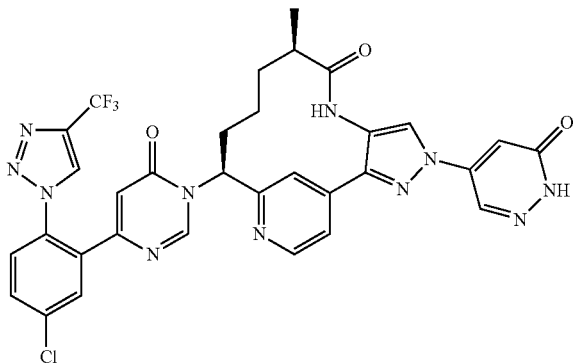 [SMILES: C[C@@H]1CCC[C@H](n2cnc(-c3cc(Cl)ccc3-n3cc(C(F)(F)F)nn3)cc2=O)c2cc(ccn2)-c2nn(-c3cn[nH]c(=O)c3)cc2NC1=O]

(9R,13S)-13-(4-{5-Chloro-2-[4-(trifluoromethyl)-1H-1,2,3-triazol-1-yl]phenyl}-6-oxo-1,6-dihydropyrimidin-1-yl)-9-methyl-4-(6-oxo-1,6-dihydropyridazin-4-yl)-3,4,7,15-tetraazatricyclo[12.3.1.0²,⁶]octadeca-1(18),2,5,14,16-pentaen-8-one trifluoroacetate (2.8 mg, 10% yield) was prepared in a similar manner as the procedure described in Example 216, by using 5-iodopyridazin-3(2H)-one (7.28 mg, 0.033 mmol) and (9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0²,⁶]octadeca-1(18),2(6),4,14,16-pentaen-8-one (20.0 mg, 0.033 mmol), prepared as described in Example 196. ¹H NMR (500 MHz, DMSO-d₆) δ 9.64 (s, 1H), 9.21 (s, 1H), 8.80 (s, 1H), 8.70 (s, 1H), 8.65 (d, J=2.4 Hz, 1H), 8.59 (d, J=4.9 Hz, 1H), 7.96 (d, J=1.8 Hz, 1H), 7.89 (s, 1H), 7.86-7.76 (m, 2H), 7.63 (d, J=5.2 Hz, 1H), 7.30-7.00 (m, 1H), 6.48 (s, 1H), 6.00 (br. s., 1H), 2.78 (br. s., 1H), 2.24 (d, J=16.2 Hz, 2H), 1.91-1.76 (m, 1H), 1.55 (br. s., 1H), 1.40 (br. s., 1H), 0.92 (d, J=6.7 Hz, 3H), 0.48 (br. s., 1H). MS(ESI) m/z: 704.0 [M+H]⁺. Analytical HPLC (Method B): RT=1.735 min, purity=98.0%; Factor XIa Ki=0.21 nM, Plasma Kallikrein Ki=9 nM.

Example 268

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-4-(6-methoxypyrazin-2-yl)-9-methyl-3,4,7,15-tetraazatricyclo[12.3.1.0²,⁶]octadeca-1(18),2,5,14,16-pentaen-8-one

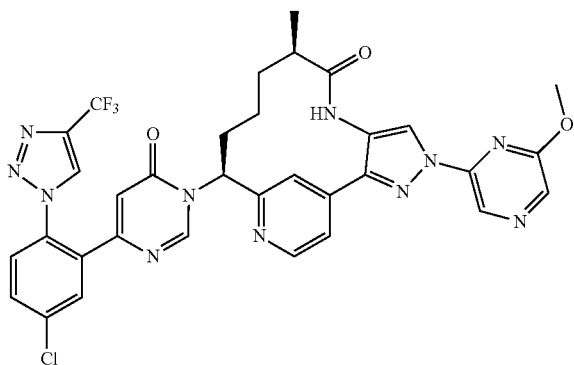 [SMILES: COc1cncc(-n2cc3c(n2)-c2ccnc(c2)[C@@H](n2cnc(-c4cc(Cl)ccc4-n4cc(C(F)(F)F)nn4)cc2=O)CCC[C@@H](C)C(=O)N3)n1]

(9R,13S)-13-(4-{5-Chloro-2-[4-(trifluoromethyl)-1H-1,2,3-triazol-1-yl]phenyl}-6-oxo-1,6-dihydropyrimidin-1-yl)-4-(6-methoxypyrazin-2-yl)-9-methyl-3,4,7,15-tetraazatricyclo[12.3.1.0²,⁶]octadeca-1(18),2,5,14,16-pentaen-8-one trifluoroacetate (10.9 mg, 16% yield) was prepared in a similar manner as the procedure described in Example 216, by using 2-iodo-6-methoxypyrazine (19.35 mg, 0.082 mmol) and (9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0²,⁶]octadeca-1(18),2(6),4,14,16-pentaen-8-one (50.0 mg, 0.082 mmol), prepared as described in Example 196. ¹H NMR (500 MHz, DMSO-d₆) δ 9.54 (s, 1H), 9.19 (s, 1H), 8.78 (s, 1H), 8.73 (s, 1H), 8.66 (s, 1H), 8.56 (d, J=4.9 Hz, 1H), 8.28 (s, 1H), 7.96-7.88 (m, 1H), 7.84-7.75 (m, 2H), 7.61 (d, J=4.6 Hz, 1H), 7.21-6.93 (m, 1H), 6.46 (s, 1H), 6.00 (br. s., 1H), 4.01 (s, 3H), 2.75 (br. s., 1H), 2.31-2.14 (m, 2H), 1.85-1.73 (m, 1H), 1.53 (br. s., 1H), 1.37 (br. s., 1H), 0.90 (d, J=6.7 Hz, 3H), 0.52 (br. s., 1H). MS(ESI) m/z: 718.0 [M+H]⁺. Analytical HPLC (Method B): RT=2.06 min, purity=100.0%; Factor XIa Ki=9 nM, Plasma Kallikrein Ki=260 nM.

Example 269

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-4-(5-fluoro-2-methoxypyridin-4-yl)-9-methyl-3,4,7,15-tetraazatricyclo[12.3.1.0²,⁶]octadeca-1(18),2,5,14,16-pentaen-8-one

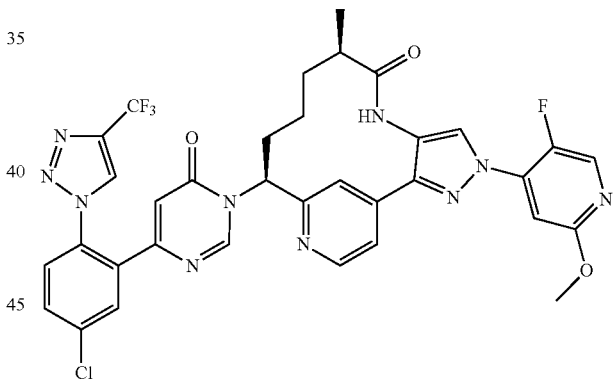

(9R,13S)-13-(4-{5-Chloro-2-[4-(trifluoromethyl)-1H-1,2,3-triazol-1-yl]phenyl}-6-oxo-1,6-dihydropyrimidin-1-yl)-4-(5-fluoro-2-methoxypyridin-4-yl)-9-methyl-3,4,7,15-tetraazatricyclo[12.3.1.0²,⁶]octadeca-1(18),2,5,14,16-pentaen-8-one (6.6 mg, 19%) was prepared in a similar manner as the procedure described in Example 216, by using 5-fluoro-4-iodo-2-methoxypyridine (21 mg, 0.082 mmol) and (9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0²,⁶]octadeca-1(18),2(6),4,14,16-pentaen-8-one (0.025 g, 0.041 mmol), prepared as described in Example 196. MS(ESI) m/z: 735.4 (M+H)⁺. ¹H NMR (500 MHz, DMSO-d₆) δ 9.60 (s, 1H), 9.23 (s, 1H), 8.72 (s, 1H), 8.60 (d, J=5.2 Hz, 1H), 8.49 (d, J=1.8 Hz, 1H), 8.43 (d, J=3.1 Hz, 1H), 8.00 (d, J=2.1 Hz, 1H), 7.92 (s, 1H), 7.90-7.80 (m, 2H), 7.64 (d, J=4.9 Hz, 1H), 7.39 (d, J=5.5 Hz, 1H), 6.51 (s, 1H), 6.12-5.90 (m, 1H), 3.93 (s, 3H), 2.79 (br. s., 1H), 2.27 (d, J=17.7 Hz, 2H), 1.84 (br. s., 1H), 1.57 (br.

s., 1H), 1.49-1.34 (m, 1H), 0.94 (d, J=6.7 Hz, 3H), 0.68-0.41 (m, 1H). Analytical HPLC (Method C): RT=2.09 min, purity=100%; Factor XIa Ki=7.4 nM, Plasma Kallikrein Ki=280 nM.

Example 270

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-3-(difluoromethyl)-9-methyl-8-oxo-3,4,7-triazatricyclo[12.3.1.0²,⁶]octadeca-1(18),2(6),4,14,16-pentaene-17-carbonitrile

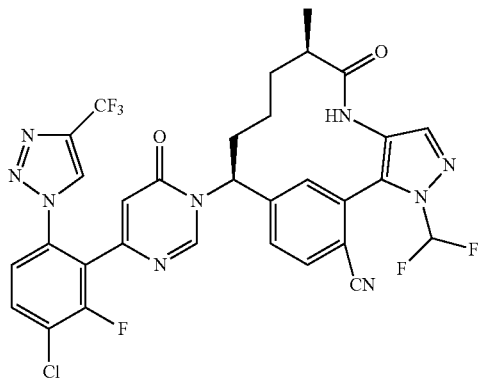 [SMILES: C[C@@H]1CCC[C@H](n2cnc(-c3c(-n4cc(C(F)(F)F)nn4)ccc(Cl)c3F)cc2=O)c2ccc(C#N)c(c2)-c2c(cnn2C(F)F)NC1=O]

270A. Preparation of Tert-Butyl N-[(9R,10E,13S)-17-cyano-3-(difluoromethyl)-9-methyl-8-oxo-3,4,7-triazatricyclo[12.3.1.0²,⁶]octadeca-1(18),2(6),4,10,14,16-hexaen-13-yl]carbamate

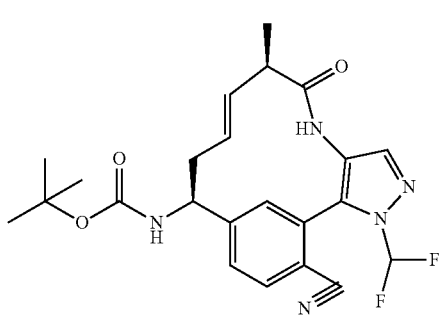 [SMILES: C[C@@H]1/C=C/C[C@H](NC(=O)OC(C)(C)C)c2ccc(C#N)c(c2)-c2c(cnn2C(F)F)NC1=O]

tert-Butyl N-[(9R,10E,13S)-17-cyano-3-(difluoromethyl)-9-methyl-8-oxo-3,4,7-triazatricyclo[12.3.1.0²,⁶]octadeca-1(18),2(6),4,10,14,16-hexaen-13-yl]carbamate (0.02 g, 45%), a dark film, was prepared in the same manner as described for Intermediate 35D, substituting 2-bromo-4-formylbenzonitrile for 3-bromobenzaldehyde. LCMS(ESI) m/z: 458.6 (M+H)⁺.

270B. Preparation of Tert-Butyl N-[(9R,13S)-17-cyano-3-(difluoromethyl)-9-methyl-8-oxo-3,4,7-triazatricyclo[12.3.1.0²,⁶]octadeca-1(18),2(6),4,14,16-pentaen-13-yl]carbamate

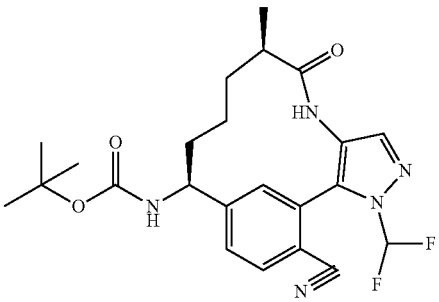 [SMILES: C[C@@H]1CCC[C@H](NC(=O)OC(C)(C)C)c2ccc(C#N)c(c2)-c2c(cnn2C(F)F)NC1=O]

tert-Butyl N-[(9R,10E,13S)-17-cyano-3-(difluoromethyl)-9-methyl-8-oxo-3,4,7-triazatricyclo[12.3.1.0²,⁶]octadeca-1(18),2(6),4,10,14,16-hexaen-13-yl]carbamate (20 mg, 0.044 mmol) in EtOH (10 ml) was added PtO₂ (0.005 g, 0.022 mmol) and the reaction was hydrogenated at 55 psi for 5 h. The reaction mixture was filtered through a plug of CELITE® and the filtrate concentrated. To the product was added DCM (2 ml), TEA (6.09 µl, 0.044 mmol) and Dess-Martin periodinane (74.2 mg, 0.175 mmol). After 1 h at rt, the reaction was quenched with sat aq Na₂S₂O₃, and extracted with EtOAc (2×15 ml). The combined organic layer was washed with brine (10 ml), dried (MgSO₄), filtered and concentrated to afford tert-butyl N-[(9R,13S)-17-cyano-3-(difluoromethyl)-9-methyl-8-oxo-3,4,7-triazatricyclo[12.3.1.0²,⁶]octadeca-1(18),2(6),4,14,16-pentaen-13-yl]carbamate (20 mg 100%). MS(ESI) m/z: 460.5 (M+H)⁺.

270C. Preparation of (9R,13S)-13-amino-3-(difluoromethyl)-9-methyl-8-oxo-3,4,7-triazatricyclo[12.3.1.0²,⁶]octadeca-1(18),2(6),4,14,16-pentaene-17-carbonitrile

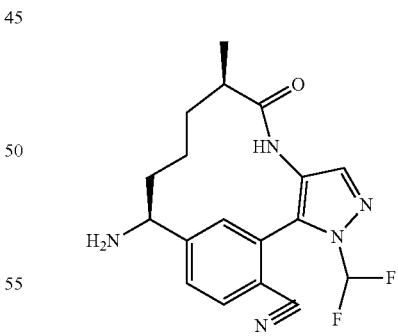

To tert-butyl N-[(9R,13S)-17-cyano-3-(difluoromethyl)-9-methyl-8-oxo-3,4,7-triazatricyclo[12.3.1.0²,⁶]octadeca-1(18),2(6),4,14,16-pentaen-13-yl]carbamate (20 mg, 0.044 mmol) was added dioxane (1 ml) followed by 1 ml of 4 N HCl in dioxane. After 3 h, the reaction was concentrated and residue dissolved in DCM/MeOH and filtered through a basic cartridge. Concentration of the filtrate afforded (9R,13S)-13-amino-3-(difluoromethyl)-9-methyl-8-oxo-3,4,7-triazatricyclo[12.3.1.0²,⁶]octadeca-1(18),2(6),4,14,16-pentaene-17-carbonitrile (12 mg, 80%) as a brown solid. MS(ESI) m/z: 360.4 (M+H)+.

270D. Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-3-(difluoromethyl)-9-methyl-8-oxo-3,4,7-triazatricyclo[12.3.1.0$^{2,6}$]octadeca-1(18),2(6),4,14,16-pentaene-17-carbonitrile (9R,13S)-13-(4-{5-Chloro-2-[4-(trifluoromethyl)-1H-1,2,3-triazol-1-yl]phenyl}-6-oxo-1,6-dihydropyrimidin-1-yl)-3-(difluoromethyl)-9-methyl-8-oxo-3,4,7-triazatricyclo[12.3.1.0$^{2,6}$]octadeca-1(18),2(6),4,14,16-pentaene-17-carbonitrile (2.2 mg, 9.6%) was prepared in a similar manner as described in Example 56 by using (9R,13S)-13-amino-3-(difluoromethyl)-9-methyl-8-oxo-3,4,7-triazatricyclo[12.3.1.0$^{2,6}$]octadeca-1(18),2(6),4,14,16-pentaene-17-carbonitrile. MS(ESI) m/z: 683.9 (M+H)+. $^1$H NMR (500 MHz, CD$_3$OD) δ 8.71 (s, 1H), 8.13 (s, 1H), 7.87 (d, J=8.0 Hz, 1H), 7.80 (m, 2H), 7.68-7.61 (m, 3H), 7.58-7.51 (m, 2H), 6.34 (s, 1H), 5.62 (d, J=12.9 Hz, 1H), 2.45-2.34 (m, 1H), 2.22 (br. s., 1H), 2.00 (d, J=16.2 Hz, 1H), 1.64 (d, J=10.2 Hz, 2H), 1.44 (d, J=7.2 Hz, 1H), 1.06 (d, J=6.6 Hz, 3H), 0.62 (br. s., 1H). Analytical HPLC (Method C) RT=1.93 min, purity=100% as a mixture of diastereomers; Factor XIa Ki=0.35 nM, Plasma Kallikrein Ki=84 nM.

Example 271

Preparation of (9R,13S)-13-{4-[5-chloro-2-(4-methyl-1H-imidazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

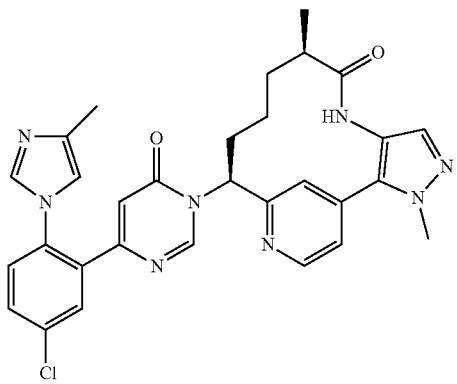 [SMILES: Cc1cn(-c2ccc(Cl)cc2-c2cc(=O)n([C@H]3CCC[C@@H](C)C(=O)Nc4cnn(C)c4-c4ccnc3c4)cn2)cn1]

(9R,13S)-13-{4-[5-Chloro-2-(4-methyl-1H-imidazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (11.7 mg, 45% yield) was a major product isolated from the preparation of (9R,13S)-13-{4-[5-chloro-2-(5-methyl-1H-imidazol-1-yl)phenyl]-6-oxo-1,6-dihydropyrimidin-1-yl}-3,9-dimethyl-3,4,7,15-tetraazatricyclo[12.3.1.0$^{2,6}$]Octadeca-1(18),2(6),4,14,16-pentaen-8-one trifluoroacetate, Example 257. MS(ESI) m/z: 569.20 (M+H)+. $^1$H NMR (500 MHz, DMSO-d$_6$) δ 9.23 (s, 1H), 9.14 (br. s., 1H), 8.77 (s, 1H), 8.68 (d, J=4.9 Hz, 1H), 7.94 (d, J=2.1 Hz, 1H), 7.85 (dd, J=8.4, 2.3 Hz, 1H), 7.76 (d, J=8.5 Hz, 1H), 7.67 (s, 1H), 7.59 (d, J=5.2 Hz, 1H), 7.52-7.47 (m, 2H), 6.60 (s, 1H), 5.90 (d, J=9.8 Hz, 1H), 4.01 (s, 3H), 2.69-2.61 (m, 1H), 2.35-2.24 (m, 4H), 2.16-2.06 (m, 1H), 1.88-1.78 (m, 1H), 1.52-1.42 (m, 1H), 1.38-1.28 (m, 1H), 0.89 (d, J=7.0 Hz, 3H), 0.53-0.38 (m, 1H). Analytical HPLC (Method C): RT=1.14 min, 100% purity; Factor XIa Ki=90 nM, Plasma Kallikrein Ki=4,600 nM.

Example 272

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-4-(5-fluoro-2-hydroxypyridin-4-yl)-9-methyl-3,4,7,15-tetraazatricyclo[12.3.1.0$^{2,6}$]octadeca-1(18),2,5,14,16-pentaen-8-one

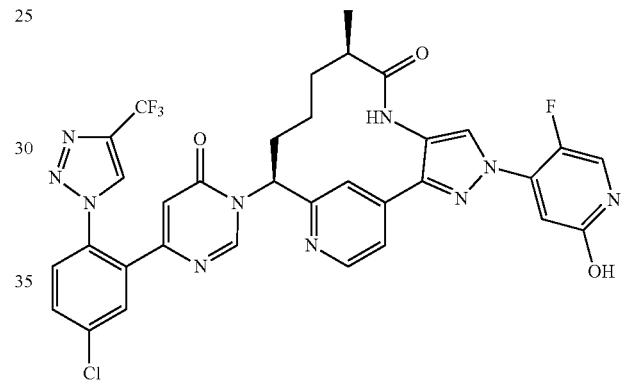

(9R,13S)-13-(4-{5-Chloro-2-[4-(trifluoromethyl)-1H-1,2,3-triazol-1-yl]phenyl}-6-oxo-1,6-dihydropyrimidin-1-yl)-4-(5-fluoro-2-methoxypyridin-4-yl)-9-methyl-3,4,7,15-tetraazatricyclo[12.3.1.0$^{2,6}$]octadeca-1(18),2,5,14,16-pentaen-8-one, prepared as described in Example 269, (0.02 g, 0.027 mmol) was dissolved in THF (2 mL) and conc. HCl (500 µl, 6.00 mmol) was added and the reaction mixture was heated to 70° C. for 16 h. After this time, the solvents were concentrated and the residue was purified by reverse phase chromatography to give (9R,13S)-13-(4-{5-chloro-2-[4-(trifluoromethyl)-1H-1,2,3-triazol-1-yl]phenyl}-6-oxo-1,6-dihydropyrimidin-1-yl)-4-(5-fluoro-2-hydroxypyridin-4-yl)-9-methyl-3,4,7,15-tetraazatricyclo[12.3.1.0$^{2,6}$]octadeca-1(18),2,5,14,16-pentaen-8-one (5.3 mg, 26%). MS(ESI) m/z: 721.2 (M+H)+. $^1$H NMR (500 MHz, DMSO-d$_6$) δ 9.59 (s, 1H), 9.24 (s, 1H), 8.73 (s, 1H), 8.60 (d, J=4.9 Hz, 1H), 8.43 (s, 1H), 8.05 (br. s., 1H), 7.98 (d, J=1.8 Hz, 1H), 7.92 (s, 1H), 7.90-7.79 (m, 2H), 7.63 (d, J=4.0 Hz, 1H), 6.96 (br. s., 1H), 6.51 (s, 1H), 6.14-5.94 (m, 1H), 2.79 (br. s., 1H), 2.27 (d, J=17.1 Hz, 2H), 1.91-1.77 (m, 1H), 1.64-1.50 (m, 1H), 1.49-1.34 (m, 1H), 0.94 (d, J=6.7 Hz, 3H), 0.64-0.42 (m, 1H). Analytical HPLC (Method C): RT=1.68 min, purity=100%; Factor XIa Ki=0.73 nM, Plasma Kallikrein Ki=130 nM.

Example 274

Preparation of (9R,13S)-13-{4-[5-chloro-2-(1,3-oxazol-2-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

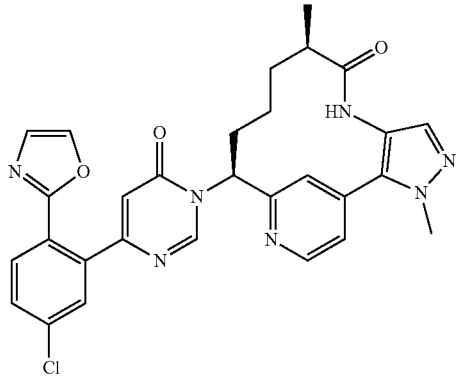 [SMILES: C[C@@H]1CCC[C@H](n2cnc(-c3cc(Cl)ccc3-c3ncco3)cc2=O)c2cc(ccn2)-c2c(cnn2C)NC1=O]

To a degassed dioxane (1 ml) solution of (9R,13S)-13-[4-(5-chloro-2-iodophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one (20 mg, 0.033 mmol), prepared as described in Example 211, was added 2-(tributylstannyl)oxazole (11.65 mg, 0.033 mmol), followed by addition of Pd(Ph$_3$P)$_4$ (3.76 mg, 3.25 μmol). The reaction was stirred at 90° C. for 2 h, then cooled to rt and concentrated. Purification by reverse phase chromatography afforded (9R,13S)-13-{4-[5-chloro-2-(1,3-oxazol-2-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (2.38 mg, 11% yield) as a white solid. MS(ESI) m/z: 556.4 (M+H)$^+$. $^1$H NMR (400 MHz, CD$_3$OD) δ 8.89 (s, 1H), 8.74 (d, J=5.1 Hz, 1H), 7.92 (d, J=8.4 Hz, 1H), 7.87 (s, 1H), 7.71 (s, 1H), 7.69 (d, J=2.2 Hz, 1H), 7.65 (dd, J=8.4, 2.2 Hz, 1H), 7.52 (dd, J=5.1, 1.5 Hz, 1H), 7.49 (s, 1H), 7.23 (s, 1H), 6.50 (s, 1H), 6.05 (dd, J=12.7, 4.1 Hz, 1H), 4.05 (s, 3H), 2.77-2.67 (m, 1H), 2.38-2.27 (m, 1H), 2.15-1.98 (m, 2H), 1.68-1.42 (m, 2H), 1.01 (d, J=7.0 Hz, 3H), 0.77-0.62 (m, 1H). Analytical HPLC (Method A): RT=7.13 min, 99.0% purity; Factor XIa Ki=100 nM, Plasma Kallikrein Ki=4,500 nM.

Example 275

Preparation of (9R,13S)-13-(4-{5-chloro-2-[(pyrazin-2-yl)amino]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one

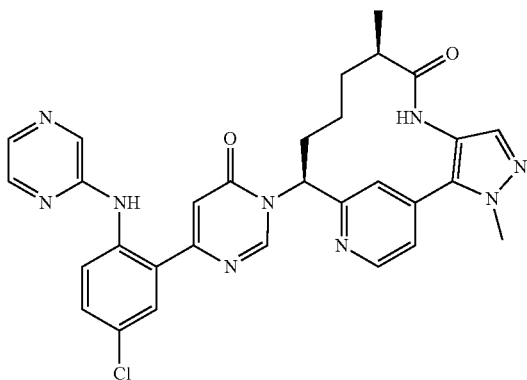 [SMILES: C[C@@H]1CCC[C@H](n2cnc(-c3cc(Cl)ccc3Nc3cnccn3)cc2=O)c2cc(ccn2)-c2c(cnn2C)NC1=O]

A sealed microwave vial containing (9R,13S)-13-[4-(2-amino-5-chlorophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one hydrochloride (0.01 g, 0.017 mmol), prepared as described in Example 313, 2-bromopyrazine (5.51 mg, 0.035 mmol) and EtOH (1 ml) was heated in a microwave at 150° C. for 30 min, cooled to rt, and concentrated. To the residue were added Cs$_2$CO$_3$ (0.030 g, 0.093 mmol), Pd(OAc)$_2$ (1.05 mg, 4.66 μmol), Xantphos (5.39 mg, 9.31 μmol), and 2-bromopyrazine (5.51 mg, 0.035 mmol), followed by dioxane (0.931 ml). The reaction mixture was degassed with Ar for 10 min. The vial was sealed and heated at 85° C. After 4 h, the reaction was cooled to rt and concentrated. Purification by reverse phase chromatography afforded (9R,13S)-13-(4-{5-chloro-2-[(pyrazin-2-yl)amino]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate (2.95 mg, 20% yield) as a yellow solid. MS(ESI) m/z: 582.5 (M+H)$^+$. $^1$H NMR (400 MHz, CD$_3$OD) δ 9.09 (s, 1H), 8.73 (d, J=5.1 Hz, 1H), 8.23-8.19 (m, 2H), 8.08 (dd, J=2.8, 1.4 Hz, 1H), 7.89 (d, J=2.6 Hz, 1H), 7.73 (s, 1H), 7.67 (d, J=2.6 Hz, 1H), 7.53 (dd, J=5.1, 1.5 Hz, 1H), 7.50 (s, 1H), 7.43 (dd, J=8.9, 2.5 Hz, 1H), 6.77 (s, 1H), 6.02 (dd, J=12.7, 4.3 Hz, 1H), 4.05 (s, 3H), 2.76-2.67 (m, 1H), 2.43-2.32 (m, 1H), 2.15-2.01 (m, 2H), 1.68-1.44 (m, 2H), 1.02 (d, J=6.8 Hz, 3H), 0.81-0.65 (m, 1H). Analytical HPLC (Method A): RT=7.06 min, 94.0% purity; Factor XIa Ki=560 nM.

Example 276

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-4-(4-hydroxypyrimidin-5-yl)-9-methyl-3,4,7,15-tetraazatricyclo[12.3.1.0$^{2,6}$]octadeca-1(18),2,5,14,16-pentaen-8-one

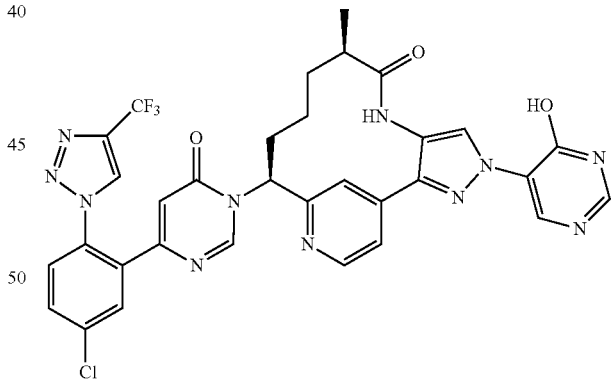

(9R,13S)-13-(4-{5-Chloro-2-[4-(trifluoromethyl)-1H-1,2,3-triazol-1-yl]phenyl}-6-oxo-1,6-dihydropyrimidin-1-yl)-4-(4-hydroxypyrimidin-5-yl)-9-methyl-3,4,7,15-tetraazatricyclo[12.3.1.0$^{2,6}$]octadeca-1(18),2,5,14,16-pentaen-8-one trifluoroacetate was prepared in a similar manner as the procedure described in Example 296, to give (9R,13S)-13-(4-{5-chloro-2-[4-(trifluoromethyl)-1H-1,2,3-triazol-1-yl]phenyl}-6-oxo-1,6-dihydropyrimidin-1-yl)-4-(4-hydroxypyrimidin-5-yl)-9-methyl-3,4,7,15-tetraazatricyclo[12.3.1.0$^{2,6}$]octadeca-1(18),2,5,14,16-pentaen-8-one trifluoroacetate (3.82 mg, 4.44 μmol, 42% yield). $^1$H NMR (400 MHz, CD$_3$OD) δ 8.85 (s, 1H), 8.75 (s, 2H), 8.71 (s, 1H), 8.67-8.62 (m, 1H), 8.27 (s, 1H), 8.00-7.93 (m, 2H), 7.82-7.69 (m, 3H), 6.49 (s, 1H), 6.13 (d, J=9.2 Hz, 1H), 2.87 (br. s., 1H), 2.29 (br. s., 2H), 2.13-2.01 (m, 1H), 1.76 (d, J=10.3 Hz, 1H), 1.59 (br. s., 1H), 1.29 (s, 1H), 1.11 (d, J=7.0 Hz, 3H), 0.91 (br. s., 1H). MS(ESI) m/z: 704.5 [M+H]¹. Analytical HPLC (Method A): RT=7.04 min, purity=>95.0%; Factor XIa Ki=2.4 nM, Plasma Kallikrein Ki=70 nM.

Example 277

Preparation of ethyl 1-(4-chloro-2-{1-[(9R,13S)-3, 9-dimethyl-8-oxo-3,4,7,15-tetraazatricyclo[12.3. 1.0$^{2,6}$]octadeca-1(18),2(6),4,14,16-pentaen-13-yl]-6-oxo-1,6-dihydropyrimidin-4-yl}phenyl)-3-methyl-1H-pyrazole-4-carboxylate

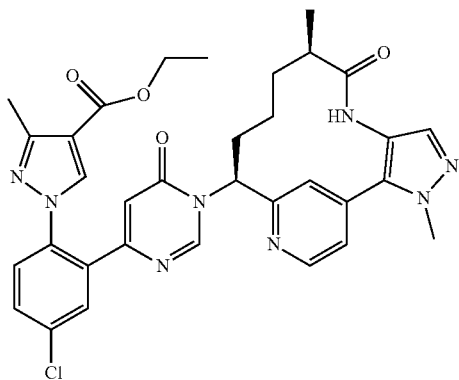 [SMILES: CCOC(=O)c1cn(-c2ccc(Cl)cc2-c2cc(=O)n([C@H]3CCC[C@@H](C)C(=O)Nc4cnn(C)c4-c4ccnc3c4)cn2)nc1C]

To a suspension of ethyl 3-methyl-1H-pyrazole-4-carboxylate (3.51 mg, 0.023 mmol), K$_3$PO$_4$ (9.79 mg, 0.046 mmol) and (9R,13S)-13-[4-(5-chloro-2-iodophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one (14 mg, 0.023 mmol) in dioxane (0.24 mL) was added (1R,2R)—N1,N2-dimethylcyclohexane-1,2-diamine (1.619 mg, 0.011 mmol). The mixture was purged with Ar, CuI (0.434 mg, 2.277 µmol) was added, and the vial was sealed. The reaction was heated at 80° C. and stirred overnight. The solution was concentrated and the residue purified by reverse phase chromatography to give ethyl 1-(4-chloro-2-{1-[(9R,13S)-3,9-dimethyl-8-oxo-3,4,7,15-tetraazatricyclo [12.3.1.0$^{2,6}$]octadeca-1(18),2(6),4,14,16-pentaen-13-yl]-6-oxo-1,6-dihydropyrimidin-4-yl}phenyl)-3-methyl-1H-pyrazole-4-carboxylate trifluoroacetate (3.21 mg, 17% yield) as a white solid. MS(ESI) m/z: 641.2 (M+H)⁺. ¹H NMR (400 MHz, CD$_3$OD) δ 8.86 (s, 1H), 8.71 (d, J=5.1 Hz, 1H), 8.20 (s, 1H), 7.84 (d, J=2.2 Hz, 1H), 7.68 (s, 1H), 7.67-7.61 (m, 1H), 7.60-7.54 (m, 1H), 7.53-7.47 (m, 2H), 6.20 (s, 1H), 6.02-5.95 (m, 1H), 4.30-4.21 (m, 2H), 4.07-4.01 (m, 3H), 2.70 (td, J=6.7, 3.2 Hz, 1H), 2.36 (s, 3H), 2.33-2.24 (m, 1H), 2.13-1.95 (m, 2H), 1.65-1.53 (m, 1H), 1.51-1.40 (m, 1H), 1.34-1.26 (m, 3H), 1.00 (d, J=7.0 Hz, 3H), 0.69 (m, 1H). Analytical HPLC (Method A): RT=7.46 min, 94% purity; Factor XIa Ki=170 nM, Plasma Kallikrein Ki=2,700 nM.

Example 278

Preparation of (9R,13S)-13-{4-[5-chloro-2-(3,4-dimethyl-1H-pyrazol-1-yl)phenyl]-6-oxo-1,6-dihydropyrimidin-1-yl}-3,9-dimethyl-3,4,7,15-tetraazatricyclo[12.3.1.0$^{2,6}$]

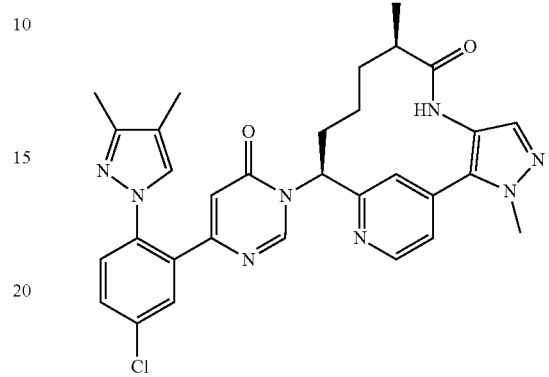

(9R,13S)-13-{4-[5-Chloro-2-(3,4-dimethyl-1H-pyrazol-1-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2 (6),4,14,16-pentaen-8-one trifluoroacetate (0.85 mg, 5% yield) was prepared in a similar manner as the procedure described in Example 277, by replacing ethyl 3-methyl-1H-pyrazole-4-carboxylate with 3,4-dimethyl-1H-pyrazole (2.189 mg, 0.023 mmol). MS(ESI) m/z: 583.2 (M+H)⁺. ¹H NMR (400 MHz, CD$_3$OD) δ 8.91 (s, 1H), 8.72 (d, J=5.1 Hz, 1H), 7.86 (d, J=2.4 Hz, 1H), 7.68 (s, 1H), 7.60 (dd, J=8.6, 2.4 Hz, 1H), 7.51 (dd, J=5.1, 1.5 Hz, 1H), 7.49-7.46 (m, 2H), 7.39 (s, 1H), 6.02-5.94 (m, 2H), 4.04 (s, 3H), 2.71 (d, J=3.1 Hz, 1H), 2.37-2.24 (m, 1H), 2.14 (s, 3H), 2.00 (s, 3H), 1.93 (s, 1H), 1.66-1.54 (m, 1H), 1.48 (m, 1H), 1.01 (d, J=6.8 Hz, 3H), 0.68 (m, 1H). Analytical HPLC (Method A): RT=6.78 min, 92% purity; Factor XIa Ki=540 nM.

Example 279

Preparation of ethyl 1-(4-chloro-2-{1-[(9R,13S)-3, 9-dimethyl-8-oxo-3,4,7,15-tetraazatricyclo[12.3. 1.0$^{2,6}$]octadeca-1(18),2(6),4,14,16-pentaen-13-yl]-6-oxo-1,6-dihydropyrimidin-4-yl}phenyl)-1H-pyrazole-4-carboxylate

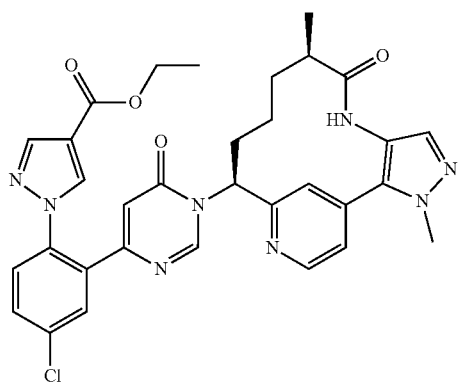 [SMILES: CCOC(=O)c1cnn(-c2ccc(Cl)cc2-c2cc(=O)n([C@H]3CCC[C@@H](C)C(=O)Nc4cnn(C)c4-c4ccnc3c4)cn2)c1]

Ethyl 1-(4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)-1H-pyrazole-4-carboxylate trifluoroacetate (9.9 mg, 56% yield) was prepared in a similar manner as the procedure described in Example 277, by replacing ethyl 3-methyl-1H-pyrazole-4-carboxylate with ethyl 1H-pyrazole-4-carboxylate (3.19 mg, 0.023 mmol). MS(ESI) m/z: 627.1 (M+H)⁺. ¹H NMR (400 MHz, methanol-d₄) δ 8.86 (s, 1H), 8.72 (d, J=5.3 Hz, 1H), 8.34 (s, 1H), 7.96 (s, 1H), 7.85 (d, J=2.2 Hz, 1H), 7.69 (s, 1H), 7.68-7.64 (m, 1H), 7.61-7.57 (m, 1H), 7.53 (dd, J=5.2, 1.7 Hz, 1H), 7.49 (s, 1H), 6.18 (s, 1H), 5.98 (dd, J=12.7, 4.3 Hz, 1H), 4.28 (q, J=7.1 Hz, 2H), 4.04 (s, 3H), 2.70 (td, J=6.7, 3.3 Hz, 1H), 2.30 (tt, J=12.7, 4.4 Hz, 1H), 2.12-1.94 (m, 2H), 1.66-1.53 (m, 1H), 1.46 (ddd, J=15.0, 9.8, 5.5 Hz, 1H), 1.32 (t, J=7.2 Hz, 3H), 1.00 (d, J=6.8 Hz, 3H), 0.69 (m, 1H). Analytical HPLC (Method A): RT=7.06 min, 99% purity; Factor XIa Ki=2.2 nM, Plasma Kallikrein Ki=960 nM.

Example 280

Preparation of (9R,13S)-13-[4-(5-chloro-2-hydroxyphenyl)-6-oxo-1,6-dihydropyrimidin-1-yl]-3,9-dimethyl-3,4,7,15-tetraazatricyclo[12.3.1.0²,⁶]octadeca-1(18),2(6),4,14,16-pentaen-8-one

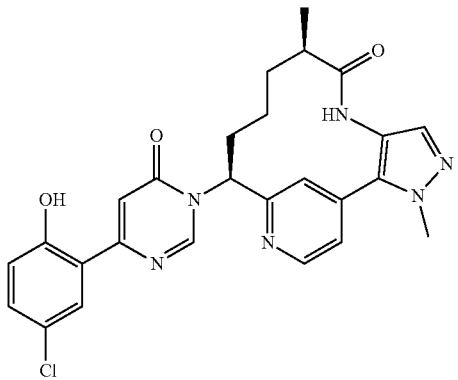 [SMILES: C[C@@H]1CCC[C@H](n2cnc(-c3cc(Cl)ccc3O)cc2=O)c2cc(ccn2)-c2c(cnn2C)NC1=O]

The mixture of 1H-imidazole (2.21 mg, 0.033 mmol), Pd(OAc)₂ (0.73 mg, 3.25 µmol) and CuI (0.012 g, 0.065 mmol) in DMF (1.63 ml) was purged with Ar (3×), and then (9R,13S)-13-[4-(5-chloro-2-iodophenyl)-6-oxo-1,6-dihydropyrimidin-1-yl]-3,9-dimethyl-3,4,7,15-tetraazatricyclo[12.3.1.0²,⁶]octadeca-1(18),2(6),4,14,16-pentaen-8-one (0.02 g, 0.033 mmol), prepared as described in Example 211, was added. The reaction was sealed and heated at 140° C. After 5 h, the reaction was cooled to rt. The solution was concentrated and the residue was purified by reverse phase chromatography afforded (9R,13S)-13-[4-(5-chloro-2-hydroxyphenyl)-6-oxo-1,6-dihydropyrimidin-1-yl]-3,9-dimethyl-3,4,7,15-tetraazatricyclo[12.3.1.0²,⁶]octadeca-1(18),2(6),4,14,16-pentaen-8-one trifluoroacetate (1.76 mg, 9% yield) as a yellow solid. MS(ESI) m/z: 505.6 (M+H)⁺. ¹H NMR (400 MHz, CD₃OD) δ 9.11 (s, 1H), 8.74 (d, J=5.1 Hz, 1H), 7.84 (d, J=2.6 Hz, 1H), 7.72 (s, 1H), 7.52 (dd, J=5.1, 1.5 Hz, 1H), 7.50 (s, 1H), 7.30 (dd, J=8.8, 2.6 Hz, 1H), 7.07 (s, 1H), 6.90 (d, J=8.8 Hz, 1H), 6.06 (dd, J=12.9, 4.5 Hz, 1H), 4.05 (s, 3H), 2.78-2.68 (m, 1H), 2.35 (tt, J=12.8, 4.3 Hz, 1H), 2.16-2.01 (m, 2H), 1.68-1.45 (m, 2H), 1.01 (d, J=7.0 Hz, 3H), 0.76-0.61 (m, 1H). Analytical HPLC (Method A): RT=8.47 min, 100% purity; Factor XIa Ki=57 nM, Plasma Kallikrein Ki=180 nM.

Example 281

Preparation of (9R,13S)-13-(4-{5-chloro-2-[4-(trifluoromethyl)-1H-imidazol-1-yl]phenyl}-6-oxo-1,6-dihydropyrimidin-1-yl)-3,9-dimethyl-3,4,7,15-tetraazatricyclo[12.3.1.0²,⁶]octadeca-1(18),2(6),4,14,16-pentaen-8-one

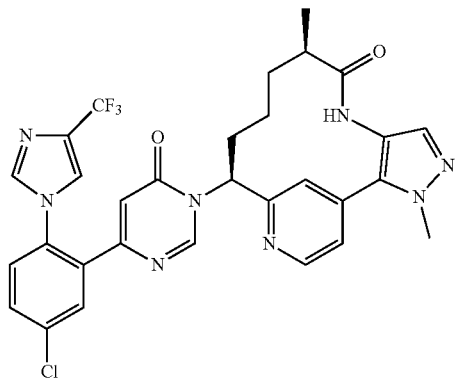

(9R,13S)-13-(4-{5-Chloro-2-[4-(trifluoromethyl)-1H-imidazol-1-yl]phenyl}-6-oxo-1,6-dihydropyrimidin-1-yl)-3,9-dimethyl-3,4,7,15-tetraazatricyclo[12.3.1.0²,⁶]octadeca-1(18),2(6),4,14,16-pentaen-8-one trifluoroacetate (4 mg, 15% yield) was prepared in a similar manner as the procedure described in Example 231, by replacing 1H-imidazole with 4-(trifluoromethyl)-1H-imidazole (0.018 g, 0.130 mmol). MS(ESI) m/z: 623.25 (M+H)⁺. ¹H NMR (500 MHz, CD₃OD) δ 8.84 (s, 1H), 8.70 (d, J=5.2 Hz, 1H), 7.86 (s, 1H), 7.83 (d, J=2.5 Hz, 1H), 7.74 (s, 1H), 7.71-7.66 (m, 2H), 7.58 (d, J=8.5 Hz, 1H), 7.52-7.47 (m, 2H), 6.40 (s, 1H), 5.99 (dd, J=12.5, 3.4 Hz, 1H), 4.04 (s, 3H), 2.70 (dt, J=6.6, 3.3 Hz, 1H), 2.33-2.23 (m, 1H), 2.12-1.92 (m, 2H), 1.65-1.55 (m, 1H), 1.52-1.41 (m, 1H), 1.01 (d, J=6.9 Hz, 3H), 0.76-0.60 (m, 1H). Analytical HPLC (Method C): RT=1.58 min, 100% purity; Factor XIa Ki=73 nM, Plasma Kallikrein Ki=4,700 nM.

Example 282

Preparation of (9R,13S)-13-{4-[5-chloro-2-(4-chloro-1H-1,2,3-triazol-1-yl)phenyl]-6-oxo-1,6-dihydropyrimidin-1-yl}-4-methanesulfonyl-9-methyl-3,4,7,15-tetraazatricyclo[12.3.1.0²,⁶]octadeca-1(18),2,5,14,16-pentaen-8-one, and Preparation of (9R,13S)-13-{4-[5-chloro-2-(4-chloro-1H-1,2,3-triazol-1-yl)phenyl]-6-oxo-1,6-dihydropyrimidin-1-yl}-3-methanesulfonyl-9-methyl-3,4,7,15-tetraazatricyclo[12.3.1.0²,⁶]octadeca-1(18),2(6),4,14,16-pentaen-8-one

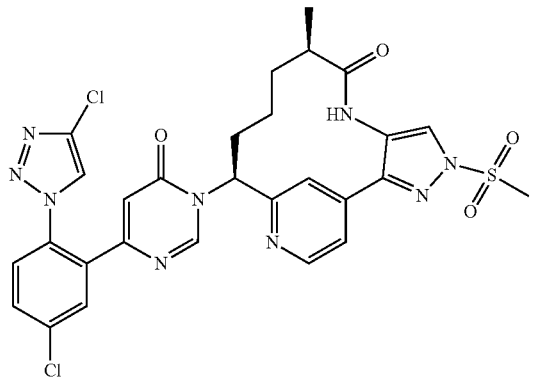

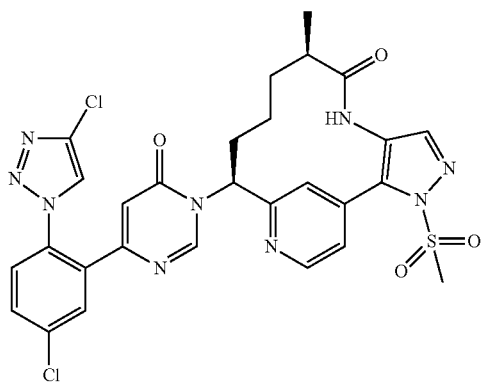

To a cooled (0° C.), clear, pale pink solution of (9R,13S)-13-{4-[5-chloro-2-(4-chloro-1H-1,2,3-triazol-1-yl)phenyl]-6-oxo-1,6-dihydropyrimidin-1-yl}-9-methyl-3,4,7,15-tetraazatricyclo[12.3.1.0$^{2,6}$]octadeca-1(18),2(6),4,14,16-pentaen-8-one trifluoroacetate (0.010 g, 0.014 mmol), prepared as described in Example 101, and pyridine (0.012 ml, 0.145 mmol) was added MsCl (1.1 µl, 0.014 mmol). The reaction was stirred for 30 min at 0° C. and then the reaction was warmed to rt. After 1 h at rt, TEA (0.020 ml, 0.145 mmol) was added followed by MsCl (1.1 µl, 0.014 mmol). After 3 h, additional TEA (0.020 ml, 0.145 mmol) was added followed by the additional of MsCl (5.5 µL, 0.070 mmol). After 1 h, the reaction was stopped, diluted with EtOAc and washed with 1.5 M K$_2$HPO$_4$, brine, dried over Na$_2$SO$_4$, filtered and concentrated to give a yellow residue. Purification by reverse phase chromatography, gave after concentration and lyophilization a 1:1 mixture of (9R,13S)-13-{4-[5-chloro-2-(4-chloro-1H-1,2,3-triazol-1-yl)phenyl]-6-oxo-1,6-dihydropyrimidin-1-yl}-4-methanesulfonyl-9-methyl-3,4,7,15-tetraazatricyclo[12.3.1.0$^{2,6}$]octadeca-1(18),2,5,14,16-pentaen-8-one trifluoroacetate and (9R,13S)-13-{4-[5-chloro-2-(4-chloro-1H-1,2,3-triazol-1-yl)phenyl]-6-oxo-1,6-dihydropyrimidin-1-yl}-3-methanesulfonyl-9-methyl-3,4,7,15-tetraazatricyclo[12.3.1.0$^{2,6}$]octadeca-1(18),2(6),4,14,16-pentaen-8-one trifluoroacetate (0.0020 g, 18%) as a white solid. MS(ESI) m/z: 654.0 (M+H)$^+$. $^1$H NMR (500 MHz, CD$_3$OD) δ 8.87 (s, 1H), 8.79 (s, 1H), 8.67 (d, J=5.2 Hz, 2H), 8.34-8.32 (m, 2H), 8.28 (s, 1H), 7.90-7.87 (m, 4H), 7.75-7.71 (m, 2H), 7.66-7.63 (m, 3H), 7.62-7.60 (m, 1H), 7.55 (dd, J=5.2, 1.7 Hz, 1H), 6.38-6.36 (m, 2H), 6.13-6.06 (m, 1H), 5.99-5.93 (m, 1H), 3.52 (s, 3H), 3.49 (s, 3H), 2.86-2.79 (m, 1H), 2.68-2.61 (m, 1H), 2.32-2.20 (m, 3H), 2.07-1.90 (m, 3H), 1.76-1.64 (m, 1H), 1.62-1.38 (m, 3H), 1.04 (d, J=6.9 Hz, 3H), 0.98 (d, J=6.9 Hz, 3H), 0.80-0.61 (m, 2H). Analytical HPLC (Method A): RT=7.98 and 8.11 min, purity=96.9%; Factor XIa Ki=1.2 nM, Plasma Kallikrein Ki=290 nM.

Example 283

Preparation of (9R,13S)-13-(4-{2,3-difluoro-6-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one

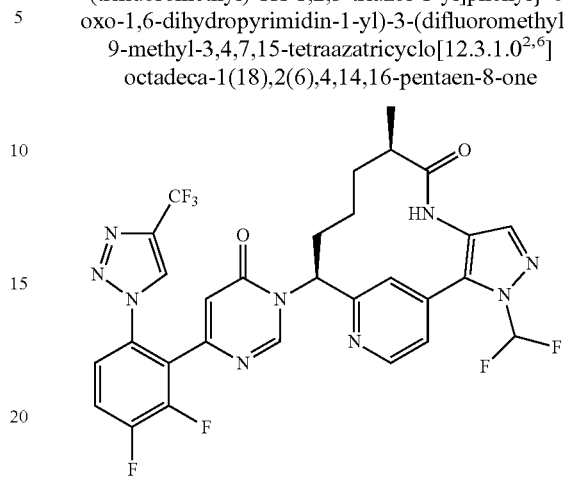

(9R,13S)-13-(4-{2,3-Difluoro-6-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one (12 mg, 100% yield) as a solid was prepared via the coupling of 6-{2,3-difluoro-6-[4-(trifluoromethyl)-1H-1,2,3-triazol-1-yl]phenyl}pyrimidin-4-ol (0.007 g, 0.02 mmol) and (9R,13S)-13-amino-3-(difluoromethyl)-9-methyl-3,4,7,15-tetraazatricyclo[12.3.1.0$^{2,6}$]octadeca-1(18),2(6), 4,14,16-pentaen-8-one (0.07 g, 0.02 mmol) using the HATU, DBU coupling methodology as described in Example 56. MS m/z=662.1(M+H)$^+$. $^1$H NMR (500 MHz, DMSO-d$_6$) δ 9.34-9.30 (m, 1H), 9.15-9.11 (m, 1H), 8.74-8.71 (m, 1H), 8.63-8.59 (m, 1H), 7.85-7.79 (m, 2H), 7.72-7.67 (m, 1H), 7.64-7.61 (m, 1H), 7.38-7.35 (m, 1H), 6.62-6.58 (m, 1H), 5.88-5.73 (m, 1H), 2.63-2.50 (m, 1H), 2.24-2.10 (m, 1H), 2.02-1.92 (m, 1H), 1.83-1.69 (m, 1H), 1.46-1.16 (m, 2H), 0.84-0.70 (d, 3H), 0.37-0.17 (m, 1H). Analytical HPLC (Method B) RT=1.73 min, purity=99%; Factor XIa Ki=2 nM, Plasma Kallikrein Ki=570 nM.

Example 284

Preparation of methyl 1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-imidazole-4-carboxylate

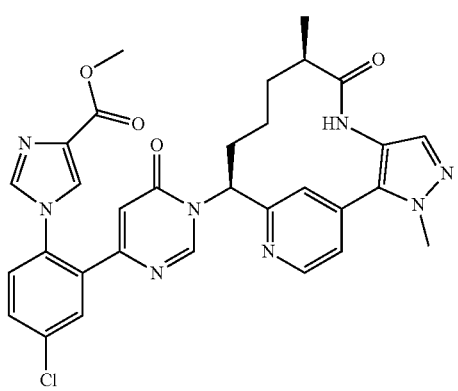 [SMILES: COC(=O)c1cn(-c2ccc(Cl)cc2-c2cc(=O)n([C@H]3CCC[C@@H](C)C(=O)Nc4cnn(C)c4-c4ccnc3c4)cn2)cn1]

Methyl 1-(4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)-1H-imidazole-4-carboxylate trifluoroacetate (10 mg, 24% yield) was prepared in a similar manner as the procedure described in Example 231, by replacing 1H-imidazole with 1H-imidazole-4-carboxylate hydrochloride (0.025 g, 0.195 mmol). MS(ESI) m/z: 613.5 (M+H)⁺. ¹H NMR (400 MHz, CD₃OD) δ 8.80 (s, 1H), 8.68 (d, J=5.3 Hz, 1H), 8.29 (s, 1H), 8.06 (s, 1H), 7.87 (d, J=2.2 Hz, 1H), 7.72 (dd, J=8.6, 2.4 Hz, 1H), 7.68 (s, 1H), 7.62 (d, J=8.4 Hz, 1H), 7.51 (dd, J=5.1, 1.5 Hz, 1H), 7.49 (s, 1H), 6.47 (s, 1H), 5.96 (dd, J=12.4, 3.9 Hz, 1H), 4.04 (s, 3H), 3.87 (s, 3H), 2.75-2.65 (m, 1H), 2.33-2.22 (m, 1H), 2.11-1.92 (m, 2H), 1.64-1.39 (m, 2H), 1.00 (d, J=6.8 Hz, 3H), 0.67 (br. s., 1H). Analytical HPLC (Method A): RT=6.10 min, 99.9% purity; Factor XIa Ki=16 nM, Plasma Kallikrein Ki=1,800 nM.

Example 285

Preparation of (9R,13S)-13-[4-(2,5-dichlorophenyl)-6-oxo-1,6-dihydropyrimidin-1-yl]-3,9-dimethyl-3,4,7,15-tetraazatricyclo[12.3.1.0²,⁶]octadeca-1(18),2(6),4,14,16-pentaen-8-one

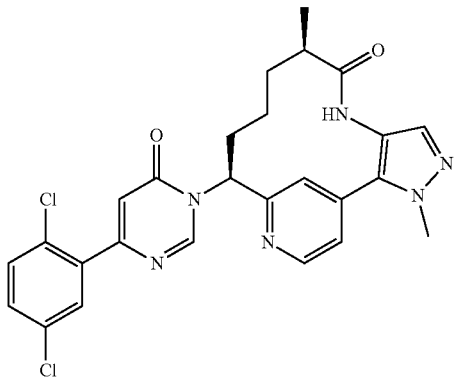

(9R,13S)-13-[4-(2,5-Dichlorophenyl)-6-oxo-1,6-dihydropyrimidin-1-yl]-3,9-dimethyl-3,4,7,15-tetraazatricyclo[12.3.1.0²,⁶]octadeca-1(18),2(6),4,14,16-pentaen-8-one trifluoroacetate (4.3 mg, 13% yield) was a minor product isolated from the preparation of methyl 1-(4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)-1H-imidazole-4-carboxylate, Example 284. MS(ESI) m/z: 523.5 (M+H)⁺. ¹H NMR (400 MHz, CD₃OD) δ 9.04 (s, 1H), 8.74 (d, J=5.3 Hz, 1H), 7.73 (s, 1H), 7.68 (d, J=2.4 Hz, 1H), 7.55-7.49 (m, 3H), 7.49-7.44 (m, 1H), 6.77 (d, J=0.7 Hz, 1H), 6.06 (dd, J=12.7, 4.1 Hz, 1H), 4.05 (s, 3H), 2.78-2.68 (m, 1H), 2.38 (tt, J=12.8, 4.3 Hz, 1H), 2.16-2.02 (m, 2H), 1.68-1.45 (m, 2H), 1.02 (d, J=6.8 Hz, 3H), 0.70 (br. s., 1H). Analytical HPLC (Method A): RT=8.29 min, 98.6% purity; Factor XIa Ki=50 nM, Plasma Kallikrein Ki=770 nM.

Example 286

Preparation of (9R,13R)-13-{4-[5-chloro-2-(4-chloro-1H-1,2,3-triazol-1-yl)phenyl]-6-oxo-1,6-dihydropyrimidin-1-yl}-3,9-dimethyl-3,4,7,18-tetraazatricyclo[12.3.1.0²,⁶]octadeca-1(18),2(6),4,14,16-pentaen-8-one Trifluoroacetate

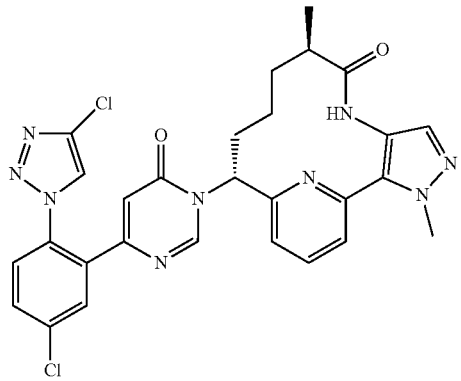 [SMILES: C[C@@H]1CCC[C@@H](n2cnc(-c3cc(Cl)ccc3-n3cc(Cl)nn3)cc2=O)c2cccc(n2)-c2c(cnn2C)NC1=O]

286A. Preparation of (9R,13R)-13-amino-3,9-dimethyl-3,4,7,18-tetraazatricyclo[12.3.1.0²,⁶]octadeca-1(18),2(6),4,14,16-pentaen-8-one

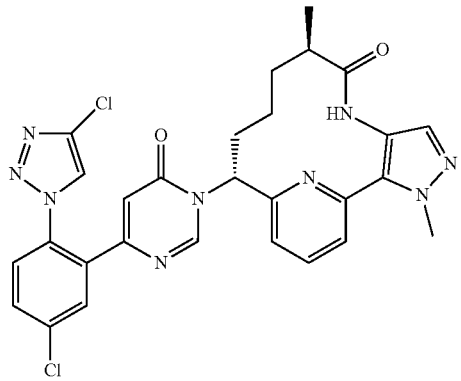 [SMILES: C[C@@H]1CCC[C@@H](n2cnc(-c3cc(Cl)ccc3-n3cc(Cl)nn3)cc2=O)c2cccc(n2)-c2c(cnn2C)NC1=O]

(9R,13R)-13-Amino-3,9-dimethyl-3,4,7,18-tetraazatricyclo[12.3.1.0²,⁶]octadeca-1(18),2(6),4,14,16-pentaen-8-one (15 mg, 100% yield) was prepared in a similar manner as the procedures described in Intermediate 28, by replacing (S)-2-methyl-N-[(1S)-1-[6-(1-methyl-4-nitro-1H-pyrazol-5-yl)pyridin-2-yl]but-3-en-1-yl]propane-2-sulfinamide (Diastereomer B) with (S)-2-methyl-N-[(1R)-1-[6-(1-methyl-4-nitro-1H-pyrazol-5-yl)pyridin-2-yl]but-3-en-1-yl]propane-2-sulfinamide (Diastereomer A). MS(ESI) m/z: 300.5 (M+H)⁺.

286B. Preparation of (9R,13R)-13-{4-[5-chloro-2-(4-chloro-1H-1,2,3-triazol-1-yl) phenyl]-6-oxo-1,6-dihydropyrimidin-1-yl}-3,9-dimethyl-3,4,7,18-tetraazatricyclo[12.3.1.0²,⁶]octadeca-1(18),2(6),4,14,16-pentaen-8-one Trifluoroacetate (9R,13R)-13-{4-[5-Chloro-2-(4-chloro-1H-1,2,3-triazol-1-yl)phenyl]-6-oxo-1,6-dihydropyrimidin-1-yl}-3,9-dimethyl-3,4,7,18-tetraazatricyclo[12.3.1.0²,⁶]octadeca-1(18),2(6),4,14,16-pentaen-8-one trifluoroacetate (7.2 mg, 19% yield) was prepared in a similar manner as the procedure described in Example 56, by using 6-(5-chloro-2-(4-chloro- 1H-1,2,3-triazol-1-yl)phenyl)pyrimidin-4-ol (15.4 mg, 0.050 mmol) and (9R,13R)-13-amino-3,9-dimethyl-3,4,7,18-tetraazatricyclo[12.3.1.0$^{2,6}$]octadeca-1(18),2(6),4,14,16-pentaen-8-one, (15 mg, 0.050 mmol), prepared as described in Example 286A. MS(ESI) m/z: 590.25 (M+H)$^+$. $^1$H NMR (500 MHz, DMSO-d$_6$) δ 9.47 (s, 1H), 8.72 (s, 1H), 8.66 (s, 1H), 7.94 (t, J=7.9 Hz, 1H), 7.90 (d, J=2.4 Hz, 1H), 7.85-7.79 (m, 1H), 7.77-7.70 (m, 2H), 7.52 (s, 1H), 7.23 (d, J=7.6 Hz, 1H), 6.48 (s, 1H), 5.89 (dd, J=12.4, 2.9 Hz, 1H), 4.10 (s, 3H), 3.91 (s, 1H), 3.08-2.94 (m, 1H), 2.74 (dt, J=11.4, 5.8 Hz, 1H), 1.70-1.57 (m, 1H), 1.50-1.29 (m, 3H), 1.05 (d, J=6.7 Hz, 3H), 0.98 (m, 1H). Analytical HPLC (Method B): RT 1.64 min, purity=95%; Factor XIa Ki=1,800 nM.

Example 287

Preparation of (9R,13S)-13-(4-{2,3-difluoro-6-[4-(trifluoromethyl)-1H-1,2,3-triazol-1-yl]phenyl}-6-oxo-1,6-dihydropyrimidin-1-yl)-3-($^2$H$_3$)methyl-9-methyl-3,4,7,17-tetraazatricyclo[12.3.1.0$^{2,6}$]octadeca-1(18),2(6),4,14,16-pentaen-8-one

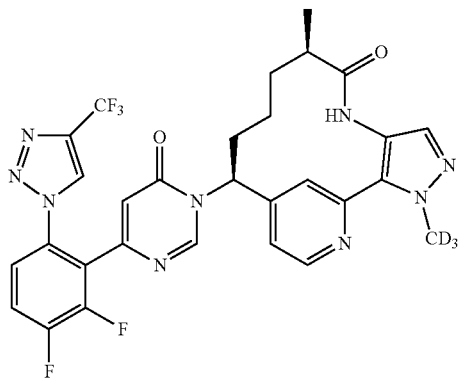 [SMILES: [2H]C([2H])([2H])n1ncc2c1-c1cc(ccn1)[C@@H](n1cnc(-c3c(-n4cc(C(F)(F)F)nn4)ccc(F)c3F)cc1=O)CCC[C@@H](C)C(=O)N2]

(9R,13S)-13-(4-{2,3-Difluoro-6-[4-(trifluoromethyl)-1H-1,2,3-triazol-1-yl]phenyl}-6-oxo-1,6-dihydropyrimidin-1-yl)-3-($^2$H$_3$)methyl-9-methyl-3,4,7,17-tetraazatricyclo[12.3.1.0$^{2,6}$]octadeca-1(18),2(6),4,14,16-pentaen-8-one (3 mg, 27% yield) as a solid was prepared via the coupling of 6-{2,3-difluoro-6-[4-(trifluoromethyl)-1H-1,2,3-triazol-1-yl]phenyl}) pyrimidin-4-ol (0.005 g, 0.015 mmol) and (9R,13S)-13-amino-3-($^2$H$_3$)methyl-9-methyl-3,4,7,17-tetraazatricyclo[12.3.1.0$^{2,6}$]octadeca-1(18),2(6),4,14,16-pentaen-8-one (0.004 g, 0.015 mmol) using the HATU, DBU coupling methodology as described in Example 56. MS m/z=629.1 (M+H)$^1$. $^1$H NMR (500 MHz, DMSO-d$_6$) δ 9.30-9.26 (m, 1H), 9.23-9.17 (m, 1H), 8.67-8.61 (m, 1H), 8.58-8.53 (m, 1H), 7.96-7.86 (m, 1H), 7.81-7.74 (m, 2H), 7.45 (s, 1H), 6.98-6.94 (m, 1H), 6.73-6.69 (m, 1H), 5.65-5.48 (m, 1H), 2.55 (s, 1H), 2.44-2.28 (m, 1H), 2.03-1.81 (m, 2H), 1.99-1.76 (m, 2H), 1.53-1.38 (m, 2H), 1.32-1.19 (m, 1H), 1.15-1.06 (d, 3H), 1.01-0.91 (m, 1H). Analytical HPLC (Method B) RT=1.55 min, purity=94%; Factor XIa Ki=4 nM, Plasma Kallikrein Ki=520 nM.

Example 288

Preparation of 1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-imidazole-4-carboxylic Acid

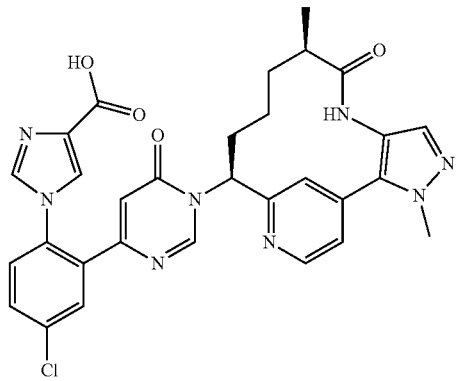 [SMILES: C[C@@H]1CCC[C@H](n2cnc(-c3cc(Cl)ccc3-n3cnc(C(=O)O)c3)cc2=O)c2cc(ccn2)-c2c(cnn2C)NC1=O]

To the solution of methyl 1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-imidazole-4-carboxylate (0.008 g, 9.51 µmol), prepared as described in Example 284, in MeOH (1 ml) was added 1 N NaOH (0.057 ml, 0.057 mmol). After stirring at rt for 24 h, the reaction was quenched with a few drops of TFA. Purification by reverse phase chromatography afforded 1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-imidazole-4-carboxylic acid trifluoroacetate (4.8 mg, 61% yield) as a white solid. MS(ESI) m/z: 599.5 (M+H)$^+$. $^1$H NMR (400 MHz, CD$_3$OD) δ 8.76 (s, 1H), 8.71-8.66 (m, 2H), 8.11 (br. s., 1H), 7.89 (d, J=2.2 Hz, 1H), 7.77-7.72 (m, 1H), 7.70-7.65 (m, 2H), 7.51-7.48 (m, 2H), 6.58 (s, 1H), 5.97 (dd, J=12.5, 4.2 Hz, 1H), 4.04 (s, 3H), 2.75-2.64 (m, 1H), 2.34-2.22 (m, 1H), 2.12-1.93 (m, 2H), 1.65-1.39 (m, 2H), 1.00 (d, J=6.8 Hz, 3H), 0.79-0.62 (m, 1H). Analytical HPLC (Method A): RT=5.13 min, 99.5% purity; Factor XIa Ki=3.7 nM, Plasma Kallikrein Ki=450 nM.

Example 289

Preparation of (9R,13S)-13-{4-[5-chloro-2-(4-chloro-1H-1,2,3-triazol-1-yl)phenyl]-6-oxo-1,6-dihydropyrimidin-1-yl}-3,9-dimethyl-3,4,7,18-tetraazatricyclo[12.3.1.0$^{2,6}$]octadeca-1(18),2(6),4,14,16-pentaen-8-one

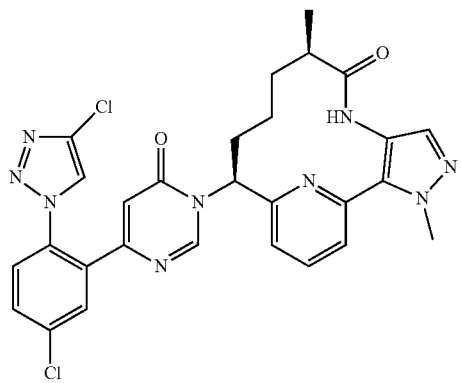 [SMILES: C[C@@H]1CCC[C@H](n2cnc(-c3cc(Cl)ccc3-n3cc(Cl)nn3)cc2=O)c2cccc(n2)-c2c(cnn2C)NC1=O]

(9R,13S)-13-{4-[5-Chloro-2-(4-chloro-1H-1,2,3-triazol-1-yl)phenyl]-6-oxo-1,6-dihydropyrimidin-1-yl}-3,9-dimethyl-3,4,7,18-tetraazatricyclo[12.3.1.0$^{2,6}$]octadeca-1(18),2(6),4,14,16-pentaen-8-one trifluoroacetate (1.8 mg, 5% yield) was prepared in a similar manner as the procedure described in Example 56, by using 6-(5-chloro-2-(4-chloro-1H-1,2,3-triazol-1-yl)phenyl)pyrimidin-4-ol (15.4 mg, 0.050 mmol) and (9R,13S)-13-amino-3,9-dimethyl-3,4,7,18-tetraazatricyclo[12.3.1.0$^{2,6}$]octadeca-1(18),2(6),4,14,16-pentaen-8-one, 15 mg, 0.050 mmol), prepared as described in Intermediate 28. MS(ESI) m/z: 590.25 (M+H)$^+$. $^1$H NMR (500 MHz, DMSO-d$_6$) δ 9.41 (s, 1H), 8.71 (s, 1H), 8.15 (s, 1H), 7.97 (t, J=7.8 Hz, 1H), 7.90 (d, J=2.4 Hz, 1H), 7.84-7.79 (m, 1H), 7.75 (dd, J=8.1, 6.0 Hz, 2H), 7.52 (s, 1H), 7.20 (d, J=7.9 Hz, 1H), 6.48 (s, 1H), 5.97 (d, J=8.5 Hz, 1H), 4.04 (s, 3H), 3.91 (s, 1H), 2.58 (m, 1H), 2.44-2.31 (m, 1H), 2.09 (d, J=7.6 Hz, 1H), 1.83-1.73 (m, 1H), 1.53-1.39 (m, 2H), 1.23 (m, 1H), 1.00 (d, J=6.7 Hz, 3H). Analytical HPLC (Method B): RT 1.59 min, purity=93%; Factor XIa Ki=2.3 nM, Plasma Kallikrein Ki=380 nM.

Example 290

Preparation of (10R,14S)-14-{4-[5-chloro-2-(4-chloro-1H-1,2,3-triazol-1-yl)phenyl]-6-oxo-1,6-dihydropyrimidin-1-yl}-10-methyl-3,5,8-triazatricyclo[13.3.1.0$^{2,7}$]nonadeca-1(19),2(7),3,5,15,17-hexaen-9-one

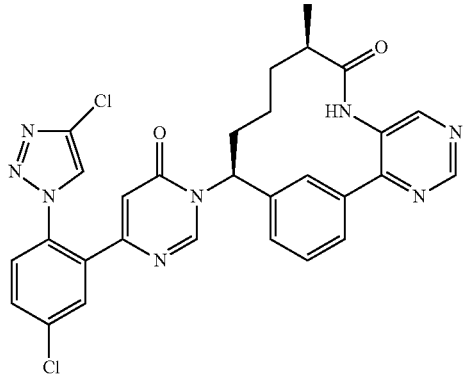 [SMILES: C[C@@H]1CCC[C@H](n2cnc(-c3cc(Cl)ccc3-n3cc(Cl)nn3)cc2=O)c2cccc(c2)-c2ncncc2NC1=O]

(10R,14S)-14-{4-[5-Chloro-2-(4-chloro-1H-1,2,3-triazol-1-yl)phenyl]-6-oxo-1,6-dihydropyrimidin-1-yl}-10-methyl-3,5,8-triazatricyclo[13.3.1.0$^{2,7}$]nonadeca-1(19),2(7),3,5,15,17-hexaen-9-one trifluoroacetate (0.004 g, 28%) was prepared according to the procedures described in Example 206 by using (10R,14S)-14-amino-10-methyl-3,5,8-triazatricyclo[13.3.1.0$^{2,7}$]nonadeca-1(19),2,4,6,15,17-hexaen-9-one, prepared as described in Intermediate 38, and 4-bromopyrimidin-5-amine in prepared as described in Intermediate 38B. MS(ESI) m/z: 587.1 (M+H)$^+$. $^1$H NMR (400 MHz, CD$_3$OD) δ 9.18 (s, 1H), 8.71 (s, 1H), 8.35-8.31 (m, 2H), 8.01 (s, 1H), 7.87 (d, J=2.4 Hz, 1H), 7.86-7.83 (m, 1H), 7.76-7.71 (m, 1H), 7.67-7.62 (m, 2H), 7.35 (d, J=7.9 Hz, 1H), 6.42 (d, J=0.7 Hz, 1H), 5.84 (dd, J=13.0, 3.7 Hz, 1H), 2.72-2.59 (m, 1H), 2.40-2.27 (m, 1H), 2.18-2.07 (m, 1H), 2.03-1.94 (m, 1H), 1.68-1.56 (m, 1H), 1.46-1.33 (m, 2H), 1.15 (d, J=7.0 Hz, 3H). Analytical HPLC (Method A): RT=8.12 min, purity>99%; Factor XIa Ki=2.4 nM, Plasma Kallikrein Ki=150 nM.

Example 292

Preparation of (9R,13S)-13-{4-[5-chloro-1-(2-hydroxyethyl)-1H-indazol-7-yl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one

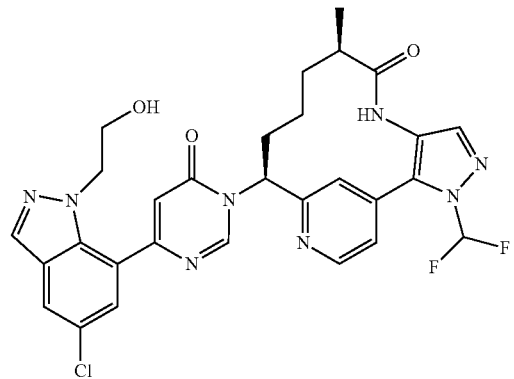 [SMILES: C[C@@H]1CCC[C@H](n2cnc(-c3cc(Cl)cc4cnn(CCO)c34)cc2=O)c2cc(ccn2)-c2c(cnn2C(F)F)NC1=O]

292A and 292B. Preparation of 7-bromo-5-chloro-1-(2-methoxyethyl)-1H-indazole, and 7-bromo-5-chloro-2-(2-methoxyethyl)-2H-indazole To a suspension of 7-bromo-5-chloro-1H-indazole (2.0 g, 8.64 mmol) and K$_2$CO$_3$ (5.97 g, 43.2 mmol) in DMSO (9.97 mL) was added 1-bromo-2-methoxyethane (0.812 mL, 8.64 mmol) at rt under a blanket of Ar. After 14 h, the reaction mixture was diluted with water, extracted with EtOAc. The combined organic layer was washed with water, brine, dried over Na$_2$SO$_4$, filtered, and concentrated. The crude mixture of regioisomers (1:1) was purified by normal phase chromatography using hexanes and EtOAc as eluants to afford 7-bromo-5-chloro-1-(2-methoxyethyl)-1H-indazole as the early eluting isomer (less polar) (0.766 g, 30%) and 7-bromo-5-chloro-2-(2-methoxyethyl)-2H-indazole as the late eluting isomer (more polar) (1.18 g, 47%).

292A. MS(ESI) m/z: 290 (M+H)$^+$ and 292 (M+2+H)$^+$. $^1$H NMR (500 MHz, CDCl$_3$) δ 7.97 (s, 1H), 7.66 (d, J=1.7 Hz, 1H), 7.56 (d, J=1.9 Hz, 1H), 4.98 (t, J=6.1 Hz, 2H), 3.85 (t, J=6.1 Hz, 2H), 3.34 (s, 3H).

292B. MS(ESI) m/z: 290 (M+H)$^+$ and 292 (M+2+H)$^+$. $^1$H NMR (400 MHz, CDCl$_3$) δ 8.08 (s, 1H), 7.60 (d, J=1.5 Hz, 1H), 7.48 (d, J=1.8 Hz, 1H), 4.64-4.59 (m, 2H), 3.89-3.84 (m, 2H), 3.34 (s, 3H).

292C. Preparation of 5-chloro-1-(2-methoxyethyl)-7-(4,4,5,5-tetramethyl-1,3,2-dioxaborolan-2-yl)-1H-indazole To a stirring solution of 7-bromo-5-chloro-1-(2-methoxyethyl)-1H-indazole (0.766 g, 2.65 mmol) in dioxane (13.23 mL) at RT was added 4,4,4',4',5,5,5',5'-octamethyl-2,2'-bi(1,3,2-dioxaborolane) (0.773 g, 3.04 mmol) and KOAc (1.194 g, 12.17 mmol) and the system was purged with Ar (3×). Pd(dppf)Cl$_2$·CH$_2$Cl$_2$ complex (0.173 g, 0.212 mmol) was added, the reaction was purged with Ar, and heated to 90° C. After stirring overnight, the reaction mixture was cooled to rt, diluted with water, extracted with EtOAc (3×). The combined organic layer was washed with water, brine, dried over Na$_2$SO$_4$, filtered, and concentrated. MS(ESI) m/z: 337 (M+H)$^+$.

292D. Preparation of 5-chloro-1-(2-methoxyethyl)-7-(6-methoxypyrimidin-4-yl)-1H-indazole 4-Chloro-6-methoxypyrimidine (0.574 g, 3.97 mmol), 5-chloro-1-(2-methoxyethyl)-7-(4,4,5,5-tetramethyl-1,3,2-dioxaborolan-2-yl)-1H-indazole (0.891 g, 2.65 mmol) and 2 M aq Na$_2$CO$_3$ (2.65 mL, 5.29 mmol) were added to DME (17.65 mL)/EtOH (2.206 mL) and purged with Ar for several min. Pd(dppf).CH$_2$Cl$_2$ Adduct (0.216 g, 0.265 mmol) was added and the reaction heated at 90° C. After 14 h, the reaction was diluted with water, extracted with EtOAc, the organic layer washed with brine, dried over Na$_2$SO$_4$, filtered, and concentrated to give a brown oil. The crude material was purified by normal phase chromatography using hexanes and EtOAc as eluents to give 5-chloro-1-(2-methoxyethyl)-7-(6-methoxypyrimidin-4-yl)-1H-indazole (0.777 g, 92% yield) brown oil. MS(ESI) m/z: 319 (M+H)$^+$.

292E. Preparation of 6-(5-chloro-1-(2-hydroxyethyl)-1H-indazol-7-yl)pyrimidin-4-ol Trifluoroacetate To a suspension of 5-chloro-1-(2-methoxyethyl)-7-(6-methoxypyrimidin-4-yl)-1H-indazole (0.300 g, 0.941 mmol) in ACN (3.14 mL) was added TMSI (1 mL, 7.35 mmol) at rt. Then, the clear yellow solution was heated to 50° C. After 4 h, the reaction mixture was cooled to rt, concentrated and purified by reverse phase chromatography (PHENOMENEX) Luna Axia C18 5µ 30×100 mm column, 10-minute gradient; Solvent A: 30% MeOH-70% H$_2$O-0.1% TFA; Solvent B: 90% MeOH-10% H$_2$O-0.1% TFA) to give 6-(5-chloro-1-(2-hydroxyethyl)-1H-indazol-7-yl)pyrimidin-4-ol trifluoroacetate (0.127 g, 33.3% yield) as a yellow solid. MS(ESI) m/z: 291 (M+H)$^1$. $^1$H NMR (400 MHz, CD$_3$OD) δ 8.52 (d, J=0.9 Hz, 1H), 8.17 (s, 1H), 7.95 (d, J=2.0 Hz, 1H), 7.47 (d, J=2.0 Hz, 1H), 6.79 (d, J=0.9 Hz, 1H), 4.45 (t, J=5.9 Hz, 2H), 3.80 (t, J=5.9 Hz, 2H).

292F. Preparation of (9R,13S)-13-{4-[5-chloro-1-(2-hydroxyethyl)-1H-indazol-7-yl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one Trifluoroacetate (9R,13S)-13-{4-[5-Chloro-1-(2-hydroxy ethyl)-1H-indazol-7-yl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one trifluoroacetate (6.6 mg, 29%) was prepared in a similar manner as Example 56 using 6-(5-chloro-1-(2-hydroxyethyl)-1H-indazol-7-yl)pyrimidin-4-ol trifluoroacetate and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one, prepared as described in Intermediate 30. MS(ESI) m/z: 609 (M+H)$^+$. $^1$H NMR (400 MHz, DMSO-d$_6$) δ 9.36 (s, 1H), 9.02 (s, 1H), 8.70 (d, J=5.1 Hz, 1H), 8.13 (s, 1H), 7.93 (d, J=2.0 Hz, 1H), 7.85 (s, 1H), 7.69 (s, 1H), 7.40-7.35 (m, 2H), 6.68 (s, 1H), 5.93 (d, J=8.6 Hz, 1H), 4.40-4.28 (m, 2H), 3.50-3.39 (m, 2H), 2.64-2.58 (m, 1H), 2.38-2.30 (m, 1H), 2.11-1.99 (m, 1H), 1.96-1.85 (m, 1H), 1.50-1.39 (m, 1H), 1.36-1.27 (m, 1H), 0.83 (d, J=7.0 Hz, 3H), 0.38-0.28 (m, 1H). Analytical HPLC (Method A): RT=7.16 min, purity=>95%; Factor XIa Ki=180 nM.

Example 293

Preparation of (9R,13S)-13-[4-(5-chloro-1-methyl-1H-indol-7-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one

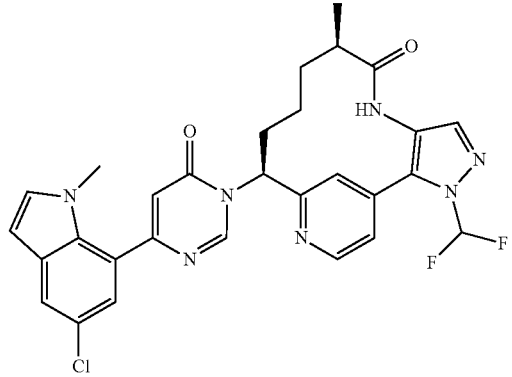 [SMILES: C[C@@H]1CCC[C@H](n2cnc(-c3cc(Cl)cc4ccn(C)c34)cc2=O)c2cc(ccn2)-c2c(cnn2C(F)F)NC1=O]

293A. Preparation of 5-chloro-7-(4,4,5,5-tetramethyl-1,3,2-dioxaborolan-2-yl)-1H-indole To a solution of 7-bromo-5-chloro-1H-indole (0.470 g, 2.039 mmol) in dioxane (10.20 mL) at rt was added 4,4,4',4',5,5,5',5'-octamethyl-2,2'-bi(1,3,2-dioxaborolane) (0.595 g, 2.345 mmol) and KOAc (0.921 g, 9.38 mmol), and the system was purged with Ar (3×). Pd(dppf)Cl$_2$. CH$_2$Cl$_2$ complex (0.133 g, 0.163 mmol) was added and the reaction mixture was again purged with Ar, and heated to 90° C. After stirring overnight, the reaction mixture was cooled to rt, diluted with water, extracted with EtOAc (3×), organics washed with water, brine, dried over Na$_2$S$_{O4}$, filtered, and concentrated and the crude material was carried forward to the next reaction. MS(ESI) m/z: 278 (M+H)$^+$.

293B. Preparation of 5-chloro-7-(6-methoxypyrimidin-4-yl)-1H-indole

4-Chloro-6-methoxypyrimidine (0.391 g, 2.70 mmol), 5-chloro-7-(4,4,5,5-tetramethyl-1,3,2-dioxaborolan-2-yl)-1H-indole (0.500 g, 1.801 mmol) and 2 M aq Na$_2$CO$_3$ (1.801 ml, 3.60 mmol) were added to DME (14.41 mL)/EtOH (1.801 mL) and purged with Ar for several min. PdCl$_2$(dppf)-CH$_2$Cl$_2$ Adduct (0.147 g, 0.180 mmol) was added and heated at 90° C. After 2 h, the reaction was diluted with water and extracted with EtOAc. The organic layer was washed with brine, dried over Na$_2$SO$_4$, filtered, and concentrated. The crude material was purified by normal phase chromatography using hexanes and EtOAc as eluants to give 5-chloro-7-(6-methoxypyrimidin-4-yl)-1H-indole (0.339 g, 72.5% yield) as an amber solid. MS(ESI) m/z: 260 (M+H)$^+$. $^1$H NMR (400 MHz, CDCl$_3$) δ 11.21 (br. s., 1H), 11.36-11.06 (m, 1H), 8.91 (d, J=1.1 Hz, 1H), 7.77-7.74 (m, 1H), 7.72 (d, J=1.8 Hz, 1H), 7.40-7.38 (m, 1H), 7.30 (d, J=1.1 Hz, 1H), 6.56 (dd, J=3.1, 2.4 Hz, 1H), 4.07 (s, 2H).

293C. Preparation of 6-(5-chloro-1-methyl-1H-indol-7-yl)pyrimidin-4-ol

MeI (0.212 ml, 3.39 mmol) was added to a suspension of 5-chloro-7-(6-methoxypyrimidin-4-yl)-1H-indole (0.339 g, 1.305 mmol) and K₂CO₃ (0.902 g, 6.53 mmol) in DMSO (5.22 mL) at rt. After stirring overnight, the reaction mixture was partitioned between dilute NH₄Cl solution and EtOAc. The organic layer was washed dilute NaHCO₃ and Na₂S₂O₃ solution, NaHCO₃, brine, then dried over MgSO₄, filtered and evaporated to dryness. The residue was dissolved in AcOH (5 mL) and treated with 45% aq HBr i (1.73 mL, 14.36 mmol) and heated to 85° C. After 2 h, the reaction was cooled to rt, then concentrated to dryness and the material was carried forward to the reaction. MS(ESI) m/z: 260 (M+H)⁺.

293D. Preparation of (9R,13S)-13-[4-(5-chloro-1-methyl-1H-indol-7-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one Trifluoroacetate (9R,13S)-13-[4-(5-Chloro-1-methyl-1H-indol-7-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one trifluoroacetate (4 mg, 18%) was prepared in a similar manner as Example 56 using 6-(5-chloro-1-methyl-1H-indol-7-yl)pyrimidin-4-ol and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one, prepared as described in Intermediate 30. MS(ESI) m/z: 578 (M+H)⁺. ¹H NMR (400 MHz, DMSO-d₆) δ 9.36 (s, 1H), 8.98 (s, 1H), 8.70 (d, J=5.1 Hz, 1H), 7.85 (s, 1H), 7.69 (s, 1H), 7.65 (d, J=2.0 Hz, 1H), 7.39-7.35 (m, 2H), 7.03 (d, J=2.0 Hz, 1H), 6.57 (s, 1H), 6.46 (d, J=3.1 Hz, 1H), 5.94-5.90 (m, 1H), 3.53 (s, 3H), 2.63-2.60 (m, 1H), 2.35-2.30 (m, 1H), 2.06-2.02 (m, 1H), 1.95-1.88 (m, 1H), 1.46-1.40 (m, 1H), 1.34-1.28 (m, 1H), 0.82 (d, J=6.8 Hz, 3H), 0.37-0.29 (m, 1H). Analytical HPLC (Method A): RT=9.19 min, purity=>95%; Factor XIa Ki=390 nM.

Example 294

Preparation of (9R,13S)-13-{4-[5-chloro-2-(2-hydroxyethyl)-2H-indazol-7-yl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one

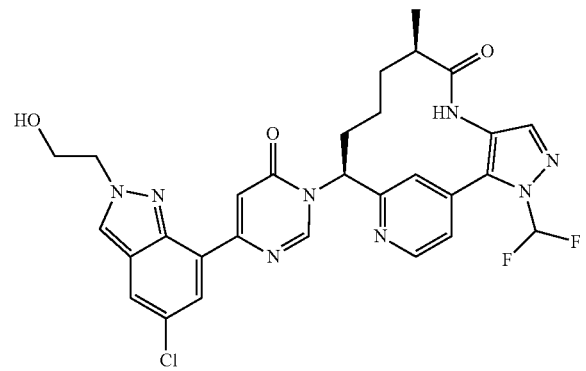 [SMILES: C[C@@H]1CCC[C@H](n2cnc(-c3cc(Cl)cc4cn(CCO)nc34)cc2=O)c2cc(ccn2)-c2c(cnn2C(F)F)NC1=O]

294A. Preparation of 5-chloro-2-(2-methoxyethyl)-7-(4,4,5,5-tetramethyl-1,3,2-dioxaborolan-2-yl)-2H-indazole 5-Chloro-2-(2-methoxyethyl)-7-(4,4,5,5-tetramethyl-1,3,2-dioxaborolan-2-yl)-2H-indazole was prepared in a similar manner as Example 292C replacing 7-bromo-5-chloro-1-(2-methoxyethyl)-1H-indazole, prepared as described in Example 292B with 7-bromo-5-chloro-2-(2-methoxyethyl)-2H-indazole, prepared as described in Example 292C. MS(ESI) m/z: 337 (M+H)⁺.

294B. Preparation of 5-chloro-2-(2-methoxyethyl)-7-(6-methoxypyrimidin-4-yl)-2H-indazole 5-Chloro-2-(2-methoxyethyl)-7-(6-methoxypyrimidin-4-yl)-2H-indazole (300 mg, 26%) was prepared in a similar manner as described in Example 292D using 5-chloro-2-(2-methoxyethyl)-7-(4,4,5,5-tetramethyl-1,3,2-dioxaborolan-2-yl)-2H-indazole. MS(ESI) m/z: 319 (M+H)⁺. ¹H NMR (400 MHz, CDCl₃) δ 8.87 (d, J=1.1 Hz, 1H), 8.39 (t, J=1.8 Hz, 2H), 8.09 (s, 1H), 7.75 (d, J=2.0 Hz, 1H), 4.63 (t, J=5.2 Hz, 2H), 4.06 (s, 3H), 3.92-3.88 (m, 2H), 3.35 (s, 3H).

294C. Preparation of 6-(5-chloro-2-(2-hydroxyethyl)-2H-indazol-7-yl)pyrimidin-4-ol 6-(5-Chloro-2-(2-hydroxyethyl)-2H-indazol-7-yl)pyrimidin-4-ol, (50 mg, 18%) was prepared in a similar manner as Example 292E using 5-chloro-2-(2-methoxyethyl)-7-(6-methoxypyrimidin-4-yl)-2H-indazole. MS(ESI) m/z: 291 (M+H)⁺ and 293 (M+2+H)⁺. ¹H NMR (400 MHz, CD₃OD) δ 8.71 (s, 1H), 8.46 (s, 1H), 8.22 (d, J=2.0 Hz, 1H), 8.05 (s, 1H), 8.01 (d, J=1.8 Hz, 1H), 4.65 (t, J=5.2 Hz, 2H), 4.14-4.09 (m, 2H).

294D. Preparation of (9R,13S)-13-{4-[5-chloro-2-(2-hydroxyethyl)-2H-indazol-7-yl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one Trifluoroacetate (9R,13S)-13-{4-[5-Chloro-2-(2-hydroxyethyl)-2H-indazol-7-yl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one trifluoroacetate was prepared (2 mg, 8.8%) in a similar manner as Example 56 using 6-(5-chloro-2-(2-hydroxyethyl)-2H-indazol-7-yl)pyrimidin-4-ol and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one, prepared as described in Intermediate 30. MS(ESI) m/z: 609 (M+H)'. 1H NMR (400 MHz, DMSO-d₆) δ 9.36 (s, 1H), 9.00 (s, 1H), 8.69 (d, J=5.1 Hz, 1H), 8.49 (s, 1H), 8.21 (d, J=2.2 Hz, 1H), 8.03-7.97 (m, 2H), 7.85 (s, 1H), 7.68 (s, 1H), 7.37 (d, J=6.2 Hz, 1H), 5.92-5.89 (m, 1H), 4.48 (t, J=5.3 Hz, 2H), 3.82 (t, J=5.3 Hz, 2H), 2.62-2.59 (m, 1H), 2.34-2.29 (m, 1H), 2.07-2.02 (m, 1H), 1.91-1.87 (m, 1H), 1.47-1.41 (m, 1H), 1.34-1.29 (m, 1H), 0.83 (d, J=6.8 Hz, 3H), 0.38-0.30 (m, 1H). Analytical HPLC (Method A): RT=7.86 min, purity=>95%; Factor XIa Ki=6,100 nM.

Example 295

Preparation of (9R,13S)-13-[4-(6-chloro-1-methyl-1H-indazol-4-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one

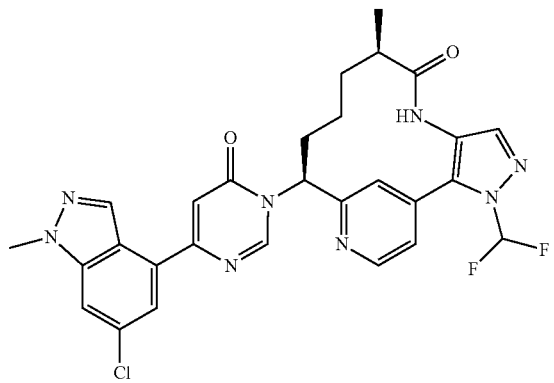 [SMILES: C[C@@H]1CCC[C@H](n2cnc(-c3cc(Cl)cc4c3cnn4C)cc2=O)c2cc(ccn2)-c2c(cnn2C(F)F)NC1=O]

295A. Preparation of 6-chloro-4-(4,4,5,5-tetramethyl-1,3,2-dioxaborolan-2-yl)-1H-indazole 6-Chloro-4-(4,4,5,5-tetramethyl-1,3,2-dioxaborolan-2-yl)-1H-indazole was prepared in a similar manner as described in Example 293A replacing 7-bromo-5-chloro-1H-indole with 4-bromo-6-chloro-1H-indazole. MS(ESI) m/z: 197 (M-C$_6$H$_{10}$+H)$^+$.

295B. Preparation of 6-chloro-4-(6-methoxypyrimidin-4-yl)-1H-indazole

6-Chloro-4-(6-methoxypyrimidin-4-yl)-1H-indazole (183 mg, 33%) was prepared in a similar manner as described in Example 293B using 6-chloro-4-(4,4,5,5-tetramethyl-1,3,2-dioxaborolan-2-yl)-1H-indazole. MS(ESI) m/z: 261 (M+H)$^+$.

295C. Preparation of 6-(6-chloro-1-methyl-1H-indazol-4-yl)pyrimidin-4-ol

MeI (0.12 mL, 1.825 mmol) was added to a suspension of 6-chloro-4-(6-methoxypyrimidin-4-yl)-1H-indazole (0.183 g, 0.702 mmol) and K$_2$CO$_3$ (0.485 g, 3.51 mmol) in DMSO (2.81 mL) at rt. After stirring overnight, the reaction mixture was partitioned between dilute aq NH$_4$Cl solution and EtOAc. The organic layer was washed with dilute NaHCO$_3$ and Na$_2$S$_2$O$_3$ solution, NaHCO$_3$, brine, then dried over MgSO$_4$, filtered, and evaporated to dryness. This mixture of regioisomers (2:1) was carried forward to the next reaction. The residue was dissolved in AcOH (3 mL), treated with 45% aq HBr (0.932 ml, 7.72 mmol), and heated to 85° C. After 1 h, the reaction mixture was concentrated to dryness, and the crude reaction mixture was purified by reverse phase chromatography (PHENOMENEX® Luna Axia C18 5µ 30×100 mm column, 10-minute gradient; Solvent A: 30% ACN-70% H$_2$O-0.1% TFA; Solvent B: 80% ACN-20% H$_2$O-0.1% TFA) to give the desired isomer, 6-(6-chloro-1-methyl-1H-indazol-4-yl)pyrimidin-4-ol (0.127 g, 69.4%) as a white solid and undesired isomer, 6-(6-chloro-2-methyl-2H-indazol-4-yl)pyrimidin-4-ol (0.051 g, 27.9%) as an off-white solid. The methyl group is more downfield for the undesired isomer than for the desired. MS(ESI) m/z: 261 (M+H)$^+$. $^1$H NMR: (400 MHz, DMSO-d$_6$) δ 12.69 (br. s., 1H), 8.51 (d, J=0.9 Hz, 1H), 8.37 (d, J=0.7 Hz, 1H), 8.03-7.99 (m, 1H), 7.77-7.74 (m, 1H), 6.99 (d, J=0.9 Hz, 1H), 4.09 (s, 3H).

295D. Preparation of (9R,13S)-13-[4-(6-chloro-1-methyl-1H-indazol-4-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one Trifluoroacetate (9R,13S)-13-[4-(6-Chloro-1-methyl-1H-indazol-4-yl)-6-oxo-1,6-dihydropyrimidin-1-yl]-3-(difluoromethyl)-9-methyl-3,4,7,15-tetraazatricyclo[12.3.1.0$^{2,6}$]octadeca-1(18),2(6),4,14,16-pentaen-8-one trifluoroacetate was prepared (1.5 mg, 6.9%) in a similar manner as Example 56 using 6-(6-chloro-1-methyl-1H-indazol-4-yl) pyrimidin-4-ol and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one, prepared as described in Intermediate 30. MS(ESI) m/z: 579 (M+H)$^+$. Analytical HPLC (Method A): RT=8.40 min, purity=>95%; Factor XIa Ki=7,400 nM.

Example 296

Preparation of (9R,13S)-13-{4-[5-chloro-2-(4-chloro-1H-1,2,3-triazol-1-yl)phenyl]-6-oxo-1,6-dihydropyrimidin-1-yl}-4-(6-hydroxypyridin-3-yl)-9-methyl-3,4,7,15-tetraazatricyclo[12.3.1.0$^{2,6}$]octadeca-1(18),2,5,14,16-pentaen-8-one

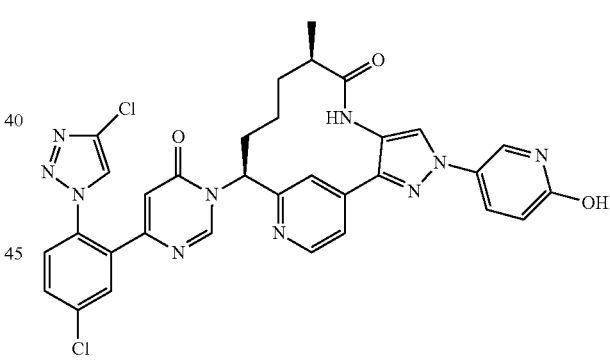

(9R,13S)-13-{4-[5-Chloro-2-(4-chloro-1H-1,2,3-triazol-1-yl)phenyl]-6-oxo-1,6-dihydropyrimidin-1-yl}-4-(6-methoxypyridin-3-yl)-9-methyl-3,4,7,15-tetraazatricyclo[12.3.1.0$^{2,6}$]octadeca-1(18),2,5,14,16-pentaen-8-one, prepared as described in Example 233, was dissolved in THF (1 mL) and HCl (0.5 mL). The solution was heated to 70° C. for 8 h, then cooled to rt, concentrated and purified by reverse phase chromatography to give (9R,13S)-13-{4-[5-chloro-2-(4-chloro-1H-1,2,3-triazol-1-yl)phenyl]-6-oxo-1,6-dihydropyrimidin-1-yl}-4-(6-hydroxypyridin-3-yl)-9-methyl-3,4,7,15-tetraazatricyclo[12.3.1.0$^{2,6}$]octadeca-1(18),2,5,14,16-pentaen-8-one trifluoroacetate (2.2 mg, 21%). MS(ESI) m/z: 669.3 (M+H)$^+$. $^1$H NMR (500 MHz, DMSO-d$_6$) δ 9.55-9.54 (m, 1H), 9.52 (s, 1H), 8.76-8.65 (m, 2H), 8.58 (d, J=5.2 Hz, 1H), 8.38 (s, 1H), 8.03 (d, J=9.8 Hz, 1H), 7.98 (d, J=2.7 Hz, 1H), 7.92 (d, J=2.1 Hz, 1H), 7.87 (s, 1H), 7.84-7.78 (m, 1H), 7.73 (d, J=8.5 Hz, 1H), 7.56 (d, J=5.2 Hz, 1H), 6.57 (d, J=9.8 Hz, 1H), 6.36 (s, 1H), 6.03-5.90 (m, 1H), 2.33-2.15 (m, 2H), 1.93-1.78 (m, 1H), 1.63-1.50 (m, 1H), 1.49-1.35 (m, 1H), 0.94 (d, J=6.7 Hz, 3H), 0.65-0.49 (m, 1H). Analytical HPLC (Method C): RT=1.41 min, purity=95%; Factor XIa Ki=1 nM, Plasma Kallikrein Ki=43 nM.

Example 297

Preparation of (9R,13S)-13-{4-[5-chloro-2-(1,2,3-thiadiazol-4-yl)phenyl]-6-oxo-1,6-dihydropyrimidin-1-yl}-3-(difluoromethyl)-9-methyl-3,4,7,15-tetraaza-tricyclo[12.3.1.0$^{2,6}$]octadeca-1(18),2(6),4,14,16-pentaen-8-one

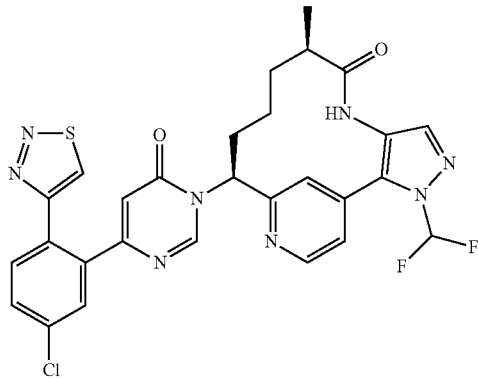 [SMILES: C[C@@H]1CCC[C@H](n2cnc(-c3cc(Cl)ccc3-c3csnn3)cc2=O)c2cc(ccn2)-c2c(cnn2C(F)F)NC1=O]

297A. Preparation of 1-[4-chloro-2-(6-methoxypy-rimidin-4-yl)phenyl]ethan-1-one

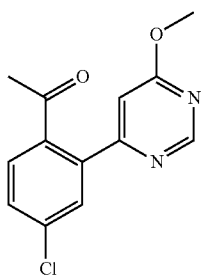 [SMILES: COc1cc(-c2cc(Cl)ccc2C(C)=O)ncn1]

A solution of 4-(2-bromo-5-chlorophenyl)-6-methoxypyrimidine (0.173 g, 0.578 mmol), CsF (0.351 g, 2.310 mmol) in ClCH$_2$CH$_2$Cl (3 mL) was purged with Ar, and Pd(PPh$_3$)$_4$ (0.033 g, 0.029 mmol) and 1-(trimethylsilyl)ethanone (0.165 mL, 1.155 mmol) were added. The reaction mixture was purged with Ar, sealed and heated at 75° C. for 2 days then cooled down to rt. Hexane (1 ml) was added, reaction mixture was filtered through a pad of CELITE®, rinsed with 10 ml EtOAc, filtrate concentrated. Purification by normal phase chromatography gave 1-[4-chloro-2-(6-methoxypy-rimidin-4-yl)phenyl]ethan-1-one (0.057 g, 38% yield). MS(ESI) m/z: 263.08 (M+H)$^+$.

297B. Preparation of N'-{1-[4-chloro-2-(6-methoxy-pyrimidin-4-yl)phenyl]ethenyl}ethoxycarbohydrazide

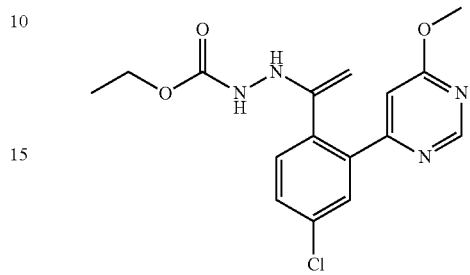

To a solution of 1-(4-chloro-2-(6-methoxypyrimidin-4-yl)phenyl)ethanone (0.057 g, 0.217 mmol) and ethyl hydrazinecarboxylate (0.022 g, 0.217 mmol) in EtOH (3 mL) was added 2 drops of conc. aq HCl. The reaction was heated at 75° C. for 2 h. After this time, the reaction mixture was concentrated to yield crude solid N'-{1-[4-chloro-2-(6-methoxypyrimidin-4-yl)phenyl]ethenyl}ethoxycarbohydrazide. MS(ESI) m/z: 349.4 (M+H)$^+$.

297C. Preparation of 4-[5-chloro-2-(1,2,3-thiadi-azol-4-yl)phenyl]-6-methoxypyrimidine

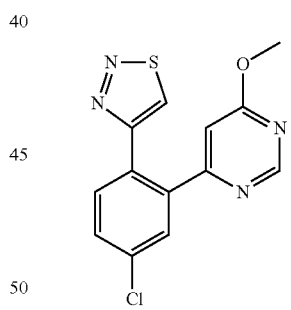

To N'-{1-[4-chloro-2-(6-methoxypyrimidin-4-yl)phenyl]ethenyl}ethoxycarbohydrazide (0.076 g, 0.217 mmol) in a vial was added SOCl$_2$ (0.32 ml, 4.34 mmol), and the resulting solution was stirred at rt for 30 min, then heated at 60° C. for 1 h. After this time, the solution was cooled to rt. To the reaction mixture was added MeOH, and the solution was concentrated. The residue was purified by reverse phase chromatography to afford 4-(4-chloro-2-(6-methoxypyrimidin-4-yl)phenyl)-1,2,3-thiadiazole (0.017 g, 26% yield) as a yellow solid. MS(ESI) m/z: 305.0 (M+H)$^+$. $^1$H NMR (400 MHz, CD$_3$OD) δ 8.87 (s, 1H), 8.63 (d, J=1.1 Hz, 1H), 7.86 (d, J=8.6 Hz, 1H), 7.76 (d, J=2.0 Hz, 1H), 7.71 (dd, J=8.4, 2.2 Hz, 1H), 6.82 (d, J=1.1 Hz, 1H), 4.02 (s, 3H).

297D. Preparation of 6-[5-chloro-2-(1,2,3-thiadiazol-4-yl)phenyl]pyrimidin-4-ol

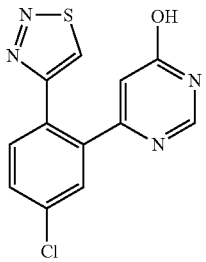 [SMILES: Oc1cc(-c2cc(Cl)ccc2-c2csnn2)ncn1]

4-(4-Chloro-2-(6-methoxypyrimidin-4-yl)phenyl)-1,2,3-thiadiazole (0.059 g, 0.194 mmol) in AcOH (2 ml) was added 48% aq HBr (1.1 ml, 9.68 mmol), and the solution was heated at 85° C. for 1 h then cooled to rt. The reaction mixture was concentrated. The residue was dissolved in EtOAc, washed with sat aq NaHCO$_3$, brine, dried over MgSO$_4$, filtered and concentrated to give 6-(5-chloro-2-(1,2,3-thiadiazol-4-yl) phenyl)pyrimidin-4-ol (0.053 g, 94% yield) as an off-white solid. MS(ESI) m/z: 291.0 (M+H)$^+$. $^1$H NMR (400 MHz, CD$_3$OD) δ 8.84 (s, 1H), 7.94 (s, 1H), 7.70 (d, J=8.1 Hz, 1H), 7.61 (d, J=2.0 Hz, 1H), 7.55 (dd, J=8.4, 2.2 Hz, 1H), 6.27 (d, J=0.7 Hz, 1H).

297E. Preparation of (9R,13S)-13-{4-[5-chloro-2-(1,2,3-thiadiazol-4-yl)phenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one trifluoroacetate (9R,13S)-13-{4-[5-Chloro-2-(1,2,3-thiadiazol-4-yl)phenyl]-6-oxo-1,6-dihydropyrimidin-1-yl)}-3-(difluoromethyl)-9-methyl-3,4,7,15-tetraazatricyclo[12.3.1.0$^{2,6}$]octadeca-1(18),2(6),4,14,16-pentaen-8-one trifluoroacetate (0.006 g, 7.7%) was prepared according to the procedures described in Example 56 by using (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one, prepared as described in Intermediate 30, and 6-[5-chloro-2-(1,2,3-thiadiazol-4-yl)phenyl]pyrimidin-4-ol, MS(ESI) m/z: 609.1 (M+H)$^+$. $^1$H NMR (400 MHz, CD$_3$OD δ 8.93 (s, 1H), 8.87 (s, 1H), 8.74 (d, J=5.1 Hz, 1H), 7.82-7.63 (m, 6H), 7.54-7.50 (m, 1H), 6.38 (s, 1H), 6.02 (dd, J=12.8, 4.8 Hz, 1H), 2.78-2.65 (m, 1H), 2.35-2.22 (m, 1H), 2.10-1.96 (m, 2H), 1.65-1.54 (m, 1H), 1.53-1.42 (m, 1H), 0.99 (d, J=7.0 Hz, 3H), 0.63 (br. s., 1H). Analytical HPLC (Method A): RT=8.80 min, purity>96%; Factor XIa Ki=1.6 nM, Plasma Kallikrein Ki=520 nM.

Example 298

Preparation of (9R,13S)-13-(4-{3-chloro-2-fluoro-6-[4-(trifluoromethyl)-1H-pyrazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one

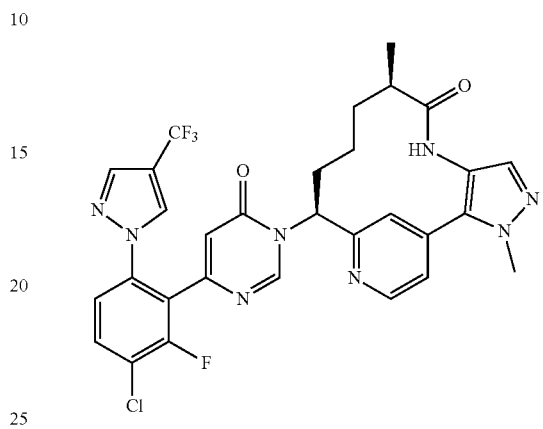

298A. Preparation of 4-(3-chloro-2-fluoro-6-(4-(trifluoromethyl)-1H-pyrazol-1-yl) phenyl)-6-methoxypyrimidine 4-(3-Chloro-2-fluoro-6-(4-(trifluoromethyl)-1H-pyrazol-1-yl)phenyl)-6-methoxypyrimidine (42 mg, 25% yield) was prepared in a similar manner as the procedure described in Example 238C, by replacing 1H-pyrazole-4-carbonitrile with 4-(trifluoromethyl)-1H-pyrazole (37.3 mg, 0.274 mmol). MS(ESI) m/z: 373.3 (M+H)$^+$. $^1$H NMR (400 MHz, CDCl$_3$) δ 8.68 (d, J=1.1 Hz, 1H), 7.76 (s, 1H), 7.70 (s, 1H), 7.62 (dd, J=8.6, 7.7 Hz, 1H), 7.36 (dd, J=8.7, 1.7 Hz, 1H), 6.78 (t, J=1.2 Hz, 1H), 4.01 (s, 3H).

298B. Preparation of 6-(3-chloro-2-fluoro-6-(4-(trifluoromethyl)-1H-pyrazol-1-yl) phenyl)pyrimidin-4-ol 6-(3-Chloro-2-fluoro-6-(4-(trifluoromethyl)-1H-pyrazol-1-yl)phenyl)pyrimidin-4-ol (0.017 g, 42.1% yield) was prepared in a similar manner as the procedure described for the preparation of 1-[4-chloro-2-(6-hydroxypyrimidin-4-yl)phenyl]-1H-1,2,3-triazole-4-carbonitrile as described in Intermediate 18C, by replacing 1-[4-chloro-2-(6-methoxypyrimidin-4-yl)phenyl]-1H-1,2,3-triazole-4-carbonitrile with 4-(3-chloro-2-fluoro-6-(4-(trifluoromethyl)-1H-pyrazol-1-yl) phenyl)-6-methoxypyrimidine (0.042 g, 0.113 mmol). MS(ESI) m/z: 359.4 (M+H)$^+$. $^1$H NMR (400 MHz, CD$_3$OD) δ 8.36 (d, J=0.9 Hz, 1H), 8.09 (d, J=1.1 Hz, 1H), 7.85 (s, 1H), 7.81-7.74 (m, 1H), 7.50 (dd, J=8.7, 1.7 Hz, 1H), 6.50 (t, J=1.1 Hz, 1H).

298C. Preparation of (9R,13S)-13-(4-{3-chloro-2-fluoro-6-[4-(trifluoromethyl)-1H-pyrazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one (9R,13S)-13-(4-{3-Chloro-2-fluoro-6-[4-(trifluoromethyl)-1H-pyrazol-1-yl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one (13 mg, 37% yield) was prepared in a similar manner as the procedure described in Example 56, by replacing 6-{5-chloro-2-[4-(trifluoromethyl)-1H-1,2,3-triazol-1-yl]phenyl}pyrimidin-4-ol with 6-(3-chloro-2-fluoro-6-(4-(trifluoromethyl)-1H-pyrazol-1-yl)phenyl)pyrimidin-4-ol (17 mg, 0.047 mmol). MS(ESI) m/z: 641.2 (M+H)$^+$. $^1$H NMR (400 MHz, CD$_3$OD) δ 9.40 (s, 1H), 8.85 (br. s., 1H), 8.72 (d, J=4.8 Hz, 1H), 8.31 (s, 1H), 7.85-7.74 (m, 2H), 7.69 (s, 1H), 7.55-7.44 (m, 3H), 6.53 (s, 1H), 6.02 (dd, J=12.4, 3.9 Hz, 1H), 4.05 (s, 3H), 2.70 (td, J=6.6, 3.1 Hz, 1H), 2.37-2.22 (m, 1H), 2.15-1.91 (m, 2H), 1.69-1.54 (m, 1H), 1.53-1.39 (m, 1H), 1.01 (d, J=6.8 Hz, 3H), 0.70 (m, 1H). Analytical HPLC (Method A): RT=8.81 min, purity=99%; Factor XIa Ki=3.8 nM, Plasma Kallikrein Ki=1,200 nM.

Example 299

Preparation of (9R,13S)-13-[4-(3-chloro-2,6-difluorophenyl)-6-oxo-1,6-dihydropyrimidin-1-yl]-9-methyl-3,4,7,15-tetraazatricyclo[12.3.1.0$^{2,6}$]octadeca-1(18),2(6),4,14,16-pentaen-8-one

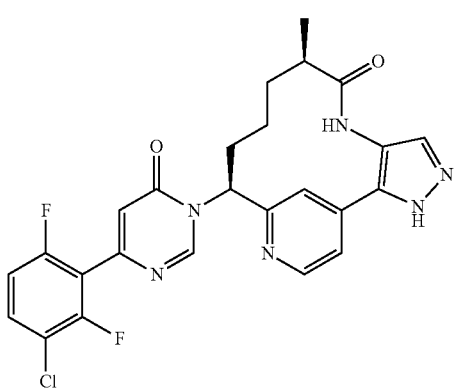 [SMILES: C[C@@H]1CCC[C@H](n2cnc(-c3c(F)ccc(Cl)c3F)cc2=O)c2cc(ccn2)-c2[nH]ncc2NC1=O]

299A. Preparation of (9R,13S)-13-[4-(3-chloro-2,6-difluorophenyl)-6-oxo-1,6-dihydropyrimidin-1-yl]-9-methyl-3-{[2-(trimethylsilyl)ethoxy]methyl}-3,4,7,15-tetraazatricyclo[12.3.1.0$^{2,6}$]octadeca-1(18),2(6),4,14,16-pentaen-8-one (9R,13S)-13-[4-(3-Chloro-2,6-difluorophenyl)-6-oxo-1,6-dihydropyrimidin-1-yl]-9-methyl-3-{[2-(trimethylsilyl)ethoxy]methyl}-3,4,7,15-tetraazatricyclo[12.3.1.0$^{2,6}$]octadeca-1(18),2(6),4,14,16-pentaen-8-one (78 mg, 89% yield) was prepared in a similar manner as the procedures described in Example 56, by using 6-(3-chloro-2,6-difluorophenyl)pyrimidin-4-ol (0.033 g, 0.137 mmol), prepared as described in Intermediate 4, and (9R,13S)-9-methyl-3-{[2-(trimethylsilyl)ethoxy]methyl}-3,4,7,15-tetraazatricyclo[12.3.1.0$^{2,6}$]octadeca-1(18),2(6),4,14,16-pentaen-8-one (0.057 g, 0.137 mmol), prepared as described in Intermediate 19. MS(ESI) m/z: 641.6 [M+H]$^+$.

299B. Preparation of (9R,13S)-13-[4-(3-chloro-2,6-difluorophenyl)-6-oxo-1,6-dihydropyrimidin-1-yl]-9-methyl-3,4,7,15-tetraazatricyclo[12.3.1.0$^{2,6}$]octadeca-1(18),2(6),4,14,16-pentaen-8-one Trifluoroacetate To a solution of (9R,13S)-13-[4-(3-chloro-2,6-difluorophenyl)-6-oxo-1,6-dihydropyrimidin-1-yl]-9-methyl-3-{[2-(trimethylsilyl)ethoxy]methyl}-3,4,7,15-tetraazatricyclo[12.3.1.0$^{2,6}$]Octadeca-1(18),2(6),4,14,16-pentaen-8-one (78 mg, 0.122 mmol), in DCM (1.6 mL) was added TFA (0.4 mL, 5.19 mmol) and the resulting solution was stirred at rt for 30 min. The reaction mixture was then concentrated and the residue was purified by prep HPLC purification to give (9R,13S)-13-[4-(3-chloro-2,6-difluorophenyl)-6-oxo-1,6-dihydropyrimidin-1-yl]-9-methyl-3,4,7,15-tetraazatricyclo[12.3.1.0$^{2,6}$]octadeca-1(18),2(6),4,14,16-pentaen-8-one trifluoroacetate (70 mg, 0.112 mmol, 92% yield). $^1$H NMR (500 MHz, DMSO-d$_6$) δ 9.31 (s, 1H), 8.95 (s, 1H), 8.57 (br. s., 1H), 7.92-7.71 (m, 3H), 7.48 (d, J=4.0 Hz, 1H), 7.31 (t, J=8.9 Hz, 1H), 6.70 (s, 1H), 5.99 (br. s., 1H), 2.73 (br. s., 1H), 2.30 (br. s., 2H), 2.01-1.88 (m, 1H), 1.60-1.37 (m, 2H), 0.93 (d, J=6.7 Hz, 3H), 0.64 (br. s., 1H). MS(ESI) m/z: 511.3 [M+H]$^+$. Analytical HPLC (Method B): RT=1.47 min, purity=94.0%; Factor XIa Ki=970 nM.

Example 300

Preparation of (9R,13S)-13-{4-[5-chloro-2-(1,2,3-thiadiazol-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

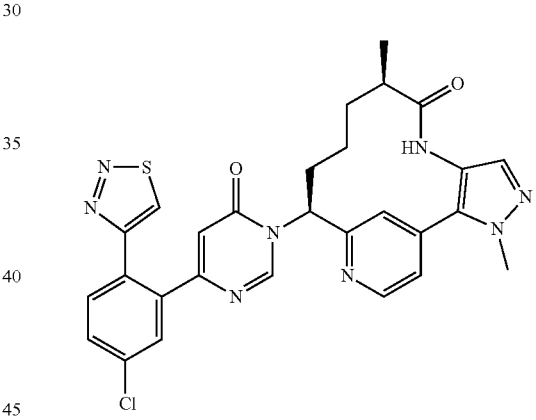

(9R,13S)-13-{4-[5-Chloro-2-(1,2,3-thiadiazol-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (0.0072 g, 37.8%) was prepared in a similar manner as the procedure described in Example 297 using (9R,13S)-13-amino-3,9-dimethyl-3,4,7,15-tetraazatricyclo[12.3.1.0$^{2,6}$]octadeca-1(18),2(6),4,14,16-pentaen-8-one, prepared as described in Intermediate 32. MS(ESI) m/z: 573.2 (M+H)$^+$. $^1$H NMR (400 MHz, CD$_3$OD) δ 8.98 (s, 1H), 8.85 (s, 1H), 8.76 (d, J=5.3 Hz, 1H), 7.82 (d, J=8.1 Hz, 1H), 7.78 (s, 1H), 7.76 (d, J=2.2 Hz, 1H), 7.68 (dd, J=8.1, 2.2 Hz, 1H), 7.61 (dd, J=5.3, 1.5 Hz, 1H), 7.52 (s, 1H), 6.40 (s, 1H), 5.99 (dd, J=12.8, 4.4 Hz, 1H), 4.07 (s, 3H), 2.77-2.67 (m, 1H), 2.39-2.27 (m, 1H), 2.14-2.00 (m, 2H), 1.69-1.56 (m, 1H), 1.55-1.41 (m, 1H), 1.03 (d, J=7.0 Hz, 3H), 0.76 (br. s., 1H). Analytical HPLC (Method A): RT=7.46 min, purity>99%; Factor XIa Ki=1.5 nM, Plasma Kallikrein Ki=280 nM.

Example 301

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-4-(2-hydroxypyridin-4-yl)-9-methyl-3,4,7,15-tetraazatricyclo[12.3.1.0$^{2,6}$]octadeca-1(18),2,5,14,16-pentaen-8-one

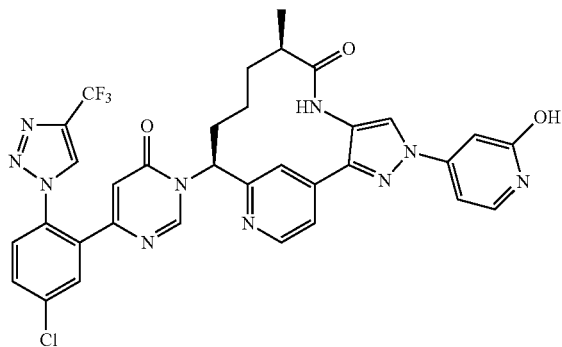 [SMILES: C[C@@H]1CCC[C@H](n2cnc(-c3cc(Cl)ccc3-n3cc(C(F)(F)F)nn3)cc2=O)c2cc(ccn2)-c2nn(-c3ccnc(O)c3)cc2NC1=O]

(9R,13S)-13-(4-{5-Chloro-2-[4-(trifluoromethyl)-1H-1,2,3-triazol-1-yl]phenyl}-6-oxo-1,6-dihydropyrimidin-1-yl)-4-(2-methoxypyridin-4-yl)-9-methyl-3,4,7,15-tetraazatricyclo[12.3.1.0$^{2,6}$]octadeca-1(18),2,5,14,16-pentaen-8-one, prepared as described in Example 323, (0.02 g, 0.027 mmol) was dissolved in THF (2 mL) and HCl (500 µl, 6.00 mmol) and heated to 70° C. for 16 h. The solvents were concentrated. The residue was purified by reverse phase chromatography to give (9R,13S)-13-(4-{5-chloro-2-[4-(trifluoromethyl)-1H-1,2,3-triazol-1-yl]phenyl}-6-oxo-1,6-dihydropyrimidin-1-yl)-4-(2-hydroxypyridin-4-yl)-9-methyl-3,4,7,15-tetraazatricyclo[12.3.1.0$^{2,6}$]octadeca-1(18),2,5,14,16-pentaen-8-one. (1.1 mg, 6%). MS(ESI) m/z: 703.0 (M+H)$^+$. $^1$H NMR (500 MHz, DMSO-d$_6$) δ 9.58 (s, 1H), 9.33-9.18 (m, 1H), 8.84-8.69 (m, 2H), 8.59 (d, J=4.6 Hz, 1H), 7.98 (br. s., 1H), 7.95-7.79 (m, 3H), 7.71-7.51 (m, 2H), 6.97-6.78 (m, 2H), 6.59-6.47 (m, 1H), 6.04 (br. s., 1H), 2.80 (br. s., 1H), 2.27 (br. s., 2H), 1.97-1.75 (m, 2H), 1.57 (br. s., 1H), 1.42 (br. s., 1H), 0.94 (d, J=6.7 Hz, 3H), 0.53 (br. s., 1H). Analytical HPLC (Method C): RT=1.58 min, purity=100%; Factor XIa Ki=0.16 nM, Plasma Kallikrein Ki=8 nM.

Example 302

Preparation of (9R,13S)-13-[4-(3-chloro-2,6-difluorophenyl)-6-oxo-1,6-dihydropyrimidin-1-yl]-9-methyl-4-(pyrimidin-5-yl)-3,4,7,15-tetraazatricyclo[12.3.1.0$^{2,6}$]octadeca-1(18),2,5,14,16-pentaen-8-one

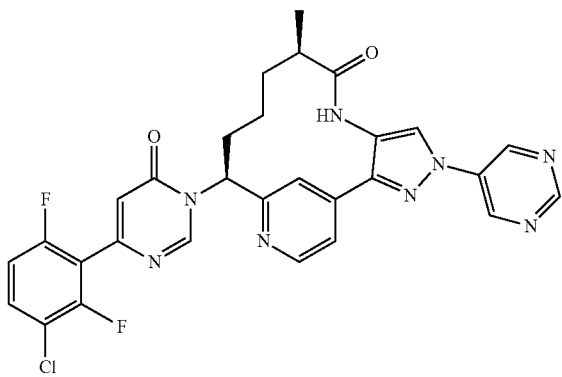 [SMILES: C[C@@H]1CCC[C@H](n2cnc(-c3c(F)ccc(Cl)c3F)cc2=O)c2cc(ccn2)-c2nn(-c3cncnc3)cc2NC1=O]

(9R,13S)-13-[4-(3-Chloro-2,6-difluorophenyl)-6-oxo-1,6-dihydropyrimidin-1-yl]-9-methyl-4-(pyrimidin-5-yl)-3,4,7,15-tetraazatricyclo[12.3.1.0$^{2,6}$]octadeca-1(18),2,5,14,16-pentaen-8-one trifluoroacetate (13.7 mg, 0.019 mmol, 33% yield) was prepared in a similar manner as the procedure described in Example 216, by using 5-iodopyrimidine (24 mg, 0.117 mmol) and (9R,13S)-13-[4-(3-chloro-2,6-difluorophenyl)-6-oxo-1,6-dihydropyrimidin-1-yl]-9-methyl-3,4,7,15-tetraazatricyclo[12.3.1.0$^{2,6}$]octadeca-1(18),2(6),4,14,16-pentaen-8-one trifluoroacetate (30 mg, 0.059 mmol), as described in Example 299. $^1$H NMR (500 MHz, DMSO-d$_6$) δ 9.58 (s, 1H), 9.35 (s, 2H), 9.15 (s, 1H), 8.97 (s, 1H), 8.76 (s, 1H), 8.63 (d, J=4.9 Hz, 1H), 7.92 (s, 1H), 7.74 (td, J=8.7, 5.8 Hz, 1H), 7.61 (d, J=4.9 Hz, 1H), 7.29 (t, J=9.0 Hz, 1H), 6.69 (s, 1H), 6.01 (d, J=11.6 Hz, 1H), 2.77 (br. s., 1H), 2.28 (br. s., 2H), 1.99-1.88 (m, 1H), 1.54 (br. s., 1H), 1.43 (br. s., 1H), 0.91 (d, J=6.7 Hz, 3H), 0.55 (br. s., 1H). MS(ESI) m/z: 589.2 [M+H]$^+$. Analytical HPLC (Method B): RT=1.64 min, purity=100.0%; Factor XIa Ki=100 nM, Plasma Kallikrein Ki=530 nM.

Example 303

Preparation of (9R,13S)-13-{4-[5-chloro-2-(pyridazin-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

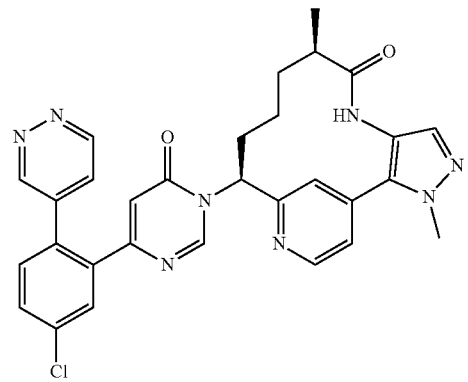 [SMILES: C[C@@H]1CCC[C@H](n2cnc(-c3cc(Cl)ccc3-c3ccnnc3)cc2=O)c2cc(ccn2)-c2c(cnn2C)NC1=O]

To a degassed solution of (9R,13S)-13-[4-(5-chloro-2-iodophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one (20 mg, 0.033 mmol), prepared as described in Example 211, 4-(tributylstannyl)pyridazine (18.01 mg, 0.049 mmol), CuI (1.24 mg, 6.51 µmol), and CsF (9.88 mg, 0.065 mmol) in ACN (1 ml) was added Pd(Ph$_3$P)$_4$ (3.76 mg, 3.25 µmol). After stirring at 45° C. for 2 h, the reaction was cooled to rt and concentrated. Purification by reverse phase chromatography afforded (9R,13S)-13-{4-[5-chloro-2-(pyridazin-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (14.9 mg, 67% yield). MS(ESI) m/z: 567.35 (M+H)$^+$. $^1$H NMR (500 MHz, DMSO-d$_6$) δ 9.27-9.19 (m, 2H), 9.09 (br. s., 1H), 8.76 (s, 1H), 8.67 (d, J=5.2 Hz, 1H), 7.80 (d, J=1.8 Hz, 1H), 7.74 (dd, J=8.2, 2.1 Hz, 1H), 7.68-7.56 (m, 4H), 7.48 (s, 1H), 6.50 (s, 1H), 5.92-5.83 (m, 1H), 4.01 (s, 3H), 2.69-2.60 (m, 1H), 2.31-2.22 (m, 1H), 2.14-2.04 (m, 1H), 1.89-1.78 (m, 1H), 1.53-1.42 (m, 1H), 1.38-1.26 (m, 1H), 0.88 (d, J=6.7 Hz, 3H), 0.50-0.32 (m, 1H). Analytical HPLC (Method C): RT=1.28 min, 100% purity; Factor XIa Ki=110 nM, Plasma Kallikrein Ki=9,300 nM.

Example 304

Preparation of (9R,13S)-13-{4-[5-chloro-2-(4-chloro-1H-1,2,3-triazol-1-yl)phenyl]-6-oxo-1,6-dihydropyrimidin-1-yl}-4-(2-hydroxypyrimidin-5-yl)-9-methyl-3,4,7,15-tetraazatricyclo[12.3.1.0$^{2,6}$]octadeca-1(18),2,5,14,16-pentaen-8-one

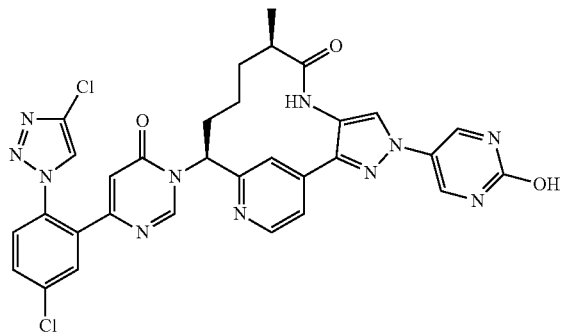 [SMILES: C[C@@H]1CCC[C@H](n2cnc(-c3cc(Cl)ccc3-n3cc(Cl)nn3)cc2=O)c2cc(ccn2)-c2nn(-c3cnc(O)nc3)cc2NC1=O]

(9R,13S)-13-{4-[5-Chloro-2-(4-chloro-1H-1,2,3-triazol-1-yl)phenyl]-6-oxo-1,6-dihydropyrimidin-1-yl}-4-(2-hydroxypyrimidin-5-yl)-9-methyl-3,4,7,15-tetraazatricyclo[12.3.1.0$^{2,6}$]octadeca-1(18),2,5,14,16-pentaen-8-one trifluoroacetate was prepared in a similar manner as the procedure described in Example 216, by using 5-iodopyrimidin-2-ol (9.63 mg, 0.043 mmol) to give (9R,13S)-13-{4-[5-chloro-2-(4-chloro-1H-1,2,3-triazol-1-yl)phenyl]-6-oxo-1,6-dihydropyrimidin-1-yl}-4-(2-hydroxypyrimidin-5-yl)-9-methyl-3,4,7,15-tetraazatricyclo[12.3.1.0$^{2,6}$]octadeca-1(18),2,5,14,16-pentaen-8-one trifluoroacetate (0.9 mg, 1.032 μmol, 2% yield). $^1$H NMR (500 MHz, DMSO-d$_6$) δ 9.44 (s, 1H), 8.85-8.66 (m, 4H), 8.55 (d, J=4.9 Hz, 1H), 8.40 (s, 1H), 7.95-7.83 (m, 2H), 7.81-7.66 (m, 2H), 7.53 (d, J=4.6 Hz, 1H), 6.34 (s, 1H), 5.95 (br. s., 1H), 2.74 (br. s., 1H), 2.24 (d, J=14.6 Hz, 2H), 1.80 (br. s., 1H), 1.51 (br. s., 1H), 1.37 (br. s., 1H), 0.89 (d, J=6.4 Hz, 3H), 0.50 (br. s., 1H). MS(ESI) m/z: 670.2 [M+H]$^+$. Analytical HPLC (Method B): RT=1.39 min, purity=90.0%; Factor XIa Ki=0.17 nM, Plasma Kallikrein Ki=14 nM.

Example 305

Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-5,8,17-triazatricyclo[13.3.1.0$^{2,7}$]nonadeca-1(19),2(7),3,5,15,17-hexaen-9-one

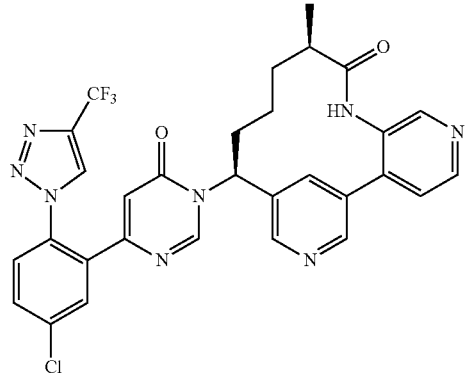 [SMILES: C[C@@H]1CCC[C@H](n2cnc(-c3cc(Cl)ccc3-n3cc(C(F)(F)F)nn3)cc2=O)c2cncc(c2)-c2ccncc2NC1=O]

305A. Preparation of (S)-tert-butyl (1-(5-(5,5-dimethyl-1,3,2-dioxaborinan-2-yl)pyridin-3-yl)but-3-en-1-yl)carbamate To a solution of 5,5,5',5'-tetramethyl-2,2'-bi(1,3,2-dioxaborinane) (2.9 g, 12.84 mmol) and (S)-tert-butyl (1-(5-bromopyridin-3-yl)but-3-en-1-yl)carbamate (3.0 g, 9.17 mmol) in toluene (38.8 mL) were added KOAc (2.70 g, 27.5 mmol) and Pd (dppf) Cl$_2$. CH$_2$Cl$_2$ Adduct (0.599 g, 0.733 mmol). The reaction was purged with Ar for 10 min and then heated at 90° C. for 12 h. The reaction mixture was diluted with EtOAc and then filtered through CELITE®. The filtrate was washed with water, brine, dried over Na$_2$SO$_4$, filtered, and concentrated. MS(ESI) m/z: 293 (M-C$_6$H$_{10}$+H)$^+$.

305B. Preparation of (S)-tert-butyl (1-(3'-amino-[3,4'-bipyridin]-5-yl)but-3-en-1-yl)carbamate (S)-tert-Butyl (1-(5-(5,5-dimethyl-1,3,2-dioxaborinan-2-yl)pyridin-3-yl)but-3-en-1-yl)carbamate (1.5 g, 4.16 mmol), 4-bromopyridin-3-amine (0.72 g, 4.16 mmol), 4 M NaHCO$_3$ (3.12 mL, 12.49 mmol) were added to dioxane (5 mL) and purged with Ar. After 15 min, Pd(PPh$_3$)$_4$ (0.241 g, 0.208 mmol) was added and the mixture heated at 90° C. overnight. The reaction mixture was diluted with water (100 ml) and extracted with EtOAc (2×50 ml), washed with brine, dried and evaporated to a black oil and was carried forward to the next reaction. MS(ESI) m/z: 341.2 (M+H)$^+$.

305C. Preparation of Tert-Butyl ((S)-1-(3'-((R)-2-methylbut-3-enamido)-[3,4'-bipyridin]-5-yl)but-3-en-1-yl)carbamate (R)-2-Methylbut-3-enoic acid (0.576 g, 5.76 mmol), (S)-tert-butyl (1-(3'-amino-[3,4'-bipyridin]-5-yl)but-3-en-1-yl)carbamate (1.4 g, 4.11 mmol), pyridine (0.998 ml, 12.34 mmol) in EtOAc (43.8 ml) was cooled to 0° C. T3PR (50% wt in EtOAc) (5.23 g, 8.23 mmol) was added and the solution allowed to gradually come to rt. After 3 h, reaction mixture was concentrated and the residue purified by normal phase chromatography using EtOAc and MeOH as eluants to give tert-butyl ((S)-1-(3'-((R)-2-methylbut-3-enamido)-[3,4'-bipyridin]-5-yl)but-3-en-1-yl)carbamate (747 mg, 43%) as a brown oil. MS(ESI) m/z: 423.2 (M+H)$^+$. $^1$H NMR (500 MHz, CDCl$_3$) δ 9.38 (br. s., 1H), 8.66 (s, 1H), 8.57-8.47 (m, 2H), 7.62 (br. s., 1H), 7.44 (br. s., 1H), 7.20 (d, J=4.1 Hz, 1H), 5.86-5.76 (m, 1H), 5.75-5.65 (m, 1H), 5.21-5.10 (m, 3H), 3.71 (d, J=11.0 Hz, 3H), 3.09 (t, J=7.3 Hz, 1H), 2.66-2.46 (m, 2H), 1.44-1.39 (m, 9H), 1.28 (d, J=7.2 Hz, 3H).

305D. Preparation of Tert-Butyl N-[(10R,11E,14S)-10-methyl-9-oxo-5,8,17-triazatricyclo[13.3.1.0$^{2,7}$]nonadeca-1(19),2(7),3,5,11,15,17-heptaen-14-yl]carbamate tert-Butyl ((S)-1-(3'-((R)-2-methylbut-3-enamido)-[3,4'-bipyridin]-5-yl)but-3-en-1-yl)carbamate (0.747 g, 1.768 mmol) and pTsOH (0.689 g, 3.62 mmol) were added to EtOAc (1040 mL) and heated to 60° C. while purging with Ar. After 1 h, Second Generation Grubbs Catalyst (0.600 g, 0.707 mmol) was added and the mixture stirred at 60° C. overnight. The reaction was quenched with sat NaHCO$_3$ (150 mL) and extracted with EtOAc (2×50 mL). The combined organic layers were washed with brine (100 mL), dried (Na$_2$SO$_4$), filtered and concentrated. The crude material was purified by normal phase chromatography DCM and MeOH as eluants to give tert-butyl N-[(10R,11E,14S)-10-methyl-9-oxo-5,8,17-triazatricyclo[13.3.1.0²,⁷]nonadeca-1(19),2(7),3,5,11,15,17-heptaen-14-yl]carbamate (0.180 g, 25.8% yield) as a tan solid. MS(ESI) m/z: 395.2 (M+H)⁺.

305E. Preparation of Tert-Butyl N-[(10R,14S)-10-methyl-9-oxo-5,8,17-triazatricyclo[13.3.1.0²,⁷]nonadeca-1(19),2(7),3,5,15,17-hexaen-14-yl]carbamate PtO₂ (10.36 mg, 0.046 mmol) was added to a solution of tert-butyl N-[(10R,11E,14S)-10-methyl-9-oxo-5,8,17-triazatricyclo[13.3.1.0²,⁷]nonadeca-1(19),2(7),3,5,11,15,17-heptaen-14-yl]carbamate (0.180 g, 0.456 mmol) in EtOH (20 mL) and subjected to a H₂ atmosphere (55 psi). After 3 h, the suspension was filtered through a plug of CELITE® and the filtrate concentrated and carried forward to the next reaction. MS(ESI) m/z: 397.2 (M+H)⁺.

305F. Preparation of (10R,14S)-14-amino-10-methyl-5,8,17-triazatricyclo[13.3.1.0²,⁷]nonadeca-1(19),2(7),3,5,15,17-hexaen-9-one TFA (0.70 mL, 9.08 mmol) was added to a stirring solution of tert-butyl N-[(10R,14S)-10-methyl-9-oxo-5,8,17-triazatricyclo[13.3.1.0²,⁷]nonadeca-1(19),2(7),3,5,15,17-hexaen-14-yl]carbamate (0.180 g, 0.454 mmol) in DCM (5 mL) at rt. After 2 h, the reaction mixture was concentrated to dryness. The residue was partitioned between EtOAc and sat NaHCO₃. The aqueous layer was extracted with EtOAc (2×). The combined organic layer was washed with brine, dried over Na₂SO₄, filtered, and concentrated to give (10R,14S)-14-amino-10-methyl-5,8,17-triazatricyclo[13.3.1.0²,⁷]nonadeca-1(19),2(7),3,5,15,17-hexaen-9-one (0.037 g, 27.5%) as a brown film. MS(ESI) m/z: 297.2 (M+H)⁺.

305G. Preparation of (10R,14S)-14-(4-{5-chloro-2-[4-(trifluoromethyl)-1H-1,2,3-triazol-1-yl]phenyl}-6-oxo-1,6-dihydropyrimidin-1-yl)-10-methyl-5,8,17-triazatricyclo[13.3.1.0²,⁷]nonadeca-1(19),2,4,6,15,17-hexaen-9-one, bis-trifluoroacetate (10R,14S)-14-(4-{5-Chloro-2-[4-(trifluoromethyl)-1H-1,2,3-triazol-1-yl]phenyl})-6-oxo-1,6-dihydropyrimidin-1-yl)-10-methyl-5,8,17-triazatricyclo[13.3.1.0²,⁷]nonadeca-1(19),2,4,6,15,17-hexaen-9-one, bis-trifluoroacetate was prepared (5.2 mg, 11%) in a similar manner as Example 56 using (10R,14S)-14-amino-10-methyl-5,8,17-triazatricyclo[13.3.1.0²,⁷]nonadeca-1(19),2(7),3,5,15,17-hexaen-9-one and 6-{5-chloro-2-[4-(trifluoromethyl)-1H-1,2,3-triazol-1-yl]phenyl}pyrimidin-4-ol, prepared as described in Intermediate 15. MS(ESI) m/z: 621.2 (M+H)⁺. ¹H NMR (400 MHz, DMSO-d₆) δ 9.69 (s, 1H), 9.19-9.13 (m, 1H), 8.64-8.55 (m, 2H), 8.49 (s, 1H), 8.41-8.38 (m, 1H), 8.03 (s, 1H), 7.87-7.84 (m, 1H), 7.79-7.73 (m, 2H), 7.64 (d, J=4.6 Hz, 1H), 6.42 (s, 1H), 5.51 (d, J=12.8 Hz, 1H), 1.90-1.84 (m, 1H), 1.75-1.67 (m, 1H), 1.39-1.32 (m, 1H), 1.14-1.02 (m, 2H), 0.95-0.85 (m, 3H). Analytical HPLC (Method A): RT=6.96 min, purity=93%; Factor XIa Ki=0.17 nM, Plasma Kallikrein Ki=25 nM.

Example 306

Preparation of (9R,13S)-13-{4-[5-chloro-2-(4-chloro-1H-1,2,3-triazol-1-yl)phenyl]-6-oxo-1,6-dihydropyrimidin-1-yl}-9-methyl-4-(piperidin-4-yl)-3,4,7,15-tetraazatricyclo[12.3.1.0²,⁶]octadeca-1(18),2,5,14,16-pentaen-8-one

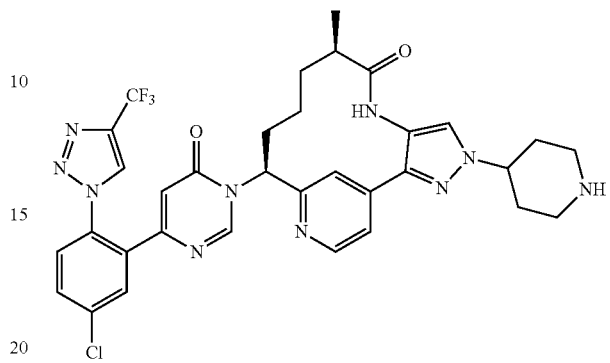

(9R,13S)-13-{4-[5-Chloro-2-(4-chloro-1H-1,2,3-triazol-1-yl)phenyl]-6-oxo-1,6-dihydropyrimidin-1-yl}-9-methyl-3,4,7,15-tetraazatricyclo[12.3.1.0²,⁶]octadeca-1(18),2(6),4,14,16-pentaen-8-one, prepared as described in Example 101, (0.020 g, 0.035 mmol), tert-butyl 4-iodopiperidine-1-carboxylate (11 mg, 0.035 mmol), Cs₂CO₃ (0.023 g, 0.069 mmol), and DMF (2 mL) were added to a vial with a Teflon septum-sealed cap. The mixture was heated to 100° C. for 12 h, at which point it was cooled to rt and DCM (2 mL) and TFA (1 mL) were added and stirred for 1 h at rt. The reaction was then concentrated and purified by reverse phase chromatography to give (9R,13S)-13-{4-[5-chloro-2-(4-chloro-1H-1,2,3-triazol-1-yl)phenyl]-6-oxo-1,6-dihydropyrimidin-1-yl}-9-methyl-4-(piperidin-4-yl)-3,4,7,15-tetraazatricyclo[12.3.1.0²,⁶]octadeca-1(18),2,5,14,16-pentaen-8-one trifluoroacetate (3 mg, 14%). MS(ESI) m/z: 659.1 (M+H)⁺. ¹H NMR (500 MHz, DMSO-d₆) δ 9.42-9.30 (m, 1H), 8.72 (s, 2H), 8.60-8.50 (m, 1H), 7.93 (s, 2H), 7.84 (s, 2H), 7.78-7.72 (m, 1H), 7.48-7.40 (m, 1H), 6.36 (s, 1H), 6.05-5.85 (m, 1H), 4.64-4.45 (m, 1H), 3.17-3.02 (m, 2H), 2.82-2.70 (m, 1H), 1.94-1.75 (m, 1H), 1.62-1.48 (m, 1H), 1.47-1.34 (m, 1H), 0.93 (d, J=7.0 Hz, 3H), 0.70-0.49 (m, 1H). Analytical HPLC (Method C): RT=1.31 min, purity=100%; Factor XIa Ki=700 nM.

Example 307

Preparation of 1-(4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}-3-fluorophenyl)-1H-pyrazole-4-carbonitrile

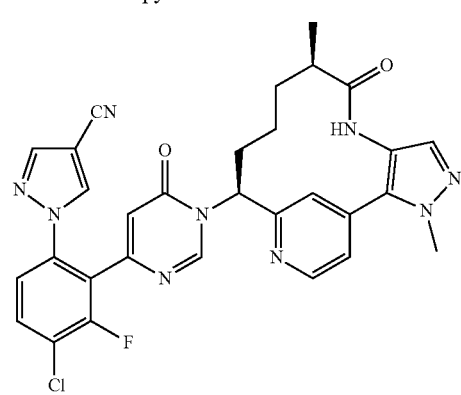

1-(4-Chloro-2-{1-[(9R,13S)-3,9-dimethyl-8-oxo-3,4,7, 15-tetraazatricyclo[12.3.1.0²,⁶]octadeca-1(18),2(6),4,14,16-pentaen-13-yl]-6-oxo-1,6-dihydropyrimidin-4-yl}-3-fluorophenyl)-1H-pyrazole-4-carbonitrile trifluoroacetate (2 mg, 43% yield) was prepared in a similar manner as the procedure described in Example 56, by replacing 6-{5-chloro-2-[4-(trifluoromethyl)-1H-1,2,3-triazol-1-yl]phenyl}pyrimidin-4-ol with 1-(4-chloro-3-fluoro-2-(6-hydroxypyrimidin-4-yl)phenyl)-1H-pyrazole-4-carbonitrile (2 mg, 6.34 μmol) prepared as described in Example 238C. MS(ESI) m/z: 598.1 (M+H)⁺. ¹H NMR (400 MHz, CD₃OD) δ 8.93-8.67 (m, 2H), 8.47 (s, 1H), 7.94 (s, 1H), 7.80 (dd, J=8.6, 7.7 Hz, 1H), 7.70 (s, 1H), 7.57-7.45 (m, 3H), 6.54 (s, 1H), 6.00 (dd, J=12.8, 4.2 Hz, 1H), 4.05 (s, 3H), 2.71 (td, J=6.6, 3.3 Hz, 1H), 2.37-2.23 (m, 1H), 2.13-1.96 (m, 2H), 1.69-1.55 (m, 1H), 1.54-1.41 (m, 1H), 1.01 (d, J=7.0 Hz, 3H), 0.71 (m, 1H). Analytical HPLC (Method A): RT=7.58 min, purity=97.1%; Factor XIa Ki=2 nM, Plasma Kallikrein Ki=1,500 nM.

Example 308

Preparation of (9R,13S)-13-{4-[5-chloro-2-(4-chloro-1H-1,2,3-triazol-1-yl)phenyl]-6-oxo-1,6-dihydropyrimidin-1-yl}-4-(1H-imidazol-4-yl)-9-methyl-3,4,7,15-tetraazatricyclo[12.3.1.0²,⁶]octadeca-1(18),2,5,14,16-pentaen-8-one

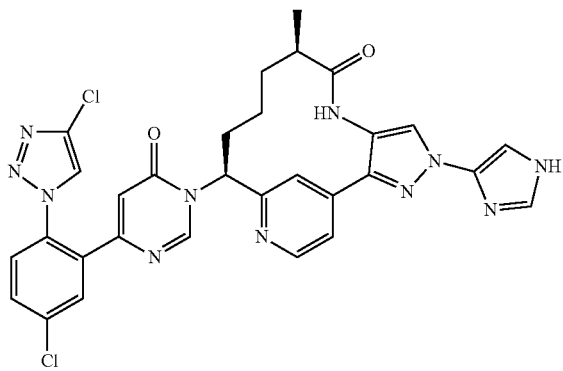 [SMILES: C[C@@H]1CCC[C@H](n2cnc(-c3cc(Cl)ccc3-n3cc(Cl)nn3)cc2=O)c2cc(ccn2)-c2nn(-c3c[nH]cn3)cc2NC1=O]

(9R,13S)-13-{4-[5-Chloro-2-(4-chloro-1H-1,2,3-triazol-1-yl)phenyl]-6-oxo-1,6-dihydropyrimidin-1-yl}-4-(1H-imidazol-4-yl)-9-methyl-3,4,7,15-tetraazatricyclo[12.3.1.0²,⁶]octadeca-1(18),2,5,14,16-pentaen-8-one trifluoroacetate was prepared in a similar manner as the procedure described in Example 216, by using 4-iodo-1-trityl-1H-imidazole (18.9 mg, 0.043 mmol) followed by deprotection using 50% TFA in DCM and Et₃SiH as scavenger to yield (9R,13S)-13-{4-[5-chloro-2-(4-chloro-1H-1,2,3-triazol-1-yl)phenyl]-6-oxo-1,6-dihydropyrimidin-1-yl}-4-(1H-imidazol-4-yl)-9-methyl-3,4,7,15-tetraazatricyclo[12.3.1.0²,⁶]octadeca-1(18),2,5,14,16-pentaen-8-one trifluoroacetate (3.3 mg, 3.5 μmol, 7% yield). ¹H NMR (400 MHz, CD₃OD) δ 8.75 (s, 1H), 8.69-8.62 (m, 1H), 8.37 (s, 1H), 8.24 (s, 1H), 8.03-7.90 (m, 3H), 7.79-7.74 (m, 1H), 7.73-7.66 (m, 2H), 7.55 (br. s., 1H), 6.41 (s, 1H), 6.11 (d, J=9.2 Hz, 1H), 2.88 (d, J=12.1 Hz, 1H), 2.31 (d, J=12.3 Hz, 2H), 2.09 (d, J=12.8 Hz, 1H), 1.74 (br. s., 1H), 1.59 (br. s., 1H), 1.11 (d, J=6.8 Hz, 3H), 0.92 (br. s., 1H). MS(ESI) m/z: 642.2 [M+H]⁺. Analytical HPLC (Method A): RT=5.74 min, purity=80.0%; Factor XIa Ki=1.9 nM, Plasma Kallikrein Ki=180 nM.

Example 309

Preparation of (9R,13S)-13-{4-[5-chloro-2-(4-chloro-1H-1,2,3-triazol-1-yl)phenyl]-6-oxo-1,6-dihydropyrimidin-1-yl}-9-methyl-4-(1H-1,2,4-triazol-5-yl)-3,4,7,15-tetraazatricyclo[12.3.1.0²,⁶]octadeca-1(18),2,5,14,16-pentaen-8-one

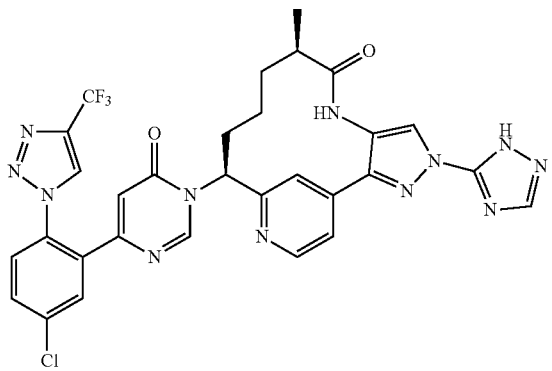 [SMILES: C[C@@H]1CCC[C@H](n2cnc(-c3cc(Cl)ccc3-n3cc(C(F)(F)F)nn3)cc2=O)c2cc(ccn2)-c2nn(-c3ncn[nH]3)cc2NC1=O]

(9R,13S)-13-{4-[5-Chloro-2-(4-chloro-1H-1,2,3-triazol-1-yl)phenyl]-6-oxo-1,6-dihydropyrimidin-1-yl}-9-methyl-4-(1H-1,2,4-triazol-5-yl)-3,4,7,15-tetraazatricyclo[12.3.1.0²,⁶]octadeca-1(18),2,5,14,16-pentaen-8-one (9 mg, 33%) as a light brown powder was prepared in a similar manner as the procedure described in Example 216, by using 5-iodo-1H-1,2,4-triazole. MS(ESI) m/z: 643.1 (M+H)⁺. ¹H NMR (500 MHz, CD₃OD) δ 8.76 (s, 1H), 8.67 (d, J=5.0 Hz, 1H), 8.58-8.48 (m, 1H), 8.41 (s, 1H), 8.36 (s, 1H), 7.98 (s, 1H), 7.91 (d, J=2.2 Hz, 1H), 7.81-7.72 (m, 2H), 7.67 (d, J=8.5 Hz, 1H), 6.40 (s, 1H), 6.18-6.04 (m, 1H), 2.92-2.80 (m, 1H), 2.38-2.22 (m, 2H), 2.13-2.01 (m, 1H), 1.81-1.68 (m, 1H), 1.65-1.52 (m, 1H), 1.10 (d, J=6.9 Hz, 3H), 0.91 (d, J=11.8 Hz, 2H). Analytical HPLC (Method A): RT=6.27 min, purity=95%; Factor XIa Ki=3 nM, Plasma Kallikrein Ki=220 nM.

Example 310

Preparation of N-(4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)-2,2,2-trifluoroacetamide

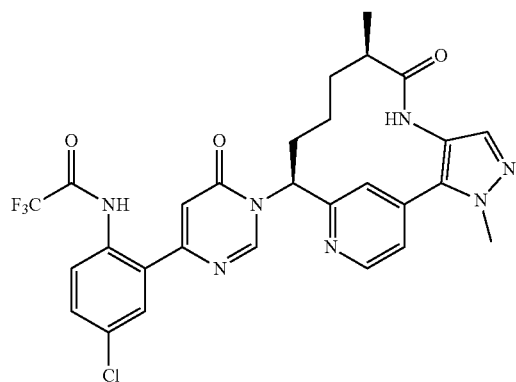 [SMILES: C[C@@H]1CCC[C@H](n2cnc(-c3cc(Cl)ccc3NC(=O)C(F)(F)F)cc2=O)c2cc(ccn2)-c2c(cnn2C)NC1=O]

310A. Preparation of N-(4-chloro-2-(6-methoxypyrimidin-4-yl)phenyl)-2,2,2-trifluoroacetamide TEA (0.71 ml, 5.09 mmol) was added to a solution of 4-chloro-2-(6-methoxypyrimidin-4-yl)aniline (1 g, 4.24 mmol), prepared as described in Intermediate 8A, and TFAA (0.72 ml, 5.09 mmol) in DCM (25 ml). After stirring at rt for 1 h, the reaction was diluted with DCM, washed with sat NaHCO$_3$, brine, dried over Na$_2$SO$_4$, filtered, and concentrated. A yellow solid was obtained as N-(4-chloro-2-(6-methoxypyrimidin-4-yl)phenyl)-2,2,2-trifluoroacetamide (1.4 g, 99% yield). MS(ESI) m/z: 332.0 (M+H)$^+$.

310B. Preparation of N-(4-chloro-2-(6-hydroxypyrimidin-4-yl)phenyl)-2,2,2-trifluoroacetamide A clear yellow solution of N-(4-chloro-2-(6-methoxypyrimidin-4-yl)phenyl)-2,2,2-trifluoroacetamide (1.4 g, 4.22 mmol) in HOAc (10 ml) and 48% aq HBr (2.39 ml, 21.10 mmol) was warmed to 60° C. for 3 h, then cooled to rt, and the reaction was concentrated. EtOAc (~400 ml) was added to the residue, followed by sat NaHCO$_3$. The layers were separated and the organic layer was washed with sat NaHCO$_3$, brine, dried over MgSO$_4$, filtered and concentrated. The residue was suspended in DCM, and the solid was filtered off. The filtrate was purified by normal phase chromatography to afford N-(4-chloro-2-(6-hydroxypyrimidin-4-yl)phenyl)-2,2,2-trifluoroacetamide (0.095 g, 7% yield) as a white solid. MS(ESI) m/z: 318.0 (M+H)$^+$.

310C. Preparation of N-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-2,2,2-trifluoroacetamide Trifluoroacetate N-(4-Chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-2,2,2-trifluoroacetamide trifluoroacetate (0.113 g, 63% yield) was prepared in a similar manner as the procedure described in Example 56, by using N-(4-chloro-2-(6-hydroxypyrimidin-4-yl)phenyl)-2,2,2-trifluoroacetamide (0.095 g, 0.301 mmol). MS(ESI) m/z: 600.0 (M+H)$^+$. $^1$H NMR (400 MHz, DMSO-d$_6$) δ 12.37 (s, 1H), 9.23 (s, 1H), 9.07 (s, 1H), 8.70 (d, J=5.1 Hz, 1H), 7.96-7.89 (m, 2H), 7.71 (s, 1H), 7.67-7.58 (m, 2H), 7.49 (s, 1H), 6.89 (br. s., 1H), 5.95 (d, J=9.5 Hz, 1H), 4.02 (s, 3H), 2.72-2.62 (m, 1H), 2.44-2.32 (m, 1H), 2.20-2.07 (m, 1H), 1.98-1.85 (m, 1H), 1.58-1.30 (m, 2H), 0.91 (d, J=6.8 Hz, 3H), 0.58-0.39 (m, 1H). Analytical HPLC (Method A): RT=9.82 min, 100% purity; Factor XIa Ki=1.7 nM, Plasma Kallikrein Ki=180 nM.

Example 311

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-4-(2-hydroxypyridin-3-yl)-9-methyl-3,4,7,15-tetraazatricyclo[12.3.1.0$^{2,6}$]octadeca-1(18),2,5,14,16-pentaen-8-one

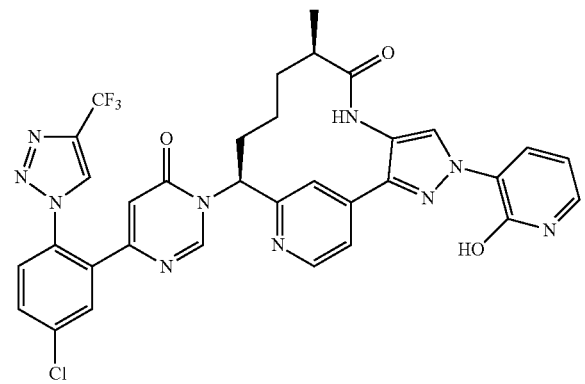 [SMILES: C[C@@H]1CCC[C@H](n2cnc(-c3cc(Cl)ccc3-n3cc(C(F)(F)F)nn3)cc2=O)c2cc(ccn2)-c2nn(-c3cccnc3O)cc2NC1=O]

(9R,13S)-13-(4-{5-Chloro-2-[4-(trifluoromethyl)-1H-1,2,3-triazol-1-yl]phenyl}-6-oxo-1,6-dihydropyrimidin-1-yl)-4-(2-methoxypyridin-3-yl)-9-methyl-3,4,7,15-tetraazatricyclo[12.3.1.0$^{2,6}$]octadeca-1(18),2,5,14,16-pentaen-8-one, prepared as described in Example 319, (0.02 g, 0.027 mmol) was dissolved in THF (2 mL) and conc. HCl (500 µl, 6.00 mmol) and heated to 70° C. for 16 h. The reaction was cooled to rt and the solution were concentrated. The residue was purified by reverse phase chromatography to give (9R,13S)-13-(4-{5-chloro-2-[4-(trifluoromethyl)-1H-1,2,3-triazol-1-yl]phenyl}-6-oxo-1,6-dihydropyrimidin-1-yl)-4-(2-hydroxypyridin-3-yl)-9-methyl-3,4,7,15-tetraazatricyclo[12.3.1.0$^{2,6}$]octadeca-1(18),2,5,14,16-pentaen-8-one (15 mg, 64%). MS(ESI) m/z: 703.2 (M+H)$^+$. $^1$H NMR (500 MHz, CD$_3$OD) δ 8.84 (s, 1H), 8.79 (s, 1H), 8.66 (s, 1H), 8.62 (d, J=5.0 Hz, 1H), 8.31 (dd, J=7.4, 1.9 Hz, 1H), 7.97 (s, 1H), 7.93 (d, J=2.2 Hz, 1H), 7.80-7.75 (m, 1H), 7.75-7.68 (m, 2H), 7.48 (dd, J=6.6, 1.9 Hz, 1H), 6.58 (dd, J=7.4, 6.3 Hz, 1H), 6.48 (d, J=0.6 Hz, 1H), 6.16-6.04 (m, 1H), 2.91-2.77 (m, 1H), 2.34-2.21 (m, 2H), 2.11-2.00 (m, 1H), 1.79-1.66 (m, 1H), 1.63-1.51 (m, 1H), 1.10 (d, J=6.9 Hz, 3H), 0.99-0.85 (m, 1H). Analytical HPLC (Method A): RT=7.36 min, purity=97.6%; Factor XIa Ki=19 nM, Plasma Kallikrein Ki=800 nM.

Example 312

Preparation of (9R,13S)-13-{4-[5-chloro-2-(4-chloro-1H-1,2,3-triazol-1-yl)phenyl]-6-oxo-1,6-dihydropyrimidin-1-yl}-9-methyl-3-(1H-pyrazol-3-yl)-3,4,7,15-tetraazatricyclo[12.3.1.0$^{2,6}$]octadeca-1(18),2(6),4,14,16-pentaen-8-one

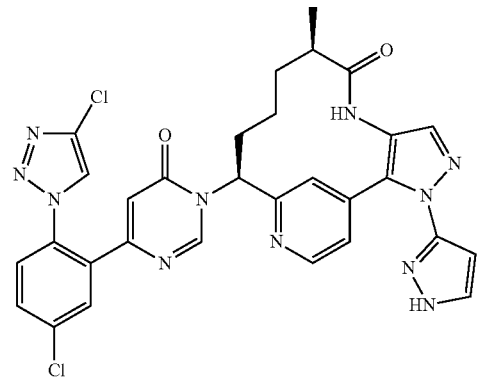 [SMILES: C[C@@H]1CCC[C@H](n2cnc(-c3cc(Cl)ccc3-n3cc(Cl)nn3)cc2=O)c2cc(ccn2)-c2c(cnn2-c2cc[nH]n2)NC1=O]

(9R,13S)-13-{4-[5-Chloro-2-(4-chloro-1H-1,2,3-triazol-1-yl)phenyl]-6-oxo-1,6-dihydropyrimidin-1-yl}-9-methyl-3-(1H-pyrazol-3-yl)-3,4,7,15-tetraazatricyclo[12.3.1.0$^{2,6}$]octadeca-1(18),2(6),4,14,16-pentaen-8-one trifluoroacetate was prepared in a similar manner as the procedure described in Example 216, by using 3-iodo-1-trityl-1H-pyrazole (18.9 mg, 0.043 mmol) followed by deprotection using 50% TFA in DCM and Et$_3$SiH as scavenger to yield (9R,13S)-13-{4-[5-chloro-2-(4-chloro-1H-1,2,3-triazol-1-yl)phenyl]-6-oxo-1,6-dihydropyrimidin-1-yl}-4-(1H-imidazol-4-yl)-9-methyl-3,4,7,15-tetraazatricyclo[12.3.1.0$^{2,6}$]octadeca-1(18),2,5,14,16-pentaen-8-one trifluoroacetate (5.3 mg, 3.5 µmol, 7% yield). $^1$H NMR (500 MHz, DMSO-d$_6$) δ 9.31 (s, 1H), 8.69 (s, 1H), 8.58 (s, 1H), 8.52 (d, J=4.9 Hz, 1H), 8.33 (s, 1H), 7.89 (br. s., 2H), 7.78 (d, J=8.5 Hz, 1H), 7.74-7.66 (m, 1H), 7.53 (d, J=4.9 Hz, 1H), 7.24-6.96 (m, 3H), 6.37 (s, 1H), 5.80 (d, J=11.6 Hz, 1H), 3.42-3.33 (m, 1H), 2.29 (br. s., 1H), 1.92 (d, J=11.3 Hz, 1H), 1.79 (br. s., 1H), 1.48 (d, J=9.8 Hz, 1H), 1.30 (br. s., 1H), 1.14 (d, J=6.7 Hz, 3H), 0.97 (br. s., 1H). MS(ESI) m/z: 642.3 [M+H]$^+$. Analytical HPLC (Method B): RT=1.48 min, purity=99.0%; Factor XIa Ki=28 nM, Plasma Kallikrein Ki=720 nM.

Example 313

Preparation of (9R,13S)-13-[4-(2-amino-5-chlorophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one

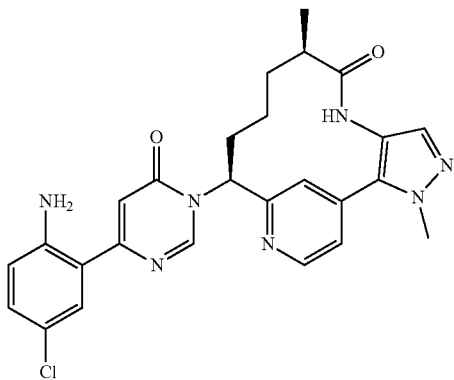

To the solution of N-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-2,2,2-trifluoroacetamide (0.111 g, 0.185 mmol), prepared as described in Example 310, in MeOH (2 ml) was added 1.25 M HCl in MeOH (0.5 ml, 0.625 mmol). After stirring at 75° C. for 1 h, the reaction was cooled to rt, concentrated and lyophilized overnight to give (9R,13S)-13-[4-(2-amino-5-chlorophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one hydrochloride (0.1 g, 94% yield) as a yellow solid. From this material, 10 mg was purified by reverse phase chromatography to afford (9R,13S)-13-[4-(2-amino-5-chlorophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one trifluoroacetate. MS(ESI) m/z: 504.4 (M+H)$^+$. $^1$H NMR (500 MHz, CD$_3$OD) δ 8.89 (br. s., 1H), 8.63 (d, J=5.0 Hz, 1H), 7.63 (s, 1H), 7.43-7.38 (m, 2H), 7.33 (s, 1H), 7.04 (d, J=8.5 Hz, 1H), 6.68 (d, J=8.8 Hz, 1H), 6.59 (s, 1H), 5.95 (d, J=9.9 Hz, 1H), 3.95 (s, 3H), 2.67-2.60 (m, 1H), 2.31-2.21 (m, 1H), 2.06-1.91 (m, 2H), 1.59-1.34 (m, 2H), 0.92 (d, J=6.9 Hz, 3H), 0.69-0.54 (m, 1H). Analytical HPLC (Method B): RT=1.45 min, 100% purity; Factor XIa Ki=57 nM, Plasma Kallikrein Ki=2,400 nM.

Example 314

Preparation of (9R,13S)-13-(4-{5-chloro-2-[(pyrimidin-4-yl)amino]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one

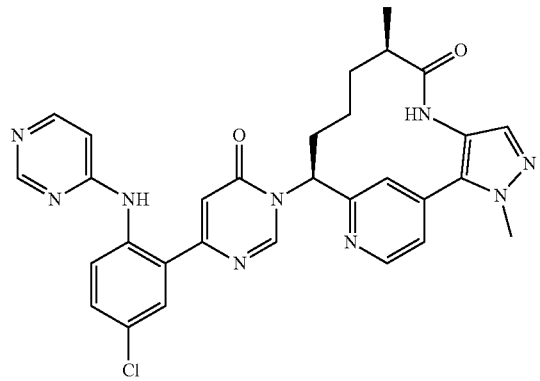 [SMILES: C[C@@H]1CCC[C@H](n2cnc(-c3cc(Cl)ccc3Nc3ccncn3)cc2=O)c2cc(ccn2)-c2c(cnn2C)NC1=O]

A mixture of (9R,13S)-13-[4-(2-amino-5-chlorophenyl)-6-oxo-1,6-dihydropyrimidin-1-yl]-3,9-dimethyl-3,4,7,15-tetraazatricyclo[12.3.1.0$^{2,6}$]octadeca-1(18),2(6),4,14,16-pentaen-8-one hydrochloride (0.01 g, 0.017 mmol), 4-bromopyrimidine hydrochloride (6.78 mg, 0.035 mmol), prepared as described in Example 313, in EtOH (1 ml) was microwaved at 150° C. for 30 min, cooled to rt and concentrated. Purification by reverse phase chromatography afforded (9R,13S)-13-(4-{5-chloro-2-[(pyrimidin-4-yl)amino]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one trifluoroacetate (6.3 mg, 45% yield). MS(ESI) m/z: 582.2 (M+H)$^+$. $^1$H NMR (500 MHz, CD$_3$OD) δ 8.88 (s, 1H), 8.61 (d, J=5.2 Hz, 1H), 8.56 (s, 1H), 8.15 (d, J=6.1 Hz, 1H), 7.73-7.67 (m, 2H), 7.62 (s, 1H), 7.48 (dd, J=8.5, 2.5 Hz, 1H), 7.43-7.39 (m, 2H), 6.85 (d, J=6.9 Hz, 1H), 6.61 (s, 1H), 5.89 (d, J=12.9 Hz, 1H), 3.97-3.92 (m, 3H), 2.66-2.59 (m, 1H), 2.28-2.19 (m, 1H), 2.03-1.89 (m, 2H), 1.56-1.34 (m, 2H), 0.92 (d, J=7.2 Hz, 3H), 0.71-0.56 (m, 1H). Analytical HPLC (Method C): RT=1.16 min, 100% purity; Factor XIa Ki=6,000 nM.

Example 315

Preparation of (9R,13S)-13-{4-[2-(aminomethyl)-5-chlorophenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one

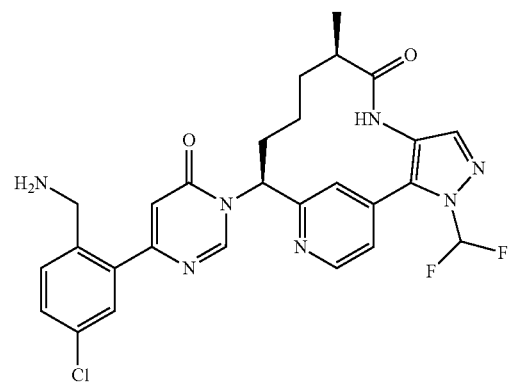 [SMILES: C[C@@H]1CCC[C@H](n2cnc(-c3cc(Cl)ccc3CN)cc2=O)c2cc(ccn2)-c2c(cnn2C(F)F)NC1=O]

315A. Preparation of Tert-Butyl 4-chloro-2-(6-hydroxypyrimidin-4-yl)benzylcarbamate

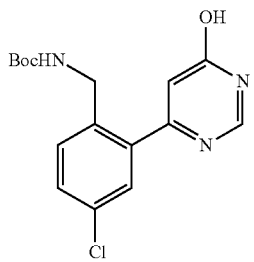 [SMILES: CC(C)(C)OC(=O)NCc1ccc(Cl)cc1-c1cc(O)ncn1]

In a microwave vial, was taken tert-butyl 2-bromo-4-chlorobenzylcarbamate (0.78 g, 2.43 mmol) and dissolved in dioxane (10 ml) and the solution was purged with Ar for 0.5 h. To this solution was then added 4,4,4',4',5,5,5',5'-octamethyl-2,2'-bi(1,3,2-dioxaborolane) (0.93 g, 3.64 mmol), followed by KOAc (0.64 g, 6.56 mmol) and Pd(dppf)Cl$_2$.CH$_2$Cl$_2$ adduct (0.06 g, 0.07 mmol) and the reaction was sealed. The microwave vial was heated at 80° C. overnight. LCMS confirmed the formation of desired boronate/boronic acid and the reaction was cooled to rt. To this was added chloromethoxypyrimidine (0.351 g, 2.43 mmol) followed by addition of 2 M aq Na$_2$CO$_3$ (3.04 ml) and the reaction mixture was purged with Ar for 0.5 h followed by the addition of Pd(dppf)Cl$_2$.CH$_2$Cl$_2$ adduct (0.06 g, 0.07 mmol) and the reaction was again sealed. The reaction was heated at 120° C. for 1 h then cooled to rt and the reaction was quenched with water (100 ml). The organics were extracted with EtOAc (2×200 ml), dried and evaporated to a blackish oil. Purified via a 40g silica gel ISCO column and eluting with Hex:EtOAc gave pure product as an oily mass. LCMS m/z=350.08 (M+H)$^+$.

315B. Preparation of Tert-Butyl 4-chloro-2-(6-hydroxypyrimidin-4-yl)benzylcarbamate The tert-butyl 4-chloro-2-(6-methoxypyrimidin-4-yl)benzylcarbamate was taken in a small vial and to this was added AcOH (1 ml) followed by 48% aq HBr (0.1 ml), sealed and heated at 80° C. for 1 h. LCMS confirmed product peak and a mass of 336 (M+H)$^+$. The solution was cooled and concentrated under a stream of N$_2$ to a oily mass and dioxane (3 ml) was added at which point solid precipitated. The solution was decanted and the residue was dissolved in DMF (3 ml) and transferred to the dioxane (2 ml) solution. To this was added Boc$_{20}$ (0.1 g) followed by TEA (2 ml) and the solution was stirred at rt overnight. To this solution was added NaOH solution (1N, 5 ml) and the reaction was stirred at rt for 0.5 h. After this time, the reaction mixture was extracted with EtOAc (2×50 ml). The combined organic layer was dried over MgSO$_4$, filtered and concentrated to a dark brown oil. Purification via prep HPLC using MeOH/water/TFA gradient afforded tert-butyl 4-chloro-2-(6-hydroxypyrimidin-4-yl)benzylcarbamate (0.05 g). $^1$H NMR (400 MHz, CDCl$_3$) δ 8.46-8.32 (m, 1H), 7.54-7.41 (m, 3H), 6.76-6.67 (m, 1H), 4.31 (s, 2H), 1.44 (s, 9H). MS m/z=236.1 (M+H)$^+$.

315C. Preparation of (9R,13S)-13-{4-[2-(aminomethyl)-5-chlorophenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one (9R,13S)-13-{4-[2-(Aminomethyl)-5-chlorophenyl]-6-oxo-1,6-dihydropyrimidin-1-yl}-3-(difluoromethyl)-9-methyl-3,4,7,15-tetraazatricyclo[12.3.1.0$^{2,6}$]octadeca-1(18),2(6),4,14,16-pentaen-8-one (4 mg, 42% yield) was prepared as a solid, via the coupling of N-{[4-chloro-2-(6-hydroxypyrimidin-4-yl)phenyl]methyl}carbamate (0.005 g, 0.015 mmol) and (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one (0.005 g, 0.015 mmol) using the HATU, DBU coupling methodology described in Example 56. MS m/z=554.1 (M+H)$^+$. $^1$H NMR (500 MHz, DMSO-d$_6$) δ 9.53-9.43 (m, 1H), 9.11-9.04 (m, 1H), 8.82-8.71 (m, 1H), 8.42-8.23 (m, 1H), 7.98-7.83 (m, 1H), 7.79-7.70 (m, 1H), 7.68-7.59 (m, 1H), 7.37-7.01 (m, 2H), 6.84-6.74 (m, 1H), 6.08-5.91 (m, 1H), 4.19-3.94 (m, 2H), 2.77-2.63 (m, 1H), 2.34-2.22 (m, 1H), 2.13-1.86 (m, 2H), 1.57-1.30 (m, 2H), 0.97-0.74 (d 3H), 0.53-0.27 (m, 1H). Analytical HPLC (Method B) RT=1.17 min, purity=96%: Factor XIa Ki=43 nM, Plasma Kallikrein Ki=4,900 nM.

Example 316

Preparation of (9R,13S)-13-{4-[5-chloro-2-(pyridin-2-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

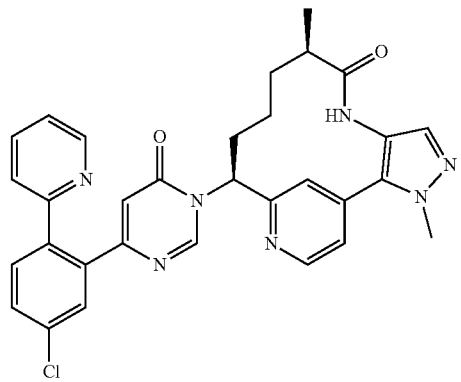 [SMILES: C[C@@H]1CCC[C@H](n2cnc(-c3cc(Cl)ccc3-c3ccccn3)cc2=O)c2cc(ccn2)-c2c(cnn2C)NC1=O]

(9R,13S)-13-{4-[5-Chloro-2-(pyridin-2-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one trifluoroacetate (13.3 mg, 51% yield) was prepared in a similar manner as the procedure described in Example 303, by replacing 4-(tributylstannyl)pyridazine with 2-(tributylstannyl)pyridine (17.96 mg, 0.049 mmol), and the reaction time was 2 h at 45° C. and then 6 h at 90° C. MS(ESI) m/z: 566.15 (M+H)$^+$. $^1$H NMR (500 MHz, DMSO-d$_6$) δ 9.23 (s, 1H), 8.72 (br. s., 1H), 8.67 (d, J=4.9 Hz, 1H), 8.52 (d, J=4.0 Hz, 1H), 7.82 (t, J=7.8 Hz, 1H), 7.72 (s, 1H), 7.67-7.62 (m, 3H), 7.56 (d, J=4.9 Hz, 1H), 7.49-7.36 (m, 3H), 6.25 (s, 1H), 5.86 (d, J=10.1 Hz, 1H), 4.00 (s, 3H), 2.68-2.59 (m, 1H), 2.30-2.21 (m, 1H), 2.14-2.03 (m, 1H), 1.86-1.76 (m, 1H), 1.50-1.40 (m, 1H), 1.37-1.26 (m, 1H), 0.87 (d, J=7.0 Hz, 3H), 0.52-0.33 (m, 1H). Analytical HPLC (Method C): RT=1.12 min, 100% purity; Factor XIa Ki=350 nM.

Example 317

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-4-(2-methoxypyridin-3-yl)-9-methyl-3,4,7,15-tetraazatricyclo[12.3.1.0²,⁶]octadeca-1(18),2,5,14,16-pentaen-8-one

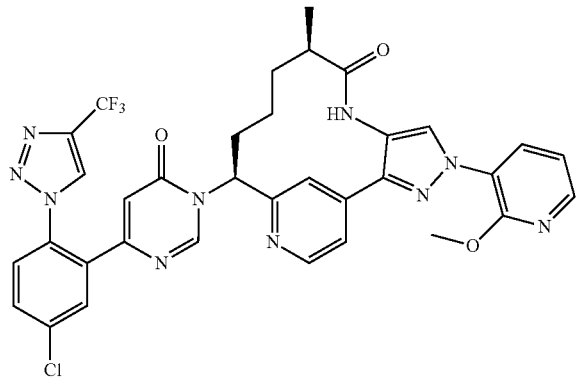 [SMILES: COc1ncccc1-n1cc2c(n1)-c1ccnc(c1)[C@@H](n1cnc(-c3cc(Cl)ccc3-n3cc(C(F)(F)F)nn3)cc1=O)CCC[C@@H](C)C(=O)N2]

(9R,13S)-13-(4-{5-Chloro-2-[4-(trifluoromethyl)-1H-1,2,3-triazol-1-yl]phenyl}-6-oxo-1,6-dihydropyrimidin-1-yl)-4-(2-methoxypyridin-3-yl)-9-methyl-3,4,7,15-tetraazatricyclo[12.3.1.0²,⁶]octadeca-1(18),2,5,14,16-pentaen-8-one was prepared in a similar manner as the procedure described in Example 216, by using 3-iodo-2-methoxypyridine (39 mg, 0.164 mmol) and (9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0²,⁶]octadeca-1(18),2(6),4,14,16-pentaen-8-one (0.05 g, 0.082 mmol), as described in Example 196, to give (9R,13S)-13-(4-{5-chloro-2-[4-(trifluoromethyl)-1H-1,2,3-triazol-1-yl]phenyl}-6-oxo-1,6-dihydropyrimidin-1-yl)-4-(2-methoxypyridin-3-yl)-9-methyl-3,4,7,15-tetraazatricyclo[12.3.1.0²,⁶]octadeca-1(18),2,5,14,16-pentaen-8-one trifluoroacetate (49 mg, 71% yield) as a light green solid. MS(ESI) m/z: 717.5 (M+H)⁺. ¹H NMR (500 MHz, DMSO-d₆) δ 9.47 (s, 1H), 9.24 (d, J=0.8 Hz, 1H), 8.70 (s, 1H), 8.56 (d, J=5.0 Hz, 1H), 8.42 (s, 1H), 8.25 (dd, J=4.8, 1.8 Hz, 1H), 8.20 (dd, J=7.7, 1.7 Hz, 1H), 7.98 (d, J=2.2 Hz, 1H), 7.91 (s, 1H), 7.89-7.81 (m, 2H), 7.58 (dd, J=5.1, 1.5 Hz, 1H), 7.24 (dd, J=7.7, 4.7 Hz, 1H), 6.51 (s, 1H), 6.10-5.95 (m, 1H), 4.02 (s, 3H), 2.84-2.70 (m, 1H), 2.35-2.18 (m, 2H), 1.91-1.75 (m, 1H), 1.63-1.50 (m, 1H), 1.48-1.32 (m, 1H), 0.95 (d, J=7.2 Hz, 3H), 0.69-0.45 (m, 1H). Analytical HPLC (Method A): RT=10.02 min, purity=99.2%; Factor XIa Ki=18 nM, Plasma Kallikrein Ki=850 nM.

Example 318

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-3-(6-methoxypyrimidin-4-yl)-9-methyl-3,4,7,15-tetraazatricyclo[12.3.1.0²,⁶]octadeca-1(18),2(6),4,14,16-pentaen-8-one

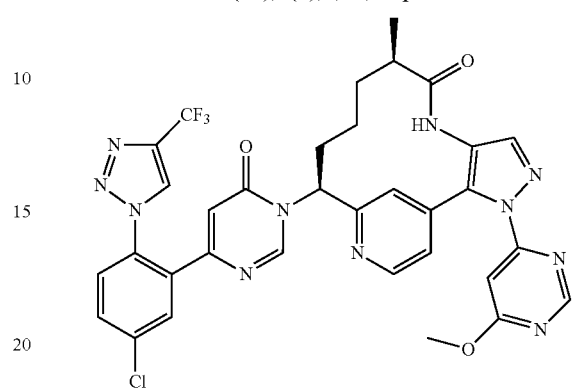

(9R,13S)-13-(4-{5-Chloro-2-[4-(trifluoromethyl)-1H-1,2,3-triazol-1-yl]phenyl}-6-oxo-1,6-dihydropyrimidin-1-yl)-3-(6-methoxypyrimidin-4-yl)-9-methyl-3,4,7,15-tetraazatricyclo[12.3.1.0²,⁶]octadeca-1(18),2(6),4,14,16-pentaen-8-one trifluoroacetate (0.83 mg, 0.908 µmol, 1% yield) as a minor product was prepared in a similar manner as the procedure described in Example 216, by using 4-iodo-6-methoxypyrimidine (19.35 mg, 0.082 mmol) and (9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0²,⁶]octadeca-1(18),2(6),4,14,16-pentaen-8-one (50 mg, 0.082 mmol), as described in Example 196. ¹H NMR (400 MHz, CD₃OD) δ 8.86 (s, 1H), 8.74 (s, 1H), 8.72 (s, 1H), 8.66 (d, J=5.3 Hz, 1H), 8.59 (s, 1H), 8.07 (s, 1H), 7.95 (d, J=2.4 Hz, 1H), 7.80 (dd, J=8.5, 2.5 Hz, 2H), 7.76-7.70 (m, 1H), 7.45 (s, 1H), 6.50 (s, 1H), 5.93 (d, J=9.0 Hz, 1H), 4.12 (s, 2H), 2.64 (s, 1H), 2.41 (s, 1H), 2.03 (s, 2H), 1.72 (s, 1H), 1.46 (br. s., 2H), 1.34 (d, J=−6.8 Hz, 3H), 1.24 (s, 1H). MS(ESI) m/z: 718.3 [M+H]⁺. Analytical HPLC (Method A): RT=9.47 min, purity=91.0%; Factor XIa Ki=280 nM, Plasma Kallikrein Ki=5,200 nM.

Example 319

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-4-(6-methoxypyrimidin-4-yl)-9-methyl-3,4,7,15-tetraazatricyclo[12.3.1.0²,⁶]octadeca-1(18),2,5,14,16-pentaen-8-one

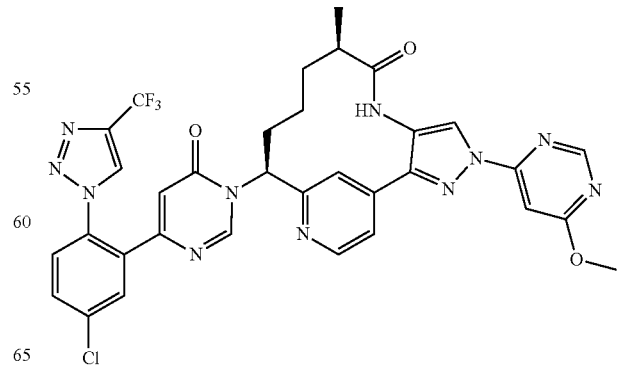

(9R,13S)-13-(4-{5-Chloro-2-[4-(trifluoromethyl)-1H-1,2,3-triazol-1-yl]phenyl}-6-oxo-1,6-dihydropyrimidin-1-yl)-4-(6-methoxypyrimidin-4-yl)-9-methyl-3,4,7,15-tetraazatricyclo[12.3.1.0$^{2,6}$]octadeca-1(18),2,5,14,16-pentaen-8-one trifluoroacetate (5.5 mg, 6.28 µmol, 7% yield) as a major product was prepared in a similar manner as the procedure described in Example 216, by using 4-iodo-6-methoxypyrimidine (19.35 mg, 0.082 mmol) and (9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0$^{2,6}$]octadeca-1(18),2(6),4,14,16-pentaen-8-one (50 mg, 0.082 mmol), as described in Example 196. $^{1}$H NMR (400 MHz, CD$_3$OD) δ 8.86 (d, J=0.9 Hz, 1H), 8.79-8.73 (m, 1H), 8.71 (s, 2H), 8.67 (d, J=5.1 Hz, 1H), 7.99-7.91 (m, 2H), 7.83-7.77 (m, 1H), 7.76-7.70 (m, 2H), 7.43 (d, J=0.9 Hz, 1H), 6.49 (d, J=0.7 Hz, 1H), 6.15 (d, J=8.1 Hz, 1H), 4.11 (s, 3H), 2.88 (d, J=3.3 Hz, 1H), 2.30 (t, J=12.7 Hz, 2H), 2.06 (t, J=11.8 Hz, 1H), 1.82-1.68 (m, 1H), 1.60 (br. s., 1H), 1.10 (d, J=7.0 Hz, 3H), 0.84 (br. s., 1H). MS(ESI) m/z: 718.3 [M+H]$^{+}$. Analytical HPLC (Method A): RT=9.90 min, purity=95.0%; Factor XIa Ki=4 nM, Plasma Kallikrein Ki=100 nM.

Example 320

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-4-(6-hydroxypyrimidin-4-yl)-9-methyl-3,4,7,15-tetraazatricyclo[12.3.1.0$^{2,6}$]octadeca-1(18),2,5,14,16-pentaen-8-one

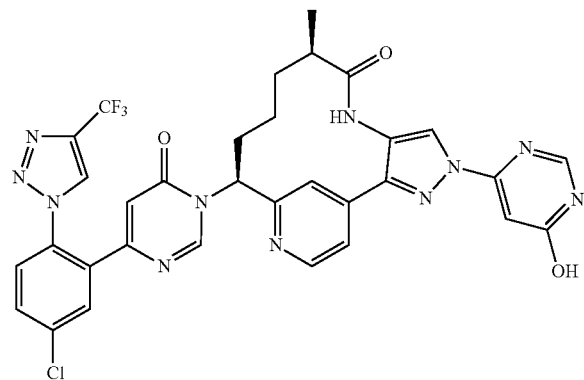 [SMILES: C[C@@H]1CCC[C@H](n2cnc(-c3cc(Cl)ccc3-n3cc(C(F)(F)F)nn3)cc2=O)c2cc(ccn2)-c2nn(-c3cc(O)ncn3)cc2NC1=O]

(9R,13S)-13-(4-{5-Chloro-2-[4-(trifluoromethyl)-1H-1,2,3-triazol-1-yl]phenyl}-6-oxo-1,6-dihydropyrimidin-1-yl)-4-(6-hydroxypyrimidin-4-yl)-9-methyl-3,4,7,15-tetraazatricyclo[12.3.1.0$^{2,6}$]octadeca-1(18),2,5,14,16-pentaen-8-one trifluoroacetate (5.4 mg, 6.47 µmol, 26% yield) was prepared in a similar manner as the procedure described in Example 296. $^{1}$H NMR (400 MHz, CD$_3$OD) δ 8.85 (d, J=0.9 Hz, 1H), 8.73 (s, 1H), 8.67 (d, J=5.3 Hz, 1H), 8.60 (s, 1H), 8.29 (d, J=0.9 Hz, 1H), 7.97 (s, 1H), 7.94 (d, J=2.4 Hz, 1H), 7.81-7.76 (m, 1H), 7.76-7.69 (m, 2H), 7.00 (d, J=0.7 Hz, 1H), 6.48 (s, 1H), 6.17-6.09 (m, 1H), 2.86 (d, J=3.5 Hz, 1H), 2.35-2.22 (m, 2H), 2.12-1.99 (m, 1H), 1.81-1.53 (m, 3H), 1.09 (d, J=7.0 Hz, 3H), 0.86 (br. s., 1H). MS(ESI) m/z: 704.5 [M+H]$^{+}$. Analytical HPLC (Method A): RT=7.47 min, purity=98.0%; Factor XIa Ki=0.2 nM, Plasma Kallikrein Ki=39 nM.

Example 321

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-4-(2-methoxypyridin-4-yl)-9-methyl-3,4,7,15-tetraazatricyclo[12.3.1.0$^{2,6}$]octadeca-1(18),2,5,14,16-pentaen-8-one

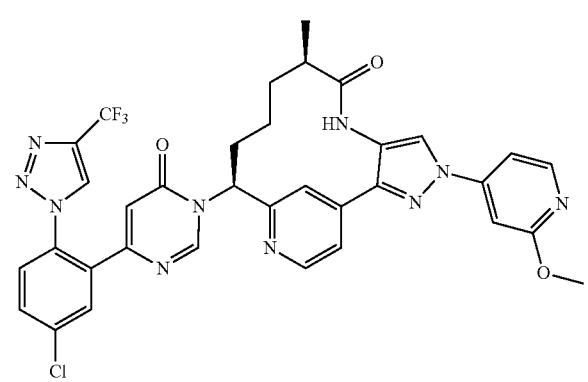 [SMILES: COc1cc(-n2cc3c(n2)-c2ccnc(c2)[C@@H](n2cnc(-c4cc(Cl)ccc4-n4cc(C(F)(F)F)nn4)cc2=O)CCC[C@@H](C)C(=O)N3)ccn1]

(9R,13S)-13-(4-{5-Chloro-2-[4-(trifluoromethyl)-1H-1,2,3-triazol-1-yl]phenyl}-6-oxo-1,6-dihydropyrimidin-1-yl)-4-(2-methoxypyridin-4-yl)-9-methyl-3,4,7,15-tetraazatricyclo[12.3.1.0$^{2,6}$]octadeca-1(18),2,5,14,16-pentaen-8-one (4 mg, 6%) was prepared in a similar manner as the procedure described in Example 216, by using 4-iodo-2-methoxypyridine (39 mg, 0.164 mmol) and (9R,13S)-13-(4-{5-chloro-2-[4-(trifluoromethyl)-1H-1,2,3-triazol-1-yl]phenyl}-6-oxo-1,6-dihydropyrimidin-1-yl)-9-methyl-3,4,7,15-tetraazatricyclo[12.3.1.0$^{2,6}$]octadeca-1(18),2(6),4,14,16-pentaen-8-one (0.05 g, 0.082 mmol), as described in Example 196. MS(ESI) m/z: 717.1 (M+H)$^{+}$. $^{1}$H NMR (500 MHz, DMSO-d$_6$) δ 9.60 (s, 1H), 9.24 (s, 1H), 8.85 (s, 1H), 8.71 (s, 1H), 8.60 (d, J=4.9 Hz, 1H), 8.31 (d, J=5.5 Hz, 1H), 7.98 (s, 1H), 7.92 (s, 1H), 7.90-7.80 (m, 2H), 7.62 (dd, J=18.3, 4.9 Hz, 2H), 7.36 (s, 1H), 6.51 (s, 1H), 6.03 (br. s., 1H), 3.94 (s, 3H), 3.46-3.27 (m, 2H), 2.81 (br. s., 1H), 2.27 (d, J=18.9 Hz, 2H), 1.85 (br. s., 1H), 1.57 (br. s., 1H), 1.42 (br. s., 1H), 0.95 (d, J=6.4 Hz, 3H), 0.54 (br. s., 1H). Analytical HPLC (Method C): RT=1.81 min, purity=100%; Factor XIa Ki=0.6 nM, Plasma Kallikrein Ki=17 nM.

Preparation of Examples 322 to 352

The following compounds were made in a parallel manner using the following procedure: Reagents were weighed into BIOTAGE® 0.5-2 mL microwave vials. Stock solutions were made for reagent addition: Dissolved 472.9 mg core in 18.6 mL 1,4-dioxane (0.04M). Dissolved 265.7 mg potassium carbonate in 6.2 mL water 0.3 M). To each microwave vial containing reagent was added Si-DPP-Pd (12.40 mg, 3.72 µmol) via ArgoScoop, 0.600 mL core solution, and 0.200 mL potassium carbonate solution. Queued the reactions to run on the BIOTAGE® Initiator (400 W) microwave for 30 min at 120° C. with 10 seconds of prestirring and using a fixed hold time.

Upon completion of the microwave run, reaction mixtures were concentrated, then redissolved in 1.8 mL DMF and filtered through a 45 µM syringe filter. Resulting clear solutions were purified via preparative LC/MS with the following conditions: Column: XBridge C18, 19×100 mm, 5-m particles; Mobile Phase A: 5:95 acetonitrile: water with 0.1% trifluoroacetic acid; Mobile Phase B: 95:5 acetonitrile:water with 0.1% trifluoroacetic acid; Gradient: 40-80% B over 10 min, then a 5-minute hold at 100% B; Flow: 20 mL/min. Fractions containing the desired product were combined and dried via centrifugal evaporation. Gradient varied for each reaction depending on polarity of compound.

Compound purity was assigned based on the methods below.

Method A: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-minute hold at 100% B; Flow: 1.11 mL/min; Detection: UV at 220 nm.

Method B: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75-minute hold at 100% B; Flow: 1.11 mL/min; Detection: UV at 220 nm.

Example 322

Preparation of (9R,13S)-13-{4-[5-chloro-2-(4-methylphenyl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

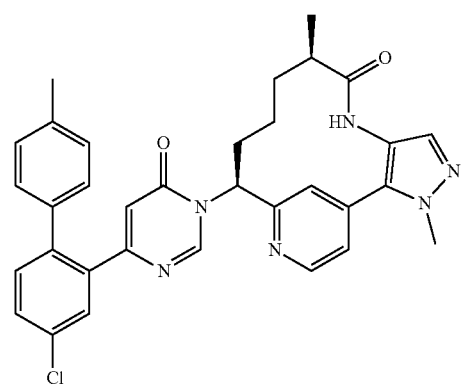 [SMILES: Cc1ccc(-c2ccc(Cl)cc2-c2cc(=O)n([C@H]3CCC[C@@H](C)C(=O)Nc4cnn(C)c4-c4ccnc3c4)cn2)cc1]

MS(ESI) m/z: 579.1 (M+H)$^+$. $^1$H NMR (500 MHz, DMSO-d$_6$) δ 9.14 (s, 1H), 8.82 (s, 1H), 8.62 (d, J=5.2 Hz, 1H), 7.61 (d, J=2.4 Hz, 1H), 7.57 (s, 1H), 7.53-7.49 (m, 2H), 7.40 (s, 1H), 7.34 (d, J=8.5 Hz, 1H), 7.10-7.03 (m, 4H), 5.99 (s, 1H), 5.79 (d, J=10.1 Hz, 1H), 3.94 (s, 3H), 2.61-2.53 (m, 1H), 2.26-2.17 (m, 4H), 2.07-1.99 (m, 1H), 1.80-1.72 (m, 1H), 1.44-1.35 (m, 1H), 1.31-1.21 (m, 1H), 0.81 (d, J=6.7 Hz, 3H), 0.41-0.26 (m, 1H). Analytical HPLC (Method A): RT=2.02 min, purity=98.7%; Factor XIa Ki=180 nM.

Example 323

Preparation of (9R,13S)-13-{4-[5-chloro-2-(3-chlorophenyl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

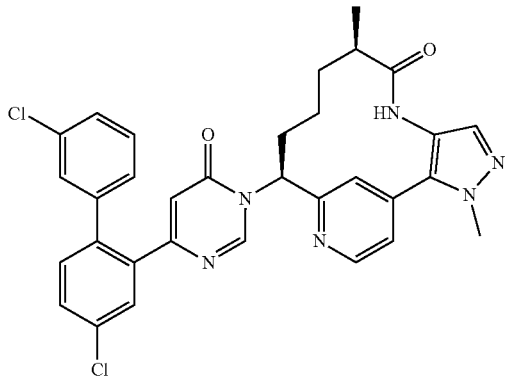 [SMILES: C[C@@H]1CCC[C@H](n2cnc(-c3cc(Cl)ccc3-c3cccc(Cl)c3)cc2=O)c2cc(ccn2)-c2c(cnn2C)NC1=O]

MS(ESI) m/z: 599.1 (M+H)$^+$; $^1$H NMR (500 MHz, DMSO-d$_6$) δ 9.15 (s, 1H), 8.76 (s, 1H), 8.60 (d, J=4.9 Hz, 1H), 7.63 (d, J=2.1 Hz, 1H), 7.59-7.54 (m, 2H), 7.50 (dd, J=5.2, 0.9 Hz, 1H), 7.43-7.39 (m, 2H), 7.34-7.26 (m, 2H), 7.23 (s, 1H), 7.09 (d, J=7.3 Hz, 1H), 6.16 (s, 1H), 5.79 (d, J=11.0 Hz, 1H), 3.94 (s, 3H), 2.61-2.53 (m, 1H), 2.27-2.17 (m, 1H), 2.07-1.97 (m, 1H), 1.80-1.70 (m, 1H), 1.44-1.34 (m, 1H), 1.31-1.20 (m, 1H), 0.81 (d, J=6.7 Hz, 3H), 0.43-0.29 (m, 1H). Analytical HPLC (Method A): RT=2.03 min, purity=94.8%; Factor XIa Ki=7,500 nM.

Example 324

Preparation of (9R,13S)-13-{4-[5-chloro-2-(3-methoxyphenyl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

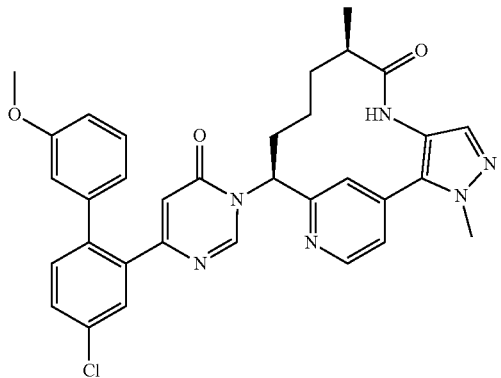 [SMILES: COc1cccc(-c2ccc(Cl)cc2-c2cc(=O)n([C@H]3CCC[C@@H](C)C(=O)Nc4cnn(C)c4-c4ccnc3c4)cn2)c1]

MS(ESI) m/z: 595.1 (M+H)$^+$; $^1$H NMR (500 MHz, DMSO-d$_6$) δ 9.15 (s, 1H), 8.81 (s, 1H), 8.61 (d, J=5.2 Hz, 1H), 7.61 (d, J=2.1 Hz, 1H), 7.58 (s, 1H), 7.55-7.49 (m, 2H), 7.41-7.37 (m, 2H), 7.18 (t, J=7.9 Hz, 1H), 6.80 (dd, J=8.2, 2.1 Hz, 1H), 6.73 (d, J=7.6 Hz, 1H), 6.69 (s, 1H), 6.04 (s,

1H), 5.78 (d, J=10.1 Hz, 1H), 3.94 (s, 3H), 3.58 (s, 3H), 2.60-2.53 (m, 1H), 2.27-2.18 (m, 1H), 2.07-1.98 (m, 1H), 1.81-1.71 (m, 1H), 1.44-1.34 (m, 1H), 1.31-1.21 (m, 1H), 0.81 (d, J=6.7 Hz, 3H), 0.43-0.29 (m, 1H); Analytical HPLC (Method A): RT=1.91 min, purity=97.5%; Factor XIa Ki=550 nM.

Example 325

Preparation of (9R,13S)-13-{4-[5-chloro-2-(2-methylphenyl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

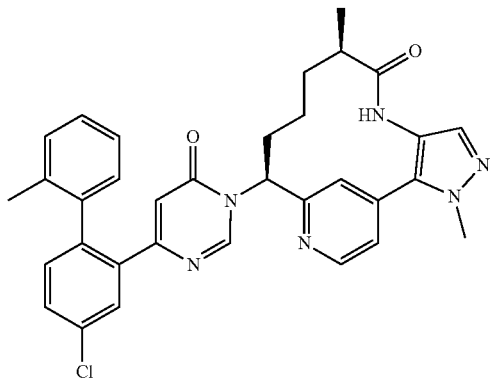 [SMILES: Cc1ccccc1-c1ccc(Cl)cc1-c1cc(=O)n([C@H]2CCC[C@@H](C)C(=O)Nc3cnn(C)c3-c3ccnc2c3)cn1]

MS(ESI) m/z: 579.1 (M+H)$^+$; $^1$H NMR (500 MHz, DMSO-d$_6$) δ 9.20 (s, 1H), 8.91 (s, 1H), 8.68 (d, J=5.2 Hz, 1H), 7.86 (d, J=2.4 Hz, 1H), 7.63-7.55 (m, 3H), 7.46 (s, 1H), 7.31-7.18 (m, 4H), 7.11 (s, 1H), 5.85-5.78 (m, 2H), 4.00 (d, J=3.1 Hz, 3H), 2.67-2.60 (m, 1H), 2.32-2.22 (m, 1H), 2.13-2.03 (m, 1H), 1.95 (d, J=12.8 Hz, 3H), 1.86-1.76 (m, 1H), 1.49-1.39 (m, 1H), 1.37-1.28 (m, 1H), 0.87 (d, J=6.7 Hz, 3H), 0.46-0.31 (m, 1H); Analytical HPLC (Method A): RT=2.05 min, purity=100%; Factor XIa Ki=3,900.

Example 326

Preparation of (9R,13S)-13-(4-{5-chloro-2-[4-(trifluoromethoxy)phenyl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one

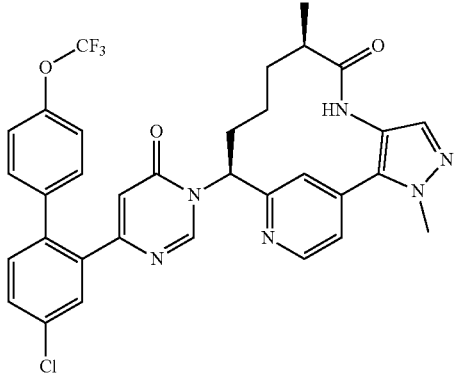 [SMILES: C[C@@H]1CCC[C@H](n2cnc(-c3cc(Cl)ccc3-c3ccc(OC(F)(F)F)cc3)cc2=O)c2cc(ccn2)-c2c(cnn2C)NC1=O]

MS(ESI) m/z: 649 (M+H)$^+$; $^1$H NMR (500 MHz, DMSO-d$_6$) δ 9.21 (s, 1H), 8.83 (s, 1H), 8.66 (d, J=4.9 Hz, 1H), 7.71 (d, J=2.1 Hz, 1H), 7.67-7.61 (m, 2H), 7.59 (d, J=4.9 Hz, 1H), 7.51-7.46 (m, 2H), 7.38-7.30 (m, 4H), 6.22 (s, 1H), 5.88 (d, J=10.4 Hz, 1H), 4.01 (s, 3H), 2.69-2.60 (m, 1H), 2.32-2.23 (m, 1H), 2.16-2.06 (m, 1H), 1.86-1.77 (m, 1H), 1.52-1.42 (m, 1H), 1.38-1.28 (m, 1H), 0.88 (d, J=7.0 Hz, 3H), 0.48-0.34 (m, 1H); Analytical HPLC (Method A): RT=2.14 min, purity=100%; Factor XIa Ki=640.

Example 327

Preparation of (9R,13S)-13-{4-[5-chloro-2-(2-chlorophenyl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

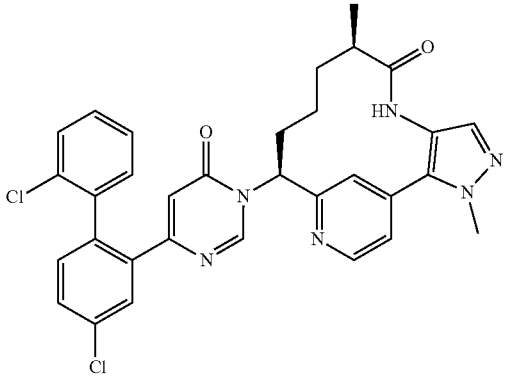 [SMILES: C[C@@H]1CCC[C@H](n2cnc(-c3cc(Cl)ccc3-c3ccccc3Cl)cc2=O)c2cc(ccn2)-c2c(cnn2C)NC1=O]

MS(ESI) m/z: 599 (M+H)$^+$; $^1$H NMR (500 MHz, DMSO-d$_6$) δ 9.20 (s, 1H), 8.89 (d, J=5.5 Hz, 1H), 8.70-8.66 (m, 1H), 7.85 (s, 1H), 7.66-7.61 (m, 2H), 7.57 (d, J=4.6 Hz, 1H), 7.52-7.46 (m, 2H), 7.43-7.29 (m, 4H), 5.93, 5.91 (2s, 1H), 5.84 (d, J=11.0 Hz, 1H), 4.01, 4.00 (2s, 3H), 2.66-2.60 (m, 1H), 2.32-2.22 (m, 1H), 2.13-2.04 (m, 1H), 1.85-1.75 (m, 1H), 1.50-1.40 (m, 1H), 1.37-1.27 (m, 1H), 0.87 (d, J=6.7 Hz, 3H), 0.45-0.31 (m, 1H); Analytical HPLC (Method A): RT=2.01 min, purity=100%; Factor XIa Ki=3,300 nM.

Example 329

Preparation of (9R,13S)-13-(4-{5-chloro-2-[4-(trifluoromethyl)phenyl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one

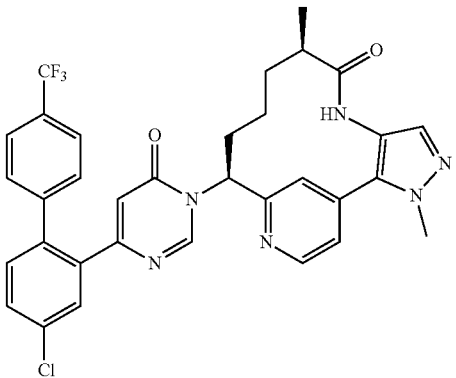

MS(ESI) m/z: 633.1 (M+H)$^+$; $^1$H NMR (500 MHz, DMSO-d$_6$) δ 9.21 (s, 1H), 8.82 (s, 1H), 8.64 (d, J=4.9 Hz,

1H), 7.74 (d, J=2.1 Hz, 1H), 7.71-7.64 (m, 4H), 7.59 (d, J=4.9 Hz, 1H), 7.53-7.44 (m, 4H), 6.26 (s, 1H), 5.88 (d, J=9.8 Hz, 1H), 4.01 (s, 3H), 2.68-2.59 (m, 1H), 2.32-2.24 (m, 1H), 2.15-2.06 (m, 1H), 1.86-1.77 (m, 1H), 1.51-1.42 (m, 1H), 1.38-1.28 (m, 1H), 0.88 (d, J=6.7 Hz, 3H), 0.48-0.32 (m, 1H); Analytical HPLC (Method A): RT=2.09 min, purity=100%; Factor XIa Ki=380 nM.

Example 330

Preparation of (9R,13S)-13-(4-{5-chloro-2-[4-(propan-2-ylsulfanyl)phenyl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one

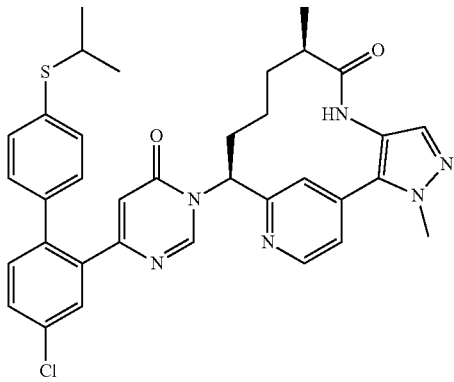 [SMILES: CC(C)Sc1ccc(-c2ccc(Cl)cc2-c2cc(=O)n([C@H]3CCC[C@@H](C)C(=O)Nc4cnn(C)c4-c4ccnc3c4)cn2)cc1]

MS(ESI) m/z: 639.1 (M+H)$^+$; $^1$H NMR (500 MHz, DMSO-d$_6$) δ 9.15 (s, 1H), 8.80 (s, 1H), 8.62 (d, J=5.2 Hz, 1H), 7.65 (d, J=2.1 Hz, 1H), 7.60 (s, 1H), 7.57-7.52 (m, 2H), 7.43-7.38 (m, 2H), 7.25 (d, J=7.9 Hz, 2H), 7.12 (d, J=8.2 Hz, 2H), 6.08 (s, 1H), 5.82 (d, J=9.8 Hz, 1H), 3.96 (s, 3H), 3.49-3.39 (m, 1H), 2.62-2.55 (m, 1H), 2.27-2.17 (m, 1H), 2.10-2.01 (m, 1H), 1.81-1.72 (m, 1H), 1.46-1.36 (m, 1H), 1.33-1.23 (m, 1H), 1.18 (dd, J=6.6, 2.0 Hz, 6H), 0.83 (d, J=7.0 Hz, 3H), 0.42-0.28 (m, 1H); Analytical HPLC (Method A): RT=2.25 min, purity=100%; Factor XIa Ki=400 nM.

Example 331

Preparation of 4-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)benzene-1-sulfonamide

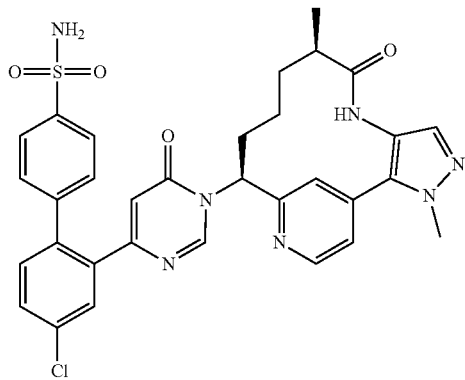 [SMILES: C[C@@H]1CCC[C@H](n2cnc(-c3cc(Cl)ccc3-c3ccc(S(N)(=O)=O)cc3)cc2=O)c2cc(ccn2)-c2c(cnn2C)NC1=O]

MS(ESI) m/z: 644 (M+H)$^+$; $^1$H NMR (500 MHz, DMSO-d$_6$) δ 9.21 (s, 1H), 8.85 (s, 1H), 8.69 (d, J=5.2 Hz, 1H), 7.78 (d, J=8.2 Hz, 2H), 7.73 (d, J=2.1 Hz, 1H), 7.67-7.64 (m, 2H), 7.58 (d, J=5.2 Hz, 1H), 7.52-7.40 (m, 6H), 6.25 (s, 1H), 5.89 (d, J=10.7 Hz, 1H), 4.01 (s, 3H), 2.68-2.60 (m, 1H), 2.33-2.24 (m, 1H), 2.15-2.06 (m, 1H), 1.88-1.78 (m, 1H), 1.51-1.42 (m, 1H), 1.39-1.28 (m, 1H), 0.88 (d, J=6.7 Hz, 3H), 0.48-0.33 (m, 1H); Analytical HPLC (Method A): RT=1.54 min, purity=100%; Factor XIa Ki=130 nM.

Example 332

Preparation of (9R,13S)-13-(4-{5-chloro-2-[4-(difluoromethoxy)phenyl]phenyl}-6-oxo-1,6-dihydropyrimidin-1-yl)-3,9-dimethyl-3,4,7,15-tetraazatricyclo[12.3.1.0$^{2,6}$]octadeca-1(18),2(6),4,14,16-pentaen-8-one

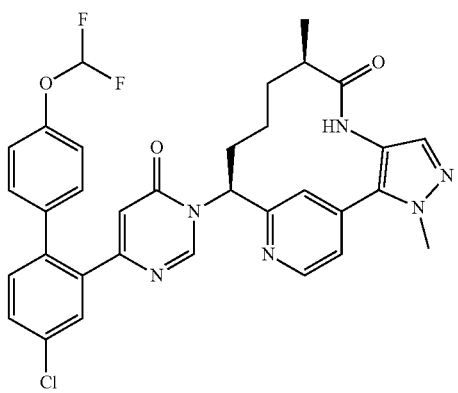 [SMILES: C[C@@H]1CCC[C@H](n2cnc(-c3cc(Cl)ccc3-c3ccc(OC(F)F)cc3)cc2=O)c2cc(ccn2)-c2c(cnn2C)NC1=O]

MS(ESI) m/z: 631 (M+H)$^+$; $^1$H NMR (500 MHz, DMSO-d$_6$) δ 9.21 (s, 1H), 8.86 (s, 1H), 8.67 (d, J=4.9 Hz, 1H), 7.70 (d, J=2.1 Hz, 1H), 7.65 (s, 1H), 7.63-7.57 (m, 2H), 7.49-7.42 (m, 2H), 7.31-7.26 (m, 3H), 7.17-7.11 (m, 2H), 6.17 (s, 1H), 5.88 (d, J=9.8 Hz, 1H), 4.01 (s, 3H), 2.69-2.60 (m, 1H), 2.34-2.24 (m, 1H), 2.16-2.06 (m, 1H), 1.88-1.79 (m, 1H), 1.51-1.42 (m, 1H), 1.39-1.28 (m, 1H), 0.88 (d, J=6.7 Hz, 3H), 0.48-0.33 (m, 1H); Analytical HPLC (Method A): RT=1.97 min, purity=100%; Factor XIa Ki=180 nM.

Example 333

Preparation of N-[3-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)phenyl]methanesulfonamide

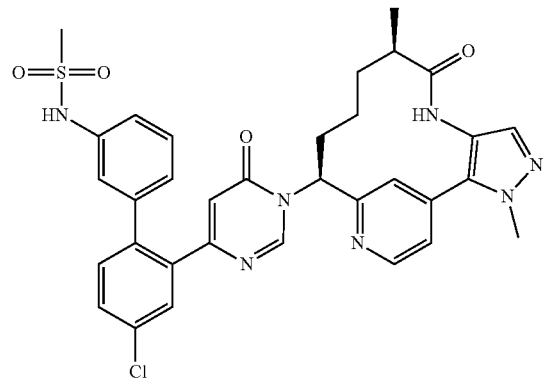 [SMILES: C[C@@H]1CCC[C@H](n2cnc(-c3cc(Cl)ccc3-c3cccc(NS(C)(=O)=O)c3)cc2=O)c2cc(ccn2)-c2c(cnn2C)NC1=O]

MS(ESI) m/z: 658 (M+H)+; 1H NMR (500 MHz, DMSO-d6) δ 9.20 (s, 1H), 8.87 (s, 1H), 8.69 (d, J=5.2 Hz, 1H), 7.70 (d, J=2.4 Hz, 1H), 7.66-7.60 (m, 3H), 7.58 (d, J=5.2 Hz, 1H), 7.48-7.44 (m, 2H), 7.38-7.33 (m, 1H), 7.16 (dd, J=8.1, 1.1 Hz, 1H), 7.06 (d, J=7.6 Hz, 1H), 7.03 (s, 1H), 6.10 (s, 1H), 5.86 (d, J=9.8 Hz, 1H), 4.01 (s, 3H), 2.80 (s, 3H), 2.70-2.60 (m, 1H), 2.34-2.24 (m, 1H), 2.15-2.05 (m, 1H), 1.88-1.78 (m, 1H), 1.51-1.42 (m, 1H), 1.39-1.28 (m, 1H), 0.89 (d, J=7.0 Hz, 3H), 0.49-0.35 (m, 1H); Analytical HPLC (Method A): RT=1.68 min, purity=100%; Factor XIa Ki=1,200 nM.

Example 334

Preparation of 3-(4-chloro-2-{1-[(9R,13S)-3,9-dimethyl-8-oxo-3,4,7,15-tetraazatricyclo[12.3.1.0²,⁶] octadeca-1(18),2(6),4,14,16-pentaen-13-yl]-6-oxo-1,6-dihydropyrimidin-4-yl}phenyl)benzonitrile

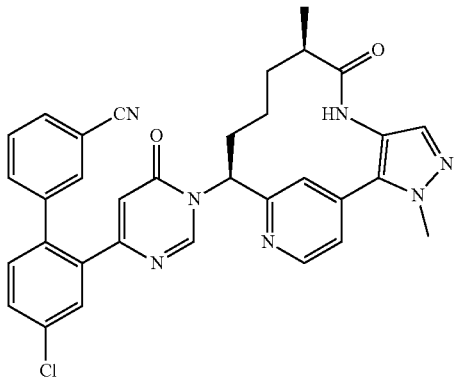 [SMILES: C[C@@H]1CCC[C@H](n2cnc(-c3cc(Cl)ccc3-c3cccc(C#N)c3)cc2=O)c2cc(ccn2)-c2c(cnn2C)NC1=O]

MS(ESI) m/z: 590.3 (M+H)+; 1H NMR (500 MHz, DMSO-d6) δ 9.21 (s, 1H), 8.78 (s, 1H), 8.68 (d, J=5.2 Hz, 1H), 7.80 (dd, J=5.3, 2.3 Hz, 1H), 7.74-7.70 (m, 2H), 7.68-7.64 (m, 2H), 7.59-7.51 (m, 4H), 7.47 (s, 1H), 6.31 (s, 1H), 5.86 (d, J=10.4 Hz, 1H), 4.01 (s, 3H), 2.70-2.59 (m, 1H), 2.33-2.23 (m, 1H), 2.14-2.04 (m, 1H), 1.86-1.77 (m, 1H), 1.51-1.41 (m, 1H), 1.38-1.28 (m, 1H), 0.88 (d, J=7.0 Hz, 3H), 0.50-0.36 (m, 1H); Analytical HPLC (Method A): RT=1.8 min, purity=100%; Factor XIa Ki=1,600 nM.

Example 335

Preparation of (9R,13S)-13-(4-{5-chloro-2-[3-(trifluoromethoxy)phenyl]phenyl}-6-oxo-1,6-dihydropyrimidin-1-yl)-3,9-dimethyl-3,4,7,15-tetraazatricyclo[12.3.1.0²,⁶]octadeca-1(18),2(6),4,14,16-pentaen-8-one

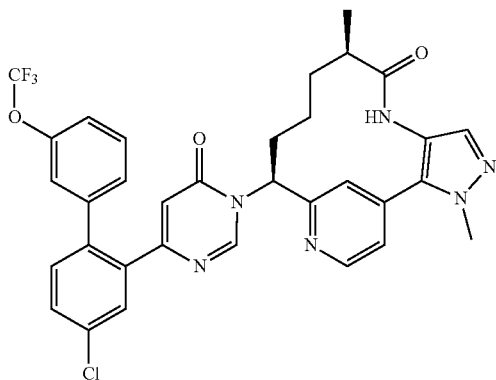 [SMILES: C[C@@H]1CCC[C@H](n2cnc(-c3cc(Cl)ccc3-c3cccc(OC(F)(F)F)c3)cc2=O)c2cc(ccn2)-c2c(cnn2C)NC1=O]

MS(ESI) m/z: 649 (M+H)+; 1H NMR (500 MHz, DMSO-d6) δ 9.20 (s, 1H), 8.84 (s, 1H), 8.67 (d, J=5.2 Hz, 1H), 7.69 (d, J=2.1 Hz, 1H), 7.67-7.62 (m, 2H), 7.58 (d, J=5.2 Hz, 1H), 7.52 (dt, J=8.1, 3.9 Hz, 2H), 7.47 (s, 1H), 7.36 (d, J=7.9 Hz, 1H), 7.32 (d, J=8.2 Hz, 1H), 7.09 (s, 1H), 6.23 (s, 1H), 5.88 (d, J=10.4 Hz, 1H), 4.00 (s, 3H), 2.69-2.60 (m, 1H), 2.33-2.24 (m, 1H), 2.14-2.05 (m, 1H), 1.82-1.72 (m, 1H), 1.51-1.41 (m, 1H), 1.37-1.27 (m, 1H), 0.88 (d, J=7.0 Hz, 3H), 0.49-0.36 (m, 1H); Analytical HPLC (Method A): RT=2.13 min, purity=100%; Factor XIa Ki=3,700 nM.

Example 336

Preparation of (9R,13S)-13-{4-[5-chloro-2-(3-methanesulfonylphenyl)phenyl]-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one

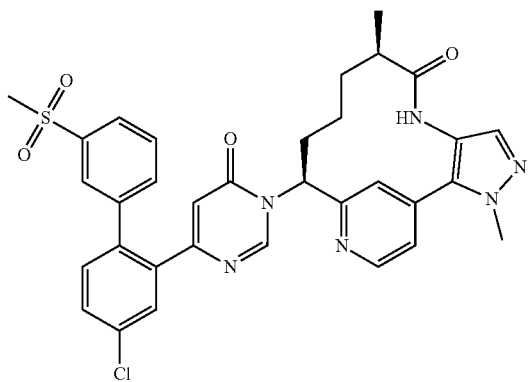 [SMILES: C[C@@H]1CCC[C@H](n2cnc(-c3cc(Cl)ccc3-c3cccc(S(C)(=O)=O)c3)cc2=O)c2cc(ccn2)-c2c(cnn2C)NC1=O]

MS(ESI) m/z: 643 (M+H)+; 1H NMR (500 MHz, DMSO-d6) δ 9.24, 9.21 (s, 1H), 9.02, 8.79 (2s, 1H), 8.71-8.63 (m, J=14.0, 4.9 Hz, 1H), 8.17-7.43 (m, 9H), 7.07, 6.32 (2s, 1H), 5.99-5.78 (m, 1H), 4.01 (d, J=1.8 Hz, 3H), 3.91, 3.11 (2s, 3H), 2.70-2.59 (m, 1H), 2.41-2.21 (m, 1H), 2.18-2.04 (m, 1H), 1.99-1.75 (m, 1H), 1.54-1.26 (m, 2H), 0.93-0.85 (m, 3H), 0.55-0.35 (m, 1H); Analytical HPLC (Method A): RT=1.65 min, purity=100%; Factor XIa Ki=1,200 nM.

Example 337

Preparation of methyl 4-(4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)benzoate

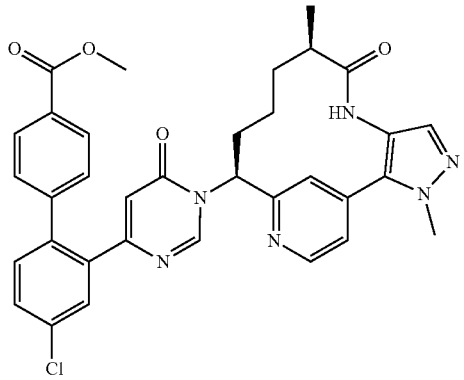 [SMILES: COC(=O)c1ccc(-c2ccc(Cl)cc2-c2cc(=O)n([C@H]3CCC[C@@H](C)C(=O)Nc4cnn(C)c4-c4ccnc3c4)cn2)cc1]

MS(ESI) m/z: 623.1 (M+H)+; 1H NMR (500 MHz, DMSO-d6) δ 9.14 (s, 1H), 8.74 (s, 1H), 8.60 (d, J=4.9 Hz,

1H), 7.84 (d, J=8.2 Hz, 2H), 7.66 (d, J=2.1 Hz, 1H), 7.60-7.56 (m, 2H), 7.51 (d, J=5.2 Hz, 1H), 7.45-7.38 (m, 2H), 7.31 (d, J=8.2 Hz, 2H), 6.12 (s, 1H), 5.82-5.75 (m, 1H), 3.94 (s, 3H), 3.80 (s, 3H), 2.61-2.53 (m, 1H), 2.26-2.16 (m, 1H), 2.09-1.97 (m, 1H), 1.80-1.71 (m, 1H), 1.44-1.19 (m, 2H), 0.81 (d, J=6.7 Hz, 3H), 0.42-0.25 (m, 1H); Analytical HPLC (Method A): RT=1.91 min, purity=98.6%; Factor XIa Ki=750 nM.

Example 338

Preparation of (9R,13S)-13-{4-[5-chloro-2-(3-methylphenyl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

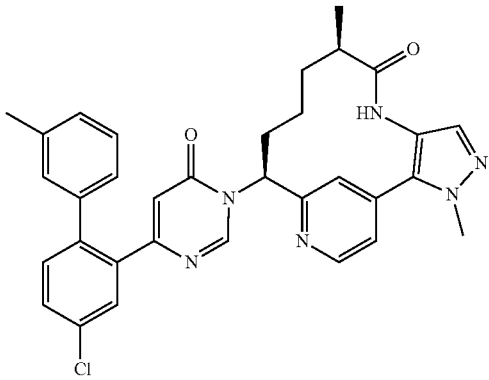 [SMILES: Cc1cccc(-c2ccc(Cl)cc2-c2cc(=O)n([C@H]3CCC[C@@H](C)C(=O)Nc4cnn(C)c4-c4ccnc3c4)cn2)c1]

MS(ESI) m/z: 579.1 (M+H)$^+$; $^1$H NMR (500 MHz, DMSO-d$_6$) δ 9.22 (s, 1H), 8.86 (s, 1H), 8.68 (d, J=5.2 Hz, 1H), 7.68 (d, J=2.1 Hz, 1H), 7.65 (s, 1H), 7.62-7.56 (m, 2H), 7.47 (s, 1H), 7.44 (d, J=8.5 Hz, 1H), 7.24-7.18 (m, 1H), 7.13 (d, J=7.6 Hz, 1H), 7.05 (s, 1H), 7.00 (d, J=7.6 Hz, 1H), 6.09 (s, 1H), 5.85 (d, J=10.4 Hz, 1H), 4.01 (s, 3H), 2.67-2.60 (m, 1H), 2.35-2.22 (m, 4H), 2.14-2.05 (m, 1H), 1.88-1.78 (m, 1H), 1.51-1.42 (m, 1H), 1.38-1.28 (m, 1H), 0.88 (d, J=7.0 Hz, 3H), 0.51-0.37 (m, 1H); Analytical HPLC (Method A): RT=2.03 min, purity=100%; Factor XIa Ki=1,400 nM.

Example 339

Preparation of 4-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)benzonitrile

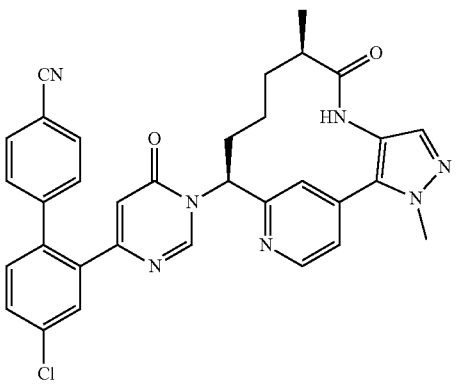 [SMILES: C[C@@H]1CCC[C@H](n2cnc(-c3cc(Cl)ccc3-c3ccc(C#N)cc3)cc2=O)c2cc(ccn2)-c2c(cnn2C)NC1=O]

MS(ESI) m/z: 590.1 (M+H)$^+$; $^1$H NMR (500 MHz, DMSO-d$_6$) δ 9.22 (s, 1H), 8.79 (s, 1H), 8.67 (d, J=4.9 Hz, 1H), 7.80 (d, J=8.2 Hz, 2H), 7.73 (d, J=2.1 Hz, 1H), 7.69-7.64 (m, 2H), 7.59 (d, J=5.2 Hz, 1H), 7.50 (d, J=8.2 Hz, 1H), 7.47 (s, 1H), 7.43 (d, J=8.5 Hz, 2H), 6.29 (s, 1H), 5.87 (d, J=10.1 Hz, 1H), 4.01 (s, 3H), 2.69-2.60 (m, 1H), 2.33-2.23 (m, 1H), 2.15-2.06 (m, 1H), 1.87-1.78 (m, 1H), 1.52-1.42 (m, 1H), 1.38-1.28 (m, 1H), 0.88 (d, J=6.7 Hz, 3H), 0.49-0.33 (m, 1H); Analytical HPLC (Method A): RT=1.8 min, purity=100%; Factor XIa Ki=290 nM.

Example 340

Preparation of (9R,13S)-13-{4-[5-chloro-2-(1-methyl-1H-indol-5-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

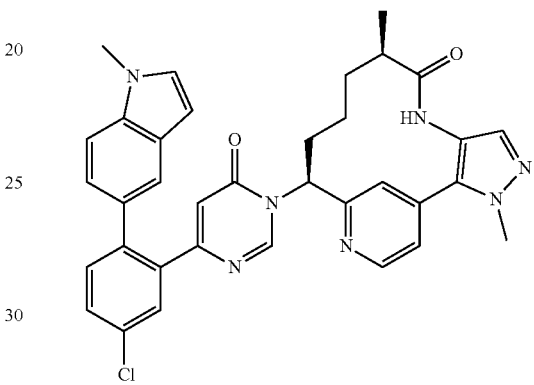

MS(ESI) m/z: 618.1 (M+H)$^+$; $^1$H NMR (500 MHz, DMSO-d$_6$) δ 9.20 (s, 1H), 8.90 (s, 1H), 8.68 (d, J=5.2 Hz, 1H), 7.72 (d, J=2.1 Hz, 1H), 7.61 (s, 1H), 7.60-7.55 (m, 2H), 7.47-7.43 (m, 3H), 7.39-7.33 (m, 2H), 6.96 (dd, J=8.5, 1.2 Hz, 1H), 6.40 (d, J=3.1 Hz, 1H), 5.98 (s, 1H), 5.82 (d, J=10.7 Hz, 1H), 4.00 (s, 3H), 3.79 (s, 3H), 2.66-2.59 (m, 1H), 2.33-2.24 (m, 1H), 2.13-2.03 (m, 1H), 1.85-1.77 (m, 1H), 1.49-1.40 (m, 1H), 1.37-1.27 (m, 1H), 0.87 (d, J=7.0 Hz, 3H), 0.45-0.32 (m, 1H); Analytical HPLC (Method A): RT=2.02 min, purity=100%; Factor XIa Ki=1,300 nM.

Example 341

Preparation of (9R,13S)-13-{4-[5-chloro-2-(isoquinolin-5-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

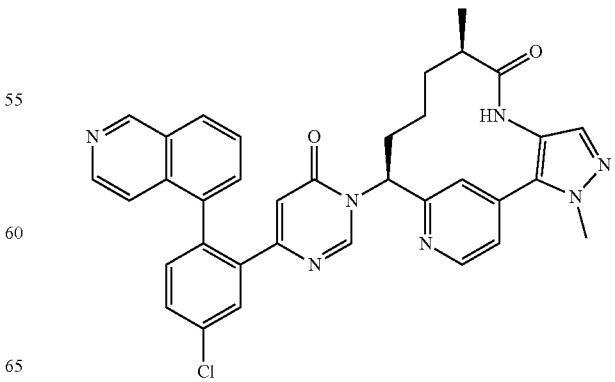

MS(ESI) m/z: 616 (M+H)+; 1H NMR (500 MHz, DMSO-d6) δ 9.48 (d, J=16.8 Hz, 1H), 9.17 (s, 1H), 8.66-8.58 (m, 2H), 8.43 (br. s., 1H), 8.24 (t, J=9.3 Hz, 1H), 7.90 (t, J=1.8 Hz, 1H), 7.82-7.69 (m, 3H), 7.56-7.51 (m, 2H), 7.48 (dd, J=8.2, 3.4 Hz, 1H), 7.45-7.38 (m, 2H), 6.00 (d, J=9.5 Hz, 1H), 5.69 (d, J=10.4 Hz, 1H), 3.99 (s, 3H), 2.63-2.57 (m, 1H), 2.19-1.96 (m, 2H), 1.73-1.59 (m, 1H), 1.45-1.34 (m, 1H), 1.31-1.20 (m, 1H), 0.85 (d, J=5.2 Hz, 3H), 0.41-0.28 (m, 1H); Analytical HPLC (Method B): RT=1.32 min, purity=100%; Factor XIa Ki=6,500 nM.

Example 342

Preparation of methyl 3-(4-chloro-2-{1-[(9R,13S)-3,9-dimethyl-8-oxo-3,4,7,15-tetraazatricyclo[12.3.1.0^{2,6}]octadeca-1(18),2(6),4,14,16-pentaen-13-yl]-6-oxo-1,6-dihydropyrimidin-4-yl}phenyl)benzoate

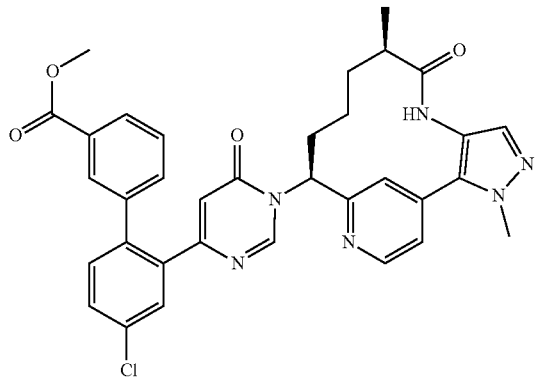 [SMILES: COC(=O)c1cccc(-c2ccc(Cl)cc2-c2cc(=O)n([C@H]3CCC[C@@H](C)C(=O)Nc4cnn(C)c4-c4ccnc3c4)cn2)c1]

MS(ESI) m/z: 623.2 (M+H)+; 1H NMR (500 MHz, DMSO-d6) δ 9.21 (s, 1H), 8.80 (s, 1H), 8.65 (d, J=5.2 Hz, 1H), 7.93-7.89 (m, 1H), 7.79 (s, 1H), 7.71 (d, J=2.1 Hz, 1H), 7.66-7.63 (m, 2H), 7.58 (d, J=5.2 Hz, 1H), 7.54-7.46 (m, 4H), 6.23 (s, 1H), 5.86 (d, J=9.8 Hz, 1H), 4.01 (s, 3H), 3.78 (s, 3H), 2.67-2.59 (m, 1H), 2.31-2.22 (m, 1H), 2.14-2.05 (m, 1H), 1.83-1.74 (m, 1H), 1.51-1.41 (m, 1H), 1.37-1.27 (m, 1H), 0.88 (d, J=7.0 Hz, 3H), 0.50-0.36 (m, 1H); Analytical HPLC (Method A): RT=1.87 min, purity=100%; Factor XIa Ki=2,200 nM.

Example 343

Preparation of N-[4-(4-chloro-2-{1-[(9R,13S)-3,9-dimethyl-8-oxo-3,4,7,15-tetraazatricyclo[12.3.1.0^{2,6}]octadeca-1(18),2(6),4,14,16-pentaen-13-yl]-6-oxo-1,6-dihydropyrimidin-4-yl}phenyl)phenyl]methanesulfonamide

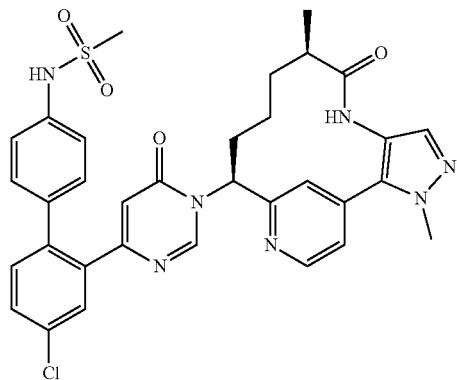 [SMILES: C[C@@H]1CCC[C@H](n2cnc(-c3cc(Cl)ccc3-c3ccc(NS(C)(=O)=O)cc3)cc2=O)c2cc(ccn2)-c2c(cnn2C)NC1=O]

MS(ESI) m/z: 657.9 (M+H)+; 1H NMR (500 MHz, DMSO-d6) δ 9.21 (s, 1H), 8.86 (s, 1H), 8.70 (d, J=5.2 Hz, 1H), 7.70 (d, J=2.4 Hz, 1H), 7.65 (s, 1H), 7.62-7.56 (m, 2H), 7.50-7.42 (m, 2H), 7.30-7.25 (m, 1H), 7.22-7.14 (m, 4H), 6.11 (s, 1H), 5.86 (d, J=8.9 Hz, 1H), 4.01 (s, 3H), 2.99 (s, 3H), 2.68-2.61 (m, 1H), 2.34-2.23 (m, 1H), 2.16-2.06 (m, 1H), 1.88-1.78 (m, 1H), 1.53-1.28 (m, 2H), 0.88 (d, J=7.0 Hz, 3H), 0.51-0.33 (m, 1H); Analytical HPLC (Method B): RT=1.63 min, purity=97.8%; Factor XIa Ki=450 nM.

Example 344

Preparation of (9R,13S)-13-(4-{5-chloro-2-[3-(trifluoromethyl)phenyl]phenyl}-6-oxo-1,6-dihydropyrimidin-1-yl)-3,9-dimethyl-3,4,7,15-tetraazatricyclo[12.3.1.0^{2,6}]octadeca-1(18),2(6),4,14,16-pentaen-8-one

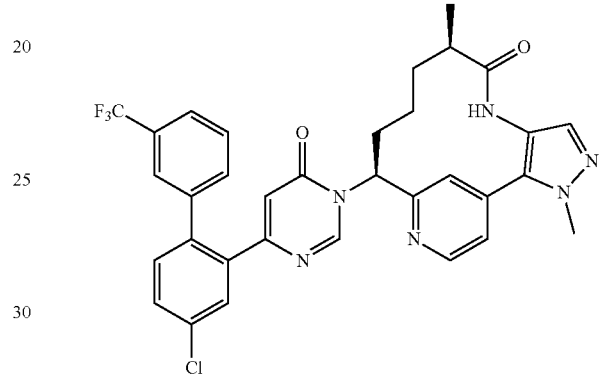

MS(ESI) m/z: 633 (M+H)+; 1H NMR (500 MHz, DMSO-d6) δ 9.21 (s, 1H), 8.79 (s, 1H), 8.65 (d, J=5.2 Hz, 1H), 7.73-7.64 (m, 4H), 7.61-7.54 (m, 4H), 7.52-7.46 (m, 2H), 6.30 (s, 1H), 5.86 (d, J=10.4 Hz, 1H), 4.01 (s, 3H), 2.67-2.59 (m, 1H), 2.33-2.23 (m, 1H), 2.14-2.05 (m, J=12.1, 12.1 Hz, 1H), 1.82-1.73 (m, 1H), 1.50-1.41 (m, 1H), 1.37-1.27 (m, 1H), 0.88 (d, J=6.7 Hz, 3H), 0.52-0.38 (m, 1H); Analytical HPLC (Method A): RT=2.06 min, purity=100%; Factor XIa Ki=4,800 nM.

Example 345

Preparation of (9R,13S)-13-{4-[5-chloro-2-(4-methoxyphenyl)phenyl]-6-oxo-1,6-dihydropyrimidin-1-yl}-3,9-dimethyl-3,4,7,15-tetraazatricyclo[12.3.1.0^{2,6}]octadeca-1(18),2(6),4,14,16-pentaen-8-one

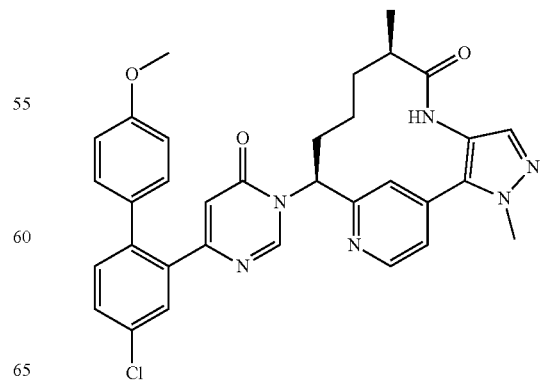

MS(ESI) m/z: 595 (M+H)+; 1H NMR (500 MHz, DMSO-d6) δ 9.22 (s, 1H), 8.89 (s, 1H), 8.69 (d, J=5.2 Hz, 1H), 7.68-7.64 (m, 2H), 7.60-7.56 (m, 2H), 7.47 (s, 1H), 7.41 (d, J=8.2 Hz, 1H), 7.15 (d, J=8.5 Hz, 2H), 6.90 (d, J=8.9 Hz, 2H), 6.08 (s, 1H), 5.87 (d, J=10.1 Hz, 1H), 4.01 (s, 3H), 3.76 (s, 3H), 2.68-2.60 (m, 1H), 2.34-2.26 (m, 1H), 2.16-2.06 (m, 1H), 1.89-1.79 (m, 1H), 1.51-1.42 (m, 1H), 1.39-1.28 (m, 1H), 0.88 (d, J=7.0 Hz, 3H), 0.48-0.35 (m, 1H); Analytical HPLC (Method A): RT=1.89 min, purity=100%; Factor XIa Ki=350 nM.

Example 346

Preparation of (9R,13S)-13-{4-[5-chloro-2-(4-chlorophenyl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

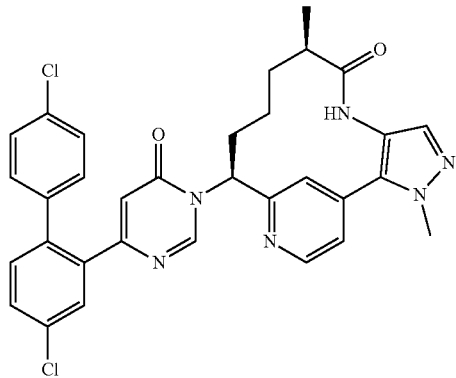

MS(ESI) m/z: 599 (M+H)+; 1H NMR (500 MHz, DMSO-d6) δ 9.22 (s, 1H), 8.85 (s, 1H), 8.68 (d, J=4.9 Hz, 1H), 7.70 (d, J=2.1 Hz, 1H), 7.66 (s, 1H), 7.63 (dd, J=8.2, 2.1 Hz, 1H), 7.59 (d, J=5.2 Hz, 1H), 7.48-7.44 (m, 2H), 7.40 (d, J=8.5 Hz, 2H), 7.25 (d, J=8.2 Hz, 2H), 6.19 (s, 1H), 5.88 (d, J=9.8 Hz, 1H), 4.01 (s, 3H), 2.69-2.60 (m, 1H), 2.34-2.25 (m, 1H), 2.15-2.06 (m, 1H), 1.88-1.79 (m, 1H), 1.52-1.42 (m, 1H), 1.39-1.28 (m, 1H), 0.88 (d, J=6.7 Hz, 3H), 0.49-0.34 (m, 1H); Analytical HPLC (Method B): RT=2 min, purity=95.5%; Factor XIa Ki=220 nM.

Example 347

Preparation of (9R,13S)-13-{4-[5-chloro-2-(pyridin-4-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

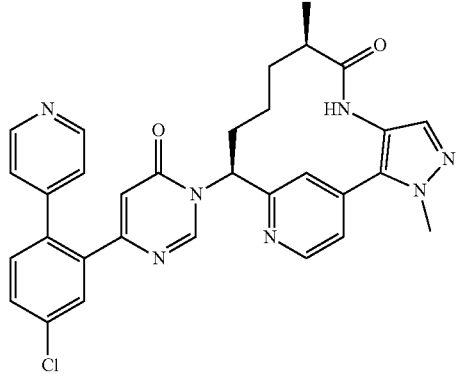 [SMILES: C[C@@H]1CCC[C@H](n2cnc(-c3cc(Cl)ccc3-c3ccncc3)cc2=O)c2cc(ccn2)-c2c(cnn2C)NC1=O]

MS(ESI) m/z: 566.1 (M+H)+; 1H NMR (500 MHz, DMSO-d6) δ 9.21 (s, 1H), 8.80 (s, 1H), 8.68 (d, J=5.2 Hz, 1H), 8.55 (d, J=5.8 Hz, 2H), 7.74 (d, J=1.8 Hz, 1H), 7.69 (dd, J=8.2, 2.1 Hz, 1H), 7.66 (s, 1H), 7.58 (d, J=5.2 Hz, 1H), 7.53 (d, J=8.2 Hz, 1H), 7.47 (s, 1H), 7.30 (d, J=5.8 Hz, 2H), 6.34 (s, 1H), 5.87 (d, J=10.7 Hz, 1H), 4.01 (s, 3H), 2.69-2.60 (m, 1H), 2.33-2.23 (m, 1H), 2.15-2.06 (m, 1H), 1.88-1.78 (m, 1H), 1.52-1.42 (m, 1H), 1.38-1.28 (m, 1H), 0.88 (d, J=7.0 Hz, 3H), 0.48-0.35 (m, 1H); Analytical HPLC (Method A): RT=1.52 min, purity=98.9%; Factor XIa Ki=2,000 nM.

Example 348

Preparation of (9R,13S)-13-{4-[5-chloro-2-(isoquinolin-7-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

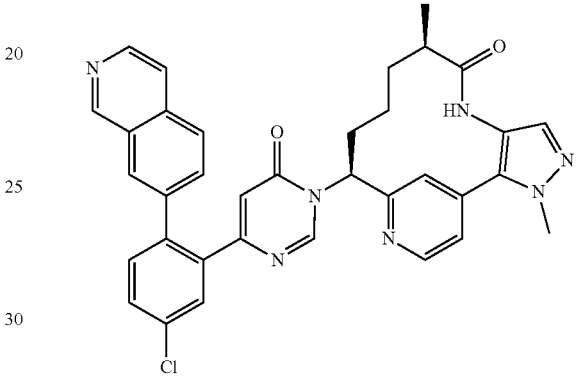

MS(ESI) m/z: 616 (M+H)+; 1H NMR (500 MHz, DMSO-d6) δ 9.25 (d, J=7.3 Hz, 2H), 8.73 (s, 1H), 8.60 (d, J=5.2 Hz, 1H), 8.50 (d, J=5.8 Hz, 1H), 8.03 (s, 1H), 7.90 (d, J=8.5 Hz, 1H), 7.86 (d, J=5.5 Hz, 1H), 7.75 (d, J=1.8 Hz, 1H), 7.70-7.66 (m, 1H), 7.63-7.56 (m, 3H), 7.53 (d, J=4.9 Hz, 1H), 7.45 (s, 1H), 6.22 (s, 1H), 5.82-5.74 (m, 1H), 3.98 (s, 3H), 2.66-2.59 (m, 1H), 2.25-2.16 (m, 1H), 2.07-1.99 (m, 1H), 1.83-1.74 (m, 1H), 1.48-1.38 (m, 1H), 1.35-1.25 (m, 1H), 0.85 (d, J=7.0 Hz, 3H), 0.47-0.32 (m, 1H); Analytical HPLC (Method A): RT=1.77 min, purity=94.8%; Factor XIa Ki=260 nM, Plasma Kallikrein Ki=3,600 nM.

Example 349

Preparation of (9R,13S)-13-{4-[5-chloro-2-(pyrimidin-5-yl)phenyl]-6-oxo-1,6-dihydropyrimidin-1-yl}-3,9-dimethyl-3,4,7,15-tetraazatricyclo[12.3.1.0$^{2,6}$]octadeca-1(18),2(6),4,14,16-pentaen-8-one

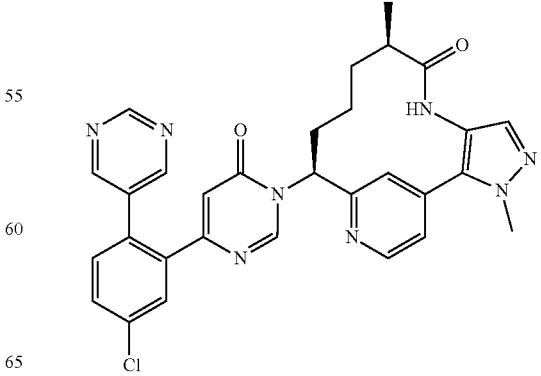

MS(ESI) m/z: 567 (M+H)+; 1H NMR (500 MHz, DMSO-d6) δ 9.22 (s, 1H), 9.16 (s, 1H), 8.80 (s, 1H), 8.71-8.66 (m, 3H), 7.79 (d, J=2.1 Hz, 1H), 7.73 (dd, J=8.2, 1.8 Hz, 1H), 7.67 (s, 1H), 7.62 (d, J=8.2 Hz, 1H), 7.58 (d, J=4.9 Hz, 1H), 7.48 (s, 1H), 6.46 (s, 1H), 5.89 (d, J=10.4 Hz, 1H), 4.02 (s, 3H), 2.69-2.61 (m, 1H), 2.33-2.23 (m, 1H), 2.16-2.07 (m, J=13.7 Hz, 1H), 1.87-1.78 (m, 1H), 1.52-1.43 (m, 1H), 1.38-1.28 (m, 1H), 0.89 (d, J=6.7 Hz, 3H), 0.48-0.35 (m, 1H); Analytical HPLC (Method A): RT=1.4 min, purity=100%; Factor XIa Ki=16 nM, Plasma Kallikrein Ki=3,000 nM.

Example 350

Preparation of ethyl 2-[4-(4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,6-dihydropyrimidin-4-yl}phenyl)-1H-pyrazol-1-yl]acetate

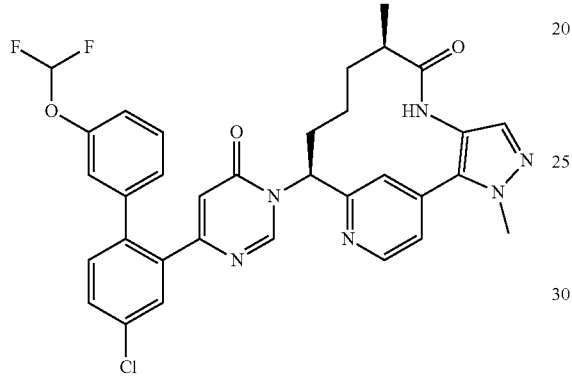

MS(ESI) m/z: 631.1 (M+H)+; 1H NMR (500 MHz, DMSO-d6) δ 9.25 (s, 1H), 8.84 (s, 1H), 8.67 (d, J=5.2 Hz, 1H), 7.69 (d, J=1.8 Hz, 1H), 7.66-7.46 (m, 6H), 7.43-7.38 (m, 1H), 7.16-7.11 (m, 2H), 7.00 (br. s., 1H), 6.20 (s, 1H), 5.89-5.82 (m, 1H), 4.01 (s, 3H), 2.68-2.60 (m, 1H), 2.33-2.23 (m, 1H), 2.13-2.04 (m, J=7.0 Hz, 1H), 1.86-1.77 (m, 1H), 1.52-1.42 (m, 1H), 1.38-1.28 (m, 1H), 0.89 (d, J=6.7 Hz, 3H), 0.51-0.37 (m, 1H); Analytical HPLC (Method A): RT=1.99 min, purity=96.9%; Factor XIa Ki=600 nM.

Example 351

Preparation of (9R,13S)-13-{4-[5-chloro-2-(1-ethyl-1H-pyrazol-4-yl)phenyl]-6-oxo-1,6-dihydropyrimidin-1-yl}-3,9-dimethyl-3,4,7,15-tetraazatricyclo[12.3.1.0²,⁶]octadeca-1(18),2(6),4,14,16-pentaen-8-one

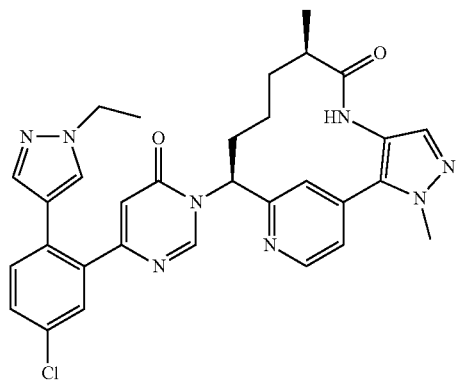 [SMILES: CCn1cc(-c2ccc(Cl)cc2-c2cc(=O)n([C@H]3CCC[C@@H](C)C(=O)Nc4cnn(C)c4-c4ccnc3c4)cn2)cn1]

MS(ESI) m/z: 583.1 (M+H)+; 1H NMR (400 MHz, CD3OD) δ 8.98 (s, 1H), 8.75 (d, J=5.1 Hz, 1H), 7.72 (s, 1H), 7.60 (s, 1H), 7.56-7.52 (m, 2H), 7.49 (s, 1H), 7.48-7.47 (m, 2H), 7.36 (s, 1H), 6.39 (s, 1H), 6.02 (dd, J=12.7, 4.3 Hz, 1H), 4.12 (q, J=7.3 Hz, 2H), 4.05 (s, 3H), 2.76-2.67 (m, 1H), 2.39-2.29 (m, 1H), 2.14-2.00 (m, 2H), 1.67-1.43 (m, 2H), 1.37 (t, J=7.3 Hz, 3H), 1.01 (d, J=6.8 Hz, 3H), 0.79-0.64 (m, 1H); Analytical HPLC (Method A): RT=1.55 min, purity=95.5%; Factor XIa Ki=96 nM.

Example 352

Preparation of (9R,13S)-13-(4-{5-chloro-2-[1-(4-fluorophenyl)-1H-pyrazol-4-yl]phenyl}-6-oxo-1,6-dihydropyrimidin-1-yl)-3,9-dimethyl-3,4,7,15-tetraazatricyclo[12.3.1.0²,⁶]octadeca-1(18),2(6),4,14,16-pentaen-8-one

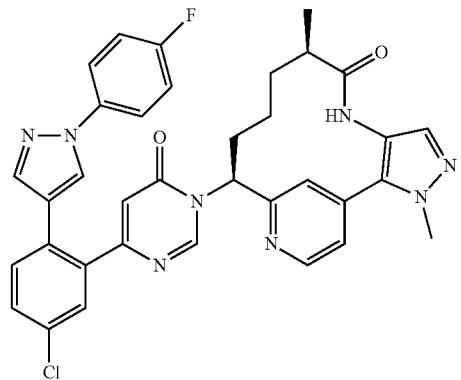 [SMILES: C[C@@H]1CCC[C@H](n2cnc(-c3cc(Cl)ccc3-c3cnn(-c4ccc(F)cc4)c3)cc2=O)c2cc(ccn2)-c2c(cnn2C)NC1=O]

MS(ESI) m/z: 649.3 (M+H)+; 1H NMR (500 MHz, DMSO-d6) δ 9.24 (s, 1H), 8.95 (s, 1H), 8.62 (d, J=5.2 Hz, 1H), 8.53 (s, 1H), 7.83 (dd, J=8.9, 4.6 Hz, 2H), 7.70 (s, 1H), 7.67-7.56 (m, 5H), 7.49 (s, 1H), 7.36 (t, J=8.7 Hz, 2H), 6.46 (s, 1H), 5.96 (d, J=10.7 Hz, 1H), 4.03 (s, 3H), 2.70-2.62 (m, 1H), 2.38-2.28 (m, 1H), 2.18-2.10 (m, 1H), 1.94-1.85 (m, 1H), 1.54-1.45 (m, 1H), 1.41-1.31 (m, 1H), 0.90 (d, J=6.7 Hz, 3H), 0.51-0.38 (m, 1H); Analytical HPLC (Method A): RT=1.99 min, purity=100%; Factor XIa Ki=7 nM.

Example 353

Preparation of (9R,13)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0²,⁶]octadeca-1(18),2(6),4,14,16-pentaen-8-one Trifluoroacetate

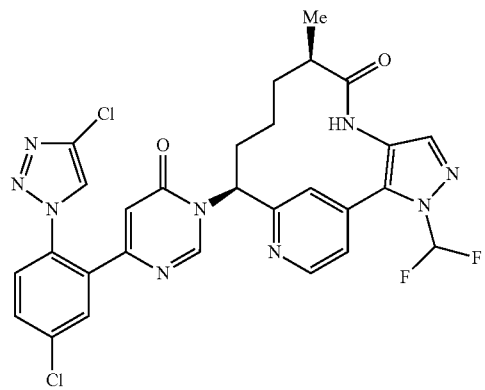 [SMILES: C[C@@H]1CCC[C@H](n2cnc(-c3cc(Cl)ccc3-n3cc(Cl)nn3)cc2=O)c2cc(ccn2)-c2c(cnn2C(F)F)NC1=O]

353A. Preparation of 1-(difluoromethyl)-4-nitro-1H-pyrazole

Cs$_2$CO$_3$ (14.41 g, 44.2 mmol) was suspended in a solution of 4-nitro-1H-pyrazole (5.00 g, 44.2 mmol) and DMF (40 mL). After heating to 120° C. for 5 min, solid sodium 2-chloro-2,2-difluoroacetate (13.48 g, 88 mmol) was added in 10 equal portions over 20 min. The reaction was complete after 10 min of additional heating. The mixture was added to a separatory funnel containing 100 mL water and extracted with Et$_2$O (2×50 mL). The combined organic layers were concentrated. Purification by normal-phase chromatography eluting with a gradient of hexanes/EtOAc yielded 1-(difluoromethyl)-4-nitro-1H-pyrazole (6.99 g, 42.9 mmol, 97% yield) as a clear, colorless oil. $^1$H NMR (500 MHz, CDCl$_3$) δ 8.58 (s, 1H), 8.22 (s, 1H), 7.39-7.05 (t, J=60 Hz, 1H).

353B. Preparation of (S)-tert-butyl (1-(4-(1-(difluoromethyl)-4-nitro-1H-pyrazol-5-yl)pyridin-2-yl)but-3-en-1-yl)carbamate To a N$_2$ flushed, 500 mL RBF was added (S)-tert-butyl (1-(4-chloropyridin-2-yl)but-3-en-1-yl)carbamate, prepared as described in Example 355, (10 g, 35.4 mmol), 1-(difluoromethyl)-4-nitro-1H-pyrazol (6.34 g, 38.9 mmol) and dioxane (100 mL). The solution was bubbled with N$_2$ for 5 min. Then Pd(OAc)$_2$ (0.40 g, 1.7 mmol), di(adamantan-1-yl)(butyl)phosphine (1.27 g, 3.5 mmol), K$_2$CO$_3$ (14.7 g, 106 mmol) and PvOH (1.08 g, 10.61 mmol) were added. The reaction mixture was bubbled with N$_2$ for 5 min then the reaction mixture was heated to 100° C. for 3 h. After this time, the solution was cooled to rt and water (200 mL) was added. The reaction mixture was then extracted with EtOAc (2×200 mL). The combined organic extracts were washed with water (200 mL), brine (200 mL), dried over Na$_2$SO$_4$, filtered and concentrated in vacuo. Purification by normal phase chromatography eluting with a gradient of hexanes/EtOAc afforded (S)-tert-butyl (1-(4-(1-(difluoromethyl)-4-nitro-1H-pyrazol-5-yl)pyridin-2-yl)but-3-en-1-yl)carbamate (12.91 g, 31.5 mmol, 89% yield) as a slightly yellow oil. MS(ESI) m/z: 410.4 [M+H]$^+$. $^1$H NMR (400 MHz, CDCl$_3$) δ 8.80 (dd, J=5.1, 0.7 Hz, 1H), 8.36 (s, 1H), 7.34 (s, 1H), 7.31 (dd, J=5.1, 1.5 Hz, 1H), 7.27-6.91 (t, J=58 Hz, 1H), 5.79-5.63 (m, 1H), 5.16-5.03 (m, 2H), 4.92 (d, J=5.9 Hz, 1H), 2.67 (t, J=6.4 Hz, 2H), 1.46 (br. s., 9H).

353C. Preparation of (S)-tert-butyl (1-(4-(4-amino-1-(difluoromethyl)-1H-pyrazol-5-yl)pyridin-2-yl)but-3-en-1-yl)carbamate To a 100 mL, 3-necked RBF was added a solution of (S)-tert-butyl (1-(4-(1-(difluoromethyl)-4-nitro-1H-pyrazol-5-yl)pyridin-2-yl)but-3-en-1-yl)carbamate (0.78 g, 1.90 mmol) in MeOH (12 mL) and a solution of NH$_4$Cl (1.02 g, 19 mmol) in water (3 mL). To the solution was added Fe (0.53 g, 9.49 mmol). The reaction mixture was heated to 65° C. for 3 h. Water (50 mL) was added. After cooling to rt, the mixture was filtered through a CELITE® pad and rinsed with MeOH (200 mL). The filtrate was concentrated in vacuo. The residue was partitioned between EtOAC (100 mL) and water (100 mL). The organic phase was separated, washed with water (100 mL), brine (100 mL), dried over Na$_2$SO$_4$, filtered and concentrated in vacuo. Purification by normal phase chromatography eluting with a gradient of DCM/MeOH yielded (S)-tert-butyl (1-(4-(4-amino-1-(difluoromethyl)-1H-pyrazol-5-yl)pyridin-2-yl)but-3-en-1-yl)carbamate (0.585 g, 1.54 mmol, 81% yield) as an oil. MS(ESI) m/z: 380.1 [M+H]$^+$. $^1$H NMR (400 MHz, CDCl$_3$) δ 8.70 (dd, J=5.0, 0.7 Hz, 1H), 7.43 (s, 1H), 7.36 (s, 1H), 7.32 (dd, J=5.1, 1.5 Hz, 1H), 7.28-6.97 (t, J=58 Hz, 1H), 5.80-5.66 (m, 1H), 5.65-5.53 (m, 1H), 5.13-5.03 (m, 2H), 4.87 (br. s., 1H), 3.22 (br. s., 2H), 2.65 (t, J=6.5 Hz, 2H), 1.52-1.37 (m, 9H).

353D. Preparation of Tert-Butyl ((S)-1-(4-(1-(difluoromethyl)-4-((R)-2-methylbut-3-enamido)-1H-pyrazol-5-yl)pyridin-2-yl)but-3-en-1-yl)carbamate To a N$_2$ flushed, 3-necked, 250 mL RBF was added a solution of (S)-tert-butyl (1-(4-(4-amino-1-(difluoromethyl)-1H-pyrazol-5-yl)pyridin-2-yl)but-3-en-1-yl)carbamate (5 g, 13.18 mmol) and EtOAc (50 ml). The solution was cooled to −10° C. and (R)-2-methylbut-3-enoic acid, as prepared in Example 354, (1.72 g, 17.13 mmol), pyridine (4.26 ml, 52.7 mmol). and T3P® (23.54 ml, 39.5 mmol) were added. The cooling bath was removed and the solution was allowed to warm to rt and then stir over a period of 20 h. Water (30 mL) and EtOAc (30 mL) were added and the mixture was stirred for 30 min. The organic phase was separated and the aqueous layer was extracted with EtOAc (30 mL). The combined organic extracts were washed with brine (50 mL), dried over Na$_2$SO$_4$, filtered and concentrated in vacuo. Purification by normal phase chromatography eluting with a gradient of hexanes/EtOAc gave tert-butyl ((S)-1-(4-(1-(difluoromethyl)-4-((R)-2-methylbut-3-enamido)-1H-pyrazol-5-yl)pyridin-2-yl)but-3-en-1-yl)carbamate (5.69 g, 12.33 mmol, 94% yield). MS(ESI) m/z: 462.2 [M+H]$^+$. $^1$H NMR (400 MHz, CDCl$_3$) δ 8.75 (dd, J=5.0, 0.6 Hz, 1H), 8.37 (s, 1H), 7.32 (t, J=59 Hz, 1H), 7.28 (br. s., 1H), 7.20 (s, 1H), 5.97-5.85 (m, 1H), 5.78-5.65 (m, 1H), 5.56-5.44 (m, 1H), 5.28-5.19 (m, 2H), 5.12 (d, J=2.0 Hz, 2H), 4.91-4.82 (m, 1H), 3.20-3.11 (m, 1H), 2.72-2.62 (m, 2H), 1.48-1.43 (s, 9H), 1.33 (d, J=6.8 Hz, 3H).

353E. Preparation of Tert-Butyl N-[(9R,10E,13S)-3-(difluoromethyl)-9-methyl-8-oxo-3,4,7,15-tetraazatricyclo[12.3.1.0$^{2,6}$]octadeca-1(18),2(6),4,10,14,16-hexaen-13-yl]carbamate To a N$_2$ flushed, 2 L, 3-necked, RBF was added a solution of tert-butyl ((S)-1-(4-(1-(difluoromethyl)-4-((R)-2-methylbut-3-enamido)-1H-pyrazol-5-yl)pyridin-2-yl)but-3-en-1-yl)carbamate (3 g, 6.50 mmol) in EtOAc (1300 ml). The solution was sparged with argon for 15 min. Grubbs II (1.38 g, 1.63 mmol) was added in one portion. The reaction mixture was heated to reflux for 24 h. After cooling to rt, the solvent was removed and the residue was purified by normal phase chromatography eluting with a gradient of DCM/MeOH to yield tert-butyl N-[(9R,10E,13S)-3-(difluoromethyl)-9-methyl-8-oxo-3,4,7,15-tetraazatricyclo[12.3.1.0$^{2,6}$]octadeca-1(18),2(6),4,10,14,16-hexaen-13-yl]carbamate (2.13 g, 4.91 mmol, 76% yield) as a tan solid. MS(ESI) m/z: 434.4 [M+H]$^+$. $^1$H NMR (400 MHz, CDCl$_3$) δ 8.71 (d, J=5.1 Hz, 1H), 7.78 (s, 1H), 7.44-7.40 (m, 1H), 7.36 (br. s., 1H), 7.27 (t, J=58 Hz, 1H), 6.87 (s, 1H), 6.49-6.39 (m, 1H), 5.78 (s, 1H), 4.80 (br. s., 2H), 3.18-3.08 (m, 1H), 3.08-2.98 (m, 1H), 2.06-1.93 (m, 1H), 1.51 (s, 9H), 1.19 (d, J=6.6 Hz, 3H).

353F. Preparation of Tert-Butyl N-[(9R,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]carbamate Pd/C (0.60 g, 0.570 mmol) was added to a 250 mL Parr hydrogenation flask containing a solution of tert-butyl N-[(9R,10E,13S)-3-(difluoromethyl)-9-methyl-8-oxo-3,4,7,15-tetraazatricyclo[12.3.1.0²,⁶]octadeca-1(18),2(6),4,10,14,16-hexaen-13-yl]carbamate (2.46 g, 5.68 mmol) in EtOH (100 mL). The flask was purged with N₂ and pressurized to 55 psi of H₂ allowed to stir for 18 h. The reaction was filtered through CELITE® and concentrated to yield tert-butyl N-[(9R,13S)-3-(difluoromethyl)-9-methyl-8-oxo-3,4,7,15-tetraazatricyclo[12.3.1.0²,⁶]octadeca-1(18),2(6),4,14,16-pentaen-13-yl]carbamate (2.17 g, 88% yield) as a tan solid. MS(ESI) m/z: 436.3 [M+H]⁺. ¹H NMR (400 MHz, DMSO-d₆) δ 9.32 (s, 1H), 8.71 (d, J=5.0 Hz, 1H), 7.96 (t, J=58 Hz, 1H), 7.43 (s, 1H), 7.32 (d, J=4.8 Hz, 1H), 7.22 (d, J=7.3 Hz, 1H), 4.66 (d, J=8.3 Hz, 1H), 2.62 (br. s., 1H), 1.88 (d, J=12.8 Hz, 1H), 1.77-1.59 (m, 2H), 1.42-1.28 (m, 9H), 1.15 (d, J=18.2 Hz, 2H), 0.83 (d, J=7.0 Hz, 3H).

353G. Preparation of (9R,13S)-13-amino-3-(difluoromethyl)-9-methyl-3,4,7,15-tetraazatricyclo[12.3.1.0²,⁶]octadeca-1(18),2(6),4,14,16-pentaen-8-one 4 N HCl in dioxane (3.88 mL, 15.5 mmol) was added to a solution of tert-butyl N-[(9R,13S)-3-(difluoromethyl)-9-methyl-8-oxo-3,4,7,15-tetraazatricyclo[12.3.1.0²,⁶]octadeca-1(18),2(6),4,14,16-pentaen-13-yl]carbamate (2.25 g, 5.2 mmol) in MeOH (10 mL). The reaction was allowed to stir at rt for 2 h. The reaction was cooled in an ice bath, and 7 N NH₃ in MeOH (13.3 mL, 93.0 mmol) was added. After 5 min, the reaction was diluted with CH₂Cl₂ (80 mL) and the solid that formed was filtered. The filtrate was concentrated to yield (9R,13S)-13-amino-3-(difluoromethyl)-9-methyl-3,4,7,15-tetraazatricyclo[12.3.1.0²,⁶]octadeca-1(18),2(6),4,14,16-pentaen-8-one (1.3 g, 3.88 mmol, 75% yield). MS(ESI) m/z: 336.3 [M+H]⁺. ¹H NMR (400 MHz, DMSO-d₆) δ 9.33 (s, 1H), 8.71 (d, J=5.0 Hz, 1H), 7.94 (t, J=58 Hz, 1H), 7.85 (s, 1H), 7.40 (s, 1H), 7.32 (d, J=5.0 Hz, 1H), 4.01 (dd, J=10.2, 5.1 Hz, 1H), 2.63-2.53 (m, 1H), 1.90-1.69 (m, 2H), 1.53-1.36 (m, 2H), 1.16-1.00 (m, 1H), 0.85 (d, J=7.0 Hz, 3H).

353H. Preparation of (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0²,⁶]Octadeca-1(18),2(6),4,14,16-pentaen-8-one To a 100 mL flask containing a white suspension of 6-(5-chloro-2-(4-chloro-1H-1,2,3-triazol-1-yl)phenyl)pyrimidin-4-ol (0.83 g, 2.7 mmol), as prepared in Example 356 in ACN (36 mL) was added HATU (1.12 g, 3.0 mmol) and DBU (0.53 mL, 3.5 mmol). The resulting clear, yellow solution was stirred at rt. After 5 min, (9R,13S)-13-amino-3-(difluoromethyl)-9-methyl-3,4,7,15-tetraazatricyclo[12.3.1.0²,⁶]octadeca-1(18),2(6),4,14,16-pentaen-8-one (0.9 g, 2.68 mmol) was added and the resulting suspension was stirred at rt for 3 h. The reaction was then concentrated and purified by normal phase silica gel chromatography, eluting with a gradient of 0% to 100% EtOAc in hexanes to yield (9R,13S)-13-{4-[5-chloro-2-(4-chloro-1H-1,2,3-triazol-1-yl)phenyl]-6-oxo-1,6-dihydropyrimidin-1-yl}-3-(difluoromethyl)-9-methyl-3,4,7,15-tetraazatricyclo[12.3.1.0²,⁶]octadeca-1(18),2(6),4,14,16-pentaen-8-one (0.87 g, 50% yield) as a white solid. MS(ESI) m/z: 626.2 [M+H]⁺. ¹H NMR (500 MHz, CD₃OD) δ 8.91-8.83 (m, 1H), 8.78-8.71 (m, 1H), 8.33 (s, 1H), 7.88 (d, J=2.5 Hz, 1H), 7.74 (s, 2H), 7.69-7.67 (m, 1H), 7.65 (s, 1H), 7.63 (t, J=58 Hz, 1H), 7.52-7.50 (m, 1H), 6.36 (d, J=0.8 Hz, 1H), 6.06-5.95 (m, 1H), 2.76-2.65 (m, 1H), 2.36-2.21 (m, 1H), 2.08-1.93 (m, 2H), 1.63-1.53 (m, 1H), 1.53-1.42 (m, 1H), 0.99 (d, J=6.9 Hz, 3H). Analytical HPLC (Method A): RT=8.87 min, purity=99.7%.

Example 354

Preparation (9R,13S)-13-{4-[5-chloro-2-(4-chloro-1H-1,2,3-triazol-1-yl)phenyl]-6-oxo-1,6-dihydropyrimidin-1-yl}-9-methyl-4-(pyridin-3-yl)-3,4,7,15-tetraazatricyclo[12.3.1.0²,⁶]octadeca-1(18),2,5,14,16-pentaen-8-one Trifluoroacetate

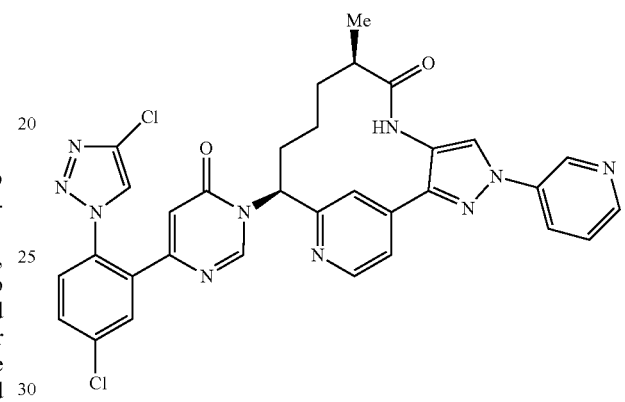

354A. Preparation of 4-nitro-1-((2-(trimethylsilyl)ethoxy)methyl)-1H-pyrazole

To a solution of 4-nitro-1H-pyrazole (5.0 g, 44.2 mmol) in THF (100 mL) at 0° C. was added N-cyclohexyl-N-methylcyclohexanamine (0.948 mL, 4.43 mmol) followed by dropwise addition of SEM-Cl (12.55 mL, 70.7 mmol). The reaction mixture was then allowed to gradually rise to rt and stirred at rt overnight. The reaction mixture was then concentrated, followed by purification using normal phase chromatography to yield 4-nitro-1-((2-(trimethylsilyl)ethoxy)methyl)-1H-pyrazole as clear oil (2.4 g, 21% yield). ¹H NMR (500 MHz, CDCl₃) δ 8.31 (s, 1H), 8.10 (s, 1H), 5.46 (s, 2H), 3.67-3.55 (m, 2H), 0.99-0.90 (m, 2H), 0.05-0.03 (m, 9H).

354B. Preparation of (S)-benzyl (1-(4-(4-nitro-1-((2-(trimethylsilyl)ethoxy)methyl)-1H-pyrazol-5-yl)pyridin-2-yl)but-3-en-1-yl)carbamate To a N₂ flushed pressure vial was added (S)-benzyl (1-(4-chloropyridin-2-yl)but-3-en-1-yl)carbamate, prepared as described in Example 357, (1.9 g, 6.00 mmol), 4-nitro-1-((2-(trimethylsilyl)ethoxy)methyl)-1H-pyrazole (1.6 g, 6.60 mmol), di(adamant-1-yl)(butyl)phosphine (0.323 g, 0.90 mmol), PvOH (0.209 mL, 1.80 mmol) and K₂CO₃ (2.48 g, 17.9 mmol). To the above mixture was then added DMA (45 mL) and the vial was purged with N₂ for 5 min. To this mixture was then added Pd(OAc)₂ (0.135 g, 0.600 mmol). The reaction mixture was again briefly purged with N₂. The vial was sealed and heated in microwave at 120° C. for 1 h. The reaction mixture was cooled to rt and partitioned between 10% aqueous LiCl (15 mL) and EtOAc (30 mL). The aqueous layer was extracted with EtOAc (2×20 mL) and the combined organic layers were washed with brine (15 mL) and dried over MgSO$_4$. The crude product was then purified using normal phase chromatography to yield (S)-benzyl (1-(4-(4-nitro-1-((2-(trimethylsilyl) ethoxy)methyl)-1H-pyrazol-5-yl)pyridin-2-yl)but-3-en-1-yl)carbamate (1.92 g, 58% yield) as a brown oil. MS(ESI) m/z: 524.2 (M+H)$^+$.

354C. Preparation of (5)-benzyl (1-(4-(4-amino-1-((2-(trimethylsilyl)ethoxy)methyl)-1H-pyrazol-5-yl) pyridin-2-yl)but-3-en-1-yl)carbamate A solution of (S)-benzyl (1-(4-(4-nitro-1-((2-(trimethylsilyl)ethoxy)methyl)-1H-pyrazol-5-yl)pyridin-2-yl)but-3-en-1-yl)carbamate (1.92 g, 3.68 mmol), prepared as described in Example 354B, in MeOH (20 mL) and AcOH (2 mL) was heated in oil bath to 40° C. To the above clear solution was then slowly added Zn (0.481 g, 7.35 mmol, in 3 portions (50:25:25%)) and allowed to stir at the same temperature for 5 min. Additional Zn was added to the reaction. The reaction mixture was monitored by LCMS and when complete, the reaction mixture was cooled and then 2.0 g of K$_2$CO$_3$ (1 g for 1 mL AcOH) and 2.0 mL water was added. The reaction mixture was then stirred for 5 min. The reaction mixture was then filtered over a pad of CELITE® and concentrated in vacuo to yield the crude product. The crude product was then partitioned between EtOAc (30 mL) and saturated NaHCO$_3$ (15 mL) solution. The organic layers were separated, dried over MgSO$_4$, filtered and concentrated. The crude product was then purified using normal phase chromatography to yield (S)-benzyl (1-(4-(4-amino-1-((2-(trimethylsilyl) ethoxy) methyl)-1H-pyrazol-5-yl)pyridin-2-yl)but-3-en-1-yl)carbamate (1.15 g, 63% yield) as pale yellow oil. MS(ESI) m/z: 494.4 (M+H)$^+$.

354D. Preparation of benzyl ((S)-1-(4-(4-((R)-2-methylbut-3-enamido)-1-((2-(trimethylsilyl)ethoxy) methyl)-1H-pyrazol-5-yl)pyridin-2-yl)but-3-en-1-yl) carbamate To a N$_2$ flushed, 3-necked, 250 mL RBF was added a solution (S)-benzyl (1-(4-(4-amino-1-((2-(trimethylsilyl) ethoxy)methyl)-1H-pyrazol-5-yl)pyridin-2-yl)but-3-en-1-yl)carbamate (1.15 g, 2.33 mmol) and EtOAc (15 mL). The solution was cooled to −10° C. and (R)-2-methylbut-3-enoic acid (350 mg, 3.49 mmol), pyridine (0.564 mL, 6.99 mmol) and T3P® (2.77 mL, 4.66 mmol) were added. The cooling bath was removed and the solution was allowed to warm to rt and then stir over a period of 20 h. Water (20 mL) and EtOAc (20 mL) were added and the mixture was stirred for 30 min. The organic phase was separated and the aqueous layer was extracted with EtOAc (20 mL). The combined organic extracts were washed with brine (15 mL), dried over Na$_2$SO$_4$, filtered and concentrated in vacuo. Purification by normal phase chromatography eluting with a gradient of hexanes/EtOAc gave benzyl ((S)-1-(4-(4-((R)-2-methylbut-3-enamido)-1-((2-(trimethylsilyl)ethoxy)methyl)-1H-pyrazol-5-yl)pyridin-2-yl)but-3-en-1-yl)carbamate (1.12 g, 79% yield). MS(ESI) m/z: 576.4 [M+H]$^+$.

354E. Preparation of Benzyl N-[(9R,10E,13S)-9-methyl-8-oxo-3-{[2-(trimethylsilyl)ethoxy]methyl}-3,4,7,15-tetraazatricyclo[12.3.1.0$^{2,6}$]octadeca-1(18),2(6),4,10,14,16-hexaen-13-yl]carbamate To a N$_2$ flushed, 250 mL, 3-necked, RBF was added a solution of benzyl ((S)-1-(4-(4-((R)-2-methylbut-3-enamido)-1-((2-(trimethylsilyl)ethoxy)methyl)-1H-pyrazol-5-yl)pyridin-2-yl)but-3-en-1-yl)carbamate (1.12 g, 1.945 mmol) in DCE (18 mL). The solution was sparged with Ar for 15 min. Grubbs II (662 mg, 0.778 mmol) was added in one portion. The reaction mixture was heated at 120° C. in microwave for 30 min. After cooling to rt, the solvent was removed and the residue was purified by normal phase chromatography eluting with a gradient of DCM/MeOH to yield benzyl N-[(9R,10E,13S)-9-methyl-8-oxo-3-{[2-(trimethylsilyl)ethoxy]methyl}-3,4,7,15-tetraazatricyclo [12.3.1.0$^{2,6}$]octadeca-1(18),2(6),4,10,14,16-hexaen-13-yl] carbamate (477 mg, 42% yield) as a tan solid. MS(ESI) m/z: 548.3 [M+H]$^+$.

354F. Preparation of Benzyl N-[(9R,13S)-9-methyl-8-oxo-3-{[2-(trimethylsilyl)ethoxy]methyl}-3,4,7,15-tetraazatricyclo[12.3.1.0$^{2,6}$]octadeca-1(18),2(6),4,14,16-pentaen-13-yl]carbamate Pd/C (0.93 g, 0.871 mmol) was added to a 250 mL Parr hydrogenation flask containing a solution of benzyl N-[(9R,10E,13S)-9-methyl-8-oxo-3-{[2-(trimethylsilyl) ethoxy] methyl}-3,4,7,15-tetraazatricyclo[12.3.1.0$^{2,6}$]octadeca-1 (18),2(6),4,10,14,16-hexaen-13-yl]carbamate (477 mg, 0.871 mmol) in EtOH (20 mL). The flask was purged with N$_2$ and pressurized to 55 psi of H$_2$ and allowed to stir for 4 h. The reaction was filtered through a pad of CELITE® and concentrated to yield benzyl N-[(9R,13S)-9-methyl-8-oxo-3-{[2-(trimethylsilyl)ethoxy]methyl}-3,4,7,15-tetraazatricyclo[12.3.1.0$^{2,6}$]octadeca-1(18),2(6),4,14,16-pentaen-13-yl]carbamate (245 mg, 64% yield) as a tan solid. MS(ESI) m/z: 416.4 [M+H]$^+$.

354G. Preparation of (9R,13S)-13-{4-[5-chloro-2-(4-chloro-1H-1,2,3-triazol-1-yl)phenyl]-6-oxo-1,6-dihydropyrimidin-1-yl}-9-methyl-3-{[2-(trimethylsilyl)ethoxy]methyl}-3,4,7,15-tetraazatricyclo [12.3.1.0$^{2,6}$]octadeca-1(18),2(6),4,14,16-pentaen-8-one To a 100 mL flask containing a white suspension of 6-(5-chloro-2-(4-chloro-1H-1,2,3-triazol-1-yl)phenyl)pyrimidin-4-ol (0.580 g, 1.88 mmol), prepared as described in Example 356 in ACN (25.0 ml) was added HATU (0.785 g, 2.06 mmol) and DBU (0.370 ml, 2.44 mmol). The resulting clear, yellow solution was stirred at rt. After 5 min, benzyl N-[(9R,13S)-9-methyl-8-oxo-3-{[2-(trimethylsilyl)ethoxy] methyl}-3,4,7,15-tetraazatricyclo[12.3.1.0$^{2,6}$]octadeca-1 (18),2(6),4,14,16-pentaen-13-yl]carbamate (0.780 g, 1.88 mmol) was added and the resulting suspension was stirred at rt for 3 h. The reaction was concentrated and the crude material was purified by normal phase silica gel chromatography to give (9R,13S)-13-{4-[5-chloro-2-(4-chloro-1H-1,2,3-triazol-1-yl)phenyl]-6-oxo-1,6-dihydropyrimidin-1-yl}-9-methyl-3-{[2-(trimethylsilyl)ethoxy]methyl}-3,4,7,15-tetraazatricyclo[12.3.1.0$^{2,6}$]octadeca-1(18),2(6),4,14,16-pentaen-8-one (0.65 g, 0.92 mmol, 49.0% yield) isolated as a purple solid. MS(ESI) m/z: 706.7 [M+H]$^+$.

354H. Preparation of (9R,13S)-13-{4-[5-chloro-2-(4-chloro-1H-1,2,3-triazol-1-yl)phenyl]-6-oxo-1,6-dihydropyrimidin-1-yl}-9-methyl-3,4,7,15-tetraazatricyclo[12.3.1.0$^{2,6}$]octadeca-1(18),2(6),4,14,16-pentaen-8-one trifluoroacetate To a solution of (9R,13S)-13-{4-[5-chloro-2-(4-chloro-1H-1,2,3-triazol-1-yl)phenyl]-6-oxo-1,6-dihydropyrimidin-1-yl}-9-methyl-3-{[2-(trimethylsilyl)ethoxy]methyl}-3,4,7, 15-tetraazatricyclo[12.3.1.0$^{2,6}$]octadeca-1(18),2(6),4,14,16-pentaen-8-one (12 mg, 0.017 mmol) in DCM (0.8 mL) was added TFA (0.2 mL, 2.60 mmol) and the reaction was stirred at rt for 30 min. The reaction mixture was then concentrated and the residue was purified by prep HPLC purification to give (9R,13S)-13-{4-[5-chloro-2-(4-chloro-1H-1,2,3-triazol-1-yl)phenyl]-6-oxo-1,6-dihydropyrimidin-1-yl}-9-methyl-3,4,7,15-tetraazatricyclo[12.3.1.0$^{2,6}$]octadeca-1(18),2(6),4,14,16-pentaen-8-one trifluoroacetate (5.3 mg, 43% yield) as a pale pink solid. $^1$H NMR (400 MHz, CD$_3$OD) δ 8.72-8.57 (m, 2H), 8.37 (s, 1H), 7.99 (s, 1H), 7.91 (d, J=2.2 Hz, 1H), 7.82-7.72 (m, 2H), 7.70-7.63 (m, 2H), 6.41 (s, 1H), 6.11-5.95 (m, 1H), 2.81 (td, J=6.8, 3.4 Hz, 1H), 2.44-2.17 (m, 2H), 2.15-2.01 (m, 1H), 1.80-1.65 (m, 1H), 1.62-1.46 (m, 1H), 1.11 (d, J=7.0 Hz, 3H), 1.01 (br. s., 1H). MS(ESI) m/z: 576.4 [M+H]$^+$. Analytical HPLC (Method A): RT=6.98 min, purity=>95.0%.

354I. Preparation (9R,13S)-13-{4-[5-chloro-2-(4-chloro-1H-1,2,3-triazol-1-yl)phenyl]-6-oxo-1,6-dihydropyrimidin-1-yl}-9-methyl-4-(pyridin-3-yl)-3,4,7,15-tetraazatricyclo[12.3.1.0$^{2,6}$]octadeca-1(18),2,5,14,16-pentaen-8-one; Trifluoroacetate (9R,13S)-13-{4-[5-Chloro-2-(4-chloro-1H-1,2,3-triazol-1-yl)phenyl]-6-oxo-1,6-dihydropyrimidin-1-yl}-9-methyl-3,4,7,15-tetraazatricyclo[12.3.1.0$^{2,6}$]octadeca-1(18),2(6),4,14,16-pentaen-8-one mono trifluoroacetate (0.09 g, 0.16 mmol), (1R,2R)—N$_1$,N$_2$-dimethylcyclohexane-1,2-diamine (0.022 g, 0.16 mmol), 3-iodopyridine (0.032 g, 0.16 mmol), CuI (2 mg, 10.5 μmol), Cs$_2$CO$_3$ (0.10 g, 0.31 mmol), and DMF (2 mL) were added to a vial containing a Teflon septum. The mixture was evacuated and back-filled with Ar three times and then heated to 100° C. for 3 h. The reaction was cooled and diluted with 2 mL of a 9:1 ACN-H$_2$O solution. After filtration through a syringe filter, the product was purified by prep HPLC to yield (9R,13S)-13-{4-[5-chloro-2-(4-chloro-1H-1,2,3-triazol-1-yl)phenyl]-6-oxo-1,6-dihydropyrimidin-1-yl}-9-methyl-4-(pyridin-3-yl)-3,4,7,15-tetraazatricyclo[12.3.1.0$^{2,6}$]octadeca-1(18),2,5,14,16-pentaen-8-one; trifluoroacetate (52 mg, 42%) as a tan solid. MS(ESI) m/z: 653.6 [M+H]$^+$. $^1$H NMR (400 MHz, CD$_3$OD) δ 9.31-9.24 (m, 1H), 8.80-8.73 (m, 1H), 8.71-8.64 (m, 2H), 8.60 (s, 2H), 8.37 (s, 1H), 8.01-7.96 (m, 1H), 7.95-7.90 (m, 1H), 7.86-7.80 (m, 1H), 7.79-7.73 (m, 2H), 7.71-7.64 (m, 1H), 6.44-6.36 (m, 1H), 6.17-6.04 (m, 1H), 2.97-2.80 (m, 1H), 2.40-2.22 (m, 2H), 2.15-2.00 (m, 1H), 1.82-1.69 (m, 1H), 1.69-1.52 (m, 1H), 1.41-1.26 (m, 1H), 1.11 (d, J=7.0 Hz, 3H). Analytical HPLC (Method A): RT=6.69 min, purity=97.5%.

Example 355

Preparation of tert-butyl N-[(1S)-1-(4-chloropyridin-2-yl)but-3-en-1-yl]carbamate

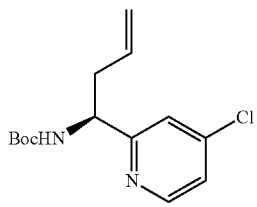 [SMILES: C=CC[C@H](NC(=O)OC(C)(C)C)c1cc(Cl)ccn1]

355A. Preparation of 4-chloro-2-[(E)-2-[(S)-2-methylpropane-2-sulfinyl]ethenyl]pyridine To a solution of S-(−)-t-butyl-sulfinamide (0.856 g, 7.06 mmol) in DCM (14.13 mL) was added sequentially CuSO$_4$ (2.481 g, 15.54 mmol) and 4-chloropicolinaldehyde [1.0 g, 7.06 mmol, prepared according to a modified described by Negi (Synthesis, 991 (1996))]. The white suspension was stirred at rt. After 3 h, the brown suspension was filtered through CELITER, eluting with DCM, to give a clear brown filtrate. Concentration gave crude product as a brown oil weighing 1.85 g. Purification by normal phase chromatography gave tert-butyl N-[(1S)-1-(4-chloropyridin-2-yl)but-3-en-1-yl]carbamate (1.31 g) as a clear, yellow oil. MS(ESI) m/z: 245.0 (M+H)$^+$.

355B. Preparation of (R)—N-[(1S)-1-(4-chloropyridin-2-yl)but-3-en-1-yl]-2-methylpropane-2-sulfinamide To a cooled (0-5° C.) mixture of InCl$_3$ (13.56 g, 61.3 mmol) in THF (170 mL) was added dropwise, over 30 min, allylmagnesium bromide (1 M in Et$_2$O) (62 mL, 61.3 mmol). The reaction was allowed to warm to rt. After 1 h at rt, a solution of 4-chloro-2-[(E)-2-[(S)-2-methylpropane-2-sulfinyl]ethenyl]pyridine (10 g, 40.9 mmol) in EtOH (170 mL) was added to the reaction mixture. After 2-3 h, the reaction was concentrated under vacuum at 50-55° C. The crude material was partitioned between EtOAc (200 ml) and water (1×50 ml) and the layers were separated. The aqueous layer was extracted with EtOAc (2×50 ml). The organic layers were combined and washed with brine (1×100 ml), dried over Na$_2$SO$_4$, filtered and concentrated to give (R)—N-[(1S)-1-(4-chloropyridin-2-yl)but-3-en-1-yl]-2-methylpropane-2-sulfinamide (13.5 g, 106%) as a yellow oil. MS(ESI) m/z: 287.2 (M+H)$^+$. This material was used in the next step without further purification.

355C. Preparation of (1S)-1-(4-chloropyridin-2-yl)but-3-en-1-amine (R)—N-[(1S)-1-(4-Chloropyridin-2-yl)but-3-en-1-yl]-2-methylpropane-2-sulfinamide (75 g, 261 mmol) was dissolved in MeOH (1500 mL). 6N HCl (750 ml, 4.5 mol) was added. The reaction was stirred at rt for 2-3 h and then was concentrated. The residue was diluted with water (2 L), washed with EtOAc (500 ml). The aqueous layer was basified with saturated Na$_2$CO$_3$ solution, then extracted into EtOAc (3×1 L). The combined organic layers were washed with water (1×1 L) and brine (1×1 L), dried over Na$_2$SO$_4$, filtered and conc. under vacuum at 50-55° C. to give (1S)-1-(4-chloropyridin-2-yl)but-3-en-1-amine (43g, 90%) which was without further purification. MS(ESI) m/z: 183.2 (M+H)$^+$.

355D. Preparation of Tert-Butyl N-[(1S)-1-(4-chloropyridin-2-yl)but-3-en-1-yl]carbamate (1S)-1-(4-Chloropyridin-2-yl)but-3-en-1-amine (42g, 230 mmol) was dissolved in DCM (420 mL). Et$_3$N (32.1 mL, 230 mmol) was added followed by dropwise addition of BOC$_2$O (53.4 mL, 230 mmol). The reaction was stirred at rt for 2-3 h. The reaction was diluted with excess DCM (1 L), washed with water (1×500 ml) and brine (1×500 ml). The organic layer was dried over Na₂SO₄, filtered, and concentrated. The crude product was then purified using silica gel chromatography to give tert-butyl N-[(1S)-1-(4-chloropyridin-2-yl)but-3-en-1-yl]carbamate (61 g, 86%) as a pale yellow solid. MS(ESI) m/z: 283.2 (M+H)⁺. ¹H NMR (500 MHz, CDCl₃) δ 8.44 (d, 1H), 7.26-7.16 (dd, 2H), 5.69-5.61 (m, 1H), 5.59 (bs, 1H), 5.07-5.03 (m, 2H), 4.76 (bs, 1H), 2.62-2.55 (m, 2H), 1.42 (s, 9H).

Example 356

Preparation of 6-[5-chloro-2-(4-chloro-1H-1,2,3-triazol-1-yl)phenyl]pyrimidin-4-ol

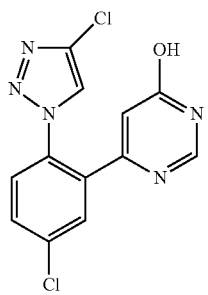

356A. Preparation of 4-chloro-2-(tetramethyl-1,3,2-dioxaborolan-2-yl)aniline

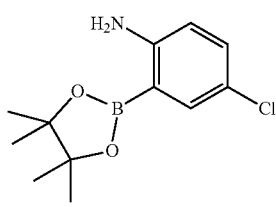 [SMILES: CC1(C)OB(c2cc(Cl)ccc2N)OC1(C)C]

In a 20 mL microwave vial was added 2-bromo-4-chloroaniline (3 g, 14.53 mmol), 4,4,5,5-tetramethyl-2-(tetramethyl-1,3,2-dioxaborolan-2-yl)-1,3,2-dioxaborolane (5.53 g, 21.80 mmol), KOAc (3.66 g, 37.3 mmol), Pd(dppf)Cl₂—CH₂Cl₂ adduct (0.32 g, 0.44 mmol) and DMSO (9 mL). The resulting suspension was purged with N₂, capped and heated at 80° C. for 22 h. The reaction was cooled to rt. Water was added to dissolve the salts, then the reaction was filtered. The remaining solid was suspended in DCM and the insoluble solid was filtered. The filtrate was concentrated and then purified by normal phase chromatography to give 4-chloro-2-(tetramethyl-1,3,2-dioxaborolan-2-yl)aniline (3.15 g, 86% yield) as a white solid. MS(ESI) m/z: 172.3 (M-C₆H₁₀+H)⁺. ¹H NMR (400 MHz, CDCl₃) δ 7.54 (d, J=2.6 Hz, 1H), 7.13 (dd, J=8.8, 2.6 Hz, 1H), 6.52 (d, J=8.6 Hz, 1H), 4.72 (br. s., 2H), 1.34 (s, 12H).

356B. Preparation of 4-chloro-2-(6-methoxypyrimidin-4-yl)aniline

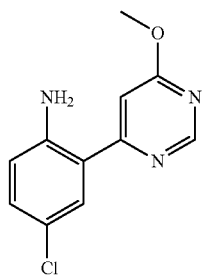 [SMILES: COc1cc(-c2cc(Cl)ccc2N)ncn1]

An RBF containing 4-chloro-6-methoxypyrimidine (3.13 g, 21.62 mmol), 4-chloro-2-(tetramethyl-1,3,2-dioxaborolan-2-yl)aniline (7.31 g, 21.62 mmol), Na₂CO₃ (2.29 g, 21.62 mmol), DME (86 ml), EtOH (10.81 ml) and water (10.81 ml) was equipped with a condenser. The mixture was purged with argon for several min, then Pd(dppf)Cl₂—CH₂Cl₂ adduct (1.77 g, 2.16 mmol) was added. The reaction was heated at 90° C. for 5 h. The reaction was cooled to rt, diluted with water and extracted with EtOAc. The organic layer was washed with brine, concentrated and purified by normal phase chromatography to give 4-chloro-2-(6-methoxypyrimidin-4-yl)aniline (2.86 g, 56.1% yield) as yellow solid. MS(ESI) m/z: 236.0 (M+H)⁺. ¹H NMR (500 MHz, CDCl₃) δ 8.78 (d, J=1.1 Hz, 1H), 7.49 (d, J=2.5 Hz, 1H), 7.15 (dd, J=8.8, 2.5 Hz, 1H), 6.99 (d, J=1.1 Hz, 1H), 6.67 (d, J=8.8 Hz, 1H), 5.89 (br. s., 2H), 4.03 (s, 3H).

356C. Preparation of 4-{5-chloro-2-[4-(trimethylsilyl)-1H-1,2,3-triazol-1-yl]phenyl}-6-methoxypyrimidine

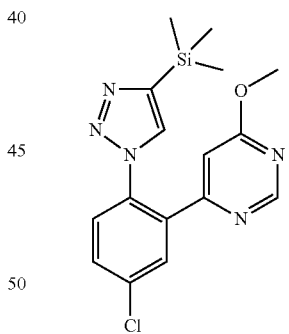

To a solution of 4-chloro-2-(6-methoxypyrimidin-4-yl) aniline (1.5 g, 6.36 mmol) in ACN (90 ml) at 0° C. was added 3-methylbutyl nitrite (1.28 ml, 9.55 mmol), followed by the dropwise addition of azidotrimethylsilane (1.26 ml, 9.55 mmol). Gas evolution was observed. After 10 min, the ice bath was removed, and the reaction was allowed to warm to rt. (Caution, aryl azides are potentially explosive.) After 1 h, ethynyltrimethylsilane (2.72 ml, 19.09 mmol) and Cu₂O (0.09 g, 0.64 mmol) were added and the reaction was stirred for an additional 1 h. The reaction was partitioned in EtOAc and sat NH₄Cl, and the layers were separated. The organic layer was washed with brine, dried over MgSO₄, filtered and concentrated. Purification by normal phase chromatography gave 4-{5-chloro-2-[4-(trimethylsilyl)-1H-1,2,3-triazol-1- yl]phenyl}-6-methoxypyrimidine (2.13 g, 5.92 mmol, 93% yield) as a yellow solid. MS(ESI) m/z: 360.3 (M+H)⁺. ¹H NMR (400 MHz, CDCl₃) δ 8.71 (d, J=1.1 Hz, 1H), 7.82 (d, J=2.2 Hz, 1H), 7.61-7.56 (m, 1H), 7.54-7.48 (m, 2H), 6.20 (d, J=1.1 Hz, 1H), 3.92 (s, 3H), 0.32-0.28 (m, 9H).

356D. Preparation of 4-[5-chloro-2-(4-chloro-1H-1,2,3-triazol-1-yl)phenyl]-6-methoxypyrimidine

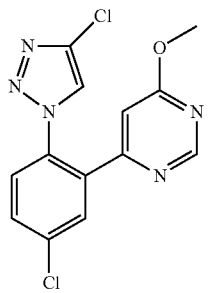 [SMILES: COc1cc(-c2cc(Cl)ccc2-n2cc(Cl)nn2)ncn1]

To a solution of 4-{5-chloro-2-[4-(trimethylsilyl)-1H-1,2,3-triazol-1-yl]phenyl}-6-methoxypyrimidine (1.56 g, 4.33 mmol) in ACN (28.9 ml) was added NCS (2.03 g, 15.17 mmol) and silica gel (6.51 g, 108 mmol). The reaction was stirred at 80° C. for 1 h. Then, the reaction was filtered to remove the silica gel and the collected silica gel was washed with EtOAc. The filtrate was washed with water (2×), brine and concentrated. Purification by normal phase chromatography gave 4-[5-chloro-2-(4-chloro-1H-1,2,3-triazol-1-yl)phenyl]-6-methoxypyrimidine (0.90 g, 64.5% yield) as a yellow foam. MS(ESI) m/z: 322.3 (M+H)⁺. ¹H NMR (400 MHz, CDCl₃) δ 8.70 (d, J=1.1 Hz, 1H), 7.75 (d, J=2.4 Hz, 1H), 7.66-7.55 (m, 2H), 7.50 (d, J=8.6 Hz, 1H), 6.52 (d, J=0.9 Hz, 1H), 3.98 (s, 3H).

356E. Preparation of 6-[5-chloro-2-(4-chloro-1H-1,2,3-triazol-1-yl)phenyl]pyrimidin-4-ol

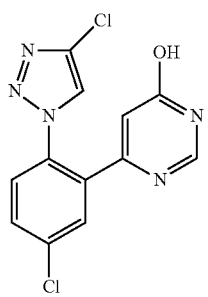

To a solution of 4-[5-chloro-2-(4-chloro-1H-1,2,3-triazol-1-yl)phenyl]-6-methoxypyrimidine (900 mg, 2.79 mmol) in AcOH (6 ml) was added 48% HBr in water (3 ml, 26.5 mmol). The mixture was stirred at 85° C. for 1 h. The reaction was concentrated to dryness and then partitioned between EtOAc and sat aqueous NaHCO₃. The mixture was separated and the aqueous layer was extracted with EtOAc (2×). The organic layers were combined, concentrated, and then the residue was purified by normal phase chromatography to give a white solid. The solid was suspended in Et₂O, filtered and washed with Et₂O to give 6-[5-chloro-2-(4-chloro-1H-1,2,3-triazol-1-yl)phenyl]pyrimidin-4-ol (610 mg, 70.9% yield) as a white solid. MS(ESI) m/z: 308.3 (M+H)⁺. ¹H NMR (400 MHz, CDCl₃) δ 7.96 (s, 1H), 7.74-7.67 (m, 2H), 7.62 (dd, J=8.5, 2.3 Hz, 1H), 7.47 (d, J=8.4 Hz, 1H), 6.44 (d, J=0.9 Hz, 1H).

Example 357

Preparation of (S)-benzyl (1-(4-chloropyridin-2-yl)but-3-en-1-yl)carbamate

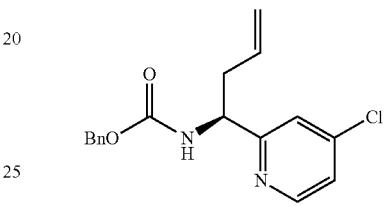

To a solution of (1S)-1-(4-chloropyridin-2-yl)but-3-en-1-amine (15.37 g, 60.1 mmol) in THF (150 mL) was added NaHCO₃ (15.16 g, 180 mmol) in H₂O (150 mL) at 0° C., followed by CBz-C₁ (12.88 mL, 90 mmol). The reaction was then stirred at 0° C. for 2 h. The reaction mixture was diluted with EtOAc (150 mL). The organic phase was separated, washed with brine (50 mL), dried over Na₂SO₄, filtered, and concentrated under reduced pressure. The crude material was purified using normal phase silica gel chromatography, eluting with a gradient of 0-20% EtOAc/petroleum ether) to obtain (S)-benzyl (1-(4-chloropyridin-2-yl)but-3-en-1-yl) carbamate (16 g, 84% yield) as a pale yellow liquid. MS(ESI) m/z: 317.5 (M+H)⁺. ¹H NMR (400 MHz, CDCl₃) δ 8.44 (d, J=5.3 Hz, 1H), 7.41-7.12 (m, 7H), 5.77 (d, J=7.0 Hz, 1H), 5.72-5.57 (m, 1H), 5.16-5.00 (m, 4H), 4.86 (q, J=6.7 Hz, 1H), 2.60 (t, J=6.2 Hz, 2H).

Example 358

Preparation of 6-[5-chloro-2-(4-chloro-1H-1,2,3-triazol-1-yl)phenyl]pyrimidin-4-ol

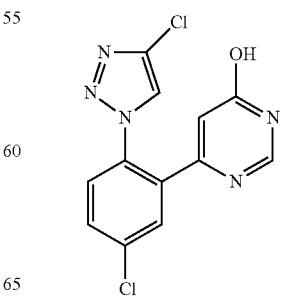

358A. Preparation of 4-chloro-2-(tetramethyl-1,3,2-dioxaborolan-2-yl)aniline

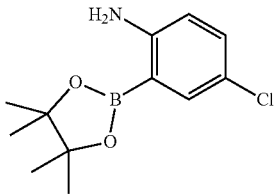 [SMILES: CC1(C)OB(c2cc(Cl)ccc2N)OC1(C)C]

In a 20 mL microwave vial was added 2-bromo-4-chloroaniline (3 g, 14.53 mmol), 4,4,5,5-tetramethyl-2-(tetramethyl-1,3,2-dioxaborolan-2-yl)-1,3,2-dioxaborolane (5.53 g, 21.80 mmol), KOAc (3.66 g, 37.3 mmol), Pd(dppf)Cl$_2$—CH$_2$Cl$_2$ adduct (0.32 g, 0.44 mmol) and DMSO (9 mL). The resulting suspension was purged with N$_2$, capped and heated at 80° C. for 22 h. The reaction was cooled to rt. Water was added to dissolve the salts, then the reaction was filtered. The remaining solid was suspended in DCM and the insoluble solid was filtered. The filtrate was concentrated and then purified by normal phase chromatography to give 4-chloro-2-(tetramethyl-1,3,2-dioxaborolan-2-yl)aniline (3.15 g, 86% yield) as a white solid. MS(ESI) m/z: 172.3 (M-C$_6$H$_{10}$+H)$^+$. $^1$H NMR (400 MHz, CDCl$_3$) δ 7.54 (d, J=2.6 Hz, 1H), 7.13 (dd, J=8.8, 2.6 Hz, 1H), 6.52 (d, J=8.6 Hz, 1H), 4.72 (br. s., 2H), 1.34 (s, 12H).

358B. Preparation of 4-chloro-2-(6-methoxypyrimidin-4-yl)aniline

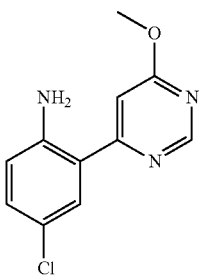

An RBF containing 4-chloro-6-methoxypyrimidine (3.13 g, 21.62 mmol), 4-chloro-2-(tetramethyl-1,3,2-dioxaborolan-2-yl)aniline (7.31 g, 21.62 mmol), Na$_2$CO$_3$ (2.29 g, 21.62 mmol), DME (86 ml), EtOH (10.81 ml) and water (10.81 ml) was equipped with a condenser. The mixture was purged with argon for several minutes then Pd(dppf)Cl$_2$—CH$_2$Cl$_2$ adduct (1.77 g, 2.16 mmol) was added. The reaction was heated at 90° C. for 5 h. The reaction was cooled to rt, diluted with water and extracted with EtOAc. The organic layer was washed with brine, concentrated and purified by normal phase chromatography to give 4-chloro-2-(6-methoxypyrimidin-4-yl)aniline (2.86 g, 56.1% yield) as yellow solid. MS(ESI) m/z: 236.0 (M+H)$^+$. $^1$H NMR (500 MHz, CDCl$_3$) δ 8.78 (d, J=–1.1 Hz, 1H), 7.49 (d, J=2.5 Hz, 1H), 7.15 (dd, J=8.8, 2.5 Hz, 1H), 6.99 (d, J=1.1 Hz, 1H), 6.67 (d, J=8.8 Hz, 1H), 5.89 (br. s., 2H), 4.03 (s, 3H).

358C. Preparation of 4-{5-chloro-2-[4-(trimethylsilyl)-1H-1,2,3-triazol-1-yl]phenyl}-6-methoxypyrimidine

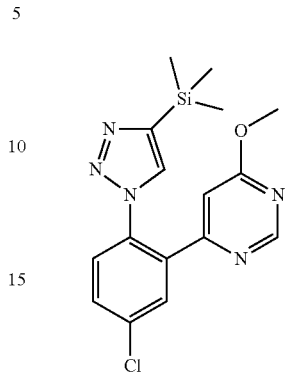

To a solution of 4-chloro-2-(6-methoxypyrimidin-4-yl)aniline (1.5 g, 6.36 mmol) in ACN (90 ml) at 0° C. was added 3-methylbutyl nitrite (1.28 ml, 9.55 mmol), followed by the dropwise addition of azidotrimethylsilane (1.26 ml, 9.55 mmol). Gas evolution was observed. After 10 min, the ice bath was removed, and the reaction was allowed to warm to rt. (Caution, aryl azides are potentially explosive.) After 1 h, ethynyltrimethylsilane (2.72 ml, 19.09 mmol) and Cu$_2$O (0.09 g, 0.64 mmol) were added and the reaction was stirred for an additional 1 h. The reaction was partitioned in EtOAc and saturated aqueous NH$_4$Cl, and the layers were separated. The organic layer was washed with brine, dried over MgSO$_4$, filtered and concentrated. Purification by normal phase chromatography gave 4-{5-chloro-2-[4-(trimethylsilyl)-1H-1,2,3-triazol-1-yl]phenyl}-6-methoxypyrimidine (2.13 g, 5.92 mmol, 93% yield) as a yellow solid. MS(ESI) m/z: 360.3 (M+H)$^+$. $^1$H NMR (400 MHz, CDCl$_3$) δ 8.71 (d, J=1.1 Hz, 1H), 7.82 (d, J=2.2 Hz, 1H), 7.61-7.56 (m, 1H), 7.54-7.48 (m, 2H), 6.20 (d, J=1.1 Hz, 1H), 3.92 (s, 3H), 0.32-0.28 (m, 9H).

358D. Preparation of 4-[5-chloro-2-(4-chloro-1H-1,2,3-triazol-1-yl)phenyl]-6-methoxypyrimidine

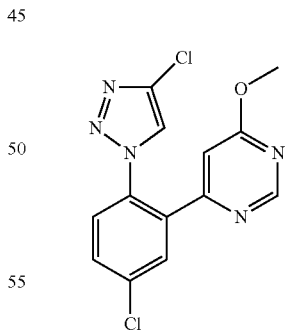

To a solution of 4-{5-chloro-2-[4-(trimethylsilyl)-1H-1,2,3-triazol-1-yl]phenyl}-6-methoxypyrimidine (1.56 g, 4.33 mmol) in ACN (28.9 ml) was added NCS (2.03 g, 15.17 mmol) and silica gel (6.51 g, 108 mmol). The reaction was stirred at 80° C. for 1 h. Then, the reaction was filtered to remove the silica gel and the collected silica gel was washed with EtOAc. The filtrate was washed with water (2×), brine and concentrated. Purification by normal phase chromatography gave 4-[5-chloro-2-(4-chloro-1H-1,2,3-triazol-1-yl)

phenyl]-6-methoxypyrimidine (0.90 g, 64.5% yield) as a yellow foam. MS(ESI) m/z: 322.3 (M+H)⁺. ¹H NMR (400 MHz, CDCl₃) δ 8.70 (d, J=1.1 Hz, 1H), 7.75 (d, J=2.4 Hz, 1H), 7.66-7.55 (m, 2H), 7.50 (d, J=8.6 Hz, 1H), 6.52 (d, J=0.9 Hz, 1H), 3.98 (s, 3H).

358E. Preparation of 6-[5-chloro-2-(4-chloro-1H-1,2,3-triazol-1-yl)phenyl]pyrimidin-4-ol

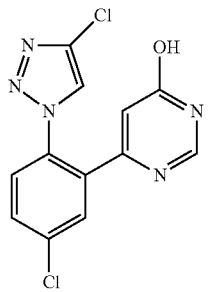 [SMILES: Oc1cc(-c2cc(Cl)ccc2-n2cc(Cl)nn2)ncn1]

To a solution of 4-[5-chloro-2-(4-chloro-1H-1,2,3-triazol-1-yl)phenyl]-6-methoxypyrimidine (900 mg, 2.79 mmol) in AcOH (6 ml) was added 48% HBr in water (3 ml, 26.5 mmol). The mixture was stirred at 85° C. for 1 h. The reaction was concentrated to dryness and then partitioned between EtOAc and saturated aqueous NaHCO₃. The mixture was separated and the aqueous layer was extracted with EtOAc (2×). The organic layers were combined, concentrated, and then the residue was purified by normal phase chromatography to give a white solid. The solid was suspended in Et₂O, filtered and washed with Et₂O to give 6-[5-chloro-2-(4-chloro-1H-1,2,3-triazol-1-yl)phenyl]pyrimidin-4-ol (610 mg, 70.9% yield) as a white solid. MS(ESI) m/z: 308.3 (M+H)⁺. ¹H NMR (400 MHz, CDCl₃) δ 7.96 (s, 1H), 7.74-7.67 (m, 2H), 7.62 (dd, J=8.5, 2.3 Hz, 1H), 7.47 (d, J=8.4 Hz, 1H), 6.44 (d, J=0.9 Hz, 1H).

Example 359

Preparation of tert-butyl N-[(1S)-1-(2-bromopyridin-4-yl)but-3-en-1-yl]carbamate

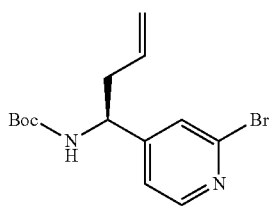

359A. Preparation of (R)—N-[(1E)-(2-bromopyridin-4-yl)methylidene]-2-methylpropane-2-sulfinamide

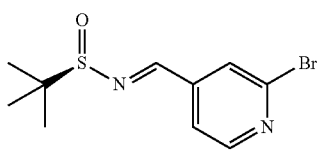

To a stirred suspension of (R)-2-methylpropane-2-sulfinamide (13.03 g, 108 mmol) and Cs₂CO₃ (52.5 g, 161 mmol) in DCM (400 ml) was added 2-bromopyridine-4-carbaldehyde (20 g, 108 mmol) over 10 min. The reaction mixture was then stirred for 18.5 h at rt. The reaction mixture was concentrated and the residue was diluted with EtOAc (50 ml) and washed with brine (3×20 ml). The organic layer was dried over MgSO₄ and filtered and then the filtrate was concentrated. The residue was purified by normal phase chromatography using hexanes and EtOAc as eluents to afford (27.2 g, 87%) of (R)—N-[(1E)-(2-bromopyridin-4-yl)methylidene]-2-methylpropane-2-sulfinamide as a white solid. MS(ESI) m/z: 289-291.0 (M+H)⁺.

359B. Preparation of (R)—N-[(1S)-1-(2-bromopyridin-4-yl)but-3-en-1-yl]-2-methylpropane-2-sulfonamide

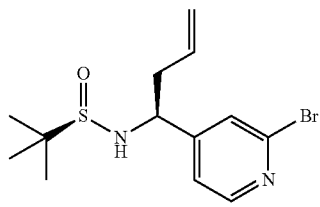 [SMILES: C=CC[C@H](N[S@](=O)C(C)(C)C)c1ccnc(Br)c1]

To a solution of (R)—N-[(1E)-(2-bromopyridin-4-yl)methylidene]-2-methylpropane-2-sulfinamide (0.73 g, 2.52 mmol) and indium (0.435 g, 3.79 mmol) in THF (6 ml) was slowly added 3-bromoprop-1-ene (0.458 g, 3.79 mmol) and resulting solution was heated at 60° C. for 18 h. The reaction mixture was cooled, filtered through CELITE® and the filtrate was concentrated. To the residue was added EtOAc (100 ml) and 5% NaHCO₃ (aq) (1000 ml) and an emulsion formed immediately. The suspension was filtered through paper. The organic layer was washed with brine, dried over Na₂SO₄ filtered, and concentrated. The resulting residue was purified by normal phase chromatography using hexanes and EtOAc as eluents to afford (0.62 g, 74%) of (R)—N-[(1S)-1-(2-bromopyridin-4-yl)but-3-en-1-yl]-2-methylpropane-2-sulfonamide as a yellow liquid. MS(ESI) m/z: 331-333.0 (M+H)⁺.

359C. Preparation of Tert-Butyl N-[(1S)-1-(2-bromopyridin-4-yl)but-3-en-1-yl]carbamate

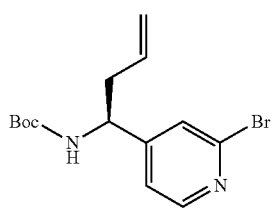 [SMILES: C=CC[C@H](NC(=O)OC(C)(C)C)c1ccnc(Br)c1]

To a solution of (R)—N-[(1S)-1-(2-bromopyridin-4-yl)but-3-en-1-yl]-2-methylpropane-2-sulfinamide (1.38 g, 4.17 mmol) in MeOH (10 ml) was added 4 N HCl in dioxane (5.21 mL, 20.83 mmol). The reaction mixture was stirred for 1.5 h at rt, then was concentrated. To the resulting residue was added ACN (10 ml), TEA (5.81 ml, 41.7 mmol) and Boc₂₀ (1.818 g, 8.33 mmol). After 18 h, the reaction mixture was concentrated and the residue was taken up in EtOAc, washed with water, brine, dried over MgSO$_4$, filtered and concentrated. The resulting residue was purified by normal phase chromatography using hexanes and EtOAc as eluents to afford (0.80 g, 58.7%) of tert-butyl N-[(1S)-1-(2-bromopyridin-4-yl)but-3-en-1-yl]carbamate as a pale yellow oil. MS(ESI) m/z: 324-326.1 (M+H)$^+$.

Example 360

Preparation of (R)-2-methylbut-3-enoic Acid

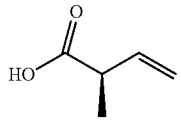

360A. Preparation of (R)-4-benzyl-3-((R)-2-methylbut-3-enoyl)oxazolidin-2-one

To the solution of 2-methylbut-3-enoic acid (5.59 g, 55.9 mmol) and NMM (6.14 mL, 55.9 mmol) in THF (62 mL) at 0° C. was added pivaloyl chloride (6.87 mL, 55.9 mmol) dropwise. The reaction mixture was cooled down to −78° C., and stirred for ~2 h. In a separate flask: To the solution of (R)-4-benzyloxazolidin-2-one (8.25 g, 46.6 mmol) in THF (126 mL) at −78° C. was added N-butyllithium (2.5 M in hexane) (20.49 mL, 51.2 mmol) dropwise. After 35 min, this reaction was transferred via cannula to the first reaction. The reaction mixture was stirred at −78° C. for 2 h, then the cold bath was removed, and the reaction was quenched with saturated NH$_4$Cl. The reaction was diluted with water and extracted with EtOAc (3×). The combined organic layers were washed with brine, dried over Na$_2$SO$_4$, filtered, and concentrated to give a yellow oil (15 g). Purification by silica gel chromatography afforded (R)-4-benzyl-3-((R)-2-methylbut-3-enoyl)oxazolidin-2-one (6.59 g, 55%) as a colorless oil. MS(ESI) m/z: 282.1 (M+Na)$^+$. $^1$H NMR (500 MHz, CDCl$_3$) δ 7.36-7.19 (m, 5H), 6.03-5.93 (m, 1H), 5.23-5.10 (m, 2H), 4.69-4.63 (m, 1H), 4.51-4.43 (m, 1H), 4.23-4.15 (m, 2H), 3.29 (dd, J 13.5, 3.3 Hz, 1H), 2.79 (dd, J=13.5, 9.6 Hz, 1H), 1.35 (d, J=6.9 Hz, 3H) ppm. The other diastereomer (R)-4-benzyl-3-((S)-2-methylbut-3-enoyl)oxazolidin-2-one (4.6 g, 38%) also obtained as a white solid. MS(ESI) m/z: 260.1 (M+H)$^+$.

360B. Preparation of (R)-2-methylbut-3-enoic Acid

To a clear colorless solution of (R)-4-benzyl-3-((R)-2-methylbut-3-enoyl) oxazolidin-2-one (6.05 g, 23.33 mmol) in THF (146 mL) at 0° C. was added dropwise 30% aqueous H$_2$O$_2$ (9.53 mL, 93 mmol) followed by 2 N LiOH (23.33 mL, 46.7 mmol). After 30 min, the reaction was quenched with 25 mL of saturated Na$_2$SO$_3$ and 25 mL of saturated NaHCO$_3$. The reaction was then concentrated to remove the THF. The residue was diluted with water and extracted with CHCl$_3$ (3×). The aqueous layer was acidified with conc. HCl to pH-3 and then it was extracted with EtOAc (3×). The EtOAc layers were combined, washed with brine, dried over MgSO$_4$, filtered and concentrated to afford (R)-2-methylbut-3-enoic acid (2.15 g, 92%) as a colorless oil. $^1$H NMR (500 MHz, CDCl$_3$) δ 10.84 (br. s., 1H), 5.94 (ddd, J 17.4, 10.1, 7.4 Hz, 1H), 5.22-5.13 (m, 2H), 3.23-3.15 (m, 1H), 1.31 (d, J=7.2 Hz, 3H) ppm.

Example 361

Preparation of (9R,13S)-13-amino-3,9-dimethyl-3,4,7,17-tetraazatricyclo[12.3.1.0$^{2,6}$]octadeca-1(18),2(6),4,14,16-pentaen-8-one

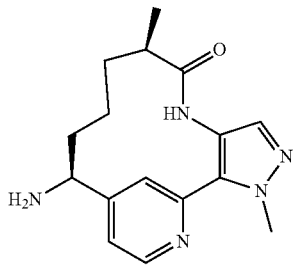 [SMILES: C[C@@H]1CCC[C@H](N)c2ccnc(c2)-c2c(cnn2C)NC1=O]

361A. Preparation of Tert-Butyl N-[(1S)-1-[2-(1-methyl-4-nitro-1H-pyrazol-5-yl)pyridin-4-yl]but-3-en-1-yl]carbamate To a large microwave vial was added tert-butyl N-[(1S)-1-(2-bromopyridin-4-yl)but-3-en-1-yl]carbamate (1.0 g, 3.06 mmol), prepared as described in Example 354, 1-methyl-4-nitro-1H-pyrazole (0.427 g, 3.36 mmol), dioxane (10 ml), di(adamantan-1-yl)(butyl)phosphine (0.164 g, 0.458 mmol), K$_2$CO$_3$ (1.267 g, 9.17 mmol) and pivalic acid (0.106 ml, 0.917 mmol). The reaction was degassed with Ar. Afterwards, Pd(OAc)$_2$ (0.069 g, 0.306 mmol) was added and the reaction was stirred at 100° C. After 4 h, heating was stopped and the reaction was stirred at rt for 72 h. The reaction was quenched with water (20 ml) and extracted with EtOAc (3×50 ml). The combined organic layers were washed with brine (20 ml), dried (MgSO$_4$), and filtered, and concentrated. The residue was purified by normal phase chromatography using heptanes and EtOAc as eluents to give tert-butyl N-[(1S)-1-[2-(1-methyl-4-nitro-1H-pyrazol-5-yl)pyridin-4-yl]but-3-en-1-yl]carbamate (0.62 g, 54%) as a white foam. MS(ESI) m/z: 374.08 (M+H)$^+$. $^1$H NMR (500 MHz, CDCl$_3$) δ 8.73 (d, J=5.2 Hz, 1H), 8.28-8.15 (m, 1H), 7.66-7.54 (m, 1H), 7.43-7.34 (m, 1H), 5.76-5.63 (m, 1H), 5.26-5.16 (m, 2H), 4.99 (br. s., 1H), 4.83 (br. s., 1H), 3.97-3.85 (m, 3H), 2.66-2.46 (m, 2H), 1.45 (br. s., 9H).

361B. Preparation of Tert-Butyl N-[(1S)-1-[2-(4-amino-1-methyl-1H-pyrazol-5-yl)pyridin-4-yl]but-3-en-1-yl]carbamate To a cooled (0° C.) acetone (40 ml)/water (12 ml) solution of tert-butyl N-[(1S)-1-[2-(1-methyl-4-nitro-1H-pyrazol-5-yl)pyridin-4-yl]but-3-en-1-yl]carbamate (0.62 g, 1.660 mmol) was added NH$_4$Cl (0.444 g, 8.30 mmol) and Zn (1.086 g, 16.60 mmol). The ice bath was removed and the reaction was stirred 18 h. The reaction was filtered through paper and partitioned with water (20 ml) and EtOAc (75 ml). The aqueous layer was extracted with EtOAc (2×50 ml). The combined organic layers were washed with brine (25 ml) and dried (MgSO$_4$). The mixture was filtered, concentrated and the residue was purified by normal phase chromatography using DCM and 0-10% MeOH as eluents to give tert-butyl N-[(1S)-1-[2-(4-amino-1-methyl-1H-pyrazol-5-yl)pyridin-4-yl]but-3-en-1-yl]carbamate (0.46 g, 60%). MS(ESI) m/z: 344.5 (M+H)⁺.

361C. Preparation of Tert-Butyl N-[(1S)-1-(2-{1-methyl-4-[(2R)-2-methylbut-3-enamido]-1H-pyrazol-5-yl}pyridin-4-yl)but-3-en-1-yl]carbamate To tert-butyl N-[(1S)-1-[2-(4-amino-1-methyl-1H-pyrazol-5-yl)pyridin-4-yl]but-3-en-1-yl]carbamate (0.6 g, 1.747 mmol) was added (R)-2-methylbut-3-enoic acid (0.189 g, 1.893 mmol), prepared as described in Example 360, in EtOAc (5.8 ml), cooled to 0° C., was added pyridine (0.0.424 ml, 5.24 mmol) and a 50% EtOAc solution of T3P® (2.1 ml, 3.49 mmol). After 24 h, the reaction was partitioned between saturated aqueous NaHCO₃(10 ml) and EtOAc (20 ml). The aqueous layer was extracted with EtOAc (2×20 ml). The combined organic layers were washed with brine (10 ml) and dried (MgSO₄). The mixture was filtered and concentrated and the residue was purified by normal phase chromatography using hexanes and EtOAc as eluents to give tert-butyl N-[(1S)-1-(2-{1-methyl-4-[(2R)-2-methylbut-3-enamido]-1H-pyrazol-5-yl}pyridin-4-yl)but-3-en-1-yl]carbamate (0.35 g, 47%). MS(ESI) m/z: 426.1 (M+H)⁺. $^1$H NMR (500 MHz, CDCl₃) δ 10.23 (br. s., 1H), 8.70-8.56 (m, 1H), 8.35 (d, J=1.1 Hz, 1H), 7.56-7.44 (m, 1H), 7.25-7.14 (m, 1H), 6.03 (ddd, J=17.2, 10.2, 8.0 Hz, 1H), 5.39-5.17 (m, 3H), 5.03-4.63 (m, 2H), 4.14-4.08 (m, 3H), 3.22 (quin, J=7.2 Hz, 1H), 2.66-2.49 (m, 1H), 1.84-1.72 (m, 1H), 1.50-1.40 (m, 9H), 1.42-1.37 (m, 3H), 1.06-0.93 (m, 1H).

361D. Preparation of Tert-Butyl N-[(9R,10E,13S)-3,9-dimethyl-8-oxo-3,4,7,17-tetraazatricyclo[12.3.1.0$^{2,6}$]octadeca-1(18),2(6),4,10,14,16-hexaen-13-yl]carbamate To a degassed DCE (20 ml) solution of tert-butyl N-[(1S)-1-(2-{1-methyl-4-[(2R)-2-methylbut-3-enamido]-1H-pyrazol-5-yl}pyridin-4-yl)but-3-en-1-yl]carbamate (0.160 g, 0.376 mmol) was added Grubbs II (0.096 g, 0.113 mmol) and the reaction mixture was heated to 120° C. for 30 min in a microwave. The reaction mixture was concentrated and the residue was purified by normal phase chromatography using DCM and MeOH as eluents to afford desired product (29 mg, 19%) as a green film. MS(ESI) m/z: 398.3 (M+H)⁺. $^1$H NMR (500 MHz, CDCl₃) δ 8.71 (d, J=4.7 Hz, 1H), 7.58 (s, 1H), 7.23 (d, J=13.8 Hz, 1H), 7.03-6.94 (m, 1H), 6.61 (s, 1H), 5.82-5.71 (m, 1H), 5.19-5.09 (m, 2H), 4.75 (br. s., 1H), 4.15-4.09 (1, 3H), 3.19-3.10 (m, 1H), 2.67 (br. s., 1H), 2.28-2.15 (m, 2H), 1.54-1.39 (m, 9H), 1.34-1.28 (m, 3H).

361E. Preparation of (9R,13S)-13-amino-3,9-dimethyl-3,4,7,17-tetraazatricyclo[12.3.1.0$^{2,6}$]octadeca-1(18),2(6),4,14,16-pentaen-8-one

To an EtOH (3 mL) solution of tert-butyl N-[(9R,10E,13S)-3,9-dimethyl-8-oxo-3,4,7,17-tetraazatricyclo[12.3.1.0$^{2,6}$]octadeca-1(18),2(6),4,10,14,16-hexaen-13-yl]carbamate (29 mg, 0.073 mmol) was added PtO₂ (4 mg). The reaction mixture was purged with hydrogen, then was hydrogenated at 55 psi. After 3 h, the reaction mixture was filtered through a 0.45 μM filter and concentrated to afford a dark solid (MS(ESI) m/z: 400.3 (M+H)⁺). The dark solid residue was dissolved in 4N HCl in dioxane (1 ml) and MeOH (1 ml). After 3 h, the mixture was concentrated and resultant HCl salt was dissolved in DCM/MeOH and passed through a basic cartridge to afford (9R,13S)-13-amino-3,9-dimethyl-3,4,7,17-tetraazatricyclo[12.3.1.0$^{2,6}$]octadeca-1(18),2(6),4,14,16-pentaen-8-one as a dark solid (21 mg, 96%), which was used in next step without further purification. MS(ESI) m/z: 300.2 (M+H)⁺.

Example 362

Preparation of (9R,13)-13-{4-[5-chloro-2-(4-chloro-1H-1,2,3-triazol-1-yl)phenyl]-6-oxo-1,6-dihydropyrimidin-1-yl}-3,9-dimethyl-3,4,7,17-tetraazatricyclo[12.3.1.0$^{2,6}$]octadeca-1(18),2(6),4,14,16-pentaen-8-one Trifluoroacetate

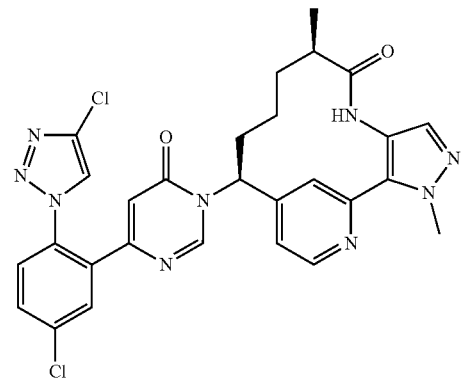 [SMILES: C[C@@H]1CCC[C@H](n2cnc(-c3cc(Cl)ccc3-n3cc(Cl)nn3)cc2=O)c2ccnc(c2)-c2c(cnn2C)NC1=O]

To a solution of 6-[5-chloro-2-(4-chloro-1H-1,2,3-triazol-1-yl)phenyl]pyrimidin-4-ol (0.019 g, 0.060 mmol), prepared as described in Example 358, in CH₃CN (0.4 ml) was added HATU (0.030 g, 0.078 mmol) and DBU (0.014 mL, 0.090 mmol). After 30 min, (9R,13S)-13-amino-3,9-dimethyl-3,4,7,17-tetraazatricyclo[12.3.1.0$^{2,6}$]octadeca-1(18),2(6),4,14,16-pentaen-8-one, prepared as described in Example 361, was added with DMF (0.2 ml). After 18 h, the reaction was diluted with DMF, filtered and concentrated. The residue was purified by reverse phase HPLC using PHENOMENEX® Luna 5U 30×100 mm (10:90 ACN/H₂O to 90:10 ACN/H₂O, 0.1% TFA) (20% B start, 14 min gradient). The desired fractions were concentrated and freeze-dried to afford (9R,13S)-13-{4-[5-chloro-2-(4-chloro-1H-1,2,3-triazol-1-yl)phenyl]-6-oxo-1,6-dihydropyrimidin-1-yl}-3,9-dimethyl-3,4,7,17-tetraazatricyclo[12.3.1.0$^{2,6}$]octadeca-1(18),2(6),4,14,16-pentaen-8-one (11.9 mg, 27%) as an off-white solid. MS(ESI) m/z: 590.3 (M+H)⁺. $^1$H NMR (400 MHz, CD₃OD) δ 8.78-8.70 (m, 1H), 8.41-8.33 (m, 2H), 7.92-7.85 (m, 2H), 7.80-7.73 (m, 1H), 7.71-7.65 (m, 1H), 7.51 (s, 1H), 7.21 (dd, J=5.3, 1.8 Hz, 1H), 6.50-6.42 (m, 1H), 5.77 (dd, J=12.5, 3.1 Hz, 1H), 4.23-4.16 (m, 3H), 2.69-2.58 (m, 1H), 2.41 (dd, J=7.5, 4.2 Hz, 1H), 2.22-2.09 (m, 1H), 2.07-1.96 (m, 1H), 1.74-1.60 (m, 1H), 1.38 (d, J=7.7 Hz, 2H), 1.15 (d, J=7.0 Hz, 3H). Analytical HPLC (Method A) RT=7.38 min, purity=96%.

Example 363

Preparation of (9R,13S)-13-{4-[5-chloro-2-(4-chloro-1H-1,2,3-triazol-1-yl)phenyl]-6-oxo-1,6-dihydropyrimidin-1-yl}-3-($^2$H$_3$)methyl-9-methyl-3,4,7,17-tetraazatricyclo[12.3.1.0$^{2,6}$]octadeca-1(18),2(6),4,14,16-pentaen-8-one Trifluoroacetate

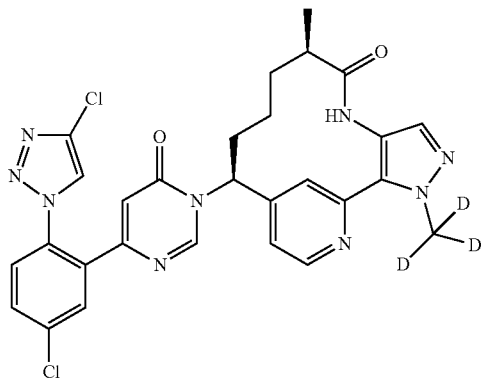 [SMILES: [2H]C([2H])([2H])n1ncc2c1-c1cc(ccn1)[C@@H](n1cnc(-c3cc(Cl)ccc3-n3cc(Cl)nn3)cc1=O)CCC[C@@H](C)C(=O)N2]

363A. Preparation of 1-($^2$H$_3$)methyl-4-nitro-1H-pyrazole

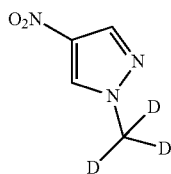

4-Nitro-1H-pyrazole (10.3g, 91 mmol) was dissolved in THF (200 ml) and cooled to 0° C. To this solution was added portionwise NaH (60%, 4.37g, 109 mmol) and stirred for an additional 0.5 h cold. To this cold milky solution was then added CD$_3$I (6.23 ml, 100 mmol) dropwise and the reaction mixture stirred cold for 3 h, then warmed to rt and stirred at this temperature overnight. The reaction mixture was quenched with cold water (200 ml), extracted with EtOAc (2×200 ml) and dried with MgSO$_4$. The solution was filtered and concentrated yielding a yellow solid. Recrystallization of the material from hexane/ethyl acetate afforded the desired compound as a yellow solid (11.5g, 97%). $^1$H NMR (CDCl$_3$) δ 8.85 (s, 1H), 8.82 (s, 1H).

363B. Preparation of Tert-Butyl N-[(1S)-1-{2-[1-($^2$H$_3$)methyl-4-nitro-1H-pyrazol-5-yl]pyridin-4-yl}but-3-en-1-yl]carbamate

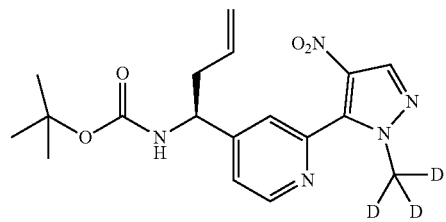 [SMILES: [2H]C([2H])([2H])n1ncc([N+](=O)[O-])c1-c1cc([C@H](CC=C)NC(=O)OC(C)(C)C)ccn1]

tert-Butyl N-[(1S)-1-{2-[1-($^2$H$_3$)methyl-4-nitro-1H-pyrazol-5-yl]pyridin-4-yl}but-3-en-1-yl]carbamate (0.80 g, 70%), a white foam, was prepared in the same manner as tert-butyl N-[(1S)-1-[2-(1-methyl-4-nitro-1H-pyrazol-5-yl)pyridin-4-yl]but-3-en-1-yl]carbamate, as described in Example 361A, by replacing 1-methyl-4-nitro-1H-pyrazole with 1-($^2$H$_3$)methyl-4-nitro-1H-pyrazole. MS(ESI) m/z: 377.5 (M+H)$^1$. $^1$H NMR (500 MHz, CDCl$_3$) δ 8.73 (d, J=5.2 Hz, 1H), 8.28-8.15 (m, 1H), 7.59 (s, 1H), 7.43-7.34 (m, 1H), 5.73-5.63 (m, 1H), 5.24-5.18 (m, 2H), 4.99 (br. s., 1H), 4.83 (br. s., 1H), 2.69-2.42 (m, 2H), 1.45 (br. s., 9H).

363C. Preparation of Tert-Butyl N-[(1S)-1-{2-[4-amino-1-($^2$H$_3$)methyl-1H-pyrazol-5-yl]pyridin-4-yl}but-3-en-1-yl]carbamate

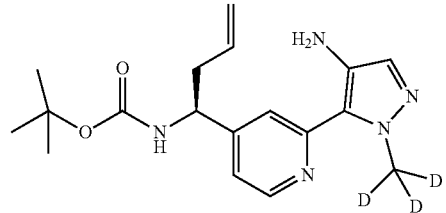 [SMILES: [2H]C([2H])([2H])n1ncc(N)c1-c1cc([C@H](CC=C)NC(=O)OC(C)(C)C)ccn1]

tert-Butyl N-[(1S)-1-{2-[4-amino-1-($^2$H$_3$)methyl-1H-pyrazol-5-yl]pyridin-4-yl}but-3-en-1-yl]carbamate (0.56 g, 76%), a tan solid, was prepared in the same manner as tert-butyl N-[(1S)-1-[2-(4-amino-1-methyl-1H-pyrazol-5-yl)pyridin-4-yl]but-3-en-1-yl]carbamate, as described in Example 361B, by replacing tert-butyl N-[(1S)-1-[2-(1-methyl-4-nitro-1H-pyrazol-5-yl)pyridin-4-yl]but-3-en-1-yl]carbamate, prepared as described in Example 361A with tert-butyl N-[(1S)-1-{2-[1-($^2$H$_3$)methyl-4-nitro-1H-pyrazol-5-yl]pyridin-4-yl}but-3-en-1-yl]carbamate. MS(ESI) m/z: 347.3 (M+H)$^+$.

363D. Preparation of Tert-Butyl N-[(1S)-1-{2-[1-($^2$H$_3$)methyl-4-[(2R)-2-methylbut-3-enamido]-1H-pyrazol-5-yl]pyridin-4-yl}but-3-en-1-yl]carbamate

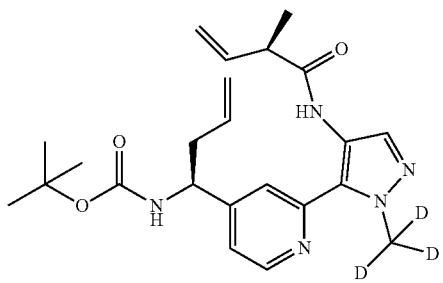 [SMILES: [2H]C([2H])([2H])n1ncc(NC(=O)[C@H](C)C=C)c1-c1cc([C@H](CC=C)NC(=O)OC(C)(C)C)ccn1]

tert-Butyl N-[(1S)-1-{2-[1-($^2$H$_3$)methyl-4-[(2R)-2-methylbut-3-enamido]-1H-pyrazol-5-yl]pyridin-4-yl}but-3-en-1-yl]carbamate (0.49 g, 72%), a yellow solid, was prepared in the same manner as tert-butyl N-[(1S)-1-(2-{1-methyl-4-[(2R)-2-methylbut-3-enamido]-1H-pyrazol-5-yl}pyridin-4-yl)but-3-en-1-yl]carbamate, as described in Example 361C, by replacing tert-butyl N-[(1S)-1-[2-(4-amino-1-methyl-1H-pyrazol-5-yl)pyridin-4-yl]but-3-en-1-yl]carbamate, prepared as described in Example 361B, with tert-butyl N-[(1S)-1-{2-[4-amino-1-($^2$H$_3$)methyl-1H-pyrazol-5-yl]pyridin-4-yl}but-3-en-1-yl]carbamate. MS(ESI) m/z: 429.08 (M+H)$^+$. $^1$H NMR (500 MHz, CDCl$_3$) δ 10.13 (br. s., 1H), 8.56-8.50 (m, 1H), 8.25 (s, 1H), 7.42-7.35 (m, 1H), 7.15-7.08 (m, 1H), 5.92 (ddd, J=17.1, 10.1, 8.0 Hz, 1H), 5.68-5.56 (m, 1H), 5.26-5.19 (m, 3H), 5.16-5.11 (m, 2H), 4.88 (br. s., 1H), 4.70 (br. s., 1H), 3.12 (quin, J=7.2 Hz, 1H), 2.57-2.39 (m, 1H), 1.36 (br. s., 9H), 1.30 (d, J=6.9 Hz, 3H).

363E. Preparation of Tert-Butyl N-[(9R,10E,13S)-3-($^2$H$_3$)methyl-9-methyl-8-oxo-3,4,7,17-tetraazatricyclo[12.3.1.0$^{2,6}$]octadeca-1(18),2(6),4,10,14,16-hexaen-13-yl]carbamate

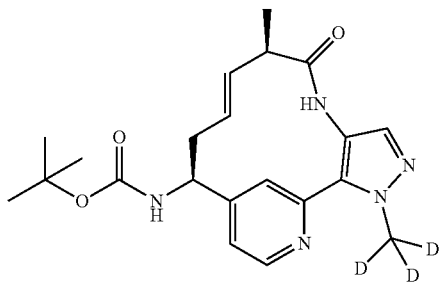 [SMILES: [2H]C([2H])([2H])n1ncc2c1-c1cc(ccn1)[C@@H](NC(=O)OC(C)(C)C)C/C=C/[C@@H](C)C(=O)N2]

tert-Butyl N-[(9R,10E,13S)-3-($^2$H$_3$)methyl-9-methyl-8-oxo-3,4,7,17-tetraazatricyclo[12.3.1.0$^{2,6}$]octadeca-1(18),2(6),4,10,14,16-hexaen-13-yl]carbamate (64 mg, 33%), a green solid, was prepared in the same manner as tert-butyl N-[(9R,10E,13S)-3,9-dimethyl-8-oxo-3,4,7,17-tetraazatricyclo[12.3.1.0$^{2,6}$]octadeca-1(18),2(6),4,10,14,16-hexaen-13-yl]carbamate as described in Example 361D, by replacing tert-butyl N-[(1S)-1-(2-{1-methyl-4-[(2R)-2-methylbut-3-enamido]-1H-pyrazol-5-yl}pyridin-4-yl)but-3-en-1-yl]carbamate, prepared as described in Example 361C, with tert-butyl N-[(1S)-1-{2-[1-($^2$H$_3$)methyl-4-[(2R)-2-methylbut-3-enamido]-1H-pyrazol-5-yl]pyridin-4-yl}but-3-en-1-yl]carbamate. MS(ESI) m/z: 401.3 (M+H)$^+$. $^1$H NMR (500 MHz, CDCl$_3$) δ 8.67 (br. s., 1H), 7.55 (s, 1H), 7.20 (br. s., 1H), 6.97 (s, 1H), 6.75 (br. s., 1H), 5.74 (br. s., 1H), 5.14 (br. s., 2H), 4.76 (br. s., 1H), 3.13 (br. s., 1H), 2.66 (br. s., 1H), 2.20 (s, 1H), 1.47 (br. s., 9H), 1.28 (br. s., 3H).

363F. Preparation of (9R,13S)-13-amino-3-($^2$H$_3$)methyl-9-methyl-3,4,7,17-tetraazatricyclo[12.3.1.0$^{2,6}$]Octadeca-1(18),2(6),4,14,16-pentaen-8-one

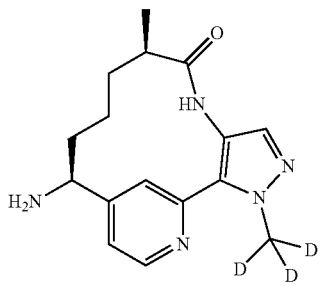 [SMILES: [2H]C([2H])([2H])n1ncc2c1-c1cc(ccn1)[C@@H](N)CCC[C@@H](C)C(=O)N2]

(9R,13S)-13-Amino-3-($^2$H$_3$)methyl-9-methyl-3,4,7,17-tetraazatricyclo[12.3.1.0$^{2,6}$]octadeca-1(18),2(6),4,14,16-pentaen-8-one (48 mgs), a brown solid, was prepared in the same manner as (9R,13S)-13-amino-3,9-dimethyl-3,4,7,17-tetraazatricyclo[12.3.1.0$^{2,6}$]octadeca-1(18),2(6),4,14,16-pentaen-8-one, as described in Example 361E, replacing tert-butyl N-[(9R,10E,13S)-3,9-dimethyl-8-oxo-3,4,7,17-tetraazatricyclo[12.3.1.0$^{2,6}$]octadeca-1(18),2(6),4,10,14,16-hexaen-13-yl]carbamate, prepared as described in Example 361D, with tert-butyl N-[(9R,10E,13S)-3-($^2$H$_3$)methyl-9-methyl-8-oxo-3,4,7,17-tetraazatricyclo[12.3.1.0$^{2,6}$]octadeca-1(18),2(6),4,10,14,16-hexaen-13-yl]carbamate. MS(ESI) m/z: 303.3 (M+H)$^+$.

363G. Preparation of (9R,13S)-13-{4-[5-chloro-2-(4-chloro-1H-1,2,3-triazol-1-yl)phenyl]-6-oxo-1,6-dihydropyrimidin-1-yl}-3-($^2$H$_3$)methyl-9-methyl-3,4,7,17-tetraazatricyclo[12.3.1.0$^{2,6}$]octadeca-1(18),2(6),4,14,16-pentaen-8-one Trifluoroacetate

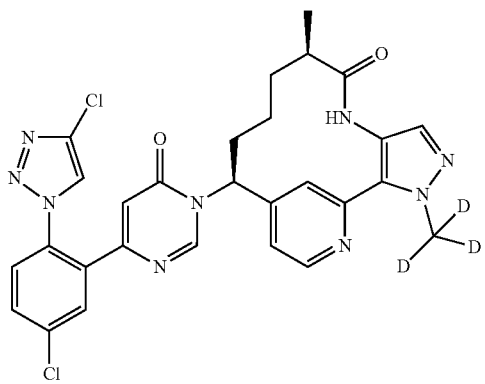 [SMILES: [2H]C([2H])([2H])n1ncc2c1-c1cc(ccn1)[C@@H](n1cnc(-c3cc(Cl)ccc3-n3cc(Cl)nn3)cc1=O)CCC[C@@H](C)C(=O)N2]

(9R,13S)-13-{4-[5-Chloro-2-(4-chloro-1H-1,2,3-triazol-1-yl)phenyl]-6-oxo-1,6-dihydropyrimidin-1-yl}-3-($^2$H$_3$) methyl-9-methyl-3,4,7,17-tetraazatricyclo[12.3.1.0$^{2,6}$]octadeca-1(18),2(6),4,14,16-pentaen-8-one trifluoroacetate, (10.8 mg, 18%), a white solid, was prepared in the same manner as (9R,13S)-13-{4-[5-chloro-2-(4-chloro-1H-1,2,3-triazol-1-yl)phenyl]-6-oxo-1,6-dihydropyrimidin-1-yl}-3,9-dimethyl-3,4,7,17-tetraazatricyclo[12.3.1.0$^{2,6}$]octadeca-1(18),2(6),4,14,16-pentaen-8-one, as described in Example 362, by replacing (9R,13S)-13-amino-3,9-dimethyl-3,4,7,17-tetraazatricyclo[12.3.1.0$^{2,6}$]octadeca-1(18),2(6),4,14,16-pentaen-8-one, prepared as described in Example 361E with (9R,13S)-13-amino-3-($^2$H$_3$)methyl-9-methyl-3,4,7,17-tetraazatricyclo[12.3.1.0$^{2,6}$]octadeca-1(18),2(6),4,14,16-pentaen-8-one, prepared as described in Example 363F. MS(ESI) m/z: 593.3 (M+H)$^+$. 1H NMR (400 MHz, CD$_3$OD) δ 8.78-8.69 (m, 1H), 8.42-8.33 (m, 2H), 7.92-7.86 (m, 2H), 7.80-7.74 (m, 1H), 7.69-7.64 (m, 1H), 7.52 (s, 1H), 7.21 (dd, J=5.3, 1.5 Hz, 1H), 6.51-6.43 (m, 1H), 5.77 (dd, J=12.5, 3.3 Hz, 1H), 2.62 (ddd, J=9.5, 6.7, 3.4 Hz, 1H), 2.48-2.38 (m, 1H), 2.22-2.11 (m, 1H), 2.06-1.97 (m, 1H), 1.69-1.59 (m, 1H), 1.42-1.33 (m, 2H), 1.15 (d, J=6.8 Hz, 3H). Analytical HPLC (Method A) RT=7.26 min, purity=96%.

Example 364

Preparation of 6-{5-chloro-2-[4-(trifluoromethyl)-1H-1,2,3-triazol-1-yl]phenyl}pyrimidin-4-ol

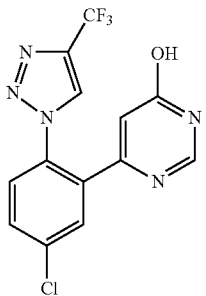 [SMILES: Oc1cc(-c2cc(Cl)ccc2-n2cc(C(F)(F)F)nn2)ncn1]

364A. Preparation of 4-{5-chloro-2-[4-(trifluoromethyl)-1H-1,2,3-triazol-1-yl]phenyl}-6-methoxypyrimidine

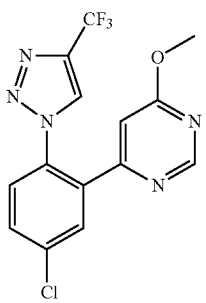 [SMILES: COc1cc(-c2cc(Cl)ccc2-n2cc(C(F)(F)F)nn2)ncn1]

To a solution of 4-chloro-2-(6-methoxypyrimidin-4-yl)aniline (1.0 g, 4.24 mmol), prepared as described in Example 358B, in ACN (60.6 ml) at 0° C. was added 3-methylbutyl nitrite (0.86 ml, 6.36 mmol) followed by the dropwise addition of azidotrimethylsilane (0.84 ml, 6.36 mmol). Gas evolution was observed. After 10 min, the ice bath was removed, and the reaction was allowed to warm to rt. (Caution, aryl azides are potentially explosive.) After 2 h, Cu$_2$O (61 mg, 0.42 mmol) was added followed by a slow bubbling of 3,3,3-trifluoroprop-1-yne gas over a period of 5 min. After an additional 10 min, the reaction was partitioned between DCM and saturated aqueous NH$_4$Cl and then the layers were separated. The organic layer was washed with brine, dried over MgSO$_4$, filtered and concentrated. Purification by normal phase chromatography gave 4-{5-chloro-2-[4-(trifluoromethyl)-1H-1,2,3-triazol-1-yl]phenyl}-6-methoxypyrimidine (1.46 g, 97% yield) as a yellow solid. MS(ESI) m/z: 356.1 (M+H)$^|$. $^1$H NMR (400 MHz, CDCl$_3$) δ 8.62 (d, J=1.1 Hz, 1H), 8.00 (d, J=0.7 Hz, 1H), 7.75 (d, J=2.4 Hz, 1H), 7.66-7.60 (m, 1H), 7.52 (d, J=8.6 Hz, 1H), 6.60 (d, J=1.1 Hz, 1H), 3.98 (s, 3H). $^{19}$F NMR (376 MHz, CDCl$_3$) δ -61.10 (s).

364B. Preparation of 6-{5-chloro-2-[4-(trifluoromethyl)-1H-1,2,3-triazol-1-yl]phenyl}pyrimidin-4-ol

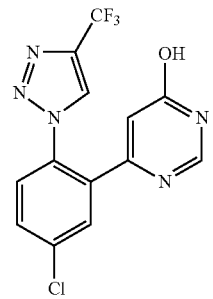 [SMILES: Oc1cc(-c2cc(Cl)ccc2-n2cc(C(F)(F)F)nn2)ncn1]

To a solution of 4-{5-chloro-2-[4-(trifluoromethyl)-1H-1,2,3-triazol-1-yl]phenyl}-6-methoxypyrimidine (1.46 g, 4.10 mmol) in AcOH (10 ml) was added 48% HBr in water (5 ml, 44.2 mmol). The mixture was stirred at 85° C. for 1 h. The reaction was concentrated to dryness and then partitioned between EtOAc and saturated aqueous NaHCO$_3$ solution. The layers were separated and the aqueous layer was extracted with EtOAc (2×). The organic layers were combined and washed with saturated aqueous NaHCO$_3$, brine, dried over MgSO$_4$, filtered and the solvent was reduced under vacuum until some solid started to form. The resulting suspension was triturated with Et$_2$O. The solid was filtered and washed with Et$_2$O to give 6-{5-chloro-2-[4-(trifluoromethyl)-1H-1,2,3-triazol-1-yl]phenyl}pyrimidin-4-ol (1 g, 71.3% yield) as a pale yellow solid. MS(ESI) m/z: 342.0 (M+H)$^+$. $^1$H NMR (400 MHz, CD$_3$OD) δ 8.83 (d, J=0.7 Hz, 1H), 7.99 (d, J=0.9 Hz, 1H), 7.87 (d, J=2.2 Hz, 1H), 7.79-7.72 (m, 1H), 7.70-7.62 (m, 1H), 6.45 (d, J=0.9 Hz, 1H). $^{19}$F NMR (376 MHz, CD$_3$OD) δ -62.61 (s).

Example 365

Preparation of (9R,13S)-13-amino-3,9-dimethyl-3,4,7,15-tetraazatricyclo[12.3.1.0$^{2,6}$]octadeca-1(18),2(6),4,14,16-pentaen-8-one

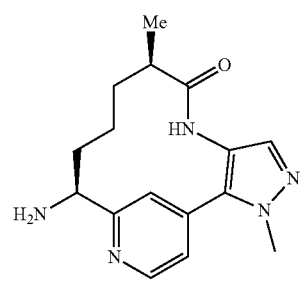 [SMILES: C[C@@H]1CCC[C@H](N)c2cc(ccn2)-c2c(cnn2C)NC1=O]

365A. Preparation of 1-methyl-4-nitro-1H-pyrazole

To a solution of 4-nitro-1H-pyrazole (2.5 g, 22.11 mmol) in THF (50 mL) was added NaH (0.973 g, 24.32 mmol) and the mixture was stirred at rt for 5 min. To this suspension was then added CH$_3$I (1.382 mL, 22.11 mmol) and stirred at rt overnight. The reaction mixture was then diluted with EtOAc (2×25 mL) and washed with brine (25 mL). The organic layer was concentrated, followed by purification using normal phase chromatography to yield 1-methyl-4-nitro-1H-pyrazole as white solid (1.9 g, 80% yield). $^1$H NMR (400 MHz, CDCl$_3$) δ ppm 8.12 (s, 1H), 8.06 (s, 1H), 3.97 (s, 3H).

365B. Preparation of (S)-tert-butyl (1-(4-(1-methyl-4-nitro-1H-pyrazol-5-yl)pyridin-2-yl)but-3-en-1-yl) carbamate To a N$_2$ flushed pressure vial was added (S)-tert-butyl (1-(4-chloropyridin-2-yl)but-3-en-1-yl)carbamate (3.0 g, 10.61 mmol), 1-methyl-4-nitro-1H-pyrazole (1.348 g, 10.61 mmol), di(adamant-1-yl)(butyl)phosphine (1.141 g, 3.18 mmol), PvOH (0.369 ml, 3.18 mmol) and K$_2$CO$_3$ (4.40 g, 31.8 mmol). To the above mixture was then added DMF (21 mL) and the vial was purged with N$_2$ for 5 min. To this mixture was then added Pd(OAc)$_2$ (0.476 g, 2.122 mmol). The reaction mixture was again briefly purged with N$_2$. The vial was sealed and heated in oil bath at 120° C. for 4 h. The reaction mixture was cooled to rt and partitioned between 10% aqueous LiCl (15 mL) and EtOAc (30 mL). The aqueous layer was extracted with EtOAc (2×20 mL) and the combined organic layers were washed with brine (15 mL), dried over MgSO$_4$, filtered and concentrated. The crude product was then purified using normal phase chromatography to yield (S)-tert-butyl (1-(4-(1-methyl-4-nitro-1H-pyrazol-5-yl)pyridin-2-yl)but-3-en-1-yl)carbamate (1.2 g, 29% yield) as a brown oil. MS(ESI) m/z: 374.4 (M+H)$^+$.

365C. Preparation of (S)-tert-butyl (1-(4-(4-amino-1-methyl-1H-pyrazol-5-yl)pyridin-2-yl)but-3-en-1-yl)carbamate A solution of (S)-tert-butyl (1-(4-(1-methyl-4-nitro-1H-pyrazol-5-yl)pyridin-2-yl)but-3-en-1-yl)carbamate (1.2 g, 3.21 mmol) in MeOH (10 mL) and AcOH (1 mL) was heated in oil bath to 40° C. To the above clear solution was then slowly added Zn (0.420 g, 6.43 mmol, in 3 portions (50:25:25%) and allowed to stir at the same temperature for 5 min. The reaction mixture was monitored by LCMS and once reaction is complete, to the cooled reaction mixture was then added 1 g of K$_2$CO$_3$ (1 g for 1 mL AcOH) and 1 mL water. The reaction mixture was then stirred for 5 min. The reaction mixture was then filtered over a pad of CELITE® and concentrated in vacuo to yield the crude product. The crude product was then partitioned between EtOAc (30 mL) and saturated aqueous NaHCO$_3$(15 mL) solution. The organic layers were separated, dried over MgSO$_4$, filtered and concentrated. The crude product was then purified using normal phase chromatography to yield (S)-tert-butyl (1-(4-(4-amino-1-methyl-1H-pyrazol-5-yl)pyridin-2-yl)but-3-en-1-yl)carbamate (0.88 g, 76% yield) as pale brown oil. MS(ESI) m/z: 344.4 (M+H)$^+$.

365D. Preparation of Tert-Butyl ((S)-1-(4-(1-methyl-4-((R)-2-methylbut-3-enamido)-1H-pyrazol-5-yl)pyridin-2-yl)but-3-en-1-yl)carbamate To a N$_2$ flushed, 3-necked, 250 mL RBF was added a solution of (S)-tert-butyl (1-(4-(4-amino-1-methyl-1H-pyrazol-5-yl)pyridin-2-yl)but-3-en-1-yl)carbamate (620 mg, 1.805 mmol) and EtOAc (15 mL). The solution was cooled to −10° C. and (R)-2-methylbut-3-enoic acid, as prepared in Example 354, (271 mg, 2.71 mmol), pyridine (0.437 mL, 5.42 mmol) and T3P® (2.149 mL, 3.61 mmol) were added. The cooling bath was removed and the solution was allowed to warm to rt and then stir over a period of 20 h. Water (15 mL) and EtOAc (15 mL) were added and the mixture was stirred for 30 min. The organic phase was separated and the aqueous layer was extracted with EtOAc (15 mL). The combined organic extracts were washed with brine (15 mL), dried over Na$_2$SO$_4$, filtered and concentrated in vacuo. Purification by normal phase chromatography eluting with a gradient of hexanes/EtOAc gave tert-butyl ((S)-1-(4-(1-methyl-4-((R)-2-methylbut-3-enamido)-1H-pyrazol-5-yl)pyridin-2-yl)but-3-en-1-yl)carbamate (0.26 g, 34% yield). MS(ESI) m/z: 426.5 [M+H]$^+$.

365E. Preparation of Tert-Butyl N-[(9R,10E,13S)-3,9-dimethyl-8-oxo-3,4,7,15-tetraazatricyclo[12.3.1.0$^{2,6}$]octadeca-1(18),2(6),4,10,14,16-hexaen-13-yl] carbamate To a N$_2$ flushed, 250 mL, 3-necked RBF was added a solution of tert-butyl ((S)-1-(4-(1-methyl-4-((R)-2-methylbut-3-enamido)-1H-pyrazol-5-yl)pyridin-2-yl)but-3-en-1-yl)carbamate (266 mg, 0.625 mmol) in DCE (18 mL). The solution was sparged with argon for 15 min. Grubbs II (213 mg, 0.250 mmol) was added in one portion. The reaction mixture was heated to 120° C. in microwave for 30 min. After cooling to rt, the solvent was removed and the residue was purified by normal phase chromatography eluting with a gradient of DCM/MeOH to yield tert-butyl N-[(9R,10E,13S)-3,9-dimethyl-8-oxo-3,4,7,15-tetraazatricyclo[12.3.1.0$^{2,6}$]octadeca-1(18),2(6),4,10,14,16-hexaen-13-yl]carbamate (60 mg, 23% yield) as a tan solid. MS(ESI) m/z: 398.4 [M+H]$^+$.

365F. Preparation of Tert-Butyl N-[(9R,13S)-3,9-dimethyl-8-oxo-3,4,7,15-tetraazatricyclo[12.3.1.0$^{2,6}$]octadeca-1(18),2(6),4,14,16-pentaen-13-yl]carbamate Pd/C (0.016 g, 0.015 mmol) was added to a 100 mL Parr hydrogenation flask containing a solution of tert-butyl N-[(9R,10E,13S)-3,9-dimethyl-8-oxo-3,4,7,15-tetraazatricyclo[12.3.1.0$^{2,6}$]octadeca-1(18),2(6),4,10,14,16-hexaen-13-yl]carbamate (60 mg, 0.151 mmol) in EtOH (6 mL). The flask was purged with N$_2$ and pressurized to 55 psi of H$_2$ and allowed to stir for 5 h. The reaction was filtered through a pad of CELITE® and concentrated to yield tert-butyl N-[(9R,13S)-3,9-dimethyl-8-oxo-3,4,7,15-tetraazatricyclo[12.3.1.0$^{2,6}$]octadeca-1(18),2(6),4,14,16-pentaen-13-yl]carbamate (48 mg, 76% yield) as a tan solid. MS(ESI) m/z: 400.5 [M+H]$^+$.

365G. Preparation of (9R,13S)-13-amino-3,9-dimethyl-3,4,7,15-tetraazatricyclo[12.3.1.0$^{2,6}$]octadeca-1(18),2(6),4,14,16-pentaen-8-one To a solution of tert-butyl N-[(9R,13)-3,9-dimethyl-8-oxo-3,4,7,15-tetraazatricyclo[12.3.1.0$^{2,6}$]octadeca-1(18),2(6),4,14,16-pentaen-13-yl]carbamate (48 mg, 0.120 mmol) in DCM (2.5 mL) was added TFA (0.6 mL, 7.79 mmol) and the reaction was stirred at rt for 1.5 h. The reaction mixture was then concentrated to give (9R,13S)-13-amino-3,9-dimethyl-3,4,7,15-tetraazatricyclo[12.3.1.0$^{2,6}$]octadeca-1(18),2(6),4,14,16-pentaen-8-one bis trifluoroacetate (63 mg, 94% yield) as a brown solid which was then dissolved in MeOH (1 mL) to give a clear, brown solution. The solution was added to a pre-rinsed AGILENT® StratoSpheres SPE PL-HCO₃ MP Resin cartridge. Gravity filtration, eluting with MeOH, gave a clear, slightly yellow filtrate. Concentration provided (9R,13S)-13-amino-3,9-dimethyl-3,4,7,15-tetraazatricyclo[12.3.1.0$^{2,6}$]octadeca-1(18),2(6),4,14,16-pentaen-8-one (25 mg, 93%) as a pale yellow solid. MS(ESI) m/z: 300.4 [M+H]⁺.

Example 366

Preparation of (9R,13S)-13-amino-3-($^2$H₃)methyl-9-methyl-3,4,7,15-tetraazatricyclo[12.3.1.0$^{2,6}$]octadeca-1(18),2(6),4,14,16-pentaen-8-one

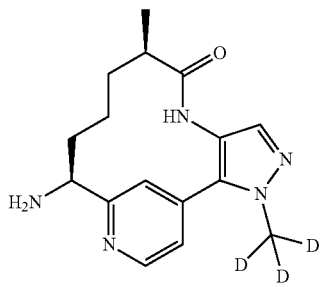 [SMILES: [2H]C([2H])([2H])n1ncc2c1-c1ccnc(c1)[C@@H](N)CCC[C@@H](C)C(=O)N2]

366A. Preparation of 1-($^2$H₃)methyl-4-nitro-1H-pyrazole

DIAD (5.59 mL, 28.7 mmol) was added to a solution of 4-nitro-1H-pyrazole (2.5 g, 22.11 mmol), CD₃OD (0.898 mL, 22.11 mmol), and Ph₃P (resin bound) (8.84 g, 26.5 mmol) in THF (40 ml) and stirred overnight. The reaction was quenched with water, extracted with EtOAc, washed with brine, dried over Na₂SO₄, filtered, and concentrated. The crude product was purified by normal phase chromatography eluting with a gradient of DCM/MeOH to afford the desired product (1.92 g, 14.76 mmol, 66.7% yield) as a white solid. MS(ESI) m/z: 131.0 (M+H)⁺. $^1$H NMR (400 MHz, CDCl₃) δ 8.13 (d, J=0.4 Hz, 1H), 8.05 (s, 1H).

366B. Preparation of Tert-Butyl N-[(1S)-1-{4-[1-($^2$H₃)methyl-4-nitro-1H-pyrazol-5-yl]pyridin-2-yl}but-3-en-1-yl]carbamate To a large microwave vial were added (S)-tert-butyl (1-(4-chloropyridin-2-yl)but-3-en-1-yl)carbamate (2.61 g, 9.22 mmol), 1-($^2$H₃)methyl-4-nitro-1H-pyrazole (1.0 g, 7.69 mmol), di(adamantanyl)(butyl)phosphine (0.413 g, 1.15 mmol), K₂CO₃ (3.19 g, 23.06 mmol) and pivalic acid (0.268 ml, 2.306 mmol) and DMF (15.37 ml). The reaction was purged with argon for 10 min, Pd(OAc)₂ (0.173 g, 0.769 mmol) was added, vial sealed, and stirred at 115° C. overnight. The reaction was then partitioned between EtOAc and H₂O. The aqueous layer was extracted with additional EtOAc (2×). The combined organic layer was washed with brine, dried over MgSO₄, filtered and concentrated. The residue was purified by normal phase chromatography eluting with a gradient of hexanes/EtOAc to give the desired product (1.49 g, 3.96 mmol, 51.5% yield) as a lavender foam. MS(ESI) m/z: 377.0 (M+H)⁺. $^1$H NMR (400 MHz, CDCl₃) δ 8.77 (d, J=4.8 Hz, 1H), 8.21 (s, 1H), 7.26 (s, 1H), 7.23 (dd, J=5.1, 1.5 Hz, 1H), 5.78-5.65 (m, 1H), 5.55 (d, J=6.8 Hz, 1H), 5.14-5.03 (m, 2H), 4.89 (d, J=6.8 Hz, 1H), 2.66 (t, J=6.6 Hz, 2H), 1.44 (s, 9H).

366C. Preparation of Tert-Butyl N-[(1S)-1-{4-[4-amino-1-($^2$H₃)methyl-1H-pyrazol-5-yl]pyridin-2-yl}but-3-en-1-yl]carbamate tert-Butyl N-[(1S)-1-{4-[1-($^2$H₃)methyl-4-nitro-1H-pyrazol-5-yl]pyridin-2-yl}but-3-en-1-yl]carbamate (1.45 g, 3.85 mmol) was dissolved in acetone (15 ml)/water (3 ml), cooled to 0° C., and added NH₄Cl (1.030 g, 19.26 mmol) and zinc (2.52 g, 38.5 mmol) followed by removal of ice bath. After 1h, the reaction was filtered and filtrate partitioned with water (30 ml) and EtOAc (50 ml). The aqueous layer was extracted with EtOAc (2×50 ml). The combined organic layers were washed with brine (20 ml), dried (MgSO₄), filtered, and concentrated. The residue was purified by normal phase eluting with a gradient of DCM/MeOH chromatography to afford the desired product (0.62 g, 46.5%). MS(ESI) m/z: 347.2 (M+H)⁺. $^1$H NMR (400 MHz, CDCl₃) δ 8.67 (dd, J=5.1, 0.7 Hz, 1H), 7.26-7.23 (m, 2H), 7.21 (dd, J=5.1, 1.5 Hz, 1H), 5.79-5.66 (m, 1H), 5.58 (d, J=7.3 Hz, 1H), 5.11-5.05 (m, 2H), 4.86 (q, J=6.6 Hz, 1H), 2.64 (t, J=6.7 Hz, 2H), 1.44 (s, 9H).

366D. Preparation of Tert-Butyl N-[(1S)-1-{4-[1-($^2$H₃)methyl-4-[(2R)-2-methylbut-3-enamido]-1H-pyrazol-5-yl]pyridin-2-yl}but-3-en-1-yl]carbamate (R)-2-Methylbut-3-enoic acid (233 mg, 2.327 mmol), tert-butyl N-[(1S)-1-{4-[4-amino-1-($^2$H₃)methyl-1H-pyrazol-5-yl]pyridin-2-yl}but-3-en-1-yl]carbamate (620 mg, 1.79 mmol), pyridine (0.433 ml, 5.37 mmol) in EtOAc (17.900 ml) was cooled to −10° C. under Ar followed by dropwise addition of T3P® (50% wt in EtOAc) (2.131 ml, 3.58 mmol) was added dropwise and then gradually warmed up to rt. After 3.5 h, the reaction mixture was diluted with EtOAc, washed with 1.5 M K₂HPO₄ followed by brine, dried over Na₂SO₄, filtered, and concentrated. The crude product was then purified by normal phase chromatography eluting with a gradient of hexanes/EtOAc to the desired product (529 mg, 1.234 mmol, 69.0% yield) as a yellow foam. MS(ESI) m/z: 429.2 (M+H)⁺.

366E. Preparation of Tert-Butyl N-[(9R,10E,13S)-3-($^2$H₃)methyl-9-methyl-8-oxo-3,4,7,15-tetraazatricyclo[12.3.1.0$^{2,6}$]octadeca-1(18),2(6),4,10,14,16-hexaen-13-yl]carbamate Five large microwave vials were charged in equal amounts with the following: tert-butyl N-[(1S)-1-{4-[1-($^2$H₃)methyl-4-[(2R)-2-methylbut-3-enamido]-1H-pyrazol-5-yl]pyridin-2-yl}but-3-en-1-yl]carbamate (0.51 g, 1.190 mmol) in degassed DCE (90 ml) was irradiated 120° C. for 30 min in the presence of Grubbs II (0.404 g, 0.476 mmol). The reactions were combined, concentrated, and the residue purified by normal phase column chromatography eluting with a gradient of hexanes/EtOAc to give the desired product (0.124 g, 26.0%) as a brown solid. MS(ESI) m/z: 401.2 (M+H)⁺. $^1$H NMR (400 MHz, CDCl₃) δ 8.66 (d, J=5.1 Hz, 1H), 7.52 (s, 1H), 7.19 (d, J=4.8 Hz, 1H), 6.80 (s, 1H), 6.37 (d, J=7.5 Hz, 1H), 5.68 (t, J=11.2 Hz, 1H), 4.82-4.63 (m, 2H), 3.12-2.93 (m, 2H), 1.93 (q, J=11.1 Hz, 1H), 1.48 (s, 9H), 1.15 (d, J=5.9 Hz, 3H).

366F. Preparation of Tert-Butyl N-[(9R,13S)-3-($^2$H₃)methyl-9-methyl-8-oxo-3,4,7,15-tetraazatricyclo[12.3.1.0$^{2,6}$]octadeca-1(18),2(6),4,14,16-pentaen-13-yl]carbamate PtO₂ (6.80 mg, 0.030 mmol) was added to a stirring solution of tert-butyl N-[(9R,10E,13S)-3-($^2$H₃)methyl-9- methyl-8-oxo-3,4,7,15-tetraazatricyclo[12.3.1.0²,⁶]octa-deca-1(18),2(6),4,10,14,16-hexaen-13-yl]carbamate (0.120 g, 0.300 mmol) in EtOH (10 ml). The suspension was subjected to a hydrogen atmosphere (55 psi) for 1 h. The catalyst was filtered off through a plug of CELITE® and the filtrate concentrated. The product (0.104 g, 86%) was carried forward to the next reaction as is without further purification. MS(ESI) m/z: 403.2 (M+H)⁺.

366G. Preparation of (9R,13S)-13-amino-3-(²H₃)methyl-9-methyl-3,4,7,15-tetraazatricyclo[12.3.1.0²,⁶]octadeca-1(18),2(6),4,14,16-pentaen-8-one A solution of 4.0 M HCl in dioxane (1.621 ml) was added to a stirring solution of tert-butyl N-[(9R,13S)-3-(²H₃)methyl-9-methyl-8-oxo-3,4,7,15-tetraazatricyclo[12.3.1.0²,⁶]octadeca-1(18),2(6),4,14,16-pentaen-13-yl]carbamate (0.100 g, 0.248 mmol) in MeOH (3 ml) and stirred overnight. The reaction mixture was concentrated to dryness and placed under high vacuum. The hydrogen chloride salt was free based by dissolution in MeOH, passed through a resin bound NaHCO₃ cartridge (StratoSpheres SPE; 500 mg, 0.90 mmol loading) and filtrate concentrated. The material was carried forward as is to next reaction. MS(ESI) m/z: 303.4 (M+H)⁺.

Example 367

Preparation of (9R,13S)-3-(4-{5-chloro-2-[4-(trifluoromethyl)-1H-1,2,3-triazol-1-yl]phenyl}-6-oxo-1,6-dihydropyrimidin-1-yl)-3,9-dimethyl-3,4,7,15-tetraazatricyclo[12.3.1.0²,⁶]octadeca-1(18),2(6),4,14,16-pentaen-8-one Trifluoroacetate

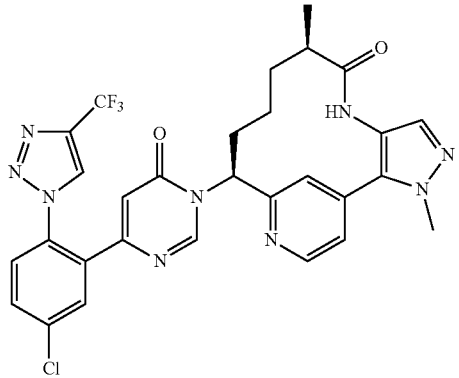 [SMILES: C[C@@H]1CCC[C@H](n2cnc(-c3cc(Cl)ccc3-n3cc(C(F)(F)F)nn3)cc2=O)c2cc(ccn2)-c2c(cnn2C)NC1=O]

To a scintillation vial containing 6-{5-chloro-2-[4-(trifluoromethyl)-1H-1,2,3-triazol-1-yl]phenyl}pyrimidin-4-ol (22.8 mg, 0.067 mmol), prepared as described in Example 364, HATU (33.0 mg, 0.087 mmol) in anhydrous ACN (0.5 mL) was added DBU (15 mL, 0.100 mmol). After 30 min, a solution of (9R,13S)-13-amino-3,9-dimethyl-3,4,7,15-tetraazatricyclo[12.3.1.0²,⁶]octadeca-1(18),2(6),4,14,16-pentaen-8-one (20 mg, 0.067 mmol), prepared as described in Example 365, in 0.5 ml CH₃CN and DMF (0.1 ml) was added. The resulting solution was stirred at rt for 2 h then purified by reverse phase chromatography to give, after concentration and lyophilization, (9R,13S)-13-(4-{5-chloro-2-[4-(trifluoromethyl)-1H-1,2,3-triazol-1-yl]phenyl}-6-oxo-1,6-dihydropyrimidin-1-yl)-3,9-dimethyl-3,4,7,15-tetraazatricyclo[12.3.1.0²,⁶]octadeca-1(18),2(6),4,14,16-pentaen-8-one trifluoroacetate (26.98 mg, 53.1% yield) as a white solid. MS(ESI) m/z: 624.3 (M+H)⁺. ¹H NMR (400 MHz, CD₃OD) δ 8.81 (d, J=0.7 Hz, 1H), 8.75 (s, 1H), 8.70 (d, J=5.3 Hz, 1H), 7.89 (d, J=2.4 Hz, 1H), 7.77-7.72 (m, 1H), 7.72-7.66 (m, 2H), 7.53 (dd, J=5.1, 1.5 Hz, 1H), 7.49 (s, 1H), 6.43 (s, 1H), 6.02-5.93 (m, 1H), 4.04 (s, 3H), 2.70 (td, J=6.7, 3.3 Hz, 1H), 2.27 (tt, J=12.7, 4.4 Hz, 1H), 2.12-1.94 (m, 2H), 1.66-1.52 (m, 1H), 1.45 (ddd, J=15.0, 9.8, 5.0 Hz, 1H), 1.00 (d, J=7.0 Hz, 3H), 0.69 (br. s., 1H). ¹⁹F NMR (376 MHz, CD₃OD) d −62.54 (s), −77.44 (s). Analytical HPLC (Method A): RT=11.02 min, purity=96.7%.

Example 368

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-3-(²H₃)methyl-9-methyl-3,4,7,15-tetraazatricyclo[12.3.1.0²,⁶]octadeca-1(18),2(6),4,14,16-pentaen-8-one Trifluoroacetate

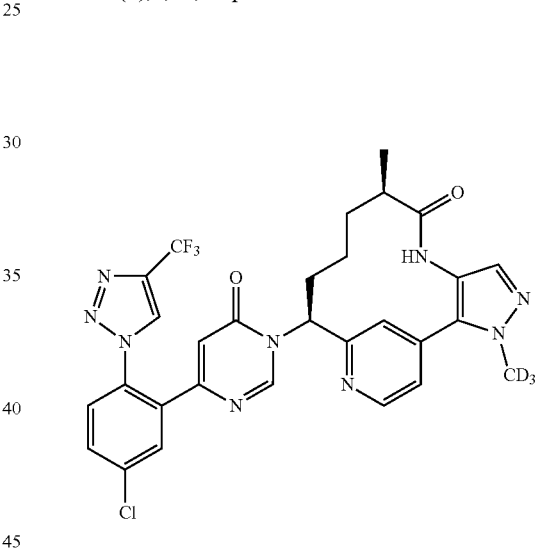

(9R,13S)-13-(4-{5-Chloro-2-[4-(trifluoromethyl)-1H-1,2,3-triazol-1-yl]phenyl}-6-oxo-1,6-dihydropyrimidin-1-yl)-3-(²H₃)methyl-9-methyl-3,4,7,15-tetraazatricyclo[12.3.1.0²,⁶]octadeca-1(18),2(6),4,14,16-pentaen-8-one trifluoroacetate (11 mg, 30% yield) was prepared in a similar manner as the procedure described in Example 367, by replacing (9R,13S)-13-amino-3,9-dimethyl-3,4,7,15-tetraazatricyclo[12.3.1.0²,⁶]octadeca-1(18),2(6),4,14,16-pentaen-8-one with (9R,13S)-13-amino-3-(²H₃)methyl-9-methyl-3,4,7,15-tetraazatricyclo[12.3.1.0²,⁶]octadeca-1(18),2(6),4,14,16-pentaen-8-one (15 mg, 0.050 mmol), prepared as described in Example 366. MS(ESI) m/z: 627.3 (M+H). ¹H NMR (400 MHz, CD₃OD) δ 8.81 (s, 1H), 8.77-8.66 (m, 2H), 7.89 (d, J=2.2 Hz, 1H), 7.79-7.64 (m, 3H), 7.59-7.51 (m, 1H), 7.49 (s, 1H), 6.44 (s, 1H), 5.97 (dd, J=12.4, 3.9 Hz, 1H), 2.76-2.62 (m, J=6.5, 3.4, 3.4 Hz, 1H), 2.34-2.21 (m, 1H), 2.12-1.94 (m, 2H), 1.68-1.53 (m, 1H), 1.51-1.39 (m, 1H), 1.00 (d, J=6.8 Hz, 3H), 0.78-0.63 (m, 1H). Analytical HPLC (Method A): RT=8.64 min, purity=99.4%.

Example 369

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one Trifluoroacetate

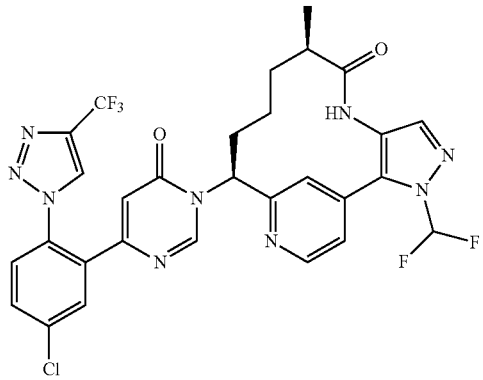

(9R,13S)-13-(4-{5-Chloro-2-[4-(trifluoromethyl)-1H-1,2,3-triazol-1-yl]phenyl}-6-oxo-1,6-dihydropyrimidin-1-yl)-3-(difluoromethyl)-9-methyl-3,4,7,15-tetraazatricyclo[12.3.1.0$^{2,6}$]octadeca-1(18),2(6),4,14,16-pentaen-8-one, trifluoroacetate (20 mg, 50% yield) was prepared in a similar manner as the procedure described in Example 367, by replacing (9R,13S)-13-amino-3,9-dimethyl-3,4,7,15-tetraazatricyclo[12.3.1.0$^{2,6}$]octadeca-1(18),2(6),4,14,16-pentaen-8-one, with (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one (17 mg, 0.051 mmol). MS(ESI) m/z: 660.3 (M+H). $^1$H NMR (400 MHz, CD$_3$OD) δ 8.81 (d, J=3.7 Hz, 2H), 8.71 (d, J=5.1 Hz, 1H), 7.89 (d, J=2.2 Hz, 1H), 7.81-7.62 (m, 5H), 7.56-7.46 (m, 1H), 6.44 (s, 1H), 6.00 (dd, J=12.7, 4.5 Hz, 1H), 2.70 (td, J=6.5, 3.0 Hz, 1H), 2.32-2.20 (m, 1H), 2.10-1.91 (m, 2H), 1.65-1.51 (m, 1H), 1.51-1.39 (m, 1H), 0.99 (d, J=6.8 Hz, 3H), 0.70-0.51 (m, 1H). Analytical HPLC (Method A): RT=9.74 min, purity=97.8%.

Example 370

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-3,9-dimethyl-3,4,7,17-tetraazatricyclo[12.3.1.0$^{2,6}$]octadeca-1(18),2(6),4,14,16-pentaen-8-one trifluoroacetate

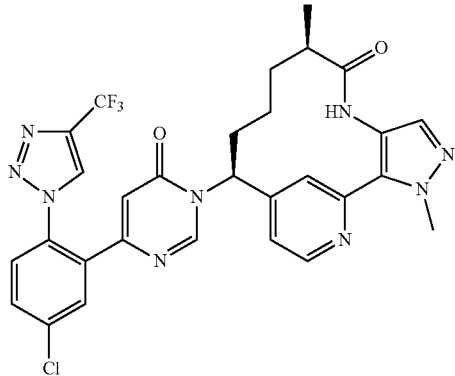 [SMILES: C[C@@H]1CCC[C@H](n2cnc(-c3cc(Cl)ccc3-n3cc(C(F)(F)F)nn3)cc2=O)c2ccnc(c2)-c2c(cnn2C)NC1=O]

(9R,13S)-13-(4-{5-Chloro-2-[4-(trifluoromethyl)-1H-1,2,3-triazol-1-yl]phenyl}-6-oxo-1,6-dihydropyrimidin-1-yl)-3,9-dimethyl-3,4,7,17-tetraazatricyclo[12.3.1.0$^{2,6}$]octadeca-1(18),2(6),4,14,16-pentaen-8-one, TFA salt (9 mg, 20%), an off-white solid, was prepared in the same manner as Example 362, replacing 6-[5-chloro-2-(4-chloro-1H-1,2,3-triazol-1-yl)phenyl]pyrimidin-4-ol, prepared as described in Example 358, with 6-{5-chloro-2-[4-(trifluoromethyl)-1H-pyrazol-1-yl]phenyl}pyrimidin-4-ol, prepared as described in Example 364B. MS(ESI) m/z: 624.3(M+H)$^+$. $^1$H NMR (400 MHz, CD$_3$OD) δ 8.84 (d, J=0.7 Hz, 1H), 8.71 (d, J=5.1 Hz, 1H), 8.29 (s, 1H), 7.91 (d, J=2.4 Hz, 1H), 7.86 (s, 1H), 7.80-7.75 (m, 1H), 7.72 (s, 1H), 7.51 (s, 1H), 7.17 (dd, J=5.3, 1.8 Hz, 1H), 6.52 (d, J=0.7 Hz, 1H), 5.77 (dd, J=12.4, 3.2 Hz, 1H), 4.18 (s, 3H), 2.64-2.56 (m, 1H), 2.38 (br. s., 1H), 2.11 (dd, J=13.1, 3.6 Hz, 1H), 2.02-1.95 (m, 1H), 1.64 (d, J=6.8 Hz, 1H), 1.39 (dd, J=16.9, 8.1 Hz, 2H), 1.14 (d, J=6.8 Hz, 3H). Analytical HPLC (Method A) RT=8.05 min, purity=95%.

Example 371

Preparation of (9R,13S)-13-(4-{5-chloro-2-[4-(trifluoromethyl)-1H-1,2,3-triazol-1-yl]phenyl}-6-oxo-1,6-dihydropyrimidin-1-yl)-3-($^2$H$_3$)methyl-9-methyl-3,4,7,17-tetraazatricyclo[12.3.1.0$^{2,6}$]octadeca-1(18),2(6),4,14,16-pentaen-8-one Trifluoroacetate

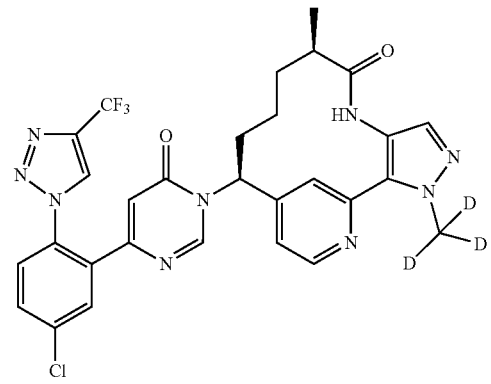 [SMILES: [2H]C([2H])([2H])n1ncc2c1-c1cc(ccn1)[C@@H](n1cnc(-c3cc(Cl)ccc3-n3cc(C(F)(F)F)nn3)cc1=O)CCC[C@@H](C)C(=O)N2]

(9R,13S)-13-(4-{5-Chloro-2-[4-(trifluoromethyl)-1H-1,2,3-triazol-1-yl]phenyl}-6-oxo-1,6-dihydropyrimidin-1-yl)-3-($^2$H$_3$)methyl-9-methyl-3,4,7,17-tetraazatricyclo[12.3.1.0$^{2,6}$]octadeca-1(18),2(6),4,14,16-pentaen-8-one trifluoroacetate (11.7 mg, 23%), an off-white solid, was prepared in the same manner as Example 362, replacing 6-[5-chloro-2-(4-chloro-H-1,2,3-triazol-1-yl)phenyl]pyrimidin-4-ol, prepared as described in Example 358, with 6-{5-chloro-2-[4-(trifluoromethyl)-1H-pyrazol-1-yl]phenyl}pyrimidin-4-ol, prepared as described in Example 364B. Also, (9R,13S)-13-amino-3,9-dimethyl-3,4,7,17-tetraazatricyclo[12.3.1.0$^{2,6}$]octadeca-1(18),2(6),4,14,16-pentaen-8-one, prepared as described in Example 361 was replaced with (9R,13S)-13-amino-3-($^2$H$_3$)methyl-9-methyl-3,4,7,17-tetraazatricyclo[12.3.1.0$^{2,6}$]octadeca-1(18),2(6),4,14,16-pentaen-8-one, prepared as described in Example 358F. MS(ESI) m/z: 627.3(M+H)$^l$. $^1$H NMR (400 MHz, CD$_3$OD) δ 8.86-8.82 (m, 1H), 8.75-8.69 (m, 1H), 8.28 (s, 1H), 7.94-7.87 (m, 1H), 7.86 (s, 1H), 7.80-7.76 (m, 1H), 7.74-7.69 (m, 1H), 7.51 (s, 1H), 7.20-7.09 (m, 1H), 6.56-6.51 (m, 1H), 5.77 (dd, J=12.5, 3.3 Hz, 1H), 2.67-2.58 (m, 1H), 2.47-2.37 (m, 2H), 2.19-

2.06 (m, 1H), 2.03-1.96 (m, 1H), 1.73-1.60 (m, 1H), 1.48-1.31 (m, 2H), 1.14 (d, J=6.8 Hz, 3H). Analytical HPLC (Method A) RT=8.02 min, purity=96%.

Example 372

Preparation of 1-(4-chloro-2-(1-((5R,9S)-21,5-dimethyl-4-oxo-21H-3-aza-1 (2,4)-pyridina-2(5,4)-pyrazolacyclononaphane-9-yl)-6-oxo-1,6-dihydropyrimidin-4-yl)phenyl)-1H-1,2,3-triazole-4-carboxylic Acid Trifluoroacetate

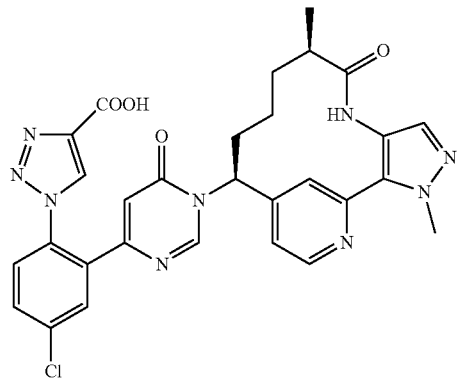 [SMILES: C[C@@H]1CCC[C@H](n2cnc(-c3cc(Cl)ccc3-n3cc(C(=O)O)nn3)cc2=O)c2ccnc(c2)-c2c(cnn2C)NC1=O]

372A. Preparation of N-(4-chloro-2-(6-methoxypyrimidin-4-yl)phenyl)-2,2,2-trifluoroacetamide

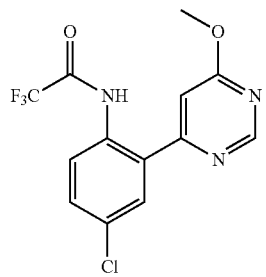 [SMILES: COc1cc(-c2cc(Cl)ccc2NC(=O)C(F)(F)F)ncn1]

TEA (0.371 ml, 2.66 mmol) was added to a solution of 4-chloro-2-(6-methoxypyrimidin-4-yl)aniline (0.523 g, 2.219 mmol), prepared as described in Example 358B, and trifluoroacetic anhydride (0.376 ml, 2.66 mmol) in DCM (17.47 ml). After 1 h, the reaction mixture was concentrated and purified by normal phase chromatography to give N-(4-chloro-2-(6-methoxypyrimidin-4-yl)phenyl)-2,2,2-trifluoroacetamide (0.684 g, 93% yield) as a white solid. MS(ESI) m/z: 332.1 (M+H)+. $^1$H NMR (400 MHz, CDCl$_3$-d) δ 13.95 (br. s., 1H), 8.83 (d, J=1.1 Hz, 1H), 8.59 (d, J=9.0 Hz, 1H), 7.76 (d, J=2.4 Hz, 1H), 7.49 (dd, J=9.0, 2.4 Hz, 1H), 7.16 (d, J=0.9 Hz, 1H), 4.09 (s, 3H).

372B. Preparation of N-(4-chloro-2-(6-hydroxypyrimidin-4-yl)phenyl)-2,2,2-trifluoroacetamide

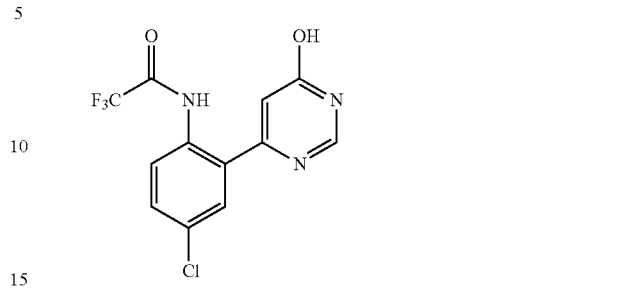

48% HBr in H$_2$O (1.693 ml, 14.97 mmol) was added to a stirring solution of N-(4-chloro-2-(6-methoxypyrimidin-4-yl)phenyl)-2,2,2-trifluoroacetamide (0.68 g, 2.05 mmol) in THF (13.67 ml) at 60° C. After 3 h, the reaction mixture was concentrated, quenched with saturated NaHCO$_3$(40 ml), and extracted with EtOAc (3×30 ml). The combined organic layers were washed with brine (15 mL) and dried (MgSO$_4$). The residue was purified by normal phase chromatography to give the desired product (0.195 g, 30%). MS(ESI) m/z: 318.1 (M+H)+. $^1$H NMR: (400 MHz, CDCl$_3$-d) δ 8.50 (d, J=9.0 Hz, 1H), 8.27 (s, 1H), 7.66 (d, J=2.4 Hz, 1H), 7.57-7.49 (m, 1H), 6.89 (s, 1H).

372C. Preparation of (5R,9S)-9-(4-(2-amino-5-chlorophenyl)-6-oxopyrimidin-1 (6H)-yl)-21,5-dimethyl-21H-3-aza-1 (2,4)-pyridina-2(5,4)-pyrazolacyclononaphan-4-one

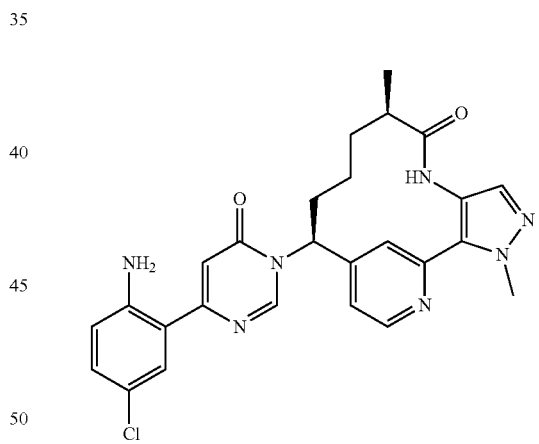

To a 1-dram vial containing a white suspension of N-(4-chloro-2-(6-hydroxypyrimidin-4-yl)phenyl)-2,2,2-trifluoroacetamide (0.035 g, 0.110 mmol) and HATU (0.054 g, 0.143 mmol) in ACN (1.10 ml) was added DBU (0.025 ml, 0.165 mmol). After 10 min, a purple solution of Example 361 (0.033 g, 0.110 mmol) in DMF (1.102 ml) was added. After stirring overnight, the reaction was diluted with water, extracted with EtOAc (3×), organics washed with brine, dried over Na$_2$SO$_4$, filtered and concentrated. The crude product was purified by normal phase chromatography to give the desired intermediate as a yellow film (30% undesired isomer also observed in $^1$H NMR). The material was carried forward to subsequent reactions. The trifluoroacetamide group was removed by dissolving the compound in MeOH (2 ml), treatment with HCl (1 ml), and heating to 75°

C. After 2 h, the organics were removed and the aqueous layer freeze dried. The HCl salt was neutralized by dissolving the residue in MeOH and passing through two successive NaHCO$_3$ cartridges (500 mg) and filtrate concentrated to give the desired product (0.040 g, 0.079 mmol, 72.0% yield) as a yellow film. MS(ESI) m/z: 504.3 (M+H)$^+$.

372D. Preparation of 1-(4-chloro-2-(1-((5R,9S)-21,5-dimethyl-4-oxo-21H-3-aza-1(2,4)-pyridina-2(5,4)-pyrazolacyclononaphane-9-yl)-6-oxo-1,6-dihydropyrimidin-4-yl)phenyl)-1H-1,2,3-triazole-4-carboxylic Acid Trifluoroacetate

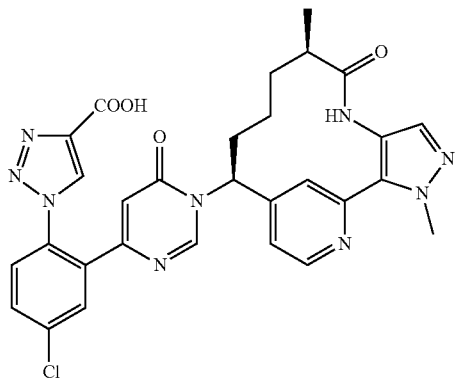 [SMILES: C[C@@H]1CCC[C@H](n2cnc(-c3cc(Cl)ccc3-n3cc(C(=O)O)nn3)cc2=O)c2ccnc(c2)-c2c(cnn2C)NC1=O]

To a yellow solution of 20 C (0.040 g, 0.079 mmol) in ACN (1.134 ml) at 0° C. was added isoamyl nitrite (0.032 ml, 0.238 mmol) in ACN (0.25 ml), followed by azidotrimethylsilane (0.031 ml, 0.238 mmol) ACN (0.25 ml), dropwise. After 10 min, the cold bath was removed, and the reaction allowed to warm to rt. After 1 h, tert-butyl propiolate (0.050 g, 0.397 mmol) ACN (0.25 ml), and Cu$_2$O (1.136 mg, 7.94 µmol) were added at rt. After 6 h, the reaction was diluted with DCM and washed with sat. NH$_4$Cl, brine, dried over MgSO$_4$, filtered and concentrated to give a yellow oil. The crude material was purified by normal phase chromatography to give the desired intermediate as a yellow film. The t-butyl ester was hydrolyzed by treatment with 50%/TFA/DCM. After 1 h, the reaction mixture was concentrated, purified by reverse phase chromatography, and freeze dried to give the desired product (15 mg, 25%). This material was subjected to chiral purification to remove any remaining residual undesired isomer. The title compound was the early eluting isomer after chiral HPLC separation using CHIRALPAK® IC, 21×250 mm ID, 5µ, using 40% MeOH:ACN:FA/60% CO$_2$ at 45.0 mL/min, 100 bar, and 40° C. MS(ESI) m/z: 600.3(M+H)$^+$. $^1$H NMR: (400 MHz, ACN-d$_3$) d 8.66 (d, J=5.1 Hz, 1H), 8.41 (s, 1H), 8.07 (s, 1H), 7.83-7.77 (m, 2H), 7.73-7.66 (m, 2H), 7.65-7.61 (m, 1H), 7.37 (s, 1H), 6.99 (d, J=4.2 Hz, 1H), 6.39 (s, 1H), 5.66-5.61 (m, 1H), 4.12 (s, 3H), 2.52 (br. s., 1H), 2.25-2.19 (m, 1H), 2.07-2.01 (m, 1H), 1.54 (dd, J=13.4, 5.5 Hz, 1H), 1.31 (d, J=7.9 Hz, 1H), 1.19-1.14 (m, 1H), 1.05 (d, J=6.8 Hz, 3H). Analytical HPLC (Method A) RT=5.31 min, purity>95%.

Example 373

Preparation of 1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-1,2,3-triazole-4-carboxylic Acid Trifluoroacetate

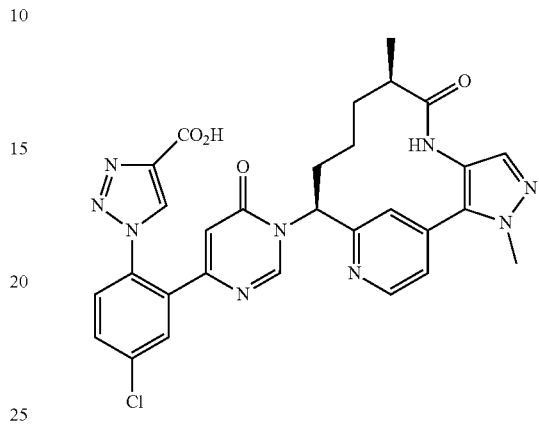

373A. Preparation of ethyl 1-[4-chloro-2-(6-methoxypyrimidin-4-yl)phenyl]-1H-1,2,3-triazole-4-carboxylate

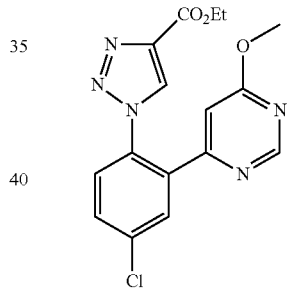

To a cooled (0° C.) clear, yellow solution of 4-chloro-2-(6-methoxypyrimidin-4-yl)aniline (0.400 g, 1.70 mmol), prepared as described in Example 356B, in CH$_3$CN (24.2 mL) was added isoamyl nitrite (0.34 mL, 2.55 mmol), followed by the dropwise addition of azidotrimethylsilane (0.34 mL, 2.55 mmol). Gas evolution was observed. After 10 min, the cold bath was removed and the reaction was allowed to warm to rt and stir at rt for 1 h. A yellow suspension formed. Next, ethyl propiolate (0.500 g, 5.09 mmol) and Cu$_2$O (0.024 g, 0.17 mmol) were added. After 1 h, the cloudy greenish reaction was diluted with DCM and washed with saturated aqueous NH$_4$Cl, brine, dried over MgSO$_4$, filtered and concentrated to give a yellow oil. Purification by normal phase chromatography gave ethyl 1-[4-chloro-2-(6-methoxypyrimidin-4-yl)phenyl]-1H-1,2,3-triazole-4-carboxylate (0.507 g, 83% yield) as a yellow solid. MS(ESI) m/z: 360.0 (M+H)$^+$. $^1$H NMR (400 MHz, CDCl$_3$) δ 8.65 (d, J=1.1 Hz, 1H), 8.19 (s, 1H), 7.75 (d, J=2.4 Hz, 1H), 7.62 (dd, J=8.4, 2.4 Hz, 1H), 7.50 (d, J=8.4 Hz, 1H), 6.56 (d, J=1.1 Hz, 1H), 4.44 (q, J=7.3 Hz, 2H), 3.96 (s, 3H), 1.42 (t, J=7.2 Hz, 3H).

373B. Preparation of ethyl 1-[4-chloro-2-(6-hydroxypyrimidin-4-yl)phenyl]-1H-1,2,3-triazole-4-carboxylate

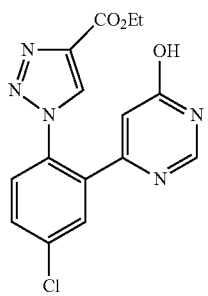 [SMILES: CCOC(=O)c1cn(-c2ccc(Cl)cc2-c2cc(O)ncn2)nn1]

To a suspension of ethyl 1-[4-chloro-2-(6-methoxypyrimidin-4-yl)phenyl]-1H-1,2,3-triazole-4-carboxylate (0.200 g, 0.56 mmol) in CH$_3$CN (3 mL) was added TMS-I (0.38 mL, 2.78 mmol). The resulting clear yellow solution was heated at 50° C. over night. The reaction was cooled to rt and then it was poured into a mixture of 10% sodium thiosulfate and saturated aqueous NaHCO$_3$. The reaction was extracted with DCM (3×). The organic layers were combined and concentrated. Purification by normal phase chromatography gave ethyl 1-[4-chloro-2-(6-hydroxypyrimidin-4-yl)phenyl]-1H-1,2,3-triazole-4-carboxylate (0.098 g, 51% yield) as a white solid. MS(ESI) m/z: 345.9 (M+H)$^+$. $^1$H NMR (400 MHz, CDCl$_3$) δ 8.30 (s, 1H), 7.97 (d, J=1.1 Hz, 1H), 7.73 (d, J=2.2 Hz, 1H), 7.62 (dd, J=8.5, 2.3 Hz, 1H), 7.49 (d, J=8.4 Hz, 1H), 6.46 (d, J=0.9 Hz, 1H), 4.44 (q, J=7.3 Hz, 2H), 1.42 (t, J=7.2 Hz, 3H).

373C. Preparation of ethyl 1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-1,2,3-triazole-4-carboxylate Trifluoroacetate

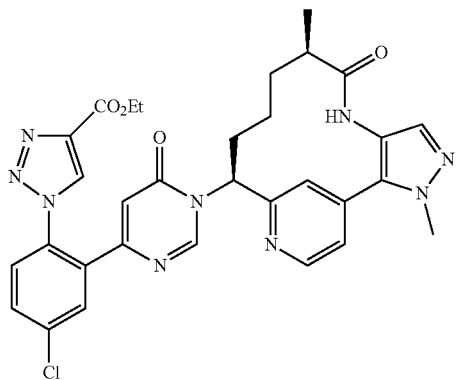 [SMILES: CCOC(=O)c1cn(-c2ccc(Cl)cc2-c2cc(=O)n([C@H]3CCC[C@@H](C)C(=O)Nc4cnn(C)c4-c4ccnc3c4)cn2)nn1]

To a 1-dram vial containing a white suspension of ethyl 1-[4-chloro-2-(6-hydroxypyrimidin-4-yl)phenyl]-1H-1,2,3-triazole-4-carboxylate (0.035 g, 0.10 mmol) and HATU (0.050 g, 0.13 mmol) in CH$_3$CN (1.0 mL) was added DBU (0.023 mL, 0.15 mmol). The resulting clear, yellow solution was stirred at rt for 20 min. Then a clear, purple solution of (9R,13S)-13-amino-3,9-dimethyl-3,4,7,15-tetraazatricyclo[12.3.1.0$^{2,6}$]octadeca-1(18),2(6),4,14,16-pentaen-8-one (0.030 g, 0.10 mmol), prepared as described in Example 365, in DMF (1.0 mL) was added. The reaction was stirred at rt. After 3 h, the reaction was stopped purified directly by reverse phase chromatography which gave, after concentration and lyophilization, ethyl 1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-1,2,3-triazole-4-carboxylate, trifluoroacetate (0.0292 g, 39% yield) as an off-white solid. MS(ESI) m/z: 628.4 (M+H)$^+$. $^1$H NMR (500 MHz, CD$_3$OD) δ 8.81 (s, 1H), 8.78 (s, 1H), 8.70 (d, J=5.2 Hz, 1H), 7.89 (d, J=2.5 Hz, 1H), 7.74 (dd, J=8.5, 2.5 Hz, 1H), 7.70-7.65 (m, 2H), 7.52 (dd, J=5.0, 1.7 Hz, 1H), 7.49 (s, 1H), 6.39 (s, 1H), 5.99-5.93 (m, 1H), 4.40 (q, J=7.2 Hz, 2H), 4.05 (s, 3H), 2.74-2.66 (m, 1H), 2.32-2.23 (m, 1H), 2.11-1.93 (m, 2H), 1.64-1.54 (m, 1H), 1.50-1.41 (m, 1H), 1.38 (t, J=7.2 Hz, 3H), 1.00 (d, J=6.9 Hz, 3H), 0.73-0.61 (m, 1H). Analytical HPLC (Method A) RT=4.90 min, purity=98.8%.

373D. Preparation of 1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-1,2,3-triazole-4-carboxylic Acid Trifluoroacetate A clear, colorless solution of ethyl 1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-1,2,3-triazole-4-carboxylate trifluoroacetate (0.020 g, 0.027 mmol) in MeOH (0.54 mL) and 1.0 M NaOH (0.14 mL, 0.14 mmol) was stirred at rt. After 2 h the reaction was stopped, neutralized with 1.0 M HCl and then the reaction was concentrated to give a white solid. Purification by reverse phase chromatography gave, after concentration and lyophilization, 1-(4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,6-dihydropyrimidin-4-yl}phenyl)-1H-1,2,3-triazole-4-carboxylic acid, trifluoroacetate (0.0126 g, 64% yield) as a white solid. MS(ESI) m/z: 600.3 (M+H)$^1$. $^1$H NMR (500 MHz, CD$_3$OD) δ 8.78 (s, 1H), 8.73 (s, 1H), 8.71 (d, J=5.2 Hz, 1H), 7.89 (d, J=2.2 Hz, 1H), 7.76-7.73 (m, 1H), 7.70-7.66 (m, 2H), 7.50 (dd, J=5.1, 1.5 Hz, 1H), 7.49 (s, 1H), 6.40 (s, 1H), 6.00-5.94 (m, 1H), 4.05 (s, 3H), 2.74-2.66 (m, 1H), 2.32-2.23 (m, 1H), 2.11-1.93 (m, 2H), 1.64-1.54 (m, 1H), 1.51-1.40 (m, 1H), 1.00 (d, J=6.9 Hz, 3H), 0.73-0.61 (m, 1H). Analytical HPLC (Method A) RT=3.37 min, purity=100%.

What is claimed is:
1. A compound having Formula (IIa):

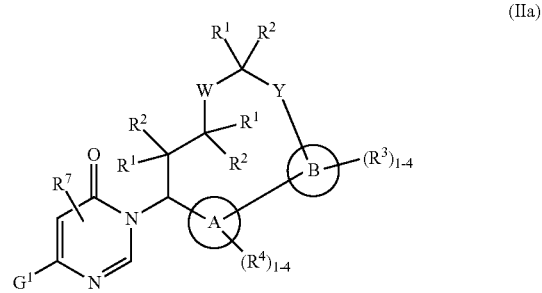

or a stereoisomer, a tautomer, a pharmaceutically acceptable salt thereof, wherein:

ring A is a 6-membered aryl or a 6-membered heteroaryl;

ring B is a 6-membered heteroaryl substituted with, where valence allows, one or more $R^3$ groups comprising carbon atoms and 1-3 heteroatoms selected from N and $NR^{3c}$;

$G^1$ is

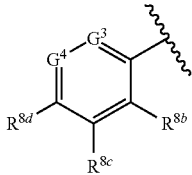

wherein $G^3$ is $CR^{8a}$ and $G^4$ is $CR^{8e}$;

W is independently selected from $(CR^1R^2)_{1-2}$, O, NH, and $N(C_{1-4}$ alkyl);

Y is independently selected from —$CHR^{13}NH$—, —NHC(=O)— and —C(=O)NH—;

$R^1$ and $R^2$ are independently selected from H, D, halogen, haloalkyl, $C_{1-6}$ alkyl (optionally substituted with $R^6$), hydroxyl, and alkoxy (optionally substituted with $R^6$), and $C_{3-5}$ cycloalkyl optionally substituted with $R^6$;

$R^3$ is independently selected from H, =O, halogen, $C_{1-4}$ alkyl (optionally substituted with $R^6$), CN, —$(CH_2)_n$—$OR^5$, —$(CH_2)_n$—$NR^5R^5$, —$(CH_2)_n$—C(=O)$R^5$, and —$(CH_2)_n$—C(=O)$OR^5$;

$R^{3c}$ is independently selected from H, haloalkyl, and $C_{1-4}$ alkyl (optionally substituted with $R^6$);

$R^4$ is independently selected from H, OH, halogen, CN, $C_{1-4}$ alkyl, $C_{1-4}$ haloalkyl, and $C_{1-4}$ alkoxy;

$R^5$ is independently selected from H, $C_{1-4}$ alkyl (optionally substituted with halogen, hydroxyl, alkoxy, carboxy, alkoxycarbonyl, amino, substituted amino), $C_{3-10}$ carbocyclyl and 4- to 10-membered heterocyclyl, wherein said carbocyclyl and heterocyclyl are optionally substituted with $R^6$;

$R^6$ is independently selected from H, —$(CH_2)_n$—OH, =O, —$(CH_2)_n NH_2$, —$(CH_2)_n CN$, halogen, $C_{1-6}$ alkyl, —$(CH_2)_n$—C(=O)OH, —$(CH_2)_n$—C(=O)O$C_{1-4}$ alkyl, —$(CH_2)_n$—O$C_{1-4}$ alkyl, —$(CH_2)_n$—C(=O)$NH_2$, —$(CH_2)_n$—$C_{3-10}$ carbocyclyl, —$(CH_2)_n$-4- to 10-membered heterocyclyl, and —O—$(CH_2)_n$-4- to 10-membered heterocyclyl, wherein said carbocyclyl and heterocyclyl are optionally substituted with $R^{10}$;

$R^7$ is independently selected from H, hydroxyl, halogen, $C_{1-2}$haloalkyl, and $C_{1-2}$alkyl;

$R^{8a}$ is a 5-membered heterocyclyl with at least 3 nitrogen atoms optionally substituted with $R^{10}$;

$R^{8b}$ is independently selected from H and F;

$R^{8c}$ is independently selected from H, F, Cl, methyl, ethyl, isopropyl, $OCHF_2$, and $OCH_3$;

$R^{8d}$ is independently selected from H, F, and Cl;

$R^{8e}$ is H;

$R^{10}$ is independently selected from H, $C_{1-6}$ alkyl (optionally substituted with $R^{11}$), $C_{2-6}$ alkenyl, $C_{2-6}$ alkynyl, aryl (optionally substituted with $R^{11}$), —$(CH_2)_n$—$C_{3-6}$ cycloalkyl (optionally substituted with $R^{11}$), —$(CH_2)_n$—O-4- to 10-membered heterocyclyl (optionally substituted with $R^{11}$), F, Cl, Br, —$(CH_2)_n CN$, $NO_2$, =O, C(=O)$N^{12}R^{12}$, —$(CH_2)_n$C(=O)$OR^{12}$, $Si(C_{1-4}$ alkyl)$_3$, —$(CH_2)_n$—$OR^{12}$, —$(CH_2)_n$—$NR^{12}R^{12}$, —S(=O)$_p C_{1-6}$ alkyl, $NR^{12}S(=O)_p C_{1-6}$ alkyl, and S(=O)$_p NR^{12}R^{12}$;

$R^{11}$, at each occurrence, is independently selected from H, halogen, $C_{1-5}$ alkyl, —$(CH_2)_n$—OH, $C_{3-6}$ cycloalkyl, and phenyl;

$R^{12}$, at each occurrence, is independently selected from H, $C_{1-5}$ alkyl optionally substituted with $R^{11}$, $C_{3-6}$ cycloalkyl, phenyl, and heterocyclyl, or $R^{12}$ and $R^{12}$ together with the nitrogen atom to which they are both attached form a heterocyclic ring optionally substituted with $C_{1-4}$alkyl;

$R^{13}$ is, independently at each occurrence, selected from H, $CF_3$, C(=O)OH, C(=O)O($C_{1-4}$ alkyl), and —C(=O)$NH_2(C_{1-4}$ alkoxy);

n, at each occurrence, is an integer independently selected from 0, 1, 2, 3, and 4; and p, at each occurrence, is an integer independently selected from 0, 1, and 2.

2. The compound of claim 1 having Formula (IIb):

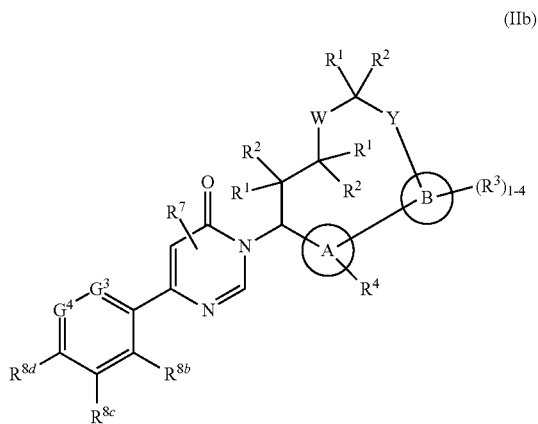

(IIb)

or a stereoisomer, a tautomer, a pharmaceutically acceptable salt thereof, wherein:

ring A is phenyl or pyridyl;

ring B is a 6-membered heteroaryl substituted with, where valence allows, one or more $R^3$ groups comprising carbon atoms and 1-3 N atoms;

W is independently selected from $(CR^1R^2)_{1-2}$, O, NH, and $N(C_{1-4}$ alkyl);

Y is independently selected from —$CH_2NH$—, —NHC(=O)— and —C(=O)NH—;

$G^3$ is $CR^{8a}$;

$G^4$ is $CR^{8c}$;

$R^1$ and $R^2$ are independently selected from H, D, halogen, $CF_3$, $C_{1-6}$ alkyl, and hydroxyl;

$R^3$ is independently selected from H, halogen, $C_{1-4}$alkyl (optionally substituted with $R^6$), CN, —$(CH_2)_n$—$OR^5$, —$(CH_2)_n$—$NR^5R^5$, —$(CH_2)_n$—C(=O)$R^5$, and —$(CH_2)_n$—C(=O)$OR^5$;

$R^4$ is independently selected from H, OH, F, Cl, Br, $C_{1-4}$ alkyl, $C_{1-4}$ alkoxy, $CF_3$, CN;

$R^5$ is independently selected from H and $C_{1-4}$ alkyl, wherein $C_{1-4}$ alkyl is optionally substituted with halogen and hydroxyl;

$R^6$ is independently selected from H, —$(CH_2)_n$—OH, =O, $NH_2$, —$(CH_2)_n$—CN, halogen, $C_{1-6}$ alkyl, —$(CH_2)_n$—C(=O)OH, —$(CH_2)_n$—C(=O)O$C_{1-4}$ alkyl, —$(CH_2)_n$—O$C_{1-4}$ alkyl, —$(CH_2)_n$—$C_{3-6}$ cycloalkyl, —(CH$_2$)$_n$-4- to 10-membered heterocyclyl, and —O—(CH$_2$)$_n$-4- to 10-membered heterocyclyl, wherein said cycloalkyl and heterocyclyl are optionally substituted with R$^{10}$;

R$^7$ is independently selected from H, F, Cl, Br, CF$_3$, and CH$_3$;

R$^{8a}$ is a 5-membered heterocyclyl with at least 3 nitrogen atoms optionally substituted with R$^{10}$;

R$^{8b}$ is independently selected from H and F;

R$^{8c}$ is independently selected from H, F, Cl, methyl, ethyl, isopropyl, OCHF$_2$, and OCH$_3$;

R$^{8d}$ is independently selected from H, F, and Cl;

R$^{8e}$ is H;

R$^{10}$ is independently selected from H, C$_{1-6}$ alkyl (optionally substituted with R$^{11}$), C$_{2-6}$ alkenyl, C$_{2-6}$ alkynyl, aryl (optionally substituted with R$^{11}$), —(CH$_2$)$_n$—C$_{3-6}$ cycloalkyl (optionally substituted with R$^{11}$), —(CH$_2$)$_n$—O-4- to 10-membered heterocyclyl (optionally substituted with R$^{11}$), F, Cl, Br, CN, NO$_2$, =O, CONR$^{12}$R$^{12}$, —(CH$_2$)$_n$C(=O)OR$^{12}$, Si(C$_{1-4}$ alkyl)$_3$, —(CH$_2$)$_n$—OR$^{12}$, —(CH$_2$)$_n$—NR$^{12}$R$^{12}$, —S(=O)$_p$C$_{1-6}$ alkyl, NR$^{12}$S(=O)$_p$C$_{1-6}$ alkyl, and S(=O)$_p$NR$^{12}$R$^{12}$;

R$^{11}$, at each occurrence, is independently selected from H, halogen, C$_{1-5}$ alkyl, —(CH$_2$)$_n$—OH, C$_{3-6}$ cycloalkyl, and phenyl;

R$^{12}$, at each occurrence, is independently selected from H, C$_{1-5}$ alkyl optionally substituted with R$^{11}$, C$_{3-6}$ cycloalkyl, phenyl, and heterocyclyl, or R$^{12}$ and R$^{12}$ together with the nitrogen atom to which they are both attached form a heterocyclic ring optionally substituted with C$_{1-4}$alkyl;

n, at each occurrence, is an integer independently selected from 0, 1, and 2; and p, at each occurrence, is an integer independently selected from 0, 1, and 2.

3. The compound of claim 2 or a stereoisomer, a tautomer, a pharmaceutically acceptable salt thereof, wherein:

ring A is phenyl or pyridyl;

ring B is a 6-membered heteroaryl comprising carbon atoms and 1-3 N atoms;

W is independently selected from (CR$^1$R$^2$)$_{1-2}$, O, NH, and N(C$_{1-4}$ alkyl);

Y is independently selected from —CH$_2$NH—, —NHC(=O)— and —C(=O)NH—;

G$^3$ is CR$^{8a}$;

G$^4$ is CR$^{8e}$;

R$^1$ and R$^2$ are independently selected from H, D, halogen, CF$_3$, C$_{1-6}$ alkyl, and hydroxyl;

R$^3$ is independently selected from H, halogen, C$_{1-4}$alkyl (optionally substituted with R$^6$), CN, —(CH$_2$)$_n$—OR$^5$, —(CH$_2$)$_n$—C(=O)R$^5$, and —(CH$_2$)$_n$—C(=O)OR$^5$;

R$^4$ is H;

R$^5$ is independently selected from H and C$_{1-4}$ alkyl;

R$^6$ is independently selected from H, —(CH$_2$)$_n$—OH, =O, NH$_2$, —(CH$_2$)$_n$—CN, halogen, and C$_{1-6}$ alkyl;

R$^7$ is independently selected from H, F, Cl, Br, and methyl;

R$^{8a}$ is a 5-membered heterocyclyl with at least 3 nitrogen atoms is optionally substituted with R$^{10}$;

R$^{8b}$ is independently selected from H and F;

R$^{8c}$ is independently selected from H, F, Cl, methyl, ethyl, isopropyl, and OCH$_3$;

R$^{8d}$ is independently selected from H, F, and Cl;

R$^{8e}$ is H;

R$^{10}$ is independently selected from H, C$_{1-6}$ alkyl (optionally substituted with R$^{11}$), C$_{2-6}$ alkenyl, C$_{2-6}$ alkynyl, aryl (optionally substituted with R$^{11}$), —(CH$_2$)$_n$—C$_{3-6}$ cycloalkyl (optionally substituted with R$^{11}$), —(CH$_2$)$_n$—O-4- to 10-membered heterocyclyl (optionally substituted with R$^{11}$), F, Cl, Br, CN, NO$_2$, =O, CONR$^{12}$R$^{12}$, —(CH$_2$)$_n$—C(=O)OR$^{12}$, Si(C$_{1-4}$ alkyl)$_3$, —(CH$_2$)$_n$—OR$^{12}$, —(CH$_2$)$_n$—NR$^{12}$R$^{12}$, —S(=O)$_p$C$_{1-6}$ alkyl, NR$^{12}$S(=O)$_p$C$_{1-6}$ alkyl, and S(=O)$_p$NR$^{12}$R$^{12}$;

R$^{11}$, at each occurrence, is independently selected from H, halogen, C$_{1-5}$ alkyl, —(CH$_2$)$_n$—OH, C$_{3-6}$ cycloalkyl, and phenyl;

R$^{12}$, at each occurrence, is independently selected from H, C$_{1-5}$ alkyl optionally substituted with R$^{11}$, C$_{3-6}$ cycloalkyl, phenyl, and heterocyclyl, or R$^{12}$ and R$^{12}$ together with the nitrogen atom to which they are both attached form a heterocyclic ring optionally substituted with C$_{1-4}$alkyl;

n, at each occurrence, is an integer independently selected from 0, 1, and 2; and p, at each occurrence, is an integer independently selected from 0, 1, and 2.

4. The compound of claim 3 having Formula (IIc):

(IIc)

or a stereoisomer, a tautomer, a pharmaceutically acceptable salt thereof, wherein:

ring A is phenyl or pyridyl;

ring B is a 6-membered heteroaryl comprising carbon atoms and 1-3 N atoms;

W is independently selected from (CR'R$^2$)$_{1-2}$, O, NH, and N(C$_{1-4}$ alkyl);

Y is independently selected from —CH$_2$NH—, —NHC(=O)— and —C(=O)NH—;

R$^1$ and R$^2$ are independently selected from H, D, F, C$_{1-4}$ alkyl, and hydroxyl;

R$^3$ is independently selected from H, halogen, haloalkyl, C$_{1-4}$alkyl (optionally substituted with R$^6$), and CN;

R$^4$ is H;

R$^6$ is independently selected from H, —(CH$_2$)$_n$—OH, =O, NH$_2$, —(CH$_2$)$_n$—CN, halogen, and C$_{1-6}$ alkyl;

R$^{8b}$ is independently selected from H and F;

R$^{8c}$ is independently selected from H, F, Cl, CH$_3$, and OCH$_3$;

R$^{10}$ is independently selected from H, C$_{1-6}$ alkyl (optionally substituted with R$^{11}$);

R$^{11}$, at each occurrence, is independently selected from H, halogen, and C$_{1-5}$ alkyl; and, n, at each occurrence, is an integer independently selected from 0, 1, and 2.

5. The compound of claim 1 having Formula (IIIb):

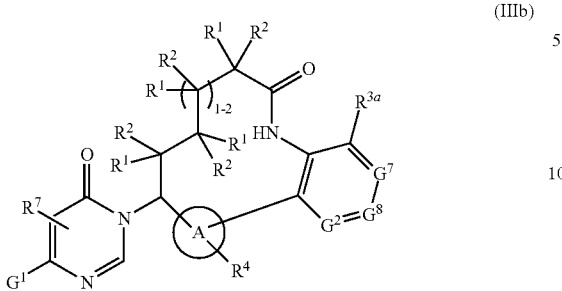

(IIIb)

or a stereoisomer, a tautomer, a pharmaceutically acceptable salt thereof, wherein:
ring A is phenyl or pyridyl;
$G_1$ is

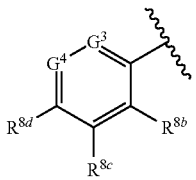

wherein $G^3$ is $CR^{8a}$ and $G^4$ is $CR^{8e}$;
$G^2$ is independently selected from N and $CR^{3b}$;
$G^7$ is independently selected from N and $CR^3$;
$G^8$ is independently selected from N and $CR^3$;
provided at least one of $G^2$, $G^7$, and $G^8$ is N;
$R^1$ and $R^2$ are independently selected from H, halogen, $CF_3$, $C_{1-6}$ alkyl, and hydroxyl;
$R^3$ is independently selected from H, halogen, $C_{1-4}$alkyl (optionally substituted with $R^6$), $C_{2-4}$alkenyl (optionally substituted with $R^6$), CN, $-(CH_2)_n-OR^5$, $-(CH_2)_n-NR^5R^5$, and $-(CH_2)_n-C(=O)OR^5$;
$R^{3a}$ is independently selected from H and halogen;
$R^{3b}$ is independently selected from H, halogen, methyl, and CN;
$R^4$ is independently selected from H, OH, F, Cl, Br, $C_{1-4}$ alkyl, $C_{1-4}$ alkoxy, $CF_3$, and CN;
$R^5$ is independently selected from H, $C_{1-4}$ alkyl (optionally substituted with halogen, hydroxyl, alkoxy, carboxy, alkoxycarbonyl, amino, substituted amino), $-C_{3-10}$ carbocyclyl and $-(CH_2)_n$-4- to 10-membered heterocyclyl, wherein said carbocyclyl and heterocyclyl are optionally substituted with $R^6$;
$R^6$ is independently selected from $-(CH_2)_n-OH$, $=O$, $NH_2$, $-(CH_2)_n-CN$, halogen, $C_{1-6}$ alkyl, $-(CH_2)_n-C(=O)OH$, $-(CH_2)_n-C(=O)OC_{1-4}$ alkyl, $-(CH_2)_n-OC_{1-4}$ alkyl, $-(CH_2)_n-C_{3-6}$ cycloalkyl, $-(CH_2)_n$-4- to 10-membered heterocyclyl, and $-O-(CH_2)_n$-4- to 10-membered heterocyclyl, wherein said cycloalkyl and heterocyclyl are optionally substituted with $R^{10}$;
$R^7$ is independently selected from H, F, Cl, and methyl;
$R^{8a}$ is a 5-membered 4 to 12 membered heterocyclyl with at least 3 nitrogen atoms optionally substituted with $R^{10}$;
$R^{8b}$ is independently selected from H and F;
$R^{8c}$ is independently selected from H, F, Cl, methyl, ethyl, isopropyl, $OCHF_2$, and $OCH_3$;
$R^{8d}$ is independently selected from H, F, and Cl;
$R^{8e}$ is H;
$R^{10}$ is independently selected from H, $C_{1-6}$ alkyl (optionally substituted with $R^{11}$), $C_{2-6}$ alkenyl, $C_{2-6}$ alkynyl, aryl, $-(CH_2)_n-C_{3-6}$ cycloalkyl (optionally substituted with $R^{11}$), $-(CH_2)_n$-O-4- to 10-membered heterocyclyl (optionally substituted with $R^{11}$), F, Cl, Br, CN, $NO_2$, $=O$, $C(=O)NR^{12}R^{12}$, $C(=O)OR^{12}$, $Si(C_{1-4}$ alkyl$)_3$, $-(CH_2)_n-OR^{12}$, $-(CH_2)_n-NR^{12}R^{12}$, $-S(=O)_pC_{1-6}$ alkyl, $NR^{12}S(=O)_pC_{1-6}$ alkyl, and $S(=O)_pNR^{12}R^{12}$;
$R^{11}$, at each occurrence, is independently selected from H, halogen, $C_{1-5}$ alkyl, $-(CH_2)_n-OH$, $C_{3-6}$ cycloalkyl, and phenyl;
$R^{12}$, at each occurrence, is independently selected from H, $C_{1-5}$ alkyl, $C_{3-6}$ cycloalkyl, phenyl, and heterocyclyl, or $R^{12}$ and $R^{12}$ together with the nitrogen atom to which they are both attached form a heterocyclic ring optionally substituted with $C_{1-4}$alkyl;
n, at each occurrence, is an integer independently selected from 0, 1, and 2; and
p, at each occurrence, is an integer independently selected from 0, 1, and 2.

6. The compound of claim 5, having Formula (IVa):

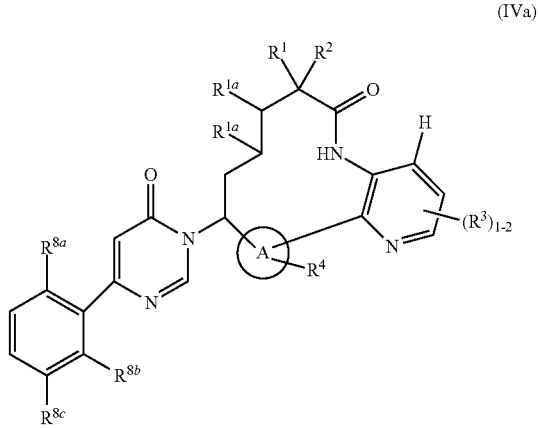

(IVa)

or a stereoisomer, a tautomer, a pharmaceutically acceptable salt thereof, wherein:
ring A is

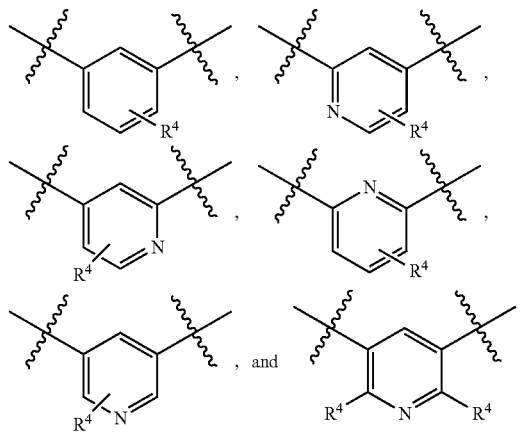

$R^1$ and $R^2$ are independently selected from H, F, $C_{1-4}$ alkyl, and OH;

$R^{1a}$, at each occurrence, is independently selected from H, F, $CH_3$, and OH;

$R^3$ is independently selected from H, F, Cl, Br, I, $C_{2-4}$alkenyl (optionally substituted with C(=O)OH), CN, and —$(CH_2)_n$—OH;

$R^4$ is independently selected from H, OH, F, $OC_{1-4}$ alkyl, $C_{1-4}$ alkyl, and CN;

$R^{8a}$ is a 5-membered heterocyclyl with at least 3 nitrogen atoms optionally substituted with $R^{10}$;

$R^{8b}$ is independently selected from H and F;

$R^{8c}$ is independently selected from H, F, Cl, $CH_3$, and $OCH_3$;

$R^{10}$ is independently selected from $C_{1-6}$ alkyl, —$C_{3-6}$ cycloalkyl, F, Cl, Br, CN, and $OC_{1-5}$ alkyl; and n, at each occurrence, is an integer independently selected from 0, 1, and 2.

7. The compound of claim 2, or a stereoisomer, a tautomer, a pharmaceutically acceptable salt thereof, wherein: ring A is independently selected from

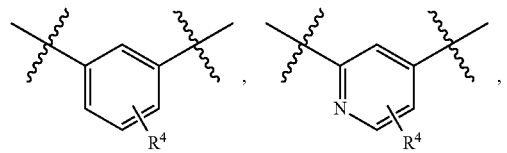

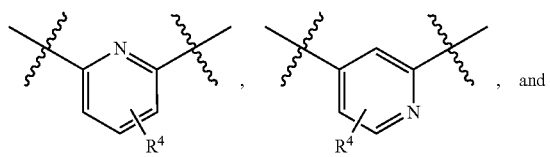, and

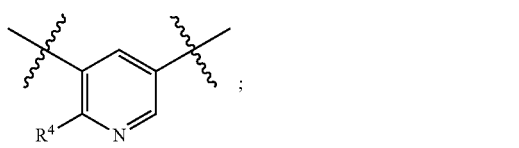;

ring B is independently selected from

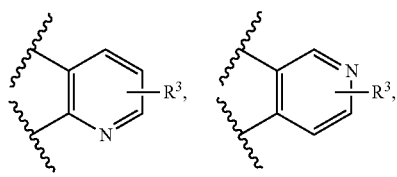

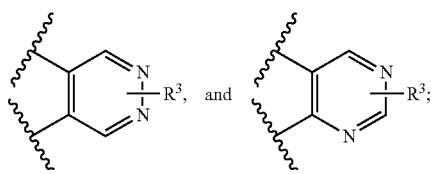

W is independently selected from $CHR^{1a}$ O, NH, and $N(C_{1-4}$ alkyl);

$R^1$ is independently selected from H and $C_{1-4}$ alkyl;

$R^{1a}$ is independently selected from H F, $CH_3$, and hydroxyl;

$R^2$ is independently selected from H and hydroxyl;

$R^3$ is independently selected from H, F, $CH_3$, CN, —$(CH_2)_{0-2}$—OH, $OC_{1-4}$ alkyl, C(=O)$C_{1-4}$ alkyl, and —$(CH_2)_{0-1}$—C(=O)OH;

$R^4$ is independently selected from H and F;

$R^{8b}$ is independently selected from H and F;

$R^{8c}$ is independently selected from H and Cl;

$R^{10}$ is independently selected from H, $C_{1-6}$ alkyl (optionally substituted with $R^{11}$), aryl, —$(CH_2)_n$—$C_{3-6}$ cycloalkyl (optionally substituted with $R^{11}$), —$(CH_2)_n$—O-4- to 10-membered heterocyclyl, F, Cl, Br, CN, C(=O)$NR^{12}R^{12}$, $Si(C_{1-4}$ alkyl$)_3$, and —$(CH_2)_n$—$OR^{12}$;

$R^{11}$, at each occurrence, is independently selected from H, halogen, and $C_{1-5}$ alkyl; and n, at each occurrence, is an integer independently selected from 0, 1, 2, 3, and 4.

8. The compound of claim 1, or a stereoisomer, a tautomer, a pharmaceutically acceptable salt thereof, wherein: ring A is independently selected from

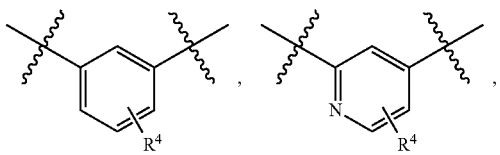

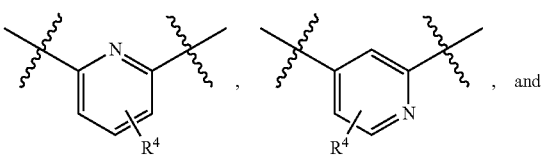, and

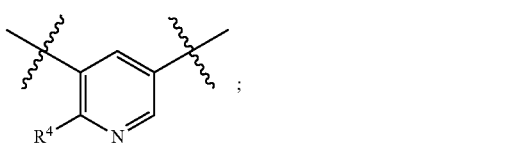;

ring B is independently selected from

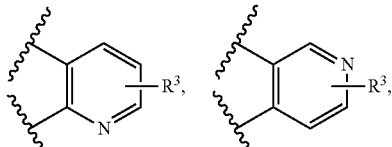

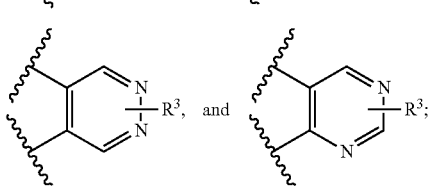

$G^1$ is independently selected from
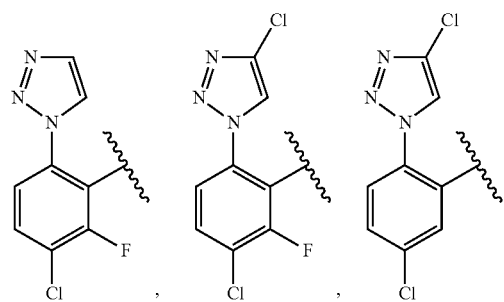
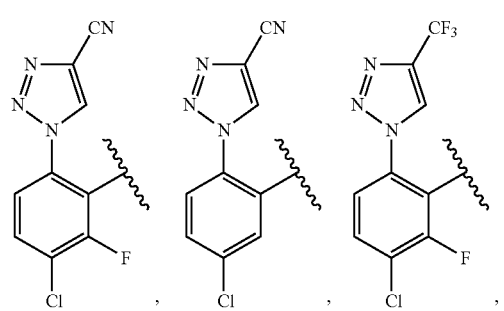
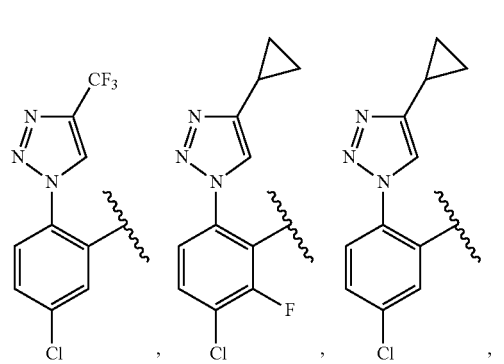
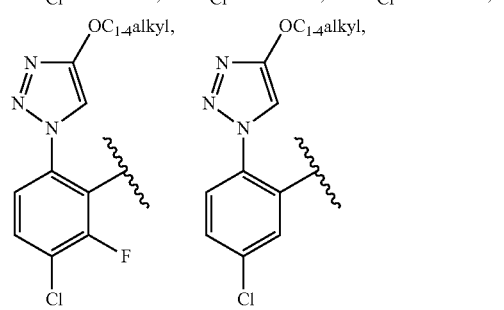
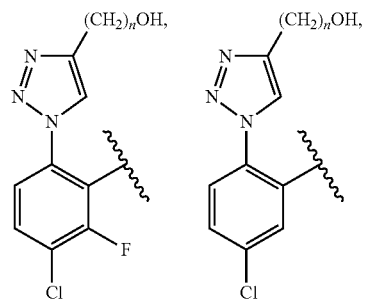
-continued
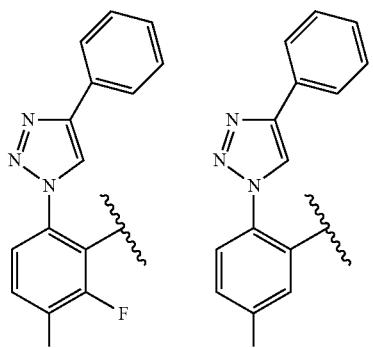
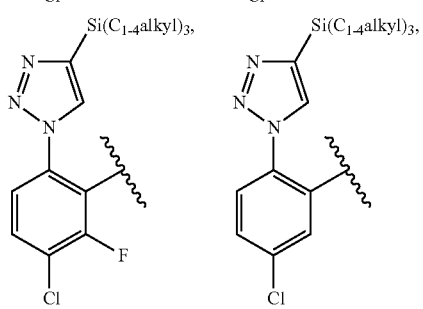
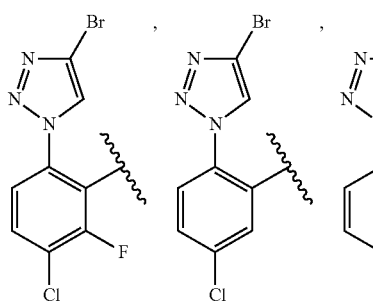
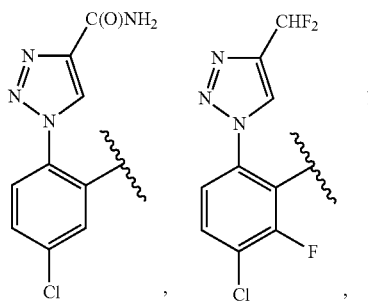
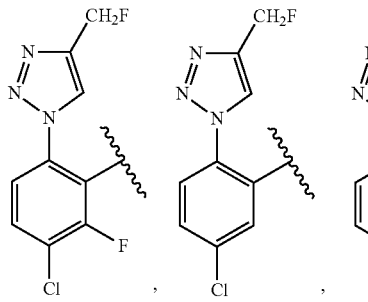

-continued

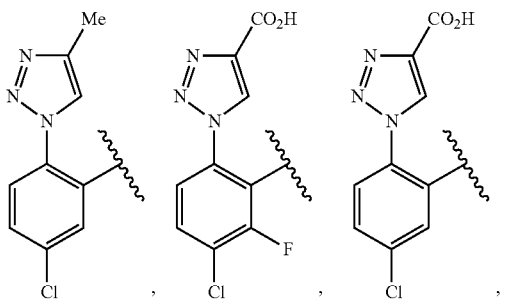

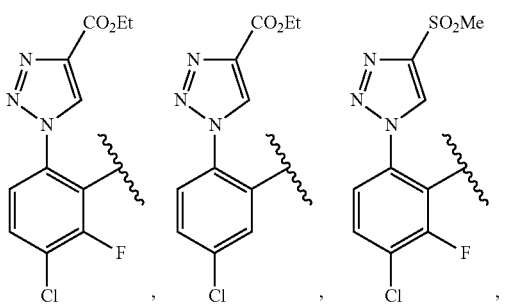

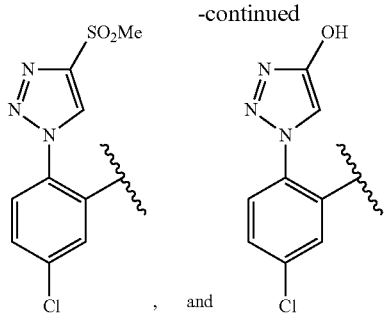

, and

W is independently selected from CHR$^1$, O, NH, and N(C$_{1-4}$ alkyl);

Y is independently selected from —NH—, —NHC(=O)— and —C(=O)NH—;

R$^1$ and R$^2$ are independently selected from H, F, C$_{1-4}$ alkyl, and hydroxyl;

R$^3$ is independently selected from H, =O, F, CH$_3$, CN, —(CH$_2$)$_{0-2}$—OH, OC$_{1-4}$ alkyl, C(=O)C$_{1-4}$ alkyl, —(CH$_2$)$_{0-1}$—C(=O)OH, and —C(=O)OC$_{1-4}$ alkyl;

R$^{3c}$ is independently selected from H, CF$_2$H, CF$_3$, and C$_{1-4}$ alkyl;

R$^4$ is independently selected from H, F, and C$_{1-4}$ alkyl; and

R$^7$ is H.

9. A pharmaceutical composition comprising one or more compounds according to claim 1 and a pharmaceutically acceptable carrier or diluent.

\* \* \* \* \*